United States Patent
Ramaswamy et al.

(10) Patent No.: US 7,105,293 B2
(45) Date of Patent: Sep. 12, 2006

(54) GENETIC MARKERS FOR TUMORS

(75) Inventors: Sridhar Ramaswamy, Brookline, MA (US); Todd R. Golub, Newton, MA (US); Pablo Tamayo, Cambridge, MA (US); Michael Angelo, San Francisco, CA (US)

(73) Assignees: Whitehead Institute for Biomedical Research, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 320 days.

(21) Appl. No.: 09/955,920

(22) Filed: Sep. 19, 2001

(65) Prior Publication Data

US 2002/0110820 A1    Aug. 15, 2002

Related U.S. Application Data

(60) Provisional application No. 60/278,749, filed on Mar. 26, 2001, provisional application No. 60/233,534, filed on Sep. 19, 2000.

(51) Int. Cl.
*C12Q 1/68* (2006.01)
*C12N 15/12* (2006.01)

(52) U.S. Cl. ........................ 435/6; 536/24.31
(58) Field of Classification Search ...................... 435/6
See application file for complete search history.

(56) References Cited

U.S. PATENT DOCUMENTS

2002/0142981 A1* 10/2002 Horne et al. ................. 514/44
2004/0033502 A1*  2/2004 Williams et al. ............ 435/6

FOREIGN PATENT DOCUMENTS

WO    WO 98/53319 A2    11/1998
WO    WO 00/55350 A1     9/2000
WO    WO 01/12781 A1     2/2001

OTHER PUBLICATIONS

Lolan et al. Lactose-binding lectin expression in human colorectal caricinomas. Relation to tumor progression. Carbohydrate Research, vol. 213, pp. 47-57, (1991).*
Golub et al. Molecular Classification of Cancer: Class Discovery and Class Prediction by Gene Expression Monitoring. Science, vol. 286, pp. 531-537 (1999).*
Buckhaults, P., et al., "Identifying Tumor Origin Using a Gene Expression-based Classification Map," *Cancer Research*, 63:4144-4149 (2003).
Nishizuka, S., et al., "Diagnostic Markers That Distinguish Colon and Ovarian Adeocarcinomas; Identification by Genomic, Proteomic, and Tissue Array Prolifting" *Cancer Research*, 63:5243-5250 (2003).
Dennis, J., et al., "Identification from Public Data of Molecular Markers of Adenocarcinoma Characteristic of the Site of Origin," *Cancer Research*, 62:5999-6005 (2002).
Su, A., et al., "Molecular Classification of Human Carcinomas by Use of Gene Expression Signatures," *Cancer Research*, 61:7388-7393 (2001).
Huflejt et al., "Striking Different Localization of Galectin-3 and Galectin-4 in Human Colon Adenocarcinoma T84 Cells," The Journal of Biological Chemistry, vol. 272, No. 22, Issue of May 30, pp. 14294-14303, 1997.
Rechreche et al., "Cloning and expression of the mRNA of human galectin-4, an S-type lectin down-regulated in colorectal cancer," Eur. J. Biochem. 248, 225-230 (1997).
Miklos and Maleszka, 2004, Microarray reality checks in the context of a complex disease, Nature Biotechnology 22(5):615-621.

* cited by examiner

*Primary Examiner*—John S. Brusca
(74) *Attorney, Agent, or Firm*—Fish & Neave IP Group, Ropes & Gray LLP

(57) ABSTRACT

Sets of genetic markers for specific tumor classes are described, as well as methods of identifying a biological sample based on these markers. Also described are diagnostic, prognostic, and therapeutic screening uses for these markers, as well as oligonucleotide arrays comprising these markers.

9 Claims, 673 Drawing Sheets

| Distinction | Distance | Perm 1% | Perm 5% | Perm (user) | Feature | Desc |
|---|---|---|---|---|---|---|
| 1) Bladder | 0.5222343 | 0.7140383 | 0.625628 | 0.469987452 | U49973_xpt_at | ORF2: function unknown from Human Tigger1 transposable element, complete consensus sequence./ntype=DNA /annot=CDS |
| 2) Bladder | 0.5004972 | 0.6663364 | 0.580119 | 0.4378299 | Z00010_at | Germ line pseudogene for immunoglobulin kappa light chain leader peptide and variable region (subgroup V kappa I) |
| 3) Bladder | 0.4811056 | 0.6442664 | 0.558641 | 0.42185774 | M31667_f_at | CYTOCHROME P450 IA2 |
| 4) Bladder | 0.4796712 | 0.6275353 | 0.545335 | 0.4101013 | U49974_f_at | Mariner2 transposable element, complete consensus sequence |
| 5) Bladder | 0.4633824 | 0.6154791 | 0.536003 | 0.40168163 | T89571_f_at | EST: ye04h07.r1 Homo sapiens cDNA clone 116797 5' similar to contains Alu repetitive element;. (from Genbank) |
| 6) Bladder | 0.4475702 | 0.6028036 | 0.527267 | 0.39502096 | L00389_f_at | Cytochrome P-450 4 gene |
| 7) Bladder | 0.437072 | 0.5972622 | 0.520689 | 0.3894528 | X52426_s_a_t | KRT13 Keratin 13 |
| 8) Bladder | 0.4328913 | 0.5927864 | 0.51606 | 0.38404244 | RC_AA3043 44_f_at | EST: EST17092 Aorta endothelial cells, TNF alpha-treated Homo sapiens cDNA 3' end similar to EST containing Alu repeat, mRNA sequence. (from Genbank) |
| 9) Bladder | 0.4179855 | 0.5864499 | 0.511478 | 0.37957391 | Z19574_rna 1_at | Cytokeratin 17 |
| 10) Bladder | 0.4038961 | 0.5632233 | 0.506805 | 0.3749016 | AA476704_a_t | EST: zw87h02.r1 Soares total fetus Nb2HF8 9w Homo sapiens cDNA clone 783987 5', mRNA sequence. (from Genbank) |
| 11) Bladder | 0.4004278 | 0.5787987 | 0.503221 | 0.37135372 | Y07755_at | S100A2 gene, exon 1, 2 and 3 |
| 12) Bladder | 0.3904162 | 0.5755673 | 0.49981 | 0.36821586 | L77563_at | DGS-F partial mRNA |
| 13) Bladder | 0.3821097 | 0.5749506 | 0.495871 | 0.36506096 | M74093_at | G1/S-SPECIFIC CYCLIN E |
| 14) Bladder | 0.3804864 | 0.5716851 | 0.492437 | 0.36227097 | U19180_at | BAGE B melanoma antigen |
| 15) Bladder | 0.3804649 | 0.5670317 | 0.489875 | 0.35994408 | U79301_at | Clone 23842 mRNA sequence |
| 16) Bladder | 0.3804649 | 0.5661115 | 0.486512 | 0.35749477 | U79301_at-2 | Human clone 23842 mRNA sequence |
| 17) Bladder | 0.3795788 | 0.5652931 | 0.484787 | 0.35480672 | S79854_at | Type 3 iodothyronine deiodinase |
| 18) Bladder | 0.3795788 | 0.5618347 | 0.482676 | 0.35260853 | S79854_at-2 | Deiodinase, iodothyronine, type III |
| 19) Bladder | 0.3735957 | 0.5615372 | 0.480288 | 0.35047776 | M65199_at | EDN2 Endothelin 2 |
| 20) Bladder | 0.3719681 | 0.5599971 | 0.479021 | 0.34866765 | M19045_f_at | LYZ Lysozyme |

FIG. 1A

| | | | | | | |
|---|---|---|---|---|---|---|
| 21 | Bladder | 0.3668245 | 0.5570917 | 0.478987 | 0.34694237 | J03801_f_at | LYZ Lysozyme |
| 22 | Bladder | 0.3617656 | 0.5544571 | 0.4744961 | 0.34511527 | RC_AA055404_f_at | EST: zf74e11.s1 Stratagene colon (#937204) Homo sapiens cDNA clone 510380 3' similar to contains Alu repetitive element;, mRNA sequence. (from Genbank) |
| 23 | Bladder | 0.3585888 | 0.5527974 | 0.473629 | AA004333_a_at | | EST: zh91a01.r1 Soares fetal liver spleen 1NFLS S1 Homo sapiens cDNA clone 428616 5', mRNA sequence. (from Genbank) |
| 24 | Bladder | 0.3546446 | 0.551398 | 0.472633 | 0.343673 | X58072_at | GATA3 GATA-binding protein 3 |
| 25 | Bladder | 0.3516819 | 0.5512844 | 0.470429 | 0.3423039 | X65614_at | S100P S100 calcium-binding protein P |
| 26 | Bladder | 0.3495828 | 0.5501952 | 0.46925 | 0.34083462 | X71135_at | Sox3 gene |
| 27 | Bladder | 0.3491402 | 0.5473553 | 0.467994 | 0.33910047 | AA059327_i_at | EST: zf65e11.r1 Soares retina N2b4HR Homo sapiens cDNA clone 381836 5', mRNA sequence. (from Genbank) |
| 28 | Bladder | 0.3422301 | 0.546696 | 0.466414 | 0.3378539 | M20530_at | SPINK1 Serine protease inhibitor, Kazal type 1 |
| 29 | Bladder | 0.3407664 | 0.5460622 | 0.465027 | 0.33637735 | X78262_f_at | H.sapiens mRNA for TRE5 |
| 30 | Bladder | 0.3378267 | 0.5434613 | 0.463984 | 0.33499768 | U14910_at | RPE-retinal G protein-coupled receptor (rgr) mRNA |
| 31 | Bladder | 0.3322129 | 0.5422407 | 0.463013 | 0.33257496 | F15197_at | EST: H. sapiens partial cDNA sequence, mRNA sequence. (from Genbank) |
| 32 | Bladder | 0.3220662 | 0.5398117 | 0.461431 | 0.33093923 | RC_AA190676_at | EST: zp89g09.s1 Stratagene HeLa cell s3 937216 Homo sapiens cDNA clone 627424 3', mRNA sequence. (from Genbank) |
| 33 | Bladder | 0.3193212 | 0.5383251 | 0.461031 | 0.3298111 | U49973_xpt1_at | ORF1; MER37; putative transposase similar to pogo element from Human Tigger1 transposable element, complete consensus sequence./ntype=DNA /annot=CDS |
| 34 | Bladder | 0.3150793 | 0.5378045 | 0.46003 | 0.3286371 | hum_alu_at | hum_alu_at (miscellaneous control) |
| 35 | Bladder | 0.3150793 | 0.5368709 | 0.458494 | 0.32739004 | hum_alu_at- 2 | No description for gene: hum_alu_at |
| 36 | Bladder | 0.3150536 | 0.5362847 | 0.457694 | 0.32661385 | J02874_at | FABP4 Fatty acid binding protein 4, adipocyte |
| 37 | Bladder | 0.3138648 | 0.5347996 | 0.456496 | 0.3250607 | S73288_at | Small proline-rich protein SPRK [human, odontogenic keratocysts, mRNA Partial, 317 nt] |
| 38 | Bladder | 0.3132269 | 0.5347996 | 0.455457 | 0.32396704 | M34344_at | ITGA2B Integrin, alpha 2b (platelet glycoprotein IIb of IIb/IIIa complex, antigen CD41B) |
| 39 | Bladder | 0.3130415 | 0.5342372 | 0.454397 | 0.32295874 | X82693_at | E48 antigen |
| 40 | Bladder | 0.3108572 | 0.5327527 | 0.452961 | 0.32202353 | W67675_at | EST: zd37c12.r1 Soares fetal heart NbHH19W Homo sapiens cDNA clone 342838 5', mRNA sequence. (from Genbank) |
| 41 | Bladder | 0.3043914 | 0.531638 | 0.452762 | 0.32140842 | X95406_at | Cyclin E gene |
| 42 | Bladder | 0.3036189 | 0.5308437 | 0.452254 | 0.32027555 | J05158_at | CARBOXYPEPTIDASE N 83 KD CHAIN |
| 43 | Bladder | 0.3028153 | 0.5293424 | 0.451048 | 0.31925225 | H02480_at | EST: yj35e11.r1 Homo sapiens cDNA clone 150764 5'. (from Genbank) |
| 44 | Bladder | 0.3026588 | 0.5274541 | 0.450491 | 0.31815872 | J00287_at | PEPSINOGEN A PRECURSOR |
| 45 | Bladder | 0.3004723 | 0.5268151 | 0.450013 | 0.31719595 | Y00705_at | SPINK1 Serine protease inhibitor, Kazal type 1 |

FIG. 1B

| # | Tissue | | | | |
|---|---|---|---|---|---|
| 46 | Bladder | 0.2944566 | 0.5259358 | 0.448763 | 0.3161997 | HG3236-HT3413_f_at Neurofibromatosis 2 Tumor Suppressor (Gb:L27065) |
| 47 | Bladder | 0.2940576 | 0.5249827 | 0.447903 | 0.31523636 | RC_AA4492 15_at EST: zx03h11.s1 Soares total fetus Nb2HF8 9w Homo sapiens cDNA clone 785445 3', mRNA sequence. (from Genbank) |
| 48 | Bladder | 0.2896088 | 0.5235943 | 0.447287 | 0.31431654 | J02871_s_at CYP4B1 Cytochrome P450 IVB1 |
| 49 | Bladder | 0.2892569 | 0.5219361 | 0.44638 | 0.31362706 | M27826_at Endogenous retroviral protease mRNA |
| 50 | Bladder | 0.2879725 | 0.5209997 | 0.44545 | 0.3127739 | RC_AA1916 47_at Ceruloplasmin (ferroxidase) |
| 51 | Bladder | 0.2878275 | 0.5197005 | 0.444737 | 0.3121669 | RC_AA4469 64_at Homo sapiens prostate stem cell antigen (PSCA) mRNA, complete cds |
| 52 | Bladder | 0.2859805 | 0.519376 | 0.443783 | 0.311148654 | M86757_s_a_t S100A7 S100 calcium-binding protein A7 (psoriasin 1) |
| 53 | Bladder | 0.2849908 | 0.5183376 | 0.443014 | 0.3106054 | M14091_at THYROXINE-BINDING GLOBULIN PRECURSOR |
| 54 | Bladder | 0.2819153 | 0.5181242 | 0.442297 | 0.3099225 | RC_AA4534 51_at EST: zx45a09.s1 Soares testis NHT Homo sapiens cDNA clone 795160 3', mRNA sequence. (from Genbank) |
| 55 | Bladder | 0.28164 | 0.5171191 | 0.441948 | 0.30888793 | RC_AA0013 59_a_t EST: zh83d11.s1 Soares fetal liver spleen 1NFLS S1 Homo sapiens cDNA clone 427893 3', mRNA sequence. (from Genbank) |
| 56 | Bladder | 0.2761128 | 0.5164211 | 0.441108 | 0.30826807 | HG2841-HT2969_s_a_t Albumin, Alt. Splice 3, Misssplicing In Alloalbumin Venezia |
| 57 | Bladder | 0.2755032 | 0.5156131 | 0.440289 | 0.30754557 | U39487_at XDH Xanthine dehydrogenase |
| 58 | Bladder | 0.2752715 | 0.5147324 | 0.439671 | 0.30675662 | AA252752_a_t EST: zs26b10.r1 NCI_CGAP_GCB1 Homo sapiens cDNA clone IMAGE:686299 5', mRNA sequence. (from Genbank) |
| 59 | Bladder | 0.275238 | 0.5142779 | 0.438724 | 0.3059757 | U51587_at Golgi complex autoantigen golgin-97 mRNA |
| 60 | Bladder | 0.2750438 | 0.5137218 | 0.438434 | 0.3053376 | M60828_at FGF7 Fibroblast growth factor 7 (keratinocyte growth factor) |
| 61 | Bladder | 0.2740574 | 0.51331107 | 0.437479 | 0.30452663 | X83618_at Clone HSH1 HMG CoA synthase mRNA, partial cds |
| 62 | Bladder | 0.272605 | 0.51126445 | 0.436951 | 0.3038781 | U05861_at DDH1 Dihydrodiol dehydrogenase |
| 63 | Bladder | 0.2710716 | 0.5120996 | 0.435736 | 0.3033949 | RC_D59354 i_at EST: Human fetal brain cDNA 3'-end GEN-020E05, mRNA sequence. (from Genbank) |
| 64 | Bladder | 0.2691142 | 0.5112219 | 0.434842 | 0.30258542 | Z78285_f_at Z78285 Homo sapiens brain fetus Homo sapiens cDNA clone 1A7, mRNA sequence |
| 65 | Bladder | 0.2685153 | 0.51103946 | 0.433993 | 0.30199873 | J00124_at KERATIN, TYPE I CYTOSKELETAL 14 |
| 66 | Bladder | 0.267924 | 0.5097284 | 0.433258 | 0.30147517 | L00137_cds 1_at GHRF gene (growth hormone releasing factor) extracted from Human growth hormone-releasing factor (GRF) gene, exon 1 ( |
| 67 | Bladder | 0.2666138 | 0.50944423 | 0.432798 | 0.3009288 | D87024_at Immunoglobulin lambda gene locus DNA, clone:92H4 |

FIG. 1C

| | | | | | |
|---|---|---|---|---|---|
| 68 | Bladder | 0.266528 | 0.5088778 | 0.432136 | 0.3002215 | RC_AA1942 57_r_at | Human DNA sequence from clone 522J7 on chromosome 22q13.3. Contains part of a 60S Ribosomal protein L5 pseudogene and a Peregrin (BR140) LIKE gene downstream of a putative CpG island. Contains ESTs, STSs and GSSs |
| 69 | Bladder | 0.2664737 | 0.5080214 | 0.431398 | 0.29978427 | T92512_at | Ye24g11.r1 Homo sapiens cDNA clone 118724 5'. (from Genbank) |
| 70 | Bladder | 0.263522 | 0.5079261 | 0.430434 | 0.29906005 | RC_AA0191 36_s_at | EST: ze58h09.s1 Soares retina N2b4HR Homo sapiens cDNA clone 363233 3', mRNA sequence. (from Genbank) |
| 71 | Bladder | 0.2633922 | 0.5076373 | 0.430079 | 0.29859278 | J02973_rna1 _at | THBD gene extracted from Human thrombomodulin gene |
| 72 | Bladder | 0.2592166 | 0.5074905 | 0.429281 | 0.2978743 | H16876_at | Ym34f05.r1 Homo sapiens cDNA clone 50123 5'. (from Genbank) |
| 73 | Bladder | 0.2590196 | 0.5071446 | 0.428868 | 0.29738238 | J04093_s_at | UDP-GLUCURONOSYLTRANSFERASE 1F PRECURSOR, MICROSOMAL |
| 74 | Bladder | 0.2589375 | 0.5064912 | 0.4281 | 0.2967745 | M31776_s_a t | BRAIN NATRIURETIC PEPTIDE PRECURSOR |
| 75 | Bladder | 0.2584704 | 0.5051627 | 0.427958 | 0.29663655 | Z48199_at | SDC1 Syndecan 1 |
| 76 | Bladder | 0.2584312 | 0.5051627 | 0.427493 | 0.29592586 | AA406087_s _at | TAL1 (SCL) interrupting locus |
| 77 | Bladder | 0.2580246 | 0.5046264 | 0.427095 | 0.2954576 | M17236_at | HLA CLASS II HISTOCOMPATIBILITY ANTIGEN, DQ(2) ALPHA CHAIN PRECURSOR |
| 78 | Bladder | 0.2548651 | 0.5038334 | 0.42671 | 0.29502822 | L78833_cds 2_at | Rho7 gene extracted from Human BRCA1, Rho7 and vatI genes, and ipf35 gene, partial cds |
| 79 | Bladder | 0.2540633 | 0.5033087 | 0.425944 | 0.29452837 | V00571_rna 1_at | Gene encoding prepro form of corticotropin releasing factor |
| 80 | Bladder | 0.2521889 | 0.5032067 | 0.425558 | 0.29398812 | M92449_at | LTR mRNA, 3' end of coding region and 3' flank |
| 81 | Bladder | 0.2482704 | 0.50215919 | 0.424709 | 0.29351172 | L40904_at | LGALS1 Ubiquinol-cytochrome c reductase core protein II |
| 82 | Bladder | 0.2482704 | 0.5016 | 0.423835 | 0.29309762 | L40904_at-2 | Peroxisome proliferative activated receptor, gamma |
| 83 | Bladder | 0.2470583 | 0.5015603 | 0.423187 | 0.2926486 | RC_AA1810 96_at | EST: zp67b07.s1 Stratagene endothelial cell 937223 Homo sapiens cDNA clone 625237 3' similar to contains element MIR repetitive element:, mRNA sequence. (from Genbank) |
| 84 | Bladder | 0.2435404 | 0.50111214 | 0.422982 | 0.29208043 | X14008_rna 1_f_at | Lysozyme gene (EC 3.2.1.17) |
| 85 | Bladder | 0.2431545 | 0.50066249 | 0.422559 | 0.291755875 | L34355_at | (clone p4) 50 kD dystrophin-associated glycoprotein mRNA |
| 86 | Bladder | 0.2431177 | 0.4993878 | 0.422214 | 0.29134393 | X78678_at | KHK Ketohexokinase (fructokinase) |
| 87 | Bladder | 0.2423082 | 0.4987399 | 0.421638 | 0.29083067 | U04313_at | PI5 Protease inhibitor 5 (maspin) |
| 88 | Bladder | 0.241649 | 0.498558 | 0.421146 | 0.29030737 | D38024_at | Facioscapulohumeral muscular dystrophy (FSHD) gene region, D4Z4 tandem repeat unit |
| 89 | Bladder | 0.237779 | 0.498558 | 0.420855 | 0.28889312 | AA365031_s _at | EST: EST75974 Pineal gland II Homo sapiens cDNA 5' end, mRNA sequence. (from Genbank) |
| 90 | Bladder | 0.2375737 | 0.4979784 | 0.420598 | 0.2895758 | H52378_at | Spectrin, alpha, erythrocytic 1 (elliptocytosis 2) |

FIG. 1D

| | | | | | | |
|---|---|---|---|---|---|---|
| 91 | Bladder | 0.2348844 | 0.4973496 | 0.42026 | 0.2891052 | RC_AA4500 06_s_at | Sulfotransferase, estrogen-preferring |
| 92 | Bladder | 0.2347219 | 0.497176 | 0.419864 | 0.2885942 | AA044946_a_t | Transcription factor 9 (binds GC-rich sequences) |
| 93 | Bladder | 0.2344337 | 0.4966071 | 0.419805 | 0.2883126 | AA480838_s_at | EST: zx87e06.r1 Soares ovary tumor NbHOT Homo sapiens cDNA clone 810754 5', mRNA sequence. (from Genbank) |
| 94 | Bladder | 0.2338483 | 0.4950363 | 0.419115 | 0.2879004 | HG3934-HT4204_at | G1 Phase-Specific Gene |
| 95 | Bladder | 0.2333825 | 0.4947473 | 0.418585 | 0.2876057 | J05459_at | GSTM3 Glutathione S-transferase M3 (brain) |
| 96 | Bladder | 0.2310942 | 0.4947179 | 0.418104 | 0.2873358 | RC_AA0195 28_at | EST: ze55b02.s1 Soares retina N2b4HR Homo sapiens cDNA clone 362859 3', mRNA sequence. (from Genbank) |
| 97 | Bladder | 0.2304104 | 0.4945694 | 0.417913 | 0.2868064 | S85963_at | Insulin receptor substrate-1 [human, skeletal muscle, mRNA, 5828 nt] |
| 98 | Bladder | 0.2269905 | 0.4937859 | 0.417057 | 0.2864820 | D14539_at | Human mRNA for LTG19. (from Genbank) |
| 99 | Bladder | 0.2261536 | 0.4934233 | 0.416613 | 0.2859405 | HG4099-HT4369_s_a_t | Adrenergic Receptor, Alpha 1b |
| 100 | Bladder | 0.2240019 | 0.493311 | 0.416367 | 0.2855534 | AFFX-BioDn-3 5_st | AFFX-BioDn-5_st (endogenous control) |
| 101 | Bladder | 0.2240019 | 0.4922493 | 0.416122 | 0.2851711 | AFFX-BioDn-5_st-2 | AFFX-BioDn-5_st (miscellaneous control - 11k chips) |
| 102 | Bladder | 0.2225575 | 0.4920135 | 0.41574 | 0.2848314 | HG880-HT880_at | Mucin 6, Gastric (Gb:L07517) |
| 103 | Bladder | 0.2222761 | 0.491765 | 0.415431 | 0.2845286 | RC_D60246 _at | EST: Human fetal brain cDNA 3'-end GEN-093H03, mRNA sequence. (from Genbank) |
| 104 | Bladder | 0.2219926 | 0.4916041 | 0.414911 | 0.2841813 | U78313_at | Myogenic repressor I-mf (MDFI) mRNA |
| 105 | Bladder | 0.2218411 | 0.4908751 | 0.414432 | 0.2839267 | HG415-HT415_at | Lectin, Galactoside-Binding, Soluble, 2 |
| 106 | Bladder | 0.220422 | 0.4906752 | 0.414305 | 0.2835213 | R80351_at | EST: yj96e02.r1 Homo sapiens cDNA clone 147098 5'. (from Genbank) |
| 107 | Bladder | 0.2185662 | 0.489544 | 0.414071 | 0.2832019 | R81217_at | Yj03b09.r1 Homo sapiens cDNA clone 147641 5' similar to gb:X54156_rna1 CELLULAR TUMOR ANTIGEN P53 (HUMAN);contains Alu repetitive element;. (from Genbank) |
| 108 | Bladder | 0.2180181 | 0.4893021 | 0.413467 | 0.2827974 | RC_AA4602 21_at | EST: zx67a02.s1 Soares total fetus Nb2HF8 9w Homo sapiens cDNA clone 796490 3', mRNA sequence. (from Genbank) |
| 109 | Bladder | 0.2163227 | 0.489161 | 0.412978 | 0.2824959 | RC_AA2931 63_at | EST: zl55e05.s1 Soares ovary tumor NbHOT Homo sapiens cDNA clone 726272 3', mRNA sequence. (from Genbank) |
| 110 | Bladder | 0.2136944 | 0.4890391 | 0.412707 | 0.2821371 | U48436_s_a_t | FMR2 Fragile X mental retardation 2 |

FIG. 1E

| # | Tissue | | | | | Description |
|---|---|---|---|---|---|---|
| 111 | Bladder | 0.2136638 | 0.4886639 | 0.412328 | RC_AA3982 0.281790557 6_at | EST: zt60c07.s1 Soares testis NHT Homo sapiens cDNA clone 726732 3', mRNA sequence. (from Genbank) |
| 112 | Bladder | 0.2124692 | 0.4883141 | 0.411691 | 0.28133968 W25945_at | EST: 17c5 Human retina cDNA randomly primed sublibrary Homo sapiens cDNA, mRNA sequence. (from Genbank) |
| 113 | Bladder | 0.2095443 | 0.4861237 | 0.411485 | 0.28107503 S82472_at | Beta -pol=DNA polymerase beta (exon alpha to exon VII region) [human, Genomic, 124 nt, segment 1 of 2] |
| 114 | Bladder | 0.2085519 | 0.4858976 | 0.41091 | 0.28061423 W27256_at | Homo sapiens mRNA for putative RING finger protein, partial |
| 115 | Bladder | 0.2051885 | 0.485773 | 0.410788 | 0.28023028 X92475_at-2 | ITBA1 gene |
| 116 | Bladder | 0.2051885 | 0.4856327 | 0.410303 | 0.28001535 X92475_at | ITBA1 protein |
| 117 | Bladder | 0.2042837 | 0.4854372 | 0.410004 | 0.27974427 L10377_s_at | (clone CTG-B37) mRNA sequence |
| 118 | Bladder | 0.203303 | 0.4847722 | 0.409887 | 0.27943683 AA167824_a t | Cell division cycle 27 |
| 119 | Bladder | 0.2025079 | 0.4846439 | 0.409387 | 0.27905178 U60521_at | Cysteine protease ICE-LAP6 mRNA |
| 120 | Bladder | 0.2005113 | 0.4836244 | 0.409351 | 0.27870348 L11369_at | Protocadherin 42 mRNA, 3' end of cds for alternative splicing PC42-8 |
| 121 | Bladder | 0.1985588 | 0.4834217 | 0.408793 | 0.2783184 HG742-HG742_at | Latent Membrane Protein Lmp1 |
| 122 | Bladder | 0.1977808 | 0.4833573 | 0.408266 | 0.27808493 HG3432-HT3621_at | Fibroblast Growth Factor Receptor K-Sam, Alt. Splice 4, K-Sam Iv |
| 123 | Bladder | 0.193588 | 0.4832549 | 0.408 | 0.27770907 HG3897-HT4167_at | Sodium Channel, Type Iii, Alpha Subunit, Brain |
| 124 | Bladder | 0.1928114 | 0.4829245 | 0.407447 | 0.27743426 L20859_at | Leukemia virus receptor 1 (GLVR1) mRNA |
| 125 | Bladder | 0.1917242 | 0.4823633 | 0.406261 | 0.27710912 M19888_at | SPRR1B Small proline-rich protein 1B (cornifin) |
| 126 | Bladder | 0.1886425 | 0.4816808 | 0.40615 | 0.27682626 M77481_rna 1_f_at | Antigen (MAGE-1) gene |
| 127 | Bladder | 0.1874011 | 0.481662 | 0.406085 | 0.27646986 U08854_s_a t | UDP glucuronosyltransferase precursor (UGT2B15) mRNA |
| 128 | Bladder | 0.1869247 | 0.4815364 | 0.405623 | 0.27613884 AA444115_a t | EST: zv51h08.r1 Soares testis NHT Homo sapiens cDNA clone 757143 5', mRNA sequence. (from Genbank) |
| 129 | Bladder | 0.1868608 | 0.4811476 | 0.405244 | 0.27586403 M68840_at | MAOA Monoamine oxidase A |
| 130 | Bladder | 0.1853088 | 0.4805843 | 0.404335 | 0.27548274 RC_D60364_at | EST: Human fetal brain cDNA 3'-end GEN-102B09, mRNA sequence. (from Genbank) |
| 131 | Bladder | 0.1851053 | 0.4805036 | 0.404256 | 0.27523914 RC_AA4213 28_at | EST: zu27d04.s1 Soares ovary tumor NbHOT Homo sapiens cDNA clone 739207 3', mRNA sequence. (from Genbank) |
| 132 | Bladder | 0.1849799 | 0.4804439 | 0.403551 | 0.2748993 R11267_at | Homo sapiens chromosome 19, cosmid F22329 |
| 133 | Bladder | 0.1838469 | 0.4800442 | 0.403114 | 0.2745337 HG3543-HT3739_at | Insulin-Like Growth Factor 2 |
| 134 | Bladder | 0.1838098 | 0.4797981 | 0.403079 | 0.27426526 AA099726_a t | EST: zk86e10.r1 Soares pregnant uterus NbHPU Homo sapiens cDNA clone 489738 5', mRNA sequence. (from Genbank) |

FIG. 1F

| | | | | | | |
|---|---|---|---|---|---|---|
| 135 | Bladder | | 0.1827677 | 0.4797327 | 0.402715 | 0.27386442 | X63755_at | High-sulphur keratin |
| 136 | Bladder | | 0.1826186 | 0.4783266 | 0.402638 | 0.27360818 | X56411_rna 1_at | ADH4 gene for class II alcohol dehydrogenase (pi subunit), exon 1 |
| 137 | Bladder | | 0.1820319 | 0.478011 | 0.402448 | 0.27323318 | RC_AA6001 50_at | EST: ae50d12.s1 Stratagene lung carcinoma 937218 Homo sapiens cDNA clone 950327 3', mRNA sequence. (from Genbank) |
| 138 | Bladder | | 0.181527 | 0.4777031 | 0.402212 | 0.2729088 | L11708_at | HSD17B2 17 beta hydroxysteroid dehydrogenase, type 2 |
| 139 | Bladder | | 0.1814934 | 0.4775387 | 0.402193 | 0.2725679 | R11710_at | Transcobalamin I (vitamin B12 binding protein, R binder family) |
| 140 | Bladder | | 0.180324 | 0.4774376 | 0.402158 | 0.27234975 | AA410786_s _at | EST: zt35b09.r1 Soares ovary tumor NbHOT Homo sapiens cDNA clone 724313 5', mRNA sequence. (from Genbank) |
| 141 | Bladder | | 0.1786799 | 0.4773319 | 0.401829 | 0.27209738 | X86163_at | BDKRB2 Bradykinin receptor B2 |
| 142 | Bladder | | 0.178492 | 0.476809 | 0.401671 | 0.27175963 | U82303_at | Unknown protein mRNA, partial cds |
| 143 | Bladder | | 0.1781216 | 0.4767463 | 0.401172 | 0.27164498 | M94856_at | FATTY ACID-BINDING PROTEIN, EPIDERMAL |
| 144 | Bladder | | 0.1779615 | 0.4756579 | 0.400715 | 0.27139875 | U21931_at | FBP1 Fructose-bisphosphatase 1 |
| 145 | Bladder | | 0.1772622 | 0.4752239 | 0.400527 | 0.2710882 | AC002450_a t | BAC clone GS244B22 from 7q21-q22, complete sequence |
| 146 | Bladder | | 0.1766272 | 0.4751216 | 0.400298 | 0.27080733 | M94167_at | HGL Heregulin alpha |
| 147 | Bladder | | 0.1763088 | 0.4748522 | 0.400075 | 0.27047795 | U61741_at | Clone 18 (HL-18), dynein heavy chain (Dnahc14) mRNA, partial cds |
| 148 | Bladder | | 0.1757367 | 0.4746358 | 0.399853 | 0.27018142 | HG4036-HT4306_at | Retinoblastoma 1 |
| 149 | Bladder | | 0.1745572 | 0.4744271 | 0.399288 | 0.26992038 | J04152_rna1 s_at | M1S1 gene extracted from Human gastrointestinal tumor-associated antigen GA733-1 protein gene, clone 05516 |
| 150 | Bladder | | 0.1732341 | 0.4741848 | 0.399178 | 0.26973486 | X95289_at | HCGIX protein |
| 151 | Bladder | | 0.1731842 | 0.473917 | 0.3989 | 0.2694124 | U13680_at | LDHC Lactate dehydrogenase C |
| 152 | Bladder | | 0.1731842 | 0.4738257 | 0.398534 | 0.26923758 | U13680_at-2 | Lactate dehydrogenase C |
| 153 | Bladder | | 0.1726749 | 0.4736018 | 0.39833 | 0.26886386 | L13286_at | Mitochondrial 1,25-dihydroxyvitamin D3 24-hydroxylase mRNA |
| 154 | Bladder | | 0.1724232 | 0.4727036 | 0.397941 | 0.26854777 | M64347_at | FGFR3 Fibroblast growth factor receptor 3 (achondroplasia, thanatophoric dwarfism) |
| 155 | Bladder | | 0.17125 | 0.4724708 | 0.39794 | 0.26832888 | W52431_at | EST: zc45b12.r1 Soares senescent fibroblasts NbHSF Homo sapiens cDNA clone 325247 5' similar to SW:WDNM_RAT P14730 WDNM1 PROTEIN. [2] PIR:S07807 ;, mRNA sequence. (from Genbank) |
| 156 | Bladder | | 0.1711476 | 0.4723066 | 0.397812 | 0.2681159 | X60483_at | H4/d gene for H4 histone |
| 157 | Bladder | | 0.1697957 | 0.4722235 | 0.397312 | 0.26771313 | S76965_at | Protein kinase inhibitor [human, neuroblastoma cell line SH-SY-5Y, mRNA, 2147 nt] |
| 158 | Bladder | | 0.1695036 | 0.4717567 | 0.396946 | 0.2675112 | L76465_at | 15-HYDROXYPROSTAGLANDIN DEHYDROGENASE |
| 159 | Bladder | | 0.1670327 | 0.4715059 | 0.396541 | 0.26719064 | RC_AA2358 03_i_at | EST: zs42g06.s1 Soares NhHMPu S1 Homo sapiens cDNA clone 687898 3', mRNA sequence. (from Genbank) |

FIG. 1G

| # | Tissue | | | | Description |
|---|---|---|---|---|---|
| 160 | Bladder | 0.1667579 | 0.471069 | 0.396142 | M14123_xpt 3_at | Gag 2 protein from Human endogenous retrovirus HERV-K10./ntype=DNA./annot=CDS |
| 161 | Bladder | 0.165794 | 0.4707031 | 0.3957335 | 0.26658645 U12775_at | AGOUTI SWITCH PROTEIN PRECURSOR |
| 162 | Bladder | 0.165392 | 0.4706222 | 0.395594 | 0.26639983 D38293_at | Clathrin-like protein |
| 163 | Bladder | 0.1650688 | 0.4704467 | 0.395311 | RC_AA4772 52_at | Homo sapiens mRNA for KIAA0664 protein, partial cds |
| 164 | Bladder | 0.1649707 | 0.4700519 | 0.395011 | 0.26575932 J00117_f_at | Chorionic gonadotropin (hcg) beta subunit mRNA |
| 165 | Bladder | 0.1644523 | 0.4697602 | 0.394673 | RC_AA0630 0.26551868_at | EST: zf67e04.s1 Soares pineal gland N3HPG Homo sapiens cDNA clone 382014 3', mRNA sequence. (from Genbank) |
| 166 | Bladder | 0.1623945 | 0.469756 | 0.393862 | 0.26522526 U30930_at | CGT UDP-galactose ceramide galactosyl transferase |
| 167 | Bladder | 0.1621248 | 0.4696752 | 0.393817 | RC_AA0071 0.26509684 70_at | EST: 13cDNA84-3.seq Soares fetal liver spleen 1NFLS Homo sapiens cDNA clone HY30-cDNA12 3', mRNA sequence. (from Genbank) |
| 168 | Bladder | 0.1610194 | 0.4695534 | 0.393633 | 0.26489165 L19314_at | HRY gene |
| 169 | Bladder | 0.1609305 | 0.4691801 | 0.393617 | 0.26462226 D43772_at | Squamous cell carcinoma of esophagus mRNA for GRB-7 SH2 domain protein |
| 170 | Bladder | 0.160833 | 0.4687603 | 0.393375 | 0.26441893 U08049_at | Peripheral myelin protein-22 (PMP22) gene, non-coding exon 1A |
| 171 | Bladder | 0.1596156 | 0.4684287 | 0.393317 | 0.2641546 U68019_at | Mad protein homolog (hMAD-3) mRNA |
| 172 | Bladder | 0.1584186 | 0.4683965 | 0.392625 | 0.26390043 M86849_at | Connexin 26 (GJB2) mRNA |
| 173 | Bladder | 0.1582625 | 0.4680306 | 0.392331 | 0.26370218 W25933_at | EST: 15b2 Human retina cDNA randomly primed sublibrary Homo sapiens mRNA sequence. (from Genbank) |
| 174 | Bladder | 0.1578183 | 0.4678046 | 0.39214 | RC_AA4300 0.26340276 36_at | EST: zw65f10.s1 Soares testis NHT Homo sapiens cDNA clone 781099 3', mRNA sequence. (from Genbank) |
| 175 | Bladder | 0.1557797 | 0.4674365 | 0.391856 | 0.26321688 M11321_at | GC Group-specific component (vitamin D binding protein) |
| 176 | Bladder | 0.155758 | 0.4671269 | 0.391327 | 0.2629987 U76456_at | Tissue inhibitor of metalloproteinase 4 mRNA |
| 177 | Bladder | 0.155758 | 0.4669263 | 0.39126 | 0.26267424 U76456_at-2 | Human tissue inhibitor of metalloproteinase 4 mRNA, complete cds. (from Genbank) |
| 178 | Bladder | 0.1554388 | 0.4665316 | 0.391237 | 0.2624343 HG4517-HT4920_s_a t | Immunoglobulin Recombination Signal Sequence Binding Protein, Alt. Splice 3 |
| 179 | Bladder | 0.1547668 | 0.4658998 | 0.391053 | 0.26221153 M96233_s_a t | GSTM4 Glutathione S-transferase M4 |
| 180 | Bladder | 0.1537927 | 0.4658607 | 0.390738 | 0.26185173 N73185_at | EST: yv46a09.r1 Homo sapiens cDNA clone 245752 5'. (from Genbank) |
| 181 | Bladder | 0.153676 | 0.4657265 | 0.390481 | 0.26164904 D80011_at | KIAA0189 gene |
| 182 | Bladder | 0.153676 | 0.464831 | 0.389918 | 0.261463 D80011_at-2 | KIAA0189 gene product |
| 183 | Bladder | 0.1534032 | 0.4648247 | 0.389628 | 0.26121077 U13369_at | Ribosomal DNA complete repeating unit |
| 184 | Bladder | 0.1533623 | 0.4643537 | 0.389501 | 0.26094857 W28734_at | EST: 51a1 Human retina cDNA randomly primed sublibrary Homo sapiens cDNA, mRNA sequence. (from Genbank) |

FIG. 1H

| # | Tissue | | | | Accession | Description |
|---|---|---|---|---|---|---|
| 185 | Bladder | 0.1523489 | 0.4640757 | 0.389374 | 0.260719931 X81836_s_a t | Dents Disease candidate gene |
| 186 | Bladder | 0.1514157 | 0.4636369 | 0.389343 | 0.260059705 U17566_at | SLC19A1 Solute carrier family 19 (folate transporter), member 1 |
| 187 | Bladder | 0.1510678 | 0.4633779 | 0.389199 | 0.26036578 AA422123_i _at | EST: zv26h12.r1 Soares NhHMPu S1 Homo sapiens cDNA clone 754823 5' similar to contains Alu repetitive element;, mRNA sequence. (from Genbank) |
| 188 | Bladder | 0.1493747 | 0.4630102 | 0.388338 | 0.260025838 U90437_at | RP1 homolog mRNA, 3'UTR region |
| 189 | Bladder | 0.1486966 | 0.4628564 | 0.387982 | 0.259980565 L13436_at | Guanylate cyclase mRNA, complete mature peptide |
| 190 | Bladder | 0.1485016 | 0.4625492 | 0.387719 | 0.259647881 U28413_at | Cockayne syndrome complementation group A CSA protein (CSA) mRNA |
| 191 | Bladder | 0.1458209 | 0.4623764 | 0.387711 | 0.259432881 RC_AA0045 21_at | Prostate cancer overexpressed gene 1 |
| 192 | Bladder | 0.1430561 | 0.4621076 | 0.387191 | 0.259229181 J03915_s_at | CHGA Chromogranin A |
| 193 | Bladder | 0.1426495 | 0.4618579 | 0.387139 | 0.258895851 X06268_at | COL2A1 Collagen, type II, alpha 1 (primary osteoarthritis, spondyloepiphyseal dysplasia, congenital) |
| 194 | Bladder | 0.1402592 | 0.4616344 | 0.386983 | 0.258833984 AA156215_a t | EST: zo48h03.r1 Stratagene endothelial cell 937223 Homo sapiens cDNA clone 590165 5' similar to contains element LTR8 repetitive element;, mRNA sequence. (from Genbank) |
| 195 | Bladder | 0.1400141 | 0.4610898 | 0.386866 | 0.258478282 D87002_cds 2_at | POM121-like 1 gene extracted from Human (lambda) DNA for immunoglobin light chain |
| 196 | Bladder | 0.1371618 | 0.4607078 | 0.386488 | 0.258194848 M27878_at | ZNF84 Zinc finger protein 84 (HPF2) |
| 197 | Bladder | 0.1359859 | 0.4605887 | 0.386441 | 0.258053316 D17793_at | DDH1 Dihydrodiol dehydrogenase |
| 198 | Bladder | 0.1359222 | 0.4602003 | 0.386036 | 0.257761661 M58297_at | ZNF42 Zinc finger protein 42 (myeloid-specific retinoic acid-responsive) |
| 199 | Bladder | 0.1358307 | 0.4598061 | 0.385885 | 0.257610951 AA122302_a t | EST: zk97d12.r1 Soares pregnant uterus NbHPU Homo sapiens cDNA clone 490775 5' similar to gb:L32179 Human arylacetamide deacetylase mRNA, complete cds. (HUMAN);, mRNA sequence. (from Genbank) |
| 200 | Bladder | 0.1357712 | 0.4596236 | 0.385622 | 0.257380431 AA427468_s _at | Claudin 4 |
| 201 | Bladder | 0.1357086 | 0.4592364 | 0.385516 | 0.257193331 L17330_at | Pre-T/NK cell associated protein (6H9A) mRNA |
| 202 | Bladder | 0.1356579 | 0.4590434 | 0.385479 | 0.256914051 S58733_at | Pp52 |
| 203 | Bladder | 0.1332773 | 0.4589572 | 0.385202 | 0.256581 J00277_at | (genomic clones lambda-[SK2-T2, HS578T]; cDNA clones RS-[3,4, 6]) c-Ha-ras1 proto-oncogene, complete coding sequence |
| 204 | Bladder | 0.1323236 | 0.4588063 | 0.385044 | 0.256345331 X99101_at | ESR Estrogen receptor |
| 205 | Bladder | 0.1323236 | 0.4584121 | 0.384958 | 0.256069691 X99101_at-2 | Estrogen receptor 2 (ER beta) |
| 206 | Bladder | 0.1321859 | 0.4583841 | 0.384709 | 0.255895081 X90579_s_a t | H.sapiens DNA for cyp related pseudogene |

FIG. 1I

| | | | | | |
|---|---|---|---|---|---|
| 207 | Bladder | 0.1321776 | 0.4583044 | 0.384104 | 0.25567436 | RC_AA1506_19_at | EST:zt46a03.s1 Soares pregnant uterus NbHPU Homo sapiens cDNA clone 504940 3', mRNA sequence. (from Genbank) |
| 208 | Bladder | 0.1318411 | 0.458298 | 0.384072 | 0.25543034 | U28055_at | MST1 Macrophage stimulating 1 (hepatocyte growth factor-like) |
| 209 | Bladder | 0.131518 | 0.4577703 | 0.383841 | 0.25529942 | U09850_at | ZNF143 Zinc finger protein 143 (clone pHZ-1) |
| 210 | Bladder | 0.131518 | 0.4575949 | 0.383579 | 0.25509372 | U09850_at-2 | Zinc finger protein 143 (clone pHZ-1) |
| 211 | Bladder | 0.1312656 | 0.4575049 | 0.383516 | 0.25483451 | X87871_s_a t | HEPATOCYTE NUCLEAR FACTOR 4 |
| 212 | Bladder | 0.1305731 | 0.4574514 | 0.382963 | 0.254658251 | M62628_s_a t | Alpha-1 Ig germline C-region membrane-coding region, 3' end |
| 213 | Bladder | 0.1301464 | 0.4573334 | 0.382934 | 0.25448054 | N40774_at | EST:yw81e10.r1 Homo sapiens cDNA clone 258666 5'. (from Genbank) |
| 214 | Bladder | 0.1291867 | 0.457138 | 0.382732 | 0.2542403 | N29076_at | EST:yx41e01.r1 Homo sapiens cDNA clone 264312 5'. (from Genbank) |
| 215 | Bladder | 0.1286372 | 0.4568807 | 0.382551 | 0.25397208 | D45370_at | ApM2 mRNA for GS2374 (unknown product specific to adipose tissue) |
| 216 | Bladder | 0.1267606 | 0.4563995 | 0.382377 | 0.25373286 | W27720_at | Protocadherin 9 |
| 217 | Bladder | 0.1251471 | 0.4563757 | 0.382213 | 0.25353587 | U66083_at | MAGE-9 antigen (MAGE9) gene |
| 218 | Bladder | 0.1228662 | 0.4560547 | 0.382141 | 0.2532871 | U03090_at | Ca2+-dependent phospholipase A2 mRNA |
| 219 | Bladder | 0.1227494 | 0.4559751 | 0.381948 | 0.25299013 | L14812_at | RBL1 Retinoblastoma-like 1 (p107) |
| 220 | Bladder | 0.1226272 | 0.4559067 | 0.381754 | 0.25286514 | Z49826_at | Hepatocyte nuclear factor 4, gamma |
| 221 | Bladder | 0.1218462 | 0.4555458 | 0.381525 | 0.25277358 | U76369_at | Cationic amino acid transporter-2B (ATRC2) mRNA, partial cds |
| 222 | Bladder | 0.1214202 | 0.4548251 | 0.381504 | 0.25235754 | HG3342-HT3519_s_a t | Id1 |
| 223 | Bladder | 0.1210718 | 0.4545756 | 0.381286 | 0.25218061 | U23430_s_a | CCKAR Cholecystokirin A receptor |
| 224 | Bladder | 0.1201641 | 0.4545501 | 0.380099 | 0.25203379 | N88827_at | EST:K5685F Fetal heart, Lambda ZAP Express Homo sapiens cDNA clone K5685 5' similar to EST(YI03A03.R1), mRNA sequence. (from Genbank) |
| 225 | Bladder | 0.1198097 | 0.4543718 | 0.3800809 | 0.2518914 | M13955_at | Mesothelial keratin K7 (type II) mRNA, 3' end |
| 226 | Bladder | 0.1197636 | 0.4541487 | 0.380737 | 0.251751 | U17033_at | 180 kDa transmembrane PLA2 receptor mRNA |
| 227 | Bladder | 0.1197636 | 0.4541327 | 0.380312 | 0.251514 | U17033_at-2 | Human 180 kDa transmembrane PLA2 receptor mRNA, complete cds |
| 228 | Bladder | 0.1195144 | 0.4540066 | 0.380061 | 0.2513110 | RC_AA4782_98_s_at | Human apM2 mRNA for GS2374 (unknown product specific to adipose tissue), complete cds |
| 229 | Bladder | 0.1191743 | 0.4539329 | 0.379897 | 0.25112566 | J03242_s_at | IGF2 Insulin-like growth factor 2 (somatomedin A) |
| 230 | Bladder | 0.1185377 | 0.4537219 | 0.379699 | 0.25089055 | RC_AA2370_34_at | Golgi SNAP receptor complex member 2 |

FIG. 1J

| | | | | | |
|---|---|---|---|---|---|
| 231 | Bladder | 0.1166809 | 0.4536924 | 0.379043 | 0.25061813 | M20030_f_at | Small proline rich protein (sprII) mRNA, clone 930 |
| 232 | Bladder | 0.1165407 | 0.4532436 | 0.378869 | 0.25044206 | L36644_at | Receptor protein-tyrosine kinase (HEK7) mRNA, 3' end |
| 233 | Bladder | 0.1160006 | 0.4531906 | 0.378785 | 0.2503087 | S66896_at | SCCA1 Squamous cell carcinoma antigen 1 |
| 234 | Bladder | 0.115523 | 0.4529906 | 0.37865 | 0.25006074 | U12139_at | Alpha1(XI) collagen (COL11A1) gene, 5' region and exon 1 |
| 235 | Bladder | 0.1153378 | 0.4528299 | 0.37847 | 0.24985552 | D79995_at | KIAA0173 gene |
| 236 | Bladder | 0.1153347 | 0.4525504 | 0.378374 | 0.24971482 | AA191072_a_t | EST: zq43c11.r1 Stratagene hNT neuron (#937233) Homo sapiens cDNA clone 632468 5', mRNA sequence. (from Genbank) |
| 237 | Bladder | 0.1151569 | 0.4521225 | 0.378062 | 0.2494406 | RC_AA2533 97_at | Homo sapiens clone 24659 mRNA sequence |
| 238 | Bladder | 0.1150993 | 0.452017 | 0.37796 | 0.24923792 | M64936_at | Retinoic acid-inducible endogenous retroviral DNA |
| 239 | Bladder | 0.1140868 | 0.4514787 | 0.377625 | 0.249107 | RC_AA5984 10_at | EST: ae48b06.s1 Stratagene lung carcinoma 937218 Homo sapiens cDNA clone 950099 3', mRNA sequence. (from Genbank) |
| 240 | Bladder | 0.1137273 | 0.451315 | 0.377383 | 0.24896084 | D50582_at | Inward rectifier K channel |
| 241 | Bladder | 0.1128431 | 0.4512457 | 0.37728 | 0.24870318 | S69369_at | PAX3 Paired box homeotic gene 3 (Waardenburg syndrome 1)[alternative products] |
| 242 | Bladder | 0.1125664 | 0.4510102 | 0.37719 | 0.24852617 | U11872_at | Interleukin-8 receptor type B (IL8RB) mRNA, splice variant IL8RB1, partial cds |
| 243 | Bladder | 0.1114162 | 0.4509441 | 0.377167 | 0.2483537 | M69225_at | Bullous pemphigoid antigen (BPAG1) mRNA |
| 244 | Bladder | 0.1107282 | 0.4506999 | 0.376905 | 0.24801525 | RC_AA4638 61_at | EST: zx97c05.s1 Soares NhHMPu S1 Homo sapiens cDNA clone 811688 3' similar to SW:RB25_RABIT P46629 RAS-RELATED PROTEIN RAB-25. ; mRNA sequence. (from Genbank) |
| 245 | Bladder | 0.1092077 | 0.4502715 | 0.376715 | 0.24789566 | U06641_s_a t | UDP glycosyltransferase 2 family, polypeptide B15 |
| 246 | Bladder | 0.1089967 | 0.4502694 | 0.376627 | 0.24755578 | RC_AA4432 77_at | Peroxisomal biogenesis factor 11A |
| 247 | Bladder | 0.1085787 | 0.4499911 | 0.376484 | 0.2473274 | M12963_s_a t | ADH1 Alcohol dehydrogenase 1 (class I), alpha polypeptide |
| 248 | Bladder | 0.1081563 | 0.4499092 | 0.376362 | 0.24715394 | X78549_at | Brk mRNA for tyrosine kinase |
| 249 | Bladder | 0.1074152 | 0.4498538 | 0.376034 | 0.24706167 | X07730_at | APS Prostate specific antigen |
| 250 | Bladder | 0.1071856 | 0.4497513 | 0.375816 | 0.24685101 | L37199_at | (clone cD24-1) Huntington's disease candidate region mRNA fragment |
| 251 | Bladder | 0.107177 | 0.4496127 | 0.375695 | 0.24649942 | AA027760_a_t | EST: HPLA_CCLEE_406ar HPLA CCLee Homo sapiens cDNA, mRNA sequence. (from Genbank) |
| 252 | Bladder | 0.1066559 | 0.4495788 | 0.375688 | 0.24634053 | Y10275_at | L-3-phosphoserine phosphatase |
| 253 | Bladder | 0.1051963 | 0.4494627 | 0.375335 | 0.24608266 | D87023_cds 2_at | J1 gene extracted from Human (lambda) DNA for immunoglobin light chain |

FIG. 1K

| | | | | | | |
|---|---|---|---|---|---|---|
| 254 | Bladder | 0.105103 | 0.4489245 | 0.374979 | 0.245835584 U43030_at | Cardiotrophin-1 (CT-1) mRNA |
| 255 | Bladder | 0.1045492 | 0.4488328 | 0.374925 | AA282944_a | EST: zt15g08.r1 NCI_CGAP_GCB1 Homo sapiens cDNA clone IMAGE:713246 5', mRNA sequence. (from Genbank) |
| | | | | | 0.24571495 t | EST: zu41a09.s1 Soares ovary tumor NbHOT Homo sapiens cDNA clone 740536 3' similar to TR:G11144330 G11144330 CREB-RP. :, mRNA sequence. (from Genbank) |
| 256 | Bladder | 0.1037243 | 0.4487698 | 0.374847 | 0.245534331 L32164_at | Zinc finger protein mRNA, 3' end |
| 257 | Bladder | 0.1036713 | 0.4487619 | 0.374716 | 0.245522878 D88422_at | CYSTATIN A |
| 258 | Bladder | 0.1033749 | 0.4489939 | 0.374597 | HG2788- HG2788_at | |
| 259 | Bladder | 0.1033559 | 0.4483132 | 0.374326 | 0.245508993 HT2896_at | Calcyclin |
| 260 | Bladder | 0.103298 | 0.4478444 | 0.37427 | 0.2448629 M17316_at | Gamma-A-crystallin gene (gamma-G5), exon 3 |
| 261 | Bladder | 0.1032866 | 0.4477599 | 0.374207 | 0.24467142 D82636_at | EST: similar to none, mRNA sequence. (from Genbank) |
| 262 | Bladder | 0.1021394 | 0.4476731 | 0.374118 | 0.24449421 M31166_at | PTX3 Pentaxin-related gene, rapidly induced by IL-1 beta |
| 263 | Bladder | 0.1017572 | 0.4475309 | 0.373963 | 0.24418119 L48211_at | Angiotensin II receptor gene |
| 264 | Bladder | 0.1002536 | 0.4472213 | 0.373903 | 0.24395847 X82279_s_a t | Fas, Apo-1 gene (promoter and exon 1) |
| | | | | | AA130614_a t | EST: zo10f02.r1 Stratagene neuroepithelium NT2RAMI 937234 Homo sapiens cDNA clone 567291 5' similar to TR:G11125026 G11125026 3-HYDROXYACYL COA DEHYDROGENASE. :, mRNA sequence. (from Genbank) |
| 265 | Bladder | 0.0978928 | 0.447211 | 0.373355 | 0.24383032 t | HISTATIN 3 PRECURSOR |
| 266 | Bladder | 0.0971292 | 0.4470733 | 0.373509 | 0.243365549 M26065_at | CENPE Centromere protein E (312kD) |
| 267 | Bladder | 0.0970921 | 0.4467145 | 0.373438 | 0.243346629 Z15005_at | B94 PROTEIN |
| 268 | Bladder | 0.09697151 | 0.4466168 | 0.373278 | 0.24331836 M92357_at | OR17-228 gene extracted from Human olfactory receptor gene cluster on chromosome 17, OR17-228 and OR17-40, and OR17-24 and OR17-25 pseudogenes |
| 269 | Bladder | 0.096796 | 0.446361 | 0.373224 | U58675_cds 1_at | |
| 270 | Bladder | 0.0965342 | 0.4462171 | 0.372896 | RC_AA4320 83_at | EST: zw89c10.s1 Soares total fetus Nb2HF8 9w Homo sapiens cDNA clone 784146 3', mRNA sequence. (from Genbank) |
| 271 | Bladder | 0.096642 | 0.4459868 | 0.372862 | 0.242286085 H08988_at | EST: yl96d07.r1 Homo sapiens cDNA clone 46139 5'. (from Genbank) |
| 272 | Bladder | 0.0961804 | 0.4457915 | 0.372837 | 0.242270768 L14565_at | PERIPHERIN |
| 273 | Bladder | 0.0961784 | 0.4456743 | 0.372527 | 0.24264991 X90908_at | Ileal lipid binding protein mRNA |
| | | | | | RC_AA1437 63_at | EST: zo31d08.s1 Stratagene colon (#937204) Homo sapiens cDNA clone 588495 3', mRNA sequence. (from Genbank) |
| 274 | Bladder | 0.0958371 | 0.4456188 | 0.372489 | 0.242239543 U39447_at | Placenta copper monamine oxidase mRNA |
| 275 | Bladder | 0.0956522 | 0.4455904 | 0.371914 | 0.24229549 M13903_at | Involucrin gene, exon 2 |
| 276 | Bladder | 0.0953885 | 0.4455382 | 0.371872 | 0.2421691 M64930_at | Protein phosphatase 2A beta subunit mRNA |
| 277 | Bladder | 0.0942626 | 0.4455047 | 0.371163 | 0.24206069 M21494_at | CKM Creatine kinase, muscle |
| 278 | Bladder | 0.0933272 | 0.4454729 | 0.371611 | 0.24419099 U82979_at | Immunoglobulin-like transcript-3 mRNA |
| 279 | Bladder | 0.09233357 | 0.4452849 | 0.371509 | 0.24171035 | |

FIG. 1L

| # | Tissue | | | | Description |
|---|---|---|---|---|---|
| 280 | Bladder | 0.0917383 | 0.4451625 | 0.371438 | 0.24149881 | AA464368_s at | EST: zx81c11.r1 Soares ovary tumor NbHOT Homo sapiens cDNA clone 810164 5', mRNA sequence. (from Genbank) |
| 281 | Bladder | 0.0916961 | 0.4451212 | 0.371286 | 0.2413914 | D10923_at | PROBABLE G PROTEIN-COUPLED RECEPTOR HM74 |
| 282 | Bladder | 0.0911681 | 0.4450832 | 0.371218 | 0.24123172 | K02054_at | GRP Gastrin-releasing peptide |
| 283 | Bladder | 0.0914684 | 0.4450159 | 0.37095 | 0.24100913 | U64863_at | HPD-1 (hPD-1) mRNA |
| 284 | Bladder | 0.0912739 | 0.4443892 | 0.370718 | 0.24080348 | Z70295_at | GCAP-II/uroguanylin precursor |
| 285 | Bladder | 0.0912671 | 0.1443661 | 0.370633 | 0.24059094 | AA398863_a t | Zt80f04.r1 Soares testis NHT Homo sapiens cDNA clone 728671 5' similar to contains Alu repetitive element;contains element L1 repetitive element .; mRNA sequence. (from Genbank) |
| 286 | Bladder | 0.0898263 | 0.4441937 | 0.370261 | 0.24038087 | AA286726_a t | EST: zs53c11.r1 NCI_CGAP_GCB1 Homo sapiens cDNA clone IMAGE:701204 5' similar to TR:G849227 G849227 SIMILAR TO PROTEINS INVOLVED IN VACUOLAR FUNCTION: S. CEREVISIAE VAC1P. ; mRNA sequence. (from Genbank) |
| 287 | Bladder | 0.0896721 | 0.4438813 | 0.370106 | 0.24018839 | D38503_at | PMS8 mRNA (yeast mismatch repair gene PMS1 homologue), partial cds (C-terminal region) |
| 288 | Bladder | 0.0895167 | 0.4438038 | 0.369734 | 0.23999457 | M24364_at | HLA-DQB1 Major histocompatibility complex, class II, DQ beta 1 |
| 289 | Bladder | 0.0894491 | 0.4433568 | 0.369659 | 0.23984064 | HG3492-HT3686_at | Uncoupling Protein Ucp |
| 290 | Bladder | 0.0892752 | 0.442713 | 0.369659 | 0.23969305 | X93330_at | RYR2 Ryanodine receptor 2 (cardiac) |
| 291 | Bladder | 0.0892752 | 0.4426481 | 0.369498 | 0.23959109 | X98330_at-2 | Ryanodine receptor 2 (cardiac) |
| 292 | Bladder | 0.0889579 | 0.442355 | 0.369191 | 0.23943353 | RC_AA2333 71_at | EST: zr48f03.s1 Soares NhHMPu S1 Homo sapiens cDNA clone 666653 3', mRNA sequence. (from Genbank) |
| 293 | Bladder | 0.0887058 | 0.4422826 | 0.369039 | 0.2391186 | U41515_at | Deleted in split hand/split foot 1 (DSS1) mRNA |
| 294 | Bladder | 0.0886999 | 0.4420766 | 0.368855 | 0.23893073 | L19183_at | MAC30 mRNA, 3' end |
| 295 | Bladder | 0.0866702 | 0.4417574 | 0.368644 | 0.23849869 | U73499_at | Hepatic nuclear factor 1-alpha (TCF-1-alpha) gene, promoter region and partial cds |
| 296 | Bladder | 0.0860137 | 0.4416733 | 0.368509 | 0.2384067 | X87159_at | Beta subunit of epithelial amiloride-sensitive sodium channel |
| 297 | Bladder | 0.0849903 | 0.4416101 | 0.368486 | 0.23819833 | J00073_at | Alpha-cardiac actin gene, 5' flank and |
| 298 | Bladder | 0.0848509 | 0.4412853 | 0.368362 | 0.23800859 | M13485_at | Metallothionein I-B gene |
| 299 | Bladder | 0.0845381 | 0.4412217 | 0.368288 | 0.23792812 | X03473_at | HISTONE H1' |
| 300 | Bladder | 0.0840654 | 0.4410428 | 0.368185 | 0.23777252 | RC_AA2564 85_at | EST: zr81e12.s1 Soares NhHMPu S1 Homo sapiens cDNA clone 682126 3', mRNA sequence. (from Genbank) |
| 301 | Bladder | 0.0838388 | 0.44074405 | 0.36778 | 0.23765811 | M11973_cds 1_at | Gamma-B-crystallin gene (gamma 1-2) |
| 302 | Bladder | 0.0835978 | 0.4406396 | 0.367632 | 0.23745807 | HG4051-HT4321_at | Choline Acetyltransferase |
| 303 | Bladder | 0.0830292 | 0.44054462 | 0.367386 | 0.23737565 | X74039_at | Variant urokinase plasminogen activator receptor (uPAR2) mRNA, partial cds |
| 304 | Bladder | 0.0825923 | 0.44053345 | 0.367176 | 0.23720981 | L08488_at | iNPP1 inositol polyphosphate-1-phosphatase |

FIG. 1M

| # | Tissue | | | | | Description |
|---|---|---|---|---|---|---|
| 305 | Bladder | 0.0825844 | 0.4404194 | 0.367128 | 0.237U51t U28758_s_a | NMDA receptor subtype 2B subunit (GRIN2B) mRNA, partial cds |
| 306 | Bladder | 0.0817482 | 0.4403704 | 0.367116 | 0.236845422 M11437_cds 2_at | KNG gene (kininogen) extracted from Human kininogen gene |
| 307 | Bladder | 0.0816293 | 0.4402723 | 0.367067 | 0.236751181 D90276_at | CGM7 Carcinoembryonic antigen gene family member 7 |
| 308 | Bladder | 0.0813425 | 0.4400959 | 0.367049 | 0.236656931 R66772_at | EST: yj33h04.r1 Homo sapiens cDNA clone 141079 5' similar to gb:X70944 cds1 MYOBLAST CELL SURFACE ANTIGEN 24.1D5 (HUMAN);. (from Genbank) |
| 309 | Bladder | 0.0811965 | 0.4400393 | 0.366988 | 0.236494561 L38517_at | Indian hedgehog protein (IHH) mRNA, 5' end |
| 310 | Bladder | 0.0798617 | 0.4395228 | 0.366917 | 0.236115982 HT4010_at HG3740- | Basic Transcription Factor 2, 34 Kda Subunit |
| 311 | Bladder | 0.079809 | 0.439356 | 0.366792 | 0.236150982 RC_AA6211 | EST: al61a05.s1 Soares NhHMPu S1 Homo sapiens cDNA clone 1046480 3', mRNA sequence. (from Genbank) |
| 312 | Bladder | 0.0791087 | 0.4392524 | 0.366712 | 0.235976143 31_at S79781_at | WT1 [antisense promoter, intron 1] [human, kidney, Genomic, 780 nt] |
| 313 | Bladder | 0.0788124 | 0.4390661 | 0.366402 | 0.235702351 S72493_s_at | KERATIN, TYPE I CYTOSKELETAL 17 |
| 314 | Bladder | 0.0784234 | 0.4389373 | 0.366081 | 0.235493931 D14520_at | GC-Box binding protein BTEB2 |
| 315 | Bladder | 0.0781659 | 0.4389108 | 0.365998 | 0.235468251 X64994_at | HGMP07I gene for olfactory receptor |
| 316 | Bladder | 0.0762364 | 0.4387546 | 0.365939 | 0.235285681 AA249611_a_t | SH3-binding domain glutamic acid-rich protein |
| 317 | Bladder | 0.0751428 | 0.4386492 | 0.365871 | 0.235119221 J00209_f_at | IFNA10 Interferon, alpha 10 |
| 318 | Bladder | 0.0748573 | 0.4384134 | 0.365573 | 0.234847871 X76059_at | YRRM1 |
| 319 | Bladder | 0.0743545 | 0.4383839 | 0.365528 | 0.234611651 M20777_at | , alpha-2 (VI) collagen |
| 320 | Bladder | 0.0743271 | 0.4382954 | 0.365182 | 0.234484871 X99142_at | Hair keratin, hHb6 |
| 321 | Bladder | 0.0730864 | 0.4382481 | 0.36508 | 0.234432651 U17760_ma 1_at | Laminin S B3 chain (LAMB3) gene |
| 322 | Bladder | 0.0719037 | 0.43813181 | 0.364999 | 0.234088111 AA018852_a_t | EST: ze55a07.r1 Soares retina N2b4HR Homo sapiens cDNA clone 362868 5', mRNA sequence. (from Genbank) |
| 323 | Bladder | 0.07168 | 0.4380594 | 0.364826 | 0.234056621 S81294_at | DCC=deleted in colorectal cancer (alternatively spliced, exon 1A) [human, brain tumor, tumor no. 245, mRNA Partial, 216 nt] |
| 324 | Bladder | 0.0716741 | 0.43790691 | 0.364758 | 0.233810961 J04760_at | TNNI1 Troponin I, skeletal, slow |
| 325 | Bladder | 0.0712361 | 0.4377245 | 0.364502 | 0.233665191 L44140_cds 4_s_at | DNL1L gene extracted from Homo sapiens chromosome X region from filamin (FLN) gene to glucose-6-phosphate dehydrogenase (G6PD) gene's |
| 326 | Bladder | 0.07119821 | 0.4374299 | 0.364284 | 0.233495531 X16666_s_a t-2 | Homeo box B1 |
| 327 | Bladder | 0.0711982 | 0.43723831 | 0.364161 | 0.233435381 X16666_s_a t | HOXB1 Homeo box B1 |

FIG. 1N

| | | | | | | |
|---|---|---|---|---|---|---|
| 328 | Bladder | 0.0710842 | 0.4370078 | 0.363812 | 0.233330604 | HG4749-HT5197_at | Calmitine Calcium-Binding Protein, Mitochondrial |
| 329 | Bladder | 0.0707451 | 0.4368897 | 0.363323 | 0.233179321 | Z80345_rna_s_at | SCAD gene, exon 1 and joining features |
| 330 | Bladder | 0.0706855 | 0.4368044 | 0.363309 | 0.233304388 | W28091_at | EST: 41h4 Human retina cDNA randomly primed sublibrary Homo sapiens cDNA, mRNA sequence. (from Genbank) |
| 331 | Bladder | 0.0701331 | 0.4364465 | 0.363263 | 0.233300986 | RC_AA6088 02_at | EST: af04e03.s1 Soares testis NHT Homo sapiens cDNA clone 1030684 3', mRNA sequence. (from Genbank) |
| 332 | Bladder | 0.0701108 | 0.4363766 | 0.36315 | 0.23290707 | U25826_at | Transcription factor (SC1) gene |
| 333 | Bladder | 0.0700822 | 0.4362766 | 0.36308 | 0.23284133 | Y00503_at | KRT19 Keratin 19 |
| 334 | Bladder | 0.069082 | 0.4360632 | 0.363032 | 0.23266093 | W02342_at | Homo sapiens putative transmembrane protein (CLN5) mRNA, complete cds |
| 335 | Bladder | 0.0688592 | 0.4359873 | 0.362743 | 0.232479961 | AA043601_a_t | Ubiquitin-conjugating enzyme E2H (homologous to yeast UBC8) |
| 336 | Bladder | 0.0679561 | 0.4357595 | 0.362692 | 0.232283329 | RC_AA4355 97_at | EST: zt85g06.s1 Soares testis NHT Homo sapiens cDNA clone 729178 3', mRNA sequence. (from Genbank) |
| 337 | Bladder | 0.0677295 | 0.4355727 | 0.362347 | 0.232111987 | R73842_at | EST: yi55f09.r1 Homo sapiens cDNA clone 143177 5' similar to contains Alu repetitive element.. (from Genbank) |
| 338 | Bladder | 0.0674489 | 0.4352745 | 0.362198 | 0.23191448 | X54925_at | MMP1 Matrix metalloproteinase 1 (interstitial collagenase) |
| 339 | Bladder | 0.0666082 | 0.4349769 | 0.362187 | 0.231724744 | RC_AA4180 46_at | EST: zv97f10.s1 Soares NhHMPu S1 Homo sapiens cDNA clone 767755 3', mRNA sequence. (from Genbank) |
| 340 | Bladder | 0.0662417 | 0.4349625 | 0.362012 | 0.2315955 | AA280228_a_t | EST: zt04c11.r1 NCI_CGAP_GCB1 Homo sapiens cDNA clone IMAGE:712148 5', mRNA sequence. (from Genbank) |
| 341 | Bladder | 0.0659497 | 0.4347339 | 0.361957 | 0.231493771 | RC_AA4820 31_at | Ribosomal protein L37 |
| 342 | Bladder | 0.0655879 | 0.4346328 | 0.361864 | 0.231305578 | HG3987-HT4257_at | Cpg-Enriched Dna, Clone E06 |
| 343 | Bladder | 0.0654644 | 0.4345666 | 0.361771 | 0.231153344 | RC_AA4195 47_at | EST: zv04a05.s1 Soares NhHMPu S1 Homo sapiens cDNA clone 752624 3', mRNA sequence. (from Genbank) |
| 344 | Bladder | 0.0654236 | 0.4344904 | 0.361669 | 0.231031844 | M20218_at | F11 Coagulation factor XI (plasma thromboplastin antecedent) |
| 345 | Bladder | 0.0652238 | 0.4344266 | 0.36154 | 0.230940524 | D83838_at | EST: similar to protein Nterminal asparagine amidohydrolase, mRNA sequence. (from Genbank) |
| 346 | Bladder | 0.0649321 | 0.434416 | 0.36138 | 0.230824988 | Z21156_at | Homo sapiens mRNA for KIAA0826 protein, partial cds |
| 347 | Bladder | 0.0649257 | 0.4343781 | 0.361287 | 0.230613636 | RC_AA1923 06_at | EST: zp97c12.s1 Stratagene muscle 937209 Homo sapiens cDNA clone 628150 3', mRNA sequence. (from Genbank) |
| 348 | Bladder | 0.0648475 | 0.4341822 | 0.36085 | 0.230555184 | D50495_at | Transcription elongation factor S-II, hS-II-T1 |
| 349 | Bladder | 0.0633066 | 0.4340169 | 0.360776 | 0.230262773 | X87344_cds 10_r_at | DMA gene extracted from H.sapiens DMA, DMB, HLA-Z1, IPP2, LMP2, TAP1, LMP7, TAP2, DOB, DQB2 and RING8, 9, 13 and 14 genes |
| 350 | Bladder | 0.0627882 | 0.4334844 | 0.360689 | 0.230166674 | X86400_at | Gamma subunit of sodium potassium ATPase |

FIG. 1O

| | | | | | | |
|---|---|---|---|---|---|---|
| 351 | Bladder | 0.0627882 | 0.433473 | 0.360542 | 0.230000255 | X86400_at-2 | ATPase, Na+/K+ transporting, gamma 1 polypeptide |
| 352 | Bladder | 0.062768 | 0.4344359 | 0.360326 | 0.22990637 | M60047_at | Heparin binding protein (HBp17) mRNA |
| 353 | Bladder | 0.0627096 | 0.4333471 | 0.359872 | 0.22973487 | RC_AA4538 15_at | EST: aa19h06.s1 Soares NhHMPu S1 Homo sapiens cDNA clone 813755 3', mRNA sequence. (from Genbank) |
| 354 | Bladder | 0.0626819 | 0.433216 | 0.359675 | 0.2295711 | M19878_s_a t | Calbindin 27 gene, exons 1 and 2, and Alu repeat |
| 355 | Bladder | 0.0626531 | 0.433179 | 0.359586 | 0.22943208 | L16464_at | ETS-RELATED PROTEIN PE-1 |
| 356 | Bladder | 0.0625535 | 0.433179 | 0.359519 | 0.2292636 | X57348_s_a t | SFN Stratifiin |
| 357 | Bladder | 0.0622724 | 0.4331583 | 0.359442 | 0.22917165 | W31287_at | EST: zb92a04.r1 Soares parathyroid tumor NbHPA Homo sapiens cDNA clone 320238 5', mRNA sequence. (from Genbank) |
| 358 | Bladder | 0.0621258 | 0.4330452 | 0.359231 | 0.22900306 | AFFX-DapX-M_at | AFFX-DapX-M_at (endogenous control) |
| 359 | Bladder | 0.0621258 | 0.4330081 | 0.359152 | 0.22889638 | AFFX-DapX-M_at-2 | AFFX-DapX-M_at (miscellaneous control - 11k chips) |
| 360 | Bladder | 0.0620866 | 0.4329309 | 0.359047 | 0.22872312 | RC_AA3720 18_at | EST: EST83940 Parathyroid gland tumor I Homo sapiens cDNA 3' end, mRNA sequence. (from Genbank) |
| 361 | Bladder | 0.0620314 | 0.4327582 | 0.358913 | 0.2285443 | R81003_at | EST: yi94e03.r1 Homo sapiens cDNA clone 146908 5'. (from Genbank) |
| 362 | Bladder | 0.0620106 | 0.4326507 | 0.358874 | 0.22842196 | HG4058-HT4328_at | Oncogene Aml1-Evi-1, Fusion Activated |
| 363 | Bladder | 0.0619291 | 0.4325385 | 0.35877 | 0.22827314 | M55153_at | PROTEIN-GLUTAMINE GAMMA-GLUTAMYLTRANSFERASE |
| 364 | Bladder | 0.0618514 | 0.4324747 | 0.35868 | 0.22817238 | RC_AA4890 63_at | EST: aa54f09.s1 NCI_CGAP_GCB1 Homo sapiens cDNA clone IMAGE:824777 3', mRNA sequence. (from Genbank) |
| 365 | Bladder | 0.061247 | 0.432313 | 0.358624 | 0.2279737 | Y07867_at | Pirin, isolate 1 |
| 366 | Bladder | 0.0608551 | 0.4322478 | 0.358535 | 0.22778153 | U31875_at | Hep27 protein mRNA |
| 367 | Bladder | 0.0608551 | 0.4321103 | 0.358316 | 0.22276842 | U31875_at-2 | Human Hep27 protein mRNA, complete cds |
| 368 | Bladder | 0.060164 | 0.4320281 | 0.358063 | 0.22754622 | RC_AA2363 56_at | EST: zf54a11.s1 Soares_NhHMPu_S1 Homo sapiens cDNA clone IMAGE:667196 3', mRNA sequence |
| 369 | Bladder | 0.0596682 | 0.4320262 | 0.357926 | 0.22742647 | X99374_s_a t | Ferritin beta mRNA |
| 370 | Bladder | 0.0593514 | 0.4319091 | 0.357907 | 0.22728266 | D84361_at | P52 and p64 isoforms of N-Shc |
| 371 | Bladder | 0.0589966 | 0.4318941 | 0.357811 | 0.22717111 | D87953_at | RTP |
| 372 | Bladder | 0.0584637 | 0.4318597 | 0.357322 | 0.22707637 | U14577_s_a t | MAP1A Microtubule-associated protein 1A |
| 373 | Bladder | 0.0577985 | 0.4317132 | 0.357159 | 0.22700034 | Z49825_s_at | HEPATOCYTE NUCLEAR FACTOR 4 |

FIG. 1P

| # | Tissue | | | | ID | Description |
|---|---|---|---|---|---|---|
| 374 | Bladder | 0.0566229 | 0.4315885 | 0.357155 | 0.22677158 | RC_AA2437 23_at | EST: zr68g10.s1 Soares NhHMPu S1 Homo sapiens cDNA clone 668610 3'; mRNA sequence. (from Genbank) |
| 375 | Bladder | 0.0563572 | 0.4315208 | 0.356886 | 0.2265718 | U67611_at-2 | Mouse transaldolase gene mRNA, complete cds. (from Genbank) |
| 376 | Bladder | 0.0563572 | 0.4314631 | 0.356767 | 0.22645459 | U67611_at | Mouse transaldolase gene mRNA |
| 377 | Bladder | 0.0563226 | 0.4310626 | 0.356688 | 0.22624591 | S77812_at | FLT1 Fms-related tyrosine kinase 1 (vascular endothelial growth factor/vascular permeability factor receptor) |
| 378 | Bladder | 0.0561582 | 0.4307508 | 0.35657 | 0.22610949 | RC_AA2321 26_at | EST: zr45b12.s1 Soares NhHMPu S1 Homo sapiens cDNA clone 666335 3'; mRNA sequence. (from Genbank) |
| 379 | Bladder | 0.0559053 | 0.4305874 | 0.356541 | 0.22594447 | HG3355-HT3532_at | Peroxisome Proliferator Activated Receptor (Gb:Z30972) |
| 380 | Bladder | 0.0556085 | 0.430546 | 0.356406 | 0.22573191 | L00205_at | KERATIN, TYPE II CYTOSKELETAL 6D |
| 381 | Bladder | 0.0554827 | 0.4302088 | 0.35631 | 0.22558264 | HG2566-HT4792_r_at | Microtubule-Associated Protein Tau, Alt. Splice 3, Exon 8 (clone 8B1) |
| 382 | Bladder | 0.0540595 | 0.4301117 | 0.356216 | 0.22254838 | L33477_at | Br-cadherin mRNA |
| 383 | Bladder | 0.0538207 | 0.4300621 | 0.356088 | 0.22544941 | M36205_at | SYNAPTOBREVIN 2 |
| 384 | Bladder | 0.0535315 | 0.4298687 | 0.356032 | 0.22524147 | HG25930-HT26386_at | Estradiol 17-beta dehydrogenase 1 |
| 385 | Bladder | 0.0532402 | 0.429824 | 0.355755 | 0.22512208 | X96754_at | GLUL Glutamate-ammonia ligase (glutamine synthase) |
| 386 | Bladder | 0.0531437 | 0.429312 | 0.35564 | 0.22495985 | Z48519_s_at | XG gene (clone RACE5) |
| 387 | Bladder | 0.0526468 | 0.4292454 | 0.355554 | 0.22488101 | RC_AA2566 68_at | EST: zr82h02.s1 Soares NhHMPu S1 Homo sapiens cDNA clone 682227 3'; mRNA sequence. (from Genbank) |
| 388 | Bladder | 0.05246 | 0.4291433 | 0.355403 | 0.22477199 | Y10209_at | CD30L protein |
| 389 | Bladder | 0.0524419 | 0.4289939 | 0.35516 | 0.2246155 | S73840_at | Type IIx myosin heavy chain (3' region) [human, skeletal muscle, mRNA Partial, 827 nt] |
| 390 | Bladder | 0.0514074 | 0.4288784 | 0.355127 | 0.22453785 | RC_AA2522 89_at | EST: zr29d01.s1 Stratagene NT2 neuronal precursor 937230 Homo sapiens cDNA clone 664801 3' similar to TR:G1060907 G1060907 QPRTASE ;; mRNA sequence. (from Genbank) |
| 391 | Bladder | 0.051141 | 0.4288498 | 0.354771 | 0.22444242 | HG3513-HT3707_at | Myosin, Heavy Polypeptide, Light Meromyosin |
| 392 | Bladder | 0.0510215 | 0.4287831 | 0.354764 | 0.22441888 | U46499_at | GLUTATHIONE S-TRANSFERASE, MICROSOMAL |
| 393 | Bladder | 0.0509701 | 0.4286442 | 0.354737 | 0.22409752 | L12060_s_at | RARG Retinoic acid receptor, gamma 1 |
| 394 | Bladder | 0.0509363 | 0.4281341 | 0.354736 | 0.2239799 | HG3495-HT3689_at | Collagen, Type lx, Alpha 1 |
| 395 | Bladder | 0.0509018 | 0.4275578 | 0.354689 | 0.22391555 | K03021_at | PLAT Plasminogen activator, tissue type (t-PA) |
| 396 | Bladder | 0.0507932 | 0.4274685 | 0.354669 | 0.22378549 | D17716_at-2 | Mannosyl (alpha-1,6-)-glycoprotein beta-1,6-N-acetyl-glucosaminyltransferase |

FIG. 1Q

| # | Tissue | | | | | Description |
|---|---|---|---|---|---|---|
| 397 | Bladder | 0.0507932 | 0.4273799 | 0.35412 | 0.223714484 D17716_at | N-acetylglucosaminyltransferase V |
| 398 | Bladder | 0.0506349 | 0.4273213 | 0.354048 | 0.22363096 S81419_at | Dystrophin, dystrophin (Purkinje promoter, alternatively spliced) [human, cortical brain and adult heart, mRNA Partial, 377 nt] |
| 399 | Bladder | 0.0498577 | 0.4271195 | 0.353917 | 0.22351193 U55258_at | HBRAVO/Nr-CAM precursor (hBRAVO/Nr-CAM) gene |
| 400 | Bladder | 0.0494496 | 0.4269797 | 0.353738 | 0.223229951 RC_AA0589 51_at | EST: zi96f07.s1 Stratagene corneal stroma (#937222) Homo sapiens cDNA clone 512485 3', mRNA sequence. (from Genbank) |
| 401 | Bladder | 0.0487522 | 0.4268143 | 0.353573 | 0.223307876 RC_AA2341 12_at | EST: zr74a05.s1 Soares NhHMPu S1 Homo sapiens cDNA clone 669104 3', mRNA sequence. (from Genbank) |
| 402 | Bladder | 0.0486552 | 0.4267403 | 0.353232 | 0.22288205 AA040628_a t | SYNAPTOTAGMIN I |
| 403 | Bladder | 0.0485486 | 0.4267225 | 0.353182 | 0.22277764 RC_AA0106 65_at | EST: ze19f06.s1 Soares fetal heart NbHH19W Homo sapiens cDNA clone 359459 3', mRNA sequence. (from Genbank) |
| 404 | Bladder | 0.0479636 | 0.4267026 | 0.352935 | 0.22226968 D86096_cds 1_s_at | EP3-IV gene extracted from Human DNA for prostaglandin E receptor EP3 subtype |
| 405 | Bladder | 0.0479196 | 0.426644 | 0.352858 | 0.22252354 C06279_at | EST: similar to none, mRNA sequence. (from Genbank) |
| 406 | Bladder | 0.0462434 | 0.426607 | 0.352725 | 0.22240618 X02874_at | OIAS (2'-5') oligoadenylate synthetase |
| 407 | Bladder | 0.0455019 | 0.4265375 | 0.352663 | 0.22217166 W27721_at | Homo sapiens KIAA0424 mRNA, partial cds |
| 408 | Bladder | 0.0445774 | 0.4264267 | 0.352595 | 0.2220572 X06825_at | Skeletal beta-tropomyosin |
| 409 | Bladder | 0.0443611 | 0.4263696 | 0.352314 | 0.221194307 M21551_rna 1_at | Neuromedin B mRNA |
| 410 | Bladder | 0.044351 | 0.4263188 | 0.362142 | 0.221175573 D78725_at | Homo sapiens mRNA for KIAA0914 protein, complete cds |
| 411 | Bladder | 0.0443297 | 0.4263149 | 0.352042 | 0.221169042 U33267_at | Glycine receptor beta subunit (GLRB) mRNA |
| 412 | Bladder | 0.0434613 | 0.4261689 | 0.352001 | 0.22152244 RC_AA6096 42_at | EST: af16a06.s1 Soares testis NHT Homo sapiens cDNA clone 1031794 3', mRNA sequence. (from Genbank) |
| 413 | Bladder | 0.0432534 | 0.425966 | 0.351828 | 0.02130874 AA071223_a t | EST: zf79f10.r1 Soares pineal gland N3HPG Homo sapiens cDNA clone 383179 5', mRNA sequence. (from Genbank) |
| 414 | Bladder | 0.042974 | 0.4258032 | 0.351756 | 0.22121264 L08424_at | Achaete scute homologous protein (ASH1) mRNA |
| 415 | Bladder | 0.0426014 | 0.4257608 | 0.351734 | 0.22114015 U15590_at | Heat shock protein 27 (HSP27) mRNA |
| 416 | Bladder | 0.0420211 | 0.4257174 | 0.351679 | 0.22105172 M28825_at | CD1A CD1a antigen (thymocyte antigen) |
| 417 | Bladder | 0.0418688 | 0.425695 | 0.351499 | 0.220955993 D87942_at | Fucosyltransferase 2 (secretor status included) |
| 418 | Bladder | 0.0418525 | 0.4256518 | 0.351361 | 0.22082242 HG3517-HT3711_at | Alpha-1-Antitrypsin, 5' End |
| 419 | Bladder | 0.0414693 | 0.4252038 | 0.351217 | 0.220076039 H24127_at | EST: ym50f03.r1 Homo sapiens cDNA clone 51827 5'. (from Genbank) |
| 420 | Bladder | 0.0414624 | 0.4250849 | 0.351122 | 0.2206557 X58377_at | Adipogenesis inhibitory factor |
| 421 | Bladder | 0.0398846 | 0.4250751 | 0.350929 | 0.22058696 M31606_at | PHKG2 Phosphorylase kinase, gamma 2 (testis) |
| 422 | Bladder | 0.0398162 | 0.4249809 | 0.35077 | 0.02044958 AF000545_a t | Putative purinergic receptor P2Y10 gene |
| 423 | Bladder | 0.0398053 | 0.4248788 | 0.350633 | 0.2202493 D90042_at | AAC2 Arylamine N-acetyltransferase, liver |

FIG. 1R

| | | | | | | |
|---|---|---|---|---|---|---|
| 424 | Bladder | 0.0394708 | 0.42473 | 0.350497 | 0.22018345 | U24266_at | Pyrroline-5-carboxylate dehydrogenase (P5CDh) mRNA, long form |
| 425 | Bladder | 0.0391943 | 0.4246208 | 0.350339 | 0.2201674 | M25322_at | SELP Selectin P (granule membrane protein 140kD, antigen CD62) |
| 426 | Bladder | 0.0391932 | 0.4244458 | 0.350104 | 0.22012138 | U73191_at | Inward rectifier potassium channel (Kir1.3) |
| 427 | Bladder | 0.0389838 | 0.4243701 | 0.350092 | 0.22000156 | L16782_at | Putative M phase phosphoprotein 1 (MPP1) mRNA, partial cds |
| 428 | Bladder | 0.0387155 | 0.4243444 | 0.349963 | 0.2198501 | D78367_at | K12 keratin |
| 429 | Bladder | 0.0384115 | 0.4241763 | 0.349917 | 0.21969792 | Y10514_s_at | CD152 protein |
| 430 | Bladder | 0.0383238 | 0.4240741 | 0.349902 | 0.2195899 | L02648_at | TCN2 Transcobalamin II |
| 431 | Bladder | 0.038302 | 0.4238106 | 0.349862 | 0.21946108 | HG1078-HT1078_at | Lamin-Like Protein (Gb:M24732) |
| 432 | Bladder | 0.0382422 | 0.4237583 | 0.349545 | 0.21935992 | RC_AA4589 52_at | EST: zx88e03.s1 Soares ovary tumor NbHOT Homo sapiens cDNA clone 810844 3', mRNA sequence. (from Genbank) |
| 433 | Bladder | 0.0381575 | 0.4235728 | 0.349446 | 0.2192598 | Y08417_s_at | CHRNB3 Cholinergic receptor, nicotinic, beta polypeptide 3 |
| 434 | Bladder | 0.0380313 | 0.4234776 | 0.349381 | 0.21914773 | AF010126_a t | Synuclein, gamma (breast cancer-specific protein 1) |
| 435 | Bladder | 0.0376956 | 0.4234432 | 0.349274 | 0.21897194 | HG273-HT273_at | Lymphocyte Antigen Hla-G3 |
| 436 | Bladder | 0.0376204 | 0.4229651 | 0.349165 | 0.21874294 | W56102_at | EST: zc58g07.r1 Soares parathyroid tumor NbHPA Homo sapiens cDNA clone 326556 5', mRNA sequence. (from Genbank) |
| 437 | Bladder | 0.0368371 | 0.4228829 | 0.348811 | 0.21873634 | Y00970_at | ACR Acrosin |
| 438 | Bladder | 0.0365929 | 0.4228408 | 0.348751 | 0.21868433 | U42408_at | Ladinin (LAD) mRNA |
| 439 | Bladder | 0.0360328 | 0.4228343 | 0.348625 | 0.21848868 | U52969_at | EST: yj53f04.r1 Homo sapiens cDNA clone 152479 5'. (from Genbank) |
| 440 | Bladder | 0.0360288 | 0.4228253 | 0.348459 | 0.2184533 | R46311_at | BRAIN SPECIFIC POLYPEPTIDE PEP-19 |
| 441 | Bladder | 0.0359417 | 0.422769 | 0.348259 | 0.21822183 | HG2271-HT2367_at | Profilaggrin |
| 442 | Bladder | 0.0358078 | 0.4227186 | 0.348095 | 0.21811951 | D49493_at | Bone morphogenetic protein-3b |
| 443 | Bladder | 0.0355552 | 0.4227005 | 0.347944 | 0.2180428 | AA017283_a t | EST: ze52b01.r1 Soares retina N2b4HR Homo sapiens cDNA clone 362569 5', mRNA sequence. (from Genbank) |
| 444 | Bladder | 0.03536 | 0.422646 | 0.347856 | 0.21785907 | D17408_s_a t | Calponin |
| 445 | Bladder | 0.0352848 | 0.422445 | 0.347728 | 0.21783351 | RC_AA3499 98_at | EST: EST57271 Infant brain Homo sapiens cDNA 3' end, mRNA sequence. (from Genbank) |
| 446 | Bladder | 0.034385 | 0.4224347 | 0.347671 | 0.21768893 | S61953_at | ERBB3 V-erb-b2 avian erythroblastic leukemia viral oncogene homolog 3 {alternative products} |

FIG. 1S

| # | Tissue | | | | ID | Description |
|---|---|---|---|---|---|---|
| 447 | Bladder | 0.0341425 | 0.4223525 | 0.347457 | AA362598_a t | EST: EST72534 Ovary II Homo sapiens cDNA 5' end, mRNA sequence. (from Genbank) |
| 448 | Bladder | 0.034139 | 0.4223475 | 0.347401 | RC_AA4545 54_at | EST: zx74e07.s1 Soares ovary tumor NbHOT Homo sapiens cDNA clone 809508 3' similar to TR:G973313 G973313 MYO-INOSITOL 1-PHOSPHATE SYNTHASE ISOZYME-2. ;, mRNA sequence. (from Genbank) |
| 449 | Bladder | 0.0336015 | 0.422094 | 0.347316 | AA426361_a t | Sortilin 1 |
| 450 | Bladder | 0.0333633 | 0.4220628 | 0.347217 | A28102_at | GABAa receptor alpha-3 subunit |
| 451 | Bladder | 0.033234 | 0.4219986 | 0.347208 | AA182909_a t | EST: zp51d08.r1 Stratagene HeLa cell s3 937216 Homo sapiens cDNA clone 612975 5', mRNA sequence. (from Genbank) |
| 452 | Bladder | 0.0325329 | 0.4218038 | 0.346788 | U13220_at | Forkhead protein FREAC-2 mRNA, partial cds |
| 453 | Bladder | 0.032036 | 0.4214408 | 0.346752 | AA292609_a t | EST: zs57g01.r1 NCI_CGAP_GCB1 Homo sapiens cDNA clone IMAGE:716616 5' similar to contains L1.t1 L1 repetitive element ;, mRNA sequence. (from Genbank) |
| 454 | Bladder | 0.0318354 | 0.4212161 | 0.346631 | RC_AA4295 71_at | EST: zw75d12.s1 Soares testis NHT Homo sapiens cDNA clone 782039 3' similar to contains element PTR7 repetitive element ;, mRNA sequence. (from Genbank) |
| 455 | Bladder | 0.0316793 | 0.4211663 | 0.346331 | M64936_f_at | Homo sapiens retinoic acid-inducible endogenous retroviral DNA |
| 456 | Bladder | 0.0316428 | 0.4209038 | 0.346211 | L02321_at | GSTM5 Glutathione S-transferase M5 |
| 457 | Bladder | 0.0315946 | 0.4208423 | 0.346184 | RC_AA4357 80_at | EST: zt77c11.s1 Soares testis NHT Homo sapiens cDNA clone 728372 3', mRNA sequence. (from Genbank) |
| 458 | Bladder | 0.0315475 | 0.4207422 | 0.345941 | HG3412-HT3593_s_a t | Blue Cone Photoreceptor Pigment |
| 459 | Bladder | 0.0313778 | 0.4204664 | 0.345855 | M21305_at | Alpha satellite and satellite 3 junction DNA sequence |
| 460 | Bladder | 0.0310702 | 0.4204147 | 0.345835 | M10051_s_a t | INSR Insulin receptor |
| 461 | Bladder | 0.030811 | 0.4202842 | 0.345747 | M93143_at | PLGL Plasminogen-like protein |
| 462 | Bladder | 0.0306993 | 0.420248 | 0.345654 | D50863_at | TESK1 |
| 463 | Bladder | 0.0306608 | 0.4202175 | 0.345593 | X73501_at-2 | KERATIN, TYPE I CYTOSKELETAL 20 |
| 464 | Bladder | 0.0306608 | 0.4200984 | 0.345498 | X73501_at | KERATIN, TYPE I CYTOSKELETAL 20 |
| 465 | Bladder | 0.0293408 | 0.420072 | 0.345338 | X82634_at | Partial mRNA for hair keratin acidic 3-II |
| 466 | Bladder | 0.0291908 | 0.4200108 | 0.345302 | AF001294_a t | IPL (IPL) mRNA |
| 467 | Bladder | 0.0287948 | 0.4199694 | 0.345229 | M21302_at | Small proline rich protein (sprl) mRNA, clone 174N |
| 468 | Bladder | 0.028752 | 0.419705 | 0.345162 | RC_AA4179 35_at | EST: zv94c08.s1 Soares NhHMPu S1 Homo sapiens cDNA clone 767438 3', mRNA sequence. (from Genbank) |

FIG. 1T

| # | Tissue | | | | ID | Description |
|---|---|---|---|---|---|---|
| 469 | Bladder | 0.0284433 | 0.4196658 | 0.345037 | 0.21497534 D26661_cds 2_at | ORF for E6 protein gene extracted from Human papillomavirus 5b genome integrated into human carcinoma DNA |
| 470 | Bladder | 0.0284737 | 0.4193523 | 0.344931 | 0.21493292 X83127_at | K+ channel beta 1a subunit mRNA, alternatively spliced |
| 471 | Bladder | 0.0283879 | 0.4193309 | 0.344806 | 0.21472059 AA478129_a t | EST: zu42c09.r1 Soares ovary tumor NbHOT Homo sapiens cDNA clone 740656 5' similar to SW:BI3_MOUSE P28662 BRAIN PROTEIN I3 ;, mRNA sequence. (from Genbank) |
| 472 | Bladder | 0.0282716 | 0.4193172 | 0.344797 | 0.21464953 RC_AA0262 80_at | EST: ze91d10.s1 Soares fetal heart NbHH19W Homo sapiens cDNA clone 366355 3', mRNA sequence. (from Genbank) |
| 473 | Bladder | 0.0277701 | 0.4192931 | 0.344426 | 0.21448617 AA459155_a t | EST: aa26h04.r1 NCI_CGAP_GCB1 Homo sapiens cDNA clone IMAGE:814423 5', mRNA sequence. (from Genbank) |
| 474 | Bladder | 0.0276949 | 0.4192291 | 0.344389 | 0.21431057 X52005_at | MYL4 Myosin, light polypeptide 4, alkali; atrial, embryonic |
| 475 | Bladder | 0.0275428 | 0.4192033 | 0.344342 | 0.21412554 HG2191- HT2261_at | Crystallin, Beta B3 (Gb:X15145) |
| 476 | Bladder | 0.0275347 | 0.4190671 | 0.344308 | 0.21405894 D00654_at | Enteric smooth muscle gamma-actin gene, 5' flank and |
| 477 | Bladder | 0.0274612 | 0.418985 | 0.344261 | 0.21401396 X78706_at | CRAT Carnitine acetyltransferase |
| 478 | Bladder | 0.0273511 | 0.4187846 | 0.344229 | 0.21383993 M65292_s_a t | HFL1 H factor (complement)-like 1 |
| 479 | Bladder | 0.0271896 | 0.4185309 | 0.344007 | 0.21370876 M98045_at | Folypolyglutamate synthetase mRNA |
| 480 | Bladder | 0.0269445 | 0.4185133 | 0.343992 | 0.21360534 N31684_at | Neuropilin 2 |
| 481 | Bladder | 0.0266457 | 0.4182184 | 0.343946 | 0.21350056 U60269_cds 2_at | Putative envelope protein; orf similar to env of Type A and Type B retroviruses and to class II HERVs gene extracted from Human endogenous retrovirus HERV-K(HML6) proviral clone HML6.17 putative polymerase and envelope genes, partial cds, and 3'LTR |
| 482 | Bladder | 0.0257196 | 0.4181826 | 0.343791 | 0.213305 M15881_at | UMOD Uromodulin (uromucoid, Tamm-Horsfall glycoprotein) |
| 483 | Bladder | 0.0257014 | 0.4181323 | 0.34375 | 0.21327646 U40371_at | 3',5' cyclic nucleotide phosphodiesterase (HSPDE1C1A) mRNA |
| 484 | Bladder | 0.025353 | 0.4179379 | 0.343665 | 0.21311559 HG4194- HT4464_at | Sodium/Hydrogen Exchanger 5 |
| 485 | Bladder | 0.0024638 | 0.4178295 | 0.3435 | 0.21307544 RC_AA4559 67_at | Neuronal PAS domain protein 2 |
| 486 | Bladder | 0.0245341 | 0.4176301 | 0.343304 | 0.21285224 U10690_f_at | MAGE-5a antigen (MAGE5a) gene |
| 487 | Bladder | 0.0244112 | 0.4176 | 0.343301 | 0.21274276 M60614_at | WT1 Wilms tumor 1 |
| 488 | Bladder | 0.0243394 | 0.4173596 | 0.343078 | 0.21262732 U31201_cds s_at | Laminin gamma2 chain gene (LAMC2) |
| 489 | Bladder | 0.0239442 | 0.4169847 | 0.343078 | 0.21257673 L11005_at | ALDEHYDE OXIDASE |
| 490 | Bladder | 0.0236619 | 0.4168963 | 0.342846 | 0.2123044 U01157_at | GI P1R Glucagon-like peptide 1 receptor |
| 491 | Bladder | 0.0235036 | 0.4168408 | 0.34279 | 0.21221857 U51003_s_a t | DLX-2 (DLX-2) gene |
| 492 | Bladder | 0.0232202 | 0.4168066 | 0.342688 | 0.21209788 M60298_at | EPB42 Erythrocyte membrane protein band 4.2 |
| 493 | Bladder | 0.0231249 | 0.4167408 | 0.342606 | 0.21192634 Z29572_at | Antisense mRNA for BCMA peptide |

FIG. 1U

| | | | | | |
|---|---|---|---|---|---|
| 494 | Bladder | 0.0231141 | 0.4166007 | 0.342364 | 0.21187279 | X75308_at | MMP13 Matrix metalloproteinase 13 (collagenase 3) |
| 495 | Bladder | 0.0229837 | 0.4165835 | 0.342346 | 0.21177591 | X63578_rna1_at | Parvalbumin |
| 496 | Bladder | 0.0229343 | 0.4164714 | 0.342058 | 0.21172091 | U55209_at | Myosin VIIa transcript 2 mRNA |
| 497 | Bladder | 0.0223716 | 0.4161491 | 0.341868 | 0.21164344 | T83397_at | Homo sapiens peroxisomal phytanoyl-CoA alpha-hydroxylase (PAHX) mRNA, complete cds |
| 498 | Bladder | 0.0212573 | 0.41609 | 0.341829 | 0.21149504 | U32499_s_at | D3 dopamine receptor mRNA |
| 499 | Bladder | 0.0211896 | 0.4158762 | 0.341796 | 0.21140356 | L20861_at | WNT5A Wingless-type MMTV integration site 5A, human homolog |
| 500 | Bladder | 0.0208589 | 0.4155853 | 0.341709 | 0.2113415 | U88902_cds11_f_at | Integrase gene extracted from Human endogenous retrovirus H clone g10.34 integrase and putative envelope protein genes, partial cds |
| 501 | Bladder | 0.0207751 | 0.4155719 | 0.341524 | 0.21124786 | Z33905_at | 43kD acetylcholine receptor-associated protein (Rapsyn) |
| 502 | Bladder | 0.0207331 | 0.4155607 | 0.341481 | 0.21116468 | X69878_at | FLT4 Fms-related tyrosine kinase 4 |
| 503 | Bladder | 0.02062 | 0.415351 | 0.341413 | 0.21099436 | RC_AA4043 81_f_at | EST: zw37a04.s1 Soares total fetus Nb2HF8 9w Homo sapiens cDNA clone 772206 3', mRNA sequence. (from Genbank) |
| 504 | Bladder | 0.0201105 | 0.4153276 | 0.341311 | 0.21092583 | U48231_at | Bradykinin receptor B1 subtype mRNA |
| 505 | Bladder | 0.0198645 | 0.4151395 | 0.341212 | 0.21076791 | Z86000_at | DNA sequence from clone RP1-151B14 on chromosome 22 Contains SSTR3 (somatostatin receptor 3) gene, pseudogene similar to ribosomal protein L39, RAC2 (ras-related C3 botulinum toxin substrate 2 (rho family, small GTP binding protein Rac2)) gene, ESTs, STSs, GSSs and CpG islands, complete sequence |
| 506 | Bladder | 0.0198612 | 0.4150705 | 0.341166 | 0.21062627 | W39573_at | EST: zc20b05.r1 Soares senescent fibroblasts NbHSF Homo sapiens cDNA clone 322833 5', mRNA sequence. (from Genbank) |
| 507 | Bladder | 0.0194261 | 0.4148907 | 0.341027 | 0.21056598 | H04627_at | EST: yj49f04.r1 Homo sapiens cDNA clone 152095 5'. (from Genbank) |
| 508 | Bladder | 0.0190298 | 0.414712 | 0.340882 | 0.21039835 | U64573_s_at | Connexin43 gap junction protein (connexin43) gene, exon 1 and promoter region |
| 509 | Bladder | 0.0190044 | 0.4147117 | 0.340794 | 0.21032225 | R14782_at | EST: yf93a01.r1 Homo sapiens cDNA clone 29972 5'. (from Genbank) |
| 510 | Bladder | 0.0187181 | 0.4146773 | 0.340765 | 0.21021667 | R51517_at | Yg72d11.r1 Homo sapiens cDNA clone 38889 5'. (from Genbank) |
| 511 | Bladder | 0.0184996 | 0.4146741 | 0.340616 | 0.21019728 | M13928_s_at | DELTA-AMINOLEVULINIC ACID DEHYDRATASE |
| 512 | Bladder | 0.0180239 | 0.4145186 | 0.340493 | 0.21004976 | M60331_at | PRM1 Protamine 1 |
| 513 | Bladder | 0.0176025 | 0.4143131 | 0.340331 | 0.20997985 | M59911_at | ITGA3 Integrin alpha-3 subunit |
| 514 | Bladder | 0.0174845 | 0.4143131 | 0.340303 | 0.20973095 | HG3936-HT4206_at | Interleukin 9 Receptor (Gb:S71404) |

FIG. 1V

| | | | | | |
|---|---|---|---|---|---|
| | 0.0174559 | 0.4139852 | 0.340278 | 0.20961878 | M24248_at | MYL3 Myosin, light polypeptide 3, alkali; ventricular, skeletal, slow |
| Bladder | 0.0173542 | 0.4137881 | 0.340195 | 0.209517 | RC_AA4656 64_at | EST: aa31b10.s1 NCI_CGAP_GCB1 Homo sapiens cDNA clone IMAGE:814843 3', mRNA sequence. (from Genbank) |
| 517 Bladder | 0.017334 | 0.4136108 | 0.340025 | 0.20947352 | U00803_s_a t | Fyn-related kinase |
| 518 Bladder | 0.0172407 | 0.4134401 | 0.339856 | 0.20936738 | U48807_at | Dual specific protein phosphatase mRNA |
| 519 Bladder | 0.0170615 | 0.4131798 | 0.339735 | 0.20925198 | D86957_at | KIAA0202 gene, partial cds |
| 520 Bladder | 0.01695 | 0.4128612 | 0.339721 | 0.20919491 | AA346065_a t | EST: EST52164 Greater omentum II Homo sapiens cDNA 5' end, mRNA sequence. (from Genbank) |
| 521 Bladder | 0.0166705 | 0.4128221 | 0.33964 | 0.2089954 | HG2730-HT2827_s_a | Fibrinogen, A Alpha Polypeptide, Alt. Splice 2, E |
| 522 Bladder | 0.0164375 | 0.4126806 | 0.339639 | 0.20886022 1_at | M63962_rna | Gastric H,K-ATPase catalytic subunit gene |
| 523 Bladder | 0.0164333 | 0.4125662 | 0.339405 | 0.20876858 | D14827_at | Tax helper protein 1 |
| 524 Bladder | 0.015948 | 0.4122615 | 0.33938 | 0.20860969 | U54804_at | Has2 mRNA |
| 525 Bladder | 0.0157191 | 0.4120875 | 0.339378 | 0.20852247 1_at | M57506_rna | SCYA1 gene (secreted protein I-309) extracted from Human secreted protein (I-309) gene |
| 526 Bladder | 0.0156512 | 0.4120398 | 0.339377 | 0.20845494 t | X13451_s_a | B-CELL ANTIGEN RECEPTOR COMPLEX ASSOCIATED PROTEIN ALPHA-CHAIN PRECURSOR |
| 527 Bladder | 0.0154402 | 0.4118176 | 0.339169 | 0.20838776 | U67784_at | Orphan G protein-coupled receptor (RDC1) mRNA, partial cds |
| 528 Bladder | 0.0153809 | 0.4117838 | 0.339033 | 0.20822155 5_at | RC_AA2364 | EST: zr75g02.s1 Soares NhHMPu S1 Homo sapiens cDNA clone 669266 3', mRNA sequence. (from Genbank) |
| 529 Bladder | 0.0152863 | 0.4115226 | 0.339024 | 0.20817296 | RC_AA0710 75_at | EST: zn58d10.s1 Stratagene fibroblast (#937212) Homo sapiens cDNA clone 529843 3', mRNA sequence. (from Genbank) |
| 530 Bladder | 0.0151383 | 0.4114377 | 0.338979 | 0.20804358 | D88532_at | P55pik |
| 531 Bladder | 0.0147889 | 0.411213 | 0.338945 | 0.207946431 t | HG1827-HT1856_s_a | Cytochrome P450, Subfamily IIc, Alt. Splice Form 2 |
| 532 Bladder | 0.0147604 | 0.4107625 | 0.338885 | 0.20775723 | S81957_at | BMP-5=bone morphogenic protein-5 [promoter] [human, Genomic, 1116 nt] |
| 533 Bladder | 0.0146777 | 0.410709 | 0.338728 | 0.2075998 1_at | U21051_rna | G protein-coupled receptor (GPR4) gene |
| 534 Bladder | 0.0138417 | 0.4106537 | 0.338702 | 0.20747581 | U51704_at | EST: Human mRNA sequence containing Alu repetitive elements. (from Genbank) |
| 535 Bladder | 0.0135856 | 0.4106054 | 0.338684 | 0.20728248 | U49857_at | Transcriptional activator mRNA |
| 536 Bladder | 0.0133775 | 0.4103409 | 0.338646 | 0.20723127 | X68314_at | GPX2 Glutathione peroxidase 2, gastrointestinal |
| 537 Bladder | 0.0131295 | 0.4101775 | 0.338527 | 0.20708442 | U62647_at | Deoxyribonuclease I-like 2 |

FIG. 1W

| | | | | | |
|---|---|---|---|---|---|
| 538 | Bladder | 0.0126058 | 0.4099266 | 0.33851 | 0.20707019 | W33035_at | EST: zc08d02.r1 Soares parathyroid tumor NbHPA Homo sapiens cDNA clone 321699 5'; mRNA sequence. (from Genbank) |
| 539 | Bladder | 0.0121411 | 0.4096319 | 0.338456 | 0.20700094 | M21389_at | KRT5 Keratin 5 (epidermolysis bullosa simplex, Dowling-Meara/Kobner/Weber-Cockayne types) |
| 540 | Bladder | 0.0117662 | 0.4094274 | 0.338338 | 0.20688418 | U76376_at | Harakiri, BCL2-interacting protein (contains only BH3 domain) |
| 541 | Bladder | 0.0117062 | 0.4093706 | 0.338327 | 0.20676461 | X54162_at | 64 KD AUTOANTIGEN D1 |
| 542 | Bladder | 0.0116682 | 0.4093685 | 0.338216 | 0.20663828 | M34041_at | Alpha-2-adrenergic receptor (alpha-2 c2) gene |
| 543 | Bladder | 0.0115933 | 0.4092691 | 0.338195 | 0.20655844 | U53442_at | P38Beta MAP kinase mRNA |
| 544 | Bladder | 0.0112006 | 0.4092419 | 0.338189 | 0.20645303 | S73885_s_at | TFAP4 Transcription factor AP-4 (activating enhancer-binding protein 4)) |
| 545 | Bladder | 0.0110582 | 0.4091745 | 0.338071 | 0.20639913 | L11353_at | NF2 Neurofibromin 2 (bilateral acoustic neuroma) |
| 546 | Bladder | 0.0108023 | 0.4090293 | 0.337971 | 0.206303 | HG2841-HT2968_s_a_t | Albumin, Alt. Splice 1 |
| 547 | Bladder | 0.0105163 | 0.4090218 | 0.337797 | 0.206241 | L35269_at | ZINC FINGER PROTEIN 35 |
| 548 | Bladder | 0.0095433 | 0.408891 | 0.337943 | 0.20611528 | U90918_at-2 | Human clone 23654 mRNA sequence |
| 549 | Bladder | 0.0095433 | 0.4086591 | 0.337897 | 0.20606282 | U90918_at | Clone 23654 mRNA sequence |
| 550 | Bladder | 0.008669 | 0.4086449 | 0.3378 | 0.20597453 | N79930_s_a_t | EST: yz86c05.r1 Homo sapiens cDNA clone 289928 5'. (from Genbank) |
| 551 | Bladder | 0.0086098 | 0.4086608 | 0.337623 | 0.2058684 | AA211295_a_t | Zq87g01.r1 Stratagene hNT neuron (#937233) Homo sapiens cDNA clone 649008 5'; mRNA sequence. (from Genbank) |
| 552 | Bladder | 0.0084219 | 0.4084829 | 0.337454 | 0.20571727 | RC_AA45/2 16_at | Interleukin enhancer binding factor 1 |
| 553 | Bladder | 0.0083111 | 0.408228 | 0.337395 | 0.20567723 | RC_AA4646 89_at | EST: zx82a03.s1 Soares ovary tumor NbHOT Homo sapiens cDNA clone 810220 3'; mRNA sequence. (from Genbank) |
| 554 | Bladder | 0.0079426 | 0.4081902 | 0.337392 | 0.20545706 | U12779_at | MAP KINASE-ACTIVATED PROTEIN KINASE 2 |
| 555 | Bladder | 0.0077511 | 0.4081057 | 0.337366 | 0.20543236 | L36463_at | Ras inhibitor mRNA, 3' end |
| 556 | Bladder | 0.0076713 | 0.4080944 | 0.337343 | 0.20527634 | RC_AA2364 76_at | EST: zr75c01.s1 Soares NhHMPu S1 Homo sapiens cDNA clone 669216 3' similar to TR:G755466 G755466 TRANSMEMBRANE PROTEIN PRECURSOR.; mRNA sequence. (from Genbank) |
| 557 | Bladder | 0.0075689 | 0.4079472 | 0.337262 | 0.2051851 | R33301_at | EST: yh81g01.r1 Homo sapiens cDNA clone 136176 5' similar to contains MSR1 repetitive element.:. (from Genbank) |
| 558 | Bladder | 0.0074166 | 0.4078634 | 0.337099 | 0.20503299 | X03363_s_a_t | ERBB2 V-erb-b2 avian erythroblastic leukemia viral oncogene homolog 2 (neuro/glioblastoma derived oncogene homolog) |
| 559 | Bladder | 0.007375 | 0.4078229 | 0.337047 | 0.20498237 | M17236_s_a_t | HLA CLASS II HISTOCOMPATIBILITY ANTIGEN, DQ(2) ALPHA CHAIN PRECURSOR |
| 560 | Bladder | 0.007343 | 0.4077794 | 0.336955 | 0.20490304 | AF000430_a_t | Dynamin-like protein mRNA |

FIG. IX

| | | | | | |
|---|---|---|---|---|---|
| 561 | Bladder | 0.0068585 | 0.407769 | 0.336934 | 0.204750064 | D45213_at | Homo sapiens mRNA for zinc finger protein, complete cds |
| 562 | Bladder | 0.0063708 | 0.4077612 | 0.33688 | RC_AA1565 0.204599959_32_at | Homo sapiens interferon regulatory factor 6 (IRF6) mRNA, complete cds |
| 563 | Bladder | 0.0060597 | 0.4076997 | 0.336814 | 0.204533353 M31165_at | TUMOR NECROSIS FACTOR-INDUCIBLE PROTEIN TSG-6 PRECURSOR |
| 564 | Bladder | 0.0058652 | 0.4076392 | 0.336689 | 0.204390062 M60278_at | DTR Diphtheria toxin receptor (heparin-binding epidermal growth factor-like growth factor) |
| 565 | Bladder | 0.0056581 | 0.4074823 | 0.336588 | RC_AA0132 0.204354543 31_at | EST: ze28h05.s1 Soares retina N2b4HR Homo sapiens cDNA clone 360345 3', mRNA sequence. (from Genbank) |
| 566 | Bladder | 0.0054524 | 0.4073624 | 0.336515 | X04602_s_a 0.204424682 t-2 | Interleukin 6 (interferon, beta 2) |
| 567 | Bladder | 0.0054524 | 0.4072766 | 0.336439 | X04602_s_a 0.204196681 t | IL6 Interleukin 6 (B cell stimulatory factor 2) |
| 568 | Bladder | 0.0054254 | 0.4072441 | 0.336385 | HG2987- 0.2041391 HT3136_s_a t | Vasoactive Intestinal Peptide |
| 569 | Bladder | 0.0053322 | 0.4069091 | 0.336249 | 0.203973389 X93017_at | Ncx2 gene (exon 2) |
| 570 | Bladder | 0.0052947 | 0.4068644 | 0.336192 | 0.203888559 L20469_s_at | Truncated dopamine D3 receptor mRNA |
| 571 | Bladder | 0.0051277 | 0.4068053 | 0.336033 | AA188555_a 0.2037977779 t | EST: zp78e11.r1 Stratagene HeLa cell s3 937216 Homo sapiens cDNA clone 626348 5', mRNA sequence. (from Genbank) |
| 572 | Bladder | 0.004953 | 0.4067128 | 0.335958 | 0.203684409 X58288_at | PTPRM Protein tyrosine phosphatase, receptor type, mu polypeptide |
| 573 | Bladder | 0.0048514 | 0.4065523 | 0.335911 | 0.203546605 Y10260_at | EYA1A gene |
| 574 | Bladder | 0.0048182 | 0.4062783 | 0.335899 | M31520_ma 0.203447111 at | Unknown protein gene extracted from Human ribosomal protein S24 mRNA |
| 575 | Bladder | 0.0044372 | 0.4062186 | 0.33578 | 0.203422268 U49928_at | TAK1 binding protein 1 (TAB1) mRNA |
| 576 | Bladder | 0.0043853 | 0.4058838 | 0.335678 | 0.203336822 L17326_s_at | Human pre-T/NK cell associated protein (1F6) mRNA, 3' end |
| 577 | Bladder | 0.0041493 | 0.4056924 | 0.33559 | M63509_s_a 0.203328908 t | Glutathione S-transferase M2 (muscle) |
| 578 | Bladder | 0.0041047 | 0.40569 | 0.335516 | 0.203220529 U55764_at | Estrogen sulfotransferase mRNA, partial cds |
| 579 | Bladder | 0.0038496 | 0.4056819 | 0.335474 | HG870- 0.203020072 HT870_at | Golgin, 165 Kda Polypeptide |
| 580 | Bladder | 0.0037646 | 0.4056769 | 0.335442 | RC_AA4183 0.202944668 94_at | EST: zv92e06.s1 Soares NhHMPu S1 Homo sapiens cDNA clone 767266 3', mRNA sequence. (from Genbank) |
| 581 | Bladder | 0.0034687 | 0.4056769 | 0.335288 | AA018418_a 0.202903211 t | EST: ze50a02.r1 Soares retina N2b4HR Homo sapiens cDNA clone 362378 5', mRNA sequence. (from Genbank) |
| 582 | Bladder | 0.0033625 | 0.4056633 | 0.335245 | 0.202718551 R14606_at | EST: yf34c12.r1 Homo sapiens cDNA clone 128758 5'. (from Genbank) |

FIG. 1Y

| | | | | | |
|---|---|---|---|---|---|
| 583 | Bladder | 0.0022909 | 0.4056633 | 0.335105 | 0.20258886 | K00629_f_at | Human kpni repeat mrna (cdna clone pcd-kpni-4), 3' end |
| 584 | Bladder | 0.0021413 | 0.4056353 | 0.335019 | 0.20258497 | U05012_s_at | NTRK3 Neurotrophic tyrosine kinase, receptor, type 3 (TrkC) |
| 585 | Bladder | 0.0020917 | 0.4056081 | 0.334994 | 0.20228115 | AA424381_s_at | EST: zv90g12.r1 Soares NbHMPu S1 Homo sapiens cDNA clone 767110 5', mRNA sequence. (from Genbank) |
| 586 | Bladder | 0.0020461 | 0.4053913 | 0.334881 | 0.20225722 | D21337_at | COL4A6 Collagen, type IV, alpha 6 |
| 587 | Bladder | 0.0019807 | 0.4052483 | 0.334872 | 0.20219491 | L41607_at | GCNT2 Glucosaminyl (N-acetyl) transferase 2, I-branching enzyme |
| 588 | Bladder | 0.0019386 | 0.4052203 | 0.334754 | 0.20212647 | AA0850059_a_at | Zn14b01.r1 Stratagene hNT neuron (#937233) Homo sapiens cDNA clone 547369 5' similar to gb:M26380 UBIQUITIN (HUMAN);, mRNA sequence. (from Genbank) |
| 589 | Bladder | 0.0016093 | 0.4051888 | 0.334483 | 0.20199428 | S72503_s_at | HRK1 |
| 590 | Bladder | 0.0015221 | 0.4051793 | 0.334442 | 0.20188577 | U43843_at | H-neuro-d4 protein mRNA |
| 591 | Bladder | 0.0011484 | 0.4050511 | 0.334408 | 0.20175707 | AA074933_a_at | Zm85b07.r1 Stratagene ovarian cancer (#937219) Homo sapiens cDNA clone 544693 5' similar to gb:J04794 ALCOHOL DEHYDROGENASE (HUMAN);, mRNA sequence. (from Genbank) |
| 592 | Bladder | 0.00110096 | 0.4049275 | 0.334242 | 0.20160204 | RC_AA464188_s_at | EST: zx83g04.s1 Soares ovary tumor NbHOT Homo sapiens cDNA clone 810390 3', mRNA sequence. (from Genbank) |
| 593 | Bladder | 8.49E-04 | 0.404859 | 0.334139 | 0.20151573 | AA285229_a_at | PMY0709 KG1-a Lambda Zap Express cDNA library Homo sapiens cDNA 5', mRNA sequence. (from Genbank) |
| 594 | Bladder | 8.17E-04 | 0.4048388 | 0.334067 | 0.2014302 | U58130_at | Bumetanide-sensitive Na-K-2Cl cotransporter (NKCC2) mRNA |
| 595 | Bladder | 7.92E-04 | 0.4048312 | 0.333876 | 0.20133114 | AF000562_a_at | Uroplakin II mRNA, partial cds |
| 596 | Bladder | 7.44E-04 | 0.4048144 | 0.333754 | 0.20125984 | X13839_at | LCAT Lecithin-cholesterol acyltransferase |
| 597 | Bladder | 4.26E-04 | 0.4045939 | 0.333694 | 0.20115615 | X89426_at | ESM-1 protein |
| 598 | Bladder | 3.76E-04 | 0.4043819 | 0.33362 | 0.20098957 | AA167340_a_at | Zp11a09.r1 Stratagene fetal retina 937202 Homo sapiens cDNA clone 609112 5', mRNA sequence. (from Genbank) |
| 599 | Bladder | 3.27E-04 | 0.4043663 | 0.333353 | 0.20093228 | U72209_at | YY1-associated factor 2 (YAF2) mRNA |
| 600 | Bladder | 1.82E-04 | 0.4042527 | 0.333504 | 0.20088567 | U73843_at | Epithelial-specific transcription factor ESE-1b (ESE-1) mRNA |
| 601 | Bladder | -4.75E-04 | 0.404138 | 0.333389 | 0.20087372 | RC_D59630_at | EST: Human fetal brain cDNA 3'-end GEN-052F04, mRNA sequence. (from Genbank) |
| 602 | Bladder | -6.02E-04 | 0.4039995 | 0.333167 | 0.20068097 | U46461_at | Dishevelled homolog (DVL) mRNA |
| 603 | Bladder | -0.001195 | 0.4039462 | 0.333118 | 0.2006507 | L07594_at | TGFBR3 Transforming growth factor, beta receptor III (betaglycan, 300kD) |
| 604 | Bladder | -0.001562 | 0.4038779 | 0.333006 | 0.20054983 | RC_D12031_at | EST: Human HepG2 3'-directed Mbol cDNA, clone s14g02, mRNA sequence. (from Genbank) |
| 605 | Bladder | -0.001612 | 0.4038751 | 0.332966 | 0.20040289 | U90716_at | Cell surface protein HCAR mRNA |

FIG. 1Z

| | | | | | | |
|---|---|---|---|---|---|---|
| 606 | Bladder | -0.001721 | 0.40038679 | 0.332934 | 0.200234473 | HG2936-HT3080_at | Immunoglobulin Heavy Chain, Enhancer Element |
| 607 | Bladder | -0.001765 | 0.40038679 | 0.332928 | 0.20013262 | S79267_at | CD4 CD4 antigen (p55) |
| 608 | Bladder | -0.001997 | 0.4035124 | 0.3329 | 0.2000781 | AA059287_s_at | EST: zf65e02.r1 Soares retina N2b4HR Homo sapiens cDNA clone 381818 5', mRNA sequence. (from Genbank) |
| 609 | Bladder | -0.002165 | 0.4034976 | 0.332767 | 0.20002142 | U39840_at | Hepatocyte nuclear factor-3 alpha (HNF-3 alpha) mRNA |
| 610 | Bladder | -0.002394 | 0.4032889 | 0.332649 | 0.19995838 | U00951_at-2 | Human clone A9A2BR11 (CAC)n/(GTG)n repeat-containing mRNA |
| 611 | Bladder | -0.002394 | 0.4032842 | 0.332649 | 0.19992596 | U00951_at | Clone A9A2BR11 (CAC)n/(GTG)n repeat-containing mRNA |
| 612 | Bladder | -0.00249 | 0.4031963 | 0.332635 | 0.19982278 | AA496083_a_at | EST: zu67c08.r1 Soares testis NHT Homo sapiens cDNA clone 743054 5', mRNA sequence. (from Genbank) |
| 613 | Bladder | -0.003573 | 0.4030942 | 0.33262 | 0.19968727 | M99063_at | KERATIN, TYPE II CYTOSKELETAL 2 ORAL |
| 614 | Bladder | -0.003698 | 0.4029892 | 0.332328 | 0.19958569 | AA488505_a_t | Human placenta (Diff33) mRNA, complete cds |
| 615 | Bladder | -0.004628 | 0.4028657 | 0.332274 | 0.19952804 | M10943_at | Metallothionein-If gene (hMT-If) |
| 616 | Bladder | -0.004662 | 0.4028616 | 0.332263 | 0.1994643 | U95626_rna1_at | Ccr2 gene (ccr2a) extracted from Homo sapiens ccr2b (ccr2), ccr2a (ccr2), ccr5 (ccr5) and ccr6 (ccr6) genes, and lactoferrin (lactoferrin) gene, partial cds, complete sequence |
| 617 | Bladder | -0.00467 | 0.4028103 | 0.332095 | 0.19938204 | M77348_rna1_s_at | Pmel 17 mRNA |
| 618 | Bladder | -0.004929 | 0.4027283 | 0.332083 | 0.19932649 | S78825_at | ID1 Inhibitor of DNA binding 1, dominant negative helix-loop-helix protein |
| 619 | Bladder | -0.004992 | 0.4026891 | 0.332083 | 0.19924726 | Z22780_at | CYLICIN |
| 620 | Bladder | -0.005389 | 0.4026367 | 0.331958 | 0.19923145 | RC_AA411351_at | EST: zv28e04.s1 Soares ovary tumor NbHOT Homo sapiens cDNA clone 754950 3', mRNA sequence. (from Genbank) |
| 621 | Bladder | -0.005719 | 0.4026367 | 0.331891 | 0.19904143 | V00535_rna2_s_at | Interferon beta 1 gene extracted from Gene for human fibroblast interferon beta 1 |
| 622 | Bladder | -0.005925 | 0.4026347 | 0.331843 | 0.19900347 | RC_AA252209_at | EST: zr63g05.s1 Soares NhHMPu S1 Homo sapiens cDNA clone 668120 3', mRNA sequence. (from Genbank) |
| 623 | Bladder | -0.006015 | 0.4025945 | 0.331716 | 0.19896111 | M94055_at | SODIUM CHANNEL PROTEIN, BRAIN II ALPHA SUBUNIT |
| 624 | Bladder | -0.006144 | 0.4025401 | 0.331552 | 0.19889551 | RC_AA001663_at | EST: zh85b09.s1 Soares fetal liver spleen 1NFLS S1 Homo sapiens cDNA clone 428057 3', mRNA sequence. (from Genbank) |
| 625 | Bladder | -0.00629 | 0.40239680 | 0.331432 | 0.19882688 | AB000584_a_t | Prostate differentiation factor mRNA |
| 626 | Bladder | -0.006568 | 0.402238 | 0.331396 | 0.1986566 | RC_AA460257_at | EST: zx67d07.s1 Soares total fetus Nb2HF8 9w Homo sapiens cDNA clone 796525 3', mRNA sequence. (from Genbank) |
| 627 | Bladder | -0.006643 | 0.4021483 | 0.331396 | 0.19847181 | RC_AA441791_at | EST: zw62c02.s1 Soares total fetus Nb2HF8 9w Homo sapiens cDNA clone 774626 3', mRNA sequence. (from Genbank) |
| 628 | Bladder | -0.007003 | 0.4021237 | 0.331287 | 0.1984411 | U62435_at | Cholinergic receptor, neuronal nicotinic, alpha polypeptide 6 |

FIG. 1A2

| | | | | | |
|---|---|---|---|---|---|
| 629 | Bladder | -0.007142 | 0.4021064 | 0.331182 | 0.19837402 | U03735_f_at | MAGE-3 antigen (MAGE-3) gene |
| 630 | Bladder | -0.007341 | 0.4020942 | 0.331057 | 0.1982545 | X99253_at | ZNF183 gene |
| 631 | Bladder | -0.007542 | 0.4020822 | 0.331042 | 0.19815795 | RC_AA4420 71_at | EST: zw63b06.s1 Soares total fetus Nb2HF8 9w Homo sapiens cDNA clone 774707 3', mRNA sequence. (from Genbank) |
| 632 | Bladder | -0.008052 | 0.402003 | 0.330863 | 0.19803475 | T61992_at | EST: yb96h08.r1 Homo sapiens cDNA clone 79071 5'. (from Genbank) |
| 633 | Bladder | -0.008352 | 0.4015873 | 0.330778 | 0.19795163 | RC_AA4365 53_at | EST: zv08c11.s1 Soares NhHMPu S1 Homo sapiens cDNA clone 753044 3', mRNA sequence. (from Genbank) |
| 634 | Bladder | -0.008408 | 0.4015569 | 0.330644 | 0.19783106 | M31651_at | SHBG Sex hormone-binding globulin |
| 635 | Bladder | -0.008503 | 0.4014916 | 0.330377 | 0.19770393 | X82324_at | POU3F4 POU domain, class 3, transcription factor 4 |
| 636 | Bladder | -0.00858 | 0.4013344 | 0.330336 | 0.1975626 | AB002314_a t-2 | KIAA0316 gene product |
| 637 | Bladder | -0.00858 | 0.4012983 | 0.330265 | 0.19748098 | AB002314_a t | KIAA0316 gene |
| 638 | Bladder | -0.008913 | 0.4012493 | 0.330188 | 0.19737568 | M80333_at | M5 muscarinic acetylcholine receptor gene |
| 639 | Bladder | -0.008955 | 0.4012289 | 0.33012 | 0.1972677 | U11870_ma 1_at | Interleukin-8 receptor type A (IL8RBA) gene, promoter and complete cds |
| 640 | Bladder | -0.009156 | 0.400803 | 0.3299999 | 0.19723135 | D13168_at | EDNRB Endothelin receptor type B |
| 641 | Bladder | -0.009259 | 0.4007721 | 0.329843 | 0.19712663 | U68162_cds 1_s_at | MPL gene (thrombopoietin receptor) extracted from Human thrombopoietin receptor (MPL) gene |
| 642 | Bladder | -0.009677 | 0.4005682 | 0.329809 | 0.19708538 | M91368_s_a t | Na+/Ca+ exchanger (CNC) mRNA |
| 643 | Bladder | -0.010218 | 0.4003349 | 0.329765 | 0.19699791 | RC_AA2428 23_at | EST: zr65e10.s1 Soares NhHMPu S1 Homo sapiens cDNA clone 668298 3', mRNA sequence. (from Genbank) |
| 644 | Bladder | -0.010399 | 0.4001721 | 0.329661 | 0.19690546 | U84540_at | Dystrobrevin isoform DTN-3 (DTN) gene, exon 11B and complete cds |
| 645 | Bladder | -0.010399 | 0.4000874 | 0.32966 | 0.19683957 | M34715_at | PSG11 Pregnancy-specific beta-1 glycoprotein 11 |
| 646 | Bladder | -0.010495 | 0.3998658 | 0.329531 | 0.19673371 | J02947_s_at | SOD3 Superoxide dismutase 3, extracellular |
| 647 | Bladder | -0.010526 | 0.3998479 | 0.329392 | 0.1965774 | N32716_at | EST: yx74h12.r1 Homo sapiens cDNA clone 267527 5' similar to PIR:S45251 S45251 SNF2alpha protein - human ;. (from Genbank) |
| 648 | Bladder | -0.010583 | 0.3997595 | 0.32936 | 0.19651204 | L27671_s_at | Intercellular adhesion molecule 4, Landsteiner-Wiener blood group |
| 649 | Bladder | -0.01127 | 0.3997316 | 0.329308 | 0.19643803 | X66839_at | MaTu MN mRNA for p54/58N protein |
| 650 | Bladder | -0.011688 | 0.3997071 | 0.329169 | 0.19629197 | RC_AA0129 53_at | EST: ze35e03.s1 Soares retina N2b4HR Homo sapiens cDNA clone 360988 3', mRNA sequence. (from Genbank) |
| 651 | Bladder | -0.011726 | 0.3996856 | 0.329158 | 0.19624645 | M99564_at | P PROTEIN |

FIG. 1B2

| # | Tissue | | | | ID | Description |
|---|---|---|---|---|---|---|
| 652 | Bladder | -0.0125 | 0.3996109 | 0.329063 | 0.19618687 | AB000114_a_t Osteomodulin |
| 653 | Bladder | -0.0125 | 0.3995068 | 0.329017 | 0.1961066 | AB000114_a_t-2 Osteomodulin |
| 654 | Bladder | -0.012651 | 0.3994813 | 0.329003 | 0.19597839 | X96783_rna1_at Syt V gene (genomic and cDNA sequence) |
| 655 | Bladder | -0.012887 | 0.3994667 | 0.328917 | 0.19588974 | H11788_at EST: ym11b06.r1 Homo sapiens cDNA clone 47577 5'. (from Genbank) |
| 656 | Bladder | -0.013006 | 0.3990419 | 0.328917 | 0.19570558 | AA393318_a_t EST: zt70d02.r1 Soares testis NHT Homo sapiens cDNA clone 727683 5', mRNA sequence. (from Genbank) |
| 657 | Bladder | -0.013401 | 0.398884 | 0.328766 | 0.1955738 | Y08134_at ASM-like phosphodiesterase 3b |
| 658 | Bladder | -0.013401 | 0.3988671 | 0.328623 | 0.19554159 | Y08134_at-2 H.sapiens mRNA for ASM-like phosphodiesterase 3b |
| 659 | Bladder | -0.013852 | 0.3988458 | 0.328581 | 0.19544278 | AA203274_a_t EST: zx55hi09.r1 Soares fetal liver spleen 1NFLS S1 Homo sapiens cDNA clone 446465 5' similar to contains element MER27 repetitive element.; mRNA sequence. (from Genbank) |
| 660 | Bladder | -0.014469 | 0.3988446 | 0.328581 | 0.19530731 | U07139_at CAB3b mRNA for calcium channel beta3 subunit |
| 661 | Bladder | -0.014503 | 0.3987374 | 0.328479 | 0.19524048 | X51602_at VASCULAR ENDOTHELIAL GROWTH FACTOR RECEPTOR 1 PRECURSOR |
| 662 | Bladder | -0.014829 | 0.3986346 | 0.32836 | 0.19514215 | U51334_at Putative RNA binding protein (RBP56) mRNA |
| 663 | Bladder | -0.015127 | 0.3985746 | 0.328318 | 0.19502036 | U09860_at PRSS7 Protease, serine, 7 (enterokinase) |
| 664 | Bladder | -0.015148 | 0.3984816 | 0.32823 | 0.19493929 | RC_AA233899_at EST: zr49c02.s1 Soares NhHMPu S1 Homo sapiens cDNA clone 666722 3' similar to TR:G469478 G469478 SM-20.; mRNA sequence. (from Genbank) |
| 665 | Bladder | -0.015468 | 0.3984666 | 0.328219 | 0.19485556 | AA401238_a_t EST: zv63f03.r1 Soares total fetus Nb2HF8 9w Homo sapiens cDNA clone 758333 5' similar to TR:G1050752 G1050752 KYNURENINE/ALPHA-AMINOADIPATE AMINOTRANSFERASE.; mRNA sequence. (from Genbank) |
| 666 | Bladder | -0.015874 | 0.3983022 | 0.327967 | 0.19475098 | D61391_at Phosphoribosypyrophosphate synthetase-associated protein 39 |
| 667 | Bladder | -0.016048 | 0.3981427 | 0.327907 | 0.19456865 | RC_AA449718_at EST: zx09b07.s1 Soares total fetus Nb2HF8 9w Homo sapiens cDNA clone 785941 3', mRNA sequence. (from Genbank) |
| 668 | Bladder | -0.01669 | 0.3975521 | 0.327902 | 0.19452329 | W04902_at EST: za43a11.r1 Soares fetal liver spleen 1NFLS Homo sapiens cDNA clone 295292 5', mRNA sequence. (from Genbank) |
| 669 | Bladder | -0.016995 | 0.3974719 | 0.327892 | 0.19443734 | U43753_cds2_at Frataxin (FRDA) gene, promoter region and |
| 670 | Bladder | -0.016758 | 0.3973807 | 0.327852 | 0.1943273 | AA024428_a_t EST: ze73e12.r1 Soares fetal heart NbHH19W Homo sapiens cDNA clone 364654 5', mRNA sequence. (from Genbank) |
| 671 | Bladder | -0.016795 | 0.3973601 | 0.327779 | 0.19419599 | U46767_at Monocyte chemoattractant protein-4 precursor (MCP-4) mRNA |
| 672 | Bladder | -0.016861 | 0.3971088 | 0.327724 | 0.19414152 | AB000462_a_t SH3 binding protein, clone RES4-23A |

FIG. 1C2

| # | Tissue | Col3 | Col4 | Col5 | Col6 | Col7 | Description |
|---|---|---|---|---|---|---|---|
| 673 | Bladder | -0.017018 | 0.3970419 | 0.327532 | 0.1941271 | U06155_at | Chromosome 1q subtelomeric sequence D1S553 |
| 674 | Bladder | -0.017086 | 0.3970003 | 0.3275253 | 0.19406258 | W27099_at | EST: 2cc4 Human retina cDNA randomly primed sublibrary Homo sapiens cDNA, mRNA sequence. (from Genbank) |
| 675 | Bladder | -0.017145 | 0.3966916 | 0.327431 | 0.19401053 | U32674_s_at | Orphan receptor GPR9 (GPR9) gene, partial cds |
| 676 | Bladder | -0.017254 | 0.3966488 | 0.327425 | 0.19378962 | M55268_at | CSNK2A2 Casein kinase 2, alpha prime polypeptide |
| 677 | Bladder | -0.017284 | 0.3966376 | 0.327413 | 0.19369626 | RC_AA488979_at | Homo sapiens cell cycle-regulated factor p78 mRNA, complete cds |
| 678 | Bladder | -0.017352 | 0.3965806 | 0.327208 | 0.19364406 | X16866_at | Cytochrome P-450IID (clone pMP33) |
| 679 | Bladder | -0.017499 | 0.3961862 | 0.32698 | 0.1935521 | T35280_at | EST: EST82450 Homo sapiens cDNA 5' end similar to None. (from Genbank) |
| 680 | Bladder | -0.018183 | 0.3961161 | 0.326855 | 0.19348507 | AA248587_at | EST: csih0559.seq.F Human fetal heart, Lambda ZAP Express Homo sapiens cDNA 5', mRNA sequence. (from Genbank) |
| 681 | Bladder | -0.018256 | 0.3961282 | 0.326837 | 0.1933749 | M58026_at | CALMODULIN-RELATED PROTEIN NB-1 |
| 682 | Bladder | -0.018479 | 0.3960434 | 0.3268812 | 0.1932798 | U87964_at | Putative G-protein (GP-1) mRNA |
| 683 | Bladder | -0.018564 | 0.3960353 | 0.326635 | 0.19324511 | X04500_at | IL1B Interleukin 1, beta |
| 684 | Bladder | -0.019007 | 0.3959516 | 0.326605 | 0.19311399 | RC_D20728_at | EST: Human HL60 3'directed Mbol cDNA, HUMGS01705, clone mp0666, mRNA sequence. (from Genbank) |
| 685 | Bladder | -0.019035 | 0.3959152 | 0.326596 | 0.1930074 | W28931_at | EST: 56f3 Human retina cDNA randomly primed sublibrary Homo sapiens cDNA, mRNA sequence. (from Genbank) |
| 686 | Bladder | -0.019274 | 0.3958722 | 0.326594 | 0.19289848 | U17579_rna1_at | Growth hormone-releasing hormone receptor form b gene extracted from Human growth hormone-releasing hormone receptor gene, alternatively spliced forms a, b, and c, partial cds |
| 687 | Bladder | -0.019286 | 0.3957672 | 0.326589 | 0.19282453 | Y14140_at | G protein gene encoding beta 3 subunit exon 1 and promoter |
| 688 | Bladder | -0.019426 | 0.3956692 | 0.326388 | 0.19273911 | X74764_at | Receptor protein tyrosine kinase |
| 689 | Bladder | -0.019641 | 0.3954331 | 0.326211 | 0.19267961 | AA203501_at | EST: zx59a01.r1 Soares fetal liver spleen 1NFLS S1 Homo sapiens cDNA clone 446760 5', mRNA sequence. (from Genbank) |
| 690 | Bladder | -0.019692 | 0.3953917 | 0.32619 | 0.19261755 | T48536_at | EST: hbc3204 Homo sapiens cDNA clone hbc32204 5'end. (from Genbank) |
| 691 | Bladder | -0.019931 | 0.3953916 | 0.326186 | 0.19253203 | RC_AA4366619_at | EST: zw55o04.s1 Soares total fetus Nb2HF8 9w Homo sapiens cDNA clone 773959 3', mRNA sequence. (from Genbank) |
| 692 | Bladder | -0.020105 | 0.3953075 | 0.326078 | 0.19241257 | U28249_at | MAT8 protein |
| 693 | Bladder | -0.020349 | 0.3952483 | 0.325988 | 0.19231294 | W26982_at | EST: 17a9 Human retina cDNA randomly primed sublibrary Homo sapiens cDNA, mRNA sequence. (from Genbank) |
| 694 | Bladder | -0.020459 | 0.3950981 | 0.325956 | 0.19227564 | RC_AA459949_at | EST: zx66b02.s1 Soares total fetus Nb2HF8 9w Homo sapiens cDNA clone 796395 3', mRNA sequence. (from Genbank) |
| 695 | Bladder | -0.020494 | 0.3950855 | 0.325728 | 0.19218242 | RC_D58185_at | EST: Human aorta cDNA 3'-end GEN-354C01, mRNA sequence. (from Genbank) |

FIG. 1D2

| | | | | | |
|---|---|---|---|---|---|
| 696 | Bladder | -0.020686 | 0.3950675 | 0.325687 | 0.19215238_t | AA367473_a Crystallin, beta B2 |
| 697 | Bladder | -0.020779 | 0.3949988 | 0.325676 | 0.19210674 | RC_AA4166 EST: zu18b03.s1 Soares NhHMPu S1 Homo sapiens cDNA clone 738317 3', mRNA sequence. (from Genbank) |
| 698 | Bladder | -0.020972 | 0.3947264 | 0.325581 | 0.19204307 | S77415_at Melanocortin-4 receptor [human, Genomic, 1671 nt] |
| 699 | Bladder | -0.020973 | 0.3946935 | 0.325541 | 0.19196393 | U93553_at Alpha1-fetoprotein transcription factor (hFTF) mRNA |
| 700 | Bladder | -0.020973 | 0.3944264 | 0.325488 | 0.19186023 | U93553_at-2 Fetoprotein-alpha 1 (AFP) transcription factor |
| 701 | Bladder | -0.021106 | 0.3943677 | 0.325313 | 0.1917311 | J03068_at APEH N-acylaminoacyl-peptide hydrolase |
| 702 | Bladder | -0.021225 | 0.3942698 | 0.32518 | 0.19171514 | J00214_f_at Messenger RNA for human leukocyte (alpha) interferon. (from Genbank) |
| 703 | Bladder | -0.021422 | 0.3942502 | 0.324955 | 0.19152829 | AC002398_c ds4_at Human DNA from chromosome 19-specific cosmid F25965, genomic sequence::Human DNA from chromosome 19-specific cosmid F25965, genomic sequence::Human DNA from chromosome 19-specific cosmid F25965, genomic sequence |
| 704 | Bladder | -0.021755 | 0.3942059 | 0.324906 | 0.19138749 | L07615_at Neuropeptide Y receptor Y1 (NPYY1) mRNA, exon 2-3 and complete cds |
| 705 | Bladder | -0.021796 | 0.394139 | 0.324811 | 0.19126722 | C00038_s_a EST: HUMGS0003443, Human Gene Signature, 3'-directed cDNA sequence, mRNA sequence. (from Genbank) |
| 706 | Bladder | -0.021852 | 0.394081 | 0.324772 | 0.19121084 | X55283_rna_1_s_at Asialoglycoprotein receptor 2 |
| 707 | Bladder | -0.022063 | 0.3940115 | 0.324642 | 0.1911793 | X75535_at 33 KD HOUSEKEEPING PROTEIN |
| 708 | Bladder | -0.022398 | 0.3938853 | 0.324625 | 0.19111119 | D50532_at Macrophage lectin 2 |
| 709 | Bladder | -0.022716 | 0.3938128 | 0.324604 | 0.19102716 | R88880_at EST: ym96h06.r1 Homo sapiens cDNA clone 166811 5' similar to gb:X07290_cds1 ZINC FINGER PROTEIN HF.12 (HUMAN). (from Genbank) |
| 710 | Bladder | -0.022777 | 0.3937911 | 0.324479 | 0.1909511 | Y09846_rna_1_at SHC (Src homology 2 domain-containing) transforming protein 1 pseudogene 1 |
| 711 | Bladder | -0.023046 | 0.3934037 | 0.324472 | 0.19085656 | AB002293_a_t Human mRNA for KIAA0295 gene, partial cds |
| 712 | Bladder | -0.023377 | 0.3933395 | 0.324467 | 0.19072703 | M16961_at AHSG Alpha-2-HS-glycoprotein alpha and beta chain |
| 713 | Bladder | -0.023552 | 0.3931407 | 0.324322 | 0.19059922 | N34697_at EST: yx81c11.r1 Homo sapiens cDNA clone 268148 5'. (from Genbank) |
| 714 | Bladder | -0.023763 | 0.3931174 | 0.324285 | 0.19053024 | RC_AA4812 66_at EST: aa35b12.s1 NCI_CGAP_GCB1 Homo sapiens cDNA clone IMAGE:815231 3', mRNA sequence. (from Genbank) |
| 715 | Bladder | -0.02385 | 0.393047 | 0.324281 | 0.19043289 | AA130284_a_t EST: zi29d04.r1 Soares pregnant uterus NbHPU Homo sapiens cDNA clone 503335 5', mRNA sequence. (from Genbank) |

FIG. 1E2

| | | | | | |
|---|---|---|---|---|---|
| 716 | Bladder | -0.023852 | 0.3929791 | 0.324155 | 0.19034865 | RC_AA0478 76_at | EST: zf50b08.s1 Soares retina N2b4HR Homo sapiens cDNA clone 3803433 3' similar to contains Alu repetitive element;contains element L1 repetitive element.;, mRNA sequence. (from Genbank) |
| 717 | Bladder | -0.024469 | 0.39297719 | 0.324041 | 0.1902926 | U52100_at | XMP mRNA |
| 718 | Bladder | -0.024848 | 0.3929131 | 0.3239925 | 0.19021156 | M97496_at | GUCA2 Guanylate cyclase activator 2 (guanylin, intestinal, heat-stable) |
| 719 | Bladder | -0.024857 | 0.3928742 | 0.3238863 | 0.19015184 | HG4243-HT4513_at | Zinc Finger Protein Znf155 |
| 720 | Bladder | -0.025077 | 0.3928663 | 0.323777 | 0.19005889 | U33317_ma 1_at | Defensin 6 (HD-6) gene |
| 721 | Bladder | -0.025122 | 0.392821 | 0.3233752 | 0.18996385 | R02207_s_a t | EST: ye83b06.r1 Homo sapiens cDNA clone 124307 5'. (from Genbank) |
| 722 | Bladder | -0.02519 | 0.3927971 | 0.32374 | 0.18992423 | AA018887_a t | EST: ze55f04.r1 Soares retina N2b4HR Homo sapiens cDNA clone 362911 5', mRNA sequence. (from Genbank) |
| 723 | Bladder | -0.025327 | 0.39249997 | 0.3233687 | 0.18986525 | U02082_at | Guanine nucleotide regulatory protein (lim1) mRNA |
| 724 | Bladder | -0.025577 | 0.3924233 | 0.3233526 | 0.18977955 | X07696_at | KRT15 Keratin 15 |
| 725 | Bladder | -0.025611 | 0.3924211 | 0.3233446 | 0.18969487 | M20137_at | Interleukin 3 (IL-3) mRNA |
| 726 | Bladder | -0.025949 | 0.3923743 | 0.3233428 | 0.18966202 | R11248_at | EST: yf41c02.r1 Homo sapiens cDNA clone 129410 5'. (from Genbank) |
| 727 | Bladder | -0.026125 | 0.3923549 | 0.3233322 | 0.18955627 | U50929_at | Betaine:homocysteine methyltransferase mRNA |
| 728 | Bladder | -0.026255 | 0.3922236 | 0.3233103 | 0.18953861 | U26914_at | Ras-responsive element binding protein (RREB-1) mRNA |
| 729 | Bladder | -0.0267 | 0.3922088 | 0.322989 | 0.18935868 | U80457_at | Transcription factor SIM2 long form mRNA |
| 730 | Bladder | -0.026902 | 0.3919809 | 0.322869 | 0.189272690 0_at | RC_AA4020 | EST: zu55b03.s1 Soares ovary tumor NbHOT Homo sapiens cDNA clone 741869 3' similar to TR:G452270 G452270 2-19 PROTEIN PRECURSOR.;, mRNA sequence. (from Genbank) |
| 731 | Bladder | -0.027084 | 0.3918091 | 0.322867 | 0.18922588 | U12140_at | Tyrosine kinase receptor p145TRK-B (TRK-B) mRNA |
| 732 | Bladder | -0.027725 | 0.3917496 | 0.322761 | 0.18916056 | L31573_at | Sulfite oxidase mRNA |
| 733 | Bladder | -0.027825 | 0.3916795 | 0.322729 | 0.1889937 | M24351_cds 3_s_at | PTHLH gene (parathyroid hormone-like protein A) extracted from Human parathyroid hormone-like protein (PLP) gene |
| 734 | Bladder | -0.028417 | 0.3916368 | 0.322684 | 0.18891996 | M15517_cds 3_s_at | TTR gene extracted from Human mutant preablumin gene directly linked to familial amyloidotic polyneuropathy (FAP) |
| 735 | Bladder | -0.028581 | 0.3916368 | 0.3226 | 0.18887882 | M32053_at | H19 RNA gene |
| 736 | Bladder | -0.028745 | 0.3916183 | 0.322572 | 0.18874364 | HG2365-HT2461_at | Glyceraldehyde-3-Phosphate Dehydrogenase (Gb:K03121) |
| 737 | Bladder | -0.028766 | 0.3915584 | 0.322522 | 0.18868731 | M31516_s_a t | DAF Decay accelerating factor for complement (CD55, Cromer blood group system) |
| 738 | Bladder | -0.029168 | 0.3915509 | 0.322458 | 0.18860404 | U61276_s_a t | Transmembrane protein Jagged 1 (HJ1) mRNA |
| 739 | Bladder | -0.029489 | 0.3915392 | 0.32233 | 0.18855678 | U18549_at | PROBABLE G PROTEIN-COUPLED RECEPTOR GPR6 |

FIG. 1F2

| | | | | | | |
|---|---|---|---|---|---|---|
| 740 | Bladder | -0.029496 | 0.3914629 | 0.3223328 | 0.1884595 | X99141_at | Hair keratin, hHb3 |
| 741 | Bladder | -0.029791 | 0.3914489 | 0.3222253 | 0.18843356 | X05997_at | Gastric lipase |
| 742 | Bladder | -0.03001 | 0.3913737 | 0.3222245 | 0.18827498 | M74096_at | ACADL Acyl-Coenzyme A dehydrogenase, long chain |
| 743 | Bladder | -0.030012 | 0.3913126 | 0.3222045 | 0.1882263 | RC_AA3496 12_s_at | KIAA0305 gene product |
| 744 | Bladder | -0.030116 | 0.3911068 | 0.3221948 | 0.18811071 | X04707_at | C-erb-A mRNA for thyroid hormone receptor |
| 745 | Bladder | -0.030421 | 0.391081 | 0.321806 | 0.18795699 | HG3242-HT4231_s_at | Calcium Channel, Voltage-Gated, Alpha 1e Subunit, Alt. Splice 3 |
| 746 | Bladder | -0.030552 | 0.3910789 | 0.321781 | 0.18789558 | X95463_s_at | FMR2 Fragile X mental retardation 2 |
| 747 | Bladder | -0.030754 | 0.3909631 | 0.321624 | 0.18777561 | M91487_at | EST: HUMRTPGEAF Homo sapiens cDNA. (from Genbank) |
| 748 | Bladder | -0.0313 | 0.3909387 | 0.32154 | 0.18773443 | W28045_at | EST: 41b8 Human retina cDNA randomly primed sublibrary Homo sapiens cDNA, mRNA sequence. (from Genbank) |
| 749 | Bladder | -0.031396 | 0.3908848 | 0.321489 | 0.1876421 | S78653_at | Mrg=mas-related [human, Genomic, 2416 nt] |
| 750 | Bladder | -0.031862 | 0.3908784 | 0.321486 | 0.18754499 | AA452625_a_t | Iduronate 2-sulfatase (Hunter syndrome) |
| 751 | Bladder | -0.031974 | 0.3907697 | 0.321404 | 0.18747654 | RC_AA2907 45_at | EST: zt22n02.s1 Soares ovary tumor NbHOT Homo sapiens cDNA clone 713907 3' similar to TR:G520469 G520469 NA+/GLUCOSE COTRANSPORTER-RELATED PROTEIN ;, mRNA sequence. (from Genbank) |
| 752 | Bladder | -0.03199 | 0.3907473 | 0.321372 | 0.18728565 | D84307_at | Phosphoethanolamine cytidylyltransferase |
| 753 | Bladder | -0.032274 | 0.3907123 | 0.321056 | 0.18721075 | M81780_cds 5_at | SMPD1 gene (acid sphingomyelinase) extracted from Homo sapiens acid sphingomyelinase (SMPD1) gene, ORF's 1-3's |
| 754 | Bladder | -0.032694 | 0.3905223 | 0.321032 | 0.18710886 | L40992_at | (clone PEBP2aA1) core-binding factor, runt domain, alpha subunit 1 (CBFA1) mRNA, 3' end of cds |
| 755 | Bladder | -0.032992 | 0.3904705 | 0.320649 | 0.18702558 | AA083797_s_at | Zm63c02.r1 Stratagene fibroblast (#937212) Homo sapiens cDNA clone 530306 5' similar to gb:X15822 CYTOCHROME C OXIDASE POLYPEPTIDE VIIA-LIVER PRECURSOR (HUMAN);, mRNA sequence. (from Genbank) |
| 756 | Bladder | -0.033267 | 0.3903749 | 0.320463 | 0.18693897 | L41668_rna1 _at | UDP-Galactose 4 epimerase (GALE) gene |
| 757 | Bladder | -0.033689 | 0.3902574 | 0.320455 | 0.1868573 | X76383_at | HE3(alpha) |
| 758 | Bladder | -0.033855 | 0.3901519 | 0.320455 | 0.18681037 | RC_AA4494 75_at | EST: zx08f10.s1 Soares total fetus Nb2HF8 9w Homo sapiens cDNA clone 785899 3' similar to contains Alu repetitive element;contains element MER22 repetitive element ;, mRNA sequence. (from Genbank) |
| 759 | Bladder | -0.033876 | 0.3900421 | 0.320433 | 0.18678343 | AA236771_a_t | EST: zr99e10.r1 NCI_CGAP_GCB1 Homo sapiens cDNA clone IMAGE:683850 5', mRNA sequence. (from Genbank) |
| 760 | Bladder | -0.034205 | 0.3900045 | 0.320416 | 0.18664177 | L42354_at | (clone 48ES4) mRNA fragment |

FIG. 1G2

| # | Tissue | | | | | Description |
|---|---|---|---|---|---|---|
| 761 | Bladder | -0.034385 | 0.3899595 | 0.320403 | 0.18657228 | U19145_s_at G antigen 4 |
| 762 | Bladder | -0.034771 | 0.38993 | 0.320403 | 0.18654964 | L78833_cds4_at Ifp35 gene extracted from Human BRCA1, Rho7 and vat1 genes, and ipf35 gene, partial cds |
| 763 | Bladder | -0.035006 | 0.3897993 | 0.320322 | 0.18653668 | L47125_s_at EEF1A1 Translation elongation factor 1-alpha-1 |
| 764 | Bladder | -0.03503 | 0.389783 | 0.320302 | 0.1864109 | AA310850_a_t EST: EST181766 Jurkat T-cells V Homo sapiens cDNA 5' end, mRNA sequence. (from Genbank) |
| 765 | Bladder | -0.035159 | 0.3897465 | 0.320166 | 0.18624996 | HG668-HT4793_at T-Cell Factor 1, A/B/C, Alt. Splice 1, A |
| 766 | Bladder | -0.035343 | 0.3897402 | 0.319963 | 0.1861345335_at | RC_AA4494 EST: zx05c11.s1 Soares total fetus Nb2HF8 9w Homo sapiens cDNA clone 785588 3', mRNA sequence. (from Genbank) |
| 767 | Bladder | -0.035349 | 0.3896959 | 0.319923 | 0.18603286_at | RC_D59362 EST: Human fetal brain cDNA 3'-end GEN-023A02, mRNA sequence. (from Genbank) |
| 768 | Bladder | -0.035574 | 0.3895944 | 0.319876 | 0.1859705364_at | RC_AA1279 EST: zl13g07.s1 Soares pregnant uterus NbHPU Homo sapiens cDNA clone 501852 3', mRNA sequence. (from Genbank) |
| 769 | Bladder | -0.035596 | 0.38957 | 0.319827 | 0.1859456755_at | RC_AA4560 EST: aa03f02.s1 Soares NhHMPu S1 Homo sapiens cDNA clone 812187 3', mRNA sequence. (from Genbank) |
| 770 | Bladder | -0.0356655 | 0.3895521 | 0.319756 | 0.18587051 | S49592_s_at Transcription factor E2F like protein [human, mRNA, 2492 nt] |
| 771 | Bladder | -0.03572 | 0.38953 | 0.319691 | 0.18582466 | X52011_at MYF6 Muscle determination factor |
| 772 | Bladder | -0.035772 | 0.3893506 | 0.319637 | 0.1857854948_at | RC_AA4614 EST: zx68b07.s1 Soares total fetus Nb2HF8 9w Homo sapiens cDNA clone 796597 3' similar to SW:BTD_HUMAN P43251 BIOTINIDASE PRECURSOR;, mRNA sequence. (from Genbank) |
| 773 | Bladder | -0.03581 | 0.3892865 | 0.319609 | 0.18569428 | U53786_at EVPL Envoplakin |
| 774 | Bladder | -0.035854 | 0.3892196 | 0.319568 | 0.18565359 | X07881_rma11_f_at Human gene PRB3L for proline-rich protein G1 |
| 775 | Bladder | -0.036148 | 0.3891827 | 0.319542 | 0.18548931_t | AA443437_a EST: zw94b07.r1 Soares total fetus Nb2HF8 9w Homo sapiens cDNA clone 784597 5', mRNA sequence. (from Genbank) |
| 776 | Bladder | -0.036155 | 0.3891742 | 0.31951 | 0.18534674 | HG1098-HT1098_at Cystatin D |
| 777 | Bladder | -0.036159 | 0.3891442 | 0.319939 | 0.18522803 | K03183_f_at Chorionic gonadotropin beta subunit gene |
| 778 | Bladder | -0.036347 | 0.389093 | 0.319212 | 0.1851617 | U37707_at DLG3 Homolog 3 of Drosophila large discs |
| 779 | Bladder | -0.036462 | 0.38901 | 0.319197 | 0.18507805 | L11238_s_at GP5 Glycoprotein V (platelet) |
| 780 | Bladder | -0.036479 | 0.3889986 | 0.319159 | 0.18501881 | X98176_at MACH-alpha-2 protein |
| 781 | Bladder | -0.037156 | 0.3889915 | 0.319064 | 0.18497732 | U36221_at Pancreatic zymogen granule membrane protein GP-2 mRNA |
| 782 | Bladder | -0.037168 | 0.3889706 | 0.319039 | 0.18496111 | J05037_at L-SERINE DEHYDRATASE |

FIG. 1H2

| | | | | | |
|---|---|---|---|---|---|
| 783 | Bladder | -0.0373352 | 0.3889239 | 0.31899 | 0.18487017 | H25982_at | EST: yl56g01.r1 Homo sapiens cDNA clone 162288 5'. (from Genbank) |
| 784 | Bladder | -0.037433 | 0.3888803 | 0.318978 | 0.18473051 | D87449_at | KIAA0260 gene, partial cds |
| 785 | Bladder | -0.037499 | 0.3888392 | 0.318944 | 0.1846395 | HG3288-HT3465_at | Xanthine Dehydrogenase (Gb:U06117) |
| 786 | Bladder | -0.037582 | 0.3888254 | 0.318744 | 0.18459739 | AA043894_at | EST: zk57b05.r1 Soares pregnant uterus NbHPU Homo sapiens cDNA clone 486897 5', mRNA sequence. (from Genbank) |
| 787 | Bladder | -0.037757 | 0.3886733 | 0.318701 | 0.18454467 | L77561_at | DGS-D mRNA, 3' end |
| 788 | Bladder | -0.037985 | 0.3885674 | 0.318692 | 0.18448463 | Y11416_at | P73 |
| 789 | Bladder | -0.038096 | 0.3885346 | 0.318689 | 0.18445788 | X52008_at | GLRA2 Glycine receptor, alpha 2 |
| 790 | Bladder | -0.038301 | 0.3884737 | 0.318592 | 0.18441501 | M19989_cds1_at | Platelet-derived growth factor (PDGFA) A chain gene |
| 791 | Bladder | -0.038347 | 0.3884653 | 0.318587 | 0.18422878 | U64197_at | CC chemokine LARC precursor |
| 792 | Bladder | -0.038464 | 0.3884125 | 0.318456 | 0.18417145 | AFFX-BioB-5_at-2 | AFFX-BioB-5_at (miscellaneous control - 11k chips) |
| 793 | Bladder | -0.038464 | 0.3883271 | 0.318448 | 0.1841414 | AFFX-BioB-5_at | AFFX-BioB-5_at (endogenous control) |
| 794 | Bladder | -0.038474 | 0.3883067 | 0.318267 | 0.1840723 | X04571_at | EGF Epidermal growth factor |
| 795 | Bladder | -0.038671 | 0.3883067 | 0.318238 | 0.18396977 | S81944_at | GABRA6 Gamma-aminobutyric acid (GABA) A receptor, alpha 6 |
| 796 | Bladder | -0.038671 | 0.3882187 | 0.318157 | 0.18393171 | S81944_at-2 | Gamma-aminobutyric acid (GABA) A receptor, alpha 6 |
| 797 | Bladder | -0.039458 | 0.3881823 | 0.318016 | 0.18389118 | M16707_rna1_at | Histone H4 gene, clone FO108 |
| 798 | Bladder | -0.039879 | 0.3881286 | 0.317849 | 0.18382502 | U89717_at | RDH1 Retinol dehydrogenase 1 (11-cis) |
| 799 | Bladder | -0.040094 | 0.3880022 | 0.317844 | 0.18379784 | U06088_at | N-ACETYLGALACTOSAMINE-6-SULFATASE PRECURSOR |
| 800 | Bladder | -0.040261 | 0.3879998 | 0.317769 | 0.183646 | D03017_s_at | Nel-related protein |
| 801 | Bladder | -0.040266 | 0.387962 | 0.317669 | 0.18359812 | U29607_at | EIF-2-associated p67 homolog mRNA |
| 802 | Bladder | -0.04041 | 0.3879417 | 0.317593 | 0.18359652 | X80878_at | R kappa B mRNA |
| 803 | Bladder | -0.040444 | 0.3878776 | 0.317503 | 0.1835336 | Z35402_rna1_s_at | Gene encoding E-cadherin, exon 3 and joined CDS |
| 804 | Bladder | -0.040452 | 0.3877505 | 0.317483 | 0.18345046 | X52282_s_at | Atrial natriuretic peptide clearance receptor (ANP-C receptor) |
| 805 | Bladder | -0.040502 | 0.3875376 | 0.317434 | 0.18332963 | U90910_at | Clone 23564 mRNA sequence |
| 806 | Bladder | -0.040502 | 0.3874456 | 0.317393 | 0.18323557 | U90910_at-2 | Human clone 23564 mRNA sequence |
| 807 | Bladder | -0.040935 | 0.3874282 | 0.317386 | 0.18320854 | U13219_at | Forkhead protein FREAC-1 mRNA |
| 808 | Bladder | -0.041346 | 0.3873323 | 0.317278 | 0.18319283 | H89896_s_at | EST: yw29e12.r1 Homo sapiens cDNA clone 253678 5'. (from Genbank) |

FIG. 1I2

| # | Tissue | | | | ID | Description |
|---|---|---|---|---|---|---|
| 809 | Bladder | -0.041386 | 0.3872941 | 0.317151 | W56463_at | EST: zc57h06.r1 Soares parathyroid tumor NbHPA Homo sapiens cDNA clone 326459 5', mRNA sequence. (from Genbank) |
| 810 | Bladder | -0.041622 | 0.3871705 | 0.317042 | RC_AA1913 23_at | EST: zp83s09.s1 Stratagene HeLa cell s3 937216 Homo sapiens cDNA clone 626777 3', mRNA sequence. (from Genbank) |
| 811 | Bladder | -0.041659 | 0.3871328 | 0.317018 | D83657_at | Calcium-binding protein in amniotic fluid 1 |
| 812 | Bladder | -0.041729 | 0.3870957 | 0.317 | U51127_at | IRF5 Interferon regulatory factor 5 |
| 813 | Bladder | -0.041926 | 0.3870679 | 0.316944 | X70340_at | TGFA Transforming growth factor, alpha |
| 814 | Bladder | -0.042023 | 0.3869889 | 0.316873 | HG1227-HT1227_s_a_t | Collagen, Type II, Alpha 1 |
| 815 | Bladder | -0.042134 | 0.3869088 | 0.316808 | L49054_at | T(3;5)(q25.1;p34) fusion gene NPM-MLF1 mRNA |
| 816 | Bladder | -0.042295 | 0.3868925 | 0.316481 | D13305_at | CCKBR Cholecystokinin B receptor |
| 817 | Bladder | -0.042412 | 0.3868674 | 0.316451 | U08198_rna 1_at | Complement C8 gamma subunit precursor (C8G) gene |
| 818 | Bladder | -0.042555 | 0.3867752 | 0.31645 | RC_D20297_at | EST: Human HL60 3'directed MboI cDNA, HUMGS01271, clone pm2024, mRNA sequence. (from Genbank) |
| 819 | Bladder | -0.042602 | 0.3864655 | 0.316264 | HG4185-HT4455_at | Estrogen Sulfotransferase, Ste |
| 820 | Bladder | -0.042682 | 0.3864215 | 0.316031 | Z38026_at | CAP-18 protein |
| 821 | Bladder | -0.042683 | 0.3864205 | 0.315881 | X06985_at | HMOX1 Heme oxygenase (decycling) 1 |
| 822 | Bladder | -0.04293 | 0.386372 | 0.315732 | M24736_s_a_t | SELE Selectin E (endothelial adhesion molecule 1) |
| 823 | Bladder | -0.043024 | 0.386258 | 0.315646 | RC_AA2362 41_at | EST: zr51e07.s1 Soares NhHMPu S1 Homo sapiens cDNA clone 666948 3', mRNA sequence. (from Genbank) |
| 824 | Bladder | -0.043058 | 0.3858043 | 0.315634 | X97230_f_at | NK receptor, clone library 4M1#6 |
| 825 | Bladder | -0.043284 | 0.3856897 | 0.315562 | RC_AA2365 33_s_at | Ecotropic viral integration site 1 |
| 826 | Bladder | -0.043347 | 0.3856251 | 0.315518 | U52077_s_a_t | Mariner1 transposase gene, complete consensus sequence |
| 827 | Bladder | -0.043517 | 0.3854914 | 0.315464 | X14085_s_a_t | GGTB2 Glycoprotein-4-beta-galactosyltransferase 2 |
| 828 | Bladder | -0.043594 | 0.3854128 | 0.315347 | U62800_at | CST6 Cystatin M |
| 829 | Bladder | -0.043648 | 0.3853718 | 0.315342 | U62392_at | Homo sapiens zinc finger protein mRNA, complete cds |
| 830 | Bladder | -0.043723 | 0.3852908 | 0.315283 | D10537_s_a_t | MPZ Myelin protein zero (Charcot-Marie-Tooth neuropathy 1B) |
| 831 | Bladder | -0.043723 | 0.3852509 | 0.315166 | D10537_t-2 | Myelin protein zero (Charcot-Marie-Tooth neuropathy 1B) |
| 832 | Bladder | -0.043962 | 0.3852447 | 0.315137 | AA504736_a_t | EST: aa63e01.r1 NCI_CGAP_GCB1 Homo sapiens cDNA clone IMAGE:825624 5', mRNA sequence. (from Genbank) |

FIG. 1J2

| # | Tissue | Col3 | Col4 | Col5 | Col6 | Col7 | Description |
|---|---|---|---|---|---|---|---|
| 833 | Bladder | -0.043993 | 0.3850881 | 0.315075 | 0.18107322 | X00949_at | Prepro-relaxin H1 |
| 834 | Bladder | -0.044235 | 0.3849595 | 0.315052 | 0.18099922 | U47050_at | Putative calcium influx channel (hltrp3) mRNA |
| 835 | Bladder | -0.044324 | 0.3849278 | 0.314931 | 0.18091089 | Z96810_at | DNA sequence from PAC 452H17 on chromosome X contains sodium and chloride-dependent glycine transporter 1 (GLYT-1) like, ESTs |
| 836 | Bladder | -0.04433 | 0.384841 | 0.3148 | 0.18087707 | U58496_s_at | Dual-specificity tyrosine-(Y)-phosphorylation regulated kinase 1 |
| 837 | Bladder | -0.044367 | 0.38848284 | 0.314751 | 0.18077473 | M35198_at | Integrin B-6 mRNA |
| 838 | Bladder | -0.04453 | 0.3848256 | 0.314651 | 0.18074639 | AA046737_at | EST: zf48a10.r1 Soares retina N2b4HR Homo sapiens cDNA clone 380154 5' similar to contains Alu repetitive element:, mRNA sequence. (from Genbank) |
| 839 | Bladder | -0.044571 | 0.3847747 | 0.314622 | 0.18052754 | AA282702_a | EST: zt15d02.r1 NCI_CGAP_GCB1 Homo sapiens cDNA clone IMAGE:713187 5', mRNA sequence. (from Genbank) |
| 840 | Bladder | -0.044802 | 0.38845988 | 0.314622 | 0.18050249 | X05615_at | Thyroglobulin |
| 841 | Bladder | -0.045069 | 0.3844741 | 0.314585 | 0.18043184 | S57296_at | HER2/neu receptor [3' region, alternatively spliced] [human, breast cancer cell line, mRNA Partial, 175 nt] |
| 842 | Bladder | -0.045081 | 0.38844155 | 0.314583 | 0.18035542 | J05253_s_at | INTERPHOTORECEPTOR RETINOID-BINDING PROTEIN PRECURSOR |
| 843 | Bladder | -0.045087 | 0.3843775 | 0.31444 | 0.18033373 | RC_AA3502 68_at | EST: EST57664 Infant brain Homo sapiens cDNA 3' end, mRNA sequence. (from Genbank) |
| 844 | Bladder | -0.045189 | 0.3840872 | 0.314393 | 0.18023264 | K03195_at | (HepG2) glucose transporter gene mRNA |
| 845 | Bladder | -0.045272 | 0.3838284 | 0.314311 | 0.18012314 | AV418320_a_t | Homo sapiens mRNA for pre-mRNA cleavage factor I subunit |
| 846 | Bladder | -0.045289 | 0.3837578 | 0.314275 | 0.18009719 | W16486_at | EST: zb11e11.r1 Soares fetal lung NbHL19W Homo sapiens cDNA clone 301772 5', mRNA sequence. (from Genbank) |
| 847 | Bladder | -0.045358 | 0.3836986 | 0.314254 | 0.18001667 | RC_AA2523 74_at | EST: zs12f12.s1 NCI_CGAP_GCB1 Homo sapiens cDNA clone IMAGE:685007 3', mRNA sequence. (from Genbank) |
| 848 | Bladder | -0.046107 | 0.383659 | 0.314223 | 0.17997743 | RC_AA0534 00_at | EST: zi71b04.s1 Stratagene colon (#937204) Homo sapiens cDNA clone 510031 3', mRNA sequence. (from Genbank) |
| 849 | Bladder | -0.046137 | 0.383646 | 0.314133 | 0.179903 | X51362_s_a t | DRD2 Dopamine D2 receptor |
| 850 | Bladder | -0.046357 | 0.383462 | 0.3141 | 0.17985399 | RC_AA4588 90_at | EST: zx88c06.s1 Soares ovary tumor NbHOT Homo sapiens cDNA clone 810826 3', mRNA sequence. (from Genbank) |
| 851 | Bladder | -0.04644 | 0.3829775 | 0.313987 | 0.1798119 | X17651_at | MYOG Myogenin (myogenic factor 4) |
| 852 | Bladder | -0.046661 | 0.3829162 | 0.313968 | 0.17971055 | RC_AA4304 96_r_at | Ferritin, light polypeptide |
| 853 | Bladder | -0.046761 | 0.3828282 | 0.313921 | 0.1796759 | AA287724_a | EST: zs53h10.r1 NCI_CGAP_GCB1 Homo sapiens cDNA clone IMAGE:701251 5', mRNA sequence. (from Genbank) |
| 854 | Bladder | -0.046776 | 0.3827492 | 0.313888 | 0.17958038 | L23852_at | (clone Z146) retinal mRNA, 3' end and repeat region |

FIG. 1K2

| | | | | | |
|---|---|---|---|---|---|
| 855 | Bladder | -0.046844 | 0.3826017 | 0.313812 | 0.17950714 | M26901_s_a t | RENIN PRECURSOR, RENAL |
| 856 | Bladder | -0.046941 | 0.382595 | 0.313789 | 0.17949066 | D64053_at | Protein-tyrosine phosphatase |
| 857 | Bladder | -0.047023 | 0.3825047 | 0.313772 | 0.17941739 | M35878_at | INSULIN-LIKE GROWTH FACTOR BINDING PROTEIN 3 PRECURSOR |
| 858 | Bladder | -0.047073 | 0.3824896 | 0.313769 | 0.17930369 | U12767_at | Mitogen induced nuclear orphan receptor (MINOR) mRNA |
| 859 | Bladder | -0.047356 | 0.3824584 | 0.313733 | 0.17921634 | L47726_at | PAH Phenylalanine hydroxylase |
| 860 | Bladder | -0.047482 | 0.3824306 | 0.31365 | 0.17918551 | U88063_at | Agouti (mouse) related protein |
| 861 | Bladder | -0.047599 | 0.3823082 | 0.313637 | 0.17913964 | D85939_at | P97 homologous protein |
| 862 | Bladder | -0.047623 | 0.3823004 | 0.31358 | 0.17903109 | X77909_at | IKBL mRNA |
| 863 | Bladder | -0.047636 | 0.38226 | 0.313358 | 0.17901021 | W05585_at | EST: za85a06.r1 Soares fetal lung NbHL19W Homo sapiens cDNA clone 299314 5', mRNA sequence. (from Genbank) |
| 864 | Bladder | -0.047699 | 0.3821859 | 0.313346 | 0.17898475 | HG2290-HT2386_at | Calcitonin |
| 865 | Bladder | -0.047809 | 0.3821023 | 0.313266 | 0.17886487 | RC_AA5211 11_at | EST: aa70h12.s1 NCI_CGAP_GCB1 Homo sapiens cDNA clone IMAGE:826343 3' similar to WP:C09F5.2 CE01774:, mRNA sequence. (from Genbank) |
| 866 | Bladder | -0.048048 | 0.3820575 | 0.313248 | 0.17877144 | RC_AA0047 01_at | EST: zh93e03.s1 Soares fetal liver spleen 1NFLS S1 Homo sapiens cDNA clone 428860 3', mRNA sequence. (from Genbank) |
| 867 | Bladder | -0.048208 | 0.3820371 | 0.313224 | 0.17862274 | L40400_at | (clone zap113) mRNA, 3' end of cds |
| 868 | Bladder | -0.048256 | 0.3820371 | 0.313171 | 0.17853734 | U31986_at | Cartilage-specific homeodomain protein Cart-1 mRNA |
| 869 | Bladder | -0.04829 | 0.3819985 | 0.313148 | 0.17841299 | J03626_rna1 s_at | UMPS gene extracted from Human UMP synthase mRNA |
| 870 | Bladder | -0.048471 | 0.3819308 | 0.313064 | 0.17836724 | AC000099_a t | Metabotropic glutamate receptor 8 mRNA |
| 871 | Bladder | -0.048607 | 0.3819386 | 0.313036 | 0.17830448 | AA465262_a t | EST: aa33b06.r1 NCI_CGAP_GCB1 Homo sapiens cDNA clone IMAGE:815027 5', mRNA sequence. (from Genbank) |
| 872 | Bladder | -0.048809 | 0.381879 | 0.312796 | 0.17826846 | U10685_at | MAGE-10 antigen (MAGE10) gene |
| 873 | Bladder | -0.048809 | 0.381844 | 0.312742 | 0.17823903 | U10685_at-2 | Melanoma antigen, family A, 10 |
| 874 | Bladder | -0.048856 | 0.3818053 | 0.312664 | 0.17816487 | M91463_rna 1_at | Glucose transporter (GLUT4) gene |
| 875 | Bladder | -0.048856 | 0.381739 | 0.312637 | 0.178019751 | M91463_rna 1_at-2 | Solute carrier family 2 (facilitated glucose transporter), member 4 |
| 876 | Bladder | -0.048856 | 0.3816713 | 0.312524 | 0.17779619 | H78886_at | EST: yu11a03.r1 Homo sapiens cDNA clone 233452 5'. (from Genbank) |
| 877 | Bladder | -0.048939 | 0.3815118 | 0.312506 | 0.17791204 | RC_AA0188 76_at | EST: ze58g07.s1 Soares retina N2b4HR Homo sapiens cDNA clone 363228 3', mRNA sequence. (from Genbank) |

FIG. 1L2

| # | Tissue | | | | | |
|---|---|---|---|---|---|---|
| 878 | Bladder | -0.048944 | 0.3814075 | 0.312483 | 0.17785856 | AA425053_a t | EST: zw06e03.r1 Soares NhHMPu S1 Homo sapiens cDNA clone 768508 5', mRNA sequence. (from Genbank) |
| 879 | Bladder | -0.049251 | 0.3813945 | 0.312483 | 0.17778562 | U79255_at | X11 protein mRNA, partial cds |
| 880 | Bladder | -0.04934 | 0.3813911 | 0.312424 | 0.17773773 | RC_AA2353 43_at | EST: zs40a08.s1 Soares NhHMPu S1 Homo sapiens cDNA clone 687638 3', mRNA sequence. (from Genbank) |
| 881 | Bladder | -0.049594 | 0.3813791 | 0.312421 | 0.17768581 | RC_AA4546 75_at | EST: zx76a07.s1 Soares ovary tumor NbHOT Homo sapiens cDNA clone 809652 3', mRNA sequence. (from Genbank) |
| 882 | Bladder | -0.049889 | 0.3813083 | 0.312421 | 0.17761421 | X95654_at | SCP1 protein |
| 883 | Bladder | -0.050145 | 0.3812536 | 0.312325 | 0.17754705 | HG4258-HT4528_at | Kinase Inhibitor P27kip1, Cyclin-Dependent |
| 884 | Bladder | -0.050162 | 0.3812413 | 0.312167 | 0.17747056 | X02176_s_a t | C9 Complement component C9 |
| 885 | Bladder | -0.050354 | 0.3812373 | 0.31216 | 0.17738837 | RC_AA0244 82_at | EST: ze76a01.s1 Soares fetal heart NbHH19W Homo sapiens cDNA clone 364872 3', mRNA sequence. (from Genbank) |
| 886 | Bladder | -0.050406 | 0.381231 | 0.31207 | 0.1773117 | D49410_at | IL3RA Interleukin 3 receptor, alpha (low affinity) |
| 887 | Bladder | -0.050043 | 0.3811915 | 0.312065 | 0.17726237 | U80987_s_a t | Transcription factor TBX5 mRNA |
| 888 | Bladder | -0.050454 | 0.3810056 | 0.311922 | 0.177218 | R14545_at | EST: yf84f08.r1 Homo sapiens cDNA clone 292219 5'. (from Genbank) |
| 889 | Bladder | -0.050779 | 0.3807295 | 0.311879 | 0.17708127 | AA479990_a t | EST: zv18a05.r1 Soares NhHMPu S1 Homo sapiens cDNA clone 753968 5', mRNA sequence. (from Genbank) |
| 890 | Bladder | -0.050831 | 0.3806762 | 0.311715 | 0.17703103 | AA053052_a t | EST: zl71a06.r1 Stratagene colon (#937204) Homo sapiens cDNA clone 510034 5', mRNA sequence. (from Genbank) |
| 891 | Bladder | -0.051018 | 0.3806182 | 0.311532 | 0.17698587 | X52611_s_a t-2 | Transcription factor AP-2 alpha (activating enhancer-binding protein 2 alpha) |
| 892 | Bladder | -0.051018 | 0.3804509 | 0.3115 | 0.17692783 | X52611_s_a t | TRANSCRIPTION FACTOR AP-2 |
| 893 | Bladder | -0.051185 | 0.380384 | 0.311436 | 0.17683215 | U83192_at | Post-synaptic density protein 95 (PSD95) mRNA |
| 894 | Bladder | -0.051415 | 0.3802967 | 0.311408 | 0.17676586 | W68464_at | Homo sapiens mRNA for ADP ribosylation factor-like LAK, complete cds |
| 895 | Bladder | -0.051567 | 0.3802684 | 0.311378 | 0.17665437 | S81914_at | IEX-1 |
| 896 | Bladder | -0.051616 | 0.3802191 | 0.311253 | 0.17657328 | RC_AA4215 72_at | EST: zu25e03.s1 Soares NhHMPu S1 Homo sapiens cDNA clone 739036 3', mRNA sequence. (from Genbank) |
| 897 | Bladder | -0.051762 | 0.3801958 | 0.311236 | 0.17655952 | L21715_at | TNNI2 Troponin I (skeletal fast) |
| 898 | Bladder | -0.051891 | 0.3801661 | 0.311175 | 0.17652261 | X59798_at | CCND1 Cyclin D1 (PRAD1; parathyroid adenomatosis 1) |
| 899 | Bladder | -0.052106 | 0.3801507 | 0.311081 | 0.17641869 | AA426525_a t | EST: zw02f08.r1 Soares NhHMPu S1 Homo sapiens cDNA clone 768135 5', mRNA sequence. (from Genbank) |
| 900 | Bladder | -0.052219 | 0.3801491 | 0.310921 | 0.17637491 | U16720_rna _s_at | Interleukin 10 (IL10) gene |

FIG. 1M2

| | | | | | |
|---|---|---|---|---|---|
| 901 | Bladder | -0.052241 | 0.3801431 | 0.310844 | 0.17628865 | RC_AA4248 06_at | Biphenyl hydrolase-like (serine hydrolase) |
| 902 | Bladder | -0.05242 | 0.380094 | 0.310809 | 0.1762216 | M19311_at | CALM1 Calmodulin 1 (phosphorylase kinase, delta) |
| 903 | Bladder | -0.052562 | 0.38005 | 0.310767 | 0.17614442 | U29091_at | Selenium-binding protein (hSBP) mRNA |
| 904 | Bladder | -0.052612 | 0.3798863 | 0.310751 | 0.17608452 | M98399_s_a t | CD36 CD36 antigen (collagen type I receptor, thrombospondin receptor) |
| 905 | Bladder | -0.053404 | 0.3798255 | 0.310744 | 0.17602567 | AB000464_a l-2 | Homo sapiens mRNA, exon 1, 2, 3, 4, clone:RES4-24A |
| 906 | Bladder | -0.053404 | 0.3798242 | 0.310695 | 0.17585273 | AB000464_a t | mRNA, clone RES4-24A, exon 1, 2, 3, 4 |
| 907 | Bladder | -0.05352 | 0.3797001 | 0.31062 | 0.17581442 | RC_AA2848 79_at | Homo sapiens incomplete cDNA for a mutated allele of a myosin class I, myh-1c |
| 908 | Bladder | -0.053525 | 0.3796234 | 0.31062 | 0.17570098 | M86933_s_a t | AMELY Amelogenin (chromosome Y encoded) |
| 909 | Bladder | -0.053631 | 0.3795871 | 0.310562 | 0.17562555 | U25997_at | Stanniocalcin precursor (STC) mRNA |
| 910 | Bladder | -0.053647 | 0.379577 | 0.31038 | 0.17554551 | U31903_s_a t | CREB-RP (creb-rp) mRNA |
| 911 | Bladder | -0.05379 | 0.3794811 | 0.310354 | 0.17550051 | X51755_cds 5_s_at | Ig light-chain, partial Ke-Oz- polypeptide; Author-given protein sequence is in conflict with the conceptual translation gene extracted from Human lambda-immunoglobulin constant region complex (germline) |
| 912 | Bladder | -0.053809 | 0.3794594 | 0.310343 | 0.175455697 | RC_AA0051 96_at | EST: zh95g08.s1 Soares fetal liver spleen 1NFLS S1 Homo sapiens cDNA clone 429086 3'; mRNA sequence. (from Genbank) |
| 913 | Bladder | -0.054179 | 0.3793585 | 0.310253 | 0.1754006 | X97261_r_at | Metallothionein isoform 1R |
| 914 | Bladder | -0.05418 | 0.3793045 | 0.310106 | 0.17536040 | RC_AA4436 01_at | Ribosomal protein S6 kinase, 90kD, polypeptide 4 |
| 915 | Bladder | -0.05418 | 0.3792672 | 0.309962 | 0.17530957 | D70830_at | Doc2 beta |
| 916 | Bladder | -0.054438 | 0.3791232 | 0.309836 | 0.17524497 | HG2320-HT2416_at | Integrin, Beta 3 Subunit |
| 917 | Bladder | -0.054711 | 0.3790096 | 0.309822 | 0.17514394 | X81788_at | DS-1 mRNA |
| 918 | Bladder | -0.054745 | 0.3789618 | 0.309768 | 0.17511037 | HG3104-HT3280_at | Serine Protease Met1 |
| 919 | Bladder | -0.054884 | 0.3789519 | 0.30971 | 0.174969 | Z22536_at | SERINE/THREONINE-PROTEIN KINASE RECEPTOR R2 PRECURSOR |
| 920 | Bladder | -0.055123 | 0.3788492 | 0.309659 | 0.17490895 | U42359_at | N33 protein form 1 (N33) gene, exon 10 and complete cds |
| 921 | Bladder | -0.055216 | 0.3787613 | 0.309571 | 0.17488223 | X59711_at | NFYA Nuclear transcription factor Y, alpha |
| 922 | Bladder | -0.055298 | 0.3787144 | 0.309571 | 0.17479552 | L24559_at | POLA DNA polymerase alpha subunit |

FIG. 1N2

| # | Tissue | | | | | Description |
|---|---|---|---|---|---|---|
| 923 | Bladder | -0.055363 | 0.3786407 | 0.309539 | 0.1747026 M23263_at | AR Androgen receptor (dihydrotestosterone receptor; testicular feminization; spinal and bulbar muscular atrophy; Kennedy disease) |
| 924 | Bladder | -0.055363 | 0.3785724 | 0.309519 | 0.1746403 M23263_at-2 | Androgen receptor (dihydrotestosterone receptor; testicular feminization; spinal and bulbar muscular atrophy; Kennedy disease) |
| 925 | Bladder | -0.055451 | 0.378455 | 0.309518 | 0.1746150 RC_AA6090 46_at | EST: af10e05.s1 Soares testis NHT Homo sapiens cDNA clone 1031264 3', mRNA sequence. (from Genbank) |
| 926 | Bladder | -0.055468 | 0.3784481 | 0.309517 | 0.1745718 M28210_at | GTP-binding protein (RAB3A) mRNA |
| 927 | Bladder | -0.056229 | 0.3783518 | 0.30948 | 0.1744981 X98833_rna 1_at | Zinc finger protein, Hsal1 |
| 928 | Bladder | -0.056404 | 0.3783108 | 0.309291 | 0.1744538 D63813_at | Rod photoreceptor protein |
| 929 | Bladder | -0.056584 | 0.378178 | 0.309255 | 0.1744019 U58675_cds 2_at | OR17-40 gene extracted from Human olfactory receptor gene cluster on chromosome 17, OR17-228 and OR17-40, and OR17-24 and OR17-25 pseudogenes |
| 930 | Bladder | -0.056686 | 0.3781688 | 0.309149 | 0.1742963 L27584_s_at | CAB3b mRNA for calcium channel beta3 subunit |
| 931 | Bladder | -0.056927 | 0.3779717 | 0.309098 | 0.1742513 D21205_at | Estrogen responsive finger protein |
| 932 | Bladder | -0.05699 | 0.3779557 | 0.309027 | 0.1741919 AA249368_a t | EST: j1535.seq.F Human fetal heart, Lambda ZAP Express Homo sapiens cDNA 5', mRNA sequence. (from Genbank) |
| 933 | Bladder | -0.057061 | 0.3779208 | 0.30902 | 0.174144 U22961_s_a t | mRNA clone with similarity to L-glycerol-3-phosphate:NAD oxidoreductase and albumin gene sequences |
| 934 | Bladder | -0.057316 | 0.3778359 | 0.309016 | 0.1740456 L20433_at | Octamer binding transcription factor 1 (OTF1) mRNA |
| 935 | Bladder | -0.057415 | 0.3777826 | 0.308978 | 0.1739998 RC_AA2583 83_at | Ash2 (absent, small, or homeotic, Drosophila, homolog)-like |
| 936 | Bladder | -0.057557 | 0.377759 | 0.308947 | 0.1739920 U03399_at | T-complex protein 10A (TCP10A) mRNA |
| 937 | Bladder | -0.057558 | 0.3777019 | 0.308836 | 0.1738913 RC_AA0253 52_at | EST: ze74h04.s1 Soares fetal heart NbHH19W Homo sapiens cDNA clone 364759 3', mRNA sequence. (from Genbank) |
| 938 | Bladder | -0.057623 | 0.3776443 | 0.308821 | 0.1738360 X02750_at | PROC Protein C (inactivator of coagulation factors Va and VIIa) |
| 939 | Bladder | -0.05776 | 0.3776403 | 0.308681 | 0.1737893 AC000115_c ds1_at | WUGSC:H_GS188P18.1a gene extracted from Human BAC clone GS188P18 |
| 940 | Bladder | -0.057776 | 0.3776232 | 0.308646 | 0.1737608 AC000115_c ds1_at-2 | Human DNA sequence from PAC 196E23 on chromosome Xq26.1-27.2. Contains the TAT-SF1 (HIV-1 transcriptional elongation factor TAT cofactor TAT-SF1) gene, the BRS3 (Bombesin Receptor subtype-3 (Uterine Bombesin Receptor, BRS-3) gene, an unknown gene coding for two isoforms, a predicted CpG island, ESTs and STSs |
| 941 | Bladder | -0.057815 | 0.3776221 | 0.308509 | 0.1735971 M93311_at | GIF |
| 942 | Bladder | -0.057903 | 0.3775278 | 0.308477 | 0.1735497 T23709_at | Seq545 Homo sapiens cDNA clone HY6cDNA2-4 5'. (from Genbank) |

FIG. 1O2

| | | | | | | |
|---|---|---|---|---|---|---|
| 943 | Bladder | -0.057932 | 0.3774667 | 0.308406 | 0.17349717 | U64871_at | G protein-coupled receptor GPR-NGA gene |
| 944 | Bladder | -0.058142 | 0.3771979 | 0.308388 | 0.17343473 | X87870_at | HEPATOCYTE NUCLEAR FACTOR 4 |
| 945 | Bladder | -0.058185 | 0.37715151 | 0.308262 | 0.17340761 | L19067_at | TRANSCRIPTION FACTOR P65 |
| 946 | Bladder | -0.058279 | 0.3770452 | 0.308247 | 0.17323422 | S77410_at | AGTR1 Angiotensin receptor 1 |
| 947 | Bladder | -0.058318 | 0.3770426 | 0.30823 | 0.17322688 | L22569_at | CTSB Cathepsin B |
| 948 | Bladder | -0.058408 | 0.3770138 | 0.308116 | 0.17310478 | W52493_at | EST: zc54a05.r1 Soares senescent fibroblasts NbHSF Homo sapiens cDNA clone 326096 5' similar to contains element MER6 repetitive element ;. mRNA sequence. (from Genbank) |
| 949 | Bladder | -0.058582 | 0.3769707 | 0.308065 | 0.17304768 | D14826_s_at | CREM cAMP responsive element modulator |
| 950 | Bladder | -0.058627 | 0.3769475 | 0.307896 | 0.17299914 | AA044095_a_t | EST: zk51a08.r1 Soares pregnant uterus NbHPU Homo sapiens cDNA clone 486326 5', mRNA sequence. (from Genbank) |
| 951 | Bladder | -0.058834 | 0.3769444 | 0.307697 | 0.17294106 | AA209239_a_t | EST: zq85h01.r1 Stratagene hNT neuron (#937233) Homo sapiens cDNA clone 648433 5', mRNA sequence. (from Genbank) |
| 952 | Bladder | -0.058922 | 0.3769048 | 0.307635 | 0.17291485 | U38276_at | Semaphorin III family homolog mRNA |
| 953 | Bladder | -0.059008 | 0.3768076 | 0.30757 | 0.17278095 | U47677_at | Transcription factor E2F like protein [human, mRNA, 2492 nt] |
| 954 | Bladder | -0.059211 | 0.3767662 | 0.307509 | 0.17274654 | RC_AA430466_at | EST: zw23d05.s1 Soares ovary tumor NbHOT Homo sapiens cDNA clone 770121 3', mRNA sequence. (from Genbank) |
| 955 | Bladder | -0.059263 | 0.3766483 | 0.3075 | 0.17272046 | L13391_at | REGULATOR OF G-PROTEIN SIGNALLING 2 |
| 956 | Bladder | -0.059276 | 0.3766062 | 0.307483 | 0.17263705 | L39064_rna1_at | Interleukin 9 receptor (IL9R) gene |
| 957 | Bladder | -0.059444 | 0.3765569 | 0.307462 | 0.17256323 | RC_AA186897_at | EST: zp74c05.s1 Stratagene HeLa cell s3 937216 Homo sapiens cDNA clone 625928 3', mRNA sequence. (from Genbank) |
| 958 | Bladder | -0.059584 | 0.3765534 | 0.307406 | 0.17248246 | W73805_at | EST: zd50g02.r1 Soares fetal heart NbHH19W Homo sapiens cDNA clone 344114 5', mRNA sequence. (from Genbank) |
| 959 | Bladder | -0.059804 | 0.3765489 | 0.307406 | 0.17239277 | X59656_at | CRKL V-crk avian sarcoma virus CT10 oncogene homolog-like |
| 960 | Bladder | -0.059808 | 0.3762352 | 0.307273 | 0.17231426 | M20778_s_at | Homo sapien, alpha-3 (VI) collagen |
| 961 | Bladder | -0.059829 | 0.376203 | 0.307194 | 0.17224173 | Y08564_at | GalNAc-T4 gene |
| 962 | Bladder | -0.05983 | 0.3759164 | 0.307152 | 0.17220227 | RC_AA398124_s_at | Growth factor receptor-bound protein 14 |
| 963 | Bladder | -0.059907 | 0.3758407 | 0.307081 | 0.17216259 | Y10256_at | Serine/threonine protein kinase, NIK |
| 964 | Bladder | -0.05993 | 0.3757221 | 0.307075 | 0.17213538 | X71125_at | Glutamine cyclotransferase |
| 965 | Bladder | -0.060048 | 0.3757021 | 0.307026 | 0.1720956 | L44538_at | EST: Homo sapiens thymus mRNA (randomly primed, normalized), single-pass sequence, mRNA sequence. (from Genbank) |
| 966 | Bladder | -0.06014 | 0.3755727 | 0.307025 | 0.171912 | M26880_at | UBA52 Ubiquitin A-52 residue ribosomal protein fusion product 1 |
| 967 | Bladder | -0.06016 | 0.3754811 | 0.306999 | 0.17185773 | HG3477-HT3670_at | Cd4 Antigen |

FIG. 1P2

| | | | | | | |
|---|---|---|---|---|---|---|
| 968 | Bladder | -0.060167 | 0.375449 | 0.306919 | 0.17173503 | M94250_at | MDK Midkine (neurite growth-promoting factor 2) |
| | | | | | | AF000177_a |
| 969 | Bladder | -0.060292 | 0.3754252 | 0.306717 | 0.17169876 | t | Sm-like protein CaSm (CaSm) mRNA |
| 970 | Bladder | -0.060331 | 0.3752748 | 0.306665 | 0.17160052 | Z32684_at | XK mRNA for membrane transport protein |
| | | | | | | RC_AA1258 | EST: zl29e12.s1 Soares pregnant uterus NbHPU Homo sapiens |
| 971 | Bladder | -0.0606 | 0.3752392 | 0.306632 | 0.171548950 | 8_at | cDNA clone 503374 3', mRNA sequence. (from Genbank) |
| 972 | Bladder | -0.060719 | 0.3752141 | 0.306472 | 0.17148261 | M35128_at | Muscarinic acetylcholine receptor gene |
| | | | | | | AA233107_a | |
| 973 | Bladder | -0.060818 | 0.3751358 | 0.306456 | 0.17145796 | t | Homo sapiens Smad6 mRNA, complete cds |
| | | | | | | N75203_s_a | EST: yw33e05.r1 Homo sapiens cDNA clone 254048 5' (from |
| 974 | Bladder | -0.0609 | 0.3750482 | 0.306445 | 0.17143147 | t | Genbank) |
| | | | | | | HG3921- | |
| 975 | Bladder | -0.060995 | 0.3749930 | 0.306344 | 0.17140122 | HT4191_f_at | Homeotic Protein C6, Class I |
| 976 | Bladder | -0.060957 | 0.3749390 | 0.306343 | 0.17129926 | M62783_at | NAGA N-acetylgalactosaminidase, alpha- |
| 977 | Bladder | -0.060983 | 0.3748452 | 0.30625 | 0.1712577 | X69090_at | Skeletal muscle 190kD protein |
| 978 | Bladder | -0.06102 | 0.3747438 | 0.306225 | 0.17117085 | X12433_at | PROTEIN PHP31-2 |
| | | | | | | RC_AA4959 | EST: zw06a03.s1 Soares NhHMPu S1 Homo sapiens cDNA clone |
| 979 | Bladder | -0.061163 | 0.3745751 | 0.306203 | 0.171076465 | 2_at | 768470 3', mRNA sequence. (from Genbank) |
| | | | | | | U22970_rna | 6-16 gene (interferon-inducible peptide precursor) extracted from |
| 980 | Bladder | -0.061183 | 0.3744806 | 0.306113 | 0.171076461 | _s_at | Human interferon-inducible peptide (6-16) gene |
| 981 | Bladder | -0.06128 | 0.3744772 | 0.30607 | 0.17108845 | D79205_at | Ribosomal protein L39 |
| | | | | | | HG4113- | |
| | | | | | | HT4383_s_a | |
| 982 | Bladder | -0.061301 | 0.3744609 | 0.306063 | 0.1708802 | t | Olfactory Receptor Or17-201 |
| | | | | | | RC_AA4790 | EST: zv17e07.s1 Soares NhHMPu S1 Homo sapiens cDNA clone |
| 983 | Bladder | -0.061365 | 0.374273 | 0.306063 | 0.170751539 | 6_at | 753924 3', mRNA sequence. (from Genbank) |
| | | | | | | AA203285_a | EST: zx57e08.r1 Soares fetal liver spleen 1NFLS S1 Homo sapiens |
| 984 | Bladder | -0.061386 | 0.3742026 | 0.305984 | 0.17071536 | t | cDNA clone 446630 5', mRNA sequence. (from Genbank) |
| | | | | | | RC_AA0252 | EST: ze81f06.s1 Soares fetal heart NbHH19W Homo sapiens cDNA |
| 985 | Bladder | -0.06139 | 0.3741972 | 0.30598 | 0.170658343 | 7_at | clone 365411 3', mRNA sequence. (from Genbank) |
| 986 | Bladder | -0.061409 | 0.3741908 | 0.30573 | 0.17058344 | U87972_at | NAD+-isocitrate dehydrogenase mRNA, partial cds |
| | | | | | | RC_AA4614 | EST: zx68d02.s1 Soares total fetus Nb2HF8.9w Homo sapiens cDNA |
| 987 | Bladder | -0.061466 | 0.3741314 | 0.305654 | 0.170540025 | 5_at | clone 796611 3', mRNA sequence. (from Genbank) |
| | | | | | | RC_AA4904 | EST: za45a12.s1 Soares NhHMPu S1 Homo sapiens cDNA clone |
| 988 | Bladder | -0.061485 | 0.3740752 | 0.305547 | 0.170491766 | 1_at | 823870 3', mRNA sequence. (from Genbank) |
| | | | | | | RC_AA4314 | EST: zw70f11.s1 Soares testis NHT Homo sapiens cDNA clone |
| 989 | Bladder | -0.06168 | 0.374063 | 0.30554 | 0.170458916 | 1_at | 781581 3', mRNA sequence. (from Genbank) |

FIG. 1Q2

| | | | | | |
|---|---|---|---|---|---|
| 990 | Bladder | -0.061822 | 0.373881 | 0.305463 | 0.170406685 | RC_AA417 98_at | EST: zw62c11.s1 Soares total fetus Nb2HF8 9w Homo sapiens cDNA clone 774644 3' similar to TR:G207250 G207250 RAT GROWTH AND TRANSFORMATION-DEPENDENT ; mRNA sequence. (from Genbank) |
| 991 | Bladder | -0.061832 | 0.3737912 | 0.305277 | 0.17037009 | AA278413_a t | EST: zs81h05.r1 NCI_CGAP_GCB1 Homo sapiens cDNA clone IMAGE:703929 5', mRNA sequence. (from Genbank) |
| 992 | Bladder | -0.061869 | 0.3737442 | 0.30521 | 0.170263421 | U04636_rna 1_at-2 | Prostaglandin-endoperoxide synthase 2 (prostaglandin G/H synthase and cyclooxygenase) |
| 993 | Bladder | -0.061869 | 0.3736545 | 0.305062 | 0.170207341 | U04636_rna 1_at | Cyclooxygenase-2 (hCox-2) gene |
| 994 | Bladder | -0.061889 | 0.3736098 | 0.305047 | 0.170193371 | M37981_at | CHRNA3 Alpha-3 neuronal nicotinic acetylcholine receptor subunit |
| 995 | Bladder | -0.061949 | 0.3734886 | 0.304825 | 0.170125291 | RC_AA4547 9_at | EST: zx77b02.s1 Soares ovary tumor NbHOT Homo sapiens cDNA clone 809739 3', mRNA sequence. (from Genbank) |
| 996 | Bladder | -0.062022 | 0.3733334 | 0.304825 | 0.169990291 | T68083_at | Short-chain dehydrogenase/reductase 1 |
| 997 | Bladder | -0.062104 | 0.3733075 | 0.304813 | 0.169943971 | S70348_at-2 | Integrin beta 3 {alternatively spliced, clone beta 3C} [human, erythroleukemia cell HEL, mRNA Partial, 409 nt] |
| 998 | Bladder | -0.062104 | 0.3733065 | 0.304801 | 0.169849231 | S70348_at | ITGB3 Integrin, beta 3 (platelet glycoprotein IIIa, antigen CD61) |
| 999 | Bladder | -0.062136 | 0.3732649 | 0.304775 | 0.169807941 | U67988_at | Guanylate kinase associated protein (GKAP) mRNA |
| 1000 | Bladder | -0.062189 | 0.3732564 | 0.304664 | 0.169725451 | AA448460_a t | EST: zw79b12.r1 Soares testis NHT Homo sapiens cDNA clone 782399 5', mRNA sequence. (from Genbank) |

FIG. 1R2

| | | | | | | |
|---|---|---|---|---|---|---|
| 1 | Breast | 0.4144211 | 0.7052603 | 0.615615 | 0.46934703 | S70585_rna_1_at | Thyroid-stimulating hormone alpha subunit [human, Genomic, 1327 nt 4 segments] |
| 2 | Breast | 0.4051815 | 0.6544581 | 0.57007 | 0.43706787 | J03460_s_at | Prolactin-induced protein |
| 3 | Breast | 0.3902984 | 0.6254832 | 0.549476 | 0.42199615 | AC002077_a_t | GUANINE NUCLEOTIDE-BINDING PROTEIN G(T), ALPHA-1 SUBUNIT |
| 4 | Breast | 0.3692085 | 0.6140406 | 0.538343 | 0.41081786 | HG1763-HT1780_s_a_t | Prolactin-Induced Protein |
| 5 | Breast | 0.3573955 | 0.601601 | 0.527243 | 0.4027538 | AA059327_i_at | EST: zf65e11.r1 Soares retina N2b4HR Homo sapiens cDNA clone 381836 5', mRNA sequence. (from Genbank) |
| 6 | Breast | 0.3370636 | 0.5946991 | 0.51971 | 0.39607754 | D90041_s_a_t | N-acetyltransferase 1 (arylamine N-acetyltransferase) |
| 7 | Breast | 0.3302206 | 0.5911745 | 0.515125 | 0.38979056 | K03192_f_at | CYP2A6 Cytochrome P450, subfamily IIA (phenobarbital-inducible), polypeptide 6 |
| 8 | Breast | 0.3302206 | 0.583999 | 0.509847 | 0.38526917 | K03192_f_at | Cytochrome P450, subfamily IIA (phenobarbital-inducible), polypeptide 6 |
| 9 | Breast | 0.3101546 | 0.5778751 | 0.504484 | 0.3807439 | M81057_at | CPB1 Carboxypeptidase B1 (tissue) |
| 10 | Breast | 0.3052343 | 0.5733255 | 0.501 | 0.37644237 | M97815_at | CRABP2 Cellular retinoic acid-binding protein 2 |

FIG. 2A

| # | Tissue | | | | ID | Gene/Description |
|---|---|---|---|---|---|---|
| 11 | Breast | 0.3039735 | 0.5713079 | 0.497555 | 0.3731388 L00389_f_at | Cytochrome P-450 4 gene |
| 12 | Breast | 0.3018422 | 0.5663985 | 0.494761 | AA393089_a 0.369807661 t | EST: zi69b10.r1 Soares testis NHT Homo sapiens cDNA clone 727579 5'. mRNA sequence. (from Genbank) |
| 13 | Breast | 0.301496 | 0.5648769 | 0.491622 | 0.36651027 X13589_at | CYP19 Cytochrome P450, subfamily XIX (aromatization of androgens) |
| 14 | Breast | 0.301386 | 0.5610314 | 0.488126 | 0.3636768 W27961_at | EST: 40a4 Human retina cDNA randomly primed sublibrary Homo sapiens cDNA, mRNA sequence. (from Genbank) |
| 15 | Breast | 0.3011417 | 0.5586313 | 0.485323 | HG2365-0.360680076 HT2461_at | Glyceraldehyde-3-Phosphate Dehydrogenase (Gb:K03121) |
| 16 | Breast | 0.2956604 | 0.5576914 | 0.483406 | AA287713_a 0.3586727 t | EST: zs53h01.r1 NCI_CGAP_GCB1 Homo sapiens cDNA clone IMAGE:701233 5' similar to TR:G1223890 G1223890 PUTATIVE T1/ST2 RECEPTOR BINDING PROTEIN PRECURSOR. ;, mRNA sequence. (from Genbank) |
| 17 | Breast | 0.2954511 | 0.5521304 | 0.480035 | 0.356413905 D16583_at | HDC Histidine decarboxylase |
| 18 | Breast | 0.2892586 | 0.5511941 | 0.477087 | HG3236-0.353864667 HT3413_f_at | Neurofibromatosis 2 Tumor Suppressor (Gb:L27065) |
| 19 | Breast | 0.2879139 | 0.5490707 | 0.475087 | 0.351197905 U22029_f_at | CYP2A7 Cytochrome P450, subfamily IIA (phenobarbital-inducible), polypeptide 7 |
| 20 | Breast | 0.2857193 | 0.5455678 | 0.474101 | HG880-0.349923 HT880_at | Mucin 6, Gastric (Gb:L07517) |
| 21 | Breast | 0.2855561 | 0.5433092 | 0.471108 | AFFX-DapX-0.348110886 5_at | AFFX-DapX-5_at (endogenous control) |
| 22 | Breast | 0.2855561 | 0.5397123 | 0.469333 | AFFX-DapX-0.346228665 5_at-2 | AFFX-DapX-5_at (miscellaneous control - 11k chips) |
| 23 | Breast | 0.2817361 | 0.5391187 | 0.467654 | M29874_s_a 0.3445486 t | CYP2B6 Cytochrome P450, subfamily IIB (phenobarbital-inducible), polypeptide 6 |
| 24 | Breast | 0.2797567 | 0.53859 | 0.465246 | 0.342962 X58072_at | GATA3 GATA-binding protein 3 |
| 25 | Breast | 0.272856 | 0.5356196 | 0.463567 | 0.3413686 U73330_at | PAC clone 85D2 from 13q12-13q13, complete sequence |
| 26 | Breast | 0.2579279 | 0.5322417 | 0.462184 | 0.339944871 M14091_at | THYROXINE-BINDING GLOBULIN PRECURSOR |
| 27 | Breast | 0.2570436 | 0.5311074 | 0.460936 | 0.33822918 T92512_at | Ye24g11.r1 Homo sapiens cDNA clone 118724 5'. (from Genbank) |
| 28 | Breast | 0.2555496 | 0.5289472 | 0.459658 | X17059_s_a 0.33666405 | AAC1 Arylamine N-acetyltransferase, liver |
| 29 | Breast | 0.2509626 | 0.5283092 | 0.458428 | M63962_ma 0.335517381 1_at | Gastric H,K-ATPase catalytic subunit gene |
| 30 | Breast | 0.2476297 | 0.527762 | 0.456917 | 0.3340632 W07430_at | EST: za96f10.r1 Soares fetal lung NbHL19W Homo sapiens cDNA clone 300427 5'; mRNA sequence. (from Genbank) |
| 31 | Breast | 0.2458172 | 0.5273711 | 0.455669 | 0.33269461 N79354_at | EST: yz73a08.r1 Homo sapiens cDNA clone 288662 5'. (from Genbank) |

FIG. 2B

| # | Type | | | | | Accession | Description |
|---|---|---|---|---|---|---|---|
| 32 | Breast | 0.245815 | 0.5269248 | 0.454783 | 0.33144146 | AA478131_at | EST: zu42c10.r1 Soares ovary tumor NbHOT Homo sapiens cDNA clone 740658 5' similar to TR:G433963 G433963 P18H-REV 107..; mRNA sequence. (from Genbank) |
| 33 | Breast | 0.2450795 | 0.5260367 | 0.452885 | 0.33000445 | L10377_s_at | (clone CTG-B37) mRNA sequence |
| 34 | Breast | 0.2396013 | 0.5247346 | 0.45194 | 0.32894969 | RC_AA1469_at | EST: zi51g10.s1 Soares pregnant uterus NbHPU Homo sapiens cDNA clone 505506 3', mRNA sequence. (from Genbank) |
| 35 | Breast | 0.2394474 | 0.5229325 | 0.450851 | 0.32772556 | RC_D59354_i_at | EST: Human fetal brain cDNA 3'-end GEN-020E05, mRNA sequence. (from Genbank) |
| 36 | Breast | 0.2387956 | 0.5228207 | 0.449647 | 0.32679677 | AFFX-PheX-3_at-2 | AFFX-PheX-3_at (miscellaneous control - 11k chips) |
| 37 | Breast | 0.2387956 | 0.5201473 | 0.448486 | 0.3256697 | AFFX-PheX-3_at | AFFX-PheX-3_at (endogenous control) |
| 38 | Breast | 0.236189 | 0.5198922 | 0.448017 | 0.32445835 | U28413_at | Cockayne syndrome complementation group A CSA protein (CSA) mRNA |
| 39 | Breast | 0.2339904 | 0.5194382 | 0.447233 | 0.32374018 | U79293_at | Clone 23948 mRNA sequence |
| 40 | Breast | 0.2310167 | 0.5187003 | 0.446593 | 0.32270935 | M60331_at | PRM1 Protamine 1 |
| 41 | Breast | 0.2294978 | 0.5172582 | 0.445578 | 0.32168627 | M29873_s_a_t | Human cytochrome P450-IIB (hIIB3) mRNA, complete cds |
| 42 | Breast | 0.2275559 | 0.5166451 | 0.444513 | 0.32078087 | RC_AA6097_95_at | EST: ac62a09.s1 Stratagene lung carcinoma 937218 Homo sapiens cDNA clone 951448 3', mRNA sequence. (from Genbank) |
| 43 | Breast | 0.2262459 | 0.5148028 | 0.443448 | 0.31968847 | M96132_at | MHC class II HLA-DR-beta-1*09012 (HLA-DRB1*09012) gene, 3'end cds |
| 44 | Breast | 0.2232326 | 0.5139468 | 0.442246 | 0.31869397 | X76059_at | YRRM1 |
| 45 | Breast | 0.2216474 | 0.51127663 | 0.441581 | 0.31773603 | S81294_at | DCC=deleted in colorectal cancer {alternatively spliced, exon 1A} [human, brain tumor, tumor no. 245, mRNA Partial, 216 nt] |
| 46 | Breast | 0.2207041 | 0.5122337 | 0.440414 | 0.31697726 | RC_AA4323_78_at | EST: zw76c08.s1 Soares testis NHT Homo sapiens cDNA clone 782126 3', mRNA sequence. (from Genbank) |
| 47 | Breast | 0.2167237 | 0.5119829 | 0.439703 | 0.31625086 | M33318_r_at | CYP2A6 Cytochrome P450, subfamily IIA (phenobarbital-inducible), polypeptide 6 |
| 48 | Breast | 0.2138934 | 0.510178 | 0.439014 | 0.315327 | M31667_f_at | CYTOCHROME P450 IA2 |
| 49 | Breast | 0.2089151 | 0.510178 | 0.438184 | 0.31431746 | X78678_at | KHK Ketohexokinase (fructokinase) |
| 50 | Breast | 0.2072929 | 0.5087296 | 0.437622 | 0.31354463 | U59877_s_a_t | |
| 51 | Breast | 0.2072783 | 0.5080157 | 0.4368857 | 0.31298834 | M19481_at | Low-Mr GTP-binding protein (RAB31) mRNA |
| 52 | Breast | 0.2059171 | 0.5078226 | 0.436084 | 0.31211993 | M87338_at | Follistatin gene |
| 53 | Breast | 0.2054884 | 0.5075588 | 0.435751 | 0.31118977 | Y09561_at | RFC2 Replication factor C (activator 1) 2, 40kD subunit |
|  |  |  |  |  |  |  | P2X7 receptor |

FIG. 2C

| # | Tissue | | | | | ID | Description |
|---|---|---|---|---|---|---|---|
| 54 | Breast | 0.2036483 | 0.507147 | 0.434863 | 0.310475777 | RC_AA0571 93_at | EST: zk79g01.s1 Soares pregnant uterus NbHPU Homo sapiens cDNA clone 489072 3', mRNA sequence. (from Genbank) |
| 55 | Breast | 0.2026314 | 0.5069917 | 0.433748 | 0.30985519 | W07461_at | EST: za97f08.r1 Soares fetal lung NbHL19W Homo sapiens cDNA clone 300519 5' similar to WP:B0491.7 CEU2109 DIPHTHINE SYNTHASE;, mRNA sequence. (from Genbank) |
| 56 | Breast | 0.2009918 | 0.5065417 | 0.433043 | 0.30905774 | M27826_at | Endogenous retroviral protease mRNA |
| 57 | Breast | 0.1930344 | 0.5063547 | 0.432044 | 0.30823 | K00629_i_at | Human kpni repeat mrna (cdna clone pcd-kpni-4), 3' end |
| 58 | Breast | 0.180382 | 0.5052289 | 0.431654 | 0.30751547 | AA428090_a_t | EST: zw32a08.r1 Soares ovary tumor NbHOT Homo sapiens cDNA clone 770966 5', mRNA sequence. (from Genbank) |
| 59 | Breast | 0.1879053 | 0.5047944 | 0.430951 | 0.30678293 | X71135_at | Sox3 gene |
| 60 | Breast | 0.1877799 | 0.5042729 | 0.4305504 | 0.30609787 | L40396_at | (clone s22i7f) mRNA fragment |
| 61 | Breast | 0.1873857 | 0.5028442 | 0.430114 | 0.3054275 | U33147_at | Mammaglobin mRNA |
| 62 | Breast | 0.1860077 | 0.5017778 | 0.429478 | 0.3047553 | X07881_rna 1_f_at | Human gene PRB3L for proline-rich protein G1 |
| 63 | Breast | 0.185097 | 0.5007832 | 0.428728 | 0.30425614 | R82528_at | EST: yf19a05.r1 Homo sapiens cDNA clone 149168 5'. (from Genbank) |
| 64 | Breast | 0.1850751 | 0.5005295 | 0.428209 | 0.30378756 | RC_AA1286 17_at | EST: zf15d10.s1 Soares pregnant uterus NbHPU Homo sapiens cDNA clone 502003 3', mRNA sequence. (from Genbank) |
| 65 | Breast | 0.1826687 | 0.5004 | 0.427635 | 0.30302867 | RC_AA4365 53_at | EST: zv08c11.s1 Soares NhHMPu S1 Homo sapiens cDNA clone 753044 3', mRNA sequence. (from Genbank) |
| 66 | Breast | 0.1818307 | 0.5002153 | 0.426603 | 0.3025784 | HG2566-HT4792_r_at | Microtubule-Associated Protein Tau, Alt. Splice 3, Exon 8 |
| 67 | Breast | 0.1809896 | 0.4988202 | 0.426546 | 0.3018145 | YEL002c/W BP1_at | No info for gene |
| 68 | Breast | 0.1806067 | 0.4987948 | 0.425947 | 0.30131826 | X83301_s_a t | SMA5 mRNA |
| 69 | Breast | 0.1776925 | 0.4979267 | 0.424989 | 0.30063042 | H18713_at | H.sapiens mRNA for aminopeptidase P-like |
| 70 | Breast | 0.1762679 | 0.4966449 | 0.424616 | 0.3001228 | S75174_at | E2F4 E2F transcription factor 4, p107/p130-binding |
| 71 | Breast | 0.1761461 | 0.4966449 | 0.42419 | 0.2995844 | RC_C14801_at | EST: Human fetal brain cDNA 3'-end GEN-089D05, mRNA sequence. (from Genbank) |
| 72 | Breast | 0.175442 | 0.4960552 | 0.42353 | 0.29917407 | W03018_at | Glucocorticoid receptor DNA binding factor 1 |
| 73 | Breast | 0.1742659 | 0.4955122 | 0.423282 | 0.29847592 | HG4099-HT4369_s_a t | Adrenergic Receptor, Alpha 1b |
| 74 | Breast | 0.1733242 | 0.4954579 | 0.422941 | 0.29794037 | N29207_at | EST: yx42h05.r1 Homo sapiens cDNA clone 264441 5'. (from Genbank) |
| 75 | Breast | 0.1718145 | 0.4949794 | 0.422192 | 0.29747328 | RC_D60394_at | EST: Human fetal brain cDNA 3'-end GEN-104E06, mRNA sequence. (from Genbank) |

FIG. 2D

| | | | | |
|---|---|---|---|---|
| 76 Breast | 0.1686359 | 0.4943706 | 0.421874 | 0.2971239 M23263_at | AR Androgen receptor (dihydrotestosterone receptor; testicular feminization; spinal and bulbar muscular atrophy; Kennedy disease) |
| 77 Breast | 0.1686359 | 0.4937092 | 0.420646 | 0.2965633 M23263_at-2 | Androgen receptor (dihydrotestosterone receptor; testicular feminization; spinal and bulbar muscular atrophy; Kennedy disease) |
| 78 Breast | 0.1672696 | 0.4930089 | 0.420364 | RC_AA1916 47_at | Ceruloplasmin (ferroxidase) |
| 79 Breast | 0.1659615 | 0.4928859 | 0.419925 | 0.2955664 U90910_at-2 | Human clone 23564 mRNA sequence |
| 80 Breast | 0.1659615 | 0.4917122 | 0.419109 | 0.2952445 U90910_at | Clone 23564 mRNA sequence |
| 81 Breast | 0.1644084 | 0.4916681 | 0.418326 | 0.2947381 W68464_at | Homo sapiens mRNA for ADP ribosylation factor-like LAK, complete cds |
| 82 Breast | 0.1636634 | 0.4907536 | 0.417955 | RC_AA0554 0.2942110 04_f_at | EST: zl74e11.s1 Stratagene colon (#937204) Homo sapiens cDNA clone 510380 3' similar to contains Alu repetitive element;, mRNA sequence. (from Genbank) |
| 83 Breast | 0.1633128 | 0.4902477 | 0.417484 | 0.2936591 W31698_at | Zinc finger protein 42 (myeloid-specific retinoic acid- responsive) |
| 84 Breast | 0.1620412 | 0.4898317 | 0.416865 | 0.2932521 D83913_at | Genethonin 1 |
| 85 Breast | 0.1580962 | 0.4897454 | 0.416215 | M14123_xpt 0.2927415 3_at | Gag 2 protein from Human endogenous retrovirus HERV-K10./ntype=DNA /annot=CDS |
| 86 Breast | 0.1580673 | 0.4880573 | 0.416033 | 0.2923667 M33317_f_at | CYP2A7 Cytochrome P450, subfamily IIA (phenobarbital-inducible), polypeptide 7 |
| 87 Breast | 0.1575966 | 0.4874969 | 0.415513 | 0.2918222 S77410_at | AGTR1 Angiotensin receptor 1 |
| 88 Breast | 0.1568142 | 0.4874758 | 0.415029 | 0.2915416 L42150_at | PDK1 Pyruvate dehydrogenase kinase, isoenzyme 1 |
| 89 Breast | 0.1552809 | 0.4866583 | 0.414581 | 0.2911139 U20325_at | Cocaine and amphetamine regulated transcript CART (hCART) mRNA |
| 90 Breast | 0.1528014 | 0.4858357 | 0.414185 | 0.2907505 X81836_s_a t | Dents Disease candidate gene |
| 91 Breast | 0.1486395 | 0.4849633 | 0.413004 | RC_AA5210 0.2902368 773_at | EST: aa72a05.s1 NCI_CGAP_GCB1 Homo sapiens cDNA clone IMAGE:826448 3', mRNA sequence. (from Genbank) |
| 92 Breast | 0.1483766 | 0.4848722 | 0.412836 | U32499_s_a 0.2889125 t | D3 dopamine receptor mRNA |
| 93 Breast | 0.1483625 | 0.4842243 | 0.412473 | 0.2894367 U62435_at | Cholinergic receptor, neuronal nicotinic, alpha polypeptide 6 |
| 94 Breast | 0.1473178 | 0.4840047 | 0.412064 | 0.2890786 L10844_at | CDC42 Cell division cycle 42 (GTP-binding protein, 25kD) |
| 95 Breast | 0.1472629 | 0.4839905 | 0.411916 | 0.2886710 W28414_at | EST: 46g7 Human retina cDNA randomly primed sublibrary Homo sapiens cDNA, mRNA sequence. (from Genbank) |
| 96 Breast | 0.146634 | 0.4839169 | 0.411477 | HG415-0.2883357 HT415_at | Lectin, Galactoside-Binding, Soluble, 2 |
| 97 Breast | 0.1462051 | 0.4833313 | 0.410845 | 0.2879375 X73079_at | GIF Polymeric immunoglobulin receptor |

FIG. 2E

| | | | | | |
|---|---|---|---|---|---|
| 98 | Breast | 0.1454632 | 0.4830362 | 0.410382 | 0.28760898 | HG3731-HT4001_r_at | Immunoglobulin Heavy Chain, Vdjrc Regions (Gb:L23566) |
| 99 | Breast | 0.1446769 | 0.4820118 | 0.410039 | 0.28726697 | M31661_at | PRLR Prolactin receptor |
| 100 | Breast | 0.142678 | 0.4817252 | 0.409762 | 0.28671452 | AA448128_a_t | Heat shock 40kD protein 2 |
| 101 | Breast | 0.1425744 | 0.480467 | 0.409464 | 0.286305 | AA398863_a_t | Zl80f04.r1 Soares testis NHT Homo sapiens cDNA clone 728671 5' similar to contains Alu repetitive element;contains element L1 repetitive element :, mRNA sequence. (from Genbank) |
| 102 | Breast | 0.1425183 | 0.4797899 | 0.408963 | 0.28593504 | U60521_at | Cysteine protease ICE-LAP6 mRNA |
| 103 | Breast | 0.1420439 | 0.4797809 | 0.408845 | 0.28553647 | X66436_at | POSSIBLE GTP-BINDING PROTEIN HSR1 |
| 104 | Breast | 0.1404123 | 0.4797016 | 0.408685 | 0.28527972 | X92475_at | ITBA1 protein |
| 105 | Breast | 0.1404123 | 0.4786941 | 0.408089 | 0.28492057 | X92475_at-2 | ITBA1 gene |
| 106 | Breast | 0.1396912 | 0.478331 | 0.407545 | 0.28458354 | AA447244_a_t | KIAA0740 gene product |
| 107 | Breast | 0.1388565 | 0.4772545 | 0.407181 | 0.28430355 | X90780_rna1_at | Cardiac troponin I gene, exons 1 to 5 |
| 108 | Breast | 0.1386668 | 0.4771094 | 0.406837 | 0.28399804 | RC_AA052947_at | EST: zl70d10.s1 Stratagene colon (#937204) Homo sapiens cDNA clone 509971 3', mRNA sequence. (from Genbank) |
| 109 | Breast | 0.1377513 | 0.4762728 | 0.406635 | 0.28356695 | RC_AA399226_at | Homo sapiens chromosome 19, cosmid R28784 |
| 110 | Breast | 0.1365907 | 0.4761649 | 0.40639 | 0.28320184 | H66367_at | EST: yu14a06.r1 Homo sapiens cDNA clone 233746 5' similar to contains Alu repetitive element;. (from Genbank) |
| 111 | Breast | 0.1361492 | 0.4755487 | 0.40572 | 0.28294975 | X55037_s_a_t | GATA3 GATA-binding protein 3 |
| 112 | Breast | 0.136135 | 0.4749816 | 0.405224 | 0.28260452 | U37519_at | ALDH8 Aldehyde dehydrogenase 8 |
| 113 | Breast | 0.1350118 | 0.4749779 | 0.405038 | 0.28233362 | RC_AA192339_at | EST: zp97g11.s1 Stratagene muscle 937209 Homo sapiens cDNA clone 628196 3', mRNA sequence. (from Genbank) |
| 114 | Breast | 0.1345174 | 0.4746602 | 0.404481 | 0.2817898 | R33301_at | EST: yh81g01.r1 Homo sapiens cDNA clone 136176 5' similar to contains MSR1 repetitive element ;. (from Genbank) |
| 115 | Breast | 0.1338865 | 0.4742993 | 0.404086 | 0.2813785 | R86920_at | EST: yq30g06.r1 Homo sapiens cDNA clone 197338 5'. (from Genbank) |
| 116 | Breast | 0.1333216 | 0.4734562 | 0.403847 | 0.28105938 | D38024_at | Facioscapulohumeral muscular dystrophy (FSHD) gene region, D4Z4 tandem repeat unit |
| 117 | Breast | 0.13306 | 0.4733514 | 0.4036658 | 0.28065583 | RC_AA084318_at | EST: zn18b04.s1 Stratagene neuroepithelium NT2RAMI 937234 Homo sapiens cDNA clone 547759 3', mRNA sequence. (from Genbank) |
| 118 | Breast | 0.1304407 | 0.4730471 | 0.402953 | 0.28038876 | RC_AA018441_at | EST: ze50a08.s1 Soares retina N2b4HR Homo sapiens cDNA clone 362390 3', mRNA sequence. (from Genbank) |

FIG. 2F

| | | | | | |
|---|---|---|---|---|---|
| 119 | Breast | 0.1301951 | 0.4724207 | 0.402594 | 0.280094566 | RC_AA2279 41_s_at | EST: zt56c12.s1 Soares NhHMPu S1 Homo sapiens cDNA clone 667414 3', mRNA sequence. (from Genbank) |
| 120 | Breast | 0.1300902 | 0.4722814 | 0.402019 | 0.279751 | S76978_s_at | Prostate-specific membrane antigen (alternatively spliced) [human, primary prostatic tissues, mRNA Partial, 251 nt] |
| 121 | Breast | 0.1299656 | 0.4716187 | 0.401658 | 0.279578454 | RC_AA2348 30_at | EST: zs38b03.s1 Soares NhHMPu S1 Homo sapiens cDNA clone 687437 3', mRNA sequence. (from Genbank) |
| 122 | Breast | 0.1299156 | 0.4715659 | 0.401536 | 0.279199 | L37378_at | Guanylyl cyclase (RetGC-2) mRNA |
| 123 | Breast | 0.1296486 | 0.4713915 | 0.400846 | 0.2789851 | J05200_s_at | Ryanodine receptor 1 (skeletal) |
| 124 | Breast | 0.1293121 | 0.471321 | 0.400395 | 0.27856982 | RC_D60715_at | EST: Human fetal brain cDNA 3'-end GEN-126H02, mRNA sequence. (from Genbank) |
| 125 | Breast | 0.1284234 | 0.470987 | 0.400225 | 0.2781939 | U97188_at | Putative RNA binding protein KOC (koc) mRNA |
| 126 | Breast | 0.1277191 | 0.4705171 | 0.399834 | 0.27790773 | X59766_at | AZGP1 Zinc-alpha-2-glycoprotein 1 |
| 127 | Breast | 0.1249595 | 0.4703271 | 0.399515 | 0.27775942 | Z21217_at | KIAA0008 gene product |
| 128 | Breast | 0.1232011 | 0.4700199 | 0.399377 | 0.27723655 | M13755_at | G1P2 Interferon, alpha-inducible protein (clone IFI-15K) |
| 129 | Breast | 0.1224186 | 0.4695616 | 0.399132 | 0.2768773 | M59815_at | C4A Complement component 4A |
| 130 | Breast | 0.1212664 | 0.4695155 | 0.398823 | 0.276449262 | RC_AA4769 22_at | EST: zu38c05.s1 Soares ovary tumor NbHOT Homo sapiens cDNA clone 740264 3', mRNA sequence. (from Genbank) |
| 131 | Breast | 0.1196906 | 0.4694306 | 0.398724 | 0.27623805 | U37221_at | Cyclophilin-like protein mRNA, partial cds |
| 132 | Breast | 0.1187918 | 0.4690452 | 0.398279 | 0.27602154 | AA203527_a_t | Homo sapiens ribonuclease P protein subunit p20 (RPP20) mRNA, complete cds |
| 133 | Breast | 0.1183818 | 0.4690452 | 0.397827 | 0.27557287 | M11321_at | GC Group-specific component (vitamin D binding protein) |
| 134 | Breast | 0.1183761 | 0.4689992 | 0.397569 | 0.275379 | Y00970_at | ACR Acrosin |
| 135 | Breast | 0.1180724 | 0.4679385 | 0.397387 | 0.275105981 | U11870_ma_at | Interleukin-8 receptor type A (IL8RBA) gene, promoter and complete cds |
| 136 | Breast | 0.1146055 | 0.4675561 | 0.397198 | 0.27480546 | U03399_at | T-complex protein 10A (TCP10A) mRNA |
| 137 | Breast | 0.1143943 | 0.4674776 | 0.396417 | 0.2745963 | X90568_at | TTN Titin |
| 138 | Breast | 0.114019 | 0.4667178 | 0.396355 | 0.2742709 | T89571_f_at | EST: ye04h07.r1 Homo sapiens cDNA clone 116797 5' similar to contains Alu repetitive element;. (from Genbank) |
| 139 | Breast | 0.113987 | 0.4665307 | 0.396175 | 0.2738823 | L15702_at | BF B-factor, properdin |
| 140 | Breast | 0.1133876 | 0.4663909 | 0.395823 | 0.27358848 | RC_AA3043 44_f_at | EST: EST17092 Aorta endothelial cells, TNF alpha-treated Homo sapiens cDNA 3' end similar to EST containing Alu repeat, mRNA sequence. (from Genbank) |
| 141 | Breast | 0.1132141 | 0.4662151 | 0.395441 | 0.2732057 | M84605_at | PUTATIVE TACHYKININ RECEPTOR |
| 142 | Breast | 0.1129674 | 0.4661736 | 0.395316 | 0.27288175 | R86180_at | EST: yp89g01.r1 Homo sapiens cDNA clone 194544 5'. (from Genbank) |
| 143 | Breast | 0.1124377 | 0.4661096 | 0.395248 | 0.27254072 | RC_AA4649 46_at | EST: aa93h11.s1 Stratagene fetal retina 937202 Homo sapiens cDNA clone 838917 3', mRNA sequence. (from Genbank) |
| 144 | Breast | 0.1117724 | 0.4658541 | 0.394866 | 0.27220443 | M17236_at | HLA CLASS II HISTOCOMPATIBILITY ANTIGEN, DQ(2) ALPHA CHAIN PRECURSOR |

FIG. 2G

| | | | | | |
|---|---|---|---|---|---|
| 145 | Breast | 0.1110564 | 0.4645429 | 0.3942259 | 0.2720548 | RC_AA0195 28_at | EST: ze55b02.s1 Soares retina N2b4HR Homo sapiens cDNA clone 362859 3', mRNA sequence. (from Genbank) |
| 146 | Breast | 0.110723 | 0.4644613 | 0.3942094 | 0.271816688 | Z33905_at | 43kD acetylcholine receptor-associated protein (Rapsyn) |
| 147 | Breast | 0.1097011 | 0.4639846 | 0.3939030 | 0.2716054 | HG2239-HT2324_at | Potassium Channel Protein (Gb:Z11585) |
| 148 | Breast | 0.1078734 | 0.4637789 | 0.3936688 | 0.271133763 | X52005_at | MYL4 Myosin, light polypeptide 4, alkali; atrial, embryonic |
| 149 | Breast | 0.106807 | 0.4637664 | 0.3935780 | 0.271058 | M88579_at | Zinc finger protein (SRE-ZBP) mRNA, 3' end |
| 150 | Breast | 0.106184 | 0.4634257 | 0.3932910 | 0.2707273 | AB000463_s_at | SH3-domain binding protein 2 |
| 151 | Breast | 0.10616657 | 0.4623278 | 0.3929320 | 0.270379780 | AA203649_a_t | EST: zx58e12.r1 Soares fetal liver spleen 1NFLS S1 Homo sapiens cDNA clone 446734 5', mRNA sequence. (from Genbank) |
| 152 | Breast | 0.10591116 | 0.4623278 | 0.3926760 | 0.26987523 | U52827_at | Cri-du-chat region mRNA, clone NIBB11 |
| 153 | Breast | 0.10557779 | 0.4622459 | 0.3925360 | 0.269873763 | X63755_at | High-sulphur keratin |
| 154 | Breast | 0.1052419 | 0.4622331 | 0.3923790 | 0.269953828 | M64936_i_at | Homo sapiens retinoic acid-inducible endogenous retroviral DNA |
| 155 | Breast | 0.1051398 | 0.4621977 | 0.3922870 | 0.2692618 | Y00064_at | CHGB Chromogranin B (secretogranin 1) |
| 156 | Breast | 0.1049577 | 0.4619075 | 0.3919210 | 0.269002696 | AA434329_a_t | EST: zw24g07.r1 Soares ovary tumor NbHOT Homo sapiens cDNA clone 770268 5' similar to contains element TAR1 repetitive element ;, mRNA sequence. (from Genbank) |
| 157 | Breast | 0.10048 | 0.4616584 | 0.3916970 | 0.268873964 | U76376_at | Harakiri, BCL2-interacting protein (contains only BH3 domain) |
| 158 | Breast | 0.1046188 | 0.4614898 | 0.3912480 | 0.268498452 | AA203236_at | EST: zx54g10.r1 Soares fetal liver spleen 1NFLS S1 Homo sapiens cDNA clone 446370 5' similar to contains element PTR5 repetitive element ;, mRNA sequence. (from Genbank) |
| 159 | Breast | 0.1034737 | 0.4614792 | 0.3912280 | 0.268145027 | RC_AA2783 73_at | Homo sapiens mRNA for KIAA0746 protein, partial cds |
| 160 | Breast | 0.1033571 | 0.4613786 | 0.3907390 | 0.267896861 | M19989_cds1_at | Platelet-derived growth factor (PDGFA) A chain gene |
| 161 | Breast | 0.1029475 | 0.461143 | 0.3901890 | 0.267515587 | Y00083_s_at | TGFB2 Transforming growth factor, beta 2 |
| 162 | Breast | 0.1025376 | 0.4610763 | 0.3901360 | 0.26735756 | U40371_at | 3',5' cyclic nucleotide phosphodiesterase (HSPDE1C1A) mRNA |
| 163 | Breast | 0.1023547 | 0.4609028 | 0.3900460 | 0.267107936 | AA418143_a_t | EST: zv97b09.r1 Soares NhHMPu S1 Homo sapiens cDNA clone 767705 5', mRNA sequence. (from Genbank) |
| 164 | Breast | 0.1014101 | 0.460869 | 0.3899661 | 0.266852475 | RC_AA0200 05_at | EST: ze62e11.s1 Soares retina N2b4HR Homo sapiens cDNA clone 363596 3', mRNA sequence. (from Genbank) |
| 165 | Breast | 0.1013909 | 0.4602697 | 0.389591 | 0.26651163 | X13930_f_at | CYTOCHROME P450 IIA6 |
| 166 | Breast | 0.1010564 | 0.4602091 | 0.3893870 | 0.266361935 | D16593_at | HPCA Hippocalcin |
| 167 | Breast | 0.100846 | 0.4598492 | 0.3890780 | 0.266036657 | U96922_at | Inositol polyphosphate 4-phosphatase type II-alpha mRNA |

FIG. 2II

| # | Type | | | | | Accession | Description |
|---|---|---|---|---|---|---|---|
| 168 | Breast | 0.10077 | 0.4594875 | 0.388973 | 0.26585692 | AA410925_at | EST: zv39e11.r1 Soares ovary tumor NbHOT Homo sapiens cDNA clone 756044 5' similar to gb:M99435 TRANSDUCIN-LIKE ENHANCER PROTEIN 1 (HUMAN);, mRNA sequence. (from Genbank) |
| 169 | Breast | 0.1002694 | 0.4593886 | 0.388742 | 0.26557794 | L36529_at | (clone N5-4) protein p84 mRNA |
| 170 | Breast | 0.0987002 | 0.4586633 | 0.388419 | 0.26536882 | M14123_xpt4_at | Neutral protease large subunit from Human endogenous retrovirus HERV-K10./ntype=DNA /annot=CDS |
| 171 | Breast | 0.0983236 | 0.4585121 | 0.388281 | 0.26500675 | D10216_s_at | POU domain, class 1, transcription factor 1 (Pit1, growth hormone factor 1) |
| 172 | Breast | 0.0980842 | 0.458134 | 0.388186 | 0.26479006 | HG4417-HT4687_f_at | Homeotic Protein Hpx-2 |
| 173 | Breast | 0.0980702 | 0.4572411 | 0.387885 | 0.26460913 | X53331_at | MGP Matrix protein gla |
| 174 | Breast | 0.0978578 | 0.4568232 | 0.387839 | 0.26442334 | C14915_at | Homo sapiens Chromosome 16 BAC clone CIT987SK-A-69G12 |
| 175 | Breast | 0.0970478 | 0.456665 | 0.387323 | 0.26423895 | HG4258-HT4528_at | Kinase Inhibitor P27kip1, Cyclin-Dependent |
| 176 | Breast | 0.0954316 | 0.456665 | 0.386864 | 0.264032 | U23070_at | Putative transmembrane protein (nma) mRNA |
| 177 | Breast | 0.0942793 | 0.4561517 | 0.386723 | 0.26381743 | AA021124_at | EST: ze67f10.r1 Soares retina N2b4HR Homo sapiens cDNA clone 364075 5' similar to contains Alu repetitive element;contains element L1 repetitive element ;, mRNA sequence. (from Genbank) |
| 178 | Breast | 0.0933483 | 0.455925 | 0.38664 | 0.26351067 | M62400_at | GABRR1 Gamma-aminobutyric acid (GABA) receptor, rho 1 |
| 179 | Breast | 0.0931456 | 0.4559138 | 0.386298 | 0.26323184 | M20137_at | Interleukin 3 (IL-3) mRNA |
| 180 | Breast | 0.0929915 | 0.45591 | 0.385822 | 0.26303378 | D26561_cds1_at | ORF for L1 protein gene extracted from Human papillomavirus 5b genome integrated into human carcinoma DNA |
| 181 | Breast | 0.0918815 | 0.4554118 | 0.38558 | 0.26274347 | U13369_at | Ribosomal DNA complete repeating unit |
| 182 | Breast | 0.0915385 | 0.4554013 | 0.385333 | 0.2625152 | W39573_at | EST: zc20b05.r1 Soares senescent fibroblasts NbHSF Homo sapiens cDNA clone 322833 5', mRNA sequence. (from Genbank) |
| 183 | Breast | 0.0906031 | 0.4553969 | 0.385171 | 0.26232597 | RC_D20426_at | EST: Human HL60 3'directed MboI cDNA, HUMGS01400, clone pm2764, mRNA sequence. (from Genbank) |
| 184 | Breast | 0.0904789 | 0.4550578 | 0.385048 | 0.26210921 | HG742-HT742_at | Latent Membrane Protein Lmp1 |
| 185 | Breast | 0.0901848 | 0.4549179 | 0.384871 | 0.26187799 | D26561_cds3_at | ORF for E7 protein gene extracted from Human papillomavirus 5b genome integrated into human carcinoma DNA |
| 186 | Breast | 0.0901116 | 0.4545414 | 0.384438 | 0.26171422 | T83444_at | Homo sapiens mRNA for KIAA0887 protein, partial cds |
| 187 | Breast | 0.0894928 | 0.4542728 | 0.384292 | 0.26138297 | RC_AA404609_s_at | EST: zf43h04.s1 Soares ovary tumor NbHOT Homo sapiens cDNA clone 725143 3', mRNA sequence. (from Genbank) |
| 188 | Breast | 0.089386 | 0.454048 | 0.383972 | 0.26089674 | HG3286-HT3463_at | Crystallin, Alpha A |

FIG. 2I

| | | | | | | |
|---|---|---|---|---|---|---|
| 189 | Breast | 0.093384 | 0.454038 | 0.383734 | 0.2607195 t | AA491376_a t | EST: aa65o11.r1 NCI_CGAP_GCB1 Homo sapiens cDNA clone IMAGE:825836 5', mRNA sequence. (from Genbank) |
| 190 | Breast | 0.0887464 | 0.4539805 | 0.383516 | 0.26041833 | T47519_at | Genethonin 1 |
| 191 | Breast | 0.0887102 | 0.4536992 | 0.383402 | 0.26013142 | HG3987-HT4257_at | Cpg Enriched Dna, Clone E06 |
| 192 | Breast | 0.0884397 | 0.45333 | 0.3832212 | 0.25995356 | RC_AA0020 06_at | EST: zh86a01.s1 Soares fetal liver spleen 1NFLS S1 Homo sapiens cDNA clone 428136 3', mRNA sequence. (from Genbank) |
| 193 | Breast | 0.0883572 | 0.4527864 | 0.383177 | 0.25966272 | HG25930-HT26386_at | Estradiol 17-beta dehydrogenase 1 |
| 194 | Breast | 0.0882548 | 0.4525867 | 0.382907 | 0.25936133 t | AA136315_a t | EST: zn82e03.r1 Stratagene lung carcinoma 937218 Homo sapiens cDNA clone 564700 5', mRNA sequence. (from Genbank) |
| 195 | Breast | 0.0881491 | 0.4525816 | 0.382771 | 0.25924832 | U43843_at | H-neuro-d4 protein mRNA |
| 196 | Breast | 0.0874548 | 0.4524845 | 0.382335 | 0.25912717 | J04621_at | SDC2 Syndecan 2 (heparan sulfate proteoglycan 1, cell surface-associated, fibroglycan) |
| 197 | Breast | 0.0874048 | 0.4523321 | 0.381941 | 0.25873658 | Z83805_at | Axonemal dynein heavy chain (partial, ID hdhc8) |
| 198 | Breast | 0.087352 | 0.4521794 | 0.381660 | 0.25856188 | M63896_at | Transcriptional enhancer factor (TEF1) DNA |
| 199 | Breast | 0.0868997 | 0.4520838 | 0.381586 | 0.25830814 | HG3729-HT3999_f_at | Homeotic Protein Hpx-5 |
| 200 | Breast | 0.0860977 | 0.4518668 | 0.381404 | 0.25818882 | RC_AA4646 96_at | EST: zx82u10.s1 Soares ovary tumor NbHOT Homo sapiens cDNA clone 810234 3', mRNA sequence. (from Genbank) |
| 201 | Breast | 0.0858226 | 0.4518275 | 0.381089 | 0.2580243 t | X72304_s_a t | Corticotropin releasing hormone receptor 1 |
| 202 | Breast | 0.085196 | 0.4518275 | 0.380869 | 0.25784394 | R22178_at | Homo sapiens CAGF28 mRNA, partial cds |
| 203 | Breast | 0.084483 | 0.4511711 | 0.380622 | 0.25766003 | L02840_at | Potassium channel Kv2.1 mRNA |
| 204 | Breast | 0.084328 | 0.4510919 | 0.380431 | 0.25742084 t | AA495729_a t | EST: zw04a10.r1 Soares NhHMPu S1 Homo sapiens cDNA clone 768282 5', mRNA sequence. (from Genbank) |
| 205 | Breast | 0.083469 | 0.45093 | 0.380043 | 0.2571851 | H66279_at | Yr72b07.r1 Homo sapiens cDNA clone 210805 5'. (from Genbank) |
| 206 | Breast | 0.0832062 | 0.4509069 | 0.379974 | 0.25698048 t | AA421370_a t | EST: zu06c06.r1 Soares testis NHT Homo sapiens cDNA clone 731074 5' similar to contains MER17.t2 MER17 repetitive element ;, mRNA sequence. (from Genbank) |
| 207 | Breast | 0.0829828 | 0.450154 | 0.379476 | 0.25673324 | U24488_s_a t | CYP21 Cytochrome P450, subfamily XXI (steroid 21-hydroxylase, congenital adrenal hyperplasia) |
| 208 | Breast | 0.0820699 | 0.450076 | 0.379348 | 0.2563814 | X16662_at | ANX8 Annexin VIII |
| 209 | Breast | 0.0811764 | 0.4498118 | 0.379243 | 0.25612888 | M35198_at | Integrin B 6 mRNA |
| 210 | Breast | 0.0809659 | 0.4497008 | 0.370873 | 0.25604665 | HG3513-HT3707_at | Myosin, Heavy Polypeptide, Light Meromyosin |

*FIG. 2J*

| # | Tissue | | | | ID | Description |
|---|---|---|---|---|---|---|
| 211 | Breast | 0.0806473 | 0.4494901 | 0.378617 | 0.25580257 R81217_at | Yj03b09.r1 Homo sapiens cDNA clone 147641 5' similar to gb:X54156_rna1 CELLULAR TUMOR ANTIGEN P53 (HUMAN);contains Alu repetitive element;. (from Genbank) |
| 212 | Breast | 0.0795012 | 0.4492681 | 0.378224 | 0.25556183 HG3264-HT3441_at | Af-6 (Gb:U02478) |
| 213 | Breast | 0.0794716 | 0.4491743 | 0.378136 | 0.25532648 L37199_at | (clone cD24-1) Huntington's disease candidate region mRNA fragment |
| 214 | Breast | 0.0788738 | 0.4490815 | 0.37803 | 0.25504974 U07225_at | P2U nucleotide receptor mRNA |
| 215 | Breast | 0.0785972 | 0.4490149 | 0.37761 | 0.25483087 HG2530-HT2626_at | Adenylyl Cyclase-Associated Protein 2 |
| 216 | Breast | 0.0782644 | 0.4489539 | 0.377537 | 0.25459158 U85265_at | Down syndrome candidate region 1 (DSCR1) gene, alternative exon 1 |
| 217 | Breast | 0.0780549 | 0.4486558 | 0.377337 | 0.25433654 U33920_at | Clone lambda 5 semaphorin mRNA |
| 218 | Breast | 0.077293 | 0.4483567 | 0.377062 | 0.25409475 R93659_at | Homo sapiens mRNA for KIAA0871 protein, complete cds |
| 219 | Breast | 0.0762319 | 0.4482782 | 0.376916 | 0.25394967 Z21244_at | Homo sapiens brain expressed ring finger protein mRNA, complete cds |
| 220 | Breast | 0.075748 | 0.4476327 | 0.37681 | 0.25383845 HG3242-HT4231_s_at | Calcium Channel, Voltage-Gated, Alpha 1e Subunit, Alt. Splice 3 |
| 221 | Breast | 0.0751439 | 0.4469373 | 0.376733 | 0.25367084 X16666_s_at | HOXB1 Homeo box B1 |
| 222 | Breast | 0.0751439 | 0.4468566 | 0.376361 | 0.2533031 X16666_s_at-2 | Homeo box B1 |
| 223 | Breast | 0.0744652 | 0.4465658 | 0.376361 | 0.253102176 RC_AA0478_at | EST: zf50b08.s1 Soares retina N2b4HR Homo sapiens cDNA clone 3803343 3' similar to contains Alu repetitive element;contains element L1 repetitive element :, mRNA sequence. (from Genbank) |
| 224 | Breast | 0.0743978 | 0.4462747 | 0.375912 | 0.25291532 N42022_at | EST: yw69g06.r1 Homo sapiens cDNA clone 257530 5'. (from Genbank) |
| 225 | Breast | 0.0741908 | 0.4457812 | 0.375763 | 0.25279006 H81340_at | EST: yu74d04.r1 Homo sapiens cDNA clone 239527 5'. (from Genbank) |
| 226 | Breast | 0.0738568 | 0.4453105 | 0.375614 | 0.25244242 HG2465-HT4871_at | Dna-Binding Protein Ap-2, Alt. Splice 3 |
| 227 | Breast | 0.0738299 | 0.4452643 | 0.375241 | 0.25228813 W36279_at | EST: HFBEST-56 Human fetal brain QBoqin2 Homo sapiens cDNA, mRNA sequence. (from Genbank) |
| 228 | Breast | 0.0728815 | 0.4451951 | 0.375201 | 0.25211945 M57506_rna1_at | SCYA1 gene (secreted protein I-309) extracted from Human secreted protein (I-309) gene |
| 229 | Breast | 0.0728505 | 0.4448771 | 0.375194 | 0.25192085 M34041_at | Alpha-2-adrenergic receptor (alpha-2 c2) gene |
| 230 | Breast | 0.0722495 | 0.4446217 | 0.375006 | 0.25160065 AA383703_i_at | EST97119 Testis I Homo sapiens cDNA 5' end similar to similar to zinc finger protein ZNF2, mRNA sequence. (from Genbank) |

FIG. 2K

| | | | | | | |
|---|---|---|---|---|---|---|
| 231 | Breast | 0.0719913 | 0.4442761 | 0.374782 | 0.25141132 | D85939_at | P97 homologous protein |
| | | | | | M30625_s_a | |
| 232 | Breast | 0.0712931 | 0.4433541 | 0.374466 | 0.251183 t | | Dopamine D2 receptor, mRNA |
| 233 | Breast | 0.0708416 | 0.4429643 | 0.374334 | 0.25102973 | D25215_at | KIAA0032 gene |
| 234 | Breast | 0.0707776 | 0.4426866 | 0.374219 | 0.2508405 | J05037_at | L-SERINE DEHYDRATASE |
| 235 | Breast | 0.0706308 | 0.4422134 | 0.373929 | 0.25060964 | L36644_at | Receptor protein-tyrosine kinase (HEK7) mRNA, 3' end |
| 236 | Breast | 0.0702981 | 0.4417023 | 0.37371 | 0.25033116 | W23474_at | EST: zb33d08.r1 Soares parathyroid tumor NbHPA Homo sapiens cDNA clone 305391 5' mRNA sequence. (from Genbank) |
| 237 | Breast | 0.0701355 | 0.4417023 | 0.373493 | 0.25025654 | D90042_at | AAC2 Arylamine N-acetyltransferase, liver |
| 238 | Breast | 0.0698778 | 0.4415626 | 0.373388 | 0.25010458 | M77235_at | Cardiac tetrodotoxin-insensitive voltage-dependent sodium channel alpha subunit (HH1) mRNA |
| 239 | Breast | 0.0692833 | 0.4412475 | 0.373298 | 0.24990846 | W28734_at | EST: 51a1 Human retina cDNA randomly primed sublibrary Homo sapiens cDNA, mRNA sequence. (from Genbank) |
| 240 | Breast | 0.0689706 | 0.4412266 | 0.373272 | 0.24972571 | U54804_at | Has2 mRNA |
| 241 | Breast | 0.0678918 | 0.4411619 | 0.372969 | 0.24958886 RC_AA2567 00_at | | Interferon (alpha, beta and omega) receptor 2 |
| 242 | Breast | 0.0677066 | 0.4408702 | 0.372733 | 0.24928777 | X03635_at | ESR Estrogen receptor |
| 243 | Breast | 0.0675199 | 0.4407296 | 0.372691 | 0.24901806 | HG3517-HT3711_at | Alpha-1-Antitrypsin, 5' End |
| 244 | Breast | 0.0664876 | 0.4403656 | 0.372384 | 0.24878873 | M77144_ma 1_at | 3-beta-hydroxysteroid dehydrogenase gene extracted from Human type II 3-beta hydroxysteroid dehydrogenase/ 5-delta - 4-delta isomerase gene |
| 245 | Breast | 0.0662882 | 0.4401698 | 0.37231 | 0.24874993 | U17327_at | NOS1 Nitric oxide synthase 1 (neuronal) |
| 246 | Breast | 0.0660346 | 0.4401118 | 0.37189 | 0.24857435 | AFFX-BioB-M_st-2 | AFFX-BioB-M_st (miscellaneous control - 11k chips) |
| 247 | Breast | 0.0660346 | 0.440044 | 0.371659 | 0.24838617 | AFFX-BioB-M_st | AFFX-BioB-M_st (endogenous control) |
| 248 | Breast | 0.0659636 | 0.4400162 | 0.371623 | 0.24821983 | N78064_at | EST: yv72a02.r1 Soares fetal liver spleen 1NFLS Homo sapiens cDNA clone 248234 5' mRNA sequence. (from Genbank) |
| 249 | Breast | 0.0656123 | 0.4399824 | 0.371388 | 0.248083 | U41060_at | Breast cancer, estrogen regulated LIV-1 protein (LIV-1) mRNA, partial cds |
| 250 | Breast | 0.0651987 | 0.4396983 | 0.371382 | 0.24775968 AA306051_a t | AB000381_s_at | DNA for GPI-anchored molecule-like protein |
| 251 | Breast | 0.0651089 | 0.4396983 | 0.371102 | 0.24764815 t | | KIAA0683 gene product |
| 252 | Breast | 0.0650498 | 0.4396549 | 0.37101 | 0.24739484 | U43408_at | Tyrosine kinase (TnkI) mRNA |
| 253 | Breast | 0.0648255 | 0.4394252 | 0.370813 | 0.24703103 t | AA167043_a | EST: zo86d03.r1 Stratagene ovarian cancer (#937219) Homo sapiens cDNA clone 593765 5' mRNA sequence. (from Genbank) |

FIG. 2L

| | | | | | |
|---|---|---|---|---|---|
| 254 | Breast | 0.064351 | 0.4391809 | 0.37063 | 0.24686624 | AA167824_a_t | Cell division cycle 27 |
| 255 | Breast | 0.0639453 | 0.4385929 | 0.370405 | 0.24679068 | AA401575_a_t | EST: zu62b07.r1 Soares testis NHT Homo sapiens cDNA clone 742549 5', mRNA sequence. (from Genbank) |
| 256 | Breast | 0.0636319 | 0.4385899 | 0.370254 | 0.2466424 | M31606_at | PHKG2 Phosphorylase kinase, gamma 2 (testis) |
| 257 | Breast | 0.0635282 | 0.4383332 | 0.370114 | 0.2463463 | U47050_at | Putative calcium influx channel (htrp3) mRNA |
| 258 | Breast | 0.0632544 | 0.4382424 | 0.369904 | 0.24618948 | D79995_at | KIAA0173 gene |
| 259 | Breast | 0.0631949 | 0.4379791 | 0.369622 | 0.24601673 | X00371_rna1_at | Myoglobin gene (exon 1) (and joined CDS) |
| 260 | Breast | 0.0631807 | 0.4376267 | 0.369486 | 0.2458327 | HG273-HT273_at | Lymphocyte Antigen I-Ia-G3 |
| 261 | Breast | 0.0622801 | 0.4371998 | 0.36945 | 0.24569954 | RC_AA485945_at | EST: ab40g02.s1 Stratagene HeLa cell s3 937216 Homo sapiens cDNA clone 843314 3' similar to SW:SOH1_YEAST P38633 SOH1 PROTEIN. [1].; mRNA sequence. (from Genbank) |
| 262 | Breast | 0.0618249 | 0.437025 | 0.369222 | 0.2455889 | U14577_s_at | MAP1A Microtubule-associated protein 1A |
| 263 | Breast | 0.0615094 | 0.4367154 | 0.36913 | 0.2452498 | M60614_at | WT1 Wilms tumor 1 |
| 264 | Breast | 0.0614224 | 0.4366623 | 0.369032 | 0.2451102 | X87870_at | HEPATOCYTE NUCLEAR FACTOR 4 |
| 265 | Breast | 0.0612097 | 0.436333 | 0.368989 | 0.24490054 | X87767_at | CD89 gene, exon S1 |
| 266 | Breast | 0.0611846 | 0.4362189 | 0.368713 | 0.24461812 | RC_AA495926_at | EST: zw05h01.s1 Soares NhHMPu S1 Homo sapiens cDNA clone 768433 3', mRNA sequence. (from Genbank) |
| 267 | Breast | 0.0608841 | 0.4361712 | 0.368417 | 0.24444053 | RC_AA176867_at | EST: zp11f06.s1 Stratagene fetal retina 937202 Homo sapiens cDNA clone 609155 3', mRNA sequence. (from Genbank) |
| 268 | Breast | 0.0608838 | 0.4361123 | 0.368366 | 0.24417712 | U79301_at-2 | Human clone 23842 mRNA sequence |
| 269 | Breast | 0.0608838 | 0.4359367 | 0.368173 | 0.24408029 | U79301_at | Clone 23842 mRNA sequence |
| 270 | Breast | 0.0600718 | 0.4357036 | 0.367956 | 0.24391416 | N76208_at | EST: yv37b01.r1 Soares fetal liver spleen 1NFLS Homo sapiens cDNA clone 244873 5' similar to contains Alu repetitive element.; mRNA sequence. (from Genbank) |
| 271 | Breast | 0.0599743 | 0.4354258 | 0.367793 | 0.24376059 | RC_AA398533_at | EST: zf73b05.s1 Soares testis NHT Homo sapiens cDNA clone 727953 3', mRNA sequence. (from Genbank) |
| 272 | Breast | 0.0594209 | 0.4353869 | 0.367737 | 0.24354558 | AA476704_a_t | EST: zw87h02.r1 Soares total fetus Nb2HF8 9w Homo sapiens cDNA clone 783987 5', mRNA sequence. (from Genbank) |
| 273 | Breast | 0.0583071 | 0.4352838 | 0.367392 | 0.24339215 | D12485_at | Plasma cell membrane glycoprotein (PC-1) mRNA |
| 274 | Breast | 0.0581647 | 0.4349373 | 0.367376 | 0.24315822 | HG961-HT961_at | Guanine Nucleotide Exchange Factor 2 |
| 275 | Breast | 0.0576567 | 0.4349053 | 0.367353 | 0.24302986 | RC_AA453794_at | EST: aa19f07.s1 Soares NhHMPu S1 Homo sapiens cDNA clone 813733 3', mRNA sequence. (from Genbank) |
| 276 | Breast | 0.0574047 | 0.4347637 | 0.36699 | 0.24288869 | L13436_at | Guanylate cyclase mRNA, complete mature peptide |

FIG. 2M

| # | Tissue | | | | ID | Description |
|---|---|---|---|---|---|---|
| 277 | Breast | 0.0572155 | 0.4346257 | 0.366675 | 0.24273749 | RC_AA0585 32_at | EST: zf56d07.s1 Soares retina N2b4HR Homo sapiens cDNA clone 3809413', mRNA sequence. (from Genbank) |
| 278 | Breast | 0.0572026 | 0.4346257 | 0.366623 | 0.24258459 | J05158_at | CARBOXYPEPTIDASE N 83 KD CHAIN |
| 279 | Breast | 0.0570774 | 0.4344572 | 0.366476 | 0.24235624 | HG862-HT862_s_at | Transition Protein 2 |
| 280 | Breast | 0.0565533 | 0.4340626 | 0.3664 | 0.24216034 | L46353_at | High-mobility group phosphoprotein (HMGI-C) gene, exons 1-3 |
| 281 | Breast | 0.0564789 | 0.4340217 | 0.366241 | 0.24203654 | W27720_at | Protocadherin 9 |
| 282 | Breast | 0.0563111 | 0.4339662 | 0.366168 | 0.24187939 | AA128724_a_t | Homo sapiens mRNA for KIAA0684 protein, partial cds |
| 283 | Breast | 0.0556628 | 0.4336168 | 0.365815 | 0.24177678 | D90359_at | TRANSCRIPTION INITIATION FACTOR TFIID 250 KD SUBUNIT |
| 284 | Breast | 0.0551652 | 0.4335797 | 0.365773 | 0.24159646 | U90065_s_a_t | Potassium channel KCNO1 mRNA |
| 285 | Breast | 0.0550014 | 0.4335654 | 0.365593 | 0.24146628 | U22970_ma 1_s_at | 6-16 gene (interferon-inducible peptide precursor) extracted from Human interferon-inducible peptide (6-16) gene |
| 286 | Breast | 0.0548055 | 0.4334755 | 0.365142 | 0.24118869 | U58496_s_a_t | Dual-specificity tyrosine-(Y)-phosphorylation regulated kinase 1 |
| 287 | Breast | 0.0533756 | 0.4332961 | 0.365029 | 0.24102162 | Z20656_rna 1_s_at | Of cardiac alpha-myosin heavy chain gene |
| 288 | Breast | 0.0531498 | 0.4329981 | 0.364834 | 0.24071202 | U49974_f_at | Mariner2 transposable element, complete consensus sequence |
| 289 | Breast | 0.052965 | 0.4329616 | 0.364589 | 0.24060303 | S74683_at | ADP-ribosyltransferase [human, skeletal muscle, mRNA, 1334 nt] |
| 290 | Breast | 0.0529083 | 0.4325464 | 0.36427 | 0.24048653 | D00003_s_at | CYP3A3 Cytochrome P450 IIIA3 (nifedipine oxidase chain 3) |
| 291 | Breast | 0.0527766 | 0.4322473 | 0.364101 | 0.24030784 | U14910_at | RPE-retinal G protein-coupled receptor (rgr) mRNA |
| 292 | Breast | 0.0526866 | 0.4320349 | 0.363995 | 0.24019569 | RC_AA6203 95_at | EST: ae57c05.s1 Stratagene lung carcinoma 937218 Homo sapiens cDNA clone 950984 3', mRNA sequence. (from Genbank) |
| 293 | Breast | 0.0526438 | 0.4317145 | 0.36396 | 0.23997691 | AA022985_a_t | EST: ze72g05.r1 Soares fetal heart NbHH19W Homo sapiens cDNA clone 364568 5', mRNA sequence. (from Genbank) |
| 294 | Breast | 0.0521825 | 0.4316921 | 0.363931 | 0.23974888 | X51755_cds 5_s_at | Ig light-chain, partial Ke-Oz- polypeptide; Author-given protein sequence is in conflict with the conceptual translation gene extracted from Human lambda-immunoglobulin constant region complex (germline) |
| 295 | Breast | 0.0515696 | 0.4314752 | 0.363878 | 0.23960805 | J04177_at | COL11A1 Collagen, type XI, alpha 1 |
| 296 | Breast | 0.0514911 | 0.4312466 | 0.363852 | 0.2394968 | D83017_s_a_t | Nel-related protein |
| 297 | Breast | 0.0513471 | 0.4312331 | 0.363752 | 0.23934166 | AA416829_a_t | EST: zu08e03.r1 Soares testis NHT Homo sapiens cDNA clone 731260 5', mRNA sequence. (from Genbank) |
| 298 | Breast | 0.0508588 | 0.4311984 | 0.363719 | 0.23911104 | U58658_at | Unknown protein mRNA within the p53 intron 1 |

FIG. 2N

| # | Tissue | | | | Description |
|---|---|---|---|---|---|
| 299 | Breast | 0.0502055 | 0.4310185 | 0.363266 | 0.233979916 U09278_at | Fibroblast activation protein mRNA |
| 300 | Breast | 0.0488758 | 0.4309234 | 0.363095 | AA085696_a_a | EST: zf83a10.r1 Stratagene colon (#937204) Homo sapiens cDNA clone 511194 5', mRNA sequence. (from Genbank) |
| 301 | Breast | 0.0479617 | 0.4307557 | 0.362373 | 0.238890045_t | |
| | | | | | 0.2387299 S85963_at | Insulin receptor substrate-1 [human, skeletal muscle, mRNA, 5828 nt] |
| 302 | Breast | 0.0476915 | 0.4306579 | 0.362356 | W92242_s_at | EST: ze14b12.r1 Soares fetal heart NbHH19W Homo sapiens cDNA clone 358943 5' similar to PIR:A49128 A49128 cell-fate determining gene Notch2 product:; mRNA sequence. (from Genbank) |
| 303 | Breast | 0.0473838 | 0.4300758 | 0.362329 | X02761_s_a_t | FN1 Fibronectin 1 |
| 304 | Breast | 0.0473665 | 0.4300495 | 0.362237 | RC_AA4304 96_r_at | Ferritin, light polypeptide |
| 305 | Breast | 0.0465526 | 0.4300495 | 0.361832 | 0.238825729 D38128_at | PTGIR Prostaglandin I2 (prostacyclin) receptor (IP) |
| 306 | Breast | 0.0465065 | 0.4299312 | 0.361756 | 0.238103/8 M14113_at | F8C Coagulation factor VIIIc (hemophilia A) |
| 307 | Breast | 0.0455725 | 0.4297436 | 0.361555 | 0.2377587 U32907_at | P37NB mRNA |
| 308 | Breast | 0.0454797 | 0.4297331 | 0.361199 | 0.237555975 L32137_at | COMP Cartilage oligomeric matrix protein |
| 309 | Breast | 0.0454438 | 0.429525 | 0.360914 | 0.237377626 M29335_at | MHC class II DO-alpha mRNA, partial cds |
| 310 | Breast | 0.0453906 | 0.4294729 | 0.360901 | 0.237177825 Y08417_s_at | CHRNB3 Cholinergic receptor, nicotinic, beta polypeptide 3 |
| 311 | Breast | 0.0453211 | 0.428889 | 0.360804 | 0.2370/376 U40215_at | SYN2 Synapsin IIb |
| 312 | Breast | 0.0447517 | 0.4288699 | 0.36077 | AA059287_s_at | EST: zf65e02.r1 Soares retina N2b4HR Homo sapiens cDNA clone 381818 5', mRNA sequence. (from Genbank) |
| 313 | Breast | 0.0447441 | 0.4284469 | 0.360739 | 0.236/3148 AA287815_a_t | EST: zs50g04.r1 NCI_CGAP_GCB1 Homo sapiens cDNA clone IMAGE:700950 5', mRNA sequence. (from Genbank) |
| 314 | Breast | 0.0444217 | 0.4283626 | 0.36061 | 0.236641/06 HG1098-HT1098_at | Cystatin D |
| 315 | Breast | 0.0436385 | 0.4283383 | 0.36046 | AA149560_a_a | EST: zo29d07.r1 Stratagene colon (#937204) Homo sapiens cDNA clone 588301 5', mRNA sequence. (from Genbank) |
| 316 | Breast | 0.0429564 | 0.4283285 | 0.360242 | 0.236358894 Z34975_at | LDLC mRNA |
| 317 | Breast | 0.0428684 | 0.4281687 | 0.36016 | 0.236202261 AA443479_a_t | Nuclear restricted protein, BTB domain-like (brain) |
| 318 | Breast | 0.0422923 | 0.4278965 | 0.360067 | 0.236600549 Z26256_at | Isoform 1 gene for L-type calcium channel, exon 1 |
| 319 | Breast | 0.0420966 | 0.4277256 | 0.35998 | 0.235589963 M94167_at | HGL Heregulin alpha |
| 320 | Breast | 0.0412446 | 0.4276507 | 0.359764 | 0.235580083 H47945_at | Lysozyme (renal amyloidosis) |
| 321 | Breast | 0.0409508 | 0.4274165 | 0.359641 | 0.235600052 R80351_at | EST: yi96e02.r1 Homo sapiens cDNA clone 147098 5'. (from Genbank) |
| 322 | Breast | 0.0409182 | 0.4274137 | 0.359524 | 0.235497/4 M11973_cds 1_at | Gamma-B-crystallin gene (gamma 1-2) |

FIG. 20

| | | | | | | |
|---|---|---|---|---|---|---|
| 323 | Breast | 0.0407245 | 0.4272869 | 0.359415 | 0.235199807 | W16700_at | EST: zb07e12.r1 Soares fetal lung NbHL19W Homo sapiens cDNA clone 301390 5', mRNA sequence. (from Genbank) |
| 324 | Breast | 0.040571 | 0.4272169 | 0.35934 | 0.235503631 | RC_D19756_at | EST: Human HL60 3'directed MboI cDNA, HUMGS00712, clone mm0970, mRNA sequence. (from Genbank) |
| 325 | Breast | 0.0405646 | 0.4269071 | 0.359249 | 0.234889252 | S69369_at | PAX3 Paired box homeotic gene 3 (Waardenburg syndrome 1){alternative products}] |
| 326 | Breast | 0.0404366 | 0.4268203 | 0.359135 | 0.234464967 | AA074897_a_t | Zm85a05.r1 Stratagene ovarian cancer (#937219) Homo sapiens cDNA clone 544688 5' similar to SW:ANRE_MOUSE P15267 KIDNEY ANDROGEN-REGULATED PROTEIN PRECURSOR ;, mRNA sequence. (from Genbank) |
| 327 | Breast | 0.0401511 | 0.4267538 | 0.358894 | 0.234496679 | X72308_at | MONOCYTE CHEMOTACTIC PROTEIN 3 PRECURSOR |
| 328 | Breast | 0.0401511 | 0.4262991 | 0.358715 | 0.2343904 | X72308_at-2 | Small inducible cytokine A7 (monocyte chemotactic protein 3) |
| 329 | Breast | 0.0399904 | 0.4257574 | 0.358466 | 0.2343198 | D21239_at | C3G protein |
| 330 | Breast | 0.0397158 | 0.4256842 | 0.358429 | 0.234412012 | AA0819995_a_t | Zn26d06.r1 Stratagene neuroepithelium NT2RAMI 937234 Homo sapiens cDNA clone 548555 5', mRNA sequence. (from Genbank) |
| 331 | Breast | 0.0396951 | 0.4256407 | 0.358341 | 0.23407412 | D14827_at | Tax helper protein 1 |
| 332 | Breast | 0.0396004 | 0.4253073 | 0.358213 | 0.233386289 | AFFX-LysX-3_at-2 | AFFX-LysX-3_at (miscellaneous control - 11k chips) |
| 333 | Breast | 0.0396004 | 0.4252924 | 0.358204 | 0.233363796 | AFFX-LysX-3_at | AFFX-LysX-3_at (endogenous control) |
| 334 | Breast | 0.0394851 | 0.4251626 | 0.358092 | 0.233353318 | D84424_at | Fetal brain mRNA for hyaluronan synthase |
| 335 | Breast | 0.0394712 | 0.4248546 | 0.358007 | 0.233343225 | U20362_at | Tg737 mRNA |
| 336 | Breast | 0.0394526 | 0.4247103 | 0.357475 | 0.23333058 | RC_AA0262180_at | EST: ze91d10.s1 Soares fetal heart NbHH19W Homo sapiens cDNA clone 363355 3', mRNA sequence. (from Genbank) |
| 337 | Breast | 0.0394317 | 0.4246177 | 0.357429 | 0.233319118 | W40374_at | DiGeorge syndrome critical region gene 2 |
| 338 | Breast | 0.0393458 | 0.424216 | 0.357374 | 0.23299167 | S73885_s_at | TFAP4 Transcription factor AP-4 (activating enhancer-binding protein 4)) |
| 339 | Breast | 0.0388353 | 0.4242154 | 0.357075 | 0.2328101 | U48807_at | Dual specific protein phosphatase mRNA |
| 340 | Breast | 0.0388174 | 0.4240757 | 0.356852 | 0.23268871 | U36501_at | SP100 Nuclear antigen Sp100 |
| 341 | Breast | 0.03860099 | 0.4239275 | 0.356795 | 0.2325892 | U03877_at | HEAT SHOCK 70 KD PROTEIN 1 |
| 342 | Breast | 0.0379743 | 0.4235694 | 0.356711 | 0.232248078 | RC_AA5995183_at | Homo sapiens mRNA for HIS1 protein, complete cds |
| 343 | Breast | 0.0377849 | 0.4235688 | 0.356475 | 0.232232062 | H16876_at | Ym34f05.r1 Homo sapiens cDNA clone 50123 5'. (from Genbank) |
| 344 | Breast | 0.037663 | 0.4235247 | 0.356319 | 0.23208803 | X52011_at | MYF6 Muscle determination factor |
| 345 | Breast | 0.0366197 | 0.4234619 | 0.3561 | 0.231193462 | X87871_s_a_t | HEPATOCYTE NUCLEAR FACTOR 4 |
| 346 | Breast | 0.0364763 | 0.4233822 | 0.3557739 | 0.23178133 | AA075998_a_t | Zm89b09.r1 Stratagene ovarian cancer (#937219) Homo sapiens cDNA clone 545081 5' similar to gb:M15887 ACYL-COA-BINDING PROTEIN (HUMAN) ;, mRNA sequence. (from Genbank) |

FIG. 2P

| | | | | | |
|---|---|---|---|---|---|
| 347 | Breast | 0.0363521 | 0.423366 | 0.355707 | 0.23166208 | S66096_at | SCCA1 Squamous cell carcinoma antigen 1 |
| 348 | Breast | 0.0360756 | 0.4233335 | 0.355642 | 0.23153605 | U08191_s_at | R kappa B mRNA |
| 349 | Breast | 0.0359679 | 0.4232217 | 0.35535 | 0.23138444 | U19180_at | BAGE B melanoma antigen |
| 350 | Breast | 0.0358032 | 0.4230258 | 0.355297 | 0.23112569 | Y00503_at | KRT19 Keratin 19 |
| 351 | Breast | 0.0355254 | 0.4230037 | 0.355119 | 0.23111542 | U60319_at | HLA-H MHC protein HLA-H (hereditary haemochromatosis) |
| 352 | Breast | 0.0353821 | 0.4228246 | 0.355104 | 0.23103241 | Z48519_s_at | XG gene (clone RACE5) |
| 353 | Breast | 0.0353715 | 0.4227985 | 0.355041 | 0.23095721 | S79267_at | CD4 CD4 antigen (p55) |
| 354 | Breast | 0.0350129 | 0.4226657 | 0.35504 | 0.23072314 | U69961_at-2 | Paired-like homeodomain transcription factor 2 |
| 355 | Breast | 0.0350129 | 0.4226657 | 0.35504 | 0.23061174 | U69961_at | RIEG Rieger syndrome (solurshin) |
| 356 | Breast | 0.034632 | 0.4225272 | 0.354839 | 0.23044913 | AA419502_a t | EST: zv03b02.r1 Soares NhHMPu S1 Homo sapiens cDNA clone 752523 5', mRNA sequence. (from Genbank) |
| 357 | Breast | 0.0343895 | 0.42246 | 0.354758 | 0.23033246 | RC_AA2564 85_at | EST: zr81e12.s1 Soares NhHMPu S1 Homo sapiens cDNA clone 682126 3', mRNA sequence. (from Genbank) |
| 358 | Breast | 0.03433283 | 0.4221102 | 0.354568 | 0.23021527 | RC_AA3427 80_at | EST: EST48360 Fetal spleen Homo sapiens cDNA 3' end, mRNA sequence. (from Genbank) |
| 359 | Breast | 0.0341753 | 0.4218956 | 0.354511 | 0.23003007 | RC_AA6101 21_at | EST: af19h05.s1 Soares total fetus Nb2HF8 9w Homo sapiens cDNA clone 1032153 3', mRNA sequence. (from Genbank) |
| 360 | Breast | 0.0333477 | 0.4217951 | 0.354484 | 0.22997577 | U82108_s_a t-2 | Solute carrier family 9 (sodium/hydrogen exchanger), isoform 3 regulatory factor 2 |
| 361 | Breast | 0.0333477 | 0.4212153 | 0.354359 | 0.22977675 | U82108_s_a t | SIP-1 mRNA |
| 362 | Breast | 0.0329759 | 0.4209298 | 0.354019 | 0.22964463 | U09770_at | Cysteine-rich heart protein (hCRHP) mRNA |
| 363 | Breast | 0.032789 | 0.4207739 | 0.353884 | 0.22948655 | U31628_at | IL15RA Interleukin 15 receptor alpha chain |
| 364 | Breast | 0.0316908 | 0.420761 | 0.353641 | 0.22928058 | RC_AA2812 95_at | EST: zt08g01.s1 NCI_CGAP_GCB1 Homo sapiens cDNA clone IMAGE:712560 3', mRNA sequence. (from Genbank) |
| 365 | Breast | 0.0316539 | 0.4205315 | 0.353108 | 0.22914945 | AA197134_a t | EST: zq11b11.r1 Stratagene muscle 937209 Homo sapiens cDNA clone 6293/3 5', mRNA sequence. (from Genbank) |
| 366 | Breast | 0.0314347 | 0.420473 | 0.353212 | 0.22899526 | AA378316_a t | Homo sapiens clone 24736 mRNA sequence |
| 367 | Breast | 0.030838 | 0.4204419 | 0.353157 | 0.22876112 | U40223_at | Uridine nucleotide receptor (UNR) gene |
| 368 | Breast | 0.0307915 | 0.420296 | 0.353041 | 0.22866301 | M86757_s_a t | S100A7 S100 calcium-binding protein A7 (psoriasin 1) |
| 369 | Breast | 0.0306809 | 0.4202093 | 0.352829 | 0.22857477 | D31417_at | EST: Human fetal-lung cDNA 5'-end sequence, mRNA sequence. (from Genbank) |
| 370 | Breast | 0.0304438 | 0.4199431 | 0.352616 | 0.22842449 | D13666_s_a t | Osteoblast specific factor 2 (OSF-2os) |

FIG. 2Q

| | | | | | | |
|---|---|---|---|---|---|---|
| 371 | Breast | 0.0297859 | 0.4198474 | 0.35261 | 0.228258277 | U63303_cds2_at | GCP-2 gene (granulocyte chemotactic protein-2) extracted from Human line-1 reverse transcriptase gene, partial cds, and granulocyte chemotactic protein-2 (GCP-2) gene |
| 372 | Breast | | 0.029558 | 0.4197755 | 0.352539 | 0.228816657t-2 | AB000464_a Homo sapiens mRNA, exon 1, 2, 3, 4, clone:RES4-24A |
| 373 | Breast | | 0.029558 | 0.4195445 | 0.352365 | 0.228809042 | AB000464_a mRNA, clone RES4-24A, exon 1, 2, 3, 4 |
| 374 | Breast | | 0.02903 | 0.4194021 | 0.352144 | 0.22790742 | T95377_at EST: ye43c01.r1 Homo sapiens cDNA clone 120480 5'. (from Genbank) |
| 375 | Breast | | 0.0283808 | 0.4192353 | 0.35209 | 0.22772473t | AA203513_a EST: zx56b11.r1 Soares fetal liver spleen 1NFLS S1 Homo sapiens cDNA clone 446493 5', mRNA sequence. (from Genbank) |
| 376 | Breast | | 0.0282599 | 0.4189481 | 0.352038 | 0.22761236 | L15309_at ZNF141 Zinc finger protein 141 (clone pHZ-44) |
| 377 | Breast | | 0.0278669 | 0.4184885 | 0.351993 | 0.2274913 | M32373_at ARSB Arylsulfatase B |
| 378 | Breast | | 0.0278168 | 0.4182043 | 0.351864 | 0.22730185 | X51602_at VASCULAR ENDOTHELIAL GROWTH FACTOR RECEPTOR 1 PRECURSOR |
| 379 | Breast | | 0.0277125 | 0.4181201 | 0.351772 | 0.22718252 | U85267_at Down syndrome candidate region 1 (DSCR1) gene, alternative exon 1 |
| 380 | Breast | | 0.027534 | 0.4180682 | 0.351692 | 0.22712643 | HG759-HT759_s_at Adrenergic Receptor, Beta 1 |
| 381 | Breast | | 0.0268083 | 0.4180588 | 0.35164 | 0.22694637 | AA488935_a EST: aa55c10.r1 NCI_CGAP_GCB1 Homo sapiens cDNA clone IMAGE:824850 5' similar to TR:G1167506 G1167506 PROTEIN KINASE.; mRNA sequence. (from Genbank) |
| 382 | Breast | | 0.0264019 | 0.4179341 | 0.351324 | 0.22681604 | RC_AA4357 20_i_at Homo sapiens (clone ch13lambda7) alpha-tubulin mRNA, complete cds |
| 383 | Breast | | 0.0261934 | 0.4175403 | 0.351252 | 0.2267451 | M17466_at F12 Coagulation factor XII (Hageman factor) |
| 384 | Breast | | 0.0261083 | 0.4175363 | 0.351205 | 0.2266237 | AA112799_a EST: zn62h02.r1 Stratagene muscle 937209 Homo sapiens cDNA clone 562803 5', mRNA sequence. (from Genbank) |
| 385 | Breast | | 0.0259383 | 0.4174866 | 0.350984 | 0.22649984 | U93553_at-2 Fetoprotein-alpha 1 (AFP) transcription factor |
| 386 | Breast | | 0.0259383 | 0.4174105 | 0.350956 | 0.22634694 | U93553_at Alpha1-fetoprotein transcription factor (hFTF) mRNA |
| 387 | Breast | | 0.0255119 | 0.4172736 | 0.35093 | 0.22619797 | N25467_at Homo sapiens mRNA for DEPP (decidual protein induced by progesterone), complete cds |
| 388 | Breast | | 0.0252955 | 0.417018 | 0.350811 | 0.22608559 | U15590_at Heat shock protein 27 (HSP27) mRNA |
| 389 | Breast | | 0.0251769 | 0.4169912 | 0.350803 | 0.22598173 | RC_AA6098 73_at EST: af08o07.s1 Soares testis NHT Homo sapiens cDNA clone 1031052 3', mRNA sequence. (from Genbank) |
| 390 | Breast | | 0.0250039 | 0.4169912 | 0.350739 | 0.22580901t | D13814_s_a AGTR1 Angiotensin receptor 1 |
| 391 | Breast | | 0.0248178 | 0.4169903 | 0.350411 | 0.22566435 | AA043157_a Zk48f06.r1 Soares pregnant uterus NbHPU Homo sapiens cDNA clone 486083 5', mRNA sequence. (from Genbank) |

FIG. 2R

| | | | | | |
|---|---|---|---|---|---|
| 392 | Breast | 0.0247007 | 0.4169742 | 0.350195 | M83712_s_a t | CHRNA5 Cholinergic receptor, nicotinic, alpha polypeptide 5 |
| 393 | Breast | 0.0243905 | 0.4164135 | 0.350134 | RC_AA5211 11_at | EST: aa70h12.s1 NCI_CGAP_GCB1 Homo sapiens cDNA clone IMAGE:826343 3' similar to WP:C09F5.2 CE01774.;, mRNA sequence. (from Genbank) |
| 394 | Breast | 0.0237124 | 0.4164081 | 0.350125 | H41895_at | EST: yo07h11.r1 Homo sapiens cDNA clone 177285 5'. (from Genbank) |
| 395 | Breast | 0.0234328 | 0.4163954 | 0.3499987 | U13220_at | Forkhead protein FREAC-2 mRNA, partial cds |
| 396 | Breast | 0.0232614 | 0.4163598 | 0.3499947 | J03068_at | APEH N-acylaminoacyl-peptide hydrolase |
| 397 | Breast | 0.0229326 | 0.4163078 | 0.3499857 | RC_AA0018 86_at | EST: zh81d12.s1 Soares fetal liver spleen 1NFLS S1 Homo sapiens cDNA clone 427703 3' similar to contains Alu repetitive element;, mRNA sequence. (from Genbank) |
| 398 | Breast | 0.0223844 | 0.4161504 | 0.3499758 | J00287_at | PEPSINOGEN A PRECURSOR |
| 399 | Breast | 0.0222027 | 0.4160872 | 0.3499684 | HG831-HT831_at | Potassium Channel (Gb:L02752) |
| 400 | Breast | 0.0219029 | 0.416043 | 0.3499574 | W78726_at | EST: zh51h04.r1 Soares fetal liver spleen 1NFLS S1 Homo sapiens cDNA clone 415639 5'. mRNA sequence. (from Genbank) |
| 401 | Breast | 0.0217941 | 0.4158326 | 0.3499547 | W26719_at | EST: 12f7 Human retina cDNA randomly primed sublibrary Homo sapiens cDNA, mRNA sequence. (from Genbank) |
| 402 | Breast | 0.0216546 | 0.4158122 | 0.3499475 | RC_AA4355 97_at | EST: zt85g06.s1 Soares testis NHT Homo sapiens cDNA clone 729178 3', mRNA sequence. (from Genbank) |
| 403 | Breast | 0.0212416 | 0.415485 | 0.349942 | M62505_at | C5R1 Complement component 5 receptor 1 (C5a ligand) |
| 404 | Breast | 0.0211948 | 0.4150932 | 0.3499384 | RC_AA2837 74_at | EST: zt18d04.s1 Soares ovary tumor NbHOT Homo sapiens cDNA clone 713479 3', mRNA sequence. (from Genbank) |
| 405 | Breast | 0.02109 | 0.4149379 | 0.349378 | AA171913_a t | Carbonic anhydrase XII |
| 406 | Breast | 0.0208901 | 0.4148989 | 0.349919 | AA0077583_a t | Homo sapiens DNA sequence from Fosmid 27C3 on chromosome 22q11.2-qter. Contains two possibly alternatively spliced unknown genes, one with homology to a worm protein. Contains ESTs |
| 407 | Breast | 0.0208811 | 0.4148851 | 0.349146 | RC_AA4342 45_r_at | EST: zw24g05.s1 Soares ovary tumor NbHOT Homo sapiens cDNA clone 770264 3', mRNA sequence. (from Genbank) |
| 408 | Breast | 0.020606 | 0.4148843 | 0.349084 | AA046737_a t | EST: zf48a10.r1 Soares retina N2b4HR Homo sapiens cDNA clone 380154 5' similar to contains Alu repetitive element;, mRNA sequence. (from Genbank) |
| 409 | Breast | 0.0204034 | 0.4147914 | 0.348608 | HG4234-HT4504_at | Methylenetetrahydrofolate Reductase |
| 410 | Breast | 0.0203722 | 0.4146491 | 0.348604 | U82532_at | GDI-dissociation inhibitor RhoGDIgamma mRNA |

FIG. 2S

| | | | | | | |
|---|---|---|---|---|---|---|
| 411 | Breast | 0.0197804 | 0.414447 | 0.348522 | U12259_cds_at | Paired box homeotic protein (PAX3) gene |
| 412 | Breast | 0.019492 | 0.4143775 | 0.34837 | AA431603_a_t | EST: zw70c11.r1 Soares testis NHT Homo sapiens cDNA clone 781556 5', mRNA sequence. (from Genbank) |
| 413 | Breast | 0.018997 | 0.4142608 | 0.348266 | RC_AA0341 79_at | EST: zl06g11.s1 Soares fetal liver spleen 1NFLS S1 Homo sapiens cDNA clone 430052 3', mRNA sequence. (from Genbank) |
| 414 | Breast | 0.0183599 | 0.414243 | 0.347872 | 0.222255002 U78166_at | Human Ras-like small GTPase RIBA mRNA, alternatively spliced, complete cds |
| 415 | Breast | 0.0183175 | 0.4141943 | 0.347631 | 0.22244968 S81914_at | IEX-1 |
| 416 | Breast | 0.0182602 | 0.414025 | 0.347608 | 0.22239153 X51757_at | HSPA6 Heat shock 70kD protein 6 (HSP70B') |
| 417 | Breast | 0.0182602 | 0.4139094 | 0.347427 | 0.22224224 X51757_at-2 | Heat shock 70kD protein 6 (HSP70B') |
| 418 | Breast | 0.0182514 | 0.4136716 | 0.346928 | RC_AA2561 53_i_at | EST: zr79a09.s1 Soares NhHMPu S1 Homo sapiens cDNA clone 681880 3', mRNA sequence. (from Genbank) |
| 419 | Breast | 0.0180122 | 0.4135433 | 0.34677 | HG2271-HT2367_at | Profilaggrin |
| 420 | Breast | 0.0176827 | 0.4135337 | 0.346748 | 0.22180723 X65724_at | NDP Norrie disease (pseudoglioma) protein |
| 421 | Breast | 0.0174744 | 0.4133748 | 0.346619 | 0.22175573 X76383_at | HE3(alpha) |
| 422 | Breast | 0.0172671 | 0.4132845 | 0.34658 | HG3044-HT3742_s_a_t | Fibronectin, Alt. Splice 1 |
| 423 | Breast | 0.0172473 | 0.4130637 | 0.346399 | RC_AA2813 37_at | EST: zs94g02.s1 NCI_CGAP_GCB1 Homo sapiens cDNA clone IMAGE:705170 3', mRNA sequence. (from Genbank) |
| 424 | Breast | 0.0163557 | 0.4130339 | 0.346391 | 0.22143744 U28055_at | MST1 Macrophage stimulating 1 (hepatocyte growth factor-like) |
| 425 | Breast | 0.0163481 | 0.4129909 | 0.34627 | AA165144_i_at | EST: zo94e09.r1 Stratagene ovarian cancer (#937219) Homo sapiens cDNA clone 594568 5', mRNA sequence. (from Genbank) |
| 426 | Breast | 0.016178 | 0.4129804 | 0.346263 | AA344417_a_t | Alpha-1-antichymotrypsin |
| 427 | Breast | 0.0160547 | 0.4126453 | 0.346189 | 0.22113090 W17400_at | EST: zb15b10.r1 Soares fetal lung NbHL19W Homo sapiens cDNA clone 302107 5', mRNA sequence. (from Genbank) |
| 428 | Breast | 0.0158821 | 0.4125003 | 0.346134 | 0.22097512 M14306_at | Beta-A3/A1 crystallin (CYRBA3/A1) mRNA, partial cds |
| 429 | Breast | 0.0157 | 0.4123595 | 0.346113 | 0.22088304 L77563_at | DGS-F partial mRNA |
| 430 | Breast | 0.0152924 | 0.4122446 | 0.346081 | 0.22075565 U82306_at | Unknown protein mRNA, partial cds |
| 431 | Breast | 0.0144867 | 0.4120733 | 0.34601 | 0.22062117 L35854_at | Dystrophin (dp140) mRNA, 5' end |
| 432 | Breast | 0.0144322 | 0.4120116 | 0.345968 | 0.22045566 N75646_at | EST: yv29a08.r1 Homo sapiens cDNA clone 244118 5'. (from Genbank) |
| 433 | Breast | 0.0142941 | 0.4117874 | 0.345957 | 0.22032975 HT3689_at | Collagen, Type Ix, Alpha 1 |

FIG. 2T

| | | | | | |
|---|---|---|---|---|---|
| 434 | Breast | 0.0141948 | 0.411621 | 0.345843 | 0.220134335 | RC_AA426584_at | EST: zw02h10.s1 Soares NhHMPu S1 Homo sapiens cDNA clone 768163 3', mRNA sequence. (from Genbank) |
| 435 | Breast | 0.0135345 | 0.4111601 | 0.3456935 | 0.21997169 | AA437153_a t | EST: zv61b01.r1 Soares testis NHT Homo sapiens cDNA clone 758089 5', mRNA sequence. (from Genbank) |
| 436 | Breast | 0.0134053 | 0.4110372 | 0.345647 | 0.21981709 | HG3187-HT3366_s_a t | Tyrosine Phosphatase 1, Non-Receptor, Alt. Splice 3 |
| 437 | Breast | 0.0133904 | 0.4109576 | 0.345536 | 0.21976164 | N31013_at | EST: yx51d01.r1 Homo sapiens cDNA clone 265249 5'. (from Genbank) |
| 438 | Breast | 0.0131763 | 0.4106325 | 0.345492 | 0.21968429 | X00368_xpt 2_at | Exon 1 from Human prolactin gene 5' region./ntype=DNA /annot=mRNA |
| 439 | Breast | 0.0131511 | 0.4105138 | 0.345208 | 0.21950255 | AA459160_a t | EST: aa26h10.r1 NCI_CGAP_GCB1 Homo sapiens cDNA clone IMAGE:814435 5', mRNA sequence. (from Genbank) |
| 440 | Breast | 0.0128706 | 0.4104281 | 0.345046 | 0.2194109 | U53442_at | P38Beta MAP kinase mRNA |
| 441 | Breast | 0.0127012 | 0.4101566 | 0.344949 | 0.21936236 | L07592_at | Peroxisome proliferator activated receptor mRNA |
| 442 | Breast | 0.0127012 | 0.4101006 | 0.344907 | 0.21919642 | L07592_at-2 | Human peroxisome proliferator activated receptor mRNA, complete cds |
| 443 | Breast | 0.012679 | 0.4100905 | 0.344813 | 0.21911365 | AA287308_a t | EST: zs52i04.r1 NCI_CGAP_GCB1 Homo sapiens cDNA clone IMAGE:701119 5' similar to contains Alu repetitive element;contains element MER1 repetitive element ;, mRNA sequence. (from Genbank) |
| 444 | Breast | 0.0124688 | 0.4100214 | 0.344684 | 0.21904598 | U26403_at | EPLG7 Eph-related receptor tyrosine kinase ligand 7 |
| 445 | Breast | 0.0120718 | 0.4099689 | 0.344567 | 0.21892244 | AFFX-BioC-3_st | AFFX-BioC-3_st (endogenous control) |
| 446 | Breast | 0.0120718 | 0.4096865 | 0.344257 | 0.21883304 | AFFX-BioC-3_st-2 | AFFX-BioC-3_st (miscellaneous control - 11k chips) |
| 447 | Breast | 0.0119039 | 0.4096225 | 0.344122 | 0.21864054 | J05068_at | TCN1 Transcobalamin I |
| 448 | Breast | 0.0118772 | 0.4094398 | 0.344072 | 0.21856806 | AA489716_a t | EST: aa43a01.r1 Soares NhHMPu S1 Homo sapiens cDNA clone 8236656 5' similar to contains element MER22 repetitive element ;, mRNA sequence. (from Genbank) |
| 449 | Breast | 0.0116967 | 0.409404 | 0.343898 | 0.21847437 | U05227_at | Rar protein mRNA |
| 450 | Breast | 0.0116866 | 0.4093491 | 0.34383 | 0.21831964 | AA406087_s_ at | TAL1 (SCL) interrupting locus |
| 451 | Breast | 0.0115896 | 0.4093473 | 0.343743 | 0.2182242464 | AA417310_a t | EST: zu07c02.r1 Soares testis NHT Homo sapiens cDNA clone 731138 5', mRNA sequence. (from Genbank) |
| 452 | Breast | 0.0108785 | 0.4092896 | 0.343489 | 0.21807055 | X16866_at | Cytochrome P-450IID (clone pMP33) |
| 453 | Breast | 0.0108434 | 0.4092376 | 0.343487 | 0.21796383 | L23852_at | (clone Z146) retinal mRNA, 3' end and repeat region |
| 454 | Breast | 0.0105127 | 0.4091721 | 0.343412 | 0.21776974 | HG4749-HT5197_at | Calmitine Calcium-Binding Protein, Mitochondrial |

FIG. 2U

| # | Tissue | | | | ID | Description |
|---|---|---|---|---|---|---|
| 455 | Breast | 0.0101699 | 0.4090603 | 0.342996 | 0.217664414 R81267_at | Yj01a05.r1 Homo sapiens cDNA clone 147440 5' similar to SP:A43336 A43336 MICROTUBULE-VESICLE LINKER CLIP-170 (from Genbank) |
| 456 | Breast | 0.0101495 | 0.4090234 | 0.342868 | 0.217761985 X98330_at-2 | Ryanodine receptor 2 (cardiac) |
| 457 | Breast | 0.0101495 | 0.4089698 | 0.342868 | 0.217748464 X98330_at | RYR2 Ryanodine receptor 2 (cardiac) |
| 458 | Breast | 0.0101174 | 0.4089017 | 0.342819 | 0.217732162 HG3740-HT4010_at | Basic Transcription Factor 2, 34 Kda Subunit |
| 459 | Breast | 0.0100586 | 0.408843 | 0.342819 | 0.217729638 M15881_at | UMOD Uromodulin (uromucoid, Tamm-Horsfall glycoprotein) |
| 460 | Breast | 0.010055 | 0.4085902 | 0.342704 | 0.2170868 AA282300_at | SET binding factor 1 |
| 461 | Breast | 0.0098453 | 0.4084224 | 0.342571 | 0.217700253 RC_AA151674_at | Carbonic anhydrase XII |
| 462 | Breast | 0.008997 | 0.4084071 | 0.342252 | 0.216899688 RC_AA485673_at | EST: zx91b06.s1 Soares ovary tumor NbHOT Homo sapiens cDNA clone 811091 3' similar to SW:YN54_CAEEL P34588 HYPOTHETICAL 80.8 KD PROTEIN ZC21.4 IN CHROMOSOME III. [1] ;, mRNA sequence. (from Genbank) |
| 463 | Breast | 0.0085265 | 0.4080169 | 0.342169 | 0.216818689 L20348_at | Oncomodulin gene |
| 464 | Breast | 0.008427 | 0.4078828 | 0.342083 | 0.216733297 U31215_s_at | Metabotropic glutamate receptor 1 alpha (mGluR1alpha) mRNA |
| 465 | Breast | 0.0076954 | 0.4078205 | 0.34204 | 0.216599407 X80878_at | R kappa B mRNA |
| 466 | Breast | 0.0075561 | 0.4077657 | 0.342004 | 0.216509694 V01514_at | AFP Alpha-fetoprotein |
| 467 | Breast | 0.0072653 | 0.4077236 | 0.341847 | 0.216406297 AA053831_at | Dual-specificity tyrosine-(Y)-phosphorylation regulated kinase 2 |
| 468 | Breast | 0.0066134 | 0.4076301 | 0.341736 | 0.216288911 L20321_at | STK2 Protein serine/threonine kinase stk2 |
| 469 | Breast | 0.0064498 | 0.4075662 | 0.34166 | 0.216170192 RC_AA243723_at | EST: zf68g10.s1 Soares NhHMPu S1 Homo sapiens cDNA clone 668610 3', mRNA sequence. (from Genbank) |
| 470 | Breast | 0.0061377 | 0.4075098 | 0.341648 | 0.216092023 RC_AA121433_s_at | Axin |
| 471 | Breast | 0.0060056 | 0.4074809 | 0.34152 | 0.2160020 M32879_at | CYP11B1 Cytochrome P450 11 beta |
| 472 | Breast | 0.0059052 | 0.407462 | 0.34152 | 0.215892463 X17651_at | MYOG Myogenin (myogenic factor 4) |
| 473 | Breast | 0.0058443 | 0.4073809 | 0.341374 | 0.215809217 HG2380-HT2476_s_at | Adp-Ribosylarginine Hydrolase |
| 474 | Breast | 0.0058419 | 0.4073646 | 0.341333 | 0.215734233 U33632_at | Two P-domain K+ channel TWIK-1 mRNA |
| 475 | Breast | 0.0058032 | 0.407364 | 0.341326 | 0.215585344 R84733_at | EST: yf68b09.r1 Soares retina N2b4HR Homo sapiens cDNA clone 275297 5', mRNA sequence. (from Genbank) |
| 476 | Breast | 0.0057447 | 0.4072518 | 0.341317 | 0.215443992 HG2538-HT2634_at | Heterogeneous Nuclear Ribonucleoprotein C |
| 477 | Breast | 0.0057106 | 0.4072251 | 0.341131 | 0.215331481 L38820_at | CD1D CD1D antigen, d polypeptide |

FIG. 2V

| | | | | | |
|---|---|---|---|---|---|
| 478 | Breast | 0.0056493 | 0.4072181 | 0.341131 | 0.21517509 | M33882_at | MX1 Myxovirus (influenza) resistance 1, homolog of murine (interferon inducible protein p78) |
| 479 | Breast | 0.0055227 | 0.4071741 | 0.341103 | 0.21508758 | U89717_at | RDH1 Retinol dehydrogenase 1 (11-cis) |
| 480 | Breast | 0.0054328 | 0.407045 | 0.34105 | 0.214911147 | RC_AA4279_at | EST: zw50e09.s1 Soares total fetus Nb2HF8 9w Homo sapiens cDNA clone 773512 3', mRNA sequence. (from Genbank) |
| 481 | Breast | 0.0050569 | 0.4069941 | 0.341034 | 0.214490355 | AA490685_at | EST: aa45b03.r1 Soares NhHMPu S1 Homo sapiens cDNA clone 823853 5', mRNA sequence. (from Genbank) |
| 482 | Breast | 0.0050467 | 0.4069175 | 0.34068 | 0.214482638 | M59941_at | CSF2RB Colony stimulating factor 2 receptor, beta, low-affinity (granulocyte-macrophage) |
| 483 | Breast | 0.0049541 | 0.4067849 | 0.340611 | 0.21457182 | H52378_at | Spectrin, alpha, erythrocytic 1 (elliptocytosis 2) |
| 484 | Breast | 0.0046402 | 0.4067706 | 0.34054 | 0.214441376 | X56667_at | CALB2 Calbindin 2, (29kD, calretinin) |
| 485 | Breast | 0.0045265 | 0.4066709 | 0.340332 | 0.214434543 | U30930_at | CGT UDP-galactose ceramide galactosyl transferase |
| 486 | Breast | 0.004522 | 0.4066148 | 0.340278 | 0.214236616 | L41351_at | Prostasin mRNA |
| 487 | Breast | 0.0044954 | 0.4065344 | 0.340149 | 0.214172495 | RC_AA5212_at | EST: aa79e10.s1 NCl_CGAP_GCB1 Homo sapiens cDNA clone IMAGE:827178 3', mRNA sequence. (from Genbank) |
| 488 | Breast | 0.0041656 | 0.4065344 | 0.340109 | 0.21397248 | S80905_f_at | PRB2 locus salivary proline-rich protein mRNA, clone cP7 |
| 489 | Breast | 0.0039722 | 0.4065061 | 0.339895 | 0.213905572 | RC_AA6096_at | EST: af15h11.s1 Soares testis NHT Homo sapiens cDNA clone 1031781 3', mRNA sequence. (from Genbank) |
| 490 | Breast | 0.0036419 | 0.406475 | 0.33983 | 0.213790113 | W28510_at | Calmodulin 1 (phosphorylase kinase, delta) |
| 491 | Breast | 0.0036291 | 0.4062729 | 0.339828 | 0.21371846 | U28131_at | HMGI-C chimeric transcript mRNA, partial cds |
| 492 | Breast | 0.0027202 | 0.4061568 | 0.339806 | 0.21361004 | AA402121_at | EST: zt67e02.r1 Soares testis NHT Homo sapiens cDNA clone 727418 5', mRNA sequence. (from Genbank) |
| 493 | Breast | 0.0025829 | 0.4061568 | 0.339632 | 0.213512214 | U13044_at | GABPA GA-binding protein transcription factor, alpha subunit (60kD) |
| 494 | Breast | 0.0024218 | 0.4059742 | 0.339487 | 0.213336308 | N48204_at | EST: yv22a08.r1 Homo sapiens cDNA clone 243446 5'. (from Genbank) |
| 495 | Breast | 0.0022413 | 0.4059293 | 0.339421 | 0.21313124 | HG1827-HT1856_s_at | Cytochrome P450, Subfamily IIc, Alt. Splice Form 2 |
| 496 | Breast | 0.0016266 | 0.4058759 | 0.339319 | 0.213307735 | U12139_at | Alpha1(XI) collagen (COL11A1) gene, 5' region and exon 1 |
| 497 | Breast | 0.0015754 | 0.405842 | 0.339132 | 0.212928447 | AA282944_at | EST: zt15g08.r1 NCl_CGAP_GCB1 Homo sapiens cDNA clone IMAGE:713246 5', mRNA sequence. (from Genbank) |
| 498 | Breast | 0.00109 | 0.405553 | 0.339124 | 0.21281794 | S82362_s_at | HRAR- beta 2=retinoic-acid-receptor beta/suspected tumor suppressor {5' region, transcription control region} [human, mRNA Partial, 1730 nt] |
| 499 | Breast | 0.0010207 | 0.4053617 | 0.339031 | 0.21276698 | L32164_at | Zinc finger protein mRNA, 3' end |
| 500 | Breast | 9.71E-04 | 0.4051561 | 0.338897 | 0.21268353 | M37981_at | CHRNA3 Alpha-3 neuronal nicotinic acetylcholine receptor subunit |
| 501 | Breast | 7.13E-04 | 0.4050444 | 0.338766 | 0.21263252 | U82303_at | Unknown protein mRNA, partial cds |

FIG. 2W

| | | | | | |
|---|---|---|---|---|---|
| 502 | Breast | 2.19E-05 | 0.4050356 | 0.338622 | 0.21245304 | U83598_s_at | Death domain receptor 3 soluble form (DDR3) mRNA, partial cds |
| 503 | Breast | -4.57E-05 | 0.404849 | 0.338375 | 0.2123711 | H11788_at | EST: ym11b06.r1 Homo sapiens cDNA clone 47577 5'. (from Genbank) |
| 504 | Breast | -3.96E-04 | 0.4047111 | 0.338312 | 0.21227753 | M27533_s_at | Ig rearranged B7 protein mRNA VC1-region |
| 505 | Breast | -4.18E-04 | 0.404682 | 0.338305 | 0.21217075 | RC_AA4339 51_at | EST: zw52h03.s1 Soares total fetus Nb2HF8 9w Homo sapiens cDNA clone 773717 3', mRNA sequence. (from Genbank) |
| 506 | Breast | -6.52E-04 | 0.4043935 | 0.338228 | 0.21205503 | RC_AA1942 57_r_at | Human DNA sequence from clone 522J7 on chromosome 22q13.3. Contains part of a 60S Ribosomal protein L5 pseudogene and a Peregrin (BR140) LIKE gene downstream of a putative CpG island. Contains ESTs, STSs and GSSs |
| 507 | Breast | -0.001026 | 0.4043892 | 0.338161 | 0.21197373 | L11372_at | Protocadherin 43 mRNA, 3' end of cds for alternative splicing PC43-12 |
| 508 | Breast | -0.001101 | 0.4042602 | 0.33796 | 0.21185085 | W51743_at | EST: zc48f12.r1 Soares senescent fibroblasts NbHSF Homo sapiens cDNA clone 325583 5', mRNA sequence. (from Genbank) |
| 509 | Breast | -0.001213 | 0.4041543 | 0.33794 | 0.21173644 | R46311_at | EST: yj53f04.r1 Homo sapiens cDNA clone 152479 5'. (from Genbank) |
| 510 | Breast | -0.001466 | 0.4041159 | 0.337509 | 0.21166414 | L11238_s_at | GP5 Glycoprotein V (platelet) |
| 511 | Breast | -0.001939 | 0.4041023 | 0.337475 | 0.21154357 | M58509_cds 1_s_at | FDXR gene (adrenodoxin reductase) extracted from Human adrenodoxin reductase gene |
| 512 | Breast | -0.002216 | 0.404023 | 0.337361 | 0.21151799 | D10656_at | CRK V-crk avian sarcoma virus CT10 oncogene homolog |
| 513 | Breast | -0.002298 | 0.4038912 | 0.337325 | 0.21140918 | W27076_at | EST: 22g11 Human retina cDNA randomly primed sublibrary Homo sapiens cDNA, mRNA sequence. (from Genbank) |
| 514 | Breast | -0.002486 | 0.4037237 | 0.33732 | 0.21122555 | RC_AA3988 92_at | EST: zf62g12.s1 Soares testis NHT Homo sapiens cDNA clone 726982 3', mRNA sequence. (from Genbank) |
| 515 | Breast | -0.002519 | 0.4035768 | 0.3372 | 0.21118708 | M19045_f_at | LYZ Lysozyme |
| 516 | Breast | -0.00258 | 0.4035298 | 0.337119 | 0.21098429 | M77481_ma 1_f_at | Antigen (MAGE-1) gene |
| 517 | Breast | -0.002677 | 0.4032174 | 0.337049 | 0.21089697 | L00137_cds 1_at | GHRF gene (growth hormone releasing factor) extracted from Human growth hormone-releasing factor (GRF) gene, exon 1 ( |

FIG. 2X

| | | | | | |
|---|---|---|---|---|---|
| 518 | Breast | -0.002713 | 0.4028361 | 0.337012 | 0.21082246 | R67702_at | Human DNA sequence from clone 283E3 on chromosome 1p36.21-36.33. Contains the alternatively spliced gene for Matrix Metalloproteinase in the Female Reproductive tract MIFR1, -2, MMP21/22A, -B and -C, a novel gene, the alternatively spliced CDC2L2 gene for Cell Division Cycle 2-Like 2 (PITSLRE, p58/GTA, Galactosyltransferase Associated Protein Kinase) beta 1, beta 2-1, beta 2-2 and alpha 2-4, a 40S Ribosomal Protein S7 pseudogene, part of the KIAA0447 gene, a novel alternatively spliced gene similar to many (archae)bacterial, worm and yeast hypothetical genes, and the GNB1 gene for Guanine Nucleotide Binding Protein (G protein), Beta polypeptide 1 (Transducin Beta chain 1). Contains putative CpG islands, ESTs, STSs and GSSs |
| 519 | Breast | -0.00283 | 0.4028219 | 0.336971 | 0.21072227 | X73501_at-2 | KERATIN, TYPE I CYTOSKELETAL 20 |
| 520 | Breast | -0.00283 | 0.4027551 | 0.336844 | 0.21064727 | X73501_at | KERATIN, TYPE I CYTOSKELETAL 20 |
| 521 | Breast | -0.002967 | 0.4027481 | 0.336707 | 0.2104736 | D50923_at | KIAA0133 gene |
| 522 | Breast | -0.00311 | 0.4026403 | 0.336636 | 0.21036582 | M16474_s_at | Butyrylcholinesterase, mRNA |
| 523 | Breast | -0.003626 | 0.4025314 | 0.336635 | 0.2102628 | J02963_at | ITGA2B Integrin, alpha 2b (platelet glycoprotein IIb of IIb/IIIa complex, antigen CD41B) |
| 524 | Breast | -0.003913 | 0.4023718 | 0.336497 | 0.21011898 | AA249119_at | Ec0276.seq.F Human fetal heart, Lambda ZAP Express Homo sapiens cDNA 5', mRNA sequence. (from Genbank) |
| 525 | Breast | -0.00414 | 0.4023425 | 0.33645 | 0.21003717 | AA075427_at | EST: zm87a05.r1 Stratagene ovarian cancer (#937219) Homo sapiens cDNA clone 544880 5', mRNA sequence. (from Genbank) |
| 526 | Breast | -0.004198 | 0.4021739 | 0.336181 | 0.20996502 | RC_AA478967_at | EST: zv18e03.s1 Soares NhHMPu S1 Homo sapiens cDNA clone 754012 3', mRNA sequence. (from Genbank) |
| 527 | Breast | -0.004209 | 0.4021293 | 0.336062 | 0.20990698 | RC_AA256162_at | EST: zr79b07.s1 Soares NhHMPu S1 Homo sapiens cDNA clone 681877 3', mRNA sequence. (from Genbank) |
| 528 | Breast | -0.004343 | 0.4021145 | 0.335997 | 0.20980309 | HG870-HT870_at | Golgin, 165 Kda Polypeptide |
| 529 | Breast | -0.004345 | 0.4019598 | 0.335815 | 0.20973794 | J05480_s_at | Protein phosphatase 3 (formerly 2B), catalytic subunit, alpha isoform (calcineurin A alpha) |
| 530 | Breast | -0.004866 | 0.4019173 | 0.33564 | 0.20961753 | RC_AA491001_f_at | EST: aa52g12.s1 NCI_CGAP_GCB1 Homo sapiens cDNA clone IMAGE:824614 3' similar to TR:G1293732 G1293732 O3625P. :; mRNA sequence. (from Genbank) |
| 531 | Breast | -0.00499 | 0.4018627 | 0.335563 | 0.20952269 | HG3934-HT4204_at | G1 Phase-Specific Gene |
| 532 | Breast | -0.005561 | 0.4016674 | 0.335514 | 0.20946181 | X96754_at | GLUL Glutamate-ammonia ligase (glutamine synthase) |

FIG. 2Y

| | | | | | |
|---|---|---|---|---|---|
| 533 | Breast | -0.005562 | 0.4016433 | 0.335492 | 0.20928715 | HG4113-HT4383_s_a_t | Olfactory Receptor Or17-201 |
| 534 | Breast | -0.005663 | 0.4015656 | 0.335262 | 0.20918314 | X77753_at | M1S1 Membrane component, chromosome 1, surface marker 1 (40kD glycoprotein, identified by monoclonal antibody GA733) |
| 535 | Breast | -0.005824 | 0.4014216 | 0.335199 | 0.2090622 | S81243_s_at | Mitogen induced nuclear orphan receptor (MINOR) mRNA |
| 536 | Breast | -0.0061 | 0.4014216 | 0.33513 | 0.20887616 | X67594_at | MC1R Melanocortin 1 receptor (alpha melanocyte stimulating hormone receptor) |
| 537 | Breast | -0.006865 | 0.4013628 | 0.335097 | 0.20877592 | Z00010_at | Germ line pseudogene for immunoglobulin kappa light chain leader peptide and variable region (subgroup V kappa I) |
| 538 | Breast | -0.006932 | 0.4013168 | 0.334864 | 0.2085361 | X52008_at | GLRA2 Glycine receptor, alpha 2 |
| 539 | Breast | -0.007039 | 0.4008135 | 0.334489 | 0.20852098 | S77812_at | FLT1 Fms-related tyrosine kinase 1 (vascular endothelial growth factor/vascular permeability factor receptor) |
| 540 | Breast | -0.007125 | 0.4006445 | 0.334404 | 0.20844536 | RC_AA2848 29_at | H.sapiens mRNA for Zinc-finger protein (ZNFpT7) |
| 541 | Breast | -0.007137 | 0.4006213 | 0.334356 | 0.20821393 | U69114_at | EST: Human Down syndrome region, YAC 152F7, mRNA sequence. (from Genbank) |
| 542 | Breast | -0.007167 | 0.4005706 | 0.334349 | 0.20809577 | X78416_s_a_t | CSN1 Casein, alpha S1 |
| 543 | Breast | -0.007179 | 0.4004878 | 0.33416 | 0.20803538 | H17239_at | EST: ym42f05.r1 Homo sapiens cDNA clone 50975 5'. (from Genbank) |
| 544 | Breast | -0.007273 | 0.4004105 | 0.334138 | 0.20793584 | AFFX-CreX-3_at | AFFX-CreX-3_at (endogenous control) |
| 545 | Breast | -0.007273 | 0.4003306 | 0.334113 | 0.20786817 | AFFX-CreX-3_at-2 | AFFX-CreX-3_at (miscellaneous control - 11k chips) |
| 546 | Breast | -0.007329 | 0.4003102 | 0.333913 | 0.20751318 | L15296_s_at | Clone hRCNC2b retinal rod cyclic nucleotide-gated cation channel gene |
| 547 | Breast | -0.00735 | 0.4003039 | 0.333825 | 0.20744857 | RC_AA0197 12_at | KIAA0735_gene product |
| 548 | Breast | -0.007536 | 0.4002044 | 0.333683 | 0.20738943 | Z15005_at | CENPE Centromere protein E (312kD) |
| 549 | Breast | -0.007571 | 0.4001838 | 0.333417 | 0.20728518 | X07696_at | KRT15 Keratin 15 |
| 550 | Breast | -0.007576 | 0.4001827 | 0.333377 | 0.2071896 | X57985_rna 2_at | GL105 gene (histone H2B) extracted from H.sapiens genes for histones H2B.1 and H2A |
| 551 | Breast | -0.007581 | 0.4000622 | 0.333334 | 0.20710509 | RC_AA6208 89_at | EST: af95g10.s1 Soares testis NHT Homo sapiens cDNA clone 1055566 3', mRNA sequence. (from Genbank) |
| 552 | Breast | -0.00775 | 0.4000337 | 0.333331 | 0.20702955 | U59057_at | CRYBA4 Beta-A4 crystallin |
| 553 | Breast | -0.00793 | 0.3999725 | 0.333312 | 0.2069242 | RC_AA2370 34_at | Golgi SNAP receptor complex member 2 |

FIG. 2Z

| | | | | | |
|---|---|---|---|---|---|
| 554 | Breast | -0.008101 | 0.3999223 | 0.333172 | 0.20689984 | T70856_at | EST: yd15f04.r1 Homo sapiens cDNA clone 108319 5' similar to SP:ME18_MOUSE P23798 DNA-BINDING PROTEIN .; (from Genbank) |
| 555 | Breast | -0.008164 | 0.3998873 | 0.33296 | 0.20680106 | RC_AA5996 99_at | EST: ag10h08.s1 Gessler Wilms tumor Homo sapiens cDNA clone 1069983 3', mRNA sequence. (from Genbank) |
| 556 | Breast | -0.008488 | 0.3998312 | 0.332933 | 0.20655969 | L12060_s_at | RARG Retinoic acid receptor, gamma 1 |
| 557 | Breast | -0.008644 | 0.3997046 | 0.332903 | 0.20652814 | U13948_at | Zinc finger/leucine zipper protein (AF10) mRNA |
| 558 | Breast | -0.008802 | 0.3995789 | 0.332877 | 0.20647828 | N32716_at | EST: yx74h12.r1 Homo sapiens cDNA clone 267527 5' similar to PIR:S45251 S45251 SNF2alpha protein - human ;. (from Genbank) |
| 559 | Breast | -0.008831 | 0.399577 | 0.332776 | 0.20638831 | AA076003_a t | Zm89c09.r1 Stratagene ovarian cancer (#937219) Homo sapiens cDNA clone 545104 5', mRNA sequence. (from Genbank) |
| 560 | Breast | -0.008894 | 0.3995217 | 0.332724 | 0.20635384 | HG3432-HT3621_at | Fibroblast Growth Factor Receptor K-Sam, Alt. Splice 4, K-Sam Iv |
| 561 | Breast | -0.009085 | 0.3994748 | 0.332559 | 0.20627391 | U20536_s_a t | Cysteine protease Mch2 isoform alpha (Mch2) mRNA |
| 562 | Breast | -0.009642 | 0.399442 | 0.33248 | 0.20620906 | U27185_at | RAR-responsive (TIG1) mRNA |
| 563 | Breast | -0.009689 | 0.3993699 | 0.332388 | 0.20605153 | AA233236_a t | Human clone p4betaGT/3 beta-1,4-galactosyltransferase mRNA, partial cds |
| 564 | Breast | -0.009812 | 0.3993147 | 0.332314 | 0.20597644 | M17446_s_a t | FGF4 Fibroblast growth factor 4 (heparin secretory transforming protein 1, Kaposi sarcoma oncogene) |
| 565 | Breast | -0.00985 | 0.3989676 | 0.332196 | 0.205751911 | X60299_s_a t | KALLMANN SYNDROME PROTEIN PRECURSOR |
| 566 | Breast | -0.009934 | 0.3988719 | 0.332023 | 0.20573328 | M62397_at | MCC Mutated in colorectal cancers |
| 567 | Breast | -0.01029 | 0.3987995 | 0.331993 | 0.20569713 | D21337_at | COL4A6 Collagen, type IV, alpha 6 |
| 568 | Breast | -0.010371 | 0.398798 | 0.331969 | 0.20551108 | Z80777_at | H2A/k gene |
| 569 | Breast | -0.010508 | 0.3986818 | 0.331845 | 0.20542865 | X60487_at | H4/h gene for H4 histone |
| 570 | Breast | -0.010621 | 0.398646 | 0.331742 | 0.20533364 | U16261_at | MDA-7 (mda-7) mRNA |
| 571 | Breast | -0.01107 | 0.3986287 | 0.331568 | 0.20523974 | RC_AA4121 s_at | Nucleoporin 88kD |
| 572 | Breast | -0.011111 | 0.3985811 | 0.331383 | 0.20516984 | RC_AA6096 2_at | EST: af16a06.s1 Soares testis NHT Homo sapiens cDNA clone 10317943', mRNA sequence. (from Genbank) |
| 573 | Breast | -0.011919 | 0.3985346 | 0.33131 | 0.20504439 | D13305_at | CCKBR Cholecystokinin B receptor |
| 574 | Breast | -0.011953 | 0.3984317 | 0.331251 | 0.20498066 | D31833_s_a t | AVPR1B Arginine vasopressin receptor 1B |
| 575 | Breast | -0.0121776 | 0.3983848 | 0.331175 | 0.20497473 | L26953_at | RMSA1 Regulator of mitotic spindle assembly 1 |
| 576 | Breast | -0.012189 | 0.398048 | 0.331033 | 0.2048766 | AA280228_a t | EST: zt04c11.r1 NCI_CGAP_GCB1 Homo sapiens cDNA clone IMAGE:712148 5', mRNA sequence. (from Genbank) |
| 577 | Breast | -0.012202 | 0.3979125 | 0.330916 | 0.20468736 | U90304_at | Iroquois-class homeodomain protein IRX-2a mRNA |

FIG. 2A2

| | | | | | |
|---|---|---|---|---|---|
| 578 | Breast | -0.01241 | 0.3977047 | 0.20455948 | X99142_at | Hair keratin, hHb6 |
| 579 | Breast | -0.012689 | 0.3976834 | 0.20444581 | D45213_at | Homo sapiens mRNA for zinc finger protein, complete cds |
| 580 | Breast | -0.013411 | 0.3976801 | 0.20436706 | RC_AA2428 23_at | EST: zr65e10.s1 Soares NhHMPu S1 Homo sapiens cDNA clone 668298 3', mRNA sequence. (from Genbank) |
| 581 | Breast | -0.013466 | 0.3976657 | 0.20426139 | M81349_at | SERUM AMYLOID A-4 PROTEIN PRECURSOR |
| 582 | Breast | -0.013784 | 0.3976527 | 0.20418884 | L43338_at | (clone JJ1a) cadherin mRNA fragment |
| 583 | Breast | -0.013949 | 0.3975537 | 0.20409729 | J03778_s_at | MICROTUBULE-ASSOCIATED PROTEIN TAU |
| 584 | Breast | -0.014154 | 0.3975345 | 0.20401117 | L77561_at | DGS-D mRNA, 3' end |
| 585 | Breast | -0.014178 | 0.3973927 | 0.20395581 | Y08134_at-2 | H.sapiens mRNA for ASM-like phosphodiesterase 3b |
| 586 | Breast | -0.014178 | 0.3973286 | 0.20383477 | Y08134_at | ASM-like phosphodiesterase 3b |
| 587 | Breast | -0.014269 | 0.3973022 | 0.20375353 | Z83745_at | DNA sequence from PAC 453A3 contains EST and STS |
| 588 | Breast | -0.014396 | 0.3973016 | 0.2036282 | M19878_s_a t | Calbindin 27 gene, exons 1 and 2, and Alu repeat |
| 589 | Breast | -0.014603 | 0.3973016 | 0.20353736 | X84746_at | Histo-blood group AB0 gene, exon 1 |
| 590 | Breast | -0.015383 | 0.3971769 | 0.20345484 | RC_AA2534 19_at | EST: zr77e01.s1 Soares NhHMPu S1 Homo sapiens cDNA clone 669432 3', mRNA sequence. (from Genbank) |
| 591 | Breast | -0.015565 | 0.3971318 | 0.20330955 | HG2730-HT2827_s_a | Fibrinogen, A Alpha Polypeptide, Alt. Splice 2, E |
| 592 | Breast | -0.015592 | 0.3970318 | 0.20321149 | RC_AA2333 71_at | EST: zx48f03.s1 Soares NhHMPu S1 Homo sapiens cDNA clone 666653 3', mRNA sequence. (from Genbank) |
| 593 | Breast | -0.015713 | 0.3970246 | 0.20315346 | M24594_at | IFI56 Interferon-induced protein 56 |
| 594 | Breast | -0.0158 | 0.3969408 | 0.20311978 | AA426304_r_at | EST: zw11g07.r1 Soares NhHMPu S1 Homo sapiens cDNA clone 769020 5', mRNA sequence. (from Genbank) |
| 595 | Breast | -0.016186 | 0.3969314 | 0.20299536 | RC_AA3464 07_at | EST: EST52587 Fetal heart II Homo sapiens cDNA 3' end, mRNA sequence. (from Genbank) |
| 596 | Breast | -0.016188 | 0.3969139 | 0.20293432 | RC_AA1913 23_at | EST: zp83b09.s1 Stratagene HeLa cell s3 937216 Homo sapiens cDNA clone 626777 3', mRNA sequence. (from Genbank) |
| 597 | Breast | -0.016196 | 0.3968759 | 0.20280564 | AA018847_a t | EST: ze57h12.r1 Soares retina N2b4HR Homo sapiens cDNA clone 363143 5', mRNA sequence. (from Genbank) |
| 598 | Breast | -0.016228 | 0.3968066 | 0.20274048 | AA253330_s_at | EST: zr72g02.r1 Soares NhHMPu S1 Homo sapiens cDNA clone 668978 5', mRNA sequence. (from Genbank) |
| 599 | Breast | -0.016304 | 0.3965611 | 0.2026461 | AA085138_a t | ZnO1a07.r1 Stratagene colon HT29 (#937221) Homo sapiens cDNA clone 546132 5' similar to gb:M34539 FK506-BINDING PROTEIN (HUMAN);, mRNA sequence. (from Genbank) |
| 600 | Breast | -0.016367 | 0.3965053 | 0.20260999 | X82279_s_a t | Fas, Apo-1 gene (promoter and exon I) |

FIG. 2B2

| | | | | | |
|---|---|---|---|---|---|
| 601 | Breast | -0.016658 | 0.3964541 | 0.32868 | 0.2025331772_at | RC_AA3994 | EST: zt53e07.s1 Soares ovary tumor NbHOT Homo sapiens cDNA clone 726084 3', mRNA sequence. (from Genbank) |
| 602 | Breast | -0.016681 | 0.3964232 | 0.328519 | 0.2023837 | AC002450_a1 | BAC clone GS244B22 from 7q21-q22, complete sequence |
| 603 | Breast | -0.016723 | 0.3964422 | 0.328416 | 0.20218068 | AA206983_a | EST: zq50h02.r1 Stratagene neuroepithelium (#937231) Homo sapiens cDNA clone 645075 5' similar to contains Alu repetitive element;contains element MER22 repetitive element :, mRNA sequence. (from Genbank) |
| 604 | Breast | -0.017051 | 0.3961465 | 0.328344 | 0.2021114 | M21188_at | INSULIN-DEGRADING ENZYME |
| 605 | Breast | -0.017133 | 0.3960699 | 0.328285 | 0.20206255 | U86755_s_at | TNF-alpha converting enzyme mRNA |
| 606 | Breast | -0.017432 | 0.3960353 | 0.328159 | 0.2019909 | U76369_at | Cationic amino acid transporter-2B (ATRC2) mRNA, partial cds |
| 607 | Breast | -0.017527 | 0.3959732 | 0.327911 | 0.20188579 | X81637_at | CLTB Clathrin, light polypeptide (Lcb) |
| 608 | Breast | -0.017668 | 0.3959027 | 0.327909 | 0.20182575 | D88667_at | Cerebroside sulfotransferase |
| 609 | Breast | -0.017948 | 0.3957879 | 0.327818 | 0.2017172 | RC_AA2243 51_f_at | EST: zr12f12.s1 Stratagene hNT neuron (#937233) Homo sapiens cDNA clone 648623 3', mRNA sequence. (from Genbank) |
| 610 | Breast | -0.018025 | 0.3957652 | 0.327752 | 0.20162672 | X00540_at | PRL Prolactin |
| 611 | Breast | -0.018058 | 0.3957646 | 0.327647 | 0.20145844 | RC_AA4373 23_at | EST: zv62f11.s1 Soares testis NHT Homo sapiens cDNA clone 758253 3', mRNA sequence. (from Genbank) |
| 612 | Breast | -0.018071 | 0.3957413 | 0.327481 | 0.20132859 | RC_D59856 _at | EST: Human fetal brain cDNA 3'-end GEN-071B10, mRNA sequence. (from Genbank) |
| 613 | Breast | -0.018516 | 0.3956075 | 0.327403 | 0.2011978 | X59798_at | CCND1 Cyclin D1 (PRAD1; parathyroid adenomatosis 1) |
| 614 | Breast | -0.018742 | 0.3954774 | 0.327229 | 0.201115829 | R18154_at | EST: yf97d10.r1 Homo sapiens cDNA clone 30728 5'. (from Genbank) |
| 615 | Breast | -0.018751 | 0.3954442 | 0.326992 | 0.20111069 | RC_AA4497 49_at | EST: zx07e10.s1 Soares total fetus Nb2HF8 9w Homo sapiens cDNA clone 785802 3', mRNA sequence. (from Genbank) |
| 616 | Breast | -0.018825 | 0.3954056 | 0.326985 | 0.20098412 | AA453136_a t | Phosphoribosyl pyrophosphate synthetase-associated protein 2 |
| 617 | Breast | -0.018881 | 0.395224 | 0.326876 | 0.20090981 | U51587_at | Golgi complex autoantigen golgin-97 mRNA |
| 618 | Breast | -0.018927 | 0.3951604 | 0.326746 | 0.20089218 | U00968_at | SREBP-1 mRNA |
| 619 | Breast | -0.019054 | 0.3951426 | 0.326707 | 0.20084654 | U48436_s_a | FMR2 Fragile X mental retardation 2 |
| 620 | Breast | -0.019157 | 0.3950504 | 0.326695 | 0.20075232 | M22403_s_a | PLATELET GLYCOPROTEIN IB ALPHA CHAIN PRECURSOR |
| 621 | Breast | -0.019218 | 0.3950452 | 0.326659 | 0.20067114 | L08044_s_at L08044_s_at | Trefoil factor 3 (intestinal) |
| 622 | Breast | -0.019218 | 0.3950284 | 0.326521 | 0.20066702 | L08044_s_at | TFF3 Trefoil factor 3 (intestinal) |
| 623 | Breast | -0.019501 | 0.3950174 | 0.326357 | 0.20043099 | L08096_s_at 2 | Tumor necrosis factor (ligand) superfamily, member 7 |

FIG. 2C2

| # | Type | | | | | Description |
|---|---|---|---|---|---|---|
| 624 | Breast | -0.019501 | 0.3950068 | 0.32634 | 0.20038226 | L08096_s_at CD70 CD70 antigen (CD27 ligand) |
| 625 | Breast | -0.019909 | 0.3944859 | 0.326315 | 0.20034094 | S49953_s_at N-cym |
| 626 | Breast | -0.019995 | 0.3947755 | 0.326173 | 0.20028324 | AA367473_a_t Crystallin, beta B2 |
| 627 | Breast | -0.020125 | 0.3947755 | 0.326162 | 0.20016424 | AA287706_a_t EST: zs53g08.r1 NCI_CGAP_GCB1 Homo sapiens cDNA clone IMAGE:701246 5', mRNA sequence. (from Genbank) |
| 628 | Breast | -0.020255 | 0.3946715 | 0.326061 | 0.20003535 | Z20777_at EST: H. sapiens putatively transcribed partial sequence; UK-HGMP sequence ID AAACVQH; single read, mRNA sequence. (from Genbank) |
| 629 | Breast | -0.020747 | 0.3946108 | 0.325809 | 0.19996712 | AA010324_a_t Zi09c03.r1 Soares fetal liver spleen 1NFLS S1 Homo sapiens cDNA clone 430276 5', mRNA sequence. (from Genbank) |
| 630 | Breast | -0.020857 | 0.394493 | 0.325747 | 0.19983742 | AA477031_a_t EST: zu38c01.r1 Soares ovary tumor NbHOT Homo sapiens cDNA clone 740256 5', mRNA sequence. (from Genbank) |
| 631 | Breast | -0.021032 | 0.3943622 | 0.325729 | 0.19974118 | U86214_at Fas-associated death domain protein interleukin-1b-converting enzyme 2 mRNA |
| 632 | Breast | -0.021106 | 0.3943285 | 0.325689 | 0.19957174 | N36040_at EST: yy01h09.r1 Homo sapiens cDNA clone 270017 5'. (from Genbank) |
| 633 | Breast | -0.021183 | 0.3942584 | 0.325387 | 0.19945112 | AB002314_a_t KIAA0316 gene |
| 634 | Breast | -0.021183 | 0.3941521 | 0.325292 | 0.19940563 | AB002314_t-2 KIAA0316 gene product |
| 635 | Breast | -0.021189 | 0.3941393 | 0.325259 | 0.19924217 | RC_AA0191 36_s_at EST: ze58h09.s1 Soares retina N2b4HR Homo sapiens cDNA clone 363233 3', mRNA sequence. (from Genbank) |
| 636 | Breast | -0.021451 | 0.3941003 | 0.325226 | 0.1991448 | D84290_s_a_t GPI anchored molecule like protein |
| 637 | Breast | -0.021632 | 0.3941003 | 0.325171 | 0.19912635 | U49928_at TAK1 binding protein 1 (TAB1) mRNA |
| 638 | Breast | -0.021685 | 0.3940784 | 0.325048 | 0.19907698 | L22647_s_at Prostaglandin E receptor 1 (subtype EP1), 42kD |
| 639 | Breast | -0.021835 | 0.3939941 | 0.325001 | 0.19896728 | X69878_at FLT4 Fms-related tyrosine kinase 4 |
| 640 | Breast | -0.02193 | 0.3937903 | 0.324902 | 0.19890364 | M60450_s_a_t KCNA4 Potassium voltage-gated channel, shaker-related subfamily, member 4 |
| 641 | Breast | -0.022125 | 0.3935908 | 0.324752 | 0.1988587 | D88795_at Cadherin, partial cds |
| 642 | Breast | -0.022222 | 0.3934328 | 0.32469 | 0.19879825 | W32012_at EST: zb96c10.r1 Soares parathyroid tumor NbHPA Homo sapiens cDNA clone 320658 5', mRNA sequence. (from Genbank) |
| 643 | Breast | -0.022357 | 0.3934026 | 0.324547 | 0.19849059 | T28246_at Hepsin (transmembrane protease, serine 1) |
| 644 | Breast | -0.022524 | 0.3932871 | 0.324482 | 0.19843242 | L16782_at Putative M phase phosphoprotein 1 (MPP1) mRNA, partial cds |

FIG. 2D2

| | | | | | |
|---|---|---|---|---|---|
| 645 | Breast | -0.022697 | 0.3932196 | 0.324427 | 0.19837774 | RC_AA2533 31_at | EST: zr72g02.s1 Soares NhHMPu S1 Homo sapiens cDNA clone 668978 3', mRNA sequence. (from Genbank) |
| 646 | Breast | -0.022712 | 0.3931201 | 0.324427 | 0.19830844 | RC_AA2274 63_at | Homo sapiens mRNA for KIAA0859 protein, complete cds |
| 647 | Breast | -0.022738 | 0.3926503 | 0.324237 | 0.19822703 | U52373_s_a t | Serine/threonine protein kinase |
| 648 | Breast | -0.02335 | 0.3926291 | 0.323959 | 0.1981594 | U31120_rna 1_at | Interleukin-13 (IL-13) precursor gene |
| 649 | Breast | -0.02364 | 0.3926286 | 0.323894 | 0.19808505 | Y09267_at | Flavin-containing monooxygenase 2 |
| 650 | Breast | -0.02373 | 0.3924801 | 0.323841 | 0.19806422 | RC_AA5214 16_at | EST: aa68d12.s1 NCI_CGAP_GCB1 Homo sapiens cDNA clone IMAGE:826103 3', mRNA sequence. (from Genbank) |
| 651 | Breast | -0.024149 | 0.3924719 | 0.323805 | 0.19800529 | RC_AA4066 40_s_at | EST: zv15e12.s1 Soares NhHMPu S1 Homo sapiens cDNA clone 753742 3', mRNA sequence. (from Genbank) |
| 652 | Breast | -0.024281 | 0.3923425 | 0.3237 | 0.19795163 | M95585_s_a t | HLF Hepatic leukemia factor |
| 653 | Breast | -0.024516 | 0.3923035 | 0.323673 | 0.19779998 | L16464_at | ETS-RELATED PROTEIN PE-1 |
| 654 | Breast | -0.024622 | 0.3920741 | 0.323593 | 0.19775112 | M13955_at | Mesothelial keratin K7 (type II) mRNA, 3' end |
| 655 | Breast | -0.024912 | 0.3920518 | 0.32347 | 0.19756006 | U13706_at | ELAV-like neuronal protein 1 isoform Hel-N2 (Hel-N1) mRNA, partial cds |
| 656 | Breast | -0.024985 | 0.3918988 | 0.323403 | 0.19750126 | X60787_s_a t | INTERLEUKIN ENHANCER-BINDING FACTOR |
| 657 | Breast | -0.025027 | 0.3918442 | 0.323208 | 0.19740452 | L07615_at | Neuropeptide Y receptor Y1 (NPYY1) mRNA, exon 2-3 and complete cds |
| 658 | Breast | -0.025098 | 0.3917643 | 0.323025 | 0.19738203 | AA461426_r _at | EST: zx63h02.r1 Soares total fetus Nb2HF8 9w Homo sapiens cDNA clone 796179 5', mRNA sequence. (from Genbank) |
| 659 | Breast | -0.025314 | 0.3917643 | 0.322916 | 0.19723244 | X06985_at | HMOX1 Heme oxygenase (decycling) 1 |
| 660 | Breast | -0.025388 | 0.3917475 | 0.32281 | 0.19711089 | U00944_at | Clone A9A2BRB6 (CAC)n/(GTG)n repeat-containing mRNA |
| 661 | Breast | -0.025593 | 0.3915833 | 0.322773 | 0.19710284 | X02176_s_a t | C9 Complement component C9 |
| 662 | Breast | -0.025744 | 0.3915815 | 0.322569 | 0.19697288 | M97639_at | Transmembrane receptor (ror2) mRNA |
| 663 | Breast | -0.025776 | 0.3911917 | 0.322529 | 0.19695029 | RC_AA4501 16_at | EST: zx42e06.s1 Soares total fetus Nb2HF8 9w Homo sapiens cDNA clone 789154 3', mRNA sequence. (from Genbank) |
| 664 | Breast | -0.025779 | 0.3911039 | 0.322486 | 0.19681126 | X14675_at | Bcr-abl mRNA 5' fragment (clone 3c) |
| 665 | Breast | -0.025896 | 0.3909376 | 0.322439 | 0.196809 | X72790_at | Endogenous retrovirus mRNA for ORF |
| 666 | Breast | -0.026019 | 0.3907685 | 0.322383 | 0.19662406 | U35407_at | Peroxisomal targeting signal import receptor (PXR1) gene, allele 5, partial cds |
| 667 | Breast | -0.026258 | 0.3907412 | 0.322342 | 0.19659062 | U18914_at | 19.8 kDa protein mRNA |
| 668 | Breast | -0.026348 | 0.3906833 | 0.322326 | 0.19647202 | S58733_at | Pp52 |
| 669 | Breast | -0.026473 | 0.390676 | 0.322237 | 0.19639546 | U10690_f_at | MAGE-5a antigen (MAGE5a) gene |

FIG. 2E2

| | | | | | |
|---|---|---|---|---|---|
| 670 | Breast | -0.027101 | 0.3906609 | 0.3222049 | 0.196299973 | AA203556_a t | EST: zx52a08.r1 Soares fetal liver spleen 1NFLS S1 Homo sapiens cDNA clone 446102 5' similar to contains element MSR1 repetitive element:, mRNA sequence. (from Genbank) |
| 671 | Breast | -0.027137 | 0.3906453 | 0.321914 | 0.196152254 | L02321_at | GSTM5 Glutathione S-transferase M5 |
| 672 | Breast | -0.027203 | 0.3904055 | 0.3217765 | 0.196056622 | AA332089_a t | EST: EST36010 Embryo, 8 week I Homo sapiens cDNA 5' end, mRNA sequence. (from Genbank) |
| 673 | Breast | -0.027253 | 0.3903644 | 0.321747 | 0.195996648 | X13100_s_a t | MYH3 Myosin, heavy polypeptide 3, skeletal muscle, embryonic |
| 674 | Breast | -0.027257 | 0.3903118 | 0.321686 | 0.195781561 | L10123_at | Surfactant protein A mRNA |
| 675 | Breast | -0.027276 | 0.3902732 | 0.321445 | 0.195569753 | M16714_at | HLA-E MHC class I antigen HLA-E |
| 676 | Breast | -0.027276 | 0.3902246 | 0.321387 | 0.195623891 | M16714_at-2 | HLA CLASS I HISTOCOMPATIBILITY ANTIGEN, E E*0101/E*0102 ALPHA CHAIN PRECURSOR |
| 677 | Breast | -0.02756 | 0.3901581 | 0.321271 | 0.195484071 | K02054_at | GRP Gastrin-releasing peptide |
| 678 | Breast | -0.0277 | 0.3901129 | 0.321269 | 0.195394961 | Z46632_at | PDE4C Phosphodiesterase 4C, cAMP-specific (dunce (Drosophila)-homolog phosphodiesterase E1) |
| 679 | Breast | -0.027774 | 0.3901016 | 0.321221 | 0.195339381 | X95238_s_a t | H.sapiens mRNA for cysteine-rich secretory protein-1 delta |
| 680 | Breast | -0.028045 | 0.3899886 | 0.32114 | 0.195279691 | U79280_at | Clone 23575 mRNA, partial cds |
| 681 | Breast | -0.028045 | 0.3898886 | 0.320961 | 0.1951904 | U79280_at-2 | Human clone 23575 mRNA, partial cds |
| 682 | Breast | -0.028417 | 0.389951 | 0.320818 | 0.195130241 | AA386297_a t | EST: EST185039 Brain IV Homo sapiens cDNA, mRNA sequence. (from Genbank) |
| 683 | Breast | -0.02848 | 0.3898881 | 0.320782 | 0.195079091 | HG4194-HT4464_at | Sodium/Hydrogen Exchanger 5 |
| 684 | Breast | -0.028502 | 0.3897989 | 0.320773 | 0.194973111 | AA393903_a t | EST: zl85e04.r1 Soares testis NHT Homo sapiens cDNA clone 729150 5', mRNA sequence. (from Genbank) |
| 685 | Breast | -0.028566 | 0.3897747 | 0.320737 | 0.194901261 | D42039_at | KIAA0081 gene, partial cds |
| 686 | Breast | -0.028601 | 0.3897689 | 0.320697 | 0.194811821 | RC_AA2851 44_s_at | EST: zs48h10.s1 NCI_CGAP_GCB1 Homo sapiens cDNA clone IMAGE:700771 3', mRNA sequence. (from Genbank) |
| 687 | Breast | -0.028804 | 0.389744 | 0.320549 | 0.194765551 | AA078906_a t | Zm94c04.r1 Stratagene colon HT29 (#937221) Homo sapiens cDNA clone 545574 5', mRNA sequence. (from Genbank) |
| 688 | Breast | -0.028867 | 0.3897027 | 0.320237 | 0.194651511 | D10537_s_a t-2 | Myelin protein zero (Charcot-Marie-Tooth neuropathy 1B) |
| 689 | Breast | -0.028867 | 0.389526 | 0.320207 | 0.194611791 | D10537_s_a t | MPZ Myelin protein zero (Charcot-Marie-Tooth neuropathy 1B) |
| 690 | Breast | -0.028964 | 0.3894779 | 0.32003 | 0.194544881 | D88532_at | P55pik |
| 691 | Breast | -0.029097 | 0.3894518 | 0.320011 | 0.194523651 | Z19702_at | EST: H. sapiens putatively transcribed partial sequence; UK-HGMP sequence ID AAAAHXT; single read, mRNA sequence. (from Genbank) |

FIG. 2F2

| | | | | | |
|---|---|---|---|---|---|
| 692 | Breast | -0.029423 | 0.3894487 | 0.319976 | 0.19443801 | M82967_s_a t | Acrosomal vesicle protein 1 |
| 693 | Breast | -0.0295 | 0.3893646 | 0.319864 | 0.19434194 | Z29572_at | Antisense mRNA for BCMA peptide |
| 694 | Breast | -0.029501 | 0.3892904 | 0.319834 | 0.19424595 | L40992_at | (clone PEBP2aA1) core-binding factor, runt domain, alpha subunit 1 (CBFA1) mRNA, 3' end of cds |
| 695 | Breast | -0.0296 | 0.3891564 | 0.319748 | 0.19413926 | AA071106_f _at | EST: zm66e11.r1 Stratagene neuroepithelium (#937231) Homo sapiens cDNA clone 530636 5' similar to SW:PA10_YEAST P48363 PAC10 PROTEIN. [1] ;_mRNA sequence. (from Genbank) |
| 696 | Breast | -0.029649 | 0.389063 | 0.319717 | 0.19406885 | R87549_at | Ym89c04.r1 Homo sapiens cDNA clone 166086 5'. (from Genbank) |
| 697 | Breast | -0.029738 | 0.389023 | 0.319563 | 0.19401522 | RC_AA4492 15_at | EST: zx03h11.s1 Soares total fetus Nb2HF8 9w Homo sapiens cDNA clone 785445 3', mRNA sequence. (from Genbank) |
| 698 | Breast | -0.029969 | 0.3889602 | 0.319435 | 0.19390024 | M11718_at | COL5A2 Collagen, type V, alpha |
| 699 | Breast | -0.030033 | 0.3888889 | 0.319365 | 0.19380666 | U87593_f_at | Endogenous retrovirus clone P1.8 polymerase mRNA, partial cds |
| 700 | Breast | -0.0301 | 0.3888714 | 0.31931 | 0.19370103 | X51699_at | Bone gamma-carboxyglutamate (gla) protein (osteocalcin) |
| 701 | Breast | -0.030433 | 0.3888714 | 0.319301 | 0.19363362 | X83127_at | K+ channel beta 1a subunit mRNA, alternatively spliced |
| 702 | Breast | -0.030521 | 0.3887397 | 0.319211 | 0.19349878 | N24988_at | EST: yx16d12.r1 Homo sapiens cDNA clone 261911 5'. (from Genbank) |
| 703 | Breast | -0.030784 | 0.3885799 | 0.319186 | 0.1934782 | HG3355-HT3532_at | Peroxisome Proliferator Activated Receptor (Gb:Z30972) |
| 704 | Breast | -0.03082 | 0.3885541 | 0.319117 | 0.19337611 | RC_AA0211 57_at | EST: zo65d11.s1 Soares retina N2b4HR Homo sapiens cDNA clone 363861 3', mRNA sequence. (from Genbank) |
| 705 | Breast | -0.030839 | 0.3885389 | 0.318897 | 0.1933438 | U09609_at | NFKB2 Nuclear factor of kappa light polypeptide gene enhancer in B-cells 2 (p49/p100) |
| 706 | Breast | -0.030947 | 0.3883018 | 0.318806 | 0.193263 | hum_alu_at | hum_alu_at (miscellaneous control) |
| 707 | Breast | -0.030947 | 0.3882127 | 0.318768 | 0.19315903 2 | hum_alu_al-hum_alu_at | No description for gene: hum_alu_at |
| 708 | Breast | -0.030952 | 0.3881313 | 0.318744 | 0.19305119 | HG3111-HT3287_at | Autoantigen (Gb:S67069) |
| 709 | Breast | -0.031107 | 0.3880803 | 0.318708 | 0.19291893 | U06711_s_a t | Mucin 5, sublype B, tracheobronchial |
| 710 | Breast | -0.031109 | 0.3880755 | 0.318662 | 0.19288558 | X83492_s_a | Fas/Apo-1 (clone pCRTM11-Fasdelta(4,7)) |
| 711 | Breast | -0.03202 | 0.3880634 | 0.318595 | 0.19276854 | U39840_at | Hepatocyte nuclear factor-3 alpha (HNF-3 alpha) mRNA |
| 712 | Breast | -0.032318 | 0.3879453 | 0.318595 | 0.1927063 | U72508_at-2 | Human B7 mRNA, complete cds |
| 713 | Breast | -0.032318 | 0.387741 | 0.318436 | 0.19259281 | U72508_at | B7 mRNA |

FIG. 2G2

| | | | | | |
|---|---|---|---|---|---|
| 714 | Breast | -0.032536 | 0.387623 | 0.318382 | 0.19242862 | U37529_at | TAC2 Tachykinin 2 (substance K, neurokinin A, neurokinin 2, neuromedin L, neurokinin alpha, neuropeptide K, neuropeptide gamma) |
| 715 | Breast | -0.032688 | 0.387188 | 0.318353 | 0.19241333 | HG2602-HT2698_at | Succinate Dehydrogenase, Flavoprotein Subunit |
| 716 | Breast | -0.033031 | 0.3871545 | 0.318248 | 0.1923692 | X53683_at | SCYA4 Small inducible cytokine A4 (homologous to mouse Mip-1b) |
| 717 | Breast | -0.033117 | 0.3871545 | 0.318154 | 0.1921061 | RC_AA4238120_at | EST: zv33l03.s1 Soares ovary tumor NbHOT Homo sapiens cDNA clone 755453 3', mRNA sequence. (from Genbank) |
| 718 | Breast | -0.033488 | 0.386972 | 0.318084 | 0.19199681 | Y13896_at | Skeletal muscle alternate 5'end of gene Kir4.2 5'UTR |
| 719 | Breast | -0.033579 | 0.3869321 | 0.318001 | 0.19199432 | U24389_s_at | Lysyl oxidase-like protein gene |
| 720 | Breast | -0.033614 | 0.3867562 | 0.317791 | 0.19187437 | T83397_at | Homo sapiens peroxisomal phytanoyl-CoA alpha-hydroxylase (PAHX) mRNA, complete cds |
| 721 | Breast | -0.03365 | 0.3867241 | 0.317856 | 0.19185448 | AA126812_a_t | Homo sapiens mRNA for KIAA0690 protein, partial cds |
| 722 | Breast | -0.033779 | 0.3866734 | 0.317836 | 0.19178328 | L47125_s_at | EEF1A1 Translation elongation factor 1-alpha-1 |
| 723 | Breast | -0.034154 | 0.3866259 | 0.317747 | 0.19174463 | X03168_at | VTN Vitronectin (serum spreading factor, somatomedin B, complement S-protein) |
| 724 | Breast | -0.034379 | 0.3866137 | 0.317631 | 0.191585 | L39060_at | Transcription factor SL1 mRNA |
| 725 | Breast | -0.034379 | 0.3866099 | 0.317515 | 0.19151199 | L39060_at-2 | Homo sapiens transcription factor SL1 mRNA, complete cds |
| 726 | Breast | -0.03445 | 0.3865914 | 0.317501 | 0.19149223 | M61176_at | BDNF Brain-derived neurotrophic factor |
| 727 | Breast | -0.034486 | 0.386584 | 0.317479 | 0.19137911 | U26446_s_at | Protoporphyrinogen oxidase |
| 728 | Breast | -0.034719 | 0.3865145 | 0.31721 | 0.19130622 | U60669_rna1_s_at | Human 1 alpha,25-dihydroxyvitamin D3 24-hydroxylase (CYP24) gene, promoter region and partial CDS. (from Genbank) |
| 729 | Breast | -0.034739 | 0.3864797 | 0.317153 | 0.19119155 | W04798_at | EST: ze81b04.r1 Soares fetal lung NbHL19W Homo sapiens cDNA clone 298927 5', mRNA sequence. (from Genbank) |
| 730 | Breast | -0.034753 | 0.3862583 | 0.316978 | 0.1911794 | M32598_at | RPS11 Ribosomal protein S11 |
| 731 | Breast | -0.034781 | 0.3862173 | 0.316917 | 0.19114253 | U63824_at | Transcription factor RTEF-1 (RTEF1) mRNA |
| 732 | Breast | -0.034781 | 0.3861283 | 0.316833 | 0.1910568 | U63824_at-2 | TEA domain family member 4 |
| 733 | Breast | -0.034847 | 0.3859254 | 0.316798 | 0.19094059 | RC_AA485055_at | Homo sapiens sperm flagellar protein Repro-SA-1 mRNA, complete cds |
| 734 | Breast | -0.034994 | 0.3858423 | 0.316716 | 0.19086787 | AA156670_f_at | Homo sapiens agrin precursor mRNA, partial cds |
| 735 | Breast | -0.035093 | 0.3857837 | 0.316631 | 0.19081274 | X04729_s_at | Plasminogen activator inhibitor type 1 N-terminus |
| 736 | Breast | -0.035134 | 0.3856858 | 0.316376 | 0.19075832 | X83412_at | B1 mRNA for mucin |

FIG. 2H2

| | | | | | | |
|---|---|---|---|---|---|---|
| 737 | Breast | -0.0351134 | 0.3856494 | 0.316271 | 0.19066155 | X83412_at-2 | H.saplens B1 mRNA for mucin |
| 738 | Breast | -0.0354 | 0.3856175 | 0.316244 | 0.19061704 | HG944-HT944_s_at | Dopamine Receptor D4 |
| 739 | Breast | -0.035602 | 0.3855714 | 0.316193 | 0.19035721 | U92074_at | RAD51 (S. cerevisiae)-like 1 |
| 740 | Breast | -0.03629 | 0.3855714 | 0.316147 | 0.19032341 | HG371-HT26388_s_at | Mucin 1, Epithelial, Alt. Splice 9 |
| 741 | Breast | -0.036315 | 0.3852958 | 0.315979 | 0.19026425 | M13485_at | Metallothionein I-B gene |
| 742 | Breast | -0.03644 | 0.3851801 | 0.315951 | 0.19018021 | U25801_at | Tax1 binding protein mRNA, partial cds |
| 743 | Breast | -0.036725 | 0.3851245 | 0.315841 | 0.19010323 | D50582_at | Inward rectifier K channel |
| 744 | Breast | -0.036862 | 0.3848574 | 0.315766 | 0.19002923 | U88667_at | ATP binding cassette transporter (ABCR) mRNA |
| 745 | Breast | -0.036925 | 0.3848563 | 0.31576 | 0.1899569638_at | RC_AA1668 | EST: zq39h04.s1 Stratagene hNT neuron (#937233) Homo sapiens cDNA clone 632119 3' similar to contains Alu repetitive element;contains element MSR1 repetitive element :, mRNA sequence. (from Genbank) |
| 746 | Breast | -0.037002 | 0.3846765 | 0.315584 | 0.18993308 | AA283662_at | EST: zt16h03.r1 NCI_CGAP_GCB1 Homo sapiens cDNA clone IMAGE:713333 5', mRNA sequence. (from Genbank) |
| 747 | Breast | -0.037156 | 0.384391 | 0.315584 | 0.18985245 | AA444115_at | EST: zv51b08.r1 Soares testis NHT Homo sapiens cDNA clone 757143 5', mRNA sequence. (from Genbank) |
| 748 | Breast | -0.037231 | 0.3843007 | 0.315368 | 0.18972932 | RC_AA1484 | Flavin containing monooxygenase 5 |
| 749 | Breast | -0.037298 | 0.3841811 | 0.315365 | 0.18967877 | HG2157-HT2227_at | Mucin 4, Tracheobronchial |
| 750 | Breast | -0.037299 | 0.3841666 | 0.315357 | 0.18952338 | U27699_at | SODIUM- AND CHLORIDE-DEPENDENT BETAINE TRANSPORTER |
| 751 | Breast | -0.037348 | 0.3839851 | 0.315349 | 0.18944152 | RC_AA6101 16_i_at | EST: af19g10.s1 Soares total fetus Nb2HF8 9w Homo sapiens cDNA clone 1032162 3', mRNA sequence. (from Genbank) |
| 752 | Breast | -0.03741 | 0.3839824 | 0.315344 | 0.18943453 | U90907_at | Clone 23907 mRNA sequence |
| 753 | Breast | -0.037521 | 0.3839673 | 0.315335 | 0.18934816 | Y10205_at | CD88 protein |
| 754 | Breast | -0.037705 | 0.3839286 | 0.315279 | 0.18925376 | M94893_at | TSPY Testis specific protein, Y-linked |
| 755 | Breast | -0.037743 | 0.3838683 | 0.315149 | 0.18915528 | Y10260_at | EYA1A gene |
| 756 | Breast | -0.037829 | 0.3837707 | 0.315115 | 0.18907477 | N45402_at | EST: yw97i08.r1 Homo sapiens cDNA clone 260199 5'. (from Genbank) |
| 757 | Breast | -0.037857 | 0.383661 | 0.315012 | 0.18900041 17_at | RC_AA5051 | EST: aa65b09.s1 NCI_CGAP_GCB1 Homo sapiens cDNA clone IMAGE:825785 3', mRNA sequence. (from Genbank) |
| 758 | Breast | -0.037981 | 0.3836543 | 0.314924 | 0.18894492 | AA043894_at | EST: zk57b05.r1 Soares pregnant uterus NbHPU Homo sapiens cDNA clone 486897 5', mRNA sequence. (from Genbank) |
| 759 | Breast | -0.038016 | 0.3835911 | 0.314865 | 0.18889864 | H25982_at | EST: yl56g01.r1 Homo sapiens cDNA clone 162288 5'. (from Genbank) |

FIG. 2I2

| | | | | | |
|---|---|---|---|---|---|
| 760 | Breast | -0.038383 | 0.3834648 | 0.314852 | 0.18882492 | HG3231-HT3408_at | Protease Receptor-1, Effector Cell |
| 761 | Breast | -0.038459 | 0.3833663 | 0.314788 | 0.18878222 | RC_AA4170 46_at | Fatty-acid-Coenzyme A ligase, very long-chain 1 |
| 762 | Breast | -0.038896 | 0.3832846 | 0.314589 | 0.18866111 | J05582_s_at | MUC1 Mucin 1, transmembrane |
| 763 | Breast | -0.039355 | 0.3829456 | 0.31455 | 0.18860418 | AA504384_a t | EST: aa59c02.r1 NCI_CGAP_GCB1 Homo sapiens cDNA clone IMAGE:825218 5' similar to contains element MIR repetitive element:; mRNA sequence. (from Genbank) |
| 764 | Breast | -0.039476 | 0.3829375 | 0.31439 | 0.18851428 | D61596_at | Human fetal brain cDNA 5'-end GEN-421F03, mRNA sequence. (from Genbank) |
| 765 | Breast | -0.039592 | 0.3829375 | 0.314274 | 0.18847165 | N73185_at | EST: yv46a09.r1 Homo sapiens cDNA clone 245752 5'. (from Genbank) |
| 766 | Breast | -0.039766 | 0.3829356 | 0.314272 | 0.18836278 | U04325_cds 3_at | PSG11 gene (pregnancy-specific beta-1-glycoprotein 11 C-A domain) extracted from Human pregnancy-specific beta-1-glycoprotein alternatively spliced C-R, C-S, C-B, and C-A domains (PSG11) gene, partial cds |
| 767 | Breast | -0.039783 | 0.3828778 | 0.314272 | 0.18828952 | RC_AA4305 52_at | Proline-rich Gla (G-carboxglutamic acid) polypeptide 2 |
| 768 | Breast | -0.039802 | 0.3828232 | 0.314235 | 0.18826889 | U32674_s_a t | Orphan receptor GPR9 (GPR9) gene, partial cds |
| 769 | Breast | -0.04008 | 0.382802 | 0.314233 | 0.1881376 | U35459_at | Bomapin mRNA |
| 770 | Breast | -0.040125 | 0.3824697 | 0.314123 | 0.18804514 | W87936_at | EST: zh68d10.r1 Soares fetal liver spleen 1NFLS S1 Homo sapiens cDNA clone 417235 5' similar to gb:M74525 UBIQUITIN-CONJUGATING ENZYME E2-17 KD (HUMAN);contains Alu repetitive element:; mRNA sequence. (from Genbank) |
| 771 | Breast | -0.040346 | 0.3824697 | 0.314053 | 0.18796603 | HG2260-HT2349_s_a t | Duchenne Muscular Dystrophy Protein (Dmd) |
| 772 | Breast | -0.0406 | 0.3824237 | 0.313974 | 0.18780902 | M11058_at | 3-HYDROXY-3-METHYLGLUTARYL-COENZYME A REDUCTASE |
| 773 | Breast | -0.040858 | 0.3822903 | 0.313893 | 0.187753 | RC_AA4060 54_at | EST: zu65a10.s1 Soares testis NHT Homo sapiens cDNA clone 742842 3', mRNA sequence. (from Genbank) |
| 774 | Breast | -0.041114 | 0.3822249 | 0.313862 | 0.1877031 | Z70218_s_at | MN1 protein (clone ICRFp507I0498) |
| 775 | Breast | -0.041126 | 0.3821041 | 0.313813 | 0.18766877 | AA004333_a t | EST: zh91a01.r1 Soares fetal liver spleen 1NFLS S1 Homo sapiens cDNA clone 428616 5', mRNA sequence. (from Genbank) |
| 776 | Breast | -0.041236 | 0.3820344 | 0.313651 | 0.18754639 | W01059_at | EST: za55e09.r1 Soares fetal liver spleen 1NFLS Homo sapiens cDNA clone 296488 5', mRNA sequence. (from Genbank) |

FIG. 2J2

| | | | | | | |
|---|---|---|---|---|---|---|
| 777 | Breast | -0.041472 | 0.3818738 | 0.313634 | 0.1874629 | Z22780_at | CYLICIN |
| 778 | Breast | -0.041654 | 0.3818504 | 0.313586 | 0.18743448 | W19984_at | EST: zb38d11.r1 Soares parathyroid tumor NbHPA Homo sapiens cDNA clone 305877 5', mRNA sequence. (from Genbank) |
| 779 | Breast | -0.041679 | 0.3817395 | 0.3135 | 0.18733877 | AA362598_a_t | EST: EST72534 Ovary II Homo sapiens cDNA 5' end, mRNA sequence. (from Genbank) |
| 780 | Breast | -0.041703 | 0.3817279 | 0.313489 | 0.18728574 | M21494_at | CKM Creatine kinase, muscle |
| 781 | Breast | -0.041738 | 0.3817012 | 0.313473 | 0.18724519 | X52003_at | TFF1 Trefoil factor 1 (breast cancer, estrogen-inducible sequence expressed in) |
| 782 | Breast | -0.04187 | 0.3816702 | 0.3134414 | 0.18713742 | RC_AA0106 17_at | EST: zl09f12.s1 Soares fetal liver spleen 1NFLS S1 Homo sapiens cDNA clone 4303193', mRNA sequence. (from Genbank) |
| 783 | Breast | -0.041888 | 0.3816606 | 0.3134414 | 0.18708766 | U73394_f_at | H.sapiens mRNA for NK receptor, clone 12.11C |
| 784 | Breast | -0.04192 | 0.381577 | 0.311335 | 0.18707192_at | D87002_cds AB000115_a | POM121-like 1 gene extracted from Human (lambda) DNA for immunoglobulin light chain |
| 785 | Breast | -0.042124 | 0.3815632 | 0.313284 | 0.18691987 | t | mRNA |
| 786 | Breast | -0.042367 | 0.3815464 | 0.313261 | 0.18682547 | Y09321_at | TAFII105 mRNA, partial |
| 787 | Breast | -0.042618 | 0.3813474 | 0.313211 | 0.18681543 | RC_AA4366 19_at | EST: zw55d04.s1 Soares total fetus Nb2HF8 9w Homo sapiens cDNA clone 7739593', mRNA sequence. (from Genbank) |
| 788 | Breast | -0.042849 | 0.3813261 | 0.313104 | 0.18677084 | M37763_at | Neurotrophin-3 (NT-3) gene |
| 789 | Breast | -0.043119 | 0.3812952 | 0.312946 | 0.18675461 | U09877_at | Helicase-like protein (HLP) mRNA |
| 790 | Breast | -0.043255 | 0.3812952 | 0.312914 | 0.1867369 | L14269_at | SLC18A2 Solute carrier family 18 (vesicular monoamine), member 2 |
| 791 | Breast | -0.0433 | 0.3812754 | 0.312909 | 0.18663359 | W28035_at | EST: 41a8 Human retina cDNA randomly primed sublibrary Homo sapiens cDNA, mRNA sequence. (from Genbank) |
| 792 | Breast | -0.043619 | 0.3811475 | 0.312854 | 0.18641348 | AA018852_a_t | EST: ze55a07.r1 Soares retina N2b4HR Homo sapiens cDNA clone 3628685', mRNA sequence. (from Genbank) |
| 793 | Breast | -0.043679 | 0.3810659 | 0.312835 | 0.18639849 | U26209_at | Solute carrier family 13 (sodium-dependent dicarboxylate transporter), member 2 |
| 794 | Breast | -0.043703 | 0.3810654 | 0.312828 | 0.18635501 | AFFX-LysX-5_at | AFFX-LysX-5_at (endogenous control) |
| 795 | Breast | -0.043703 | 0.3808901 | 0.31271 | 0.18621843 | AFFX-LysX-5_at-2 | AFFX-LysX-5_at (miscellaneous control - 11k chips) |
| 796 | Breast | -0.043819 | 0.3807985 | 0.312639 | 0.18615448 | N28643_at | Melastatin 1 |
| 797 | Breast | -0.043947 | 0.3807322 | 0.312404 | 0.18608798 | HT4163_at | Phosphoglucomutase 1, Alt. Splice |
| 798 | Breast | -0.043956 | 0.3806689 | 0.312303 | 0.18603803 | X81420_at | MLN137 mRNA |
| 799 | Breast | -0.044317 | 0.3805767 | 0.312237 | 0.18601997 | D87012_at | Immunoglobulin lambda gene locus DNA, clone:61D6 |

FIG. 2K2

| # | Tissue | | | | ID | Description |
|---|---|---|---|---|---|---|
| 800 | Breast | -0.04437 | 0.38056695 | 0.312191 | 0.18586798 | X04898_rna1_at | Apolipoprotein AII |
| 801 | Breast | -0.044387 | 0.38056693 | 0.312105 | 0.18585421 | X98405_at | Myelin associated glycoprotein |
| 802 | Breast | -0.044589 | 0.3804854 | 0.312079 | 0.18581752 | X82125_at | HOK-2 mRNA for zinc finger protein |
| 803 | Breast | -0.045062 | 0.3804589 | 0.311941 | 0.18564828 | U29091_at | Selenium-binding protein (hSBP) mRNA |
| 804 | Breast | -0.045064 | 0.3804506 | 0.311941 | 0.18558545 | AA070545_at | Zm70c03.r1 Stratagene neuroepithelium (#937231) Homo sapiens cDNA clone 530980 5', mRNA sequence. (from Genbank) |
| 805 | Breast | -0.045145 | 0.3803745 | 0.311858 | 0.18545094 | W26635_at | Core-binding factor, runt domain, alpha subunit 2; translocated to, 2 |
| 806 | Breast | -0.045175 | 0.3802944 | 0.311818 | 0.18541189 | U80982_rna1_s_at | CCAAT/enhancer binding protein (C/EBP), epsilon |
| 807 | Breast | -0.045283 | 0.3802944 | 0.311811 | 0.18533006 | U49973_xpt2_at | ORF2: function unknown from Human Tigger1 transposable element, complete consensus sequence./ntype=DNA /annot=CDS |
| 808 | Breast | -0.045317 | 0.3802663 | 0.311809 | 0.18527262 | M81780_cds5_at | SMPD1 gene (acid sphingomyelinase) extracted from Homo sapiens acid sphingomyelinase (SMPD1) gene, ORF's 1-3's |
| 809 | Breast | -0.045327 | 0.38021 | 0.311772 | 0.1851911 | X95463_s_at | FMR2 Fragile X mental retardation 2 |
| 810 | Breast | -0.045598 | 0.3801895 | 0.311642 | 0.18512306 | D49490_at | Protein disulfide isomerase-related protein (PDIR) |
| 811 | Breast | -0.045622 | 0.380162 | 0.31164 | 0.18500948 | M65199_at | EDN2 Endothelin 2 |
| 812 | Breast | -0.045629 | 0.3801511 | 0.311621 | 0.18489403 | X83857_s_at | PTGER3 Prostaglandin E receptor 3 (subtype EP3) (alternative products) |
| 813 | Breast | -0.045709 | 0.3800442 | 0.311497 | 0.18474871 | AA422123_i_at | EST: zv26h12.r1 Soares NhHMPu S1 Homo sapiens cDNA clone 754823 5' similar to contains Alu repetitive element;, mRNA sequence. (from Genbank) |
| 814 | Breast | -0.045846 | 0.3800312 | 0.311447 | 0.18473122 | AF010126_a_at | Synuclein, gamma (breast cancer-specific protein 1) |
| 815 | Breast | -0.045977 | 0.3800042 | 0.311387 | 0.18463843 | D17716_at-2 | Mannosyl (alpha-1,6-)-glycoprotein beta-1,6-N-acetyl-glucosaminyltransferase |
| 816 | Breast | -0.045977 | 0.379957 | 0.311354 | 0.18455261 | D17716_at | N-acetylglucosaminyltransferase V |
| 817 | Breast | -0.046085 | 0.3798629 | 0.311285 | 0.18446992 | Z83802_at | Axonemal dynein heavy chain (partial, ID hdhc3) |
| 818 | Breast | -0.046102 | 0.3796748 | 0.311238 | 0.18439811 | D82286_at | EST: similar to none, mRNA sequence. (from Genbank) |
| 819 | Breast | -0.046132 | 0.3796173 | 0.311175 | 0.18430896 | L04791_s_at | Excision repair cross-complementing rodent repair deficiency, complementation group 6 |
| 820 | Breast | -0.046141 | 0.379601 | 0.311125 | 0.1842122 | RC_AA6217 18_at | EST: af54f07.s1 Soares total fetus Nb2H F8 9w Homo sapiens cDNA clone 1035493 3', mRNA sequence. (from Genbank) |
| 821 | Breast | -0.046276 | 0.3795269 | 0.311086 | 0.18408595 | RC_AA5989 51_at | EST: ae37h03.s1 Gessler Wilms tumor Homo sapiens cDNA clone 898037 3', mRNA sequence. (from Genbank) |
| 822 | Breast | -0.046374 | 0.3794265 | 0.310965 | 0.18405467 | X66839_at | MaTu MN mRNA for p54/58N protein |
| 823 | Breast | -0.046503 | 0.3794064 | 0.310964 | 0.183937 | P-Select_at | No description for gene: P-Select_at |

FIG. 2L2

| | | | | | |
|---|---|---|---|---|---|
| 824 | Breast | -0.046598 | 0.3793238 | 0.310916 | 0.18382798 | X87344_cds 10_r_at | DMA gene extracted from H.sapiens DMA, DMB, HLA-Z1, IPP2, LMP2, TAP1, LMP7, TAP2, DOB, DQB2 and RING8, 9, 13 and 14 genes |
| 825 | Breast | -0.046808 | 0.3792819 | 0.31084 | 0.18379238 | L41147_at | 5-HT6 serotonin receptor mRNA |
| 826 | Breast | -0.047033 | 0.3790966 | 0.310591 | 0.18376642 | U12140_at | Tyrosine kinase receptor p145TRK-B (TRK-B) mRNA |
| 827 | Breast | -0.04711 | 0.3790465 | 0.310565 | 0.18370172 | M99063_at | KERATIN, TYPE II CYTOSKELETAL 2 ORAL |
| 828 | Breast | -0.047221 | 0.3788799 | 0.310537 | 0.18354703 | X91653_s_a t | DNA for exon encoding for N-acetylglucosaminyltransferase V (340 bp) |
| 829 | Breast | -0.047427 | 0.3788275 | 0.310493 | 0.18350817 | AA099995_a t | Zn65e06.r1 Stratagene fibroblast (#937212) Homo sapiens cDNA clone 530530 5', mRNA sequence. (from Genbank) |
| 830 | Breast | -0.047494 | 0.3786335 | 0.310455 | 0.18347153 | M31651_at | SHBG Sex hormone-binding globulin |
| 831 | Breast | -0.047503 | 0.3785127 | 0.310432 | 0.18340471 | U58675_cds_at | OR17-228 gene extracted from Human olfactory receptor gene cluster on chromosome 17, OR17-228 and OR17-40, and OR17-24 and OR17-25 pseudogenes |
| 832 | Breast | -0.047893 | 0.3785102 | 0.310279 | 0.18335998 | R78309_at | EST: yi82b05.r1 Homo sapiens cDNA clone 145713 5'. (from Genbank) |
| 833 | Breast | -0.048011 | 0.3785049 | 0.310219 | 0.18329163 | RC_AA0019 08_at | EST: zh83a05.s1 Soares fetal liver spleen 1NFLS S1 Homo sapiens cDNA clone 427856 3', mRNA sequence. (from Genbank) |
| 834 | Breast | -0.048012 | 0.3783343 | 0.310149 | 0.18323077 | AA249437_a t HG4272- | EST: j3966.seq.F Human fetal heart, Lambda ZAP Express Homo sapiens cDNA 5', mRNA sequence. (from Genbank) |
| 835 | Breast | -0.048071 | 0.3783139 | 0.310091 | 0.183159 | HT4542_at | Hepatocyte Growth Factor Receptor |
| 836 | Breast | -0.048148 | 0.378209 | 0.30999 | 0.18310912 | H47161_at | Acyl-Coenzyme A dehydrogenase, short/branched chain |
| 837 | Breast | -0.048182 | 0.3781759 | 0.309966 | 0.18330362 | U34044_at | Selenium donor protein (selD) mRNA |
| 838 | Breast | -0.048856 | 0.3781345 | 0.309846 | 0.18286031 | H78886_at | EST: yu11a03.r1 Homo sapiens cDNA clone 233452 5'. (from Genbank) |
| 839 | Breast | -0.048856 | 0.3780817 | 0.3098 | 0.18285431 | M91463_rna_at-2 M91463_rna | Solute carrier family 2 (facilitated glucose transporter), member 4 |
| 840 | Breast | -0.048856 | 0.3779767 | 0.309789 | 0.18269047 | _at | Glucose transporter (GLUT4) gene |
| 841 | Breast | -0.048877 | 0.377887 | 0.309704 | 0.18265112 | RC_AA4777 39_at | EST: zu34a07.s1 Soares ovary tumor NbHOT Homo sapiens cDNA clone 739860 3', mRNA sequence. (from Genbank) |
| 842 | Breast | -0.048953 | 0.377817 | 0.309605 | 0.18256605 | AA251078_a t | EST: zs01b12.r1 NCI_CGAP_GCB1 Homo sapiens cDNA clone IMAGE:683903 5', mRNA sequence. (from Genbank) |
| 843 | Breast | -0.0491 | 0.3777879 | 0.309457 | 0.18247831 | X83863_at | PTGER3 Prostaglandin E receptor 3 (subtype EP3) {alternative products} |
| 844 | Breast | -0.049134 | 0.3777756 | 0.309446 | 0.18239106 | U70136_at | THPO Thrombopoietin (myeloproliferative leukemia virus oncogene ligand, megakaryocyte growth and development factor) |

FIG. 2M2

| | | | | | |
|---|---|---|---|---|---|
| 845 | Breast | -0.049186 | 0.377745 | 0.30937 | 0.18238877 | RC_AA0114 41_at | EST: zi03a02.s1 Soares fetal liver spleen 1NFLS S1 Homo sapiens cDNA clone 429674 3' similar to gb:J02931 TISSUE FACTOR PRECURSOR (HUMAN);, mRNA sequence. (from Genbank) |
| 846 | Breast | -0.049221 | 0.3777053 | 0.309295 | 0.18227758 | M60828_at | FGF7 Fibroblast growth factor 7 (keratinocyte growth factor) |
| 847 | Breast | -0.049375 | 0.3774585 | 0.309253 | 0.18225089 | M58597_at | FUT4 Fucosyltransferase 4 (alpha (1,3) fucosyltransferase, myeloid-specific) |
| 848 | Breast | -0.049551 | 0.3774023 | 0.309077 | 0.1822192 | D42123_at | ESP1/CRP2 |
| 849 | Breast | -0.049976 | 0.3773491 | 0.308997 | 0.18214276 | C17139_at | EST: Human placenta cDNA 5'-end GEN-539G01, mRNA sequence. (from Genbank) |
| 850 | Breast | -0.05026 | 0.3773456 | 0.30899 | 0.18202047 | Z49825_s_at | HEPATOCYTE NUCLEAR FACTOR 4 |
| 851 | Breast | -0.050272 | 0.3772548 | 0.308935 | 0.1819276 | U03115_cds 10_at | Human V beta T-cell receptor (TCRBV) gene locus |
| 852 | Breast | -0.050367 | 0.3771961 | 0.308833 | 0.18181373 | AA434506_a_t | EST: zw31c06.r1 Soares ovary tumor NbHOT Homo sapiens cDNA clone 770890 5', mRNA sequence. (from Genbank) |
| 853 | Breast | -0.050384 | 0.3771682 | 0.308774 | 0.18173163 | AA094735_a_t | EST: cp14z2.seq.F Fetal heart, Lambda ZAP Express Homo sapiens cDNA 5', mRNA sequence. (from Genbank) |
| 854 | Breast | -0.05043 | 0.3770363 | 0.308741 | 0.18171063 | U60987_s_a_t | Transcription factor TBX5 mRNA |
| 855 | Breast | -0.050445 | 0.3769881 | 0.308637 | 0.18159907 | U94354_at | Lunatic fringe (Drosophila) homolog |
| 856 | Breast | -0.050511 | 0.3767901 | 0.308632 | 0.18153572 | H53555_at | EST: yq86g10.r1 Homo sapiens cDNA clone 202722 5' similar to contains L1 repetitive element.: (from Genbank) |
| 857 | Breast | -0.050779 | 0.3766713 | 0.308521 | 0.1814945 | AA479990_a_t | EST: zv18a05.r1 Soares NhHMPu S1 Homo sapiens cDNA clone 753968 5', mRNA sequence. (from Genbank) |
| 858 | Breast | -0.050786 | 0.3764956 | 0.308514 | 0.1814329 | M98528_at | BRAIN NEURON CYTOPLASMIC PROTEIN 1 |
| 859 | Breast | -0.050916 | 0.3764089 | 0.308414 | 0.1813518 | U33849_at | Lymphoma proprotein convertase (LPC) mRNA |
| 860 | Breast | -0.051229 | 0.3763587 | 0.308362 | 0.18123317 | AC002076_c ds2_at | WUGSC:GS345D13.2 gene (G-protein gamma-1 subunit) extracted from Human BAC clone GS345D13 from 7q31-q32 |
| 861 | Breast | -0.051249 | 0.3763434 | 0.308293 | 0.18114 | AA043160_a_t | EST: zk49g01.r1 Soares pregnant uterus NbHPU Homo sapiens cDNA clone 486096 5', mRNA sequence. (from Genbank) |
| 862 | Breast | -0.051305 | 0.3762389 | 0.308195 | 0.18112722 | L35269_at | ZINC FINGER PROTEIN 35 |
| 863 | Breast | -0.051386 | 0.3762241 | 0.308156 | 0.18098173 | RC_AA0046 37_at | EST: zh92b04.s1 Soares fetal liver spleen 1NFLS S1 Homo sapiens cDNA clone 428719 3', mRNA sequence. (from Genbank) |
| 864 | Breast | -0.051656 | 0.3762117 | 0.308058 | 0.1809893 | W28988_at | EST: 54f5 Human retina cDNA randomly primed sublibrary Homo sapiens cDNA, mRNA sequence. (from Genbank) |
| 865 | Breast | -0.051685 | 0.3760914 | 0.30799 | 0.18084933 | T57140_s_at | Paraoxonase 3 |

FIG. 2N2

| # | Tissue | | | | Description |
|---|---|---|---|---|---|
| 866 | Breast | -0.051717 | 0.3760565 | 0.307867 | 0.180776622 D79603_at | EST: Human aorta cDNA 5'-end GEN-286H04, mRNA sequence. (from Genbank) |
| 867 | Breast | -0.051809 | 0.3760473 | 0.307774 | 0.180711191 M57730_at | EPH-RELATED RECEPTOR TYROSINE KINASE LIGAND 1 PRECURSOR |
| 868 | Breast | -0.051955 | 0.3760147 | 0.307765 | 0.180639480 RC_AA0339 95_at | EST: zi05f09.s1 Soares fetal liver spleen 1NFLS S1 Homo sapiens cDNA clone 429929 3', mRNA sequence. (from Genbank) |
| 869 | Breast | -0.052036 | 0.3759982 | 0.307725 | 0.180548270 RC_D51215 f_at | STATHMIN |
| 870 | Breast | -0.052444 | 0.3758713 | 0.307713 | 0.180486132_at M14159_cds | T-cell receptor beta-chain J2.1 gene extracted from Human T-cell receptor germline beta-chain D2.1 and J2.1 to J2.7 genes |
| 871 | Breast | -0.052563 | 0.375773 | 0.30766 | 0.180332736 W28545_at | EST: 48c7 Human retina cDNA randomly primed sublibrary Homo sapiens cDNA, mRNA sequence. (from Genbank) |
| 872 | Breast | -0.052619 | 0.375601 | 0.307577 | 0.180282520 D50495_at | Transcription elongation factor S-II, hS-II-T1 |
| 873 | Breast | -0.052717 | 0.3755494 | 0.307448 | 0.180202380 M88279_at | FKBP4 FK506-binding protein 4 (59kD) |
| 874 | Breast | -0.05291 | 0.3755172 | 0.307386 | 0.180181820 RC_AA0373 57_r_at | EST: zc03c04.s1 Soares parathyroid tumor NbHPA Homo sapiens cDNA clone 3212223 3' similar to contains Alu repetitive element;, mRNA sequence. (from Genbank) |
| 875 | Breast | -0.053207 | 0.3754799 | 0.307262 | 0.180107360 D14539_at | Human mRNA for LTG19. (from Genbank) |
| 876 | Breast | -0.053207 | 0.375448 | 0.307159 | 0.180058260 X74837_at | HUMM9 mRNA |
| 877 | Breast | -0.053401 | 0.375428 | 0.307144 | 0.179947170 X53961_at | LTF Lactotransferrin |
| 878 | Breast | -0.053461 | 0.3754231 | 0.307083 | 0.179872380 HG4178- HT4448_at | Af-17 |
| 879 | Breast | -0.0535 | 0.3752009 | 0.307001 | 0.179859190 J03801_f_at | LYZ Lysozyme |
| 880 | Breast | -0.053545 | 0.3751927 | 0.306998 | 0.179770419_at RC_AA2428 | Phospholipase C, beta 4 |
| 881 | Breast | -0.053661 | 0.3750678 | 0.306919 | 0.179699850 HG1067- HT1067_r_at | Mucin (Gb:M22406) |
| 882 | Breast | -0.053938 | 0.3749172 | 0.30687 | 0.179679130 H81241_at | EST: yu73c07.r1 Homo sapiens cDNA clone 239436 5' similar to SP:S35643 S35643 BTEB2 PROTEIN -;. (from Genbank) |
| 883 | Breast | -0.053999 | 0.3748842 | 0.306867 | 0.179567130 D86425_at | Osteoblast mRNA for osteonidogen |
| 884 | Breast | -0.05418 | 0.3748797 | 0.306807 | 0.179472090 D70830_at | Doc2 beta |
| 885 | Breast | -0.05418 | 0.3748206 | 0.306802 | 0.179403830_at RC_AA4436 | Ribosomal protein S6 kinase, 90kD, polypeptide 4 |
| 886 | Breast | -0.054343 | 0.3747226 | 0.306767 | 0.179356340 M19159_at | ALPP Alkaline phosphatase, placental (Regan isozyme) |
| 887 | Breast | -0.054421 | 0.374623 | 0.306743 | 0.179258992_at L78833_cds | Rho7 gene extracted from Human BRCA1, Rho7 and vat1 genes, and ipf35 gene, partial cds |
| 888 | Breast | -0.054652 | 0.3745989 | 0.306688 | 0.179148470 HG180- HT180_at | Ahnak-A Nucleoprotein Ahnak-A |

FIG. 2O2

| # | Tissue | | | | | Description |
|---|---|---|---|---|---|---|
| 889 | Breast | -0.054693 | 0.3745569 | 0.306619 | 0.17790261 | X06268_at | COL2A1 Collagen, type II, alpha 1 (primary osteoarthritis, spondyloepiphyseal dysplasia, congenital) |
| 890 | Breast | -0.054745 | 0.3745835 | 0.306541 | 0.17898135 | HG3104-HT3280_at | Serine Protease Met1 |
| 891 | Breast | -0.05484 | 0.3745231 | 0.306418 | 0.1789223 | M55998_s_a_t | Alpha-1 collagen type I gene, 3' end |
| 892 | Breast | -0.054841 | 0.3745231 | 0.306286 | 0.17885049 | D86968_at | KIAA0213 gene, partial cds |
| 893 | Breast | -0.055135 | 0.3743204 | 0.306183 | 0.17877047 | X81333_at | PPH beta subunit protein |
| 894 | Breast | -0.055178 | 0.3743001 | 0.306167 | 0.17868887 | RC_AA2436 17_at | EST: zs16c08.s1 NCI_CGAP_GCB1 Homo sapiens cDNA clone IMAGE:685358 3', mRNA sequence. (from Genbank) |
| 895 | Breast | -0.055237 | 0.3742955 | 0.306089 | 0.17864491 | L02867_at | 62 kDa paraneoplastic antigen mRNA, 3' end |
| 896 | Breast | -0.055254 | 0.3742814 | 0.306064 | 0.17860605 | L10955_cds 1_s_at | Carbonic anhydrase IV gene extracted from Human carbonic anhydrase IV gene, promoter region and |
| 897 | Breast | -0.055465 | 0.374211 | 0.305976 | 0.17845528 | M20218_at | F11 Coagulation factor XI (plasma thromboplastin antecedent) |
| 898 | Breast | -0.055468 | 0.3740773 | 0.30588 | 0.17838494 | M28210_at | GTP-binding protein (RAB3A) mRNA |
| 899 | Breast | -0.05553 | 0.3740075 | 0.305778 | 0.17836434 | HG732-HT732_at | Serum Amyloid A1 |
| 900 | Breast | -0.055584 | 0.3739264 | 0.305723 | 0.17826432 | RC_AA2434 42_at | Homo sapiens clone 192 Rer1 mRNA, complete cds |
| 901 | Breast | -0.055911 | 0.3738658 | 0.305512 | 0.17819955 | X75535_at | 33 KD HOUSEKEEPING PROTEIN |
| 902 | Breast | -0.05631 | 0.3737828 | 0.305512 | 0.17817293 | L34060_at | Cadherin-8 mRNA |
| 903 | Breast | -0.056686 | 0.3735604 | 0.305508 | 0.17813462 | L27584_s_at | CAB3b mRNA for calcium channel beta3 subunit |
| 904 | Breast | -0.0568 | 0.3734772 | 0.305397 | | U79549_rna 1_s_at | Human Xp22 BAC CT-285115 (from CalTech/Research Genetics), PAC RPCI1-27C22 (from Roswell Park Cancer Center), and Cosmid U35B5 (from Lawrence Livermore), complete sequence. (from Genbank) |
| 905 | Breast | -0.056874 | 0.3734614 | 0.305338 | 0.17801876 | AA401605_a_t | Homo sapiens BAC clone RG060N22 from 7q21 |
| 906 | Breast | -0.056927 | 0.3734582 | 0.305299 | 0.17792776 | D21205_at | Estrogen responsive finger protein |
| 907 | Breast | -0.057185 | 0.3732237 | 0.305228 | 0.17791052 | U21051_rna 1_at | G protein-coupled receptor (GPR4) gene |
| 908 | Breast | -0.057302 | 0.3731872 | 0.305169 | 0.17789173 | U02019_at | Heterogeneous nuclear ribonucleoprotein D (hnRNP D), partial cds, clone cDx4 |
| 909 | Breast | -0.057316 | 0.3731569 | 0.304987 | 0.17780292 | L20433_at | Octamer binding transcription factor 1 (OTF1) mRNA |
| 910 | Breast | -0.057436 | 0.3730936 | 0.304807 | 0.17773566 | L09190_rna1_at | Trichohyalin (TRHY) gene |
| 911 | Breast | -0.057506 | 0.3729651 | 0.304797 | 0.17764536 | HG3405-HT3586_at | Zinc Finger Protein Hzf3 (Gb:X60153) |

FIG. 2P2

| # | Tissue | Val1 | Val2 | Val3 | ID1 | ID2 | Description |
|---|---|---|---|---|---|---|---|
| 912 | Breast | -0.057529 | 0.3728566 | 0.304769 | 0.1775865 | D45370_at | ApM2 mRNA for GS2374 (unknown product specific to adipose tissue) |
| 913 | Breast | -0.057863 | 0.3728035 | 0.304581 | 0.1775261 | RC_AA1578 14_at | EST: zo35h03.s1 Stratagene colon (#937204) Homo sapiens cDNA clone 588917 3', mRNA sequence. (from Genbank) |
| 914 | Breast | -0.057876 | 0.3727866 | 0.304545 | 0.1774321 | HG2479-HT2575_at | Helix-Loop-Helix Protein Sef2-1d |
| 915 | Breast | -0.057903 | 0.3727756 | 0.304495 | 0.1773515 | T23709_at | Seq545 Homo sapiens cDNA clone HY6cDNA2-4 5'. (from Genbank) |
| 916 | Breast | -0.057974 | 0.3727756 | 0.304477 | 0.1773095 | U53506_at | Type II iodothyronine deiodinase mRNA |
| 917 | Breast | -0.058242 | 0.3727748 | 0.304462 | 0.1772061 | X05246_at | Testis-specific PGK-2 gene for phosphoglycerate kinase (ATP:.3-phospho-D-glycerate 1-phosphotransferase, EC 2.7.2.3) |
| 918 | Breast | -0.058318 | 0.3725462 | 0.304454 | 0.1771598 | L22569_at | CTSB Cathepsin B |
| 919 | Breast | -0.058393 | 0.3724536 | 0.304373 | 0.1770531 | S73288_at | Small proline-rich protein SPRK [human, odontogenic keratocysts, mRNA Partial, 317 nt] |
| 920 | Breast | -0.058404 | 0.3724106 | 0.304293 | 0.1770109 | Z74616_s_at | COL1A2 Collagen, type I, alpha-2 |
| 921 | Breast | -0.058513 | 0.372294 | 0.304228 | 0.1769284 | W26666_at | EST: 11a12 Human retina cDNA randomly primed sublibrary Homo sapiens cDNA, mRNA sequence. (from Genbank) |
| 922 | Breast | -0.058533 | 0.372294 | 0.304204 | 0.1768551 | AA258463_a_t | N-ethylmaleimide-sensitive factor attachment protein, gamma |
| 923 | Breast | -0.058547 | 0.3722833 | 0.304159 | 0.1768307 | M77836_at | PYCR1 Pyrroline-5-carboxylate reductase 1 |
| 924 | Breast | -0.058582 | 0.3722216 | 0.304096 | 0.1766529 | RC_AA1645 89_at | EST: zo92f10.s1 Stratagene ovarian cancer (#937219) Homo sapiens cDNA clone 594379 3', mRNA sequence. (from Genbank) |
| 925 | Breast | -0.058613 | 0.3721394 | 0.304029 | 0.1766114 | N48927_at | EST: yy75e09.r1 Homo sapiens cDNA clone 279400 5'. (from Genbank) |
| 926 | Breast | -0.058835 | 0.3721014 | 0.303903 | 0.1765902 | J03060_at | GBA Glucosidase, beta; acid (includes glucosylceramidase) |
| 927 | Breast | -0.059035 | 0.3720605 | 0.303854 | 0.1765170 | X13238_at | COX6C Cytochrome c oxidase subunit VIc |
| 928 | Breast | -0.059042 | 0.3719516 | 0.303847 | 0.1764732 | D37965_at | PDGF receptor beta-like tumor suppressor (PRLTS) |
| 929 | Breast | -0.059211 | 0.3719358 | 0.303798 | 0.1763551 | RC_AA4304 66_at | EST: zw23d05.s1 Soares ovary tumor NbHOT Homo sapiens cDNA clone 770121 3', mRNA sequence. (from Genbank) |
| 930 | Breast | -0.059753 | 0.3718463 | 0.303788 | 0.1762906 | D31764_at | KIAA0064 gene |
| 931 | Breast | -0.059829 | 0.3718428 | 0.303701 | 0.1762623 | Y08564_at | GalNAc-T4 gene |
| 932 | Breast | -0.059846 | 0.3716371 | 0.303597 | 0.1761759 | D50645_at | SDF2 |
| 933 | Breast | -0.059907 | 0.3715959 | 0.303532 | 0.1760991 | Y10256_at | Serine/threonine protein kinase, NIK |
| 934 | Breast | -0.059971 | 0.3715022 | 0.303524 | 0.1760808 | AA476894_a_t | Neuronal PAS domain protein 2 |
| 935 | Breast | -0.060106 | 0.3714699 | 0.303492 | 0.1759779 | U25771_at | ARF4L ADP-ribosylation factor 4-like |
| 936 | Breast | -0.06016 | 0.3714579 | 0.303449 | 0.1759481 | HG3477-HT3670_at | Cd4 Antigen |

FIG. 2Q2

| | | | | | |
|---|---|---|---|---|---|
| 937 | Breast | -0.060673 | 0.3713124 | 0.303449 | AA191072_a t | EST: zq43c11.r1 Stratagene hNT neuron (#937233) Homo sapiens cDNA clone 632468 5', mRNA sequence. (from Genbank) |
| 938 | Breast | -0.060823 | 0.371236 | 0.303367 | X12662_rna 1_at | Arginase gene exon 1 and flanking regions (EC 3.5.3.1) (and joined CDS) |
| 939 | Breast | -0.060912 | 0.3712209 | 0.303222 | 0.17572095 L48211_at | Angiotensin II receptor gene |
| 940 | Breast | -0.060921 | 0.3710788 | 0.303183 | RC_AA4439 93_at | EST: zv44b09.s1 Soares ovary tumor NbHOT Homo sapiens cDNA clone 756473 3', mRNA sequence. (from Genbank) |
| 941 | Breast | -0.060959 | 0.3710275 | 0.303071 | 0.17565605 M93311_at | GIF |
| 942 | Breast | -0.060983 | 0.3709529 | 0.302986 | 0.17546663 X69090_at | Skeletal muscle 190kD protein |
| 943 | Breast | -0.061105 | 0.3709426 | 0.302914 | 0.17536747 S74445_at | Cellular retinoic acid-binding protein [human, skin, mRNA, 735 nt] |
| 944 | Breast | -0.061163 | 0.3709199 | 0.302914 | RC_AA4959 52_at | EST: zw06a08.s1 Soares NhHMPu S1 Homo sapiens cDNA clone 768470 3', mRNA sequence. (from Genbank) |
| 945 | Breast | -0.06129 | 0.3707676 | 0.302878 | 0.17528987 U55258_at | HBRAVO/Nr-CAM precursor (hBRAVO/Nr-CAM) gene |
| 946 | Breast | -0.061732 | 0.3707493 | 0.302854 | 0.17517972 U18288_at | Clone CIITA-10 MHC class II transactivator CIITA mRNA |
| 947 | Breast | -0.061797 | 0.3707097 | 0.302781 | 0.17510882 M37190_at | Ras inhibitor mRNA, 3' end |
| 948 | Breast | -0.061829 | 0.370707 | 0.302686 | 0.17505069 M81830_at | Somatostatin receptor isoform 2 (SSTR2) gene |
| 949 | Breast | -0.061922 | 0.3706661 | 0.302646 | 0.17495133 H05559_at | EST: yl75c08.r1 Homo sapiens cDNA clone 43873 5'. (from Genbank) |
| 950 | Breast | -0.061938 | 0.3705689 | 0.30257 | AA090632_a t | EST: yl1095.seq.F Fetal heart, Lambda ZAP Express Homo sapiens cDNA 5', mRNA sequence. (from Genbank) |
| 951 | Breast | -0.062256 | 0.3705308 | 0.302568 | 0.17481978 AFFX-CreX-3_st-2 | AFFX-CreX-3_st (miscellaneous control - 11k chips) |
| 952 | Breast | -0.062256 | 0.3704386 | 0.302537 | 0.17477928 AFFX-CreX-3_st | AFFX-CreX-3_st (endogenous control) |
| 953 | Breast | -0.06229 | 0.3703011 | 0.302469 | 0.17471492 X58399_at | L2-9 transcript of unrearranged immunoglobulin V(H)5 pseudogene |
| 954 | Breast | -0.062453 | 0.3701737 | 0.302447 | 0.17470723 D38535_at | PK-120 |
| 955 | Breast | -0.062493 | 0.3701396 | 0.302427 | 0.17463356 M18731_at | GALT Galactose-1-phosphate uridyltransferase |
| 956 | Breast | -0.062691 | 0.3701046 | 0.302365 | RC_AA4339 50_at | EST: zw52h02.s1 Soares total fetus Nb2HF8.9w Homo sapiens cDNA clone 773715 3', mRNA sequence. (from Genbank) |
| 957 | Breast | -0.062832 | 0.3700884 | 0.302321 | 0.17443383 S81419_at | Dystrophin, dystrophin (Purkinje promoter, alternatively spliced) [human, cortical brain and adult heart, mRNA Partial, 377 nt] |
| 958 | Breast | -0.062943 | 0.370081 | 0.302229 | 0.17437036 M34344_at | ITGA2B Integrin, alpha 2b (platelet glycoprotein IIb of IIb/IIIa complex, antigen CD41B) |
| 959 | Breast | -0.063046 | 0.370081 | 0.302219 | AA209290_a t | EST: zq85c01.r1 Stratagene hNT neuron (#937233) Homo sapiens cDNA clone 648384 5' similar to contains element MER22 repetitive element ;, mRNA sequence. (from Genbank) |
| 960 | Breast | -0.063085 | 0.3700262 | 0.302186 | 0.17429526 HG67-HT67_f_at | Zinc Finger Protein (Gb:X61870) |

FIG. 2R2

| | | | | | |
|---|---|---|---|---|---|
| 961 | Breast | -0.063111 | 0.3699893 | 0.30215 | 0.17419226 | RC_AA4420 78_at | EST: zw63c01.s1 Soares total fetus Nb2HF8 9w Homo sapiens cDNA clone 774720 3', mRNA sequence. (from Genbank) |
| 962 | Breast | -0.063122 | 0.3697913 | 0.302081 | 0.17412324 | R19997_at | Homo sapiens exportin t mRNA, complete cds |
| 963 | Breast | -0.063124 | 0.3696035 | 0.30205 | 0.17409343 | AA338308_a t | Homo sapiens mRNA for KIAA0524 protein, partial cds |
| 964 | Breast | -0.063188 | 0.3693799 | 0.301999 | 0.17401792 | D14686_at | AMT Glycine cleavage system protein T (aminomethyltransferase) |
| 965 | Breast | -0.063234 | 0.3693226 | 0.301975 | 0.1740153 | X72879_at | 14A2AK DNA sequence |
| 966 | Breast | -0.063301 | 0.3692876 | 0.301924 | 0.1739759 | X00237_at | F variable segment 5' to antithrombin III gene (AT III) |
| 967 | Breast | -0.063334 | 0.3692851 | 0.301749 | 0.17383315 | RC_AA3982 76_at | EST: zf60c07.s1 Soares testis NHT Homo sapiens cDNA clone 726732 3', mRNA sequence. (from Genbank) |
| 968 | Breast | -0.063366 | 0.3690902 | 0.301673 | 0.17379622 | S82185_at | Escherichia coli unknown mRNA |
| 969 | Breast | -0.063421 | 0.3689872 | 0.301622 | 0.17370985 | U87972_at | NAD+-isocitrate dehydrogenase mRNA, partial cds |
| 970 | Breast | -0.063576 | 0.3689599 | 0.301593 | 0.17365451 | U01157_at | GLP1R Glucagon-like peptide 1 receptor |
| 971 | Breast | -0.063648 | 0.3689208 | 0.30154 | 0.17359863 | AA280253_a t | Human activated p21cdc42Hs kinase (ack) mRNA, complete cds |
| 972 | Breast | -0.063373 | 0.3689103 | 0.301485 | 0.17348851 | U79295_at-2 | Human clone 23961 mRNA sequence |
| 973 | Breast | -0.063373 | 0.3688502 | 0.301454 | 0.17340961 | U79295_at | Clone 23961 mRNA sequence |
| 974 | Breast | -0.063895 | 0.3687235 | 0.301433 | 0.1733959 | X58401_at | CLL-12 transcript of unrearranged immunoglobulin V(H)5 gene |
| 975 | Breast | -0.063945 | 0.3686968 | 0.301324 | 0.17334343 | M60315_at | BONE MORPHOGENETIC PROTEIN 6 PRECURSOR |
| 976 | Breast | -0.064086 | 0.368655 | 0.301296 | 0.17332555 | M20778_s_a t | Homo sapien, alpha-3 (VI) collagen |
| 977 | Breast | -0.064148 | 0.3686425 | 0.301285 | 0.17321171 | U20816_s_a t | Nuclear factor kappa-B2 (NF-KB2) gene, partial cds |
| 978 | Breast | -0.064266 | 0.3684953 | 0.301243 | 0.17309964 | RC_AA0013 59_at | EST: zh83d11.s1 Soares fetal liver spleen 1NFLS S1 Homo sapiens cDNA clone 427893 3', mRNA sequence. (from Genbank) |
| 979 | Breast | -0.064439 | 0.3684856 | 0.301199 | 0.17302833 | L04569_at | Calcium channel L-type alpha 1 subunit (CACNL1A1) mRNA |
| 980 | Breast | -0.064448 | 0.368409 | 0.301142 | 0.17300284 | X16282_at-2 | Human mRNA for zinc finger protein (clone 647) |
| 981 | Breast | -0.064448 | 0.3684041 | 0.301017 | 0.17287046 | X16282_at | Zinc finger protein (clone 647) |
| 982 | Breast | -0.064584 | 0.3683977 | 0.300911 | 0.17282745 | M87313_s_a t | DM Dystrophia myotonica (includes dystrophia myotonia protein kinase) |
| 983 | Breast | -0.064461 | 0.3682191 | 0.300874 | 0.17275523 | M86933_at | AMELY Amelogenin (chromosome Y encoded) |
| 984 | Breast | -0.064813 | 0.3681234 | 0.300776 | 0.17264907 | AA399432_a t | EST: zf60b01.r1 Soares testis NHT Homo sapiens cDNA clone 726697 5' similar to TR:G541730 G541730 IGD B-CELL RECEPTOR-ASSOCIATED PROTEIN ;, mRNA sequence. (from Genbank) |
| 985 | Breast | -0.06488 | 0.3681157 | 0.300766 | 0.17253389 | L33477_at | (clone 8B1) Br-cadherin mRNA |

FIG. 2S2

| | | | | |
|---|---|---|---|---|
| 986 | Breast | -0.064963 | 0.3680508 | 0.17245314 | U15197_at-2 | ABO blood group (transferase A, alpha 1-3-N-acetylgalactosaminyltransferase; transferase B, alpha 1-3-galactosyltransferase) |
| 987 | Breast | -0.064963 | 0.3680224 | 0.17244586 | U15197_at | ABO ABO blood group (transferase A, alpha 1-3-N-acetylgalactosaminyltransferase; transferase B, alpha 1-3-galactosyltransferase) |
| 988 | Breast | -0.065004 | 0.3680146 | 0.17225446 | U66036_at | Sulfotransferase mRNA |
| 989 | Breast | -0.065035 | 0.3679706 | 0.17221446 | S74720_at | DAX-1 |
| 990 | Breast | -0.065074 | 0.367948 | 0.17218089 | U51333_s_at | HK3 Hexokinase 3 (white cell) |
| 991 | Breast | -0.065074 | 0.36794 | 0.17210503 | U51333_s_at-2 | Hexokinase 3 (white cell) |
| 992 | Breast | -0.065317 | 0.3679378 | 0.17209774 | AA285229_a_t | EST: PMY0709 KG1-a Lambda Zap Express cDNA library Homo sapiens cDNA 5', mRNA sequence. (from Genbank) |
| 993 | Breast | -0.06542 | 0.3679375 | 0.17203608 | X97261_r_at | Metallothionein isoform 1R |
| 994 | Breast | -0.065506 | 0.3678798 | 0.3001 | V00535_rna1_s_at | Interferon, beta 1, fibroblast |
| 995 | Breast | -0.065569 | 0.3677944 | 0.17185599 | HG4185-HT4455_at | Estrogen Sulfotransferase, Ste |
| 996 | Breast | -0.065598 | 0.3677728 | 0.17183031 | AA248747_a_t | EST: hp0672.seq.F Human fetal heart, Lambda ZAP Express Homo sapiens cDNA 5', mRNA sequence. (from Genbank) |
| 997 | Breast | -0.065611 | 0.367685 | 0.17176764 | U50315_at | EZH1 Enhancer of zeste (Drosophila) homolog 1 |
| 998 | Breast | -0.065632 | 0.3676511 | 0.17155029 | T08870_at | EST: EST06762 Homo sapiens cDNA clone HIBBL42 5' end. (from Genbank) |
| 999 | Breast | -0.065684 | 0.3675023 | 0.17152813 | H19258_at | Yn50b11.r1 Homo sapiens cDNA clone 171837 5' similar to contains PTR5 repetitive element ;. (from Genbank) |
| 1000 | Breast | -0.065685 | 0.3674599 | 0.17149578 | D83885_at | Tumor protein D52-like 2 |

FIG. 2Γ2

| | | | | |
|---|---|---|---|---|
| 1 CNS | 1.5821122 | 0.5227835 | 0.466243 | 0.36578274 | RC_AA4320 87_at | EST: zw89d03.s1 Soares total fetus Nb2HF8 9w Homo sapiens cDNA clone 784133 3', mRNA sequence. (from Genbank) |
| 2 CNS | 1.3601404 | 0.4887298 | 0.435394 | 0.3433382 | D54949_at | Calmodulin 1 (phosphorylase kinase, delta) |
| 3 CNS | 1.3382851 | 0.471399 | 0.420481 | 0.330668585 | RC_AA0097 44_at | EST: ze82g01.s1 Soares fetal heart NbHH19W Homo sapiens cDNA clone 365520 3', mRNA sequence. (from Genbank) |
| 4 CNS | 1.3208506 | 0.4620444 | 0.411019 | 0.321190722 | AA093923_a t | Tissue inhibitor of metalloproteinase 2 |
| 5 CNS | 1.3130109 | 0.4570996 | 0.402494 | 0.315200544 | RC_AA2623 40_at | EST: zr71g09.s1 Soares NhHMPu S1 Homo sapiens cDNA clone 668896 3', mRNA sequence. (from Genbank) |
| 6 CNS | 1.2842487 | 0.4508557 | 0.398151 | 0.310184274 | RC_AA2335 41_at | EST: zr30h08.s1 Stratagene NT2 neuronal precursor 937230 Homo sapiens cDNA clone 664959 3', mRNA sequence. (from Genbank) |

FIG. 3A

| | | | | | |
|---|---|---|---|---|---|
| 7 CNS | 1.2712225 | 0.4456711 | 0.392711 | 0.305967181 RC_AA3386 46_f_at | Homo sapiens mRNA for APCL protein, complete cds |
| 8 CNS | 1.2365611 | 0.4426227 | 0.389566 | 0.302136541 RC_AA4494 41_at | EST: zx05d05.s1 Soares total fetus Nb2HF8.9w Homo sapiens cDNA clone 785577 3', mRNA sequence. (from Genbank) |
| 9 CNS | 1.236307 | 0.4378117 | 0.385896 | 0.298884660 U04811_at-2 | Trophinin |
| 10 CNS | 1.236307 | 0.4335288 | 0.383609 | 0.295745701 U04811_at | Trophinin mRNA |
| 11 CNS | 1.2355561 | 0.4291814 | 0.380423 | 0.293382141 AA046593_a t | EST: zk62g01.r1 Soares pregnant uterus Nb-HPU Homo sapiens cDNA clone 487440 5', mRNA sequence. (from Genbank) |
| 12 CNS | 1.2335474 | 0.4288096 | 0.3783 | 0.291201031 AA464334_s at | EST: zx78f01.r1 Soares ovary tumor NbHOT Homo sapiens cDNA clone 809881 5', mRNA sequence. (from Genbank) |
| 13 CNS | 1.2186718 | 0.4267445 | 0.375897 | 0.288680461 T08879_at | Cathepsin F |
| 14 CNS | 1.2162564 | 0.4235237 | 0.37428 | 0.286005121 H29161_at | EST: ym59h02.r1 Homo sapiens cDNA clone 52919 5'. (from Genbank) |
| 15 CNS | 1.2048391 | 0.421496 | 0.37261 | 0.284578861 AB002357_a t | Kinesin family protein 3B |
| 16 CNS | 1.199385 | 0.4192172 | 0.370695 | 0.282702831 R10931_at | Discs, large (Drosophila) homolog 5 |
| 17 CNS | 1.1938953 | 0.417314 | 0.369058 | 0.281051611 D31289_at | EST: Human fetal-lung cDNA 5'-end sequence, mRNA sequence. (from Genbank) |
| 18 CNS | 1.1865215 | 0.4153346 | 0.367431 | 0.279249941 U12597_s_a t | TNF receptor-associated factor 2 |
| 19 CNS | 1.1835281 | 0.4138258 | 0.366073 | 0.277536331 C01257_at | EST: HUMGS0007992, Human Gene Signature, 3'-directed cDNA sequence, mRNA sequence. (from Genbank) |
| 20 CNS | 1.1815939 | 0.4126025 | 0.364142 | 0.276082131 RC_AA4602 70_at | Midline 1 (Opitz/BBB syndrome) |
| 21 CNS | 1.1729355 | 0.4111149 | 0.363086 | 0.274758311 R70976_at | EST: yi50c01.r1 Homo sapiens cDNA clone 142656 5'. (from Genbank) |
| 22 CNS | 1.1597135 | 0.4084373 | 0.361936 | 0.273269741 N98707_at | Kinesin family member 5C |
| 23 CNS | 1.1538289 | 0.4080156 | 0.360021 | 0.271993711 RC_AA4901 82_at | EST: ab06e01.s1 Stratagene fetal retina 937202 Homo sapiens cDNA clone 840024 3', mRNA sequence. (from Genbank) |
| 24 CNS | 1.1504455 | 0.4070224 | 0.359134 | 0.270686981 AA393961_a t | EST: zf78b10.r1 Soares testis NHT Homo sapiens cDNA clone 728443 5', mRNA sequence. (from Genbank) |
| 25 CNS | 1.1500549 | 0.4061916 | 0.357859 | 0.269554171 T09191_at | Homo sapiens Luman mRNA, complete cds |
| 26 CNS | 1.1481502 | 0.4050371 | 0.356555 | 0.268271151 H59008_at | Homo sapiens mRNA for NIK, partial cds |
| 27 CNS | 1.1449691 | 0.4050371 | 0.355957 | 0.267320451 RC_AA3982 55_at | EST: zf60a06.s1 Soares testis NHT Homo sapiens cDNA clone 726706 3' similar to contains element MER22 repetitive element ;, mRNA sequence. (from Genbank) |
| 28 CNS | 1.1443744 | 0.4035838 | 0.35473 | 0.266267781 RC_AA2565 56_f_at | EST: zf86f05.s1 Soares NhHMPu S1 Homo sapiens cDNA clone 682593 3', mRNA sequence. (from Genbank) |

FIG. 3B

| # | Tissue | Val1 | Val2 | Val3 | ID | Description |
|---|---|---|---|---|---|---|
| 29 | CNS | 1.1437584 | 0.4022301 | 0.265305507 | H66988_at | EST:yu17c10.r1 Homo sapiens cDNA clone 234066 5'. (from Genbank) |
| 30 | CNS | 1.1396248 | 0.4010547 | 0.2642311 | RC_AA4118 19_at | Homo sapiens mRNA for KIAA0898 protein, partial cds |
| 31 | CNS | 1.139285 | 0.3999776 | 0.2632767 | L44416_at | Human DEAD-box protein p72 (P72) mRNA, complete cds |
| 32 | CNS | 1.1370252 | 0.3990943 | 0.26244372 | RC_AA4521 13_at | EST:zx15b11.s1 Soares total fetus Nb2HF8 9w Homo sapiens cDNA clone 786525 3', mRNA sequence. (from Genbank) |
| 33 | CNS | 1.1369255 | 0.3988254 | 0.261485163_at | RC_AA1133 | Homo sapiens mRNA for KIAA0810 protein, partial cds |
| 34 | CNS | 1.1351925 | 0.3984377 | 0.2606674 | RC_AA2580 22_at | Tissue inhibitor of metalloproteinase 1 (erythroid potentiating activity, collagenase inhibitor) |
| 35 | CNS | 1.134893 | 0.3973183 | 0.25975117 | AA310328_a t | EST:EST181171 Jurkat T-cells V Homo sapiens cDNA 5' end, mRNA sequence. (from Genbank) |
| 36 | CNS | 1.1326729 | 0.3964586 | 0.25880587 | AA481723_a t | Deleted in oral cancer-1 |
| 37 | CNS | 1.1260254 | 0.39439 | 0.25786522 | RC_AA4800 45_at | EST:zv41a04.s1 Soares ovary tumor NbHOT Homo sapiens cDNA clone 756174 3', mRNA sequence. (from Genbank) |
| 38 | CNS | 1.125968 | 0.3938153 | 0.25702432 | H12112_at | Ym16e10.r1 Homo sapiens cDNA clone 47942 5'. (from Genbank) |
| 39 | CNS | 1.1251478 | 0.3936734 | 0.2562541 | AB002368_a t | Human mRNA for KIAA0370 gene, partial cds |
| 40 | CNS | 1.1242508 | 0.393288 | 0.25542974 | AA401052_a t | EST:zu50f11.r1 Soares ovary tumor NbHOT Homo sapiens cDNA clone 741453 5', mRNA sequence. (from Genbank) |
| 41 | CNS | 1.1216179 | 0.3927719 | 0.2546986 | Y09836_at | 3'UTR of unknown protein |
| 42 | CNS | 1.1213297 | 0.3917421 | 0.25389153 | RC_AA4169 70_at | EST:zt94g03.s1 Soares testis NHT Homo sapiens cDNA clone 730036 3', mRNA sequence. (from Genbank) |
| 43 | CNS | 1.1199872 | 0.3906457 | 0.25319153 | RC_AA3996 63_at | EST:zt86c04.s1 Soares testis NHT Homo sapiens cDNA clone 729222 3', mRNA sequence. (from Genbank) |
| 44 | CNS | 1.1183511 | 0.3902271 | 0.25241002 | RC_AA2847 67_at | EST:zt21h07.s1 Soares ovary tumor NbHOT Homo sapiens cDNA clone 713821 3', mRNA sequence. (from Genbank) |
| 45 | CNS | 1.116263 | 0.3897033 | 0.25163272 | RC_AA4264 54_s_at | Homo sapiens I-1 receptor candidate protein mRNA, complete cds |
| 46 | CNS | 1.116161 | 0.3896734 | 0.25093027 | RC_AA4639 78_at | EST:zx86f03.s1 Soares ovary tumor NbHOT Homo sapiens cDNA clone 810653 3', mRNA sequence. (from Genbank) |
| 47 | CNS | 1.1098641 | 0.3879441 | 0.2504129 | W01587_s_at | EST:za80f11.r1 Soares fetal lung NbHL19W Homo sapiens cDNA clone 298993 5', mRNA sequence. (from Genbank) |
| 48 | CNS | 1.1091572 | 0.3878151 | 0.24985288 | RC_AA3981 67_at | Glutathione S-transferase A4 |
| 49 | CNS | 1.1086977 | 0.3875319 | 0.24928012 | RC_AA2868 62_at | IMAGE:701651 3', mRNA sequence. (from Genbank) |

FIG. 3C

| | | | | | | |
|---|---|---|---|---|---|---|
| 50 | CNS | 1.1070427 | 0.3873824 | 0.338023 | 0.2487205 | RC_AA6213 25_at | HNK-1 sulfotransferase |
| 51 | CNS | 1.1003532 | 0.3867391 | 0.337495 | 0.24813242 | D12676_at | Lysosomal sialoglycoprotein |
| 52 | CNS | 1.0997258 | 0.3867343 | 0.337093 | 0.24741161 | N76496_at | Small inducible cytokine A5 (RANTES) |
| 53 | CNS | 1.099367 | 0.3853312 | 0.336166 | 0.24681646 | AA425719_a at | EST: zv47f04.r1 Soares ovary tumor NbHOT Homo sapiens cDNA clone 756799 5', mRNA sequence. (from Genbank) |
| 54 | CNS | 1.0993154 | 0.3852245 | 0.335525 | 0.24623369 | RC_AA4562 89_at | EST: aa13e06.s1 Soares NhHMPu S1 Homo sapiens cDNA clone 813154 3', mRNA sequence. (from Genbank) |
| 55 | CNS | 1.0952227 | 0.3839721 | 0.334967 | 0.24563473 | AB002323_a t | Human mRNA for KIAA0325 gene, partial cds. (from Genbank) |
| 56 | CNS | 1.0949132 | 0.383254 | 0.334556 | 0.24498488 | Z43594_at | EST: H. sapiens partial cDNA sequence, clone c-1fh06, mRNA sequence. (from Genbank) |
| 57 | CNS | 1.093505 | 0.3831663 | 0.333862 | 0.24429488 | RC_AA6002 46_at | Phosphatidylinositol-4-phosphate 5-kinase, type II, beta |
| 58 | CNS | 1.0932192 | 0.3822998 | 0.333433 | 0.24380438 | D31483_at | Homo sapiens clone 23565 unknown mRNA, partial cds |
| 59 | CNS | 1.091907 | 0.3822985 | 0.333183 | 0.24319646 | RC_D59321 f_at | Homo sapiens mRNA for APCL protein, complete cds |
| 60 | CNS | 1.0909321 | 0.382079 | 0.332454 | 0.24263969 | RC_AA4811 43_at | Homo sapiens mRNA for KIAA0515 protein, partial cds |
| 61 | CNS | 1.0856 | 0.3814946 | 0.332056 | 0.24220833 | RC_AA4356 33_at | Homo sapiens clone 23965 mRNA sequence |
| 62 | CNS | 1.0843205 | 0.38056644 | 0.331863 | 0.24175566 | W07195_at | EST: za95c12.r1 Soares fetal lung NbHL19W Homo sapiens cDNA clone 300310 5', mRNA sequence. (from Genbank) |
| 63 | CNS | 1.082367 | 0.3804849 | 0.331076 | 0.2411023 | RC_AA4265 18_at | EST: zw11a09.s1 Soares NhHMPu S1 Homo sapiens cDNA clone 768952 3', mRNA sequence. (from Genbank) |
| 64 | CNS | 1.0819024 | 0.380351 | 0.330858 | 0.24066082 | W26817_at | Homo sapiens ornithine decarboxylase antizyme 2 (OAZ2) mRNA, complete cds |
| 65 | CNS | 1.0809634 | 0.3795781 | 0.330074 | 0.24011303 | C00155_at | Homo sapiens clone 24658 mRNA sequence |
| 66 | CNS | 1.0803376 | 0.37861 | 0.329968 | 0.23959897 | RC_AA4244 84_at | EST: zv90a09.s1 Soares NhHMPu S1 Homo sapiens cDNA clone 767032 3', mRNA sequence. (from Genbank) |
| 67 | CNS | 1.0800035 | 0.37855376 | 0.329124 | 0.2390876 | N90328_at | EST: yz88b05.r1 Soares multiple sclerosis 2NbHMSP Homo sapiens cDNA clone 290097 5' similar to contains element MER11 repetitive element :, mRNA sequence. (from Genbank) |
| 68 | CNS | 1.0787363 | 0.3784324 | 0.328476 | 0.23850404 | H49222_s_a t | EST: yq19g03.r1 Soares fetal liver spleen 1NFLS Homo sapiens cDNA clone 274349 5', mRNA sequence. (from Genbank) |
| 69 | CNS | 1.077306 | 0.37761164 | 0.328069 | 0.2380899 | W28390_at | EST: 46c8 Human retina cDNA randomly primed sublibrary Homo sapiens cDNA, mRNA sequence. (from Genbank) |
| 70 | CNS | 1.0749671 | 0.37761164 | 0.327955 | 0.23774487 | D81925_at | Heterogeneous nuclear ribonucleoprotein D-like |
| 71 | CNS | 1.0745177 | 0.3772638 | 0.327613 | 0.23728606 | RC_AA4366 55_at | EST: zv57c03.s1 Soares testis NHT Homo sapiens cDNA clone 757732 3', mRNA sequence. (from Genbank) |

FIG. 3D

| # | | | | | |
|---|---|---|---|---|---|
| 72 CNS | 1.0732971 | 0.3765062 | 0.327109 | RC_AA4902 61_s_at | EST: aa44c08.s1 Soares NhHMPu S1 Homo sapiens cDNA clone 823790 3', mRNA sequence. (from Genbank) |
| 73 CNS | 1.072461 | 0.3761596 | 0.326687 | AA351923_a_t | EST: EST59835 Infant brain Homo sapiens cDNA 5' end, mRNA sequence. (from Genbank) |
| 74 CNS | 1.0717345 | 0.3758686 | 0.326149 | RC_AA4026 85_at | EST: zu49g09.s1 Soares ovary tumor NbHOT Homo sapiens cDNA clone 741376 3', mRNA sequence. (from Genbank) |
| 75 CNS | 1.0696682 | 0.3757239 | 0.3261105 | RC_AA2934 36_s_at | EST: zt54c07.s1 Soares ovary tumor NbHOT Homo sapiens cDNA clone 726156 3' similar to WP:R13A5.1 CE01370 :, mRNA sequence. (from Genbank) |
| 76 CNS | 1.0683788 | 0.3756529 | 0.325567 | RC_AA0853 199_at | Homo sapiens mRNA for JM4 protein, complete CDS (clone IMAGE 546750 and LLNLc110F1857Q7 (RZPD Berlin)) |
| 77 CNS | 1.068823 | 0.3749681 | 0.325105 | AA311931_s_at | Ras-related C3 botulinum toxin substrate 3 (rho family, small GTP binding protein Rac3) |
| 78 CNS | 1.0663271 | 0.3745332 | 0.324472 | W81301_at | EST: zd85a12.r1 Soares fetal heart NbHH19W Homo sapiens cDNA clone 347422 5', mRNA sequence. (from Genbank) |
| 79 CNS | 1.0657293 | 0.3743767 | 0.32441 | D31550_at | EST: Human fetal-lung cDNA 5'-end sequence, mRNA sequence. (from Genbank) |
| 80 CNS | 1.0650709 | 0.3742216 | 0.323926 | W26376_at | Homo sapiens ornithine decarboxylase antizyme 2 (OAZ2) mRNA, complete cds |
| 81 CNS | 1.0650405 | 0.3739961 | 0.323725 | AA455208_a_t | D site of albumin promoter (albumin D-box) binding protein |
| 82 CNS | 1.0640874 | 0.3729959 | 0.323476 | AA136360_a_t | EST: zk93c02.r1 Soares pregnant uterus NbHPU Homo sapiens cDNA clone 490370 5', mRNA sequence. (from Genbank) |
| 83 CNS | 1.0633168 | 0.3728446 | 0.323225 | RC_AA0593 86_at | EST: zf66c03.s1 Soares retina N2b4HR Homo sapiens cDNA clone 381892 3', mRNA sequence. (from Genbank) |
| 84 CNS | 1.0599332 | 0.3725329 | 0.322862 | AA431268_a_t | EST: zw78g06.r1 Soares testis NHT Homo sapiens cDNA clone 782362 5', mRNA sequence. (from Genbank) |
| 85 CNS | 1.0580418 | 0.3719045 | 0.322629 | Y12711_at-2 | H.sapiens mRNA for putative progesterone binding protein |
| 86 CNS | 1.0580418 | 0.3716327 | 0.322019 | Y12711_at | Putative progesterone binding protein |
| 87 CNS | 1.0576942 | 0.3712107 | 0.321699 | RC_AA1338 96_s_at | Homo sapiens clone 24812 mRNA sequence |
| 88 CNS | 1.057471 | 0.3711056 | 0.321566 | T99604_at | Ye65g07.r1 Homo sapiens cDNA clone 122652 5' similar to SP:NECD_MOUSE P25233 :. (from Genbank) |
| 89 CNS | 1.0572321 | 0.3704442 | 0.321222 | RC_AA2275 41_at | Homo sapiens mRNA for KIAA0850 protein, complete cds |
| 90 CNS | 1.056566 | 0.3702271 | 0.320691 | N77151_at | Homo sapiens mRNA for KIAA0799 protein, partial cds |
| 91 CNS | 1.0474865 | 0.3702271 | 0.32043 | RC_AA4476 17_at | EST: zw97a02.s1 Soares total fetus Nb2HF8 9w Homo sapiens cDNA clone 784874 3', mRNA sequence. (from Genbank) |

FIG. 3E

| # | Tissue | | | | ID | Description |
|---|---|---|---|---|---|---|
| 92 | CNS | 1.0471169 | 0.37000851 | 0.320289 | 0.228937181 | AA284647_a_at EST: zt23g10.r1 Soares ovary tumor NbHOT Homo sapiens cDNA clone 714018 5', mRNA sequence. (from Genbank) |
| 93 | CNS | 1.0466598 | 0.3899072 | 0.319766 | 0.228629564_3_at | RC_AA2522 EST: zr64g05.s1 Soares NhHMPu S1 Homo sapiens cDNA clone 668216 3', mRNA sequence. (from Genbank) |
| 94 | CNS | 1.046282 | 0.3688252 | 0.319169 | 0.22830428 W26496_at | EST: 30d2 Human retina cDNA randomly primed sublibrary Homo sapiens cDNA, mRNA sequence. (from Genbank) |
| 95 | CNS | 1.0460862 | 0.3688252 | 0.319049 | 0.22791341_5_at | RC_AA4851 KIAA0793 gene product |
| 96 | CNS | 1.0454617 | 0.3885715 | 0.318571 | 0.227515717_1_at | RC_AA1358 EST: zn93h05.s1 Stratagene lung carcinoma 937218 Homo sapiens cDNA clone 565785 3', mRNA sequence. (from Genbank) |
| 97 | CNS | 1.0453646 | 0.3685071 | 0.318375 | 0.2271155 Y09616_at-2 | Intestinal carboxylesterase; liver carboxylesterase-2 |
| 98 | CNS | 1.0453646 | 0.368468 | 0.317733 | 0.22669233 Y09616_at | Carboxylesterase (hCE-2) mRNA |
| 99 | CNS | 1.045011 | 0.3683571 | 0.317416 | 0.22630712_t | AA095791_a EST: 15920.seq.F Fetal heart, Lambda ZAP Express Homo sapiens cDNA 5', mRNA sequence. (from Genbank) |
| 100 | CNS | 1.0439073 | 0.3682889 | 0.317273 | 0.225958231 | AA455403_a EST: aa03d07.r1 Soares NhHMPu S1 Homo sapiens cDNA clone 812173 5', mRNA sequence. (from Genbank) |
| 101 | CNS | 1.0416962 | 0.3661786 | 0.316998 | 0.225725341 | RC_AA1268 EST: zn88f12.s1 Stratagene lung carcinoma 937218 Homo sapiens cDNA clone 565295 3', mRNA sequence. (from Genbank) |
| 102 | CNS | 1.0412948 | 0.3677616 | 0.316626 | 0.22547339 S40719_s_at | GFAP Glial fibrillary acidic protein |
| 103 | CNS | 1.0408907 | 0.3673216 | 0.316375 | 0.22521017 N77574_i_at | Human DNA sequence from clone 341E18 on chromosome 6p11.2-12.3. Contains a Serine/Threonine Protein Kinase gene (presumptive isolog of a Rat gene) and a novel alternatively spliced gene. Contains a putative CpG island, ESTs and GSSs |
| 104 | CNS | 1.04008 | 0.3668905 | 0.316224 | 0.22484718 U46116_at-2 | Protein tyrosine phosphatase, receptor type, gamma polypeptide |
| 105 | CNS | 1.04008 | 0.3668033 | 0.316088 | 0.22457357 U46116_at | PTPRG Protein tyrosine phosphatase, receptor type, gamma polypeptide |
| 106 | CNS | 1.0399616 | 0.3668033 | 0.315721 | 0.224270853_3_at | RC_AA4257 EST: zv47a10.s1 Soares ovary tumor NbHOT Homo sapiens cDNA clone 756762 3', mRNA sequence. (from Genbank) |
| 107 | CNS | 1.039451 | 0.3667739 | 0.31546 | 0.22389305_t | AA410200_a EST: zv32d11.r1 Soares ovary tumor NbHOT Homo sapiens cDNA clone 755349 5', mRNA sequence. (from Genbank) |
| 108 | CNS | 1.03611865 | 0.3664435 | 0.3150048 | 0.22352216 N71215_f_at | KIAA0587 gene product |
| 109 | CNS | 1.033165 | 0.3658772 | 0.314954 | 0.22316662_9_at | RC_AA4636 Homo sapiens mRNA for KIAA0721 protein, partial cds |

FIG. 3F

| | | | | | |
|---|---|---|---|---|---|
| 110 | CNS | 1.03153240 | 0.3657871 | 0.314699 | 0.2229604 | S76756_s_at | 4R-MAP2=microtubule-associated protein 2 4R isoform [human, brain, mRNA Partial, 1012 nt] |
| 111 | CNS | 1.0313895 | 0.3645982 | 0.314543 | 0.2227114 | W27023_at | Homo sapiens mRNA for KIAA0886 protein, complete cds |
| 112 | CNS | 1.0301079 | 0.3645953 | 0.314168 | 0.222235774 | AA046674_a_t | EST: zf12d12.r1 Soares fetal heart NbHH19W Homo sapiens cDNA clone 376727 5', mRNA sequence. (from Genbank) |
| 113 | CNS | 1.029867 | 0.3645953 | 0.314026 | 0.222210413 | AA405775_s_at | EST: zu57c10.r1 Soares ovary tumor NbHOT Homo sapiens cDNA clone 742098 5', mRNA sequence. (from Genbank) |
| 114 | CNS | 1.028171 | 0.3645804 | 0.313575 | 0.22171398 | Y10746_at | H.sapiens mRNA for protein containing MBD 1 |
| 115 | CNS | 1.0272713 | 0.3645103 | 0.313343 | 0.22148871 | RC_AA2071 03_at | EST: zq81b03.s1 Stratagene hNT neuron (#937233) Homo sapiens cDNA clone 647981 3', mRNA sequence. (from Genbank) |
| 116 | CNS | 1.0283342 | 0.364446 | 0.313005 | 0.2211354 | C14203_s_a t | EST: Human fetal brain cDNA 5'-end GEN-037E11, mRNA sequence. (from Genbank) |
| 117 | CNS | 1.0267732 | 0.3642832 | 0.312996 | 0.220949995 | RC_AA1890 83_at | EST: zq45b09.s1 Stratagene hNT neuron (#937233) Homo sapiens cDNA clone 632633 3', mRNA sequence. (from Genbank) |
| 118 | CNS | 1.0264816 | 0.3642044 | 0.312879 | 0.22065304 | RC_AA2348 31_at | EST: zs38b04.s1 Soares NhHMPu S1 Homo sapiens cDNA clone 687439 3', mRNA sequence. (from Genbank) |
| 119 | CNS | 1.0247778 | 0.3639924 | 0.312635 | 0.22034481 | W26436_s_ at | Microtubule-associated protein 1B |
| 120 | CNS | 1.0243666 | 0.3638694 | 0.312468 | 0.22003654 | D86981_at | KIAA0228 gene, partial cds |
| 121 | CNS | 1.0243666 | 0.3626002 | 0.311862 | 0.21983251 | D86981_at-2 | Human mRNA for KIAA0228 gene, partial cds |
| 122 | CNS | 1.0219347 | 0.3622816 | 0.311694 | 0.21958862 | D80897_at | Homo sapiens clone 24736 mRNA sequence |
| 123 | CNS | 1.0215923 | 0.3622252 | 0.311444 | 0.21930876 | N77277_at | EST: yv43a07.r1 Soares fetal liver spleen 1NFLS Homo sapiens cDNA clone 245460 5', mRNA sequence. (from Genbank) |
| 124 | CNS | 1.0211011 | 0.3621407 | 0.31142 | 0.21915452 | X99802_at-2 | H.sapiens mRNA for ZYG homologue |
| 125 | CNS | 1.0211011 | 0.3619148 | 0.311078 | 0.21886241 | X99802_at | ZYG homologue |
| 126 | CNS | 1.0209804 | 0.3615916 | 0.310755 | 0.21862793 | M62302_at-2 | Human growth/differentiation factor 1 (GDF-1) mRNA, complete cds. |
| 127 | CNS | 1.0209804 | 0.3613792 | 0.310566 | 0.21845424 | M62302_at | Growth/differentiation factor 1 (GDF-1) mRNA |
| 128 | CNS | 1.0205418 | 0.361154 | 0.310433 | 0.21814896 | AA130156_a_t | EST: zi35d12.r1 Soares pregnant uterus NbHPU Homo sapiens cDNA clone 503927 5', mRNA sequence. (from Genbank) |
| 129 | CNS | 1.0176283 | 0.3607447 | 0.310396 | 0.217969905 | AA393666_a_t | Mannose-6-phosphate receptor (cation dependent) |
| 130 | CNS | 1.0173213 | 0.3604674 | 0.310363 | 0.21763197 | RC_AA4275 53_at | EST: zw22e04.s1 Soares ovary tumor NbHOT Homo sapiens cDNA clone 770046 3', mRNA sequence. (from Genbank) |
| 131 | CNS | 1.0170012 | 0.3600439 | 0.310338 | 0.21742667 | RC_AA5986 80_at | KIAA0618 gene product |

FIG. 3G

| # | Tissue | | | | Description |
|---|---|---|---|---|---|
| 132 | CNS | 1.0154105 | 0.3599196 | 0.309925 | 0.217234311 RC_AA4598 55_at | EST: zx51g08.s1 Soares testis NHT Homo sapiens cDNA clone 795806 3', mRNA sequence. (from Genbank) |
| 133 | CNS | 1.0151407 | 0.3599196 | 0.309806 | 0.21685941 AA480828_a t | EST: zx87d05.r1 Soares ovary tumor NbHOT Homo sapiens cDNA clone 810729 5' similar to TR:G1262329 G1262329 RETICULOCALBIN PRECURSOR. ;contains Alu repetitive element;, mRNA sequence. (from Genbank) |
| 134 | CNS | 1.0147551 | 0.3596523 | 0.309613 | 0.21663097 AA252381_a t | KH-type splicing regulatory protein |
| 135 | CNS | 1.0146048 | 0.3595884 | 0.309218 | 0.2165199 RC_AA4372 25_at | EST: zv54b11.s1 Soares testis NHT Homo sapiens cDNA clone 757437 3', mRNA sequence. (from Genbank) |
| 136 | CNS | 1.0141691 | 0.3590856 | 0.308927 | 0.21612594 N49353_at | EST: yy23h12.r1 Homo sapiens cDNA clone 272135 5'. (from Genbank) |
| 137 | CNS | 1.0136988 | 0.3587981 | 0.308914 | 0.21589483 U58856_at | Endocytic receptor (macrophage mannose receptor family) |
| 138 | CNS | 1.0132961 | 0.3587409 | 0.308868 | 0.21567686 AB002360_a t | Human mRNA for KIAA0362 gene, partial cds |
| 139 | CNS | 1.012922 | 0.3584979 | 0.308692 | 0.21550402 RC_AA0072 14_at | EST: 13cDNA52-3.seq Soares infant brain 1NIB Homo sapiens cDNA clone HY18-117,159,251 3', mRNA sequence. (from Genbank) |
| 140 | CNS | 1.012517 | 0.3581604 | 0.308384 | 0.21535349 AA058759_a t | Homo sapiens mRNA for KIAA0461 perotein, partial cds |
| 141 | CNS | 1.0120515 | 0.3578871 | 0.308102 | 0.21505221 AA040512_a t | Homo sapiens KIAA0431 mRNA, partial cds |
| 142 | CNS | 1.0117236 | 0.3576369 | 0.307855 | 0.21491116 RC_AA4528 65_at | UDP-Gal:betaGlcNAc beta 1,4- galactosyltransferase, polypeptide 2 |
| 143 | CNS | 1.0104562 | 0.3573959 | 0.307447 | 0.21471475 RC_AA4355 71_at | EST: zf73g10.s1 Soares testis NHT Homo sapiens cDNA clone 728034 3', mRNA sequence. (from Genbank) |
| 144 | CNS | 1.0101736 | 0.357391 | 0.307317 | 0.21445861 RC_AA5996 43_at | EST: ag10b05.s1 Gessler Wilms tumor Homo sapiens cDNA clone 1069905 3', mRNA sequence. (from Genbank) |
| 145 | CNS | 1.009497 | 0.3573434 | 0.307087 | 0.21425956 RC_AA4794 98_at | EST: zv21d10.s1 Soares NhHMPu S1 Homo sapiens cDNA clone 754291 3', mRNA sequence. (from Genbank) |
| 146 | CNS | 1.0094161 | 0.3567238 | 0.306915 | 0.21403474 RC_AA4851 47_at | EST: aa40h06.s1 NCI_CGAP_GCB1 Homo sapiens cDNA clone IMAGE:815771 3', mRNA sequence. (from Genbank) |
| 147 | CNS | 1.0084629 | 0.3566788 | 0.306705 | 0.21390297 AA096178_a t | EST: I8434.seq.F Fetal heart, Lambda ZAP Express Homo sapiens cDNA 5', mRNA sequence. (from Genbank) |
| 148 | CNS | 1.0050942 | 0.3563182 | 0.306324 | 0.21358328 H46787_at | Aconitase 2, mitochondrial |
| 149 | CNS | 1.0044037 | 0.3562298 | 0.306123 | 0.21333948 AA095885_a t | EST: I6748.seq.F Fetal heart, Lambda ZAP Express Homo sapiens cDNA 5', mRNA sequence. (from Genbank) |
| 150 | CNS | 1.0027878 | 0.3559859 | 0.306029 | 0.21311955 RC_AA0266 17_at | EST: ze93c06.s1 Soares fetal heart NbHH19W Homo sapiens cDNA clone 366538 3', mRNA sequence. (from Genbank) |

FIG. 3H

| | | | | | |
|---|---|---|---|---|---|
| 151 | CNS | 1.0027362 | 0.3559338 | 0.305807 | 0.21281919 | RC_AA4599 68_at | EST: zx66c12.s1 Soares total fetus Nb2HF8 9w Homo sapiens cDNA clone 796438 3', mRNA sequence. (from Genbank) |
| 152 | CNS | 1.001813 | 0.3558437 | 0.305651 | 0.21255636 | AA496526_s_at | EST: zv36h01.r1 Soares ovary tumor NbHOT Homo sapiens cDNA clone 755761 5', mRNA sequence. (from Genbank) |
| 153 | CNS | 1.0015508 | 0.35575779 | 0.305465 | 0.21238591 | AB002308_at | KIAA0310 gene product |
| 154 | CNS | 1.0015498 | 0.3556455 | 0.305414 | 0.21222307 | RC_AA4029 82_f_at | EST: zu55a06.s1 Soares ovary tumor NbHOT Homo sapiens cDNA clone 741874 3', mRNA sequence. (from Genbank) |
| 155 | CNS | 1.0014266 | 0.3552023 | 0.305358 | 0.21205635 | RC_AA4313 99_at | Homo sapiens chromosome 1 atrophin-1 related protein (DRPLA) mRNA, complete cds |
| 156 | CNS | 1.0001297 | 0.3551805 | 0.305155 | 0.21181707 | H14744_at | EST: ym24e06.r1 Homo sapiens cDNA clone 48792 5'. (from Genbank) |
| 157 | CNS | 0.9978548 | 0.3544163 | 0.304786 | 0.21166652 | C01747_at | EST: HUMGS0003679, Human Gene Signature, 3'-directed cDNA sequence, mRNA sequence. (from Genbank) |
| 158 | CNS | 0.9975388 | 0.3540663 | 0.304638 | 0.21140084 | RC_AA2591 35_at | EST: zx30d01.s1 NCI_CGAP_GCB1 Homo sapiens cDNA clone IMAGE:6866689 3', mRNA sequence. (from Genbank) |
| 159 | CNS | 0.9969791 | 0.3540631 | 0.304243 | 0.21119729 | AA092968_a_t | EST: m0992.seq.F Fetal heart, Lambda ZAP Express Homo sapiens cDNA 5', mRNA sequence. (from Genbank) |
| 160 | CNS | 0.9959125 | 0.3539636 | 0.304213 | 0.21102984 | RC_AA4286 32_at | EST: zw69a09.s1 Soares testis NHT Homo sapiens cDNA clone 781432 3', mRNA sequence. (from Genbank) |
| 161 | CNS | 0.9954314 | 0.3539217 | 0.303825 | 0.21094486 | D31091_at | EST: Human fetal-lung cDNA 5'-end sequence, mRNA sequence. (from Genbank) |
| 162 | CNS | 0.9949913 | 0.35538704 | 0.303576 | 0.21063513 | RC_AA1473 64_at | Homo sapiens clone 23714 mRNA sequence |
| 163 | CNS | 0.9945802 | 0.3538354 | 0.303531 | 0.21045855 | H08068_at | Homo sapiens clone 23967 unknown mRNA, partial cds |
| 164 | CNS | 0.9939117 | 0.3537598 | 0.303407 | 0.21030046 | RC_AA4636 37_at | EST: zx98h04.s1 Soares NhHMPu S1 Homo sapiens cDNA clone 811831 3', mRNA sequence. (from Genbank) |
| 165 | CNS | 0.9938311 | 0.3531174 | 0.303171 | 0.21001343 | H83527_s_at | KIAA0618 gene product |
| 166 | CNS | 0.9918591 | 0.3530565 | 0.303078 | 0.20985535 | AA203628_a_t | Insulin-like growth factor binding protein 6 |
| 167 | CNS | 0.9918453 | 0.3530507 | 0.302795 | 0.20973378 | RC_AA4066 10_at | EST: zv15b10.s1 Soares NhHMPu S1 Homo sapiens cDNA clone 753691 3' similar to gb:X02067 H.sapiens mRNA for 7SL RNA pseudogene (HUMAN);contains Alu repetitive element;, mRNA sequence. (from Genbank) |
| 168 | CNS | 0.9899077 | 0.3530362 | 0.302619 | 0.20951113 | AA032048_a_t | EST: zk15c03.r1 Soares pregnant uterus NbHPU Homo sapiens cDNA clone 470596 5', mRNA sequence. (from Genbank) |
| 169 | CNS | 0.9897113 | 0.3528417 | 0.302469 | 0.20928946 | RC_AA4372 35_s_at | EST: zv54c11.s1 Soares testis NHT Homo sapiens cDNA clone 757460 3', mRNA sequence. (from Genbank) |

FIG. 3I

| # | Tissue | | | | ID | Description |
|---|---|---|---|---|---|---|
| 170 | CNS | 0.9876819 | 0.3527185 | 0.302273 | 0.209022368 | RC_AA4432 72_at | EST: zw87e10.s1 Soares total fetus Nb2HF8 9w Homo sapiens cDNA clone 783978 3', mRNA sequence. (from Genbank) |
| 171 | CNS | 0.9876165 | 0.3526356 | 0.302148 | 0.208749071 | AA094107_at | EST: cl1862.seq.F Fetal heart, Lambda ZAP Express Homo sapiens cDNA 5', mRNA sequence. (from Genbank) |
| 172 | CNS | 0.9864547 | 0.352388 | 0.301841 | 0.208609746 | RC_AA2521 61_at | EST: zr64c03.s1 Soares NhHMPu S1 Homo sapiens cDNA clone 668164 3', mRNA sequence. (from Genbank) |
| 173 | CNS | 0.9853885 | 0.3522965 | 0.301695 | 0.208426243 | RC_AA5388 31_f_at | EST: ae40f06.s1 Gessler Wilms tumor Homo sapiens cDNA clone 898307 3', mRNA sequence. (from Genbank) |
| 174 | CNS | 0.984585 | 0.3521034 | 0.301486 | 0.208287731 | RC_AA4355 07_at | Homo sapiens mRNA for KIAA0731 protein, partial cds |
| 175 | CNS | 0.984182 | 0.35197411 | 0.301375 | 0.208018691 | AA479995_at | Discs, large (Drosophila) homolog 5 |
| 176 | CNS | 0.9826071 | 0.3519678 | 0.301088 | 0.207899621 | AA279561_at | EST: zs92a09.r1 NCI_CGAP_GCB1 Homo sapiens cDNA clone IMAGE:704920 5', mRNA sequence. (from Genbank) |
| 177 | CNS | 0.9821494 | 0.351353 | 0.300896 | 0.207688211 | AA248802_at | EST: j4151.seq.F Human fetal heart, Lambda ZAP Express Homo sapiens cDNA 5', mRNA sequence. (from Genbank) |
| 178 | CNS | 0.9818472 | 0.35122219 | 0.30076 | 0.207543259 | RC_AA4798 92_at | EST: zw44b02.s1 Soares total fetus Nb2HF8 9w Homo sapiens cDNA clone 772875 3', mRNA sequence. (from Genbank) |
| 179 | CNS | 0.9817755 | 0.3509987 | 0.3006619 | 0.207333339 | RC_AA1338 91_at | EST: zn86b06.s1 Stratagene lung carcinoma 937218 Homo sapiens cDNA clone 565043 3'. mRNA sequence. (from Genbank) |
| 180 | CNS | 0.981034 | 0.3509861 | 0.300501 | 0.207234551 | U95822_at | Human putative transmembrane GTPase mRNA, partial cds |
| 181 | CNS | 0.9809778 | 0.350864 | 0.300296 | 0.207056431 | C01394_at | H.sapiens gene from PAC 426l6, similar to syntaxin / |
| 182 | CNS | 0.9802766 | 0.3508498 | 0.3000095 | 0.206785343 | RC_AA4477 32_at | Glutathione peroxidase 3 (plasma) |
| 183 | CNS | 0.9787967 | 0.3507122 | 0.2999869 | 0.206462761 | H51057_at | EST: yp84f11.r1 Homo sapiens cDNA clone 194157 5'. (from Genbank) |
| 184 | CNS | 0.9780007 | 0.3506287 | 0.299772 | 0.206233278 | RC_AA4881 78_at | EST: ad08c04.s1 Soares NbHFB Homo sapiens cDNA clone 877638 3', mRNA sequence. (from Genbank) |
| 185 | CNS | 0.9763234 | 0.3503568 | 0.299606 | 0.206061027 | RC_AA0704 37_at | Human smoothened mRNA, complete cds |
| 186 | CNS | 0.9762463 | 0.3501048 | 0.299352 | 0.205811107 | D49958_at | Fetus brain mRNA for membrane glycoprotein M6 |
| 187 | CNS | 0.9759226 | 0.3500681 | 0.299038 | 0.205655492 | RC_AA1498 26_at | EST: zi48d11.s1 Soares pregnant uterus NbHPU Homo sapiens cDNA clone 505173 3', mRNA sequence. (from Genbank) |
| 188 | CNS | 0.9755471 | 0.3500381 | 0.298731 | 0.205579741 | RC_AA4781 06_at | EST: zt89d01.s1 Soares testis NHT Homo sapiens cDNA clone 729505 3', mRNA sequence. (from Genbank) |
| 189 | CNS | 0.9751933 | 0.3492295 | 0.298574 | 0.205360381 | RC_AA2558 22_at | EST: zx84g09.s1 Soares NhHMPu S1 Homo sapiens cDNA clone 682432 3', mRNA sequence. (from Genbank) |
| 190 | CNS | 0.9742862 | 0.3497171 | 0.298399 | 0.205322041 | AA453917_at | EST: zx32f02.r1 Soares total fetus Nb2HF8 9w Homo sapiens cDNA clone 788187 5', mRNA sequence. (from Genbank) |

FIG. 3J

| | | | | | | |
|---|---|---|---|---|---|---|
| 191 | CNS | 0.9736393 | 0.3495999 | 0.298081 | 0.20513378 | AA194766_a_t | Homo sapiens mRNA for KIAA0850 protein, complete cds |
| 192 | CNS | 0.9729598 | 0.3495284 | 0.297923 | 0.20495585 | W75980_at | KIAA0214 gene product |
| 193 | CNS | 0.9700761 | 0.3494426 | 0.297858 | 0.20476721 | RC_AA5987 18_at | EST: ae49e04.s1 Stratagene lung carcinoma 937218 Homo sapiens cDNA clone 950238 3', mRNA sequence. (from Genbank) |
| 194 | CNS | 0.9689111 | 0.3490906 | 0.297712 | 0.20461504 | AFFX-HSAC07/X0 0351_5_at-2 | No info for gene |
| 195 | CNS | 0.9689111 | 0.3490325 | 0.297574 | 0.20446858 | AFFX-HSAC07/X0 0351_5_at | AFFX-HSAC07/X00351_5_at (endogenous control) |
| 196 | CNS | 0.9686173 | 0.3487854 | 0.297364 | 0.20433103 | RC_AA2583 78_at | EST: zr62a09.s1 Soares NhHMPu S1 Homo sapiens cDNA clone 667960 3', mRNA sequence. (from Genbank) |
| 197 | CNS | 0.968174 | 0.3483558 | 0.297352 | 0.20413762 | R37560_at | Myotubularin related protein 4 |
| 198 | CNS | 0.9678751 | 0.3482869 | 0.297182 | 0.20401448 | RC_AA2325 49_f_at | EST: zt24c06.s1 Stratagene NT2 neuronal precursor 937230 Homo sapiens cDNA clone 664330 3', mRNA sequence. (from Genbank) |
| 199 | CNS | 0.9668545 | 0.3482148 | 0.29691 | 0.20380266 | AA371121_a t | EST82873 Prostate gland I Homo sapiens cDNA 5' end, mRNA sequence. (from Genbank) |
| 200 | CNS | 0.9663124 | 0.3481166 | 0.296769 | 0.20354801 | RC_AA3982 21_at | EST: zt59e10.s1 Soares testis NHT Homo sapiens cDNA clone 726666 3' similar to SW:KCCB_MOUSE P28652 CALCIUM/CALMODULIN-DEPENDENT PROTEIN KINASE TYPE II BETA CHAIN. ;; mRNA sequence. (from Genbank) |
| 201 | CNS | 0.9657993 | 0.3481166 | 0.29672 | 0.2033493 | AF006012_a t | Homo sapiens dishevelled 2 (DVL2) mRNA, complete cds. (from Genbank) |
| 202 | CNS | 0.9657444 | 0.3479804 | 0.296447 | 0.20317283 | RC_AA6203 07_at | EST: af05g12.s1 Soares testis NHT Homo sapiens cDNA clone 1030822 3', mRNA sequence. (from Genbank) |
| 203 | CNS | 0.9655124 | 0.347499 | 0.296332 | 0.20302619 | RC_AA4644 23_at | EST: zx78g08.s1 Soares ovary tumor NbHOT Homo sapiens cDNA clone 809918 3', mRNA sequence. (from Genbank) |
| 204 | CNS | 0.9654415 | 0.347289 | 0.296199 | 0.20292503 | R67297_at | EST: yh08d12.r2 Homo sapiens cDNA clone 42704 5'. (from Genbank) |
| 205 | CNS | 0.9654146 | 0.3472382 | 0.296072 | 0.20278879 | C00808_s_a t | EST: HUMGS0003083, Human Gene Signature, 3'-directed cDNA sequence, mRNA sequence. (from Genbank) |
| 206 | CNS | 0.9651779 | 0.3466997 | 0.295929 | 0.20262823 | RC_AA2845 06_s_at | EST: zi20o02.s1 Soares ovary tumor NbHOT Homo sapiens cDNA clone 713691 3', mRNA sequence. (from Genbank) |
| 207 | CNS | 0.9650673 | 0.3463053 | 0.295638 | 0.20250314 | RC_AA4253 54_at | EST: zw46e02.s1 Soares total fetus Nb2HF8 9w Homo sapiens cDNA clone 773114 3', mRNA sequence. (from Genbank) |
| 208 | CNS | 0.9637535 | 0.3461667 | 0.29544 | 0.20228057 | RC_AA4304 81_at | EST: zw23e02.s1 Soares ovary tumor NbHOT Homo sapiens cDNA clone 770138 3', mRNA sequence. (from Genbank) |

FIG. 3K

| | | | | | | |
|---|---|---|---|---|---|---|
| 209 | CNS | 0.9636452 | 0.3461488 | 0.295341 | 0.2019788 | AA092716_a t | HLA-B associated transcript-3 |
| 210 | CNS | 0.963081 | 0.3461072 | 0.295329 | 0.20185208 | D82603_at | EST: similar to F26F4.1, mRNA sequence. (from Genbank) |
| 211 | CNS | 0.9624962 | 0.3459891 | 0.295164 | 0.2017906 | RC_AA3499 15_at | Homo sapiens brain expressed ring finger protein mRNA, complete cds |
| 212 | CNS | 0.962081 | 0.3458137 | 0.295137 | 0.20153604 | W28214_at | EST: 45f7 Human retina cDNA randomly primed sublibrary Homo sapiens cDNA, mRNA sequence. (from Genbank) |
| 213 | CNS | 0.962053 | 0.3457714 | 0.294782 | 0.20141575 | AA496423_a t | EST: zv37d02.r1 Soares ovary tumor NbHOT Homo sapiens cDNA clone 755811 5', mRNA sequence. (from Genbank) |
| 214 | CNS | 0.9610634 | 0.3456965 | 0.294619 | 0.20122379 | RC_AA4608 49_at | EST: zx64h08.s1 Soares total fetus Nb2HF8 9w Homo sapiens cDNA clone 796287 3', mRNA sequence. (from Genbank) |
| 215 | CNS | 0.960719 | 0.3456629 | 0.294597 | 0.20109265 | RC_AA2335 29_at | EST: zr30g05.s1 Stratagene NT2 neuronal precursor 937230 Homo sapiens cDNA clone 664952 3', mRNA sequence. (from Genbank) |
| 216 | CNS | 0.9597902 | 0.345295 | 0.294418 | 0.2009026 | H58970_at | EST: yr40b03.r1 Homo sapiens cDNA clone 207725 5' similar to contains Alu repetitive element;. (from Genbank) |
| 217 | CNS | 0.9591184 | 0.3451828 | 0.294213 | 0.2008066 | RC_AA1672 73_at | KIAA0468 gene product |
| 218 | CNS | 0.9584609 | 0.3451705 | 0.294118 | 0.20062812 | RC_AA2054 31_at | EST: zq66a10.s1 Stratagene neuroepithelium (#937231) Homo sapiens cDNA clone 646554 3', mRNA sequence. (from Genbank) |
| 219 | CNS | 0.958143 | 0.345123 | 0.293841 | 0.20043863 | AA083572_a t | V-ral simian leukemia viral oncogene homolog A (ras related) |
| 220 | CNS | 0.957246 | 0.3451031 | 0.293708 | 0.20033564 | AA278412_a t | EST: zs81h03.r1 NCI_CGAP_GCB1 Homo sapiens cDNA clone IMAGE:703925 5', mRNA sequence. (from Genbank) |
| 221 | CNS | 0.9560762 | 0.3450495 | 0.293603 | 0.20015222 | RC_AA2344 69_s_at | EST: zr74h07.s1 Soares NhHMPu S1 Homo sapiens cDNA clone 669181 3', mRNA sequence. (from Genbank) |
| 222 | CNS | 0.9552402 | 0.3450189 | 0.293351 | 0.19985208 | RC_AA4764 48_at | EST: zx02f06.s1 Soares total fetus Nb2HF8 9w Homo sapiens cDNA clone 785315 3', mRNA sequence. (from Genbank) |
| 223 | CNS | 0.9550276 | 0.3448438 | 0.293246 | 0.1998251 | C01139_at | EST: HUMGS0007818, Human Gene Signature, 3'-directed cDNA sequence, mRNA sequence. (from Genbank) |
| 224 | CNS | 0.9548962 | 0.344729 | 0.293192 | 0.19957082 | AA401850_a t | Homo sapiens clone 23856 unknown mRNA, partial cds |
| 225 | CNS | 0.9546772 | 0.3445809 | 0.29308 | 0.19940169 | RC_AA0820 41_at | EST: zn21c01.s1 Stratagene neuroepithelium NT2RAMI 937234 Homo sapiens cDNA clone 548064 3', mRNA sequence. (from Genbank) |
| 226 | CNS | 0.9545261 | 0.3445375 | 0.292985 | 0.19928686 | RC_AA4639 46_at | Pigment epithelium-derived factor |
| 227 | CNS | 0.9541986 | 0.3443775 | 0.292878 | 0.19915034 | T68246_at | EST: yc40f01.r1 Homo sapiens cDNA clone 83161 5' similar to contains PTR5 repetitive element;. (from Genbank) |

FIG. 3L

| | | | | | |
|---|---|---|---|---|---|
| 228 | CNS | 0.9539833 | 0.3441235 | 0.292525 | 0.19897382 | RC_AA2915 51_at | Human ets domain protein ERF mRNA, complete cds |
| 229 | CNS | 0.9537966 | 0.3440925 | 0.292477 | 0.19883154 | RC_AA5898 59_at | EST: ag33g02.s1 Jia bone marrow stroma Homo sapiens cDNA clone 1091378 3', mRNA sequence. (from Genbank) |
| 230 | CNS | 0.9537156 | 0.3440479 | 0.292464 | 0.1906734 | AA298180_a t | EST: EST113862 Bone VII Homo sapiens cDNA 5' end, mRNA sequence. (from Genbank) |
| 231 | CNS | 0.9517934 | 0.3439757 | 0.292362 | 0.19844995 | RC_AA4875 10_at | EST: aa95c11.s1 Stratagene fetal retina 937202 Homo sapiens cDNA clone 839060 3', mRNA sequence. (from Genbank) |
| 232 | CNS | 0.9498384 | 0.3438279 | 0.292062 | 0.19834196 | RC_AA4240 25_at | Sperm surface protein |
| 233 | CNS | 0.9498376 | 0.3436411 | 0.291944 | 0.19825117 | AA255918_a t | Homo sapiens mRNA for putative vacuolar proton ATPase membrane sector associated protein M8-9 |
| 234 | CNS | 0.9495384 | 0.3433476 | 0.291763 | 0.19812670 | RC_AA6217 20_at | Glutathione peroxidase 3 (plasma) |
| 235 | CNS | 0.9486534 | 0.3430688 | 0.291685 | 0.19803612 | RC_AA4872 18_at | EST: ab19g10.s1 Stratagene lung (#937210) Homo sapiens cDNA clone 841314 3', mRNA sequence. (from Genbank) |
| 236 | CNS | 0.9483126 | 0.3430532 | 0.291409 | 0.19791976 | AA085463_a t | Tropomyosin 4 |
| 237 | CNS | 0.9479108 | 0.342795 | 0.291383 | 0.19784653 | AA091278_a t | EST: cchn24o4.seq.F Fetal heart, Lambda 7AP Express Homo sapiens cDNA 5', mRNA sequence. (from Genbank) |
| 238 | CNS | 0.9479089 | 0.3426282 | 0.291289 | 0.19759142 | C02472_at | Homo sapiens RanBP7/importin 7 mRNA, complete cds |
| 239 | CNS | 0.9476763 | 0.3424581 | 0.291017 | 0.19745554 | RC_AA4252 96_at | EST: zw48c01.s1 Soares total fetus Nb2HF8 9w Homo sapiens cDNA clone 773280 3', mRNA sequence. (from Genbank) |
| 240 | CNS | 0.9469206 | 0.3422883 | 0.290786 | 0.19736661 | W81268_at | Eukaryotic translation initiation factor 2, subunit 3 (gamma, 52kD) |
| 241 | CNS | 0.9465747 | 0.3420135 | 0.290734 | 0.1971762 | RC_AA0846 40_at | EST: zn20d05.s1 Stratagene neuroepithelium NT2RAMI 937234 Homo sapiens cDNA clone 547977 3', mRNA sequence. (from Genbank) |
| 242 | CNS | 0.9459087 | 0.3417914 | 0.290513 | 0.1970026 | RC_AA4799 10_at | EST: zw44c09.s1 Soares total fetus Nb2HF8 9w Homo sapiens cDNA clone 772912 3', mRNA sequence. (from Genbank) |
| 243 | CNS | 0.9442487 | 0.3417354 | 0.290365 | 0.19690289 | RC_AA4321 77_at | EST: zw71f12.s1 Soares testis NHT Homo sapiens cDNA clone 781679 3', mRNA sequence. (from Genbank) |
| 244 | CNS | 0.9438028 | 0.3414481 | 0.290133 | 0.19674788 | RC_AA6208 99_at | Homo sapiens clone 24684 mRNA sequence |
| 245 | CNS | 0.9437864 | 0.3414093 | 0.289991 | 0.19663103 | AA458602_a t | EST: aa12f12.r1 Soares NhHMPu S1 Homo sapiens cDNA clone 813071 5', mRNA sequence. (from Genbank) |
| 246 | CNS | 0.9413137 | 0.3413717 | 0.289945 | 0.19639803 | RC_AA3982 00_at | Homo sapiens mRNA for KIAA0875 protein, partial cds |
| 247 | CNS | 0.9421586 | 0.3412744 | 0.289842 | 0.19626512 | RC_AA6085 37_at | EST: ae53c08.s1 Stratagene lung carcinoma 937218 Homo sapiens cDNA clone 950806 3', mRNA sequence. (from Genbank) |

FIG. 3M

| # | Tissue | | | | ID | Description |
|---|---|---|---|---|---|---|
| 248 | CNS | 0.9420937 | 0.3411845 | 0.289833 | 0.19611757 | AA436315_a t | EST: zv22e11.r1 Soares NhHMPu S1 Homo sapiens cDNA clone 754412 5', mRNA sequence. (from Genbank) |
| 249 | CNS | 0.9417201 | 0.3410694 | 0.289742 | 0.19601606 76_at | RC_AA1507 | Homo sapiens clone 24405 mRNA sequence |
| 250 | CNS | 0.9415796 | 0.3408538 | 0.28967 | 0.19587982 81_at | RC_AA4545 | Homo sapiens mRNA for KIAA0602 protein, partial cds |
| 251 | CNS | 0.9413161 | 0.3407871 | 0.289447 | 0.19560473 42_at | RC_AA4552 | EST: ua30i08.s1 NCI_CGAP_GCB1 Homo sapiens cDNA clone IMAGE:814791 3' similar to TR:G933 G933 CANINE 68KDA SUBUNIT OF SIGNAL RECOGNITION PARTICLE.; mRNA sequence. (from Genbank) |
| 252 | CNS | 0.9404758 | 0.3405388 | 0.289226 | 0.19550174 30_r_at | RC_AA4342 | EST: zw24e10.s1 Soares ovary tumor NbHOT Homo sapiens cDNA clone 770250 3', mRNA sequence. (from Genbank) |
| 253 | CNS | 0.9404371 | 0.3404388 | 0.289111 | 0.19542396 42_at | RC_AA0453 | EST: zk58g01.s1 Soares pregnant uterus NbHPU Homo sapiens cDNA clone 487152 3', mRNA sequence. (from Genbank) |
| 254 | CNS | 0.9396198 | 0.3403753 | 0.289044 | 0.19523694 16_at | RC_AA2281 | Homo sapiens mRNA for KIAA0551 protein, partial cds |
| 255 | CNS | 0.9383699 | 0.3402981 | 0.288912 | 0.19516522 | MIP1-B_at | No info for gene |
| 256 | CNS | 0.9378721 | 0.3402134 | 0.288737 | 0.19501172 t | AA488230_a | EST: ad08c03.r1 Soares NbHFB Homo sapiens cDNA clone 877636 5', mRNA sequence. (from Genbank) |
| 257 | CNS | 0.9373376 | 0.3399583 | 0.288536 | 0.19486225 t | AA427783_a | EST: zw49b02.r1 Soares total fetus Nb2HF8 9w Homo sapiens cDNA clone 773355 5', mRNA sequence. (from Genbank) |
| 258 | CNS | 0.9370789 | 0.3398952 | 0.288328 | 0.19476531 40_at | RC_AA4790 | EST: zu36b12.s1 Soares ovary tumor NbHOT Homo sapiens cDNA clone 740063 3', mRNA sequence. (from Genbank) |
| 259 | CNS | 0.9357977 | 0.3397292 | 0.28827 | 0.19459064 64_at | RC_AA4584 | EST: zx73g05.s1 Soares ovary tumor NbHOT Homo sapiens cDNA clone 809432 3', mRNA sequence. (from Genbank) |
| 260 | CNS | 0.9340786 | 0.3394536 | 0.288203 | 0.19435151 | U24183_s_a t | PFKM Phosphofructokinase, muscle |
| 261 | CNS | 0.9340054 | 0.3394105 | 0.288132 | 0.19425146 | W72943_at | EST: zd54f12.r1 Soares fetal heart NbHH19W Homo sapiens cDNA clone 344495 5', mRNA sequence. (from Genbank) |
| 262 | CNS | 0.9336692 | 0.3391886 | 0.287951 | 0.19410947 42_at | RC_AA0578 | EST: zl95e03.s1 Stratagene corneal stroma (#937222) Homo sapiens cDNA clone 512380 3', mRNA sequence. (from Genbank) |
| 263 | CNS | 0.9329568 | 0.3388807 | 0.287827 | 0.19397263 21_at | RC_AA1211 | EST: zl88c03.s1 Stratagene colon (#937204) Homo sapiens cDNA clone 511684 3', mRNA sequence. (from Genbank) |
| 264 | CNS | 0.9326395 | 0.338879 | 0.287653 | 0.19390693 53_at | RC_AA0071 | EST: 13cDNA40-3.seq Soares infant brain 1NIB Homo sapiens cDNA clone HY18-44 3', mRNA sequence. (from Genbank) |
| 265 | CNS | 0.9322209 | 0.3388363 | 0.287586 | 0.19379193 t | AA405937_a | EST: zu66a10.r1 Soares testis NHT Homo sapiens cDNA clone 742038 5', mRNA sequence. (from Genbank) |
| 266 | CNS | 0.9318144 | 0.3385669 | 0.287567 | 0.19363035 42_at | RC_AA0355 | EST: ze24c03.s1 Soares fetal heart NbHH19W Homo sapiens cDNA clone 359908 3', mRNA sequence. (from Genbank) |

FIG. 3N

| # | Tissue | | | | Probe ID | Description |
|---|---|---|---|---|---|---|
| 267 | CNS | 0.9313584 | 0.3385087 | 0.287174 | 0.11935239 | RC_AA2243 28_at | EST: zr12f02.s1 Stratagene hNT neuron (#937233) Homo sapiens cDNA clone 648603 3', mRNA sequence. (from Genbank) |
| 268 | CNS | 0.9310966 | 0.3383984 | 0.28691 | 0.193413401 | AA056361_a t | EST: ze24f10.r1 Soares fetal heart NbHH19W Homo sapiens cDNA clone 359947 5' similar to contains element PTR5 repetitive element.; mRNA sequence. (from Genbank) |
| 269 | CNS | 0.9305229 | 0.3383817 | 0.286848 | 0.193282254 | D85815_at-2 | Homo sapiens DNA for rhoHP1, complete cds |
| 270 | CNS | 0.9305229 | 0.3382067 | 0.286778 | 0.1930946 | D85815_at | DNA for rhoHP1 |
| 271 | CNS | 0.9304102 | 0.3382044 | 0.286756 | 0.193022273 | RC_AA4361 49_at | EST: zv22h03.s1 Soares NhHMPu S1 Homo sapiens cDNA clone 754349 3', mRNA sequence. (from Genbank) |
| 272 | CNS | 0.9293105 | 0.33881902 | 0.286566 | 0.19289578 93_at | RC_AA4311 | Homo sapiens mRNA for KIAA0544 protein, partial cds |
| 273 | CNS | 0.9287321 | 0.33881902 | 0.286395 | 0.19279495 41_at | RC_AA4177 | EST: zv01c10.s1 NCI_CGAP_GCB1 Homo sapiens cDNA clone IMAGE:746226 3', mRNA sequence. (from Genbank) |
| 274 | CNS | 0.9287133 | 0.3379416 | 0.286327 | 0.19269516 t | AA464918_a | EST: aa92h11.r1 Stratagene fetal retina 937202 Homo sapiens cDNA clone 838821 5' similar to contains Alu repetitive element;, mRNA sequence. (from Genbank) |
| 275 | CNS | 0.9286905 | 0.3378868 | 0.286307 | 0.19256726_at | AA384184_s | EST: EST97722 Thyroid Homo sapiens cDNA 5' end, mRNA sequence. (from Genbank) |
| 276 | CNS | 0.9286417 | 0.3378617 | 0.286265 | 0.19246061 37_at | RC_AA4790 | EST: zu36b09.s1 Soares ovary tumor NbHOT Homo sapiens cDNA clone 740057 3', mRNA sequence. (from Genbank) |
| 277 | CNS | 0.9286303 | 0.3376463 | 0.286237 | 0.19237445 32_at | RC_AA5987 | EST: ae49g02.s1 Stratagene lung carcinoma 937218 Homo sapiens cDNA clone 950258 3', mRNA sequence. (from Genbank) |
| 278 | CNS | 0.9284996 | 0.3375374 | 0.286153 | 0.19229238 96_at | RC_AA2113 | EST: zq88d01.s1 Stratagene hNT neuron (#937233) Homo sapiens cDNA clone 649057 3' similar to TR:G257387 G257387 HTS1:;, mRNA sequence. (from Genbank) |
| 279 | CNS | 0.9275916 | 0.3375039 | 0.286033 | 0.19206153 48_at | RC_AA4211 | Solute carrier family 5 (sodium/glucose cotransporter), member 2 |
| 280 | CNS | 0.927029 | 0.3373744 | 0.285955 | 0.19195415 46_at | RC_AA1715 | EST: zp22d10.s1 Stratagene neuroepithelium (#937231) Homo sapiens cDNA clone 610195 3', mRNA sequence. (from Genbank) |
| 281 | CNS | 0.9268475 | 0.3372175 | 0.285828 | 0.191180332 | H05871_at | EST: yl73f05.r1 Homo sapiens cDNA clone 43723 5'. (from Genbank) |
| 282 | CNS | 0.9262156 | 0.3372084 | 0.285681 | 0.19169898 t | AA436926_a | EST: zv72a04.r1 Soares total fetus Nb2HF8 9w Homo sapiens cDNA clone 759150 5', mRNA sequence. (from Genbank) |
| 283 | CNS | 0.9258798 | 0.3369707 | 0.285609 | 0.19150257 59_at | RC_AA4894 | EST: ae31b11.s1 Gessler Wilms tumor Homo sapiens cDNA clone 897405 3', mRNA sequence. (from Genbank) |
| 284 | CNS | 0.9252191 | 0.3365977 | 0.285513 | 0.19140908 | N24994_at | KIAA0710 gene product |

FIG. 3O

| # | Tissue | | | | ID | Description |
|---|---|---|---|---|---|---|
| 285 | CNS | 0.9250717 | 0.33644383 | 0.285466 | 0.191124807 | RC_AA2847 20_at | EST: zt24a08.s1 Soares ovary tumor NbHOT Homo sapiens cDNA clone 714038 3', mRNA sequence. (from Genbank) |
| 286 | CNS | 0.9248542 | 0.33663085 | 0.285314 | 0.191117658 | RC_AA4763 55_s_at | EST: zw99e11.s1 Soares total fetus Nb2HF8 9w Homo sapiens cDNA clone 785132 3', mRNA sequence. (from Genbank) |
| 287 | CNS | 0.9247506 | 0.33662466 | 0.28505 | 0.19106659 | C15772_at | EST: Human fetal brain cDNA 5'-end GEN-169G03, mRNA sequence. (from Genbank) |
| 288 | CNS | 0.9243805 | 0.33624201 | 0.28487 | 0.190818888 | RC_AA4240 33_at | H.sapiens mRNA for serine palmitoyltransferase, subunit I |
| 289 | CNS | 0.9239809 | 0.336111 | 0.284727 | 0.190685786 | RC_AA4518 65_at | H. sapiens RNA for CLCN3 |
| 290 | CNS | 0.9230045 | 0.33660803 | 0.284606 | 0.190589966 | RC_AA0289 42_at | EST: zk08f11.s1 Soares pregnant uterus NbHPU Homo sapiens cDNA clone 469965 3', mRNA sequence. (from Genbank) |
| 291 | CNS | 0.9224028 | 0.33359724 | 0.284461 | 0.190512735 | S76992_at-2 | Vav 2 oncogene |
| 292 | CNS | 0.9224028 | 0.33359576 | 0.28424 | 0.190355325 | S76992_at | VAV2 Vav 2 oncogene |
| 293 | CNS | 0.9222903 | 0.33570340 | 0.284199 | 0.19023727 | R12974_at | EST: yf70c09.r1 Homo sapiens cDNA clone 27660 5' similar to contains Alu repetitive element;contains MER22 repetitive element.. (from Genbank) |
| 294 | CNS | 0.9221217 | 0.33514485 | 0.284089 | 0.19008848 | R67290_at | Homo sapiens clone 24607 mRNA sequence |
| 295 | CNS | 0.9212725 | 0.33507445 | 0.283978 | 0.18996776 | AA151569_s_at | EST: zl39h08.r1 Soares pregnant uterus NbHPU Homo sapiens cDNA clone 504351 5' similar to SW:CPT1_RAT P32198 MITOCHONDRIAL CARNITINE PALMITOYLTRANSFERASE I ;contains element PTR5 repetitive element.; mRNA sequence. (from Genbank) |
| 296 | CNS | 0.9202628 | 0.334947 | 0.283856 | 0.189948659 | RC_AA4792 99_at | EST: zv21f04.s1 Soares NbHMPu S1 Homo sapiens cDNA clone 754303 3', mRNA sequence. (from Genbank) |
| 297 | CNS | 0.9199286 | 0.33487220 | 0.283763 | 0.18974149 | RC_AA4356 44_s_at | EST: zt85d09.s1 Soares testis NHT Homo sapiens cDNA clone 729137 3', mRNA sequence. (from Genbank) |
| 298 | CNS | 0.9197363 | 0.33482875 | 0.283562 | 0.18965021 | RC_AA4482 19_at | KIAA0705 gene product |
| 299 | CNS | 0.9194799 | 0.33481555 | 0.283511 | 0.18949175 | RC_AA4245 43_s_at | EST: zv91b10.s1 Soares NbHMPu S1 Homo sapiens cDNA clone 767131 3', mRNA sequence. (from Genbank) |
| 300 | CNS | 0.9193137 | 0.33467706 | 0.283378 | 0.189391520 | T08287_at | EST: EST06178 Homo sapiens cDNA clone HIBBB85 5' end. (from Genbank) |
| 301 | CNS | 0.9188231 | 0.33464140 | 0.283279 | 0.18928197 | N56625_at | Low density lipoprotein receptor (familial hypercholesterolemia) |
| 302 | CNS | 0.9178692 | 0.33456390 | 0.283251 | 0.189151635 | RC_AA4033 05_at | EST: zt44e03.s1 Soares ovary tumor NbHOT Homo sapiens cDNA clone 725212 3', mRNA sequence. (from Genbank) |
| 303 | CNS | 0.9177618 | 0.33439685 | 0.283042 | 0.189000767 | RC_AA5998 76_s_at | EST: ag32e02.s1 Jia bone marrow stroma Homo sapiens cDNA clone 1091258 3', mRNA sequence. (from Genbank) |

FIG. 3P

| | | | | | |
|---|---|---|---|---|---|
| 304 | CNS | 0.9171396 | 0.3343027 | 0.282852 | 0.18889138 | RC_AA6100 82_at | EST: af08g08.s1 Soares testis NHT Homo sapiens cDNA clone 1031102 3', mRNA sequence. (from Genbank) |
| 305 | CNS | 0.9167273 | 0.334239 | 0.282845 | 0.18869998 | RC_AA2369 50_at | EST: zs43f01.s1 Soares NhHMPu S1 Homo sapiens cDNA clone 687961 3', mRNA sequence. (from Genbank) |
| 306 | CNS | 0.9167028 | 0.3341688 | 0.282792 | 0.18861105 | M25667_at | GAP43 Growth associated protein 43 |
| 307 | CNS | 0.9165799 | 0.3341104 | 0.28262 | 0.18844490 | RC_AA4103 136_at | EST: zv16d12.s1 Soares NhHMPu S1 Homo sapiens cDNA clone 753815 3', mRNA sequence. (from Genbank) |
| 308 | CNS | 0.9148403 | 0.3340688 | 0.282468 | 0.18831897 | C00771_at | ATPase type IV, phospholipid-transporting (P-type),(putative) |
| 309 | CNS | 0.9146573 | 0.3340074 | 0.282468 | 0.18816735 | AA476564_s_at | EST: zx02f07.r1 Soares total fetus Nb2HF8 9w Homo sapiens cDNA clone 785317 5' similar to TR:G553813 G553813 DNA-BINDING PROTEIN ;, mRNA sequence. (from Genbank) |
| 310 | CNS | 0.9145317 | 0.3336863 | 0.282425 | 0.18808039 | AA042991_s_at | EST: zk56a01.r1 Soares pregnant uterus NbHPU Homo sapiens cDNA clone 486792 5', mRNA sequence. (from Genbank) |
| 311 | CNS | 0.9137443 | 0.3335142 | 0.282071 | 0.18799073 | RC_AA4789 68_at | EST: zv18e04.s1 Soares NhHMPu S1 Homo sapiens cDNA clone 754014 3', mRNA sequence. (from Genbank) |
| 312 | CNS | 0.9131467 | 0.3335136 | 0.282054 | 0.18788114 | RC_AA2354 65_at | EST: zt31b07.s1 Soares ovary tumor NbHOT Homo sapiens cDNA clone 723925 3', mRNA sequence. (from Genbank) |
| 313 | CNS | 0.9129232 | 0.3333525 | 0.281906 | 0.18771234 | S74039_s_at | Homo sapiens creatine transporter mRNA, complete cds |
| 314 | CNS | 0.9121473 | 0.3333097 | 0.281872 | 0.18753573 | W68255_at | EST: zd33f12.r1 Soares fetal heart NbHH19W Homo sapiens cDNA clone 342479 5', mRNA sequence. (from Genbank) |
| 315 | CNS | 0.9120022 | 0.3331609 | 0.281775 | 0.18745464 | RC_AA4637 12_at | EST: aa07d06.s1 Soares NhHMPu S1 Homo sapiens cDNA clone 812555 3', mRNA sequence. (from Genbank) |
| 316 | CNS | 0.9119647 | 0.3329263 | 0.281751 | 0.1873864 | RC_AA4298 09_at | EST: zw64a12.s1 Soares testis NHT Homo sapiens cDNA clone 780958 3', mRNA sequence. (from Genbank) |
| 317 | CNS | 0.9115763 | 0.3328778 | 0.281611 | 0.18718566 | RC_AA6208 06_at | EST: af95c05.s1 Soares testis NHT Homo sapiens cDNA clone 1055528 3', mRNA sequence. (from Genbank) |
| 318 | CNS | 0.9114778 | 0.3326972 | 0.281528 | 0.18717408 | R56383_at | CDC23 (cell division cycle 23, yeast, homolog) |
| 319 | CNS | 0.9113318 | 0.3326895 | 0.281254 | 0.18709591 | RC_AA5996 79_s_at | Homo sapiens clone 23584 mRNA sequence |
| 320 | CNS | 0.9113081 | 0.3326083 | 0.281196 | 0.18692344 | W27301_at | EST: 27b5 Human retina cDNA randomly primed sublibrary Homo sapiens cDNA, mRNA sequence. (from Genbank) |
| 321 | CNS | 0.9112123 | 0.3324861 | 0.281118 | 0.18681057 | RC_AA2879 17_at | EST: zs55b10.s1 NCI_CGAP_GCB1 Homo sapiens cDNA clone IMAGE:701371 3', mRNA sequence. (from Genbank) |
| 322 | CNS | 0.9109531 | 0.3322273 | 0.28104 | 0.18673289 | D82277_s_at | EST: similar to none, mRNA sequence. (from Genbank) |
| 323 | CNS | 0.9108422 | 0.3319761 | 0.280885 | 0.18652676 | RC_AA6214 47_at | Af36h03.s1 Soares_total_fetus_Nb2HF8_9w Homo sapiens cDNA clone IMAGE:1033781 3', mRNA sequence |
| 324 | CNS | 0.9107899 | 0.3319129 | 0.280718 | 0.18647857 | C14228_f_at | EST: Human fetal brain cDNA 5'-end GEN-039B03, mRNA sequence. (from Genbank) |

FIG. 3Q

| | | | | | | |
|---|---|---|---|---|---|---|
| 325 | CNS | 0.910032 | 0.3318965 | 0.280575 | 0.18641502 | Z82022_at | Dolichyl-phosphate N-acetylglucosaminephosphotransferase 2 (GlcNAc-1-P transferase) |
| 326 | CNS | 0.9097309 | 0.331785 | 0.280535 | 0.18616481 | RC_AA4220 47_at | EST: zv28e08.s1 Soares ovary tumor NbHOT Homo sapiens cDNA clone 754982 3', mRNA sequence. (from Genbank) |
| 327 | CNS | 0.9096921 | 0.3312781 | 0.280476 | 0.18604225 | RC_AA4049 88_at | Homo sapiens mRNA for KIAA0674 protein, partial cds |
| 328 | CNS | 0.9092219 | 0.3317064 | 0.28033 | 0.18590525 | RC_AA4482 80_at | EST: zw83h05.s1 Soares testis NHT Homo sapiens cDNA clone 782841 3', mRNA sequence. (from Genbank) |
| 329 | CNS | 0.9089643 | 0.331525 | 0.280272 | 0.18578438 | AA477214_a t | EST: zu28h04.r1 Soares ovary tumor NbHOT Homo sapiens cDNA clone 739351 5' similar to contains Alu repetitive element; mRNA sequence. (from Genbank) |
| 330 | CNS | 0.908928 | 0.3314865 | 0.280125 | 0.18565504 | AA232738_a t | Sarcoglycan, epsilon |
| 331 | CNS | 0.9086279 | 0.3314186 | 0.279951 | 0.185556 | AA461215_a t | EST: zx61a09.r1 Soares total fetus Nb2HF8 9w Homo sapiens cDNA clone 795928 5', mRNA sequence. (from Genbank) |
| 332 | CNS | 0.9083716 | 0.3312341 | 0.279915 | 0.18536836 | RC_AA2531 93_at | EST: zr52g02.s1 Soares NhHMPu S1 Homo sapiens cDNA clone 667058 3', mRNA sequence. (from Genbank) |
| 333 | CNS | 0.9080692 | 0.3311848 | 0.279744 | 0.18529294 | RC_AA2530 00_at | EST: zr52h04.s1 Soares NhHMPu S1 Homo sapiens cDNA clone 667063 3', mRNA sequence. (from Genbank) |
| 334 | CNS | 0.9076743 | 0.3311738 | 0.2797 | 0.18512663 | RC_AA4560 80_at | EST: aa17c01.s1 Soares NhHMPu S1 Homo sapiens cDNA clone 813504 3', mRNA sequence. (from Genbank) |
| 335 | CNS | 0.9074756 | 0.3310127 | 0.279582 | 0.18508771 | RC_AA2580 28_at | EST: zs76a05.s1 NCI_CGAP_GCB1 Homo sapiens cDNA clone IMAGE:703376 3', mRNA sequence. (from Genbank) |
| 336 | CNS | 0.9070862 | 0.3309577 | 0.279347 | 0.1850575 | RC_AA4651 94_at | EST: aa33g02.s1 NCI_CGAP_GCB1 Homo sapiens cDNA clone IMAGE:815090 3'; mRNA sequence. (from Genbank) |
| 337 | CNS | 0.9070412 | 0.3308105 | 0.279284 | 0.18494342 | AA378597_a t | EST: EST91316 Synovial sarcoma Homo sapiens cDNA 5' end, mRNA sequence. (from Genbank) |
| 338 | CNS | 0.906994 | 0.3307675 | 0.279115 | 0.18485843 | RC_AA4366 15_at | EST: zw55c09.s1 Soares total fetus Nb2HF8 9w Homo sapiens cDNA clone 773968 3', mRNA sequence. (from Genbank) |
| 339 | CNS | 0.9067808 | 0.3306317 | 0.279067 | 0.18477507 | AB002302_a t | KIAA0304 gene product |
| 340 | CNS | 0.9065295 | 0.3304749 | 0.279055 | 0.1845846 | RC_AA4537 95_at | EST: aa19l08.s1 Soares NhHMPu S1 Homo sapiens cDNA clone 813735 3', mRNA sequence. (from Genbank) |
| 341 | CNS | 0.9058477 | 0.3304187 | 0.278969 | 0.18450525 | RC_AA4439 62_at | EST: zv51f04.s1 Soares testis NHT Homo sapiens cDNA clone 757183 3', mRNA sequence. (from Genbank) |
| 342 | CNS | 0.904971 | 0.330216 | 0.278722 | 0.1843542 | U55312_rna 1_s_at | G protein-coupled receptor 19 |
| 343 | CNS | 0.9045503 | 0.3300984 | 0.278706 | 0.18422922 | AA460511_a t | EST: zx51h09.r1 Soares testis NHT Homo sapiens cDNA clone 795809 5', mRNA sequence. (from Genbank) |

FIG. 3R

| # | Tissue | | | | ID | Description |
|---|---|---|---|---|---|---|
| 344 | CNS | 0.9041189 | 0.3300789 | 0.278551 | 0.18408261 | N79674_s_at | EST: yz81h05.r1 Homo sapiens cDNA clone 289497 5'. (from Genbank) |
| 345 | CNS | 0.9035726 | 0.32992 | 0.278538 | 0.18400048 | RC_AA4772_at | EST: zu39a12.s1 Soares ovary tumor NbHOT Homo sapiens cDNA clone 740350 3', mRNA sequence. (from Genbank) |
| 346 | CNS | 0.9034963 | 0.3299009 | 0.27839 | 0.1839901 | AB002310_at | Upstream regulatory element binding protein 1 |
| 347 | CNS | 0.9027182 | 0.3298551 | 0.278296 | 0.18374318 | AA089559_a_at | Homo sapiens mRNA, chromosome 1 specific transcript KIAA0488 |
| 348 | CNS | 0.9026671 | 0.329793 | 0.278196 | 0.18368259 | RC_AA4285_88_at | EST: zw74d07.s1 Soares testis NHT Homo sapiens cDNA clone 781933 3', mRNA sequence. (from Genbank) |
| 349 | CNS | 0.9026005 | 0.3296566 | 0.278156 | 0.18358363 | RC_AA2561_71_at | EST: zr79c08.s1 Soares NhHMPu S1 Homo sapiens cDNA clone 681902 3', mRNA sequence. (from Genbank) |
| 350 | CNS | 0.9025773 | 0.3296487 | 0.277928 | 0.18345508 | RC_AA4339_07_at | EST: zw52c04.s1 Soares total fetus Nb2HF8 9w Homo sapiens cDNA clone 773670 3', mRNA sequence. (from Genbank) |
| 351 | CNS | 0.9023477 | 0.3295342 | 0.277892 | 0.18339877 | RC_AA2438_42_at | EST: zr68a03.s1 Soares NhHMPu S1 Homo sapiens cDNA clone 668524 3', mRNA sequence. (from Genbank) |
| 352 | CNS | 0.9019314 | 0.3292249 | 0.277728 | 0.18323226 | RC_AA4301_79_s_at | Putative Ac-like transposon |
| 353 | CNS | 0.9010252 | 0.3292249 | 0.27766 | 0.1831334 | RC_AA4433_21_at | EST: zw94e05.s1 Soares total fetus Nb2HF8 9w Homo sapiens cDNA clone 784640 3', mRNA sequence. (from Genbank) |
| 354 | CNS | 0.9009711 | 0.3291293 | 0.277515 | 0.1830403 | J03544_s_at | Phosphorylase, glycogon; brain |
| 355 | CNS | 0.8999703 | 0.3291293 | 0.277487 | 0.18285912 | AA166776_a_at | Homo sapiens mRNA for KIAA0869 protein, partial cds |
| 356 | CNS | 0.8999657 | 0.3289509 | 0.277332 | 0.18271835 | RC_AA3994_45_at | EST: zi53a02.s1 Soares ovary tumor NbHOT Homo sapiens cDNA clone 726026 3', mRNA sequence. (from Genbank) |
| 357 | CNS | 0.8995807 | 0.328941 | 0.277227 | 0.18260302 | RC_AA6211_88_at | EST: zu81a08.s1 Soares testis NHT Homo sapiens cDNA clone 744374 3', mRNA sequence. (from Genbank) |
| 358 | CNS | 0.8993013 | 0.3289307 | 0.277036 | 0.1825605 | AA236286_a_at | EST: zr51a03.r1 Soares NhHMPu S1 Homo sapiens cDNA clone 666892 5' similar to SW:GCN5_YEAST Q03330 TRANSCRIPTIONAL ACTIVATOR GCN5. [1].; mRNA sequence. (from Genbank) |
| 359 | CNS | 0.898236 | 0.328855 | 0.276939 | 0.1823823 | RC_AA4970_50_at | EST: aa42c03.s1 Soares NhHMPu S1 Homo sapiens cDNA clone 823588 3', mRNA sequence. (from Genbank) |
| 360 | CNS | 0.8979144 | 0.3287333 | 0.276899 | 0.1823516 | AA258972_a_at | EST: zs34d01.r1 NCI_CGAP_GCB1 Homo sapiens cDNA clone IMAGE:687073 5', mRNA sequence. (from Genbank) |
| 361 | CNS | 0.8975303 | 0.3285351 | 0.276747 | 0.18219829 | H67964_at | Yu53g07.r1 Soares fetal liver spleen 1NFLS Homo sapiens cDNA clone IMAGE:2238884 5', mRNA sequence |
| 362 | CNS | 0.8968484 | 0.3285141 | 0.276611 | 0.1821126 | H01766_s_at | Homo sapiens mRNA for KIAA0829 protein, partial cds |

FIG. 3S

| | | | | | | |
|---|---|---|---|---|---|---|
| 363 | CNS | 0.89648 | 0.3285013 | 0.276578 | 0.1820782 | W28106_at | EST: 42b12 Human retina cDNA randomly primed sublibrary Homo sapiens cDNA, mRNA sequence. (from Genbank) |
| 364 | CNS | 0.8955314 | 0.3284345 | 0.276376 | 0.18196289 | RC_AA4493 20_at | EST: zx06e03.s1 Soares total fetus Nb2HF8 9w Homo sapiens cDNA clone 785692 3', mRNA sequence. (from Genbank) |
| 365 | CNS | 0.8949432 | 0.3282835 | 0.276316 | 0.18192057 | AA214730_a t | Human DNA sequence from clone 431H6 on chromosome 16. Contains a novel gene with some homology to mouse HN1 (Hematological and Neurological expressed sequence 1) downstream of a putative CpG island. Contains ESTs and GSSs |
| 366 | CNS | 0.8945633 | 0.3282348 | 0.276249 | 0.18180585 | RC_AA4566 67_at | EST: aa01f07.s1 Soares NhHMPu S1 Homo sapiens cDNA clone 812005 3', mRNA sequence. (from Genbank) |
| 367 | CNS | 0.8944442 | 0.3281789 | 0.276193 | 0.18170495 | RC_AA6216 24_at | Homo sapiens clone 24515 mRNA sequence |
| 368 | CNS | 0.8941941 | 0.3280276 | 0.276176 | 0.18155804 | RC_AA1582 51_at | Human growth factor-regulated tyrosine kinase substrate |
| 369 | CNS | 0.8938357 | 0.3278598 | 0.276056 | 0.18141976 | RC_AA1950 31_at | EST: zl35f08.s1 Soares NhHMPu S1 Homo sapiens cDNA clone 665415 3', mRNA sequence. (from Genbank) |
| 370 | CNS | 0.89349 | 0.3277756 | 0.275925 | 0.18128863 | RC_D59847 _at | EST: Human fetal brain cDNA 3'-end GEN-070G07, mRNA sequence. (from Genbank) |
| 371 | CNS | 0.8932131 | 0.3276595 | 0.275889 | 0.1811862 | D82346_at | HNSPC |
| 372 | CNS | 0.8927829 | 0.3274034 | 0.275694 | 0.18107748 | AA059401_a t | EST: zl96c05.r1 Stratagene corneal stroma (#937222) Homo sapiens cDNA clone 512456 5', mRNA sequence. (from Genbank) |
| 373 | CNS | 0.8924663 | 0.3272977 | 0.275688 | 0.1809682 | W28255_at | EST: 44b8 Human retina cDNA randomly primed sublibrary Homo sapiens cDNA, mRNA sequence. (from Genbank) |
| 374 | CNS | 0.8917642 | 0.3272079 | 0.275685 | 0.18079548 | RC_AA4257 77_at | EST: zv83d10.s1 Soares total fetus Nb2HF8 9w Homo sapiens cDNA clone 760243 3', mRNA sequence. (from Genbank) |
| 375 | CNS | 0.8915897 | 0.3271901 | 0.275632 | 0.18075244 | RC_AA4262 20_at | Homo sapiens mRNA for KIAA0523 protein, partial cds |
| 376 | CNS | 0.8912345 | 0.3271645 | 0.275514 | 0.18056559 | RC_AA6087 72_at | EST: af04b05.s1 Soares testis NHT Homo sapiens cDNA clone 1030641 3' similar to contains element TAR1 repetitive element :, mRNA sequence. (from Genbank) |
| 377 | CNS | 0.8905333 | 0.3268903 | 0.275492 | 0.18052281 | RC_AA2362 09_at | EST: zr49g05.s1 Soares NhHMPu S1 Homo sapiens cDNA clone 666776 3', mRNA sequence. (from Genbank) |
| 378 | CNS | 0.8904765 | 0.3268522 | 0.275312 | 0.18042365 | RC_AA6214 30_at | Doublecortex; lissencephaly, X-linked (doublecortin) |
| 379 | CNS | 0.8900428 | 0.3267535 | 0.275277 | 0.1802816 | RC_AA4599 16_at | Bradykinin receptor B2 |
| 380 | CNS | 0.8896193 | 0.3267422 | 0.275069 | 0.18015333 | AA436304_a t | GTP-BINDING NUCLEAR PROTEIN RAN |

FIG. 3T

| | | | | | |
|---|---|---|---|---|---|
| 381 | CNS | 0.8894191 | 0.3267285 | 0.275025 | 0.18008366 | C00314_at | EST: HUMGS0006018, Human Gene Signature, 3'-directed cDNA sequence, mRNA sequence. (from Genbank) |
| 382 | CNS | 0.8891949 | 0.3264561 | 0.274652 | 0.17998132 | RC_AA2279 60_at | EST: ze56d10.s1 Soares NhHMPu S1 Homo sapiens cDNA clone 667411 3', mRNA sequence. (from Genbank) |
| 383 | CNS | 0.8891608 | 0.3263621 | 0.274565 | 0.17989685 | AB002322_a t | Human mRNA for KIAA0324 gene, partial cds. (from Genbank) |
| 384 | CNS | 0.8889532 | 0.3263038 | 0.274444 | 0.17983982 | RC_AA3484 85_at | KIAA0438 gene product |
| 385 | CNS | 0.8889151 | 0.3262521 | 0.274436 | 0.17962293 | RC_AA5987 46_at | EST: ae49h07.s1 Stratagene lung carcinoma 937218 Homo sapiens cDNA clone 950269 3', mRNA sequence. (from Genbank) |
| 386 | CNS | 0.8888409 | 0.3260302 | 0.274367 | 0.17955106 | RC_AA2814 75_s_at | EST: zs96e10.s1 NCI_CGAP_GCB1 Homo sapiens cDNA clone IMAGE:711498 3', mRNA sequence. (from Genbank) |
| 387 | CNS | 0.8884828 | 0.325856 | 0.274356 | 0.17944467 | RC_AA2812 14_s_at | EST: zs94c04.s1 NCI_CGAP_GCB1 Homo sapiens cDNA clone IMAGE:705126 3', mRNA sequence. (from Genbank) |
| 388 | CNS | 0.8882795 | 0.3258103 | 0.274279 | 0.17926483 | RC_AA2591 47_at | EST: zs30f01.s1 NCI_CGAP_GCB1 Homo sapiens cDNA clone IMAGE:686713 3', mRNA sequence. (from Genbank) |
| 389 | CNS | 0.8880609 | 0.3254135 | 0.27424 | 0.17920062 | H09364_s_a t | EST: yl95a06.r1 Homo sapiens cDNA clone 45792 5' similar to SP:A42792 A42792 SUCCINATE DEHYDROGENASE :. (from Genbank) |
| 390 | CNS | 0.8879383 | 0.3253922 | 0.274204 | 0.17909473 | RC_AA0260 46_s_at | EST: ze86a02.s1 Soares fetal heart NbHH19W Homo sapiens cDNA clone 365834 3', mRNA sequence. (from Genbank) |
| 391 | CNS | 0.8876537 | 0.3251919 | 0.274136 | 0.17899898 | RC_AA3981 41_at | EST: zt58g11.s1 Soares testis NHT Homo sapiens cDNA clone 726596 3', mRNA sequence. (from Genbank) |
| 392 | CNS | 0.8865256 | 0.3249258 | 0.27395 | 0.17885493 | W58709_at | PHD finger protein 2 |
| 393 | CNS | 0.8860795 | 0.3248851 | 0.273847 | 0.17878127 | RC_AA4253 09_at | EST: zw46c01.s1 Soares total fetus Nb2HF8 9w Homo sapiens cDNA clone 773088 3', mRNA sequence. (from Genbank) |
| 394 | CNS | 0.8857641 | 0.3246657 | 0.273404 | 0.17868166 | AA090687_a t | EST: y1297.seq.F Fetal heart, Lambda ZAP Express Homo sapiens cDNA 5', mRNA sequence. (from Genbank) |
| 395 | CNS | 0.8857103 | 0.3246276 | 0.273296 | 0.17858195 | R88228_at | Homo sapiens mRNA for JM4 protein, complete CDS (clone IMAGE 546750 and LLNLc110F1857G7 (RZPD Berlin)) |
| 396 | CNS | 0.8855347 | 0.3243329 | 0.273236 | 0.17844316 | R80573_at | EST: yl92f11.r1 Homo sapiens cDNA clone 146733 5'. (from Genbank) |
| 397 | CNS | 0.8854269 | 0.3242738 | 0.273236 | 0.17834364 | RC_AA1575 06_at | EST: zo55d01.s1 Stratagene pancreas (#937208) Homo sapiens cDNA clone 590785 3', mRNA sequence. (from Genbank) |
| 398 | CNS | 0.8853662 | 0.3241518 | 0.273015 | 0.17825201 | RC_AA2519 82_at | Homo sapiens clone 23770 mRNA sequence |
| 399 | CNS | 0.8842993 | 0.3240429 | 0.272988 | 0.17815068 | RC_AA4609 39_at | EST: zx61d03.s1 Soares total fetus Nb2HF8 9w Homo sapiens cDNA clone 795941 3', mRNA sequence. (from Genbank) |

FIG. 3U

| | | | | | |
|---|---|---|---|---|---|
| 400 | CNS | 0.8842527 | 0.3238381 | 0.27289 | 0.17804533 | RC_AA2349 95_at | EST: zf50c05.s1 Soares NhHMPu S1 Homo sapiens cDNA clone 666824 3', mRNA sequence. (from Genbank) |
| 401 | CNS | 0.8831623 | 0.3238223 | 0.272841 | 0.17790111 | RC_AA4532 89_at | H.sapiens mRNA for ZYG homologue |
| 402 | CNS | 0.8831182 | 0.3237092 | 0.272721 | 0.17786632 | AA363338_a t | Ubiquitin protein ligase E3A (human papilloma virus E6-associated protein, Angelman syndrome) |
| 403 | CNS | 0.8823555 | 0.3235939 | 0.27271 | 0.1776822 | AA094441_a t | Glutathione peroxidase 3 (plasma) |
| 404 | CNS | 0.8822184 | 0.3234656 | 0.272652 | 0.17756717 | RC_AA4022 68_at | KIAA0652 gene product |
| 405 | CNS | 0.8816973 | 0.3233967 | 0.272648 | 0.17751234 | RC_AA4433 34_at | EST: zw94g05.s1 Soares total fetus Nb2HF8 9w Homo sapiens cDNA clone 784664 3', mRNA sequence. (from Genbank) |
| 406 | CNS | 0.8815104 | 0.3233528 | 0.272591 | 0.17746037 | AA044715_a t | EST: zk75g11.r1 Soares pregnant uterus NbHPU Homo sapiens cDNA clone 488708 5' similar to PIR:B54857 B54857 transcription factor NF-AT 90K chain - human .; mRNA sequence. (from Genbank) |
| 407 | CNS | 0.8812974 | 0.3233399 | 0.272553 | 0.17724355 | RC_AA3985 72_at | EST: zf73g07.s1 Soares testis NHT Homo sapiens cDNA clone 728028 3', mRNA sequence. (from Genbank) |
| 408 | CNS | 0.8811587 | 0.3231237 | 0.272441 | 0.17714423 | S82024_at | SCG10 |
| 409 | CNS | 0.8811452 | 0.3230982 | 0.272346 | 0.17701282 | W03178_at | EST: za54c04.r1 Soares fetal liver spleen 1NFLS Homo sapiens cDNA clone 296358 5', mRNA sequence. (from Genbank) |
| 410 | CNS | 0.8810003 | 0.322961 | 0.272159 | 0.17695235 | RC_AA4253 02_at | EST: zw46b05.s1 Soares total fetus Nb2HF8 9w Homo sapiens cDNA clone 773073 3', mRNA sequence. (from Genbank) |
| 411 | CNS | 0.8803201 | 0.3229579 | 0.272097 | 0.17683512 | RC_AA4637 45_at | EST: aa07h08.s1 Soares NhHMPu S1 Homo sapiens cDNA clone 812607 3', mRNA sequence. (from Genbank) |
| 412 | CNS | 0.880312 | 0.322877 | 0.272077 | 0.1767594 | AA410480_a t | EST: zv23b05.r1 Soares NhHMPu S1 Homo sapiens cDNA clone 754449 5', mRNA sequence. (from Genbank) |
| 413 | CNS | 0.880078 | 0.3228021 | 0.271953 | 0.17672397 | AA399200_a t | EST: zt52e04.r1 Soares ovary tumor NbHOT Homo sapiens cDNA clone 725982 5', mRNA sequence. (from Genbank) |
| 414 | CNS | 0.8795734 | 0.3226229 | 0.271833 | 0.17666355 | RC_AA4892 45_at | EST: aa57h06.s1 NCI_CGAP_GCB1 Homo sapiens cDNA clone IMAGE:825083 3', mRNA sequence. (from Genbank) |
| 415 | CNS | 0.8790923 | 0.3224933 | 0.271693 | 0.17653482 | H46831_at | EST: yo18b06.r1 Homo sapiens cDNA clone 178259 5' similar to contains MER29 repetitive element ;. (from Genbank) |
| 416 | CNS | 0.8790079 | 0.3224571 | 0.271669 | 0.17636923 | RC_AA2562 08_at | EST: zr80a08.s1 Soares NhHMPu S1 Homo sapiens cDNA clone 681974 3', mRNA sequence. (from Genbank) |
| 417 | CNS | 0.8786764 | 0.3224205 | 0.271527 | 0.17619815 | AA455331_a t | EST: aa30d12.r1 NCI_CGAP_GCB1 Homo sapiens cDNA clone IMAGE:814775 5', mRNA sequence. (from Genbank) |
| 418 | CNS | 0.8783413 | 0.3221654 | 0.271518 | 0.17617007 | U06863_at-2 | Human follistatin-related protein precursor mRNA, complete cds. (from Genbank) |
| 419 | CNS | 0.8783413 | 0.3221408 | 0.271384 | 0.17601943 | U06863_at | Follistatin-related protein precursor mRNA |

FIG. 3V

| | | | | | |
|---|---|---|---|---|---|
| 420 | CNS | 0.8781272 | 0.3220042 | 0.271285 | 0.175846419 | RC_AA3791 26_s_at | EST: EST91932 Skin tumor I Homo sapiens cDNA 3' end, mRNA sequence. (from Genbank) |
| 421 | CNS | 0.8744802 | 0.3219739 | 0.271118 | 0.175790371 | H21148_s_a t | EST: yn65e06.r1 Homo sapiens cDNA clone 173314 5'. (from Genbank) |
| 422 | CNS | 0.8764464 | 0.3219698 | 0.270948 | 0.175711886 | D82477_at | EST: similar to none, mRNA sequence. (from Genbank) |
| 423 | CNS | 0.8764378 | 0.3218825 | 0.270816 | 0.175683161 0_s_at | RC_AA2627 | Homo sapiens mRNA for KIAA0627 protein, partial cds |
| 424 | CNS | 0.8760315 | 0.3218065 | 0.270742 | 0.175553825_s_at | RC_AA4061 | EST: zu65b07.s1 Soares testis NHT Homo sapiens cDNA clone 742837 3', mRNA sequence. (from Genbank) |
| 425 | CNS | 0.8759868 | 0.3217611 | 0.270706 | 0.17553158 69_at | RC_AA4477 | EST: aa20e01.s1 Soares NhHMPu S1 Homo sapiens cDNA clone 813816 3', mRNA sequence. (from Genbank) |
| 426 | CNS | 0.8757927 | 0.3216643 | 0.270654 | 0.17547399 | AA482453_a t | EST: zv05b12.r1 Soares NhHMPu S1 Homo sapiens cDNA clone 752735 5', mRNA sequence. (from Genbank) |
| 427 | CNS | 0.8753265 | 0.3216557 | 0.2705 | 0.17532202 | W26883_at | Homo sapiens chromosome 1 atrophin-1 related protein (DRPLA) mRNA, complete cds |
| 428 | CNS | 0.8752369 | 0.3216257 | 0.270446 | 0.175223258 0_at | RC_AA0864 | EST: zl83d11.s1 Stratagene colon (#937204) Homo sapiens cDNA clone 511221 3' similar to contains Alu repetitive element;contains element MER22 repetitive element :, mRNA sequence. (from Genbank) |
| 429 | CNS | 0.8751909 | 0.3216005 | 0.270426 | 0.175131514 6_f_at | RC_AA4361 | EST: zv22a12.s1 Soares NhHMPu S1 Homo sapiens cDNA clone 754366 3', mRNA sequence. (from Genbank) |
| 430 | CNS | 0.8749581 | 0.3215883 | 0.270391 | 0.1749306 | AA459536_a t | Procollagen-lysine, 2-oxoglutarate 5-dioxygenase 3 |
| 431 | CNS | 0.8749492 | 0.3211414 | 0.270369 | 0.17488008367_at | RC_AA2136 | EST: zr93e10.s1 NCI_CGAP_GCB1 Homo sapiens cDNA clone IMAGE:683274 3', mRNA sequence. (from Genbank) |
| 432 | CNS | 0.873919 | 0.3210794 | 0.27031 | 0.17477958_at | AA091412_s | Homo sapiens mRNA containing (CAG)4 repeat, clone CZ-CAG-7 |
| 433 | CNS | 0.8736669 | 0.3209994 | 0.270221 | 0.1747426265_at | RC_AA5211 | EST: aa73d12.s1 NCI_CGAP_GCB1 Homo sapiens cDNA clone IMAGE:826583 3', mRNA sequence. (from Genbank) |
| 434 | CNS | 0.8734883 | 0.3208085 | 0.270152 | 0.17464387 | AA094023_a t | Homo sapiens exportin t mRNA, complete cds |
| 435 | CNS | 0.873412 | 0.3205961 | 0.270125 | 0.17457251_at | RC_D59420 | Homo sapiens mRNA for KIAA0865 protein, partial cds |
| 436 | CNS | 0.8730769 | 0.3204384 | 0.270095 | 0.17443305 47_at | RC_AA2322 | EST: zr75g08.s1 Soares NhHMPu S1 Homo sapiens cDNA clone 669278 3', mRNA sequence. (from Genbank) |
| 437 | CNS | 0.8726217 | 0.3202697 | 0.269996 | 0.17429751 | T87560_at | EST: yd83b10.r1 Homo sapiens cDNA clone 114811 5'. (from Genbank) |
| 438 | CNS | 0.8723564 | 0.3201354 | 0.269974 | 0.17421918 | AB002348_a t | Human mRNA for KIAA0350 gene, partial cds |

FIG. 3W

| | | | | | |
|---|---|---|---|---|---|
| 439 | CNS | 0.8722791 | 0.3200499 | 0.269941 | 0.1741314 | AA195678_a_t | Homo sapiens mRNA for KIAA0465 protein, partial cds |
| 440 | CNS | 0.8722293 | 0.3200105 | 0.269872 | 0.17402827 | RC_AA6091 72_at | EST: af12b02.s1 Soares testis NHT Homo sapiens cDNA clone 1031403 3', mRNA sequence. (from Genbank) |
| 441 | CNS | 0.8719453 | 0.3199683 | 0.269846 | 0.17384979 | RC_AA4785 90_at | EST: zv14c07.s1 Soares NhHMPu S1 Homo sapiens cDNA clone 753612 3', mRNA sequence. (from Genbank) |
| 442 | CNS | 0.8718835 | 0.3199524 | 0.269722 | 0.17383437 | AA247643_a_t | EST: csg4860.seq.F Human fetal heart, Lambda ZAP Express Homo sapiens cDNA 5', mRNA sequence. (from Genbank) |
| 443 | CNS | 0.8715387 | 0.3198913 | 0.26968 | 0.17376097 | AA0403 94_at | EST: zi05h02.s1 Soares fetal heart NbHH19W Homo sapiens cDNA clone 376083 3', mRNA sequence. (from Genbank) |
| 444 | CNS | 0.8714629 | 0.319016 | 0.269605 | 0.17367683 | AA126592_a_t | EST: zi17g05.r1 Soares pregnant uterus NbHPU Homo sapiens cDNA clone 502232 5', mRNA sequence. (from Genbank) |
| 445 | CNS | 0.8712021 | 0.3196343 | 0.269508 | 0.17358626 | RC_AA2588 01_s_at | C-terminal binding protein 1 |
| 446 | CNS | 0.8705825 | 0.3195301 | 0.269379 | 0.17352396 | D82284_at | Homo sapiens mRNA for KIAA0733 protein, partial cds |
| 447 | CNS | 0.8704747 | 0.319455 | 0.269258 | 0.17337993 | AA194146_a_t | EST: zr37g05.r1 Soares NhHMPu S1 Homo sapiens cDNA clone 665624 5', mRNA sequence. (from Genbank) |
| 448 | CNS | 0.8700701 | 0.3192615 | 0.269095 | 0.17325737 | AA092765_a_t | EST: Il8569.seq.F Fetal heart, Lambda ZAP Express Homo sapiens cDNA 5', mRNA sequence. (from Genbank) |
| 449 | CNS | 0.8696395 | 0.3192508 | 0.269074 | 0.17315294 | R78991_at | Lactate dehydrogenase B |
| 450 | CNS | 0.8695718 | 0.3192241 | 0.268958 | 0.17306668 | RC_AA4257 82_at | Homo sapiens mRNA for KIAA0874 protein, partial cds |
| 451 | CNS | 0.8694489 | 0.3191114 | 0.268946 | 0.17293209 | AA448522_a_t | Human smoothened mRNA, complete cds |
| 452 | CNS | 0.8693954 | 0.3189533 | 0.268897 | 0.17288527 | RC_AA0189 76_at | EST: ze55e09.s1 Soares retina N2b4HR Homo sapiens cDNA clone 362920 3' similar to contains Alu repetitive element;, mRNA sequence. (from Genbank) |
| 453 | CNS | 0.8690352 | 0.3188826 | 0.268884 | 0.17284723 | AA172242_a_t | Mannose-6-phosphate receptor (cation dependent) |
| 454 | CNS | 0.8682405 | 0.3188277 | 0.268773 | 0.1726802 | AA465434_a_t | Karyopherin (importin) beta 2 |
| 455 | CNS | 0.8680446 | 0.3186049 | 0.26873 | 0.17261161 | T34896_s_at | EST: EST78547 Homo sapiens cDNA 5' end similar to None. (from Genbank) |
| 456 | CNS | 0.8679949 | 0.3185938 | 0.268597 | 0.17253341 | AA093862_a_t | EST: cf1256.seq.F Fetal heart, Lambda ZAP Express Homo sapiens cDNA 5', mRNA sequence. (from Genbank) |
| 457 | CNS | 0.8677273 | 0.3185546 | 0.268574 | 0.172453 | AA43011_a_t | Radixin |
| 458 | CNS | 0.8673101 | 0.3183403 | 0.268467 | 0.17226339 | RC_AA1348 24_at | EST: zi20e10.s1 Soares pregnant uterus NbHPU Homo sapiens cDNA clone 502506 3', mRNA sequence. (from Genbank) |

FIG. 3X

| | | | | | | |
|---|---|---|---|---|---|---|
| 459 | CNS | 0.8672912 | 0.3182977 | 0.268361 | 0.172333655 | AA195457_a t | EST: zr36a12.r1 Soares NhHMPu S1 Homo sapiens cDNA clone 665470 5', mRNA sequence. (from Genbank) |
| 460 | CNS | 0.8672099 | 0.3182463 | 0.268304 | 0.172225803 | W40410_at | EST: zb74f10.r1 Soares fetal lung NbHL19W Homo sapiens cDNA clone 309355 5', mRNA sequence. (from Genbank) |
| 461 | CNS | 0.8672053 | 0.3180966 | 0.268213 | 0.172251154 | H78550_at | EST: yu13g03.r1 Homo sapiens cDNA clone 233716 5'. (from Genbank) |
| 462 | CNS | 0.8671424 | 0.3179736 | 0.268052 | 0.17211534 | R20031_at | EST: yg31g03.r1 Homo sapiens cDNA clone 20078 5'. (from Genbank) |
| 463 | CNS | 0.8671183 | 0.3178086 | 0.267951 | 0.171989934 | RC_AA6091 63_at | Small inducible cytokine A5 (RANTES) |
| 464 | CNS | 0.8668292 | 0.3178054 | 0.267817 | 0.171855512 | RC_AA2155 85_s_at | Homo sapiens clone 486790 diphosphoinositol polyphosphate phosphohydrolase mRNA, complete cds |
| 465 | CNS | 0.8666653 | 0.3176784 | 0.267752 | 0.171717201 | W26395_at | EST: 29h10 Human retina cDNA randomly primed sublibrary Homo sapiens cDNA, mRNA sequence. (from Genbank) |
| 466 | CNS | 0.8665986 | 0.3175967 | 0.267715 | 0.171703099 | RC_AA6202 95_s_at | EST: af04h10.s1 Soares testis NHT Homo sapiens cDNA clone 1030723 3', mRNA sequence. (from Genbank) |
| 467 | CNS | 0.866149 | 0.3175961 | 0.267637 | 0.17159374 | C02016_at | KIAA0447 gene product |
| 468 | CNS | 0.8657075 | 0.3174503 | 0.267563 | 0.171519074 | RC_AA0708 41_at | Homo sapiens mRNA, complete cds, similar to yeast pre-mRNA splicing factors, Prp1/Zer1 and Prp6 |
| 469 | CNS | 0.8656745 | 0.3173472 | 0.267298 | 0.171437415 | D78012_at | CRMP1 Collapsin response mediator protein 1 |
| 470 | CNS | 0.8653678 | 0.3172293 | 0.26727 | 0.171279161 | AA400643_s _at | H.sapiens mRNA for GAR22 protein |
| 471 | CNS | 0.866512 | 0.3171641 | 0.26721 | 0.171215271 | AA095021_a t | Glioblastoma amplified sequence |
| 472 | CNS | 0.8644858 | 0.3171121 | 0.267112 | 0.171173951 | X82207_at | BETA-CENTRACTIN |
| 473 | CNS | 0.8644858 | 0.3170405 | 0.267079 | 0.171095271 | X82207_at-2 | BETA-CENTRACTIN |
| 474 | CNS | 0.8644258 | 0.3169101 | 0.267004 | 0.170946121 | AA134028_a t | EST: zi34c12.r1 Soares pregnant uterus NbHPU Homo sapiens cDNA clone 503830 5', mRNA sequence. (from Genbank) |
| 475 | CNS | 0.8637341 | 0.3168535 | 0.266916 | 0.170886641 | AA504549_a t | EST: aa60c12.r1 NCI_CGAP_GCB1 Homo sapiens cDNA clone IMAGE:825334 5', mRNA sequence. (from Genbank) |
| 476 | CNS | 0.8630804 | 0.3167527 | 0.266839 | 0.170776591 | AA278829_a t | Homo sapiens mRNA for KIAA0871 protein, complete cds |
| 477 | CNS | 0.862962 | 0.3167299 | 0.26682 | 0.170759841 | AA488103_a t | EST: ad07a08.r1 Soares NbHFB Homo sapiens cDNA clone 877526 5' similar to SW:YAH8_YEAST P39707 HYPOTHETICAL 31.3 KD PROTEIN IN RFA1-ADE1 INTERGENIC REGION.; mRNA sequence. (from Genbank) |
| 478 | CNS | 0.8629395 | 0.31663 | 0.266738 | 0.170630841 | RC_AA4536 28_at | EST: zx48c06.s1 Soares testis NHT Homo sapiens cDNA clone 795466 3', mRNA sequence. (from Genbank) |

FIG. 3Y

| | | | | | | |
|---|---|---|---|---|---|---|
| 479 | CNS | 0.8628446 | 0.3165369 | 0.266682 | 0.170583 W52638_at | EST: zc49f01.r1 Soares senescent fibroblasts NbHSF Homo sapiens cDNA clone 325657 5', mRNA sequence. (from Genbank) |
| 480 | CNS | 0.8624148 | 0.316419 | 0.266576 | 0.170496 RC_AA411014_at | EST: zv40a08.s1 Soares ovary tumor NbI IOT Homo sapiens cDNA clone 756086 3', mRNA sequence. (from Genbank) |
| 481 | CNS | 0.8614368 | 0.316418 | 0.266474 | 0.170443 RC_AA4358 53_67_at | EST: zt80f08.s1 Soares testis NHT Homo sapiens cDNA clone 728679 3', mRNA sequence. (from Genbank) |
| 482 | CNS | 0.861293 | 0.3163188 | 0.266444 | 0.170312 RC_AA4522 17 45_s_at | EST: zx15f06.s1 Soares total fetus Nb2HF8 9w Homo sapiens cDNA clone 786663 3', mRNA sequence. (from Genbank) |
| 483 | CNS | 0.8607888 | 0.3160881 | 0.266116 | 0.170237 RC_AA4341 903_at | EST: zw24a08.s1 Soares ovary tumor NbHOT Homo sapiens cDNA clone 770198 3', mRNA sequence. (from Genbank) |
| 484 | CNS | 0.8607813 | 0.3160742 | 0.266069 | 0.170150 RC_AA4503 16_02_s_at | Peroxisomal biogenesis factor 14 |
| 485 | CNS | 0.8607601 | 0.3160489 | 0.265969 | 0.170059 RC_AA1502 59_05_at | Ubiquitous Kruppel-like transcription factor |
| 486 | CNS | 0.8603923 | 0.3160449 | 0.265911 | 0.169949 RC_AA4781 65_04_at | EST: zt89c03.s1 Soares testis NHT Homo sapiens cDNA clone 729508 3', mRNA sequence. (from Genbank) |
| 487 | CNS | 0.8603262 | 0.3160376 | 0.265752 | 0.169878 AA490192_a 35_at | EST: aa13f10.r1 Soares NhHMPu S1 Homo sapiens cDNA clone 823723 5', mRNA sequence. (from Genbank) |
| 488 | CNS | 0.8599824 | 0.3159898 | 0.265608 | 0.169792 AB002304_a 4_t | Human mRNA for KIAA0306 gene, partial cds |
| 489 | CNS | 0.8597012 | 0.3159038 | 0.265555 | 0.169680 RC_AA2370 83_34_at | Golgi SNAP receptor complex member 2 |
| 490 | CNS | 0.8595918 | 0.3158009 | 0.265396 | 0.169598 W25847_at | Homo sapiens mRNA for GEF-2 protein |
| 491 | CNS | 0.8588387 | 0.3156932 | 0.265364 | 0.169522 RC_AA4596 76_57_at | Homo sapiens clone 23570 mRNA sequence |
| 492 | CNS | 0.8587751 | 0.3156571 | 0.265339 | 0.169457 RC_AA2916 78_29_at | EST: zt45f05.s1 Soares ovary tumor NbHOT Homo sapiens cDNA clone 725313 3', mRNA sequence. (from Genbank) |
| 493 | CNS | 0.8586209 | 0.3156269 | 0.265235 | 0.169345 W60181_at | P311 protein |
| 494 | CNS | 0.8583674 | 0.3156097 | 0.265107 | 0.169259 M93426_at | PTPRZ Protein tyrosine phosphatase, receptor-type, zeta polypeptide |
| 495 | CNS | 0.8581185 | 0.3155079 | 0.26509 | 0.169176 W46192_at | EST: zc30d03.r1 Soares senescent fibroblasts NbHSF Homo sapiens cDNA clone 323813 5', mRNA sequence. (from Genbank) |
| 496 | CNS | 0.8579005 | 0.3155886 | 0.265009 | 0.169125 RC_AA4118 85_25_s_at | EST: zt67c03.s1 Soares testis NHT Homo sapiens cDNA clone 727396 3', mRNA sequence. (from Genbank) |
| 497 | CNS | 0.8575531 | 0.3155774 | 0.264968 | 0.169026 RC_AA0533 94_41_at | EST: zf60e10.s1 Soares retina N2b4HR Homo sapiens cDNA clone 381354 3' similar to contains Alu repetitive element;contains element MER22 repetitive element ;., mRNA sequence. (from Genbank) |

FIG. 3Z

| | | | | | | |
|---|---|---|---|---|---|---|
| 498 | CNS | 0.8573443 | 0.3154531 | 0.264789 | RC_AA4550 97_i_at | EST: aa04f08.s1 Soares NhHMPu S1 Homo sapiens cDNA clone 812295 3', mRNA sequence. (from Genbank) |
| 499 | CNS | 0.8570634 | 0.3153619 | 0.264617 | AA464639_a t | Ribosome binding protein 1 (dog 180kD homolog) |
| 500 | CNS | 0.8564378 | 0.3153363 | 0.264546 | RC_AA2868 07_at | EST: zs54a01.s1 NCI_CGAP_GCB1 Homo sapiens cDNA clone IMAGE:701256 3', mRNA sequence. (from Genbank) |
| 501 | CNS | 0.8562839 | 0.3152781 | 0.264451 | AA261884_a t | Homo sapiens mRNA for KIAA0788 protein, partial cds |
| 502 | CNS | 0.8558524 | 0.3152213 | 0.264347 | RC_AA2060 23_at | EST: zq77c12.s1 Stratagene hNT neuron (#937233) Homo sapiens cDNA clone 647638 3', mRNA sequence. (from Genbank) |
| 503 | CNS | 0.8558478 | 0.3152061 | 0.264324 | W02253_at | EST: zs57f05.r1 Soares fetal liver spleen 1NFLS Homo sapiens cDNA clone 296673 5', mRNA sequence. (from Genbank) |
| 504 | CNS | 0.8555413 | 0.3150941 | 0.264212 | AA455606_s _at | EST: aa17e06.r1 Soares NhHMPu S1 Homo sapiens cDNA clone 813538 5', mRNA sequence. (from Genbank) |
| 505 | CNS | 0.8551045 | 0.3150696 | 0.264109 | T86796_at | EST: yd86e07.r1 Homo sapiens cDNA clone 115140 5' similar to contains TAR1 repetitive element :. (from Genbank) |
| 506 | CNS | 0.8549647 | 0.3149992 | 0.264041 | AA418351_a t | EST: zx96e07.r1 Soares NhHMPu S1 Homo sapiens cDNA clone 767652 5', mRNA sequence. (from Genbank) |
| 507 | CNS | 0.8548502 | 0.314909 | 0.263969 | RC_AA0763 26_at | Ribosomal protein L32 |
| 508 | CNS | 0.8547452 | 0.3148094 | 0.263928 | RC_AA0562 47_at | Homo sapiens clone 24511 mRNA sequence |
| 509 | CNS | 0.854447 | 0.3145937 | 0.263857 | RC_AA4358 38_s_at | EST: zt80b06.s1 Soares testis NHT Homo sapiens cDNA clone 728627 3', mRNA sequence. (from Genbank) |
| 510 | CNS | 0.854466 | 0.3143011 | 0.263817 | AA452957_a t | EST: zx36c01.r1 Soares total fetus Nb2HF8 9w Homo sapiens cDNA clone 788544 5' similar to gb:X52354 ZINC FINGER PROTEIN KOX23 (HUMAN), mRNA sequence. (from Genbank) |
| 511 | CNS | 0.8543346 | 0.3140812 | 0.263778 | RC_AA1635 02_at | EST: zx72c09.s1 Soares total fetus Nb2HF8 9w Homo sapiens cDNA clone 797008 3', mRNA sequence. (from Genbank) |
| 512 | CNS | 0.8539971 | 0.3140491 | 0.263695 | D16181_at | PMP2 Peripheral myelin protein 2 |
| 513 | CNS | 0.8536553 | 0.3139249 | 0.263619 | RC_AA4534 73_at | EST: zx45d07.s1 Soares testis NHT Homo sapiens cDNA clone 795181 3', mRNA sequence. (from Genbank) |
| 514 | CNS | 0.8534239 | 0.3139046 | 0.263609 | RC_AA2794 39_at | EST: zs85f09.s1 NCI_CGAP_GCB1 Homo sapiens cDNA clone IMAGE:704297 3', mRNA sequence. (from Genbank) |
| 515 | CNS | 0.8530401 | 0.3134361 | 0.263497 | RC_AA4063 19_at | Midline 1 (Opitz/BBB syndrome) |
| 516 | CNS | 0.8529968 | 0.3132913 | 0.263496 | RC_AA2624 72_at | EST: zs17g03.s1 NCI_CGAP_GCB1 Homo sapiens cDNA clone IMAGE:685492 3', mRNA sequence. (from Genbank) |

FIG. 3A2

| # | Tissue | | | | ID | Description |
|---|---|---|---|---|---|---|
| 517 | CNS | 0.8523769 | 0.3130742 | 0.263365 | 0.1673256 | RC_AA4529 28_at | EST: zx41h05.s1 Soares total fetus Nb2HF8 9w Homo sapiens cDNA clone 789081 3', mRNA sequence. (from Genbank) |
| 518 | CNS | 0.8521363 | 0.3130189 | 0.263313 | 0.16722212 | RC_AA2788 60_at | EST: zs77h05.s1 NCI_CGAP_GCB1 Homo sapiens cDNA clone IMAGE:7035453 3', mRNA sequence. (from Genbank) |
| 519 | CNS | 0.851822 | 0.312805 | 0.263223 | 0.16715606 | H27232_at | Yi63e12.r1 Homo sapiens cDNA clone 162958 5'. (from Genbank) |
| 520 | CNS | 0.8517499 | 0.3127979 | 0.263124 | 0.16709167 | D81655_at | EST: Human fetal brain cDNA 5'-end GEN-181D03, mRNA sequence. (from Genbank) |
| 521 | CNS | 0.8513388 | 0.3127483 | 0.26309 | 0.16702446 | HG3638-HT3849_s_a t | Amyloid Beta (A4) Precursor Protein, Alt. Splice 2, A4(751) |
| 522 | CNS | 0.8511856 | 0.3127445 | 0.26303 | 0.16692969 | RC_AA6030 11_at | EST: af05f10.s1 Soares testis NHT Homo sapiens cDNA clone 1030795 3', mRNA sequence. (from Genbank) |
| 523 | CNS | 0.8509063 | 0.3126426 | 0.262916 | 0.16687898 | RC_AA4648 44_at | EST: zx44g03.s1 Soares total fetus Nb2HF8 9w Homo sapiens cDNA clone 789364 3', mRNA sequence. (from Genbank) |
| 524 | CNS | 0.8506628 | 0.3125913 | 0.262904 | 0.1667924 | RC_AA4593 10_f_at | EST: zx89d06.s1 Soares ovary tumor NbHOT Homo sapiens cDNA clone 810923 3', mRNA sequence. (from Genbank) |
| 525 | CNS | 0.8502092 | 0.3124628 | 0.262827 | 0.16674112 | AA056681_a t | EST: zk80g05.r1 Soares pregnant uterus NbHPU Homo sapiens cDNA clone 489176 5', mRNA sequence. (from Genbank) |
| 526 | CNS | 0.8501516 | 0.3124199 | 0.262785 | 0.16660722 | F15210_at | Hexosaminidase B (beta polypeptide) |
| 527 | CNS | 0.8500838 | 0.312153 | 0.262637 | 0.16654107 | RC_AA4241 40_at | Carbonic anhydrase XI |
| 528 | CNS | 0.8496226 | 0.3120626 | 0.262544 | 0.16649167 | RC_AA0042 11_at | EST: zh97c05.s1 Soares fetal liver spleen 1NFLS S1 Homo sapiens cDNA clone 429224 3', mRNA sequence. (from Genbank) |
| 529 | CNS | 0.8495781 | 0.3118795 | 0.262489 | 0.16637972 | RC_AA0295 97_at | Bone morphogenetic protein 7 (osteogenic protein 1) |
| 530 | CNS | 0.8491106 | 0.3118793 | 0.262465 | 0.1663110 | AA465553_a t | EST: Aa33g05.r1 NCI_CGAP_GCB1 Homo sapiens cDNA clone IMAGE:815096 5', mRNA sequence. (from Genbank) |
| 531 | CNS | 0.8489354 | 0.3117518 | 0.262405 | 0.16618398 | RC_AA4896 87_at | EST: aa50c11.s1 NCI_CGAP_GCB1 Homo sapiens cDNA clone IMAGE:824372 3', mRNA sequence. (from Genbank) |
| 532 | CNS | 0.848788 | 0.3116835 | 0.262311 | 0.16610803 | R51401_at | Homo sapiens chromosome 19, fosmid 39554 |
| 533 | CNS | 0.84858 | 0.3115251 | 0.26225 | 0.16601504 | RC_AA0695 71_at | Homo sapiens clone 24616 mRNA sequence |
| 534 | CNS | 0.8485167 | 0.3114922 | 0.262184 | 0.16595986 | RC_AA6085 46_at | EST: ac53d06.s1 Stratagene lung carcinoma 937218 Homo sapiens cDNA clone 950603 3', mRNA sequence. (from Genbank) |
| 535 | CNS | 0.8484812 | 0.3114693 | 0.262158 | 0.16591097 | AA471221_a t | EST: PMY2200 KG1-a Lambda Zap Express cDNA library Homo sapiens cDNA 5', mRNA sequence. (from Genbank) |
| 536 | CNS | 0.8481967 | 0.3113906 | 0.262115 | 0.15583134 | S72043_rna 1_at | GIF=growth inhibitory factor [human, brain, Genomic, 2015 nt] |

FIG. 3B2

| | | | | | |
|---|---|---|---|---|---|
| 537 | CNS | 0.8477377 | 0.3113883 | 0.26205 | 0.165799989_at | RC_AA4471 | EST: zw91e01.s1 Soares total fetus Nb2HF8 9w Homo sapiens cDNA clone 784344 3', mRNA sequence. (from Genbank) |
| 538 | CNS | 0.8476792 | 0.311379 | 0.261956 | 0.165749312_at | RC_AA1817 | Homo sapiens TRIAD1 type I mRNA, complete cds |
| 539 | CNS | 0.8473674 | 0.3113439 | 0.261867 | 0.165671860351_M_at-2 | AFFX-HSAC07/X0 | No info for gene |
| 540 | CNS | 0.8473674 | 0.3113068 | 0.261841 | 0.165578190351_M_at | AFFX-HSAC07/X0 | AFFX-HSAC07/X00351_M_at (endogenous control) |
| 541 | CNS | 0.8471552 | 0.3112805 | 0.261841 | 0.165480292_at | RC_AA4559 | EST: aa16g12.s1 Soares NhHMPu S1 Homo sapiens cDNA clone 813478 3', mRNA sequence. (from Genbank) |
| 542 | CNS | 0.8470684 | 0.3110745 | 0.261713 | 0.165462157_at | RC_AA2427 | EST: zr65b05.s1 Soares NhHMPu S1 Homo sapiens cDNA clone 668241 3', mRNA sequence. (from Genbank) |
| 543 | CNS | 0.8468567 | 0.3110506 | 0.261658 | 0.165366984_at | RC_AA5043 | EST: aa61e03.s1 NCI_CGAP_GCB1 Homo sapiens cDNA clone IMAGE:825436 3', mRNA sequence. (from Genbank) |
| 544 | CNS | 0.8463649 | 0.3109135 | 0.261592 | 0.165278820_W26770_at | | EST: 12g4 Human retina cDNA randomly primed sublibrary Homo sapiens cDNA, mRNA sequence. (from Genbank) |
| 545 | CNS | 0.846257 | 0.3108082 | 0.261491 | 0.16516191 H83573_r_at | | Tumor protein D52-like 2 |
| 546 | CNS | 0.8462 | 0.3107384 | 0.261437 | 0.1650961 AA013042_a_t | | EST: zo35d03.r1 Soares retina N2b4HR Homo sapiens cDNA clone 360965 5', mRNA sequence. (from Genbank) |
| 547 | CNS | 0.8455775 | 0.3105439 | 0.261189 | 0.165073368_at | RC_AA0846 | EST: zn20e08.s1 Stratagene neuroepithelium NT2RAMI 937234 Homo sapiens cDNA clone 548006 3', mRNA sequence. (from Genbank) |
| 548 | CNS | 0.8456679 | 0.3105175 | 0.261126 | 0.164979269_s_at | RC_AA4278 | Homo sapiens clone 24703 beta-tubulin mRNA, complete cds |
| 549 | CNS | 0.8455085 | 0.3103857 | 0.261124 | 0.164900596_at | RC_AA2054 | EST: zq66f07.s1 Stratagene neuroepithelium (#937231) Homo sapiens cDNA clone 646597 3', mRNA sequence. (from Genbank) |
| 550 | CNS | 0.8453791 | 0.3103805 | 0.261079 | 0.164859497097_at | | Tetraspan 5 |
| 551 | CNS | 0.8447517 | 0.3102813 | 0.260999 | 0.164750650_at | RC_AA2361 | 3-prime-phosphoadenosine 5-prime-phosphosulfate synthase 1 |
| 552 | CNS | 0.8446667 | 0.3102381 | 0.260894 | 0.164675856_at | RC_AA5986 | EST: ae39h03.s1 Gessler Wilms tumor Homo sapiens cDNA clone 898229 3', mRNA sequence. (from Genbank) |
| 553 | CNS | 0.8454458 | 0.3100374 | 0.260835 | 0.164649231 AA419186_a_t | | EST: zv34f07.r1 Soares ovary tumor NbHOT Homo sapiens cDNA clone 755557 5', mRNA sequence. (from Genbank) |
| 554 | CNS | 0.8442358 | 0.3099558 | 0.260756 | 0.164530231 AA287973_a_t | | Homo sapiens clone 24582 mRNA sequence |

FIG. 3C2

| # | Tissue | | | | ID | Description |
|---|---|---|---|---|---|---|
| 555 | CNS | 0.8441979 | 0.3099062 | 0.26069 | 0.16448729 | AA091017_a_t | EST: yy1646.seq.F Fetal heart, Lambda ZAP Express Homo sapiens cDNA 5', mRNA sequence. (from Genbank) |
| 556 | CNS | 0.8441081 | 0.3098175 | 0.260595 | 0.1644242 | RC_AA4122 51_at | EST: zu10a07.s1 Soares testis NHT Homo sapiens cDNA clone 731412 3', mRNA sequence. (from Genbank) |
| 557 | CNS | 0.8439533 | 0.3096205 | 0.26049 | 0.16439494 | RC_AA1730 80_at | EST: zp21g07.s1 Stratagene neuroepithelium (#937231) Homo sapiens cDNA clone 610140 3', mRNA sequence. (from Genbank) |
| 558 | CNS | 0.8438715 | 0.3094766 | 0.260432 | 0.16430289 | AA478704_a_t | Interleukin 13 receptor, alpha 1 |
| 559 | CNS | 0.8432761 | 0.3094406 | 0.260363 | 0.16416588 | RC_AA3507 29_at | EST: EST58150 Infant brain Homo sapiens cDNA 3' end, mRNA sequence. (from Genbank) |
| 560 | CNS | 0.8428872 | 0.309363 | 0.260262 | 0.16408171 | RC_AA5999 78_s_at | EST: ag28g07.s1 Jia bone marrow stroma Homo sapiens cDNA clone 1090908 3', mRNA sequence. (from Genbank) |
| 561 | CNS | 0.8426119 | 0.3093524 | 0.260262 | 0.16400689 | RC_AA1761 64_f_at | EST: zp23h11.s1 Stratagene neuroepithelium (#937231) Homo sapiens cDNA clone 610341 3', mRNA sequence. (from Genbank) |
| 562 | CNS | 0.8426043 | 0.3091897 | 0.260153 | 0.16390994 | RC_AA6092 13_at | EST: af12f09.s1 Soares testis NHT Homo sapiens cDNA clone 1031465 3', mRNA sequence. (from Genbank) |
| 563 | CNS | 0.8425161 | 0.3090431 | 0.260142 | 0.16384247 | Z68092_s_at | Cell division cycle 25B |
| 564 | CNS | 0.8423365 | 0.3090026 | 0.260069 | 0.16372354 | RC_AA1363 45_at | EST: zn89h06.s1 Stratagene lung carcinoma 937218 Homo sapiens cDNA clone 565403 3', mRNA sequence. (from Genbank) |
| 565 | CNS | 0.8421232 | 0.3089875 | 0.260015 | 0.16364752 | RC_AA1123 61_at | EST: zn68c10.s1 Stratagene HeLa cell s3 937216 Homo sapiens cDNA clone 563346 3', mRNA sequence. (from Genbank) |
| 566 | CNS | 0.8419783 | 0.3088945 | 0.2599965 | 0.1635746 | RC_AA6214 71_at | EST: af92d09.s1 Soares total fetus Nb2HF8 9w Homo sapiens cDNA clone 1055249 3', mRNA sequence. (from Genbank) |
| 567 | CNS | 0.8414637 | 0.3088441 | 0.2599935 | 0.16351797 | T34963_at | Homo sapiens clone 24523 mRNA sequence |
| 568 | CNS | 0.8410502 | 0.3087117 | 0.2599816 | 0.16342008 | AB002324_a_t | Human mRNA for KIAA0326 gene, partial cds |
| 569 | CNS | 0.8408773 | 0.3086928 | 0.2599815 | 0.16336168 | RC_AA4258 79_s_at | EST: zw49e02.s1 Soares total fetus Nb2HF8 9w Homo sapiens cDNA clone 773402 3', mRNA sequence. (from Genbank) |
| 570 | CNS | 0.8408421 | 0.3086294 | 0.2599698 | 0.16328335 | AF005038_a_t | Secretory carrier membrane protein 2 |
| 571 | CNS | 0.8407771 | 0.3085646 | 0.2599674 | 0.16320334 | D86062_s_a t-2 | |
| 572 | CNS | 0.8407771 | 0.3084042 | 0.2599591 | 0.16303906 | D86062_s_a t | Human mRNA for KNP-Ib, complete cds KNP-Ib |
| 573 | CNS | 0.840645 | 0.3083106 | 0.259547 | 0.16299616 | RC_D51172 _at | EST: Human fetal brain cDNA 3' end GEN-015G07, mRNA sequence. (from Genbank) |

FIG. 3D2

| # | Tissue | | | | | Description |
|---|---|---|---|---|---|---|
| 574 | CNS | 0.8401902 | 0.3081848 | 0.259513 | 0.16288611 | R23293_at FK506-binding protein 2 (13kD) |
| 575 | CNS | 0.8400458 | 0.3081639 | 0.259459 | 0.1628367 | RC_AA6001 14_at KIAA0455 gene product |
| 576 | CNS | 0.8396528 | 0.3081607 | 0.259373 | 0.16277693 | RC_AA4549 37_at EST: aa30c07.s1 NCI_CGAP_GCB1 Homo sapiens cDNA clone IMAGE:814764 3', mRNA sequence. (from Genbank) |
| 577 | CNS | 0.839603 | 0.308064 | 0.259277 | 0.16273163 | N23801_at EST: yx36b12.r1 Homo sapiens cDNA clone 263807 5'. (from Genbank) |
| 578 | CNS | 0.8395087 | 0.30796999 | 0.259274 | 0.16263796 | U00802_s_a t Drebrin E |
| 579 | CNS | 0.8390283 | 0.3079161 | 0.259176 | 0.16259329 | RC_AA4418 02_at EST: zw62d04.s1 Soares total fetus Nb2HF8 9w Homo sapiens cDNA clone 774631 3', mRNA sequence. (from Genbank) |
| 580 | CNS | 0.8388993 | 0.3078571 | 0.259159 | 0.16249704 | C01688_s_a t EST: HUMGS0002068, Human Gene Signature, 3'-directed cDNA sequence, mRNA sequence. (from Genbank) |
| 581 | CNS | 0.8388622 | 0.307803 | 0.259141 | 0.16235134 | RC_AA4525 36_at V-ral simian leukemia viral oncogene homolog A (ras related) |
| 582 | CNS | 0.8384658 | 0.3077509 | 0.259122 | 0.16231601 | RC_AA0393 58_at EST: zf05d10.s1 Soares fetal heart NbHH19W Homo sapiens cDNA clone 376051 3', mRNA sequence. (from Genbank) |
| 583 | CNS | 0.8380725 | 0.3077364 | 0.259063 | 0.16226761 | N98799_at EST: yy69n03.r1 Homo sapiens cDNA clone 278837 5' similar to contains element THR repetitive element ;. (from Genbank) |
| 584 | CNS | 0.8379745 | 0.3077118 | 0.258961 | 0.16214316 | R54897_at Untitled |
| 585 | CNS | 0.8377281 | 0.3076383 | 0.258961 | 0.1620365 | AA484997_a t Manic fringe (Drosophila) homolog |
| 586 | CNS | 0.8376226 | 0.3075781 | 0.258925 | 0.16197784 | R69700_at EST: yl45a03.r1 Homo sapiens cDNA clone 142156 5'. (from Genbank) |
| 587 | CNS | 0.8370836 | 0.3075253 | 0.258793 | 0.16196665 | S72422_s_at E2k |
| 588 | CNS | 0.8365548 | 0.3074768 | 0.258715 | 0.16190551 | Y13622_at Latent transforming growth factor beta binding protein 4 |
| 589 | CNS | 0.8365279 | 0.30746443 | 0.258664 | 0.1617889 | W27237_at EST: 24c11 Human retina cDNA randomly primed sublibrary Homo sapiens cDNA, mRNA sequence. (from Genbank) |
| 590 | CNS | 0.8360968 | 0.307357 | 0.258604 | 0.16175145 | RC_AA2838 23_at EST: zs49e08.s1 NCI_CGAP_GCB1 Homo sapiens cDNA clone IMAGE:700838 3', mRNA sequence. (from Genbank) |
| 591 | CNS | 0.8360176 | 0.3073144 | 0.258495 | 0.16170447 | AA426168_a t Homo sapiens mRNA for KIAA0805 protein, partial cds |
| 592 | CNS | 0.8360081 | 0.307299 | 0.258468 | 0.16165869 | RC_AA3572 04_s_at EST: EST65911 Jurkat T-cells I Homo sapiens cDNA 3' end, mRNA sequence. (from Genbank) |
| 593 | CNS | 0.8359247 | 0.3072293 | 0.258425 | 0.16158219 | RC_AA1498 33_at EST: zl47e11.s1 Soares pregnant uterus NbHPU Homo sapiens cDNA clone 505100 3', mRNA sequence. (from Genbank) |
| 594 | CNS | 0.8358825 | 0.3070409 | 0.258409 | 0.16151380 | RC_AA2583 08_at EST: zr60g11.s1 Soares NhHMPu S1 Homo sapiens cDNA clone 667844 3', mRNA sequence. (from Genbank) |

FIG. 3E2

| | | | | | |
|---|---|---|---|---|---|
| 595 | CNS | 0.8352098 | 0.3070316 | 0.258341 | 0.16141116630_at RC_AA2526 | Tankyrase, TRF1-interacting ankyrin-related ADP-ribose polymerase |
| 596 | CNS | 0.8346335 | 0.3069953 | 0.258305 | 0.16132928t AA248283_a | EST: csg2234.seq.F Human fetal heart, Lambda ZAP Express Homo sapiens cDNA 5', mRNA sequence. (from Genbank) |
| 597 | CNS | 0.8335921 | 0.3067779 | 0.258263 | 0.16132928t D83883_s_a | Human tip associating protein (TAP) mRNA, complete cds |
| 598 | CNS | 0.8334558 | 0.3067616 | 0.258238 | 0.16112344t AA096491_a | EST: k0190.seq.F Fetal heart, Lambda ZAP Express Homo sapiens cDNA 5', mRNA sequence. (from Genbank) |
| 599 | CNS | 0.8333895 | 0.3066787 | 0.258063 | 0.16120675t AA437171_a | Homo sapiens transcriptional regulatory protein p54 mRNA, complete cds |
| 600 | CNS | 0.8325222 | 0.3065542 | 0.258037 | 0.16111238 T34752_s_at | EST: EST74662 Homo sapiens cDNA 5' end similar to None. (from Genbank) |
| 601 | CNS | 0.8325188 | 0.3065297 | 0.258015 | 0.160962461 H43286_s_a | Gamma-aminobutyric acid (GABA) B receptor, 1 |
| 602 | CNS | 0.8324813 | 0.3064551 | 0.257811 | 0.16087097_at AA259021_s | EST: zs33b03.r1 NCI_CGAP_GCB1 Homo sapiens cDNA clone IMAGE:686957 5', mRNA sequence. (from Genbank) |
| 603 | CNS | 0.8323581 | 0.3062807 | 0.257705 | 0.1608120500_at RC_AA2529 | EST: zr76f01.s1 Soares NhHMPu S1 Homo sapiens cDNA clone 669337 3', mRNA sequence. (from Genbank) |
| 604 | CNS | 0.8323335 | 0.3062381 | 0.257639 | 0.1608087385_at RC_AA2353 | EST: zt30h10.s1 Soares ovary tumor NbHOT Homo sapiens cDNA clone 723907 3', mRNA sequence. (from Genbank) |
| 605 | CNS | 0.8321369 | 0.3062159 | 0.257631 | 0.1607354404_s_at RC_AA2801 | EST: zt05h09.s1 NCI_CGAP_GCB1 Homo sapiens cDNA clone IMAGE:712289 3', mRNA sequence. (from Genbank) |
| 606 | CNS | 0.8317393 | 0.3061822 | 0.257606 | 0.16054262 Y12478_at | CHD5 protein |
| 607 | CNS | 0.8317165 | 0.3061796 | 0.257581 | 0.16043402t AA379742_a | EST: EST92623 Skin tumor I Homo sapiens cDNA 5' end, mRNA sequence. (from Genbank) |
| 608 | CNS | 0.8306666 | 0.3060078 | 0.257496 | 0.16035496 W44681_at | Zc29g11.r1 Soares senescent fibroblasts NbHSF Homo sapiens cDNA clone 323780 5', mRNA sequence. (from Genbank) |
| 609 | CNS | 0.8306291 | 0.3059836 | 0.257404 | 0.16033968 W03008_at | EST: ze02h03.r1 Soares melanocyte 2NbHM Homo sapiens cDNA clone 291413 5' similar to PIR:S33957 S33957 coat protein gamma-COP - bovine.; mRNA sequence. (from Genbank) |
| 610 | CNS | 0.8305032 | 0.3059652 | 0.257391 | 0.1603174 W80658_at | EST: zd82b12.r1 Soares fetal heart NbHH19W Homo sapiens cDNA clone 347135 5', mRNA sequence. (from Genbank) |
| 611 | CNS | 0.8304488 | 0.3058153 | 0.257739 | 0.16031574t H89133_s_a | KIAA0618 gene product |
| 612 | CNS | 0.8303629 | 0.305801 | 0.257313 | 0.16021173 R51809_at | EST: yg77g09.r1 Homo sapiens cDNA clone 39567 5'. (from Genbank) |
| 613 | CNS | 0.830255 | 0.3057611 | 0.257306 | 0.16008936 RC_D52154_s_at | Iduronate 2-sulfatase (Hunter syndrome) |

FIG. 3172

| | | | | | | |
|---|---|---|---|---|---|---|
| 614 | CNS | 0.8298565 | 0.3057225 | 0.257296 | 0.15999512 | RC_AA0791 35_at | EST: zm98f06.s1 Stratagene colon HT29 (#937221) Homo sapiens cDNA clone 545987 3', mRNA sequence. (from Genbank) |
| 615 | CNS | 0.829702 | 0.3055946 | 0.257213 | 0.15995744 | RC_AA6001 40_at | Deleted in oral cancer-1 |
| 616 | CNS | 0.8290605 | 0.3055408 | 0.256933 | 0.15990305 | AA095812_a t | Density-regulated protein |
| 617 | CNS | 0.8290556 | 0.3054445 | 0.256876 | 0.15990305 | RC_AA2329 42_at | EST: zr46e02.s1 Soares NhHMPu S1 Homo sapiens cDNA clone 666458 3' similar to contains element L1 repetitive element :, mRNA sequence. (from Genbank) |
| 618 | CNS | 0.8289711 | 0.3053838 | 0.256852 | 0.15977687 | T31862_at | EST: EST40163 Homo sapiens cDNA 5' end similar to None. (from Genbank) |
| 619 | CNS | 0.8289131 | 0.3050947 | 0.256769 | 0.15974285 | AB002313_a t | Human mRNA for KIAA0315 gene, partial cds |
| 620 | CNS | 0.8286154 | 0.3050558 | 0.256741 | 0.15964518 | RC_AA3985 22_at | EST: zt47d11.s1 Soares ovary tumor NbHOT Homo sapiens cDNA clone 725493 3', mRNA sequence. (from Genbank) |
| 621 | CNS | 0.8286033 | 0.3049647 | 0.256714 | 0.15957911 | W26984_at | Calmodulin 1 (phosphorylase kinase, delta) |
| 622 | CNS | 0.8286032 | 0.3049378 | 0.256682 | 0.15943897 | AFFX-HUMGAPDH/M33197_5_at | AFFX-HUMGAPDH/M33197_5_at (endogenous control) |
| 623 | CNS | 0.8286032 | 0.3049011 | 0.256651 | 0.159379 | AFFX-HUMGAPDH/M33197_5_at-2 | Glyceraldehyde-3-phosphate dehydrogenase |
| 624 | CNS | 0.8283285 | 0.3047462 | 0.256591 | 0.15929787 | AA033543_a t | Homo sapiens Chromosome 16 BAC clone CIT987SK-A-69G12 |
| 625 | CNS | 0.8281773 | 0.3046939 | 0.256558 | 0.15922712 | RC_AA4560 73_at | Human amino acid transport-related protein mRNA, complete cds |
| 626 | CNS | 0.8281543 | 0.3046188 | 0.256551 | 0.15922263 | R83496_at | EST: yp15c07.r1 Homo sapiens cDNA clone 187500 5'. (from Genbank) |
| 627 | CNS | 0.8280532 | 0.3045814 | 0.256515 | 0.15915386 | RC_AA0355 46_at | EST: ze24c07.s1 Soares fetal heart NbHH19W Homo sapiens cDNA clone 359916 3', mRNA sequence. (from Genbank) |
| 628 | CNS | 0.8279582 | 0.3044593 | 0.256404 | 0.15907359 | RC_AA0708 62_at | EST: zn58c10.s1 Stratagene fibroblast (#937212) Homo sapiens cDNA clone 529842 3' similar to TR:G998813 G998813 TIF1. [1] ;, mRNA sequence. (from Genbank) |
| 629 | CNS | 0.8279355 | 0.3043807 | 0.256362 | 0.15899748 | W69964_at | Homo sapiens mRNA, chromosome 1 specific transcript KIAA0495 |
| 630 | CNS | 0.8278584 | 0.3043257 | 0.256346 | 0.15890592 | L11373_at | Protocadherin 43 mRNA for abbreviated PC43 |

FIG. 3G2

| | | | | | |
|---|---|---|---|---|---|
| 631 | CNS | 0.8275738 | 0.3043096 | 0.256312 | 0.15886128 | RC_AA2325 49_i_at | EST: zr24c06.s1 Stratagene NT2 neuronal precursor 937230 Homo sapiens cDNA clone 664330 3', mRNA sequence. (from Genbank) |
| 632 | CNS | 0.8273299 | 0.3042676 | 0.256253 | 0.15877318 | R80333_at | EST: yj96b06.r1 Homo sapiens cDNA clone 147059 5'. (from Genbank) |
| 633 | CNS | 0.8269027 | 0.3042376 | 0.256251 | 0.15862796 | RC_AA4285 94_at | EST: zw75g12.s1 Soares testis NHT Homo sapiens cDNA clone 782086 3', mRNA sequence. (from Genbank) |
| 634 | CNS | 0.8267392 | 0.3042368 | 0.256119 | 0.15855484 | AA149543_a t | EST: zl28g06.r1 Soares pregnant uterus NbHPU Homo sapiens cDNA clone 503290 5', mRNA sequence. (from Genbank) |
| 635 | CNS | 0.8263632 | 0.3039806 | 0.256093 | 0.15850711 | RC_AA2924 27_s_at | EST: zt28g07.s1 Soares ovary tumor NbHOT Homo sapiens cDNA clone 714492 3' similar to TR:E91187 E91187 NMDA RECEPTOR GLUTAMATE-BINDING SUBUNIT.;, mRNA sequence. (from Genbank) |
| 636 | CNS | 0.8261754 | 0.3037881 | 0.256087 | 0.15847576 | D82534_at | Homo sapiens clone 23765 mRNA sequence |
| 637 | CNS | 0.8261409 | 0.3037502 | 0.25607 | 0.158348 | R15268_at | EST: yf89f02.r1 Homo sapiens cDNA clone 29665 5'. (from Genbank) |
| 638 | CNS | 0.8259348 | 0.3034252 | 0.256001 | 0.15829577 | AA256355_a t | EST: zr80b02.r1 Soares NhHMPu S1 Homo sapiens cDNA clone 681963 5', mRNA sequence. (from Genbank) |
| 639 | CNS | 0.825903 | 0.3033613 | 0.255951 | 0.15825278 | RC_AA0260 54_at | EST: ze86b05.s1 Soares fetal heart NbHH19W Homo sapiens cDNA clone 365841 3', mRNA sequence. (from Genbank) |
| 640 | CNS | 0.8257268 | 0.3032471 | 0.255938 | 0.15816386 | RC_AA1483 18_s_at | Human mRNA for KIAA0069 gene, partial cds |
| 641 | CNS | 0.8255546 | 0.3031608 | 0.255883 | 0.15812258 | RC_AA4217 89_at | EST: zu26e07.s1 Soares ovary tumor NbHOT Homo sapiens cDNA clone 739140 3', mRNA sequence. (from Genbank) |
| 642 | CNS | 0.8254309 | 0.3030926 | 0.255796 | 0.15805726 | RC_AA4259 43_at | Acyl-Coenzyme A dehydrogenase, very long chain |
| 643 | CNS | 0.8253813 | 0.3030733 | 0.255702 | 0.15801959 | W26589_at | EST: 33d9 Human retina cDNA randomly primed sublibrary Homo sapiens cDNA, mRNA sequence. (from Genbank) |
| 644 | CNS | 0.8252641 | 0.3030448 | 0.255632 | 0.15787694 | RC_AA4820 77_at | EST: zv43d08.s1 Soares ovary tumor NbHOT Homo sapiens cDNA clone 756399 3', mRNA sequence. (from Genbank) |
| 645 | CNS | 0.8250298 | 0.3030217 | 0.255574 | 0.15780035 | RC_AA4314 82_s_at | Homo sapiens mRNA for KIAA0465 protein, partial cds |
| 646 | CNS | 0.8249951 | 0.302834 | 0.255532 | 0.15772638 | RC_AA4548 53_at | EST: zx79e11.s1 Soares ovary tumor NbHOT Homo sapiens cDNA clone 809996 3', mRNA sequence. (from Genbank) |
| 647 | CNS | 0.8241409 | 0.3028197 | 0.255446 | 0.15759073 | H29992_at | EST: yp44g05.r1 Homo sapiens cDNA clone 190328 5'. (from Genbank) |
| 648 | CNS | 0.8240151 | 0.3027892 | 0.255333 | 0.15747163 | D45278_at | EST: Human brain cDNA, mRNA sequence. (from Genbank) |
| 649 | CNS | 0.8239818 | 0.3026509 | 0.255147 | 0.15740249 | RC_AA4959 63_at | EST: zw06b08.s1 Soares NhHMPu S1 Homo sapiens cDNA clone 768471 3', mRNA sequence. (from Genbank) |

FIG. 3H2

| | | | | | | |
|---|---|---|---|---|---|---|
| 650 | CNS | 0.823882 | 0.3025819 | 0.255044 | RC_AA4777_at | Breakpoint cluster region protein, uterine leiomyoma, 1; barrier to autointegration factor |
| 651 | CNS | 0.8238664 | 0.3025027 | 0.254904 | 0.15737307 L20814_at | GRIA2 Glutamate receptor, ionotropic, AMPA 2 |
| 652 | CNS | 0.8238664 | 0.3024769 | 0.254869 | 0.15728155 L20814_at-2 | Glutamate receptor, ionotropic, AMPA 2 |
| 653 | CNS | 0.8238363 | 0.3023984 | 0.254841 | 0.15722528 T30687_s_at | Human PDGF associated protein mRNA, complete cds |
| 654 | CNS | 0.8234683 | 0.3023061 | 0.254837 | 0.15714197 AA046865_a t | EST: zf12b09.r1 Soares fetal heart NbHH19W Homo sapiens cDNA clone 376697 5', mRNA sequence. (from Genbank) |
| 655 | CNS | 0.823076 | 0.3021786 | 0.254755 | 0.15704006 RC_AA3507 96_at | EST: EST58251 Infant brain Homo sapiens cDNA 3' end, mRNA sequence. (from Genbank) |
| 656 | CNS | 0.8227399 | 0.3021742 | 0.254625 | 0.15699892 L13435_at | Human chromosome 3p21.1 gene sequence |
| 657 | CNS | 0.8226515 | 0.3021401 | 0.254621 | 0.1568895 M60346_s_a t | ATPase, H+ transporting, lysosomal (vacuolar proton pump), beta polypeptide, 56/58kD, isoform 2 |
| 658 | CNS | 0.8225755 | 0.3020018 | 0.254592 | 0.15687397 R77159_at | EST: yi65a07.r1 Homo sapiens cDNA clone 144084 5'. (from Genbank) |
| 659 | CNS | 0.8224721 | 0.3019881 | 0.254545 | 0.156817 R87373_s_a t | Iduronate 2-sulfatase (Hunter syndrome) |
| 660 | CNS | 0.8224141 | 0.3019762 | 0.254505 | 0.15674943 AB002374_a t | Human mRNA for KIAA0376 gene, partial cds |
| 661 | CNS | 0.8220636 | 0.3018619 | 0.254256 | 0.15667441 RC_AA4784 _at | Cathepsin F |
| 662 | CNS | 0.8220327 | 0.3018507 | 0.254219 | 0.15665807 RC_AA4854 43_at | Homo sapiens hypothetical SBBI03 protein mRNA, complete cds |
| 663 | CNS | 0.8220047 | 0.30158831 | 0.254202 | 0.1565604 AA147144_a t | Zo32c06.r1 Stratagene colon (#937204) Homo sapiens cDNA clone 588586 5' similar to WP:C14B1.4 CE00901 GUANINE NUCLEOTIDE BINDING PROTEIN :; mRNA sequence. (from Genbank) |
| 664 | CNS | 0.8219892 | 0.301553 | 0.254415 | 0.15649949 RC_AA4029 84_at | EST: zu55b08.s1 Soares ovary tumor NbHOT Homo sapiens cDNA clone 741879 3', mRNA sequence. (from Genbank) |
| 665 | CNS | 0.821766 | 0.301447 | 0.254016 | 0.15643784 N36619_at | EST: yx98c08.r1 Homo sapiens cDNA clone 268814 5'. (from Genbank) |
| 666 | CNS | 0.8213825 | 0.30144454 | 0.254002 | 0.15631226 N27670_at | Homo sapiens mRNA for putative progesterone binding protein |
| 667 | CNS | 0.8213707 | 0.30141148 | 0.253988 | 0.15627375 RC_AA0564 _at | EST: zl69d05.s1 Stratagene colon (#937204) Homo sapiens cDNA clone 509865 3', mRNA sequence. (from Genbank) |
| 668 | CNS | 0.821304 | 0.3013967 | 0.2539 | 0.15619285 AA046768_a t | Homo sapiens clone TUA8 Cri-du-chat region mRNA |
| 669 | CNS | 0.8212514 | 0.3013807 | 0.253736 | 0.15610074 AA490648_a t | Aa01g06.r1 Soares NhHMPu S1 Homo sapiens cDNA clone 812026 5', mRNA sequence. (from Genbank) |
| 670 | CNS | 0.8212333 | 0.3012483 | 0.253577 | 0.15602048 RC_AA5990 37_s_at | SWI/SNF related, matrix associated, actin dependent regulator of chromatin, subfamily a, member 5 |

FIG. 312

| # | Tissue | | | | ID | Description |
|---|---|---|---|---|---|---|
| 671 | CNS | 0.821083 | 0.3012019 | 0.253545 | 0.15594865 | RC_AA4881 66_s_at | EST: ad08b01.s1 Soares NbHFB Homo sapiens cDNA clone 877609 3', mRNA sequence. (from Genbank) |
| 672 | CNS | 0.8208385 | 0.3011568 | 0.253524 | 0.1558727 | RC_D60296_at | EST: Human fetal brain cDNA 3'-end GEN-097D06, mRNA sequence. (from Genbank) |
| 673 | CNS | 0.8204764 | 0.3010707 | 0.253456 | 0.15580075 | RC_AA0226 15_at | EST: ze72h10.s1 Soares fetal heart NbHH19W Homo sapiens cDNA clone 364579 3', mRNA sequence. (from Genbank) |
| 674 | CNS | 0.8203406 | 0.3009537 | 0.253417 | 0.15573676 | RC_AA1477 19_at | EST: zo44b06.s1 Stratagene endothelial cell 937223 Homo sapiens cDNA clone 589715 3', mRNA sequence. (from Genbank) |
| 675 | CNS | 0.82015 | 0.3008483 | 0.253315 | 0.15566185 | RC_AA4282 04_at | EST: zw51c11.s1 Soares total fetus Nb2HF8 9w Homo sapiens cDNA clone 773588 3', mRNA sequence. (from Genbank) |
| 676 | CNS | 0.8199686 | 0.3007678 | 0.253241 | 0.15553867 | W38663_at | Galactokinase 1 |
| 677 | CNS | 0.8198898 | 0.3007077 | 0.253157 | 0.15551578 | RC_AA0434 48_at | EST: zk54a10.s1 Soares pregnant uterus NbHPU Homo sapiens cDNA clone 486618 3', mRNA sequence. (from Genbank) |
| 678 | CNS | 0.8196563 | 0.3006394 | 0.253157 | 0.15549669 | RC_AA4045 43_at | EST: zw37h03.s1 Soares total fetus Nb2HF8 9w Homo sapiens cDNA clone 772277 3', mRNA sequence. (from Genbank) |
| 679 | CNS | 0.8194774 | 0.3006275 | 0.253109 | 0.15542647 | RC_AA2580 68_at | EST: zs76d12.s1 NCI_CGAP_GCB1 Homo sapiens cDNA clone IMAGE:703415 3' similar to contains MER28.t1 MER28 repetitive element;, mRNA sequence. (from Genbank) |
| 680 | CNS | 0.8193989 | 0.3004805 | 0.253104 | 0.1553556 | H19063_at | EST: yn51b01.r1 Homo sapiens cDNA clone 171913 5'. (from Genbank) |
| 681 | CNS | 0.8193691 | 0.3004341 | 0.253047 | 0.15529554 | RC_AA4881 77_at | EST: ad08c03.s1 Soares NbHFB Homo sapiens cDNA clone 877636 3', mRNA sequence. (from Genbank) |
| 682 | CNS | 0.8188886 | 0.3003271 | 0.25297 | 0.15524507 | AA436102_a t | EST: zu03b11.r1 Soares testis NHT Homo sapiens cDNA clone 730749 5', mRNA sequence. (from Genbank) |
| 683 | CNS | 0.8188499 | 0.3002946 | 0.252903 | 0.15521008 | RC_AA4958 03_at | EST: zw05b10.s1 Soares NhHMPu S1 Homo sapiens cDNA clone 768379 3', mRNA sequence. (from Genbank) |
| 684 | CNS | 0.8187499 | 0.3002751 | 0.252865 | 0.15511067 | R82229_at | Homo sapiens clone 23956 mRNA, partial cds |
| 685 | CNS | 0.8186795 | 0.3000532 | 0.252771 | 0.15503395 | RC_AA4525 51_at | EST: zx35f06.s1 Soares total fetus Nb2HF8 9w Homo sapiens cDNA clone 788483 3', mRNA sequence. (from Genbank) |
| 686 | CNS | 0.8186256 | 0.30004451 | 0.252765 | 0.15492807 | RC_AA4497 73_at | EST: zx07h07.s1 Soares total fetus Nb2HF8 9w Homo sapiens cDNA clone 785821 3', mRNA sequence. (from Genbank) |
| 687 | CNS | 0.8185136 | 0.2995589 | 0.252719 | 0.1549017 | RC_AA4302 08_at | EST: zw59e02.s1 Soares total fetus Nb2HF8 9w Homo sapiens cDNA clone 774362 3', mRNA sequence. (from Genbank) |
| 688 | CNS | 0.8184393 | 0.2998772 | 0.252638 | 0.15483402 | AA127605_a t | Homo sapiens mRNA for KIAA0829 protein, partial cds |
| 689 | CNS | 0.8181421 | 0.2998648 | 0.252551 | 0.15480909 | D31134_at | EST: Human fetal-lung cDNA 5'-end sequence, mRNA sequence. (from Genbank) |
| 690 | CNS | 0.8175545 | 0.2998346 | 0.252538 | 0.15472803 | RC_AA0695 49_at | EST: zm52e03.s1 Stratagene fibroblast (#937212) Homo sapiens cDNA clone 529276 3', mRNA sequence. (from Genbank) |

FIG. 3J2

| | | | | | | |
|---|---|---|---|---|---|---|
| 691 | CNS | 0.817362 | 0.2998277 | 0.252479 | 0.15468344 04_f_at | RC_AA4121 | EST: zt69a05.s1 Soares testis NHT Homo sapiens cDNA clone 727568 3', mRNA sequence. (from Genbank) |
| 692 | CNS | 0.8171154 | 0.2997645 | 0.252342 | 0.15458314 295636_at | | H.sapiens mRNA for laminin alpha 5 chain |
| 693 | CNS | 0.817001 | 0.2993721 | 0.252311 | 0.15454395 H60501_at | | EST: yr42g01.r1 Homo sapiens cDNA clone 207984 5'. (from Genbank) |
| 694 | CNS | 0.8166563 | 0.2993583 | 0.252271 | 0.15448625 AA313653_a t | | EST: EST185526 Colon carcinoma (HCC) cell line Homo sapiens cDNA 5' end, mRNA sequence. (from Genbank) |
| 695 | CNS | 0.8165445 | 0.2992305 | 0.252208 | 0.15435196 41_at | RC_AA4438 | Homo sapiens Sprouty 2 (SPRY2) mRNA, complete cds |
| 696 | CNS | 0.8165259 | 0.2990672 | 0.252125 | 0.15427282 W76399_at | | EST: zd66d05.r1 Soares fetal heart NbHH19W Homo sapiens cDNA clone 345609 5' similar to SW:A33_PLEWA Q02084 ZINC-BINDING PROTEIN A33. [1] ;. mRNA sequence. (from Genbank) |
| 697 | CNS | 0.8162547 | 0.2990464 | 0.252058 | 0.15425204 S76942_s_at 2 | | Dopamine receptor D4 |
| 698 | CNS | 0.8162547 | 0.2989794 | 0.252013 | 0.15419286 S76942_s_at | | Dopamine D4 receptor {exon 1} [human, brain tumor tissue, mRNA Partial Mutant, 386 nt] |
| 699 | CNS | 0.8162507 | 0.2988867 | 0.251922 | 0.15403028 97_at | RC_AA2793 | EST: zs85d04.s1 NCI_CGAP_GCB1 Homo sapiens cDNA clone IMAGE:704263 3', mRNA sequence. (from Genbank) |
| 700 | CNS | 0.8161736 | 0.2987502 | 0.251853 | 0.15400504 R01949_at | | Homo sapiens mRNA for KIAA0855 protein, partial cds |
| 701 | CNS | 0.8159177 | 0.2987489 | 0.251826 | 0.153949 04_i_at | RC_AA4766 | EST: zx03d08.s1 Soares total fetus Nb2HF8 9w Homo sapiens cDNA clone 785391 3', mRNA sequence. (from Genbank) |
| 702 | CNS | 0.8156514 | 0.2986366 | 0.251785 | 0.15392488 AA091467_s _at | | Homo sapiens CAGH1a (CAGH1) mRNA, partial cds |
| 703 | CNS | 0.8156021 | 0.298605 | 0.251733 | 0.153819 L44334_at | | EST: Homo sapiens thymus mRNA (randomly primed, normalized), single-pass sequence. mRNA sequence. (from Genbank) |
| 704 | CNS | 0.8154852 | 0.2985106 | 0.251703 | 0.15376309 AA316036_a t | | CASP8 and FADD-like apoptosis regulator |
| 705 | CNS | 0.8154646 | 0.2984948 | 0.251622 | 0.15371522 AA442054_s _at | | Phospholipase C, gamma 1 (formerly subtype 148) |
| 706 | CNS | 0.8148758 | 0.2983965 | 0.251537 | 0.15365468 N46577_at | | EST: yy48b04.r1 Homo sapiens cDNA clone 276751 5'. (from Genbank) |
| 707 | CNS | 0.814853 | 0.2983666 | 0.25151 | 0.15354574 AA094999_a t | | Homo sapiens zinc finger protein 216 splice variant 2 (ZNF216) mRNA, complete cds |
| 708 | CNS | 0.8147036 | 0.2983133 | 0.25149 | 0.15349714 AA459189_s _at | | EST: zx88g08.r1 Soares ovary tumor NbHOT Homo sapiens cDNA clone 810878 5', mRNA sequence. (from Genbank) |
| 709 | CNS | 0.8145073 | 0.2982905 | 0.251426 | 0.15345654 38_at | RC_AA3985 | EST: zt73c02.s1 Soares testis NHT Homo sapiens cDNA clone 727970 3', mRNA sequence. (from Genbank) |
| 710 | CNS | 0.8144894 | 0.298214 | 0.251287 | 0.15338401 AA454214_a t | | Homo sapiens clone 23631 mRNA sequence |

FIG. 3K2

| | | | | | |
|---|---|---|---|---|---|
| 711 | CNS | 0.8144709 | 0.2981073 | 0.251261 | 0.1533421 | AA447349_a t | EST: zw93g08.r1 Soares total fetus Nb2HF8 9w Homo sapiens cDNA clone 784574 5', mRNA sequence. (from Genbank) |
| 712 | CNS | 0.8144354 | 0.298103 | 0.251176 | 0.15333316 | RC_AA0636 18_at | EST: ze87g04.s1 Soares fetal heart NbHH19W Homo sapiens cDNA clone 366006 3', mRNA sequence. (from Genbank) |
| 713 | CNS | 0.8140076 | 0.2980999 | 0.251103 | 0.15325634 | RC_AA1581 62_at | EST: zo55h11.s1 Stratagene pancreas (#937208) Homo sapiens cDNA clone 590853 3', mRNA sequence. (from Genbank) |
| 714 | CNS | 0.8139586 | 0.2980237 | 0.250998 | 0.15316522 | RC_AA6203 55_at | EST: af07d01.s1 Soares testis NHT Homo sapiens cDNA clone 1030945 3', mRNA sequence. (from Genbank) |
| 715 | CNS | 0.8136003 | 0.2979746 | 0.250928 | 0.15304327 | AA291444_a t | Novel centrosomal protein RanBPM |
| 716 | CNS | 0.8135234 | 0.2979568 | 0.250879 | 0.15300635 | AB002306_a t | Human mRNA for KIAA0308 gene, partial cds |
| 717 | CNS | 0.8133059 | 0.2978435 | 0.250846 | 0.15295824 | AA449376_a t | EST: zx04c11.r1 Soares total fetus Nb2HF8 9w Homo sapiens cDNA clone 785492 5', mRNA sequence. (from Genbank) |
| 718 | CNS | 0.8131968 | 0.2977865 | 0.250795 | 0.15286915 | W72770_s_ at | EST: zd77c10.r1 Soares fetal heart NbHH19W Homo sapiens cDNA clone 346674 5', mRNA sequence. (from Genbank) |
| 719 | CNS | 0.8131241 | 0.2976297 | 0.250746 | 0.15279359 | U32169_rna 2_s_at | Collagen, type XI, alpha 2 |
| 720 | CNS | 0.8130422 | 0.2975648 | 0.250619 | 0.15276536 | RC_AA2831 80_at | EST: zt17c12.s1 Soares ovary tumor NbHOT Homo sapiens cDNA clone 713398 3', mRNA sequence. (from Genbank) |
| 721 | CNS | 0.8126917 | 0.2974907 | 0.250572 | 0.15275177 | RC_AA4358 99_at | Homo sapiens mRNA for KIAA0462 protein, partial cds |
| 722 | CNS | 0.8126193 | 0.2974826 | 0.250566 | 0.15271162 | RC_AA6096 14_at | EST: af15f12.s1 Soares testis NHT Homo sapiens cDNA clone 1031759 3', mRNA sequence. (from Genbank) |
| 723 | CNS | 0.8125814 | 0.2973941 | 0.250559 | | RC_AA0820 57_at | EST: zn21f01.s1 Stratagene neuroepithelium NT2RAMI 937234 Homo sapiens cDNA clone 548089 3', mRNA sequence. (from Genbank) |
| 724 | CNS | 0.8120902 | 0.2973632 | 0.250516 | 0.15253317 | RC_AA5984 41_at | EST: ae48f01.s1 Stratagene lung carcinoma 937218 Homo sapiens cDNA clone 950137 3', mRNA sequence. (from Genbank) |
| 725 | CNS | 0.81174 | 0.2973608 | 0.25051 | 0.15245025 | RC_D60608 _at | EST: Human fetal brain cDNA 3'-end GEN-120A10, mRNA sequence. (from Genbank) |
| 726 | CNS | 0.8112771 | 0.2972956 | 0.250432 | 0.15242274 | RC_AA2871 04_at | Homo sapiens mRNA for PRP8 protein, complete cds |
| 727 | CNS | 0.8109133 | 0.2972147 | 0.250361 | 0.15242274 | AA486831_s _at | KIAA0618 gene product |
| 728 | CNS | 0.8108686 | 0.2968683 | 0.250225 | 0.15227762 | RC_AA4494 19_at | EST: zx05b03.s1 Soares total fetus Nb2HF8 9w Homo sapiens cDNA clone 785549 3', mRNA sequence. (from Genbank) |

FIG. 3L2

| | | | | | |
|---|---|---|---|---|---|
| 729 CNS | 0.8108075 | 0.2968556 | 0.250212 | 0.152163 W24319_at | EST: zb81b11.r1 Soares senescent fibroblasts NbHSF Homo sapiens cDNA clone 309981 5', mRNA sequence. (from Genbank) |
| 730 CNS | 0.8106909 | 0.2968284 | 0.250197 | 0.15214102 RC_C21123_at | EST: HUMGS0002071, Human Gene Signature, 3'-directed cDNA sequence, mRNA sequence. (from Genbank) |
| 731 CNS | 0.8103234 | 0.2968175 | 0.25017 | 0.15206029 W79850_at | EST: zd75e07.r1 Soares fetal heart NbHH19W Homo sapiens cDNA clone 346500 5', mRNA sequence. (from Genbank) |
| 732 CNS | 0.8099455 | 0.2968099 | 0.250136 | 0.15205514 RC_AA1327 46_at | EST: zo21a03.s1 Stratagene colon (#937204) Homo sapiens cDNA clone 587500 3', mRNA sequence. (from Genbank) |
| 733 CNS | 0.8098899 | 0.296799 | 0.250134 | 0.15197249 RC_AA4060 56_at | Homo sapiens CAGH32 mRNA, partial cds |
| 734 CNS | 0.8098409 | 0.2967913 | 0.250019 | 0.1519263 RC_D59316_f_at | EST: Human fetal brain cDNA 3'-end GEN-014B03, mRNA sequence. (from Genbank) |
| 735 CNS | 0.809783 | 0.2967666 | 0.249945 | 0.15189499 M57399_at | PTN Pleiotrophin (heparin binding growth factor 8, neurite growth-promoting factor 1) |
| 736 CNS | 0.8095502 | 0.2966725 | 0.249794 | 0.151788 AA135328_s_at | EST: zo28e00.r1 Stratagene colon (#937204) Homo sapiens cDNA clone 588230 5', mRNA sequence. (from Genbank) |
| 737 CNS | 0.8093398 | 0.2966647 | 0.249761 | 0.1517824 M63379_at | CLU Clusterin (complement lysis inhibitor; testosterone-repressed prostate message 2; apolipoprotein J) |
| 738 CNS | 0.8092362 | 0.2962177 | 0.249673 | 0.15174271 H44269_at | EST: yp17b05.r1 Homo sapiens cDNA clone 187665 5' similar to contains Alu repetitive element; (from Genbank) |
| 739 CNS | 0.8092039 | 0.2962093 | 0.249655 | 0.15173368 RC_AA4486 55_at | H.sapiens mRNA for RP3 gene |
| 740 CNS | 0.8091561 | 0.2960731 | 0.249597 | 0.15165432 Z11584_s_at | H.sapiens NuMA gene (Clone T33) |
| 741 CNS | 0.809099 | 0.2959747 | 0.249574 | 0.15157907 RC_AA4500 78_at | EST: zx42a07.s1 Soares total fetus Nb2HF8 9w Homo sapiens cDNA clone 789108 3', mRNA sequence. (from Genbank) |
| 742 CNS | 0.8089281 | 0.2959734 | 0.249558 | 0.1515625 AA058376_a_t | Sjogren syndrome antigen A2 (60kD, ribonucleoprotein autoantigen SS-A/Ro) |
| 743 CNS | 0.8088711 | 0.2959734 | 0.249555 | 0.1514404 AA251693_a_t | EST: zs04a09.r1 NCI_CGAP_GCB1 Homo sapiens cDNA clone IMAGE:684184 5', mRNA sequence. (from Genbank) |
| 744 CNS | 0.8088388 | 0.2958687 | 0.249495 | 0.1513642 RC_AA4501 18_at | EST: zx42e09.s1 Soares total fetus Nb2HF8 9w Homo sapiens cDNA clone 789160 3', mRNA sequence. (from Genbank) |
| 745 CNS | 0.8086565 | 0.2958662 | 0.249449 | 0.15125836 RC_AA2624 85_at | EST: zs17h07.s1 NCI_CGAP_GCB1 Homo sapiens cDNA clone IMAGE:685501 3', mRNA sequence. (from Genbank) |
| 746 CNS | 0.8085643 | 0.2958061 | 0.24936 | 0.15118259 AA307471_a_t | Homo sapiens Chromosome 16 BAC clone CIT987SK-A-152E5 |
| 747 CNS | 0.8084993 | 0.2957328 | 0.249333 | 0.15110232 T95813_f_at | Karyopherin alpha 4 (importin alpha 3) |
| 748 CNS | 0.8084518 | 0.2956044 | 0.249305 | 0.15103455 RC_AA2339 24_at | EST: zr49e08.s1 Soares NhHMPu S1 Homo sapiens cDNA clone 666758 3', mRNA sequence. (from Genbank) |

FIG. 3M2

| # | Tissue | | | | Accession | Description |
|---|---|---|---|---|---|---|
| | | | | | AB002349_a | KIAA0351 gene product |
| 749 | CNS | 0.808348 | 0.249267 | 0.1509965 | t | |
| 750 | CNS | 0.8081766 | 0.29557 | 0.15093213 | H91564_at | EST: yw29b04.r1 Homo sapiens cDNA clone 253615 5'. (from Genbank) |
| 751 | CNS | 0.808082 | 0.29555176 | 0.15086646 | AA249175_a | EST: hfe0150.seq.F Human fetal heart, Lambda ZAP Express Homo sapiens cDNA 5', mRNA sequence. (from Genbank) |
| 752 | CNS | 0.8078888 | 0.2953989 | 0.15077727 | RC_AA1017 | EST: zk96e11.s1 Soares pregnant uterus NbHPU Homo sapiens cDNA clone 490700 3', mRNA sequence. (from Genbank) |
| 753 | CNS | 0.8075836 | 0.2953879 | 0.15074073 | H06982_at | TRANSCRIPTION INITIATION FACTOR IIE, ALPHA SUBUNIT |
| 754 | CNS | 0.8075659 | 0.2953691 | 0.15064792 | RC_AA4210 52_at | Homo sapiens branched chain alpha-ketoacid dehydrogenase kinase precursor, mRNA, nuclear gene encoding mitochondrial protein, complete cds |
| 755 | CNS | 0.807376 | 0.2952259 | 0.15059124 | R86859_at | EST: ym86a02.r1 Homo sapiens cDNA clone 165770 5'. (from Genbank) |
| 756 | CNS | 0.8071907 | 0.29551218 | 0.15052259 | RC_AA4364 59_at | Nuclear factor I/X (CCAAT-binding transcription factor) |
| 757 | CNS | 0.8068485 | 0.2950774 | 0.15052259 | N89302_s_a t | HLA-B associated transcript-3 |
| 758 | CNS | 0.8068011 | 0.2950059 | 0.15047899 | AA486335_a t | EST: ab13a09.r1 Stratagene lung (#937210) Homo sapiens cDNA clone 840664 5'. (from Genbank) |
| 759 | CNS | 0.8067973 | 0.2949879 | 0.15034461 | W00904_at | EST: za52d12.r1 Soares fetal liver spleen 1NFLS Homo sapiens cDNA clone 296183 5', mRNA sequence. (from Genbank) |
| 760 | CNS | 0.8065688 | 0.2949433 | 0.1502955 | N23817_at | Homo sapiens clone 23675 mRNA sequence |
| 761 | CNS | 0.8065649 | 0.2949147 | 0.15023437 | D31381_at | H.sapiens novel gene, similar to mouse Dynein light chain AB010031 |
| 762 | CNS | 0.8064374 | 0.294886 | 0.15016064 | W32305_f_a t | EST: zc67a06.r1 Soares fetal heart NbHH19W Homo sapiens cDNA clone 327346 5', mRNA sequence. (from Genbank) |
| 763 | CNS | 0.8061346 | 0.2948833 | 0.15011425 | RC_AA6093 46_at | EST: zu71b11.s1 Soares testis NHT Homo sapiens cDNA clone 743421 3', mRNA sequence. (from Genbank) |
| 764 | CNS | 0.8061283 | 0.2948734 | 0.1500928 | AA448456_a t | EST: zw96h10.r1 Soares total fetus Nb2HF8 9w Homo sapiens cDNA clone 784867 5', mRNA sequence. (from Genbank) |
| 765 | CNS | 0.8059463 | 0.2945857 | 0.14999449 | RC_AA4650 93_at | TIA1 cytotoxic granule-associated RNA-binding protein |
| 766 | CNS | 0.8058006 | 0.2945691 | 0.1499445 | D31313_s_a t | EST: Human fetal-lung cDNA 5'-end sequence, mRNA sequence. (from Genbank) |
| 767 | CNS | 0.8056954 | 0.2945454 | 0.14994087 | RC_AA4436 76_at | EST: zw86c05.s1 Soares total fetus Nb2HF8 9w Homo sapiens cDNA clone 783848 3', mRNA sequence. (from Genbank) |
| 768 | CNS | 0.8053963 | 0.2944939 | 0.14980794 | AB002305_a t | KIAA0307 gene product |

FIG. 3N2

| | | | | | |
|---|---|---|---|---|---|
| 769 | CNS | 0.8050146 | 0.2943942 | 0.247984 | 0.14976819 | AB002369_at | Myotubularin related protein 3 |
| 770 | CNS | 0.8048108 | 0.2943849 | 0.247922 | 0.14964971 | R64534_at | EST: yl36c12.r1 Homo sapiens cDNA clone 141334 5'. (from Genbank) |
| 771 | CNS | 0.8046038 | 0.2943849 | 0.247859 | 0.1496261 | AA248582_at | KIAA0737 gene product |
| 772 | CNS | 0.8044031 | 0.2943227 | 0.247847 | 0.14958866 | AB002378_at | KIAA0380 gene product |
| 773 | CNS | 0.8042371 | 0.2943177 | 0.247776 | 0.14946802 | AA478512_at | Homo sapiens EVI5 homolog mRNA, complete cds |
| 774 | CNS | 0.8041161 | 0.2943097 | 0.247702 | 0.14939196 | RC_AA4304_f_at | Ferritin, light polypeptide |
| 775 | CNS | 0.8039966 | 0.2942551 | 0.247681 | 0.14934379 | RC_AA4339_13_at | EST: zw52c11.s1 Soares total fetus Nb2HF8 9w Homo sapiens cDNA clone 773684 3', mRNA sequence. (from Genbank) |
| 776 | CNS | 0.8039872 | 0.2942532 | 0.247619 | 0.14931679 | D82399_at | Homo sapiens clone 23714 mRNA sequence |
| 777 | CNS | 0.8037524 | 0.2941536 | 0.247619 | 0.14927964 | AA482390_at | EST: zv05h05.r1 Soares NhHMPu S1 Homo sapiens cDNA clone 752793 5', mRNA sequence. (from Genbank) |
| 778 | CNS | 0.8036697 | 0.2939619 | 0.247563 | 0.14924994 | RC_AA1696_40_at | Homo sapiens mRNA for KIAA0643 protein, partial cds |
| 779 | CNS | 0.8033497 | 0.2939619 | 0.24754 | 0.14916542 | L44403_at | EST: Homo sapiens thymus mRNA (randomly primed, normalized), single-pass sequence, mRNA sequence. (from Genbank) |
| 780 | CNS | 0.8033435 | 0.2935595 | 0.247499 | 0.14910783 | RC_AA2436_92_at | EST: zr68e05.s1 Soares NhHMPu S1 Homo sapiens cDNA clone 668576 3', mRNA sequence. (from Genbank) |
| 781 | CNS | 0.8028711 | 0.2938561 | 0.247449 | 0.14905417 | RC_AA5995_52_s_at | EST: ag08a06.s1 Gessler Wilms tumor Homo sapiens cDNA clone 1069714 3', mRNA sequence. (from Genbank) |
| 782 | CNS | 0.8028511 | 0.2938471 | 0.247383 | 0.14902623 | AA281677_at | EST: zt03c01.r1 NCI_CGAP_GCB1 Homo sapiens cDNA clone IMAGE:712032 5', mRNA sequence. (from Genbank) |
| 783 | CNS | 0.8028113 | 0.2938412 | 0.2473 | 0.14900622 | N91193_at | EST: za13b03.r1 Soares fetal liver spleen 1NFLS Homo sapiens cDNA clone 292397 5', mRNA sequence. (from Genbank) |
| 784 | CNS | 0.8026431 | 0.2938411 | 0.247205 | 0.14898409 | H15314_at | EST: yn28c02.r1 Homo sapiens cDNA clone 49413 5'. (from Genbank) |
| 785 | CNS | 0.8026617 | 0.2938121 | 0.247184 | 0.1489192 | RC_AA1293_11_at | EST: zn84d06.s1 Stratagene lung carcinoma 937218 Homo sapiens cDNA clone 564875 3', mRNA sequence. (from Genbank) |
| 786 | CNS | 0.8025582 | 0.2937814 | 0.247167 | 0.14884889 | RC_AA4481_77_at | EST: zw83b12.s1 Soares testis NHT Homo sapiens cDNA clone 782783 3', mRNA sequence. (from Genbank) |
| 787 | CNS | 0.8025266 | 0.2937437 | 0.247044 | 0.14883143 | RC_AA5989_30_at | EST: ae37e06.s1 Gessler Wilms tumor Homo sapiens cDNA clone 898018 3', mRNA sequence. (from Genbank) |

FIG. 302

| | | | | | |
|---|---|---|---|---|---|
| 788 | CNS | 0.8024967 | 0.2936523 | 0.247023 | 0.14874522 | C14290_s_a t | EST: Human fetal brain cDNA 5'-end GEN-043C09, mRNA sequence. (from Genbank) |
| 789 | CNS | 0.8019133 | 0.2936039 | 0.24696 | 0.14487379 | RC_AA6098 69_at | EST: af08c02.s1 Soares testis NHT Homo sapiens cDNA clone 1031042 3', mRNA sequence. (from Genbank) |
| 790 | CNS | 0.8018189 | 0.2935399 | 0.246913 | 0.14869091 | RC_AA0842 86_at | Homo sapiens mRNA for KIAA0287 gene, partial cds |
| 791 | CNS | 0.8018161 | 0.2935148 | 0.246868 | 0.14863922 | W24039_at | Homo sapiens clone 24700 unknown mRNA, partial cds |
| 792 | CNS | 0.8017443 | 0.2934496 | 0.246823 | 0.14853682 | R88021_at | EST: ym87d05.r1 Homo sapiens cDNA clone 165897 5'. (from Genbank) |
| 793 | CNS | 0.8016132 | 0.2934448 | 0.246782 | 0.14852412 | U72507_at-2 | Human 40871 mRNA partial sequence. (from Genbank) |
| 794 | CNS | 0.8016132 | 0.2933306 | 0.246711 | 0.14844613 | U72507_at | 40871 mRNA partial sequence |
| 795 | CNS | 0.8015544 | 0.2932595 | 0.246696 | 0.14831293 | AA236441_a t | Homo sapiens chromosome 9, P1 clone 11659 |
| 796 | CNS | 0.8014099 | 0.2932074 | 0.246643 | 0.1483084 | U95018_at | Cysteine and glycine-rich protein 2 (LIM domain only, smooth muscle) |
| 797 | CNS | 0.8012898 | 0.2932045 | 0.246576 | 0.1482562 | RC_D59981 _s_at | EST: Human fetal brain cDNA 3'-end GEN-079C04, mRNA sequence. (from Genbank) |
| 798 | CNS | 0.801284 | 0.2932003 | 0.246501 | 0.14813866 | AA214085_a t | EST: zn57h08.r1 Stratagene muscle 937209 Homo sapiens cDNA clone 562335 5', mRNA sequence. (from Genbank) |
| 799 | CNS | 0.8010261 | 0.2931294 | 0.246443 | 0.1480573 | RC_AA4657 20_at | EST: aa32f08.s1 NCI_CGAP_GCB1 Homo sapiens cDNA clone IMAGE:814983 3', mRNA sequence. (from Genbank) |
| 800 | CNS | 0.8009084 | 0.2929629 | 0.246361 | 0.14803538 | W04732_at | EST: za76b09.r1 Soares fetal lung NbHL.19W Homo sapiens cDNA clone 293457 5' similar to contains element MER22 repetitive element ;, mRNA sequence. (from Genbank) |
| 801 | CNS | 0.8007942 | 0.2929077 | 0.246331 | 0.14799511 | RC_AA4652 40_at | EST: aa24h03.s1 NCI_CGAP_GCB1 Homo sapiens cDNA clone IMAGE:814229 3', mRNA sequence. (from Genbank) |
| 802 | CNS | 0.8002412 | 0.2928834 | 0.24628 | 0.14789902 | AA134178_s _at | EST: zo18f10.r1 Stratagene colon (#937204) Homo sapiens cDNA clone 587275 5', mRNA sequence. (from Genbank) |
| 803 | CNS | 0.7999758 | 0.2928348 | 0.24624 | 0.14783496 | RC_AA6091 45_at | EST: af11g09.s1 Soares testis NHT Homo sapiens cDNA clone 1031392 3', mRNA sequence. (from Genbank) |
| 804 | CNS | 0.7999215 | 0.2928279 | 0.246186 | 0.14780673 | X74142_at | HBF-1 mRNA for transcription factor |
| 805 | CNS | 0.7999215 | 0.2928088 | 0.246184 | 0.14774841 | X74142_at-2 | Forkhead (Drosophila)-like 1 |
| 806 | CNS | 0.79992 | 0.2927665 | 0.246137 | 0.14768411 | W27984_at | EST: 40f11 Human retina cDNA randomly primed sublibrary Homo sapiens cDNA, mRNA sequence. (from Genbank) |
| 807 | CNS | 0.7998202 | 0.2926448 | 0.246097 | 0.14763619 | RC_AA4786 14_at | EST: zv19c10.s1 Soares NhHMPu S1 Homo sapiens cDNA clone 754098 3', mRNA sequence. (from Genbank) |
| 808 | CNS | 0.7997556 | 0.2926099 | 0.245953 | 0.14759286 | AA046908_a t | EST: zf47f09.r1 Soares retina N2b4HR Homo sapiens cDNA clone 380105 5', mRNA sequence. (from Genbank) |

FIG. 3P2

| | | | | | |
|---|---|---|---|---|---|
| 809 | CNS | 0.7994891 | 0.2925932 | 0.245904 | 0.14749941 | RC_AA1366 60_i_at | EST: zk99a04.s1 Soares pregnant uterus NbHPU Homo sapiens cDNA clone 490926 3', mRNA sequence. (from Genbank) |
| 810 | CNS | 0.7993264 | 0.2924895 | 0.245896 | 0.14745213 | RC_AA4317 73_at | Homo sapiens clone 23716 mRNA sequence |
| 811 | CNS | 0.7993043 | 0.2924828 | 0.245862 | 0.14732514 | N44756_at | EST: yy38c09.r1 Homo sapiens cDNA clone 273520 5' similar to contains Alu repetitive element;. (from Genbank) |
| 812 | CNS | 0.7992892 | 0.2924341 | 0.245835 | 0.14729407 | D87458_at | KIAA0282 gene, partial cds |
| 813 | CNS | 0.7991949 | 0.2923353 | 0.24579 | 0.14726983 | X78932_f_at | H.sapiens HZF9 mRNA for zinc finger protein |
| 814 | CNS | 0.799068 | 0.2923172 | 0.245753 | 0.14725854 | AA112941_a_t | Citrate synthase |
| 815 | CNS | 0.7987962 | 0.2922759 | 0.245688 | 0.14725018 | X95073_at-2 | H.sapiens mRNA for translin associated protein X |
| 816 | CNS | 0.7987962 | 0.2922645 | 0.245662 | 0.14716852 | X95073_at | Translin associated protein X |
| 817 | CNS | 0.79853 | 0.2921798 | 0.245622 | 0.14708227 | RC_AA5985 75_at | EST: ae35e11.s1 Gessler Wilms tumor Homo sapiens cDNA clone 897836 3', mRNA sequence. (from Genbank) |
| 818 | CNS | 0.7984864 | 0.2921749 | 0.245433 | 0.147022 | RC_AA4117 11_at | EST: zv16d08.s1 Soares NhHMPu S1 Homo sapiens cDNA clone 753807 3', mRNA sequence. (from Genbank) |
| 819 | CNS | 0.7981759 | 0.2921284 | 0.24541 | 0.1469538 | RC_AA2367 90_at | EST: zr76e12.s1 Soares NhHMPu S1 Homo sapiens cDNA clone 669358 3', mRNA sequence. (from Genbank) |
| 820 | CNS | 0.7981136 | 0.2921042 | 0.245316 | 0.1468983 | RC_AA4614 58_at | EST: zx68d06.s1 Soares total fetus Nb2HF8 9w Homo sapiens cDNA clone 796619 3', mRNA sequence. (from Genbank) |
| 821 | CNS | 0.79803 | 0.2920942 | 0.245267 | 0.14684244 | AA324825_a_t | Homo sapiens polyadenylate binding protein-interacting protein-1 (PAIP1) mRNA, complete cds |
| 822 | CNS | 0.7979968 | 0.2920861 | 0.245251 | 0.14682845 | RC_AA4422 61_at | EST: zv61h04.s1 Soares testis NHT Homo sapiens cDNA clone 758167 3', mRNA sequence. (from Genbank) |
| 823 | CNS | 0.7978979 | 0.2919534 | 0.24524 | 0.14672877 | T55688_s_at | EST: yb39g06.r1 Homo sapiens cDNA clone 73594 5'. (from Genbank) |
| 824 | CNS | 0.79788 | 0.2917496 | 0.245204 | 0.1466592 | RC_AA4000 22_at | EST: zu68e12.s1 Soares testis NHT Homo sapiens cDNA clone 743182 3', mRNA sequence. (from Genbank) |
| 825 | CNS | 0.797752 | 0.2917179 | 0.245168 | 0.14663151 | RC_AA4278 89_at | H.sapiens gene from PAC 426I6, similar to syntaxin 7 |
| 826 | CNS | 0.7976823 | 0.2916305 | 0.245124 | 0.14652792 | U37408_at-2 | C-terminal binding protein 1 |
| 827 | CNS | 0.7976823 | 0.2914804 | 0.24507 | 0.14647587 | U37408_at | CtBP mRNA |
| 828 | CNS | 0.7974007 | 0.2914502 | 0.244943 | 0.14640293 | RC_AA4117 95_at | EST: zt67d11.s1 Soares testis NHT Homo sapiens cDNA clone 727413 3', mRNA sequence. (from Genbank) |
| 829 | CNS | 0.7971985 | 0.2914463 | 0.244917 | 0.14635049 | RC_AA2626 59_at | EST: zs21b09.s1 NCI_CGAP_GCB1 Homo sapiens cDNA clone IMAGE:685817 3', mRNA sequence. (from Genbank) |
| 830 | CNS | 0.797021 | 0.2914377 | 0.244781 | 0.14631762 | W28235_at | EST: 43h8 Human retina cDNA randomly primed sublibrary Homo sapiens cDNA, mRNA sequence. (from Genbank) |

FIG. 3Q2

| | | | | | | |
|---|---|---|---|---|---|---|
| 831 | CNS | 0.7969728 | 0.2914265 | 0.244764 | 0.14626573 | RC_AA4634 17_at | EST: zx71g06.s1 Soares total fetus Nb2HF8 9w Homo sapiens cDNA clone 796954 3', mRNA sequence. (from Genbank) |
| 832 | CNS | 0.798841 | 0.2913662 | 0.244712 | 0.14461599 | AA248199_s _at | EST: csg11153.seq.F Human fetal heart, Lambda ZAP Express Homo sapiens cDNA 5', mRNA sequence. (from Genbank) |
| 833 | CNS | 0.7965409 | 0.29112585 | 0.244695 | 0.14605246 | RC_AA4260 89_at | EST: zv52d02.s1 Soares testis NHT Homo sapiens cDNA clone 757251 3' similar to contains Alu repetitive element;, mRNA sequence. (from Genbank) |
| 834 | CNS | 0.7955123 | 0.29112573 | 0.244592 | 0.146002 | RC_AA1495 86_at | EST: zl39e03.s1 Soares pregnant uterus NbHPU Homo sapiens cDNA clone 504316 3', mRNA sequence. (from Genbank) |
| 835 | CNS | 0.7963432 | 0.29112249 | 0.244574 | 0.14597984 | W28406_at | EST: 46e2 Human retina cDNA randomly primed sublibrary Homo sapiens cDNA, mRNA sequence. (from Genbank) |
| 836 | CNS | 0.79622375 | 0.29118711 | 0.244552 | 0.14596465 | C00100_at | EST: HUMGS0005724, Human Gene Signature, 3'-directed cDNA sequence, mRNA sequence. (from Genbank) |
| 837 | CNS | 0.7960093 | 0.291157 | 0.244528 | 0.14584789 | H08939_at | KIAA0331 gene product |
| 838 | CNS | 0.79528884 | 0.29111394 | 0.244485 | 0.14584789 | RC_AA4258 55_s_at | EST: zw47h02.s1 Soares total fetus Nb2HF8 9w Homo sapiens cDNA clone 7773235 3', mRNA sequence. (from Genbank) |
| 839 | CNS | 0.7951386 | 0.291138 | 0.244295 | 0.14580399 | AA446785_a t | EST: zw89e05.r1 Soares total fetus Nb2HF8 9w Homo sapiens cDNA clone 784160 5', mRNA sequence. (from Genbank) |
| 840 | CNS | 0.7950217 | 0.291111 | 0.244289 | 0.14573152 | M24899_at | THRA Thyroid hormone receptor, alpha (avian erythroblastic leukemia viral (v-erb-a) oncogene homolog) |
| 841 | CNS | 0.79481155 | 0.28110655 | 0.244273 | 0.14568089 | RC_AA2816 17_at | EST: zt03b09.s1 NCI_CGAP_GCB1 Homo sapiens cDNA clone IMAGE:712025 3' similar to SW:ADAC_MOUSE P17427 ALPHA-ADAPTIN ;, mRNA sequence. (from Genbank) |
| 842 | CNS | 0.79447549 | 0.2909977 | 0.244186 | 0.1455829 | C01750_at | EST: HUMGS0003693, Human Gene Signature, 3'-directed cDNA sequence, mRNA sequence. (from Genbank) |
| 843 | CNS | 0.79447477 | 0.2908929 | 0.244031 | 0.1455699 | H05401_at | EST: yl80d09.r1 Homo sapiens cDNA clone 44434 5'. (from Genbank) |
| 844 | CNS | 0.794266 | 0.29108313 | 0.244013 | 0.1453979 | RC_AA2813 61_at | EST: zs96a03.s1 NCI_CGAP_GCB1 Homo sapiens cDNA clone IMAGE:711436 3', mRNA sequence. (from Genbank) |
| 845 | CNS | 0.7942234 | 0.2807926 | 0.244013 | 0.14535981 | RC_AA4500 40_s_at | ADP-ribosylation factor-like 2 |
| 846 | CNS | 0.79418335 | 0.2906865 | 0.243945 | 0.14531973 | RC_AA2790 68_at | EST: zs82a03.s1 NCI_CGAP_GCB1 Homo sapiens cDNA clone IMAGE:703948 3' similar to WP:T19A5.1 CE07509 ;, mRNA sequence. (from Genbank) |
| 847 | CNS | 0.7941307 | 0.2906424 | 0.243908 | 0.14524797 | W35309_at | EST: zc70e09.r1 Soares fetal heart NbHH19W I Homo sapiens cDNA clone 327688 5', mRNA sequence. (from Genbank) |
| 848 | CNS | 0.7941172 | 0.2906041 | 0.243854 | 0.14520562 | RC_AA2281 22_at | ATPase, H+ transporting, lysosomal (vacuolar proton pump), alpha polypeptide, 70kD, isoform 1 |
| 849 | CNS | 0.7941078 | 0.2905922 | 0.243839 | 0.14515156 | RC_AA4061 04_at | EST: zu20a06.s1 Soares NhHMPu S1 Homo sapiens cDNA clone 738514 3', mRNA sequence. (from Genbank) |

FIG. 3R2

| | | | | | |
|---|---|---|---|---|---|
| 850 | CNS | 0.7938355 | 0.2904645 | 0.14511038 | X98834_rna1_at | Zinc finger protein Hsal2 gene extracted from H.sapiens mRNA for zinc finger protein, Hsal2 |
| 851 | CNS | 0.7935988 | 0.2904433 | 0.14509714 | RC_AA4548 40_s_at | EST: zx79d09.s1 Soares ovary tumor NbHOT Homo sapiens cDNA clone 809969 3', mRNA sequence. (from Genbank) |
| 852 | CNS | 0.7935311 | 0.2904395 | 0.14499152 | U43083_at-2 | Guanine nucleotide binding protein (G protein), q polypeptide |
| 853 | CNS | 0.7935311 | 0.2904395 | 0.1449714 | U43083_at | GNAQ Guanine nucleotide binding protein (G protein), q polypeptide |
| 854 | CNS | 0.7934907 | 0.2904244 | 0.14493316 | RC_AA2561 80_at | Dihydropyrimidinase-like 2 |
| 855 | CNS | 0.7931503 | 0.290382 | 0.14490317 | AA282702_a_at | EST: zf15d02.r1 NCI_CGAP_GCB1 Homo sapiens cDNA clone IMAGE:713187 5', mRNA sequence. (from Genbank) |
| 856 | CNS | 0.7931114 | 0.2903816 | 0.14483695 | RC_AA6003 02_at | EST: ag04a07.s1 Gessler Wilms tumor Homo sapiens cDNA clone 1069332 3', mRNA sequence. (from Genbank) |
| 857 | CNS | 0.7930369 | 0.2903816 | 0.14472346 | T66762_at | Homo sapiens clone 23914 mRNA sequence |
| 858 | CNS | 0.7929705 | 0.2903469 | 0.14468367 | RC_AA0470 34_at | EST: zf50b11.s1 Soares retina N2b4HR Homo sapiens cDNA clone 380349 3', mRNA sequence. (from Genbank) |
| 859 | CNS | 0.7929339 | 0.2903374 | 0.14463335 | AA258286_a_t | Homo sapiens mRNA for KIAA0877 protein, partial cds |
| 860 | CNS | 0.792861 | 0.2903341 | 0.14456643 | RC_AA4437 16_at | EST: zw88c05.s1 Soares total fetus Nb2HF8 9w Homo sapiens cDNA clone 784040 3', mRNA sequence. (from Genbank) |
| 861 | CNS | 0.7928296 | 0.2902932 | 0.14450252 | AA248734_a_t | EST: hfe0796.seq.F Human fetal heart, Lambda ZAP Express Homo sapiens cDNA 5', mRNA sequence. (from Genbank) |
| 862 | CNS | 0.79251 | 0.2902331 | 0.14443891 | RC_AA4566 10_at | EST: zx75s09.s1 Soares ovary tumor NbHOT Homo sapiens cDNA clone 809561 3', mRNA sequence. (from Genbank) |
| 863 | CNS | 0.7924936 | 0.2901875 | 0.14440922 | RC_AA2243 24_at | EST: zr12e05.s1 Stratagene hNT neuron (#937233) Homo sapiens cDNA clone 646608 3', mRNA sequence. (from Genbank) |
| 864 | CNS | 0.7911196 | 0.2900868 | 0.1443214 | RC_AA4053 79_at | EST: zu66b01.s1 Soares testis NHT Homo sapiens cDNA clone 742921 3', mRNA sequence. (from Genbank) |
| 865 | CNS | 0.7910059 | 0.2899154 | 0.1412823 | U42390_at | Trio mRNA |
| 866 | CNS | 0.7906377 | 0.2899146 | 0.144206 | W28462_at | Secreted protein, acidic, cysteine-rich (osteonectin) |
| 867 | CNS | 0.7903458 | 0.2899036 | 0.14415523 | AA419507_a_t | EST: zv03b07.r1 Soares NhHMPu S1 Homo sapiens cDNA clone 752533 5', mRNA sequence. (from Genbank) |
| 868 | CNS | 0.7915512 | 0.2896226 | 0.14411739 | RC_AA0567 56_at | EST: zk81g03.s1 Soares pregnant uterus NbHPU Homo sapiens cDNA clone 489268 3', mRNA sequence. (from Genbank) |
| 869 | CNS | 0.7901413 | 0.2895369 | 0.14405075 | RC_AA4004 82_at | EST: zu64g10.s1 Soares testis NHT Homo sapiens cDNA clone 742818 3', mRNA sequence. (from Genbank) |
| 870 | CNS | 0.789775 | 0.2894742 | 0.14400978 | RC_AA2911 62_at | EST: zs46d07.s1 NCI_CGAP_GCB1 Homo sapiens cDNA clone IMAGE:700525 3', mRNA sequence. (from Genbank) |

FIG. 3S2

| | | | | | |
|---|---|---|---|---|---|
| 871 | CNS | 0.7897602 | 0.2893994 | 0.14393917 | RC_AA0859 18_at | H.sapiens HUNK1 mRNA |
| 872 | CNS | 0.789265 | 0.28926 | 0.1438543 | H19570_s_a t | EST: yn59b03.r1 Homo sapiens cDNA clone 172685 5' similar to contains Alu repetitive element;contains PTR5 repetitive element (from Genbank) |
| 873 | CNS | 0.7889618 | 0.289226 | 0.14383705 | RC_AA6095 40_at | EST: af14h01.s1 Soares testis NHT Homo sapiens cDNA clone 1031665 3', mRNA sequence. (from Genbank) |
| 874 | CNS | 0.7888299 | 0.2891739 | 0.14379609 | R61154_at | EST: yh10d07.r1 Homo sapiens cDNA clone 43071 5'. (from Genbank) |
| 875 | CNS | 0.7886787 | 0.2891345 | 0.14373153 | H19378_at | EST: ym46e01.r1 Homo sapiens cDNA clone 51292 5'. (from Genbank) |
| 876 | CNS | 0.788366 | 0.2891033 | 0.14369497 | C00180_f_at | Synaptic glycoprotein SC2 |
| 877 | CNS | 0.7875977 | 0.2890145 | 0.1435807 | D56558_at | H.sapiens mRNA for p40 |
| 878 | CNS | 0.7875876 | 0.2889892 | 0.14356026 | RC_AA2787 20_at | EST: zs77e07.s1 NCI_CGAP_GCB1 Homo sapiens cDNA clone IMAGE:703524 3', mRNA sequence. (from Genbank) |
| 879 | CNS | 0.7875552 | 0.288822 | 0.14343849 | L43631_at | Scaffold attachment factor (SAF-B) gene, partial cds |
| 880 | CNS | 0.7875552 | 0.2887696 | 0.14331226 | L43631_at-2 | Scaffold attachment factor B |
| 881 | CNS | 0.7875167 | 0.28875 | 0.14324279 | RC_AA0016 04_at | EST: zh82d12.s1 Soares fetal liver spleen 1NFLS S1 Homo sapiens cDNA clone 427799 3', mRNA sequence. (from Genbank) |
| 882 | CNS | 0.7873678 | 0.2886144 | 0.14319625 | W52581_at | EST: zc91g02.r1 Soares fetal Islet Homo sapiens cDNA clone 338546 5' similar to contains Alu repetitive element; mRNA sequence. (from Genbank) |
| 883 | CNS | 0.7871386 | 0.2885805 | 0.143086 | AA024641_a t | EST: ze79a04.r1 Soares fetal heart NbHH19W Homo sapiens cDNA clone 365166 5', mRNA sequence. (from Genbank) |
| 884 | CNS | 0.787109 | 0.2885481 | 0.14305142 | AA316272_a t | Fatty-acid-Coenzyme A ligase, long-chain 3 |
| 885 | CNS | 0.7868788 | 0.2885302 | 0.14300299 | RC_AA4289 95_at | H.sapiens mRNA for nuclear protein SA-2 |
| 886 | CNS | 0.7865008 | 0.2885273 | 0.14294165 | C02050_at | Homo sapiens mRNA for beta-tubulin folding cofactor D |
| 887 | CNS | 0.7864874 | 0.2885086 | 0.14284727 | AA278243_a t | EST: zs77b11.r1 NCI_CGAP_GCB1 Homo sapiens cDNA clone IMAGE:703485 5', mRNA sequence. (from Genbank) |
| 888 | CNS | 0.7862121 | 0.2884736 | 0.14280447 | AA253232_a t | EST: zr53e12.r1 Soares NhHMPu S1 Homo sapiens cDNA clone 667150 5', mRNA sequence. (from Genbank) |
| 889 | CNS | 0.7861354 | 0.28836 | 0.14276288 | X81006_at | H.sapiens HCG I mRNA |
| 890 | CNS | 0.7861137 | 0.2883279 | 0.14262506 | AA044781_a t | EST: zk74b09.r1 Soares pregnant uterus NbHPU Homo sapiens cDNA clone 488537 5', mRNA sequence. (from Genbank) |

FIG. 3T2

| | | | | | | |
|---|---|---|---|---|---|---|
| 891 | CNS | 0.7860966 | 0.2882715 | 0.241612 | 0.14256547 | W37583_at | EST: zc10e03.r1 Soares parathyroid tumor NbHPA Homo sapiens cDNA clone 32:1916 5' similar to contains Alu repetitive element;, mRNA sequence. (from Genbank) |
| 892 | CNS | 0.7858892 | 0.2882437 | 0.241604 | 0.14249413 | AA436291_a_t | EST: zv22c07.r1 Soares NhHMPu S1 Homo sapiens cDNA clone 754380 5', mRNA sequence. (from Genbank) |
| 893 | CNS | 0.7857466 | 0.2882239 | 0.241551 | 0.14246006 | RC_AA4026 37_at | EST: zu49e02.s1 Soares ovary tumor NbHOT Homo sapiens cDNA clone 741338 3', mRNA sequence. (from Genbank) |
| 894 | CNS | 0.7856637 | 0.2882152 | 0.241537 | 0.14241967 | R79265_at | EST: yi84b08.r1 Homo sapiens cDNA clone 145911 5'. (from Genbank) |
| 895 | CNS | 0.7856381 | 0.2881519 | 0.241531 | 0.14233994 | RC_AA1653 69_at | EST: zq49c07.s1 Stratagene hNT neuron (#937233) Homo sapiens cDNA clone 633036 3', mRNA sequence. (from Genbank) |
| 896 | CNS | 0.7853615 | 0.2881604 | 0.241473 | 0.14225884 | RC_AA4960 45_s_at | EST: zv72e04.s1 Soares total fetus Nb2HF8 9w Homo sapiens cDNA clone 759198 3', mRNA sequence. (from Genbank) |
| 897 | CNS | 0.7850708 | 0.2881426 | 0.241455 | 0.14216 | AA131547_a_t | Homo sapiens phosphatidylinositol synthase (PIS) mRNA, complete cds |
| 898 | CNS | 0.7849888 | 0.2881242 | 0.241351 | 0.14213224 | RC_AA2340 94_at | Homo sapiens clone 24800 mRNA sequence |
| 899 | CNS | 0.7843437 | 0.2881106 | 0.241334 | 0.14210561 | H38727_at | Ribosomal protein L37 |
| 900 | CNS | 0.7843323 | 0.2881069 | 0.24131 | 0.14204784 | H15219_at | EST: ym30i02.r1 Homo sapiens cDNA clone 49693 5'. (from Genbank) |
| 901 | CNS | 0.7841904 | 0.288061 | 0.241258 | 0.142023 74 | RC_AA2588_at | Homo sapiens clone 24422 mRNA sequence |
| 902 | CNS | 0.7841194 | 0.2880256 | 0.241164 | 0.14196818 | RC_AA2555 46_at | EST: zr85c12.s1 Soares NhHMPu S1 Homo sapiens cDNA clone 682486 3', mRNA sequence. (from Genbank) |
| 903 | CNS | 0.7838343 | 0.2879909 | 0.241084 | 0.14193803 | N75238_s_a_t | EST: yz73f12.r1 Homo sapiens cDNA clone 288719 5' similar to contains Alu repetitive element;. (from Genbank) |
| 904 | CNS | 0.7835919 | 0.2879909 | 0.241071 | 0.14190811 | RC_AA4764 50_at | Homo sapiens cyclophilin-33A (CYP-33) mRNA, complete cds |
| 905 | CNS | 0.7834707 | 0.2879443 | 0.241026 | 0.14188066 | AB002300_a_t | Human mRNA for KIAA0302 gene, partial cds. (from Genbank) |
| 906 | CNS | 0.7833451 | 0.2878872 | 0.241007 | 0.14184291 2_at | EST: zu39e05.s1 Soares ovary tumor NbHOT Homo sapiens cDNA clone 740384 3', mRNA sequence. (from Genbank) |
| 907 | CNS | 0.7832259 | 0.2878077 | 0.240985 | 0.14182705 87_at | RC_AA4465 | EST: zw84e01.s1 Soares total fetus Nb2HF8 9w Homo sapiens cDNA clone 783672 3', mRNA sequence. (from Genbank) |
| 908 | CNS | 0.7831872 | 0.2877817 | 0.240982 | 0.14173692 | R50247_s_a_t | EST: yj58b01.r1 Homo sapiens cDNA clone 152905 5'. (from Genbank) |
| 909 | CNS | 0.7828515 | 0.2877749 | 0.240955 | 0.14171316 70_at | RC_AA4257 | EST: zw47g06.s1 Soares total fetus Nb2HF8 9w Homo sapiens cDNA clone 773242 3', mRNA sequence. (from Genbank) |

FIG. 3U2

| | | | | | | |
|---|---|---|---|---|---|---|
| 910 | CNS | 0.7825069 | 0.2876664 | 0.240933 | 0.14169355 | W28167_at | EST: 43a1 Human retina cDNA randomly primed sublibrary Homo sapiens cDNA, mRNA sequence. (from Genbank) |
| 911 | CNS | 0.7820613 | 0.2876557 | 0.240922 | 0.14168084 | RC_AA0828 48_at | Suppressor of actin mutations 2, yeast, homolog-like |
| 912 | CNS | 0.7818281 | 0.2876338 | 0.240778 | 0.14161229 | AA133244_a t | EST: zt17g11.r1 Soares pregnant uterus NbHPU Homo sapiens cDNA clone 502244 5', mRNA sequence. (from Genbank) |
| 913 | CNS | 0.7817494 | 0.2875974 | 0.240768 | 0.14157207 | RC_AA4418 00_at | Protein kinase inhibitor [human, neuroblastoma cell line SH-SY-5Y, mRNA, 2147 nt] |
| 914 | CNS | 0.7816512 | 0.2875651 | 0.240735 | 0.14147417 | RC_AA4238 38_at | EST: zv79a11.s1 Soares total fetus Nb2HF8 9w Homo sapiens cDNA clone 759836 3', mRNA sequence. (from Genbank) |
| 915 | CNS | 0.7815679 | 0.2874509 | 0.240735 | 0.14143275 | RC_AA4960 48_at | EST: zv72e10.s1 Soares total fetus Nb2HF8 9w Homo sapiens cDNA clone 759210 3', mRNA sequence. (from Genbank) |
| 916 | CNS | 0.7816552 | 0.2874491 | 0.240673 | 0.14137876 | R24294_at | EST: yg32a08.r1 Homo sapiens cDNA clone 33873 5'. (from Genbank) |
| 917 | CNS | 0.7814773 | 0.2874133 | 0.240678 | 0.14132595 | U57316_at | GCN5 (hGCN5) gene |
| 918 | CNS | 0.7814773 | 0.2873927 | 0.240617 | 0.14120653 | U57316_at-2 | Homo sapiens histone acetyltransferase (GCN5) mRNA, partial cds |
| 919 | CNS | 0.781007 | 0.2873369 | 0.240546 | 0.1411887 | RC_AA4881 99_at | EST: ad08f06.s1 Soares NbHFB Homo sapiens cDNA clone 877667 3', mRNA sequence. (from Genbank) |
| 920 | CNS | 0.7808299 | 0.2873094 | 0.240521 | 0.14109704 | AA247453_a t | EST: csg2876.seq.F Human fetal heart, Lambda ZAP Express Homo sapiens cDNA 5', mRNA sequence. (from Genbank) |
| 921 | CNS | 0.7807418 | 0.2872988 | 0.240442 | 0.1410737 | AA484982_a t | EST: aa39b02.r1 NCI_CGAP_GCB1 Homo sapiens cDNA clone IMAGE:815595 5', mRNA sequence. (from Genbank) |
| 922 | CNS | 0.7805461 | 0.2872551 | 0.240423 | 0.14104229 | RC_AA2533 90_s_at | Tetraspan 5 |
| 923 | CNS | 0.7802509 | 0.2872551 | 0.240411 | 0.14103632 | RC_AA2364 77_at | EST: zt75c02.s1 Soares NhHMPu S1 Homo sapiens cDNA clone 669218 3', mRNA sequence. (from Genbank) |
| 924 | CNS | 0.7800378 | 0.2871554 | 0.240378 | 0.14090821 | RC_AA2825 21_at | Platelet-activating factor acetylhydrolase, isoform Ib, alpha subunit (45kD) |
| 925 | CNS | 0.779781 | 0.2871186 | 0.240331 | 0.14085378 | RC_AA2620 32_at | EST: zs21c03.s1 NCI_CGAP_GCB1 Homo sapiens cDNA clone IMAGE:685829 3', mRNA sequence. (from Genbank) |
| 926 | CNS | 0.7797489 | 0.287107 | 0.240306 | 0.14071286 | RC_AA0650 94_at | EST: zf75e12.s1 Soares pineal gland N3HPG Homo sapiens cDNA clone 382798 3', mRNA sequence. (from Genbank) |
| 927 | CNS | 0.77963359 | 0.2868305 | 0.240267 | 0.14064182 | C01169_at | Karyopherin alpha 4 (importin alpha 3) |
| 928 | CNS | 0.7793308 | 0.2868064 | 0.240184 | 0.14054224 | AA436202_a t | EST: zv23g01.r1 Soares NhHMPu S1 Homo sapiens cDNA clone 754512 5', mRNA sequence. (from Genbank) |
| 929 | CNS | 0.7792648 | 0.2867799 | 0.240186 | 0.14053299 | D17530_s_a t | Drebrin 1 |
| 930 | CNS | 0.7790957 | 0.2866837 | 0.240022 | 0.14048333 | RC_AA1502 62_at | EST: zl07e02.s1 Soares pregnant uterus NbHPU Homo sapiens cDNA clone 491642 3', mRNA sequence. (from Genbank) |

FIG. 3V2

| # | Tissue | | | | ID | Description |
|---|---|---|---|---|---|---|
| 931 | CNS | 0.7787081 | 0.2866019 | 0.240016 | RC_AA4289 0.14038512 02_at | EST: zv49d11.s1 Soares ovary tumor NbHOT Homo sapiens cDNA clone 756981 3', mRNA sequence. (from Genbank) |
| 932 | CNS | 0.7785296 | 0.2865944 | 0.240015 | RC_AA4652 0.14038512 14_at | EST: aa24e06.s1 NCI_CGAP_GCB1 Homo sapiens cDNA clone IMAGE:814210 3', mRNA sequence. (from Genbank) |
| 933 | CNS | 0.7784938 | 0.2865575 | 0.239996 | 0.14033404 N30908_at | EST: yx51a06.r1 Homo sapiens cDNA clone 265234 5'. (from Genbank) |
| 934 | CNS | 0.7784748 | 0.2865575 | 0.239992 | RC_AA5992 0.1402985 11_at | Short-chain dehydrogenase/reductase 1 |
| 935 | CNS | 0.7783558 | 0.2864201 | 0.23995 | 0.14029352 W26958_at | EST: 16g8 Human retina cDNA randomly primed sublibrary Homo sapiens cDNA, mRNA sequence. (from Genbank) |
| 936 | CNS | 0.778171 | 0.2863807 | 0.239937 | RC_AA4189 0.14026922 36_s_at | Homo sapiens mRNA for KIAA0795 protein, partial cds |
| 937 | CNS | 0.7778792 | 0.2863567 | 0.239931 | RC_AA0395 0.14019565 95_at | EST: zf08d12.s1 Soares fetal heart NbHH19W Homo sapiens cDNA clone 376343 3', mRNA sequence. (from Genbank) |
| 938 | CNS | 0.7774258 | 0.2863567 | 0.239911 | RC_AA0398 0.14014171 54_at | EST: zf03c08.s1 Soares fetal heart NbHH19W Homo sapiens cDNA clone 375854 3', mRNA sequence. (from Genbank) |
| 939 | CNS | 0.777338 | 0.2863043 | 0.239848 | 0.14006734 W27503_at | Homo sapiens mRNA for KIAA0679 protein, partial cds |
| 940 | CNS | 0.7773348 | 0.2862876 | 0.239794 | RC_AA4118 0.13999467 82_at | EST: zu01g11.s1 Soares testis NHT Homo sapiens cDNA clone 730628 3', mRNA sequence. (from Genbank) |
| 941 | CNS | 0.7769022 | 0.2862852 | 0.239719 | RC_AA2871 0.13997345 07_s_at | EST: zs58f12.s1 NCI_CGAP_GCB1 Homo sapiens cDNA clone IMAGE:701711 3', mRNA sequence. (from Genbank) |
| 942 | CNS | 0.7769451 | 0.2862736 | 0.23964 | 0.1399609 M97252_at | KALLMANN SYNDROME PROTEIN PRECURSOR |
| 943 | CNS | 0.7769451 | 0.286258 | 0.239622 | 0.13986395 M97252_at-2 | Kallmann syndrome 1 sequence |
| 944 | CNS | 0.7768155 | 0.2862105 | 0.239479 | RC_AA4853 0.13983353 49_at | EST: zx90a05.s1 Soares ovary tumor NbHOT Homo sapiens cDNA clone 810992 3', mRNA sequence. (from Genbank) |
| 945 | CNS | 0.7767715 | 0.2862201 | 0.239459 | RC_AA4486 0.13981009 44_at | EST: zx10c06.s1 Soares total fetus Nb2HF8 9w Homo sapiens cDNA clone 786058 3', mRNA sequence. (from Genbank) |
| 946 | CNS | 0.7767122 | 0.2861985 | 0.239421 | RC_AA3985 0.13974254 52_at | Homo sapiens mRNA for KIAA0639 protein, partial cds |
| 947 | CNS | 0.776687 | 0.2861978 | 0.239379 | RC_AA2800 0.13969864 32_at | EST: zs93c02.s1 NCI_CGAP_GCB1 Homo sapiens cDNA clone IMAGE:705026 3', mRNA sequence. (from Genbank) |
| 948 | CNS | 0.7766538 | 0.2861658 | 0.239275 | RC_AA6101 0.13963245 14_at | EST: af19g07.s1 Soares total fetus Nb2HF8 9w Homo sapiens cDNA clone 1032156 3', mRNA sequence. (from Genbank) |
| 949 | CNS | 0.776552 | 0.2861149 | 0.239275 | RC_AA4438 0.13957366 44_at | EST: zw88g09.s1 Soares total fetus Nb2HF8 9w Homo sapiens cDNA clone 784096 3', mRNA sequence. (from Genbank) |
| 950 | CNS | 0.7765047 | 0.2861035 | 0.239163 | RC_AA0592 0.13954109 14_at | EST: zf64g11.s1 Soares retina N2b4HR Homo sapiens cDNA clone 381764 3' similar to TR:G508424 G508424 NEUROPHILIN.; mRNA sequence. (from Genbank) |

FIG. 3W2

| | | | | | | |
|---|---|---|---|---|---|---|
| 951 | CNS | 0.776407 | 0.2860858 | 0.239149 | 0.13948356 | RC_AA2340 89_at | Serine/threonine kinase 17a (apoptosis-inducing) |
| 952 | CNS | 0.7763682 | 0.2860685 | 0.239107 | 0.1394616 | RC_AA4431 47_at | Homo sapiens mRNA for KIAA0582 protein, partial cds |
| 953 | CNS | 0.7761444 | 0.2858928 | 0.239094 | 0.13941881 | U35234_at | Protein tyrosine phosphatase sigma mRNA |
| 954 | CNS | 0.7761444 | 0.2857713 | 0.239066 | 0.13939281 | U35234_at-2 | Protein tyrosine phosphatase, receptor type, S |
| 955 | CNS | 0.7758534 | 0.2857562 | 0.239064 | 0.13934022 | RC_AA4968 98_at | EST: ae33d05.s1 Gessler Wilms tumor Homo sapiens cDNA clone 897609 3', mRNA sequence. (from Genbank) |
| 956 | CNS | 0.7757993 | 0.285754 | 0.238992 | 0.13229884 | W92836_at | EST: zd92g04.r1 Soares fetal heart NbHH19W Homo sapiens cDNA clone 356982 5', mRNA sequence. (from Genbank) |
| 957 | CNS | 0.7757189 | 0.2856855 | 0.238992 | 0.13917425 | RC_AA2566 04_at | EST: zr86g02.s1 Soares NhHMPu S1 Homo sapiens cDNA clone 682610 3', mRNA sequence. (from Genbank) |
| 958 | CNS | 0.7755565 | 0.2856752 | 0.238785 | 0.13910772 | RC_AA1950 77_at | EST: zr35g12.s1 Soares NhHMPu S1 Homo sapiens cDNA clone 665446 3', mRNA sequence. (from Genbank) |
| 959 | CNS | 0.7755209 | 0.285663 | 0.238785 | 0.13910772 | RC_AA4214 76_at | EST: zu06d10.s1 Soares testis NHT Homo sapiens cDNA clone 731059 3', mRNA sequence. (from Genbank) |
| 960 | CNS | 0.7753943 | 0.2855165 | 0.238715 | 0.13906229 | RC_AA1575 37_at | EST: zo55e02.s1 Stratagene pancreas (#937208) Homo sapiens cDNA clone 590810 3', mRNA sequence. (from Genbank) |
| 961 | CNS | 0.7753196 | 0.2854844 | 0.23862 | 0.13904567 | H67195_s_a t | Notch (Drosophila) homolog 3 |
| 962 | CNS | 0.7753158 | 0.2853704 | 0.238603 | 0.1389666 | U95740_rna 2_at | 362G6.2 gene extracted from Human chromosome 16p13.1 BAC clone CIT987SK-362G6 complete sequence |
| 963 | CNS | 0.7751086 | 0.2853686 | 0.238579 | 0.1389276 | RC_AA4641 80_at | EST: zx83f04.s1 Soares ovary tumor NbHOT Homo sapiens cDNA clone 810367 3' similar to gb:M38188 OVARIAN GRANULOSA CELL 13.0 KD PROTEIN HGR74 (HUMAN);, mRNA sequence. (from Genbank) |
| 964 | CNS | 0.7749978 | 0.2853333 | 0.238568 | 0.13891321 | RC_AA2825 28_at | KIAA0675 gene product |
| 965 | CNS | 0.7748278 | 0.2852866 | 0.238559 | 0.13887075 | RC_AA4042 77_at | EST: zv63e04.s1 Soares total fetus Nb2HF8 9w Homo sapiens cDNA clone 758334 3', mRNA sequence. (from Genbank) |
| 966 | CNS | 0.7745657 | 0.2852629 | 0.23853 | 0.13883941 | AA479996_a t | EST: zv18b06.r1 Soares NhHMPu S1 Homo sapiens cDNA clone 753971 5', mRNA sequence. (from Genbank) |
| 967 | CNS | 0.7744977 | 0.2852601 | 0.238499 | 0.13880026 | RC_AA2527 59_at | EST: zs27c08.s1 NCI_CGAP_GCB1 Homo sapiens cDNA clone IMAGE:686414 3', mRNA sequence. (from Genbank) |
| 968 | CNS | 0.7744122 | 0.2852188 | 0.23844 | 0.13876756 | RC_AA2821 40_at | EST: zt02b01.s1 NCI_CGAP_GCB1 Homo sapiens cDNA clone IMAGE:711913 3', mRNA sequence. (from Genbank) |
| 969 | CNS | 0.7739148 | 0.2852054 | 0.238428 | 0.1387426 | W86706_at | EST: zh63d02.r1 Soares fetal liver spleen 1NFLS S1 Homo sapiens cDNA clone 416739 5', mRNA sequence. (from Genbank) |

FIG. 3X2

| | | | | | | |
|---|---|---|---|---|---|---|
| 970 | CNS | | 0.7738523 | 0.2851265 | 0.238423 | 0.13862507 | AA452003_at | EST: zv75e04.r1 Soares total fetus Nb2HF8 9w Homo sapiens cDNA clone 759486 5' similar to contains Alu repetitive element;contains element MER22 repetitive element :, mRNA sequence. (from Genbank) |
| 971 | CNS | | 0.7737186 | 0.2850772 | 0.238368 | 0.13853648 | S69790_at | Brush-1 |
| 972 | CNS | | 0.7736881 | 0.2850699 | 0.238296 | 0.13845417 | W69582_at | Homo sapiens mRNA for KIAA0696 protein, partial cds |
| 973 | CNS | | 0.7735992 | 0.2850409 | 0.238292 | 0.13840705 | W26520_at | EST: 32g10 Human retina cDNA randomly primed sublibrary Homo sapiens cDNA, mRNA sequence. (from Genbank) |
| 974 | CNS | | 0.7733082 | 0.2850273 | 0.238261 | 0.13835496 | AA263028_at | Homo sapiens malate dehydrogenase precursor (MDH) mRNA, nuclear gene encoding mitochondrial protein, complete cds |
| 975 | CNS | | 0.7731788 | 0.285026 | 0.238109 | 0.13832414 | W27299_at | Homo sapiens clone 23685 mRNA sequence |
| 976 | CNS | | 0.773162 | 0.2849931 | 0.238027 | 0.13825244 | RC_AA2922 90_at | EST: zt51c08.s1 Soares ovary tumor NbHOT Homo sapiens cDNA clone 725870 3', mRNA sequence. (from Genbank) |
| 977 | CNS | | 0.7726568 | 0.284988 | 0.237937 | 0.1382138 | AA232156_a t | Insulin-like growth factor 2 (somatomedin A) |
| 978 | CNS | | 0.7725179 | 0.2849739 | 0.237914 | 0.1381877 | RC_AA4437 91_f_at | EST: zw86e09.s1 Soares total fetus Nb2HF8 9w Homo sapiens cDNA clone 783880 3', mRNA sequence. (from Genbank) |
| 979 | CNS | | 0.772334 | 0.2848958 | 0.237905 | 0.13813432 | M28219_at-2 | Homo sapiens low density lipoprotein receptor (FH 10 mutant causing familial hypercholesterolemia) mRNA, 3' end |
| 980 | CNS | | 0.772334 | 0.2848958 | 0.237861 | 0.1380858 | M28219_at | LDLR Low density lipoprotein receptor (familial hypercholesterolemia) |
| 981 | CNS | | 0.7722658 | 0.2848463 | 0.237842 | 0.13806406 | W27054_at | APOLIPOPROTEIN AI REGULATORY PROTEIN-1 |
| 982 | CNS | | 0.772213 | 0.2848381 | 0.237797 | 0.13805005 | AA304566_a t | EST: EST17372 Aorta endothelial cells, TNF alpha-treated Homo sapiens cDNA 5' end, mRNA sequence. (from Genbank) |
| 983 | CNS | | 0.7721638 | 0.2848311 | 0.237741 | 0.13797128 | D52791_at | Human clone iota unknown protein mRNA, complete cds |
| 984 | CNS | | 0.7721435 | 0.2847193 | 0.237675 | 0.13793764 | RC_AA3995 38_at | EST: zt88e11.s1 Soares testis NHT Homo sapiens cDNA clone 729452 3', mRNA sequence. (from Genbank) |
| 985 | CNS | | 0.771937 | 0.2847083 | 0.237637 | 0.13785812 | R62894_at | EST: yi11h08.r1 Homo sapiens cDNA clone 138975 5'. (from Genbank) |
| 986 | CNS | | 0.7718838 | 0.2846935 | 0.237631 | 0.13778081 | RC_AA4169 65_s_at | Gap junction protein, alpha 1, 43kD (connexin 43) |
| 987 | CNS | | 0.7717063 | 0.2846898 | 0.237586 | 0.13776186 | RC_AA2279 86_at | EST: zr58c12.s1 Soares NhHMPu S1 Homo sapiens cDNA clone 667606 3', mRNA sequence. (from Genbank) |
| 988 | CNS | | 0.7717017 | 0.2845522 | 0.237586 | 0.13769595 | X58431_ma 2_s_at | HOX 2.2 gene extracted from Human Hox2.2 gene for a homeobox protein |
| 989 | CNS | | 0.7717017 | 0.2845313 | 0.237496 | 0.13767721 | X58431_ma 2_s_at-2 | HOMEOBOX PROTEIN HOX-B6::HOMEOBOX PROTEIN HOX-B6 |
| 990 | CNS | | 0.7713846 | 0.2845313 | 0.237412 | 0.13761114 | RC_AA1913 36_at | EST: zp88c05.s1 Stratagene HeLa cell s3 937216 Homo sapiens cDNA clone 627272 3' similar to contains Alu repetitive element;, mRNA sequence. (from Genbank) |

FIG. 3Y2

| | | | | | |
|---|---|---|---|---|---|
| 991 | CNS | 0.7713515 | 0.2844337 | 0.237373 | 0.137578621 | RC_AA4322_92_at | EST:zw69e03.s1 Soares testis NHT Homo sapiens cDNA clone 781468 3', mRNA sequence. (from Genbank) |
| 992 | CNS | 0.7711845 | 0.2844117 | 0.237298 | 0.137542891 | RC_AA4120_28_s_at | Homo sapiens mRNA for Fe65L2, complete cds |
| 993 | CNS | 0.7710287 | 0.2843574 | 0.237275 | 0.13747811 | AF007165_a_t | Homo sapiens nuclear DEAF-1 related transcriptional regulator protein mRNA, complete cds |
| 994 | CNS | 0.7709872 | 0.2843531 | 0.237197 | 0.13747366 | AA247455_a_t | EST: csg2890.seq.F Human fetal heart, Lambda ZAP Express Homo sapiens cDNA 5', mRNA sequence. (from Genbank) |
| 995 | CNS | 0.770958 | 0.2843426 | 0.23715 | 0.137426111 | RC_AA4372_78_at | EST: zv62b04.s1 Soares testis NHT Homo sapiens cDNA clone 758191 3', mRNA sequence. (from Genbank) |
| 996 | CNS | 0.770297 | 0.2842931 | 0.237146 | 0.137389621 | AA039762_a_t | EST: zf10a09.r1 Soares fetal heart NbHH19W Homo sapiens cDNA clone 376504 5', mRNA sequence. (from Genbank) |
| 997 | CNS | 0.7702879 | 0.284291 | 0.237111 | 0.137257371 | RC_AA4468_58_at | EST: zw84h11.s1 Soares total fetus Nb2HF8 9w Homo sapiens cDNA clone 783717 3', mRNA sequence. (from Genbank) |
| 998 | CNS | 0.7701257 | 0.2842826 | 0.237099 | 0.13722234 | N40320_at | EST: yx80g06.r1 Homo sapiens cDNA clone 268090 5'. (from Genbank) |
| 999 | CNS | 0.7700138 | 0.2842266 | 0.236811 | 0.137170821 | RC_AA4421_42_at | EST: zw56h02.s1 Soares total fetus Nb2HF8 9w Homo sapiens cDNA clone 774099 3', mRNA sequence. (from Genbank) |
| 1000 | CNS | 0.7700077 | 0.2842197 | 0.236729 | 0.13708031 | RC_AA2566_06_at | EST: zr86g04.s1 Soares NhHMPu S1 Homo sapiens cDNA clone 682614 3', mRNA sequence. (from Genbank) |

FIG. 3Z2

| | | | | | |
|---|---|---|---|---|---|
| 1 | Colorectal | 1.3304546 | 0.6979361 | 0.61841 | 0.46926254 | AB006781_s_at | Galectin-4 |
| 2 | Colorectal | 0.9893228 | 0.6466596 | 0.573452 | 0.43697375 | U51095_at | CDX1 Caudal type homeo box transcription factor 1 |
| 3 | Colorectal | 0.9447319 | 0.6240295 | 0.551708 | 0.42068958 | X83228_at | LI-cadherin |
| 4 | Colorectal | 0.9219171 | 0.6074118 | 0.539086 | 0.40901852 | M29540_at | CARCINOEMBRYONIC ANTIGEN PRECURSOR |
| 5 | Colorectal | 0.8310602 | 0.5984152 | 0.52723 | 0.40071398 | M35252_at | TUMOR-ASSOCIATED ANTIGEN CO-029 |
| 6 | Colorectal | 0.7965425 | 0.5912129 | 0.520434 | 0.39418483 | D14520_at | GC-Box binding protein BTEB2 |
| 7 | Colorectal | 0.772929 | 0.5859177 | 0.514771 | 0.38826877 | X98311_at | Carcinoembryonic antigen family member 2, CGM2 |
| 8 | Colorectal | 0.7369248 | 0.5797341 | 0.509057 | 0.38285961 | X74929_s_at | KRT8 Keratin 8 |
| 9 | Colorectal | 0.710591 | 0.5760404 | 0.503801 | 0.37822562 | M10050_at | HBG2 Hemoglobin gamma-G |
| 10 | Colorectal | 0.7019893 | 0.5677402 | 0.500434 | 0.37441394 | M57710_at | LGALS3 Lectin, galactoside-binding, soluble, 3 (galectin 3) (NOTE: redefinition of symbol) |
| 11 | Colorectal | 0.6896882 | 0.5667345 | 0.495918 | 0.37061206 | L02785_at | DRA Down-regulated in adenoma |
| 12 | Colorectal | 0.6816363 | 0.5633355 | 0.491975 | 0.36677584 | RC_AA053660_at | EST: zl74e07.s1 Stratagene colon (#937204) Homo sapiens cDNA clone 510372 3' similar to contains Alu repetitive element., mRNA sequence. (from Genbank) |
| 13 | Colorectal | 0.6661732 | 0.5606063 | 0.488131 | 0.36401525 | L08044_s_at | Trefoil factor 3 (intestinal) |

FIG. 4A

| # | Tissue | | | | | | Description |
|---|---|---|---|---|---|---|---|
| 14 | Colorectal | 0.6661732 | 0.557618 | 0.485725 | 0.3609329 | L08044_s_at | TFF3 Trefoil factor 3 (intestinal) |
| 15 | Colorectal | 0.6645613 | 0.5556119 | 0.483527 | 0.35857078 | U07969_s_a_t | Intestinal peptide-associated transporter HPT-1 mRNA |
| 16 | Colorectal | 0.6597598 | 0.5527974 | 0.481477 | 0.3561044 | X12901_at | VILLIN |
| 17 | Colorectal | 0.6488326 | 0.5484788 | 0.478819 | 0.3537182 | D87292_at | Rhodanese |
| 18 | Colorectal | 0.6443836 | 0.5457429 | 0.476623 | 0.351588 | M55998_s_a_t | Alpha-1 collagen type I gene, 3' end |
| 19 | Colorectal | 0.639657 | 0.5418932 | 0.4746 | 0.34959665 | M77349_at | Transforming growth factor-beta induced gene product (BIGH3) mRNA |
| 20 | Colorectal | 0.6345016 | 0.5388692 | 0.472279 | 0.34737322 | M93036_at | MAJOR GASTROINTESTINAL TUMOR-ASSOCIATED PROTEIN GA733-2 PRECURSOR |
| 21 | Colorectal | 0.6183873 | 0.5373365 | 0.470427 | 0.34542933 | X93036_at | MAT8 protein |
| 22 | Colorectal | 0.6162866 | 0.5337368 | 0.460914 | 0.34354696 | X16354_at | BGP Biliary glycoprotein (alternative products) |
| 23 | Colorectal | 0.6135939 | 0.5322881 | 0.467634 | 0.34195346 | X79882_at | Lrp mRNA |
| 24 | Colorectal | 0.604686 | 0.5295914 | 0.466112 | 0.34027967 | X68314_at | GPX2 Glutathione peroxidase 2, gastrointestinal |
| 25 | Colorectal | 0.5409228 | 0.5289235 | 0.464264 | 0.3388225 | X12876_s_a_t | KRT18 Keratin 18 |
| 26 | Colorectal | 0.5346139 | 0.5278842 | 0.463016 | 0.3370235 | L03840_s_at | FGFR4 Fibroblast growth factor receptor 4 |
| 27 | Colorectal | 0.5314592 | 0.5263897 | 0.461656 | 0.33576262 | J04469_at | Mitochondrial creatine kinase (CKMT) gene |
| 28 | Colorectal | 0.5262153 | 0.5252495 | 0.459832 | 0.33431423 | U27333_s_a_t | Alpha-1,3 fucosyltransferase 6 (FCT3A) mRNA |
| 29 | Colorectal | 0.5178417 | 0.5230292 | 0.458503 | 0.3330468 | X73501_at-2 | KERATIN, TYPE I CYTOSKELETAL 20 |
| 30 | Colorectal | 0.5178417 | 0.521027 | 0.457537 | 0.33154407 | X73501_at | KERATIN, TYPE I CYTOSKELETAL 20 |
| 31 | Colorectal | 0.5177953 | 0.5197674 | 0.455465 | 0.33026433 | U51096_at | Homeobox protein Cdx2 mRNA |
| 32 | Colorectal | 0.5161443 | 0.5194929 | 0.453944 | 0.32879257 | L23808_at | MMP12 Matrix metalloproteinase 12 (macrophage elastase) |
| 33 | Colorectal | 0.5147349 | 0.5184934 | 0.452769 | 0.32764837 | L20826_at | I-plastin mRNA |
| 34 | Colorectal | 0.5127617 | 0.5174283 | 0.452021 | 0.32639337 | X54925_at | MMP1 Matrix metalloproteinase 1 (interstitial collagenase) |
| 35 | Colorectal | 0.5102813 | 0.5169292 | 0.450713 | 0.32528314 | RC_AA2534 71_at | EST: zr77g09.s1 Soares NhHMPu S1 Homo sapiens cDNA clone 669472 3', mRNA sequence. (from Genbank) |
| 36 | Colorectal | 0.5056632 | 0.514767 | 0.449718 | 0.32434413 | L10343_at | PI3 Protease inhibitor 3, skin-derived (SKALP) |
| 37 | Colorectal | 0.5009919 | 0.5137439 | 0.448466 | 0.3232134 | X05232_at | MMP3 Stromelysin |
| 38 | Colorectal | 0.4974572 | 0.5122448 | 0.447924 | 0.32208204 | HG2788-HT2896_at | Calcyclin |
| 39 | Colorectal | 0.4731978 | 0.5109233 | 0.446611 | 0.32114545 | U78556_at | Cisplatin resistance associated alpha protein (hCRA alpha) mRNA |
| 40 | Colorectal | 0.4665764 | 0.5103841 | 0.445483 | 0.31993556 | L41668_rna1_at | UDP-Galactose 4 epimerase (GALE) gene |
| 41 | Colorectal | 0.4652342 | 0.5094581 | 0.445063 | 0.31906912 | U53786_at | EVPL Envoplakin |

FIG. 4B

| # | Type | | | | | Description |
|---|---|---|---|---|---|---|
| 42 | Colorectal | 0.4642504 | 0.5088035 | 0.44383 | 0.31810844 | U04313_at | PI5 Protease inhibitor 5 (maspin) |
| 43 | Colorectal | 0.4639263 | 0.5078172 | 0.44311 | 0.3172188 | J04164_at | RPS3 Ribosomal protein S3 |
| 44 | Colorectal | 0.458828 | 0.5067757 | 0.442532 | 0.3161517 | M18728_at | NCA Non-specific cross reacting antigen |
| 45 | Colorectal | 0.4568794 | 0.5051471 | 0.441531 | 0.31544325 | U68488_at | HTR7 5-hydroxytryptamine (serotonin) receptor 7 (adenylate cyclase-coupled) |
| 46 | Colorectal | 0.449968 | 0.5047656 | 0.440184 | 0.31469578 | U21128_at | LUM Lumican |
| 47 | Colorectal | 0.4476498 | 0.5042585 | 0.439301 | 0.31340513 | X67325_at | INTERFERON-ALPHA INDUCED 11.5 KD PROTEIN |
| 48 | Colorectal | 0.4456659 | 0.5026614 | 0.438598 | 0.3125313 | RC_AA1349 85_at | EST: zo26i05.s1 Stratagene colon (#937204) Homo sapiens cDNA clone 588057 3', mRNA sequence. (from Genbank) |
| 49 | Colorectal | 0.4447622 | 0.5019999 | 0.438107 | 0.311380951_s_at | S71043_rna | Ig alpha 2=immunoglobulin A heavy chain allotype 2 {constant region, germ line} [human, peripheral blood neutrophils, Genomic, 1799 nt] |
| 50 | Colorectal | 0.442524 | 0.5009725 | 0.437162 | 0.3110768447_s_at | RC_AA1310 | KIAA0698 gene product |
| 51 | Colorectal | 0.439528 | 0.4998462 | 0.436568 | 0.31014428 | L21998_at | MUC2 Mucin 2, intestinal/tracheal |
| 52 | Colorectal | 0.4371672 | 0.4986036 | 0.43558 | 0.30930987 | RC_AA1349 68_at | EST: zo23g08.s1 Stratagene colon (#937204) Homo sapiens cDNA clone 587774 3', mRNA sequence. (from Genbank) |
| 53 | Colorectal | 0.4348819 | 0.4982730 | 0.434647 | 0.308269 | U55206_at | Gamma-glutamyl hydrolase (hGH) mRNA |
| 54 | Colorectal | 0.4298149 | 0.4982425 | 0.433883 | 0.30752197 | AA427468_s _at | Claudin 4 |
| 55 | Colorectal | 0.4282036 | 0.4979363 | 0.433556 | 0.306933734 | D13666_s_a t | Osteoblast specific factor 2 (OSF-2os) |
| 56 | Colorectal | 0.4248353 | 0.4975193 | 0.432558 | 0.30608693 | RC_AA1000 26_at | EST: zl79c09.s1 Stratagene colon (#937204) Homo sapiens cDNA clone 510832 3', mRNA sequence. (from Genbank) |
| 57 | Colorectal | 0.4248332 | 0.4966319 | 0.431647 | 0.3053618 | AF001294_a t | IPL (IPL) mRNA |
| 58 | Colorectal | 0.4147611 | 0.4957649 | 0.431022 | 0.3047288 | U42408_at | Ladinin (LAD) mRNA |
| 59 | Colorectal | 0.4099886 | 0.4956147 | 0.430292 | 0.30399632 | M95787_at | 22kDa smooth muscle protein (SM22) mRNA |
| 60 | Colorectal | 0.4092692 | 0.4948158 | 0.429676 | 0.30328473 | RC_AA1325 23_at | NF-E2-related factor 3 |
| 61 | Colorectal | 0.4084193 | 0.4941933 | 0.429105 | 0.3026381 | U89606_at | Pyridoxal kinase mRNA |
| 62 | Colorectal | 0.4080049 | 0.4931263 | 0.428411 | 0.30198815 | M32886_at | SRI Sorcin |
| 63 | Colorectal | 0.4006579 | 0.4925519 | 0.427544 | 0.30146047 | M76180_at | DDC Dopa decarboxylase (aromatic L-amino acid decarboxylase) |
| 64 | Colorectal | 0.4005646 | 0.4919929 | 0.427107 | 0.30097124 | X57348_s_a t | SFN Stratifin |
| 65 | Colorectal | 0.3981035 | 0.4917975 | 0.426731 | 0.3003053 | U73843_at | Epithelial-specific transcription factor ESE-1b (ESE-1) mRNA |
| 66 | Colorectal | 0.3958408 | 0.4912443 | 0.425976 | 0.29989058 | RC_AA4541 13_s_at | Human N-benzoyl-L-tyrosyl-p-amino-benzoic acid hydrolase alpha subunit (PPH alpha) mRNA, complete cds |
| 67 | Colorectal | 0.3938758 | 0.4906323 | 0.425471 | 0.29939732 | J04813_s_at | Cytochrome P450, subfamily IIIA (niphedipine oxidase), polypeptide 5 |

FIG. 4C

| # | Tissue | | | | Accession | Description |
|---|---|---|---|---|---|---|
| 68 | Colorectal | 0.3937155 | 0.4900717 | 0.424572 | 0.2987325 | RC_AA4043_38_at | EST: zv63a12.s1 Soares total fetus Nb2HF8 9w Homo sapiens cDNA clone 758302 3', mRNA sequence. (from Genbank) |
| 69 | Colorectal | 0.3925914 | 0.4894687 | 0.423703 | 0.298146 | Y09022_at | Not56-like protein |
| 70 | Colorectal | 0.3919728 | 0.4893894 | 0.423178 | 0.29754966 | AA443499_f_at | Keratin 8 |
| 71 | Colorectal | 0.390575 | 0.4882457 | 0.422642 | 0.29705 | RC_AA2428_19_at | Phospholipase C, beta 4 |
| 72 | Colorectal | 0.3899017 | 0.4871914 | 0.422398 | 0.2963615 | L77886_at | Protein tyrosine phosphatase mRNA |
| 73 | Colorectal | 0.3869763 | 0.4864893 | 0.421963 | 0.29599983 | RC_AA0244_82_at | EST: ze76a01.s1 Soares fetal heart NbHH19W Homo sapiens cDNA clone 364872 3', mRNA sequence. (from Genbank) |
| 74 | Colorectal | 0.3859425 | 0.4861084 | 0.421373 | 0.295498 | RC_AA4572_35_at | EST: aa91c07.s1 Stratagene fetal retina 937202 Homo sapiens cDNA clone 838668 3', mRNA sequence. (from Genbank) |
| 75 | Colorectal | 0.3857464 | 0.4858298 | 0.42087 | 0.2950936 | M63438_s_a_t | GLUL Glutamate-ammonia ligase (glutamine synthase) |
| 76 | Colorectal | 0.3840961 | 0.4853059 | 0.420502 | 0.2946229 | RC_AA1325_54_at | EST: zo20g08.s1 Stratagene colon (#937204) Homo sapiens cDNA clone 587486 3' similar to SW:MDCE_MOUSE P21271 MYOSIN-LIKE PROTEIN. ; mRNA sequence. (from Genbank) |
| 77 | Colorectal | 0.3831372 | 0.4846798 | 0.420144 | 0.29408625 | M38591_at | S100A10 S100 calcium-binding protein A10 (annexin II ligand, calpactin I, light polypeptide (p11)) |
| 78 | Colorectal | 0.3798282 | 0.4844075 | 0.419905 | 0.2937528 | U11862_s_a_t | ABP1 Amiloride binding protein 1 (amine oxidase (copper-containing)) |
| 79 | Colorectal | 0.379074 | 0.483671 | 0.419346 | 0.2933345 | X02874_at | OIAS (2'-5') oligoadenylate synthetase |
| 80 | Colorectal | 0.3790067 | 0.4823856 | 0.418853 | 0.29283714 | RC_AA1007_19_s_at | Non-specific cross reacting antigen |
| 81 | Colorectal | 0.3773377 | 0.4818361 | 0.418217 | 0.29226494 | X53587_at | ITGB4 Integrin beta-4 subunit |
| 82 | Colorectal | 0.37023305 | 0.4804687 | 0.41777 | 0.2918897 | RC_AA6085_79_s_at | Paired-like homeodomain transcription factor 2 |
| 83 | Colorectal | 0.3644778 | 0.4795685 | 0.417505 | 0.29132295 | H89551_s_a_t | EST: yw28e07.r1 Homo sapiens cDNA clone 253572 5'. (from Genbank) |
| 84 | Colorectal | 0.3638102 | 0.4783426 | 0.416981 | 0.29090998 | RC_AA3720_18_at | EST: EST83940 Parathyroid gland tumor I Homo sapiens cDNA 3' end, mRNA sequence. (from Genbank) |
| 85 | Colorectal | 0.3617361 | 0.4776064 | 0.416761 | 0.2904227 | S81914_at | IEX-1 |
| 86 | Colorectal | 0.3590579 | 0.4771514 | 0.416175 | 0.2899723 | RC_AA2629_43_at | EST: zr71a09.s1 Soares NhHMPu S1 Homo sapiens cDNA clone 668824 3', mRNA sequence. (from Genbank) |
| 87 | Colorectal | 0.3587444 | 0.4769289 | 0.415651 | 0.28951192 | D00017_at | ANX2 Annexin II (lipocortin II) |
| 88 | Colorectal | 0.3571036 | 0.4762957 | 0.415184 | 0.28911367 | M34516_r_at | Omega light chain protein 14.1 (Ig lambda chain related) gene, exon 3 |
| 89 | Colorectal | 0.355448 | 0.4760904 | 0.414942 | 0.28869188 | RC_AA2563_65_s_at | Homo sapiens mRNA expressed in thyroid gland |

FIG. 4D

| # | Type | | | | Description |
|---|---|---|---|---|---|
| 90 | Colorectal | 0.3529292 | 0.4758498 | 0.41475 | 0.2882023 U12595_at | Tumor necrosis factor type 1 receptor associated protein (TRAP1) mRNA, partial cds |
| 91 | Colorectal | 0.3526995 | 0.4754698 | 0.414083 | 0.28780922 Z74616_s_at | COL1A2 Collagen, type I, alpha-2 |
| 92 | Colorectal | 0.3494644 | 0.4751242 | 0.413578 | 0.28752562 X87767_at | CD89 gene, exon S1 |
| 93 | Colorectal | 0.3475012 | 0.4731991 | 0.412799 | 0.28716025 X57351_s_a t | RPS3 Ribosomal protein S3 |
| 94 | Colorectal | 0.3461418 | 0.4731492 | 0.412449 | 0.28667745 HT2324_at HG2239- | Potassium Channel Protein (Gb:Z11585) |
| 95 | Colorectal | 0.345997 | 0.4731211 | 0.412154 | 0.28619328 X54489_rna 1_at | Melanoma growth stimulatory activity (MGSA) |
| 96 | Colorectal | 0.3454008 | 0.472999 | 0.411772 | 0.28581673 M87789_s_a t | (hybridoma H210) anti-hepatitis A IgG variable region, constant region, complementarity-determining regions mRNA |
| 97 | Colorectal | 0.3453316 | 0.4727896 | 0.411117 | 0.2852261 X01630_at | ASS Argininosuccinate synthetase |
| 98 | Colorectal | 0.3439322 | 0.4719834 | 0.41076 | 0.28488582 L41351_at | Prostasin mRNA |
| 99 | Colorectal | 0.3426999 | 0.4712013 | 0.410335 | 0.28456652 M73489_at | Heat-stable enterotoxin receptor mRNA |
| 100 | Colorectal | 0.3426407 | 0.4704531 | 0.410025 | 0.2843162 X87342_at | Giant larvae homolog |
| 101 | Colorectal | 0.3403187 | 0.4703058 | 0.409773 | 0.28386307 L25081_at | ARH9 Aplysia ras-related homolog 9 |
| 102 | Colorectal | 0.3398675 | 0.4700763 | 0.408981 | 0.28356016 U79725_at | A33 antigen precursor mRNA |
| 103 | Colorectal | 0.3396676 | 0.4699301 | 0.408855 | 0.2831329 J05257_at | DPEP1 Dipeptidase 1 (renal) |
| 104 | Colorectal | 0.3390883 | 0.4898633 | 0.408365 | RC_AA1595 01_at | EST: zo72c02.s1 Stratagene pancreas (#937208) Homo sapiens cDNA clone 592418 3' similar to TR:G1199669 G1199669 PROTEIN KINASE C-BINDING PROTEIN BETA 15.; mRNA sequence. (from Genbank) |
| 105 | Colorectal | 0.3363895 | 0.4693615 | 0.408 | 0.28241677 M34309_at | ERBB3 V-erb-b2 avian erythroblastic leukemia viral oncogene homolog 3 (alternative products) |
| 106 | Colorectal | 0.335006 | 0.4687567 | 0.407503 | 0.28186926 J02854_at | 20-kDa myosin light chain (MLC-2) mRNA |
| 107 | Colorectal | 0.3345018 | 0.4683488 | 0.407073 | 0.28154293 D63486_at | KIAA0152 gene |
| 108 | Colorectal | 0.3338831 | 0.4679911 | 0.406902 | 0.28122646 M86808_at | Pyruvate dehydrogenase complex (PDHA2) gene |
| 109 | Colorectal | 0.3337304 | 0.4678407 | 0.406638 | 0.28081584 X06700_s_a 1_at | COL3A1 Alpha-1 type 3 collagen |
| 110 | Colorectal | 0.3322153 | 0.4665029 | 0.406117 | 0.2805408 X60382_rna 1_at | COL10A1 gene for collagen (alpha-1 type X) |
| 111 | Colorectal | 0.3313465 | 0.4662139 | 0.405724 | 0.28016385 S85655_at | PHB Prohibitin |
| 112 | Colorectal | 0.3309523 | 0.4660988 | 0.405248 | 0.27988875 L41349_at | PLCB4 Phospholipase C, beta 4 |
| 113 | Colorectal | 0.3309307 | 0.465658 | 0.405215 | 0.27941817 RC_AA1428 49_at | EST: zl40h02.s1 Soares pregnant uterus NbHPU Homo sapiens cDNA clone 504435 3', mRNA sequence. (from Genbank) |

FIG. 4E

| | | | | | | |
|---|---|---|---|---|---|---|
| 114 | Colorectal | 0.3291652 | 0.4649201 | 0.405046 | 0.27907494 | RC_AA4638 61_at | EST: zx97c05.s1 Soares NhHMPu S1 Homo sapiens cDNA clone 811688 3' similar to SW:RB25_RABIT P46629 RAS-RELATED PROTEIN RAB-25.;, mRNA sequence. (from Genbank) |
| 115 | Colorectal | 0.3265352 | 0.4645526 | 0.404425 | 0.27874827 | M82962_at | N-benzoyl-L-tyrosyl-p-amino-benzoic acid hydrolase alpha subunit (pPH alpha) mRNA |
| 116 | Colorectal | 0.3253648 | 0.4636824 | 0.404211 | 0.27784384 | M14218_at | ASL Arginosuccinate lyase |
| 117 | Colorectal | 0.3246478 | 0.4634886 | 0.403958 | 0.27809417 | X05409_at | ALDH2 Aldehyde dehydrogenase 2, mitochondrial |
| 118 | Colorectal | 0.3246213 | 0.4632541 | 0.402969 | 0.27778419 | Z29067_at | Nek3 mRNA for protein kinase |
| 119 | Colorectal | 0.3245217 | 0.4629836 | 0.40271 | 0.2775136 | X65614_at | S100P S100 calcium-binding protein P |
| 120 | Colorectal | 0.3238286 | 0.4625747 | 0.402542 | 0.2771918 | X97335_at | Kinase A anchor protein |
| 121 | Colorectal | 0.3229135 | 0.4622362 | 0.402366 | 0.27693212 | U27326_s_a t | FUT3 Alpha (1,3/1,4) fucosyltransferase |
| 122 | Colorectal | 0.322097 | 0.4621217 | 0.40199 | 0.27653858 | RC_AA6211 31_at | EST: af61a05.s1 Soares NhHMPu S1 Homo sapiens cDNA clone 1046480 3', mRNA sequence. (from Genbank) |
| 123 | Colorectal | 0.3202075 | 0.4618764 | 0.401657 | 0.27603555 | HG4115-HT4385_at | Olfactory Receptor Or17-210 |
| 124 | Colorectal | 0.3202045 | 0.4615341 | 0.401187 | 0.27578703 | AA147510_s _at | EST: zl50c12.r1 Soares pregnant uterus NbHPU Homo sapiens cDNA clone 505366 5', mRNA sequence. (from Genbank) |
| 125 | Colorectal | 0.3201549 | 0.4614542 | 0.400854 | 0.27553368 | RC_AA1506 19_at | EST: zl46a03.s1 Soares pregnant uterus NbHPU Homo sapiens cDNA clone 504940 3', mRNA sequence. (from Genbank) |
| 126 | Colorectal | 0.3193956 | 0.4609241 | 0.400546 | 0.27525836 | D38583_at | Calgizzarin |
| 127 | Colorectal | 0.3180397 | 0.4604949 | 0.400246 | 0.27491027 | U72882_s_a t | Interferon-induced leucine zipper protein (IFP35) mRNA, partial cds |
| 128 | Colorectal | 0.3174135 | 0.4602224 | 0.399963 | 0.27458924 | H78628_at | EST: yu26c05.r1 Homo sapiens cDNA clone 234920 5'. (from Genbank) |
| 129 | Colorectal | 0.3153257 | 0.4601988 | 0.3995575 | 0.27425927 | RC_AA4306 74_at | EST: zw26d12.s1 Soares ovary tumor NbHOT Homo sapiens cDNA clone 770423 3', mRNA sequence. (from Genbank) |
| 130 | Colorectal | 0.3151839 | 0.4598908 | 0.399164 | 0.2739331 | D00408_s_a t | CYP3A7 Cytochrome P450 IIIA7 (P450-HFLa) |
| 131 | Colorectal | 0.3145525 | 0.4597153 | 0.398937 | 0.27358411 | U90716_at | Cell surface protein HCAR mRNA |
| 132 | Colorectal | 0.3144143 | 0.459702 | 0.39867 | 0.27337873 | M34516_at | Omega light chain protein 14.1 (Ig lambda chain related) gene, exon 3 |
| 133 | Colorectal | 0.3142386 | 0.4593249 | 0.39844 | 0.27305278 | U56418_at | Lysophosphatidic acid acyltransferase-beta mRNA |
| 134 | Colorectal | 0.3121006 | 0.4590579 | 0.398107 | 0.27280134 | L40379_at | Thyroid receptor interactor (TRIP10) mRNA, 3' end of cds |
| 135 | Colorectal | 0.3117978 | 0.4584834 | 0.397758 | 0.27248895 | L20591_at | ANX3 Annexin III (lipocortin III) |
| 136 | Colorectal | 0.3106408 | 0.4581681 | 0.397164 | 0.27219298 | RC_AA2906 79_at | Selenium binding protein 1 |
| 137 | Colorectal | 0.3104196 | 0.4574646 | 0.396861 | 0.27192706 | X82153_at | CATHEPSIN K PRECURSOR |

FIG. 4F

| | | | | | |
|---|---|---|---|---|---|
| 138 | Colorectal | 0.3085437 | 0.4570568 | 0.396583 | 0.27174953 | AD000684_c ds1_at | LISCH7 gene (liver-specific bHLH-Zip transcription factor) extracted from Homo sapiens DNA from chromosome 19-cosmid R30879 containing USF2, genomic sequence |
| 139 | Colorectal | 0.3082213 | 0.4568923 | 0.396073 | 0.27174976 | L05144_at | PCK1 Phosphoenolpyruvate carboxykinase 1 (soluble) |
| 140 | Colorectal | 0.3080792 | 0.4566876 | 0.395992 | 0.27115154 | J03258_at | VDR Vitamin D (1,25- dihydroxyvitamin D3) receptor |
| 141 | Colorectal | 0.3077637 | 0.4562675 | 0.395825 | 0.2708481 | S80343_at | RARS Arginyl-tRNA synthetase |
| 142 | Colorectal | 0.3052971 | 0.4562675 | 0.395391 | 0.27061194 | RC_AA1868 97_at | EST: zp74c05.s1 Stratagene HeLa cell s3 937216 Homo sapiens cDNA clone 625928 3', mRNA sequence. (from Genbank) |
| 143 | Colorectal | 0.3052922 | 0.4560627 | 0.395019 | 0.2703553 | RC_AA4577 18_at | EST: zx87d04.s1 Soares ovary tumor NbHOT Homo sapiens cDNA clone 810727 3', mRNA sequence. (from Genbank) |
| 144 | Colorectal | 0.3033279 | 0.4555158 | 0.394745 | 0.27002838 | HG1980-HT2023_at | Tubulin, Beta 2 |
| 145 | Colorectal | 0.3019452 | 0.4554212 | 0.394414 | 0.26973784 | W27721_at | Homo sapiens KIAA0424 mRNA, partial cds |
| 146 | Colorectal | 0.3006995 | 0.4547286 | 0.394342 | 0.26945966 | X83618_at | Clone HSH1 HMG CoA synthase mRNA, partial cds |
| 147 | Colorectal | 0.2979128 | 0.4546229 | 0.394139 | 0.26923937 | U17760_rna 1_at | Laminin S B3 chain (LAMB3) gene |
| 148 | Colorectal | 0.2978341 | 0.4542575 | 0.393862 | 0.2688789777_at | RC_AA4275 | EST: zw54b05.s1 Soares total fetus Nb2HF8 9w Homo sapiens cDNA clone 773841 3', mRNA sequence. (from Genbank) |
| 149 | Colorectal | 0.2976009 | 0.4541483 | 0.393468 | 0.26853278 | X13839_at | LCAT Lecithin-cholesterol acyltransferase |
| 150 | Colorectal | 0.2964177 | 0.4539721 | 0.393296 | 0.26832888 | U47025_s_a t | PYGB Glycogen phosphorylase B (brain form) |
| 151 | Colorectal | 0.2960429 | 0.4536237 | 0.392712 | 0.26817298 | X07979_at | ITGB1 Integrin, beta 1 (fibronectin receptor, beta polypeptide, antigen CD29 includes MDF2, MSK12) |
| 152 | Colorectal | 0.2944463 | 0.4532687 | 0.392651 | 0.26798746 | RC_AA3992 26_at | Homo sapiens chromosome 19, cosmid R28784 |
| 153 | Colorectal | 0.2905926 | 0.4529879 | 0.392145 | 0.26754314 | C00038_s_a t | EST: HUMGS0003443, Human Gene Signature, 3'-directed cDNA sequence, mRNA sequence. (from Genbank) |
| 154 | Colorectal | 0.2944404 | 0.4526705 | 0.391782 | 0.26732546 | RC_AA4289 90_at | EST: zw19c12.s1 Soares ovary tumor NbHOT Homo sapiens cDNA clone 769750 3' similar to contains element MER22 repetitive element ;, mRNA sequence. (from Genbank) |
| 155 | Colorectal | 0.2900507 | 0.4525525 | 0.391414 | 0.26712176 | RC_AA6211 69_at | EST: af61h05.s1 Soares NhHMPu S1 Homo sapiens cDNA clone 1046553 3', mRNA sequence. (from Genbank) |
| 156 | Colorectal | 0.2897171 | 0.4518591 | 0.391375 | 0.26678312 | U17077_at | BENE mRNA, partial cds |
| 157 | Colorectal | 0.2893714 | 0.4517718 | 0.39108 | 0.2665894 | RC_AA3938 03_at | EST: zv64c05.s1 Soares total fetus Nb2HF8 9w Homo sapiens cDNA clone 7584408 3', mRNA sequence. (from Genbank) |
| 158 | Colorectal | 0.2889066 | 0.4512376 | 0.390989 | 0.2663623 | RC_AA4594 20_at | EST: zx89h11.s1 Soares ovary tumor NbHOT Homo sapiens cDNA clone 810981 3', mRNA sequence. (from Genbank) |
| 159 | Colorectal | 0.2880846 | 0.4511261 | 0.390634 | 0.2661315 | L15344_at | High molecular weight B cell growth factor mRNA sequence |
| 160 | Colorectal | 0.2879694 | 0.4509095 | 0.389813 | 0.26583395 | U34683_at | GSS Glutathione synthetase |
| 161 | Colorectal | 0.2874484 | 0.4503436 | 0.389714 | 0.26558763 | M34057_at | LTBP1 Latent transforming growth factor beta binding protein 1 |

FIG. 4G

| # | Tissue | | | | | Accession | Description |
|---|---|---|---|---|---|---|---|
| 162 | Colorectal | 0.2873897 | 0.4498679 | 0.38927 | 0.26524404 | M22960_at | PPGB Protective protein for beta-galactosidase (galactosialidosis) |
| 163 | Colorectal | 0.2868318 | 0.4493014 | 0.389084 | 0.26505816 | U18018_at | ETV4 Ets variant gene 4 (E1A enhancer-binding protein, E1AF) |
| 164 | Colorectal | 0.2863423 | 0.4492515 | 0.38901 | 0.26473483 | H89806_s_at | EST: yw29e12.r1 Homo sapiens cDNA clone 25367 8 5'. (from Genbank) |
| 165 | Colorectal | 0.286018 | 0.4488575 | 0.388819 | 0.2644313 | T62771_s_at | Homo sapiens nucleoplasmin-3 (NPM3) mRNA, complete cds |
| 166 | Colorectal | 0.2854559 | 0.4487699 | 0.388603 | 0.26419505 | X97675_rna1_at | Plakophilin 2a gene extracted from H.sapiens mRNA for plakophilin 2a and b |
| 167 | Colorectal | 0.2842944 | 0.4487521 | 0.388407 | 0.26396865 | X82125_at | HOK-2 mRNA for zinc finger protein |
| 168 | Colorectal | 0.2842561 | 0.4486165 | 0.388128 | 0.26379237 | RC_AA025352_at | EST: ze74h04.s1 Soares fetal heart NbHH19W Homo sapiens cDNA clone 364759 3', mRNA sequence. (from Genbank) |
| 169 | Colorectal | 0.284068 | 0.4482635 | 0.388014 | 0.26358816 | X81420_at | MLN137 mRNA |
| 170 | Colorectal | 0.2838166 | 0.4480006 | 0.387653 | 0.26333362 | U52100_at | XMP mRNA |
| 171 | Colorectal | 0.2830422 | 0.4479057 | 0.3874 | 0.26311921 | RC_AA394121_at | EST: zt52g05.s1 Soares ovary tumor NbHOT Homo sapiens cDNA clone 726008 3', mRNA sequence. (from Genbank) |
| 172 | Colorectal | 0.2826245 | 0.4473684 | 0.387096 | 0.26288193 | AA090778_a_at | EST: yy0416.seq.F Fetal heart, Lambda ZAP Express Homo sapiens cDNA 5', mRNA sequence. (from Genbank) |
| 173 | Colorectal | 0.2825118 | 0.446785 | 0.38669 | 0.26256222 | U01062_at | ITPR3 Inositol 1,4,5-triphosphate receptor, type 3 |
| 174 | Colorectal | 0.2821878 | 0.4466844 | 0.38613 | 0.26241365 | M14949_at | RAS-RELATED PROTEIN R-RAS |
| 175 | Colorectal | 0.2817878 | 0.4464111 | 0.385698 | 0.2621385 | X52022_at | RNA for type VI collagen alpha3 chain |
| 176 | Colorectal | 0.2797018 | 0.4460374 | 0.385651 | 0.26181865 | M98343_at | Amplaxin (EMS1) mRNA |
| 177 | Colorectal | 0.2795155 | 0.4457014 | 0.38521 | 0.26166266 | U09564_at | Serine kinase mRNA |
| 178 | Colorectal | 0.2794765 | 0.4454948 | 0.385072 | 0.26140434 | Z24727_at | TPM1 Tropomyosin alpha chain (skeletal muscle) |
| 179 | Colorectal | 0.2790382 | 0.4452392 | 0.384537 | 0.26109293 | M18079_at | FATTY ACID-BINDING PROTEIN, INTESTINAL |
| 180 | Colorectal | 0.2784429 | 0.4450501 | 0.384364 | 0.26088074 | U89942_at | Lysyl oxidase-related protein (WS9-14) mRNA |
| 181 | Colorectal | 0.2777302 | 0.4450202 | 0.384312 | 0.26068738 | HG2797-HT2906_s_at | Clathrin, Light Polypeptide B, Alt. Splice 2 |
| 182 | Colorectal | 0.2775453 | 0.4446172 | 0.383921 | 0.26043087 | W28414_at | EST: 46g7 Human retina cDNA randomly primed sublibrary Homo sapiens cDNA, mRNA sequence. (from Genbank) |
| 183 | Colorectal | 0.2760558 | 0.4445678 | 0.383729 | 0.2602868 | L07548_at | ACY1 Aminoacylase 1 |
| 184 | Colorectal | 0.2758841 | 0.4436831 | 0.383468 | 0.25991017 | D79206_s_at | SDC4 Syndecan 4 (amphiglycan, ryudocan) |
| 185 | Colorectal | 0.2758695 | 0.4432321 | 0.383229 | 0.2596775 | M27826_at | Endogenous retroviral protease mRNA |
| 186 | Colorectal | 0.2744746 | 0.4427031 | 0.382959 | 0.25948972 | X14253_s_at | TDGF1 Teratocarcinoma-derived growth factor 1 |

FIG. 4H

| # | Type | | | | ID | Description |
|---|---|---|---|---|---|---|
| 187 | Colorectal | 0.27738329 | 0.4426029 | 0.382903 | 0.259229181 U79549_s_at ma | Human Xp22 BAC CT-285I15 (from CalTech/Research Genetics), PAC RPCI1-27C22 (from Roswell Park Cancer Center), and Cosmid U35B5 (from Lawrence Livermore), complete sequence. (from Genbank) |
| 188 | Colorectal | 0.27723998 | 0.4424643 | 0.382794 | 0.25900492 RC_AA4820 15_at | EST: zu98d08.s1 NCI_CGAP_GCB1 Homo sapiens cDNA clone IMAGE:746031 3', mRNA sequence. (from Genbank) |
| 189 | Colorectal | 0.2716996 | 0.4423659 | 0.382073 | 0.2587583 U29091_at | Selenium-binding protein (hSBP) mRNA |
| 190 | Colorectal | 0.2699324 | 0.4422453 | 0.362073 | 0.25852776 AA479990_a t | EST: zv18a05.r1 Soares NhHMPu S1 Homo sapiens cDNA clone 753968 5', mRNA sequence. (from Genbank) |
| 191 | Colorectal | 0.2699285 | 0.4420108 | 0.38191 | 0.25829273 RC_AA1437 63_at | EST: zo31d08.s1 Stratagene colon (#937204) Homo sapiens cDNA clone 588495 3', mRNA sequence. (from Genbank) |
| 192 | Colorectal | 0.2698754 | 0.4420007 | 0.381861 | 0.2580638 AA056958_a t | Tumor suppressing subtransferable candidate 3 |
| 193 | Colorectal | 0.2696778 | 0.441814 | 0.381845 | 0.25789955 RC_AA4044 87_at | EST: zw38a06.s1 Soares total fetus Nb2HF8 9w Homo sapiens cDNA clone 772306 3', mRNA sequence. (from Genbank) |
| 194 | Colorectal | 0.2695739 | 0.4415602 | 0.381413 | 0.25747073 D79999_at | KIAA0177 gene, partial cds |
| 195 | Colorectal | 0.2692404 | 0.4415602 | 0.381157 | 0.25727057 D55696_at | Cysteine protease |
| 196 | Colorectal | 0.2686886 | 0.4413927 | 0.380887 | 0.2571191 AA298786_a t | EST: EST114389 Activated T-cells I Homo sapiens cDNA 5' end, mRNA sequence. (from Genbank) |
| 197 | Colorectal | 0.2669644 | 0.4412214 | 0.380592 | 0.2569419 H46617_at | Yp19h01.r1 Homo sapiens cDNA clone 187921 5'. (from Genbank) |
| 198 | Colorectal | 0.2655602 | 0.4409944 | 0.380361 | 0.25677538 AA0774933_a t | Zm85b07.r1 Stratagene ovarian cancer (#937219) Homo sapiens cDNA clone 544693 5' similar to gb:J04794 ALCOHOL DEHYDROGENASE (HUMAN);. mRNA sequence. (from Genbank) |
| 199 | Colorectal | 0.26581 | 0.44089 | 0.38018 | 0.25657907 RC_AA4259 06_at | EST: zw17h06.s1 Soares ovary tumor NbHOT Homo sapiens cDNA clone 769595 3', mRNA sequence. (from Genbank) |
| 200 | Colorectal | 0.2637967 | 0.4408184 | 0.380009 | 0.25637132 AA215333_a t | EST: zr94d06.r1 NCI_CGAP_GCB1 Homo sapiens cDNA clone IMAGE:683339 5', mRNA sequence. (from Genbank) |
| 201 | Colorectal | 0.2629061 | 0.4406756 | 0.379693 | 0.25609446 M77140_at | GALN Galanin |
| 202 | Colorectal | 0.26272252 | 0.4403952 | 0.379252 | 0.255912 L16842_at | UQCRC1 Ubiquinol-cytochrome c reductase core protein I |
| 203 | Colorectal | 0.2626974 | 0.4401701 | 0.378853 | 0.25564706 X78687_at | G9 gene encoding sialidase |
| 204 | Colorectal | 0.26179 | 0.4401267 | 0.378731 | 0.25546265 U24169_at | JTV-1 (JTV-1) mRNA |
| 205 | Colorectal | 0.2610115 | 0.4400005 | 0.378718 | 0.25539052 X74039_at | Variant urokinase plasminogen activator receptor (uPAR2) mRNA, partial cds |
| 206 | Colorectal | 0.2615691 | 0.4393005 | 0.378664 | 0.25512356 M29335_at | MHC class II DO-alpha mRNA, partial cds |
| 207 | Colorectal | 0.2610115 | 0.4384362 | 0.378569 | 0.25493538 X02761_s_a t | FN1 Fibronectin 1 |
| 208 | Colorectal | 0.2609527 | 0.4384202 | 0.378164 | 0.25460264 L42176_at | (clone 35.3) DRAL mRNA |

FIG. 4I

| | | | | | |
|---|---|---|---|---|---|
| 209 | Colorectal | 0.2599319 | 0.4384187 | 0.377939 | 0.25448507 | R39374_at | EST: yh95a06.r1 Homo sapiens cDNA clone 137458 5' similar to gb:M55542 INTERFERON-INDUCED GUANYLATE-BINDING PROTEIN 1 (HUMAN);. (from Genbank) |
| 210 | Colorectal | 0.2595176 | 0.4380884 | 0.377698 | 0.25419658 | X90579_s_at | H.sapiens DNA for cyp related pseudogene |
| 211 | Colorectal | 0.2590499 | 0.4379003 | 0.377596 | 0.25403702 | X59434_at | TST Thiosulfate sulfurtransferase (rhodanese) |
| 212 | Colorectal | 0.2578857 | 0.4377968 | 0.377096 | 0.25384232 | X82224_at | Glutamine transaminase K |
| 213 | Colorectal | 0.2567741 | 0.4373914 | 0.377075 | 0.25355202 | M11147_at | FTL Ferritin, light polypeptide |
| 214 | Colorectal | 0.2558351 | 0.4373853 | 0.376938 | 0.25339845 | N94824_at | Homo sapiens Chromosome 16 BAC clone CIT987SK-A-67A1 |
| 215 | Colorectal | 0.2546034 | 0.4373848 | 0.376324 | 0.25324994 | J04444_at | CYC1 Cytochrome c-1 |
| 216 | Colorectal | 0.2538757 | 0.4372188 | 0.376225 | 0.25295016 | RC_AA0529 59_at | EST: zl70b07.s1 Stratagene colon (#937204) Homo sapiens cDNA clone 509941 3' similar to TR:G762826 G762826 PHOSPHOLIPASE C BETA 4.;. mRNA sequence. (from Genbank) |
| 217 | Colorectal | 0.2526687 | 0.4369767 | 0.375947 | 0.25274342 | M33772_s_at | TNNC2 Troponin C2 (fast skeletal) |
| 218 | Colorectal | 0.2526022 | 0.4368653 | 0.37592 | 0.25253441 | M22382_at | HSPD1 Heat shock 60 kD protein 1 (chaperonin) |
| 219 | Colorectal | 0.2525422 | 0.4368289 | 0.375285 | 0.25236521 | HG1102-HT1102_at | Ras-Related C3 Botulinum Toxin Substrate |
| 220 | Colorectal | 0.2524923 | 0.4368103 | 0.375253 | 0.25223481 | D86956_at | KIAA0201 gene |
| 221 | Colorectal | 0.2523198 | 0.4367228 | 0.375132 | 0.25207108 | RC_AA3982 76_at | EST: zt60c07.s1 Soares testis NHT Homo sapiens cDNA clone 726732 3'. mRNA sequence. (from Genbank) |
| 222 | Colorectal | 0.2513914 | 0.436644 | 0.374928 | 0.25187638 | RC_AA1612 92_s_at | Interferon, alpha-inducible protein 27 |
| 223 | Colorectal | 0.2509154 | 0.4366248 | 0.374735 | 0.25159131 | R33301_at | EST: yh81g01.r1 Homo sapiens cDNA clone 136176 5' similar to contains MSR1 repetitive element;. (from Genbank) |
| 224 | Colorectal | 0.2504406 | 0.4364291 | 0.374661 | 0.25143181 | M12125_at | Skeletal beta-tropomyosin |
| 225 | Colorectal | 0.2499405 | 0.4363218 | 0.374254 | 0.25130941 | M62403_s_at | IGFBP4 Insulin-like growth factor-binding protein 4 |
| 226 | Colorectal | 0.2497276 | 0.4345914 | 0.373718 | 0.25105903 | M17466_at | F12 Coagulation factor XII (Hageman factor) |
| 227 | Colorectal | 0.2493821 | 0.4345358 | 0.373431 | 0.25075394 | D49372_s_a_t | SCYA11 Small inducible cytokine A11 (eotaxin) |
| 228 | Colorectal | 0.2487971 | 0.4343934 | 0.373305 | 0.25066942 | AA090632_at | EST: y1095.scq.F Fetal heart, Lambda ZAP Express Homo sapiens cDNA 5';. mRNA sequence. (from Genbank) |
| 229 | Colorectal | 0.2482375 | 0.4343443 | 0.373143 | 0.25029984 | L77567_s_at | RPS11 Ribosomal protein S11 |
| 230 | Colorectal | 0.2482352 | 0.4338554 | 0.373037 | 0.2501696 | Z49989_at | Smoothelin |
| 231 | Colorectal | 0.2473214 | 0.4334525 | 0.372948 | 0.25012305 | L04490_at | (clone CC6) NADH-ubiquinone oxidoreductase subunit mRNA, 3' end cds |

FIG. 4J

| | | | | | |
|---|---|---|---|---|---|
| 232 | Colorectal | 0.2464403 | 0.4333727 | 0.372917 | 0.24978833 J03464_s_at | Collagen, type I, alpha 2 |
| 233 | Colorectal | 0.245648 | 0.4332904 | 0.372874 | 0.24959934 U73514_at | Short-chain alcohol dehydrogenase (XH98G2) mRNA |
| 234 | Colorectal | 0.2454265 | 0.4332613 | 0.372658 | 0.24930625 Z36714_at | CCNF Cyclin F |
| 235 | Colorectal | 0.2437817 | 0.4329935 | 0.372345 | 0.24919015 X63573_at | ARSE mRNA |
| 236 | Colorectal | 0.2435387 | 0.4329534 | 0.372097 | 0.24900725 U51711_at | DESMOCOLLIN 2A/BB PRECURSOR |
| 237 | Colorectal | 0.2432521 | 0.432789 | 0.371909 | 0.24886379 U27655_at | RGP3 mRNA |
| 238 | Colorectal | 0.2432249 | 0.43276 | 0.371716 | 0.24866241 Y00503_at | KRT19 Keratin 19 |
| 239 | Colorectal | 0.2417218 | 0.4325721 | 0.37156 | 0.24847391 RC_AA4045 04_at | EST: zw38t09.s1 Soares total fetus Nb2HF8 9w Homo sapiens cDNA clone 772313 3', mRNA sequence. (from Genbank) |
| 240 | Colorectal | 0.2417041 | 0.4324356 | 0.371416 | 0.2482578 H87671_at | Yw15d02.r1 Homo sapiens cDNA clone 252291 5'. (from Genbank) |
| 241 | Colorectal | 0.2415092 | 0.4319491 | 0.371012 | 0.24800336 RC_AA4632 34_at | KIAA0792 gene product |
| 242 | Colorectal | 0.2408507 | 0.4318435 | 0.370947 | 0.24770266 RC_AA0745 14_at | EST: zm17f04.s1 Stratagene pancreas (#937208) Homo sapiens cDNA clone 525919 3', mRNA sequence. (from Genbank) |
| 243 | Colorectal | 0.2404307 | 0.4316835 | 0.370675 | 0.24766117 RC_AA4027 20_at | EST: zu47e05.s1 Soares ovary tumor NbHOT Homo sapiens cDNA clone 741152 3', mRNA sequence. (from Genbank) |
| 244 | Colorectal | 0.2398451 | 0.4314801 | 0.370532 | 0.24746579 RC_D20426_at | EST: Human HL60 3'directed MboI cDNA, HUMGS01400, clone pm2764, mRNA sequence. (from Genbank) |
| 245 | Colorectal | 0.2390578 | 0.4313634 | 0.370171 | 0.24717106 AA376468_a t | EST: EST88890 HSC172 cells II Homo sapiens cDNA 5' end, mRNA sequence. (from Genbank) |
| 246 | Colorectal | 0.2384494 | 0.4312794 | 0.370054 | 0.24704532 L06499_at | RPL37A Ribosomal protein L37a |
| 247 | Colorectal | 0.237877 | 0.4309956 | 0.369792 | 0.24696982 M11437_cds 2_at | KNG gene (kininogen) extracted from Human kininogen gene |
| 248 | Colorectal | 0.2378171 | 0.4309435 | 0.369634 | 0.24669023 X63422_at | ATP5D ATP synthase, H+ transporting, mitochondrial F1 complex, delta subunit |
| 249 | Colorectal | 0.2378171 | 0.430421 | 0.369634 | 0.24649552 X63422_at-2 | ATP synthase, H+ transporting, mitochondrial F1 complex, delta subunit |
| 250 | Colorectal | 0.237445 | 0.4297348 | 0.36938 | 0.24822984 U09278_at | Fibroblast activation protein mRNA |
| 251 | Colorectal | 0.2367845 | 0.4294908 | 0.369047 | 0.24601284 RC_AA2435 82_at | Hemoglobin, gamma A |
| 252 | Colorectal | 0.236753 | 0.4294153 | 0.368688 | 0.24585667 RC_AA4017 63_at | EST: zl53g11.s1 Soares ovary tumor NbHOT Homo sapiens cDNA clone 726116 3', mRNA sequence. (from Genbank) |
| 253 | Colorectal | 0.236711 | 0.4292812 | 0.368341 | 0.24566157 X17093_at | HLA CLASS I HISTOCOMPATIBILITY ANTIGEN, F ALPHA CHAIN PRECURSOR |
| 254 | Colorectal | 0.2356256 | 0.4289072 | 0.368288 | 0.24541639 L25286_s_at | COL15A1 Collagen, type XV, alpha 1 |
| 255 | Colorectal | 0.2355853 | 0.4283096 | 0.368126 | 0.24515241 RC_AA1564 50_at | EST: zl51f03.s1 Soares pregnant uterus NbHPU Homo sapiens cDNA clone 505469 3', mRNA sequence. (from Genbank) |

FIG. 4K

| # | Type | | | | ID | Description |
|---|---|---|---|---|---|---|
| 256 | Colorectal | 0.2355099 | 0.4282645 | 0.368043 | 0.24499446 | AA454908_s_at | EST: zx79c12.r1 Soares ovary tumor NbHOT Homo sapiens cDNA clone 809974 5', mRNA sequence. (from Genbank) |
| 257 | Colorectal | 0.235389 | 0.4282106 | 0.368027 | 0.24482329 | U66674_at | Canicular multispecific organic anion transporter |
| 258 | Colorectal | 0.2353334 | 0.4281947 | 0.367738 | 0.24457671 | D79997_at | KIAA0175 gene |
| 259 | Colorectal | 0.2351394 | 0.4280374 | 0.367488 | 0.24429834 | M34423_at | GLB1 Beta-D-galactosidase |
| 260 | Colorectal | 0.2346506 | 0.4277001 | 0.367443 | 0.24400778 | RC_AA477106_s_at | D21S2056E, novel nuclear protein 1 |
| 261 | Colorectal | 0.2344479 | 0.4276524 | 0.367328 | 0.24392831 | RC_AA479044_s_at | EST: zu36d09.s1 Soares ovary tumor NbHOT Homo sapiens cDNA clone 740081 3', mRNA sequence. (from Genbank) |
| 262 | Colorectal | 0.234363 | 0.4270255 | 0.367017 | 0.24378608 | X15882_at | COL6A2 Collagen, type VI, alpha 2 |
| 263 | Colorectal | 0.2343158 | 0.4270182 | 0.366612 | 0.24356449 | AA431505_at | Homo sapiens mRNA for putative Sqv-7-like protein, partial |
| 264 | Colorectal | 0.2310646 | 0.4259951 | 0.366507 | 0.243444 | M61764_at | TUBG Tubulin, gamma polypeptide |
| 265 | Colorectal | 0.2328659 | 0.4269734 | 0.36626 | 0.24322260 | RC_AA458899_at | EST: zx88d07.s1 Soares ovary tumor NbHOT Homo sapiens cDNA clone 810829 3', mRNA sequence. (from Genbank) |
| 266 | Colorectal | 0.2326066 | 0.426753 | 0.366193 | 0.24302162 | X05610_at | COL4A2 Collagen, type IV, alpha 2 |
| 267 | Colorectal | 0.2325791 | 0.4266124 | 0.366087 | 0.24289443 | RC_AA157814_at | EST: zo35h03.s1 Stratagene colon (#937204) Homo sapiens cDNA clone 588917 3', mRNA sequence. (from Genbank) |
| 268 | Colorectal | 0.2313208 | 0.4262463 | 0.365986 | 0.24273828 | RC_AA412284_s_at | Human poliovirus receptor mRNA, clone H20A |
| 269 | Colorectal | 0.2312584 | 0.4261007 | 0.365818 | 0.24250843 | RC_AA464935_at | Homo sapiens mRNA for KIAA0517 protein, partial cds |
| 270 | Colorectal | 0.2308645 | 0.4260578 | 0.365768 | 0.24237236 | X51755_cds5_s_at | Ig light-chain, partial Ke-Oz- polypeptide; Author-given protein sequence is in conflict with the conceptual translation gene extracted from Human lambda-immunoglobulin constant region complex (germline) |
| 271 | Colorectal | 0.2305032 | 0.4258721 | 0.365586 | 0.24222004 | RC_AA054561_at | EST: zk83h03.s1 Soares pregnant uterus NbHPU Homo sapiens cDNA clone 489461 3', mRNA sequence. (from Genbank) |
| 272 | Colorectal | 0.2292832 | 0.4258433 | 0.365569 | 0.24206237 | M3445565_at | EST: ab04a05.s1 Stratagene fetal retina 937202 Homo sapiens cDNA clone 839792 3', mRNA sequence. (from Genbank) |
| 273 | Colorectal | 0.2292013 | 0.4257856 | 0.365314 | 0.24192263 | M34455_at | IDO Indole 2,3-dioxygenase |
| 274 | Colorectal | 0.2291508 | 0.4255351 | 0.365299 | 0.24173522 | U64197_at | CC chemokine LARC precursor |
| 275 | Colorectal | 0.2271702 | 0.425261 | 0.364932 | 0.24157457 | D28124_at | Unknown product |
| 276 | Colorectal | 0.2267513 | 0.4250637 | 0.364844 | 0.24143389 | RC_AA470145_at | EST: zu11f02.s1 Soares testis NHT Homo sapiens cDNA clone 731547 3', mRNA sequence. (from Genbank) |
| 277 | Colorectal | 0.2259522 | 0.4248984 | 0.364784 | 0.24119541 | U91316_at | Acyl-CoA thioester hydrolase mRNA |
| 278 | Colorectal | 0.2252225 | 0.4247543 | 0.364533 | 0.24092536 | M54995_at | PPBP Connective tissue activation peptide III |
| 279 | Colorectal | 0.2250794 | 0.424666 | 0.364342 | 0.24080605 | RC_AA010530_at | Human BAC clone GS025M02 from 7q21-q22 |

FIG. 4L

| | | | | | |
|---|---|---|---|---|---|
| 280 | Colorectal | 0.2244888 | 0.4244825 | 0.364282 | 0.24061918 | U46692_rna 1_at | Cystatin B gene |
| 281 | Colorectal | 0.2243395 | 0.4242902 | 0.364256 | 0.24049804 | U16799_s_a t | Na,K-ATPase beta-1 subunit mRNA |
| 282 | Colorectal | 0.2237412 | 0.4242748 | 0.364061 | 0.24029635 | RC_AA4212 68_at | Homo sapiens putative tumor suppressor protein (101F6) mRNA, complete cds |
| 283 | Colorectal | 0.2237204 | 0.4241056 | 0.363926 | 0.240143 | AF001548_r na1_at | 815A9.1 gene (myosin heavy chain) extracted from Homo sapiens chromosome 16 BAC clone CIT987SK-815A9 complete sequence |
| 284 | Colorectal | 0.2236298 | 0.4240391 | 0.363811 | 0.24003637 | M55131_at | CFTR Cystic fibrosis conductance regulator |
| 285 | Colorectal | 0.2229676 | 0.4240391 | 0.363704 | 0.23991685 | S65738_at | Actin depolymerizing factor [human, fetal brain, mRNA, 1452 nt] |
| 286 | Colorectal | 0.2229479 | 0.4240344 | 0.363612 | 0.23977596 | RC_AA4525 98_s_at | Genethonin 1 |
| 287 | Colorectal | 0.2224907 | 0.4238209 | 0.363478 | 0.2396546 | U80184_rna 1_at | FLII gene |
| 288 | Colorectal | 0.2217537 | 0.4238209 | 0.363226 | 0.23938963 | L04751_at | CYP4A11 Cytochrome P450, subfamily IVA, polypeptide 11 |
| 289 | Colorectal | 0.2212446 | 0.4237679 | 0.363004 | 0.2392877 | RC_AA1914 95_at | EST: zp88e03.s1 Stratagene HeLa cell s3 937216 Homo sapiens cDNA clone 627292 3' similar to contains Alu repetitive element;, mRNA sequence. (from Genbank) |
| 290 | Colorectal | 0.2212011 | 0.4236443 | 0.362807 | 0.23915909 | L09708_at | C2 Complement component C2 |
| 291 | Colorectal | 0.2201314 | 0.4234047 | 0.362739 | 0.23889286 | L13210_at | Mac-2 binding protein mRNA |
| 292 | Colorectal | 0.2199767 | 0.4232847 | 0.362534 | 0.23878038 | J02645_at | EIF2A Eukaryotic translation initiation factor 2A |
| 293 | Colorectal | 0.2197534 | 0.4230354 | 0.362369 | 0.2385777 | M16364_s_a t | CKB Creatine kinase B |
| 294 | Colorectal | 0.2195442 | 0.4229702 | 0.362228 | 0.23831792 | HG3517-HT3711_at | Alpha-1-Antitrypsin, 5' End |
| 295 | Colorectal | 0.2191761 | 0.4229702 | 0.362136 | 0.23813273 | U03100_at | CTNNA1 Catenin (cadherin-associated protein), alpha 1 (102kD) |
| 296 | Colorectal | 0.2174458 | 0.4229226 | 0.361876 | 0.23799877 | U53445_at | Ovarian cancer downregulated myosin heavy chain homolog (Doc1) mRNA |
| 297 | Colorectal | 0.2171963 | 0.4227956 | 0.361476 | 0.23774703 | W25933_at | EST: 15b2 Human retina cDNA randomly primed sublibrary Homo sapiens cDNA, mRNA sequence. (from Genbank) |
| 298 | Colorectal | 0.2170434 | 0.4227762 | 0.361382 | 0.23764469 | RC_AA4486 63_at | EST: zx10e03.s1 Soares total fetus Nb2HF8 9w Homo sapiens cDNA clone 786076 3'; mRNA sequence. (from Genbank) |
| 299 | Colorectal | 0.2166066 | 0.4226796 | 0.361363 | 0.23748411 | RC_AA1864 27_s_at | Human hTRIP (hTRIP) mRNA, complete cds |
| 300 | Colorectal | 0.213646 | 0.4225038 | 0.36121 | 0.23731422 | RC_AA0558 09_at | EST: zl76c05.s1 Stratagene colon (#937204) Homo sapiens cDNA clone 510536 3'; mRNA sequence. (from Genbank) |
| 301 | Colorectal | 0.2160157 | 0.4223527 | 0.361095 | 0.23715094 | RC_AA5048 14_at | Ribosomal protein L14 |

FIG. 4M

| # | Tissue | | | | ID | Description |
|---|---|---|---|---|---|---|
| 302 | Colorectal | 0.215741 | 0.4220851 | 0.360948 | RC_AA2623 51_f_at | EST: zr44g03.s1 Soares NhHMPu S1 Homo sapiens cDNA clone 666292 3', mRNA sequence. (from Genbank) |
| 303 | Colorectal | 0.2156857 | 0.4220488 | 0.360862 | M63391_rna1_at | Desmin gene |
| 304 | Colorectal | 0.2156719 | 0.422039 | 0.360712 | 0.23663089 Z35307_at | ECE1 Endothelin converting enzyme 1 |
| 305 | Colorectal | 0.2155447 | 0.4217475 | 0.360675 | 0.23642176 U21049_at | DD96 mRNA |
| 306 | Colorectal | 0.2154369 | 0.4213895 | 0.360544 | 0.23622829 D16217_at | CAST Calpastatin |
| 307 | Colorectal | 0.2138341 | 0.4213895 | 0.360115 | 0.2360938 M97936_at | SIGNAL TRANSDUCER AND ACTIVATOR OF TRANSCRIPTION 1-ALPHA/BETA |
| 308 | Colorectal | 0.2137431 | 0.4211144 | 0.360033 | RC_AA2241 62_at | EST: zr15d05.s1 Stratagene NT2 neuronal precursor 937230 Homo sapiens cDNA clone 663465 3', mRNA sequence. (from Genbank) |
| 309 | Colorectal | 0.2128677 | 0.4206799 | 0.359827 | 0.23592868 X52003_at | TFF1 Trefoil factor 1 (breast cancer, estrogen-inducible sequence expressed in) |
| 310 | Colorectal | 0.2127371 | 0.4205355 | 0.359526 | 0.23569235 AA372630_s_at | Homo sapiens GW112 protein (GW112) mRNA, complete cds |
| 311 | Colorectal | 0.2123357 | 0.4205039 | 0.359493 | 0.23553297 U66359_at | T54 protein (T54) mRNA |
| 312 | Colorectal | 0.2112828 | 0.4203111 | 0.359427 | 0.23532106 X99133_at | NGAL gene |
| 313 | Colorectal | 0.2110833 | 0.4202541 | 0.359337 | 0.23521934 U13219_at | Forkhead protein FREAC-1 mRNA |
| 314 | Colorectal | 0.2107744 | 0.4201149 | 0.359146 | 0.23504303 HG4058-HT4328_at | Oncogene Aml1-Evi-1, Fusion Activated |
| 315 | Colorectal | 0.2107521 | 0.4200316 | 0.358913 | W38597_i_at | EST: zb20c11.r1 Soares fetal lung NbHL19W Homo sapiens cDNA clone 302612 5', mRNA sequence. (from Genbank) |
| 316 | Colorectal | 0.2106079 | 0.419534 | 0.358858 | 0.23470141 AA295819_s_at | EST: EST101121 Thymus III Homo sapiens cDNA 5' end, mRNA sequence. (from Genbank) |
| 317 | Colorectal | 0.2093179 | 0.4193819 | 0.358727 | RC_AA0019 36_at | EST: zh86b04.s1 Soares fetal liver spleen 1NFLS S1 Homo sapiens cDNA clone 428143 3', mRNA sequence. (from Genbank) |
| 318 | Colorectal | 0.2082233 | 0.4186259 | 0.358555 | 0.23423612 HG1153-HT1153_at | Nucleoside Diphosphate Kinase Nnn23-H2s |
| 319 | Colorectal | 0.2074357 | 0.4184691 | 0.3584 | 0.23401211 N76904_at | Occludin |
| 320 | Colorectal | 0.2073005 | 0.4177268 | 0.358214 | 0.23385955 D45906_at | LIMK-2 |
| 321 | Colorectal | 0.2071615 | 0.417504 | 0.358084 | 0.23338088 U63824_at | Transcription factor RTEF-1 (RTEF1) mRNA |
| 322 | Colorectal | 0.20716115 | 0.4174936 | 0.3578 | 0.23372023 U63824_at-2 | TEA domain family member 4 |
| 323 | Colorectal | 0.2067716 | 0.4173119 | 0.357707 | 0.23361337 W78726_at | EST: zh51h04.r1 Soares fetal liver spleen 1NFLS S1 Homo sapiens cDNA clone 415639 5', mRNA sequence. (from Genbank) |
| 324 | Colorectal | 0.2065829 | 0.4172798 | 0.3577 | 0.23349696 U61262_at | NEO1 Neogenin (chicken) homolog 1 |

FIG. 4N

| | | | | | | |
|---|---|---|---|---|---|---|
| 325 | Colorectal | 0.2064035 | 0.4172628 | 0.357524 | RC_AA1133 87_at | EST: zn70g06.s1 Stratagene HeLa cell s3 937216 Homo sapiens cDNA clone 563578 3', mRNA sequence. (from Genbank) |
| 326 | Colorectal | 0.2062532 | 0.4169118 | 0.357353 | 0.2331365 U67963_at | Lysophospholipase homolog (HU-K5) mRNA |
| 327 | Colorectal | 0.2062282 | 0.4164088 | 0.357309 | 0.23298869 722533_s_at | Activin A receptor type II-like 1 |
| 328 | Colorectal | 0.2060922 | 0.4161472 | 0.357238 | 0.23277271 L12350_at | THBS2 Thrombospondin 2 |
| 329 | Colorectal | 0.2056696 | 0.4159612 | 0.356886 | 0.23265688 X02419_rna 1_s_at | UPA gene |
| 330 | Colorectal | 0.2052573 | 0.41591195 | 0.356819 | 0.2325496 U78581_s_a t | Human type I phosphatidylinositol-4-phosphate 5-kinase beta (STM7) mRNA, partial cds |
| 331 | Colorectal | 0.2050409 | 0.4158197 | 0.356782 | 0.23249404 X78342_at | (clone PK2J) CDC2-related protein kinase (PISSLRE) mRNA |
| 332 | Colorectal | 0.2049733 | 0.4156097 | 0.356451 | 0.23237406 N56451_at | Human zinc-finger domain-containing protein mRNA, partial cds |
| 333 | Colorectal | 0.2048363 | 0.4151186 | 0.356439 | 0.23220895 M20471_at | CLTA Clathrin light chain A |
| 334 | Colorectal | 0.2039772 | 0.414631 | 0.356359 | AA422029_a 0.23198506 t | EST: zv26g08.r1 Soares NhHMPu S1 Homo sapiens cDNA clone 754814 5', mRNA sequence. (from Genbank) |
| 335 | Colorectal | 0.2038375 | 0.4145514 | 0.356263 | 0.23184581 X53586_rna 1_at | Integrin alpha 6 (or alpha E) protein gene extracted from Human mRNA for integrin alpha 6 |
| 336 | Colorectal | 0.2036814 | 0.4144842 | 0.356139 | 0.23161034 U28249_at | MAT8 protein |
| 337 | Colorectal | 0.2032533 | 0.4142972 | 0.355944 | 0.23149377 X57522_at | TAP1 Transporter 1, ABC (ATP binding cassette) |
| 338 | Colorectal | 0.2031472 | 0.4142688 | 0.355504 | AA129547_a 0.23135382 t | EST: zn83f01.r1 Stratagene lung carcinoma 937218 Homo sapiens cDNA clone 564793 5', mRNA sequence. (from Genbank) |
| 339 | Colorectal | 0.2026946 | 0.4140218 | 0.355413 | 0.23124467 C01782_at | EST: HUMGS0003737, Human Gene Signature, 3'-directed cDNA sequence, mRNA sequence. (from Genbank) |
| 340 | Colorectal | 0.2024833 | 0.4138213 | 0.354958 | 0.23104405 X86163_at | BDKRB2 Bradykinin receptor B2 |
| 341 | Colorectal | 0.2022269 | 0.4137722 | 0.354941 | 0.23096722 W38597_s_ at | EST: zb20c11.r1 Soares fetal lung NbHL19W Homo sapiens cDNA clone 302612 5', mRNA sequence. (from Genbank) |
| 342 | Colorectal | 0.202178 | 0.4136169 | 0.35492 | RC_AA4294 0.23090212 72_at | EST: zw34b09.s1 Soares ovary tumor NbHOT Homo sapiens cDNA clone 771161 3', mRNA sequence. (from Genbank) |
| 343 | Colorectal | 0.201821 | 0.4133649 | 0.354737 | RC_AA6217 0.23067464 14_at | EST: af54e12.s1 Soares total fetus Nb2HF8 9w Homo sapiens cDNA clone 1035502 3', mRNA sequence. (from Genbank) |
| 344 | Colorectal | 0.2011614 | 0.41331035 | 0.354531 | RC_AA4190 0.23058137 26_at | EST: zv34e11.s1 Soares ovary tumor NbHOT Homo sapiens cDNA clone 755564 3' similar to SW:PTN2_RAT P35233 PROTEIN-TYROSINE PHOSPHATASE PTP-S ;, mRNA sequence. (from Genbank) |
| 345 | Colorectal | 0.2006981 | 0.4127873 | 0.354427 | 0.23037542 X02875_s_a t | OIAS (2'-5') oligoadenylate synthetase |
| 346 | Colorectal | 0.2002416 | 0.4127589 | 0.354305 | 0.23012887 X01060_at | TFRC Transferrin receptor (p90, CD71) |
| 347 | Colorectal | 0.1999146 | 0.4126949 | 0.354284 | 0.2299653 AA355059_a t | EST: EST63401 Jurkat T-cells V Homo sapiens cDNA 5' end, mRNA sequence. (from Genbank) |

FIG. 4O

| # | | | | | | |
|---|---|---|---|---|---|---|
| 348 | Colorectal | 0.1994864 | 0.4126626 | 0.354107 | 0.22979686 | J05401_at | CKM12 Creatine kinase, mitochondrial 2 (sarcomeric) |
| 349 | Colorectal | 0.198993 | 0.412455 | 0.354044 | 0.22969289 | D79985_at | A cell surface protein |
| 350 | Colorectal | 0.1987864 | 0.4124333 | 0.353879 | 0.22952573 | U31201_cds2_s_at | Laminin gamma2 chain gene (LAMC2) |
| 351 | Colorectal | 0.1983433 | 0.4124333 | 0.353696 | 0.2294468 | RC_AA088458_at | EST: zl82ra09.s1 Stratagene colon (#937204) Homo sapiens cDNA clone 511096 3' similar to contains element MER27 repetitive element ; mRNA sequence. (from Genbank) |
| 352 | Colorectal | 0.1979193 | 0.4121242 | 0.353635 | 0.22929068 | X57766_at | PSG11 Pregnancy-specific beta-1 glycoprotein 11 |
| 353 | Colorectal | 0.1968851 | 0.4118455 | 0.35351 | 0.22914132 | U33286_at | Chromosome segregation gene homolog CAS mRNA |
| 354 | Colorectal | 0.1967153 | 0.4115963 | 0.353262 | 0.22902222 | RC_AA491001_f_at | EST: aa52g12.s1 NCI_CGAP_GCB1 Homo sapiens cDNA clone IMAGE:824614 3' similar to TR:G1293732 G1293732 O3625P. ;. mRNA sequence. (from Genbank) |
| 355 | Colorectal | 0.1965384 | 0.4113627 | 0.352762 | 0.22883533 | D00761_at | PSMA5 Proteasome component C5 |
| 356 | Colorectal | 0.1964374 | 0.4113368 | 0.352707 | 0.22865196 | RC_AA447671_at | EST: aa18b05.s1 Soares NhHMPu S1 Homo sapiens cDNA clone 813585 3'; mRNA sequence. (from Genbank) |
| 357 | Colorectal | 0.1962046 | 0.4112994 | 0.35265 | 0.22844285 | D87682_at | KIAA0241 gene, partial cds |
| 358 | Colorectal | 0.195363 | 0.4109364 | 0.352528 | 0.22834799 | J00231_f_at | Immunoglobulin gamma 3 (Gm marker) |
| 359 | Colorectal | 0.1951849 | 0.4109121 | 0.352301 | 0.22821721 | RC_AA621122_at | Chromosome 21 leucine-rich protein |
| 360 | Colorectal | 0.1949294 | 0.4107072 | 0.352261 | 0.2282048 | AA303711_at | Ephrin-B1 |
| 361 | Colorectal | 0.1943457 | 0.4106107 | 0.352152 | 0.22797549 | U23942_at | CYP51 Cytochrome P450, 51 (lanosterol 14-alpha-demethylase) |
| 362 | Colorectal | 0.1942743 | 0.4104415 | 0.351993 | 0.22775424 | U90913_at | Clone 23665 mRNA sequence |
| 363 | Colorectal | 0.1940673 | 0.4099687 | 0.351867 | 0.2277458 | RC_AA280670_at | EST: zs97a07.s1 NCI_CGAP_GCB1 Homo sapiens cDNA clone IMAGE:711540 3'; mRNA sequence. (from Genbank) |
| 364 | Colorectal | 0.1937847 | 0.4099687 | 0.351845 | 0.22772816 | Z35402_ma1_s_at | Gene encoding E-cadherin, exon 3 and joined CDS |
| 365 | Colorectal | 0.1937249 | 0.409967 | 0.351808 | 0.22743449 | M59807_at | NATURAL KILLER CELLS PROTEIN 4 PRECURSOR |
| 366 | Colorectal | 0.1926037 | 0.4096152 | 0.351762 | 0.2273894 | AA306051_at | KIAA0683 gene product |
| 367 | Colorectal | 0.1920891 | 0.4095695 | 0.351529 | 0.22722417 | M19961_at | COX5B Cytochrome c oxidase subunit Vb |
| 368 | Colorectal | 0.1920275 | 0.4095139 | 0.351012 | 0.22708957 | L34155_at-2 | Laminin, alpha 3 (nicein (150kD), kalinin (165kD), BM600 (150kD), epilegrin) |
| 369 | Colorectal | 0.1920275 | 0.4092352 | 0.350929 | 0.22692518 | L34155_at | Laminin-related protein (LamA3) mRNA |
| 370 | Colorectal | 0.1918812 | 0.4090524 | 0.350716 | 0.22681259 | S79219_s_at | PCCA Propionyl-coA carboxylase alpha chain |
| 371 | Colorectal | 0.1917144 | 0.4087796 | 0.35068 | 0.22655553 | L41559_at | PCBD 6 pyruvoyl-tetrahydropterin synthase/dimerization cofactor of hepatocyte nuclear factor 1 alpha (TCF1) |
| 372 | Colorectal | 0.1903125 | 0.4087658 | 0.350592 | 0.22649843 | RC_AA465211_f_at | EST: aa24e01.s1 NCI_CGAP_GCB1 Homo sapiens cDNA clone IMAGE:814200 3'; mRNA sequence. (from Genbank) |

FIG. 4P

| | | | | | | |
|---|---|---|---|---|---|---|
| 373 | Colorectal | 0.1891975 | 0.4087521 | 0.350427 | 0.22262772 | L41143_at | Expressed pseudo TCTA mRNA at t(1;3) translocation site |
| 374 | Colorectal | 0.1890445 | 0.4087355 | 0.350345 | 0.22617792 | Z12962_at | EEF1A1 Translation elongation factor 1-alpha-1 |
| 375 | Colorectal | 0.1888832 | 0.4087213 | 0.350135 | 0.22604753 | U82987_at-2 | Human Bcl-2 binding component 3 (bbc3) mRNA, partial cds |
| 376 | Colorectal | 0.1888832 | 0.4085137 | 0.350092 | 0.225852 | U82987_at | Bcl-2 binding component 3 (bbc3) mRNA, partial cds |
| 377 | Colorectal | 0.1876353 | 0.4084984 | 0.349963 | 0.22572815 | D64154_at | Mr 110,000 antigen |
| 378 | Colorectal | 0.1876054 | 0.4082678 | 0.349675 | 0.22552337 | D44466_at | Proteasome subunit p112 |
| 379 | Colorectal | 0.1874838 | 0.407953 | 0.349602 | 0.22254372 | U61263_at | Acetolactate synthase homolog mRNA |
| 380 | Colorectal | 0.1871072 | 0.4079152 | 0.349583 | 0.22533056 | X54162_at | 64 KD AUTOANTIGEN D1 |
| 381 | Colorectal | 0.1870685 | 0.4078227 | 0.349375 | 0.22522818 | RC_AA2619 07_at | EST: zs17d04.s1 NCI_CGAP_GCB1 Homo sapiens cDNA clone IMAGE:685447 3', mRNA sequence. (from Genbank) |
| 382 | Colorectal | 0.1868834 | 0.4077731 | 0.349374 | 0.22511148 | Z16411_s_at | 1-PHOSPHATIDYLINOSITOL-4,5-BISPHOSPHATE PHOSPHODIESTERASE BETA 3 |
| 383 | Colorectal | 0.1868124 | 0.4075659 | 0.349318 | 0.22494116 | RC_AA2365 33_s_at | Ecotropic viral integration site 1 |
| 384 | Colorectal | 0.1864537 | 0.4075027 | 0.349237 | 0.22488289 | AF000177_a t | Sm-like protein CaSm (CaSm) mRNA |
| 385 | Colorectal | 0.1861585 | 0.4074602 | 0.349048 | 0.22485767 | L41066_at | NF-AT3 mRNA |
| 386 | Colorectal | 0.1857376 | 0.407424 | 0.34889 | 0.22459504 | L04270_at | LYMPHOTOXIN-BETA RECEPTOR PRECURSOR |
| 387 | Colorectal | 0.1856037 | 0.4073818 | 0.348803 | 0.22455119 | Z28407_at | RPL8 Ribosomal protein L8 |
| 388 | Colorectal | 0.1855529 | 0.4072997 | 0.348803 | 0.22433567 | U78525_at | Eukaryotic translation initiation factor (eIF3) mRNA |
| 389 | Colorectal | 0.1845051 | 0.4072956 | 0.348771 | 0.22418927 | M25629_at | Kallikrein mRNA, clone phKK25 |
| 390 | Colorectal | 0.1841088 | 0.4072678 | 0.348563 | 0.22406629 | HG3431-HT3616_s_a t | Decorin, Alt. Splice 1 |
| 391 | Colorectal | 0.1839668 | 0.4072191 | 0.348524 | 0.22398557 | RC_AA2561 57_at | EST: zr79b01.s1 Soares NhHMPu S1 Homo sapiens cDNA clone 681865 3', mRNA sequence. (from Genbank) |
| 392 | Colorectal | 0.1839458 | 0.4071069 | 0.348513 | 0.22382079 | S78187_at | M-PHASE INDUCER PHOSPHATASE 2 |
| 393 | Colorectal | 0.1827556 | 0.406673 | 0.348215 | 0.22360696 | AA412620_s _at | EST: zt97b10.r1 Soares testis NHT Homo sapiens cDNA clone 730267 5', mRNA sequence. (from Genbank) |
| 394 | Colorectal | 0.1826154 | 0.4065993 | 0.348046 | 0.22350992 | AA421370_a t | EST: zu06e06.r1 Soares testis NHT Homo sapiens cDNA clone 731074 5' similar to contains MER17.12 MER17 repetitive element ;, mRNA sequence. (from Genbank) |
| 395 | Colorectal | 0.1824051 | 0.4063293 | 0.347987 | 0.22325791 | J04080_at | C1S Complement component 1, s subcomponent |
| 396 | Colorectal | 0.1815284 | 0.4062979 | 0.347759 | 0.22320338 | HG417-HT417_s_at | Cathepsin B |
| 397 | Colorectal | 0.1811393 | 0.4062636 | 0.347713 | 0.22308592 | RC_AA5042 70_at | EST: aa61c10.s1 NCI_CGAP_GCB1 Homo sapiens cDNA clone IMAGE:825426 3', mRNA sequence. (from Genbank) |
| 398 | Colorectal | 0.1812437 | 0.4062599 | 0.347371 | 0.22298136 | M97935_s_a t | SIGNAL TRANSDUCER AND ACTIVATOR OF TRANSCRIPTION 1-ALPHA/BETA |

FIG. 4Q

| # | Tissue | | | | Description |
|---|---|---|---|---|---|
| 399 | Colorectal | 0.180716 | 0.4062513 | 0.347154 | 0.22276407 | M91083_at | DNA-binding protein (HRC1) mRNA |
| 400 | Colorectal | 0.1804325 | 0.4060873 | 0.347066 | 0.22268288 | HG2147-HT2217_r_at | Mucin 3, Intestinal (Gb:M55405) |
| 401 | Colorectal | 0.179763 | 0.405745 | 0.347016 | 0.22253454 | RC_AA4005_91_at | Proteasome (prosome, macropain) 26S subunit, non-ATPase, 13 |
| 402 | Colorectal | 0.1796245 | 0.4052811 | 0.346881 | 0.22236669 | RC_AA4962_04_at | EST: zx70a12.s1 Soares total fetus Nb2HF8 9w Homo sapiens cDNA clone 796798 3', mRNA sequence. (from Genbank) |
| 403 | Colorectal | 0.1794001 | 0.4052002 | 0.346808 | 0.22232442 | L29433_at | COAGULATION FACTOR X PRECURSOR |
| 404 | Colorectal | 0.1792444 | 0.4051298 | 0.34653 | 0.22216293 | Z83821_cds1_at | Keratin 8 |
| 405 | Colorectal | 0.1786292 | 0.4050372 | 0.346425 | 0.22211528 | RC_AA0843_18_at | EST: zn18b04.s1 Stratagene neuroepithelium NT2RAMI 937234 Homo sapiens cDNA clone 547759 3', mRNA sequence. (from Genbank) |
| 406 | Colorectal | 0.1782558 | 0.4049873 | 0.34629 | 0.22198282 | AB002332_a_t | KIAA0334 gene |
| 407 | Colorectal | 0.1778101 | 0.4047728 | 0.346028 | 0.22189309 | L48513_at | Paraoxonase (PON2) mRNA |
| 408 | Colorectal | 0.1756461 | 0.4041274 | 0.345895 | 0.22167064 | RC_AA6212_39_at | EST: zu81h12.s1 Soares testis NHT Homo sapiens cDNA clone 744455 3', mRNA sequence. (from Genbank) |
| 409 | Colorectal | 0.1755425 | 0.4039614 | 0.345841 | 0.2215906 | M29536_at | Translational initiation factor 2 beta subunit (eIF-2-beta) mRNA |
| 410 | Colorectal | 0.1755385 | 0.403747 | 0.345809 | 0.22148977 | RC_AA2629_69_f_at | EST: zr71c02.s1 Soares NhHMPu S1 Homo sapiens cDNA clone 668334 3' similar to TR:G969170 G969170 PX19. :, mRNA sequence (from Genbank) |
| 411 | Colorectal | 0.1754513 | 0.4036137 | 0.345559 | 0.22132495 | D50914_at | KIAA0124 gene, partial cds |
| 412 | Colorectal | 0.1754297 | 0.403425 | 0.345539 | 0.22113867 | RC_D60026_at | EST: Human fetal brain cDNA 3'-end GEN-081G02, mRNA sequence (from Genbank) |
| 413 | Colorectal | 0.1752464 | 0.4033151 | 0.345449 | 0.22104083 | X55448_cds2_at | 2-19 gene (2-19 protein) extracted from H.sapiens G6PD gene for glucose-6-phosphate dehydrogenase |
| 414 | Colorectal | 0.1746087 | 0.4032273 | 0.345159 | 0.22090986 | AA465016_a_t | EST: zx80d02.r1 Soares ovary tumor NbHOT Homo sapiens cDNA clone 810051 5' similar to TR:G1020091 G1020091 NEUROPSIN. ;contains element LTR3 repetitive element :, mRNA sequence. (from Genbank) |
| 415 | Colorectal | 0.174411 | 0.4031603 | 0.345106 | 0.22074215 | X87159_at | Beta subunit of epithelial amiloride-sensitive sodium channel |
| 416 | Colorectal | 0.1741242 | 0.4030842 | 0.344993 | 0.22059147 | RC_D20171_at | EST: Human HL60 3'directed MboI cDNA, HUMGS01145, clone pm2260, mRNA sequence. (from Genbank) |
| 417 | Colorectal | 0.1739448 | 0.4029589 | 0.344983 | 0.22042492 | RC_AA4534_31_at | EST: zx32g10.s1 Soares total fetus Nb2HF8 9w Homo sapiens cDNA clone 788226 3', mRNA sequence. (from Genbank) |
| 418 | Colorectal | 0.1738675 | 0.4027393 | 0.344892 | 0.22032273 | M17733_at | Thymosin beta-4 mRNA |
| 419 | Colorectal | 0.1738624 | 0.4026335 | 0.344861 | 0.22023967 | RC_AA4017_21_s_at | EST: zt6c01.s1 Soares testis NHT Homo sapiens cDNA clone 727296 3', mRNA sequence. (from Genbank) |

FIG. 4R

| # | Type | | | | | Description |
|---|---|---|---|---|---|---|
| 420 | Colorectal | 0.173791 | 0.4025816 | 0.344774 | 0.22017785/ RC_AA4518 77_at | EST: zx16e06.s1 Soares total fetus Nb2IIF8 9w Homo sapiens cDNA clone 786658 3', mRNA sequence. (from Genbank) |
| 421 | Colorectal | 0.1737058 | 0.4025284 | 0.344748 | 0.2200681 1 C00125_s_a t | EST: HUMGS0005758, Human Gene Signature, 3'-directed cDNA sequence, mRNA sequence. (from Genbank) |
| 422 | Colorectal | 0.1736943 | 0.402457 | 0.344624 | 0.21985555 RC_AA0355 14_at | EST: zk26b02.s1 Soares pregnant uterus NbHPU Homo sapiens cDNA clone 471627 3', mRNA sequence. (from Genbank) |
| 423 | Colorectal | 0.1734535 | 0.4022192 | 0.344613 | 0.21979126 L13923_at | FBN1 Fibrillin 1 (Marfan syndrome) |
| 424 | Colorectal | 0.1733749 | 0.4020973 | 0.344613 | 0.2197131 M14758_at | MULTIDRUG RESISTANCE PROTEIN 1 |
| 425 | Colorectal | 0.1729153 | 0.4019776 | 0.344399 | 0.21963376 RC_AA5050 95_at | EST: aa64g12.s1 NCI_CGAP_GCB1 Homo sapiens cDNA clone IMAGE:825766 3', mRNA sequence. (from Genbank) |
| 426 | Colorectal | 0.1725793 | 0.4019096 | 0.344266 | 0.21955204 Z24680_at | Garp gene mRNA |
| 427 | Colorectal | 0.1724256 | 0.4018521 | 0.344226 | 0.2193254 D26129_at | RNS1 Ribonuclease A (pancreatic) |
| 428 | Colorectal | 0.1721121 | 0.4018173 | 0.34413 | 0.21914238 W05585_at | EST: za85a06.r1 Soares fetal lung NbHL19W Homo sapiens cDNA clone 299314 5', mRNA sequence. (from Genbank) |
| 429 | Colorectal | 0.1718734 | 0.4016974 | 0.344024 | 0.21904136 X63629_at | CDH3 Cadherin 3 (P-cadherin) |
| 430 | Colorectal | 0.1715397 | 0.4016271 | 0.343953 | 0.21898192 RC_AA6100 70_at | EST: af08e11.s1 Soares testis NHT Homo sapiens cDNA clone 1031084 3', mRNA sequence. (from Genbank) |
| 431 | Colorectal | 0.1744253 | 0.4015857 | 0.343903 | 0.21882729 M55593_at | MMP2 Matrix metalloproteinase 2 (gelatinase A, 72kD gelatinase, 72kD type IV collagenase) |
| 432 | Colorectal | 0.1710495 | 0.4014494 | 0.343864 | 0.21877955 U46767_at | Monocyte chemoattractant protein-4 precursor (MCP-4) mRNA |
| 433 | Colorectal | 0.1708696 | 0.4012243 | 0.343732 | 0.21860664 AA157623_s _at | KIAA0750 gene product |
| 434 | Colorectal | 0.1703653 | 0.4009031 | 0.343707 | 0.21848814 L20348_at | Oncomodulin gene |
| 435 | Colorectal | 0.1699524 | 0.4007933 | 0.343571 | 0.21833302 M74093_at | G1/S-SPECIFIC CYCLIN E |
| 436 | Colorectal | 0.1699521 | 0.4007216 | 0.343368 | 0.2181762 U41766_s_a t | Metalloprotease/disintegrin/cysteine-rich protein precursor (MDC9) mRNA |
| 437 | Colorectal | 0.1695515 | 0.4006932 | 0.342891 | 0.21804747 L02326_f_at | [clone Hu lambda-17] lambda-like gene |
| 438 | Colorectal | 0.169787 | 0.400523 | 0.342879 | 0.21784674 Z18948_at | S100A3 S100 calcium-binding protein A3 (formerly S100E) |
| 439 | Colorectal | 0.1695879 | 0.4003103 | 0.342845 | 0.21777372 X53002_s_ a t | ITGB5 Integrin beta-5 subunit |
| 440 | Colorectal | 0.1695 | 0.4002795 | 0.34271 | 0.21767299 D87716_s_a t | KIAA0007 gene, partial cds |
| 441 | Colorectal | 0.1694984 | 0.4001872 | 0.342653 | 0.21764944 X06956_at | TUBULIN ALPHA-4 CHAIN |
| 442 | Colorectal | 0.1691347 | 0.4001326 | 0.342397 | 0.21743883 HG3227- HT3404_at | Guanine Nucleotide-Binding Protein Hsr1 |
| 443 | Colorectal | 0.1690883 | 0.4000302 | 0.342304 | 0.21731475 RC_AA2332 57_at | Transforming growth factor beta 1 induced transcript 1 |
| 444 | Colorectal | 0.1690355 | 0.3999129 | 0.342197 | 0.21725959 D45248_at | Proteasome activator hPA28 subunit beta |
| 445 | Colorectal | 0.1688801 | 0.3999087 | 0.342043 | 0.21716623 U28386_at | RCH1 RAG (recombination activating gene) cohort 1 |

FIG. 4S

| # | Type | | | | Accession | Description |
|---|---|---|---|---|---|---|
| 446 | Colorectal | 0.1688689 | 0.3997103 | 0.341902 | 0.21708882 RC_AA1499 40_at | GLUT1 C-terminal binding protein |
| 447 | Colorectal | 0.1688496 | 0.3996964 | 0.341726 | 0.21691293 D50683_at | TGFBR2 Transforming growth factor, beta receptor II (70-80kD) |
| 448 | Colorectal | 0.1685865 | 0.3996956 | 0.341626 | 0.21675077 HG3954-HT4224_s_a t | Landsteiner-Wiener Blood Group Glycoprotein (Lw) (Gb:L27671) |
| 449 | Colorectal | 0.1683068 | 0.3995984 | 0.341542 | 0.21665724 D49824_s_a t | HLA-B null allele mRNA |
| 450 | Colorectal | 0.1681806 | 0.3995227 | 0.341513 | 0.21657811 RC_AA4256 37_at | Homo sapiens mRNA, complete cds, similar to yeast pre-mRNA splicing factors, Prp1/Zer1 and Prp6 |
| 451 | Colorectal | 0.1679135 | 0.3994782 | 0.341478 | 0.21637894 U80034_at | Mitochondrial intermediate peptidase precursor (MIPEP) mRNA, mitochondrial gene encoding mitochondrial protein |
| 452 | Colorectal | 0.1678417 | 0.3994775 | 0.341415 | 0.21628368 RC_AA0353 66_at | EST: zk26d12.s1 Soares pregnant uterus NbHPU Homo sapiens cDNA clone 471671 3', mRNA sequence. (from Genbank) |
| 453 | Colorectal | 0.1676434 | 0.3994277 | 0.341415 | 0.21623326 RC_AA2363 56_at | Zr54a11.s1 Soares_NhHMPu_S1 Homo sapiens cDNA clone IMAGE:667196 3', mRNA sequence |
| 454 | Colorectal | 0.1673252 | 0.3993781 | 0.341386 | 0.21608981 N79354_at | EST: yz73a08.r1 Homo sapiens cDNA clone 288662 5'. (from Genbank) |
| 455 | Colorectal | 0.1672328 | 0.3993452 | 0.341352 | 0.21594298 HG2259-HT2348_s_a t | Tubulin, Alpha 1, Isoform 44 |
| 456 | Colorectal | 0.1672166 | 0.399217 | 0.341283 | 0.21577172 RC_AA6095 92_at | EST: af15d11.s1 Soares testis NHT Homo sapiens cDNA clone 1031733 3', mRNA sequence. (from Genbank) |
| 457 | Colorectal | 0.1671251 | 0.3991573 | 0.341063 | 0.21577172 C00476_at | EST: HUMGS0007866, Human Gene Signature, 3'-directed cDNA sequence, mRNA sequence. (from Genbank) |
| 458 | Colorectal | 0.1667122 | 0.3991136 | 0.341022 | 0.21566679 RC_AA1739 81_at | EST: zp03e05.s1 Stratagene ovarian cancer (#937219) Homo sapiens cDNA clone 595328 3', mRNA sequence. (from Genbank) |
| 459 | Colorectal | 0.1665861 | 0.3991324 | 0.340981 | 0.21561334 M55543_at | INTERFERON-INDUCED GUANYLATE-BINDING PROTEIN 2 |
| 460 | Colorectal | 0.1665606 | 0.399104 | 0.340873 | 0.21540578 X92493_s_a t | STM-7 protein |
| 461 | Colorectal | 0.166446 | 0.3990471 | 0.340803 | 0.21533175 RC_AA5048 03_at | EST: aa64a06.s1 NCI_CGAP_GCB1 Homo sapiens cDNA clone IMAGE:825682 3', mRNA sequence. (from Genbank) |
| 462 | Colorectal | 0.165736 | 0.3990317 | 0.340778 | 0.21517071 RC_AA4365 60_at | EST: zv08e10.s1 Soares NhHMPu S1 Homo sapiens cDNA clone 753066 3', mRNA sequence. (from Genbank) |
| 463 | Colorectal | 0.1655869 | 0.3987303 | 0.340543 | 0.21506318 J05633_at | ITGB5 Integrin beta-5 subunit |
| 464 | Colorectal | 0.1655231 | 0.3987299 | 0.340353 | 0.21480893 L03411_s_at | RD Radin blood group |
| 465 | Colorectal | 0.1653327 | 0.3984724 | 0.340172 | 0.21468474 RC_AA1351 85_at | EST: zo27a05.s1 Stratagene colon (#937204) Homo sapiens cDNA clone 588080 3', mRNA sequence. (from Genbank) |

FIG. 4T

| # | Tissue | Value1 | Value2 | Value3 | ID | Description |
|---|---|---|---|---|---|---|
| 466 | Colorectal | 0.1651904 | 0.3984437 | 0.340161 | RC_AA4191 39_at | EST: zv34h05.s1 Soares ovary tumor NbHOT Homo sapiens cDNA clone 755577 3', mRNA sequence. (from Genbank) |
| 467 | Colorectal | 0.1648333 | 0.3982009 | 0.340157 | X71874_cds 1_at | Proteasome-like subunit MECL-1 gene extracted from H.sapiens genes for proteasome-like subunit (MECL-1), chymotrypsin-like protease (CTRL-1) and protein serine kinase (PSK-H1) last exon |
| 468 | Colorectal | 0.1646377 | 0.3980459 | 0.34013 | 0.21445012 S71018_at-2 | Peptidylprolyl Isomerase C (cyclophilin C) |
| 469 | Colorectal | 0.1646377 | 0.3979631 | 0.339942 | 0.21437135 S71018_at | Cyclophilin C [human, kidney, mRNA, 883 nt] |
| 470 | Colorectal | 0.1645432 | 0.3979631 | 0.33993 | RC_AA2509 0.21426827 68_s_at | Ran GTPase activating protein 1 |
| 471 | Colorectal | 0.1643057 | 0.3977973 | 0.339658 | 0.21414681 L11369_at | Protocadherin 42 mRNA, 3' end of cds for alternative splicing PC42-8 |
| 472 | Colorectal | 0.1637872 | 0.3977175 | 0.339517 | 0.21399806 L33930_s_at | CD24 signal transducer mRNA and 3' region |
| 473 | Colorectal | 0.163628 | 0.397591 | 0.33943 | C00225_s_a 0.21393126 t | EST: HUMGS0005889, Human Gene Signature, 3'-directed cDNA sequence, mRNA sequence. (from Genbank) |
| 474 | Colorectal | 0.1635248 | 0.3975688 | 0.339319 | HG3044-HT3742_s_a 0.21368803 t | Fibronectin, Alt. Splice 1 |
| 475 | Colorectal | 0.1631892 | 0.3975664 | 0.339238 | RC_AA2357 0.21362731 07_at | EST: zt31e08.s1 Soares ovary tumor NbHOT Homo sapiens cDNA clone 723974 3', mRNA sequence. (from Genbank) |
| 476 | Colorectal | 0.1630999 | 0.3973875 | 0.339172 | 0.21351211 L21954_at | PERIPHERAL-TYPE BENZODIAZEPINE RECEPTOR |
| 477 | Colorectal | 0.1629482 | 0.3973582 | 0.33907 | RC_AA4565 0.21338874 95_at | EST: zx73d11.s1 Soares ovary tumor NbHOT Homo sapiens cDNA clone 809397 3', mRNA sequence. (from Genbank) |
| 478 | Colorectal | 0.1628553 | 0.3972327 | 0.339057 | 0.21317948 X17644_s_a t | GSPT1 G1 to S phase transition 1 |
| 479 | Colorectal | 0.1628099 | 0.397137 | 0.339043 | 0.21299042 D89501_at-2 | Human PBI gene, complete cds |
| 480 | Colorectal | 0.1628099 | 0.397121 | 0.338872 | 0.21293436 D89501_at | PBI gene |
| 481 | Colorectal | 0.1628895 | 0.3969455 | 0.338842 | RC_AA4436 0.21288554 67_at | EST: zw86b07.s1 Soares total fetus Nb2HF8 9w Homo sapiens cDNA clone 783829 3', mRNA sequence. (from Genbank) |
| 482 | Colorectal | 0.162363 | 0.3967438 | 0.338644 | RC_D60354 0.21277869 s_at | Human mRNA for KIAA0007 gene, partial cds |
| 483 | Colorectal | 0.1623051 | 0.3966425 | 0.338479 | 0.21261954 U82535_at | Fatty acid amide hydrolase mRNA |
| 484 | Colorectal | 0.1619627 | 0.3965244 | 0.338403 | 0.21245596 K01160_s_at | HLA-DQA1 MHC class II DQ alpha |
| 485 | Colorectal | 0.1616623 | 0.396479 | 0.338365 | 0.21236816 M91493_at | EST: HUMRTPGEAL Homo sapiens cDNA. (from Genbank) |
| 486 | Colorectal | 0.1616189 | 0.3963925 | 0.338334 | RC_AA4030 0.21234865 41_at | Cellular retinoic acid-binding protein 1 |

FIG. 4U

| | | | | | |
|---|---|---|---|---|---|
| 487 | Colorectal | 0.1615999 | 0.3963835 | 0.33828 | 0.212094381 | RC_AA2364_at | EST: zr75d02.s1 Soares NhHMPu S1 Homo sapiens cDNA clone 669219 3' similar to gb:L27670 Human Landsteiner-Wiener blood group glycoprotein (HUMAN);contains Alu repetitive element;, mRNA sequence. (from Genbank) |
| 488 | Colorectal | 0.1606803 | 0.3963129 | 0.338205 | 0.212080075 | RC_AA2362_at | EST: zr51108.s1 Soares NhHMPu S1 Homo sapiens cDNA clone 666951 3', mRNA sequence. (from Genbank) |
| 489 | Colorectal | 0.1602888 | 0.3962475 | 0.338097 | 0.211967768 | RC_AA2584_82_s_at | Homo sapiens mRNA for zinc finger protein, complete cds |
| 490 | Colorectal | 0.1602171 | 0.3959201 | 0.338003 | 0.211731091 | U78095_at | Placental bikunin mRNA |
| 491 | Colorectal | 0.1601474 | 0.3958512 | 0.337912 | 0.211720991 | M74447_at | TAP2 Transporter 2, ABC (ATP binding cassette) |
| 492 | Colorectal | 0.1595165 | 0.3958136 | 0.33787 | 0.211669286 | U62317_rna | Hypothetical protein 384D8_6 gene extracted from Chromosome 22q13 BAC Clone CIT987SK-384D8 complete sequence |
| 493 | Colorectal | 0.1591935 | 0.3957578 | 0.337795 | 0.211574811 | U79775_at | D21S2056E, novel nuclear protein 1 |
| 494 | Colorectal | 0.1590418 | 0.3956529 | 0.337721 | 0.211329186 | RC_AA0464_at | EST: zk70b10.s1 Soares pregnant uterus NbHPU Homo sapiens cDNA clone 488155 3' similar to contains element MER9 repetitive element;, mRNA sequence. (from Genbank) |
| 495 | Colorectal | 0.1589532 | 0.3954982 | 0.337613 | 0.211194373 | RC_AA0789_32_at | EST: zm95f07.s1 Stratagene colon HT29 (#937221) Homo sapiens cDNA clone 545701 3', mRNA sequence. (from Genbank) |
| 496 | Colorectal | 0.15849 | 0.3954701 | 0.3373 | 0.211111012 | AA481201_at | EST: aa34c12.r1 NCI_CGAP_GCB1 Homo sapiens cDNA clone IMAGE:815158 5', mRNA sequence. (from Genbank) |
| 497 | Colorectal | 0.1575591 | 0.3954353 | 0.3373 | 0.211103315 | RC_AA6097_95_at | EST: ae62a09.s1 Stratagene lung carcinoma 937218 Homo sapiens cDNA clone 951448 3', mRNA sequence. (from Genbank) |
| 498 | Colorectal | 0.1569468 | 0.3953815 | 0.337048 | 0.210879671 | U50330_at | BMP1 Bone morphogenetic protein 1 |
| 499 | Colorectal | 0.1565222 | 0.395285 | 0.33704 | 0.210702181 | X65633_at | ACTH-R gene for adrenocorticotropic hormone receptor |
| 500 | Colorectal | 0.1564706 | 0.3951381 | 0.336887 | 0.210594521 | L22524_s_at | MATRILYSIN PRECURSOR |
| 501 | Colorectal | 0.1564513 | 0.3950984 | 0.33687 | 0.210552591 | U48959_at | Myosin light chain kinase (MLCK) mRNA |
| 502 | Colorectal | 0.1561238 | 0.3950417 | 0.336793 | 0.210496817 | RC_AA4516_76_at | EST: zx44b03.s1 Soares total fetus Nb2HF8 9w Homo sapiens cDNA clone 789293 3', mRNA sequence. (from Genbank) |
| 503 | Colorectal | 0.1559671 | 0.3949231 | 0.336636 | 0.210453550 | RC_AA4783_00_at | CD39-like 2 |
| 504 | Colorectal | 0.1557691 | 0.3948976 | 0.336509 | 0.210336251 | U77594_at | Tazarotene-induced gene 2 (TIG2) mRNA |
| 505 | Colorectal | 0.1557269 | 0.3946397 | 0.336328 | 0.210191431 | M22430_at | PLA2G2A Phospholipase A2, group IIA (platelets, synovial fluid) |
| 506 | Colorectal | 0.1556963 | 0.3945324 | 0.336225 | 0.210074041 | AA091231_a_t | EST: cchn2158.seq.F Fetal heart, Lambda ZAP Express Homo sapiens cDNA 5', mRNA sequence. (from Genbank) |
| 507 | Colorectal | 0.15532 | 0.3944851 | 0.336171 | 0.210000372 | X59798_at | CCND1 Cyclin D1 (PRAD1; parathyroid adenomatosis 1) |
| 508 | Colorectal | 0.1552322 | 0.3944281 | 0.336089 | 0.209900541 | M90516_at | GFPT Glutamine-fructose-6-phosphate transaminase |

FIG. 4V

| | | | | | |
|---|---|---|---|---|---|
| 509 | Colorectal | 0.1549872 | 0.3943015 | 0.335977 | 0.2098014 | L44538_at | EST: Homo sapiens thymus mRNA (randomly primed, normalized), single-pass sequence, mRNA sequence. (from Genbank) |
| 510 | Colorectal | 0.1547511 | 0.3942341 | 0.335733 | 0.209638876_t | AA251078_a | EST: zs01b12.r1 NCI_CGAP_GCB1 Homo sapiens cDNA clone IMAGE:683903 5', mRNA sequence. (from Genbank) |
| 511 | Colorectal | 0.1547084 | 0.3941278 | 0.335589 | 0.20959847 | RC_AA0749 19_at | EST: zm82b10.s1 Stratagene ovarian cancer (#937219) Homo sapiens cDNA clone 544411 3', mRNA sequence. (from Genbank) |
| 512 | Colorectal | 0.1544632 | 0.3940334 | 0.335471 | 0.20944932 | D84454_at | UDP-galactose translocator |
| 513 | Colorectal | 0.1542577 | 0.3939991 | 0.335392 | 0.2093829 | AA094752_a_t | Protein phosphatase 3 (formerly 2B), catalytic subunit, beta isoform (calcineurin A beta) |
| 514 | Colorectal | 0.1541217 | 0.3939991 | 0.335234 | 0.20931253 | M32405_at | Protein kinase (JNK2) mRNA |
| 515 | Colorectal | 0.1536185 | 0.3939194 | 0.335224 | 0.20914608 | RC_AA4170 79_at | EST: zu13c03.s1 Soares testis NHT Homo sapiens cDNA clone 731716 3', mRNA sequence. (from Genbank) |
| 516 | Colorectal | 0.1535545 | 0.3939163 | 0.335085 | 0.20904989 | RC_AA2337 90_at | EST: zr44c08.s1 Soares NhHMPu S1 Homo sapiens cDNA clone 666254 3', mRNA sequence. (from Genbank) |
| 517 | Colorectal | 0.1534945 | 0.393889 | 0.334907 | 0.20900838 | M63835_at | HIGH AFFINITY IMMUNOGLOBULIN GAMMA FC RECEPTOR I "A FORM" PRECURSOR |
| 518 | Colorectal | 0.1533766 | 0.3938167 | 0.334854 | 0.20896049 | D15049_at | PTPRH Protein tyrosine phosphatase |
| 519 | Colorectal | 0.1533382 | 0.3935947 | 0.334761 | 0.2088442 | U75370_at | Mitochondrial RNA polymerase mRNA, nuclear gene encoding mitochondrial protein |
| 520 | Colorectal | 0.153082 | 0.3935785 | 0.334744 | 0.20866127 | RC_AA4005 28_at | EST: zu70f09.s1 Soares testis NHT Homo sapiens cDNA clone 743369 3', mRNA sequence. (from Genbank) |
| 521 | Colorectal | 0.1524428 | 0.3933713 | 0.334698 | 0.20855671 | RC_AA1222 17_at | EST: zn83a11.s1 Stratagene lung carcinoma 937218 Homo sapiens cDNA clone 564764 3', mRNA sequence. (from Genbank) |
| 522 | Colorectal | 0.1517651 | 0.3933333 | 0.334573 | 0.20852254 | S75256_s_at | HNL=neutrophil lipocalin [human, ovarian cancer cell line OC6, mRNA Partial, 534 nt] |
| 523 | Colorectal | 0.1517395 | 0.3933051 | 0.334548 | 0.20836028 | X15880_at | COL6A1 Collagen, type VI, alpha 1 |
| 524 | Colorectal | 0.1510072 | 0.393215 | 0.334422 | 0.20830275 | AA338573_i_at | Zinc finger protein 200 |
| 525 | Colorectal | 0.1509668 | 0.3931952 | 0.334397 | 0.20818146 | C01811_f_at | EST: HUMGS0003774, Human Gene Signature, 3'-directed cDNA sequence, mRNA sequence. (from Genbank) |
| 526 | Colorectal | 0.1506593 | 0.3931735 | 0.334314 | 0.20797463 | X15822_at | COX7A2 Cytochrome c oxidase VIIa subunit (liver specific) |
| 527 | Colorectal | 0.150431 | 0.3931355 | 0.334227 | 0.20793276 | Z32684_at | XK mRNA for membrane transport protein |
| 528 | Colorectal | 0.1503324 | 0.3930886 | 0.33414 | 0.20788004 | D31764_at | KIAA0064 gene |
| 529 | Colorectal | 0.1502032 | 0.3930462 | 0.334034 | 0.20771392 | RC_AA2340 66_at | EST: zr74b07.s1 Soares NhHMPu S1 Homo sapiens cDNA clone 669109 3', mRNA sequence. (from Genbank) |
| 530 | Colorectal | 0.1498392 | 0.3927834 | 0.333964 | 0.20758401 | M25753_at | G2/MITOTIC-SPECIFIC CYCLIN B1 |

FIG. 4W

| | | | | | | |
|---|---|---|---|---|---|---|
| 531 | Colorectal | 0.1491762 | 0.3927706 | 0.2074444 | RC_AA4546_54_at | EST: zx99i06.s1 Soares NhHMPu S1 Homo sapiens cDNA clone 811907 3', mRNA sequence. (from Genbank) |
| 532 | Colorectal | 0.1491703 | 0.3926815 | 0.20730981 | U53446_at | Mitogen-responsive phosphoprotein (DOC-2) mRNA |
| 533 | Colorectal | 0.1491638 | 0.3926589 | 0.20723232 | RC_AA0226_32_at | EST: ze73a01.s1 Soares fetal heart NbHH19W Homo sapiens cDNA clone 364584 3', mRNA sequence. (from Genbank) |
| 534 | Colorectal | 0.1487316 | 0.3924795 | 0.20715122 | M19267_s_a_t | TPM1 Tropomyosin alpha chain (skeletal muscle) |
| 535 | Colorectal | 0.1486853 | 0.3924395 | 0.20699231 | AA071381_a_t | EST: zm61d03.r1 Stratagene fibroblast (#937212) Homo sapiens cDNA clone 530117 5', mRNA sequence. (from Genbank) |
| 536 | Colorectal | 0.148371 | 0.392371 | 0.20698786 | U40572_at | Beta2-syntrophin (SNT B2) mRNA |
| 537 | Colorectal | 0.1473992 | 0.3923646 | 0.20688641 | RC_AA0183_46_at | EST: ze41d12.s1 Soares retina N2b4HR Homo sapiens cDNA clone 361559 3', mRNA sequence. (from Genbank) |
| 538 | Colorectal | 0.1472546 | 0.3923127 | 0.2067851 | AF008442_a_t | RNA polymerase I subunit |
| 539 | Colorectal | 0.1469579 | 0.3922158 | 0.20672369 | M74558_at | SiL mRNA |
| 540 | Colorectal | 0.1465781 | 0.3921879 | 0.20663773 | D13243_s_a_t | Pyruvate kinase, liver and RBC |
| 541 | Colorectal | 0.1465549 | 0.3919869 | 0.20652114 | RC_AA1957_20_at | 33 kDa transcriptional co-activator |
| 542 | Colorectal | 0.1464579 | 0.3918662 | 0.2062354 | U18919_at | Chromosome 17q12-21 mRNA, clone pOV-2, partial cds |
| 543 | Colorectal | 0.1464099 | 0.3918206 | 0.20618701 | RC_AA4859_65_at | EST: ab40h12.s1 Stratagene HeLa cell s3 937216 Homo sapiens cDNA clone 843335 3' similar to SW:SUCA_RAT P13086 SUCCINYL-COA LIGASE ; mRNA sequence. (from Genbank) |
| 544 | Colorectal | 0.1459415 | 0.3918171 | 0.20604913 | AA406433_a_t | EST: zv12d10.r1 Soares NhHMPu S1 Homo sapiens cDNA clone 753427 5', mRNA sequence. (from Genbank) |
| 545 | Colorectal | 0.1459308 | 0.3915806 | 0.20598646 | J03626_rna1_s_at | UMPS gene extracted from Human UMP synthase mRNA |
| 546 | Colorectal | 0.1456732 | 0.3914018 | 0.20578396 | X57809_s_a_t | IGL@ Immunoglobulin lambda light chain |
| 547 | Colorectal | 0.1454744 | 0.3912747 | 0.20566429 | L34600_at | INITIATION FACTOR IF-2, MITOCHONDRIAL PRECURSOR |
| 548 | Colorectal | 0.1453867 | 0.3911521 | 0.20552492 | X74801_at | T-COMPLEX PROTEIN 1, GAMMA SUBUNIT |
| 549 | Colorectal | 0.1452846 | 0.3910876 | 0.20553958 | M11718_at | COL5A2 Collagen, type V, alpha |
| 550 | Colorectal | 0.1449539 | 0.39098 | 0.20541492 | U40223_at | Uridine nucleotide receptor (UNR) gene |
| 551 | Colorectal | 0.1449419 | 0.3909658 | 0.20538235 | J00220_cds_at | IGHA1 gene extracted from Human Ig germline H-chain G-E-A region A: gamma-3 5' flank |
| 552 | Colorectal | 0.1447022 | 0.3908173 | 0.20522827 | RC_AA4777_01_at | Homo sapiens mRNA for p27, complete cds |
| 553 | Colorectal | 0.1445668 | 0.3908009 | 0.20515011 | RC_AA2367_47_at | Mitogen-activated protein kinase-activated protein kinase 5 |
| 554 | Colorectal | 0.1444047 | 0.3908004 | 0.20508054 | M30496_at | UBIQUITIN CARBOXYL-TERMINAL HYDROLASE ISOZYME L3 |

FIG. 4X

| # | Tissue | | | | | | Description |
|---|---|---|---|---|---|---|---|
| 555 | Colorectal | 0.1443297 | 0.3908004 | 0.331393 | 0.205004661 | M93425_at | PTPN12 Protein tyrosine phosphatase, non-receptor type 12 |
| 556 | Colorectal | 0.1442873 | 0.3907617 | 0.331163 | 0.20497122 | M14058_at | C1R Complement component C1r |
| 557 | Colorectal | 0.1441881 | 0.3907539 | 0.331074 | 0.20479114 | AA424897_s_at | EST: zv47b09.r1 Soares ovary tumor NbHOT Homo sapiens cDNA clone 756761 5', mRNA sequence. (from Genbank) |
| 558 | Colorectal | 0.1438796 | 0.3907445 | 0.330982 | 0.20469745 | AA165144_i_at | EST: zo94e09.r1 Stratagene ovarian cancer (#937219) Homo sapiens cDNA clone 594568 5', mRNA sequence. (from Genbank) |
| 559 | Colorectal | 0.1433866 | 0.3905691 | 0.330963 | 0.20456348 | RC_AA4366 08_at | EST: zw55b04.s1 Soares total fetus Nb2HF8 9w Homo sapiens cDNA clone 773935 3', mRNA sequence. (from Genbank) |
| 560 | Colorectal | 0.1433587 | 0.3904927 | 0.330919 | 0.20444244 | RC_AA4339 30_at | EST: zw52e11.s1 Soares total fetus Nb2HF8 9w Homo sapiens cDNA clone 773708 3' similar to contains Alu repetitive element;, mRNA sequence. (from Genbank) |
| 561 | Colorectal | 0.1430477 | 0.3904657 | 0.330634 | 0.20435798 | HG4683-HT5108_s_a_t | Tumor Necrosis Factor Receptor 2 Associated Protein Trap3 |
| 562 | Colorectal | 0.1429431 | 0.3904283 | 0.330462 | 0.20420091 | HG880-HT880_at | Mucin 6, Gastric (Gb:L07517) |
| 563 | Colorectal | 0.1428845 | 0.3900456 | 0.330301 | 0.20406649 | RC_AA2430 58_at | EST: zr24h08.s1 Stratagene NT2 neuronal precursor 937230 Homo sapiens cDNA clone 664383 3', mRNA sequence. (from Genbank) |
| 564 | Colorectal | 0.1425521 | 0.3899879 | 0.330168 | 0.20393468 | RC_AA2349 25_at | EST: zr78g10.s1 Soares NhHMPu S1 Homo sapiens cDNA clone 669570 3' similar to contains Alu repetitive element;, mRNA sequence. (from Genbank) |
| 565 | Colorectal | 0.1424765 | 0.3899682 | 0.330084 | 0.20380616 | RC_AA6211 59_at | EST: af61g01.s1 Soares NhHMPu S1 Homo sapiens cDNA clone 1046544 3', mRNA sequence. (from Genbank) |
| 566 | Colorectal | 0.1423671 | 0.3899612 | 0.33005 | 0.20371859 | X79483_at | ERK6 mRNA for extracellular signal regulated kinase |
| 567 | Colorectal | 0.1423272 | 0.3898947 | 0.330029 | 0.20368525 | W38778_s_at | EST: zb27g04.r1 Soares parathyroid tumor NbHPA Homo sapiens cDNA clone 304854 5', mRNA sequence. (from Genbank) |
| 568 | Colorectal | 0.1421333 | 0.3898051 | 0.329971 | 0.20360702 | AA262132_a_t | EST: zs23b10.r1 NCI_CGAP_GCB1 Homo sapiens cDNA clone IMAGE:686011 5' similar to SW:YHH6_YEAST P32793 HYPOTHETICAL 41.8 KD PROTEIN IN SPO13-ARG4 INTERGENIC REGION.;, mRNA sequence. (from Genbank) |
| 569 | Colorectal | 0.1419172 | 0.3897153 | 0.329914 | 0.20345855 | AC002115_c ds1_at | COX6B gene (COXG) extracted from Human DNA from overlapping chromosome 19 cosmids R31396, F25451, and R31076 containing COX6B and UPKA, genomic sequence |
| 570 | Colorectal | 0.1417995 | 0.3895923 | 0.329662 | 0.20338286 | M17885_at | RPLP0 Ribosomal protein, large, P0 |
| 571 | Colorectal | 0.1416053 | 0.3895293 | 0.329598 | 0.20327981 | L38487_at | Estrogen receptor-related protein (hERRa1) mRNA, 3' end, partial cds |

FIG. 4Y

| | | | | | | |
|---|---|---|---|---|---|---|
| 572 | Colorectal | 0.1415465 | 0.3894798 | 0.329568 | 0.20315456 | RC_AA1890_15_at | Homo sapiens mRNA for cytochrome b5, partial cds |
| 573 | Colorectal | 0.1413702 | 0.3892001 | 0.329534 | 0.20301951 | U40380_at | PSEN1 Presenilin 1 (Alzheimer disease 3) |
| 574 | Colorectal | 0.1412662 | 0.3891311 | 0.329402 | 0.20286448 | M92299_s_at | Homeo box B5 |
| 575 | Colorectal | 0.1405472 | 0.3890792 | 0.329446 | 0.20278817 | U02082_at | Guanine nucleotide regulatory protein (lirm1) mRNA |
| 576 | Colorectal | 0.1399544 | 0.3889351 | 0.329138 | 0.20276329 | X53800_s_a_t | GRO3 GRO3 oncogene |
| 577 | Colorectal | 0.1397436 | 0.3888428 | 0.329065 | 0.20262466 | RC_AA4266_16_at | EST: zv47f11.s1 Soares ovary tumor NbHOT Homo sapiens cDNA clone 756813 3', mRNA sequence. (from Genbank) |
| 578 | Colorectal | 0.1396057 | 0.3886772 | 0.328977 | 0.20261255 | Z48541_at | Protein tyrosine phosphatase |
| 579 | Colorectal | 0.139491 | 0.388648 | 0.328856 | 0.20243344 | M22877_at | CYC1 Cytochrome c-1 |
| 580 | Colorectal | 0.1391638 | 0.3886307 | 0.328688 | 0.20236476 | AA447876_a_t | EST: aa20c09.r1 Soares NhHMPu S1 Homo sapiens cDNA clone 813808 5', mRNA sequence. (from Genbank) |
| 581 | Colorectal | 0.1390463 | 0.3886001 | 0.328376 | 0.20220411 | X12517_at | U1 small nuclear RNP-specific C protein |
| 582 | Colorectal | 0.1389986 | 0.3885009 | 0.328314 | 0.20216668 | RC_AA4318_73_at | Homo sapiens clone 24711 mRNA sequence |
| 583 | Colorectal | 0.1388823 | 0.3883795 | 0.328271 | 0.20212127 | M38690_at | CD9 CD9 antigen |
| 584 | Colorectal | 0.1385709 | 0.3882337 | 0.328149 | 0.2020956 | U66468_at | Cell growth regulator CGR11 mRNA |
| 585 | Colorectal | 0.138408 | 0.3880641 | 0.32807 | 0.20199909 | RC_AA1431_90_s_at | EST: zo36a01.s1 Stratagene endothelial cell 937223 Homo sapiens cDNA clone 588936 3' similar to SW:YBF7_YEAST P34222 HYPOTHETICAL 23.1 KD PROTEIN IN SHP1-SEC17 INTERGENIC REGION. ;, mRNA sequence. (from Genbank) |
| 586 | Colorectal | 0.1380976 | 0.3880465 | 0.327987 | 0.20181869 | X52773_at-2 | Retinoid X receptor, alpha |
| 587 | Colorectal | 0.1380976 | 0.3879883 | 0.327915 | 0.20177579 | X52773_at | RXRA Retinoid X receptor, alpha |
| 588 | Colorectal | 0.1377286 | 0.3878684 | 0.327874 | 0.20167392 | AA059327_i_at | EST: zf65e11.r1 Soares retina N2b4HR Homo sapiens cDNA clone 381836 5', mRNA sequence. (from Genbank) |
| 589 | Colorectal | 0.1375699 | 0.3877516 | 0.327844 | 0.20156671 | U37689_at | RNA polymerase II subunit (hsRPB8) mRNA |
| 590 | Colorectal | 0.1375565 | 0.3877516 | 0.327734 | 0.20151506 | HG3415-HT3598_at | Poliovirus Receptor |
| 591 | Colorectal | 0.1374446 | 0.3877117 | 0.327664 | 0.2014449 | HG4757-HT5207_s_a_t | Oncogene Mll-Af4, Fusion Activated |
| 592 | Colorectal | 0.1372264 | 0.3875924 | 0.327518 | 0.20134012 | U09210_at | SLC18A3 Solute carrier family 18 (vesicular acetylcholine), member 3 |
| 593 | Colorectal | 0.136795 | 0.3875116 | 0.327616 | 0.20129351 | S62696_s_at | EBV/C3d receptor [alternatively spliced, exons 8a,9,10) [human, Jurkat T cells, mRNA Partial, 151 nt] |
| 594 | Colorectal | 0.1367271 | 0.3874195 | 0.327313 | 0.2012092 | J03040_at | SPARC SPARC/osteonectin |
| 595 | Colorectal | 0.1361887 | 0.3872636 | 0.327248 | 0.20110364 | K03430_at | C1QB Complement component 1, q subcomponent, beta polypeptide |

FIG. 4Z

| | | | | | | |
|---|---|---|---|---|---|---|
| 596 | Colorectal | 0.1361352 | 0.3872297 | 0.327209 | 0.201031195 | Z29066_s_at | Nek2 mRNA for protein kinase |
| 597 | Colorectal | 0.1357074 | 0.3871917 | 0.32718 | 0.20093626 | L17128_at | GGCX Gamma-glutamyl carboxylase |
| 598 | Colorectal | 0.1355016 | 0.3871591 | 0.327043 | 0.20082115 | L27476_at | X104 mRNA |
| 599 | Colorectal | 0.1351314 | 0.3869832 | 0.327043 | 0.20075868 | S59184_at | RYK RYK receptor-like tyrosine kinase |
| 600 | Colorectal | 0.1346302 | 0.3869177 | 0.326995 | 0.20071375 | RC_AA2566 68_at | EST: zr82h02.s1 Soares NhHMPu S1 Homo sapiens cDNA clone 682227 3', mRNA sequence. (from Genbank) |
| 601 | Colorectal | 0.1344563 | 0.3867928 | 0.326888 | 0.20064518 | RC_AA0010 49_at | EST: ze47c08.s1 Soares retina N2b4HR Homo sapiens cDNA clone 362126 3', mRNA sequence. (from Genbank) |
| 602 | Colorectal | 0.1343301 | 0.3867714 | 0.326833 | 0.20058395 | M58597_at | FUT4 Fucosyltransferase 4 (alpha (1,3) fucosyltransferase, myeloid-specific) |
| 603 | Colorectal | 0.1342465 | 0.3867035 | 0.326833 | 0.20053466 | M23294_at | HEXB Hexosaminidase B (beta polypeptide) |
| 604 | Colorectal | 0.1341348 | 0.3864796 | 0.326715 | 0.2004496 | RC_AA4241 48_at | EST: zv81c03.s1 Soares total fetus Nb2HF8 9w Homo sapiens cDNA clone 760036 3', mRNA sequence. (from Genbank) |
| 605 | Colorectal | 0.134009 | 0.3863635 | 0.326534 | 0.20043641 | HG2157-HT2227_at | Mucin 4, Tracheobronchial |
| 606 | Colorectal | 0.1335087 | 0.3863466 | 0.326356 | 0.2002967 | U39447_at | Placenta copper monamine oxidase mRNA |
| 607 | Colorectal | 0.1332906 | 0.3862258 | 0.326333 | 0.20024462 | RC_AA1590 25_at | EST: zo57h03.s1 Stratagene pancreas (#937208) Homo sapiens cDNA clone 591029 3', mRNA sequence. (from Genbank) |
| 608 | Colorectal | 0.133234 | 0.3861477 | 0.32632 | 0.20009403 | AA447244_a at-2 | KIAA0740 gene product |
| 609 | Colorectal | 0.1328404 | 0.3861477 | 0.326233 | 0.1999966 | RC_AA4282 43_at | Integrin beta 4 binding protein |
| 610 | Colorectal | 0.1328117 | 0.3859375 | 0.326124 | 0.19978234 | X68487_at | ADORA2B Adenosine A2b receptor |
| 611 | Colorectal | 0.1325887 | 0.3858976 | 0.326026 | 0.1997248 | AFFX-M27830_M_ at-2 | Human 28S ribosomal RNA gene, complete cds. (from Genbank) |
| 612 | Colorectal | 0.1325887 | 0.3858492 | 0.325844 | 0.19956233 | AFFX-M27830_M_ at | AFFX-M27830_M_at (endogenous control) |
| 613 | Colorectal | 0.1325647 | 0.3858044 | 0.325824 | 0.19954881 | J03934_s_at | NMOR1 NAD(P)H:menadione oxidoreductase |
| 614 | Colorectal | 0.1325387 | 0.38577 | 0.325781 | 0.19947852 | RC_AA1349 65_i_at | EST: zo23g05.s1 Stratagene colon (#937204) Homo sapiens cDNA clone 587768 3', mRNA sequence. (from Genbank) |
| 615 | Colorectal | 0.1322557 | 0.3856998 | 0.325676 | 0.1993915 | L04483_s_at | RPS21 Ribosomal protein S21 |
| 616 | Colorectal | 0.1321966 | 0.3856872 | 0.325661 | 0.19930212 | N78005_at | Homo sapiens SRp46 splicing factor retropseudogene mRNA |
| 617 | Colorectal | 0.1320532 | 0.3855746 | 0.325637 | 0.19923906 | L33799_at | PCOLCE Procollagen C-endopeptidase enhancer |
| 618 | Colorectal | 0.1320363 | 0.3854617 | 0.325485 | 0.1991721 | M62895_s_a t | Annexin II (lipocortin II) pseudogene 2 |

FIG. 4A2

| | | | | | |
|---|---|---|---|---|---|
| 619 | Colorectal | 0.1320046 | 0.3854173 | 0.325461 | 0.19910981 | D10923_at | PROBABLE G PROTEIN-COUPLED RECEPTOR HM74 |
| 620 | Colorectal | 0.1318774 | 0.3854134 | 0.325455 | 0.19888614 | HG3342-HT3519_s_at | Id1 |
| 621 | Colorectal | 0.1316323 | 0.3854109 | 0.325355 | 0.19897164 | U66661_at | GABA-A receptor epsilon subunit mRNA |
| 622 | Colorectal | 0.1314177 | 0.3852747 | 0.325296 | 0.19893168 | X63469_at | GTF2E2 General transcription factor TFIIE beta subunit, 34 kD |
| 623 | Colorectal | 0.131403 | 0.3852558 | 0.325212 | 0.19884351 | D86960_at | KIAA0205 gene |
| 624 | Colorectal | 0.1310938 | 0.3851432 | 0.325175 | 0.19873777 | U25182_at | Antioxidant enzyme AOE37-2 mRNA |
| 625 | Colorectal | 0.130975 | 0.3850127 | 0.324892 | 0.1984489 | RC_AA4762 35_at | EST: zw35h03.s1 Soares ovary tumor NbHOT Homo sapiens cDNA clone 771317 3', mRNA sequence. (from Genbank) |
| 626 | Colorectal | 0.1308969 | 0.3850087 | 0.324847 | 0.19836508 | AA206902_a_t | EST: zq80d01.r1 Stratagene hNT neuron (#937233) Homo sapiens cDNA clone 647905 5', mRNA sequence. (from Genbank) |
| 627 | Colorectal | 0.1306295 | 0.3848691 | 0.324709 | 0.19824855 | Z26317_at | DSG2 Desmoglein 2 |
| 628 | Colorectal | 0.1304023 | 0.3848485 | 0.324543 | 0.198172 | J02947_s_at | SOD3 Superoxide dismutase 3, extracellular |
| 629 | Colorectal | 0.1302964 | 0.3848429 | 0.324512 | 0.19814177 | X01038_rna1_s_at | Fetal gene for apolipoprotein AI precursor |
| 630 | Colorectal | 0.1300966 | 0.3848258 | 0.324477 | 0.19801326 | RC_AA4002 92_at | EST: zu63f03.s1 Soares testis NHT Homo sapiens cDNA clone 742685 3', mRNA sequence. (from Genbank) |
| 631 | Colorectal | 0.1299563 | 0.3847184 | 0.324361 | 0.19793893 | X85740_at | C-C chemokine receptor-4 |
| 632 | Colorectal | 0.1296325 | 0.3847076 | 0.324352 | 0.19790396 | Z11502_at | ANNEXIN XIII |
| 633 | Colorectal | 0.1296167 | 0.3846676 | 0.324267 | 0.19777966 | X58298_s_at | IL6R Interleukin 6 receptor |
| 634 | Colorectal | 0.1294602 | 0.3845975 | 0.324255 | 0.19771707 | RC_AA0998 76_s_at | EST: zl79a05.s1 Stratagene colon (#937204) Homo sapiens cDNA clone 510800 3', mRNA sequence. (from Genbank) |
| 635 | Colorectal | 0.1293851 | 0.3845743 | 0.324044 | 0.1976412 | U16997_at | Orphan receptor ROR gamma mRNA |
| 636 | Colorectal | 0.1293384 | 0.3843444 | 0.323956 | 0.19749188 | M11313_s_at | A2M Alpha-2-macroglobulin |
| 637 | Colorectal | 0.1291705 | 0.3842438 | 0.323791 | 0.19742991 | J02783_at | P4HB Procollagen-proline, 2-oxoglutarate 4-dioxygenase (proline 4-hydroxylase), beta polypeptide (protein disulfide isomerase; thyroid hormone binding protein p55) |
| 638 | Colorectal | 0.1288984 | 0.3842206 | 0.323788 | 0.19735324 | HG2815-HT2931_at | Myosin, Light Chain, Alkali, Smooth Muscle (Gb:U02629), Non-Muscle, Alt. Splice 2 |
| 639 | Colorectal | 0.1287086 | 0.3841534 | 0.323614 | 0.19722882 | RC_AA4033 12_s_at | EST: zt44f05.s1 Soares ovary tumor NbHOT Homo sapiens cDNA clone 725217 3', mRNA sequence. (from Genbank) |
| 640 | Colorectal | 0.1286121 | 0.3840573 | 0.323566 | 0.1971586 | X51801_at | BMP7 Bone morphogenetic protein 7 (osteogenic protein 1) |
| 641 | Colorectal | 0.128513 | 0.3839508 | 0.323522 | 0.1969965 | U46025_at | Chromosome 16p11.2 BAC Clone CIT987SK-234F9 complete sequence |
| 642 | Colorectal | 0.1285114 | 0.383938 | 0.323442 | 0.19691062 | L27943_at | CDA Cytidine deaminase |

FIG. 4B2

| | | | | | | |
|---|---|---|---|---|---|---|
| 643 | Colorectal | 0.1278501 | 0.383938 | 0.323345 | 0.19687009 | D21163_at | KIAA0031 gene |
| 644 | Colorectal | 0.1277185 | 0.3836695 | 0.3233343 | 0.19670084 | HG2191-HT2261_at | Crystallin, Beta B3 (Gb:X15145) |
| 645 | Colorectal | 0.1276059 | 0.3837974 | 0.3233289 | 0.19663636 | U23028_at | EIF2B Eukaryotic translation initiation factor 2B epsilon |
| 646 | Colorectal | 0.1275945 | 0.3836988 | 0.3233274 | 0.19653714 | RC_AA226919_at | EST: zr21a09.s1 Stratagene NT2 neuronal precursor 937230 Homo sapiens cDNA clone 664024 3', mRNA sequence. (from Genbank) |
| 647 | Colorectal | 0.1274344 | 0.3836536 | 0.3233257 | 0.19649628 | RC_AA426640_at | EST: zv47h07.s1 Soares ovary tumor NbHOT Homo sapiens cDNA clone 756829 3', mRNA sequence. (from Genbank) |
| 648 | Colorectal | 0.1272982 | 0.383612 | 0.3233222 | 0.1963967 | U85611_at | Snk interacting protein 2-28 mRNA |
| 649 | Colorectal | 0.1271576 | 0.3835005 | 0.3233184 | 0.19628575 | RC_AA004811_at | EST: zh94a05.s1 Soares fetal liver spleen 1NFLS S1 Homo sapiens cDNA clone 428912 3', mRNA sequence. (from Genbank) |
| 650 | Colorectal | 0.1271194 | 0.3834495 | 0.3233146 | 0.19620813 | X52638_at | PFKFB1 6-phosphofructo-2-kinase/fructose-2,6-biphosphatase 1 |
| 651 | Colorectal | 0.1270278 | 0.3833269 | 0.3233142 | 0.19610842 | D63391_at | Platelet activating factor acetylhydrolase IB gamma-subunit |
| 652 | Colorectal | 0.1269114 | 0.3832566 | 0.3233086 | 0.19604763 | L13720_at | Growth-arrest-specific protein (gas) mRNA |
| 653 | Colorectal | 0.1267173 | 0.3832378 | 0.3232973 | 0.19599566 | U66075_at | Transcription factor hGATA-6 mRNA |
| 654 | Colorectal | 0.1266405 | 0.3831516 | 0.3228999 | 0.1959323 | RC_AA243695_at | Deoxynucleotidyltransferase, terminal |
| 655 | Colorectal | 0.1263899 | 0.3831516 | 0.3228885 | 0.19583826 | AB000584_at | Prostate differentiation factor mRNA |
| 656 | Colorectal | 0.1261906 | 0.3830174 | 0.3228823 | 0.19570024 | M88458_at | ELP-1 mRNA sequence |
| 657 | Colorectal | 0.1261373 | 0.3829249 | 0.32273 | 0.19567592 | AA059287_s_at | EST: zf65e02.r1 Soares retina N2b4HR Homo sapiens cDNA clone 381818 5', mRNA sequence. (from Genbank) |
| 658 | Colorectal | 0.1260684 | 0.3828082 | 0.3228638 | 0.19560139 | RC_AA449720_s_at | Homo sapiens clone 24706 mRNA sequence |
| 659 | Colorectal | 0.1260647 | 0.3827462 | 0.3224451 | 0.19553293 | U17886_at | SDH1 Succinate dehydrogenase, iron sulphur (Ip) subunit |
| 660 | Colorectal | 0.1256548 | 0.3826842 | 0.3223551 | 0.19541393 | X02152_at | LDHA Lactate dehydrogenase A |
| 661 | Colorectal | 0.1253074 | 0.3823456 | 0.3222195 | 0.19537848 | RC_AA056735_at | KIAA0755 gene product |
| 662 | Colorectal | 0.1251066 | 0.3821932 | 0.3222123 | 0.19524361 | L38517_at | Indian hedgehog protein (IHH) mRNA, 5' end |
| 663 | Colorectal | 0.1250249 | 0.3821478 | 0.3222082 | 0.19524361 | AA320369_s_at | GLUT1 C-terminal binding protein |
| 664 | Colorectal | 0.1249676 | 0.3821197 | 0.3222072 | 0.19508958 | RC_AA252893_at | EST: zr76e01.s1 Soares NhHMPu S1 Homo sapiens cDNA clone 669336 3', mRNA sequence. (from Genbank) |
| 665 | Colorectal | 0.1244854 | 0.3821174 | 0.3222068 | 0.19503415 | D86961_at | KIAA0206 gene, partial cds |
| 666 | Colorectal | 0.124412 | 0.38205 | 0.3222033 | 0.19493294 | RC_AA243442_at | Homo sapiens clone 192 Rer1 mRNA, complete cds |
| 667 | Colorectal | 0.1243377 | 0.3818007 | 0.321918 | 0.19484964 | RC_AA058846_at | EST: zf64c05.s1 Soares retina N2b4HR Homo sapiens cDNA clone 381704 3', mRNA sequence. (from Genbank) |

FIG. 4C2

| | | | | | | |
|---|---|---|---|---|---|---|
| 668 | Colorectal | 0.12411185 | 0.3817327 | 0.321866 | 0.19469456 | M73077_at | Glucocorticoid receptor repression factor 1 (GRF-1) mRNA |
| 669 | Colorectal | 0.1240252 | 0.3816356 | 0.321767 | 0.19466443 | U96094_at | Sarcolipin (SLN) mRNA |
| 670 | Colorectal | 0.1239886 | 0.3816297 | 0.32164 | 0.1945989 | AA279633_a t | EST: zs86h10.r1 NCI_CGAP_GCB1 Homo sapiens cDNA clone IMAGE:704419 5' similar to contains element L1 repetitive element;, mRNA sequence. (from Genbank) |
| 671 | Colorectal | 0.1237255 | 0.3814003 | 0.321519 | 0.1944212 | X14787_at | THBS1 Thrombospondin 1 |
| 672 | Colorectal | 0.1237255 | 0.3813465 | 0.321428 | 0.19439913 | X14787_at-2 | Thrombospondin 1 |
| 673 | Colorectal | 0.1237121 | 0.3813404 | 0.321418 | 0.19432822 | U09813_at | Mitochondrial ATP synthase subunit 9, P3 gene copy, mRNA, nuclear gene encoding mitochondrial protein |
| 674 | Colorectal | 0.1236289 | 0.3812598 | 0.321297 | 0.19428834 | X77584_at | TXN Thioredoxin |
| 675 | Colorectal | 0.1234703 | 0.3810924 | 0.321227 | 0.19422735 | RC_AA4421 25_at | KIAA0331 gene product |
| 676 | Colorectal | 0.123212 | 0.381041 | 0.321201 | 0.1940369 | RC_AA4258 52_s_at | EST: zw47g11.s1 Soares total fetus Nb2HF8_9w Homo sapiens cDNA clone 773252 3', mRNA sequence. (from Genbank) |
| 677 | Colorectal | 0.1231618 | 0.3808966 | 0.321196 | 0.19395724 | U43519_at | DRP2 Dystrophin related protein 2 |
| 678 | Colorectal | 0.1230573 | 0.3808346 | 0.321145 | 0.19385812 | AA131127_a t | Cathepsin Z |
| 679 | Colorectal | 0.1229442 | 0.3807745 | 0.321119 | 0.19382109 | X92814_at | Rat HREV107-like protein |
| 680 | Colorectal | 0.1228716 | 0.380758 | 0.321081 | 0.19368309 | D38293_at | Clathrin-like protein |
| 681 | Colorectal | 0.1227563 | 0.3807509 | 0.320973 | 0.19358245 | D43950_at | T-COMPLEX PROTEIN 1, EPSILON SUBUNIT |
| 682 | Colorectal | 0.1225971 | 0.3806008 | 0.320966 | 0.1934891 | D25274_at | Randomly sequenced mRNA |
| 683 | Colorectal | 0.1224722 | 0.3805043 | 0.320837 | 0.19335964 | D26018_at | KIAA0039 gene, partial cds |
| 684 | Colorectal | 0.1223172 | 0.3804649 | 0.320789 | 0.1932318 | U27328_s_a t | Fucosyltransferase 3 (galactoside 3(4)-L-fucosyltransferase, Lewis blood group included) |
| 685 | Colorectal | 0.1222639 | 0.3804564 | 0.320783 | 0.19322662 | RC_AA1470 67_at | EST: zo32a02.s1 Stratagene colon (#937204) Homo sapiens cDNA clone 588554 3', mRNA sequence. (from Genbank) |
| 686 | Colorectal | 0.1220887 | 0.3803847 | 0.320777 | 0.19317591 | M10277_s_a t | ACTB Actin, beta |
| 687 | Colorectal | 0.1220792 | 0.3803649 | 0.320685 | 0.19308423 | RC_AA2570 74_at | EST: zr82c03.s1 Soares NhHMPu_S1 Homo sapiens cDNA clone 682180 3', mRNA sequence. (from Genbank) |
| 688 | Colorectal | 0.1218589 | 0.3803211 | 0.320593 | 0.19302863 | U95006_at | D9 splice variant A mRNA |
| 689 | Colorectal | 0.1217905 | 0.3802693 | 0.320566 | 0.1930049 | AA094507_s _at | EST: cp0543.seq.F Fetal heart, Lambda ZAP Express Homo sapiens cDNA 5', mRNA sequence. (from Genbank) |
| 690 | Colorectal | 0.121765 | 0.3801889 | 0.320555 | 0.19295281 | RC_AA4028 00_at | EST: zu49d12.s1 Soares ovary tumor NbHOT Homo sapiens cDNA clone 741335 3' similar to contains Alu repetitive element;, mRNA sequence. (from Genbank) |
| 691 | Colorectal | 0.1215827 | 0.3801688 | 0.320296 | 0.19282936 | X92720_at | Phosphoenolpyruvate carboxykinase |
| 692 | Colorectal | 0.1215787 | 0.3800073 | 0.320113 | 0.19273862 | M83751_at | Arginine-rich protein (ARP) gene |

FIG. 4D2

| | | | | | |
|---|---|---|---|---|---|
| 693 | Colorectal | 0.1215052 | 0.3799817 | 0.320062 | 0.19265793 | AA173597_a t | EST: zp03c08.r1 Stratagene ovarian cancer (#937219) Homo sapiens cDNA clone 595310 5', mRNA sequence. (from Genbank) |
| 694 | Colorectal | 0.1213798 | 0.3799744 | 0.319914 | 0.19256769 | HG1103-HT1103_at | Guanine Nucleotide-Binding Protein Ral, Ras-Oncogene Related |
| 695 | Colorectal | 0.1212289 | 0.3799523 | 0.319875 | 0.19248337 | D00654_at | Enteric smooth muscle gamma-actin gene, 5' flank and |
| 696 | Colorectal | 0.1210308 | 0.3799256 | 0.319713 | 0.19233952 | RC_AA1674 36_i_at | EST: zp08l09.s1 Stratagene ovarian cancer (#937219) Homo sapiens cDNA clone 595817 3', mRNA sequence. (from Genbank) |
| 697 | Colorectal | 0.1209356 | 0.379987 | 0.319691 | 0.19229622 | RC_AA4357 69_s_at | EST: zl79h07.s1 Soares testis NHT Homo sapiens cDNA clone 728605 3', mRNA sequence. (from Genbank) |
| 698 | Colorectal | 0.1209061 | 0.3798532 | 0.319689 | 0.19213337 | M16937_at | Homeo box c1 protein, mRNA |
| 699 | Colorectal | 0.1208698 | 0.3798241 | 0.319609 | 0.19205002 | U12535_at | Epidermal growth factor receptor kinase substrate (Eps8) mRNA |
| 700 | Colorectal | 0.1206551 | 0.3797887 | 0.319526 | 0.19187795 | D13636_at | KIAA0011 gene |
| 701 | Colorectal | 0.1206173 | 0.3797084 | 0.319314 | 0.19184203 | L06845_at | CARS Cysteinyl-tRNA synthetase |
| 702 | Colorectal | 0.1204419 | 0.3796654 | 0.319127 | 0.1918137 | U84720_at | mRNA export protein Rae1 (RAE1) mRNA |
| 703 | Colorectal | 0.1204366 | 0.3795269 | 0.319112 | 0.19169855 | U10550_at | Gem GTPase (gem) mRNA |
| 704 | Colorectal | 0.1203954 | 0.3794884 | 0.319098 | 0.19165988 | HG174-HT174_at | Desmoplakin I |
| 705 | Colorectal | 0.1201526 | 0.3793192 | 0.319069 | 0.1915b694 | RC_C14898_at | EST: Human fetal brain cDNA 3'-end GEN-098C12, mRNA sequence. (from Genbank) |
| 706 | Colorectal | 0.1200641 | 0.3793083 | 0.319056 | 0.19140579 | RC_AA1267 19_at | EST: zk95b03.s1 Soares pregnant uterus NbHPU Homo sapiens cDNA clone 490541 3', mRNA sequence. (from Genbank) |
| 707 | Colorectal | 0.1198904 | 0.3792779 | 0.318937 | 0.19129631 | RC_AA2058 03_at | Homo sapiens mRNA for nebulette |
| 708 | Colorectal | 0.119448 | 0.3792536 | 0.318931 | 0.19127026 | AA380393_a t | EST: EST93352 Supt cells Homo sapiens cDNA 5' end, mRNA sequence. (from Genbank) |
| 709 | Colorectal | 0.1188506 | 0.3791769 | 0.318815 | 0.1911793 | X66401_cds 1_at | LMP2 gene extracted from H.sapiens genes TAP1, TAP2, LMP2, LMP7 and DOB |
| 710 | Colorectal | 0.1183064 | 0.3791715 | 0.318644 | 0.19111046 | RC_AA1521 03_at | Human Chromosome 16 BAC clone CIT987SK-A-735G6 |
| 711 | Colorectal | 0.118229 | 0.3790575 | 0.318574 | 0.19102597 | AA456471_s _at | EST: zx74g11.r1 Soares ovary tumor NbHOT Homo sapiens cDNA clone 809540 5', mRNA sequence. (from Genbank) |
| 712 | Colorectal | 0.1179214 | 0.3789529 | 0.318574 | 0.19099104 | RC_AA0558 41_at | EST: zf20c08.s1 Soares fetal heart NbHH19W Homo sapiens cDNA clone 377486 3', mRNA sequence. (from Genbank) |
| 713 | Colorectal | 0.1178902 | 0.3789345 | 0.318568 | 0.19093734 | RC_AA4494 75_at | EST: zx08l10.s1 Soares total fetus Nb2HF8 9w Homo sapiens cDNA clone 785899 3' similar to contains Alu repetitive element;contains element MER22 repetitive element ;; mRNA sequence. (from Genbank) |

FIG. 4E2

| # | Type | | | | Accession | Description |
|---|---|---|---|---|---|---|
| 714 | Colorectal | 0.1175263 | 0.378897 | 0.318468 | 0.19087711 | RC_AA4499 42_at | EST: zx38a01.s1 Soares total fetus Nb2HF8 9w Homo sapiens cDNA clone 788712 3', mRNA sequence. (from Genbank) |
| 715 | Colorectal | 0.1174486 | 0.3788644 | 0.318365 | 0.19075918 | RC_AA4173 73_at | EST: zu05a12.s1 Soares testis NHT Homo sapiens cDNA clone 730942 3' similar to contains element MER31 repetitive element ;, mRNA sequence. (from Genbank) |
| 716 | Colorectal | 0.1174355 | 0.3788196 | 0.318296 | 0.19057879 | RC_AA4056 12_at | Interferon-related developmental regulator 1 |
| 717 | Colorectal | 0.1174113 | 0.3788065 | 0.318253 | 0.19052759 | RC_AA4057 44_at | EST: zu66f10.s1 Soares testis NHT Homo sapiens cDNA clone 742987 3', mRNA sequence. (from Genbank) |
| 718 | Colorectal | 0.1173908 | 0.3786251 | 0.318239 | 0.19046406 | X66839_at | MaTu MN mRNA for p54/58N protein |
| 719 | Colorectal | 0.1173887 | 0.3784709 | 0.318184 | 0.19038299 | U07550_at | HSPE1 Heat shock 10 kD protein 1 (chaperonin 10) |
| 720 | Colorectal | 0.1171897 | 0.378439 | 0.317972 | 0.19029583 | X54941_at | CKS1 CDC28 protein kinase 1 |
| 721 | Colorectal | 0.117116 | 0.378436 | 0.317922 | 0.19015858 | HG987-HT987_at | Mac25 |
| 722 | Colorectal | 0.1170865 | 0.378394 | 0.317814 | 0.19011314 | D81608_at | Polymerase (RNA) II (DNA directed) polypeptide L (7.6kD) |
| 723 | Colorectal | 0.1168432 | 0.3781567 | 0.317737 | 0.1900737 | Y08639_at | Nuclear orphan receptor ROR-beta |
| 724 | Colorectal | 0.1165629 | 0.3781449 | 0.317715 | 0.18990482 | X76534_at | NMB Neuromedin B |
| 725 | Colorectal | 0.1162928 | 0.3780906 | 0.317655 | 0.18984148 | N72380_s_at | EST: yv38f12.r1 Soares fetal liver spleen 1NFLS Homo sapiens cDNA clone 245039 5', mRNA sequence. (from Genbank) |
| 726 | Colorectal | 0.1161021 | 0.3780412 | 0.317634 | 0.18976343 | W49521_at | Procollagen-proline, 2-oxoglutarate 4-dioxygenase (proline 4-hydroxylase), alpha polypeptide II |
| 727 | Colorectal | 0.1159714 | 0.3779147 | 0.317588 | 0.18965365 | X13334_at | CD14 CD14 antigen |
| 728 | Colorectal | 0.1149368 | 0.377831 | 0.31775 | 0.18956053 | RC_AA1567 92_at | EST: zl18h06.s1 Soares pregnant uterus NbHPU Homo sapiens cDNA clone 502331 3', mRNA sequence. (from Genbank) |
| 729 | Colorectal | 0.1147768 | 0.3777796 | 0.317498 | 0.18949509 | RC_AA2360 18_at | EST: zs05b10.s1 NCI_CGAP_GCB1 Homo sapiens cDNA clone IMAGE:684283 3', mRNA sequence. (from Genbank) |
| 730 | Colorectal | 0.114763 | 0.3777811 | 0.317325 | 0.18942805 | J04162_at | FCGR3 Fc fragment of IgG, low affinity IIIa, receptor for (CD16) |
| 731 | Colorectal | 0.11451 | 0.3777578 | 0.317125 | 0.18937059 | RC_AA4192 17_at | EST: zv34h10.s1 Soares ovary tumor NbHOT Homo sapiens cDNA clone 755587 3', mRNA sequence. (from Genbank) |
| 732 | Colorectal | 0.1144905 | 0.3777307 | 0.317088 | 0.18931441 | X02530_at | INP10 Interferon (gamma)-induced cell line; protein 10 from |
| 733 | Colorectal | 0.1141271 | 0.3777167 | 0.316991 | 0.18925394 | X70040_at | MST1R Protein-tyrosine kinase RON |
| 734 | Colorectal | 0.1139887 | 0.3777167 | 0.316929 | 0.18907441 | M22632_at | GOT2 Glutamic-oxaloacetic transaminase 2, mitochondrial (aspartate aminotransferase 2) |
| 735 | Colorectal | 0.1137097 | 0.3776079 | 0.316806 | 0.18901491 | Z37986_al | Phenylalkylamine binding protein |
| 736 | Colorectal | 0.1136393 | 0.3774442 | 0.316676 | 0.18888438 | HG742-HT742_at | Latent Membrane Protein Lmp1 |
| 737 | Colorectal | 0.113539 | 0.3773945 | 0.316721 | 0.18892474 | RC_AA1568 73_at | EST: zl20h08.s1 Soares pregnant uterus NbHPU Homo sapiens cDNA clone 502527 3', mRNA sequence. (from Genbank) |
| 738 | Colorectal | 0.1134186 | 0.377328 | 0.316529 | 0.18888468 | RC_AA0472 90_at | EST: zk74f05.s1 Soares pregnant uterus NbHPU Homo sapiens cDNA clone 488577 3', mRNA sequence. (from Genbank) |

FIG. 4F2

| # | Tissue | | | | | Description |
|---|---|---|---|---|---|---|
| 739 | Colorectal | 0.1132421 | 0.3772997 | 0.316489 | 0.18871331 U46751_at | Phosphotyrosine independent ligand p62 for the Lck SH2 domain mRNA |
| 740 | Colorectal | 0.1128246 | 0.3772854 | 0.316455 | 0.1886412 D11094_at | 26S PROTEASE REGULATORY SUBUNIT 7 |
| 741 | Colorectal | 0.1127841 | 0.377231 | 0.316398 | 0.18851288 RC_AA4357 20_f_at | Homo sapiens (clone ch13lambda7) alpha-tubulin mRNA, complete cds |
| 742 | Colorectal | 0.1127803 | 0.3772103 | 0.316278 | 0.18840776 M22760_at | CYTOCHROME C OXIDASE POLYPEPTIDE VA PRECURSOR |
| 743 | Colorectal | 0.1126677 | 0.3770899 | 0.316247 | 0.18837102 RC_AA2925 33_at | EST: zs59b05.s1 NCI_CGAP_GCB1 Homo sapiens cDNA clone IMAGE:7017745 3', mRNA sequence. (from Genbank) |
| 744 | Colorectal | 0.1120379 | 0.3770616 | 0.316134 | 0.18832907 X17567_s_a t | SNRPB Small nuclear ribonucleoprotein polypeptides B and B1 |
| 745 | Colorectal | 0.1120189 | 0.3770135 | 0.316068 | 0.18818274 U93205_at | Nuclear chloride ion channel protein (NCC27) mRNA |
| 746 | Colorectal | 0.1117057 | 0.3769751 | 0.316004 | 0.18809533 Z74615_at | COL1A1 Collagen, type I, alpha 1 |
| 747 | Colorectal | 0.1116607 | 0.3769163 | 0.315769 | 0.1880267 X81832_s_a t | GIPR Gastric inhibitory polypeptide receptor |
| 748 | Colorectal | 0.1116565 | 0.3769163 | 0.315752 | 0.18788427 D62600_s_a t | EST: Human aorta cDNA 5'-end GEN-304G05, mRNA sequence. (from Genbank) |
| 749 | Colorectal | 0.1115345 | 0.3768666 | 0.315714 | 0.18781038 L27080_at | Melanocortin 5 receptor (MC5R) gene |
| 750 | Colorectal | 0.1113154 | 0.376859 | 0.315634 | 0.18766183 U09587_at | GARS Glycyl-tRNA synthetase |
| 751 | Colorectal | 0.1111667 | 0.376736 | 0.315621 | 0.18762258 RC_AA0106 19_at | EST: zi09g09.s1 Soares fetal liver spleen 1NFLS S1 Homo sapiens cDNA clone 430336 3', mRNA sequence. (from Genbank) |
| 752 | Colorectal | 0.1110516 | 0.3766674 | 0.315578 | 0.18740402 RC_AA2331 70_al | Interleukin 13 receptor, alpha 1 |
| 753 | Colorectal | 0.1110429 | 0.3766201 | 0.315546 | 0.18737254 M92934_at | CTGF Connective tissue growth factor |
| 754 | Colorectal | 0.1110066 | 0.3766073 | 0.315458 | 0.1873025 RC_AA1160 36_at | EST: zm79a11.s1 Stratagene neuroepithelium (#937231) Homo sapiens cDNA clone 531836 3', mRNA sequence. (from Genbank) |
| 755 | Colorectal | 0.1108751 | 0.3765291 | 0.315199 | 0.1872338 RC_AA3218 33_at | EST: EST24395 Cerebellum II Homo sapiens cDNA 3' end, mRNA sequence. (from Genbank) |
| 756 | Colorectal | 0.1107573 | 0.3764139 | 0.315182 | 0.18718122 RC_AA4789 67_at | EST: zv18e03.s1 Soares NhHMPu S1 Homo sapiens cDNA clone 754012 3', mRNA sequence. (from Genbank) |
| 757 | Colorectal | 0.1107559 | 0.3763478 | 0.315154 | 0.18709068 D86968_at | KIAA0213 gene, partial cds |
| 758 | Colorectal | 0.110665 | 0.3763036 | 0.315107 | 0.18704936 D21853_at | EUKARYOTIC INITIATION FACTOR 4A-LIKE NUK-34 |
| 759 | Colorectal | 0.1105232 | 0.3762199 | 0.315103 | 0.18690695 T35341_s_at | EST: EST83074 Homo sapiens cDNA 5' end similar to None. (from Genbank) |
| 760 | Colorectal | 0.1105111 | 0.3760927 | 0.314993 | 0.18681534 L07597_at | RPS6KA2 Ribosomal protein S6 kinase, 90kD, polypeptide 2 |
| 761 | Colorectal | 0.110045 | 0.3760301 | 0.314982 | 0.18676004 J04823_ma1 _at | Cytochrome c oxidase subunit VIII (COX8) mRNA |

FIG. 4G2

| | | | | | |
|---|---|---|---|---|---|
| 762 | Colorectal | 0.1102982 | 0.3760109 | 0.314861 | 0.1866799 | RC_AA0395 76_at | EST: zf07h12.s1 Soares fetal heart NbHH19W Homo sapiens cDNA clone 376295 3' similar to contains Alu repetitive element;contains element PTR5 repetitive element ;, mRNA sequence. (from Genbank) |
| 763 | Colorectal | 0.1101836 | 0.37759728 | 0.314826 | 0.1866324 | RC_AA2364 60_at | EST: zr75h04.s1 Soares NhHMPu S1 Homo sapiens cDNA clone 669271 3', mRNA sequence. (from Genbank) |
| 764 | Colorectal | 0.1101059 | 0.3758947 | 0.31479 | 0.18651803 | X59812_at | CYP27 Cytochrome P450, subfamily XXVII (steroid 27-hydroxylase, cerebrotendinous xanthomatosis) |
| 765 | Colorectal | 0.1096608 | 0.3758305 | 0.31479 | 0.18645349 | Z11793_at | Selenoprotein P |
| 766 | Colorectal | 0.1095469 | 0.3757923 | 0.314749 | 0.18636103 | U59309_at | FH Fumarate hydratase |
| 767 | Colorectal | 0.1094853 | 0.3757726 | 0.314526 | 0.18633045 | RC_AA2523 95_at | EST: zs12g10.s1 NCI_CGAP_GCB1 Homo sapiens cDNA clone IMAGE:685026 3', mRNA sequence. (from Genbank) |
| 768 | Colorectal | 0.1094749 | 0.3757363 | 0.31446 | 0.18620825 | M57732_at | TCF1 Transcription factor 1, hepatic; LF-B1, hepatic nuclear factor (HNF1), albumin proximal factor |
| 769 | Colorectal | 0.1094025 | 0.3756432 | 0.314306 | 0.18616688 | RC_AA4417 98_at | EST: zw62c11.s1 Soares total fetus Nb2HF8 9w Homo sapiens cDNA clone 774644 3' similar to TR:G207250 G207250 RAT GROWTH AND TRANSFORMATION-DEPENDENT ;, mRNA sequence. (from Genbank) |
| 770 | Colorectal | 0.1086783 | 0.3754573 | 0.314255 | 0.18606272 | D14659_at | KIAA0103 gene |
| 771 | Colorectal | 0.1085378 | 0.3754449 | 0.314135 | 0.18603663 | RC_AA4559 67_at | Neuronal PAS domain protein 2 |
| 772 | Colorectal | 0.1083784 | 0.3754011 | 0.314118 | 0.18593888 | X16666_s_a t-2 | Homeo box B1 |
| 773 | Colorectal | 0.1083784 | 0.3751272 | 0.314106 | 0.18587461 | X16666_s_a t | HOXB1 Homeo box B1 |
| 774 | Colorectal | 0.1082166 | 0.3750993 | 0.314064 | 0.185880322 | AA195893_a t | EST: zp97e03.r1 Stratagene muscle 937209 Homo sapiens cDNA clone 628156 5', mRNA sequence. (from Genbank) |
| 775 | Colorectal | 0.1082015 | 0.3750481 | 0.314014 | 0.18572451 | Z25821_rna 1_s_at | Dodecenoyl-Coenzyme A delta isomerase (3,2 trans-enoyl-Coenzyme A isomerase) |
| 776 | Colorectal | 0.1081496 | 0.3749245 | 0.313833 | 0.18563227 | HG658-HT658_f_at | Major Histocompatibility Complex, Class I, C (Gb:X58536) |
| 777 | Colorectal | 0.1080974 | 0.3747783 | 0.313822 | 0.18554266 | X84709_at | Mediator of receptor-induced toxicity |
| 778 | Colorectal | 0.1080925 | 0.3747637 | 0.31351 | 0.18540493 | RC_AA4821 26_at | Claudin 3 |
| 779 | Colorectal | 0.1080379 | 0.3747521 | 0.313519 | 0.18532212 | L24203_at | EST: zs80b08.s1 NCI_CGAP_GCB1 Homo sapiens cDNA clone IMAGE:703767 3', mRNA sequence. (from Genbank) |
| 780 | Colorectal | 0.1080002 | 0.3747438 | 0.313463 | 0.1852719 | L24203_at | Ataxia-telangiectasia group D-associated protein mRNA |
| 781 | Colorectal | 0.1079596 | 0.3745598 | 0.313458 | 0.18518591 | RC_AA4502 33_at | EST: zx43d06.s1 Soares total fetus Nb2HF8 9w Homo sapiens cDNA clone 789227 3', mRNA sequence. (from Genbank) |

FIG. 4H2

| | | | | | |
|---|---|---|---|---|---|
| 782 | Colorectal | 0.1078156 | 0.3744406 | 0.313386 | RC_AA4248 0.18515852 81_at | EST: zw03c10.s1 Soares NhHMPu S1 Homo sapiens cDNA clone 768210 3', mRNA sequence. (from Genbank) |
| 783 | Colorectal | 0.1076643 | 0.3744339 | 0.313304 | AA489716_a 0.18505086 t | EST: aa43a01.r1 Soares NhHMPu S1 Homo sapiens cDNA clone 823656 5' similar to contains element MER22 repetitive element ;, mRNA sequence. (from Genbank) |
| 784 | Colorectal | 0.1075382 | 0.3742585 | 0.3133234 | 0.18496718 L35854_at | Dystrophin (dp140) mRNA, 5' end |
| 785 | Colorectal | 0.1073138 | 0.3742047 | 0.313205 | 0.18489441 U79277_at | Clone 23548 mRNA sequence |
| 786 | Colorectal | 0.107282 | 0.3741384 | 0.313172 | 0.1848114 S69272_s_at | Cytoplasmic antiproteinase |
| 787 | Colorectal | 0.1071564 | 0.3740613 | 0.313067 | RC_AA5984 0.18476222 44_at | Homo sapiens clone 486790 diphosphoinositol polyphosphate phosphohydrolase mRNA, complete cds |
| 788 | Colorectal | 0.1071265 | 0.3740326 | 0.313037 | RC_AA4908 0.18471572 85_at | EST: aa48d05.s1 NCI_CGAP_GCB1 Homo sapiens cDNA clone IMAGE:824169 3', mRNA sequence. (from Genbank) |
| 789 | Colorectal | 0.1069943 | 0.3740277 | 0.313037 | 0.18461254 L09260_at | (chromosome 3p25) membrane protein mRNA |
| 790 | Colorectal | 0.1069878 | 0.3739299 | 0.312959 | 0.18451354 D45213_at | Homo sapiens mRNA for zinc finger protein, complete cds |
| 791 | Colorectal | 0.1068639 | 0.3739 | 0.312854 | 0.18444666 J03460_s_at | Prolactin-induced protein |
| 792 | Colorectal | 0.1064241 | 0.3736877 | 0.312743 | AA081209_a 0.18432246 t | Regulator of G-protein signalling 5 |
| 793 | Colorectal | 0.1060864 | 0.3736441 | 0.312695 | 0.18428504 U26726_at | 11 beta-hydroxysteroid dehydrogenase type II mRNA |
| 794 | Colorectal | 0.1058599 | 0.373621 | 0.31266 | RC_AA4279 0.18425202 78_at | EST: zw32f12.s1 Soares ovary tumor NbHOT Homo sapiens cDNA clone 771023 3' similar to contains Alu repetitive element;contains element OFR repetitive element ;, mRNA sequence. (from Genbank) |
| 795 | Colorectal | 0.1056269 | 0.3735119 | 0.312572 | AA036794_a 0.18417485 t | EST: zk29a01.r1 Soares pregnant uterus NbHPU Homo sapiens cDNA clone 471912 5' similar to WP:T20B12.3 CE01409 ;, mRNA sequence. (from Genbank) |
| 796 | Colorectal | 0.10558 | 0.3734322 | 0.312513 | X03794_s_a 0.18413731 t | HOXB5 Homeo box B5 (2.1 protein) |
| 797 | Colorectal | 0.1055759 | 0.3732599 | 0.312471 | 0.18404259 J04058_at | ETFA Electron-transfer-flavoprotein, alpha polypeptide (glutaric aciduria II) |
| 798 | Colorectal | 0.1055733 | 0.3731474 | 0.312384 | RC_AA2812 0.18397607 45_at | EST: zs94d07.s1 NCI_CGAP_GCB1 Homo sapiens cDNA clone IMAGE:705133 3', mRNA sequence. (from Genbank) |
| 799 | Colorectal | 0.1054405 | 0.3730889 | 0.31236 | 0.18394175 U47105_at | H105e3 mRNA |
| 800 | Colorectal | 0.1052258 | 0.3730461 | 0.312333 | 0.18386884 S82447_s_at | GCN5-like 1 |
| 801 | Colorectal | 0.1050332 | 0.3730134 | 0.312306 | 0.18372026 D82348_at | 5-aminoimidazole-4-carboxamide-1-beta-D-ribonucleoti de transformylase/inosinicase |
| 802 | Colorectal | 0.1050332 | 0.3729946 | 0.312253 | 0.18366866 D82348_at-2 | Homo sapiens mRNA for 5-aminoimidazole-4-carboxamide-1-beta-D-ribon ucleotide transformylase/inosinicase, complete cds |

FIG. 4I2

| # | Tissue | | | | ID | Description |
|---|---|---|---|---|---|---|
| 803 | Colorectal | 0.1047495 | 0.3729363 | 0.312239 | RC_AA4599 | EST: zx66c02.s1 Soares total fetus Nb2HF8 9w Homo sapiens cDNA clone 796418 3', mRNA sequence. (from Genbank) |
| 804 | Colorectal | 0.1047429 | 0.3728766 | 0.312205 | 0.18349603 | M63603_at PLN Phospholamban |
| 805 | Colorectal | 0.1046492 | 0.3728493 | 0.312186 | HG2190-HT2260_at | Crystallin, Beta B3 (Gb:X15144) |
| 806 | Colorectal | 0.1045248 | 0.372826 | 0.312176 | RC_AA1714 88_at | Homo sapiens clone 24778 unknown mRNA |
| 807 | Colorectal | 0.1043271 | 0.3727079 | 0.312153 | D17793_at | DDH1 Dihydrodiol dehydrogenase |
| 808 | Colorectal | 0.1041077 | 0.3725623 | 0.312098 | RC_AA1514 35_at | EST: zl43h11.s1 Soares pregnant uterus NbHPU Homo sapiens cDNA clone 504741 3', mRNA sequence. (from Genbank) |
| 809 | Colorectal | 0.103823 | 0.3724439 | 0.312098 | D45371_at | ApM1 mRNA for GS3109 (novel adipose specific collagen-like factor) |
| 810 | Colorectal | 0.1037316 | 0.372392 | 0.312058 | RC_AA2837 74_at | EST: zt18d04.s1 Soares ovary tumor NbHOT Homo sapiens cDNA clone 713479 3', mRNA sequence. (from Genbank) |
| 811 | Colorectal | 0.1036369 | 0.3723761 | 0.311945 | HG4716-HT5158_at | Guanosine 5'-Monophosphate Synthase |
| 812 | Colorectal | 0.1034785 | 0.3723377 | 0.311896 | AA402298_s_at | Actinin, alpha 4 |
| 813 | Colorectal | 0.1034678 | 0.3721637 | 0.311779 | RC_AA2339 57_at | EST: zr27e04.s1 Stratagene NT2 neuronal precursor 937230 Homo sapiens cDNA clone 664638 3', mRNA sequence. (from Genbank) |
| 814 | Colorectal | 0.1033997 | 0.372103 | 0.311453 | Z56281_at | Interferon regulatory factor 3 |
| 815 | Colorectal | 0.103123 | 0.3719171 | 0.311318 | AA247685_a_at | Desmoplakin (DPI, DPII) |
| 816 | Colorectal | 0.103017 | 0.3717969 | 0.311197 | RC_AA4890 91_at | EST: aa56g08.s1 NCI_CGAP_GCB1 Homo sapiens cDNA clone IMAGE:824990 3', mRNA sequence. (from Genbank) |
| 817 | Colorectal | 0.1028238 | 0.3717966 | 0.31111 | RC_AA4245 17_at | EST: zv90f06.s1 Soares NhHMPu S1 Homo sapiens cDNA clone 767075 3', mRNA sequence. (from Genbank) |
| 818 | Colorectal | 0.1026596 | 0.3716924 | 0.311072 | M10321_s_at | VON WILLEBRAND FACTOR PRECURSOR |
| 819 | Colorectal | 0.1023984 | 0.3716767 | 0.311008 | X87870_at | HEPATOCYTE NUCLEAR FACTOR 4 |
| 820 | Colorectal | 0.1022189 | 0.3716735 | 0.310788 | J03910_rna1_at | (clone 14VS) metallothionein-IG (MT1G) gene |
| 821 | Colorectal | 0.1020303 | 0.3716703 | 0.310763 | L33801_at | Protein kinase mRNA |
| 822 | Colorectal | 0.1019609 | 0.3715265 | 0.310696 | D83260_s_at | HXC-26 mRNA |
| 823 | Colorectal | 0.1016902 | 0.3714274 | 0.310641 | D80009_at | KIAA0187 gene |
| 824 | Colorectal | 0.1016138 | 0.3714401 | 0.310531 | AA329542_a_at | EST: EST33182 Embryo, 12 week II Homo sapiens cDNA 5' end, mRNA sequence. (from Genbank) |

FIG. 4J2

| | | | | | | |
|---|---|---|---|---|---|---|
| 825 | Colorectal | 0.1015356 | 0.3712717 | 0.310431 | 0.18188469 | N89563_s_a t | EST: HFBEST-40 Human fetal brain QBoqin2 Homo sapiens cDNA, mRNA sequence. (from Genbank) |
| 826 | Colorectal | 0.1015221 | 0.3711679 | 0.310429 | 0.18179104 | Z80345_rna 1_s_at | SCAD gene, exon 1 and joining features |
| 827 | Colorectal | 0.1015099 | 0.3710451 | 0.310315 | 0.18177584 | U67849_at | Beta-galactoside alpha2,6-sialyltransferase (SIAT1) mRNA, exon W |
| 828 | Colorectal | 0.1014571 | 0.371024 | 0.310299 | 0.181682 | X57579_s_a t | Activin beta-A subunit (exon 2) |
| 829 | Colorectal | 0.1013914 | 0.3709471 | 0.310279 | 0.18161505 | RC_AA4777 29_at | EST: zu44g09.s1 Soares ovary tumor NbHOT Homo sapiens cDNA clone 740896 3', mRNA sequence. (from Genbank) |
| 830 | Colorectal | 0.1011125 | 0.3708007 | 0.310261 | 0.181525 | D83782_at | KIAA0199 gene, partial cds |
| 831 | Colorectal | 0.1010276 | 0.3706148 | 0.310255 | 0.18142752 | M31013_at | MYH9 Myosin, heavy polypeptide 9, non-muscle |
| 832 | Colorectal | 0.1010108 | 0.3704874 | 0.310231 | 0.18137753 | AA461426_r at | EST: zx63h02.r1 Soares total fetus Nb2HF8 9w Homo sapiens cDNA clone 796179 5', mRNA sequence. (from Genbank) |
| 833 | Colorectal | 0.1008865 | 0.3704431 | 0.310156 | 0.18131231 | RC_AA4364 77_at | EST: zv08f05.s1 Soares NhHMPu S1 Homo sapiens cDNA clone 753057 3', mRNA sequence. (from Genbank) |
| 834 | Colorectal | 0.1005393 | 0.370402 | 0.309907 | 0.18125597 | X04366_at | CALPAIN 1, LARGE |
| 835 | Colorectal | 0.1004137 | 0.3703068 | 0.30984 | 0.18108182 | RC_AA4569 81_at | EST: aa90h11.s1 Stratagene fetal retina 937202 Homo sapiens cDNA clone 838629 3' similar to contains Alu repetitive element;, mRNA sequence. (from Genbank) |
| 836 | Colorectal | 0.1001854 | 0.3702498 | 0.309749 | 0.18106878 | RC_AA4286 03_at | EST: zw69c02.s1 Soares testis NHT Homo sapiens cDNA clone 781442 3', mRNA sequence. (from Genbank) |
| 837 | Colorectal | 0.0999086 | 0.3702316 | 0.309709 | 0.18103768 | AA425251_a t | EST: zw47g05.r1 Soares total fetus Nb2HF8 9w Homo sapiens cDNA clone 773240 5' similar to SW:ALG5_YEAST P40350 DOLICHYL-PHOSPHATE BETA-GLUCOSYLTRANSFERASE :, mRNA sequence. (from Genbank) |
| 838 | Colorectal | 0.0998011 | 0.3701576 | 0.309696 | 0.18103768 | RC_AA4477 22_at | EST: aa20d05.s1 Soares NhHMPu S1 Homo sapiens cDNA clone 813801 3', mRNA sequence. (from Genbank) |
| 839 | Colorectal | 0.099793 | 0.3701058 | 0.309655 | 0.1809571 | U56998_at | Putative serine/threonine protein kinase PRK (prk) mRNA |
| 840 | Colorectal | 0.0994662 | 0.3700781 | 0.309578 | 0.18090901 | AA418214_a t | EST: zv97f07.r1 Soares NhHMPu S1 Homo sapiens cDNA clone 767749 5' similar to TR:G633926 G633926 APK1 ANTIGEN. :, mRNA sequence. (from Genbank) |
| 841 | Colorectal | 0.0993424 | 0.36998 | 0.309522 | 0.1807964 | AA442428_a t | EST: zv70f08.r1 Soares total fetus Nb2HF8 9w Homo sapiens cDNA clone 759015 5' similar to SW:YB72_YEAST P38137 HYPOTHETICAL 60.5 KD PROTEIN IN PDB1-ABD1 INTERGENIC REGION. :, mRNA sequence. (from Genbank) |
| 842 | Colorectal | 0.0993158 | 0.3699015 | 0.309516 | 0.18072318 | X17098_at | PSG6 Pregnancy-specific beta-1 glycoprotein 6 |
| 843 | Colorectal | 0.0993145 | 0.3698788 | 0.30951 | 0.18071891 | D86479_at | Non-lens beta gamma-crystallin like protein (AIM1) mRNA, partial cds |

FIG. 4K2

| | | | | | | |
|---|---|---|---|---|---|---|
| 844 | Colorectal | 0.0992493 | 0.3696489 | 0.30944 | 0.18059304 | HG491-HT491_at | Fc Receptor IIb3 For Igg, Low Affinity |
| 845 | Colorectal | 0.0990316 | 0.3695954 | 0.309379 | 0.18051022 | RC_AA4344 41_at | Frizzled (Drosophila) homolog 7 |
| 846 | Colorectal | 0.0986173 | 0.3695771 | 0.309305 | 0.18046694 | RC_AA4525 38_at | EST: zx35e05.s1 Soares total fetus Nb2HF8 9w I homo sapiens cDNA clone 788480 3', mRNA sequence. (from Genbank) |
| 847 | Colorectal | 0.0983304 | 0.3695127 | 0.30928 | 0.18033491 | M18391_s_at | TYROSINE-PROTEIN KINASE RECEPTOR EPH PRECURSOR |
| 848 | Colorectal | 0.0982712 | 0.3694668 | 0.30924 | 0.18029409 | M85289_at | HSPG2 Heparan sulfate proteoglycan |
| 849 | Colorectal | 0.098265 | 0.3694266 | 0.30923 | 0.18029442 | AB002294_a t | KIAA0296 gene product |
| 850 | Colorectal | 0.0981109 | 0.3693816 | 0.309186 | 0.18021777 | M24485_s_a t | SAT Spermidine/spermine N1-acetyltransferase |
| 851 | Colorectal | 0.098003 | 0.3693463 | 0.308989 | 0.18018626 | C00032_at | EST: HUMGS0003377, Human Gene Signature, 3'-directed cDNA sequence, mRNA sequence. (from Genbank) |
| 852 | Colorectal | 0.0979339 | 0.3692421 | 0.308892 | 0.18003461 | M57730_at | EPH-RELATED RECEPTOR TYROSINE KINASE LIGAND 1 PRECURSOR |
| 853 | Colorectal | 0.0974983 | 0.3691822 | 0.308848 | 0.17996137 | U65579_at | Mitochondrial NADH dehydrogenase-ubiquinone Fe-S protein 8, 23 kDa subunit precursor (NDUFS8) nuclear mRNA encoding mitochondrial protein |
| 854 | Colorectal | 0.0974748 | 0.3691728 | 0.308817 | 0.17996034 | RC_AA5996 83_at | EST: ag10f09.s1 Gessler Wilms tumor Homo sapiens cDNA clone 1069961 3', mRNA sequence. (from Genbank) |
| 855 | Colorectal | 0.0970471 | 0.369114 | 0.308816 | 0.17992407 | L06132_at | VDAC1 Voltage-dependent anion channel 1 |
| 856 | Colorectal | 0.0968551 | 0.3690573 | 0.308801 | 0.17986096 | RC_AA6085 45_at | EST: ae53d05.s1 Stratagene lung carcinoma 937218 Homo sapiens cDNA clone 950601 3', mRNA sequence. (from Genbank) |
| 857 | Colorectal | 0.0968151 | 0.3690652 | 0.308709 | 0.17981024 | L22548_at | COL18A1 Collagen, type XVIII, alpha 1 |
| 858 | Colorectal | 0.0964766 | 0.3686484 | 0.308689 | 0.17975925 | AA287289_a t | EST: zs49g10.r1 NCI_CGAP_GCB1 Homo sapiens cDNA clone IMAGE:700866 5', mRNA sequence. (from Genbank) |
| 859 | Colorectal | 0.0964245 | 0.3686215 | 0.308553 | 0.17965844 | RC_AA0288 90_at | EST: zk11f01.s1 Soares pregnant uterus NbHPU Homo sapiens cDNA clone 470233 3', mRNA sequence. (from Genbank) |
| 860 | Colorectal | 0.096186 | 0.3685744 | 0.308479 | 0.17955196 | D30756_at | KIAA0108 gene |
| 861 | Colorectal | 0.0960368 | 0.3685397 | 0.308426 | 0.17949271 | RC_AA0106 17_at | EST: zl09f12.s1 Soares fetal liver spleen 1NFLS S1 Homo sapiens cDNA clone 430319 3', mRNA sequence. (from Genbank) |
| 862 | Colorectal | 0.0960401 | 0.3685113 | 0.308416 | 0.17947358 | D79601_f_at | EST: Human aorta cDNA 5'-end GEN-286G10, mRNA sequence. (from Genbank) |
| 863 | Colorectal | 0.0959868 | 0.3684908 | 0.308004 | 0.17935272 | M63967_at | ALDEHYDE DEHYDROGENASE, MITOCHONDRIAL X PRECURSOR |
| 864 | Colorectal | 0.0959166 | 0.3682811 | 0.307925 | 0.17928286 | X69150_at | Ribosomal protein S18 |

FIG. 4I.2

| | | | | | | |
|---|---|---|---|---|---|---|
| 865 | Colorectal | 0.0958927 | 0.36823 | 0.307918 | 0.17928061 | L36983_at | Dynamin (DNM) mRNA |
| 866 | Colorectal | 0.0957509 | 0.3681307 | 0.307852 | 0.17913303 | L07493_at | RECA Replication protein A (E coli RecA homolog, RAD51 homolog) |
| 867 | Colorectal | 0.0956532 | 0.3681182 | 0.307757 | 0.17790809 | X81788_at | DS-1 mRNA |
| 868 | Colorectal | 0.0956037 | 0.3680734 | 0.307734 | 0.17905654 | D86957_at | KIAA0202 gene, partial cds |
| 869 | Colorectal | 0.095559 | 0.3680191 | 0.307553 | 0.17895895 | U50383_at | Retinoic acid-responsive protein (NN8-4AG) mRNA |
| 870 | Colorectal | 0.0953243 | 0.3679965 | 0.30753 | 0.17886594 | X59405_at | MCP Membrane cofactor protein (CD46, trophoblast-lymphocyte cross-reactive antigen) |
| 871 | Colorectal | 0.0951026 | 0.3679407 | 0.307494 | 0.17874716 | D80002_at | KIAA0180 gene, partial cds |
| 872 | Colorectal | 0.0951026 | 0.3678478 | 0.307336 | 0.1786732 | D80002_at-2 | Human mRNA for KIAA0180 gene, partial cds. (from Genbank) |
| 873 | Colorectal | 0.0950603 | 0.3677385 | 0.307336 | 0.17857422 | AA478674_a_t | EST: zv19f08.r1 Soares NhHMPu S1 Homo sapiens cDNA clone 754119 5', mRNA sequence. (from Genbank) |
| 874 | Colorectal | 0.0950569 | 0.3676296 | 0.307263 | 0.17852655 | U29195_at | NPTX2 Neuronal pentraxin II |
| 875 | Colorectal | 0.0950386 | 0.3676104 | 0.307229 | 0.17783631 | M55621_at | MGAT1 N-acetylglucosaminyltransferase I |
| 876 | Colorectal | 0.0949239 | 0.3675207 | 0.30722 | 0.17836049 | RC_AA4300 74_at | EST: zw59c03.s1 Soares total fetus Nb2HF8_9w Homo sapiens cDNA clone 774340 3', mRNA sequence. (from Genbank) |
| 877 | Colorectal | 0.0947793 | 0.3674794 | 0.30714 | 0.17826907 | X71345_f_at | PRSS3 Protease, serine, 3 (trypsin 3) |
| 878 | Colorectal | 0.0946479 | 0.3672888 | 0.307072 | 0.17823921 | M32373_at | ARSB Arylsulfatase B |
| 879 | Colorectal | 0.0944786 | 0.3672148 | 0.306854 | 0.178051 23_at | RC_AA4373 | EST: zv62f11.s1 Soares testis NHT Homo sapiens cDNA clone 758253 3', mRNA sequence. (from Genbank) |
| 880 | Colorectal | 0.0944084 | 0.3672111 | 0.306816 | 0.17802346 50_at | RC_AA6088 | EIF4E-like cap-binding protein |
| 881 | Colorectal | 0.0943732 | 0.3671756 | 0.306712 | 0.17794147 61_at | RC_AA2622 | EST: zs25e01.s1 NCI_CGAP_GCB1 Homo sapiens cDNA clone IMAGE:686232 3' similar to WP:R05G6.4 CE07417:, mRNA sequence. (from Genbank) |
| 882 | Colorectal | 0.094198 | 0.3671325 | 0.306548 | 0.17781886 | U90915_at | COX4 Cytochrome c oxidase subunit IV |
| 883 | Colorectal | 0.0941319 | 0.3670834 | 0.306247 | 0.1777522 46_at | RC_AA12/9 | EST: zi13d08.s1 Soares pregnant uterus NbHPU Homo sapiens cDNA clone 501807 3', mRNA sequence. (from Genbank) |
| 884 | Colorectal | 0.0940872 | 0.3670663 | 0.306184 | 0.17766105 t | AA248169_a | EST: csg1676.seq.F Human fetal heart, Lambda ZAP Express Homo sapiens cDNA 5', mRNA sequence. (from Genbank) |
| 885 | Colorectal | 0.0938772 | 0.3670338 | 0.306132 | 0.17762522 20_at | RC_AA4063 | EST: zv24f04.s1 Soares NhHMPu S1 Homo sapiens cDNA clone 754591 3', mRNA sequence. (from Genbank) |
| 886 | Colorectal | 0.093848 | 0.3668634 | 0.306122 | 0.17757253 87_at | RC_AA2797 | EST: zs87f02.s1 NCI_CGAP_GCB1 Homo sapiens cDNA clone IMAGE:704475 3', mRNA sequence. (from Genbank) |
| 887 | Colorectal | 0.0931873 | 0.3665892 | 0.306098 | 0.17743365 | D21262_at | KIAA0035 gene, partial cds |
| 888 | Colorectal | 0.0927504 | 0.366504 | 0.306016 | 0.17741808 | AA078862_s_at | EST: zm92d02.r1 Stratagene ovarian cancer (#937219) Homo sapiens cDNA clone 545379 5', mRNA sequence. (from Genbank) |
| 889 | Colorectal | 0.0921649 | 0.3664064 | 0.305938 | 0.17734616 | S76463_at | ELONGATION FACTOR TU, MITOCHONDRIAL PRECURSOR |

FIG. 4M2

| | | | | | | |
|---|---|---|---|---|---|---|
| 890 | Colorectal | 0.0919764 | 0.3661593 | 0.305894 | 0.17725754 | X53331_at | MGP Matrix protein gla |
| 891 | Colorectal | 0.091899 | 0.3661587 | 0.305843 | 0.17721215 | U45285_at | Specific 116-kDa vacuolar proton pump subunit (OC-116KDa) mRNA |
| 892 | Colorectal | 0.0918772 | 0.3661394 | 0.305724 | 0.17709394 | AA090842_a_t | EST: yy0444.seq.F Fetal heart, Lambda ZAP Express Homo sapiens cDNA 5', mRNA sequence. (from Genbank) |
| 893 | Colorectal | 0.0917985 | 0.3661088 | 0.305633 | 0.17704633 | RC_AA4427 63_at | EST: zv60c04.s1 Soares testis NHT Homo sapiens cDNA clone 758022 3' similar to SW:CGB2_MESAU P37883 G2/MITOTIC-SPECIFIC CYCLIN B2.;, mRNA sequence. (from Genbank) |
| 894 | Colorectal | 0.0916026 | 0.3660908 | 0.305611 | 0.17696834 | D30755_at | VIM Vimentin |
| 895 | Colorectal | 0.0916026 | 0.3659485 | 0.305539 | 0.17690636 | D30755_at-2 | Human mRNA for KIAA0113 gene, partial cds |
| 896 | Colorectal | 0.0915553 | 0.3658933 | 0.305526 | 0.176859721 | AA478131_a_t | EST: zu42c10.r1 Soares ovary tumor NbHOT Homo sapiens cDNA clone 740658 5' similar to TR:G433963 G433963 P18H-REV 107..; mRNA sequence. (from Genbank) |
| 897 | Colorectal | 0.0915244 | 0.3658475 | 0.305441 | 0.17679666 | RC_AA3977 79_at | EST: zt72d01.s1 Soares testis NHT Homo sapiens cDNA clone 727873 3', mRNA sequence. (from Genbank) |
| 898 | Colorectal | 0.0911797 | 0.3658407 | 0.305382 | 0.17671314 | D82060_at | Kidney mRNA for putative membrane protein with histidine rich charge clusters |
| 899 | Colorectal | 0.0910688 | 0.3658318 | 0.305334 | 0.17667067 | RC_D51235 f_at AA343629_a_t | Tumor rejection antigen (gp96) 1 |
| 900 | Colorectal | 0.0907928 | 0.3656176 | 0.30528 | 0.17658818 | | Homo sapiens mRNA for neuropsin, complete cds |
| 901 | Colorectal | 0.0907866 | 0.3656066 | 0.305222 | 0.17648873 | L10413_at | FNTA Farnesyltransferase, CAAX box, alpha |
| 902 | Colorectal | 0.0907267 | 0.3655602 | 0.305185 | 0.17641185 | V01514_at | AFP Alpha-fetoprotein |
| 903 | Colorectal | 0.0905193 | 0.3654815 | 0.305185 | 0.17637348 | RC_AA4421 44_at | EST: zw56h03.s1 Soares total fetus Nb2HF8 9w Homo sapiens cDNA clone 774101 3', mRNA sequence. (from Genbank) |
| 904 | Colorectal | 0.0904557 | 0.365401 | 0.305034 | 0.17626467 | M95178_at | ALPHA-ACTININ 1, CYTOSKELETAL ISOFORM |
| 905 | Colorectal | 0.0904479 | 0.365397 | 0.304976 | 0.17623897 | RC_AA2365 59_at | EST: zs39e02.s1 Soares NhHMPu S1 Homo sapiens cDNA clone 687578 3', mRNA sequence. (from Genbank) |
| 906 | Colorectal | 0.090388 | 0.3653446 | 0.304942 | 0.17616539 | U70212_at | Single-minded (Drosophila) homolog 1 |
| 907 | Colorectal | 0.0903135 | 0.3653211 | 0.304911 | 0.17611153 | RC_AA4901 42_at | EST: ab05f07.s1 Stratagene fetal retina 937202 Homo sapiens cDNA clone 839941 3', mRNA sequence. (from Genbank) |
| 908 | Colorectal | 0.0901215 | 0.3652385 | 0.304868 | 0.17608988 | X70649_at | Cl:1042 mRNA of DEAD box protein family |
| 909 | Colorectal | 0.0899683 | 0.3651849 | 0.304849 | 0.1759395 | H25982_at | EST: yl56g01.r1 Homo sapiens cDNA clone 162288 5'. (from Genbank) |
| 910 | Colorectal | 0.0899229 | 0.3651123 | 0.304843 | 0.17591423 | X51362_s_a_t | DRD2 Dopamine D2 receptor |
| 911 | Colorectal | 0.0898177 | 0.3650917 | 0.3047 | 0.1758407 | C00180_f_at | Synaptic glycoprotein SC2 |

FIG. 4N2

| # | Tissue | | | | | | Description |
|---|---|---|---|---|---|---|---|
| 912 | Colorectal | 0.089772 | 0.3649236 | 0.304618 | RC_AA1792 98_at | 0.1757794 | Homo sapiens chromosome 9, P1 clone 11659 |
| 913 | Colorectal | 0.0895391 | 0.3646752 | 0.304544 | Z37544_rna 1_s_at | 0.17571668 | Phospholipase C, beta 3 (phosphatidylinositol-specific) |
| 914 | Colorectal | 0.0894386 | 0.3646393 | 0.304365 | RC_AA2365 16_at | 0.17566574 | 33 kDa transcriptional co-activator |
| 915 | Colorectal | 0.0893178 | 0.3646026 | 0.304321 | N81162_at | 0.17563848 | EST: yw36d01.r1 Homo sapiens cDNA clone 254305 5'. (from Genbank) |
| 916 | Colorectal | 0.0892828 | 0.3645176 | 0.304219 | M62994_at | 0.17551358 | Thyroid autoantigen (truncated actin-binding protein) mRNA |
| 917 | Colorectal | 0.0891553 | 0.3644964 | 0.304209 | D61871_r_at | 0.17554635 | EST: Human aorta cDNA 5'-end GEN-218G01, mRNA sequence. (from Genbank) |
| 918 | Colorectal | 0.0891149 | 0.3644176 | 0.304189 | X71125_at | 0.17542724 | Glutamine cyclotransferase |
| 919 | Colorectal | 0.0890112 | 0.364372 | 0.304127 | D87071_at | 0.17539804 | KIAA0233 gene |
| 920 | Colorectal | 0.0889243 | 0.3642209 | 0.304073 | S62028_s_at | 0.17527397 | RCV1 Recoverin |
| 921 | Colorectal | 0.0889151 | 0.3641273 | 0.303965 | M38193_rna 1_s_at | 0.17524418 | Granzyme B (granzyme 2, cytotoxic T-lymphocyte-associated serine esterase 1) |
| 922 | Colorectal | 0.0888401 | 0.3640126 | 0.303907 | RC_AA4594 02_s_at | 0.1751563 | EST: zx89g02.s1 Soares ovary tumor NbHOT Homo sapiens cDNA clone 810962 3' similar to SW:MV10_MOUSE P23249 PUTATIVE GTP-BINDING PROTEIN MOV10.; mRNA sequence. (from Genbank) |
| 923 | Colorectal | 0.0887433 | 0.3638175 | 0.303854 | H81448_s_at | 0.17509894 | EST: yr75e04.r1 Homo sapiens cDNA clone 211134 5'. (from Genbank) |
| 924 | Colorectal | 0.0886368 | 0.36377 | 0.303745 | AFFX-CreX-5_at-2 | 0.17493787 | AFFX-CreX-5_at (miscellaneous control - 11k chips) |
| 925 | Colorectal | 0.0886368 | 0.3637284 | 0.303736 | AFFX-CreX-5_at | 0.17491248 | AFFX-CreX-5_at (endogenous control) |
| 926 | Colorectal | 0.0885625 | 0.3636926 | 0.303637 | X52599_at | 0.17478826 | NGFB Nerve growth factor beta |
| 927 | Colorectal | 0.0885268 | 0.3636769 | 0.303548 | AA053096_a | 0.1747111 | EST: zi71h06.r1 Stratagene colon (#937204) Homo sapiens cDNA clone 510107 5', mRNA sequence. (from Genbank) |
| 928 | Colorectal | 0.0884516 | 0.3636729 | 0.303543 | RC_AA2358 03_f_at | 0.17463842 | EST: zs42g06.s1 Soares NhHMPu S1 Homo sapiens cDNA clone 687898 3', mRNA sequence. (from Genbank) |
| 929 | Colorectal | 0.0882725 | 0.3636514 | 0.303457 | L19183_at | 0.17458098 | MAC30 mRNA, 3' end |
| 930 | Colorectal | 0.0881408 | 0.3636181 | 0.303353 | U18291_at | 0.17449743 | CDC16Hs mRNA |
| 931 | Colorectal | 0.0880567 | 0.3635748 | 0.303279 | RC_AA0590 14_at | 0.17445114 | EST: z63e06.s1 Soares retina N2b4HR Homo sapiens cDNA clone 381634 3', mRNA sequence. (from Genbank) |
| 932 | Colorectal | 0.0880195 | 0.3635722 | 0.303247 | Z27113_at | 0.17441405 | DNA-DIRECTED RNA POLYMERASE II 14.4 KD POLYPEPTIDE |
| 933 | Colorectal | 0.0880064 | 0.3635193 | 0.303244 | U79295_at | 0.174368 | Clone 23961 mRNA sequence |
| 934 | Colorectal | 0.0880064 | 0.3634415 | 0.303191 | U79295_at-2 | 0.17442654 | Human clone 23961 mRNA sequence |

FIG. 4O2

| # | Type | | | | | Description |
|---|---|---|---|---|---|---|
| 935 | Colorectal | 0.0879879 | 0.3633758 | 0.303137 | 0.1742237 | AF007875_a_t Dolichol monophosphate mannose synthase (DPM1) mRNA, partial cds |
| 936 | Colorectal | 0.0879218 | 0.363332 | 0.303102 | 0.174179127 RC_AA2921 28_at | EST: zr58h06.s1 Soares NhHMPu S1 Homo sapiens cDNA clone 667643 3', mRNA sequence. (from Genbank) |
| 937 | Colorectal | 0.0878082 | 0.3632222 | 0.303034 | 0.174113254 J03909_at | GAMMA-INTERFERON-INDUCIBLE PROTEIN IP-30 PRECURSOR |
| 938 | Colorectal | 0.0877665 | 0.36322 | 0.303016 | 0.173999655 HG2855-HT2995_at | Heat Shock Protein, 70 Kda (Gb:Y00371) |
| 939 | Colorectal | 0.0877215 | 0.3629631 | 0.302755 | 0.173996699 X12447_at | ALDOA Aldolase A |
| 940 | Colorectal | 0.087407 | 0.3629171 | 0.302719 | 0.173883345 M36821_s_a_t | GRO3 oncogene |
| 941 | Colorectal | 0.0873162 | 0.3629123 | 0.302714 | 0.1738302 D83174_s_a_t | CBP1 Collagen-binding protein 1 |
| 942 | Colorectal | 0.087166 | 0.3628711 | 0.302681 | 0.173677642 M29277_at | CELL SURFACE GLYCOPROTEIN MUC18 PRECURSOR |
| 943 | Colorectal | 0.0866665 | 0.3628308 | 0.302587 | 0.173655606 RC_AA2338 56_at | EST: zr47a06.s1 Soares NhHMPu S1 Homo sapiens cDNA clone 666514 3', mRNA sequence. (from Genbank) |
| 944 | Colorectal | 0.0866092 | 0.3628222 | 0.302511 | 0.1736013 X15940_at | RPL31 Ribosomal protein L31 |
| 945 | Colorectal | 0.066558 | 0.3627926 | 0.302477 | 0.173578646 RC_AA3983_at | EST: zt61d08.s1 Soares testis NHT Homo sapiens cDNA clone 726831 3', mRNA sequence. (from Genbank) |
| 946 | Colorectal | 0.0862218 | 0.3627847 | 0.302364 | 0.17352836 RC_AA1328 74_at | EST: zo19e03.s1 Stratagene colon (#937204) Homo sapiens cDNA clone 587356 3', mRNA sequence. (from Genbank) |
| 947 | Colorectal | 0.0857385 | 0.3626874 | 0.302362 | 0.173398268 RC_AA1488 59_s_at | EST: zo01d11.s1 Stratagene colon (#937204) Homo sapiens cDNA clone 566421 3' similar to contains Alu repetitive element;contains element MER22 repetitive element ;, mRNA sequence. (from Genbank) |
| 948 | Colorectal | 0.0856766 | 0.3625927 | 0.302272 | 0.173324327 AA477375_s_at | Homo sapiens clone 640 unknown mRNA, complete sequence |
| 949 | Colorectal | 0.0856655 | 0.3625132 | 0.302128 | 0.17325146 RC_AA4436 83_at | EST: zw86c12.s1 Soares total fetus Nb2HF8 9w Homo sapiens cDNA clone 783862 3' similar to WP:B0303.15 CE00004 RIBOSOMAL PROTEIN L11 ;, mRNA sequence. (from Genbank) |
| 950 | Colorectal | 0.0854834 | 0.3624399 | 0.30205 | 0.173190337 RC_AA2849_at | Human ets domain protein ERF mRNA, complete cds |
| 951 | Colorectal | 0.0852693 | 0.3624357 | 0.30205 | 0.173145064 RC_AA4651_at | Chromosome 1 specific transcript KIAA0491 |
| 952 | Colorectal | 0.0852481 | 0.3624297 | 0.302022 | 0.173065 L32137_at | COMP Cartilage oligomeric matrix protein |
| 953 | Colorectal | 0.0849922 | 0.3624032 | 0.30198 | 0.173007785 RC_AA4221 46_at | EST: zy28g12.s1 Soares ovary tumor NbHOT Homo sapiens cDNA clone 7550143', mRNA sequence. (from Genbank) |
| 954 | Colorectal | 0.0849299 | 0.362243 | 0.301954 | 0.172961158 T48536_at | EST: hbc3204 Homo sapiens cDNA clone hbc3204 5'end. (from Genbank) |

FIG. 4P2

| # | Type | | | | | Description |
|---|---|---|---|---|---|---|
| 955 | Colorectal | 0.0849143 | 0.3622086 | 0.301933 | RC_AA4655 0.17286918 27_at | EST: aa32c07.s1 NCI_CGAP_GCB1 Homo sapiens cDNA clone IMAGE:814956 3', mRNA sequence. (from Genbank) |
| 956 | Colorectal | 0.0849125 | 0.3622 | 0.301841 | 0.17278965 Z19899_at | EST: H. sapiens putatively transcribed partial sequence; UK-HGMP sequence ID AAAAYRK; single read, mRNA sequence. (from Genbank) |
| 957 | Colorectal | 0.0848168 | 0.3621617 | 0.301779 | RC_AA5988 0.17271367 72_at | EST: ae37b10.s1 Gessler Wilms tumor Homo sapiens cDNA clone 897979 3', mRNA sequence. (from Genbank) |
| 958 | Colorectal | 0.0847012 | 0.3621331 | 0.301708 | RC_AA4028 0.17264414 49_at | EST: zu54a01.s1 Soares ovary tumor NbHOT Homo sapiens cDNA clone 741768 3', mRNA sequence. (from Genbank) |
| 959 | Colorectal | 0.0846797 | 0.3620108 | 0.301649 | RC_AA1289 0.17260127 02_at | EST: zn90a05.s1 Stratagene lung carcinoma 937218 Homo sapiens cDNA clone 565424 3', mRNA sequence. (from Genbank) |
| 960 | Colorectal | 0.0844689 | 0.3619776 | 0.301585 | RC_AA4165 0.17255814 38_at | EST: zu05b09.s1 Soares testis NHT Homo sapiens cDNA clone 730937 3', mRNA sequence. (from Genbank) |
| 961 | Colorectal | 0.0844638 | 0.3619716 | 0.301514 | RC_AA1478 0.17252336 84_at | EST: zl50b04.s1 Soares pregnant uterus NbHPU Homo sapiens cDNA clone 505327 3', mRNA sequence. (from Genbank) |
| 962 | Colorectal | 0.0842947 | 0.3619229 | 0.301471 | AA093834_a 0.17244168 t | EST: cl1190.seq.F Fetal heart, Lambda ZAP Express Homo sapiens cDNA 5', mRNA sequence. (from Genbank) |
| 963 | Colorectal | 0.0837558 | 0.3618484 | 0.301333 | 0.17243756 X79440_at | NADP¹-dependent malic enzyme |
| 964 | Colorectal | 0.0834329 | 0.3618044 | 0.301325 | 0.17233664 C011765_at | EST: HUMGS0003713, Human Gene Signature, 3'-directed cDNA sequence, mRNA sequence. (from Genbank) |
| 965 | Colorectal | 0.0833271 | 0.3616668 | 0.301297 | 0.17230633 Z30644_at | Chloride channel (putative) 2163bp |
| 966 | Colorectal | 0.0833202 | 0.3616422 | 0.301159 | 0.17222661 Y12065_at | Homo sapiens mRNA for nucleolar protein hNop56 |
| 967 | Colorectal | 0.0833189 | 0.3616004 | 0.301092 | R84594_at 0.17216685 HG3214- | EST: yo37b10.r1 Homo sapiens cDNA clone 180091 5'. (from Genbank) |
| 968 | Colorectal | 0.0832619 | 0.3615744 | 0.30106 | 0.17210557 HT3391_at | Metallopanstimulin 1 |
| 969 | Colorectal | 0.0832096 | 0.3614558 | 0.30099 | 0.17205548 D42073_at | Reticulocalbin |
| 970 | Colorectal | 0.083063 | 0.3614467 | 0.300959 | HG3033- 0.17200057 HT3194_at | Spliceosomal Protein Sap 62 |
| 971 | Colorectal | 0.0830454 | 0.3612629 | 0.300927 | 0.17180516 M68864_at | ORF mRNA |
| 972 | Colorectal | 0.0830167 | 0.3612629 | 0.300821 | RC_AA4538 0.17172186 54_at | Homo sapiens pt-wd mRNA for WD-40 repeat protein, complete cds |
| 973 | Colorectal | 0.0829826 | 0.3612551 | 0.300808 | RC_AA5999 0.17170094 36_at | EST: ag28h05.s1 Jia bone marrow stroma Homo sapiens cDNA clone 1090905 3', mRNA sequence. (from Genbank) |
| 974 | Colorectal | 0.0826057 | 0.3611782 | 0.300777 | AA410925_a 0.17162094 t | EST: zv39e11.r1 Soares ovary tumor NbHOT Homo sapiens cDNA clone 7556044 5' similar to gb:M99435 TRANSDUCIN-LIKE ENHANCER PROTEIN 1 (HUMAN);, mRNA sequence. (from Genbank) |

FIG. 4Q2

| | | | | | | |
|---|---|---|---|---|---|---|
| 975 | Colorectal | 0.0826014 | 0.3611596 | | 0.300759 | 0.171530011 RC_AA6213 40_at | EST: af85c04.s1 Soares testis NHT Homo sapiens cDNA clone 1048806 3' similar to SW:YK61_YEAST P36160 HYPOTHETICAL 39.6 KD PROTEIN IN MTD1-NUP133 INTERGENIC REGION.; mRNA sequence. (from Genbank) |
| 976 | Colorectal | 0.0825341 | 0.3611034 | | 0.300675 | 0.17137393 RC_AA4787 94_at | EST: zv20e01.s1 Soares NhHMPu S1 Homo sapiens cDNA clone 754200 3', mRNA sequence. (from Genbank) |
| 977 | Colorectal | 0.0823935 | 0.3610455 | | 0.300651 | 0.171346861 RC_AA1329 69_s_at | Homo sapiens metalloprotease 1 (MP1) mRNA, complete cds |
| 978 | Colorectal | 0.0822751 | 0.3609324 | | 0.300548 | 0.17134237 RC_AA0019 08_at | EST: zh83a05.s1 Soares fetal liver spleen 1NFLS S1 Homo sapiens cDNA clone 427856 3', mRNA sequence. (from Genbank) |
| 979 | Colorectal | 0.0821848 | 0.3608286 | | 0.300528 | 0.17131984 RC_AA6212 77_at | EST: zu83d08.s1 Soares testis NHT Homo sapiens cDNA clone 744591 3', mRNA sequence. (from Genbank) |
| 980 | Colorectal | 0.0820697 | 0.3607682 | | 0.300427 | 0.17125268 D84239_at-2 | IgG Fc binding protein |
| 981 | Colorectal | 0.0820697 | 0.3607292 | | 0.300341 | 0.17122382 D84239_at | IgG Fc binding protein |
| 982 | Colorectal | 0.0820426 | 0.3606988 | | 0.300314 | 0.17103413 RC_AA4614 76_at | EST: zx68g01.s1 Soares total fetus Nb2HF8 9w Homo sapiens cDNA clone 796656 3' similar to TR:G577189 G577189 SIMILAR TO DEAD BOX RNA HELICASES.; mRNA sequence. (from Genbank) |
| 983 | Colorectal | 0.082042 | 0.360618 | | 0.3002581 | 0.17090756 M54994_f_at | Carboxyl ester lipase (bile salt-stimulated lipase) |
| 984 | Colorectal | 0.0819521 | 0.360422 | | 0.300247 | 0.17090331 D16350_at | SA mRNA for SA gene product |
| 985 | Colorectal | 0.0818907 | 0.360386 | | 0.300223 | 0.17084618 R56678_at | EST: yl04d08.r1 Homo sapiens cDNA clone 138255 5' similar to contains Alu repetitive element:. (from Genbank) |
| 986 | Colorectal | 0.0815508 | 0.3603115 | | 0.300179 | 0.17077523 AA365742_s_at | EST: ES76593 Pineal gland II Homo sapiens cDNA 5' end, mRNA sequence. (from Genbank) |
| 987 | Colorectal | 0.0815452 | 0.3802785 | | 0.300112 | 0.17070991 RC_AA0404 65_at | EST: zk46h09.s1 Soares pregnant uterus NbHPU Homo sapiens cDNA clone 485921 3', mRNA sequence. (from Genbank) |
| 988 | Colorectal | 0.0812312 | 0.360204 | | 0.300108 | 0.17066623 M86737_at | SSRP1 High mobility group box |
| 989 | Colorectal | 0.0810845 | 0.3601831 | | 0.300046 | 0.17061129 RC_AA2808 65_at | EST: zt01b06.s1 NCI_CGAP_GCB1 Homo sapiens cDNA clone IMAGE:711827 3', mRNA sequence. (from Genbank) |
| 990 | Colorectal | 0.0809646 | 0.3601299 | | 0.299982 | 0.17054886 RC_AA4372 58_at | EST: zv54f03.s1 Soares testis NHT Homo sapiens cDNA clone 757469 3', mRNA sequence. (from Genbank) |
| 991 | Colorectal | 0.0807475 | 0.3599102 | | 0.299923 | 0.17046368 Z48199_at | SDC1 Syndecan 1 |
| 992 | Colorectal | 0.0806754 | 0.3597956 | | 0.299824 | 0.17039213 RC_AA4364 20_at | EST: zv44e06.s1 Soares ovary tumor NbHOT Homo sapiens cDNA clone 755514 3', mRNA sequence. (from Genbank) |
| 993 | Colorectal | 0.0803246 | 0.3597343 | | 0.299777 | 0.17034793 M91222_at | EST: HUMRTPGEG Homo sapiens cDNA. (from Genbank) |
| 994 | Colorectal | 0.0803047 | 0.3596878 | | 0.299688 | 0.17030239 RC_AA0071 60_at | EST: 13cDNA30A-3.seq Soares infant brain 1NIB Homo sapiens cDNA clone HY18-3.3', mRNA sequence. (from Genbank) |

FIG. 4R2

| | | | | | |
|---|---|---|---|---|---|
| 995 | Colorectal | 0.0802925 | 0.3596844 | 0.29966 | 0.17026065 | U02680_at | Protein tyrosine kinase mRNA |
| 996 | Colorectal | 0.0802769 | 0.3596664 | 0.299503 | 0.17017648 | RC_AA0756 66_at | EST: zm88e09.s1 Stratagene ovarian cancer (#937219) Homo sapiens cDNA clone 545032 3', mRNA sequence. (from Genbank) |
| 997 | Colorectal | 0.0796214 | 0.35939957 | 0.299492 | 0.1700276 | W27770_at | EST: 3719 Human retina cDNA randomly primed sublibrary Homo sapiens cDNA, mRNA sequence. (from Genbank) |
| 998 | Colorectal | 0.0793234 | 0.3593702 | 0.299491 | 0.16996102 | X61970_at | PROTEASOME ZETA CHAIN |
| 999 | Colorectal | 0.0791645 | 0.3593253 | 0.299452 | 0.16988634 | HG2743-HT2846_s_a t | Caldesmon 1, Alt. Splice 4, Non-Muscle |
| 1000 | Colorectal | 0.0791311 | 0.3592957 | 0.299448 | 0.16984347 | Z96810_at | DNA sequence from PAC 452H17 on chromosome X contains sodium and chloride-dependent glycine transporter 1 (GLYT-1) like, ESTs |

FIG. 4S2

| # | Class | | | | ID | Description |
|---|---|---|---|---|---|---|
| 1 | Leukemia | 2.1245492 | 0.4423031 | 0.398474 | 0.3168242 | L20688_at | GDP-dissociation Inhibitor protein (Ly-GDI) mRNA |
| 2 | Leukemia | 1.7983353 | 0.4104766 | 0.37298 | 0.2975146 | X03689_s_at | mRNA fragment for elongation factor TU (N-terminus) |
| 3 | Leukemia | 1.770247 | 0.3996912 | 0.36131 | 0.28735778 | M26708_s_at | PTMA Prothymosin alpha |
| 4 | Leukemia | 1.7262069 | 0.3928716 | 0.35268 | 0.27946351 | U43901_rna1_s_at | 37 kD laminin receptor precursor/p40 ribosome associated protein gene |
| 5 | Leukemia | 1.626872 | 0.3870009 | 0.347355 | 0.27421996 | HT821_at | Ribosomal Protein S13 |
| 6 | Leukemia | 1.5929008 | 0.381187 | 0.343753 | 0.26967597 | U67369_at | Growth factor independence-1 (Gfi-1) mRNA |
| 7 | Leukemia | 1.5842817 | 0.3790399 | 0.339392 | 0.26589945 | X04347_s_at | Liver mRNA fragment DNA binding protein UP1 homologue (C-terminus) |
| 8 | Leukemia | 1.5754955 | 0.3753435 | 0.336293 | 0.26270148 | D87735_at | CAG-isl 7 (trinucleotide repeat-containing sequence) [human, pancreas, mRNA Partial, 701 nt] |
| 9 | Leukemia | 1.5749655 | 0.3715162 | 0.333566 | 0.25968373 | RC_AA280630_at | Glia maturation factor, gamma |
| 10 | Leukemia | 1.5748247 | 0.3701863 | 0.330908 | 0.25715446 | U14970_at | RPS5 Ribosomal protein S5 |
| 11 | Leukemia | 1.5661684 | 0.3673442 | 0.329057 | 0.25483343 | HG4319-HT4589_at | Ribosomal Protein L5 |
| 12 | Leukemia | 1.5449955 | 0.3640238 | 0.326474 | 0.252562 | Z49148_s_at | Enhancer of rudimentary homolog mRNA |
| 13 | Leukemia | 1.5306438 | 0.3631739 | 0.324161 | 0.2505693 | X78817_at | KIAA0131 gene, partial cds |
| 14 | Leukemia | 1.5063082 | 0.3615369 | 0.323043 | 0.24852082 | HG1428-HT1428_s_at | Globin, Beta |
| 15 | Leukemia | 1.4976654 | 0.3610132 | 0.321369 | 0.24683218 | HG613-HT613_at | Ribosomal Protein S12 |

FIG. 5A

| | | | | | |
|---|---|---|---|---|---|
| 16 | Leukemia | 1.4975446 | 0.3599675 | 0.245550068 | X67247_rna1_at | RpS8 gene for ribosomal protein S8 |
| 17 | Leukemia | 1.4961206 | 0.3587279 | 0.24399225 | X62691_at | 40S RIBOSOMAL PROTEIN S15A |
| 18 | Leukemia | 1.4926745 | 0.3580288 | 0.24209743 | L19527_at | RPL27 Ribosomal protein L27 |
| 19 | Leukemia | 1.4878429 | 0.3560807 | 0.31536 | HG4542-HT4947_at | Ribosomal Protein L10 |
| 20 | Leukemia | 1.4762723 | 0.3536887 | 0.24142163 | X55954_at | RPL17 Ribosomal protein L17 |
| 21 | Leukemia | 1.4723858 | 0.3529107 | 0.23992863 | X60489_at | Elongation factor-1-beta |
| 22 | Leukemia | 1.466343 | 0.3522405 | 0.23885897 | L22009_at | HnRNP H mRNA |
| 23 | Leukemia | 1.4643947 | 0.3514966 | 0.23763658 | M14483_rna1_s_at | PTMA gene extracted from Human prothymosin alpha mRNA |
| 24 | Leukemia | 1.4440879 | 0.3501856 | 0.23648864 | X89399_s_a t | Ins(1,3,4,5)P4-binding protein |
| 25 | Leukemia | 1.4405453 | 0.3491933 | 0.23545831 | M61827_rna1_s_at | Leukosialin (CD43) gene |
| 26 | Leukemia | 1.4365484 | 0.3488895 | 0.23415814 | HG3549-HT3751_at | Wilm'S Tumor-Related Protein |
| 27 | Leukemia | 1.4194885 | 0.3472533 | 0.23311779 | M24194_at | Alpha-tubulin mRNA |
| 28 | Leukemia | 1.4186814 | 0.3468086 | 0.23221248 | L49380_at | Transcription factor ZFM1 isoform B3 mRNA, complete cds |
| 29 | Leukemia | 1.4112004 | 0.3455588 | 0.23130439 | D14530_at | 40S RIBOSOMAL PROTEIN S23 |
| 30 | Leukemia | 1.4087023 | 0.3441794 | 0.23045073 | X55715_at | RPS3 Ribosomal protein S3 |
| 31 | Leukemia | 1.4042301 | 0.3435043 | 0.22946984 | X78136_at | HnRNP-E2 mRNA |
| 32 | Leukemia | 1.4035159 | 0.3429812 | 0.22863418 | D87017_cds3_at | C7 segment gene extracted from Human (lambda) DNA for immunoglobin light chain |
| 33 | Leukemia | 1.4016054 | 0.3421459 | 0.22776406 | U64105_at | Guanine nucleotide exchange factor p115-RhoGEF mRNA, partial cds |
| 34 | Leukemia | 1.3964151 | 0.3416564 | 0.22693126 | RC_AA410338_at | EST: zv16e02.s1 Soares NhHMPu S1 Homo sapiens cDNA clone 753818 3', mRNA sequence. (from Genbank) |
| 35 | Leukemia | 1.3906124 | 0.3411185 | 0.22612083 | M77232_ma1_at | Ribosomal protein S6 gene and flanking regions |
| 36 | Leukemia | 1.3863678 | 0.3411087 | 0.22543746 | M94630_at | Heterogeneous nuclear ribonucleoprotein D (hnRNP D), partial cds, clone cDx4 |
| 37 | Leukemia | 1.3846071 | 0.3409466 | 0.22468512 | U39318_at | AF-4 mRNA |
| 38 | Leukemia | 1.3846068 | 0.3401984 | 0.22423486 | U52112_rna5_a t | RbP gene (renin-binding protein) extracted from Human Xq28 genomic DNA in the region of the L1CAM locus containing the genes for neural cell adhesion molecule L1 (L1CAM), arginine-vasopressin receptor (AVPR2), C1 p115 (C1), ARD1 N-acetyltransferase related protein (TE2), renin-binding protein (RbP), host cell factor 1 (HCF1), and interleukin-1 receptor-associated kinase (IRAK) genes, and Xq28u2 gene |

FIG. 5B

| # | Disease | | | | ID | Gene Description |
|---|---|---|---|---|---|---|
| 39 | Leukemia | 1.3838786 | 0.3394182 | 0.297997 | 0.22289166 M31520_at | Ribosomal protein S24 |
| 40 | Leukemia | 1.3748674 | 0.3388236 | 0.297157 | 0.2221128 D28416_at | Esterase D, 5'UTR (sequence from the 5'cap to the start codon) |
| 41 | Leukemia | 1.3730975 | 0.3376064 | 0.296632 | 0.22166494 M81757_at | 40S RIBOSOMAL PROTEIN S19 |
| 42 | Leukemia | 1.3722514 | 0.3368563 | 0.296028 | 0.22101909 X69391_at | RPL6 Ribosomal protein L6 |
| 43 | Leukemia | 1.3657826 | 0.3364973 | 0.295686 | 0.2202277 U12707_s_a t | WAS Wiskott-Aldrich syndrome (ecezema-thrombocytopenia) |
| 44 | Leukemia | 1.3647323 | 0.3356295 | 0.2952 | 0.2196382 HG3521-HT3715_at | Ras-Related Protein Rap1b |
| 45 | Leukemia | 1.3643132 | 0.3351825 | 0.29476 | 0.21912986 HG33-HT33_at | Ribosomal Protein S4, X-Linked |
| 46 | Leukemia | 1.3597206 | 0.3349617 | 0.294228 | 0.21848115 D89377_at | Adult tooth pulp of third molar fibroblast mRNA for MSX-2 |
| 47 | Leukemia | 1.3564804 | 0.3341963 | 0.293438 | 0.21794002 HG1515-HT1515_f_at | Transcription Factor Btf3b |
| 48 | Leukemia | 1.3508657 | 0.3337646 | 0.29314 | 0.21725152 U77827_at | Orphan G protein-coupled receptor (CEPR) gene |
| 49 | Leukemia | 1.3496966 | 0.3336978 | 0.29247 | 0.21683167 U09412_at | ZNF134 Zinc finger protein 134 (clone pHZ-15) |
| 50 | Leukemia | 1.3491246 | 0.332831 | 0.291981 | 0.21625845 U53209_at | Transformer-2 alpha (htra-2 alpha) mRNA |
| 51 | Leukemia | 1.3461856 | 0.3326592 | 0.291352 | 0.21564445 Z48950_at | HISTONE H3.3 |
| 52 | Leukemia | 1.3405137 | 0.3325948 | 0.290999 | 0.21519908 L11566_at | RPL18 Ribosomal protein L18 |
| 53 | Leukemia | 1.3404096 | 0.3322822 | 0.290489 | 0.214751691 M14199_s_a t | LAMR1 Laminin receptor (2H5 epitope) |
| 54 | Leukemia | 1.3380556 | 0.3308695 | 0.289863 | 0.21426661 U00947_s_a t | HNRPA1 Heterogeneous nuclear ribonucleoprotein A1 |
| 55 | Leukemia | 1.3378556 | 0.3303914 | 0.289567 | 0.21375991 U21858_at | HISTONE H3.3 |
| 56 | Leukemia | 1.335347 | 0.3303539 | 0.289176 | 0.21330257 L10838_at | PRE-MRNA SPLICING FACTOR SRP20 |
| 57 | Leukemia | 1.3338704 | 0.3297808 | 0.288817 | 0.21283817 X63527_at | GAPD Glyceraldehyde-3-phosphate dehydrogenase |
| 58 | Leukemia | 1.3322679 | 0.3296065 | 0.288213 | 0.21224543 X95325_s_a t | DNA-BINDING PROTEIN A |
| 59 | Leukemia | 1.3307991 | 0.3290623 | 0.287875 | 0.21185458 U90426_at | Nuclear RNA helicase |
| 60 | Leukemia | 1.3305861 | 0.3285775 | 0.287329 | 0.211432 D86977_at | KIAA0224 gene |
| 61 | Leukemia | 1.3293155 | 0.3281694 | 0.287109 | 0.21089818 U89336_cds 1_at | Unknown gene extracted from Human HLA class III region containing NOTCH4 gene, partial sequence, homeobox PBX2 (HPBX) gene, receptor for advanced glycosylation end products (RAGE) gene, and 6 unidentified cds, complete sequence |
| 62 | Leukemia | 1.3287177 | 0.3274569 | 0.286675 | 0.21047243 S63912_at | D10S102 |
| 63 | Leukemia | 1.3287088 | 0.3264629 | 0.286344 | 0.20998995 U33839_at | No description available for U33839 |
| 64 | Leukemia | 1.3256675 | 0.3262613 | 0.285917 | 0.20959294 X79781_at | Ray mRNA |
| 65 | Leukemia | 1.3228076 | 0.3259309 | 0.285761 | 0.20919704 S72024_s_at | EIF5A Eukaryotic translation initiation factor 5A |

FIG. 5C

| | | | | | | |
|---|---|---|---|---|---|---|
| 66 | Leukemia | 1.3218347 | 0.3257203 | 0.285293 | AA263044_s_at | Histone macroH2A1.2 |
| 67 | Leukemia | 1.3217292 | 0.3253897 | 0.284732 | 0.2087115 | |
| | | | | | 0.2083298 | Z48501_s_at Polyadenylate binding protein II |
| 68 | Leukemia | 1.319648 | 0.3251419 | 0.284595 | M13934_cds | RPS14 gene (ribosomal protein S14) extracted from Human ribosomal protein S14 gene |
| 69 | Leukemia | 1.3171527 | 0.3251179 | 0.284022 | 0.20792985 2_at | |
| | | | | | 0.20752583 | X51466_at EEF2 Eukaryotic translation elongation factor 2 |
| 70 | Leukemia | 1.313569 | 0.3247116 | 0.28373 | 0.20721667 | J03827_at DbpB-like protein mRNA |
| 71 | Leukemia | 1.3122482 | 0.3244752 | 0.283491 | M30448_s_a 0.20684773 t | Casein kinase II beta subunit mRNA |
| | | | | | AC002477_s | |
| 72 | Leukemia | 1.3112588 | 0.3239575 | 0.283081 | 0.20650867 at | PAC clone DJ327A19 from Xq25-q26, complete sequence |
| 73 | Leukemia | 1.3101391 | 0.3237865 | 0.282486 | 0.20622943 | X79234_at Ribosomal protein L11 |
| 74 | Leukemia | 1.3070394 | 0.3234769 | 0.282166 | 0.20574908 | U25789_at Ribosomal protein L21 mRNA |
| 75 | Leukemia | 1.305753 | 0.3233392 | 0.281745 | 0.20532413 | X73460_at RPL3 Ribosomal protein L3 |
| 76 | Leukemia | 1.3044971 | 0.3231521 | 0.281408 | 0.20504147 | M97388_at DR1 Down-regulator of transcription 1, TBP-binding (negative cofactor 2) |
| 77 | Leukemia | 1.3021654 | 0.3229449 | 0.280964 | 0.20466115 | M36072_at RPL7A Ribosomal protein L7a |
| 78 | Leukemia | 1.301706 | 0.3228099 | 0.280547 | 0.20427912 | M86667_at HnRNP C2 protein mRNA |
| 79 | Leukemia | 1.2998625 | 0.3222751 | 0.280518 | 0.20391798 | M69066_at MSN Moesin |
| 80 | Leukemia | 1.2951708 | 0.3218956 | 0.280106 | 0.20345482 | U89896_at Casein kinase I gamma 2 mRNA |
| 81 | Leukemia | 1.2942455 | 0.3216935 | 0.279725 | 0.20312321 | M65214_s_a TCF3 Transcription factor 3 (E2A immunoglobulin enhancer binding t factors E12/E47) |
| 82 | Leukemia | 1.293594 | 0.3216367 | 0.279465 | 0.20284069 | M82882_at ETS-RELATED TRANSCRIPTION FACTOR ELF-1 |
| 83 | Leukemia | 1.2920842 | 0.321365 | 0.279157 | 0.20253761 | U45328_s_ at UBE2I Ubiquitin-conjugating enzyme E2I (homologous to yeast UBC9) |
| 84 | Leukemia | 1.2897642 | 0.3211166 | 0.278852 | 0.20219538 | Z25749_rna 1_at Ribosomal protein S7 |
| 85 | Leukemia | 1.2887139 | 0.3210614 | 0.278569 | 0.20186739 | U34962_at Transcription factor HCSX (hCsx) mRNA |
| 86 | Leukemia | 1.288485 | 0.3207896 | 0.278239 | 0.20149012 | Z50781_at Leucine zipper protein |
| 87 | Leukemia | 1.2877283 | 0.3204255 | 0.278079 | 0.2011626 | X80822_at 60S RIBOSOMAL PROTEIN L18A |
| 88 | Leukemia | 1.2869029 | 0.320231 | 0.27764 | 0.20073877 | D16581_at MTH1 MutT (E. coli) human homolog (8-oxo-7,8-dihydroguanosine triphosphatase) |
| 89 | Leukemia | 1.2857012 | 0.3199184 | 0.277469 | 0.20041728 | M23613_at NPM1 Nucleophosmin (nucleolar phosphoprotein B23, numatrin) |
| 90 | Leukemia | 1.2837796 | 0.3198457 | 0.277198 | 0.20001605 | X92106_at Bleomycin hydrolase |
| 91 | Leukemia | 1.2827122 | 0.3184036 | 0.276953 | 0.19982909 | HG3076-HT3238_s_a t Heterogeneous Nuclear Ribonucleoprotein K, Alt. Splice 1 |
| 92 | Leukemia | 1.2816616 | 0.3181081 | 0.276445 | 0.199949242 | Y08265_s_at DAN26 protein, partial |

FIG. 5D

| # | Class | Val1 | Val2 | Val3 | ID1 | ID2 | Description |
|---|---|---|---|---|---|---|---|
| 93 | Leukemia | 1.2812127 | 0.3177329 | 0.276329 | 0.19895412 | U14971_at | RPS9 Ribosomal protein S9 |
| 94 | Leukemia | 1.2800206 | 0.3174081 | 0.276123 | 0.19871943 | L13852_at | UBE1L Ubiquitin-activating enzyme E1, like |
| 95 | Leukemia | 1.2775177 | 0.3173306 | 0.275844 | 0.19844005 | S79522_at | UBA52 Ubiquitin A-52 residue ribosomal protein fusion product 1 |
| 96 | Leukemia | 1.2774563 | 0.317319 | 0.275632 | 0.19803672 | U12404_at | HSPB1 Heat shock 27kD protein 1 |
| 97 | Leukemia | 1.2768223 | 0.3170365 | 0.275542 | 0.1978352 | U37012_at | Cleavage and polyadenylation specificity factor mRNA |
| 98 | Leukemia | 1.2726396 | 0.3167291 | 0.274817 | 0.19756457 | X62055_at | PTPN6 Protein tyrosine phosphatase, non-receptor type 6 |
| 99 | Leukemia | 1.2718357 | 0.3164518 | 0.274614 | 0.19721243 | M55409_s_at | EEF1G Translation elongation factor 1 gamma |
| 100 | Leukemia | 1.2717494 | 0.3162562 | 0.274329 | 0.1969168 | HG36-HT4101_s_at | Polymyositis/Scleroderma (Pm-Scl) Autoantigen, Alt. Splice 2 |
| 101 | Leukemia | 1.2699975 | 0.3158728 | 0.273812 | 0.19663824 | Z26876_at | LTBP1 Latent transforming growth factor beta binding protein 1 |
| 102 | Leukemia | 1.2677157 | 0.3158027 | 0.27367 | 0.1963362 | X06617_at | RPS11 Ribosomal protein S11 |
| 103 | Leukemia | 1.2674696 | 0.3155016 | 0.273483 | 0.19596829 | X60036_at | PHC Phosphate carrier, mitochondrial |
| 104 | Leukemia | 1.2672986 | 0.3154532 | 0.273116 | 0.19557589 | X16064_at | TRANSLATIONALLY CONTROLLED TUMOR PROTEIN |
| 105 | Leukemia | 1.2671504 | 0.3152389 | 0.273052 | 0.19547707 | X15940_at | RPL31 Ribosomal protein L31 |
| 106 | Leukemia | 1.2663616 | 0.3149523 | 0.272233 | 0.19529337 | M76766_at | GTF2B General transcription factor IIB |
| 107 | Leukemia | 1.264089 | 0.3143916 | 0.272124 | 0.1949968 | X83973_at | TTF-I |
| 108 | Leukemia | 1.2637813 | 0.3142614 | 0.272198 | 0.19482134 | X01677_f_at | GAPD Glyceraldehyde-3-phosphate dehydrogenase |
| 109 | Leukemia | 1.2630478 | 0.3133051 | 0.271745 | 0.19504041 | D13370_at | DNA-(APURINIC OR APYRIMIDINIC SITE) LYASE |
| 110 | Leukemia | 1.2616616 | 0.3136495 | 0.271575 | 0.19421531 | Z67743_at | Chloride channel protein (CLCN7) mRNA, partial cds |
| 111 | Leukemia | 1.2582569 | 0.3135749 | 0.271285 | 0.19394386 | M37755_f_at | PSG7 Pregnancy-specific beta 1-glycoprotein 7 |
| 112 | Leukemia | 1.257142 | 0.3134559 | 0.271263 | 0.19372667 | AB002533_at | RPLP2 Hemoglobin, beta |
| 113 | Leukemia | 1.2566258 | 0.3132273 | 0.27105 | 0.19342288 | D86976_at | KIAA0223 gene, partial cds |
| 114 | Leukemia | 1.2562734 | 0.3128719 | 0.271012 | 0.19323882 | HG846-HT846_at | Cyclophilin-Related Protein |
| 115 | Leukemia | 1.2530344 | 0.312642 | 0.270433 | 0.19292504 | U93205_at | Nuclear chloride ion channel protein (NCC27) mRNA |
| 116 | Leukemia | 1.2519416 | 0.3124534 | 0.270143 | 0.19268094 | X83705_s_a | C-sis proto-oncogene |
| 117 | Leukemia | 1.2511085 | 0.3121829 | 0.270386 | 0.19247775 | HG3514-HT3708_at | Tropomyosin Tm30nm, Cytoskeletal |
| 118 | Leukemia | 1.2506273 | 0.3121381 | 0.270127 | 0.19223426 | K03189_f_at | Chorionic gonadotropin (hcg) beta subunit mRNA |
| 119 | Leukemia | 1.2503483 | 0.3115241 | 0.269744 | 0.19194281 | X52966_at | RPL35A Ribosomal protein L35a |
| 120 | Leukemia | 1.2476224 | 0.311298 | 0.269552 | 0.19175446 | HG1804-HT1829_at | Ornithine Aminotransferase-Like 3 |
| 121 | Leukemia | 1.2473154 | 0.3108951 | 0.269261 | 0.19160299 | X75091_s_a | SET PROTEIN |

FIG. 5E

| # | | | | | | | Description |
|---|---|---|---|---|---|---|---|
| 122 | Leukemia | 1.2453121 | 0.310659 | 0.269195 | 0.19137341 | X13482_at | U2 SMALL NUCLEAR RIBONUCLEOPROTEIN A' |
| 123 | Leukemia | 1.2451864 | 0.3103134 | 0.26876 | 0.19105348 | L03532_at | M4 protein mRNA |
| 124 | Leukemia | 1.2445465 | 0.31006 | 0.268479 | 0.1907233 | X62534_s_at | HMG2 High-mobility group (nonhistone chromosomal) protein 2 |
| 125 | Leukemia | 1.2416011 | 0.309915 | 0.268381 | 0.19047858 | D13748_at | EIF4A1 Eukaryotic translation initiation factor 4A (eIF-4A) isoform 1 |
| 126 | Leukemia | 1.24125741 | 0.309801 | 0.268106 | 0.19029194 | U38980_at | PMS8 mRNA (yeast mismatch repair gene PMS1 homologue), partial cds (C-terminal region) |
| 127 | Leukemia | 1.2404771 | 0.3097689 | 0.26777 | 0.19008814 | U52101_at | YMP mRNA |
| 128 | Leukemia | 1.239503 | 0.3094296 | 0.267647 | 0.18987389 | M64716_at | RPS25 Ribosomal protein S25 |
| 129 | Leukemia | 1.2388306 | 0.3093489 | 0.267582 | 0.18956022 | D31846_at | AQP2 Aquaporin 2 (collecting duct) |
| 130 | Leukemia | 1.2368712 | 0.3091966 | 0.267336 | 0.18940248 | Z49107_s_at | Galectin |
| 131 | Leukemia | 1.2361124 | 0.3090251 | 0.267149 | 0.18916345 | HG3636-HT3846_at | Myosin, Heavy Polypeptide 9, Non-Muscle |
| 132 | Leukemia | 1.234553 | 0.3089393 | 0.266949 | 0.18897024 | D14661_at | KIAA0105 gene |
| 133 | Leukemia | 1.2333759 | 0.3089393 | 0.266628 | 0.18873556 | U45448_s_at | P2x1 receptor mRNA |
| 134 | Leukemia | 1.2330676 | 0.3086549 | 0.265953 | 0.18856694 | U49869_rna1_at | Ubiquitin gene |
| 135 | Leukemia | 1.2300403 | 0.3084783 | 0.265902 | 0.18825643 | Z23064_at | HNRPG Heterogeneous nuclear ribonucleoprotein G |
| 136 | Leukemia | 1.2289646 | 0.3084368 | 0.266405 | 0.18810901 | D64142_at | Histone H1x |
| 137 | Leukemia | 1.2281015 | 0.3083881 | 0.265953 | 0.1877856 | X15729_s_at | P68 PROTEIN |
| 138 | Leukemia | 1.227778 | 0.308223 | 0.265902 | 0.18754287 | M94046_at | Zinc finger protein (MAZ) mRNA |
| 139 | Leukemia | 1.2270217 | 0.3081307 | 0.265615 | 0.18737027 | U02493_at | 54 kDa protein mRNA |
| 140 | Leukemia | 1.2268015 | 0.307945 | 0.265308 | 0.18716872 | M84711_at | RPS3A Ribosomal protein S3A |
| 141 | Leukemia | 1.226043 | 0.3075525 | 0.265289 | 0.1869955 | M64925_at | MPP1 Membrane protein, palmitoylated 1 (55kD) |
| 142 | Leukemia | 1.2259189 | 0.3072892 | 0.265239 | 0.18672927 | D63482_at | KIAA0148 gene |
| 143 | Leukemia | 1.2257375 | 0.3072786 | 0.264834 | 0.1865288 | L20316_at | GCGR Glucagon receptor |
| 144 | Leukemia | 1.2243629 | 0.3072769 | 0.264665 | 0.18633565 | X03484_at | RAF1 V-raf-1 murine leukemia viral oncogene homolog 1 |
| 145 | Leukemia | 1.2234674 | 0.3072298 | 0.264574 | 0.18613164 | X00351_f_at | ACTB Actin, beta |
| 146 | Leukemia | 1.2231642 | 0.3064514 | 0.264219 | 0.18589729 | U10323_at | Nuclear factor NF45 mRNA |
| 147 | Leukemia | 1.221944 | 0.3063171 | 0.264126 | 0.185669 | U01038_at | PLK mRNA |
| 148 | Leukemia | 1.22046 | 0.3061257 | 0.263962 | 0.18543686 | Z84721_cds2_at | Alpha-globin 1 gene extracted from Human DNA sequence from cosmid GG1 from a contig from the tip of the short arm of chromosome 16, spanning 2Mb of 16p13.3 Contains alpha and zeta globin genes and ESTs |
| 149 | Leukemia | 1.2170087 | 0.3060651 | 0.263775 | 0.18518446 | L38941_at | RPL37 Ribosomal protein L37 |

FIG. 5F

| # | | | | | | |
|---|---|---|---|---|---|---|
| 150 | Leukemia | 1.2162648 | 0.3055604 | 0.263688 | 0.18505192 | HG3527-HT3721_f_at | Luteinizing Hormone, Beta Subunit |
| 151 | Leukemia | 1.2150172 | 0.3054116 | 0.263523 | 0.1847654 | U40343_at | CDK inhibitor p19INK4d mRNA |
| 152 | Leukemia | 1.2147936 | 0.3052923 | 0.263206 | 0.18455225 | X75755_rna1_s_at | PR264 gene |
| 153 | Leukemia | 1.2147683 | 0.3052791 | 0.262911 | 0.18449408 | X83368_at | PIK3CG Phosphatidylinositol 3-kinase, catalytic, gamma polypeptide |
| 154 | Leukemia | 1.2133484 | 0.3051662 | 0.262766 | 0.18434271 | U45974_at | Phosphatidylinositol (4,5) bisphosphate 5-phosphatase homolog mRNA, partial cds |
| 155 | Leukemia | 1.2129612 | 0.3044576 | 0.262685 | 0.18408845 | X78338_at | MULTIDRUG RESISTANCE-ASSOCIATED PROTEIN 1 |
| 156 | Leukemia | 1.2126172 | 0.3044128 | 0.26255 | 0.1839925 | HG273-HT273_s_at | Lymphocyte Antigen Hla-G3 |
| 157 | Leukemia | 1.2123963 | 0.3043453 | 0.262463 | 0.18379508 | U12465_at | RPS11 Ribosomal protein S11 |
| 158 | Leukemia | 1.2120221 | 0.3042996 | 0.262444 | 0.18357657 | M74715_s_at | IDUA Iduronidase, alpha-L- |
| 159 | Leukemia | 1.211662 | 0.3041582 | 0.262131 | 0.18344717 | U30827_s_at | Splicing factor SRp40-1 (SRp40) mRNA |
| 160 | Leukemia | 1.2107162 | 0.3037405 | 0.262124 | 0.18331046 | M60854_at | RPS16 Ribosomal protein S16 |
| 161 | Leukemia | 1.2101176 | 0.3033187 | 0.261628 | 0.18297808 | HG4336-HT4606_at | Bactericidal Bpi Gene |
| 162 | Leukemia | 1.209184 | 0.3032731 | 0.261532 | 0.18280509 | HG662-HT662_at | Epstein-Barr Virus Small Rna-Associated Protein |
| 163 | Leukemia | 1.2083427 | 0.3031735 | 0.261374 | 0.18265115 | L07633_at | INTERFERON GAMMA UP-REGULATED I-5111 PROTEIN PRECURSOR |
| 164 | Leukemia | 1.2083071 | 0.3029563 | 0.261311 | 0.1824216 | HG2463-HT2559_at | Guanine Nucleotide-Binding Protein G25k |
| 165 | Leukemia | 1.2072864 | 0.3028952 | 0.261227 | 0.18232065 | D28423_at | Pre-mRNA splicing factor SRp20, 5'UTR (sequence from the 5'cap to the start codon) |
| 166 | Leukemia | 1.2069051 | 0.302875 | 0.261225 | 0.1821297 | X16135_at | HETEROGENEOUS NUCLEAR RIBONUCLEOPROTEIN L |
| 167 | Leukemia | 1.206428 | 0.3025334 | 0.261093 | 0.18200736 | X92396_at | Novel gene in Xq28 region |
| 168 | Leukemia | 1.2061185 | 0.3024052 | 0.260629 | 0.1818137 | HT5011_at | Centractin, Alpha |
| 169 | Leukemia | 1.2060547 | 0.3022202 | 0.260627 | 0.18170589 | U07132_at | Orphan receptor mRNA, partial cds |
| 170 | Leukemia | 1.2057818 | 0.3022002 | 0.260431 | 0.18147752 | U57341_r_at | Neurofilament triplet L protein mRNA, partial cds |
| 171 | Leukemia | 1.2052876 | 0.3020866 | 0.260324 | 0.18126565 | Y08765_s_at | ZFM1 protein alternatively spliced product |
| 172 | Leukemia | 1.2034352 | 0.3020802 | 0.260214 | 0.18116085 | X76013_at | GLUTAMINYL-TRNA SYNTHETASE |
| 173 | Leukemia | 1.2028148 | 0.3019385 | 0.259985 | 0.18110165 | U77718_at | Desmosome associated protein pinin mRNA |

FIG. 5G

| # | Type | | | | | Description |
|---|---|---|---|---|---|---|
| 174 | Leukemia | 1.20266554 | 0.3018221 | 0.259953 | 0.180877 U14969_at | Ribosomal protein L28 mRNA |
| 175 | Leukemia | 1.20026693 | 0.30172521 | 0.259672 | 0.180757921 HG384- HT384_at | Ribosomal Protein L26 |
| 176 | Leukemia | 1.19823791 | 0.30125116 | 0.259541 | 0.180562731 M16342_at | HnRNP C2 protein mRNA |
| 177 | Leukemia | 1.19803171 | 0.30111774 | 0.259325 | 0.180454271 L25080_at | ARH12 Aplysia ras-related homolog 12 |
| 178 | Leukemia | 1.19729031 | 0.30102321 | 0.259146 | 0.180326691 X86012_at | DNA sequence from intron 22 of the factor VIII gene, Xq28. Contains the end of a 9.5kb repeated region, int22h-1, involved in many cases of haemophilia |
| 179 | Leukemia | 1.197249 | 0.30066991 | 0.259119 | 0.1801582911 M96954_s_a_t | TIAL1 TIA1 cytotoxic granule-associated RNA-binding protein-like 1 |
| 180 | Leukemia | 1.19633191 | 0.30044674 | 0.258796 | 0.179994481 U95040_at | Unknown protein mRNA, partial cds |
| 181 | Leukemia | 1.19632661 | 0.30039811 | 0.258699 | 0.179894911 Y00486_rna1_at | Adenine phosphoribosyltransferase (aprt) gene extracted from Human APRT gene for adenine phosphoribosyltransferase |
| 182 | Leukemia | 1.19506431 | 0.30030661 | 0.258696 | 0.17973361 M31303_rna1_at | Oncoprotein 18 (Op18) gene |
| 183 | Leukemia | 1.19443831 | 0.3000982 | 0.2586 | 0.17950111 Y10807_s_at | Suppressor for yeast mutant |
| 184 | Leukemia | 1.193796 | 0.30000552 | 0.258512 | 0.179282081 Y11251_at | Novel member of serine-arginine domain protein, SRrp129 |
| 185 | Leukemia | 1.19237291 | 0.29996951 | 0.258254 | 0.179115041 M97856_at | NASP Nuclear autoantigenic sperm protein (histone-binding) |
| 186 | Leukemia | 1.19211721 | 0.29898111 | 0.258052 | 0.178948881 J03191_at | Profilin mRNA |
| 187 | Leukemia | 1.19047251 | 0.29899804 | 0.25766 | 0.178778951 M88108_at | P62 mRNA |
| 188 | Leukemia | 1.189373 | 0.28891271 | 0.257539 | 0.178512721 D86974_at | KIAA0220 gene, partial cds |
| 189 | Leukemia | 1.18891887 | 0.29885681 | 0.257515 | 0.178433881 Z19554_s_at | VIM Vimentin |
| 190 | Leukemia | 1.18880521 | 0.29875451 | 0.257308 | 0.178205421 X59244_f_at | ZNF43 Zinc finger protein 43 (HTF6) |
| 191 | Leukemia | 1.18879181 | 0.29884471 | 0.257169 | 0.178028051 M24069_at | DNA-BINDING PROTEIN A |
| 192 | Leukemia | 1.1865348 | 0.298375 | 0.257051 | 0.177782216 X96506_s_a_t | NC2 alpha subunit |
| 193 | Leukemia | 1.18555811 | 0.29982459 | 0.256846 | 0.17775615 M25079_s_a_t | Sickle cell beta-globin mRNA |
| 194 | Leukemia | 1.18506061 | 0.29823941 | 0.2566 | 0.177599091 L13848_at | LKP DEAD/H (Asp-Glu-Ala-Asp/His) box polypeptide 9 (RNA helicase A) |
| 195 | Leukemia | 1.18436071 | 0.29820891 | 0.256475 | 0.177411681 X80909_at | Alpha NAC mRNA |
| 196 | Leukemia | 1.18182441 | 0.29980891 | 0.256634 | 0.177333831 S75213_s_at | PDE4A Phosphodiesterase 4A, cAMP-specific (dunce (Drosophila)-homolog phosphodiesterase E2) |
| 197 | Leukemia | 1.1804932 | 0.2980198 | 0.256007 | 0.177761081 D87673_at | Heat shock transcription factor 4 |

FIG. 5H

| | | | | | | |
|---|---|---|---|---|---|---|
| 198 | Leukemia | 1.1794626 | 0.2979992 | 0.255954 | 0.17698868 | Z68280_cds2_s_at | Erythrocyte adducin alpha subunit gene extracted from Human DNA sequence from cosmid L25A3, Huntington's Disease Region, chromosome 4p16.3 contains Human tetracycline transporter-like protein and erythrocyte adducin alpha subunit, multiple ESTs and a putative CpG island |
| 199 | Leukemia | 1.1791159 | 0.2979146 | 0.255882 | 0.17682564 | X95404_at | CFL1 Cofilin 1 (non-muscle) |
| 200 | Leukemia | 1.179037 | 0.2977709 | 0.25568 | 0.17666484 | AC002115_cds3_at | F25451_3 gene extracted from Human DNA from overlapping chromosome 19 cosmids R31396, F25451, and R31076 containing COX6B and UPKA, genomic sequence |
| 201 | Leukemia | 1.1767216 | 0.2977417 | 0.255529 | 0.17665575 | X56997_rna1_at | UbA52 gene coding for ubiquitin-52 amino acid fusion protein |
| 202 | Leukemia | 1.1761341 | 0.2976536 | 0.255337 | 0.17640434 | X52851_rna1_at | Peptidylprolyl isomerase gene extracted from Human cyclophilin gene for cyclophilin (EC 5.2.1.8) |
| 203 | Leukemia | 1.1748629 | 0.2975881 | 0.255318 | 0.1762864 | U48405_at | G protein coupled receptor OGR1 gene |
| 204 | Leukemia | 1.1744432 | 0.2975271 | 0.255305 | 0.17621805 | HG2873-HT3017_at | Ribosomal Protein L30 Homolog |
| 205 | Leukemia | 1.1728004 | 0.297279 | 0.255236 | 0.17605063 | AF008937_a_t | Syntaxin-16C mRNA |
| 206 | Leukemia | 1.17196639 | 0.2970226 | 0.254878 | 0.17584848 | HG1602-HT1602_at | Utrophin |
| 207 | Leukemia | 1.1710877 | 0.2969898 | 0.254833 | 0.17570893 | X64044_at | SPLICING FACTOR U2AF 65 KD SUBUNIT |
| 208 | Leukemia | 1.1708757 | 0.2969872 | 0.254613 | 0.17564848 | U42412_at | 5'-AMP-activated protein kinase, gamma-1 subunit mRNA |
| 209 | Leukemia | 1.169984 | 0.296758 | 0.2545525 | 0.17551471 | M34338_s_a_t | SRM Spermidine synthase |
| 210 | Leukemia | 1.1699051 | 0.2967441 | 0.25445 | 0.17527379 | X07948_at | TNP1 Transition protein 1 (TP1) |
| 211 | Leukemia | 1.1689916 | 0.2966667 | 0.254308 | 0.17519422 | L49173_at | OCP2 gene, partial cds |
| 212 | Leukemia | 1.1694614 | 0.2963972 | 0.2540447 | 0.17505342 | HG3364-HT3541_at | Ribosomal Protein L37 |
| 213 | Leukemia | 1.1687437 | 0.2962276 | 0.253936 | 0.17484337 | M64992_at | PSMA2 Proteasome component C2 |
| 214 | Leukemia | 1.1685725 | 0.2961727 | 0.253817 | 0.1747057 | U79262_at | DHPS Deoxyhypusine synthase |
| 215 | Leukemia | 1.1681709 | 0.2961308 | 0.253788 | 0.17453593 | M21812_at | MYL2 Myosin, light polypeptide 2, regulatory, cardiac, slow |
| 216 | Leukemia | 1.1674801 | 0.2956751 | 0.253683 | 0.17440426 | HG2868-HT3012_s_a_t | Xe7, Pseudoautosomal Gene, Alt. Splice 2 |
| 217 | Leukemia | 1.166249 | 0.2956078 | 0.253556 | 0.17428826 | M90356_f_at | BTF3 protein homologue gene |
| 218 | Leukemia | 1.1653548 | 0.2955859 | 0.253489 | 0.17409502 | C02386_s_a_t | EST: HUMGS0010652, Human Gene Signature, 3'-directed cDNA sequence, mRNA sequence. (from Genbank) |
| 219 | Leukemia | 1.1652404 | 0.2955517 | 0.253221 | 0.17396985 | Y09216_at | Protein kinase, Dyrk2 |
| 220 | Leukemia | 1.164727 | 0.2955114 | 0.25302 | 0.17379431 | X53777_at | 60S RIBOSOMAL PROTEIN L23 |

FIG. 51

| | | | | | | |
|---|---|---|---|---|---|---|
| 221 | Leukemia | 1.16472 | 0.2954747 | 0.2529 | 0.173711538 | L04483_s_at | RPS21 Ribosomal protein S21 |
| 222 | Leukemia | 1.1645837 | 0.295445 | 0.252744 | 0.173358968 | X03342_at | RPL32 Ribosomal protein L32 |
| 223 | Leukemia | 1.163055 | 0.295334 | 0.252679 | 0.17340413 | U86529_at | Glutathione transferase Zeta 1 (GSTZ1) mRNA |
| 224 | Leukemia | 1.1629171 | 0.2953216 | 0.252541 | 0.17327225 | M13829_s_at | PKS PROTO-ONCOGENE SERINE/THREONINE-PROTEIN KINASE |
| 225 | Leukemia | 1.1612717 | 0.2948614 | 0.252418 | 0.17315453 | X57152_rna 1_s_at | Casein kinase II subunit beta (EC 2.7.1.37) |
| 226 | Leukemia | 1.1608988 | 0.2948278 | 0.252273 | 0.17299987 | X63679_at | TRAMP protein |
| 227 | Leukemia | 1.1608714 | 0.2948162 | 0.252142 | 0.17293733 | J00105_s_at | BETA-2-MICROGLOBULIN PRECURSOR |
| 228 | Leukemia | 1.1600969 | 0.2943476 | 0.251937 | 0.17276658 | U66617_at | SWI/SNF complex 60 KDa subunit (BAF60a) mRNA, alternatively spliced |
| 229 | Leukemia | 1.158937 | 0.29419959 | 0.251846 | 0.17262106 | X80754_at | GTP-binding protein |
| 230 | Leukemia | 1.1582055 | 0.294134 | 0.251816 | 0.172409629 | U94855_at | Translation initiation factor 3 47 kDa subunit mRNA |
| 231 | Leukemia | 1.1581177 | 0.2940536 | 0.25164 | 0.172384493 | X99585_at | SMT3B protein |
| 232 | Leukemia | 1.1572137 | 0.2940494 | 0.25143 | 0.17228387 | X76770_at | PAP mRNA |
| 233 | Leukemia | 1.1547911 | 0.2938658 | 0.251312 | 0.17205808 | X89984_at | BCL7 B cell lymphoma protein 7A |
| 234 | Leukemia | 1.1547556 | 0.2938606 | 0.251109 | 0.17190476 | Y10376_at | SIRP-beta1 |
| 235 | Leukemia | 1.1544577 | 0.2938364 | 0.251017 | 0.17184833 | U72206_at | Guanine nucleotide regulatory factor (LFP40) mRNA |
| 236 | Leukemia | 1.1535186 | 0.29374 | 0.250765 | 0.1717438 | Y08409_at | Spot14 gene |
| 237 | Leukemia | 1.153308 | 0.2932648 | 0.25073 | 0.171566641 | M80629_at | Cdc2-related protein kinase (CHED) mRNA |
| 238 | Leukemia | 1.1521839 | 0.2932485 | 0.250634 | 0.17146523 | X52943_at | TRANSCRIPTION FACTOR ATF-A AND ATF-A-DELTA |
| 239 | Leukemia | 1.1517979 | 0.2931118 | 0.250517 | 0.17136452 | AB004884_a t | PKU-alpha, partial cds |
| 240 | Leukemia | 1.1517426 | 0.2930953 | 0.250361 | 0.17113084 | D29012_at | PSMB6 Proteasome (prosome, macropain) subunit, beta type, 6 |
| 241 | Leukemia | 1.1515728 | 0.2928733 | 0.250361 | 0.17104958 | X83928_at | Transcription factor TFIID subunit TAFII28 |
| 242 | Leukemia | 1.1513697 | 0.2928099 | 0.250215 | 0.17093512 | HG1800-HT1823_at | Ribosomal Protein S20 |
| 243 | Leukemia | 1.1509783 | 0.2928011 | 0.24996 | 0.17085531 | X80818_at | GRM4 Glutamate receptor, metabotropic 4 |
| 244 | Leukemia | 1.1502827 | 0.2924913 | 0.249748 | 0.17060931 | M60858_rna 1_at | Nucleolin gene |
| 245 | Leukemia | 1.1493975 | 0.2923627 | 0.249664 | 0.17051846 | Y13115_at | Serine/threonine protein kinase SAK |
| 246 | Leukemia | 1.1491419 | 0.29235355 | 0.249577 | 0.17034017 | X97544_at | TIM17 preprotein translocase |
| 247 | Leukemia | 1.1472197 | 0.29232228 | 0.249483 | 0.17026886 | D13118_at | ATP SYNTHASE LIPID-BINDING PROTEIN P1 PRECURSOR |
| 248 | Leukemia | 1.145702 | 0.2921904 | 0.249302 | 0.17016792 | U14972_at | Ribosomal protein S10 mRNA |
| 249 | Leukemia | 1.145148 | 0.2919355 | 0.249189 | 0.1700586 | X70218_at | PPP4C Protein phosphatase 4 (formerly X), catalytic subunit |
| 250 | Leukemia | 1.1450238 | 0.2919342 | 0.249064 | 0.16992874 | U37139_at | Beta 3-endonexin mRNA, long form and short form |
| 251 | Leukemia | 1.1445582 | 0.2919332 | 0.249011 | 0.16978043 | U09953_at | RPL9 Ribosomal protein L9 |

FIG. 5J

| # | | | | | | | |
|---|---|---|---|---|---|---|---|
| 252 | Leukemia | 1.1441656 | 0.2917726 | 0.248939 | 0.16970333 | X52730_rna1_at | Phenylethanolamine n-methyltransferase gene extracted from Human gene for phenylethanolamine N-methylase (PNMT) (EC 2.1.1.28) |
| 253 | Leukemia | 1.1434027 | 0.2916956 | 0.248889 | 0.16957933 | L32831_s_at | PROBABLE G PROTEIN-COUPLED RECEPTOR GPR3 |
| 254 | Leukemia | 1.1433293 | 0.2916355 | 0.248731 | 0.16944677 | X16316_at | Vav oncogene |
| 255 | Leukemia | 1.1432002 | 0.2914688 | 0.248649 | 0.16930853 | Z84497_s_at HG2059-HG2059 | RING3 PROTEIN |
| 256 | Leukemia | 1.1431863 | 0.2914579 | 0.248564 | 0.16926442 | HT2114_at | Arrestin, Beta 2 |
| 257 | Leukemia | 1.1428101 | 0.2913958 | 0.248308 | 0.16917129 | U28886_at | Putative RNA binding protein RNPL mRNA |
| 258 | Leukemia | 1.1425124 | 0.2913019 | 0.248132 | 0.16901068 | Z47038_s_at | Partial cDNA sequence, clone x101, putative microtubule-associated; protein 1A (MAP1A) |
| 259 | Leukemia | 1.1424148 | 0.2912244 | 0.248045 | 0.1689065 | M36430_s_a_t | GNB1 Guanine nucleotide binding protein (G protein), beta polypeptide 1 |
| 260 | Leukemia | 1.1423041 | 0.2911485 | 0.248027 | 0.16879904 | U71203_s_a_t | Rit mRNA |
| 261 | Leukemia | 1.1422026 | 0.2909852 | 0.247932 | 0.16862282 | U38268_at | Cytochrome b pseudogene, partial cds |
| 262 | Leukemia | 1.140583 | 0.2908772 | 0.247711 | 0.1685722 | U78678_at | Thioredoxin mRNA, nuclear gene encoding mitochondrial protein |
| 263 | Leukemia | 1.1400883 | 0.2908703 | 0.247667 | 0.16841552 | U22376_cds2_s_at | C-myb gene extracted from Human (c-myb) gene, complete primary cds, and five complete alternatively spliced cds |
| 264 | Leukemia | 1.1394109 | 0.2906564 | 0.247481 | 0.16832282 | X90761_at | HHKa2 protein |
| 265 | Leukemia | 1.1385344 | 0.2905794 | 0.247445 | 0.1682302 | D87437_at | KIAA0250 gene |
| 266 | Leukemia | 1.1381584 | 0.2904616 | 0.247389 | 0.16806996 | X84740_at | DNA ligase III |
| 267 | Leukemia | 1.1376195 | 0.290294 | 0.247327 | 0.16799949 | U30825_at | Splicing factor SRp30c mRNA |
| 268 | Leukemia | 1.1369768 | 0.2902518 | 0.247178 | 0.16778138 | X69550_at | Rho GDP-dissociation Inhibitor 1 |
| 269 | Leukemia | 1.1359952 | 0.2899953 | 0.247145 | 0.16771683 | U65416_rna1_s_at | MHC class I molecule (MICB) gene |
| 270 | Leukemia | 1.1358911 | 0.2898581 | 0.247101 | 0.16763291 | K01383_at | Metallothionein-I-A gene, complete coding sequence |
| 271 | Leukemia | 1.1348935 | 0.2898518 | 0.247063 | 0.16755845 | U70439_s_at | PHAPI2b protein |
| 272 | Leukemia | 1.1348822 | 0.289834 | 0.246941 | 0.16746695 | Z69915_at | mRNA (clone ICRFp507L1876) |
| 273 | Leukemia | 1.1346132 | 0.2898124 | 0.246783 | 0.16731027 | M11353_at | EEF1G Translation elongation factor 1 gamma |
| 274 | Leukemia | 1.1344482 | 0.2896539 | 0.246705 | 0.16714419 | X14448_at | ALPHA-GALACTOSIDASE A PRECURSOR |
| 275 | Leukemia | 1.1329956 | 0.2895347 | 0.246608 | 0.16702329 | Z47727_at | RNA polymerase II subunit |
| 276 | Leukemia | 1.1327214 | 0.2895107 | 0.246482 | 0.16685395 | X98411_at | Myosin-IE |
| 277 | Leukemia | 1.1322469 | 0.2894479 | 0.246296 | 0.16671152 | U62962_at | Int-6 mRNA |
| 278 | Leukemia | 1.1322204 | 0.2893198 | 0.246168 | 0.16659564 | L12711_s_at | TKT Transketolase (Wernicke-Korsakoff syndrome) |

FIG. 5K

| | | | | | | |
|---|---|---|---|---|---|---|
| 279 | Leukemia | 1.1309122 | 0.289316 | 0.246081 | 0.166539 | X52979_rna 1_s_at | SmB protein gene extracted from Human gene for small nuclear ribonucleoproteins SmB and SmB' |
| 280 | Leukemia | 1.1302959 | 0.2892097 | 0.246048 | 0.16643462 | Z49878_at | Guanidinoacetate N-methyltransferase |
| 281 | Leukemia | 1.129755 | 0.2891943 | 0.245944 | 0.16633128 | X56932_at | LCAT Lecithin-cholesterol acyltransferase |
| 282 | Leukemia | 1.129514 | 0.2891271 | 0.245777 | 0.16616645 | X74795_at | CDC46 HOMOLOG |
| 283 | Leukemia | 1.1291142 | 0.2890729 | 0.245471 | 0.1660515 | X69150_at | Ribosomal protein S18 |
| 284 | Leukemia | 1.128326 | 0.289037 | 0.245425 | 0.16587387 | M91592_at | ZNF76 Zinc finger protein 76 |
| 285 | Leukemia | 1.1265644 | 0.2890178 | 0.24531 | 0.16584118 | U86409_at | Hyaluronan synthase 3 (HAS3) gene, partial cds |
| 286 | Leukemia | 1.1255598 | 0.2888225 | 0.245509 | 0.16578884 | M58285_at | Membrane-associated protein (HEM-1) mRNA |
| 287 | Leukemia | 1.125383 | 0.2887524 | 0.245046 | 0.16564767 | Z69720_at | MPG N-methylpurine-DNA glycosylase |
| 288 | Leukemia | 1.1252847 | 0.2887193 | 0.244955 | 0.16557367 | M34276_at | Plasminogen mRNA |
| 289 | Leukemia | 1.1246662 | 0.2885988 | 0.244946 | 0.16534217 | RC_AA6099 177_at | EST: af09h02.s1 Soares testis NHT Homo sapiens cDNA clone 1031187 3', mRNA sequence. (from Genbank) |
| 290 | Leukemia | 1.1225882 | 0.2885784 | 0.244732 | 0.16520637 | U58682_at | RPS28 Ribosomal protein S28 |
| 291 | Leukemia | 1.12252 | 0.2885706 | 0.244406 | 0.16510895 | C06269_at | EST: similar to none, mRNA sequence. (from Genbank) |
| 292 | Leukemia | 1.1220155 | 0.2881413 | 0.244355 | 0.16498981 | X79536_at | HNRPA1 Heterogeneous nuclear ribonucleoprotein A1 |
| 293 | Leukemia | 1.1216736 | 0.2881277 | 0.244247 | 0.16487932 | X62025_rna 1_at | Rod cG-PDE G gene for 3', 5'-cyclic nucleotide phosphodiesterase |
| 294 | Leukemia | 1.1208966 | 0.288098 | 0.244105 | 0.1647394 | U34038_at | Proteinase-activated receptor-2 mRNA |
| 295 | Leukemia | 1.1203524 | 0.2880561 | 0.244053 | 0.16465314 | Z48042_at | mRNA encoding GPI-anchored protein p137 |
| 296 | Leukemia | 1.1181958 | 0.2880113 | 0.243974 | 0.16453451 | M37583_at | H2AZ H2AZ histone |
| 297 | Leukemia | 1.118027 | 0.2876341 | 0.243849 | 0.16442089 | U80073_at | Tip associating protein (TAP) mRNA |
| 298 | Leukemia | 1.1172501 | 0.2874497 | 0.243731 | 0.16428559 | M25269_at | ELK1 ELK1, member of ETS oncogene family |
| 299 | Leukemia | 1.1160593 | 0.2872661 | 0.243696 | 0.16425402 | X57959_at | RPL17 Ribosomal protein L7 |
| 300 | Leukemia | 1.1154639 | 0.28722085 | 0.24362 | 0.1641192 | X82434_at | EMD Emerin (Emery-Dreifuss muscular dystrophy) |
| 301 | Leukemia | 1.1154184 | 0.2870454 | 0.243597 | 0.16401269 | X56741_at | RAS-RELATED PROTEIN RAB-8 |
| 302 | Leukemia | 1.115225 | 0.2869661 | 0.243358 | 0.16385859 | U34301_r_at | Nonmuscle myosin heavy chain IIB gene, promoter region and exon 1 |
| 303 | Leukemia | 1.1151443 | 0.2868831 | 0.243254 | 0.16379945 | HG2149-HT2219_at | Mucin (Gb:M57417) |
| 304 | Leukemia | 1.1151345 | 0.2868296 | 0.243167 | 0.16370875 | M63483_at | MATRIN 3 |
| 305 | Leukemia | 1.1150829 | 0.2868095 | 0.243116 | 0.16360624 | HG3319-HT3496_s_at | Split Gene 1 Enhancer, Tup1-Like |
| 306 | Leukemia | 1.1149789 | 0.2866643 | 0.24297 | 0.16349174 | M92642_at | COL16A1 Alpha-1 type XVI collagen |
| 307 | Leukemia | 1.1149035 | 0.2866307 | 0.242931 | 0.16341172 | U14968_at | Ribosomal protein L27a mRNA |
| 308 | Leukemia | 1.1143427 | 0.2865572 | 0.242904 | 0.16325933 | U78521_at | Immunophilin homolog ARA9 mRNA |
| 309 | Leukemia | 1.1130372 | 0.286514 | 0.242683 | 0.16320764 | X98001_at | Geranylgeranyl transferase II |
| 310 | Leukemia | 1.1129369 | 0.2860844 | 0.24256 | 0.16314812 | U66618_at | SWI/SNF complex 60 KDa subunit (BAF60b) mRNA |

FIG. 5L

| | | | | | | |
|---|---|---|---|---|---|---|
| 311 | Leukemia | 1.1116054 | 0.2860316 | 0.242532 | 0.16304502 | Y08766_s_at | Splicing factor, SF1-Bo isoform |
| 312 | Leukemia | 1.1099217 | 0.2859941 | 0.242456 | 0.16300045 | U15552_at | Acidic 82 kDa protein mRNA |
| 313 | Leukemia | 1.109396 | 0.2859084 | 0.242401 | 0.16284847 | X16663_at | HEMATOPOIETIC LINEAGE CELL SPECIFIC PROTEIN |
| 314 | Leukemia | 1.1093055 | 0.2858837 | 0.242191 | 0.16271928 | M93651_at | SET PROTEIN |
| 315 | Leukemia | 1.1090453 | 0.2857677 | 0.242167 | 0.16261557 | L00635_at | FNTB Farnesyltransferase, CAAX box, beta |
| 316 | Leukemia | 1.1078787 | 0.2857232 | 0.242129 | 0.16255267 | U70671_at | Ataxin-2 related protein mRNA, partial cds |
| 317 | Leukemia | 1.1077245 | 0.2856785 | 0.242026 | 0.16251051 | D16105_at | LTK Leukocyte tyrosine kinase |
| 318 | Leukemia | 1.1053149 | 0.2856439 | 0.242026 | 0.16236947 | M17886_at | RPLP1 Ribosomal protein, large, P1 |
| 319 | Leukemia | 1.1050891 | 0.2855242 | 0.241824 | 0.16231644 | U24186_at | EB1 mRNA |
| 320 | Leukemia | 1.1044514 | 0.285508 | 0.241823 | 0.16226187 | X56681_s_a t | JunD mRNA |
| 321 | Leukemia | 1.1036431 | 0.2855046 | 0.241479 | 0.16211317 | U28963_at | Gps2 (GPS2) mRNA |
| 322 | Leukemia | 1.103209 | 0.2854269 | 0.241475 | 0.16199353 | U19713_s_a t | Allograft inflammatory factor-1 (AIF-1) mRNA |
| 323 | Leukemia | 1.1026112 | 0.2854197 | 0.241386 | 0.16191407 | X54637_at | TYK2 Protein-tyrosine kinase tyk2 (non-receptor) |
| 324 | Leukemia | 1.1022385 | 0.2853949 | 0.241294 | 0.16181475 | HG2566-HT4867_at | Microtubule-Associated Protein Tau, Alt. Splice 5, Exon 4a |
| 325 | Leukemia | 1.1014911 | 0.2852632 | 0.241189 | 0.16174133 | U31930_at | DUT DUTP pyrophosphatase |
| 326 | Leukemia | 1.1013687 | 0.2851508 | 0.240994 | 0.16165617 | M86400_at | YWHAZ Tyrosine 3-monooxygenase/tryptophan 5-monooxygenase activation protein, zeta polypeptide |
| 327 | Leukemia | 1.1007587 | 0.2850826 | 0.24097 | 0.1615375 | M97287_at | SATB1 Special AT-rich sequence binding protein 1 (binds to nuclear matrix/scaffold-associating DNA's) |
| 328 | Leukemia | 1.100501 | 0.2850741 | 0.240704 | 0.1614906 | M29581_at | ZNF8 Zinc finger protein 8 (clone HF.18) |
| 329 | Leukemia | 1.09952275 | 0.2849745 | 0.240689 | 0.1613819 | J02621_s_at | Non-histone chromosomal protein HMG-14 mRNA |
| 330 | Leukemia | 1.0994701 | 0.2848574 | 0.240563 | 0.16126516 | X65488_at | HETEROGENOUS NUCLEAR RIBONUCLEOPROTEIN U |
| 331 | Leukemia | 1.0991381 | 0.2847856 | 0.240506 | 0.16118191 | U60325_at | POLG DNA polymerase gamma |
| 332 | Leukemia | 1.09899913 | 0.2846162 | 0.240408 | 0.16106379 | U80017_ma 3_at | Smn gene (survival motor neuron protein SMN) extracted from Human basic transcription factor 2 p44 (btf2p44) gene, partial cds, neuronal apoptosis inhibitory protein (naip) and survival motor neuron protein (smn) genes |
| 333 | Leukemia | 1.0977106 | 0.2845467 | 0.240344 | 0.16101246 | U14187_at | Receptor tyrosine kinase ligand LERK-3 (EPLG3) mRNA |
| 334 | Leukemia | 1.0972737 | 0.2843184 | 0.240279 | 0.16095036 | U75679_at | Histone stem-loop binding protein (SLBP) mRNA |
| 335 | Leukemia | 1.0961341 | 0.2842417 | 0.240263 | 0.16085316 | M93718_at | NOS3 Nitric oxide synthase 3 (endothelial cell) |
| 336 | Leukemia | 1.0950685 | 0.2842359 | 0.240138 | 0.16074711 | X73113_at | Fast MyBP-C |
| 337 | Leukemia | 1.09447922 | 0.2842085 | 0.240079 | 0.16063266 | AB002356_s _at | DENN mRNA |
| 338 | Leukemia | 1.0938666 | 0.2840985 | 0.240079 | 0.1605167 | U40714_at | Tyrosyl-tRNA synthetase mRNA |
| 339 | Leukemia | 1.0935458 | 0.2840951 | 0.23998 | 0.1603849 | D84557_at | P105MCM mRNA |

FIG. 5M

| | | | | | | |
|---|---|---|---|---|---|---|
| 340 | Leukemia | 1.0925126 | 0.2839587 | 0.239966 | 0.1602867 | U15008_at | SnRNP core protein Sm D2 mRNA |
| 341 | Leukemia | 1.0912216 | 0.2837795 | 0.239957 | 0.16017373 | HG1322-HT5143_s_a t | Small Nuclear Ribonucleoprotein, Polypeptide C, Alt. Splice 2 |
| 342 | Leukemia | 1.090349 | 0.283724 | 0.239968 | 0.16009448 | U03634_at | P47 LBC oncogene mRNA |
| 343 | Leukemia | 1.0900426 | 0.2837193 | 0.239958 | 0.1599969 | X70944_s_a t | PTB-ASSOCIATED SPLICING FACTOR |
| 344 | Leukemia | 1.0900426 | 0.2834316 | 0.239435 | 0.15983514 | X70944_s_a t-2 | Splicing factor proline/glutamine rich (polypyrimidine tract-binding protein-associated) |
| 345 | Leukemia | 1.0900408 | 0.2832874 | 0.239184 | 0.15980089 | AB000460_a t | mRNA, clone RES4-22A |
| 346 | Leukemia | 1.089713 | 0.2832874 | 0.239166 | 0.15969242 | U71088_at | MAP kinase kinase MEK5c mRNA |
| 347 | Leukemia | 1.0895984 | 0.2832694 | 0.239049 | 0.15958636 | M29610_at | GYPE Glycophorin E |
| 348 | Leukemia | 1.0886735 | 0.2829181 | 0.238994 | 0.15941343 | X94754_at | Yeast methionyl-tRNA synthetase homologue |
| 349 | Leukemia | 1.088289 | 0.2828893 | 0.238961 | 0.15933315 | U25988_at | PSG13 Pregnancy-specific beta-1 glycoprotein 13 |
| 350 | Leukemia | 1.0879525 | 0.2827407 | 0.238896 | 0.15922646 | U38904_at | Zinc finger protein C2H2-25 mRNA |
| 351 | Leukemia | 1.0875225 | 0.282674 | 0.238829 | 0.15917763 | U51240_at | KIAA0085 gene, partial cds |
| 352 | Leukemia | 1.0874597 | 0.2825215 | 0.238803 | 0.15904178 | X66417_at | KAPPA CASEIN PRECURSOR |
| 353 | Leukemia | 1.0868907 | 0.2824906 | 0.23865 | 0.15895419 | D23660_at | RPL4 Ribosomal protein L4 |
| 354 | Leukemia | 1.0868239 | 0.2823955 | 0.238625 | 0.15887953 | L36151_at | PHOSPHATIDYLINOSITOL 4-KINASE ALPHA |
| 355 | Leukemia | 1.0866914 | 0.282215 | 0.238568 | 0.15882437 | L17131_rna1_at | High mobility group protein (HMG-I(Y)) gene exons 1-8 |
| 356 | Leukemia | 1.086631 | 0.2822067 | 0.23841 | 0.15879697 | HG210-HT210_s_at | Galactokinase 2 |
| 357 | Leukemia | 1.0865532 | 0.2821873 | 0.238393 | 0.15859085 | V00599_s_at | mRNA fragment encoding beta-tubulin. (from clone D-beta-1) |
| 358 | Leukemia | 1.0865134 | 0.2821048 | 0.238265 | 0.15852426 | U69546_at | RNA binding protein Etr-3 mRNA |
| 359 | Leukemia | 1.086487 | 0.2820638 | 0.238105 | 0.15842809 | M18000_at | 40S RIBOSOMAL PROTEIN S17 |
| 360 | Leukemia | 1.0860066 | 0.2819287 | 0.237934 | 0.1583713 | U17894_at | Alpha(1,2)fucosyltransferase |
| 361 | Leukemia | 1.0855914 | 0.2817653 | 0.2378 | 0.1582572 | X66142_s_a t | PDE6B Phosphodiesterase 6B, cGMP-specific, rod, beta |
| 362 | Leukemia | 1.084546 | 0.2816694 | 0.237714 | 0.15824796 | U06155_s_a t | Chromosome 1q subtelomeric sequence D1S553 |
| 363 | Leukemia | 1.0832771 | 0.2816178 | 0.23764 | 0.15811275 | Y00433_at | GPX1 Glutathione peroxidase 1 |
| 364 | Leukemia | 1.0829148 | 0.2815631 | 0.237594 | 0.15802062 | X55733_at | EUKARYOTIC INITIATION FACTOR 4B |
| 365 | Leukemia | 1.0828974 | 0.2815472 | 0.237576 | 0.15797698 | U50839_at | G16 protein (g16) mRNA, partial cds |
| 366 | Leukemia | 1.0821224 | 0.2814679 | 0.237377 | 0.15787955 | U25750_at | Chromosome 17q21 mRNA clone 1046:1-1 |
| 367 | Leukemia | 1.0815961 | 0.2813997 | 0.237317 | 0.1577719 | U18300_at | DDB2 Damage-specific DNA binding protein 2 (48 kD) |
| 368 | Leukemia | 1.0813627 | 0.2813408 | 0.237194 | 0.15763296 | M28215_at | RAS-RELATED PROTEIN RAB-5A |
| 369 | Leukemia | 1.0792134 | 0.2813205 | 0.237048 | 0.15751874 | U45982_at | G protein-coupled receptor GPR-9-6 gene |

FIG. 5N

| # | Type | | | | | Description |
|---|---|---|---|---|---|---|
| 370 | Leukemia | 1.0787251 | 0.2812586 | 0.236997 | 0.15741014 D50918_at-2 | Human mRNA for KIAA0128 gene, partial cds |
| 371 | Leukemia | 1.0787251 | 0.281104 | 0.236944 | 0.1573883 D50918_at | KIAA0128 gene, partial cds |
| 372 | Leukemia | 1.0784053 | 0.2809657 | 0.235929 | 0.15736118 M95678_at | PLCB2 Phospholipase C, beta 2 |
| 373 | Leukemia | 1.0783503 | 0.2808356 | 0.236821 | 0.15715927 X51435_s_a | HIVEP1 Human immunodeficiency virus type I enhancer-binding protein 1 |
| 374 | Leukemia | 1.0782131 | 0.2807015 | 0.236772 | 0.15707237 U66615_at | SWI/SNF complex 155 KDa subunit (BAF155) mRNA |
| 375 | Leukemia | 1.0781792 | 0.2805625 | 0.236697 | 0.15702824 U44059_at | Thyrotroph embryonic factor (TEF) mRNA |
| 376 | Leukemia | 1.0777758 | 0.2804482 | 0.236674 | 0.15689361 U49441_at | Mitochondrial trifunctional protein beta subunit mRNA, partial cds |
| 377 | Leukemia | 1.0770123 | 0.2802991 | 0.236507 | 0.15677965 D87462_at | KIAA0272 gene, partial cds |
| 378 | Leukemia | 1.0766983 | 0.2802726 | 0.236465 | 0.1567085 M94362_at | LAMB2 Laminin, beta 2 (laminin S) |
| 379 | Leukemia | 1.0764946 | 0.2802726 | 0.2364 | 0.15662755 W95348_at | EST: ze06b01.r1 Soares fetal heart NbHH19W Homo sapiens cDNA clone 358153 5' similar to PIR:A40533 A40533 cAMP-dependent protein kinase major membrane substrate :: mRNA sequence. (from Genbank) |
| 380 | Leukemia | 1.0764494 | 0.2800324 | 0.236382 | 0.15656048 D26535_s_a | DLST Dihydrolipoamide S-succinyltransferase (E2 component of 2-oxo-glutarate complex) |
| 381 | Leukemia | 1.0760711 | 0.2799436 | 0.236354 | 0.1564418 U09411_at | ZNF132 Zinc finger protein 132 (clone pHZ-12) |
| 382 | Leukemia | 1.0755459 | 0.2798555 | 0.236255 | 0.15637726 D14657_at | KIAA0101 gene |
| 383 | Leukemia | 1.0754781 | 0.2796672 | 0.236173 | 0.15636076 HG2147-HT2217_at | Mucin 3, Intestinal (Gb:M55405) |
| 384 | Leukemia | 1.0753374 | 0.2796137 | 0.23607 | 0.15619878 X52192_at | FES Feline sarcoma (Snyder-Theilen) viral (v-fes)/Fujinami avian sarcoma (PRCII) viral (v-fps) oncogene homolog |
| 385 | Leukemia | 1.0752034 | 0.2794659 | 0.235834 | 0.15618761 L15409_at | VON HIPPEL-LINDAU DISEASE TUMOR SUPPRESSOR |
| 386 | Leukemia | 1.0750905 | 0.2793669 | 0.235646 | 0.1560759 U27330_at | FUT5 Fucosyltransferase 5 (alpha (1,3) fucosyltransferase) |
| 387 | Leukemia | 1.0734849 | 0.2792756 | 0.23551 | 0.1559421 U37219_at | Cyclophilin-like protein CyP-60 mRNA |
| 388 | Leukemia | 1.0731243 | 0.2792509 | 0.235474 | 0.15589432 M60784_s_a | U1 SMALL NUCLEAR RIBONUCLEOPROTEIN A |
| 389 | Leukemia | 1.0726568 | 0.2791381 | 0.23536 | 0.15576376 M37033_at | CD53 CD53 antigen |
| 390 | Leukemia | 1.0722156 | 0.2790708 | 0.235346 | 0.15568334 X92518_s_a | HMGI-C |
| 391 | Leukemia | 1.07211 | 0.2790005 | 0.235173 | 0.15565534 D16562_at | ATP SYNTHASE GAMMA CHAIN, MITOCHONDRIAL PRECURSOR |
| 392 | Leukemia | 1.0717362 | 0.278919 | 0.235096 | 0.15561327 M96995_s_a | GRB2 Growth factor receptor-bound protein 2 |
| 393 | Leukemia | 1.0717136 | 0.278905 | 0.235051 | 0.15551986 D79986_at | KIAA0164 gene |
| 394 | Leukemia | 1.0713031 | 0.2787188 | 0.234949 | 0.15548089 HG2379-HT3997_s_a | Serine Hydroxymethyltransferase, Cytosolic, Alt. Splice 3 |
| 395 | Leukemia | 1.0712078 | 0.2786824 | 0.234896 | 0.15535207 X02750_at | PROC Protein C (inactivator of coagulation factors Va and VIIIa) |

FIG. 50

| # | Type | | | | | | Description |
|---|---|---|---|---|---|---|---|
| 396 | Leukemia | 1.07069685 | 0.2786484 | 0.234745 | | 0.15531787 | X17206_at | PTB Ribosomal protein L26 |
| 397 | Leukemia | 1.0690673 | 0.2785358 | 0.234722 | | 0.155257 | Y00477_at | Bone marrow serine protease gene (medullasin) (leukocyte neutrophil elastase gene) |
| 398 | Leukemia | 1.0693145 | 0.2784956 | 0.234595 | | 0.15510282 | U79273_at | Clone 23933 mRNA sequence |
| 399 | Leukemia | 1.06919 | 0.2784782 | 0.23456 | D13413_ma 1_s_at | 0.15501659 | | Tumor-associated 120 kDa nuclear protein p120, partial cds(carboxyl terminus) |
| 400 | Leukemia | 1.0688711 | 0.2778449 | 0.234555 | | 0.15492117 | X60221_at | ATP5F1 ATP synthase, H+ transporting, mitochondrial F0 complex, subunit b, isoform 1 |
| 401 | Leukemia | 1.0677823 | 0.2784211 | 0.234422 | | 0.15486541 | L05072_s_at | IRF1 Interferon regulatory factor 1 |
| 402 | Leukemia | 1.0676644 | 0.2783461 | 0.234388 | | 0.15477511 | U57650_at | Signaling inositol polyphosphate 5 phosphatase SIP-110 mRNA |
| 403 | Leukemia | 1.0675877 | 0.2781927 | 0.234335 | | 0.1546605 | L14076_at | PRE-MRNA SPLICING FACTOR SRP75 |
| 404 | Leukemia | 1.0671936 | 0.2781853 | 0.234281 | | 0.15459642 | D63478_at | KIAA0144 gene |
| 405 | Leukemia | 1.0657507 | 0.2780446 | 0.234156 | | 0.1544765 | D13988_at | Rab GDI mRNA |
| 406 | Leukemia | 1.0657132 | 0.277993 | 0.2341 | | 0.15434417 | Z37166_at | BAT1 mRNA for nuclear RNA helicase (DEAD family) |
| 407 | Leukemia | 1.0655652 | 0.2778528 | 0.234076 | | 0.15428428 | M19283_at | ACTG1 Actin, gamma 1 |
| 408 | Leukemia | 1.0653403 | 0.2776999 | 0.234001 | | 0.15423803 | U62739_at | Branched-chain amino acid aminotransferase (ECA40) mRNA |
| 409 | Leukemia | 1.0651479 | 0.2776266 | 0.233977 | | 0.15412694 | U43148_at | PTCH Patched (Drosophila) homolog |
| 410 | Leukemia | 1.0646759 | 0.2776266 | 0.233895 | | 0.15408665 | U15177_at | Cosmid CRI-JC2015 at D10S289 in 10sp13 |
| 411 | Leukemia | 1.0642318 | 0.2773876 | 0.233791 | | 0.1539706 | M85247_at | Dopamine D1A receptor gene, complete exon 1, and exon 2, 5' end |
| 412 | Leukemia | 1.063674 | 0.2772995 | 0.233751 | | 0.15389264 | X14789_at | CRYAA Crystallin alpha-A |
| 413 | Leukemia | 1.0615326 | 0.2772919 | 0.233641 | | 0.15381987 | M31642_at | HPRT1 Hypoxanthine phosphoribosyltransferase 1 (Lesch-Nyhan syndrome) |
| 414 | Leukemia | 1.0612599 | 0.2770811 | 0.233519 | | 0.15372121 | X71428_at | RNA-BINDING PROTEIN FUS/TLS |
| 415 | Leukemia | 1.06085 | 0.2770085 | 0.233364 | D30930_s_a t | 0.153625886 | | EST: Human fetal-lung cDNA 5'-end sequence, mRNA sequence. (from Genbank) |
| 416 | Leukemia | 1.0605729 | 0.2769749 | 0.233336 | | 0.15353741 | M91585_at | Br140 mRNA |
| 417 | Leukemia | 1.0595994 | 0.2769749 | 0.233204 | | 0.15345937 | HT2621_at | Helix-Loop-Helix Protein Delta Max, Alt. Splice 1 |
| 418 | Leukemia | 1.0595453 | 0.2769176 | 0.233075 | | 0.15338008 | Z72499_at | Herpesvirus associated ubiquitin-specific protease (HAUSP) |
| 419 | Leukemia | 1.0581961 | 0.2767587 | 0.233013 | | 0.15328898 | S74221_at | IK |
| 420 | Leukemia | 1.0580108 | 0.276747 | 0.232995 | M33684_s_a t | 0.15313345 | | (clone lambda-16-1) non-receptor tyrosine phosphatase 1 (PTPN1) gene, exon x+4 and 5' end cds |
| 421 | Leukemia | 1.0577866 | 0.2767044 | 0.232923 | | 0.15302981 | U27831_at | Striatum-enriched phosphatase (STEP) mRNA, partial cds |
| 422 | Leukemia | 1.057281 | 0.2765918 | 0.232909 | | 0.15296148 | M74002_at | Arginine-rich nuclear protein mRNA |
| 423 | Leukemia | 1.0571856 | 0.2765358 | 0.23286 | | 0.15292238 | U92436_at | Mutated in multiple advanced cancers protein (MMAC1) mRNA |
| 424 | Leukemia | 1.0567095 | 0.2765085 | 0.232751 | | 0.15283552 | U26312_s_a t | Heterochromatin protein HP1Hs-gamma mRNA |
| 425 | Leukemia | 1.0551009 | 0.2764401 | 0.232722 | | 0.15273067 | U66052_at | Clone W2-6 mRNA from chromosome X |

FIG. 5P

| # | Type | V1 | V2 | V3 | ID1 | ID2 | Description |
|---|---|---|---|---|---|---|---|
| 426 | Leukemia | 1.0545149 | 0.276352 | 0.232625 | 0.15270753 | AA461140_a t | EST: zx64f12.r1 Soares total fetus Nb2HF8 9w Homo sapiens cDNA clone 796271 5', mRNA sequence. (from Genbank) |
| 427 | Leukemia | 1.0544431 | 0.2763338 | 0.232553 | 0.15260927 | HG2325-HT2421_at | Retinoic Acid Receptor, Gamma 2 |
| 428 | Leukemia | 1.0544137 | 0.2761261 | 0.232497 | 0.15254888 | Y12856_at | AMP-activated protein kinase alpha-1, partial |
| 429 | Leukemia | 1.0544074 | 0.2761194 | 0.232414 | 0.15247752 | J04102_at | ETS2 V-ets avian erythroblastosis virus E26 oncogene homolog 2 |
| 430 | Leukemia | 1.0542761 | 0.2760035 | 0.232393 | 0.15239303 | D38076_at | RANBP1 RAN binding protein 1 |
| 431 | Leukemia | 1.0539241 | 0.2758793 | 0.23235 | 0.1522458 | D21261_at | SM22-ALPHA HOMOLOG |
| 432 | Leukemia | 1.0537413 | 0.2758634 | 0.232301 | 0.15223864 | S82297_at | BETA-2-MICROGLOBULIN PRECURSOR |
| 433 | Leukemia | 1.0536019 | 0.2758448 | 0.232237 | 0.15216245 | X58521_at | NUCLEAR PORE GLYCOPROTEIN P62 |
| 434 | Leukemia | 1.0533165 | 0.275672 | 0.232159 | 0.15205857 | U62317_rna 3_at | Choline kinase isolog 384D8_3 gene extracted from Chromosome 22q13 BAC Clone CIT987SK-384D8 complete sequence |
| 435 | Leukemia | 1.0530785 | 0.2756116 | 0.232066 | 0.15198444 | HG2705-HT2801_s_a t | Serine/Threonine Kinase (Gb:Z25427) |
| 436 | Leukemia | 1.0516443 | 0.2755635 | 0.231966 | 0.15195596 | L38932_at | GT197 partial ORF mRNA, 3' end of cds |
| 437 | Leukemia | 1.0512185 | 0.2754828 | 0.231956 | 0.15186423 | L31801_at | SLC16A1 Solute carrier family 16 (monocarboxylic acid transporters), member 1 |
| 438 | Leukemia | 1.0496935 | 0.2754662 | 0.231905 | 0.151854 | L24804_at | (p23) mRNA |
| 439 | Leukemia | 1.049624 | 0.275438 | 0.231852 | 0.1517252 | Y08302_at | MAP kinase phosphatase 4 |
| 440 | Leukemia | 1.0492315 | 0.2753522 | 0.231656 | 0.15156926 | U10117_at | CALMODULIN |
| 441 | Leukemia | 1.0487151 | 0.2752825 | 0.23164 | 0.15154754 | X60003_s_a t | CAMP-RESPONSE ELEMENT BINDING PROTEIN |
| 442 | Leukemia | 1.0486447 | 0.2751431 | 0.231605 | 0.1514889 | L37368_at | (clone E5.1) RNA-binding protein mRNA |
| 443 | Leukemia | 1.048322 | 0.275055 | 0.231562 | 0.15140463 | HG3214-HT3391_at | Metallopanstimulin 1 |
| 444 | Leukemia | 1.0478345 | 0.2750196 | 0.231534 | 0.15132624 | L43579_s_at | L43579 Soares fetal liver spleen 1NFLS Homo sapiens cDNA clone 110298, mRNA sequence |
| 445 | Leukemia | 1.0478203 | 0.2750187 | 0.231424 | 0.151089 | U70064_s_a t | |
| 446 | Leukemia | 1.0443496 | 0.2750171 | 0.231419 | 0.15104818 | D86550_at | Serine/threonine protein kinase |
| 447 | Leukemia | 1.0442094 | 0.2750001 | 0.231389 | 0.15101625 | U78027_rna 3_at | Lysosomal trafficking regulator (LYST) mRNA, partial cds |
| 448 | Leukemia | 1.0440782 | 0.2749421 | 0.231361 | 0.15099755 | X99687_at | L44L gene (L44L-like ribosomal protein) extracted from Human Bruton's tyrosine kinase (BTK), alpha-D-galactosidase A (GLA), L44-like ribosomal protein (L44L) and FTP3 (FTP3) genes |
| 449 | Leukemia | 1.043317 | 0.2749179 | 0.231219 | 0.1508406 | U16812_s_a t | Methyl-CpG-binding protein 2, intron 2 |
| 450 | Leukemia | 1.0429516 | 0.274821 | 0.23114 | 0.15076965 | U90543_s_a t | Bak protein mRNA |
| 451 | Leukemia | 1.0428103 | 0.2747208 | 0.231121 | 0.15073861 | L14813_at | Butyrophilin (BTF1) mRNA / CELL Carboxyl ester lipase like protein |

FIG. 5Q

| | | | | | | |
|---|---|---|---|---|---|---|
| 452 | Leukemia | 1.0425364 | 0.2746482 | 0.231051 | 0.15064266 | D12775_s_a t | AMPD3 Adenosine monophosphate deaminase (isoform E) |
| 453 | Leukemia | 1.0421929 | 0.2745978 | 0.231018 | 0.15060385 | L13434_at | Chromosome 3p21.1 gene sequence |
| 454 | Leukemia | 1.0419241 | 0.2745805 | 0.230926 | 0.1504897 | M13792_at | ADA Adenosine deaminase |
| 455 | Leukemia | 1.041905 | 0.2745036 | 0.230858 | 0.15043059 | X13546_rna 1_at | Put. HMG-17 protein gene extracted from Human HMG-17 gene for non-histone chromosomal protein HMG-17 |
| 456 | Leukemia | 1.0416474 | 0.2744603 | 0.230701 | 0.15036479 | HG311-HT311_at | Ribosomal Protein L30 |
| 457 | Leukemia | 1.0408605 | 0.2743904 | 0.23067 | 0.1502489 | D42085_at | KIAA0095 gene |
| 458 | Leukemia | 1.040831 | 0.2743227 | 0.230606 | 0.15015577 | X66894_s_a t | FACC Fanconi anemia complementation group C |
| 459 | Leukemia | 1.0405996 | 0.2743053 | 0.2305 | 0.15008208 | X97249_at | Leucine-rich primary response protein 1 |
| 460 | Leukemia | 1.040179 | 0.2742777 | 0.230493 | 0.15002976 | Y13247_at | Fb19 mRNA |
| 461 | Leukemia | 1.0398366 | 0.2742304 | 0.230481 | 0.14999582 | RC_AA2625 83_at | EST: zs22c11.s1 NCI_CGAP_GCB1 Homo sapiens cDNA clone IMAGE:685940 3', mRNA sequence. (from Genbank) |
| 462 | Leukemia | 1.039826 | 0.2741962 | 0.230423 | 0.14993085 | M95627_at | Angio-associated migratory cell protein (AAMP) mRNA |
| 463 | Leukemia | 1.0397133 | 0.2741746 | 0.230299 | 0.14983393 | Z36715_at | Net transcription factor |
| 464 | Leukemia | 1.0395787 | 0.2739714 | 0.23025 | 0.14977348 | RC_AA4970 03_at | EST: ae32f03.s1 Gessler Wilms tumor Homo sapiens cDNA clone 897533 3', mRNA sequence. (from Genbank) |
| 465 | Leukemia | 1.0393805 | 0.2739418 | 0.230143 | 0.14968655 | M68895_rna 1_at | Alcohol dehydrogenase 6 gene |
| 466 | Leukemia | 1.0383989 | 0.2738793 | 0.230089 | 0.14955644 | U49082_at | Transporter protein (g17) mRNA |
| 467 | Leukemia | 1.0373524 | 0.2738793 | 0.230078 | 0.14946723 | RC_AA3484 12_at | EST: EST54858 Hippocampus II Homo sapiens cDNA 3' end, mRNA sequence. (from Genbank) |
| 468 | Leukemia | 1.036781 | 0.273836 | 0.229964 | 0.14934695 | M91467_at | HTR1E 5-hydroxytryptamine (serotonin) receptor 1E |
| 469 | Leukemia | 1.0366333 | 0.2738238 | 0.229915 | 0.14922723 | D29675_s_a t | Inducible nitric oxide synthase gene, promoter and exon 1 |
| 470 | Leukemia | 1.0365255 | 0.2736316 | 0.229899 | 0.14918478 | M31525_at | HLA-DNA Major histocompatibility complex, class II, DN alpha |
| 471 | Leukemia | 1.0360969 | 0.2736087 | 0.2298 | 0.14909622 | HG830-HG1112-HT830_at | Potassium Channel (Gb:L02750) |
| 472 | Leukemia | 1.0360832 | 0.2735961 | 0.229773 | 0.14906603 | HT1112_at | Ras-Like Protein Tc4 |
| 473 | Leukemia | 1.0355002 | 0.2734777 | 0.229663 | 0.14898454 | X89985_at | BCL7 B cell lymphoma protein 7B |
| 474 | Leukemia | 1.0348488 | 0.2734151 | 0.229658 | 0.14863312 | J02923_at | LCP1 Lymphocyte cytosolic protein 1 (L-plastin) |
| 475 | Leukemia | 1.0345237 | 0.273225 | 0.229605 | 0.14880955 | Y08200_at | Rab geranylgeranyl transferase, alpha-subunit |
| 476 | Leukemia | 1.0342258 | 0.2731077 | 0.229446 | 0.14873521 | M28983_at | IL1A Interleukin 1, alpha |
| 477 | Leukemia | 1.0341363 | 0.2730961 | 0.229382 | 0.14866818 | X64229_at | DEK PROTEIN |
| 478 | Leukemia | 1.0338426 | 0.2730424 | 0.22932 | 0.14866136 | U50553_at | Helicase like protein 2 mRNA |
| 479 | Leukemia | 1.0335699 | 0.2730189 | 0.229256 | 0.14856339 | M64595_at | RAC2 Ras-related C3 botulinum toxin substrate 2 |
| 480 | Leukemia | 1.0329919 | 0.273002 | 0.229248 | 0.14849466 | L40411_at | Thyroid receptor interactor (TRIP8) mRNA, 3' end of cds |

FIG. 5R.

| # | | | | | | | |
|---|---|---|---|---|---|---|---|
| 481 | Leukemia | 1.0326773 | 0.2729941 | 0.22911 | 0.14841114 | J03592_at | ANT3 Adenine nucleotide translocator 3 (liver) |
| 482 | Leukemia | 1.0326481 | 0.2729941 | 0.2291 | 0.14837883 | X74614_at | ODF2 (allele 2) gene for outer dense fiber protein |
| 483 | Leukemia | 1.0317615 | 0.27291103 | 0.229048 | 0.1483176 | U03486_at | Connexin40 gene |
| 484 | Leukemia | 1.0317472 | 0.2728589 | 0.229027 | 0.14821225 | U85430_at | Transcription factor NFATx4 mRNA |
| 485 | Leukemia | 1.0310644 | 0.2727933 | 0.228894 | 0.14812903 | U46571_at | Tetratricopeptide repeat protein (tpr2) mRNA |
| 486 | Leukemia | 1.0302689 | 0.2727467 | 0.228818 | 0.14805987 | X13461_s_at | CALMODULIN-RELATED PROTEIN NB-1 |
| 487 | Leukemia | 1.0301299 | 0.2727061 | 0.228695 | 0.14797784 | HG3088-HT3263_at | Splicing Factor Sc35, Alt Splice Form 3 |
| 488 | Leukemia | 1.0298699 | 0.2725866 | 0.228628 | 0.14787337 | HG1595-HT4788_s_a | Heterogeneous Nuclear Ribonucleoprotein I, Alt. Splice 2, Ptb-1 |
| 489 | Leukemia | 1.0297264 | 0.27249335 | 0.228598 | 0.1478017 | X60188_at | EXTRACELLULAR SIGNAL-REGULATED KINASE 1 |
| 490 | Leukemia | 1.0294064 | 0.2724558 | 0.228523 | 0.14767988 | X98085_at | TNR Tenascin R (restrictin, janusin) |
| 491 | Leukemia | 1.0292233 | 0.2724338 | 0.228461 | 0.14762366 | S49592_s_at | Transcription factor E2F like protein [human, mRNA, 2492 nt] |
| 492 | Leukemia | 1.0275176 | 0.27235585 | 0.228377 | 0.14754903 | AFFX-HUMGAPDH/M33197_5_at | AFFX-HUMGAPDH/M33197_5_at (endogenous control) |
| 493 | Leukemia | 1.0275176 | 0.2722869 | 0.228249 | 0.14741684 | AFFX-HUMGAPDH/M33197_5_at-2 | Glyceraldehyde-3-phosphate dehydrogenase |
| 494 | Leukemia | 1.0268674 | 0.2722254 | 0.228172 | 0.14733319 | S75989_at | Gamma-aminobutyric acid transporter type 3 [human, fetal brain, mRNA, 1991 nt] |
| 495 | Leukemia | 1.0266908 | 0.2721809 | 0.228101 | 0.14730573 | M13450_at | ESD Esterase D/formylglutathione hydrolase |
| 496 | Leukemia | 1.0261896 | 0.27221535 | 0.228052 | 0.14727719 | J02683_s_at | ANT2 Adenine nucleotide translocator 2 (fibroblast) |
| 497 | Leukemia | 1.0255388 | 0.27214463 | 0.228036 | 0.14723867 | M21064_at | S100A9 S100 calcium-binding protein A9 (calgranulin B) |
| 498 | Leukemia | 1.025359 | 0.27199812 | 0.227913 | 0.14717765 | U15009_at | SnRNP core protein Sm D3 mRNA |
| 499 | Leukemia | 1.0239787 | 0.2719609 | 0.227896 | 0.14708897 | X04391_at | CD5 CD5 antigen (p56-62) |
| 500 | Leukemia | 1.023952 | 0.2717978 | 0.227861 | 0.14702606 | U59752_at | Sec7p-like protein mRNA, partial cds |
| 501 | Leukemia | 1.0237935 | 0.2717784 | 0.227816 | 0.14696284 | M65217_at | HEAT SHOCK FACTOR PROTEIN 2 |
| 502 | Leukemia | 1.0235388 | 0.2717668 | 0.227801 | 0.14691241 | X62573_at | FCGR2B Fc fragment of IgG, low affinity IIb, receptor for (CD32) |
| 503 | Leukemia | 1.0225275 | 0.2717126 | 0.227563 | 0.14687638 | X98260_at | M-phase phosphoprotein, mpp11 |
| 504 | Leukemia | 1.0220897 | 0.2716422 | 0.227443 | 0.14680432 | U38545_at | ARF-activated phosphatidylcholine-specific phospholipase D1a (hPLD1) mRNA |
| 505 | Leukemia | 1.0218117 | 0.2715317 | 0.227359 | 0.14674473 | X90978_at | An acute myeloid leukaemia protein (1793bp) |

FIG. 5S

| | | | | | | |
|---|---|---|---|---|---|---|
| 506 | Leukemia | 1.0214908 | 0.2712591 | 0.227302 | 0.1466067 | Y00414_s_at | TH Tyrosine hydroxylase |
| 507 | Leukemia | 1.0212971 | 0.271244 | 0.227212 | 0.1465708 | Z14000_at | RING1 Ring finger protein 1 |
| 508 | Leukemia | 1.0204877 | 0.2711166 | 0.227133 | 0.1465158 | D87073_at | KIAA0236 gene |
| 509 | Leukemia | 1.0195603 | 0.2710729 | 0.227066 | 0.14639397 | Y10871_at | Twist gene |
| 510 | Leukemia | 1.0194591 | 0.270876 | 0.227055 | 0.14633761 | X80907_at | P85 beta subunit of phosphatidyl-inositol-3-kinase |
| 511 | Leukemia | 1.0191745 | 0.2707692 | 0.226955 | 0.14623317 | L34820_at | NAD+-dependent succinate-semialdehyde dehydrogenase (SSADH) mRNA, 3' end |
| 512 | Leukemia | 1.0187136 | 0.2706109 | 0.226861 | 0.14619271 | U85245_at | Phosphatidylinositol-4-phosphate 5-kinase type II beta mRNA |
| 513 | Leukemia | 1.0184958 | 0.27059 | 0.22677 | 0.14607468 | U79718_at | Endonuclease III homolog mRNA |
| 514 | Leukemia | 1.0181412 | 0.270484 | 0.226723 | 0.14601307 | X86681_at | Nucleolar protein, HNP36 |
| 515 | Leukemia | 1.0180436 | 0.2704655 | 0.226658 | 0.14594299 | U25165_at | Fragile X mental retardation protein 1 homolog FXR1 mRNA |
| 516 | Leukemia | 1.017392 | 0.2704442 | 0.226655 | 0.14586835 | HG2441-HT2537_s_a_t | Retinoblastoma Protein, Mutated |
| 517 | Leukemia | 1.0171125 | 0.2704426 | 0.226608 | 0.14581361 | U05040_at | FUSE binding protein mRNA |
| 518 | Leukemia | 1.0170559 | 0.2703212 | 0.22658 | 0.1457779 | U45975_at | Phosphatidylinositol (4,5)bisphosphate 5-phosphatase homolog mRNA, partial cds |
| 519 | Leukemia | 1.0166558 | 0.2702766 | 0.226507 | 0.14567302 | H51825_at | EST: yp83a08.r1 Homo sapiens cDNA clone 194006 5' similar to contains L1 repetitive element :. (from Genbank) |
| 520 | Leukemia | 1.016489 | 0.2700983 | 0.226478 | 0.14554566 | RC_AA4906 20_at | EST: aa47h07.s1 NCI_CGAP_GCB1 Homo sapiens cDNA clone IMAGE:824125 3', mRNA sequence. (from Genbank) |
| 521 | Leukemia | 1.0157963 | 0.2700755 | 0.226348 | 0.1455456 | X85137_s_a_t | Kinesin-related protein |
| 522 | Leukemia | 1.0152906 | 0.2700124 | 0.226342 | 0.14545943 | M22490_at | BMP4 Bone morphogenetic protein 4 |
| 523 | Leukemia | 1.015287 | 0.2698444 | 0.22629 | 0.14542662 | M20747_s_a_t | SLC2A4 Solute carrier family 2 (facilitated glucose transporter), member 4 |
| 524 | Leukemia | 1.0150449 | 0.2696536 | 0.226121 | 0.14531155 | X98248_rna 1_at | Sortilin |
| 525 | Leukemia | 1.0141498 | 0.2695359 | 0.226105 | 0.14525439 | L20298_at | Transcription factor (CBFB) mRNA, 3' end |
| 526 | Leukemia | 1.0135081 | 0.2694713 | 0.22607 | 0.14516947 | U05659_at | HSD17B3 Hydroxysteroid (17-beta) dehydrogenase 3 |
| 527 | Leukemia | 1.0129399 | 0.2694492 | 0.226601 | 0.1451109 | X12671_rna 61_at | Hnrnp a1 protein gene extracted from Human gene for heterogeneous nuclear ribonucleoprotein (hnRNP) core protein A1 |
| 528 | Leukemia | 1.0113257 | 0.2694393 | 0.225782 | 0.14498425 | U36759_s_a_t | Pre-T cell receptor alpha-type chain precursor, mRNA |
| 529 | Leukemia | 1.01091441 | 0.2693585 | 0.225767 | 0.14488634 | X85372_at | Sm protein F |
| 530 | Leukemia | 1.0109369 | 0.2691579 | 0.225767 | 0.14479294 | X99586_s_a_t | Ubiquitin-homology domain protein PIC1 mRNA |
| 531 | Leukemia | 1.010581 | 0.2691335 | 0.225623 | 0.14475243 | U69141_at | GCDH Glutaryl-Coenzyme A dehydrogenase |
| 532 | Leukemia | 1.0102822 | 0.2690669 | 0.2255512 | 0.14469753 | U72511_at | B-cell receptor associated protein (hBAP) mRNA, partial cds |

FIG. 5T

| # | | | | | | |
|---|---|---|---|---|---|---|
| 533 | Leukemia | 1.0097235 | 0.2690202 | 0.225238 | 0.14462133 | Z15114_at | PRKCG Protein kinase C, gamma |
| 534 | Leukemia | 1.0094302 | 0.2689514 | 0.225205 | 0.14460185 | X91809_at | GAIP protein |
| 535 | Leukemia | 1.0094115 | 0.2688449 | 0.225154 | 0.14450201 | HG3426-HT3610_s_a t | Zinc Finger Protein Hzf-16, Kruppel-Like, Alt. Splice 1 |
| 536 | Leukemia | 1.0091236 | 0.2687259 | 0.225114 | 0.14444768 | D17427_at | DSC3 Desmocollin 3 |
| 537 | Leukemia | 1.008249 | 0.2686367 | 0.225089 | 0.1444042 | U72512_at | B-cell receptor associated protein (hBAP) alternatively spliced mRNA, partial 3'UTR |
| 538 | Leukemia | 1.0080675 | 0.2685562 | 0.225052 | 0.14434643 | X82877_at | Na+-D-glucose cotransport regulator gene |
| 539 | Leukemia | 1.0080395 | 0.2685473 | 0.224985 | 0.14426583 | D26068_at | KIAA0038 gene, partial cds |
| 540 | Leukemia | 1.0068061 | 0.2684391 | 0.224962 | 0.14419374 | L22342_at | Nuclear phosphoprotein mRNA |
| 541 | Leukemia | 1.0063766 | 0.2684355 | 0.224962 | 0.14416265 | S66427_at | RBBP1 Retinoblastoma-binding protein 1(alternative products) |
| 542 | Leukemia | 1.0063581 | 0.2683736 | 0.224901 | 0.14407249 | U50079_s_a t | Histone deacetylase HD1 mRNA |
| 543 | Leukemia | 1.006167 | 0.2683364 | 0.224838 | 0.14393923 | D14878_at | Protein D123 |
| 544 | Leukemia | 1.005878 | 0.2683569 | 0.224802 | 0.14393562 | D14889_at | Small GTP-binding protein, S10 |
| 545 | Leukemia | 1.0052041 | 0.2683213 | 0.224739 | 0.14380881 | RC_AA2053 34_at | EST: zq79d12.s1 Stratagene hNT neuron (#937233) Homo sapiens cDNA clone 647831 3', mRNA sequence. (from Genbank) |
| 546 | Leukemia | 1.0041918 | 0.2682143 | 0.224679 | 0.1437358 | RC_AA2563 80_at | EST: zr80h01.s1 Soares NhHMPu S1 Homo sapiens cDNA clone 682033 3', mRNA sequence. (from Genbank) |
| 547 | Leukemia | 1.003964 | 0.2681164 | 0.224553 | 0.14366606 | U43965_at | ANK3 Ankyrin 3, node of Ranvier (ankyrin G) |
| 548 | Leukemia | 1.0037664 | 0.2680817 | 0.224473 | 0.14355526 | D86965_at | KIAA0210 gene |
| 549 | Leukemia | 1.0036104 | 0.2679925 | 0.224413 | 0.14348514 | U59736_at | Transcription factor (NFATc.b) mRNA |
| 550 | Leukemia | 1.0035161 | 0.2678291 | 0.224413 | 0.14342432 | U71601_at | Zinc finger protein zfp47 (zf47) mRNA, partial cds |
| 551 | Leukemia | 1.0030602 | 0.2677229 | 0.224385 | 0.14339615 | U49070_at | Peptidyl-prolyl isomerase and essential mitotic regulator (PIN1) mRNA |
| 552 | Leukemia | 1.0029913 | 0.2675588 | 0.224244 | 0.14334439 | Z12830_at | SSR1 Signal sequence receptor, alpha |
| 553 | Leukemia | 1.0027859 | 0.2673999 | 0.224198 | 0.14328918 | AB006782_a t | Galectin-9 isoform |
| 554 | Leukemia | 1.0025429 | 0.2673563 | 0.224189 | 0.14317745 | L26247_at | RPL3 Ribosomal protein L3 |
| 555 | Leukemia | 1.0021206 | 0.267208 | 0.224188 | 0.14307486 | U48730_at | Transcription factor Stat5b (stat5b) mRNA |
| 556 | Leukemia | 1.001407 | 0.2671715 | 0.224109 | 0.14300162 | L12392_at | HD Huntingtin (Huntington disease) |
| 557 | Leukemia | 1.000783 | 0.267164 | 0.224084 | 0.14297684 | U33936_s_a t | Adenosine kinase mRNA |
| 558 | Leukemia | 1.0006218 | 0.2671063 | 0.224084 | 0.14293385 | AA306121_a t | EST: EST177101 Jurkat T-cells VI Homo sapiens cDNA 5' end, mRNA sequence. (from Genbank) |

FIG. 5U

| # | | | | | | | |
|---|---|---|---|---|---|---|---|
| 559 | Leukemia | 1.0003803 | 0.2670581 | 0.223965 | 0.1428782 | RC_AA4488 63_at | EST: zx11d03.s1 Soares total fetus Nb2HF8 9w Homo sapiens cDNA clone 786149 3' similar to TR:E246888 E246888 CHROMOSOME XVI READING FRAME ORF YPL146C.; mRNA sequence. (from Genbank) |
| 560 | Leukemia | 1.0003021 | 0.267023 | 0.223924 | 0.14276932 | U33838_s_at | NF-kappa-B p65delta3 mRNA, spliced transcript lacking exons 6 and 7, partial cds |
| 561 | Leukemia | 1.0001686 | 0.2669815 | 0.223792 | 0.14270826 | M21142_cds2_s_at | Guanine nucleotide-binding protein G-s-alpha-3 mRNA Human guanine nucleotide-binding protein alpha-subunit gene (G-s-alpha) |
| 562 | Leukemia | 0.9993553 | 0.2668725 | 0.223738 | 0.14259373 | S78271_s_at | SB1.8/DXS423E |
| 563 | Leukemia | 0.9983326 | 0.2668605 | 0.223724 | 0.14251819 | U33053_at | Lipid-activated protein kinase PRK1 mRNA |
| 564 | Leukemia | 0.9983302 | 0.2668501 | 0.223595 | 0.14248449 | U09477_at | Clone 53BP1 p53-binding protein mRNA, partial cds |
| 565 | Leukemia | 0.9980555 | 0.2667705 | 0.223556 | 0.14242002 | Z29505_at | Alpha-CP1 mRNA |
| 566 | Leukemia | 0.9979395 | 0.2666691 | 0.223426 | 0.14235973 | M32405_at | Protein kinase (JNK2) mRNA |
| 567 | Leukemia | 0.997848 | 0.2665188 | 0.223363 | 0.14231849 | M29932_s_a t | ADRB3 Adrenergic, beta-3-, receptor |
| 568 | Leukemia | 0.997359 | 0.2663442 | 0.223345 | 0.14224017 | M74099_at | CUTL1 Cut (Drosophila)-like 1 (CCAAT displacement protein) |
| 569 | Leukemia | 0.9971064 | 0.2663127 | 0.223304 | 0.14221362 | L13972_at | SIAT4A Sialyltransferase 4A (beta-galactosidase alpha-2,3-sialyltransferase) |
| 570 | Leukemia | 0.997104 | 0.2662605 | 0.223269 | 0.14204963 | U48936_at | Amiloride-sensitive epithelial sodium channel gamma subunit mRNA, 5' end, partial cds |
| 571 | Leukemia | 0.9964346 | 0.266175 | 0.223243 | 0.14198643 | M17885_at | RPLP0 Ribosomal protein, large, P0 |
| 572 | Leukemia | 0.996066 | 0.2661211 | 0.22316 | 0.14191216 | U27325_s_a t | TBXA2R Thromboxane A2 receptor |
| 573 | Leukemia | 0.9954985 | 0.2661073 | 0.223138 | 0.14183213 | X02751_at | NRAS Neuroblastoma RAS viral (v-ras) oncogene homolog |
| 574 | Leukemia | 0.995369 | 0.2660707 | 0.223133 | 0.14178798 | X65867_at | ADENYLOSUCCINATE LYASE |
| 575 | Leukemia | 0.9946226 | 0.2660021 | 0.223013 | 0.14172333 | M95712_at | BRAF V-raf murine sarcoma viral oncogene homolog B1 |
| 576 | Leukemia | 0.9946206 | 0.2658814 | 0.222993 | 0.14165999 | AC000063_s _at | Clone lambda 5 semaphorin mRNA |
| 577 | Leukemia | 0.9945748 | 0.2658759 | 0.222843 | 0.14163777 | HG2028-HT2082_at | Laminin, A Polypeptide |
| 578 | Leukemia | 0.9943095 | 0.2658689 | 0.222837 | 0.14156242 | U61166_at | SH3 domain-containing protein SH3P17 mRNA |
| 579 | Leukemia | 0.9942491 | 0.2657645 | 0.222741 | 0.14151382 | M15205_at | TK1 Thymidine kinase 1, soluble |
| 580 | Leukemia | 0.9941995 | 0.2657613 | 0.222645 | 0.14139701 | U88898_r_at | Endogenous retroviral H protease/integrase-derived ORF1 mRNA, and putative envelope protein mRNA, partial cds |
| 581 | Leukemia | 0.993485 | 0.2657197 | 0.222483 | 0.14136915 | U43522_at | Protein tyrosine kinase PYK2 mRNA |
| 582 | Leukemia | 0.9930201 | 0.265673 | 0.222478 | 0.14127295 | X96484_at | DGCR6 protein |
| 583 | Leukemia | 0.9928292 | 0.265554 | 0.222402 | 0.14120594 | R73164_at | EST: yj91a03.r1 Homo sapiens cDNA clone 156076 5'. (from Genbank) |

FIG. 5V

| # | Type | | | | ID | Description |
|---|---|---|---|---|---|---|
| 584 | Leukemia | 0.9924133 | 0.2655222 | 0.222399 | 0.1411309 U65402_at | Seven transmembrane G-coupled receptor (GPR31) gene |
| 585 | Leukemia | 0.9923522 | 0.2654958 | 0.222351 | 0.1410583 M19483_at | ATP5B ATP synthase, H+ transporting, mitochondrial F1 complex, beta polypeptide |
| 586 | Leukemia | 0.9922085 | 0.265288 | 0.222326 | 0.1410289 Z93784_at | DNA sequence from clone RP3-398C22 on chromosome 22q13 Contains part of the gene for a novel protein (the ortholog of mouse brain protein E46), ESTs, STSs and GSSs, complete sequence |
| 587 | Leukemia | 0.991748 | 0.2652486 | 0.222252 | 0.1409723 D50917_at | KIAA0127 gene |
| 588 | Leukemia | 0.9908701 | 0.265223 | 0.222072 | 0.1409411 X82895_at | DLG2 Homolog 2 of Drosophila large discs |
| 589 | Leukemia | 0.9904501 | 0.2650642 | 0.221918 | 0.14086024 L07261_s_at | Alpha adducin mRNA, partial cds including alternate exons A and B |
| 590 | Leukemia | 0.9902272 | 0.2650642 | 0.221815 | 0.1408185 AB006190_a_t | Aquaporin 6 |
| 591 | Leukemia | 0.9900854 | 0.2650486 | 0.221796 | 0.14071418 X52882_at | T-COMPLEX PROTEIN 1, ALPHA SUBUNIT |
| 592 | Leukemia | 0.9894392 | 0.2650143 | 0.221781 | 0.14069244 U25029_at | GRL Glucocorticoid receptor alpha (alternative products) |
| 593 | Leukemia | 0.9892231 | 0.2648208 | 0.221759 | 0.14060097 D88613_at | HGCMa |
| 594 | Leukemia | 0.9888067 | 0.2648111 | 0.2217 | 0.14056556 M26683_at | SCYA2 Small inducible cytokine A2 (monocyte chemotactic protein 1, homologous to mouse Sig-je) |
| 595 | Leukemia | 0.988426 | 0.2647232 | 0.221685 | 0.1405043 L43575_s_at | (clone EST02946) mRNA |
| 596 | Leukemia | 0.9883249 | 0.2645627 | 0.221627 | 0.14045231 AA091752_a_t | Homo sapiens histone H2A.F/Z variant (H2AV) mRNA, complete cds |
| 597 | Leukemia | 0.9883074 | 0.2645522 | 0.221519 | 0.14043207 RC_AA4482 55_at | EST: zw83e08.s1 Soares testis NHT Homo sapiens cDNA clone 782822 3', mRNA sequence. (from Genbank) |
| 598 | Leukemia | 0.9878091 | 0.2644228 | 0.221464 | 0.14031926 HG3578-HT3781_at | Autoimmune Antigen, Thyroid Disease-Related Antigen |
| 599 | Leukemia | 0.9871443 | 0.2644068 | 0.221449 | 0.14023927 Z37986_at | Phenylalkylamine binding protein |
| 600 | Leukemia | 0.9866265 | 0.2643496 | 0.221425 | 0.14017594 U14973_at | 40S RIBOSOMAL PROTEIN S29 |
| 601 | Leukemia | 0.986596 | 0.2643457 | 0.221401 | 0.14011833 X65873_at | KINESIN HEAVY CHAIN |
| 602 | Leukemia | 0.9865959 | 0.2643395 | 0.221173 | 0.14008595 X98534_s_a_t | VASP gene, exons 4 to 13 |
| 603 | Leukemia | 0.986397 | 0.2642563 | 0.221171 | 0.14002734 M88468_at | MVK Mevalonate kinase |
| 604 | Leukemia | 0.9860925 | 0.2641815 | 0.221118 | 0.13993791 D38047_at | 26S PROTEASOME REGULATORY SUBUNIT P31 |
| 605 | Leukemia | 0.9859214 | 0.2641769 | 0.221008 | 0.13999155 X63692_at | DNMT DNA methyltransferase |
| 606 | Leukemia | 0.9854552 | 0.2640545 | 0.220998 | 0.13987409 U90313_at | Glutathione-S-transferase homolog mRNA |
| 607 | Leukemia | 0.9852542 | 0.2640231 | 0.220894 | 0.13979514 Y14140_at | G protein gene encoding beta 3 subunit exon 1 and promoter |
| 608 | Leukemia | 0.9849866 | 0.2640067 | 0.220879 | 0.13975918 D79991_at | KIAA0169 gene, partial cds |
| 609 | Leukemia | 0.9843043 | 0.2639483 | 0.220787 | 0.13967182 Z22951_rna1_s_at | Of p65 gene encoding p65 subunit of transcription factor NF-kappaB |
| 610 | Leukemia | 0.983847 | 0.2639208 | 0.220699 | 0.13959935 U41387_at | Gu protein mRNA, partial cds |

FIG. 5W

| | | | | | | |
|---|---|---|---|---|---|---|
| 611 | Leukemia | 0.9836288 | 0.2698364 | 0.220683 | 0.1395252 | U60063_at | Putative splice factor transformer2-beta mRNA |
| 612 | Leukemia | 0.982669 | 0.2638177 | 0.220683 | 0.1394362 | HG3523-HT4899_s_at | Proto-Oncogene C-Myc, Alt. Splice 3, Orf 114 |
| 613 | Leukemia | 0.9820164 | 0.2637265 | 0.22053 | 0.1393854 | D55716_at | DNA REPLICATION LICENSING FACTOR CDC47 HOMOLOG |
| 614 | Leukemia | 0.9819489 | 0.2637265 | 0.220465 | 0.1392838 | M21259_at | SNRPE Small nuclear ribonucleoprotein polypeptide E |
| 615 | Leukemia | 0.9817628 | 0.2637195 | 0.220452 | 0.1392286 | U96131_at | HPV16 E1 protein binding protein mRNA |
| 616 | Leukemia | 0.9815141 | 0.2636281 | 0.220045 | 0.1391888 | S78771_s_at | RING3 PROTEIN |
| 617 | Leukemia | 0.9809588 | 0.2635061 | 0.220441 | 0.1391322 | U96915_at | Sin3 associated polypeptide p18 (SAP18) mRNA |
| 618 | Leukemia | 0.9795336 | 0.2634919 | 0.220345 | 0.1390966 | J05249_at | RPA2 Replication protein A2 (32kD) |
| 619 | Leukemia | 0.979215 | 0.2634905 | 0.220288 | 0.1389068 | S83364_at | Putative Rab5-interacting protein [clone L1-57] [human, HeLa cells, mRNA Partial, 366 nt] |
| 620 | Leukemia | 0.9791006 | 0.2634052 | 0.220201 | 0.1388705 | AFFX-HSAC07/X00351_5_at | AFFX-HSAC07/X00351_5_at (endogenous control) |
| 621 | Leukemia | 0.9791006 | 0.2633874 | 0.220063 | 0.1387728 | AFFX-HSAC07/X00351_5_at-2 | No info for gene |
| 622 | Leukemia | 0.9787955 | 0.2631836 | 0.220025 | 0.1387009 | L08187_at | Cytokine receptor (EBI3) mRNA |
| 623 | Leukemia | 0.978353 | 0.2631825 | 0.22001 | 0.1386441 | D14663_at | KIAA0107 gene |
| 624 | Leukemia | 0.9781168 | 0.2631512 | 0.219925 | 0.1385524 | D86966_at | KIAA0211 gene |
| 625 | Leukemia | 0.9778667 | 0.2630597 | 0.21988 | 0.1385327 | X62153_s_at | MCM3 Minichromosome maintenance deficient (S. cerevisiae) 3 |
| 626 | Leukemia | 0.9777743 | 0.2629488 | 0.219873 | 0.138449 | U15172_at | Nip1 (NIP1) mRNA |
| 627 | Leukemia | 0.9777672 | 0.2628915 | 0.219816 | 0.1383435 | HG4297-HT4567_at | Transcriptional Coactivator Pc4 |
| 628 | Leukemia | 0.9772505 | 0.262822 | 0.219774 | 0.1383181 | U58766_at | FX protein mRNA |
| 629 | Leukemia | 0.9771581 | 0.2627907 | 0.219743 | 0.1382532 | U12622_at | Beaded intermediate filament protein CP115 mRNA, partial cds |
| 630 | Leukemia | 0.9771571 | 0.2627664 | 0.219734 | 0.1381844 | J02906_at | CYTOCHROME P450 IIF1 |
| 631 | Leukemia | 0.9769992 | 0.2627564 | 0.219641 | 0.1381045 | M34182_at | CAMP-DEPENDENT PROTEIN KINASE, GAMMA-CATALYTIC SUBUNIT |
| 632 | Leukemia | 0.9768394 | 0.2626424 | 0.219598 | 0.1380271 | U34343_at | 13kD differentiation-associated protein mRNA, partial cds |
| 633 | Leukemia | 0.9766697 | 0.2626297 | 0.219579 | 0.1379632 | X52889_at | MYH7 Myosin, heavy polypeptide 7, cardiac muscle, beta |
| 634 | Leukemia | 0.9765207 | 0.2625327 | 0.219511 | 0.1379050 | L27841_at | Autoantigen pericentriol material 1 (PCM-1) mRNA |
| 635 | Leukemia | 0.9764954 | 0.2625091 | 0.219493 | 0.1378188 | M32334_at | ICAM2 Intercellular adhesion molecule 2 |
| 636 | Leukemia | 0.9760385 | 0.2624117 | 0.2194 | 0.1378033 | L40410_at | Thyroid receptor interactor (TRIP3) mRNA, 3' end of cds |
| 637 | Leukemia | 0.976019 | 0.2623586 | 0.219373 | 0.1376895 | M64174_at | TYROSINE-PROTEIN KINASE JAK1 |
| 638 | Leukemia | 0.9757196 | 0.2623353 | 0.21937 | 0.1376517 | X76538_at | MPV17 MpV17 transgene, murine homolog, glomerulosclerosis |

FIG. 5X

| | | | | | | |
|---|---|---|---|---|---|---|
| 639 | Leukemia | 0.9752443 | 0.262287 | 0.219365 | 0.13759807 | U13045_at | GABPB2 GA-binding protein transcription factor, beta subunit 2 (47kD) |
| 640 | Leukemia | 0.9752169 | 0.2622797 | 0.219279 | 0.13754712 | D29954_at | HYPOTHETICAL MYELOID CELL LINE PROTEIN 6 |
| 641 | Leukemia | 0.97521 | 0.2622731 | 0.219261 | 0.13752021 | X54304_at | Myosin regulatory light chain mRNA |
| 642 | Leukemia | 0.9751254 | 0.2622283 | 0.219926 | 0.13747294 | D00860_at | PRPS1 Phosphoribosyl pyrophosphate synthetase subunit I |
| 643 | Leukemia | 0.9747022 | 0.2621803 | 0.219174 | 0.13735367 | D86979_at | KIAA0226 gene |
| 644 | Leukemia | 0.9746139 | 0.2620894 | 0.219118 | 0.13735338 | U66828_s_at | Carnitine palmitoyltransferase I (CPTI) mRNA |
| 645 | Leukemia | 0.9743862 | 0.2620511 | 0.219061 | 0.13724798 | U40391_rna1_at | Serotonin N-acetyltransferase gene |
| 646 | Leukemia | 0.9731653 | 0.2620101 | 0.219031 | 0.13724132 | X07024_at | TRANSCRIPTION INITIATION FACTOR TFIID 250 KD SUBUNIT |
| 647 | Leukemia | 0.9730851 | 0.2619634 | 0.218993 | 0.13720119 | M60830_at | EVI2B PROTEIN PRECURSOR TROPIC VIRAL INTEGRATION SITE 2B PROTEIN) |
| 648 | Leukemia | 0.9730682 | 0.2619074 | 0.218949 | 0.13714243 | D00596_at | TYMS Thymidylate synthase |
| 649 | Leukemia | 0.9729919 | 0.2617965 | 0.218936 | 0.13706204 | Y07829_xpt4_at | Exon A2 from H.sapiens gene encoding RING finger protein./ntype=DNA /annot=exon |
| 650 | Leukemia | 0.9729461 | 0.2617878 | 0.2189 | 0.13694704 | S87759_at | Protein phosphatase 2C alpha (human, teratocarcinoma, mRNA, 2346 nt) |
| 651 | Leukemia | 0.9728951 | 0.2617784 | 0.218828 | 0.1368517 | U61234_at | Tubulin-folding cofactor C mRNA |
| 652 | Leukemia | 0.9719777 | 0.2617541 | 0.218817 | 0.13678911 | L09604_at | INTESTINAL MEMBRANE A4 PROTEIN |
| 653 | Leukemia | 0.9710791 | 0.2617541 | 0.218652 | 0.13676417 | U32849_at | Hou mRNA |
| 654 | Leukemia | 0.9710065 | 0.2616389 | 0.2186 | 0.13665572 | U51241_at | CMKBR3 Chemokine (C-C) receptor 3 |
| 655 | Leukemia | 0.9708858 | 0.2615778 | 0.218598 | 0.13659933 | M81601_at | TRANSCRIPTION ELONGATION FACTOR S-II |
| 656 | Leukemia | 0.9701346 | 0.2615139 | 0.218563 | 0.13654675 | U41068_cds2_s_at | Retinoid X receptor beta (RXRbeta) gene, partial 3' transcript, and collagen alpha2(XI) (COL11A2) gene |
| 657 | Leukemia | 0.9697877 | 0.2615116 | 0.218419 | 0.1364635 | M16282_at | Fragile X locus M2C containing an unidentified open reading frame, 3' end |
| 658 | Leukemia | 0.969676 | 0.2613365 | 0.218308 | 0.1363978 | U25435_at | Transcriptional repressor (CTCF) mRNA |
| 659 | Leukemia | 0.9696209 | 0.2612992 | 0.218243 | 0.1363728 | U52830_at | Cri-du-chat region mRNA, clone CSC8 |
| 660 | Leukemia | 0.9692056 | 0.2610472 | 0.218234 | 0.13633299 | M13058_s_a_t | PRH1 Proline-rich protein HaeIII subfamily 1 |
| 661 | Leukemia | 0.9688708 | 0.2610467 | 0.218224 | 0.13622816 | U32581_at | Lambda/iota-protein kinase C-interacting protein mRNA |
| 662 | Leukemia | 0.9686209 | 0.2610361 | 0.218216 | 0.13619027 | J04948_at | Alkaline phosphatase |
| 663 | Leukemia | 0.9685306 | 0.2609873 | 0.218163 | 0.13613686 | U79252_at | Clone 23679 mRNA |
| 664 | Leukemia | 0.9681338 | 0.2609831 | 0.218139 | 0.13607603 | D86958_at | KIAA0203 gene |
| 665 | Leukemia | 0.9675313 | 0.2609794 | 0.218102 | 0.1360675 | U60666_at | Testis specific leucine rich repeat protein (TSLRP) |
| 666 | Leukemia | 0.9675012 | 0.2609684 | 0.218006 | 0.13601229 | M14764_at | NGFR Nerve growth factor receptor |
| 667 | Leukemia | 0.9672784 | 0.2609606 | 0.217996 | 0.13590613 | U51477_at | Diacylglycerol kinase zeta mRNA |
| 668 | Leukemia | 0.9669724 | 0.2608967 | 0.217986 | 0.13586837 | U19345_at | AR1 protein (AR) mRNA |

FIG. 5Y

| | | | | | | |
|---|---|---|---|---|---|---|
| 669 | Leukemia | 0.9659351 | 0.2608065 | 0.217973 | 0.135718336 | HG982-HT982_s_at | Pte-T/Nk-Cell-Associated Protein 1f6 |
| 670 | Leukemia | 0.9656111 | 0.2607265 | 0.217936 | 0.135699464 | M90366_at | Zona pellucida glycoprotein 2 (ZP2) mRNA |
| 671 | Leukemia | 0.9655321 | 0.2606816 | 0.217932 | 0.1356712 | M36200_at | SYNAPTOBREVIN 1 |
| 672 | Leukemia | 0.9650875 | 0.2606805 | 0.217889 | 0.135627725 | X92715_at | ZNF74 Zinc finger protein 74 (Cos52) |
| 673 | Leukemia | 0.9648359 | 0.2606419 | 0.217845 | 0.135536767 | M57464_s_a t | RET Ret proto-oncogene (multiple endocrine neoplasia MEN2A, MEN2B and medullary thyroid carcinoma 1, Hirschsprung disease) |
| 674 | Leukemia | 0.9646308 | 0.2606378 | 0.217693 | 0.135453358 | U79528_s_a t | Sigma receptor mRNA |
| 675 | Leukemia | 0.9645846 | 0.260536 | 0.217769 | 0.135433331 | U18271_cds s_at | Thymopoietin (TMPO) gene |
| 676 | Leukemia | 0.9643321 | 0.2604676 | 0.217666 | 0.135349081 | L42373_at | Protein phosphatase 2A B56-alpha mRNA |
| 677 | Leukemia | 0.9643776 | 0.2604107 | 0.2176 | 0.135331955 | D28383_at | ATP synthase B chain, 5'UTR (sequence from the 5'cap to the start codon) |
| 678 | Leukemia | 0.9643621 | 0.260329 | 0.217553 | 0.135265421 | U47677_at | Transcription factor E2F like protein [human, mRNA, 2492 nt] |
| 679 | Leukemia | 0.9643193 | 0.2602753 | 0.217538 | 0.135207831 | U82010_rna 1_at | Heme A: farnesyltransferase (COX10) gene promoter region and |
| 680 | Leukemia | 0.9643027 | 0.2601953 | 0.217453 | 0.135112626 | X17567_s_a t | SNRPB Small nuclear ribonucleoprotein polypeptides B and B1 |
| 681 | Leukemia | 0.9641039 | 0.2601803 | 0.217444 | 0.135050605 | U83239_s_a t | CC chemokine STCP-1 mRNA |
| 682 | Leukemia | 0.9636247 | 0.2601281 | 0.217416 | 0.1349893 | X36798_at | CGMP-inhibited cAMP phosphodiesterase mRNA |
| 683 | Leukemia | 0.9632511 | 0.2600382 | 0.217369 | 0.134493621 | J05614_at | Proliferating cell nuclear antigen (PCNA) gene, promoter region |
| 684 | Leukemia | 0.9631376 | 0.2599831 | 0.217339 | 0.134491368 | Z30643_at | Chloride channel (putative) 2139bp |
| 685 | Leukemia | 0.9631153 | 0.2599669 | 0.21732 | 0.1347831 | HG960-HT960_at | Guanine Nucleotide Exchange Factor 1 |
| 686 | Leukemia | 0.9630808 | 0.259932 | 0.217247 | 0.134476059 | X01388_at | APOC3 Apolipoprotein C-III |
| 687 | Leukemia | 0.9630649 | 0.2598941 | 0.217211 | 0.134470088 | U43923_at | Transcription factor SUPT4H mRNA |
| 688 | Leukemia | 0.9622974 | 0.2598401 | 0.217169 | 0.134458802 | M73780_at | ITGB8 Integrin, beta 8 |
| 689 | Leukemia | 0.9620204 | 0.2596897 | 0.216952 | 0.1345693 | RC_AA0175 17_at | EST: ze39h02.s1 Soares retina N2b4HR Homo sapiens cDNA clone 361395 3', mRNA sequence. (from Genbank) |
| 690 | Leukemia | 0.9619097 | 0.259655 | 0.216931 | 0.134451157 | X59417_at | PROTEASOME IOTA CHAIN |
| 691 | Leukemia | 0.9618215 | 0.2596369 | 0.216913 | 0.134411157 | L05187_at | Small proline-rich protein 1 (SPRR1A) gene |
| 692 | Leukemia | 0.9614296 | 0.2595855 | 0.216764 | 0.134437547 | X97302_at | Pig-1 protein |
| 693 | Leukemia | 0.9614214 | 0.2595796 | 0.216747 | 0.134343368 | L06797_s_at | PROBABLE G PROTEIN-COUPLED RECEPTOR LCR1 HOMOLOG |
| 694 | Leukemia | 0.9612474 | 0.2595498 | 0.21673 | 0.134426182 | U70451_at | Myeloid differentiation primary response protein MyD88 mRNA |
| 695 | Leukemia | 0.9611721 | 0.2595474 | 0.216691 | 0.134420233 | U61145_at | Enhancer of zeste homolog 2 (EZH2) mRNA |

FIG. 5Z

| | | | | | | |
|---|---|---|---|---|---|---|
| 696 | Leukemia | 0.9611367 | 0.2594988 | 0.216662 | 0.134122261 | U73477_s_a t | HLA-DR ASSOCIATED PROTEIN 1 |
| 697 | Leukemia | 0.961077 | 0.2594677 | 0.216644 | 0.13406864 | J04168_at | SPN Sialophorin (gpL115, leukosialin, CD43) |
| 698 | Leukemia | 0.9610701 | 0.25945 | 0.216573 | 0.13402414 | X74330_at | PRIM1 DNA primase polypeptide 1 (49kD) |
| 699 | Leukemia | 0.9608819 | 0.2594353 | 0.216656 | 0.13398458 | M86917_at | OSBP Oxysterol binding protein |
| 700 | Leukemia | 0.9600694 | 0.2593376 | 0.216548 | 0.13393667 | X16983_at | ITGA4 Integrin, alpha 4 (antigen CD49D, alpha 4 subunit of VLA-4 receptor) |
| 701 | Leukemia | 0.9599679 | 0.2593346 | 0.216479 | 0.13387573 | Z70759_at | Mitochondrial 16S rRNA gene (partial) |
| 702 | Leukemia | 0.959936 | 0.2592751 | 0.216423 | 0.13386457 | L37360_s_at | (clone hEHK1-L) EHK1 receptor tyrosine kinase ligand (EFL-2) mRNA |
| 703 | Leukemia | 0.9598551 | 0.2592553 | 0.21639 | 0.13377103 | U67122_s_a t | Ubiquitin-homology domain protein PIC1 mRNA |
| 704 | Leukemia | 0.9597926 | 0.2592183 | 0.21629 | 0.13376018 | X98172_at | MACH-alpha-2 protein |
| 705 | Leukemia | 0.9597082 | 0.2591952 | 0.216254 | 0.13371414 | HT33339_at | Transcription Factor IIa |
| 706 | Leukemia | 0.9594044 | 0.2591648 | 0.21621 | 0.13363767 | X93511_s_a t | Telomeric repeat binding factor (TRF1) mRNA |
| 707 | Leukemia | 0.9588862 | 0.2591352 | 0.216188 | 0.13356024 | U76366_s_a t | TCOF1 Treacher Collins syndrome susceptibility protein |
| 708 | Leukemia | 0.9586842 | 0.2591317 | 0.216152 | 0.13345881 | X78992_at | ERF-2 mRNA |
| 709 | Leukemia | 0.9584196 | 0.2591147 | 0.216116 | 0.13340378 | Z30426_at | CD69 CD69 antigen (early T cell activation antigen) |
| 710 | Leukemia | 0.9578203 | 0.2591139 | 0.216085 | 0.1333872 | AF000562_a t | Uroplakin II mRNA, partial cds |
| 711 | Leukemia | 0.9575109 | 0.259071 | 0.216084 | 0.13332965 | U34844_at | Mercurial-insensitive water-channel gene, 5' region and partial exon 1 |
| 712 | Leukemia | 0.9573796 | 0.2590636 | 0.215986 | 0.13322223 | U51004_at | Putative protein kinase C inhibitor (PKCI-1) mRNA |
| 713 | Leukemia | 0.9571899 | 0.2590485 | 0.215943 | 0.13316225 | D86988_at | KIAA0221 gene |
| 714 | Leukemia | 0.9571832 | 0.2589642 | 0.215898 | 0.13314246 | U72517_at | Alternatively spliced variant C7f (C3f) mRNA, partial 3'UTR |
| 715 | Leukemia | 0.9567441 | 0.2588719 | 0.215849 | 0.13311845 | HT2376_at | D-Amino-Acid Oxidase |
| 716 | Leukemia | 0.9563329 | 0.2587676 | 0.215798 | 0.13308531 | D38491_at | HYPOTHETICAL MYELOID CELL LINE PROTEIN 7 |
| 717 | Leukemia | 0.9561603 | 0.2587351 | 0.21569 | 0.13300404 | HT3924_at | Spermidine/Spermine N1-Acetyltransferase, Alt. Splice 2 |
| 718 | Leukemia | 0.9558069 | 0.2586827 | 0.215662 | 0.13294743 | L36922_at | Met-ase gene, exon 1 |
| 719 | Leukemia | 0.9557663 | 0.2586317 | 0.215662 | 0.13287725 | X99584_at | SMT3A protein |
| 720 | Leukemia | 0.9552177 | 0.2583399 | 0.215651 | 0.13283037 | Z48054_at | PXR1 Peroxisome receptor 1 |
| 721 | Leukemia | 0.9551695 | 0.2583044 | 0.215635 | 0.13277273 | X14329_at | ACBP Arginine carboxypeptidase (carboxypeptidase N) |
| 722 | Leukemia | 0.9545414 | 0.2581682 | 0.215605 | 0.13267013 | L38696_at | Autoantigen p542 mRNA, 3' end of cds |
| 723 | Leukemia | 0.9543055 | 0.2581291 | 0.215605 | 0.13263838 | Z32765_at | CD36 gene exon 15 |
| 724 | Leukemia | 0.9542512 | 0.2580179 | 0.215573 | 0.13253841 | U29607_at | EIF-2-associated p67 homolog mRNA |

FIG. 5A2

| | | | | | | |
|---|---|---|---|---|---|---|
| 725 | Leukemia | 0.9540494 | 0.2579221 | 0.215509 | 0.132248448 | HG4541-HT4946_s_a_t | Transformation-Related Protein |
| | | | | | | | TCRBV1S1A1N1 gene extracted from Human germline T-cell receptor beta chain Dopamine-beta-hydroxylase-like, TRY1, TRY2, TRY3, TCRBV27S1P, TCRBV22S1A2N1T, TCRBV9S1A1T, TCRBV7S1A1N2T, TCRBV5S1A1T, TCRBV13S3, TCRBV6S7P, TCRBV7S3A2T, TCRBV13S2A1T, TCRBV9S2A2PT, TCRBV7S2A1N4T, TCRBV13S9/13S2A1T, TCRBV6S5A1N1, TCRBV30S1P, TCRBV31S1, TCRBV13S5, TCRBV6S1A1N1, TCRBV32S1P, TCRBV5S5P, TCRBV1S1A1N1, TCRBV12S2A1T, TCRBV21S1, TCRBV8S4P, TCRBV12S3, TCRBV21S3A2N2T, TCRBV8S5P, TCRBV13S1 genes from bases 1 to 267156 (section 1 of 3) |
| 726 | Leukemia | 0.9538851 | 0.2578969 | 0.215386 | 0.132244924 | U66059_cds7_at | CCND3 Cyclin D3 |
| 727 | Leukemia | 0.9535385 | 0.257876 | 0.215378 | 0.13203396 | M92287_at | EST: EST181264 Jurkal T-cells V Homo sapiens cDNA 5' end, mRNA sequence. (from Genbank) |
| 728 | Leukemia | 0.9532822 | 0.2577776 | 0.215375 | 0.13236117 | AA310450_a | Chromatin assembly factor-I p150 subunit mRNA |
| 729 | Leukemia | 0.952901 | 0.2577533 | 0.215314 | 0.132233696 | U20979_at | |
| 730 | Leukemia | 0.9526573 | 0.2577446 | 0.215302 | 0.132232188 | HG1728-HT1734_s_a | Non-Specific Cross Reacting Antigen (Gb:D90277), Alt. Splice Form 2 |
| 731 | Leukemia | 0.952324 | 0.2577249 | 0.215274 | 0.13226175 | Y08976_at | FEV protein |
| 732 | Leukemia | 0.9517539 | 0.2577067 | 0.215239 | 0.1321784 | M55040_at | ACHE Acetylcholinesterase (YT blood group) |
| 733 | Leukemia | 0.9515842 | 0.2576606 | 0.215236 | 0.13211556 | X05855_s_a | EEF1G Translation elongation factor 1 gamma |
| 734 | Leukemia | 0.951547 | 0.2576326 | 0.215131 | 0.13202384 | X79865_at | Mrp17 mRNA |
| 735 | Leukemia | 0.9515334 | 0.2576096 | 0.215048 | 0.13195118 | X76942_s_a_t | 72.1 protein |
| 736 | Leukemia | 0.9514253 | 0.2576096 | 0.214993 | 0.13191958 | J02888_at | NMOR2 Quinone oxidoreductase (NQO2) |
| 737 | Leukemia | 0.9511837 | 0.2575435 | 0.214969 | 0.1318432 | X80822_f_at | Ribosomal protein L18a |
| 738 | Leukemia | 0.9504594 | 0.2574744 | 0.214803 | 0.13181144 | L25876_at | Protein tyrosine phosphatase (CIP2)mRNA |
| 739 | Leukemia | 0.9503995 | 0.2574296 | 0.214731 | 0.13175596 | D63485_at | KIAA0151 gene |
| 740 | Leukemia | 0.9502459 | 0.2574226 | 0.214725 | 0.1316795 | M38449_s_a | Transforming growth factor-beta mRNA, clone pTGF-beta-trp114 |
| 741 | Leukemia | 0.9500089 | 0.2573983 | 0.214666 | 0.131628 | D64154_at | Mr 110,000 antigen |
| 742 | Leukemia | 0.9494914 | 0.2573048 | 0.214582 | 0.1315667 | X98482_r_at | TNNT2 gene exon 11 |
| 743 | Leukemia | 0.9492815 | 0.2571852 | 0.214458 | 0.13155843 | Y11681_at | Mitochondrial ribosomal protein S12 |
| 744 | Leukemia | 0.9492169 | 0.25716 | 0.214448 | 0.13153282 | M17733_at | Thymosin beta-4 mRNA |
| 745 | Leukemia | 0.9491857 | 0.2571572 | 0.214379 | 0.13147467 | M64108_at | Udulin 1 mRNA, 3' end |

FIG. 5B2

| | | | | | |
|---|---|---|---|---|---|
| 746 | Leukemia | 0.9485521 | 0.2571007 | 0.214312 | 0.131457412_at | U93237_rna MEN1 gene (menin) extracted from Human menin (MEN1) gene |
| 747 | Leukemia | 0.948005 | 0.2569411 | 0.214171 | 0.13136622653_at | RC_AA1692 EST: zp19e02.s1 Stratagene fetal retina 937202 Homo sapiens cDNA clone 609914 3', mRNA sequence. (from Genbank) |
| 748 | Leukemia | 0.9478705 | 0.2568509 | 0.214148 | 0.131290321 | Y09306_at Protein kinase, Dyrk6, partial |
| 749 | Leukemia | 0.9471102 | 0.256695 | 0.214105 | 0.131236271 | D89858_at D-aspartate oxidase |
| 750 | Leukemia | 0.9469397 | 0.2565837 | 0.213986 | 0.131199961 | M87284_at 69/71 KD |
| 751 | Leukemia | 0.9469295 | 0.2565386 | 0.213943 | 0.131095221 | U68105_s_a t PABPL1 Poly(A)-binding protein-like 1 |
| 752 | Leukemia | 0.9466168 | 0.2564689 | 0.213905 | 0.131100201 | HG1723-HT1729_at Macrophage Scavenger Receptor, Alt. Splice 2 |
| 753 | Leukemia | 0.9462191 | 0.2564689 | 0.213876 | 0.130987821 | U07857_at SRP14 Signal recognition particle 14 kD protein |
| 754 | Leukemia | 0.9458166 | 0.2563617 | 0.213673 | 0.130929921 | U94352_at Manic fringe (Drosophila) homolog |
| 755 | Leukemia | 0.9456153 | 0.2563515 | 0.21364 | 0.130818591 | X67235_s_a PRHX Proline-rich homeodomain-containing transcription factor (symbol provisional) |
| 756 | Leukemia | 0.9454326 | 0.2563449 | 0.213599 | 0.130791291 | M19720_rna L-myc gene (L-myc protein) extracted from Human L-myc protein gene |
| 757 | Leukemia | 0.9452218 | 0.2562236 | 0.213529 | 0.130750161 | AB002318_a t KIAA0320 gene, partial cds |
| 758 | Leukemia | 0.9448673 | 0.2561809 | 0.213526 | 0.130678 | D25218_at KIAA0112 gene, partial cds |
| 759 | Leukemia | 0.9438434 | 0.2561624 | 0.213466 | 0.130595451 | H19089_at EST: yn51f04.r1 Homo sapiens cDNA clone 171967 5'. (from Genbank) |
| 760 | Leukemia | 0.94359 | 0.2561117 | 0.21344 | 0.130529731 | X80695_at RPL27 Ribosomal protein L27 |
| 761 | Leukemia | 0.9433434 | 0.2560663 | 0.213436 | 0.130503861 | X90763_at Type I keratin, hHa5 |
| 762 | Leukemia | 0.9432901 | 0.2559605 | 0.213416 | 0.130480571 | U67092_s_a Ataxia-telangiectasia locus protein (ATM) gene, exons 1a, 1b, 2, 3 and 4, partial cds |
| 763 | Leukemia | 0.9425031 | 0.2559222 | 0.213254 | 0.130407971 | U46570_at Tetratricopeptide repeat protein (tpr1) mRNA |
| 764 | Leukemia | 0.9424257 | 0.2558673 | 0.213177 | 0.130352171 | U89336_cds_ at RAGE gene (receptor for advanced glycosylation end products) extracted from Human HLA class III region containing NOTCH4 gene, partial sequence, homeobox PBX2 (HPBX) gene, receptor for advanced glycosylation end products (RAGE) gene, and 6 unidentified cds, complete sequence |
| 765 | Leukemia | 0.9422259 | 0.2558335 | 0.213038 | 0.130280031 | M55265_at CSNK2A1 Casein kinase 2, alpha 1 polypeptide |
| 766 | Leukemia | 0.9418556 | 0.2556983 | 0.212996 | 0.130218611 | S75168_rna _at Matk=megakaryocyte-associated tyrosine kinase [human, Genomic, 2677 nt 13 segments] |
| 767 | Leukemia | 0.941465 | 0.2556794 | 0.212986 | 0.130183011 | U12471_cds Thrombospondin-p50 gene extracted from Human thrombospondin-1 gene, partial cds |
| 768 | Leukemia | 0.9410585 | 0.2556603 | 0.212861 | 0.130150681 | D28588_at SP2 Sp2 transcription factor |
| 769 | Leukemia | 0.9407791 | 0.2555643 | 0.212698 | 0.130122041 | M15182_at GUSB Glucuronidase, beta |

FIG. 5C2

| # | | | | | | Description |
|---|---|---|---|---|---|---|
| 770 | Leukemia | 0.9405844 | 0.2553623 | 0.212625 | U52112_rna1_at | L1CAM gene (neural cell adhesion molecule L1) extracted from Human Xq28 genomic DNA in the region of the L1CAM locus containing the genes for neural cell adhesion molecule L1 (L1CAM), arginine-vasopressin receptor (AVPR2), C1 p115 (C1), ARD1 N-acetyltransferase related protein (TE2), renin-binding protein (RbP), host cell factor 1 (HCF1), and interleukin-1 receptor-associated kinase (IRAK) genes, and Xq28lu2 gene |
| 771 | Leukemia | 0.9399531 | 0.2553393 | 0.212597 | 0.130006857 | |
| 772 | Leukemia | 0.9396234 | 0.2552619 | 0.212595 | 0.13000831 U35459_at | Bomapin mRNA |
| 773 | Leukemia | 0.939461 | 0.2552339 | 0.212486 | 0.1299605 M55422_at | Krueppel-related zinc finger protein (H-plk) mRNA |
| | | | | | 0.1299194 D87453_at | KIAA0264 gene, partial cds |
| 774 | Leukemia | 0.9388696 | 0.2552214 | 0.212377 | 0.12987974 D30758_at-2 | KIAA0050 gene product |
| 775 | Leukemia | 0.9388696 | 0.2551937 | 0.212352 | 0.12981263 D30758_at | KIAA0050 gene |
| 776 | Leukemia | 0.9384459 | 0.2551932 | 0.212205 | 0.12975152 Y10055_at | Phosphoinositide 3-kinase |
| 777 | Leukemia | 0.9384245 | 0.2551447 | 0.212176 | 0.12971516 X64037_at | GTF2F1 General transcription factor IIF, polypeptide 1 (74kD subunit) |
| 778 | Leukemia | 0.9381435 | 0.2550916 | 0.212133 | 0.12968494 U91327_at | Chromosome 12p15 BAC clone CIT987SK-99D8 complete sequence |
| 779 | Leukemia | 0.9378268 | 0.2549949 | 0.212125 | 0.12960064 HG4332-HT4602_at | Zinc Finger Protein Znfpt1 |
| 780 | Leukemia | 0.9368298 | 0.2549747 | 0.21209 | 0.12954417 X80497_at | PHOSPHORYLASE B KINASE ALPHA REGULATORY CHAIN, LIVER ISOFORM |
| 781 | Leukemia | 0.9364706 | 0.2547897 | 0.212073 | 0.12952755 S72487_at | Platelet-derived endothelial cell growth factor mRNA |
| 782 | Leukemia | 0.9364332 | 0.2546488 | 0.212023 | 0.12942292 M91029_cds2_at | AMP deaminase (AMPD2) mRNA |
| 783 | Leukemia | 0.9363817 | 0.254637 | 0.211194 | 0.1294122 L35263_at | CSaids binding protein (CSBP1) mRNA |
| 784 | Leukemia | 0.9349624 | 0.2546057 | 0.211892 | 0.12931158 D79992_at | KIAA0170 gene |
| 785 | Leukemia | 0.9349452 | 0.2544778 | 0.211864 | 0.12928033 U76992_at | Tat-SF1 mRNA |
| 786 | Leukemia | 0.9347235 | 0.254467 | 0.211837 | 0.12921658 U50535_at | BRCA2 region, mRNA sequence CG005 |
| 787 | Leukemia | 0.9344146 | 0.2544412 | 0.211825 | 0.12920801 U85946_at | Brain secretory protein hSec10p (HSEC10) mRNA |
| 788 | Leukemia | 0.9343216 | 0.2542936 | 0.211786 | 0.12910709 U72066_at | CtBP interacting protein (CtIP) mRNA |
| 789 | Leukemia | 0.9341505 | 0.2542551 | 0.211669 | 0.12908219 D50405_at | RPD3 protein |
| 790 | Leukemia | 0.933996 | 0.2542496 | 0.211644 | 0.12902167 HG37-HT37_at | Iron-Responsive Element-Binding Protein |
| 791 | Leukemia | 0.9336405 | 0.2542437 | 0.211528 | 0.12899572 D38437_f_at | PMS8 mRNA (yeast mismatch repair gene PMS1 homologue), partial cds (C-terminal region) |
| 792 | Leukemia | 0.9334282 | 0.2539729 | 0.211521 | 0.12895635 J02986_cds1_at | FGF4 gene (transforming protein) extracted from Human transforming protein (hst) gene |
| 793 | Leukemia | 0.933028 | 0.2538656 | 0.211474 | 0.12888967 U24056_s_at | Inward rectifier K+ channel protein (hirk2) mRNA |

FIG. 5D2

| # | | | | | | |
|---|---|---|---|---|---|---|
| 794 | Leukemia | 0.932901 | 0.2538239 | 0.211457 | 0.12884386 | L34075_at | FRAP FK506 binding protein 12-rapamycin associated protein |
| 795 | Leukemia | 0.9324823 | 0.2538115 | 0.211143 | 0.1288017 | U83843_at | HIV-1 Nef interacting protein (Nip7-1) mRNA, partial cds |
| 796 | Leukemia | 0.9324226 | 0.2537694 | 0.211416 | 0.12870218 | AB003102_at | Proteasome subunit p44.5 |
| 797 | Leukemia | 0.9322655 | 0.2537421 | 0.211372 | 0.12869667 | HG1116-HT1116_at | Proliferating-Cell Nucleolar Antigen, 120 Kda |
| 798 | Leukemia | 0.9321988 | 0.2537384 | 0.21125 | 0.12863126 | U23803_at | Heterogeneous ribonucleoprotein A0 mRNA |
| 799 | Leukemia | 0.9319191 | 0.2537329 | 0.211221 | 0.12862206 | U05681_s_at | Proto-oncogene BCL3 gene |
| 800 | Leukemia | 0.9317335 | 0.2536258 | 0.211174 | 0.12851934 | M21186_at | CYBA Cytochrome b-245, alpha polypeptide |
| 801 | Leukemia | 0.9312192 | 0.2535904 | 0.211075 | 0.12850428 | X04085_rna1_at | Catalase (EC 1.11.1.6) 5'flank and exon 1 mapping to chromosome 11, band p13 (and joined CDS) |
| 802 | Leukemia | 0.9310812 | 0.2533555 | 0.211001 | 0.12842086 | Z15115_at | TOP2B Topoisomerase (DNA) II beta (180kD) |
| 803 | Leukemia | 0.9309754 | 0.2534992 | 0.210981 | 0.12839296 | U88726_at | Symplekin mRNA, partial cds |
| 804 | Leukemia | 0.9309714 | 0.2534063 | 0.210918 | 0.12833275 | R67468_at | EST: yi33b11.r1 Homo sapiens cDNA clone 141021 5'. (from Genbank) |
| 805 | Leukemia | 0.9308714 | 0.2533648 | 0.210861 | 0.1282823 | X07315_at | NUCLEAR TRANSPORT FACTOR 2 |
| 806 | Leukemia | 0.9307855 | 0.2533316 | 0.210856 | 0.12820283 | AFFX-HUMGAPDH/M33197_M_at-2 | Glyceraldehyde-3-phosphate dehydrogenase |
| 807 | Leukemia | 0.9307855 | 0.2533222 | 0.210815 | 0.12815712 | AFFX-HUMGAPDH/M33197_M_at | AFFX-HUMGAPDH/M33197_M_at (endogenous control) |
| 808 | Leukemia | 0.9303823 | 0.2532826 | 0.210732 | 0.12813866 | AFFX-HSAC07/X00351_M_at-2 | No info for gene |
| 809 | Leukemia | 0.9303823 | 0.2532705 | 0.210646 | 0.12808098 | AFFX-HSAC07/X00351_M_at | AFFX-HSAC07/X00351_M_at (endogenous control) |
| 810 | Leukemia | 0.9298865 | 0.2532493 | 0.210593 | 0.12805413 | J03071_cds_f_at | Chorionic somatomammotropin CS-1 gene extracted from Human growth hormone (GH-1 and GH-2) and chorionic somatomammotropin (CS-1, CS-2 and CS-5) genes |
| 811 | Leukemia | 0.929739 | 0.2532407 | 0.210573 | 0.12801737 | HG2415-HT2511_at | Transcription Factor E2f-2 |
| 812 | Leukemia | 0.9296195 | 0.253229 | 0.210521 | 0.12797187 | X01715_at | Gene fragment for the acetylcholine receptor gamma subunit precursor (exons 1 and 2) |

FIG. 5E2

| | | | | | |
|---|---|---|---|---|---|
| 813 | Leukemia | 0.9293427 | 0.2532007 | 0.210444 | 0.1278722 | Y00796_at | ITGAL Integrin, alpha L (antigen CD11A (p180), lymphocyte function-associated antigen 1; alpha polypeptide) |
| 814 | Leukemia | 0.9292374 | 0.2531587 | 0.210428 | 0.1277986 | X05276_at | TPM4 Tropomyosin 4 (fibroblast) |
| 815 | Leukemia | 0.9290455 | 0.2531378 | 0.21038 | 0.1277862B | U29343_at | HMMR Hyaluronan-mediated motility receptor (RHAMM) |
| 816 | Leukemia | 0.9282318 | 0.2531251 | 0.210347 | 0.12769698 | X80923_at | Nov gene |
| 817 | Leukemia | 0.9280504 | 0.253066 | 0.210265 | 0.12767504 | L37112_at | AVPR1B Arginine vasopressin receptor 1B |
| 818 | Leukemia | 0.9277813 | 0.2530074 | 0.210207 | 0.12758462 | N75236_s_a t | EST: yz73l09.r1 Homo sapiens cDNA clone 288713 5' similar to gb:M93426 PROTEIN-TYROSINE PHOSPHATASE ZETA PRECURSOR (HUMAN);.. (from Genbank) |
| 819 | Leukemia | 0.9268097 | 0.2529157 | 0.210183 | 0.12754938 | S56151_s_at | HMFG |
| 820 | Leukemia | 0.926567 | 0.252894 | 0.210126 | 0.12751465 | RC_AA4254 44_at | Human Chromosome 16 BAC clone CIT987SK-A-61E3 |
| 821 | Leukemia | 0.9258676 | 0.2528772 | 0.21003 | 0.12748271 | HG881-HT881_at | Mucin 6, Gastric (Gb:L07518) |
| 822 | Leukemia | 0.9254375 | 0.2527884 | 0.209956 | 0.12741031 | U24105_at | Coatomer protein (COPA) mRNA |
| 823 | Leukemia | 0.9253108 | 0.2527033 | 0.209936 | 0.127369905 | AF015913_a t | SKB1Hs mRNA |
| 824 | Leukemia | 0.9251571 | 0.2526872 | 0.209902 | 0.12734005 | Z97054_xpt2_at | DNA binding protein from Human DNA sequence from PAC 339A18 on chromosome Xp11.1-Xp11.4. Contains KIAA0178 gene, similar to mitosis-specific chromosome segregation protein SMC1 of S.cerevisiae, DNA binding protein similar to URE-B1, EST's and STS./ntype=DNA /annot=CDS |
| 825 | Leukemia | 0.9248518 | 0.2526051 | 0.209799 | 0.12727316 | J04988_at | 90-kDa heat-shock protein gene, cDNA |
| 826 | Leukemia | 0.9245867 | 0.2525653 | 0.209732 | 0.12725383 | L29218_at | Clk2 mRNA |
| 827 | Leukemia | 0.924313 | 0.2525025 | 0.209677 | 0.12721066 | X82206_s_a t | ALPHA-CENTRACTIN |
| 828 | Leukemia | 0.9242564 | 0.2524944 | 0.209639 | 0.12714967 | M63175_at | AMFR Autocrine motility factor receptor |
| 829 | Leukemia | 0.9237095 | 0.2523848 | 0.209601 | 0.12709698 | HG2668-HT2764_at | Bradykinin Receptor |
| 830 | Leukemia | 0.9236971 | 0.252359 | 0.209558 | 0.12702425 | X94232_at | Novel T-cell activation protein |
| 831 | Leukemia | 0.9236835 | 0.2522356 | 0.209534 | 0.12699181 | U79266_at | Clone 23627 mRNA |
| 832 | Leukemia | 0.9236469 | 0.2522339 | 0.209501 | 0.12695965 | U78107_at | Gamma SNAP mRNA |
| 833 | Leukemia | 0.9233001 | 0.2521981 | 0.209437 | 0.12690812 | U09410_at | ZNF131 Zinc finger protein 131 (clone pHZ-10) |
| 834 | Leukemia | 0.9232395 | 0.2521025 | 0.209388 | 0.12684312 | U07158_at | Syntaxin mRNA |
| 835 | Leukemia | 0.9231622 | 0.2520845 | 0.209383 | 0.12681586 | D83004_at | Epidermoid carcinoma mRNA for ubiquitin-conjugating enzyme E2 similar to Drosophila bendless gene product |
| 836 | Leukemia | 0.9229325 | 0.2520746 | 0.209367 | 0.12675379 | M57763_at | ARF6 ADP-ribosylation factor 6 |
| 837 | Leukemia | 0.9228348 | 0.25207 | 0.209304 | 0.12673043 | X12791_at | SRP19 Signal recognition particle 19 kD protein |

FIG. 5F2

| # | Type | | | | ID | Description |
|---|---|---|---|---|---|---|
| 838 | Leukemia | 0.9227675 | 0.2520623 | 0.209269 | 0.12667598 | X97160_rna1_at TFE3 transcription factor gene extracted from H.sapiens TFE3 gene, exons 1,2,3 (and joined CDS) |
| 839 | Leukemia | 0.9227372 | 0.2520438 | 0.209255 | 0.12658852 | U73328_at DLX7 Distal-less homoebox 7 |
| 840 | Leukemia | 0.9226273 | 0.2520294 | 0.209225 | 0.12652707 | X68486_at ADENOSINE A2A RECEPTOR |
| 841 | Leukemia | 0.9221103 | 0.2520043 | 0.20922 | 0.12648968 | RC_AA431502_at Homo sapiens lok mRNA for protein kinase, complete cds |
| 842 | Leukemia | 0.921907 | 0.2519141 | 0.209099 | 0.1264545 | D11086_at IL2RG Interleukin 2 receptor gamma chain |
| 843 | Leukemia | 0.921872 | 0.2518983 | 0.209092 | 0.12641974 | X80763_s_at HTR2C 5-hydroxytryptamine (serotonin) receptor 2C |
| 844 | Leukemia | 0.9214814 | 0.2518263 | 0.209065 | 0.12634583 | D79993_at KIAA0171 gene |
| 845 | Leukemia | 0.9213948 | 0.2517596 | 0.209003 | 0.12629886 | M99439_at Transducin-like enhancer protein (TLE4) mRNA, 3' end |
| 846 | Leukemia | 0.9212307 | 0.251704 | 0.208911 | 0.12628059 | J03930_at ALKALINE PHOSPHATASE, INTESTINAL PRECURSOR |
| 847 | Leukemia | 0.9205834 | 0.2516705 | 0.208886 | 0.12626049 | U60269_cds3_at Putative envelope protein; orf similar to env of Type A and Type B retroviruses and to class II HERVs gene extracted from Human endogenous retrovirus HERV-K(HML6) proviral clone HML6.17 putative polymerase and envelope genes, partial cds, and 3'LTR |
| 848 | Leukemia | 0.9205387 | 0.2516325 | 0.208859 | 0.12620391 | X68985_s_at HLF Hepatic leukemia factor |
| 849 | Leukemia | 0.9201732 | 0.2516317 | 0.208841 | 0.12618372 | U13395_at Oxidoreductase (HHCMA56) mRNA |
| 850 | Leukemia | 0.9199151 | 0.2515667 | 0.208515 | 0.12613171 | X98178_s_a MACH-beta-4 protein |
| 851 | Leukemia | 0.9197949 | 0.2514162 | 0.208497 | 0.12609671 | X80230_at mRNA (clone C-2k) mRNA for serine/threonine protein kinase |
| 852 | Leukemia | 0.9192909 | 0.2514091 | 0.208476 | 0.1260078 | U07802_at ERF-2 mRNA |
| 853 | Leukemia | 0.9192454 | 0.251401 | 0.208428 | 0.12593469 | HG4312-HT4582_s_at Transcription Factor IIa |
| 854 | Leukemia | 0.9189531 | 0.251372 | 0.208339 | 0.12589332 | X83218_at ATP5O ATP synthase, H+ transporting, mitochondrial F1 complex, O subunit (oligomycin sensitivity conferring protein) |
| 855 | Leukemia | 0.9188577 | 0.2513019 | 0.208312 | 0.12582584 | U47742_at Monocytic leukaemia zinc finger protein (MOZ) mRNA |
| 856 | Leukemia | 0.9187594 | 0.251271 | 0.208303 | 0.1257509 | X61970_at PROTEASOME ZETA CHAIN |
| 857 | Leukemia | 0.9183492 | 0.2512485 | 0.20829 | 0.12571183 | U54644_at TUB Tubby (mouse) homolog |
| 858 | Leukemia | 0.9181675 | 0.2510666 | 0.208235 | 0.12568446 | U37251_at ZNF177 KRAB zinc finger protein (alternative products) |
| 859 | Leukemia | 0.9181059 | 0.2510518 | 0.208206 | 0.12562774 | U51478_at Sodium/potassium-transporting ATPase beta-3 subunit mRNA |
| 860 | Leukemia | 0.917455 | 0.2510499 | 0.208184 | 0.12556652 | 270219_at 5'UTR for unknown protein (clone ICRFp507C0696) |
| 861 | Leukemia | 0.9174279 | 0.2510319 | 0.208161 | 0.12551421 | X96401_at ROX protein |
| 862 | Leukemia | 0.9173979 | 0.2510196 | 0.208133 | 0.12549268 | AA010933_s_at EST: ze23a09.r1 Soares fetal heart NbHH19W Homo sapiens cDNA clone 359800 5', mRNA sequence. (from Genbank) |
| 863 | Leukemia | 0.916873 | 0.2509506 | 0.208118 | 0.12541647 | X14085_s_a GGTB2 Glycoprotein-4-beta-galactosyltransferase 2 |

FIG. 5G2

| | | | | | |
|---|---|---|---|---|---|
| 864 | Leukemia | 0.9162998 | 0.2509272 | 0.1253755 | D50930_at | KIAA0140 gene |
| 865 | Leukemia | 0.9162563 | 0.2509267 | 0.1252812 | Y00097_s_at | ANX6 Annexin VI (p68) |
| 866 | Leukemia | 0.916611 | 0.2509249 | 0.12522379 | X57303_at | ERR Ecotropic retroviral receptor |
| 867 | Leukemia | 0.9159824 | 0.2509166 | 0.1251646 | X76732_at | DNA-BINDING PROTEIN NEFA PRECURSOR |
| 868 | Leukemia | 0.9156048 | 0.2508907 | 0.12511995 | M34079_at | PROBABLE 26S PROTEASE SUBUNIT TBP-1 |
| 869 | Leukemia | 0.9155746 | 0.2508762 | 0.12508899 | D50924_at | KIAA0134 gene |
| 870 | Leukemia | 0.9151861 | 0.2507992 | 0.12504318 | U73824_at | P97 mRNA |
| 871 | Leukemia | 0.9148254 | 0.2507789 | 0.12503134 | M37984_rna1_at | Slow twitch skeletal muscle/cardiac muscle troponin C gene |
| 872 | Leukemia | 0.9141761 | 0.2507533 | 0.1249382 | D21235_at | HHR23A protein |
| 873 | Leukemia | 0.9140734 | 0.2507013 | 0.12490247 | L12535_at | RSU-1/RSP-1 mRNA |
| 874 | Leukemia | 0.9134827 | 0.2506689 | 0.12485853 | AA129373_at | EST: zn84h08.r1 Stratagene lung carcinoma 937218 Homo sapiens cDNA clone 564927 5' similar to SW:RADI_HUMAN P35241 RADIXIN.; mRNA sequence. (from Genbank) |
| 875 | Leukemia | 0.9133811 | 0.2506634 | 0.12480323 | U43753_cds2_at | Frataxin (FRDA) gene, promoter region and |
| 876 | Leukemia | 0.9125423 | 0.2506206 | 0.12473374 | U01877_at | P300 protein mRNA |
| 877 | Leukemia | 0.9123278 | 0.250594 | 0.12465767 | U94585_at | Requiem homolog (hsReq) mRNA |
| 878 | Leukemia | 0.9120681 | 0.2505587 | 0.124619 | M73047_at | TPP2 Tripeptidyl peptidase II |
| 879 | Leukemia | 0.9120664 | 0.250536 | 0.12460999 | M90299_at | GCK Glucokinase (hexokinase 4, maturity onset diabetes of the young 2) |
| 880 | Leukemia | 0.9119291 | 0.2505176 | 0.12460559 | D83779_at | KIAA0195 gene |
| 881 | Leukemia | 0.9117222 | 0.2504415 | 0.12456699 | D86964_at | KIAA0209 gene, partial cds |
| 882 | Leukemia | 0.9116874 | 0.2504058 | 0.12445831 | X78924_at | HZF1 mRNA for zinc finger protein |
| 883 | Leukemia | 0.9115527 | 0.2503907 | 0.1244223 | M63904_at | GNA15 Guanine nucleotide binding protein (G protein), alpha 15 (Gq class) |
| 884 | Leukemia | 0.9114603 | 0.2503713 | 0.12435378 | X14675_at | Bcr-abl mRNA 5' fragment (clone 3c) |
| 885 | Leukemia | 0.9108548 | 0.2503697 | 0.12433449 | U44975_at | DNA-binding protein CPBP (CPBP) mRNA, partial cds |
| 886 | Leukemia | 0.9105541 | 0.2503389 | 0.1242954 | U52426_at | GOK (STIM1) mRNA |
| 887 | Leukemia | 0.9103949 | 0.2503051 | 0.1242269 | AA194091_s_at | EST: zr37a11.r1 Soares NhHMPu S1 Homo sapiens cDNA clone 665564 5', mRNA sequence. (from Genbank) |
| 888 | Leukemia | 0.9100632 | 0.2502275 | 0.12416199 | L49219_f_at | Retinoblastoma susceptibility protein (RB1) L486W 4 bp deletion mutant (resulting in premature stop at amino acid 490) gene, exon 16 (L11910 bases 76983-77136) |
| 889 | Leukemia | 0.909886 | 0.2502447 | 0.12411578 | U09414_at | ZNF137 Zinc finger protein 137 (clone pHZ-30) |
| 890 | Leukemia | 0.9090841 | 0.2502021 | 0.12407053 | M60284_s_at | Neurokinin A receptor (NK-2R) gene, exon 5 |
| 891 | Leukemia | 0.9090649 | 0.2501522 | 0.12396943 | U64444_at | Ubiquitin fusion-degradation protein (UFD1L) mRNA |
| 892 | Leukemia | 0.908672 | 0.2501059 | 0.12395518 | Y09443_at | Alkyl-dihydroxyacetonephosphate synthase precursor |

FIG. 5H2

| | | | | | | |
|---|---|---|---|---|---|---|
| 893 | Leukemia | 0.9085007 | 0.2500552 | 0.20701 | HG3255-HT3432_at | Gamma-Aminobutyric Acid (Gaba) A Receptor Beta 2 Subunit |
| 894 | Leukemia | 0.9083749 | 0.2500305 | 0.207008 | 0.12394436 RC_AA3571 89_at | EST: EST65883 Jurkat T-cells I Homo sapiens cDNA 3' end similar to arrestin, beta 2, mRNA sequence. (from Genbank) |
| 895 | Leukemia | 0.9083691 | 0.2499692 | 0.206897 | 0.123871215 | Clone 23947 mRNA, partial cds |
| 896 | Leukemia | 0.9078417 | 0.2499512 | 0.206861 | 0.123833939 U79275_at | AKT1 V-akt murine thymoma viral oncogene homolog 1 |
| 897 | Leukemia | 0.9070624 | 0.249745 | 0.206853 | 0.12380146 M63167_at | mRNA sequence (15q11-13) |
| 898 | Leukemia | 0.9066877 | 0.2497446 | 0.206845 | 0.123785995 X69636_at | Zinc-finger protein mRNA |
| 899 | Leukemia | 0.9066489 | 0.2496952 | 0.206832 | 0.123669334 U18543_at | Anti-mullerian hormone type II receptor precursor gene |
| 900 | Leukemia | 0.9065944 | 0.2496435 | 0.206811 | 0.123598896 U29700_at HG4114-HT4384_at | Olfactory Receptor Or17-209 |
| 901 | Leukemia | 0.9064214 | 0.2496424 | 0.206803 | 0.123566066 L19401_at | MYO5A Myosin VA (heavy polypeptide 12, myoxin) |
| 902 | Leukemia | 0.9062026 | 0.2496363 | 0.206775 | 0.123485933 Z30644_at | Chloride channel (putative) 2163bp |
| 903 | Leukemia | 0.9059651 | 0.2495985 | 0.206745 | 0.12342701 HG3725-HT3981_s_at | Insulin-Like Leydig Hormone |
| 904 | Leukemia | 0.9058428 | 0.2494001 | 0.206739 | U64661_rna | Human poly(A)-binding protein processed pseudogene3. (from Genbank) |
| 905 | Leukemia | 0.905811 | 0.2493704 | 0.206667 | 0.123403981_f_at 0.123305822 X69115_at | ZNF37A Zinc finger protein 37a (KOX 21) |
| 906 | Leukemia | 0.9051306 | 0.2492801 | 0.206647 | 0.123328922 HG919-HT919_at | Dna Polymerase, Epsilon, Catalytic Subunit |
| 907 | Leukemia | 0.9046862 | 0.2491589 | 0.206585 | 0.123227194 M84332_at | ARF1 ADP-ribosylation factor 1 |
| 908 | Leukemia | 0.9045205 | 0.2491176 | 0.206558 | 0.123319439 X07109_at | (clones lambda-hPKC-beta[15,802]) protein kinase C-beta-1 (PRKCB1) mRNA |
| 909 | Leukemia | 0.9044616 | 0.2491112 | 0.206507 | 0.123168916 L20010_at | HCF1 gene related mRNA sequence |
| 910 | Leukemia | 0.9044505 | 0.2490465 | 0.206445 | 0.123104403 Z35085_s_at | KIAA0203 gene |
| 911 | Leukemia | 0.9040746 | 0.2490419 | 0.206425 | 0.1230509 M29960_at | Steroid receptor (TR2-11) mRNA |
| 912 | Leukemia | 0.904036 | 0.2490419 | 0.206387 | 0.123002544 Z25884_at | ClC-1 muscle chloride channel protein |
| 913 | Leukemia | 0.9039833 | 0.2490404 | 0.206373 | 0.122962216 HG2917-HT3061_f_at | Major Histocompatibility Complex, Class I, E (Gb:M21533) |
| 914 | Leukemia | 0.9039499 | 0.2490275 | 0.206358 | 0.122293968 HG4557-HT4962_r_at | Small Nuclear Ribonucleoprotein U1, 1snrp |
| 915 | Leukemia | 0.9033574 | 0.2490068 | 0.206338 | 0.122292261 S81003_at | L-UBC |
| 916 | Leukemia | 0.9030672 | 0.2488888 | 0.206245 | 0.1228631 U16127_at | GRIK5 Glutamate receptor, ionotropic, kainate 5 |
| 917 | Leukemia | 0.9026195 | 0.2488687 | 0.206211 | 0.122841224 X13794_rna 1_at | Lactate dehydrogenase B gene exon 1 and 2 (EC 1.1.1.27) (and joined CDS) |
| 918 | Leukemia | 0.9026141 | 0.2487737 | 0.206191 | 0.122282235 X77094_at | P40phox |

FIG. 5I2

| # | Tissue | | | | Description |
|---|---|---|---|---|---|
| 919 | Leukemia | 0.9024842 | 0.2487425 | 0.12275525 X93499_at | RAB7 protein |
| 920 | Leukemia | 0.9024774 | 0.2487323 | 0.12266299 L06505_at | RPL12 Ribosomal protein L12 |
| 921 | Leukemia | 0.9020752 | 0.248686 | 0.12263145 X69654_at | RPS26 Ribosomal protein S26 |
| 922 | Leukemia | 0.9011635 | 0.2486772 | 0.122584395 D78361_at | Ornithine decarboxylase antizyme, ORF 1 and ORF 2 |
| 923 | Leukemia | 0.9011166 | 0.2486669 | 0.12254101 Y07683_at | P2X3 purinoceptor |
| 924 | Leukemia | 0.9010781 | 0.2486655 | 0.122518761 X15393_rna1_at | Motilin gene exon 2 (and joined CDS) |
| 925 | Leukemia | 0.9008008 | 0.2486445 | 0.12245452 M81829_at | Somatostatin receptor isoform 1 gene |
| 926 | Leukemia | 0.9003726 | 0.2486363 | 0.122392185 K02574_at | NP Nucleoside phosphorylase |
| 927 | Leukemia | 0.9003377 | 0.2486186 | 0.122306354 HG243-HT243_s_at | Lowe Oculocerebrorenal Syndrome Protein |
| 928 | Leukemia | 0.9002245 | 0.2485976 | AA455706_a t | EST: aa22d08.r1 NCI_CGAP_GCB1 Homo sapiens cDNA clone IMAGE:813999 5' similar to TR:G473407 G473407 NST-1.;, mRNA sequence. (from Genbank) |
| 929 | Leukemia | 0.899919 | 0.2485244 | 0.1222 U49395_at | Ionotropic ATP receptor P2X5a mRNA |
| 930 | Leukemia | 0.8998531 | 0.2485087 | 0.12218475 W27182_at | EST: 23d11 Human retina cDNA randomly primed sublibrary Homo sapiens cDNA, mRNA sequence. (from Genbank) |
| 931 | Leukemia | 0.8895121 | 0.2484315 | 0.12217356 X92098_at | Transmembrane protein rnp24 |
| 932 | Leukemia | 0.8986859 | 0.2484161 | 0.12210798 U01212_at | Olfactory marker protein (OMP) gene |
| 933 | Leukemia | 0.8986375 | 0.2483782 | 0.122053765 RC_AA2628 81_at | EST: zs26b03.s1 NCI_CGAP_GCB1 Homo sapiens cDNA clone IMAGE:686285 3' similar to contains Alu repetitive element;contains element MIR repetitive element.;, mRNA sequence. (from Genbank) |
| 934 | Leukemia | 0.8976372 | 0.2483499 | 0.122034065 HG2915-HT3059_f_at | Major Histocompatibility Complex, Class I, E (Gb:M20022) |
| 935 | Leukemia | 0.897563 | 0.2483039 | 0.122006361 X15673_s_a t | PTR2 mRNA for repetitive sequence |
| 936 | Leukemia | 0.8974713 | 0.2482811 | 0.121927254 RC_AA2869 11_at | EST: zs56d09.s1 NCI_CGAP_GCB1 Homo sapiens cDNA clone IMAGE:701489 3' similar to contains Alu repetitive element;, mRNA sequence. (from Genbank) |
| 937 | Leukemia | 0.8973967 | 0.248277 | 0.121908285 X92720_at | Phosphoenolpyruvate carboxykinase |
| 938 | Leukemia | 0.8972819 | 0.2482292 | 0.12183682 U11090_at | Hydroxyindole-O-methyltransferase promoter B-derived (HIOMT) mRNA |
| 939 | Leukemia | 0.8972813 | 0.2481745 | 0.12179965 AA455812_a t | Human transformer-2 alpha (htra-2 alpha) mRNA, complete cds |
| 940 | Leukemia | 0.8956457 | 0.2481677 | 0.12175766 D79205_at | Ribosomal protein L39 |
| 941 | Leukemia | 0.8952812 | 0.2481598 | 0.12173874 AA422160_a t | Nucleosome assembly protein 1-like 1 |

FIG. 5J2

| | | | | | |
|---|---|---|---|---|---|
| 942 | Leukemia | 0.8952051 | 0.2481435 | 0.205145 | 0.12165498 | RC_AA281478_at | EST: zs96i03.s1 NCI_CGAP_GCB1 Homo sapiens cDNA clone IMAGE:711485 3', mRNA sequence. (from Genbank) |
| 943 | Leukemia | 0.8950702 | 0.2480213 | 0.205083 | 0.12159608 | D49738_at | Cytoskeleton associated protein (CG22) mRNA |
| 944 | Leukemia | 0.8947564 | 0.2479769 | 0.205081 | 0.12154622 | AB003177_a_t | Proteasome subunit p27 |
| 945 | Leukemia | 0.8946782 | 0.2479715 | 0.205025 | 0.12150546 | M96082_at | SPLICING FACTOR U2AF 35 KD SUBUNIT |
| 946 | Leukemia | 0.8945187 | 0.2479644 | 0.205015 | 0.12145257 | U11791_at | CCNH Cyclin H |
| 947 | Leukemia | 0.8938792 | 0.2479413 | 0.204998 | 0.12140477 | U23143_at | Mitochondrial serine hydroxymethyltransferase gene, nuclear encoded mitochondrion protein |
| 948 | Leukemia | 0.8938088 | 0.2479376 | 0.204938 | 0.12134344 | D43949_at | KIAA0082 gene, partial cds |
| 949 | Leukemia | 0.8938009 | 0.2478486 | 0.204907 | 0.12130175 | D38145_at | Prostacyclin synthase |
| 950 | Leukemia | 0.893652 | 0.247844 | 0.204864 | 0.12127993 | U58032_at | Myotubularin related protein 1 (MTMR1) mRNA, partial cds |
| 951 | Leukemia | 0.8931956 | 0.2478319 | 0.204808 | 0.12124140 | U83246_at | Copine I mRNA |
| 952 | Leukemia | 0.893191 | 0.2478187 | 0.204665 | 0.12119114 | M63582_at | THYROLIBERIN PRECURSOR |
| 953 | Leukemia | 0.8930505 | 0.2478007 | 0.204653 | 0.12118194 | U67932_s_a_t | cAMP phosphodiesterase mRNA, 3' end |
| 954 | Leukemia | 0.8924748 | 0.2475665 | 0.204621 | 0.12111723 | M31520_rna41_s_at | Unknown protein gene extracted from Human ribosomal protein S24 mRNA |
| 955 | Leukemia | 0.8924127 | 0.2474866 | 0.204548 | 0.12107544 | U81802_at | Phosphatidylinositol 4-kinase |
| 956 | Leukemia | 0.8923035 | 0.2474573 | 0.204532 | 0.12104357 | M55150_at | FAH Fumarylacetoacetate |
| 957 | Leukemia | 0.8922968 | 0.2474407 | 0.204504 | 0.12102167 | X53793_at | MULTIFUNCTIONAL PROTEIN ADE2 |
| 958 | Leukemia | 0.8920471 | 0.247371 | 0.204501 | 0.12096786 | U58334_at | Bcl2, p53 binding protein Bbp/53BP2 (BBP/53BP2) mRNA |
| 959 | Leukemia | 0.8917607 | 0.2473075 | 0.204473 | 0.12094204 | U09607_at | JAK3 Janus kinase 3 (a protein tyrosine kinase, leukocyte) |
| 960 | Leukemia | 0.891744 | 0.2472879 | 0.204473 | 0.12092417 | AA247497_a_t | EST: csg3770.seq.F Human fetal heart, Lambda ZAP Express Homo sapiens cDNA 5', mRNA sequence. (from Genbank) |
| 961 | Leukemia | 0.8912273 | 0.2471743 | 0.204416 | 0.12086799 | D26599_at | Proteasome subunit HsC7-I |
| 962 | Leukemia | 0.8908304 | 0.247164 | 0.204407 | 0.12077982 | R84329_at | EST: yq23c06.r1 Soares retina N2b4HR Homo sapiens cDNA clone 274547 5' similar to SP:A44264 A44264 ALL-1=TRITHORAX HOMOLOG - HUMAN ;, mRNA sequence. (from Genbank) |
| 963 | Leukemia | 0.8904554 | 0.247153 | 0.204351 | 0.12073386 | AB002559_a_t | Hunc18b2 |
| 964 | Leukemia | 0.8899966 | 0.2470384 | 0.204282 | 0.12068668 | L37033_at | FK-506 binding protein homologue (FKBP38) mRNA |
| 965 | Leukemia | 0.8899022 | 0.2470313 | 0.204257 | 0.12064418 | U82275_s_a_t | Homo sapiens leucocyte immunoglobulin-like receptor-7 (LIR-7) mRNA, complete cds |
| 966 | Leukemia | 0.8898465 | 0.2470211 | 0.204217 | 0.12061267 | X56468_at | 14-3-3 PROTEIN TAU |
| 967 | Leukemia | 0.8897659 | 0.2469349 | 0.204202 | 0.12057196 | U09367_at | ZNF136 Zinc finger protein 136 (clone pHZ-20) |
| 968 | Leukemia | 0.8896914 | 0.246684 | 0.204057 | 0.12051495 | D00762_at | PROTEASOME COMPONENT C8 |
| 969 | Leukemia | 0.8895212 | 0.2468418 | 0.204041 | 0.1204946 | D85376_at | TRHR Thyrotropin-releasing hormone receptor |

FIG. 5K2

| # | Type | | | | | Description |
|---|---|---|---|---|---|---|
| 970 | Leukemia | 0.8883051 | 0.2467485 | 0.203998 | 0.120472044 | D13720_s_at TYROSINE-PROTEIN KINASE ITK/TSK |
| 971 | Leukemia | 0.887951 | 0.2466843 | 0.203982 | 0.12043469 | M94880_f_at HLA-A MHC class I protein HLA-A (HLA-A28,-B40,-Cw3) |
| 972 | Leukemia | 0.8871638 | 0.2466339 | 0.20398 | 0.12039278 | U02632_at Calcium-activated potassium channel mRNA, partial cds |
| 973 | Leukemia | 0.8865705 | 0.2465873 | 0.203948 | 0.120345 | M34667_at PLCG1 Phospholipase C, gamma 1 (formerly subtype 148) |
| 974 | Leukemia | 0.8857626 | 0.2465504 | 0.203894 | 0.12031882 | M22638_at LYL-1 protein gene |
| 975 | Leukemia | 0.8853456 | 0.2465305 | 0.203789 | 0.12025077 | RC_AA4653 42_at EST: aa23a09.s1 NCI_CGAP_GCB1 Homo sapiens cDNA clone IMAGE:814072 3', mRNA sequence. (from Genbank) |
| 976 | Leukemia | 0.8847793 | 0.2465275 | 0.203749 | 0.120215066 | L15189_s_at MITOCHONDRIAL STRESS-70 PROTEIN PRECURSOR |
| 977 | Leukemia | 0.8847271 | 0.2465051 | 0.203659 | 0.12017999 | D49824_s_a t HLA-B null allele mRNA |
| 978 | Leukemia | 0.8843932 | 0.2464889 | 0.203648 | 0.120152734 | HG2715-HT2811_at Tyrosine Kinase (Gb:Z25437) |
| 979 | Leukemia | 0.8842357 | 0.2464766 | 0.203593 | 0.12012257 | M60750_f_at Histone H2B.1 (H2B) gene |
| 980 | Leukemia | 0.8840365 | 0.2464487 | 0.203545 | 0.12006155 | X69433_at IDH2 Isocitrate dehydrogenase 2 (NADP+), mitochondrial |
| 981 | Leukemia | 0.8836122 | 0.2464101 | 0.203503 | 0.12003669 | U73379_at Cyclin-selective ubiquitin carrier protein mRNA |
| 982 | Leukemia | 0.8835117 | 0.2462968 | 0.2035 | 0.11999413 | X70040_at MST1R Protein-tyrosine kinase RON |
| 983 | Leukemia | 0.8833022 | 0.2461633 | 0.203456 | 0.11991956 | RC_AA4787 81_at EST: zv20c01.s1 Soares NhHMPu S1 Homo sapiens cDNA clone 754176 3' similar to WP:ZK546.2 CE07632 ADENYLATE CYCLASE.; mRNA sequence. (from Genbank) |
| 984 | Leukemia | 0.8822857 | 0.2460937 | 0.203434 | 0.11987577 | U59878_at Low-Mr GTP-binding protein (RAB32) mRNA, partial cds |
| 985 | Leukemia | 0.8821642 | 0.24607 | 0.203419 | 0.11983562 | M14328_s_a t ENO1 Enolase 1, (alpha) |
| 986 | Leukemia | 0.8820331 | 0.2460543 | 0.203318 | 0.11981014 | RC_AA4364 73_s_at EST: zv08e08.s1 Soares NhHMPu S1 Homo sapiens cDNA clone 753062 3', mRNA sequence. (from Genbank) |
| 987 | Leukemia | 0.8820094 | 0.2460309 | 0.203298 | 0.11976837 | M15465_s_a t PKLR Pyruvate kinase, liver |
| 988 | Leukemia | 0.8817014 | 0.2460168 | 0.203272 | 0.119759604 | X89267_at UROD Uroporphyrinogen decarboxylase |
| 989 | Leukemia | 0.8817 | 0.2460154 | 0.2032 | 0.11970311 | Z35102_at Ndr protein kinase |
| 990 | Leukemia | 0.8812661 | 0.2459939 | 0.203158 | 0.11967517 | L35035_at Ribose 5-phosphate isomerase (RPI) mRNA |
| 991 | Leukemia | 0.8810147 | 0.2459908 | 0.203149 | 0.11962340 | S54005_s_at THYMOSIN BETA-10 |
| 992 | Leukemia | 0.8809319 | 0.2459807 | 0.203117 | 0.119620466 | U44839_at Putative ubiquitin C-terminal hydrolase (UHX1) mRNA |
| 993 | Leukemia | 0.8808945 | 0.2459711 | 0.203058 | 0.11957671 | X92521_at Clone rasi-1 matrix metalloproteinase RASI-1 mRNA |
| 994 | Leukemia | 0.8808035 | 0.2459466 | 0.203051 | 0.11950822 | U20428_at SNC19 mRNA sequence |
| 995 | Leukemia | 0.8806957 | 0.245915 | 0.202959 | 0.11945892 | D86963_at PTB Ribosomal protein L26 |
| 996 | Leukemia | 0.8805698 | 0.2459047 | 0.202943 | 0.119402386 | Y08612_at RABAPTIN-5 protein |

FIG. 5J.2

| | | | | | |
|---|---|---|---|---|---|
| 997 | Leukemia | 0.8804677 | 0.2458731 | 0.202934 | 0.11938382 | D10995_at | Serotonin 1B receptor |
| 998 | Leukemia | 0.8800616 | 0.2458545 | 0.202911 | 0.11930436 | M69039_at | PRE-MRNA SPLICING FACTOR SF2, P32 SUBUNIT PRECURSOR |
| 999 | Leukemia | 0.879728 | 0.2457946 | 0.202783 | 0.119274154 | AA247450_at | EST: csg2873.seq,F Human fetal heart, Lambda ZAP Express Homo sapiens cDNA 5', mRNA sequence. (from Genbank) |
| 1000 | Leukemia | 0.879577 | 0.2457878 | 0.202777 | 0.119230516 | HG945-HT945_s_at | Nucleic Acid-Binding Protein (Gb:L12693) |

FIG. 5M2

| # | | | | | | |
|---|---|---|---|---|---|---|
| 1 | Lung | 0.9519866 | | | 0.469326471 | M68519_rna1_at | Pulmonary surfactant-associated protein SP-A (SFTP1) gene |
| 2 | Lung | 0.7843286 | 0.6722338 | 0.623983 | 0.43865538 | J03890_rna1_at | SP-C1 gene (pulmonary surfactant protein SP-C) extracted from Human pulmonary surfactant protein C (SP-C) and pulmonary surfactant protein C1 (SP-C1) genes |
| 3 | Lung | 0.7770512 | 0.6453148 | 0.575029 | 0.422221874 | M24461_at | PULMONARY SURFACTANT-ASSOCIATED PROTEIN B PRECURSOR |
| 4 | Lung | 0.70441 | 0.6270386 | 0.555386 | 0.411103396 | M30838_at | PULMONARY SURFACTANT-ASSOCIATED PROTEIN A PRECURSOR |
| 5 | Lung | 0.5994884 | 0.6157392 | 0.543154 | 0.4015687 | RC_AA5211 95_at | EST: aa74c01.s1 NCI_CGAP_GCB1 Homo sapiens cDNA clone IMAGE:826656 3', mRNA sequence. (from Genbank) |
| 6 | Lung | 0.5743588 | 0.6103535 | 0.534078 | 0.395522386 | W36279_at | EST: HFBEST-56 Human fetal brain QBoqin2 Homo sapiens cDNA, mRNA sequence. (from Genbank) |
| 7 | Lung | 0.5524321 | 0.6019864 | 0.526218 | 0.388435218 | RC_AA4602 57_at | EST: zx67d07.s1 Soares total fetus Nb2HF8 9w Homo sapiens cDNA clone 796525 3', mRNA sequence. (from Genbank) |
| 8 | Lung | 0.5518032 | 0.5969788 | 0.521174 | 0.383850049 | M34516_at | Omega light chain protein 14.1 (Ig lambda chain related) gene, exon 3 |
| 9 | Lung | 0.5428825 | 0.5915497 | 0.515836 | 0.379284081 | M34516_r_at | Omega light chain protein 14.1 (Ig lambda chain related) gene, exon 3 |
| 10 | Lung | 0.5341072 | 0.5888677 | 0.510164 | 0.375525790_f_at | RC_AA4868 90_f_at | EST: ab17g09.s1 Stratagene lung (#937210) Homo sapiens cDNA clone 841120 3' similar to contains LTR7.b2 LTR7 repetitive element ;, mRNA sequence. (from Genbank) |
| 11 | Lung | 0.5240091 | 0.5847114 | 0.506043 | 0.371629061 | S71043_rna 1_s_at | Ig alpha 2=immunoglobulin A heavy chain allotype 2 {constant region, germ line} [human, peripheral blood neutrophils, Genomic, 1799 nt] |
| 12 | Lung | 0.4905479 | 0.5814767 | 0.501227 | 0.368662181 | RC_D60670 _at | EST: Human fetal brain cDNA 3'-end GEN-124C08, mRNA sequence. (from Genbank) |
| 13 | Lung | 0.4863556 | 0.5791841 | 0.499201 | 0.365805771 | V00563_at | Immunoglobulin mu, part of exon 8 |
| 14 | Lung | 0.4858377 | 0.5730248 | 0.495004 | 0.362679031 | AA197134_a_at | EST: zq11b11.r1 Stratagene muscle 937209 Homo sapiens cDNA clone 629373 5', mRNA sequence. (from Genbank) |
| 15 | Lung | 0.4805647 | 0.5705465 | 0.489537 | 0.359583111 | M87789_s_a_t | Ig (hybridoma H210) anti-hepatitis A IgG variable region, constant region, complementarity-determining regions mRNA |

FIG. 6A

| # | Tissue | | | | ID | Description |
|---|---|---|---|---|---|---|
| 16 | Lung | 0.4702581 | 0.5673447 | 0.486664 | RC_AA1007 19_s_at | Non-specific cross reacting antigen |
| 17 | Lung | 0.4672205 | 0.5657846 | 0.48479 | 0.3572573 X02419_rna1_s_at | UPA gene |
| 18 | Lung | 0.4516379 | 0.563507 | 0.482806 | 0.3546987 Z48475_at | GCKR Glucokinase regulator |
| 19 | Lung | 0.4516379 | 0.5620012 | 0.480666 | 0.3525911 0.35044992 Z48475_at-2 | Glucokinase (hexokinase 4) regulatory protein |
| 20 | Lung | 0.4462894 | 0.5588728 | 0.477576 | RC_AA0102 0.34818494 11_at | EST: zi08f07.s1 Soares fetal liver spleen 1NFLS S1 Homo sapiens cDNA clone 430213 3', mRNA sequence. (from Genbank) |
| 21 | Lung | 0.4449928 | 0.5572204 | 0.476154 | U43203_s_a 0.34659567 t | TTF1 Transcription termination factor, RNA polymerase I |
| 22 | Lung | 0.4406842 | 0.5546945 | 0.474644 | 0.34489632 AA479567_a t | EST: zu42b02.r1 Soares ovary tumor NbHOT Homo sapiens cDNA clone 740619 5', mRNA sequence. (from Genbank) |
| 23 | Lung | 0.4359149 | 0.5527822 | 0.472729 | 0.3429253 AA470056_a t | EST: zt94g06.r1 Soares testis NHT Homo sapiens cDNA clone 730042 5', mRNA sequence. (from Genbank) |
| 24 | Lung | 0.4341773 | 0.550931 | 0.470869 | RC_AA1215 0.34167862 43_at | Homo sapiens mRNA for KIAA0758 protein, partial cds |
| 25 | Lung | 0.4233249 | 0.5500904 | 0.46862 | RC_AA2333 0.34006745 22_at | EST: zr69h06.s1 Soares NhHMPu S1 Homo sapiens cDNA clone 668699 3', mRNA sequence. (from Genbank) |
| 26 | Lung | 0.4227949 | 0.54962 | 0.467713 | 0.33858126 M24283_at | ICAM1 Intercellular adhesion molecule 1 (CD54), human rhinovirus receptor |
| 27 | Lung | 0.4223579 | 0.5486178 | 0.46604 | HG2755- 0.33672774 HT2862_at | T-Plastin |
| 28 | Lung | 0.4220618 | 0.5476252 | 0.464088 | 0.33349742 W69970_at | EST: zu52f04.r1 Soares fetal heart NbHH19W Homo sapiens cDNA clone 344287 5', mRNA sequence. (from Genbank) |
| 29 | Lung | 0.4215533 | 0.5470738 | 0.462975 | 0.33381 AA495729_a 11 t | EST: zw04a10.r1 Soares NhHMPu S1 Homo sapiens cDNA clone 768282 5', mRNA sequence. (from Genbank) |
| 30 | Lung | 0.4206589 | 0.5458446 | 0.461234 | 0.33233383 U52153_at | Inwardly rectifying potassium channel Kir3.2 mRNA |
| 31 | Lung | 0.4203652 | 0.5446066 | 0.460066 | RC_AA0558 0.33100665 41_at | EST: zf20c08.s1 Soares fetal heart NbHH19W Homo sapiens cDNA clone 377486 3', mRNA sequence. (from Genbank) |
| 32 | Lung | 0.4199409 | 0.543772 | 0.458873 | M63438_s_a 0.32952955 t | GLUL Glutamate-ammonia ligase (glutamine synthase) |
| 33 | Lung | 0.4194065 | 0.5382584 | 0.457402 | 0.32864657 N94824_at | Homo sapiens Chromosome 16 BAC clone CIT987SK-A-67A1 |
| 34 | Lung | 0.4181941 | 0.53775 | 0.456676 | M29873_s_a 0.32748097 t | Human cytochrome P450-IIB (hIIB3) mRNA, complete cds |
| 35 | Lung | 0.4126502 | 0.5359457 | 0.455358 | RC_AA1668 0.32613403 38_at | EST: zq39h04.s1 Stratagene hNT neuron (#937233) Homo sapiens cDNA clone 632119 3' similar to contains Alu repetitive element;contains element MSR1 repetitive element ;, mRNA sequence. (from Genbank) |
| 36 | Lung | 0.4124332 | 0.5346007 | 0.453866 | 0.32512194 J00231_f_at | Immunoglobulin gamma 3 (Gm marker) |

FIG. 6B

| | | | | | |
|---|---|---|---|---|---|
| 37 | Lung | 0.4114928 | 0.5323453 | 0.452733 | 0.32375416 | U78735_at | ABC3 ATP-binding cassette 3 |
| 38 | Lung | 0.4040549 | 0.5316177 | 0.451402 | 0.3226801 | R29657_at | Eukaryotic translation elongation factor 1 delta (guanine nucleotide exchange protein) |
| 39 | Lung | 0.4038739 | 0.5313253 | 0.449812 | 0.3217235 | AA249437_a t | EST: j3966.seq.F Human fetal heart, Lambda ZAP Express Homo sapiens cDNA 5', mRNA sequence. (from Genbank) |
| 40 | Lung | 0.3929638 | 0.529942 | 0.449059 | 0.32088184 | HG2809-HT2920_s_a t | Lung Surfactant Protein D |
| 41 | Lung | 0.3905684 | 0.5297486 | 0.448258 | 0.31966977 | R53717_at | EST: yi02e03.r1 Homo sapiens cDNA clone 138076 5'. (from Genbank) |
| 42 | Lung | 0.3883479 | 0.5291454 | 0.447251 | 0.31863177 | RC_AA4417 91_at | EST: zw62c02.s1 Soares total fetus Nb2HF8 9w Homo sapiens cDNA clone 774626 3', mRNA sequence. (from Genbank) |
| 43 | Lung | 0.3872517 | 0.5283682 | 0.44688 | 0.31748506 | AA410925_a t | EST: zv39e11.r1 Soares ovary tumor NbHOT Homo sapiens cDNA clone 756044 5' similar to gb:M99435 TRANSDUCIN-LIKE ENHANCER PROTEIN 1 (HUMAN);. mRNA sequence. (from Genbank) |
| 44 | Lung | 0.3841993 | 0.5267935 | 0.446479 | 0.3165925 | W28151_at | EST: 43f5 Human retina cDNA randomly primed sublibrary Homo sapiens cDNA, mRNA sequence. (from Genbank) |
| 45 | Lung | 0.38344 | 0.5267584 | 0.445467 | 0.31577778 | U05861_at | DDH1 Dihydrodiol dehydrogenase |
| 46 | Lung | 0.3819989 | 0.5253698 | 0.444204 | 0.31499106 | M10014_cds 1_at | Fibrinogen gamma chain and gamma-prime chain genes |
| 47 | Lung | 0.381848 | 0.5251259 | 0.443824 | 0.3141115 | AA075427_a t | EST: zm87a05.r1 Stratagene ovarian cancer (#937219) Homo sapiens cDNA clone 544880 5', mRNA sequence. (from Genbank) |
| 48 | Lung | 0.3791217 | 0.524534 | 0.443207 | 0.31338766 | M28874_s_a t | CYP2B6 Cytochrome P450, subfamily IIB (phenobarbital-inducible), polypeptide 6 |
| 49 | Lung | 0.3786208 | 0.5232443 | 0.441875 | 0.3125411 | M20778_s_a t | Homo sapien, alpha-3 (VI) collagen |
| 50 | Lung | 0.3782215 | 0.5219135 | 0.441396 | 0.31187356 | M11313_s_a t | A2M Alpha-2-macroglobulin |
| 51 | Lung | 0.3763703 | 0.5215501 | 0.440206 | 0.3109486 | AA447811_a t | Regulator of G-protein signalling 16 |
| 52 | Lung | 0.375766 | 0.5213429 | 0.439549 | 0.31013918 | X16349_s_a t | Sex hormone-binding globulin |
| 53 | Lung | 0.3726443 | 0.5211844 | 0.43922 | 0.30944195 | AA282327_a t | EST: zt12c07.r1 NCI_CGAP_GCB1 Homo sapiens cDNA clone IMAGE:712908 5', mRNA sequence. (from Genbank) |
| 54 | Lung | 0.3725365 | 0.5204216 | 0.438463 | 0.30875623 | AA329542_a t | EST: EST33182 Embryo, 12 week II Homo sapiens cDNA 5' end, mRNA sequence. (from Genbank) |
| 55 | Lung | 0.3704493 | 0.5193016 | 0.437929 | 0.30792156 | X80062_at-2 | Human SA mRNA for SA gene product, complete cds |
| 56 | Lung | 0.3704493 | 0.5187517 | 0.437446 | 0.30730021 | X80062_at | SA mRNA |

FIG. 6C

| # | Tissue | | | | ID | Description |
|---|---|---|---|---|---|---|
| 57 | Lung | 0.3685979 | 0.5173218 | 0.436855 | 0.30647877 | D10216_s_at | POU domain, class 1, transcription factor 1 (Pit1, growth hormone factor 1) |
| 58 | Lung | 0.3647298 | 0.5162718 | 0.436384 | 0.30571705 | M93221_at | M6PR Mannose receptor |
| 59 | Lung | 0.3634779 | 0.5160826 | 0.434849 | 0.305072781 | AA122302_a t | EST: zk97d12.r1 Soares pregnant uterus NbHPU Homo sapiens cDNA clone 490775 5' similar to gb:L32179 Human arylacetamide deacetylase mRNA, complete cds. (HUMAN);, mRNA sequence. (from Genbank) |
| 60 | Lung | 0.3618056 | 0.5157224 | 0.434509 | 0.30417424 | AA206236_a t | Zq54c06.r1 Stratagene neuroepithelium (#937231) Homo sapiens cDNA clone 645418 5' similar to TR:G1229022 G1229022 ALLOGRAFT INFLAMMATORY FACTOR-1.;, mRNA sequence. (from Genbank) |
| 61 | Lung | 0.3602638 | 0.5155481 | 0.433437 | 0.30350277 | AA419502_a t | EST: zv03b02.r1 Soares NhHMPu S1 Homo sapiens cDNA clone 752523 5', mRNA sequence. (from Genbank) |
| 62 | Lung | 0.3599641 | 0.5151172 | 0.432445 | 0.30296737 | D82675_at | EST: similar to none, mRNA sequence. (from Genbank) |
| 63 | Lung | 0.3595377 | 0.5140513 | 0.43226 | 0.302277515 | X81832_s_a t | GIPR Gastric inhibitory polypeptide receptor |
| 64 | Lung | 0.3595038 | 0.513129 | 0.431413 | 0.301771113 | RC_AA0106 17_at | EST: zt09f12.s1 Soares fetal liver spleen 1NFLS S1 Homo sapiens cDNA clone 430319 3', mRNA sequence. (from Genbank) |
| 65 | Lung | 0.3559342 | 0.5122271 | 0.430571 | 0.30128786 | U01102_at | UGB Uteroglobin |
| 66 | Lung | 0.3551648 | 0.5118072 | 0.429952 | 0.3006298 | L38025_at | CNTFR Ciliary neurotrophic factor receptor |
| 67 | Lung | 0.3545549 | 0.5115729 | 0.429614 | 0.3000475 | Y09858_at-2 | H.sapiens mRNA for unknown protein. (from Genbank) |
| 68 | Lung | 0.3545549 | 0.5113397 | 0.429585 | 0.2995665 | Y09858_at | Unknown protein |
| 69 | Lung | 0.3529823 | 0.5100895 | 0.429083 | 0.2991551 | X98330_at-2 | RYR2 Ryanodine receptor 2 (cardiac) |
| 70 | Lung | 0.3529823 | 0.5099303 | 0.428567 | 0.29860464 | X98330_at | RYR2 Ryanodine receptor 2 (cardiac) |
| 71 | Lung | 0.3496571 | 0.5090852 | 0.428254 | 0.29803205 | U21128_at | LUM Lumican |
| 72 | Lung | 0.3483737 | 0.5089282 | 0.427949 | 0.2975029 | X87159_at | Beta subunit of epithelial amiloride-sensitive sodium channel |
| 73 | Lung | 0.3478406 | 0.5087081 | 0.427465 | 0.296093455 | RC_AA4781 12_at | EST: zt89e03.s1 Soares testis NHT Homo sapiens cDNA clone 729532 3', mRNA sequence. (from Genbank) |
| 74 | Lung | 0.3472209 | 0.5081029 | 0.426163 | 0.296325451 | AB002328_a t | Human mRNA for KIAA0330 gene, partial cds. (from Genbank) |
| 75 | Lung | 0.3460515 | 0.5066884 | 0.425931 | 0.295752611 | HG3242-HT4231_s_a t | Calcium Channel, Voltage-Gated, Alpha 1e Subunit, Alt. Splice 3 |
| 76 | Lung | 0.3454287 | 0.506658 | 0.425813 | 0.29526493 | D17793_at | DDH1 Dihydrodiol dehydrogenase |
| 77 | Lung | 0.3416797 | 0.5061578 | 0.425146 | 0.294682 | U17077_at | BENE mRNA, partial cds |
| 78 | Lung | 0.3394485 | 0.5054468 | 0.425012 | 0.29430637 | W16804_at | NCK adaptor protein 1 |
| 79 | Lung | 0.3377888 | 0.5051784 | 0.423829 | 0.29379308 | AA046840_a t | CCAAT/enhancer binding protein (C/EBP), delta |

FIG. 6D

| | | | | | |
|---|---|---|---|---|---|
| 80 | Lung | 0.337722 | 0.5046392 | 0.423658 | 0.29332182 | U25041_at | 5C5 mRNA, putative complete cds |
| 81 | Lung | 0.337722 | 0.5041449 | 0.423195 | 0.2927943 | U25041_at-2 | Ribosomal protein, mitochondrial, L12 |
| 82 | Lung | 0.3370443 | 0.5037944 | 0.42275 | 0.29232162 | X76342_at | ADH7 Alcohol dehydrogenase 7 sigma subunit (class IV) |
| 83 | Lung | 0.3366936 | 0.5035952 | 0.422723 | 0.29176375 | AA411756_a_t | EST: zv11b06.r1 Soares Nhl-HMPu S1 Homo sapiens cDNA clone 753299 5', mRNA sequence. (from Genbank) |
| 84 | Lung | 0.3350614 | 0.5032396 | 0.42207 | 0.291327924 | RC_AA4537_at | EST: aa19f07.s1 Soares Nhl-HMPu S1 Homo sapiens cDNA clone 813733 3', mRNA sequence. (from Genbank) |
| 85 | Lung | 0.3310624 | 0.5027466 | 0.421176 | 0.29098588 | L09708_at | C2 Complement component C2 |
| 86 | Lung | 0.3308455 | 0.5016013 | 0.420608 | 0.29039747 | D10925_at | CMKBR1 Chemokine (C-C) receptor 1 |
| 87 | Lung | 0.3299923 | 0.5009126 | 0.420179 | 0.28996912 | D13666_s_a_t | Osteoblast specific factor 2 (OSF-2os) |
| 88 | Lung | 0.3295958 | 0.5008838 | 0.419688 | 0.28965738 | U43944_at | MALATE OXIDOREDUCTASE |
| 89 | Lung | 0.3281576 | 0.5007371 | 0.419574 | 0.2890436 | AB000221_a_t | Small inducible cytokine subfamily A (Cys-Cys), member 18, pulmonary and activation-regulated |
| 90 | Lung | 0.3276698 | 0.5007095 | 0.419325 | 0.2885606 | U46767_at | Monocyte chemoattractant protein-4 precursor (MCP-4) mRNA |
| 91 | Lung | 0.3271097 | 0.5006619 | 0.419012 | 0.28807667 | W73544_at | Ribosomal protein S29 |
| 92 | Lung | 0.3245924 | 0.499564 | 0.418708 | 0.28771874 | W67675_at | EST: zd37c12.r1 Soares fetal heart NbHH19W Homo sapiens cDNA clone 342838 5', mRNA sequence. (from Genbank) |
| 93 | Lung | 0.323945 | 0.4990037 | 0.418117 | 0.28740541 | RC_AA4539_97_at | EST: zx46a12.s1 Soares testis NHT Homo sapiens cDNA clone 795262 3', mRNA sequence. (from Genbank) |
| 94 | Lung | 0.3238139 | 0.4987492 | 0.417838 | 0.28704917 | AA461426_r_at | EST: zx63h02.s1 Soares total fetus Nb2HF8 9w Homo sapiens cDNA clone 796179 5', mRNA sequence. (from Genbank) |
| 95 | Lung | 0.323352 | 0.4984739 | 0.417477 | 0.2865247 | L13286_at | Mitochondrial 1,25-dihydroxyvitamin D3 24-hydroxylase mRNA |
| 96 | Lung | 0.3228559 | 0.4976095 | 0.416854 | 0.286220550_9_at | RC_AA0098 | EST: zi04g05.s1 Soares fetal liver spleen 1NFLS S1 Homo sapiens cDNA clone 429848 3', mRNA sequence. (from Genbank) |
| 97 | Lung | 0.3203585 | 0.4973751 | 0.416236 | 0.2857988 | AA479826_a_t | Solute carrier family 16 (monocarboxylic acid transporters), member 3 |
| 98 | Lung | 0.3191871 | 0.4964509 | 0.416063 | 0.285523868 | RC_AA0555_60_r_at | EST: zf21f02.s1 Soares fetal heart NbHH19W Homo sapiens cDNA clone 377595 3', mRNA sequence. (from Genbank) |
| 99 | Lung | 0.3191325 | 0.4959161 | 0.41583 | 0.28482866 | L48516_at | Paraoxonase 3 (PON3) mRNA, 3' end of cds |
| 100 | Lung | 0.3189789 | 0.4948879 | 0.415777 | 0.284589772 | RC_AA4305_at | Proline-rich Gla (G-carboxyglutamic acid) polypeptide 2 |
| 101 | Lung | 0.3187366 | 0.4935881 | 0.41495 | 0.28418133 | RC_AA2806_87_at | EST: zs95h08.s1 NCI_CGAP_GCB1 Homo sapiens cDNA clone IMAGE:705279 3', mRNA sequence. (from Genbank) |
| 102 | Lung | 0.3185722 | 0.4923228 | 0.414412 | 0.2838734 | AA227621_a_t | EST: zr57e11.r1 Soares Nhl-HMPu S1 Homo sapiens cDNA clone 667532 5', mRNA sequence. (from Genbank) |
| 103 | Lung | 0.3164977 | 0.4920196 | 0.414252 | 0.28347975 | RC_D20888_at | EST: Human HL60 3'directed Mbol cDNA, HUMGS01869, clone mp0836, mRNA sequence. (from Genbank) |

FIG. 6E

| # | Tissue | | | | | Description |
|---|---|---|---|---|---|---|
| 104 | Lung | 0.3163303 | 0.4917606 | 0.413722 | 0.283173362 RC_AA2561 53_at | EST: zr79a09.s1 Soares NhHMPu S1 Homo sapiens cDNA clone 681880 3', mRNA sequence. (from Genbank) |
| 105 | Lung | 0.3162777 | 0.4915778 | 0.413415 | 0.282917962 X52773_at | RXRA Retinoid X receptor, alpha |
| 106 | Lung | 0.3162777 | 0.4912373 | 0.413415 | 0.282432288 X52773_at-2 | Retinoid X receptor, alpha |
| 107 | Lung | 0.3148296 | 0.4909871 | 0.413058 | 0.282022888 M59499_at | TISSUE FACTOR PATHWAY INHIBITOR PRECURSOR |
| 108 | Lung | 0.3135461 | 0.4905869 | 0.412112 | 0.281646136 RC_AA4914 66_at | EST: ab04a05.s1 Stratagene fetal retina 937202 Homo sapiens cDNA clone 839792 3', mRNA sequence. (from Genbank) |
| 109 | Lung | 0.3131494 | 0.4901651 | 0.411985 | 0.281385547 RC_AA4257 3_at | EST: zw47g09.s1 Soares total fetus Nb2HF8 9w Homo sapiens cDNA clone 773248 3', mRNA sequence. (from Genbank) |
| 110 | Lung | 0.311157 | 0.4901148 | 0.411572 | 0.28100762 HG2614-HT2710_at | Collagen, Type Viii, Alpha 1 |
| 111 | Lung | 0.3114029 | 0.4900665 | 0.411247 | 0.280655530 RC_AA1484 s_at | Flavin containing monooxygenase 5 |
| 112 | Lung | 0.3118804 | 0.4891412 | 0.410739 | 0.280394000 RC_AA0400_at | EST: zk46c08.s1 Soares pregnant uterus NbHPU Homo sapiens cDNA clone 485870 3', mRNA sequence. (from Genbank) |
| 113 | Lung | 0.3110718 | 0.4890689 | 0.409566 | 0.280084977 W28035_at | EST: 41a8 Human retina cDNA randomly primed sublibrary Homo sapiens cDNA, mRNA sequence. (from Genbank) |
| 114 | Lung | 0.3106906 | 0.488937 | 0.408829 | 0.279488157 M74542_at | ALDH3 Aldehyde dehydrogenase 3 |
| 115 | Lung | 0.3106895 | 0.4885725 | 0.408537 | 0.279228729 RC_AA4304 96_r_at | Ferritin, light polypeptide |
| 116 | Lung | 0.3102291 | 0.4885174 | 0.408111 | 0.278847460 RC_AA6208 89_at | EST: af95g10.s1 Soares testis NHT Homo sapiens cDNA clone 1055586 3', mRNA sequence. (from Genbank) |
| 117 | Lung | 0.3101891 | 0.4883973 | 0.407751 | 0.278600781 W25781_at | Homo sapiens clone 23698 mRNA sequence |
| 118 | Lung | 0.3093511 | 0.4877547 | 0.407374 | 0.27821991 RC_AA0355 14_at | EST: zk26b02.s1 Soares pregnant uterus NbHPU Homo sapiens cDNA clone 471627 3', mRNA sequence. (from Genbank) |
| 119 | Lung | 0.3090108 | 0.487529 | 0.407007 | 0.278063369 RC_AA3473 3_at | EST: EST53685 Fetal heart II Homo sapiens cDNA 3' end, mRNA sequence. (from Genbank) |
| 120 | Lung | 0.3083132 | 0.4872079 | 0.406611 | 0.277772397 Y09267_at | Flavin-containing monooxygenase 2 |
| 121 | Lung | 0.308141 | 0.4869405 | 0.406687 | 0.277434350 U66674_at | Canicular multispecific organic anion transporter |
| 122 | Lung | 0.3077937 | 0.486472 | 0.40635 | 0.277073861 AA448101_a_t | EST: zw82c11.r1 Soares testis NHT Homo sapiens cDNA clone 702708 5' similar to SW:A412_PLAFA P15847 41-2 PROTEIN ANTIGEN PRECURSOR.; mRNA sequence. (from Genbank) |
| 123 | Lung | 0.3073474 | 0.4859758 | 0.405686 | 0.276710630 D50550_at | LLGL mRNA |
| 124 | Lung | 0.3072634 | 0.4856305 | 0.405303 | 0.276269266 AA043894_a_t | EST: zk57b05.r1 Soares pregnant uterus NbHPU Homo sapiens cDNA clone 486897 5', mRNA sequence. (from Genbank) |
| 125 | Lung | 0.3069983 | 0.4848718 | 0.404571 | 0.275880493 RC_AA2628 87_at | EST: zs26b12.s1 NCI_CGAP_GCB1 Homo sapiens cDNA clone IMAGE:6863033 3' similar to contains Alu repetitive element; mRNA sequence. (from Genbank) |
| 126 | Lung | 0.3066799 | 0.4848718 | 0.404176 | 0.275552160 U93868_at | Human RNA polymerase III subunit (RPC32) mRNA, complete cds |

| | | | | | |
|---|---|---|---|---|---|
| 127 | Lung | 0.3065006 | 0.4846845 | 0.403754 | 0.27539155 | H46074_at | EST: yo13f07.r1 Homo sapiens cDNA clone 177829 5'. (from Genbank) |
| 128 | Lung | 0.3056957 | 0.4841858 | 0.403345 | 0.27508694 | L44574_at | EST: Homo sapiens thymus mRNA (randomly primed, normalized), single-pass sequence, mRNA sequence. (from Genbank) |
| 129 | Lung | 0.3042333 | 0.4836007 | 0.403323 | 0.27474338 | AA490685_a_t | EST: aa45b03.r1 Soares NhHMPu S1 Homo sapiens cDNA clone 823853 5', mRNA sequence. (from Genbank) |
| 130 | Lung | 0.3041266 | 0.4833055 | 0.402314 | 0.27447408 | AA206983_a_t | EST: zq50h02.r1 Stratagene neuroepithelium (#937231) Homo sapiens cDNA clone 645075 5' similar to contains Alu repetitive element;contains element MER22 repetitive element ;. mRNA sequence. (from Genbank) |
| 131 | Lung | 0.302548 | 0.4830999 | 0.40207 | 0.27427304 | U62435_at | Cholinergic receptor, neuronal nicotinic, alpha polypeptide 6 |
| 132 | Lung | 0.3023016 | 0.4830277 | 0.401581 | 0.2738723 | RC_AA2358 03_i_at | EST: zs42g06.s1 Soares NhHMPu S1 Homo sapiens cDNA clone 687898 3', mRNA sequence. (from Genbank) |
| 133 | Lung | 0.3022544 | 0.4825101 | 0.401088 | 0.27348357 | N48204_at | EST: yv22a08.r1 Homo sapiens cDNA clone 243446 5'. (from Genbank) |
| 134 | Lung | 0.3016735 | 0.4821407 | 0.400811 | 0.2732604 | U91618_at | Proneurotensin/proneuromedin N mRNA |
| 135 | Lung | 0.3014633 | 0.4815175 | 0.400427 | 0.27292356 | T57140_s_at | Paraoxonase 3 |
| 136 | Lung | 0.2994365 | 0.481468 | 0.400271 | 0.27270302 | L02326_f_at | (clone Hu lambda-17) lambda-like gene |
| 137 | Lung | 0.2989464 | 0.4812913 | 0.400164 | 0.27240446 | RC_AA2930 96_at | EST: zt55b05.s1 Soares ovary tumor NbHOT Homo sapiens cDNA clone 726225 3', mRNA sequence. (from Genbank) |
| 138 | Lung | 0.2985752 | 0.4812542 | 0.399905 | 0.27210814 | RC_AA4774 59_at | EST: zu44c08.s1 Soares ovary tumor NbHOT Homo sapiens cDNA clone 740846 3', mRNA sequence. (from Genbank) |
| 139 | Lung | 0.2965464 | 0.4810946 | 0.39948 | 0.27188435 | RC_AA4537 61_at | Homo sapiens mRNA for KIAA0770 protein, partial cds |
| 140 | Lung | 0.2961333 | 0.4806972 | 0.399182 | 0.27159443 | M16973_at | C8B Complement component 8, beta polypeptide |
| 141 | Lung | 0.2960797 | 0.4802434 | 0.39881 | 0.2712451 | U17760_ma_1_at | Laminin S B3 chain (LAMB3) gene |
| 142 | Lung | 0.2951559 | 0.479978 | 0.398544 | 0.27090091 | RC_AA4166 85_at | Homo sapiens Munc13 mRNA, complete cds |
| 143 | Lung | 0.2951044 | 0.4799131 | 0.398312 | 0.2707115 | AA011479_a_t | EST: zi01b10.r1 Soares fetal liver spleen 1NFLS S1 Homo sapiens cDNA clone 429499 5', mRNA sequence. (from Genbank) |
| 144 | Lung | 0.2948266 | 0.4796198 | 0.398208 | 0.27045232 | M62505_at | C5R1 Complement component 5 receptor 1 (C5a ligand) |
| 145 | Lung | 0.2944621 | 0.4792813 | 0.397764 | 0.27002499 | RC_AA4775 41_at | EST: zu41a09.s1 Soares ovary tumor NbHOT Homo sapiens cDNA clone 740536 3' similar to TR:G1144330 G1144330 CREB-RP mRNA sequence. (from Genbank) |
| 146 | Lung | 0.2939202 | 0.4790747 | 0.397602 | 0.26977727 | D79206_s_a_t | SDC4 Syndecan 4 (amphiglycan, ryudocan) |

| | | | | | | |
|---|---|---|---|---|---|---|
| 147 | Lung | 0.2914589 | 0.4786702 | 0.397298 | 0.28932248 | D10537_s_at | MPZ Myelin protein zero (Charcot-Marie-Tooth neuropathy 1B) |
| 148 | Lung | 0.2914589 | 0.4783935 | 0.39646 | 0.2690792 | D10537_s_at-2 | Myelin protein zero (Charcot-Marie-Tooth neuropathy 1B) |
| 149 | Lung | 0.2898674 | 0.4781693 | 0.396126 | 0.26867762 | RC_AA4546 67_at | EST: zx99h03.s1 Soares NhHMPu S1 Homo sapiens cDNA clone 811925 3', mRNA sequence. (from Genbank) |
| 150 | Lung | 0.2898594 | 0.4780451 | 0.395776 | 0.26845086 | U08021_at | Nicotinamide N-methyltransferase (NNMT) mRNA |
| 151 | Lung | 0.2892954 | 0.477616 | 0.395687 | 0.2681705 | R86178_at | EST: yp88f07.r1 Homo sapiens cDNA clone 194533 5' similar to contains Alu repetitive element;contains L1 repetitive element ;. (from Genbank) |
| 152 | Lung | 0.2885685 | 0.4775392 | 0.395578 | 0.26800632 | M55998_s_at | Alpha-1 collagen type I gene, 3' end |
| 153 | Lung | 0.288322 | 0.4771822 | 0.394955 | 0.26776683 | RC_AA2339 57_at | EST: zr27e04.s1 Stratagene NT2 neuronal precursor 937230 Homo sapiens cDNA clone 664638 3', mRNA sequence. (from Genbank) |
| 154 | Lung | 0.2881756 | 0.477153 | 0.394793 | 0.28756203 | AA082023_a_at | EST: zn35d10.r1 Stratagene endothelial cell 937223 Homo sapiens cDNA clone 549427 5', mRNA sequence. (from Genbank) |
| 155 | Lung | 0.2880437 | 0.4766433 | 0.394412 | 0.26727933 | N72380_s_at | EST: yv38f12.r1 Soares fetal liver spleen 1NFLS Homo sapiens cDNA clone 245039 5', mRNA sequence. (from Genbank) |
| 156 | Lung | 0.2880289 | 0.476529 | 0.394247 | 0.26688108 | RC_AA6085 79_s_at | Paired-like homeodomain transcription factor 2 |
| 157 | Lung | 0.2879598 | 0.4765055 | 0.394054 | 0.2667261 | RC_AA0478 76_at | EST: zf50b08.s1 Soares retina N2b4HR Homo sapiens cDNA clone 380343 3' similar to contains Alu repetitive element;contains element L1 repetitive element ;. mRNA sequence. (from Genbank) |
| 158 | Lung | 0.2872478 | 0.4762169 | 0.393871 | 0.26648134 | RC_AA4588 99_at | EST: zx88d07.s1 Soares ovary tumor NbHOT Homo sapiens cDNA clone 810829 3', mRNA sequence. (from Genbank) |
| 159 | Lung | 0.2870744 | 0.475351 | 0.392849 | 0.2661549 | U58496_s_at | Dual-specificity tyrosine-(Y)-phosphorylation regulated kinase 1 |
| 160 | Lung | 0.2869344 | 0.4750723 | 0.392529 | 0.2658185 | M17183_s_at | Parathyroid hormone-related protein mRNA |
| 161 | Lung | 0.2849524 | 0.4749866 | 0.392386 | 0.26562515 | RC_AA6209 65_at | EST: af88f01.s1 Soares testis NHT Homo sapiens cDNA clone 1049113 3' similar to SW:PUA1_MOUSE P28650 ADENYLOSUCCINATE SYNTHETASE, MUSCLE ISOZYME ;contains Alu repetitive element;. mRNA sequence. (from Genbank) |
| 162 | Lung | 0.2849164 | 0.4746312 | 0.392209 | 0.2653295 | RC_D20171_at | EST: Human HL60 3'directed MboI cDNA, HUMGS01145, clone pm2260, mRNA sequence. (from Genbank) |

FIG. 6H

| # | Tissue | | | | ID | Description |
|---|---|---|---|---|---|---|
| 163 | Lung | 0.2847362 | 0.4743328 | 0.2651191752_at | RC_AA4014 | EST: zu56e12.s1 Soares ovary tumor NbHOT Homo sapiens cDNA clone 742030 3', mRNA sequence. (from Genbank) |
| 164 | Lung | 0.2846965 | 0.4735598 | 0.264953731_at | RC_AA4534 | EST: zx32g10.s1 Soares total fetus Nb2HF8 9w Homo sapiens cDNA clone 788226 3', mRNA sequence. (from Genbank) |
| 165 | Lung | 0.2844742 | 0.4733726 | 0.264642695_at | RC_AA0170 | EST: ze3f7h12.s1 Soares retina N2b4HR Homo sapiens cDNA clone 361223 3', mRNA sequence. (from Genbank) |
| 166 | Lung | 0.2829887 | 0.4731536 | 0.26436642 35_at | RC_AA1960 | EST: zv72d06.s1 Soares total fetus Nb2HF8 9w Homo sapiens cDNA clone 759179 3', mRNA sequence. (from Genbank) |
| 167 | Lung | 0.2827876 | 0.4730274 | 0.26403245 11_at | RC_AA4958 | EST: zw05c08.s1 Soares NhHMPu S1 Homo sapiens cDNA clone 768398 3', mRNA sequence. (from Genbank) |
| 168 | Lung | 0.282494 | 0.472829 | 0.26365912 | AA485585_a t | EST: zx90e01.r1 Soares ovary tumor NbHOT Homo sapiens cDNA clone 811032 5', mRNA sequence. (from Genbank) |
| 169 | Lung | 0.2821531 | 0.4727932 | 0.2633431 03_f_at | RC_AA2358 | EST: zs42g06.s1 Soares NhHMPu S1 Homo sapiens cDNA clone 687898 3', mRNA sequence. (from Genbank) |
| 170 | Lung | 0.2819685 | 0.4727181 | 0.26310006 | M20902_at | APOC1 Apolipoprotein CI |
| 171 | Lung | 0.2817782 | 0.4723372 | 0.26284868 | M21305_at | Alpha satellite and satellite 3 junction DNA sequence |
| 172 | Lung | 0.2811393 | 0.4723207 | 0.2626506 | J04056_at | CBR Carbonyl reductase |
| 173 | Lung | 0.2810333 | 0.4720445 | 0.26250052 | X15954_ma 1_s_at | MBP1 gene, exon 1 (and joined CDS) |
| 174 | Lung | 0.279982 | 0.4719756 | 0.26218 | AA383703_i_at | EST97119 Testis I Homo sapiens cDNA 5' end similar to similar to zinc finger protein ZNF2, mRNA sequence. (from Genbank) |
| 175 | Lung | 0.279511 | 0.471948 | 0.26192585 12_at | RC_AA2341 | EST: zr74a05.s1 Soares NhHMPu S1 Homo sapiens cDNA clone 669104 3', mRNA sequence. (from Genbank) |
| 176 | Lung | 0.2792959 | 0.471922 | 0.2616987 76_at | RC_AA4875 | EST: ab23g01.s1 Stratagene lung (#937210) Homo sapiens cDNA clone 841680 3', mRNA sequence. (from Genbank) |
| 177 | Lung | 0.2788754 | 0.4717746 | 0.2615070 6_at | RC_AA2279 | EST: zr57d06.s1 Soares NhHMPu S1 Homo sapiens cDNA clone 667499 3', mRNA sequence. (from Genbank) |
| 178 | Lung | 0.2788578 | 0.471641 | 0.26125085 | AA416829_a t | EST: zu08e03.r1 Soares testis NHT Homo sapiens cDNA clone 731260 5', mRNA sequence. (from Genbank) |
| 179 | Lung | 0.278733 | 0.4715191 | 0.26096424 | AA027760_a t | EST: HPLA_CCLEE_40i6ar HPLA CCLee Homo sapiens cDNA, mRNA sequence. (from Genbank) |
| 180 | Lung | 0.2786865 | 0.471338 | 0.26075655 1_s_at | U37055_ma | Hepatocyte growth factor-like protein gene |
| 181 | Lung | 0.2786642 | 0.4710641 | 0.26057864 7_at | RC_AA4195 | EST: zv04a05.s1 Soares NhHMPu S1 Homo sapiens cDNA clone 752624 3', mRNA sequence. (from Genbank) |
| 182 | Lung | 0.278047 | 0.4709638 | 0.26028854 | U30999_at | U30999 Homo sapiens MV3 melanoma Homo sapiens cDNA clone memd, mRNA sequence |
| 183 | Lung | 0.276639 | 0.4708279 | 0.2600507 3_at-2 | AFFX-PheX- | AFFX-PheX-3_at (miscellaneous control - 11k chips) |

FIG. 6I

| | | | | | |
|---|---|---|---|---|---|
| 184 | Lung | 0.276639 | 0.4699768 | 0.386803 | 0.259858343 | AFFX-PheX-3_at | AFFX-PheX-3_at (endogenous control) |
| 185 | Lung | 0.2762696 | 0.4693944 | 0.386732 | 0.259533461 | AA017045_a_t | EST: zf50d12.r1 Soares retina N2b4HR Homo sapiens cDNA clone 380375 5' similar to contains Alu repetitive element;, mRNA sequence. (from Genbank) |
| 186 | Lung | 0.2761711 | 0.4692693 | 0.386704 | 0.2593366 | RC_C20545_at | EST: HUMGS0002073, Human Gene Signature, 3'-directed cDNA sequence, mRNA sequence. (from Genbank) |
| 187 | Lung | 0.2756152 | 0.4688733 | 0.386704 | 0.25915623 | RC_AA4062 18_at | EST: zu65e08.s1 Soares testis NHT Homo sapiens cDNA clone 742886 3', mRNA sequence. (from Genbank) |
| 188 | Lung | 0.2753333 | 0.4688594 | 0.386171 | 0.2589496 | L27671_s_at | Intercellular adhesion molecule 4, Landsteiner-Wiener blood group |
| 189 | Lung | 0.2745251 | 0.4685253 | 0.386088 | 0.2587298 | AA367473_a_t | Crystallin, beta B2 |
| 190 | Lung | 0.2743412 | 0.4680363 | 0.385394 | 0.258824875 | AA437153_a_t | EST: zv61b01.r1 Soares testis NHT Homo sapiens cDNA clone 758089 5', mRNA sequence. (from Genbank) |
| 191 | Lung | 0.2739779 | 0.4680098 | 0.385391 | 0.2581156 | U35340_at | CRYBB1 Crystallin beta-B1 |
| 192 | Lung | 0.2733802 | 0.4676982 | 0.385331 | 0.257826926_at | U20391_rna | Folate receptor (FOLR1) gene |
| 193 | Lung | 0.2732106 | 0.4673478 | 0.385189 | 0.25753233 | J03934_s_at | NMOR1 NAD(P)H:menadione oxidoreductase |
| 194 | Lung | 0.2726639 | 0.4672887 | 0.384898 | 0.25737914 | W27099_at | EST: 20c4 Human retina cDNA randomly primed sublibrary Homo sapiens cDNA, mRNA sequence. (from Genbank) |
| 195 | Lung | 0.2724477 | 0.4671862 | 0.384725 | 0.257127348 | RC_AA6207 82_at | EST: af90f08.s1 Soares testis NHT Homo sapiens cDNA clone 1049319 3', mRNA sequence. (from Genbank) |
| 196 | Lung | 0.2721126 | 0.4670309 | 0.384471 | 0.25696772 | J04970_at | CPM Carboxypeptidase M |
| 197 | Lung | 0.2709255 | 0.4665315 | 0.384406 | 0.25674567 | RC_AA4594 02_s_at | EST: zx89g02.s1 Soares ovary tumor NbHOT Homo sapiens cDNA clone 810962 3' similar to SW:MV10_MOUSE P23249 PUTATIVE GTP-BINDING PROTEIN MOV10. ;, mRNA sequence. (from Genbank) |
| 198 | Lung | 0.2701913 | 0.4665315 | 0.384145 | 0.25656185 | HG491-HT491_at | Fc Receptor IIb3 For Igg, Low Affinity |
| 199 | Lung | 0.2690204 | 0.4664357 | 0.384121 | 0.258433161 | RC_AA3720 18_at | EST: EST83940 Parathyroid gland tumor I Homo sapiens cDNA 3' end, mRNA sequence. (from Genbank) |
| 200 | Lung | 0.2685316 | 0.4654056 | 0.383995 | 0.2560336 | M87499_at | UNG Uracil-DNA glycosylase |
| 201 | Lung | 0.2683346 | 0.4653634 | 0.383518 | 0.2558822 | AB002366_a_t | KIAA0368 gene, partial cds |
| 202 | Lung | 0.2682895 | 0.4647388 | 0.383131 | 0.25561267 | AC002086_a_t | PAC clone DJ525N14 from Xq23, complete sequence |
| 203 | Lung | 0.2682696 | 0.4646515 | 0.382982 | 0.25542003 | X74039_at | Variant urokinase plasminogen activator receptor (uPAR2) mRNA, partial cds |

FIG. 6J

| # | Tissue | | | | | Description |
|---|---|---|---|---|---|---|
| 204 | Lung | 0.2681348 | 0.4644563 | 0.382882 | 0.2552324 X54925_at | MMP1 Matrix metalloproteinase 1 (interstitial collagenase) |
| 205 | Lung | 0.2668635 | 0.464408 | 0.382328 | 0.2550093 D26129_at | RNS1 Ribonuclease A (pancreatic) |
| 206 | Lung | 0.2667076 | 0.4642426 | 0.382286 | 0.25474834 RC_AA4192 17_at | EST: zv34h10.s1 Soares ovary tumor NbHOT Homo sapiens cDNA clone 755587 3'; mRNA sequence. (from Genbank) |
| 207 | Lung | 0.2660186 | 0.4642034 | 0.382111 | 0.2544974 X52228_at | MUC1 Mucin 1, transmembrane |
| 208 | Lung | 0.2652287 | 0.4641261 | 0.381949 | 0.2543377 D79565_at | Human aorta cDNA 5'-end GEN-281C02, mRNA sequence. (from Genbank) |
| 209 | Lung | 0.2652253 | 0.4638998 | 0.381842 | 0.25415117 M18728_at | NCA Non-specific cross reacting antigen |
| 210 | Lung | 0.2649988 | 0.4635157 | 0.381611 | 0.2538488 U95301_at | Phospholipase A2, group X |
| 211 | Lung | 0.264782 | 0.4631853 | 0.381359 | 0.25370955 RC_AA5211 11_at | EST: aa70h12.s1 NCI_CGAP_GCB1 Homo sapiens cDNA clone IMAGE:826343 3' similar to WP:C09F5.2 CE01774 :; mRNA sequence. (from Genbank) |
| 212 | Lung | 0.2638549 | 0.4631186 | 0.381114 | 0.25355068 X07820_at | MMP10 Matrix metalloproteinase 10 (stromelysin 2) |
| 213 | Lung | 0.2636834 | 0.4629812 | 0.381042 | 0.25328225 X57809_at | IGL@ Immunoglobulin lambda light chain |
| 214 | Lung | 0.2634412 | 0.4626113 | 0.38087 | 0.25311196 RC_AA4042 41_at | EST: zv63c01.s1 Soares total fetus Nb2HF8 9w Homo sapiens cDNA clone 758304 3' similar to TR:G412267 G412267 UNCOUPLING PROTEIN :; mRNA sequence. (from Genbank) |
| 215 | Lung | 0.263259 | 0.4623666 | 0.380829 | 0.25283435 RC_AA4769 22_at | EST: zu38c05.s1 Soares ovary tumor NbHOT Homo sapiens cDNA clone 740264 3'; mRNA sequence. (from Genbank) |
| 216 | Lung | 0.2632494 | 0.4620025 | 0.380665 | 0.25262985 J04080_at | C1S Complement component 1, s subcomponent |
| 217 | Lung | 0.2631691 | 0.4618928 | 0.380591 | 0.25234178 AA480025_a t | EST: zv18f06.r1 Soares NhHMPu S1 Homo sapiens cDNA clone 754019 5'; mRNA sequence. (from Genbank) |
| 218 | Lung | 0.2630112 | 0.4618654 | 0.380522 | 0.25200328 U90910_at-2 | Human clone 23564 mRNA sequence |
| 219 | Lung | 0.2630112 | 0.4618502 | 0.380008 | 0.2518673 U90910_at | Clone 23564 mRNA sequence |
| 220 | Lung | 0.2627808 | 0.4612269 | 0.379785 | 0.25163764 RC_AA4549 80_r_at | Homo sapiens zinc-finger helicase (hZFH) mRNA, complete cds |
| 221 | Lung | 0.2627209 | 0.4611526 | 0.379452 | 0.25145218 AA400044_a t | Human clone 23803 mRNA, partial cds |
| 222 | Lung | 0.2625929 | 0.4610807 | 0.379284 | 0.2512403 W68464_at | Homo sapiens mRNA for ADP ribosylation factor-like LAK, complete cds |
| 223 | Lung | 0.2623043 | 0.460708 | 0.379116 | 0.2510612 AA147510_s_at | EST: zl50c12.r1 Soares pregnant uterus NbHPU Homo sapiens cDNA clone 505366 5'; mRNA sequence. (from Genbank) |
| 224 | Lung | 0.2619781 | 0.4603861 | 0.378938 | 0.250855554 W26091_at | EST: 20n8 Human retina cDNA randomly primed sublibrary Homo sapiens cDNA, mRNA sequence. (from Genbank) |
| 225 | Lung | 0.2616963 | 0.4602705 | 0.378533 | 0.25066435 AA477715_a t | EST: zu44e10.r1 Soares ovary tumor NbHOT Homo sapiens cDNA clone 740874 5'; mRNA sequence. (from Genbank) |
| 226 | Lung | 0.2611458 | 0.4598296 | 0.378524 | 0.25050667 AA096343_a t | EST: l9342.seq,F Fetal heart, Lambda ZAP Express Homo sapiens cDNA 5'; mRNA sequence. (from Genbank) |
| 227 | Lung | 0.2611255 | 0.4596179 | 0.378396 | 0.2502798 U57721_at | L-kynurenine hydrolase mRNA |

FIG. 6K

| | | | | | |
|---|---|---|---|---|---|
| 228 | Lung | 0.260941 | 0.4594376 | 0.378269 | 0.2501868 | M19481_at | Follistatin gene |
| 229 | Lung | 0.2606874 | 0.4589527 | 0.377927 | 0.2499718 | U89717_at | RDH1 Retinol dehydrogenase 1 (11-cis) |
| 230 | Lung | 0.2604209 | 0.4583586 | 0.377671 | 0.24980038 | RC_AA5987 02_at | Bone morphogenetic protein 6 |
| 231 | Lung | 0.2603552 | 0.4582492 | 0.377406 | 0.24960165 | RC_AA1820 01_i_at | EST: zp62f10.s1 Stratagene endothelial cell 937223 Homo sapiens cDNA clone 624811 3', mRNA sequence. (from Genbank) |
| 232 | Lung | 0.2600594 | 0.4581787 | 0.3772 | 0.24940409 | AA431603_a t | EST: zw70c11.r1 Soares testis NHT Homo sapiens cDNA clone 781556 5', mRNA sequence. (from Genbank) |
| 233 | Lung | 0.2599597 | 0.4577981 | 0.377166 | 0.24916701 | RC_AA4878 79_at | EST: ab12a04.s1 Stratagene lung (#937210) Homo sapiens cDNA clone 840558 3', mRNA sequence. (from Genbank) |
| 234 | Lung | 0.2595257 | 0.4577897 | 0.377067 | 0.24900065 | W94795_at | Zinc finger protein 143 (clone pHZ-1) |
| 235 | Lung | 0.2589462 | 0.4576144 | 0.376934 | 0.24892284 | RC_AA6098 73_at | EST: af08c07.s1 Soares testis NHT Homo sapiens cDNA clone 1031052 3', mRNA sequence. (from Genbank) |
| 236 | Lung | 0.2588362 | 0.4575812 | 0.376602 | 0.24865182 | M13686_s_a t | PULMONARY SURFACTANT-ASSOCIATED PROTEIN A PRECURSOR |
| 237 | Lung | 0.2588171 | 0.4571579 | 0.376432 | 0.24852368 | RC_AA0745 14_at | EST: zm17f04.s1 Stratagene pancreas (#937208) Homo sapiens cDNA clone 525919 3', mRNA sequence. (from Genbank) |
| 238 | Lung | 0.2587827 | 0.4570878 | 0.376238 | 0.24832734 | AA427468_s _at | Claudin 4 |
| 239 | Lung | 0.2586628 | 0.4570521 | 0.376141 | 0.24815279 | YEL019c/M MS21_at | No info for gene |
| 240 | Lung | 0.2571341 | 0.4570198 | 0.375894 | 0.24797288 | U75272_s_a t | PGC Gastricsin (pepsinogen C) |
| 241 | Lung | 0.257126 | 0.4567713 | 0.37581 | 0.24773003 | L15388_at | G PROTEIN-COUPLED RECEPTOR KINASE GRK5 |
| 242 | Lung | 0.257074 | 0.4567229 | 0.375642 | 0.24751052 | N41669_at | EST: yw90d03.r1 Homo sapiens cDNA clone 259493 5'. (from Genbank) |
| 243 | Lung | 0.2569361 | 0.4564265 | 0.37563 | 0.24729508 | RC_AA0354 82_at | Homo sapiens clone 24655 mRNA sequence |
| 244 | Lung | 0.2565171 | 0.4562251 | 0.375295 | 0.24719368 | RC_AA0019 28_at | EST: zh83t05.s1 Soares fetal liver spleen 1NFLS S1 Homo sapiens cDNA clone 427905 3', mRNA sequence. (from Genbank) |
| 245 | Lung | 0.2564692 | 0.4560823 | 0.375261 | 0.24699226 | M11147_at | FTL Ferritin, light polypeptide |
| 246 | Lung | 0.2564633 | 0.4554453 | 0.375238 | 0.24680512 | AA477891_a t | EST: zu34e12.r1 Soares ovary tumor NbHOT Homo sapiens cDNA clone 739918 5', mRNA sequence. (from Genbank) |
| 247 | Lung | 0.2562718 | 0.4553228 | 0.374868 | 0.24652603 | M83667_rna 1_s_at | NF-IL6-beta protein mRNA |
| 248 | Lung | 0.2558699 | 0.4548869 | 0.374733 | 0.24635512 | RC_AA0106 65_at | EST: ze19f06.s1 Soares fetal heart NbHH19W Homo sapiens cDNA clone 359459 3', mRNA sequence. (from Genbank) |

FIG. 6L

| | | | | | |
|---|---|---|---|---|---|
|249|Lung|0.2553934|0.4483366|0.374488|RC_D25718_at|EST: Human colon 3'directed MboI cDNA, HUMGS04084, clone cm1380, mRNA sequence. (from Genbank)|
|250|Lung|0.2547548|0.4546747|0.374416|RC_AA6217|EST: af54e12.s1 Soares total fetus Nb2HF8 9w Homo sapiens cDNA clone 1035502 3', mRNA sequence. (from Genbank)|
|251|Lung|0.2542415|0.4546261|0.374077|0.24600837 14_at|Epoxide hydrolase 1, microsomal (xenobiotic)|
|252|Lung|0.2542169|0.4543322|0.373829|0.24583699 L25880_s_at|EST: ye04h07.r1 Homo sapiens cDNA clone 116797 5' similar to contains Alu repetitive element;. (from Genbank)|
| | | | | |0.24568415 T89571_f_at| |
|253|Lung|0.2539989|0.4542571|0.373699|0.24545069 X76180_at|SLC9A1 Solute carrier family 9 (sodium/hydrogen exchanger), isoform 1 (antiporter, Na+/H+, amiloride sensitive)|
|254|Lung|0.2537951|0.4540571|0.373522|0.2453531 X87843_at|Cyclin H assembly factor|
|255|Lung|0.2536495|0.4539768|0.373385|0.24507011 HT3579_at|Nestin|
| | | | | |J1G3400-| |
|256|Lung|0.2536239|0.4537005|0.373333|0.24477062 R81003_at|EST: yj94e03.r1 Homo sapiens cDNA clone 146908 5'. (from Genbank)|
|257|Lung|0.2532515|0.453271|0.373097|0.24461727 33_at|EST: aa68f12.s1 NCI_CGAP_GCB1 Homo sapiens cDNA clone IMAGE:826127 3', mRNA sequence. (from Genbank)|
|258|Lung|0.2532487|0.4531776|0.372902|0.244472 52_at|EST: ze74h04.s1 Soares fetal heart NbHH19W Homo sapiens cDNA clone 364759 3', mRNA sequence. (from Genbank)|
| | | | | |RC_AA0253| |
|259|Lung|0.2526551|0.4531004|0.372707|0.24432798 94_at|EST: zv92e06.s1 Soares NhHMPu S1 Homo sapiens cDNA clone 767266 3', mRNA sequence. (from Genbank)|
| | | | | |RC_AA4183| |
|260|Lung|0.2525689|0.4530408|0.372399|0.24411121 M60047_at|Heparin binding protein (HBp17) mRNA|
|261|Lung|0.2520721|0.4524183|0.372217|0.24392939 L42601_f_at|KERATIN, TYPE II CYTOSKELETAL 6D|
|262|Lung|0.2515372|0.4522601|0.372131|0.24384682 X03350_at|ADH2 Alcohol dehydrogenase 2 (class I), beta polypeptide|
|263|Lung|0.2514899|0.4521827|0.372052|0.24344471 79_at|EST: zt51h09.s1 Soares ovary tumor NbHOT Homo sapiens cDNA clone 725921 3', mRNA sequence. (from Genbank)|
| | | | | |RC_AA2923| |
|264|Lung|0.2512445|0.45218|0.371709|0.24330086 79_at|EST: zl06g11.s1 Soares fetal liver spleen 1NFLS S1 Homo sapiens cDNA clone 430052 3', mRNA sequence. (from Genbank)|
| | | | | |RC_AA3937| |
|265|Lung|0.2510947|0.4520143|0.371691|0.24313627 66_at|EST: zv64f06.s1 Soares total fetus Nb2HF8 9w Homo sapiens cDNA clone 758435 3', mRNA sequence. (from Genbank)|
|266|Lung|0.2510839|0.4518847|0.371511|0.24289817 D21239_at|C3G protein|
| | | | | |HG3517-| |
|267|Lung|0.251063|0.4518838|0.371467|0.24273656 HT3711_at|Alpha-1-Antitrypsin, 5' End|
|268|Lung|0.2508122|0.4518792|0.371246|0.24254175 AA095022_a t|EST: cp2494.seq.F Fetal heart, Lambda ZAP Express Homo sapiens cDNA 5', mRNA sequence. (from Genbank)|
| | | | | |RC_AA2567| |
|269|Lung|0.2506688|0.4518583|0.371176|0.24230699 00_at|Interferon (alpha, beta and omega) receptor 2|
|270|Lung|0.2501076|0.4517699|0.370847|0.24218002 69_at|EST: zl85c04.s1 Stratagene colon (#937204) Homo sapiens cDNA clone 511398 3', mRNA sequence. (from Genbank)|

FIG. 6M

| | | | | | |
|---|---|---|---|---|---|
| 271 | Lung | 0.2493669 | 0.4517632 | 0.37067 | AA490758_a_t | No info for gene |
| 272 | Lung | 0.2492503 | 0.4517419 | 0.37066 | 0.241965 RC_AA4030 41_at | Cellular retinoic acid-binding protein 1 |
| 273 | Lung | 0.2488994 | 0.4512726 | 0.37039 | 0.2418305 RC_AA2563 67_s_at | Paraoxonase 3 |
| 274 | Lung | 0.2485074 | 0.4512726 | 0.370234 | 0.2416419 RC_AA4366 19_at | EST: zw55d04.s1 Soares total fetus Nb2HF8 9w Homo sapiens cDNA clone 773959 3', mRNA sequence. (from Genbank) |
| 275 | Lung | 0.2479668 | 0.4508612 | 0.370041 | 0.2414275 RC_AA1470 67_at | EST: zo32a02.s1 Stratagene colon (#937204) Homo sapiens cDNA clone 588554 3', mRNA sequence. (from Genbank) |
| 276 | Lung | 0.2470958 | 0.4508456 | 0.369826 | 0.2411011 R39467_f_at | EST: yh95a09.r1 Homo sapiens cDNA clone 137464 5'. (from Genbank) |
| 277 | Lung | 0.2469302 | 0.4508456 | 0.369599 | 0.240089013 X02761_s_a t | FN1 Fibronectin 1 |
| 278 | Lung | 0.2468594 | 0.450728 | 0.369407 | 0.24080303 U18991_at | RPE65 Retinal pigment epithelium-specific protein (65kD) |
| 279 | Lung | 0.2464644 | 0.4505417 | 0.369224 | 0.24056235 M83772_at | FMO2 Flavin-containing monooxygenase 2 |
| 280 | Lung | 0.2463113 | 0.4504213 | 0.369217 | 0.24039806 L07765_at | CES2 Carboxylesterase 2 (liver) |
| 281 | Lung | 0.2452243 | 0.4496022 | 0.368663 | 0.24017109 Y12556_at | AMP-activated protein kinase beta-1 |
| 282 | Lung | 0.2450168 | 0.4494774 | 0.368508 | 0.2400353 M32578_at | HLA-DRB1 Major histocompatibility complex, class II, DR beta 1 |
| 283 | Lung | 0.2449677 | 0.4493105 | 0.368338 | 0.23982677 H18713_at | H.sapiens mRNA for aminopeptidase P-like |
| 284 | Lung | 0.2449493 | 0.4492599 | 0.368215 | 0.2397169657_at RC_AA4528 | EST: zx41c04.s1 Soares total fetus Nb2HF8 9w Homo sapiens cDNA clone 789030 3', mRNA sequence. (from Genbank) |
| 285 | Lung | 0.2447449 | 0.449254 | 0.3677 | 0.2396555 AA114949_a t | UDP-N-acteylglucosamine pyrophosphorylase 1; Sperm associated antigen 2 |
| 286 | Lung | 0.244619 | 0.4490928 | 0.367492 | 0.23940934 AA248169_a t | EST: csg1676.seq.F Human fetal heart, Lambda ZAP Express Homo sapiens cDNA 5', mRNA sequence. (from Genbank) |
| 287 | Lung | 0.2439476 | 0.4490151 | 0.367249 | 0.239271971 HG3431-HT3616_s_a t | Decorin, Alt. Splice 1 |
| 288 | Lung | 0.2435338 | 0.448953 | 0.366966 | 0.23907928 R25944_f_at | EST: yh44b01.r1 Homo sapiens cDNA clone 132553 5'. (from Genbank) |
| 289 | Lung | 0.2421348 | 0.4489121 | 0.366873 | 0.23886372 D79603_at | EST: Human aorta cDNA 5'-end GEN-286H04, mRNA sequence. |
| 290 | Lung | 0.2421101 | 0.4486721 | 0.366676 | 0.2387215505_at RC_AA0200 | EST: ze62e11.s1 Soares retina N2b4HR Homo sapiens cDNA clone 363596 3', mRNA sequence. (from Genbank) |

FIG. 6N

| | | | | | |
|---|---|---|---|---|---|
| 291 | Lung | 0.2418224 | 0.4483815 | 0.23854859 | R67702_at | Human DNA sequence from clone 283E3 on chromosome 1p36.21-36.33. Contains the alternatively spliced gene for Matrix Metalloproteinase in the Female Reproductive tract MIFR1, -2, MMP21/22A, -B and -C, a novel gene, the alternatively spliced CDC2L2 gene for Cell Division Cycle 2-Like 2 (PITSLRE, p58/GTA, Galactosyltransferase Associated Protein Kinase) beta 1, beta 2-1, beta 2-2 and alpha 2-4, a 40S Ribosomal Protein S7 pseudogene, part of the KIAA0447 gene, a novel alternatively spliced gene similar to many (archae)bacterial, worm and yeast hypothetical genes, and the GNB1 gene for Guanine Nucleotide Binding Protein (G protein), Beta polypeptide 1 (Transducin Beta chain 1). Contains putative CpG islands, ESTs, STSs and GSSs |
| 292 | Lung | 0.241485 | 0.4482195 | 0.23836564 | RC_AA2364 60_at | EST: zr75h04.s1 Soares NhHMPu S1 Homo sapiens cDNA clone 669271 3', mRNA sequence. (from Genbank) |
| 293 | Lung | 0.2410591 | 0.4480375 | 0.23823951 | RC_AA4493 06_at | EST: zx08c12.s1 Soares total fetus Nb2HF8 9w Homo sapiens cDNA clone 785878 3', mRNA sequence. (from Genbank) |
| 294 | Lung | 0.2407021 | 0.4478584 | 0.2380642 | RC_AA4240 13_at | Homo sapiens clone 23767 and 23782 mRNA sequences |
| 295 | Lung | 0.2406482 | 0.4476039 | 0.23789497 | N27054_at | EST: yx19f02.r1 Homo sapiens cDNA clone 262203 5'. (from Genbank) |
| 296 | Lung | 0.2405345 | 0.4472519 | 0.23780748 | RC_AA1131 66_at | EST: zm27e01.s1 Stratagene pancreas (#937208) Homo sapiens cDNA clone 526872 3', mRNA sequence. (from Genbank) |
| 297 | Lung | 0.2402408 | 0.4472004 | 0.23751338 | U90905_at | Clone 23574 mRNA sequence |
| 298 | Lung | 0.240171 | 0.4470855 | 0.23746502 | RC_AA1279 64_at | EST: zl13g07.s1 Soares pregnant uterus NbHPU Homo sapiens cDNA clone 501852 3', mRNA sequence. (from Genbank) |
| 299 | Lung | 0.2398486 | 0.4470855 | 0.23732695 | K01396_at | PI Protease inhibitor 1 (anti-elastase), alpha-1-antitrypsin |
| 300 | Lung | 0.2393439 | 0.4470831 | 0.23717211 | U93869_at | Human RNA polymerase III subunit (RPC39) mRNA, complete cds |
| 301 | Lung | 0.2393215 | 0.4469072 | 0.23687358 | AA418143_a t | EST: zv97b09.r1 Soares NhHMPu S1 Homo sapiens cDNA clone 767705 5', mRNA sequence. (from Genbank) |
| 302 | Lung | 0.2392817 | 0.4468811 | 0.23681135 | D26561_cds 2_at | ORF for E6 protein gene extracted from Human papillomavirus 5b genome integrated into human carcinoma DNA |
| 303 | Lung | 0.2389897 | 0.4466466 | 0.23660107 | Z47553_at | FMO5 Flavin containing monooxygenase 5 |
| 304 | Lung | 0.2389653 | 0.4465462 | 0.23645553 | M82967_s_a t | Acrosomal vesicle protein 1 |
| 305 | Lung | 0.2389139 | 0.4464949 | 0.2361749 | H81340_at | EST: yu74d04.r1 Homo sapiens cDNA clone 239527 5'. (from Genbank) |
| 306 | Lung | 0.2387406 | 0.4463466 | 0.23596013 | AA397616_a t | EST: zt79c08.r1 Soares testis NHT Homo sapiens cDNA clone 728558 5' similar to TR:G57649 G57649 VOLTAGE-GATED POTASSIUM CHANNEL.; mRNA sequence. (from Genbank) |

FIG. 6O

| # | Tissue | | | | ID | Description |
|---|---|---|---|---|---|---|
| 307 | Lung | 0.2386606 | 0.4461591 | 0.364413 | 0.23576084 J04430_s_at | ACP5 Acid phosphatase 5, tartrate resistant |
| 308 | Lung | 0.2384605 | 0.4459762 | 0.363926 | 0.23568334 AA421370_a_t | EST: zu06e06.r1 Soares testis NHT Homo sapiens cDNA clone 731074 5' similar to contains MER17.t2 MER17 repetitive element :, mRNA sequence. (from Genbank) |
| 309 | Lung | 0.2381974 | 0.4458249 | 0.363899 | 0.23559451 X66358_at | mRNA KKIALRE for serine/threonine protein kinase |
| 310 | Lung | 0.2377942 | 0.4455868 | 0.363651 | 0.23553509 RC_AA0075 22_at | EST: zh98f09.s1 Soares fetal liver spleen 1NFLS S1 Homo sapiens cDNA clone 429353 3' similar to contains Alu repetitive element;, mRNA sequence. (from Genbank) |
| 311 | Lung | 0.2377663 | 0.4454852 | 0.363403 | 0.23538382 RC_AA1646 33_at | EST: zo93d04.s1 Stratagene ovarian cancer (#937219) Homo sapiens cDNA clone 594439 3', mRNA sequence. (from Genbank) |
| 312 | Lung | 0.2376308 | 0.4451729 | 0.363267 | 0.23522367 RC_AA2625 56_at | EST: zs22b09.s1 NCI_CGAP_GCB1 Homo sapiens cDNA clone IMAGE:685913 3', mRNA sequence. (from Genbank) |
| 313 | Lung | 0.2373599 | 0.4451073 | 0.363244 | 0.23511253 AA287815_a_t | EST: zs50g04.r1 NCI_CGAP_GCB1 Homo sapiens cDNA clone IMAGE:700950 5', mRNA sequence. (from Genbank) |
| 314 | Lung | 0.2373353 | 0.4449089 | 0.363137 | 0.23500282 RC_D25984 _at | EST: Human colon 3'directed MboI cDNA, HUMGS06759, clone cm3106, mRNA sequence. (from Genbank) |
| 315 | Lung | 0.2369185 | 0.4447673 | 0.362995 | 0.23480712 RC_AA0531 39_at | EST: zl73e05.s1 Stratagene colon (#937204) Homo sapiens cDNA clone 510272 3' similar to TR:E243948 E243948 CHROMOSOME VII READING FRAME ORF YGL054C. :, mRNA sequence. (from Genbank) |
| 316 | Lung | 0.2366281 | 0.4447151 | 0.36291 | 0.23457296 RC_AA4889 79_at | Homo sapiens cell cycle-regulated factor p78 mRNA, complete cds |
| 317 | Lung | 0.2361669 | 0.4447031 | 0.362812 | 0.23443899 RC_AA0322 50_at | EST: zk19f06.s1 Soares pregnant uterus NbHPU Homo sapiens cDNA clone 471011 3', mRNA sequence. (from Genbank) |
| 318 | Lung | 0.2361647 | 0.4445837 | 0.362637 | 0.23431237 AA478131_a_t | EST: zu42c10.r1 Soares ovary tumor NbHOT Homo sapiens cDNA clone 740658 5' similar to TR:G433963 G433963 P18H-REV 107. :, mRNA sequence. (from Genbank) |
| 319 | Lung | 0.2359319 | 0.4444797 | 0.362621 | 0.23421793 X57348_s_a_t | SFN Stratifin |
| 320 | Lung | 0.235862 | 0.4444004 | 0.362557 | 0.23400162 N34697_at | EST: yx81c11.r1 Homo sapiens cDNA clone 268148 5'. (from Genbank) |
| 321 | Lung | 0.2356288 | 0.4443508 | 0.362268 | 0.2338126 RC_AA6095 92_at | EST: af15d11.s1 Soares testis NHT Homo sapiens cDNA clone 1031733 3', mRNA sequence. (from Genbank) |
| 322 | Lung | 0.2352507 | 0.4443409 | 0.362126 | 0.23375657 X76534_at | NMB Neuromedin B |
| 323 | Lung | 0.2352127 | 0.4442597 | 0.361905 | 0.23355637 RC_AA1560 97_s_at | EST: zo45d03.s1 Stratagene endothelial cell 937223 Homo sapiens cDNA clone 589829 3', mRNA sequence. (from Genbank) |

FIG. 6P

| | | | | | |
|---|---|---|---|---|---|
| 324 | Lung | | 0.2351494 | 0.4441127 | 0.23342706 | AA476517_a t | Human DNA sequence from clone 431H6 on chromosome 16. Contains a novel gene with some homology to mouse HN1 (Hematological and Neurological expressed sequence 1) downstream of a putative CpG island. Contains ESTs and GSSs |
| 325 | Lung | 0.2344142 | 0.4440047 | 0.23331495 | AF004709_a t | Protein kinase mitogen- activated 13 |
| 326 | Lung | 0.234278 | 0.4439402 | 0.23319076 | X93921_at | Protein-tyrosine-phosphatase (tissue type: testis) |
| 327 | Lung | 0.234278 | 0.4439402 | 0.23330621 | X93921_at-2 | Dual specificity phosphatase 7 |
| 328 | Lung | 0.233664 | 0.4434984 | 0.23292959 | HG537-HT537_at | Collagen, Type Viii, Alpha 2 |
| 329 | Lung | 0.2334355 | 0.4433608 | 0.23277782 | L10125_s_at | Human serine/threonine kinase receptor-2-2 (SKR2-2) mRNA, complete cds. (from Genbank) |
| 330 | Lung | 0.2333466 | 0.4432385 | 0.23255797 | HG3242-HT3419_s_a t | Calcium Channel, Voltage-Gated, Alpha 1e Subunit, Alt. Splice 2 |
| 331 | Lung | 0.2333421 | 0.4431269 | 0.23243879 | AA128724_a t | Homo sapiens mRNA for KIAA0684 protein, partial cds |
| 332 | Lung | 0.2329953 | 0.4429795 | 0.23223354 | U21931_at | FBP1 Fructose-bisphosphatase 1 |
| 333 | Lung | 0.2328587 | 0.442692 | 0.23213045 | RC_AA4314 61_at | EST: zw70f11.s1 Soares testis NHT Homo sapiens cDNA clone 781581 3', mRNA sequence. (from Genbank) |
| 334 | Lung | 0.2320017 | 0.4426331 | 0.23200329 | Z83745_at | DNA sequence from PAC 453A3 contains EST and STS |
| 335 | Lung | 0.2317447 | 0.4423266 | 0.23182687 | L48513_at | Paraoxonase (PON2) mRNA |
| 336 | Lung | 0.2314258 | 0.4422433 | 0.23169434 | AA399299_a t | EST: zt52e09.r1 Soares ovary tumor NbHOT Homo sapiens cDNA clone 725992 5' similar to contains element PTR5 repetitive element ;, mRNA sequence. (from Genbank) |
| 337 | Lung | 0.2313241 | 0.4421065 | 0.23157692 | M90656_at | GLCLC Glutamate-cysteine ligase (gamma-glutamylcysteine synthetase), catalytic (72.8kD) |
| 338 | Lung | 0.2312668 | 0.4420143 | 0.23138015 | D11151_at | EDNRA Endothelin receptor type A |
| 339 | Lung | 0.2312089 | 0.4416896 | 0.2312995 | X07696_at | KRT15 Keratin 15 |
| 340 | Lung | 0.2312077 | 0.4415183 | 0.23117815 | YEL002c/W BP1_at | No info for gene |
| 341 | Lung | 0.2310319 | 0.4413874 | 0.23102877 | X92475_at | ITBA1 protein |
| 342 | Lung | 0.2310319 | 0.4409662 | 0.35918 | 0.23085321 | X92475_at-2 | ITBA1 gene |
| 343 | Lung | 0.2309153 | 0.4409024 | 0.23061915 | H66367_at | EST: yu14a06.r1 Homo sapiens cDNA clone 233746 5' similar to contains Alu repetitive element;. (from Genbank) |
| 344 | Lung | 0.2308357 | 0.4406858 | 0.23040917 | AA081995_a t | Zn26d06.r1 Stratagene neuroepithelium NT2RAMI 937234 Homo sapiens cDNA clone 548555 5', mRNA sequence. (from Genbank) |
| 345 | Lung | 0.2303604 | 0.4405938 | 0.23034495 | AA248964_a t | EST: kk6741.seq,F Human fetal heart, Lambda ZAP Express Homo sapiens cDNA 5', mRNA sequence. (from Genbank) |

FIG. 6Q

| | | | | | |
|---|---|---|---|---|---|
| 346 | Lung | 0.230249 | 0.4402882 | 0.358379 | 0.23023087 | RC_AA4904_at | EST: aa45a12.s1 Soares NhHMPu S1 Homo sapiens cDNA clone 823870 3', mRNA sequence. (from Genbank) |
| 347 | Lung | 0.2302438 | 0.4401727 | 0.358266 | 0.23003279 | RC_AA4314_at | EST: zw70g01.s1 Soares testis NHT Homo sapiens cDNA clone 781584 3', mRNA sequence. (from Genbank) |
| 348 | Lung | 0.2300901 | 0.4399342 | 0.358028 | 0.2299746 | M16714_at | HLA-E MHC class I antigen HLA-E |
| 349 | Lung | 0.2300901 | 0.4399039 | 0.357847 | 0.22978345 | M16714_at-2 | HLA CLASS I HISTOCOMPATIBILITY ANTIGEN, E E*0101/E*0102 ALPHA CHAIN PRECURSOR |
| 350 | Lung | 0.2293386 | 0.4398891 | 0.357632 | 0.22963841 | RC_AA6098_at | EST: ae62e05.s1 Stratagene lung carcinoma 937218 Homo sapiens cDNA clone 951488 3', mRNA sequence. (from Genbank) |
| 351 | Lung | 0.2297726 | 0.4398626 | 0.357595 | 0.2293974 | T28246_at | Hepsin (transmembrane protease, serine 1) |
| 352 | Lung | 0.2293905 | 0.4395745 | 0.357466 | 0.22927545 | D26561_cds1_at | ORF for L1 protein gene extracted from Human papillomavirus 5b genome integrated into human carcinoma DNA |
| 353 | Lung | 0.2282414 | 0.4395595 | 0.357359 | 0.2292258 | M20786_at | PLI Alpha-2-plasmin inhibitor (alpha-2-PI) |
| 354 | Lung | 0.2279826 | 0.4392837 | 0.357342 | 0.22907254 | D17716_at | N-acetylglucosaminyltransferase V |
| 355 | Lung | 0.2279826 | 0.4390499 | 0.35719 | 0.22897726 | D17716_at-2 | Mannosyl (alpha-1,6-)-glycoprotein beta-1,6-N-acetyl-glucosaminyltransferase |
| 356 | Lung | 0.2276511 | 0.4389308 | 0.357114 | 0.22876048 | RC_AA4656_at | EST: aa31b01.s1 NCI_CGAP_GCB1 Homo sapiens cDNA clone IMAGE:814825 3', mRNA sequence. (from Genbank) |
| 357 | Lung | 0.227571 | 0.4387819 | 0.35707 | 0.22858873 | U15197_at-2 | ABO blood group (transferase A, alpha 1-3-N-acetylgalactosaminyltransferase; transferase B, alpha 1-3-galactosyltransferase) |
| 358 | Lung | 0.227571 | 0.4383889 | 0.356992 | 0.22850904 | U15197_at | ABO ABO blood group (transferase A, alpha 1-3-N-acetylgalactosaminyltransferase; transferase B, alpha 1-3-galactosyltransferase) |
| 359 | Lung | 0.2274778 | 0.4382982 | 0.356905 | 0.22833458 | X60787_s_at | INTERLEUKIN ENHANCER-BINDING FACTOR |
| 360 | Lung | 0.2274309 | 0.4382207 | 0.356582 | 0.22816384 | H16876_at | Ym34f05.r1 Homo sapiens cDNA clone 50123 5'. (from Genbank) |
| 361 | Lung | 0.227429 | 0.4382066 | 0.356479 | 0.22797966 | RC_AA6203_at | EST: af07d11.s1 Soares testis NHT Homo sapiens cDNA clone 1030965 3', mRNA sequence. (from Genbank) |
| 362 | Lung | 0.2274029 | 0.4381657 | 0.356466 | 0.22778736 | HT417_s_at | Cathepsin B |
| 363 | Lung | 0.2267194 | 0.4379906 | 0.356311 | 0.2277485 | U52100_at | XMP mRNA |
| 364 | Lung | 0.2261014 | 0.4379368 | 0.356146 | 0.22767206 | AA489716_at | EST: aa43a01.r1 Soares NhHMPu S1 Homo sapiens cDNA clone 823656 5' similar to contains element MER22 repetitive element ;, mRNA sequence. (from Genbank) |
| 365 | Lung | 0.2259946 | 0.4379368 | 0.356036 | 0.22752677 | H55437_at | EST: CHR220376 Homo sapiens genomic clone C22_491 5'. (from Genbank) |
| 366 | Lung | 0.2259833 | 0.4379004 | 0.356011 | 0.22730403 | M15856_at | LPL Lipoprotein lipase |

FIG. 6R

| # | Tissue | Col3 | Col4 | Col5 | Col6 | Description |
|---|---|---|---|---|---|---|
| 367 | Lung | 0.2257753 | 0.4379004 | 0.35571 | R33961_at | EST: yh74b06.r1 Homo sapiens cDNA clone 135443 5'. (from Genbank) |
| 368 | Lung | 0.2249175 | 0.4378383 | 0.355655 | U93553_at | Alpha1-fetoprotein transcription factor (hFTF) mRNA |
| 369 | Lung | 0.2249175 | 0.4378307 | 0.355551 | U93553_at-2 | Fetoprotein-alpha 1 (AFP) transcription factor |
| 370 | Lung | 0.2248085 | 0.4377857 | 0.355499 | RC_AA446944_at | EST: zw85c11.s1 Soares total fetus Nb2HF8 9w Homo sapiens cDNA clone 783764 3', mRNA sequence. (from Genbank) |
| 371 | Lung | 0.2240313 | 0.4377154 | 0.355092 | X67698_at | Tissue specific mRNA |
| 372 | Lung | 0.2232322 | 0.43761 | 0.355025 | AA167824_a_t | Cell division cycle 27 |
| 373 | Lung | 0.2231333 | 0.4375583 | 0.355006 | J04513_at | Basic fibroblast growth factor (bFGF) 22.5 kd, 21 kd and 18 kd protein mRNA |
| 374 | Lung | 0.2231237 | 0.4375517 | 0.354993 | D30954_at | EST: Human fetal-lung cDNA 5'-end sequence, mRNA sequence. (from Genbank) |
| 375 | Lung | 0.2230321 | 0.4374047 | 0.354758 | M68840_at | MAOA Monoamine oxidase A |
| 376 | Lung | 0.2226568 | 0.4373781 | 0.354701 | W28902_r_at | KIAA0736 gene product |
| 377 | Lung | 0.2224297 | 0.4372591 | 0.354173 | W37398_at | EST: zc11a10.r1 Soares parathyroid tumor NbHPA Homo sapiens cDNA clone 321978 5', mRNA sequence. (from Genbank) |
| 378 | Lung | 0.222415 | 0.4371029 | 0.354148 | AA442274_a_t | EST: zv54a06.r1 Soares testis NHT Homo sapiens cDNA clone 757426 5', mRNA sequence. (from Genbank) |
| 379 | Lung | 0.2223091 | 0.4370776 | 0.354106 | RC_AA487558_at | EST: ab23e01.s1 Stratagene lung (#937210) Homo sapiens cDNA clone 841656 3', mRNA sequence. (from Genbank) |
| 380 | Lung | 0.2221375 | 0.4370183 | 0.354049 | U72513_at | Human RPL13-2 pseudogene mRNA, complete cds |
| 381 | Lung | 0.2221208 | 0.4369998 | 0.353864 | U16799_s_at | Na,K-ATPase beta-1 subunit mRNA |
| 382 | Lung | 0.2219176 | 0.4369082 | 0.353735 | AFFX-DapX-5_at-2 | AFFX-DapX-5_at (miscellaneous control - 11k chips) |
| 383 | Lung | 0.2219176 | 0.4365304 | 0.353641 | AFFX-DapX-5_at | AFFX-DapX-5_at (endogenous control) |
| 384 | Lung | 0.2218542 | 0.4363941 | 0.353457 | X52022_at | RNA for type VI collagen alpha3 chain |
| 385 | Lung | 0.2216734 | 0.4362356 | 0.353429 | T85532_f_at | EST: yd78g02.r1 Homo sapiens cDNA clone 114386 5' similar to contains Alu repetitive element;. (from Genbank) |
| 386 | Lung | 0.2216565 | 0.4361902 | 0.353312 | X68314_at | GPX2 Glutathione peroxidase 2, gastrointestinal |
| 387 | Lung | 0.2214257 | 0.436033 | 0.353193 | L07592_at-2 | Human peroxisome proliferator activated receptor mRNA, complete cds |
| 388 | Lung | 0.2214257 | 0.4360034 | 0.353074 | L07592_at | Peroxisome proliferator activated receptor mRNA |
| 389 | Lung | 0.221295 | 0.4359591 | 0.352986 | U25801_at | Tax1 binding protein mRNA, partial cds |

FIG. 6S

| # | Tissue | | | | ID | Description |
|---|---|---|---|---|---|---|
| 390 | Lung | 0.2212361 | 0.4356104 | 0.352714 | RC_AA1286 0.22414272 17_at | EST: zl15d10.s1 Soares pregnant uterus NbHPU Homo sapiens cDNA clone 502003 3', mRNA sequence. (from Genbank) |
| 391 | Lung | 0.2211314 | 0.4355704 | 0.352636 | T55087_s_at 0.22241315 | EST: yb45c08.r1 Homo sapiens cDNA clone 74126 5'. (from Genbank) |
| 392 | Lung | 0.2201063 | 0.4355692 | 0.352476 | AA364267_a 0.22397614 t | EST: EST74873 Pineal gland II Homo sapiens cDNA 5' end, mRNA sequence. (from Genbank) |
| 393 | Lung | 0.2199532 | 0.4354602 | 0.352393 | D83017_s_a 0.22389945 t | Nel-related protein |
| 394 | Lung | 0.2196524 | 0.4352692 | 0.352348 | RC_AA4221 0.22381282 46_at | EST: zv28g12.s1 Soares ovary tumor NbHOT Homo sapiens cDNA clone 755014 3', mRNA sequence. (from Genbank) |
| 395 | Lung | 0.2196019 | 0.4349499 | 0.352305 | 0.22361091 W28763_at | Homo sapiens KIAA0431 mRNA, partial cds |
| 396 | Lung | 0.2193915 | 0.4348034 | 0.352102 | RC_AA0172 0.22356348 54_at | EST: ze52b08.s1 Soares retina N2b4HR Homo sapiens cDNA clone 362583 3', mRNA sequence. (from Genbank) |
| 397 | Lung | 0.2190742 | 0.4344841 | 0.352101 | 0.22330593 Y00443_at | Protamine 1 |
| 398 | Lung | 0.2190497 | 0.4342092 | 0.351846 | 0.22316453 U46689_at | Microsomal aldehyde dehydrogenase (ALD10) mRNA |
| 399 | Lung | 0.2181691 | 0.4341459 | 0.351689 | U26446_s_a 0.2222905 t | Protoporphyrinogen oxidase |
| 400 | Lung | 0.2181218 | 0.4339353 | 0.351536 | RC_AA2906 0.22288755 79_at | Selenium binding protein 1 |
| 401 | Lung | 0.2178215 | 0.4337802 | 0.351477 | X85116_rna 0.22280458 1_s_at | Epb72 gene exon 1 |
| 402 | Lung | 0.2177523 | 0.4333646 | 0.351422 | X56411_rna 0.22265434 1_at | ADH4 gene for class II alcohol dehydrogenase (pi subunit), exon 1 |
| 403 | Lung | 0.2172694 | 0.4333493 | 0.351059 | AA504384_a 0.2224586 t | EST: aa59c02.r1 NCI_CGAP_GCB1 Homo sapiens cDNA clone IMAGE:825218 5' similar to contains element MIR repetitive element :, mRNA sequence. (from Genbank) |
| 404 | Lung | 0.2167519 | 0.4331934 | 0.351059 | RC_AA6090 0.22227941 60_at | EST: af10g04.s1 Soares testis NHT Homo sapiens cDNA clone 1031286 3', mRNA sequence. (from Genbank) |
| 405 | Lung | 0.2165043 | 0.4331761 | 0.350608 | 0.22222474 W25933_at | EST: 15b2 Human retina cDNA randomly primed sublibrary Homo sapiens cDNA, mRNA sequence. (from Genbank) |
| 406 | Lung | 0.2163794 | 0.43271711 | 0.3506 | 0.2220807 U40434_at | Pre-pro-megakaryocyte potentiating factor |
| 407 | Lung | 0.2160962 | 0.4327111 | 0.350465 | RC_AA0211 0.22189234 57_at | EST: ze65d11.s1 Soares retina N2b4HR Homo sapiens cDNA clone 363861 3', mRNA sequence. (from Genbank) |
| 408 | Lung | 0.2158367 | 0.4323317 | 0.350414 | RC_AA4065 0.22180302 99_at | EST: zv15a07.s1 Soares retina NhHMPu S1 Homo sapiens cDNA clone 753684 3', mRNA sequence. (from Genbank) |
| 409 | Lung | 0.2158337 | 0.4322483 | 0.349979 | AA028976_a 0.22170478 l | EST: zk11a03.r1 Soares pregnant uterus NbHPU Homo sapiens cDNA clone 470188 5', mRNA sequence. (from Genbank) |
| 410 | Lung | 0.2156631 | 0.4319767 | 0.349961 | 0.22155166 Z33905_at | 43kD acetylcholine receptor-associated protein (Rapsyn) |
| 411 | Lung | 0.2156629 | 0.4319547 | 0.349961 | 0.22126713 L25878_s_at | EPHX1 Epoxide hydrolase 1, microsomal (xenobiotic) |

FIG. 6T

| # | Tissue | | | | ID | Description |
|---|---|---|---|---|---|---|
| 412 | Lung | 0.2154811 | 0.4317628 | 0.349921 | 0.22112909 | AA310301_a_t KIAA0331 gene product |
| 413 | Lung | 0.2153825 | 0.4317125 | 0.349745 | 0.22102222 | U80811_at Lysophosphatidic acid receptor homolog mRNA |
| 414 | Lung | 0.2149317 | 0.4316894 | 0.349359 | 0.22088535 | AA442383_a_t EST: zv62d10.r1 Soares testis NHT Homo sapiens cDNA clone 758227 5', mRNA sequence. (from Genbank) |
| 415 | Lung | 0.2144865 | 0.431473 | 0.349329 | 0.22075154 | RC_D60272_i_at EST: Human fetal brain cDNA 3'-end GEN-095A07, mRNA sequence. (from Genbank) |
| 416 | Lung | 0.2142058 | 0.431373 | 0.349289 | 0.22066022 | AA452428_a_t EST: zx15g01.r1 Soares total fetus Nb2HF8 9w Homo sapiens cDNA clone 786576 5', mRNA sequence. (from Genbank) |
| 417 | Lung | 0.2140577 | 0.4313075 | 0.349188 | 0.22053619 | D38163_s_a_t-2 Collagen, type XIX, alpha 1 |
| 418 | Lung | 0.2140577 | 0.4312895 | 0.349178 | 0.22047408 | D38163_s_a_t COL19A1 Collagen, type XIX, alpha 1 |
| 419 | Lung | 0.213926 | 0.4310879 | 0.349085 | 0.22033271 | AA365742_s_at EST: EST76593 Pineal gland II Homo sapiens cDNA 5' end, mRNA sequence. (from Genbank) |
| 420 | Lung | 0.2138369 | 0.4310526 | 0.348985 | 0.22024357 | RC_AA1478_84_at EST: zi50b04.s1 Soares pregnant uterus NbHPU Homo sapiens cDNA clone 505327 3', mRNA sequence. (from Genbank) |
| 421 | Lung | 0.213747 | 0.4309248 | 0.348899 | 0.22010231 | RC_AA2365_33_s_at Ecotropic viral integration site 1 |
| 422 | Lung | 0.2131875 | 0.4308415 | 0.348601 | 0.21998385 | X57809_s_a_t IGL@ Immunoglobulin lambda light chain |
| 423 | Lung | 0.2128338 | 0.4306715 | 0.348535 | 0.2198807 | L42583_f_at KERATIN, TYPE II CYTOSKELETAL 6D |
| 424 | Lung | 0.2124133 | 0.430651 | 0.34851 | 0.21979778 | RC_AA6096_50_s_at EST: af16b03.s1 Soares testis NHT Homo sapiens cDNA clone 1031789 3', mRNA sequence. (from Genbank) |
| 425 | Lung | 0.2120543 | 0.4305704 | 0.348472 | 0.219668 | M91368_s_a_t Na+/Ca+ exchanger (CNC) mRNA |
| 426 | Lung | 0.2119022 | 0.430404 | 0.348394 | 0.21951333 | RC_AA1868_04_at EST: zp73h02.s1 Stratagene HeLa cell s3 937216 Homo sapiens cDNA clone 625875 3', mRNA sequence. (from Genbank) |
| 427 | Lung | 0.2117596 | 0.4303828 | 0.348296 | 0.21937673 | N75274_at EST: yw36a03.r1 Homo sapiens cDNA clone 254284 5'. (from Genbank) |
| 428 | Lung | 0.2109902 | 0.4303189 | 0.348236 | 0.21920326 | RC_AA5214_54_at EST: aa69e04.s1 NCI_CGAP_GCB1 Homo sapiens cDNA clone IMAGE:826206 3', mRNA sequence. (from Genbank) |
| 429 | Lung | 0.2103204 | 0.4303102 | 0.34806 | 0.21908234 | RC_AA4170_86_at EST: zu13c11.s1 Soares testis NHT Homo sapiens cDNA clone 731732 3', mRNA sequence. (from Genbank) |
| 430 | Lung | 0.2102232 | 0.4301371 | 0.347818 | 0.21889462 | RC_AA4602_21_at EST: zx67a02.s1 Soares total fetus Nb2HF8 9w Homo sapiens cDNA clone 796490 3', mRNA sequence. (from Genbank) |
| 431 | Lung | 0.2101254 | 0.4299512 | 0.347725 | 0.21885294 | U46499_at GLUTATHIONE S-TRANSFERASE, MICROSOMAL |
| 432 | Lung | 0.2099159 | 0.4297647 | 0.347623 | 0.2187152 | HG4058-HT4328_at Oncogene Aml1-Evi-1, Fusion Activated |

FIG. 6U

| | | | | | |
|---|---|---|---|---|---|
| 433 | Lung | 0.2097635 | 0.4295103 | 0.347362 | 0.218362651 | M31516_s_at | DAF Decay accelerating factor for complement (CD55, Cromer blood group system) |
| 434 | Lung | 0.2097511 | 0.429289 | 0.347286 | 0.218449224 | U78294_at | Arachidonate 15-lipoxygenase, second type |
| 435 | Lung | 0.209544 | 0.4290964 | 0.347251 | 0.218392114_at | RC_AA1578 | EST: zo35h03.s1 Stratagene colon (#937204) Homo sapiens cDNA clone 588917 3', mRNA sequence. (from Genbank) |
| 436 | Lung | 0.2095305 | 0.4289351 | 0.347231 | 0.218364022 | M95740_at | IDUA Iduronidase, alpha-L- |
| 437 | Lung | 0.2094368 | 0.4287938 | 0.347176 | 0.218221811 | M10321_s_a_t | VON WILLEBRAND FACTOR PRECURSOR |
| 438 | Lung | 0.2090187 | 0.4287123 | 0.346952 | 0.218105477 1_at | RC_AA2917 | EST: zt45g06.s1 Soares ovary tumor NbHOT Homo sapiens cDNA clone 725338 3', mRNA sequence. (from Genbank) |
| 439 | Lung | 0.2082064 | 0.428611 | 0.346904 | 0.217994189_at | RC_AA4646 | EST: zx82a03.s1 Soares ovary tumor NbHOT Homo sapiens cDNA clone 810220 3', mRNA sequence. (from Genbank) |
| 440 | Lung | 0.2078301 | 0.4284413 | 0.34687 | 0.217850954 6_at | RC_AA4180 | EST: zv97f10.s1 Soares NhHMPu S1 Homo sapiens cDNA clone 767755 3', mRNA sequence. (from Genbank) |
| 441 | Lung | 0.2068907 | 0.4283747 | 0.346675 | 0.217726082 6_at | RC_AA2279 | EST: zr56a07.s1 Soares NhHMPu S1 Homo sapiens cDNA clone 667380 3', mRNA sequence. (from Genbank) |
| 442 | Lung | 0.2068767 | 0.4283747 | 0.346674 | 0.217595333 t | AA085138_a | ZnO1a07.r1 Stratagene colon HT29 (#937221) Homo sapiens cDNA clone 546132 5' similar to gb:M34539 FK506-BINDING PROTEIN (HUMAN);, mRNA sequence. (from Genbank) |
| 443 | Lung | 0.2061588 | 0.4282722 | 0.346576 | 0.217421084 HT4232_at | HG3962- | Sialyltransferase, Slx |
| 444 | Lung | 0.2059874 | 0.428027 | 0.346462 | 0.217316755 HT5197_at | HG4749- | Calmitine Calcium-Binding Protein, Mitochondrial |
| 445 | Lung | 0.2056971 | 0.4277479 | 0.346384 | 0.2172754645_at | RC_AA4634 | Homo sapiens KIAA0439 mRNA, partial cds |
| 446 | Lung | 0.2056753 | 0.4277385 | 0.346345 | 0.2171322293_at | U89336_cds | RAGE gene (receptor for advanced glycosylation end products) extracted from Human HLA class III region containing NOTCH4 gene, partial sequence, homeobox PBX2 (HPBX) gene, receptor for advanced glycosylation end products (RAGE) gene, and 6 unidentified cds, complete sequence |
| 447 | Lung | 0.2055376 | 0.427707 | 0.345998 | 0.217052247 | D87937_at | Alpha(1,2)fucosyltransferase, 5'UTR partial sequence |
| 448 | Lung | 0.2055319 | 0.4276571 | 0.345845 | 0.216980316 1_at | RC_AA0545 | EST: zk83lo3.s1 Soares pregnant uterus NbHPU Homo sapiens cDNA clone 489461 3', mRNA sequence. (from Genbank) |
| 449 | Lung | 0.2052905 | 0.4274889 | 0.345738 | 0.216893378 | L44367_at | EST: Homo sapiens thymus mRNA (randomly primed, normalized), single-pass sequence, mRNA sequence. (from Genbank) |
| 450 | Lung | 0.2050517 | 0.4274542 | 0.345642 | 0.216673831 t | H81448_s_a | EST: yr75e04.r1 Homo sapiens cDNA clone 211134 5'. (from Genbank) |
| 451 | Lung | 0.2050112 | 0.4274464 | 0.345535 | 0.216564971 1_at-2 | U65437_ma | Homeo box gene expressed in ES cells; Rathke pouch homeo box |

FIG. 6V

| # | Tissue | | | | ID | Description |
|---|---|---|---|---|---|---|
| 452 | Lung | 0.2050112 | 0.4272526 | 0.345447 | 0.216447981 U65437_rna 1_at | Homeodomain-containing protein (HANF) gene, partial cds |
| 453 | Lung | 0.2049606 | 0.4272433 | 0.345363 | 0.21627795 RC_AA4960 53_at | EST: zv72f05.s1 Soares total fetus Nb2HF8 9w Homo sapiens cDNA clone 759201 3' similar to SW:RSP5_YEAST P39940 RSP5 PROTEIN ;, mRNA sequence. (from Genbank) |
| 454 | Lung | 0.2048765 | 0.4272302 | 0.345348 | 0.21620359 U89995_at | DNA binding protein FKHL15 (FKHL15) mRNA |
| 455 | Lung | 0.2048765 | 0.4271686 | 0.345056 | 0.21611412 U89995_at-2 | Forkhead (Drosophila)-like 15 |
| 456 | Lung | 0.2048381 | 0.4270829 | 0.345007 | 0.21604095 AA112799_a t | EST: zn62h02.r1 Stratagene muscle 937209 Homo sapiens cDNA clone 562803 5', mRNA sequence. (from Genbank) |
| 457 | Lung | 0.2047669 | 0.4269871 | 0.34491 | 0.21596743 RC_AA4494 16_at | EST: zx05a09.s1 Soares total fetus Nb2HF8 9w Homo sapiens cDNA clone 785560 3', mRNA sequence. (from Genbank) |
| 458 | Lung | 0.2043166 | 0.4265874 | 0.344875 | 0.21581881 RC_AA4248 06_at | Biphenyl hydrolase-like (serine hydrolase) |
| 459 | Lung | 0.2038577 | 0.4265876 | 0.344738 | 0.21564978 Y08134_at | ASM-like phosphodiesterase 3b |
| 460 | Lung | 0.2038577 | 0.4265278 | 0.344567 | 0.21552551 Y08134_at-2 | H.sapiens mRNA for ASM-like phosphodiesterase 3b |
| 461 | Lung | 0.2034993 | 0.4264408 | 0.344288 | 0.21540318 D55696_at | Cysteine protease |
| 462 | Lung | 0.2032563 | 0.4263962 | 0.344231 | 0.21521159 L42354_at | (clone 48ES4) mRNA fragment |
| 463 | Lung | 0.203038 | 0.4263259 | 0.344101 | 0.21512045 RC_AA2349 76_at | EST: zr50b04.s1 Soares NhHMPu S1 Homo sapiens cDNA clone 666799 3', mRNA sequence. (from Genbank) |
| 464 | Lung | 0.2026887 | 0.4263107 | 0.344042 | 0.21504399 HG1078-HT1078_at | Lamin-Like Protein (Gb:M24732) |
| 465 | Lung | 0.2025169 | 0.4262234 | 0.343966 | 0.21492204 RC_AA2243 51_f_at | EST: zr12f12.s1 Stratagene hNT neuron (#937233) Homo sapiens cDNA clone 648623 3', mRNA sequence. (from Genbank) |
| 466 | Lung | 0.2024834 | 0.4261604 | 0.343913 | 0.21481012 RC_AA3043 44_f_at | EST: EST17092 Aorta endothelial cells, TNF alpha-treated Homo sapiens cDNA 3' end similar to EST containing Alu repeat, mRNA sequence. (from Genbank) |
| 467 | Lung | 0.2021588 | 0.426129 | 0.343761 | 0.2146979 S37730_s_at | Insulin-like growth factor binding protein-2 [human, placenta, Genomic, 1342 nt, segment 4 of 4] |
| 468 | Lung | 0.2020334 | 0.4260459 | 0.343703 | 0.21461599 RC_AA4787 26_at | EST: zv14d09.s1 Soares NhHMPu S1 Homo sapiens cDNA clone 753617 3', mRNA sequence. (from Genbank) |
| 469 | Lung | 0.2019281 | 0.4260064 | 0.343596 | 0.21446498 U27328_s_a t | Fucosyltransferase 3 (galactoside 3(4)-L-fucosyltransferase, Lewis blood group included) |
| 470 | Lung | 0.2017605 | 0.425509 | 0.343584 | 0.21434529 U50330_at | BMP1 Bone morphogenetic protein 1 |
| 471 | Lung | 0.2015055 | 0.4254967 | 0.34353 | 0.21422687 L11353_at | NF2 Neurofibromin 2 (bilateral acoustic neuroma) |
| 472 | Lung | 0.2014937 | 0.4253253 | 0.343355 | 0.21413274 IL4_at | No info for gene |
| 473 | Lung | 0.2014057 | 0.4252684 | 0.343285 | 0.2141196 U29091_at | Selenium-binding protein (hSBP) mRNA |
| 474 | Lung | 0.2014027 | 0.4250385 | 0.34312 | 0.21393813 M31606_at | PHKG2 Phosphorylase kinase, gamma 2 (testis) |

FIG. 6W

| # | Tissue | Col3 | Col4 | Col5 | ID | Description |
|---|---|---|---|---|---|---|
| 475 | Lung | 0.2013618 | 0.4249189 | 0.342704 | 0.21381254 T61997_at | EST: yb97a01.r1 Homo sapiens cDNA clone 79080 5'. (from Genbank) |
| 476 | Lung | 0.2013092 | 0.4247117 | 0.342651 | 0.21372266 RC_AA4436 67_at | EST: zw86b07.s1 Soares total fetus Nb2HF8 9w Homo sapiens cDNA clone 783829 3', mRNA sequence. (from Genbank) |
| 477 | Lung | 0.2011409 | 0.4244892 | 0.342415 | 0.2136602 RC_AA4056 98_at | EST: zu66e10.s1 Soares testis NHT Homo sapiens cDNA clone 742986 3', mRNA sequence. (from Genbank) |
| 478 | Lung | 0.2008185 | 0.4244482 | 0.342406 | 0.21353971 W29115_at | EST: 56e8 Human retina cDNA randomly primed sublibrary Homo sapiens cDNA, mRNA sequence. (from Genbank) |
| 479 | Lung | 0.2000599 | 0.4243616 | 0.342179 | 0.21345186 AA279513_a t | EST: zs87g12.r1 NCI_CGAP_GCB1 Homo sapiens cDNA clone IMAGE:704518 5' similar to SW:CAH5_HUMAN P35218 CARBONIC ANHYDRASE V PRECURSOR ;. mRNA sequence. (from Genbank) |
| 480 | Lung | 0.1999584 | 0.4242009 | 0.342091 | 0.21336243 W28988_at | EST: 54f5 Human retina cDNA randomly primed sublibrary Homo sapiens cDNA, mRNA sequence. (from Genbank) |
| 481 | Lung | 0.1998813 | 0.4241411 | 0.342084 | 0.21318842 RC_AA4238 20_at | EST: zv33f03.s1 Soares ovary tumor NbHOT Homo sapiens cDNA clone 755453 3', mRNA sequence. (from Genbank) |
| 482 | Lung | 0.1996655 | 0.424125 | 0.342075 | 0.21297514 M14123_xpt _at | Neutral protease large subunit from Human endogenous retrovirus HERV-K10./ntype=DNA./annot=CDS |
| 483 | Lung | 0.1993467 | 0.4239705 | 0.341954 | 0.21283978 M86849_at | Connexin 26 (GJB2) mRNA |
| 484 | Lung | 0.1991327 | 0.4239197 | 0.341923 | 0.2127732 RC_D19672 _at | EST: Human HL60 3'directed MboI cDNA, HUMGS00627, clone mm2330, mRNA sequence. (from Genbank) |
| 485 | Lung | 0.1990886 | 0.4238464 | 0.341905 | 0.21264641 K02882_cds 1_s_at | IGHD gene (immunoglobulin delta-chain) extracted from Human germline IgD chain gene, C-region, C-delta-1 domain |
| 486 | Lung | 0.1987727 | 0.4236789 | 0.341905 | 0.21245435 RC_AA4771 33_at | EST: zu37f05.s1 Soares ovary tumor NbHOT Homo sapiens cDNA clone 740193 3', mRNA sequence. (from Genbank) |
| 487 | Lung | 0.1982116 | 0.4234348 | 0.341777 | 0.21233281 L22647_s_at | Prostaglandin E receptor 1 (subtype EP1), 42kD |
| 488 | Lung | 0.1981918 | 0.4233534 | 0.34173 | 0.21229628 X99977_at | H.sapiens ARS gene, component B |
| 489 | Lung | 0.1977862 | 0.4232468 | 0.341715 | 0.21220071 RC_AA4188 57_at | EST: zv98g02.s1 Soares NhHMPu S1 Homo sapiens cDNA clone 767858 3', mRNA sequence. (from Genbank) |
| 490 | Lung | 0.1976121 | 0.423027 | 0.341614 | 0.21207762 J02876_at | FOLATE RECEPTOR BETA PRECURSOR |
| 491 | Lung | 0.1972662 | 0.422857 | 0.341331 | 0.21199884 RC_AA4282 40_at | EST: zw51d04.s1 Soares total fetus Nb2HF8 9w Homo sapiens cDNA clone 773575 3', mRNA sequence. (from Genbank) |
| 492 | Lung | 0.1969504 | 0.4227888 | 0.341322 | 0.2119403 X16832_at | CTSH Cathepsin H |
| 493 | Lung | 0.1968705 | 0.4227419 | 0.341281 | 0.2118858 X02612_at | CYP1A1 Cytochrome P450, subfamily I (aromatic compound-inducible), polypeptide 1 |
| 494 | Lung | 0.1964423 | 0.4227419 | 0.341161 | 0.21168528 U10099_s_a t | ZONA PELLUCIDA SPERM-BINDING PROTEIN 3A PRECURSOR |
| 495 | Lung | 0.1958027 | 0.4226115 | 0.341156 | 0.21165162 Y08417_s_at | CHRNB3 Cholinergic receptor, nicotinic, beta polypeptide 3 |

FIG. 6X

| | | | | | | |
|---|---|---|---|---|---|---|
| 496 | Lung | 0.1954674 | 0.4225632 | 0.340968 | 0.211149278 | RC_AA216589_at | EST: zq94e07.s1 Stratagene NT2 neuronal precursor 937230 Homo sapiens cDNA clone 649668 3', mRNA sequence. (from Genbank) |
| 497 | Lung | 0.1951269 | 0.4224565 | 0.340791 | 0.211134602 | M19888_at | SPRR1B Small proline-rich protein 1B (cornifin) |
| 498 | Lung | 0.1950906 | 0.422343 | 0.340617 | 0.211125698 | RC_AA251845_at | EST: zs09e08.s1 NCI_CGAP_GCB1 Homo sapiens cDNA clone IMAGE:684710 3', mRNA sequence. (from Genbank) |
| 499 | Lung | 0.1949839 | 0.4218061 | 0.340504 | 0.211116346 | RC_AA085851_at | Homo sapiens clone 24658 mRNA sequence |
| 500 | Lung | 0.1947545 | 0.4217045 | 0.340486 | 0.21103089 | H87671_at | Yw15d02.r1 Homo sapiens cDNA clone 252291 5'. (from Genbank) |
| 501 | Lung | 0.1946286 | 0.4215694 | 0.340345 | 0.210094948 | AA478129_a_at | EST: zu42c09.r1 Soares ovary tumor NbHOT Homo sapiens cDNA clone 740656 5' similar to SW:BI3_MOUSE P28662 BRAIN PROTEIN I3.; mRNA sequence. (from Genbank) |
| 502 | Lung | 0.1945925 | 0.4215353 | 0.340341 | 0.210076483 | RC_AA005262_at | Homo sapiens DNA sequence from PAC 262D12 on chromosome 1q23.3-24.3. Contains a Tenascin (Hexabrachion, Cytotactin, Neuronectin, Myotendinous antigen)-LIKE gene and a mitochondrial/chloroplast 30S ribosomal protein S14-LIKE gene preceeded by a CpG island. Contains ESTs, genomic marker D1S2691 and STSs |
| 503 | Lung | 0.1945421 | 0.4215321 | 0.340195 | 0.210675972 | AA099995_a_at | Zm65e06.r1 Stratagene fibroblast (#937212) Homo sapiens cDNA clone 530530 5', mRNA sequence. (from Genbank) |
| 504 | Lung | 0.1940139 | 0.4213465 | 0.340048 | 0.210476216_at | RC_AA2566 | EST: zf86h05.s1 Soares NhHMPu S1 Homo sapiens cDNA clone 682617 3', mRNA sequence. (from Genbank) |
| 505 | Lung | 0.1938162 | 0.4213312 | 0.340048 | 0.210359562 | U64871_at | G protein-coupled receptor GPR-NGA gene |
| 506 | Lung | 0.1930866 | 0.4210407 | 0.340033 | 0.21014266 | RC_AA045136_at | EST: zk66e05.s1 Soares pregnant uterus NbHPU Homo sapiens cDNA clone 487808 3', mRNA sequence. (from Genbank) |
| 507 | Lung | 0.1927703 | 0.4209378 | 0.339926 | 0.210052273_at | RC_AA4065 | EST: zv11b09.s1 Soares NhHMPu S1 Homo sapiens cDNA clone 753305 3', mRNA sequence. (from Genbank) |
| 508 | Lung | 0.1927402 | 0.420889 | 0.339847 | 0.209981116_t | U51010_s_a | Nicotinamide N-methyltransferase gene, exon 1 and 5' flanking region |
| 509 | Lung | 0.192631 | 0.420854 | 0.339827 | 0.209829115_t | AA402121_a | EST: zt67e02.r1 Soares testis NHT Homo sapiens cDNA clone 727418 5', mRNA sequence. (from Genbank) |
| 510 | Lung | 0.1925233 | 0.4208244 | 0.339741 | 0.20967957_at | RC_AA0402 | EST: zf05e04.s1 Soares fetal heart NbHH19W Homo sapiens cDNA clone 376062 3', mRNA sequence. (from Genbank) |
| 511 | Lung | 0.1922924 | 0.4208244 | 0.339713 | 0.20962334 | RC_AA621159_at | EST: af61g01.s1 Soares NhHMPu S1 Homo sapiens cDNA clone 1046544 3', mRNA sequence. (from Genbank) |
| 512 | Lung | 0.1921844 | 0.4208062 | 0.339543 | 0.20954446 | RC_AA262308_at | EST: zr70g10.s1 Soares NhHMPu S1 Homo sapiens cDNA clone 668802 3', mRNA sequence. (from Genbank) |
| 513 | Lung | 0.1919594 | 0.4204926 | 0.339518 | 0.209378859 | R78309_at | EST: yi82b05.r1 Homo sapiens cDNA clone 145713 5'. (from Genbank) |

FIG. 6Y

| | | | | | | |
|---|---|---|---|---|---|---|
| 514 | Lung | 0.1915305 | 0.4203872 | 0.339457 | 0.20929658 | RC_AA3938 03_at | EST: zv64c05.s1 Soares total fetus Nb2HF8 9w Homo sapiens cDNA clone 758408 3', mRNA sequence. (from Genbank) |
| 515 | Lung | 0.1912515 | 0.4203647 | 0.339416 | 0.20924446 | L00205_at | KERATIN, TYPE II CYTOSKELETAL 6D |
| 516 | Lung | 0.1910615 | 0.4202727 | 0.33931 | 0.20910385 | RC_AA0629 15_at | Endothelin converting enzyme 1 |
| 517 | Lung | 0.19082 | 0.4200797 | 0.339181 | 0.20906146 | M24351_cds 3_s_at | PTHLH gene (parathyroid hormone-like protein A) extracted from Human parathyroid hormone-like protein (PLP) gene |
| 518 | Lung | 0.1908086 | 0.4199697 | 0.339056 | 0.20893884 | V01516_f_at | KERATIN, TYPE II CYTOSKELETAL 6D |
| 519 | Lung | 0.1906331 | 0.4197833 | 0.338948 | 0.20886692 | RC_AA4592 78_s_at | Homo sapiens connector enhancer of KSR-like protein CNK1 mRNA, complete cds |
| 520 | Lung | 0.1901662 | 0.4195934 | 0.33871 | 0.20881905 | RC_AA2846 87_at | EST: zt24a02.s1 Soares ovary tumor NbHOT Homo sapiens cDNA clone 714026 3', mRNA sequence. (from Genbank) |
| 521 | Lung | 0.1897348 | 0.4194072 | 0.338614 | 0.2086687 | AA447410_s_at | EST: zw93c10.r1 Soares total fetus Nb2HF8 9w Homo sapiens cDNA clone 784530 5', mRNA sequence. (from Genbank) |
| 522 | Lung | 0.1896246 | 0.4193492 | 0.338557 | 0.20855269 | M92449_at | LTR mRNA, 3' end of coding region and 3' flank |
| 523 | Lung | 0.1895064 | 0.4192633 | 0.338511 | 0.20846142 | U70370_at-2 | Human hindlimb expressed homeobox protein backfoot (Bft) mRNA, complete cds |
| 524 | Lung | 0.1895064 | 0.4192346 | 0.338359 | 0.20838776 | U70370_at | Hindlimb expressed homeobox protein backfoot (Bft) mRNA |
| 525 | Lung | 0.1844303 | 0.4190782 | 0.338218 | 0.20826498 | AA149008_a_t | EST: zn99g10.r1 Stratagene colon (#937204) Homo sapiens cDNA clone 566370 5' similar to contains Alu repetitive element;, mRNA sequence. (from Genbank) |
| 526 | Lung | 0.1891232 | 0.4189568 | 0.338168 | 0.20808844 | D31628_s_a_t | 4-HYDROXYPHENYLPYRUVATE DIOXYGENASE |
| 527 | Lung | 0.1889508 | 0.418781 | 0.33799 | 0.20796324 | RC_AA4822 24_f_at | EST: ab15c03.s1 Stratagene lung (#937210) Homo sapiens cDNA clone 840868 3', mRNA sequence. (from Genbank) |
| 528 | Lung | 0.1886343 | 0.4187364 | 0.33796 | 0.20783304 | RC_AA2932 66_at | EST: zt28b08.s1 Soares ovary tumor NbHOT Homo sapiens cDNA clone 714423 3', mRNA sequence. (from Genbank) |
| 529 | Lung | 0.188535 | 0.418455 | 0.337843 | 0.20773321 | X60382_rna 1_at | COL10A1 gene for collagen (alpha-1 type X) |
| 530 | Lung | 0.1884349 | 0.4182237 | 0.337771 | 0.20767878 | RC_AA4190 26_at | EST: zv34e11.s1 Soares ovary tumor NbHOT Homo sapiens cDNA clone 755564 3' similar to SW:PTN2_RAT P35233 PROTEIN-TYROSINE PHOSPHATASE PTP-S ;, mRNA sequence. (from Genbank) |
| 531 | Lung | 0.187921 | 0.4181424 | 0.337637 | 0.20753266 | U90437_at | RP1 homolog mRNA, 3'UTR region |
| 532 | Lung | 0.1875216 | 0.4179251 | 0.337637 | 0.20746535 | AA059489_a_t | EST: zl96b08.r1 Stratagene corneal stroma (#937222) Homo sapiens cDNA clone 512439 5', mRNA sequence. (from Genbank) |
| 533 | Lung | 0.1875204 | 0.4178397 | 0.337493 | 0.20733769 | RC_AA3986 06_at | EST: zt74a08.s1 Soares testis NHT Homo sapiens cDNA clone 728054 3', mRNA sequence. (from Genbank) |

FIG. 6Z

| | | | | | |
|---|---|---|---|---|---|
| 534 | Lung | 0.1874888 | 0.4178062 | 0.337434 | 0.20723632 | U92971_at | Protease-activated receptor 3 (PAR3) mRNA |
| 535 | Lung | 0.1874888 | 0.4177079 | 0.337288 | 0.2071424 | U92971_at-2 | Coagulation factor II (thrombin) receptor-like 2 |
| 536 | Lung | 0.1870525 | 0.417677 | 0.337274 | 0.20709419 | AA115605_a_t | HEAT SHOCK 70 KD PROTEIN 1 |
| 537 | Lung | 0.1865084 | 0.4173896 | 0.337251 | 0.20700532 | D49742_at | HGF activator like protein |
| 538 | Lung | 0.1864699 | 0.4173372 | 0.337199 | 0.20678568 | U79258_at | Clone 23732 mRNA, partial cds |
| 539 | Lung | 0.1863133 | 0.4168765 | 0.337039 | 0.20670204 | N78005_at | Homo sapiens SRp46 splicing factor retropseudogene mRNA |
| 540 | Lung | 0.1862135 | 0.4167521 | 0.336992 | 0.20556496 | AA250804_a_t | EST: zs06a01.r1 NCI_CGAP_GCB1 Homo sapiens cDNA clone IMAGE:684360 5', mRNA sequence. (from Genbank) |
| 541 | Lung | 0.186195 | 0.4166836 | 0.336973 | 0.2064239 | RC_AA2363 56_at | Zr54a11.s1 Soares_NhHMPu_S1 Homo sapiens cDNA clone IMAGE:667196 3', mRNA sequence |
| 542 | Lung | 0.1859639 | 0.4165951 | 0.336705 | 0.20635933 | D31417_at | EST: Human fetal-lung cDNA 5'-end sequence, mRNA sequence. (from Genbank) |
| 543 | Lung | 0.1857352 | 0.4163893 | 0.336634 | 0.20627302 | X85781_s_a_t | NOS2 gene, exon 27 |
| 544 | Lung | 0.1855199 | 0.4163481 | 0.336564 | 0.20614211 | R46311_at | EST: yj53f04.r1 Homo sapiens cDNA clone 152479 5'. (from Genbank) |
| 545 | Lung | 0.185402 | 0.416087 | 0.336356 | 0.20605162 | RC_AA4303 88_at | EST: zw23c04.s1 Soares ovary tumor NbHOT Homo sapiens cDNA clone 770118 3' similar to TR:E243387 E243387 ORF YGR038W.; mRNA sequence. (from Genbank) |
| 546 | Lung | 0.1852733 | 0.4160021 | 0.336139 | 0.20597522 | RC_AA4460 27_s_at | Early growth response 2 (Krox-20 (Drosophila) homolog) |
| 547 | Lung | 0.1849999 | 0.41589 | 0.336061 | 0.20589226 | U03056_at | Hyaluronoglucosaminidase 1 (HYAL1) mRNA |
| 548 | Lung | 0.1849384 | 0.4157496 | 0.335964 | 0.20574966 | RC_AA0630 68_at | EST: zf67e04.s1 Soares pineal gland N3HPG Homo sapiens cDNA clone 382014 3', mRNA sequence. (from Genbank) |
| 549 | Lung | 0.184717 | 0.4155971 | 0.335957 | 0.20566192 | RC_AA2338 41_at | EST: zr49a12.s1 Soares NhHMPu_S1 Homo sapiens cDNA clone 666718 3', mRNA sequence. (from Genbank) |
| 550 | Lung | 0.1845714 | 0.4154634 | 0.335825 | 0.20564336 | RC_AA1612 92_s_at | Interferon, alpha-inducible protein 27 |
| 551 | Lung | 0.1843069 | 0.4154162 | 0.335694 | 0.2055074 | AA249611_a_t | SH3-binding domain glutamic acid-rich protein |
| 552 | Lung | 0.1839211 | 0.4152409 | 0.335685 | 0.20543978 | AA431876_a_t | EST: zw51h07.r1 Soares total fetus Nb2HF8 9w Homo sapiens cDNA clone 773629 5', mRNA sequence. (from Genbank) |
| 553 | Lung | 0.1837888 | 0.4150792 | 0.33558 | 0.20533098 | AB000381_s_at | DNA for GPI-anchored molecule-like protein |
| 554 | Lung | 0.1837856 | 0.4150223 | 0.335482 | 0.20513515 | RC_AA2349 25_at | EST: zr78g10.s1 Soares NhHMPu_S1 Homo sapiens cDNA clone 669570 3' similar to contains Alu repetitive element., mRNA sequence. (from Genbank) |

FIG. 6A2

| | | | | | |
|---|---|---|---|---|---|
| 555 | Lung | 0.1834805 | 0.4149307 | 0.33542 | 0.205113742 | RC_AA4469 6_s_at | UDP-Gal:betaGlcNAc beta 1,4- galactosyltransferase, polypeptide 4 |
| 556 | Lung | 0.183406 | 0.4149191 | 0.335395 | 0.2050176 | W28045_at | EST: 41b8 Human retina cDNA randomly primed sublibrary Homo sapiens cDNA, mRNA sequence. (from Genbank) |
| 557 | Lung | 0.1832835 | 0.4147922 | 0.335371 | 0.204966723 93_at | RC_AA0561 | EST: zl65e03.s1 Stratagene colon (#937204) Homo sapiens cDNA clone 509500 3' similar to TR:G809573 G809573 GLUTAREDOXIN. ;. mRNA sequence. (from Genbank) |
| 558 | Lung | 0.1828422 | 0.4147421 | 0.335312 | 0.204857321_at | RC_AA1485 | EST: zl06h05.s1 Soares pregnant uterus NbHPU Homo sapiens cDNA clone 491577 3' similar to contains L1.t1 L1 repetitive element ;. mRNA sequence. (from Genbank) |
| 559 | Lung | 0.1825209 | 0.4147089 | 0.335161 | 0.204774893 2_at | RC_AA2554 | EST: zr85f08.s1 Soares NhHMPu S1 Homo sapiens cDNA clone 682503 3'. mRNA sequence. (from Genbank) |
| 560 | Lung | 0.1824035 | 0.414677 | 0.335147 | 0.204644043 t | AA443479_a | Nuclear restricted protein, BTB domain-like (brain) |
| 561 | Lung | 0.1823459 | 0.414663 | 0.335126 | 0.204532120 31883_at | | KIAA0059 gene |
| 562 | Lung | 0.1822367 | 0.4146355 | 0.335104 | 0.204522294 U01062_at | | ITPR3 Inositol 1,4,5-triphosphate receptor, type 3 |
| 563 | Lung | 0.1822326 | 0.4145642 | 0.33488 | 0.2043247 t | AA203296_a | EST: zx58g04.r1 Soares fetal liver spleen 1NFLS S1 Homo sapiens cDNA clone 446742 5' similar to contains element MER11 repetitive element ;. mRNA sequence. (from Genbank) |
| 564 | Lung | 0.182101 | 0.4143828 | 0.334771 | 0.204238746 9_at | RC_AA4900 | EST: ab05d09.s1 Stratagene fetal retina 937202 Homo sapiens cDNA clone 839921 3'. mRNA sequence. (from Genbank) |
| 565 | Lung | 0.1820915 | 0.4141098 | 0.334768 | 0.204159751 | AA309871_a | H.sapiens mRNA for M-phase phosphoprotein, mpp9 |
| 566 | Lung | 0.1819542 | 0.4140379 | 0.334706 | 0.204067421 | X87870_at | HEPATOCYTE NUCLEAR FACTOR 4 |
| 567 | Lung | 0.1817741 | 0.4139458 | 0.334614 | 0.203957429 5_at | RC_AA2436 | Deoxynucleotidyltransferase, terminal |
| 568 | Lung | 0.1815623 | 0.413831 | 0.334419 | 0.203890877 7_at | RC_AA4566 | EST: aa01h03.s1 Soares NhHMPu S1 Homo sapiens cDNA clone 812021 3'. mRNA sequence. (from Genbank) |
| 569 | Lung | 0.1812931 | 0.4138197 | 0.334331 | 0.203802081 | N48927_at | EST: yy75e09.r1 Homo sapiens cDNA clone 279400 5'. (from Genbank) |
| 570 | Lung | 0.1809925 | 0.4136798 | 0.334273 | 0.203726370 6_at | RC_AA4240 | EST: zv79n09.s1 Soares total fetus Nb2HF8 9w l Homo sapiens cDNA clone 759905 3' similar to WP:B0024.13 CE05157 ;. mRNA sequence. (from Genbank) |
| 571 | Lung | 0.1807894 | 0.4136576 | 0.334175 | 0.203669321 M33666_at | | Pregnancy specific beta-1-glycoprotein 11 |
| 572 | Lung | 0.1801156 | 0.4135804 | 0.334084 | 0.2035926 1t | HG2090- HT2152_s_a | External Membrane Protein, 130 Kda (Gb:Z22971) |
| 573 | Lung | 0.1796636 | 0.4132178 | 0.333913 | 0.203441181 66_at | RC_AA4812 | IMAGE:815231 3'. mRNA sequence. (from Genbank) |

FIG. 6B2

| # | Tissue | | | | ID | Description |
|---|---|---|---|---|---|---|
| 574 | Lung | 0.1792251 | 0.4130711 | 0.333878 | AF001294_a_t | IPL (IPL) mRNA |
| 575 | Lung | 0.1789774 | 0.4130512 | 0.333833 | RC_AA2321 28_at | Sarcoglycan, epsilon |
| 576 | Lung | 0.1788631 | 0.4129976 | 0.333741 | RC_AA1957 20_at | 33 kDa transcriptional co-activator |
| 577 | Lung | 0.1786308 | 0.4128208 | 0.336676 | U41163_s_a t | Creatine transporter (SLC6A10) gene, partial cds |
| 578 | Lung | 0.1784864 | 0.412656 | 0.333362 | 0.20299609 J03258_at | VDR Vitamin D (1,25- dihydroxyvitamin D3) receptor |
| 579 | Lung | 0.1784352 | 0.4125812 | 0.333453 | RC_AA0228 84_at | EST: ze71c10.s1 Soares fetal heart NbHH19W Homo sapiens cDNA clone 364434 3', mRNA sequence. (from Genbank) |
| 580 | Lung | 0.1779975 | 0.4124382 | 0.333382 | RC_AA1499 40_at | GLUT1 C-terminal binding protein |
| 581 | Lung | 0.1779472 | 0.4124382 | 0.333313 | AA459545_f _at | EST: zx89d12.r1 Soares ovary tumor NbHOT Homo sapiens cDNA clone 810935 5', mRNA sequence. (from Genbank) |
| 582 | Lung | 0.1777566 | 0.4124372 | 0.333262 | 0.2027197 X51757_at | HSPA6 Heat shock 70kD protein 6 (HSP70B') |
| 583 | Lung | 0.1777566 | 0.4123559 | 0.333143 | 0.20251761 X51757_at-2 | Heat shock 70kD protein 6 (HSP70B') |
| 584 | Lung | 0.1775776 | 0.4123455 | 0.333082 | RC_AA6091 68_at | EST: af12a10.s1 Soares testis NHT Homo sapiens cDNA clone 1031418 3', mRNA sequence. (from Genbank) |
| 585 | Lung | 0.1773938 | 0.4123455 | 0.332971 | RC_AA1565 32_at | Homo sapiens interferon regulatory factor 6 (IRF6) mRNA, complete cds |
| 586 | Lung | 0.1773851 | 0.4122714 | 0.332968 | RC_AA0558 29_at | EST: zf21d10.s1 Soares fetal heart NbIHH19W Homo sapiens cDNA clone 377587 3' similar to contains Alu repetitive element; mRNA sequence. (from Genbank) |
| 587 | Lung | 0.1770672 | 0.4121855 | 0.332893 | 0.20211531 J02871_s_at | CYP4B1 Cytochrome P450 IVB1 |
| 588 | Lung | 0.1769539 | 0.4120433 | 0.332842 | RC_AA2435 62_at | EST: zs15h06.s1 NCI_CGAP_GCB1 Homo sapiens cDNA clone IMAGE:685307 3', mRNA sequence. (from Genbank) |
| 589 | Lung | 0.1767123 | 0.411992 | 0.332838 | RC_AA6091 31_at | EST: af11f03.s1 Soares testis NHT Homo sapiens cDNA clone 1031357 3', mRNA sequence. (from Genbank) |
| 590 | Lung | 0.1766792 | 0.4119014 | 0.332786 | RC_AA2581 30_at | EST: zs35f03.s1 NCI_CGAP_GCB1 Homo sapiens cDNA clone IMAGE:687197 3', mRNA sequence. (from Genbank) |
| 591 | Lung | 0.1765536 | 0.4116339 | 0.332738 | M62896_i_at | Human lipocortin (LIP) 2 pseudogene mRNA, complete cds-like region. (from Genbank) |
| 592 | Lung | 0.176391 | 0.4115647 | 0.332615 | AA094752_a t | Protein phosphatase 3 (formerly 2B), catalytic subunit, beta isoform (calcineurin A beta) |
| 593 | Lung | 0.1758538 | 0.4114534 | 0.332574 | 0.20171952 U32114_at | Caveolin-2 mRNA |
| 594 | Lung | 0.1756858 | 0.4112209 | 0.332498 | AFFX-LysX-3_at | AFFX-LysX-3_at (endogenous control) |

FIG. 6C2

| | | | | | | |
|---|---|---|---|---|---|---|
| 595 | Lung | 0.1756858 | 0.4110661 | 0.3323317 | 0.201569573_at-2 | AFFX-LysX-3_at | AFFX-LysX-3_at (miscellaneous control - 11k chips) |
| 596 | Lung | 0.1756189 | 0.4108433 | 0.332238 | 0.201147029 | D53639_at | Ribosomal protein S26 |
| 597 | Lung | 0.1754493 | 0.4108122 | 0.3322225 | 0.2012877 | AA074407_a_t | EST: zm15c08.r1 Stratagene pancreas (#937208) Homo sapiens cDNA clone 525710 5', mRNA sequence. (from Genbank) |
| 598 | Lung | 0.1751292 | 0.4106699 | 0.332118 | 0.20117259 | X05409_at | ALDH2 Aldehyde dehydrogenase 2, mitochondrial |
| 599 | Lung | 0.1751191 | 0.4106699 | 0.332109 | 0.201130526 2 | RC_AA2241 | EST: zr15d05.s1 Stratagene NT2 neuronal precursor 937230 Homo sapiens cDNA clone 663465 3', mRNA sequence. (from Genbank) |
| 600 | Lung | 0.1749851 | 0.4106589 | 0.331931 | 0.201109573_at | RC_D20490_at | EST: Human HL60 3'directed MboI cDNA, HUMGS01464, clone pm1439, mRNA sequence. (from Genbank) |
| 601 | Lung | 0.1749773 | 0.4106361 | 0.331699 | 0.201100032 | U34877_at | Biliverdin-IXalpha reductase mRNA |
| 602 | Lung | 0.1746583 | 0.4105441 | 0.331498 | 0.20092951 | M12963_s_a_t | ADH1 Alcohol dehydrogenase 1 (class I), alpha polypeptide |
| 603 | Lung | 0.1742481 | 0.4104374 | 0.331449 | 0.200814576_at | RC_AA4178_at | EST: zv05f04.s1 Soares NhHMPu S1 Homo sapiens cDNA clone 752767 3', mRNA sequence. (from Genbank) |
| 604 | Lung | 0.174243 | 0.4103815 | 0.331397 | 0.200749899 t | AA256220_a_t | EST: zr79b07.r1 Soares NhHMPu S1 Homo sapiens cDNA clone 681877 5', mRNA sequence. (from Genbank) |
| 605 | Lung | 0.1741477 | 0.4103065 | 0.331345 | 0.200588128 | D11428_at | PMP22 Peripheral myelin protein 22 |
| 606 | Lung | 0.1741265 | 0.4102918 | 0.3312 | 0.2005417 | M73077_at | Glucocorticoid receptor repression factor 1 (GRF-1) mRNA |
| 607 | Lung | 0.1740455 | 0.4101519 | 0.331197 | 0.200480894_at | RC_AA4787_at | EST: zv20o01.s1 Soares NhHMPu S1 Homo sapiens cDNA clone 754200 3', mRNA sequence. (from Genbank) |
| 608 | Lung | 0.174037 | 0.4101184 | 0.3311 | 0.200327133 | R77382_at | EST: yi75d09.r1 Homo sapiens cDNA clone 145073 5'. (from Genbank) |
| 609 | Lung | 0.1740171 | 0.4100366 | 0.331065 | 0.2002879 | W27334_at | Amyloid beta (A4) precursor protein (protease nexin-II, Alzheimer disease) |
| 610 | Lung | 0.1738587 | 0.4100316 | 0.330924 | 0.20021597 t | AA465601_a_t | EST: aa24h10.r1 NCI_CGAP_GCB1 Homo sapiens cDNA clone IMAGE:814243 5', mRNA sequence. (from Genbank) |
| 611 | Lung | 0.1738566 | 0.4099948 | 0.330884 | 0.2001832 | X56677_at | MYOD1 Myogenic factor 3 |
| 612 | Lung | 0.1736328 | 0.4098567 | 0.330859 | 0.20007320 8_at | RC_AA2343_at | EST: zr72a08.s1 Soares NhHMPu S1 Homo sapiens cDNA clone 668918 3', mRNA sequence. (from Genbank) |
| 613 | Lung | 0.1735341 | 0.4098147 | 0.330803 | 0.199926644_at | RC_AA4614_at | EST: zx68b01.s1 Soares total fetus Nb2HF8 9w Homo sapiens cDNA clone 796585 3', mRNA sequence. (from Genbank) |
| 614 | Lung | 0.1730271 | 0.4097906 | 0.330705 | 0.199980459 | R70086_at | Inhibitor of growth 1-like |
| 615 | Lung | 0.1729905 | 0.4097636 | 0.330516 | 0.199747744 0_at | RC_AA4358_at | High-mobility group (nonhistone chromosomal) protein 4 |
| 616 | Lung | 0.172933 | 0.4096595 | 0.330497 | 0.199626333_s_at | U47011 cds | Fibroblast growth factor 8 (androgen-induced) |
| 617 | Lung | 0.1727754 | 0.4096222 | 0.330496 | 0.1995362 | U62392_at | Homo sapiens zinc finger protein mRNA, complete cds |

FIG. 6D2

| | | | | | | |
|---|---|---|---|---|---|---|
| 618 | Lung | 0.1726794 | 0.4096209 | 0.330155 | 0.199457705 | RC_AA1820 01_r_at | EST: zp62f10.s1 Stratagene endothelial cell 937223 Homo sapiens cDNA clone 624811 3', mRNA sequence. (from Genbank) |
| 619 | Lung | 0.1726431 | 0.4095511 | 0.330045 | 0.199405495 | AA024428_a_t | EST: ze73e12.r1 Soares fetal heart NbHH19W Homo sapiens cDNA clone 364654 5', mRNA sequence. (from Genbank) |
| 620 | Lung | 0.172183 | 0.4095104 | 0.329832 | 0.199307933 | X17644_s_a_t | GSPT1 G1 to S phase transition 1 |
| 621 | Lung | 0.17712534 | 0.4094931 | 0.329715 | 0.199235518_s_at | RC_AA4498 | Human modulator recognition factor I (MRF-1) mRNA, 3' end |
| 622 | Lung | 0.1710514 | 0.4094373 | 0.329715 | 0.199105657 6_at | RC_AA6095 | KIAA0331 gene product |
| 623 | Lung | 0.1710219 | 0.4093424 | 0.329587 | 0.199041298 | R33301_at | EST: yh81g01.r1 Homo sapiens cDNA clone 136176 5' similar to contains MSR1 repetitive element ;. (from Genbank) |
| 624 | Lung | 0.1709628 | 0.409292 | 0.329483 | 0.198991223 5_at | RC_AA0567 | KIAA0755 gene product |
| 625 | Lung | 0.1709038 | 0.4091597 | 0.329393 | 0.198894871_at | X68264_rna | MUC18 gene (melanoma associated glycoprotein) extracted from H.sapiens MGF gene exons 1&2 |
| 626 | Lung | 0.1709003 | 0.4091567 | 0.329025 | 0.1987667 | AF003521_a_t | Jagged 2 |
| 627 | Lung | 0.1706247 | 0.4090712 | 0.328994 | 0.198727703 | U95090_at | Chromosome 19 cosmid F19541 |
| 628 | Lung | 0.1706247 | 0.4090124 | 0.328987 | 0.198673311 | U95090_at-2 | Homo sapiens chromosome 19 cosmid F19541 |
| 629 | Lung | 0.1705484 | 0.4088767 | 0.328945 | 0.198568724 9_at | RC_AA4497 | EST: zx07fe10.s1 Soares total fetus Nb2HF8_9w Homo sapiens cDNA clone 785802 3', mRNA sequence. (from Genbank) |
| 630 | Lung | 0.1705396 | 0.4088519 | 0.328934 | 0.198433470 8_at | RC_AA4286 | EST: zw69c09.s1 Soares testis NHT Homo sapiens cDNA clone 781456 3', mRNA sequence. (from Genbank) |
| 631 | Lung | 0.1699309 | 0.4088212 | 0.328932 | 0.198352639 1_at | RC_AA5999 | EST: ag28h10.s1 Jia bone marrow stroma Homo sapiens cDNA clone 1090915 3', mRNA sequence. (from Genbank) |
| 632 | Lung | 0.1697518 | 0.4087344 | 0.328778 | 0.198218_at | U21943_at | Organic anion transporting polypeptide (OATP) mRNA |
| 633 | Lung | 0.1696738 | 0.4086568 | 0.328629 | 0.198103225 1_at | RC_AA0253 | EST: ze74h03.s1 Soares fetal heart NbHH19W Homo sapiens cDNA clone 364757 3' similar to contains OFR.t1 OFR repetitive element ;. mRNA sequence. (from Genbank) |
| 634 | Lung | 0.1695444 | 0.4085296 | 0.32833 | 0.197898053 9_at | RC_AA1322 | EST: zo06h05.s1 Stratagene endothelial cell 937223 Homo sapiens cDNA clone 566937 3' similar to SW:YBF5_YEAST P34220 HYPOTHETICAL 47.4 KD PROTEIN IN SHP1-SEC17 INTERGENIC REGION. ;. mRNA sequence. (from Genbank) |
| 635 | Lung | 0.1693365 | 0.408468 | 0.32826 | 0.197802655 | Z11793_at | Selenoprotein P |
| 636 | Lung | 0.1693141 | 0.408138 | 0.328115 | 0.197695554 4_at | RC_AA4314 | EST: zw70f01.s1 Soares testis NHT Homo sapiens cDNA clone 781561 3', mRNA sequence. (from Genbank) |

FIG. 6E2

| # | Tissue | | | | ID | Description |
|---|---|---|---|---|---|---|
| 637 | Lung | 0.1692346 | 0.4080117 | 0.328104 | 0.19759662 | AA482319_f_at | EST: ab15c03.r1 Stratagene lung (#937210) Homo sapiens cDNA clone 840868 5', mRNA sequence. (from Genbank) |
| 638 | Lung | 0.1691924 | 0.4079298 | 0.328041 | 0.19753116 | W58612_at | EST: zd19g10.r1 Soares fetal heart NbHH19W Homo sapiens cDNA clone 341154 5', mRNA sequence. (from Genbank) |
| 639 | Lung | 0.1691511 | 0.4079298 | 0.32799 | 0.19742571 | L20860_at | Glycoprotein Ib beta mRNA |
| 640 | Lung | 0.168735 | 0.4078622 | 0.327851 | 0.19733652 | C01782_at | EST: HUMGS003737, Human Gene Signature, 3'-directed cDNA sequence, mRNA sequence. (from Genbank) |
| 641 | Lung | 0.1679861 | 0.4078375 | 0.327775 | 0.19730447 | RC_AA4482_38_at | Homo sapiens mRNA for KIAA0915 protein, complete cds |
| 642 | Lung | 0.1679423 | 0.4078113 | 0.327645 | 0.19723177 | RC_AA2923_05_s_at | EST: zt51f07.s1 Soares ovary tumor NbHOT Homo sapiens cDNA clone 725893 3', mRNA sequence. (from Genbank) |
| 643 | Lung | 0.1678808 | 0.4077995 | 0.327494 | 0.1971215 | RC_AA0016_63_at | EST: zh85b09.s1 Soares fetal liver spleen 1NFLS S1 Homo sapiens cDNA clone 428057 3', mRNA sequence. (from Genbank) |
| 644 | Lung | 0.1678641 | 0.4077946 | 0.327396 | 0.19702789 | M28249_at | ITGA2 Integrin, alpha 2 (CD49B, alpha 2 subunit of VLA-2 receptor) |
| 645 | Lung | 0.1678427 | 0.4076892 | 0.327369 | 0.19693778 | S82472_at | Beta-pol=DNA polymerase beta {exon alpha to exon VII region} [human, Genomic, 124 nt, segment 1 of 2] |
| 646 | Lung | 0.1677564 | 0.4076728 | 0.327288 | 0.19683264 | M88461_s_a | NPY1R Neuropeptide Y receptor Y1 |
| 647 | Lung | 0.1676219 | 0.4076345 | 0.327237 | 0.19676338 | HG429-HT429_at | B-Cell Growth Factor 1 |
| 648 | Lung | 0.1674928 | 0.4076067 | 0.32714 | 0.19671354 | HG371-HT26388_s_at | Mucin 1, Epithelial, Alt. Splice 9 |
| 649 | Lung | 0.1670751 | 0.4075646 | 0.326983 | 0.19662581 | RC_AA0265_97_at | EST: ze92h11.s1 Soares fetal heart NbHH19W Homo sapiens cDNA clone 366501 3', mRNA sequence. (from Genbank) |
| 650 | Lung | 0.1670111 | 0.4071792 | 0.326947 | 0.19656013 | RC_AA4120_82_at | EST: zt66g12.s1 Soares testis NHT Homo sapiens cDNA clone 727366 3', mRNA sequence. (from Genbank) |
| 651 | Lung | 0.1668522 | 0.4069711 | 0.326899 | 0.19653678 | AFFX-HUMGAPDH/M33197_3_st-2 | Glyceraldehyde-3-phosphate dehydrogenase |
| 652 | Lung | 0.1668522 | 0.4069277 | 0.326872 | 0.19647944 | AFFX-HUMGAPDH/M33197_3_st | AFFX-HUMGAPDH/M33197_3_st (endogenous control) |
| 653 | Lung | 0.1667838 | 0.4068303 | 0.326832 | 0.19635656 | RC_AA4656_87_at | RNA binding motif, single stranded interacting protein 1 |

FIG. 6F2

| # | Tissue | | | | ID | Description |
|---|---|---|---|---|---|---|
| 654 | Lung | 0.1667251 | 0.4068004 | 0.32665 | 0.19628835 | RC_AA6217 51_at | EST: af06c06.s1 Soares testis NHT Homo sapiens cDNA clone 1030858 3', mRNA sequence. (from Genbank) |
| 655 | Lung | 0.1666787 | 0.4067025 | 0.32664 | 0.1961289 | M58286_s_a t | TNFR1 Tumor necrosis factor receptor 1 (55kD) |
| 656 | Lung | 0.1663081 | 0.4065947 | 0.326593 | 0.19605476 | M69225_at | Bullous pemphigoid antigen (BPAG1) mRNA |
| 657 | Lung | 0.1662385 | 0.4065902 | 0.326535 | 0.19599803 | AA328993_s _at | EST: EST32546 Embryo, 12 week I Homo sapiens cDNA 5' end, mRNA sequence. (from Genbank) |
| 658 | Lung | 0.1658361 | 0.4064042 | 0.326349 | 0.19586013 | U33749_s_a t | Transcription termination factor, RNA polymerase I |
| 659 | Lung | 0.1654775 | 0.4063645 | 0.326348 | 0.19579284 | X82850_s_a t | TTF1 Transcription termination factor, RNA polymerase I |
| 660 | Lung | 0.1654435 | 0.4063256 | 0.326299 | 0.19572937 | RC_AA0163 06_at | EST: ze38e03.s1 Soares retina N2b4HR Homo sapiens cDNA clone 361276 3', mRNA sequence. (from Genbank) |
| 661 | Lung | 0.1653326 | 0.4063256 | 0.326291 | 0.19564575 | U11862_s_a t | ABP1 Amiloride binding protein 1 (amine oxidase (copper-containing)) |
| 662 | Lung | 0.1652815 | 0.4062697 | 0.325892 | 0.19548824 | RC_AA0209 25_at | EST: ze64b11.s1 Soares retina N2b4HR Homo sapiens cDNA clone 363741 3', mRNA sequence. (from Genbank) |
| 663 | Lung | 0.1650641 | 0.4061297 | 0.325863 | 0.19539194 | AA059327_i _at | EST: zf65e11.r1 Soares retina N2b4HR Homo sapiens cDNA clone 381836 5', mRNA sequence. (from Genbank) |
| 664 | Lung | 0.1647899 | 0.4061297 | 0.325836 | 0.19532411 | RC_AA3983 68_at | EST: zf60g04.s1 Soares testis NHT Homo sapiens cDNA clone 726774 3', mRNA sequence. (from Genbank) |
| 665 | Lung | 0.164668 | 0.406011 | 0.325815 | 0.1952033 | M21389_at | KRT5 Keratin 5 (epidermolysis bullosa simplex, Dowling-Meara/Kobner/Weber-Cockayne types) |
| 666 | Lung | 0.1643513 | 0.405869 | 0.325575 | 0.19513659 | N28707_at | EST: yx66d11.r1 Homo sapiens cDNA clone 266709 5'. (from Genbank) |
| 667 | Lung | 0.1641693 | 0.4057203 | 0.325569 | 0.19505616 | AF000959_a t | Transmembrane protein mRNA |
| 668 | Lung | 0.1641491 | 0.4056871 | 0.325556 | 0.19498733 | RC_AA4785 17_at | EST: zw95d09.s1 Soares total fetus Nb2HF8 9w Homo sapiens cDNA clone 784721 3', mRNA sequence. (from Genbank) |
| 669 | Lung | 0.1641174 | 0.4056812 | 0.325556 | 0.19492373 | RC_AA4534 58_at | EST: zx45b04.s1 Soares testis NHT Homo sapiens cDNA clone 795151 3', mRNA sequence. (from Genbank) |
| 670 | Lung | 0.1638896 | 0.4056676 | 0.325412 | 0.19482031 | W26652_at | EST: 34c6 Human retina cDNA randomly primed sublibrary Homo sapiens cDNA, mRNA sequence. (from Genbank) |
| 671 | Lung | 0.1637483 | 0.4055148 | 0.32536 | 0.19481373 | RC_AA0859 34_at | EST: zn54c11.s1 Stratagene muscle 937209 Homo sapiens cDNA clone 562004 3' similar to WP:B0035.3 CE05161 VIRAL NON-STRUCTURAL PROTEIN LIKE ;, mRNA sequence. (from Genbank) |
| 672 | Lung | 0.1636582 | 0.4054967 | 0.325529 | 0.19469741 | X95715_at | EST: zu81d06.s1 Soares testis NHT Homo sapiens cDNA clone 744395 3', mRNA sequence. (from Genbank) |
| 673 | Lung | 0.1635511 | 0.4054483 | 0.325278 | 0.19450822 | RC_AA6212 02_at | Anthracycline resistance associated protein |

FIG. 6G2

| # | Tissue | | | | ID | Description |
|---|---|---|---|---|---|---|
| 674 | Lung | 0.1635163 | 0.4053991 | 0.325183 | C00125_s_at | EST; HUMGS0005758, Human Gene Signature, 3'-directed cDNA sequence, mRNA sequence. (from Genbank) |
| 675 | Lung | 0.1634756 | 0.4053788 | 0.325151 | RC_AA3656 91_at | EST: EST76520 Pineal gland II Homo sapiens cDNA 3' end, mRNA sequence. (from Genbank) |
| 676 | Lung | 0.1633382 | 0.4052712 | 0.325131 | R81773_at | EST: yj05h02.r1 Homo sapiens cDNA clone 147891 5'. (from Genbank) |
| 677 | Lung | 0.1629665 | 0.4052194 | 0.325131 | RC_AA2271 37_at | Homo sapiens mRNA for KIAA0828 protein, partial cds |
| 678 | Lung | 0.1629425 | 0.4051319 | 0.325034 | W73205_at | H.sapiens mRNA for ITBA2 protein |
| 679 | Lung | 0.162857 | 0.405015 | 0.324802 | S67325_at | PCCB Propionyl Coenzyme A carboxylase, beta polypeptide |
| 680 | Lung | 0.1628385 | 0.4049314 | 0.32464 | U00951_at | Clone A9A2BR11 (CAC)n/(GTG)n repeat-containing mRNA |
| 681 | Lung | 0.1628385 | 0.4046706 | 0.324633 | U00951_at-2 | Human clone A9A2BR11 (CAC)n/(GTG)n repeat-containing mRNA |
| 682 | Lung | 0.1626987 | 0.404662 | 0.324588 | RC_AA4638 61_at | EST: zx97c05.s1 Soares NhHMPu S1 Homo sapiens cDNA clone 8116888 3' similar to SW:RB25_RABIT P46629 RAS-RELATED PROTEIN RAB-25. ;, mRNA sequence. (from Genbank) |
| 683 | Lung | 0.1625888 | 0.4046579 | 0.324578 | M22976_at | CYB5 Cytochrome b-5 |
| 684 | Lung | 0.1625832 | 0.4046481 | 0.324551 | N57397_at | EST: yw82a03.r1 Homo sapiens cDNA clone 258700 5' similar to contains Alu repetitive element;. (from Genbank) |
| 685 | Lung | 0.1625642 | 0.4045725 | 0.324433 | RC_AA2817 43_r_at | EST: zt06h05.s1 NCI_CGAP_GCB1 Homo sapiens cDNA clone IMAGE:712377 3';, mRNA sequence. (from Genbank) |
| 686 | Lung | 0.1625272 | 0.4044692 | 0.324433 | AA393903_a t | EST: zt85e04.r1 Soares testis NHT Homo sapiens cDNA clone 729150 5', mRNA sequence. (from Genbank) |
| 687 | Lung | 0.1624313 | 0.4044175 | 0.324413 | RC_AA4859 45_at | EST: ab40g02.s1 Stratagene HeLa cell s3 937216 Homo sapiens cDNA clone 843314 3' similar to SW:SOH1_YEAST P38633 SOH1 PROTEIN. [1] ;, mRNA sequence. (from Genbank) |
| 688 | Lung | 0.162345 | 0.4044085 | 0.324361 | M90820_at | FKBP3 FK506-binding protein 3 (25kD) |
| 689 | Lung | 0.1622701 | 0.4043581 | 0.324304 | L02870_s_at | Collagen, type VII, alpha 1 (epidermolysis bullosa, dystrophic, dominant and recessive) |
| 690 | Lung | 0.1622288 | 0.4043215 | 0.323979 | Y10260_at | EYA1A gene |
| 691 | Lung | 0.162208 | 0.4043183 | 0.323945 | U83668_ma 1_at | Human beta-tubulin (TUB4q) gene, complete cds. (from Genbank) |
| 692 | Lung | 0.1620144 | 0.4042932 | 0.323915 | U39447_at | Placenta copper monamine oxidase mRNA |
| 693 | Lung | 0.1619355 | 0.4042848 | 0.323732 | RC_AA4781 09_at | EST: zt89d04.s1 Soares testis NHT Homo sapiens cDNA clone 729511 3', mRNA sequence. (from Genbank) |
| 694 | Lung | 0.1618381 | 0.4042658 | 0.323732 | J04076_at | EGR2 Early growth response 2 (Krox-20 (Drosophila) homolog) |
| 695 | Lung | 0.1618337 | 0.4041261 | 0.323615 | J04093_s_at | UDP-GLUCURONOSYLTRANSFERASE 1F PRECURSOR, MICROSOMAL |

FIG. 6H2

| # | Tissue | | | | | Description |
|---|---|---|---|---|---|---|
| 696 | Lung | 0.1617138 | 0.4039294 | 0.323484 | AA488793_a t | Aa54d11.r1 NCI_CGAP_GCB1 Homo sapiens cDNA clone IMAGE:824757 5', mRNA sequence. (from Genbank) |
| 697 | Lung | 0.161703 | 0.4039294 | 0.323406 | 0.19232956 RC_AA4497 20_s_at | Homo sapiens clone 24706 mRNA sequence |
| 698 | Lung | 0.1616854 | 0.4038564 | 0.32339 | 0.19225854 L36531_at-2 | Integrin, alpha 8 |
| 699 | Lung | 0.1616854 | 0.4038201 | 0.3223158 | 0.19220842 L36531_at | Integrin alpha 8 subunit mRNA, 3' end |
| 700 | Lung | 0.1616846 | 0.403772 | 0.323007 | 0.19208887 RC_AA1906 76_at | EST: zp89g09.s1 Stratagene HeLa cell s3 937216 Homo sapiens cDNA clone 627424 3', mRNA sequence. (from Genbank) |
| 701 | Lung | 0.1614686 | 0.4037253 | 0.323001 | 0.19196852 X04741_at | UBIQUITIN CARBOXYL-TERMINAL HYDROLASE ISOZYME L1 |
| 702 | Lung | 0.1614486 | 0.4035651 | 0.322985 | 0.19181742 N56451_at | Human zinc-finger domain-containing protein mRNA, partial cds |
| 703 | Lung | 0.1614016 | 0.4034808 | 0.322871 | 0.19169772 RC_AA4191 39_at | EST: zv34h05.s1 Soares ovary tumor NbHOT Homo sapiens cDNA clone 755577 3', mRNA sequence. (from Genbank) |
| 704 | Lung | 0.1612047 | 0.4034688 | 0.322788 | 0.19163692 RC_AA2619 07_at | EST: zs17d04.s1 NCI_CGAP_GCB1 Homo sapiens cDNA clone IMAGE:685447 3', mRNA sequence. (from Genbank) |
| 705 | Lung | 0.1611828 | 0.4034121 | 0.322782 | 0.19158146 RC_AA2343 84_s_at | EST: zr75a11.s1 Soares NhHMPu S1 Homo sapiens cDNA clone 669212 3', mRNA sequence. (from Genbank) |
| 706 | Lung | 0.1611738 | 0.4032412 | 0.322646 | 0.19145317 M26665_at | HISTATIN 3 PRECURSOR |
| 707 | Lung | 0.160806 | 0.4030387 | 0.322293 | 0.19143632 HG3492-HT3686_at | Uncoupling Protein Ucp |
| 708 | Lung | 0.1607893 | 0.4029555 | 0.322293 | 0.19137366 X91247_at | TXNRD1 Thioredoxin reductase |
| 709 | Lung | 0.1607136 | 0.4028861 | 0.322226 | 0.19128461 RC_AA0338 74_at | EST: zk20h04.s1 Soares pregnant uterus NbHPU Homo sapiens cDNA clone 471127 3', mRNA sequence. (from Genbank) |
| 710 | Lung | 0.1605828 | 0.4028777 | 0.322216 | 0.19121543 X55330_at | AGA Aspartylglucosaminidase |
| 711 | Lung | 0.16058 | 0.402876 | 0.322182 | 0.19113089 U10868_at | ALDH7 Aldehyde dehydrogenase 7 |
| 712 | Lung | 0.160527 | 0.4026759 | 0.322157 | 0.19104183 M60315_at | BONE MORPHOGENETIC PROTEIN 6 PRECURSOR |
| 713 | Lung | 0.1604544 | 0.4025697 | 0.322078 | 0.19097774 X04011_at-2 | Cytochrome b-245, beta polypeptide (chronic granulomatous disease) |
| 714 | Lung | 0.1604544 | 0.4025488 | 0.322062 | 0.19093066 X04011_at | CYBB Chronic granulomatous disease |
| 715 | Lung | 0.160289 | 0.4025015 | 0.321903 | 0.19076052 M63138_at | CTSD Cathepsin D (lysosomal aspartyl protease) |
| 716 | Lung | 0.1595668 | 0.4024216 | 0.321638 | 0.19063103 RC_AA2232 37_at | EST: zr06g04.s1 Stratagene NT2 neuronal precursor 937230 Homo sapiens cDNA clone 650742 3', mRNA sequence. (from Genbank) |
| 717 | Lung | 0.1595563 | 0.4023925 | 0.321515 | 0.19051693 Z49155_at | HD Huntingtin (Huntington disease) |
| 718 | Lung | 0.1595394 | 0.4023082 | 0.321482 | 0.19048667 RC_AA4323 78_at | EST: zw76c08.s1 Soares testis NHT Homo sapiens cDNA clone 782126 3', mRNA sequence. (from Genbank) |
| 719 | Lung | 0.1594579 | 0.4021936 | 0.321442 | 0.19042654 M85220_at | Germline Ig alpha mutant chain gene C-alpha-3 region of the secreted protein, 3' end |
| 720 | Lung | 0.1594037 | 0.4021498 | 0.321401 | 0.19039536 RC_AA4559 87_at | EST: aa02c04.s1 Soares NhHMPu S1 Homo sapiens cDNA clone 812070 3', mRNA sequence. (from Genbank) |

FIG. 612

| | | | | | | |
|---|---|---|---|---|---|---|
| 721 | Lung | 0.1591712 | 0.4021483 | 0.321135 | 0.19019453 | RC_D25786_at | Myosin, heavy polypeptide-like (110kD) |
| 722 | Lung | 0.1590312 | 0.4021243 | 0.321342 | 0.19007705 | AB000464_a_t | mRNA, clone RES4-24A, exon 1, 2, 3, 4 |
| 723 | Lung | 0.1590312 | 0.4021043 | 0.320959 | 0.19000174 | AB000464_a_t-2 | Homo sapiens mRNA, exon 1, 2, 3, 4, clone:RES4-24A |
| 724 | Lung | 0.1583903 | 0.4019773 | 0.320935 | 0.18894969 | RC_AA1590 25_at | EST: zs57h03.s1 Stratagene pancreas (#937208) Homo sapiens cDNA clone 591029 3', mRNA sequence. (from Genbank) |
| 725 | Lung | 0.1583357 | 0.4019668 | 0.320838 | 0.18990836 | U40380_at | PSEN1 Presenilin 1 (Alzheimer disease 3) |
| 726 | Lung | 0.1582281 | 0.4018503 | 0.320718 | 0.18983312 | M14058_at | C1R Complement component C1r |
| 727 | Lung | 0.1580057 | 0.4018459 | 0.320644 | 0.18977161 | AA195179_s_at | EST: zr35h11.r1 Soares NhHMPu S1 Homo sapiens cDNA clone 665445 5', mRNA sequence. (from Genbank) |
| 728 | Lung | 0.1576287 | 0.4017893 | 0.320586 | 0.189721 | H55741_at | EST: 121G4T7 Homo sapiens cDNA. (from Genbank) |
| 729 | Lung | 0.1576098 | 0.4016997 | 0.320539 | 0.18970075 | RC_AA2848 44_at | EST: zt22d02.s1 Soares ovary tumor NbHOT Homo sapiens cDNA clone 713859 3', mRNA sequence. (from Genbank) |
| 730 | Lung | 0.1574292 | 0.4016899 | 0.3204 | 0.18959823 | RC_AA2926 94_at | EST: zf21e10.s1 Soares ovary tumor NbHOT Homo sapiens cDNA clone 713802 3', mRNA sequence. (from Genbank) |
| 731 | Lung | 0.1573876 | 0.4016082 | 0.320353 | 0.18954493 | RC_AA0184 41_at | EST: ze50a08.s1 Soares retina N2b4HR Homo sapiens cDNA clone 362390 3', mRNA sequence. (from Genbank) |
| 732 | Lung | 0.1573741 | 0.4013513 | 0.320338 | 0.18941864 | RC_AA4573_at | EST: aa86a02.s1 Stratagene fetal retina 937202 Homo sapiens cDNA clone 838154 3', mRNA sequence. (from Genbank) |
| 733 | Lung | 0.1573352 | 0.40129 | 0.320289 | 0.18934537 | AA157623_s_at | KIAA0750 gene product |
| 734 | Lung | 0.1572465 | 0.4011589 | 0.320137 | 0.18920316 | AA203649_a_t | EST: zx58e12.r1 Soares fetal liver spleen 1NFLS S1 Homo sapiens cDNA clone 446734 5', mRNA sequence. (from Genbank) |
| 735 | Lung | 0.1572429 | 0.4011586 | 0.320012 | 0.18914019 | X82125_at | HOK-2 mRNA for zinc finger protein |
| 736 | Lung | 0.1572165 | 0.4010572 | 0.319602 | 0.18911028 | RC_AA4868 68_s_at | Slit (Drosophila) homolog 2 |
| 737 | Lung | 0.1571014 | 0.4010132 | 0.31955 | 0.18895441 | W26989_at | EST: 19b2 Human retina cDNA randomly primed sublibrary Homo sapiens cDNA, mRNA sequence. (from Genbank) |
| 738 | Lung | 0.1568871 | 0.4009562 | 0.31955 | 0.18892865 | RC_AA1943 84_at | EST: zq05e05.s1 Stratagene muscle 937209 Homo sapiens cDNA clone 628832 3', mRNA sequence. (from Genbank) |
| 739 | Lung | 0.1567547 | 0.400949 | 0.319524 | 0.18886289 | Y10506_at | CD110 protein |
| 740 | Lung | 0.1566631 | 0.400864 | 0.319524 | 0.18866336 | J05582_s_at | MUC1 Mucin 1, transmembrane |
| 741 | Lung | 0.1566456 | 0.4008102 | 0.319467 | 0.18861495 | L02648_at | TCN2 Transcobalamin II |
| 742 | Lung | 0.1560733 | 0.400767 | 0.319298 | 0.1885562 | U55206_at | Gamma-glutamyl hydrolase (hGH) mRNA |
| 743 | Lung | 0.1560259 | 0.4006851 | 0.319279 | 0.18846686 | RC_AA2925 33_at | EST: zs59b05.s1 NCI_CGAP_GCB1 Homo sapiens cDNA clone IMAGE:701745 3', mRNA sequence. (from Genbank) |

FIG. 6J2

| | | | | | |
|---|---|---|---|---|---|
| 744 | Lung | 0.1559986 | 0.4005281 | 0.319185 | 0.18843009 | M84349_at | CD59 CD59 antigen p18-20 (antigen identified by monoclonal antibodies 16.3A5, EJ16, EJ30, EL32 and G344) |
| 745 | Lung | 0.1558058 | 0.4004261 | 0.319159 | 0.18829513 | Y07868_s_at | Pirin |
| 746 | Lung | 0.1556983 | 0.4003758 | 0.319139 | 0.1882475 | RC_AA3026 57_at | EST: EST10120 Adipose tissue, white I Homo sapiens cDNA 3' end, mRNA sequence. (from Genbank) |
| 747 | Lung | 0.1556242 | 0.4002338 | 0.319108 | 0.1881709 | D62600_s_a t | EST: Human aorta cDNA 5'-end GEN-304G05, mRNA sequence. (from Genbank) |
| 748 | Lung | 0.1552696 | 0.4001185 | 0.318991 | 0.18811509 | U58096_at | TSPY Testis specific protein, Y-linked |
| 749 | Lung | 0.1552629 | 0.4000708 | 0.318924 | 0.18804002 | RC_AA4169 69_at | EST: zl51g10.s1 Soares pregnant uterus NbHPU Homo sapiens cDNA clone 505506 3', mRNA sequence. (from Genbank) |
| 750 | Lung | 0.1552509 | 0.3999682 | 0.31887 | 0.18799718 | M55593_at | MMP2 Matrix metalloproteinase 2 (gelatinase A, 72kD gelatinase, 72kD type IV collagenase) |
| 751 | Lung | 0.1511079 | 0.3999066 | 0.318843 | 0.18787578 | RC_AA1270 45_at | EST: zl22b06.s1 Soares pregnant uterus NbHPU Homo sapiens cDNA clone 502643 3', mRNA sequence. (from Genbank) |
| 752 | Lung | 0.1545847 | 0.3998266 | 0.318843 | 0.18784082 | Z18951_at | CAV Caveolin, caveolae protein, 22kD |
| 753 | Lung | 0.1540695 | 0.3997752 | 0.31874 | 0.18773164 | W26915_s_ at | Eukaryotic translation initiation factor 2, subunit 3 (gamma, 52kD) |
| 754 | Lung | 0.1539735 | 0.3997752 | 0.318708 | 0.187645 | W26567_at | EST: 33b11 Human retina cDNA randomly primed sublibrary Homo sapiens cDNA, mRNA sequence. (from Genbank) |
| 755 | Lung | 0.1537301 | 0.3997269 | 0.318562 | 0.18760176 | N36588_at | Ubiquitin-conjugating enzyme E2I (homologous to yeast UBC9) |
| 756 | Lung | 0.1536131 | 0.3996654 | 0.318283 | 0.18752524 | W23474_at | EST: zb33d08.r1 Soares parathyroid tumor NbHPA Homo sapiens cDNA clone 305391 5', mRNA sequence. (from Genbank) |
| 757 | Lung | 0.1534358 | 0.3995398 | 0.318269 | 0.18741755 | RC_AA0646 27_at | EST: zf72b06.s1 Soares pineal gland N3HPG Homo sapiens cDNA clone 382451 3', mRNA sequence. (from Genbank) |
| 758 | Lung | 0.1533692 | 0.3994352 | 0.318262 | 0.18732724 | RC_AA1370 73_at | EST: zl02g02.s1 Soares pregnant uterus NbHPU Homo sapiens cDNA clone 491186 3', mRNA sequence. (from Genbank) |
| 759 | Lung | 0.1533027 | 0.3994141 | 0.318128 | 0.18726963 | RC_AA1316 92_at | EST: zl34f04.s1 Soares pregnant uterus NbHPU Homo sapiens cDNA clone 503839 3', mRNA sequence. (from Genbank) |
| 760 | Lung | 0.1532162 | 0.3993481 | 0.318068 | 0.18714279 | HG544-HT544_at | Endothelial Cell Growth Factor 1 |
| 761 | Lung | 0.1529874 | 0.399235 | 0.318043 | 0.18711495 | HG2157-HT2227_at | Mucin 4, Tracheobronchial |
| 762 | Lung | 0.1528723 | 0.3990953 | 0.317774 | 0.18703292 | RC_AA0373 57_f_at | EST: zc03c04.s1 Soares parathyroid tumor NbHPA Homo sapiens cDNA clone 321222 3' similar to contains Alu repetitive element;, mRNA sequence. (from Genbank) |
| 763 | Lung | 0.1528113 | 0.3990846 | 0.317755 | 0.18696521 | X67785_i_at | Dihydrolipoamide branched chain transacylase (E2 component of branched chain keto acid dehydrogenase complex; maple syrup urine disease) |

FIG. 6K2

| # | Tissue | | | | ID | Description |
|---|---|---|---|---|---|---|
| 764 | Lung | 0.1528054 | 0.3989059 | 0.317662 | M64358_at | Rhom-3 gene, exon |
| 765 | Lung | 0.1527564 | 0.3989051 | 0.317638 | RC_AA4486 88_at | EST: zx11g04.s1 Soares total fetus Nb2HF8 9w Homo sapiens cDNA clone 786198 3', mRNA sequence. (from Genbank) |
| 766 | Lung | 0.1527243 | 0.3988705 | 0.317583 | RC_AA4275 79_at | Homo sapiens regulator of G protein signaling RGS14 mRNA, complete cds |
| 767 | Lung | 0.1526961 | 0.3987791 | 0.317416 | C16161_s_a t | EST: Human aorta cDNA 5'-end GEN-234B03, mRNA sequence. (from Genbank) |
| 768 | Lung | 0.1524764 | 0.3987571 | 0.317406 | N75215_s_a t | EST: yw33h05.r1 Homo sapiens cDNA clone 254073 5'. (from Genbank) |
| 769 | Lung | 0.1524361 | 0.398697 | 0.317302 | M65292_s_a t | HFL1 H factor (complement)-like 1 |
| 770 | Lung | 0.1520901 | 0.398609 | 0.317201 | M23254_at | CAPN2 Calpain, large polypeptide L2 |
| 771 | Lung | 0.1519963 | 0.3985269 | 0.317098 | U67368_s_a t | EXT2 Exostoses (multiple) 2 |
| 772 | Lung | 0.1519496 | 0.3985269 | 0.317048 | X66785_f_at | Dihydrolipoamide branched chain transacylase (E2 component of branched chain keto acid dehydrogenase complex; maple syrup urine disease) |
| 773 | Lung | 0.151612 | 0.3985259 | 0.316931 | U47621_at | Nucleolar autoantigen No55 mRNA |
| 774 | Lung | 0.1515783 | 0.3984929 | 0.316921 | RC_AA2353 43_at | EST: zs40a08.s1 Soares NhHMPu S1 Homo sapiens cDNA clone 687638 3', mRNA sequence. (from Genbank) |
| 775 | Lung | 0.1515639 | 0.3984426 | 0.31687 | RC_AA0042 74_at | EST: zh97f02.s1 Soares fetal liver spleen 1NFLS S1 Homo sapiens cDNA clone 429243 3' similar to contains element MER22 repetitive element ;, mRNA sequence. (from Genbank) |
| 776 | Lung | 0.1514965 | 0.3984395 | 0.316869 | U77845_at | HTRIP (hTRIP) mRNA |
| 777 | Lung | 0.1514965 | 0.3984088 | 0.316807 | U77845_at-2 | Human hTRIP (hTRIP) mRNA, complete cds |
| 778 | Lung | 0.1513683 | 0.3983211 | 0.316739 | AA495865_a t | EST: zw05c07.r1 Soares NhHMPu S1 Homo sapiens cDNA clone 768396 5', mRNA sequence. (from Genbank) |
| 779 | Lung | 0.151318 | 0.3982729 | 0.316642 | RC_AA4279 44_at | EST: zw53d11.s1 Soares total fetus Nb2HF8 9w Homo sapiens cDNA clone 773781 3', mRNA sequence. (from Genbank) |
| 780 | Lung | 0.1510057 | 0.3981962 | 0.316614 | R69417_at | EST: yj83f12.r1 Homo sapiens cDNA clone 155375 5'. (from Genbank) |
| 781 | Lung | 0.1509293 | 0.3981314 | 0.316604 | U09850_at | ZNF143 Zinc finger protein 143 (clone pHZ-1) |
| 782 | Lung | 0.1509293 | 0.3980586 | 0.316573 | U09850_at-2 | Zinc finger protein 143 (clone pHZ-1) |
| 783 | Lung | 0.1507461 | 0.397989 | 0.316551 | RC_AA6101 16_i_at | EST: af19g10.s1 Soares total fetus Nb2HF8 9w Homo sapiens cDNA clone 1032162 3', mRNA sequence. (from Genbank) |
| 784 | Lung | 0.1507385 | 0.3979667 | 0.316389 | U00956_at | Human clone KDB5.1 (CAC)n/(GTG)n repeat-containing mRNA |
| 785 | Lung | 0.1506853 | 0.3979476 | 0.316352 | RC_AA2817 53_at | Inositol 1,4,5-triphosphate receptor, type 3 |

FIG. 6L2

| # | Tissue | Col3 | Col4 | Col5 | ID | Description |
|---|---|---|---|---|---|---|
| 786 | Lung | 0.1502941 | 0.3979133 | 0.316342 | RC_AA4300 0.185059 47_at | EST: zw65g09.s1 Soares testis NHT Homo sapiens cDNA clone 781120 3', mRNA sequence. (from Genbank) |
| 787 | Lung | 0.1499348 | 0.397889 | 0.316231 | 0.18496215 W32012_at | EST: zb96c10.r1 Soares parathyroid tumor NbHPA Homo sapiens cDNA clone 320658 5', mRNA sequence. (from Genbank) |
| 788 | Lung | 0.1498905 | 0.3978485 | 0.316113 | 0.18491895 Y07512_at | CGMP-DEPENDENT PROTEIN KINASE, BETA ISOZYME |
| 789 | Lung | 0.1496778 | 0.3977398 | 0.315923 | AA236610_a 0.1848029 t | EST: Zr99c11.r1 NCI_CGAP_GCB1 Homo sapiens cDNA clone IMAGE:683828 5', mRNA sequence. (from Genbank) |
| 790 | Lung | 0.1496476 | 0.3977167 | 0.315849 | 0.18474285 U08998_at | TAR RNA binding protein (TRBP) mRNA |
| 791 | Lung | 0.1496134 | 0.3976829 | 0.315731 | AA027766_a 0.18466112 t | EST: HPLA_CCLEE_69a10u HPLA CCLee Homo sapiens cDNA, mRNA sequence. (from Genbank) |
| 792 | Lung | 0.1493918 | 0.3974153 | 0.315663 | 0.18450275 U02019_at | Heterogeneous nuclear ribonucleoprotein D (hnRNP D), partial cds, clone cDx4 |
| 793 | Lung | 0.1493561 | 0.3973715 | 0.315554 | RC_AA2919 0.18436338 27_at | EST: zr58g09.s1 Soares NhHMPu S1 Homo sapiens cDNA clone 667648 3', mRNA sequence. (from Genbank) |
| 794 | Lung | 0.1491333 | 0.3973623 | 0.315552 | AA325107_a 0.1843022 t | EST: EST28057 Cerebellum II Homo sapiens cDNA 5' end, mRNA sequence. (from Genbank) |
| 795 | Lung | 0.1489923 | 0.3973177 | 0.31547 | 0.18423311 S57296_at | HER2/neu receptor (3' region, alternatively spliced) [human, breast cancer cell line, mRNA Partial, 175 nt] |
| 796 | Lung | 0.1488607 | 0.3973136 | 0.315457 | 0.18412714 K03204_f_at | PRB1 locus salivary proline-rich protein mRNA, clone cP3 |
| 797 | Lung | 0.1488371 | 0.3972763 | 0.315437 | RC_AA5987 0.1840994 25_at | Endothelial differentiation-related factor 1 |
| 798 | Lung | 0.1487754 | 0.3972615 | 0.315287 | 0.18404418 D45213_at | Homo sapiens mRNA for zinc finger protein, complete cds |
| 799 | Lung | 0.1487648 | 0.3971662 | 0.315236 | 0.18393572 D13643_at | KIAA0018 gene |
| 800 | Lung | 0.1487514 | 0.3970928 | 0.315228 | RC_AA2268 0.18380356 79_at | EST: zr19g09.s1 Stratagene NT2 neuronal precursor 937230 Homo sapiens cDNA clone 683856 3' similar to contains Alu repetitive element, mRNA sequence. (from Genbank) |
| 801 | Lung | 0.148632 | 0.3970898 | 0.315058 | 0.18375574 U49065_at-2 | Interleukin 1 receptor-like 2 |
| 802 | Lung | 0.148632 | 0.3970818 | 0.315025 | 0.18369785 U49065_at | Interleukin-1 receptor-related protein mRNA |
| 803 | Lung | 0.1485932 | 0.3970102 | 0.315008 | U80982_ma 0.18358205 1_s_at | CCAAT/enhancer binding protein (C/EBP), epsilon |
| 804 | Lung | 0.1485731 | 0.3970102 | 0.314974 | 0.18351021 M94547_at | HUMMLC2At; Homo sapiens,; 593 base pairs |
| 805 | Lung | 0.1481089 | 0.3968687 | 0.314831 | RC_AA3986 0.18348065 74_at | EST: zf70d05.s1 Soares testis NHT Homo sapiens cDNA clone 727689 3' similar to SW:YKU7_YEAST P36039 HYPOTHETICAL 29.4 KD PROTEIN IN STE6-LOS1 INTERGENIC REGION..., mRNA sequence. (from Genbank) |
| 806 | Lung | 0.1479293 | 0.3968554 | 0.314773 | AA278413_a 0.1833788 t | EST: zs81h05.r1 NCI_CGAP_GCB1 Homo sapiens cDNA clone IMAGE:703929 5', mRNA sequence. (from Genbank) |

FIG. 6M2

| # | Tissue | Col3 | Col4 | Col5 | ID | Description |
|---|---|---|---|---|---|---|
| 807 | Lung | 0.1474223 | 0.3968059 | 0.314682 | 0.1832981 | U27655_at | RGP3 mRNA |
| 808 | Lung | 0.1472143 | 0.3966435 | 0.314641 | 0.183235572 5_at | RC_AA2554 | EST: zr85f01.s1 Soares NhHMPu S1 Homo sapiens cDNA clone 682489 3' similar to contains MER32.b2 MER32 repetitive element ., mRNA sequence. (from Genbank) |
| 809 | Lung | 0.1467867 | 0.3965822 | 0.314596 | 0.18315269 | AA491376_a t | EST: aa65e11.r1 NCI_CGAP_GCB1 Homo sapiens cDNA clone IMAGE:825836 5', mRNA sequence. (from Genbank) |
| 810 | Lung | 0.146693 | 0.3965822 | 0.314504 | 0.183114771_s_at | X55448_cds | G6PD gene (glucose-6-phosphate dehydrogenase) extracted from H.sapiens G6PD gene for glucose-6-phosphate dehydrogenase |
| 811 | Lung | 0.1466552 | 0.3962835 | 0.314498 | 0.18300815194_at | RC_AA4528 | EST: zx36h04.s1 Soares total fetus Nb2HF8 9w Homo sapiens cDNA clone 788599 3' similar to SW:RS16_HAEIN P44382 30S RIBOSOMAL PROTEIN S16. ;; mRNA sequence. (from Genbank) |
| 812 | Lung | 0.1465183 | 0.3961302 | 0.314475 | 0.1829082 | U65533_s_a t | KIAA0221 gene |
| 813 | Lung | 0.1460573 | 0.3960912 | 0.314452 | 0.18277606 | S72493_s_at | KERATIN, TYPE I CYTOSKELETAL 17 |
| 814 | Lung | 0.1459976 | 0.3960102 | 0.31436 | 0.18271177 | N71503_s_a t | EST: yw32b10.r1 Homo sapiens cDNA clone 253915 5'. (from Genbank) |
| 815 | Lung | 0.1459156 | 0.3060102 | 0.314255 | 0.182681190_at | RC_AA1884 | EST: zq44d08.s1 Stratagene hNT neuron (#937233) Homo sapiens cDNA clone 632559 3', mRNA sequence. (from Genbank) |
| 816 | Lung | 0.1458645 | 0.3959216 | 0.314163 | 0.182623557 5_at | RC_AA4494 | EST: zx08f10.s1 Soares total fetus Nb2HF8 9w Homo sapiens cDNA clone 785899 3' similar to contains Alu repetitive element;contains element MER22 repetitive element ., mRNA sequence. (from Genbank) |
| 817 | Lung | 0.1457587 | 0.3957494 | 0.314094 | 0.182501480 | U57094_at | Small GTP-binding protein mRNA |
| 818 | Lung | 0.1456036 | 0.3956778 | 0.314067 | 0.18238007 | X87767_at | CD89 gene, exon S1 |
| 819 | Lung | 0.1455633 | 0.3956626 | 0.313971 | 0.182315333 | R50247_s_a t | EST: yj58b01.r1 Homo sapiens cDNA clone 152905 5'. (from Genbank) |
| 820 | Lung | 0.1454501 | 0.3956354 | 0.313935 | 0.182236732_s_at | V00535_rna | Interferon beta 1 gene extracted from Gene for human fibroblast interferon beta 1 |
| 821 | Lung | 0.1454397 | 0.3956173 | 0.31384 | 0.18218815 | U63973_at | Rhodopsin kinase |
| 822 | Lung | 0.1452974 | 0.3956606 | 0.313818 | 0.18215128 | D87468_at-2 | Human mRNA for KIAA0278 gene, partial cds |
| 823 | Lung | 0.1452974 | 0.3956012 | 0.313758 | 0.18206927 | D87468_at | KIAA0278 gene, partial cds |
| 824 | Lung | 0.1452601 | 0.3955233 | 0.313689 | 0.182024095 7_at | RC_AA4319 | EST: zw77a01.s1 Soares testis NHT Homo sapiens cDNA clone 782184 3', mRNA sequence. (from Genbank) |
| 825 | Lung | 0.1452288 | 0.3954939 | 0.313687 | 0.18196057 | R15917_at | Homo sapiens clone 24629 mRNA sequence |
| 826 | Lung | 0.1447495 | 0.3954457 | 0.313662 | 0.18187064 | RC_D60033_at | EST: Human fetal brain cDNA 3'-end GEN-082A12, mRNA sequence. (from Genbank) |

FIG. 6N2

| | | | | | |
|---|---|---|---|---|---|
| 827 | Lung | 0.1445389 | 0.3951472 | 0.313558 | 0.18178140351_3_st | AFFX-HSAC07/X00351_3_st (endogenous control) |
| 828 | Lung | 0.1445389 | 0.3950982 | 0.313508 | 0.181723460351_3_st-2 | No info for gene |
| 829 | Lung | 0.1443453 | 0.3950662 | 0.313404 | RC_AA2812 | EST: zt08g01.s1 NCI_CGAP_GCB1 Homo sapiens cDNA clone IMAGE:712560 3', mRNA sequence. (from Genbank) |
| 830 | Lung | 0.144337 | 0.3950602 | 0.313378 | AA074933_a_t | Zm85b07.r1 Stratagene ovarian cancer (#937219) Homo sapiens cDNA clone 544693 5' similar to gb:J04794 ALCOHOL DEHYDROGENASE (HUMAN);, mRNA sequence. (from Genbank) |
| 831 | Lung | 0.1440862 | 0.3950484 | 0.313332 | 0.18137286 W25821_at | EST: 14e10 Human retina cDNA randomly primed sublibrary Homo sapiens cDNA, mRNA sequence. (from Genbank) |
| 832 | Lung | 0.1439097 | 0.3949648 | 0.313265 | 0.18132702 W26105_at | EST: 2217 Human retina cDNA randomly primed sublibrary Homo sapiens cDNA, mRNA sequence. (from Genbank) |
| 833 | Lung | 0.1435464 | 0.3948618 | 0.3132 | 0.18126038 RC_AA2332_at | Transforming growth factor beta 1 induced transcript 1 |
| 834 | Lung | 0.1433436 | 0.3948143 | 0.313104 | AA303745_s_at | TAP binding protein (tapasin) |
| 835 | Lung | 0.1433351 | 0.3947946 | 0.313059 | 0.18113275 U84971_at | Homo sapiens fetal unknown mRNA, complete cds |
| 836 | Lung | 0.1432472 | 0.394746 | 0.313022 | 0.18100575 H66279_at | Yr72b07.r1 Homo sapiens cDNA clone 210805 5'. (from Genbank) |
| 837 | Lung | 0.1431472 | 0.394642 | 0.312932 | 0.18092379 L27071_at | TXK TXK tyrosine kinase |
| 838 | Lung | 0.1431143 | 0.3946405 | 0.312908 | RC_AA4546 75_at | EST: zx76a07.s1 Soares ovary tumor NbHOT Homo sapiens cDNA clone 809652 3', mRNA sequence. (from Genbank) |
| 839 | Lung | 0.1429422 | 0.3944924 | 0.312861 | 0.18073787 M28585_f_at | IFNA16 Interferon, alpha 16 |
| 840 | Lung | 0.1428676 | 0.3944664 | 0.312838 | 0.18064416 X75308_at | MMP13 Matrix metalloproteinase 13 (collagenase 3) |
| 841 | Lung | 0.1425217 | 0.3944664 | 0.312753 | AA070326_a_t | EST: zm68e02.r1 Stratagene neuroepithelium (#937231) Homo sapiens cDNA clone 530810 5', mRNA sequence. (from Genbank) |
| 842 | Lung | 0.1420535 | 0.3943546 | 0.312741 | 0.18053092 RC_AA2794 67_at | EST: zs85g09.s1 NCI_CGAP_GCB1 Homo sapiens cDNA clone IMAGE:704320 3', mRNA sequence. (from Genbank) |
| 843 | Lung | 0.1420401 | 0.3942473 | 0.31271 | 0.18047878 RC_AA4890 12_at | Human pre-B cell enhancing factor (PBEF) mRNA, complete cds |
| 844 | Lung | 0.1418682 | 0.3942029 | 0.312684 | 0.18039018 Z74616_s_at | COL1A2 Collagen, type I, alpha-2 |
| 845 | Lung | 0.1417904 | 0.3941631 | 0.312604 | 0.18030953 M63835_at | HIGH AFFINITY IMMUNOGLOBULIN GAMMA FC RECEPTOR I "A FORM" PRECURSOR |
| 846 | Lung | 0.1417589 | 0.3940368 | 0.312477 | 0.18023316 U90913_at | Clone 23665 mRNA sequence |

FIG. 6O2

| # | Tissue | | | | ID | Accession | Description |
|---|---|---|---|---|---|---|---|
| 847 | Lung | 0.1415097 | 0.3939755 | 0.312368 | 0.18021257 | RC_AA1324 53_at | EST: zo20b01.s1 Stratagene colon (#937204) Homo sapiens cDNA clone 587401 3', mRNA sequence. (from Genbank) |
| 848 | Lung | 0.1409441 | 0.3939252 | 0.312358 | 0.1802085 | U32499_s_a t | D3 dopamine receptor mRNA |
| 849 | Lung | 0.1407871 | 0.3938699 | 0.312355 | 0.18008693 | R71205_at | EST: yi53g09.r1 Homo sapiens cDNA clone 143008 5' similar to gb:M15182 BETA-GLUCURONIDASE PRECURSOR (HUMAN);. (from Genbank) |
| 850 | Lung | 0.1405638 | 0.3938529 | 0.312304 | 0.18005024 | RC_AA1868 97_at | EST: zp74c05.s1 Stratagene HeLa cell s3 937216 Homo sapiens cDNA clone 625928 3', mRNA sequence. (from Genbank) |
| 851 | Lung | 0.1405437 | 0.3938106 | 0.3122133 | 0.17999251 | D50312_at | UKATP-1 |
| 852 | Lung | 0.1405437 | 0.3937709 | 0.312133 | 0.17990473 | D50312_at-2 | Potassium inwardly-rectifying channel, subfamily J, member 8 |
| 853 | Lung | 0.1404124 | 0.3937604 | 0.311989 | 0.17979872 | HG880-HT880_s_at | Mucin 6, Gastric (Gb:L07517) |
| 854 | Lung | 0.1400175 | 0.3937507 | 0.311905 | 0.17965975 | RC_AA4026 13_at | EST: zu49c05.s1 Soares ovary tumor NbHOT Homo sapiens cDNA clone 741320 3', mRNA sequence. (from Genbank) |
| 855 | Lung | 0.1398231 | 0.3936025 | 0.311902 | 0.17961605 | J04177_at | COL11A1 Collagen, type XI, alpha 1 |
| 856 | Lung | 0.13971 | 0.3936008 | 0.311875 | 0.17954832 | D82344_at-2 | Paired mesoderm homeobox 2b |
| 857 | Lung | 0.13971 | 0.3935396 | 0.311804 | 0.17941953 | D82344_at | NBPhox |
| 858 | Lung | 0.1396988 | 0.3935351 | 0.311684 | 0.17938818 | AA043223_a t | Homo sapiens clone 486790 diphosphoinositol polyphosphate phosphohydrolase mRNA, complete cds |
| 859 | Lung | 0.1395714 | 0.3935319 | 0.311583 | 0.17927533 | AA220236_a t | EST: PMY0284 KG1-a Lambda Zap Express cDNA library Homo sapiens cDNA 5', mRNA sequence. (from Genbank) |
| 860 | Lung | 0.1395243 | 0.3933778 | 0.311509 | 0.17921414 | RC_AA2333 45_at | EST: zr48e02.s1 Soares NhHMPu S1 Homo sapiens cDNA clone 666650 3', mRNA sequence. (from Genbank) |
| 861 | Lung | 0.1393928 | 0.3933545 | 0.311498 | 0.17915927 | U67611_at-2 | Mouse transaldolase gene mRNA, complete cds. (from Genbank) |
| 862 | Lung | 0.1393928 | 0.3933477 | 0.311439 | 0.17913035 | U67611_at | Mouse transaldolase gene mRNA |
| 863 | Lung | 0.1391306 | 0.3931039 | 0.311411 | 0.17905445 | AA305116_a t | EST176117 Colon carcinoma (Caco-2) cell line II Homo sapiens cDNA 5' end, mRNA sequence. (from Genbank) |
| 864 | Lung | 0.1388959 | 0.3930995 | 0.311372 | 0.17902942 | U74324_at | Guanine nucleotide exchange factor mss4 mRNA |
| 865 | Lung | 0.1386277 | 0.3930599 | 0.311349 | 0.17896973 | RC_AA5984 10_at | EST: ae48b06.s1 Stratagene lung carcinoma 937218 Homo sapiens cDNA clone 950099 3', mRNA sequence. (from Genbank) |
| 866 | Lung | 0.1385029 | 0.3930414 | 0.31132 | 0.17883463 | AA447876_a t | EST: aa20c09.r1 Soares NhHMPu S1 Homo sapiens cDNA clone 813808 5', mRNA sequence. (from Genbank) |
| 867 | Lung | 0.1382243 | 0.3930365 | 0.311314 | 0.17876777 | L23808_at | MMP12 Matrix metalloproteinase 12 (macrophage elastase) |
| 868 | Lung | 0.1379621 | 0.3929079 | 0.311286 | 0.17861361 | AA252752_a t | EST: zs26b10.r1 NCI_CGAP_GCB1 Homo sapiens cDNA clone IMAGE:686299 5', mRNA sequence. (from Genbank) |

FIG. 6P2

| | | | | | |
|---|---|---|---|---|---|
| 869 | Lung | 0.1378872 | 0.39285575 | 0.311257 | 0.17855059 | R86224_at | Human mRNA for KIAA0143 gene, partial cds |
| 870 | Lung | 0.1378637 | 0.3927889 | 0.311181 | 0.17849697 | RC_AA2429 31_at | EST: zr26a02.s1 Stratagene NT2 neuronal precursor 937230 Homo sapiens cDNA clone 664490 3', mRNA sequence. (from Genbank) |
| 871 | Lung | 0.1378305 | 0.3926302 | 0.311137 | 0.17841657 | RC_AA4245 92_at | EST: zv91h10.s1 Soares NhHMPu S1 Homo sapiens cDNA clone 767203 3', mRNA sequence. (from Genbank) |
| 872 | Lung | 0.1378245 | 0.392598 | 0.3111 | 0.17837992 | H38727_at | Ribosomal protein L37 |
| 873 | Lung | 0.1377806 | 0.3925767 | 0.311 | 0.17833771 | W92283_at | EST: ze44e02.r1 Soares retina N2b4HR Homo sapiens cDNA clone 361850 5' similar to PIR:S47327 S47327 chloride channel protein - rat ;contains Alu repetitive element., mRNA sequence. (from Genbank) |
| 874 | Lung | 0.1377016 | 0.3923748 | 0.310914 | 0.17829916 | R63981_at | EST: yi19a02.r1 Homo sapiens cDNA clone 139658 5'. (from Genbank) |
| 875 | Lung | 0.1373288 | 0.3921245 | 0.310836 | 0.17810999 | M69238_at | ARNT Aryl hydrocarbon receptor nuclear translocator |
| 876 | Lung | 0.1373148 | 0.3920416 | 0.310819 | 0.17808872 | RC_AA2338 07_at | EST: zr44f10.s1 Soares NhHMPu S1 Homo sapiens cDNA clone 666283 3', mRNA sequence. (from Genbank) |
| 877 | Lung | 0.1372945 | 0.3919544 | 0.310804 | 0.17799254 | AA419464_a t | Zv01h10.r1 NCI_CGAP_GCB1 Homo sapiens cDNA clone IMAGE:746275 5' similar to gb:J04422 ISLET AMYLOID POLYPEPTIDE PRECURSOR (HUMAN);, mRNA sequence. (from Genbank) |
| 878 | Lung | 0.1372899 | 0.3919135 | 0.310783 | 0.17792772 | RC_AA2554 80_at | EST: zs83c09.s1 Soares NhHMPu S1 Homo sapiens cDNA clone 682288 3', mRNA sequence. (from Genbank) |
| 879 | Lung | 0.1372118 | 0.3919072 | 0.310725 | 0.17783602 | AF009426_a t | Clone 22 mRNA, alternative splice variant alpha-1 |
| 880 | Lung | 0.1366392 | 0.3918499 | 0.310577 | 0.17775199 | RC_AA2824 05_at | EST: zs90e06.s1 NCI_CGAP_GCB1 Homo sapiens cDNA clone IMAGE:704770 3', mRNA sequence. (from Genbank) |
| 881 | Lung | 0.136649 | 0.3918078 | 0.310491 | 0.17773938 | U33849_at | Lymphoma proprotein convertase (LPC) mRNA |
| 882 | Lung | 0.1363433 | 0.3917604 | 0.310473 | 0.17760064 | RC_AA0053 08_at | EST: zh93e11.s1 Soares fetal liver spleen 1NFLS S1 Homo sapiens cDNA clone 428876 3', mRNA sequence. (from Genbank) |
| 883 | Lung | 0.1363078 | 0.3917021 | 0.310403 | 0.17755325 | RC_AA6209 98_at | EST: ag03a06.s1 Soares testis NHT Homo sapiens cDNA clone 1056178 3' similar to WP:C16A3.1 CE04002 HELICASES OF SNF2/RAD54 FAMILY ;, mRNA sequence. (from Genbank) |
| 884 | Lung | 0.1362718 | 0.3915954 | 0.310382 | 0.17743315 | RC_AA3502 68_at | EST: EST57664 Infant brain Homo sapiens cDNA 3' end, mRNA sequence. (from Genbank) |
| 885 | Lung | 0.136194 | 0.3915414 | 0.310321 | 0.17736258 | RC_AA1349 68_at | EST: zo23g08.s1 Stratagene colon (#937204) Homo sapiens cDNA clone 587774 3', mRNA sequence. (from Genbank) |
| 886 | Lung | 0.1359219 | 0.3915151 | 0.31032 | 0.17730825 | RC_AA4365 53_at | EST: zv08c11.s1 Soares NhHMPu S1 Homo sapiens cDNA clone 753044 3', mRNA sequence. (from Genbank) |

FIG. 6Q2

| | | | | | | |
|---|---|---|---|---|---|---|
| 887 | Lung | 0.1356629 | 0.3914748 | 0.310294 | 0.17729716 | HG2788-HT2896_at | Calcyclin |
| 888 | Lung | 0.1355367 | 0.3914444 | 0.3102 | 0.17727546 | U84487_at | CX3C chemokine precursor, mRNA, alternatively spliced |
| 889 | Lung | 0.135506 | 0.3913298 | 0.310173 | 0.17714317 | W78726_at | EST: zh51h04.r1 Soares fetal liver spleen 1NFLS S1 Homo sapiens cDNA clone 415639 5', mRNA sequence. (from Genbank) |
| 890 | Lung | 0.1354359 | 0.3911431 | 0.310171 | 0.17708886 | AA287749_a t | Zs51b11.r1 NCI_CGAP_GCB1 Homo sapiens cDNA clone IMAGE:700989 5', mRNA sequence. (from Genbank) |
| 891 | Lung | 0.134941 | 0.3911431 | 0.31009 | 0.17695856 | L40401_at | (clone zap128) mRNA, 3' end of cds |
| 892 | Lung | 0.134941 | 0.391041 | 0.310059 | 0.17691125 | L40401_at-2 | Homo sapiens (clone zap128) mRNA, 3' end of cds |
| 893 | Lung | 0.134924 | 0.3908235 | 0.309886 | 0.17685232 | RC_AA4653 67_at | EST: aa23d09.s1 NCI_CGAP_GCB1 Homo sapiens cDNA clone IMAGE:814097 3', mRNA sequence. (from Genbank) |
| 894 | Lung | 0.1349052 | 0.3907831 | 0.309859 | 0.17679831 | RC_AA4501 14_at | EST: zx42e04.s1 Soares total fetus Nb2HF8 9w Homo sapiens cDNA clone 789150 3' similar to TR:G641819 G641819 HHEB HALOHYDRIN EPOXIDASE B. ;. mRNA sequence. (from Genbank) |
| 895 | Lung | 0.1347468 | 0.390618 | 0.309829 | 0.17666917 | RC_AA4166 31_at | EST: zu08h02.s1 Soares testis NHT Homo sapiens cDNA clone 731283 3', mRNA sequence. (from Genbank) |
| 896 | Lung | 0.1346701 | 0.3905833 | 0.309774 | 0.17666431 | X00695_s_a t | INTERLEUKIN-2 PRECURSOR |
| 897 | Lung | 0.1345473 | 0.3905473 | 0.309742 | 0.17662485 | RC_AA1564 50_at | EST: zf51f03.s1 Soares pregnant uterus NbHPU Homo sapiens cDNA clone 505469 3', mRNA sequence. (from Genbank) |
| 898 | Lung | 0.1344081 | 0.3905444 | 0.309651 | 0.17650172 | U82532_at | GDI-dissociation inhibitor RhoGDIgamma mRNA |
| 899 | Lung | 0.1343923 | 0.3905425 | 0.309636 | 0.17639622 | H89551_s_a t | EST: yw28e07.r1 Homo sapiens cDNA clone 253572 5'. (from Genbank) |
| 900 | Lung | 0.1343647 | 0.3905393 | 0.309552 | 0.17634879 | AA481201_a t | EST: aa34c12.r1 NCI_CGAP_GCB1 Homo sapiens cDNA clone IMAGE:815158 5', mRNA sequence. (from Genbank) |
| 901 | Lung | 0.1342043 | 0.3904809 | 0.309495 | 0.1761804 | RC_AA5999 54_at | Phosphatidylinositol glycan, class B |
| 902 | Lung | 0.1339174 | 0.390442 | 0.309467 | 0.17617229 | X62654_ma 1_at | ME491 gene extracted from H.sapiens gene for Me491/CD63 antigen |
| 903 | Lung | 0.1339078 | 0.3904411 | 0.309342 | 0.17615084 | RC_AA0630 70_at | EST: zf67e06.s1 Soares pineal gland N3HPG Homo sapiens cDNA clone 382018 3', mRNA sequence. (from Genbank) |
| 904 | Lung | 0.1337781 | 0.3903035 | 0.309254 | 0.17608719 | AA451992_a t | EST: zv75b06.r1 Soares total fetus Nb2HF8 9w Homo sapiens cDNA clone 759443 5', mRNA sequence. (from Genbank) |
| 905 | Lung | 0.1337706 | 0.3902964 | 0.309218 | 0.17608485 | AA133029_a t | Homo sapiens TACC2 protein (TACC2) mRNA, partial cds |
| 906 | Lung | 0.1335578 | 0.3902025 | 0.309142 | 0.17591514 | RC_AA0215 92_at | EST: ze67c01.s1 Soares retina N2b4HR Homo sapiens cDNA clone 364032 3', mRNA sequence. (from Genbank) |

FIG. 6R2

| | | | | | | |
|---|---|---|---|---|---|---|
| 907 | Lung | 0.1335346 | 0.3902683 | 0.309127 | 0.17587863 | RC_AA1499 87_at | Homo sapiens thymus specific serine peptidase mRNA, complete cds |
| 908 | Lung | 0.1334101 | 0.390258 | 0.309082 | 0.17573065 | N75870_s_a t | Dual specificity phosphatase 1 |
| 909 | Lung | 0.1330162 | 0.3901953 | 0.309075 | 0.1757209 | AA287289_a t | EST: zs49g10.r1 NCI_CGAP_GCB1 Homo sapiens cDNA clone IMAGE:700866 5', mRNA sequence. (from Genbank) |
| 910 | Lung | 0.1329259 | 0.3901625 | 0.309031 | 0.17561547 | U92314_s_a t | Hydroxysteroid sulfotransferase SULT2B1a (HSST2) mRNA |
| 911 | Lung | 0.1329259 | 0.3901141 | 0.308994 | 0.17554384 | U92314_s_a t-2 | Sulfotransferase family 2B, member 1 |
| 912 | Lung | 0.1327966 | 0.389808 | 0.308832 | 0.17546465 | H47269_at | Splicing factor, arginine/serine-rich 7 (35kD) |
| 913 | Lung | 0.1326064 | 0.3897879 | 0.30876 | 0.17545015 | L17075_s_at | SERINE/THREONINE-PROTEIN KINASE RECEPTOR R3 PRECURSOR |
| 914 | Lung | 0.1325038 | 0.3897435 | 0.308648 | 0.17541745 | H29683_at | EST: ym61b06.r1 Homo sapiens cDNA clone 52750 5' similar to contains Alu repetitive element;contains KER repetitive element :. (from Genbank) |
| 915 | Lung | 0.1322415 | 0.3896492 | 0.308552 | 0.17525758 | RC_AA4615 05_at | EST: zx60b05.s1 Soares testis NHT Homo sapiens cDNA clone 795825 3', mRNA sequence. (from Genbank) |
| 916 | Lung | 0.132051 | 0.389627 | 0.308516 | 0.17521381 | L35546_at | GLCLR Glutamate-cysteine ligase (gamma-glutamylcysteine synthetase), regulatory (30.8kD) |
| 917 | Lung | 0.132051 | 0.3896247 | 0.308413 | 0.17515075 | L35546_at-2 | Glutamate-cysteine ligase (gamma-glutamylcysteine synthetase), regulatory (30.8kD) |
| 918 | Lung | 0.1317424 | 0.3894547 | 0.308356 | 0.1750737 | Z48511_at | XG mRNA (clone PEP11) |
| 919 | Lung | 0.1317297 | 0.3894403 | 0.308273 | 0.17505275 | RC_AA2905 99_at | EST: zs45c01.s1 NCI_CGAP_GCB1 Homo sapiens cDNA clone IMAGE:700416 3', mRNA sequence. (from Genbank) |
| 920 | Lung | 0.1317241 | 0.3894375 | 0.308189 | 0.17495969 | RC_D60354 s_at | Human mRNA for KIAA0007 gene, partial cds |
| 921 | Lung | 0.13166 | 0.38941 | 0.308047 | 0.17494038 | W60965_at | EST: zd30c02.r1 Soares fetal heart NbHH19W Homo sapiens cDNA clone 342146 5', mRNA sequence. (from Genbank) |
| 922 | Lung | 0.1313929 | 0.3893816 | 0.307999 | 0.17481253 | RC_AA4793 50_at | EST: zv17d09.s1 Soares NhHMPu S1 Homo sapiens cDNA clone 753905 3' similar to contains element TAR1 TAR1 repetitive element :, mRNA sequence. (from Genbank) |
| 923 | Lung | 0.1312947 | 0.3892777 | 0.307939 | 0.17476411 | U50196_at-2 | Adenosine kinase |
| 924 | Lung | 0.1312947 | 0.3891819 | 0.307904 | 0.17476411 | U50196_at | ADK Adenosine kinase |
| 925 | Lung | 0.1309666 | 0.389154 | 0.307904 | 0.174739 | H29723_at | EST: yp02a10.r1 Homo sapiens cDNA clone 186234 5'. (from Genbank) |
| 926 | Lung | 0.1309821 | 0.3890771 | 0.307831 | 0.17461346 | RC_AA4007 66_at | Homo sapiens mRNA for KIAA0556 protein, partial cds |

FIG. 6S2

| | | | | | | |
|---|---|---|---|---|---|---|
| 927 | Lung | 0.1306174 | 0.38903314 | 0.307767 | 0.1744603 | RC_AA4572_at | Etoposide-induced mRNA |
| 928 | Lung | 0.1305526 | 0.3889823 | 0.307697 | 0.17444946 | RC_AA4598_at | EST: zx73e01.s1 Soares ovary tumor NbHOT Homo sapiens cDNA clone 809400 3', mRNA sequence. (from Genbank) |
| 929 | Lung | 0.1304886 | 0.38897799 | 0.307609 | 0.17444946 | L76227_at | Metabotropic glutamate receptor 1 alpha (mGluR1alpha) mRNA |
| 930 | Lung | 0.1303417 | 0.38889908 | 0.307532 | 0.17425461 | AA313891_a_t | EST: EST185749 Colon carcinoma (HCC) cell line II Homo sapiens cDNA 5' end, mRNA sequence. (from Genbank) |
| 931 | Lung | 0.1300526 | 0.38886381 | 0.307508 | 0.17422016 | RC_AA3987_43_s_at | H.sapiens mRNA for inogen 38 |
| 932 | Lung | 0.1298359 | 0.38887812 | 0.307462 | 0.17418523 | AA115572_s_at | EST: zl05d11.r1 Soares pregnant uterus NbHPU Homo sapiens cDNA clone 491445 5' similar to TR:G895845 G895845 PUTATIVE P64 CLCP PROTEIN. ; mRNA sequence. (from Genbank) |
| 933 | Lung | 0.1297109 | 0.38866485 | 0.307426 | 0.17416929 | RC_AA4063_71_at | EST: zv10c09.s1 Soares NhHMPu S1 Homo sapiens cDNA clone 753232 3', mRNA sequence. (from Genbank) |
| 934 | Lung | 0.1297049 | 0.38886058 | 0.307394 | 0.17412226 | Y07867_at | Pirin, isolate 1 |
| 935 | Lung | 0.1295984 | 0.38885302 | 0.307354 | 0.17402734 | AA248582_a_t | KIAA0737 gene product |
| 936 | Lung | 0.1295821 | 0.3885271 | 0.307221 | 0.17402734 | W27770_at | EST: 3719 Human retina cDNA randomly primed sublibrary Homo sapiens cDNA, mRNA sequence. (from Genbank) |
| 937 | Lung | 0.1295575 | 0.38884376 | 0.307131 | 0.17395227 | AF000573_r_na1_at | Homogentisate 1,2-dioxygenase gene |
| 938 | Lung | 0.1292838 | 0.38841172 | 0.307044 | 0.17390133 | RC_AA0349_25_at | EST: zk25e01.s1 Soares pregnant uterus NbHPU t homo sapiens cDNA clone 471576 3', mRNA sequence. (from Genbank) |
| 939 | Lung | 0.1291031 | 0.38883853 | 0.306079 | 0.17388447 | AF002672_a_t | Loss of heterozygosity, 11, chromosomal region 2, gene A |
| 940 | Lung | 0.1289948 | 0.38834495 | 0.306928 | 0.17382503 | H50178_at | EST: yo27h07.r1 Homo sapiens cDNA clone 179197 5' similar to SP:2ABB_RABIT Q00006 PROTEIN PHOSPHATASE PP2A, 55 KD REGULATORY SUBUNIT, NEURONAL ISOFORM ;. (from Genbank) |
| 941 | Lung | 0.1289946 | 0.38833451 | 0.306859 | 0.17377426 | U40223_at | Uridine nucleotide receptor (UNR) gene |
| 942 | Lung | 0.1288898 | 0.38821189 | 0.306802 | 0.17367938 | RC_AA4969_80_at | KIAA0331 gene product |
| 943 | Lung | 0.12876 | 0.3882018 | 0.306745 | 0.17367345 | RC_AA4870_54_at | EST: ab18e01.s1 Stratagene lung (#937210) Homo sapiens cDNA clone 841176 3', mRNA sequence. (from Genbank) |
| 944 | Lung | 0.1287164 | 0.3881793 | 0.306732 | 0.17361404 | J03909_at | GAMMA-INTERFERON-INDUCIBLE PROTEIN IP-30 PRECURSOR |
| 945 | Lung | 0.1284487 | 0.3881031 | 0.306679 | 0.1735835 | L17128_at | GGCX Gamma-glutamyl carboxylase |
| 946 | Lung | 0.1283728 | 0.3880736 | 0.30667 | 0.17343584 | U78313_at | Myogenic repressor I-mf (MDFI) mRNA |

FIG. 6T2

| # | Tissue | Val1 | Val2 | Val3 | ID1 | ID2 | Description |
|---|---|---|---|---|---|---|---|
| 947 | Lung | 0.1280852 | 0.3880158 | 0.306551 | 0.17336771 | RC_AA2792 15_at | EST: zs83f06.s1 NCI_CGAP_GCB1 Homo sapiens cDNA clone IMAGE:704099 3', mRNA sequence. (from Genbank) |
| 948 | Lung | 0.1276563 | 0.3880053 | 0.306549 | 0.17325802 | RC_AA1914 95_at | EST: zp88e03.s1 Stratagene HeLa cell s3 937216 Homo sapiens cDNA clone 627292 3' similar to contains Alu repetitive element;;, mRNA sequence. (from Genbank) |
| 949 | Lung | 0.1276523 | 0.3879883 | 0.3065 | 0.17317784 | AA130614_a t | Zo10f02.r1 Stratagene neuroepithelium NT2RAMI 937234 Homo sapiens cDNA clone 567291 5' similar to TR:G1125026 G1125026 3-HYDROXYACYL COA DEHYDROGENASE.;. mRNA sequence. (from Genbank) |
| 950 | Lung | 0.1275981 | 0.3879795 | 0.30647 | 0.17313856 | D62633_f_at | EST: Human aorta cDNA 5'-end GEN-308H02, mRNA sequence. (from Genbank) |
| 951 | Lung | 0.1274128 | 0.3879569 | 0.306458 | 0.17309685 | L34774_s_at | Opioid-binding protein/cell adhesion molecule-like |
| 952 | Lung | 0.1272099 | 0.3878615 | 0.306198 | 0.17297521 | RC_AA0073 12_at | EST: zh98d02.s1 Soares fetal liver spleen 1NFLS S1 Homo sapiens cDNA clone 429315 3' similar to SW:POL1_HUMAN P10266 RETROVIRUS-RELATED POL POLYPROTEIN.;, mRNA sequence. (from Genbank) |
| 953 | Lung | 0.1263195 | 0.3878511 | 0.306185 | 0.17286539 | X96698_at | D1075-like gene |
| 954 | Lung | 0.1262246 | 0.3877869 | 0.306117 | 0.17275044 | M62486_at | C4BPA Complement component 4-binding protein, alpha |
| 955 | Lung | 0.1257587 | 0.3876841 | 0.306105 | 0.1726566 | RC_AA4341 13_at | EST: zw24b11.s1 Soares ovary tumor NbHOT Homo sapiens cDNA clone 770205 3' similar to contains element TAR1 repetitive element;;, mRNA sequence. (from Genbank) |
| 956 | Lung | 0.1254499 | 0.3875594 | 0.306035 | 0.17260979 | L10844_at | CDC42 Cell division cycle 42 (GTP-binding protein, 25kD) |
| 957 | Lung | 0.1254446 | 0.3875257 | 0.306019 | 0.17259628 | RC_AA4856 55_at | Human low-Mr GTP-binding protein (RAB31) mRNA, complete cds |
| 958 | Lung | 0.1254216 | 0.3874441 | 0.305979 | 0.17256227 | RC_AA5983 97_at | EST: ae40d12.s1 Gessler Wilms tumor Homo sapiens cDNA clone 898295 3', mRNA sequence. (from Genbank) |
| 959 | Lung | 0.1254068 | 0.3874079 | 0.305966 | 0.17243433 | RC_D51069 f_at | CELL SURFACE GLYCOPROTEIN MUC18 PRECURSOR |
| 960 | Lung | 0.1252746 | 0.3873117 | 0.305966 | 0.17240111 | U44754_at | PSE-binding factor PTF gamma subunit mRNA |
| 961 | Lung | 0.1250318 | 0.3872659 | 0.305922 | 0.1723387 | U40671_at | Ligase III, DNA, ATP-dependent |
| 962 | Lung | 0.1249987 | 0.3872496 | 0.30588 | 0.17226854 | M13994_s_a t | BCL2 B-cell CLL/lymphoma 2 |
| 963 | Lung | 0.124497 | 0.3871949 | 0.305836 | 0.1721731 | AA402109_a t | EST: zu55a06.r1 Soares ovary tumor NbHOT Homo sapiens cDNA clone 741874 5', mRNA sequence. (from Genbank) |
| 964 | Lung | 0.1244043 | 0.3871296 | 0.305697 | 0.17214946 | M80647_at | THROMBOXANE-A SYNTHASE |
| 965 | Lung | 0.124252 | 0.387122 | 0.305601 | 0.17208278 | Z96810_at | DNA sequence from PAC 452H17 on chromosome X contains sodium and chloride-dependent glycine transporter 1 (GLYT-1) like, ESTs |

FIG. 6U2

| # | Tissue | Col3 | Col4 | Col5 | Col6 | Description |
|---|---|---|---|---|---|---|
| 966 | Lung | 0.1242019 | 0.3871163 | 0.305554 | 0.17207249 | K00629_f_at Human kpni repeat mrna (cdna clone pcd-kpni-4), 3' end |
| 967 | Lung | 0.1238909 | 0.3870255 | 0.305541 | 0.17202947 | U62647_at Deoxyribonuclease I-like 2 |
| 968 | Lung | 0.1236748 | 0.3868947 | 0.305494 | 0.17199479 | U31929_s_at DAX-1 |
| 969 | Lung | 0.1230902 | 0.3868854 | 0.305437 | 0.17190056 | AA393318_a_t EST: zt70␣d02.r1 Soares testis NHT Homo sapiens cDNA clone 727683 5', mRNA sequence. (from Genbank) |
| 970 | Lung | 0.1229971 | 0.3868721 | 0.305389 | 0.17182809 | U21051_rna1_at G protein-coupled receptor (GPR4) gene |
| 971 | Lung | 0.1229522 | 0.3868671 | 0.305355 | 0.17176127 | RC_AA040158_at EST: zk47b05.s1 Soares pregnant uterus NbHPU I homo sapiens cDNA clone 485937 3', mRNA sequence. (from Genbank) |
| 972 | Lung | 0.1226257 | 0.3867807 | 0.305329 | 0.17171474 | RC_AA001970_at EST: zh83f07.s1 Soares fetal liver spleen 1NFLS S1 Homo sapiens cDNA clone 427909 3', mRNA sequence. (from Genbank) |
| 973 | Lung | 0.1224771 | 0.3866769 | 0.305187 | 0.17170125 | RC_AA348014_at EST: EST54433 Fetal heart II Homo sapiens cDNA 3' end, mRNA sequence. (from Genbank) |
| 974 | Lung | 0.1224594 | 0.3865044 | 0.304926 | 0.17164434 | AFFX-BioB-5_st-2 AFFX-BioB-5 st (miscellaneous control - 11k chips) |
| 975 | Lung | 0.1224594 | 0.3864811 | 0.304843 | 0.17153297 | AFFX-BioB-5_st AFFX-BioB-5 st (endogenous control) |
| 976 | Lung | 0.1223678 | 0.3863987 | 0.304826 | 0.17149651 | AA180854_a_t EST: zp35h03.r1 Stratagene muscle 937209 Homo sapiens cDNA clone 611477 5', mRNA sequence. (from Genbank) |
| 977 | Lung | 0.1223618 | 0.3862045 | 0.30478 | 0.17141947 | RC_AA599144_at Myosin phosphatase, target subunit 1 |
| 978 | Lung | 0.1222019 | 0.3861229 | 0.304721 | 0.17141365 | L19437_at TALDO Transaldolase |
| 979 | Lung | 0.1221612 | 0.3860507 | 0.304685 | 0.17136844 | M34057_at LTBP1 Latent transforming growth factor beta binding protein 1 |
| 980 | Lung | 0.1221165 | 0.3859938 | 0.304685 | 0.17126703 | AA070545_a_t EST: Zm70c03.r1 Stratagene neuroepithelium (#937231) Homo sapiens cDNA clone 530980 5', mRNA sequence. (from Genbank) |
| 981 | Lung | 0.1220644 | 0.3859637 | 0.304642 | 0.17120038 | U62325_at FE65-like protein (hFE65L) mRNA, partial cds |
| 982 | Lung | 0.1220164 | 0.3858567 | 0.304574 | 0.17111775 | RC_AA464722_s_at EST: zx82d05.s1 Soares ovary tumor NbHOT Homo sapiens cDNA clone 810249 3', mRNA sequence. (from Genbank) |
| 983 | Lung | 0.1219493 | 0.3858268 | 0.304524 | 0.171055 | M57710_at LGALS3 Lectin, galactoside-binding, soluble, 3 (galectin 3) (NOTE: redefinition of symbol) |
| 984 | Lung | 0.1217599 | 0.3857487 | 0.304382 | 0.17098396 | RC_AA101965_at Homo sapiens growth suppressor related (DOC-1R) mRNA, complete cds |
| 985 | Lung | 0.1216273 | 0.3856391 | 0.304372 | 0.17090636 | HG4169-HT4439_s_a_t Syntaxin 1b |
| 986 | Lung | 0.1215411 | 0.3856391 | 0.304342 | 0.17085183 | X62078_at GM2A GM2 ganglioside activator protein |

FIG. 6V2

| # | Tissue | | | | | Description |
|---|---|---|---|---|---|---|
| 987 | Lung | 0.1214343 | 0.3854686 | 0.30434 | 0.17079692 | AA453331_a t | EST: zx44g02.r1 Soares total fetus Nb2HF8 9w Homo sapiens cDNA clone 789362 5' similar to contains L1.t1 L1 repetitive element :, mRNA sequence. (from Genbank) |
| 988 | Lung | 0.1213893 | 0.3854203 | 0.304246 | 0.17073461 | D50663_at | CW-1 mRNA |
| 989 | Lung | 0.1212679 | 0.3854169 | 0.304236 | 0.17069243 | U13369_at | Ribosomal DNA complete repeating unit |
| 990 | Lung | 0.120995 | 0.3853394 | 0.304202 | 0.17062272 | RC_AA4571 40_at | EST: zx84f04.s1 Soares ovary tumor NbHOT Homo sapiens cDNA clone 810463 3', mRNA sequence. (from Genbank) |
| 991 | Lung | 0.1209776 | 0.3852518 | 0.304124 | 0.17052606 | AA316868_a t | EST: EST188529 HCC cell line (metastasis to liver in mouse) II Homo sapiens cDNA 5' end, mRNA sequence. (from Genbank) |
| 992 | Lung | 0.1209395 | 0.3852305 | 0.304115 | 0.17046939 | L76687_at-2 | Growth factor receptor-bound protein 14 |
| 993 | Lung | 0.1209395 | 0.3851693 | 0.3041 | 0.17040393 | L76687_at | Grb14 mRNA |
| 994 | Lung | 0.1208849 | 0.3851602 | 0.304031 | 0.17037708 | X90840_at | Axonal transporter of synaptic vesicles |
| 995 | Lung | 0.1208708 | 0.3850391 | 0.303897 | 0.17034759 | AA203236_a t | EST: zx54g10.r1 Soares fetal liver spleen 1NFLS S1 Homo sapiens cDNA clone 446370 5' similar to contains element PTR5 repetitive element :, mRNA sequence. (from Genbank) |
| 996 | Lung | 0.1208458 | 0.385016 | 0.30381 | 0.17030604 | D25539_at | KIAA0040 gene |
| 997 | Lung | 0.1206311 | 0.3849609 | 0.303802 | 0.17018099 | M91490_s_a t | EST: HUMRTPGEAI Homo sapiens cDNA. (from Genbank) |
| 998 | Lung | 0.1205743 | 0.3848771 | 0.303762 | 0.17011455 | C17139_at | EST: Human placenta cDNA 5'-end GEN-539G01, mRNA sequence. (from Genbank) |
| 999 | Lung | 0.1205573 | 0.3848463 | 0.303699 | 0.1700299 | RC_D60386 _at | EST: Human fetal brain cDNA 3'-end GEN-103H09, mRNA sequence. (from Genbank) |
| 1000 | Lung | 0.1205492 | 0.3848313 | 0.303637 | 0.16997482 | M59916_at | SMPD1 Sphingomyelin phosphodiesterase 1, acid lysosomal (acid sphingomyelinase) |

FIG. 6W2

| | | | | | |
|---|---|---|---|---|---|
| 1 Lymphoma | 1.3723106 | 0.5039521 | 0.449323 | 0.3534761 | RC_AA0246 58_at | Ribosomal protein S19 |
| 2 Lymphoma | 1.1656398 | 0.4679987 | 0.418099 | 0.33133417 | S82297_at | BETA-2-MICROGLOBULIN PRECURSOR |
| 3 Lymphoma | 1.1079978 | 0.4555078 | 0.404835 | 0.31944063 | AA297912_a_t | EST: EST113641 T-cell lymphoma Homo sapiens cDNA 5' end, mRNA sequence. (from Genbank) |
| 4 Lymphoma | 1.02126 | 0.446076 | 0.395554 | 0.31117448 | RC_AA1218 79_s_at | Proteasome (prosome, macropain) subunit, beta type, 9 (large multifunctional protease 2) |
| 5 Lymphoma | 0.9422403 | 0.4394731 | 0.388355 | 0.30497497 | U37546_s_a t | IAP homolog C (MIHC) mRNA |
| 6 Lymphoma | 0.9422403 | 0.4337181 | 0.384047 | 0.2999395 | U37546_s_a t-2 | Apoptosis inhibitor 1 |
| 7 Lymphoma | 0.9388786 | 0.4286351 | 0.380023 | 0.29578 | RC_AA4045 12_at | EST: zw38d02.s1 Soares total fetus Nb2HF8 9w Homo sapiens cDNA clone 772323 3', mRNA sequence. (from Genbank) |
| 8 Lymphoma | 0.9387285 | 0.4249089 | 0.37583 | 0.29255435 | D83597_at | RP105 |

FIG. 7A

| | | | | | |
|---|---|---|---|---|---|
| 9 Lymphoma | 0.9387285 | 0.4220441 | 0.372734 | 0.28904745 | D83597_at-2 | Lymphocyte antigen 64 (mouse) homolog, radioprotective, 105kD |
| 10 Lymphoma | 0.9386553 | 0.419515 | 0.369998 | 0.286588897 | RC_AA5212 62_at | EST: aa75e08.s1 NCI_CGAP_GCB1 Homo sapiens cDNA clone IMAGE:826790 3', mRNA sequence. (from Genbank) |
| 11 Lymphoma | 0.9383826 | 0.4159639 | 0.367165 | 0.284062958 | RC_AA4889 87_s_at | Synaptogyrin 2 |
| 12 Lymphoma | 0.9362829 | 0.4131206 | 0.364741 | 0.2815551 | M27394_s_a t | B-lymphocyte cell-surface antigen B1 (CD20) |
| 13 Lymphoma | 0.9303746 | 0.4113689 | 0.363488 | 0.27958748 | X72755_at | Humig mRNA |
| 14 Lymphoma | 0.9268587 | 0.4102988 | 0.361547 | 0.277747554 | AA397670_a t | EST: zt85h10.r1 Soares testis NHT Homo sapiens cDNA clone 729187 5' similar to TR:E243441 E243441 CHROMOSOME VII READING FRAME ORF YGR096W.; mRNA sequence. (from Genbank) |
| 15 Lymphoma | 0.9205939 | 0.4093482 | 0.360768 | 0.275558842 | M89957_at | IGB Immunoglobulin-associated beta (B29) |
| 16 Lymphoma | 0.9205939 | 0.4074558 | 0.358498 | 0.27373374 | M89957_at-2 | CD79B antigen (immunoglobulin-associated beta) |
| 17 Lymphoma | 0.9166188 | 0.4050154 | 0.357199 | 0.271198726 | X12530_s_a t | CD20 RECEPTOR |
| 18 Lymphoma | 0.8950695 | 0.4046188 | 0.355364 | 0.270132345 | U77180_at | EBI1-ligand chemokine |
| 19 Lymphoma | 0.8916236 | 0.4028494 | 0.35319 | 0.268660675 | X07203_at | CD20 RECEPTOR |
| 20 Lymphoma | 0.8882251 | 0.4017093 | 0.351473 | 0.267711926 | U26174_at | GZMK Granzyme K (serine protease, granzyme 3) |
| 21 Lymphoma | 0.8726038 | 0.3992052 | 0.349987 | 0.265841044 | RC_AA4642 40_s_at | EST: zx81a05.s1 Soares ovary tumor NbHOT Homo sapiens cDNA clone 810128 3', mRNA sequence. (from Genbank) |
| 22 Lymphoma | 0.8619036 | 0.3984305 | 0.348683 | 0.264651972 | U03754_f_at | Major histocompatibility complex, class I, A |
| 23 Lymphoma | 0.8616518 | 0.3970168 | 0.347764 | 0.2633116 | K02405_f_at | HLA CLASS II HISTOCOMPATIBILITY ANTIGEN, DQ(1) BETA CHAIN PRECURSOR |
| 24 Lymphoma | 0.8555751 | 0.3959627 | 0.346265 | 0.26218455 | RC_AA2336 20_at | EST: zr43d08.s1 Soares NhHMPu S1 Homo sapiens cDNA clone 666159 3', mRNA sequence. (from Genbank) |
| 25 Lymphoma | 0.8492417 | 0.3948609 | 0.345184 | 0.26096663 | L11015_s_at | Lymphotoxin beta (TNF superfamily, member 3) |
| 26 Lymphoma | 0.8464394 | 0.3942199 | 0.343726 | 0.259829920 | RC_AA4189 00_f_at | EST: zw01g02.s1 Soares NhHMPu S1 Homo sapiens cDNA clone 768050 3', mRNA sequence. (from Genbank) |

FIG. 7B

| # | | | | | | |
|---|---|---|---|---|---|---|
| 27 | Lymphoma | 0.8429168 | 0.3928429 | 0.342734 | 0.25865674 | AFFX-HSAC07/X00351_5_at | AFFX-HSAC07/X00351_5_at (endogenous control) |
| 28 | Lymphoma | 0.8429168 | 0.3918851 | 0.341933 | 0.25756688 | AFFX-HSAC07/X00351_5_at-2 | No info for gene |
| 29 | Lymphoma | 0.8387807 | 0.3902384 | 0.341365 | 0.2561314 | H20906_at | Homo sapiens mRNA for KIAA0746 protein, partial cds |
| 30 | Lymphoma | 0.8276051 | 0.389963 | 0.340044 | 0.25533625 | AF006083_at | Actin-related protein 3 |
| 31 | Lymphoma | 0.8237535 | 0.3887247 | 0.339399 | 0.2545945 | AA234791_at | Human DNA sequence from clone 753P9 on chromosome Xq25-26.1. Contains the gene coding for Aminopeptidase P (EC 3.4.11.9, XAA-Pro/X-Pro/Proline/Aminoacylproline Aminopeptidase) and a novel gene. Contains ESTs, STSs, GSSs and a gaaa repeat polymorphism |
| 32 | Lymphoma | 0.822552 | 0.3874336 | 0.338579 | 0.25371173 | T80746_s_at | Ferritin, light polypeptide |
| 33 | Lymphoma | 0.8151091 | 0.3867773 | 0.337949 | 0.252441 | AA281696_at | Human MDA-7 (mda-7) mRNA, complete cds |
| 34 | Lymphoma | 0.8145876 | 0.3853702 | 0.337296 | 0.25170222 | RC_AA4057742967_at | EST: zu66d12.s1 Soares testis NHT Homo sapiens cDNA clone 742967 3', mRNA sequence. (from Genbank) |
| 35 | Lymphoma | 0.8091871 | 0.3853414 | 0.336841 | 0.25094026 | R10770_at | EST: yf36a08.r1 Homo sapiens cDNA clone 128918 5'. (from Genbank) |
| 36 | Lymphoma | 0.8019967 | 0.3847336 | 0.335767 | 0.2501192 | U66464_at | Hematopoietic progenitor kinase (HPK1) mRNA |
| 37 | Lymphoma | 0.8019967 | 0.3836153 | 0.335362 | 0.24929732 | U66464_at-2 | Human hematopoietic progenitor kinase (HPK1) mRNA, complete cds |
| 38 | Lymphoma | 0.8008153 | 0.3828973 | 0.33447 | 0.24850619 | RC_AA4004743310_at | EST: zu70a04.s1 Soares testis NHT Homo sapiens cDNA clone 743310 3', mRNA sequence. (from Genbank) |
| 39 | Lymphoma | 0.8000225 | 0.3816113 | 0.334149 | 0.24769732 | AFFX-HSAC07/X00351_M_at-2 | No info for gene |
| 40 | Lymphoma | 0.8000225 | 0.3814741 | 0.333599 | 0.24692726 | AFFX-HSAC07/X00351_M_at | AFFX-HSAC07/X00351_M_at (endogenous control) |
| 41 | Lymphoma | 0.7972664 | 0.380874 | 0.332567 | 0.24620968 | RC_AA2369687936_at | EST: zs43c01.s1 Soares NhHMPu S1 Homo sapiens cDNA clone 687936 3', mRNA sequence. (from Genbank) |
| 42 | Lymphoma | 0.7929604 | 0.3798588 | 0.332131 | 0.24549004 | R72037_at | EST: yj86c09.r1 Homo sapiens cDNA clone 155632 5'. (from Genbank) |

FIG. 7C

| # | Type | | | | Accession | Description |
|---|---|---|---|---|---|---|
| 43 | Lymphoma | 0.7912974 | 0.3792441 | 0.24464384 | RC_AA2620 30_at | EST: zs21d01.s1 NCI_CGAP_GCB1 Homo sapiens cDNA clone IMAGE:685825 3', mRNA sequence. (from Genbank) |
| 44 | Lymphoma | 0.79105557 | 0.3786599 | 0.331334 | M21121_s_a t | Small inducible cytokine A5 (RANTES) |
| 45 | Lymphoma | 0.7906493 | 0.3780693 | 0.243996555 | H61295_s_a t | EST: yu40tg11.r1 Homo sapiens cDNA clone 236324 5'. (from Genbank) |
| 46 | Lymphoma | 0.7894109 | 0.3774717 | 0.2431649 | RC_AA4117 | EST: zu02b12.s1 Soares testis NHT Homo sapiens cDNA clone 730655 3' similar to contains Alu repetitive element;contains element TAR1 repetitive element ;, mRNA sequence. (from Genbank) |
| 47 | Lymphoma | 0.7892708 | 0.3771496 | 0.242247827 | RC_AA4541 | EST: zx46f10.s1 Soares testis NHT Homo sapiens cDNA clone 795307 3', mRNA sequence. (from Genbank) |
| 48 | Lymphoma | 0.7890263 | 0.3763106 | 0.241179948 | AA284380_s | Neutrophil cytosolic factor 1 (47kD, chronic granulomatous disease, autosomal 1) |
| 49 | Lymphoma | 0.7852181 | 0.3758696 | 0.2412768 | X62466_at | CDW52 CDW52 antigen (CAMPATH-1 antigen) |
| 50 | Lymphoma | 0.78374459 | 0.3755993 | 0.24079382 | M91391_at | Human mRNA for KIAA0179 gene, partial cds |
| 51 | Lymphoma | 0.7835063 | 0.37528 | 0.24013416 | AA285290_a | Pinin, desmosome associated protein |
| 52 | Lymphoma | 0.7833535 | 0.3751609 | 0.23944487 | M91196_at | ICSBP1 Interferon consensus sequence binding protein 1 |
| 53 | Lymphoma | 0.779577 | 0.3747905 | 0.23892252 | RC_AA4240 | Core-binding factor, runt domain, alpha subunit 2; translocated to, 2 |
| 54 | Lymphoma | 0.77767535 | 0.3747272 | 0.23836167 | RC_AA3423 | EST: EST48084 Fetal spleen Homo sapiens cDNA 3' end, mRNA sequence. (from Genbank) |
| 55 | Lymphoma | 0.7658663 | 0.3740414 | 0.23770358 | AA336515_a | EST141354 Endometrial tumor Homo sapiens cDNA 5' end, mRNA sequence. (from Genbank) |
| 56 | Lymphoma | 0.7642185 | 0.3738239 | 0.23737576 | X80822_f_at | Ribosomal protein L18a |
| 57 | Lymphoma | 0.7626857 | 0.3737581 | 0.23674928 | W56046_at | Homo sapiens mRNA for KIAA0746 protein, partial cds |
| 58 | Lymphoma | 0.7604024 | 0.3729435 | 0.23622586 | X00274_at | HLA CLASS II HISTOCOMPATIBILITY ANTIGEN, DR ALPHA CHAIN PRECURSOR |
| 59 | Lymphoma | 0.7560449 | 0.3709495 | 0.23569952 | RC_AA4651 | EST: aa33d09.s1 NCI_CGAP_GCB1 Homo sapiens cDNA clone IMAGE:815057 3', mRNA sequence. (from Genbank) |
| 60 | Lymphoma | 0.7557885 | 0.3707112 | 0.23535301 | RC_AA4559 | Serine/threonine kinase 17a (apoptosis-inducing) |
| 61 | Lymphoma | 0.7537171 | 0.3706513 | 0.23485571 | U36499_s_a | Human lymphoid-specific SP100 homolog (LYSP100-A) mRNA, complete cds |

FIG. 7D

| # | Tissue | | | | Probe | Description |
|---|---|---|---|---|---|---|
| 62 | Lymphoma | 0.7490465 | 0.3702929 | 0.32174 | T67231_at | Succinate dehydrogenase complex, subunit D, integral membrane protein |
| 63 | Lymphoma | 0.7488897 | 0.3698789 | 0.321022 | RC_AA4063 63_at | EST: zv10b11.s1 Soares NhHMPu S1 Homo sapiens cDNA clone 753213 3', mRNA sequence. (from Genbank) |
| 64 | Lymphoma | 0.7479789 | 0.3698091 | 0.320927 | C02143_s_a t | EST: HUMGS0006474, Human Gene Signature, 3'-directed cDNA sequence, mRNA sequence. (from Genbank) |
| 65 | Lymphoma | 0.7438281 | 0.3697601 | 0.320471 | RC_AA4821 12_at | EST: zv43b10.s1 Soares ovary tumor NbHOT Homo sapiens cDNA clone 756379 3', mRNA sequence. (from Genbank) |
| 66 | Lymphoma | 0.7400417 | 0.3696365 | 0.319486 | RC_AA2360 13_at | Cathepsin S |
| 67 | Lymphoma | 0.7389721 | 0.3694383 | 0.318992 | RC_AA4210 49_at | EST: zu09f12.s1 Soares testis NHT Homo sapiens cDNA clone 731375 3', mRNA sequence. (from Genbank) |
| 68 | Lymphoma | 0.7383922 | 0.3687783 | 0.318945 | AB002409_a t | SLC |
| 69 | Lymphoma | 0.7375007 | 0.3676483 | 0.318928 | AA214710_a t | ATPase, H+ transporting, lysosomal (vacuolar proton pump) 9kD |
| 70 | Lymphoma | 0.7357451 | 0.3676318 | 0.318476 | RC_AA4320 69_at | EST: zw89b06.s1 Soares total fetus Nb2HF8 9w Homo sapiens cDNA clone 784115 3', mRNA sequence. (from Genbank) |
| 71 | Lymphoma | 0.7281507 | 0.367251 | 0.317995 | RC_AA2340 89_at | Serine/threonine kinase 17a (apoptosis-inducing) |
| 72 | Lymphoma | 0.7273517 | 0.3669045 | 0.317629 | AA095867_a t | EST: l6224.seq.F Fetal heart, Lambda ZAP Express Homo sapiens cDNA 5', mRNA sequence. (from Genbank) |
| 73 | Lymphoma | 0.72724 | 0.3664121 | 0.317261 | M34996_s_a t | MHC cell surface glycoprotein (HLA-DQA) mRNA, 3'end |
| 74 | Lymphoma | 0.7252355 | 0.3655395 | 0.316948 | RC_AA4599 61_at | EST: zx66c03.s1 Soares total fetus Nb2HF8 9w Homo sapiens cDNA clone 796420 3', mRNA sequence. (from Genbank) |
| 75 | Lymphoma | 0.7243797 | 0.365009 | 0.31675 | M13560_s_a t | PROBABLE PROTEIN DISULFIDE ISOMERASE ER-60 PRECURSOR |
| 76 | Lymphoma | 0.7197233 | 0.3646756 | 0.316547 | AA095867_a W28944_at | EST: 54h12 Human retina cDNA randomly primed sublibrary Homo sapiens cDNA, mRNA sequence. (from Genbank) |
| 77 | Lymphoma | 0.717179 | 0.3640513 | 0.316154 | U22662_at | Nuclear orphan receptor LXR-alpha mRNA |
| 78 | Lymphoma | 0.7169247 | 0.3638963 | 0.315407 | AA291334_a t | EST: zs20g02.r1 NCI_CGAP_GCB1 Homo sapiens cDNA clone IMAGE:685778 5' similar to gb:U02570 !!!! ALU CLASS C WARNING ENTRY !!!! (HUMAN);contains Alu repetitive element;, mRNA sequence. (from Genbank) |
| 79 | Lymphoma | 0.7155678 | 0.363647 | 0.315193 | RC_AA4902 37_at | EST: aa44a02.s1 Soares NhHMPu S1 Homo sapiens cDNA clone 823754 3', mRNA sequence. (from Genbank) |
| 80 | Lymphoma | 0.7154263 | 0.3626657 | 0.314872 | X61072_at-2 | Human mRNA for T cell receptor, clone IGRA17 |

FIG. 7E

| # | Type | | | | | | Description |
|---|---|---|---|---|---|---|---|
| 81 | Lymphoma | 0.7154263 | 0.362527 | 0.314302 | 0.22549337 | X61072_at | T cell receptor, clone IGRA17 |
| 82 | Lymphoma | 0.7141152 | 0.3623878 | 0.314074 | 0.22510928 | RC_AA4888 78_at | EST: aa55f02.s1 NCI_CGAP_GCB1 Homo sapiens cDNA clone IMAGE:824859 3', mRNA sequence. (from Genbank) |
| 83 | Lymphoma | 0.7134766 | 0.3619762 | 0.313771 | 0.22480145 | U88326_at | JAK binding protein |
| 84 | Lymphoma | 0.7129324 | 0.3617928 | 0.31336 | 0.22441822 | Y11215_at | SKAP55 protein |
| 85 | Lymphoma | 0.7129324 | 0.361472 | 0.313013 | 0.22408882 | Y11215_at-2 | Src kinase-associated phosphoprotein of 55 kDa |
| 86 | Lymphoma | 0.7126781 | 0.3611044 | 0.31275 | 0.22381018 | X63380_at | MYOCYTE-SPECIFIC ENHANCER FACTOR 2 |
| 87 | Lymphoma | 0.7099217 | 0.3610381 | 0.312303 | 0.22342225 | RC_AA2812 198_at | EST: zs94h08.s1 NCI_CGAP_GCB1 Homo sapiens cDNA clone IMAGE:705183 3', mRNA sequence. (from Genbank) |
| 88 | Lymphoma | 0.7096631 | 0.3609484 | 0.31202 | 0.22305155 | RC_AA1324 09_at | EST: zo28g12.s1 Stratagene colon (#937204) Homo sapiens cDNA clone 588262 3' similar to contains OFR.t3 OFR repetitive element :, mRNA sequence. (from Genbank) |
| 89 | Lymphoma | 0.7088466 | 0.36074 | 0.31183 | 0.22272788 | AA383520_a t | EST: EST97097 Testis I Homo sapiens cDNA 5' end, mRNA sequence. (from Genbank) |
| 90 | Lymphoma | 0.7084061 | 0.360584 | 0.311597 | 0.22246407 | AA505198_a t | EST: aa58c03.r1 NCI_CGAP_GCB1 Homo sapiens cDNA clone IMAGE:825124 5', mRNA sequence. (from Genbank) |
| 91 | Lymphoma | 0.7072436 | 0.3604647 | 0.31127 | 0.22205266 | RC_AA2153 83_at | EST: zr97d02.s1 NCI_CGAP_GCB1 Homo sapiens cDNA clone IMAGE:6836193', mRNA sequence. (from Genbank) |
| 92 | Lymphoma | 0.7022232 | 0.3601423 | 0.311203 | 0.22166076 | M37033_at | CD53 CD53 antigen |
| 93 | Lymphoma | 0.698978 | 0.3597812 | 0.31089 | 0.22127011 | D29642_at | HYPOTHETICAL MYELOID CELL LINE PROTEIN 3 |
| 94 | Lymphoma | 0.6976923 | 0.3594759 | 0.3104419 | 0.22086833 | M84371_rna 1_s_at-2 | CD19 antigen |
| 95 | Lymphoma | 0.6976923 | 0.3594306 | 0.310245 | 0.22043738 | M84371_rna 1_s_at | CD19 gene |
| 96 | Lymphoma | 0.6940824 | 0.3581286 | 0.309563 | 0.22016425 | RC_AA4217 15_at | EST: zu24b05.s1 Soares NhHMPu S1 Homo sapiens cDNA clone 738897 3', mRNA sequence. (from Genbank) |
| 97 | Lymphoma | 0.6936843 | 0.3580173 | 0.309263 | 0.21994573 | F07806_at | EST: H. sapiens partial cDNA sequence; clone c-2ie11, mRNA sequence. (from Genbank) |
| 98 | Lymphoma | 0.6927738 | 0.357708 | 0.309017 | 0.21974152 | AA431017_a t | EST: PMY0907 KG1-a Lambda Zap Express cDNA library Homo sapiens cDNA 5', mRNA sequence. (from Genbank) |
| 99 | Lymphoma | 0.6918063 | 0.3572623 | 0.308849 | 0.21929313 | RC_AA4177 18_at | EST: zv01e07.s1 NCI_CGAP_GCB1 Homo sapiens cDNA clone IMAGE:746244 3', mRNA sequence. (from Genbank) |

FIG. 7F

| | | | | | | |
|---|---|---|---|---|---|---|
| 100 | Lymphoma | 0.6888455 | 0.3571636 | 0.308808 | RC_AA5987 12_at | EST: ae49b06.s1 Stratagene lung carcinoma 937218 Homo sapiens cDNA clone 950219 3', mRNA sequence. (from Genbank) |
| 101 | Lymphoma | 0.6857551 | 0.3569513 | 0.308332 | 0.21895884 AA306911_a t | EST: EST178043 Colon carcinoma (HCC) cell line Homo sapiens cDNA 5' end, mRNA sequence. (from Genbank) |
| 102 | Lymphoma | 0.68516 | 0.3568401 | 0.308055 | 0.2185397 T81141_at | Yd24d03.r1 Homo sapiens cDNA clone 109157 5'. (from Genbank) |
| 103 | Lymphoma | 0.6833432 | 0.3568399 | 0.307825 | 0.21811858 M26062_at | IL2RB Interleukin 2 receptor beta chain |
| 104 | Lymphoma | 0.68047 | 0.356657 | 0.307504 | 0.21779063 U77942_at | Syntaxin 7 |
| 105 | Lymphoma | 0.6790842 | 0.356305 | 0.307406 | 0.21762482 RC_AA4257_at | Homo sapiens mRNA for KIAA0874 protein, partial cds |
| 106 | Lymphoma | 0.6786397 | 0.355918 | 0.307023 | 0.21729909 L02547_at-2 | Cleavage stimulation factor, 3' pre-RNA, subunit 1, 50kD |
| 107 | Lymphoma | 0.6786397 | 0.3555491 | 0.306949 | 0.21709678 L02547_at | CSTF1 Cleavage stimulation factor, 3' pre-RNA, subunit 1, 50kD |
| 108 | Lymphoma | 0.6782053 | 0.3554905 | 0.306665 | 0.21669526 M17733_at | Thymosin beta-4 mRNA |
| 109 | Lymphoma | 0.6744419 | 0.3553441 | 0.306365 | 0.21625909 RC_AA1734 23_at | EST: zp02d07.s1 Stratagene ovarian cancer (#937219) Homo sapiens cDNA clone 595213 3', mRNA sequence. (from Genbank) |
| 110 | Lymphoma | 0.6743678 | 0.3552281 | 0.30619 | 0.21605416 RC_AA4170 68_s_at | EST: zu13b04.s1 Soares testis NHT Homo sapiens cDNA clone 731695 3', mRNA sequence. (from Genbank) |
| 111 | Lymphoma | 0.6742196 | 0.3548612 | 0.306033 | 0.2157826 M16336_s_a t-2 | CD2 antigen (p50), sheep red blood cell receptor |
| 112 | Lymphoma | 0.6742196 | 0.3547999 | 0.305769 | 0.21552713 M16336_s_a t | CD2 CD2 antigen (p50), sheep red blood cell receptor |
| 113 | Lymphoma | 0.6740577 | 0.354766 | 0.305437 | 0.21527074 N56493_at | EST: JJ9988F Homo sapiens cDNA clone JJ9988 5'. (from Genbank) |
| 114 | Lymphoma | 0.6727566 | 0.3545109 | 0.305173 | 0.21508488 RC_AA4637_at | EST: aa07g07.s1 Soares Nhl-hMPu S1 Homo sapiens cDNA clone 812604 3', mRNA sequence. (from Genbank) |
| 115 | Lymphoma | 0.671299 | 0.3544803 | 0.304897 | 0.21466826 RC_AA2113 88_at | EST: zq88c04.s1 Stratagene hNT neuron (#937233) Homo sapiens cDNA clone 649062 3', mRNA sequence. (from Genbank) |
| 116 | Lymphoma | 0.6700794 | 0.35404454 | 0.3046614 | 0.21431512 IL2_at | No info for gene |
| 117 | Lymphoma | 0.6651887 | 0.3536434 | 0.30452 | 0.21374978 H71130_at | Ys13d10.r1 Homo sapiens cDNA clone 214675 5'. (from Genbank) |

FIG. 7G

| | | | | | |
|---|---|---|---|---|---|
| 118 | Lymphoma | 0.6646953 | 0.3535279 | 0.304173 | 0.213349148 | Z35227_at | TTF mRNA for small G protein |
| 119 | Lymphoma | 0.6646953 | 0.3535053 | 0.303992 | 0.213316981 | Z35227_at-2 | Ras homolog gene family, member H |
| 120 | Lymphoma | 0.6639841 | 0.3532871 | 0.303462 | 0.21294783 | M63262_at-2 | Arachidonate 5-lipoxygenase-activating protein |
| 121 | Lymphoma | 0.6639841 | 0.353156 | 0.303305 | 0.21268576 | M63262_at | 5-lipoxygenase activating protein (FLAP) gene, exon 5 |
| 122 | Lymphoma | 0.6630213 | 0.3531548 | 0.30319 | 0.212245892 | L10717_at | TYROSINE-PROTEIN KINASE ITK/TSK |
| 123 | Lymphoma | 0.6630213 | 0.3529035 | 0.302925 | 0.2120807 | L10717_at-2 | Homo sapiens T cell-specific tyrosine kinase mRNA, complete cds. (from Genbank) |
| 124 | Lymphoma | 0.6608869 | 0.3527711 | 0.30257 | 0.21180731 RC_AA2119 09_at | EST: zq85a03.s1 Stratagene hNT neuron (#937233) Homo sapiens cDNA clone 646364 3', mRNA sequence. (from Genbank) |
| 125 | Lymphoma | 0.6594682 | 0.3524892 | 0.302472 | 0.21156668 AA091605_a t | Sparc/osteonectin, cwcv and kazal-like domains proteoglycan (testican) |
| 126 | Lymphoma | 0.6590121 | 0.3521232 | 0.302291 | 0.21127483 | X14046_at | CD37 CD37 antigen |
| 127 | Lymphoma | 0.6584869 | 0.35183 | 0.301832 | 0.21110134 RC_AA4176 04_at | EST: zu99g07.s1 NCI_CGAP_GCB1 Homo sapiens cDNA clone IMAGE:746172 3', mRNA sequence. (from Genbank) |
| 128 | Lymphoma | 0.655122 | 0.3515028 | 0.301643 | 0.21090299 RC_AA5044 85_at | EST: aa60e03.s1 NCI_CGAP_GCB1 Homo sapiens cDNA clone IMAGE:825340 3', mRNA sequence. (from Genbank) |
| 129 | Lymphoma | 0.6542777 | 0.3511734 | 0.301447 | 0.21066643 | L38928_at | 5,10-methenyltetrahydrofolate synthetase mRNA |
| 130 | Lymphoma | 0.6542777 | 0.3508883 | 0.301241 | 0.2103295 | L38928_at-2 | Homo sapiens 5,10-methenyltetrahydrofolate synthetase mRNA, complete cds |
| 131 | Lymphoma | 0.6540586 | 0.3508499 | 0.301194 | 0.2101158 RC_AA2434 43_at | RNA guanylyltransferase and 5' phosphatase |
| 132 | Lymphoma | 0.6504417 | 0.3504031 | 0.301062 | 0.20980906 AA127696_a t | EST: zk89d09.r1 Soares pregnant uterus NbHPU Homo sapiens cDNA clone 490001 5', mRNA sequence. (from Genbank) |
| 133 | Lymphoma | 0.6490832 | 0.3499805 | 0.300933 | 0.20949921 | H45382_at | EST: yn99b12.r1 Homo sapiens cDNA clone 176543 5' similar to contains LTR6 repetitive element :. (from Genbank) |
| 134 | Lymphoma | 0.6488603 | 0.3499138 | 0.300729 | 0.20930217 RC_AA4241 71_at | Human SNARE protein Ykt6 (YKT6) mRNA, complete cds |
| 135 | Lymphoma | 0.648008 | 0.3495892 | 0.300447 | 0.20915093 | X80822_at | 60S RIBOSOMAL PROTEIN L18A |

FIG. 7H

| | | | | | |
|---|---|---|---|---|---|
| 136 | Lymphoma | 0.647913 | 0.3493336 | 0.300173 | AFFX-HUMISGF3A/M97935_3_at-2 | No info for gene |
| 137 | Lymphoma | 0.647913 | 0.3488649 | 0.300137 | AFFX-HUMISGF3A/M97935_3_at | AFFX-HUMISGF3A/M97935_3_at (endogenous control) |
| 138 | Lymphoma | 0.6457862 | 0.3484443 | 0.299881 | AA228107_at | EST: zr58b05.r1 Soares NhHMPu S1 Homo sapiens cDNA clone 667569 5', mRNA sequence. (from Genbank) |
| 139 | Lymphoma | 0.6457266 | 0.3483919 | 0.299642 | L42621_at | Ly-9 mRNA |
| 140 | Lymphoma | 0.6457266 | 0.3483879 | 0.299378 | L42621_at-2 | Lymphocyte antigen 9 |
| 141 | Lymphoma | 0.6451268 | 0.3481848 | 0.299244 | RC_AA4548 74_at | EST: zx79h01.s1 Soares ovary tumor NbHOT Homo sapiens cDNA clone 810001 3', mRNA sequence. (from Genbank) |
| 142 | Lymphoma | 0.6450587 | 0.3475847 | 0.299102 | X16832_at | CTSH Cathepsin H |
| 143 | Lymphoma | 0.6445535 | 0.3472823 | 0.298944 | RC_AA4500 92_at | Homo sapiens clones 24718 and 24825 mRNA sequence |
| 144 | Lymphoma | 0.6427078 | 0.3471331 | 0.29888 | AA456343_a t | Scaffold attachment factor B |
| 145 | Lymphoma | 0.6420125 | 0.3469061 | 0.298694 | RC_AA4314 70_at | EST: zw70h05.s1 Soares testis NHT Homo sapiens cDNA clone 781593 3', mRNA sequence. (from Genbank) |
| 146 | Lymphoma | 0.6414065 | 0.3468661 | 0.298532 | T95430_at | Homo sapiens mRNA for putative glucosyltransferase, partial cds |
| 147 | Lymphoma | 0.6410974 | 0.3467815 | 0.298457 | H84451_at | Homo sapiens mRNA for hypothetical protein, clone YR-29 |
| 148 | Lymphoma | 0.6409587 | 0.3466618 | 0.297992 | RC_AA2828 86_at | EST: zs91g01.s1 NCI_CGAP_GCB1 Homo sapiens cDNA clone IMAGE:704880 3', mRNA sequence. (from Genbank) |
| 149 | Lymphoma | 0.6392438 | 0.3466069 | 0.297976 | M86868_at | GABRR2 Gamma-aminobutyric acid (GABA) receptor, rho 2 |
| 150 | Lymphoma | 0.6392438 | 0.3462975 | 0.297942 | M86868_at-2 | Gamma-aminobutyric acid (GABA) receptor, rho 2 |
| 151 | Lymphoma | 0.6388556 | 0.3460721 | 0.297942 | T89815_at | EST: ye11d01.r1 Homo sapiens cDNA clone 117409 5'. (from Genbank) |
| 152 | Lymphoma | 0.6377919 | 0.3458356 | 0.297691 | X87212_at | CTSC Cathepsin C |
| 153 | Lymphoma | 0.6376922 | 0.3457728 | 0.297532 | AA464386_t | EST: zx81f01.r1 Soares ovary tumor NbHOT Homo sapiens cDNA clone 810169 5', mRNA sequence. (from Genbank) |

FIG. 7I

| | | | | | |
|---|---|---|---|---|---|
| 154 | Lymphoma | 0.6367463 | 0.3457412 | 0.297307 | 0.205135376_at | RC_AA2325 | EST: zr45d09.s1 Soares NhHMPu S1 Homo sapiens cDNA clone 666353 3', mRNA sequence. (from Genbank) |
| 155 | Lymphoma | 0.6362119 | 0.345283 | 0.29715 | 0.20476702 N23786_at | | EST: yx35f11.r1 Homo sapiens cDNA clone 263757 5' similar to SP:S28583 S28583 RFBG PROTEIN - YERSINIA.; (from Genbank) |
| 156 | Lymphoma | 0.6356936 | 0.3448143 | 0.296967 | 0.20462623 V00478_s_at | | Actin, beta |
| 157 | Lymphoma | 0.6348108 | 0.3447667 | 0.296798 | 0.20436633 C16652_at | | KIAA0575 gene product |
| 158 | Lymphoma | 0.6334174 | 0.3445712 | 0.296551 | 0.20423472 M90391_s_a t-2 | | Interleukin 16 (lymphocyte chemoattractant factor) |
| 159 | Lymphoma | 0.6334174 | 0.3445046 | 0.296512 | 0.20408845 M90391_s_a t | | Putative IL-16 protein precursor, mRNA |
| 160 | Lymphoma | 0.6323038 | 0.3437625 | 0.2963 | 0.2038871 | AA090608_a | EST: y0994.seq.F Fetal heart, Lambda ZAP Express Homo sapiens cDNA 5', mRNA sequence. (from Genbank) |
| 161 | Lymphoma | 0.6322891 | 0.3434948 | 0.295897 | 0.2035471 X93996_rna _at-2 | | H.sapiens mRNA for AFX protein |
| 162 | Lymphoma | 0.6322891 | 0.3434582 | 0.295745 | 0.20334846 X93996_rna 1_at | | AFX protein |
| 163 | Lymphoma | 0.6318573 | 0.343134 | 0.295562 | 0.20316143 X68149_at | | BLR1 Burkitt lymphoma receptor 1, GTP-binding protein |
| 164 | Lymphoma | 0.6317993 | 0.3429457 | 0.295356 | 0.2029678 | RC_D59337 _at | EST: Human fetal brain cDNA 3'-end GEN-017C09, mRNA sequence. (from Genbank) |
| 165 | Lymphoma | 0.6316616 | 0.3428134 | 0.295166 | 0.2026821418_at | RC_AA0444 | EST: zk52g04.s1 Soares pregnant uterus NbHPU Homo sapiens cDNA clone 486486 3', mRNA sequence. (from Genbank) |
| 166 | Lymphoma | 0.6299456 | 0.3420202 | 0.294892 | 0.20256962 W26322_at | | Homo sapiens mRNA for KIAA0745 protein, partial cds |
| 167 | Lymphoma | 0.6292235 | 0.3418647 | 0.294834 | 0.20239066 W28167_at | | EST: 43a1 Human retina cDNA randomly primed sublibrary Homo sapiens cDNA, mRNA sequence. (from Genbank) |
| 168 | Lymphoma | 0.6284909 | 0.3418586 | 0.294624 | 0.2022289576_s_at | RC_AA2783 | EST: zt08a12.s1 NCI_CGAP_GCB1 Homo sapiens cDNA clone IMAGE:712510 3', mRNA sequence. (from Genbank) |
| 169 | Lymphoma | 0.6275017 | 0.3416064 | 0.294517 | 0.20202437 M63438_s_a t | | GLUL Glutamate-ammonia ligase (glutamine synthase) |
| 170 | Lymphoma | 0.6260822 | 0.3415106 | 0.29442 | 0.20180394 W03796_at | | EST: za60c08.r1 Soares fetal liver spleen 1NFLS Homo sapiens cDNA clone 296942 5', mRNA sequence. (from Genbank) |
| 171 | Lymphoma | 0.6259733 | 0.3413357 | 0.294323 | 0.2016492238_at | RC_AA5991 | EST: ae52c11.s1 Stratagene lung carcinoma 937218 Homo sapiens cDNA clone 950516 3', mRNA sequence. (from Genbank) |
| 172 | Lymphoma | 0.6259022 | 0.3409944 | 0.294272 | 0.2013956626_at | RC_AA4568 | EST: aa38i01.s1 NCI_CGAP_GCB1 Homo sapiens cDNA clone IMAGE:815545 3', mRNA sequence. (from Genbank) |

FIG. 7J

| # | Type | | | | | Description |
|---|---|---|---|---|---|---|
| 173 | Lymphoma | 0.6239243 | 0.3409797 | 0.29411 | 0.201249958 | RC_AA2798 27_at | EST: zs92f08.s1 NCI_CGAP_GCB1 Homo sapiens cDNA clone IMAGE:704967 3', mRNA sequence. (from Genbank) |
| 174 | Lymphoma | 0.6238103 | 0.3407115 | 0.29403 | 0.201057797 | RC_AA4009 79_at | Homo sapiens mRNA encoding RAMP3 |
| 175 | Lymphoma | 0.6236455 | 0.3404308 | 0.293811 | 0.200849909 | RC_AA4520 20_at | EST: zw57b10.s1 Soares total fetus Nb2HF8 9w Homo sapiens cDNA clone 774139 3' similar to SW:YHS2_YEAST P38829 HYPOTHETICAL 25.7 KD PROTEIN IN MSH1-EPT1 INTERGENIC REGION.;, mRNA sequence. (from Genbank) |
| 176 | Lymphoma | 0.6235814 | 0.3402013 | 0.293805 | 0.200711124 | RC_AA4361 56_s_at | EST: zv22b10.s1 Soares NhHMPu S1 Homo sapiens cDNA clone 754363 3', mRNA sequence. (from Genbank) |
| 177 | Lymphoma | 0.6234056 | 0.3400871 | 0.293326 | 0.200411151 | RC_AA4910 01_i_at | EST: aa52g12.s1 NCI_CGAP_GCB1 Homo sapiens cDNA clone IMAGE:824614 3' similar to TR:G1293732 G1293732 O3625P.;, mRNA sequence. (from Genbank) |
| 178 | Lymphoma | 0.6212004 | 0.3400037 | 0.293177 | 0.200222374 | AA095041_a t | EST: cp2556.seq.F Fetal heart, Lambda ZAP Express Homo sapiens cDNA 5', mRNA sequence. (from Genbank) |
| 179 | Lymphoma | 0.620492 | 0.339471 | 0.293074 | 0.20008999 | L00022_s_at | IG EPSILON CHAIN C REGION |
| 180 | Lymphoma | 0.6197528 | 0.3393022 | 0.292957 | 0.19990304 | U15085_at | HLA-DMB Major histocompatibility complex, class II, DM beta |
| 181 | Lymphoma | 0.6196789 | 0.3392795 | 0.292582 | 0.1997247 | W76097_at | EST: zd59e04.r1 Soares fetal heart NbHH19W Homo sapiens cDNA clone 344958 5' similar to contains element MIR repetitive element.;, mRNA sequence. (from Genbank) |
| 182 | Lymphoma | 0.6179242 | 0.3392694 | 0.29256 | 0.19949141 | R51954_at | EST: yj71g02.r1 Homo sapiens cDNA clone 154226 5'. (from Genbank) |
| 183 | Lymphoma | 0.6176816 | 0.3391704 | 0.292396 | 0.19938862 | M57466_s_a t | MHC class II HLA-DP light chain mRNA |
| 184 | Lymphoma | 0.6168518 | 0.3389453 | 0.292239 | 0.19923042 | RC_AA2794 42_at | EST: zs84g01.s1 NCI_CGAP_GCB1 Homo sapiens cDNA clone IMAGE:704208 3', mRNA sequence. (from Genbank) |
| 185 | Lymphoma | 0.6168244 | 0.3388142 | 0.292137 | 0.199089542 | RC_AA4265 21_at | Nuclear autoantigen of 14 kDa |
| 186 | Lymphoma | 0.616739 | 0.3387973 | 0.291794 | 0.198880931 | M37766_at | CD48 CD48 antigen (B-cell membrane protein) |
| 187 | Lymphoma | 0.6158703 | 0.3385852 | 0.291628 | 0.198736581 | W60268_at | EST: zd29g01.r1 Soares fetal heart NbHH19W Homo sapiens cDNA clone 342096 5', mRNA sequence. (from Genbank) |
| 188 | Lymphoma | 0.6157668 | 0.3384735 | 0.291159 | 0.198567 | RC_AA2533 69_s_at | EST: zr77b01.s1 Soares NhHMPu S1 Homo sapiens cDNA clone 693385 3' similar to SW:YIAE_ECOLI P37666 PUTATIVE 2-HYDROXYACID DEHYDROGENASE IN BISC-CSPA INTERGENIC REGION.;, mRNA sequence. (from Genbank) |
| 189 | Lymphoma | 0.6150584 | 0.338334 | 0.291581 | 0.198412057 | RC_AA4639 78_at | EST: zx86f03.s1 Soares ovary tumor NbHOT Homo sapiens cDNA clone 810653 3', mRNA sequence. (from Genbank) |

FIG. 7K

| | | | | | |
|---|---|---|---|---|---|
| 190 | Lymphoma | 0.6147595 | 0.337978 | 0.291436 | 0.19824977 | RC_AA2923 28_at | EST: zt51f09.s1 Soares ovary tumor NbHOT Homo sapiens cDNA clone 725897 3' similar to SW:ATF4_MOUSE Q06507 CYCLIC-AMP-DEPENDENT TRANSCRIPTION FACTOR ATF-4 ;contains Alu repetitive element;contains element MER22 repetitive element ;, mRNA sequence. (from Genbank) |
| 191 | Lymphoma | 0.614148 | 0.3378646 | 0.291109 | 0.19796516 | AA418341_a t | EST: zv96d05.r1 Soares NhHMPu S1 Homo sapiens cDNA clone 767625 5' similar to TR:G790473 G790473 GLYCINE RICH PROTEIN. ;, mRNA sequence. (from Genbank) |
| 192 | Lymphoma | 0.6124772 | 0.3377244 | 0.291011 | 0.19785275 | AA308998_a t | Endothelial differentiation-related factor 1 |
| 193 | Lymphoma | 0.610876 | 0.33776651 | 0.29081 | 0.19771034 | RC_AA0051 35_at | EST: zh95e02.s1 Soares fetal liver spleen 1NFLS S1 Homo sapiens cDNA clone 429050 3' similar to contains MER10.t3 MER10 repetitive element ;, mRNA sequence. (from Genbank) |
| 194 | Lymphoma | 0.6104602 | 0.3376215 | 0.290698 | 0.1976103 | L41067_at | Transcription factor NFATx mRNA |
| 195 | Lymphoma | 0.6104602 | 0.3375353 | 0.290568 | 0.19727501 | L41067_at-2 | Nuclear factor of activated T-cells, cytoplasmic 4 |
| 196 | Lymphoma | 0.6075186 | 0.337166 | 0.290138 | 0.19712873 | W52821_at | EST: zc55c07.r1 Soares senescent fibroblasts NbHSF Homo sapiens cDNA clone 326220 5' similar to SW:AMPL_BOVIN P00727 CYTOSOL AMINOPEPTIDASE.;, mRNA sequence. (from Genbank) |
| 197 | Lymphoma | 0.6060559 | 0.3365648 | 0.290047 | 0.196988 | W42818_at | EST: zc24d03.r1 Soares senescent fibroblasts NbHSF Homo sapiens cDNA clone 323237 5', mRNA sequence. (from Genbank) |
| 198 | Lymphoma | 0.6056334 | 0.3365406 | 0.289922 | 0.19679432 | U88964_at | HEM45 mRNA |
| 199 | Lymphoma | 0.6049919 | 0.3365244 | 0.289816 | 0.19655175 | RC_AA2355 3_at | EST: zt30f07.s1 Soares ovary tumor NbHOT Homo sapiens cDNA clone 723877 3', mRNA sequence. (from Genbank) |
| 200 | Lymphoma | 0.6041677 | 0.3362633 | 0.289676 | 0.19634266 | RC_AA2367 02_at | EST: zi29b02.s1 Soares ovary tumor NbHOT Homo sapiens cDNA clone 723723 3', mRNA sequence. (from Genbank) |
| 201 | Lymphoma | 0.6035701 | 0.3358352 | 0.289296 | 0.19620346 | RC_AA4473 68_s_at | EST: zw87b08.s1 Soares total fetus Nb2HF8 9w Homo sapiens cDNA clone 783927 3'; mRNA sequence. (from Genbank) |
| 202 | Lymphoma | 0.6022907 | 0.3356193 | 0.288951 | 0.19611338 | RC_AA4875 63_at | EST: ab23e08.s1 Stralagene lung (#937210) Homo sapiens cDNA clone 841670 3', mRNA sequence. (from Genbank) |
| 203 | Lymphoma | 0.602225 | 0.3354623 | 0.288896 | 0.19592279 | AA131252_a t | EST: zi31g02.r1 Soares pregnant uterus NbHPU Homo sapiens cDNA clone 503570 5', mRNA sequence. (from Genbank) |
| 204 | Lymphoma | 0.6014947 | 0.3354379 | 0.288708 | 0.19566914 | AA417129_a t | Variably charged, Y chromosome |
| 205 | Lymphoma | 0.6010132 | 0.3351582 | 0.288657 | 0.19546083 | AB002340_a t | KIAA0342 gene product |

FIG. 7L

| | | | | | |
|---|---|---|---|---|---|
| 206 | Lymphoma | 0.599709 | 0.3351251 | 0.288444 | 0.1954222 | D25278_at-2 | KIAA0036 gene product |
| 207 | Lymphoma | 0.599709 | 0.3350765 | 0.28827 | 0.19531766 | D25278_at | KIAA0036 gene |
| 208 | Lymphoma | 0.5991827 | 0.3349007 | 0.288268 | 0.19515973 | AA095959_a t | Homo sapiens clone 24649 mRNA sequence |
| 209 | Lymphoma | 0.5991587 | 0.3348074 | 0.288017 | 0.19504936 | RC_D20846 _at | EST: Human HL60 3'directed Mbol cDNA, HUMGS01827, clone mp0825, mRNA sequence. (from Genbank) |
| 210 | Lymphoma | 0.5977535 | 0.3346944 | 0.287906 | 0.19488768 | Z36531_at | FGL1 Fibrinogen-like 1 |
| 211 | Lymphoma | 0.5977535 | 0.3346194 | 0.287781 | 0.1946968 | Z36531_at-2 | H.sapiens mRNA for fibrinogen-like protein (pT49 protein) |
| 212 | Lymphoma | 0.5973118 | 0.334581 | 0.287659 | 0.19457611 | AA249434_a t | EST: j3922.seq.F Human fetal heart, Lambda ZAP Express Homo sapiens cDNA 5', mRNA sequence. (from Genbank) |
| 213 | Lymphoma | 0.5970908 | 0.3345466 | 0.287581 | 0.19445857 | RC_AA2526 16_at | EST: zs14d03.s1 NCI_CGAP_GCB1 Homo sapiens cDNA clone IMAGE:685157 3', mRNA sequence. (from Genbank) |
| 214 | Lymphoma | 0.5963791 | 0.3343524 | 0.287261 | 0.19427946 | RC_AA2337 07_at | EST: zr47e07.s1 Soares NhHMPu S1 Homo sapiens cDNA clone 666564 3', mRNA sequence. (from Genbank) |
| 215 | Lymphoma | 0.5962955 | 0.3340617 | 0.287076 | 0.19412436 | W55958_at | EST: zd13e09.r1 Soares fetal heart NbHH19W Homo sapiens cDNA clone 340552 5' similar to PIR:S55053 S55053 Sm protein F - human ., mRNA sequence. (from Genbank) |
| 216 | Lymphoma | 0.5962682 | 0.3338244 | 0.286832 | 0.19404012 | RC_AA4811 69_at | EST: aa34h11.s1 NCI_CGAP_GCB1 Homo sapiens cDNA clone IMAGE:815205 3', mRNA sequence. (from Genbank) |
| 217 | Lymphoma | 0.5958921 | 0.3337846 | 0.286737 | 0.19387074 | AA471278_a t | BUB3 (budding uninhibited by benzimidazoles 3, yeast) homolog |
| 218 | Lymphoma | 0.5953891 | 0.333382 | 0.286269 | 0.1936752 | AB002307_a t | Human mRNA for KIAA0309 gene, partial cds |
| 219 | Lymphoma | 0.5953296 | 0.3332205 | 0.286233 | 0.19348125 | RC_AA2428 29_s_at | EST: zr65f12.s1 Soares NhHMPu S1 Homo sapiens cDNA clone 668303 3', mRNA sequence. (from Genbank) |
| 220 | Lymphoma | 0.5944234 | 0.3331291 | 0.285955 | 0.19333233 | AA463311_a t | EST: zx71d12.r1 Soares total fetus Nb2HF8 9w Homo sapiens cDNA clone 796919 5', mRNA sequence. (from Genbank) |
| 221 | Lymphoma | 0.5943639 | 0.3331268 | 0.285802 | 0.19319665 | AA174152_f _at | EST: PTH078 HTCDL1 Homo sapiens cDNA 5'/3', mRNA sequence. (from Genbank) |
| 222 | Lymphoma | 0.5939278 | 0.3328537 | 0.285801 | 0.19291164 | RC_AA2326 86_i_at | EST: zr75d05.s1 Soares NhHMPu S1 Homo sapiens cDNA clone 669225 3', mRNA sequence. (from Genbank) |
| 223 | Lymphoma | 0.5929736 | 0.3326703 | 0.285705 | 0.19276343 | AA263061_s _at | EST: PMY0414 KG1-a Lambda Zap Express cDNA library Homo sapiens cDNA 5', mRNA sequence. (from Genbank) |
| 224 | Lymphoma | 0.5908444 | 0.3324568 | 0.285656 | 0.19259624 | RC_AA4528 73_at | EST: zx36e07.s1 Soares total fetus Nb2HF8 9w Homo sapiens cDNA clone 788580 3' similar to TR:G1255172 G1255172 MATERNAL TRANSCRIPT.; mRNA sequence. (from Genbank) |

FIG. 7M

| | | | | | |
|---|---|---|---|---|---|
| 225 | Lymphoma | 0.5894775 | 0.3324449 | 0.285575 | 0.19248536 | RC_AA5041 10_at | EST: aa59a08.s1 NCI_CGAP_GCB1 Homo sapiens cDNA clone IMAGE:825206 3', mRNA sequence. (from Genbank) |
| 226 | Lymphoma | 0.5891589 | 0.3324449 | 0.285233 | 0.19236875 | RC_AA4592 55_at | EST: aa27b08.s1 NCI_CGAP_GCB1 Homo sapiens cDNA clone IMAGE:814455 3', mRNA sequence. (from Genbank) |
| 227 | Lymphoma | 0.5891118 | 0.3322842 | 0.285134 | 0.1922476 | RC_AA5984 60_s_at | EST: ae48g12.s1 Stratagene lung carcinoma 937218 Homo sapiens cDNA clone 950182 3', mRNA sequence. (from Genbank) |
| 228 | Lymphoma | 0.5882627 | 0.3322307 | 0.284957 | 0.19209908 | RC_AA2619 54_at | EST: zs23e06.s1 NCI_CGAP_GCB1 Homo sapiens cDNA clone IMAGE:686050 3', mRNA sequence. (from Genbank) |
| 229 | Lymphoma | 0.5881668 | 0.3321207 | 0.284852 | 0.19189425 | RC_AA4763 26_at | EST: zw99b11.s1 Soares total fetus Nb2HF8 9w Homo sapiens cDNA clone 785085 3', mRNA sequence. (from Genbank) |
| 230 | Lymphoma | 0.5854048 | 0.3320767 | 0.28468 | 0.19179058 | D30851_at | EST: Human fetal-lung cDNA 5'-end sequence, mRNA sequence. (from Genbank) |
| 231 | Lymphoma | 0.5850233 | 0.3320094 | 0.28468 | 0.19164877 | M38193_ma 1_s_at | Granzyme B (granzyme 2, cytotoxic T-lymphocyte-associated serine esterase 1) |
| 232 | Lymphoma | 0.5842319 | 0.3319556 | 0.284494 | 0.19146943 | RC_AA3941 40_at | EST: zt49e08.s1 Soares ovary tumor NbHOT Homo sapiens cDNA clone 725702 3', mRNA sequence. (from Genbank) |
| 233 | Lymphoma | 0.5838729 | 0.3318547 | 0.28426 | 0.1913584 | AA292417_a t | EST: zt51f12.r1 Soares ovary tumor NbHOT Homo sapiens cDNA clone 725903 5', mRNA sequence. (from Genbank) |
| 234 | Lymphoma | 0.5827766 | 0.331796 | 0.284246 | 0.19117041 | RC_AA0105 40_at | EST: ze18c10.s1 Soares fetal heart NbHH19W Homo sapiens cDNA clone 353346 3', mRNA sequence. (from Genbank) |
| 235 | Lymphoma | 0.5825497 | 0.3317198 | 0.283924 | 0.19104208 | R10266_at | EST: yf36a10.r1 Homo sapiens cDNA clone 128922 5'. (from Genbank) |
| 236 | Lymphoma | 0.5823731 | 0.3316788 | 0.283786 | 0.19090241 | RC_AA4103 04_at | EST: zv23b12.s1 Soares NhHMPu S1 Homo sapiens cDNA clone 754463 3', mRNA sequence. (from Genbank) |
| 237 | Lymphoma | 0.581524 | 0.331614 | 0.283705 | 0.19078937 | U73531_at | Human G protein-coupled receptor STRL33.1 (STRL33) mRNA, complete cds |
| 238 | Lymphoma | 0.5810957 | 0.33144471 | 0.283572 | 0.19063637 | W46488_at | EST: zc32a07.r1 Soares senescent fibroblasts NbHSF Homo sapiens cDNA clone 323988 5', mRNA sequence. (from Genbank) |
| 239 | Lymphoma | 0.5796109 | 0.33144471 | 0.283544 | 0.19043598 | RC_AA4905 22_at | EST: aa51g08.s1 NCI_CGAP_GCB1 Homo sapiens cDNA clone IMAGE:824510 3' similar to SW:YHS2_YEAST P38829 HYPOTHETICAL 25.7 KD PROTEIN IN MSH1-EPT1 INTERGENIC REGION. ;, mRNA sequence. (from Genbank) |
| 240 | Lymphoma | 0.5790964 | 0.3314118 | 0.283496 | 0.1903317 | W73859_at | Transcription factor 21 |
| 241 | Lymphoma | 0.5790461 | 0.3313564 | 0.283341 | 0.19014046 | U36500_at | Lymphoid-specific SP100 homolog (LYSP100-A) mRNA |
| 242 | Lymphoma | 0.5780443 | 0.3307783 | 0.28316 | 0.19001247 | RC_AA4963 74_at | EST: zv37f09.s1 Soares ovary tumor NbHOT Homo sapiens cDNA clone 755849 3', mRNA sequence. (from Genbank) |

FIG. 7N

| | | | | | | |
|---|---|---|---|---|---|---|
| 243 | Lymphoma | 0.5779289 | 0.3303202 | 0.283016 | 0.18985632 | U77664_at | RNaseP protein p38 (RPP38) mRNA |
| 244 | Lymphoma | 0.5779289 | 0.3302951 | 0.283001 | 0.1897808 | U77664_at-2 | Human RNaseP protein p38 (RPP38) mRNA, complete cds |
| 245 | Lymphoma | 0.5773971 | 0.3302223 | 0.282936 | 0.18964787 | J05070_at | MMP2 Matrix metalloproteinase 2 (gelatinase A; collagenase type IV) |
| 246 | Lymphoma | 0.5759504 | 0.330207 | 0.282876 | 0.18952262 | RC_AA2521 72_at | EST: zr64d03.s1 Soares NhHMPu S1 Homo sapiens cDNA clone 668165 3', mRNA sequence. (from Genbank) |
| 247 | Lymphoma | 0.5754765 | 0.3301813 | 0.282529 | 0.18941422 | RC_D59367 _at | EST: Human fetal brain cDNA 3'-end GEN-023H06, mRNA sequence. (from Genbank) |
| 248 | Lymphoma | 0.5747802 | 0.3301446 | 0.282478 | 0.189284 | RC_AA4321 78_at | EST: zw71g02.s1 Soares testis NHT Homo sapiens cDNA clone 781682 3', mRNA sequence. (from Genbank) |
| 249 | Lymphoma | 0.5742781 | 0.3300333 | 0.282335 | 0.18921274 | RC_AA4054 49_at | EST: zw36a04.s1 Soares total fetus Nb2HF8 9w Homo sapiens cDNA clone 772110 3', mRNA sequence. (from Genbank) |
| 250 | Lymphoma | 0.5737209 | 0.3298904 | 0.2823 | 0.18912192 | W03361_at | EST: za06g11.r1 Soares melanocyte 2NbHM Homo sapiens cDNA clone 291812 5', mRNA sequence. (from Genbank) |
| 251 | Lymphoma | 0.573499 | 0.3298328 | 0.282069 | 0.18901318 | AA405119_a t | EST: zu65c11.r1 Soares testis NHT Homo sapiens cDNA clone 742868 5' similar to TR:G1066392 G1066392 T(3;5)(Q25.1;P34) FUSION GENE NPM-MLF1.;; mRNA sequence. (from Genbank) |
| 252 | Lymphoma | 0.5728199 | 0.3297132 | 0.282033 | 0.18875816 | RC_AA5987 24_at | EST: ae49j01.s1 Stratagene lung carcinoma 937218 Homo sapiens cDNA clone 950233 3', mRNA sequence. (from Genbank) |
| 253 | Lymphoma | 0.5720688 | 0.3295716 | 0.281966 | 0.18853574 | RC_AA4279 20_at | EST: zw53d01.s1 Soares total fetus Nb2HF8 9w Homo sapiens cDNA clone 773761 3', mRNA sequence. (from Genbank) |
| 254 | Lymphoma | 0.5719351 | 0.3294361 | 0.281912 | 0.18845333 | RC_AA2629 93_at | ATPase, H+ transporting, lysosomal (vacuolar proton pump), subunit 1 |
| 255 | Lymphoma | 0.571813 | 0.3291288 | 0.281904 | 0.18835653 | AA256638_a t | Thioredoxin-like, 32kD |
| 256 | Lymphoma | 0.5717578 | 0.3290648 | 0.281579 | 0.18819246 | AF000575_s _at | Human clone HL9 monocyte inhibitory receptor precursor mRNA, complete cds |
| 257 | Lymphoma | 0.5716004 | 0.3290647 | 0.281549 | 0.18809885 | H26812_at | EST: yf63d06.r1 Homo sapiens cDNA clone 162923 5'. (from Genbank) |
| 258 | Lymphoma | 0.5714207 | 0.3282786 | 0.281293 | 0.18795352 | RC_AA0407 59_s_at | NADH dehydrogenase (ubiquinone) 1 beta subcomplex, 3 (12kD, B12) |
| 259 | Lymphoma | 0.5712059 | 0.3281435 | 0.281256 | 0.18780105 | X15949_at-2 | Interferon regulatory factor 2 |
| 260 | Lymphoma | 0.5712059 | 0.3279782 | 0.281226 | 0.18766367 | X15949_at | IRF2 Interferon regulatory factor 2 |
| 261 | Lymphoma | 0.5705517 | 0.3279154 | 0.281109 | 0.18754422 | N23801_at | EST: yx36b12.r1 Homo sapiens cDNA clone 263807 5'. (from Genbank) |

FIG. 7O

| # | | | | | | |
|---|---|---|---|---|---|---|
| 262 | Lymphoma | 0.569451 | 0.3278902 | 0.281022 | 0.18746755_t | AA424111_a | EST: zv80e06.r1 Soares total fetus Nb2HF8 9w Homo sapiens cDNA clone 759970 5', mRNA sequence. (from Genbank) |
| 263 | Lymphoma | 0.5688793 | 0.3278369 | 0.280947 | 0.1872783 | X97267_rna 1_s_at | LPAP gene |
| 264 | Lymphoma | 0.5686818 | 0.3277679 | 0.280859 | 0.18711482_t | AA075989_a | EST: zm75h04.r1 Stratagene neuroepithelium (#937231) Homo sapiens cDNA clone 531511 5', mRNA sequence. (from Genbank) |
| 265 | Lymphoma | 0.5663061 | 0.327684 | 0.280859 | 0.1870206_t | AA384220_a | EST: EST97923 Thyroid Homo sapiens cDNA 5' end, mRNA sequence. (from Genbank) |
| 266 | Lymphoma | 0.5657781 | 0.3276105 | 0.280496 | 0.1868456_t | AF006086_a | ARP2/3 protein complex subunit p21 |
| 267 | Lymphoma | 0.5650608 | 0.3275834 | 0.280325 | 0.18664779 | W28798_at | EST: 52g10 Human retina cDNA randomly primed sublibrary Homo sapiens cDNA, mRNA sequence. (from Genbank) |
| 268 | Lymphoma | 0.5635439 | 0.3275833 | 0.280251 | 0.18659721 | W28548_at | EST: 48d1 Human retina cDNA randomly primed sublibrary Homo sapiens cDNA, mRNA sequence. (from Genbank) |
| 269 | Lymphoma | 0.5632062 | 0.3273261 | 0.280156 | 0.18644811_t | RC_AA4589 09_at | EST: aa26e06.s1 NCI_CGAP_GCB1 Homo sapiens cDNA clone IMAGE:814402 3', mRNA sequence. (from Genbank) |
| 270 | Lymphoma | 0.5631544 | 0.3267421 | 0.279981 | 0.18632442 | HG1872-HT1907_at | Major Histocompatibility Complex, Dg |
| 271 | Lymphoma | 0.5631071 | 0.3267267 | 0.279891 | 0.18621527_at | RC_AA5045 07_at | EST: aa60g07.s1 NCI_CGAP_GCB1 Homo sapiens cDNA clone IMAGE:825372 3', mRNA sequence. (from Genbank) |
| 272 | Lymphoma | 0.5615543 | 0.3267019 | 0.279781 | 0.18598068 | D82712_at | EST: similar to none, mRNA sequence. (from Genbank) |
| 273 | Lymphoma | 0.5614649 | 0.3266508 | 0.279691 | 0.185870291 | AA306192_a | Homo sapiens mRNA for NOR1-1, complete cds |
| 274 | Lymphoma | 0.5610402 | 0.3264535 | 0.279555 | 0.18581972_t | M69245_s_a | Human pregnancy-specific beta-1 glycoprotein (PSG) mRNA, complete cds. (from Genbank) |
| 275 | Lymphoma | 0.5609091 | 0.3263791 | 0.279481 | 0.1856473 | R55902_at | Yg92d05.r1 Homo sapiens cDNA clone 41017 5'. (from Genbank) |
| 276 | Lymphoma | 0.5597442 | 0.3261644 | 0.279422 | 0.18547653_at | RC_AA2837 59_at | EST: zs48b05.s1 NCI_CGAP_GCB1 Homo sapiens cDNA clone IMAGE:700689 3', mRNA sequence. (from Genbank) |
| 277 | Lymphoma | 0.5596944 | 0.3261329 | 0.279363 | 0.18535453_t | AA263146_a | EST: PMY0511 KG1-a Lambda Zap Express cDNA library Homo sapiens cDNA 5', mRNA sequence. (from Genbank) |
| 278 | Lymphoma | 0.5590776 | 0.3260188 | 0.279128 | 0.18519531_t | AA431398_a | EST: zw76d12.r1 Soares testis NHT Homo sapiens cDNA clone 782135 5' similar to WP:M01F1.6 CE01034 :, mRNA sequence. (from Genbank) |
| 279 | Lymphoma | 0.5573739 | 0.3257908 | 0.279059 | 0.18508475 | X17206_at | PTB Ribosomal protein L26 |
| 280 | Lymphoma | 0.5573096 | 0.3256352 | 0.279051 | 0.18497077 | U43586_at | Kinase suppressor of ras-1 (KSR1) mRNA, partial cds |

FIG. 7P

| # | | | | | |
|---|---|---|---|---|---|
| 281 | Lymphoma | 0.5573096 | 0.3255421 | 0.278842 | 0.18484868 | U43586_at-2 | Kinase suppressor of ras |
| 282 | Lymphoma | 0.5573081 | 0.3253575 | 0.278809 | 0.1847214 | H44262_at | Peroxisomal biogenesis factor 11B |
| 283 | Lymphoma | 0.556936 | 0.3251653 | 0.278721 | 0.18465897 | Z19751_at | H. sapiens putatively transcribed partial sequence; UK-HGMP sequence ID AAAALMt; single read, mRNA sequence. (from Genbank) |
| 284 | Lymphoma | 0.5567452 | 0.3250759 | 0.278661 | 0.18452433 | AA314466_a_t | Homo sapiens chromosome 9, P1 clone 11659 |
| 285 | Lymphoma | 0.5565508 | 0.3249639 | 0.278435 | 0.1843503 | RC_AA3978 25_at | EST: zt47g02.s1 Soares ovary tumor NbHOT Homo sapiens cDNA clone 725522 3', mRNA sequence. (from Genbank) |
| 286 | Lymphoma | 0.5547744 | 0.3248133 | 0.278231 | 0.18423972 | M62324_at | Modulator recognition factor I (MRF-1) mRNA, 3' end |
| 287 | Lymphoma | 0.5547744 | 0.3247504 | 0.278214 | 0.18410148 | M62324_at-2 | Human modulator recognition factor I (MRF-1) mRNA, 3' end |
| 288 | Lymphoma | 0.5547602 | 0.3245162 | 0.278047 | 0.18400207 | M26315_cds 2_s_at | CD8 antigen, alpha polypeptide (p32) |
| 289 | Lymphoma | 0.5543321 | 0.3244596 | 0.277864 | 0.18387945 | RC_AA4864 44_at | EST: ab36f11.s1 Stratagene HeLa cell s3 937216 Homo sapiens cDNA clone 842925 3', mRNA sequence. (from Genbank) |
| 290 | Lymphoma | 0.5541011 | 0.3244254 | 0.277701 | 0.18381476 | RC_AA4589 04_at | EST: aa26e01.s1 NCI_CGAP_GCB1 Homo sapiens cDNA clone IMAGE:814392 3', mRNA sequence. (from Genbank) |
| 291 | Lymphoma | 0.5535236 | 0.3242706 | 0.277548 | 0.18366623 | AA092898_a t | EST: m0386.seq.F Fetal heart, Lambda ZAP Express Homo sapiens cDNA 5', mRNA sequence. (from Genbank) |
| 292 | Lymphoma | 0.5532835 | 0.3241949 | 0.277424 | 0.18358295 | RC_AA4794 98_at | EST: zv21d10.s1 Soares NhHMPu S1 Homo sapiens cDNA clone 754291 3', mRNA sequence. (from Genbank) |
| 293 | Lymphoma | 0.5528798 | 0.3240677 | 0.277262 | 0.183454 | RC_AA0454 81_at | EST: zk67h05.s1 Soares pregnant uterus NbHPU Homo sapiens cDNA clone 487929 3', mRNA sequence. (from Genbank) |
| 294 | Lymphoma | 0.5501466 | 0.3239683 | 0.277146 | 0.18342124 | RC_AA4586 44_at | EST: aa16b12.s1 Soares NhHMPu S1 Homo sapiens cDNA clone 813407 3', mRNA sequence. (from Genbank) |
| 295 | Lymphoma | 0.5494753 | 0.3238952 | 0.277144 | 0.18323193 | U19261_at | Epstein-Barr virus-induced protein mRNA |
| 296 | Lymphoma | 0.5492095 | 0.3238064 | 0.27699 | 0.18313983 | R34531_at | KIAA0480 gene product |
| 297 | Lymphoma | 0.547767 | 0.323739 | 0.276752 | 0.18298216 | AA279359_a t | EST: zs84d01.r1 NCI_CGAP_GCB1 Homo sapiens cDNA clone IMAGE:704161 5', mRNA sequence. (from Genbank) |
| 298 | Lymphoma | 0.5453966 | 0.3235079 | 0.276724 | 0.18288116 | X62744_at | CLASS II HISTOCOMPATIBILITY ANTIGEN, M ALPHA CHAIN PRECURSOR |

FIG. 7Q

| | | | | | |
|---|---|---|---|---|---|
| 299 | Lymphoma | 0.5449806 | 0.3234495 | 0.27637 | AA082926_a t | EST: zn07f11.r1 Stratagene hNT neuron (#937233) Homo sapiens cDNA clone 546765 5' similar to SW:RBB1_HUMAN P29374 RETINOBLASTOMA BINDING PROTEIN 1:, mRNA sequence. (from Genbank) |
| 300 | Lymphoma | 0.5448306 | 0.3232553 | 0.27633 | RC_AA4356 64_at | EST: zi75a11.s1 Soares testis NHT Homo sapiens cDNA clone 728156 3' similar to contains Alu repetitive element;, mRNA sequence. (from Genbank) |
| 301 | Lymphoma | 0.5441038 | 0.3231901 | 0.276223 | AA478704_a t | Interleukin 13 receptor, alpha 1 |
| 302 | Lymphoma | 0.54387 | 0.3231352 | 0.276121 | RC_AA2359 85_at | EST: zs41g07.s1 Soares NhHMPu S1 Homo sapiens cDNA clone 687804 3', mRNA sequence. (from Genbank) |
| 303 | Lymphoma | 0.5428686 | 0.3231352 | 0.276086 | U62438_at-2 | Cholinergic receptor, nicotinic, beta polypeptide 3 |
| 304 | Lymphoma | 0.5428686 | 0.3231124 | 0.275978 | U62438_at | CHRNB3 Cholinergic receptor, nicotinic, beta polypeptide 3 |
| 305 | Lymphoma | 0.542415 | 0.3230177 | 0.275975 | RC_AA2792 94_at | Homo sapiens mRNA for LAK-4p, complete cds |
| 306 | Lymphoma | 0.5419941 | 0.3228915 | 0.275671 | R68846_at | EST: yj37a05.r1 Homo sapiens cDNA clone 141392 5'. (from Genbank) |
| 307 | Lymphoma | 0.5417521 | 0.322812 | 0.275545 | X03066_at | HLA-DOB MHC class II protein HLA-DO beta chain |
| 308 | Lymphoma | 0.541656 | 0.3227486 | 0.275461 | AA400632_s _at | EST: zu70f01.r1 Soares testis NHT Homo sapiens cDNA clone 743353 5', mRNA sequence. (from Genbank) |
| 309 | Lymphoma | 0.541371 | 0.3227011 | 0.275363 | RC_AA6205 98_at | EST: ae60h08.s1 Stratagene lung carcinoma 937218 Homo sapiens cDNA clone 951327 3', mRNA sequence. (from Genbank) |
| 310 | Lymphoma | 0.5413337 | 0.3226111 | 0.275177 | AA247275_a t | EST: csg0884.seq.F Human fetal heart, Lambda ZAP Express Homo sapiens cDNA 5', mRNA sequence. (from Genbank) |
| 311 | Lymphoma | 0.5410871 | 0.3225508 | 0.274999 | RC_AA0157 51_at | EST: ze30d05.s1 Soares retina N2b4HR Homo sapiens cDNA clone 360489 3', mRNA sequence. (from Genbank) |
| 312 | Lymphoma | 0.540953 | 0.3223176 | 0.274977 | M64322_s_a t | Protein tyrosine phosphatase, non-receptor type 7 |
| 313 | Lymphoma | 0.5408223 | 0.322289 | 0.27479 | M83664_at | HLA-DPB1 Major histocompatibility complex, class II, DP beta 1 |
| 314 | Lymphoma | 0.5405091 | 0.3222151 | 0.27474 | AA249385_a t | EST: j2332.seq.F Human fetal heart, Lambda ZAP Express Homo sapiens cDNA 5', mRNA sequence. (from Genbank) |
| 315 | Lymphoma | 0.5403914 | 0.3221422 | 0.274633 | W27440_at | Homo sapiens mRNA for KIAA0914 protein, complete cds |

FIG. 7R

| | | | | | |
|---|---|---|---|---|---|
| 316 | Lymphoma | 0.5399377 | 0.3219896 | 0.274563 | 0.180770358 7_at | RC_AA2321 | EST: zr25c10.s1 Stratagene NT2 neuronal precursor 937230 Homo sapiens cDNA clone 664434 3', mRNA sequence. (from Genbank) |
| 317 | Lymphoma | 0.5395976 | 0.3219346 | 0.274349 | 0.180634054 84_at | RC_AA4064 | EST: zv11e05.s1 Soares NhHMPu S1 Homo sapiens cDNA clone 753344 3', mRNA sequence. (from Genbank) |
| 318 | Lymphoma | 0.5392029 | 0.3219346 | 0.274267 | 0.180613431 t | AA431011_a | EST: PMY0900 KG1-a Lambda Zap Express cDNA library Homo sapiens cDNA 5', mRNA sequence. (from Genbank) |
| 319 | Lymphoma | 0.5390996 | 0.3219073 | 0.274168 | 0.180454 at | AA136382_s | EST: zn89a06.r1 Stratagene lung carcinoma 937218 Homo sapiens cDNA clone 565330 5', mRNA sequence. (from Genbank) |
| 320 | Lymphoma | 0.5385078 | 0.3217716 | 0.274093 | 0.180424844 54_at | RC_AA4440 | EST: zv45f09.s1 Soares ovary tumor NbHOT Homo sapiens cDNA clone 756617 3', mRNA sequence. (from Genbank) |
| 321 | Lymphoma | 0.5380406 | 0.3216421 | 0.274008 | 0.180246162 M55267_at-2 | EVI2A PROTEIN PRECURSOR TROPIC VIRAL INTEGRATION SITE 2A PROTEIN) |
| 322 | Lymphoma | 0.5380406 | 0.3213662 | 0.273923 | 0.180199711 | M55267_at | EVI2A PROTEIN PRECURSOR TROPIC VIRAL INTEGRATION SITE 2A PROTEIN) |
| 323 | Lymphoma | 0.5377693 | 0.3212344 | 0.273556 | 0.180034854 99_at | RC_AA1152 | EST: zl09d11.s1 Soares pregnant uterus NbHPU Homo sapiens cDNA clone 501429 3', mRNA sequence. (from Genbank) |
| 324 | Lymphoma | 0.5374493 | 0.3211493 | 0.2735 | 0.179953875 55_at | RC_AA4471 | Dihydropyrimidinase-like 2 |
| 325 | Lymphoma | 0.5370858 | 0.3211397 | 0.273392 | 0.179817354 at-2 | U56814 | Deoxyribonuclease I-like 3 |
| 326 | Lymphoma | 0.5370858 | 0.3210295 | 0.273257 | 0.179743193 at | U56814 | DNase1-Like III protein (DNAS1L3) mRNA |
| 327 | Lymphoma | 0.536853 | 0.3207765 | 0.273078 | 0.179619164 at | M98539 | Prostaglandin D2 synthase gene |
| 328 | Lymphoma | 0.5361224 | 0.3206471 | 0.273057 | 0.179532712 at-2 | M12759 | Human Ig J chain gene |
| 329 | Lymphoma | 0.5361224 | 0.3206168 | 0.273045 | 0.179351154 at | M12759 | IMMUNOGLOBULIN J CHAIN |
| 330 | Lymphoma | 0.535921 | 0.3205697 | 0.272735 | 0.179314912 at | H10321 | EST: ym03e10.r1 Homo sapiens cDNA clone 46636 5'. (from Genbank) |
| 331 | Lymphoma | 0.535593 | 0.3205252 | 0.272261 | 0.179208174 at | RC_AA4969 | EST: ae33d12.s1 Gessler Wilms tumor Homo sapiens cDNA clone 897623 3', mRNA sequence. (from Genbank) |
| 332 | Lymphoma | 0.5352778 | 0.3205205 | 0.272604 | 0.179100562 at | H72388 | EST: ys06b05.r1 Homo sapiens cDNA clone 213969 5'. (from Genbank) |
| 333 | Lymphoma | 0.5347686 | 0.3203815 | 0.272567 | 0.179082621 t | AA187814_a | Homo sapiens GA17 protein mRNA, complete cds |
| 334 | Lymphoma | 0.5335506 | 0.320185 | 0.272547 | 0.178996674 at | D82422 | EST: similar to none, mRNA sequence. (from Genbank) |

FIG. 7S

| # | Type | | | | ID | Description |
|---|---|---|---|---|---|---|
| 335 | Lymphoma | 0.5334873 | 0.320165 | | RC_AA2786 72_at | Homo sapiens mRNA for Fln29, complete cds |
| 336 | Lymphoma | 0.5333529 | 0.3201314 | 0.27233 | RC_AA4492 67_at | EST: zx04f03.s1 Soares total fetus Nb2HF8.9w Homo sapiens cDNA clone 785501 3', mRNA sequence. (from Genbank) |
| 337 | Lymphoma | 0.532409 | 0.3200808 | 0.272285 | RC_AA2278 84_at | EST: zr57a09.s1 Soares NhHMPu S1 Homo sapiens cDNA clone 667480 3', mRNA sequence. (from Genbank) |
| 338 | Lymphoma | 0.5308081 | 0.3199861 | 0.272271 | S80310_s_at | Acidic epididymal glycoprotein-like 1 |
| 339 | Lymphoma | 0.5300815 | 0.3199687 | 0.272122 | RC_AA4480 02_at | Human membrane-associated lectin type-C mRNA |
| 340 | Lymphoma | 0.5298708 | 0.3198687 | 0.272017 | AA151328_a t | Human Hpast (HPAST) mRNA, complete cds |
| 341 | Lymphoma | 0.5298174 | 0.3197521 | 0.271951 | AF006082_a t | Actin-related protein 2 |
| 342 | Lymphoma | 0.5294091 | 0.3196618 | 0.271693 | RC_AA1717 36_at | EST: zc01e01.r1 Soares parathyroid tumor NbHPA Homo sapiens cDNA clone 321048 5', mRNA sequence. (from Genbank) |
| 343 | Lymphoma | 0.5290833 | 0.3193594 | 0.271625 | W56875_at | RPS25 Ribosomal protein S25 |
| 344 | Lymphoma | 0.5272148 | 0.3193445 | 0.271611 | M64716_at | EST: zo97h05.s1 Stratagene ovarian cancer (#937219) Homo sapiens cDNA clone 594873 3', mRNA sequence. (from Genbank) |
| 345 | Lymphoma | 0.5264043 | 0.3193396 | 0.271569 | RC_AA4262 61_at | EST: zw17a10.s1 Soares ovary tumor NbHOT Homo sapiens cDNA clone 769530 3', mRNA sequence. (from Genbank) |
| 346 | Lymphoma | 0.5254951 | 0.3193243 | 0.271514 | HG3576-HT3779_f_at | Major Histocompatibility Complex, Class Ii Beta W52 |
| 347 | Lymphoma | 0.5251394 | 0.3191913 | 0.271474 | H02675_at | EST: yj36g07.r1 Homo sapiens cDNA clone 150876 5'. (from Genbank) |
| 348 | Lymphoma | 0.5242806 | 0.3190549 | 0.271442 | RC_AA2810 74_at | EST: zs98b03.s1 NCI_CGAP_GCB1 Homo sapiens cDNA clone IMAGE:711629 3', mRNA sequence. (from Genbank) |
| 349 | Lymphoma | 0.5240557 | 0.3189265 | 0.271328 | AA424307_a t | EST: zv90c09.r1 Soares NhHMPu S1 Homo sapiens cDNA clone 767056 5', mRNA sequence. (from Genbank) |
| 350 | Lymphoma | 0.5237947 | 0.3189065 | 0.271254 | AA174149_a t | EST: PTH056 HTCDL1 Homo sapiens cDNA 5/3', mRNA sequence. (from Genbank) |
| 351 | Lymphoma | 0.523415 | 0.3188125 | 0.271125 | RC_AA0113 10_s_at | EST: ze22e11.s1 Soares fetal heart NbHH19W Homo sapiens cDNA clone 359756 3', mRNA sequence. (from Genbank) |
| 352 | Lymphoma | 0.5231271 | 0.3187657 | 0.271226 | X69150_at | Ribosomal protein S18 |

FIG. 7T

| # | | | | | | |
|---|---|---|---|---|---|---|
| 353 | Lymphoma | 0.5231077 | 0.3186295 | 0.271061 | 0.17685358 | D31544_s_at | EST: Human fetal-lung cDNA 5'-end sequence, mRNA sequence. (from Genbank) |
| 354 | Lymphoma | 0.5230388 | 0.3186067 | 0.27105 | 0.17671913 | AA247989_at | K8033.seq.F Human fetal heart, Lambda ZAP Express Homo sapiens cDNA 5', mRNA sequence. (from Genbank) |
| 355 | Lymphoma | 0.5224261 | 0.3185857 | 0.270919 | 0.17669219 | R80333_at | EST: yl96b06.r1 Homo sapiens cDNA clone 147059 5'. (from Genbank) |
| 356 | Lymphoma | 0.5222992 | 0.318229 | 0.270632 | 0.17656825 | U90550_at | Butyrophilin (BTF2) mRNA |
| 357 | Lymphoma | 0.5222992 | 0.3182206 | 0.27061 | 0.17641424 | U90550_at-2 | Human butyrophilin (BTF2) mRNA, complete cds |
| 358 | Lymphoma | 0.5222184 | 0.3181455 | 0.270411 | 0.1763235 | X98261_at | M-phase phosphoprotein, mpp5 |
| 359 | Lymphoma | 0.5222184 | 0.3179763 | 0.270101 | 0.1762672 | X98261_at-2 | H.sapiens mRNA for M-phase phosphoprotein, mpp5 |
| 360 | Lymphoma | 0.5219629 | 0.3177496 | 0.269929 | 0.17608501 | W52638_at | EST: zo49f01.r1 Soares senescent fibroblasts NbHSF Homo sapiens cDNA clone 325657 5', mRNA sequence. (from Genbank) |
| 361 | Lymphoma | 0.5215229 | 0.3176373 | 0.269903 | 0.17606878 | AF006088_at | Arp2/3 protein complex subunit p16 |
| 362 | Lymphoma | 0.521315 | 0.3176319 | 0.269903 | 0.17596549 | AA090695_at | EST: y1365.seq.F Fetal heart, Lambda ZAP Express Homo sapiens cDNA 5', mRNA sequence. (from Genbank) |
| 363 | Lymphoma | 0.5206098 | 0.3175233 | 0.269778 | 0.17582078 | AA453381_at | EST: zx47e08.r1 Soares testis NHT Homo sapiens cDNA clone 795398 5', mRNA sequence. (from Genbank) |
| 364 | Lymphoma | 0.5204284 | 0.3174847 | 0.269759 | 0.17573975 | RC_AA476450_at | Homo sapiens cyclophilin-33A (CYP-33) mRNA, complete cds |
| 365 | Lymphoma | 0.5199574 | 0.3171968 | 0.26974 | 0.17565858 | D49950_at | Liver mRNA for interferon-gamma inducing factor(IGIF) |
| 366 | Lymphoma | 0.5199574 | 0.3167492 | 0.269683 | 0.17554952 | D49950_at-2 | Interleukin 18 (interferon-gamma-inducing factor) |
| 367 | Lymphoma | 0.519936 | 0.316647 | 0.269651 | 0.17545503 | RC_AA412700_at | Ubiquitin-conjugating enzyme E2L 6 |
| 368 | Lymphoma | 0.5196908 | 0.3166144 | 0.269485 | 0.17532094 | RC_AA047034_at | EST: zf50b11.s1 Soares retina N2b4HR Homo sapiens cDNA clone 380349 3', mRNA sequence. (from Genbank) |
| 369 | Lymphoma | 0.5188556 | 0.3165132 | 0.269302 | 0.17525198 | RC_AA282147_at | EST: zt02b12.s1 NCI_CGAP_GCB1 Homo sapiens cDNA clone IMAGE:711935 3', mRNA sequence. (from Genbank) |
| 370 | Lymphoma | 0.5183544 | 0.3164794 | 0.269223 | 0.17516522 | W26898_at | EST: 16a4 Human retina cDNA randomly primed sublibrary Homo sapiens cDNA, mRNA sequence. (from Genbank) |
| 371 | Lymphoma | 0.5178661 | 0.3164333 | 0.269117 | 0.17503932 | AA248994_at | EST: l2187.seq.F Human fetal heart, Lambda ZAP Express Homo sapiens cDNA 5', mRNA sequence. (from Genbank) |

FIG. 7U

| | | | | | |
|---|---|---|---|---|---|
| 372 | Lymphoma | 0.517763 | 0.3163402 | 0.268918 | 0.17499232 | AFFX-HUMISGF3A/M97935_MB_at-2 | No info for gene |
| 373 | Lymphoma | 0.517763 | 0.3162571 | 0.268878 | 0.17484179 | AFFX-HUMISGF3A/M97935_MB_at | AFFX-HUMISGF3A/M97935_MB_at (endogenous control) |
| 374 | Lymphoma | 0.5177347 | 0.316151 | 0.268846 | 0.17476134 | J00105_s_at | BETA-2-MICROGLOBULIN PRECURSOR |
| 375 | Lymphoma | 0.5174834 | 0.3161171 | 0.26868 | 0.17462955 | RC_AA0258 87_at | EST: ze86h12.s1 Soares fetal heart NbHH19W Homo sapiens cDNA clone 365927 3', mRNA sequence. (from Genbank) |
| 376 | Lymphoma | 0.5172433 | 0.3160481 | 0.268629 | 0.17458479 | M33600_f_at | HLA-DRB1 Major histocompatibility complex, class II, DR beta 5 |
| 377 | Lymphoma | 0.5170456 | 0.3160433 | 0.268579 | 0.17443602 | RC_AA4767 20_at | EST: zw92g06.s1 Soares total fetus Nb2HF8 9w Homo sapiens cDNA clone 784474 3', mRNA sequence. (from Genbank) |
| 378 | Lymphoma | 0.5165935 | 0.3157479 | 0.268451 | 0.17432834 | RC_AA2355 05_at | EST: zt35f12.s1 Soares ovary tumor NbHOT Homo sapiens cDNA clone 724367 3', mRNA sequence. (from Genbank) |
| 379 | Lymphoma | 0.5161895 | 0.3156834 | 0.268346 | 0.17418513 | RC_D59362 _at | EST: Human fetal brain cDNA 3'-end GEN-023A02, mRNA sequence. (from Genbank) |
| 380 | Lymphoma | 0.5157975 | 0.315461 | 0.268291 | 0.17410155 | AA148094_a t | Homo sapiens CC3 (CC3) mRNA, complete cds |
| 381 | Lymphoma | 0.5156616 | 0.3154143 | 0.26819 | 0.17407674 | RC_AA6209 70_at | Syntaxin 7 |
| 382 | Lymphoma | 0.5155967 | 0.3153643 | 0.268183 | 0.17390539 | AA091085_a t | Homo sapiens PAC clone DJ0905J08 from 7p12-p14 |
| 383 | Lymphoma | 0.5146776 | 0.3153214 | 0.26811 | 0.17380425 | X62078_at | GM2A GM2 ganglioside activator protein |
| 384 | Lymphoma | 0.5143648 | 0.3150509 | 0.268018 | 0.17336784 | H69440_at | EST: yr88c02.r1 Homo sapiens cDNA clone 212354 5' similar to SP:C18F10.7 CE00784 :; (from Genbank) |
| 385 | Lymphoma | 0.5140838 | 0.3149224 | 0.267843 | 0.17359237 | X04011_at-2 | Cytochrome b-245, beta polypeptide (chronic granulomatous disease) |
| 386 | Lymphoma | 0.5140838 | 0.3147598 | 0.267796 | 0.1735137 | X04011_at | CYBB Chronic granulomatous disease |
| 387 | Lymphoma | 0.513625 | 0.3147093 | 0.267731 | 0.173426 | AA426168_a t | Homo sapiens mRNA for KIAA0805 protein, partial cds |
| 388 | Lymphoma | 0.5134165 | 0.3147078 | 0.267596 | 0.17331235 | M28170_at | CD19 CD19 antigen |
| 389 | Lymphoma | 0.5131865 | 0.3146439 | 0.26745 | 0.17324805 | H23893_at | Yn71g12.r1 Homo sapiens cDNA clone 173926 5' similar to contains Alu repetitive element; (from Genbank) |

FIG. 7V

| # | | | | | | Description |
|---|---|---|---|---|---|---|
| 390 | Lymphoma | 0.5125923 | 0.314557 | 0.267448 | 0.1731813 | X89109_s_a t | MacMarcks mRNA |
| 391 | Lymphoma | 0.5120077 | 0.3144499 | 0.267411 | 0.1730083 | RC_AA4188 78_at | EST: zv98g08.s1 Soares NhHMPu S1 Homo sapiens cDNA clone 767870 3', mRNA sequence. (from Genbank) |
| 392 | Lymphoma | 0.5118421 | 0.314287 | 0.267219 | 0.17292859 | RC_D20483 _i_at | BING4 |
| 393 | Lymphoma | 0.5115662 | 0.3142125 | 0.266892 | 0.17286152 | AA262458_a t | EST: zs16h04.r1 NCI_CGAP_GCB1 Homo sapiens cDNA clone IMAGE:685399 5', mRNA sequence. (from Genbank) |
| 394 | Lymphoma | 0.5110772 | 0.3139595 | 0.266783 | 0.17281915 | AA313677_a t | Proteasome (prosome, macropain) subunit, alpha type, 7 |
| 395 | Lymphoma | 0.5106558 | 0.3139546 | 0.266657 | 0.17270983 | RC_AA4433 34_at | EST: zw94g05.s1 Soares total fetus Nb2HF8 9w Homo sapiens cDNA clone 784664 3', mRNA sequence. (from Genbank) |
| 396 | Lymphoma | 0.5106116 | 0.3139471 | 0.266551 | 0.17264234 | RC_AA4826 20_at | EST: zt34h11.s1 Soares ovary tumor NbHOT Homo sapiens cDNA clone 724293 3', mRNA sequence. (from Genbank) |
| 397 | Lymphoma | 0.5102195 | 0.3137436 | 0.266505 | 0.17254676 | RC_AA2511 29_at | EST: zs03a10.s1 NCI_CGAP_GCB1 Homo sapiens cDNA clone IMAGE:684090 3', mRNA sequence. (from Genbank) |
| 398 | Lymphoma | 0.5097103 | 0.3136233 | 0.266485 | 0.17243212 | RC_AA1952 29_s_at | EST: zr34g09.s1 Soares NhHMPu S1 Homo sapiens cDNA clone 665344 3', mRNA sequence. (from Genbank) |
| 399 | Lymphoma | 0.5096799 | 0.3135579 | 0.266339 | 0.17234933 | RC_AA1739 72_at | EST: zp03d01.s1 Stratagene ovarian cancer (#937219) Homo sapiens cDNA clone 595297 3', mRNA sequence. (from Genbank) |
| 400 | Lymphoma | 0.5094477 | 0.3135192 | 0.266292 | 0.17218779 | H43250_at | EST: yp05f06.r1 Homo sapiens cDNA clone 186563 5'. (from Genbank) |
| 401 | Lymphoma | 0.5086533 | 0.3135053 | 0.266267 | 0.17206582 | RC_AA4238 92_at | EST: zv79f11.s1 Soares total fetus Nb2HF8 9w Homo sapiens cDNA clone 759885 3', mRNA sequence. (from Genbank) |
| 402 | Lymphoma | 0.5085723 | 0.3134845 | 0.2662 | 0.1720013 | U57847_s_a t | Ribosomal protein S27 (metallopanstimulin 1) |
| 403 | Lymphoma | 0.5082719 | 0.3134545 | 0.266173 | 0.17181213 | H72650_at | Yu05d11.r1 Homo sapiens cDNA clone 232917 5'. (from Genbank) |
| 404 | Lymphoma | 0.5080409 | 0.3134458 | 0.266584 | 0.17167278 | U36787_at-2 | Holocytochrome c synthase (cytochrome c heme-lyase) |
| 405 | Lymphoma | 0.5080409 | 0.3134357 | 0.265783 | 0.17162815 | U36787_at | Putative holocytochrome c-type synthetase mRNA |
| 406 | Lymphoma | 0.5080199 | 0.3133913 | 0.265779 | 0.17152633 | RC_AA2435 74_at | EST: zr67h10.s1 Soares NhHMPu S1 Homo sapiens cDNA clone 668515 3', mRNA sequence. (from Genbank) |
| 407 | Lymphoma | 0.507296 | 0.3132858 | 0.265722 | 0.17150238 | X56841_at | HLA-E MHC class I antigen HLA-E |
| 408 | Lymphoma | 0.5071035 | 0.3131756 | 0.265683 | 0.17133912 | AB000221_a t | Small inducible cytokine subfamily A (Cys-Cys), member 18, pulmonary and activation-regulated |

FIG. 7W

| | | | | | | |
|---|---|---|---|---|---|---|
| 409 | Lymphoma | 0.5063697 | 0.3131256 | 0.265678 | 0.17120236 | RC_AA6090 17_s_at | Forkhead (Drosophila) homolog 1 (rhabdomyosarcoma) |
| 410 | Lymphoma | 0.5060639 | 0.3129837 | 0.265662 | 0.17119241 | AA152069_a t | H.sapiens mRNA for galectin-8 |
| 411 | Lymphoma | 0.5057313 | 0.3129317 | 0.26561 | 0.17110251 | Z20462_at | EST: H. sapiens putatively transcribed partial sequence; UK-HGMP sequence ID AAACEEP; single read, mRNA sequence. (from Genbank) |
| 412 | Lymphoma | 0.5054904 | 0.3128771 | 0.265535 | 0.17105994 | L01087_at | PRKCQ Protein kinase C-theta |
| 413 | Lymphoma | 0.5054904 | 0.312776 | 0.265431 | 0.17099616 | L01087_at-2 | Protein kinase C, theta |
| 414 | Lymphoma | 0.5050198 | 0.3127317 | 0.26536 | 0.17082238 | RC_AA4303 68_at | Cyclin E2 |
| 415 | Lymphoma | 0.5046549 | 0.3126153 | 0.265319 | 0.17077254 | D32002_s_a t | NCBP Nuclear cap binding protein, 80kD |
| 416 | Lymphoma | 0.5046649 | 0.3125323 | 0.26526 | 0.17066024 | D32002_s_a t-2 | Nuclear cap binding protein, 80kD |
| 417 | Lymphoma | 0.504543 | 0.3125193 | 0.262255 | 0.1705426 | D30758_at | KIAA0050 gene |
| 418 | Lymphoma | 0.504543 | 0.3124014 | 0.265055 | 0.1704065 | D30758_at-2 | KIAA0050 gene product |
| 419 | Lymphoma | 0.504483 | 0.3123792 | 0.265036 | 0.17033322 | RC_AA4861 83_at | EST: ab35a02.s1 Stratagene HeLa cell s3 937216 Homo sapiens cDNA clone 842762 3', mRNA sequence. (from Genbank) |
| 420 | Lymphoma | 0.5041115 | 0.3122508 | 0.264821 | 0.17023356 | RC_AA2851 53_at | EST: zs48d06.s1 NCI_CGAP_GCB1 Homo sapiens cDNA clone IMAGE:700715 3', mRNA sequence. (from Genbank) |
| 421 | Lymphoma | 0.5040442 | 0.3119722 | 0.264781 | 0.1701263 | HG3214-HT3391_at | Metallopanstimulin 1 |
| 422 | Lymphoma | 0.5030366 | 0.3119158 | 0.264639 | 0.16999939 | AA406435_a t | EST: zv12d12.r1 Soares NhHMPu S1 Homo sapiens cDNA clone 753431 5', mRNA sequence. (from Genbank) |
| 423 | Lymphoma | 0.5027992 | 0.3118224 | 0.264565 | 0.16993955 | D50840_at | Ceramide glucosyltransferase |
| 424 | Lymphoma | 0.5027992 | 0.3118178 | 0.264382 | 0.16980603 | D50840_at-2 | UDP-glucose ceramide glucosyltransferase |
| 425 | Lymphoma | 0.502516 | 0.3118013 | 0.264362 | 0.16969074 | T10792_at | EST: hbc1281 Homo sapiens cDNA clone hbc1281 5'end. (from Genbank) |
| 426 | Lymphoma | 0.5022289 | 0.3115675 | 0.264213 | 0.16961645 | RC_AA3940 02_at | EST: zl49e09.s1 Soares ovary tumor NbHOT Homo sapiens cDNA clone 725704 3', mRNA sequence. (from Genbank) |
| 427 | Lymphoma | 0.50081 | 0.3115324 | 0.264089 | 0.16948557 | RC_AA4044 83_at | EST: zw38a02.s1 Soares total fetus Nb2HF8.9w Homo sapiens cDNA clone 772298 3', mRNA sequence. (from Genbank) |

FIG. 7X

| # | Type | | | ID | | Description |
|---|---|---|---|---|---|---|
| 428 | Lymphoma | 0.5005394 | 0.3114094 | 0.16939183 | U81600_at-2 | Human paired-like homeodomain protein PRX-2 mRNA, partial cds |
| 429 | Lymphoma | 0.5005394 | 0.3114066 | 0.16929416 | U81600_at | Paired-like homeodomain protein PRX-2 mRNA, partial cds |
| 430 | Lymphoma | 0.5004904 | 0.311302 | 0.16914 | U43628_at | Human mucosal addressin cell adhesion molecule-1 (MAdCAM-1) mRNA, complete cds |
| 431 | Lymphoma | 0.5001035 | 0.3112432 | 0.16902278 | D30921_at | EST: Human fetal-lung cDNA 5'-end sequence, mRNA sequence. (from Genbank) |
| 432 | Lymphoma | 0.4994837 | 0.3110908 | 0.16899772 | RC_AA043360_at | EST: zk62e11.s1 Soares pregnant uterus NbHPU Homo sapiens cDNA clone 487436 3', mRNA sequence. (from Genbank) |
| 433 | Lymphoma | 0.4976719 | 0.3109495 | 0.16891159 | V00536_rna1_at | IFNG gene extracted from Human immune interferon (IFN-gamma) gene |
| 434 | Lymphoma | 0.497312 | 0.3107717 | 0.1688343 | RC_AA459686_at | EST: zx49d11.s1 Soares testis NHT Homo sapiens cDNA clone 795573 3', mRNA sequence. (from Genbank) |
| 435 | Lymphoma | 0.497059 | 0.3106807 | 0.16877133 | RC_AA423991_at | EST: zv79h06.s1 Soares total fetus Nb2HF8 9w Homo sapiens cDNA clone 759899 3', mRNA sequence. (from Genbank) |
| 436 | Lymphoma | 0.4961176 | 0.310636 | 0.16862732 | AA410942_at | EST: Zt32h02.r1 Soares ovary tumor NbHOT Homo sapiens cDNA clone 724083 5', mRNA sequence. (from Genbank) |
| 437 | Lymphoma | 0.4959831 | 0.310609 | 0.16851622 | RC_AA292930_at | Homo sapiens mRNA for KIAA0692 protein, partial cds |
| 438 | Lymphoma | 0.4957578 | 0.3104923 | 0.16842414 | W26355_at | EST: 26d2 Human retina cDNA randomly primed sublibrary Homo sapiens cDNA, mRNA sequence. (from Genbank) |
| 439 | Lymphoma | 0.4956735 | 0.3104841 | 0.1683926 | X52425_at | IL4R Interleukin 4 receptor |
| 440 | Lymphoma | 0.4956305 | 0.3104491 | 0.1682848 | AA430981_at | EST: PMY0792 KG1-a Lambda Zap Express cDNA library Homo sapiens cDNA 5', mRNA sequence. (from Genbank) |
| 441 | Lymphoma | 0.4956121 | 0.3103143 | 0.16815613 | RC_AA252374_at | EST: zs12f12.s1 NCI_CGAP_GCB1 Homo sapiens cDNA clone IMAGE:685007 3', mRNA sequence. (from Genbank) |
| 442 | Lymphoma | 0.495161 | 0.3102812 | 0.1680757 | AA423926_at | EST: zv79d10.r1 Soares total fetus Nb2HF8 9w Homo sapiens cDNA clone 759859 5', mRNA sequence. (from Genbank) |
| 443 | Lymphoma | 0.4947857 | 0.3101506 | 0.16803156 | W28230_at | EST: 43h12 Human retina cDNA randomly primed sublibrary Homo sapiens cDNA, mRNA sequence. (from Genbank) |
| 444 | Lymphoma | 0.4947764 | 0.3101238 | 0.16793925 | C16420_s_at | EST: Human aorta cDNA 5'-end GEN-312H05, mRNA sequence. (from Genbank) |
| 445 | Lymphoma | 0.494471 | 0.3100637 | 0.16788293 | RC_AA054152_at | EST: zf54g07.s1 Soares retina N2b4HR Homo sapiens cDNA clone 380796 3', mRNA sequence. (from Genbank) |
| 446 | Lymphoma | 0.4941604 | 0.3100385 | 0.16783653 | L42324_at | (clone GPCR W) G protein-linked receptor gene (GPCR) gene, 5' end of cds |
| 447 | Lymphoma | 0.4938051 | 0.3100236 | 0.16770528 | M12272_s_at | Alcohol dehydrogenase 3 (class I), gamma polypeptide |

FIG. 7Y

| | | | | | |
|---|---|---|---|---|---|
| 448 | Lymphoma | 0.4937576 | 0.3099369 | 0.262329 | 0.16763712 | RC_AA2431 73_at | EST: zr26d11.s1 Stratagene NT2 neuronal precursor 937230 Homo sapiens cDNA clone 664533 3', mRNA sequence. (from Genbank) |
| 449 | Lymphoma | 0.4937521 | 0.3099326 | 0.262319 | 0.16757235 | W92678_at | EST: zd92a04.r1 Soares fetal heart NbHH19W Homo sapiens cDNA clone 356910 5' similar to contains element LTR3 repetitive element ;; mRNA sequence. (from Genbank) |
| 450 | Lymphoma | 0.4933912 | 0.3099232 | 0.26227 | 0.1673887 | M60854_at | RPS16 Ribosomal protein S16 |
| 451 | Lymphoma | 0.4931738 | 0.3099209 | 0.26227 | 0.1673447 | AA007264_a t | EST: zh97e06.r1 Soares fetal liver spleen 1NFLS S1 Homo sapiens cDNA clone 429250 5', mRNA sequence. (from Genbank) |
| 452 | Lymphoma | 0.4931697 | 0.3098009 | 0.262239 | 0.16725726_at | RC_AA2563 | EST: zr80i08.s1 Soares NhHMPu S1 Homo sapiens cDNA clone 682023 3', mRNA sequence. (from Genbank) |
| 453 | Lymphoma | 0.4924473 | 0.3096889 | 0.262112 | 0.16713656 | H04627_at | EST: yj49f04.r1 Homo sapiens cDNA clone 152095 5'. (from Genbank) |
| 454 | Lymphoma | 0.4923333 | 0.309602 | 0.262067 | 0.16709335 52_at | RC_AA3985 | Homo sapiens mRNA for KIAA0639 protein, partial cds |
| 455 | Lymphoma | 0.4918718 | 0.3095457 | 0.262043 | 0.16700849 70_at | RC_AA4365 | Homo sapiens mRNA for pre-mRNA cleavage factor I subunit |
| 456 | Lymphoma | 0.4915474 | 0.3094899 | 0.261998 | 0.16696228 | RC_AA4018 09_at | EST: zv65g11.s1 Soares total fetus Nb2HF8 9w Homo sapiens cDNA clone 758564 3', mRNA sequence. (from Genbank) |
| 457 | Lymphoma | 0.4913811 | 0.3094322 | 0.261953 | 0.16687767 | AA291444_a t | Novel centrosomal protein RanBPM |
| 458 | Lymphoma | 0.4911034 | 0.3094218 | 0.261703 | 0.1668405 | U15460_at | BZip protein B-ATF mRNA |
| 459 | Lymphoma | 0.4905382 | 0.309218 | 0.261677 | 0.1666771 | M55067_at | NCF1 47 kD autosomal chronic granulomatous disease protein |
| 460 | Lymphoma | 0.4903538 | 0.3092141 | 0.26163 | 0.16657688 | H19562_at | EST: yn54h07.r1 Homo sapiens cDNA clone 172285 5'. (from Genbank) |
| 461 | Lymphoma | 0.4899899 | 0.3091564 | 0.2615 | 0.1664923 | RC_AA2629 69_f_at | EST: zr71c02.s1 Soares NhHMPu S1 Homo sapiens cDNA clone 668834 3' similar to TR:G969170 G969170 PX19. ;; mRNA sequence. (from Genbank) |
| 462 | Lymphoma | 0.4897799 | 0.3091098 | 0.261147 | 0.16338966 32_at | RC_AA4300 | Pituitary tumor-transforming 1 |
| 463 | Lymphoma | 0.4884768 | 0.3090815 | 0.261467 | 0.16330822 3_at | RC_AA2060 | EST: zq77c12.s1 Stratagene hNT neuron (#937233) Homo sapiens cDNA clone 647638 3', mRNA sequence. (from Genbank) |
| 464 | Lymphoma | 0.4884109 | 0.3090539 | 0.261306 | 0.16624503 | X03068_f_at | HLA CLASS II HISTOCOMPATIBILITY ANTIGEN, DQ(W1.1) BETA CHAIN PRECURSOR |

FIG. 7Z

| | | | | |
|---|---|---|---|---|
| 465 | Lymphoma | 0.4880095 | 0.3089931 | 0.261044 | RC_AA4901 07_at | Homo sapiens mRNA for JM5 protein, complete CDS (clone IMAGE 53337, LLNLc110F1857Q7 (RZPD Berlin) and LLNLc110G0913Q7 (RZPD Berlin)) |
| 466 | Lymphoma | 0.4876634 | 0.3089661 | 0.260952 | 0.16607879 W79409_at | Hydroxyacyl-Coenzyme A dehydrogenase/3-ketoacyl-Coenzyme A thiolase/enoyl-Coenzyme A hydratase (trifunctional protein), beta subunit |
| 467 | Lymphoma | 0.4876027 | 0.3089148 | 0.260943 | 0.16598448 AFFX-BioC-5_at | AFFX-BioC-5_at (endogenous control) |
| 468 | Lymphoma | 0.4876027 | 0.3086642 | 0.260745 | 0.16594674 AFFX-BioC-5_at-2 | AFFX-BioC-5_at (miscellaneous control - 11k chips) |
| 469 | Lymphoma | 0.487177 | 0.3088585 | 0.260678 | 0.1657831 X17093_at | HLA CLASS I HISTOCOMPATIBILITY ANTIGEN, F ALPHA CHAIN PRECURSOR |
| 470 | Lymphoma | 0.4863153 | 0.3085575 | 0.260678 | RC_AA2929 0.16556568 31_at | EST: zt54e06.s1 Soares ovary tumor NbHOT Homo sapiens cDNA clone 726178 3', mRNA sequence. (from Genbank) |
| 471 | Lymphoma | 0.4863762 | 0.3088156 | 0.260618 | RC_AA2997 0.16556922 89_at | EST: EST12356 Uterus tumor I Homo sapiens cDNA 3' end, mRNA sequence. (from Genbank) |
| 472 | Lymphoma | 0.4860996 | 0.3087816 | 0.260354 | X03100_cds 0.16551088 2_at | HLA-SB alpha gene (class II antigen) extracted from Human HLA-SB(DP) alpha gene |
| 473 | Lymphoma | 0.4852366 | 0.3087606 | 0.260329 | X01038_rna 0.16539599 1_s_at | Fetal gene for apolipoprotein AI precursor |
| 474 | Lymphoma | 0.4851981 | 0.3086963 | 0.260327 | 0.1652655 S65761_at | Anti-colorectal carcinoma heavy chain |
| 475 | Lymphoma | 0.4847626 | 0.3086499 | 0.26022 | RC_AA0259 0.16522494 05_f_at | Homo sapiens TNF-inducible protein CG12-1 mRNA, complete cds |
| 476 | Lymphoma | 0.484688 | 0.3086315 | 0.260204 | 0.1651336 S76992_at | VAV2 Vav 2 oncogene |
| 477 | Lymphoma | 0.484688 | 0.3084959 | 0.260192 | 0.16508189 S76992_at-2 | Vav 2 oncogene |
| 478 | Lymphoma | 0.4834751 | 0.3084716 | 0.260188 | AA234259_a 0.1650337 t | EST: zr71c08.r1 Soares_NhHMPu_S1 Homo sapiens cDNA clone IMAGE:668846 5', mRNA sequence |
| 479 | Lymphoma | 0.4827471 | 0.3082822 | 0.260032 | RC_AA2368 0.16497533 53_at | EST: zs01b04.s1 NCI_CGAP_GCB1 Homo sapiens cDNA clone IMAGE:683887 3', mRNA sequence. (from Genbank) |
| 480 | Lymphoma | 0.4826184 | 0.3082234 | 0.259715 | RC_AA0437 0.16482487 90_at | EST: zk59f12.s1 Soares pregnant uterus NbHPU Homo sapiens cDNA clone 487151 3', mRNA sequence. (from Genbank) |
| 481 | Lymphoma | 0.4820257 | 0.3081968 | 0.259625 | 0.16475107 W73663_at | EST: zd55e07.r1 Soares fetal heart NbHH19W Homo sapiens cDNA clone 344580 5', mRNA sequence. (from Genbank) |
| 482 | Lymphoma | 0.4818273 | 0.3079852 | 0.259513 | AA3105110_a 0.16462675 t | Human mRNA expressed in HC/HCC livers and MolT-4 proliferating cells, partial sequence |
| 483 | Lymphoma | 0.4811449 | 0.3079478 | 0.259374 | 0.16458634 H21219_at | RAB6, member RAS oncogene family |

FIG. 7A2

| | | | | | |
|---|---|---|---|---|---|
| 484 | Lymphoma | 0.4810958 | 0.3077937 | 0.259318 | 0.16445291 | AA248079_a_t | EST: cp2131.seq.F Human fetal heart, Lambda ZAP Express Homo sapiens cDNA 5', mRNA sequence. (from Genbank) |
| 485 | Lymphoma | 0.480833 | 0.3077875 | 0.259285 | 0.16439046 | RC_AA2359 80_at | EST: zs05e09.s1 NCI_CGAP_GCB1 Homo sapiens cDNA clone IMAGE:684328 3', mRNA sequence. (from Genbank) |
| 486 | Lymphoma | 0.4806607 | 0.3076404 | 0.259227 | 0.16425137 | RC_AA4001 83_at | EST: zu64d03.s1 Soares testis NHT Homo sapiens cDNA clone 742757 3', mRNA sequence. (from Genbank) |
| 487 | Lymphoma | 0.4800119 | 0.3076221 | 0.259079 | 0.16419928 | AA055361_a_t | EST: zf20a04.r1 Soares fetal heart NbHH19W Homo sapiens cDNA clone 377454 5', mRNA sequence. (from Genbank) |
| 488 | Lymphoma | 0.4799957 | 0.3075579 | 0.259018 | 0.16415285 | AA340215_a_t | EST: EST45566 Fetal brain III Homo sapiens cDNA 5' end, mRNA sequence. (from Genbank) |
| 489 | Lymphoma | 0.4798849 | 0.3075241 | 0.258976 | 0.16406794 | M26004_s_a_t | CR2 Complement component (3d/Epstein Barr virus) receptor 2 |
| 490 | Lymphoma | 0.4796203 | 0.3075202 | 0.2589 | 0.16401476 | AA091296_a_t | Phosphatidylinositol glycan, class F |
| 491 | Lymphoma | 0.4795759 | 0.3075014 | 0.258892 | 0.16398475 | AB000114_a_t | Osteomodulin |
| 492 | Lymphoma | 0.4795759 | 0.3073728 | 0.258844 | 0.16388205 | AB000114_a_t-2 | Osteomodulin |
| 493 | Lymphoma | 0.47956 | 0.3073222 | 0.258716 | 0.16381769 | RC_AA4013 05_at | EST: zu68c01.s1 Soares testis NHT Homo sapiens cDNA clone 743136 3', mRNA sequence. (from Genbank) |
| 494 | Lymphoma | 0.4793671 | 0.3072074 | 0.258555 | 0.16363816 | AFFX-HUMGAPDH /M33197_5_at | AFFX-HUMGAPDH/M33197_5_at (endogenous control) |
| 495 | Lymphoma | 0.4793671 | 0.3071489 | 0.258479 | 0.16356792 | AFFX-HUMGAPDH /M33197_5_at-2 | Glyceraldehyde-3-phosphate dehydrogenase |
| 496 | Lymphoma | 0.4786223 | 0.3071241 | 0.258464 | 0.16346438 | AA135452_a_t | CGG triplet repeat binding protein 1 |
| 497 | Lymphoma | 0.4786626 | 0.3071182 | 0.258365 | 0.16345115 | R25043_at | Yg41h10.r1 Homo sapiens cDNA clone 35408 5'. (from Genbank) |
| 498 | Lymphoma | 0.4777667 | 0.3070644 | 0.258306 | 0.1633898 | H62426_at | Ribosomal protein S25 |
| 499 | Lymphoma | 0.477442 | 0.3068466 | 0.258276 | 0.16332293 | RC_AA0860 57_s_at | Ribosomal protein, mitochondrial, S12 |
| 500 | Lymphoma | 0.4773842 | 0.3068204 | 0.258203 | 0.16318329 | U38864_at-2 | Human zinc-finger protein C2H2-150 mRNA, complete cds |
| 501 | Lymphoma | 0.4773842 | 0.3067706 | 0.258188 | 0.16313538 | U38864_at | Zinc-finger protein C2H2-150 mRNA |

FIG. 7B2

| # | Type | | | | ID | Description |
|---|---|---|---|---|---|---|
| 502 | Lymphoma | 0.4773721 | 0.3063737 | 0.16302575 | RC_AA4258 36_at | EST: zv48d10.s1 Soares ovary tumor NbHOT Homo sapiens cDNA clone 756883 3', mRNA sequence. (from Genbank) |
| 503 | Lymphoma | 0.4772288 | 0.3062795 | 0.16296189 | AA417126_a t | EST: zu13c10.r1 Soares testis NHT Homo sapiens cDNA clone 731730 5', mRNA sequence. (from Genbank) |
| 504 | Lymphoma | 0.4764133 | 0.3061908 | 0.16290188 | X81900_rna 1_at | H.sapiens mRNA for NADH dehydrogenase |
| 505 | Lymphoma | 0.4763579 | 0.3061358 | 0.16287763 | RC_AA4418 02_at | EST: zw62d04.s1 Soares total fetus Nb2HF8.9w Homo sapiens cDNA clone 774631 3', mRNA sequence. (from Genbank) |
| 506 | Lymphoma | 0.4757499 | 0.3061316 | 0.16273604 | U94352_at | Manic fringe (Drosophila) homolog |
| 507 | Lymphoma | 0.4756461 | 0.3060992 | 0.16269724 | RC_AA4165 51_at | EST: zu05e01.s1 Soares testis NHT Homo sapiens cDNA clone 730968 3', mRNA sequence. (from Genbank) |
| 508 | Lymphoma | 0.475554 | 0.3060649 | 0.16258064 | Z12962_at | EEF1A1 Translation elongation factor 1-alpha-1 |
| 509 | Lymphoma | 0.4752049 | 0.3060094 | 0.16243859 | W95793_at | EST: ze07h05.r1 Soares fetal heart NbHH19W Homo sapiens cDNA clone 358329 5' similar to PIR:A56724 A56724 cni protein - fruit fly.; mRNA sequence. (from Genbank) |
| 510 | Lymphoma | 0.4752024 | 0.3059767 | 0.16239354 | AA484997_a t | Manic fringe (Drosophila) homolog |
| 511 | Lymphoma | 0.4748591 | 0.3058469 | 0.16233556 | RC_AA1211 23_at | EST: zl88c05.s1 Stratagene colon (#937204) Homo sapiens cDNA clone 511688 3' similar to contains Alu repetitive element;contains element L1 repetitive element.;, mRNA sequence. (from Genbank) |
| 512 | Lymphoma | 0.4743813 | 0.3056891 | 0.16227311 | RC_AA4005 12_at | EST: zu70g04.s1 Soares testis NHT Homo sapiens cDNA clone 743382 3', mRNA sequence. (from Genbank) |
| 513 | Lymphoma | 0.4740894 | 0.3055018 | 0.1622346 | W44973_at | Homo sapiens mRNA for transducin (beta) like 1 protein |
| 514 | Lymphoma | 0.4738022 | 0.3053692 | 0.16215807 | H14879_at | EST: ym25f01.r1 Homo sapiens cDNA clone 48919 5'. (from Genbank) |
| 515 | Lymphoma | 0.4734473 | 0.3053502 | 0.16209751 | U57057_at | WD protein IR10 mRNA |
| 516 | Lymphoma | 0.4734473 | 0.3052999 | 0.16209228 | U57057_at-2 | WD repeat domain 2 |
| 517 | Lymphoma | 0.4730473 | 0.3052734 | 0.16198546 | RC_AA0630 70_at | EST: zf67e06.s1 Soares pineal gland N3HPG Homo sapiens cDNA clone 382018 3', mRNA sequence. (from Genbank) |
| 518 | Lymphoma | 0.472722 | 0.3050946 | 0.16190626 | X66401_cds 1_at | LMP2 gene extracted from H.sapiens genes TAP1, TAP2, LMP2, LMP7 and DOB |
| 519 | Lymphoma | 0.4724755 | 0.3050545 | 0.16184361 | RC_AA2906 30_at | EST: zs45f10.s1 NCI_CGAP_GCB1 Homo sapiens cDNA clone IMAGE:700459 3', mRNA sequence. (from Genbank) |

FIG. 7C2

| # | Type | | | | | Description |
|---|---|---|---|---|---|---|
| 520 | Lymphoma | 0.4724245 | 0.3050371 | 0.256713 | 0.16173892 | RC_AA4114 65_at | EST: zv30g06.s1 Soares ovary tumor NbHOT Homo sapiens cDNA clone 755194 3', mRNA sequence. (from Genbank) |
| 521 | Lymphoma | 0.4722337 | 0.3050129 | 0.256713 | 0.16167134 | R12040_at | EST: yf53e11.r1 Homo sapiens cDNA clone 25730 5'. (from Genbank) |
| 522 | Lymphoma | 0.4719347 | 0.304992 | 0.256689 | 0.16155617 | AA016186_a t | EST: ze32f10.r1 Soares retina N2b4HR Homo sapiens cDNA clone 360715 5', mRNA sequence. (from Genbank) |
| 523 | Lymphoma | 0.4716279 | 0.3049868 | 0.256599 | 0.16150951 | AA362594_s _at | Human Chromosome 16 BAC clone CIT987SK-A-735G6 |
| 524 | Lymphoma | 0.471304 | 0.304973 | 0.256365 | 0.16140717 | N41849_at | EST: yw72c02.r1 Homo sapiens cDNA clone 257762 5'. (from Genbank) |
| 525 | Lymphoma | 0.4709064 | 0.3049176 | 0.256313 | 0.16127142 | RC_AA4784 16_at | EST: zu46d07.s1 Soares ovary tumor NbHOT Homo sapiens cDNA clone 741037 3', mRNA sequence. (from Genbank) |
| 526 | Lymphoma | 0.4687017 | 0.3049164 | 0.256158 | 0.16123068 | W67213_at | EST: zd40h08.r1 Soares fetal heart NbHH19W Homo sapiens cDNA clone 343167 5' similar to SW:SARA_MOUSE P36536 GTP-BINDING PROTEIN SARA. [1] ;. mRNA sequence. (from Genbank) |
| 527 | Lymphoma | 0.4685468 | 0.3048878 | 0.256032 | 0.16114485 | T50262_at | Human ribosomal protein L35 mRNA, complete cds |
| 528 | Lymphoma | 0.4681419 | 0.3048064 | 0.256024 | 0.16103706 | RC_AA4028 14_at | EST: zu56g05.s1 Soares ovary tumor NbHOT Homo sapiens cDNA clone 742040 3', mRNA sequence. (from Genbank) |
| 529 | Lymphoma | 0.4680364 | 0.3047638 | 0.255882 | 0.16098247 | RC_AA4466 18_at | EST: zw85h03.s1 Soares total fetus Nb2HF8 9w Homo sapiens cDNA clone 783797 3', mRNA sequence. (from Genbank) |
| 530 | Lymphoma | 0.4680113 | 0.3047031 | 0.255845 | 0.16091307 | AA456895_a t | Aa38d10.r1 NCI_CGAP_GCB1 Homo sapiens cDNA clone IMAGE:815539 5' similar to TR:G544492 G544492 LYMPHOID-RESTRICTED MEMBRANE PROTEIN. ;. mRNA sequence. (from Genbank) |
| 531 | Lymphoma | 0.4676941 | 0.304619 | 0.255795 | 0.16080336 | RC_AA4499 90_at | Homo sapiens acyl-protein thioesterase mRNA, complete cds |
| 532 | Lymphoma | 0.4676563 | 0.3046067 | 0.255766 | 0.16073586 | X79563_at | H.sapiens 8.2kDa differentiation factor mRNA |
| 533 | Lymphoma | 0.4674477 | 0.3045258 | 0.255628 | 0.16064318 | AA410480_a t | EST: zv23b05.r1 Soares NhHMPu S1 Homo sapiens cDNA clone 754449 5', mRNA sequence. (from Genbank) |
| 534 | Lymphoma | 0.4671531 | 0.3044692 | 0.255609 | 0.16056718 | RC_AA3572 04_s_at | EST: EST65911 Jurkat T-cells I Homo sapiens cDNA 3' end, mRNA sequence. (from Genbank) |
| 535 | Lymphoma | 0.4670663 | 0.3044614 | 0.255588 | 0.16052161 | U07563_cds 1_at:2 | V-abl Abelson murine leukemia viral oncogene homolog 1::Human ABL gene, exon 1b and intron 1b, and putative M8604 Met protein (M8604 Met) gene |
| 536 | Lymphoma | 0.4670663 | 0.3043981 | 0.255501 | 0.16043113 | U07563_cds 1_at | ABL gene, exon 1b and intron 1b, and putative M8604 Met protein (M8604 Met) gene |

FIG. 7D2

| # | Type | | | | | Description |
|---|---|---|---|---|---|---|
| 537 | Lymphoma | 0.4667269 | 0.3043245 | 0.255498 | 0.16032003 | RC_AA4358 38_s_at | EST: zt80b06.s1 Soares testis NHT Homo sapiens cDNA clone 728627 3', mRNA sequence. (from Genbank) |
| 538 | Lymphoma | 0.4666877 | 0.3043076 | 0.255379 | 0.16025187 | AA315935_a t | EST: EST187738 Colon carcinoma (HCC) cell line II Homo sapiens cDNA 5' end, mRNA sequence. (from Genbank) |
| 539 | Lymphoma | 0.4666053 | 0.3040862 | 0.25529 | 0.16021876 | RC_AA4293 49_at | H.sapiens HUNK1 mRNA |
| 540 | Lymphoma | 0.466091 | 0.3040809 | 0.255257 | 0.16015346 | RC_AA4611 69_at | EST: zx70u06.s1 Soares total fetus Nb2HF8.9w Homo sapiens cDNA clone 796787 3', mRNA sequence. (from Genbank) |
| 541 | Lymphoma | 0.4658765 | 0.3039914 | 0.255254 | 0.16006778 | R56183_s_a t | Eukaryotic translation initiation factor 3, subunit 6 (48kD) |
| 542 | Lymphoma | 0.4658882 | 0.3039583 | 0.255116 | 0.15999661 | RC_AA2522 42_at | EST: zr64g04.s1 Soares NhHMPu S1 Homo sapiens cDNA clone 668214 3', mRNA sequence. (from Genbank) |
| 543 | Lymphoma | 0.464892 | 0.3039196 | 0.255075 | 0.15985727 | X13810_s_a t | POU2F2 POU domain, class 2, transcription factor 2 |
| 544 | Lymphoma | 0.464866 | 0.3038801 | 0.254904 | 0.15975219 | AA3110450_a t | EST: EST181264 Jurkat T-cells V Homo sapiens cDNA 5' end, mRNA sequence. (from Genbank) |
| 545 | Lymphoma | 0.4642687 | 0.303831 | 0.254822 | 0.15972471 | X02530_1_at | INP10 Interferon (gamma)-induced cell line; protein 10 from |
| 546 | Lymphoma | 0.4640793 | 0.3037289 | 0.254805 | 0.15960481 | M98776_rna 1_at | Keratin 1 gene |
| 547 | Lymphoma | 0.4640793 | 0.303667 | 0.25474 | 0.15954456 | M98776_rna 1_at-2 | KERATIN, TYPE II CYTOSKELETAL 1 |
| 548 | Lymphoma | 0.4640741 | 0.3035232 | 0.254596 | 0.15948603 | M91487_at | EST: HUMRTPGEAF Homo sapiens cDNA. (from Genbank) |
| 549 | Lymphoma | 0.4638918 | 0.3034747 | 0.254594 | 0.15940909 | AA046908_a t | EST: zf47109.r1 Soares retina N2b4HR Homo sapiens cDNA clone 380105 5', mRNA sequence. (from Genbank) |
| 550 | Lymphoma | 0.4637519 | 0.3034005 | 0.254584 | 0.15929358 | K02777_s_at | T-cell receptor active alpha-chain mRNA from Jurkat cell line |
| 551 | Lymphoma | 0.4636858 | 0.3033223 | 0.254538 | 0.15922879 | Y08915_at | Alpha 4 protein |
| 552 | Lymphoma | 0.4636558 | 0.3031284 | 0.254519 | 0.15916905 | Y08915_at-2 | Immunoglobulin (CD79A) binding protein 1 |
| 553 | Lymphoma | 0.4634713 | 0.3031206 | 0.254482 | 0.15910397 | H02666_at | Yj36l05.r1 Homo sapiens cDNA clone 150849 5' (from Genbank) |
| 554 | Lymphoma | 0.4625644 | 0.3028916 | 0.254461 | 0.1590877 | N34096_at | Ubiquitin-conjugating enzyme E2F.1 (homologous to yeast UBC4/5) |
| 555 | Lymphoma | 0.4625415 | 0.3028912 | 0.254453 | 0.15902767 | X66079_at | SPIB Spi-B transcription factor (Spi-1/PU.1 related) |

FIG. 7E2

| | | | | | |
|---|---|---|---|---|---|
| 556 | Lymphoma | 0.4622544 | 0.30286 | 0.25432 | 0.15895781 | RC_AA6100 52_at | EST: af18h05.s1 Soares testis NHT Homo sapiens cDNA clone 1032057 3' similar to TR:G168081 G168081 UNIDENTIFIED GENE.; mRNA sequence. (from Genbank) |
| 557 | Lymphoma | 0.4622276 | 0.3028352 | 0.254316 | 0.1588391 | W00405_at | Apg12 (autophagy, yeast) homolog |
| 558 | Lymphoma | 0.462168 | 0.3026753 | 0.254244 | 0.15874623 | RC_AA4170 68_r_at | EST: zu13b04.s1 Soares testis NHT Homo sapiens cDNA clone 731695 3', mRNA sequence. (from Genbank) |
| 559 | Lymphoma | 0.4620487 | 0.3025678 | 0.254161 | 0.15859039 | H10482_at | EST: yl90d12.r1 Homo sapiens cDNA clone 45664 5'. (from Genbank) |
| 560 | Lymphoma | 0.4617675 | 0.3025008 | 0.254106 | 0.15850651 | RC_AA4315 02_at | Homo sapiens lok mRNA for protein kinase, complete cds |
| 561 | Lymphoma | 0.4615154 | 0.3024307 | 0.254045 | 0.15845156 | RC_AA2830 66_at | EST: zs91h04.s1 NCI_CGAP_GCB1 Homo sapiens cDNA clone IMAGE:704887 3', mRNA sequence. (from Genbank) |
| 562 | Lymphoma | 0.4614739 | 0.3024224 | 0.253987 | 0.1583368 | C01687_s_a t | F1Fo-ATPase synthase f subunit |
| 563 | Lymphoma | 0.4612488 | 0.3024081 | 0.253954 | 0.15828967 | RC_AA2588 19_s_at | EST: zs32f05.s1 NCI_CGAP_GCB1 Homo sapiens cDNA clone IMAGE:686913 3', mRNA sequence. (from Genbank) |
| 564 | Lymphoma | 0.4611935 | 0.3023944 | 0.253871 | 0.15823747 | RC_AA4634 17_at | EST: zx71g06.s1 Soares total fetus Nb2HF8 9w Homo sapiens cDNA clone 796954 3', mRNA sequence. (from Genbank) |
| 565 | Lymphoma | 0.4611105 | 0.3022851 | 0.253803 | 0.15815136 | RC_AA2625 87_at | EST: zs22d03.s1 NCI_CGAP_GCB1 Homo sapiens cDNA clone IMAGE:685925 3', mRNA sequence. (from Genbank) |
| 566 | Lymphoma | 0.4608573 | 0.3022542 | 0.253783 | 0.15806161 | RC_AA2624 17_at | EST: zs16g02.s1 NCI_CGAP_GCB1 Homo sapiens cDNA clone IMAGE:685394 3', mRNA sequence. (from Genbank) |
| 567 | Lymphoma | 0.4607934 | 0.3020549 | 0.253771 | 0.15796278 | N78018_at | EST: yv71a07.r1 Soares fetal liver spleen 1NFLS Homo sapiens cDNA clone 248148 5' similar to gb:M18533 DYSTROPHIN (HUMAN).; mRNA sequence. (from Genbank) |
| 568 | Lymphoma | 0.4605532 | 0.3019942 | 0.253771 | 0.15791476 | RC_AA4364 73_s_at | EST: zv08e08.s1 Soares NhHMPu S1 Homo sapiens cDNA clone 753062 3', mRNA sequence. (from Genbank) |
| 569 | Lymphoma | 0.4604169 | 0.3019727 | 0.253767 | 0.15788807 | H06532_at | Homo sapiens chromosome 11, BAC CIT-HSP-311e8 (BC269730) containing the hFEN1 gene |
| 570 | Lymphoma | 0.460272 | 0.3018751 | 0.253747 | 0.15775098 | D82797_at | EST: similar to none, mRNA sequence. (from Genbank) |
| 571 | Lymphoma | 0.4601813 | 0.3018087 | 0.253723 | 0.15766673 | X00351_f_at | ACTB Actin, beta |
| 572 | Lymphoma | 0.4599361 | 0.301758 | 0.253718 | 0.15756141 | U05259_rna _at | MB-1 gene |
| 573 | Lymphoma | 0.4595795 | 0.3015964 | 0.253689 | 0.15753362 | AA234657_a t | EST: zr75g08.r1 Soares NhHMPu S1 Homo sapiens cDNA clone 669278 5', mRNA sequence. (from Genbank) |
| 574 | Lymphoma | 0.4593212 | 0.3015783 | 0.253636 | 0.15748420 | RC_AA0187 00_at | EST: ze54e06.s1 Soares retina N2b4HR Homo sapiens cDNA clone 362818 3', mRNA sequence. (from Genbank) |

FIG. 7F2

| | | | | | |
|---|---|---|---|---|---|
| 575 | Lymphoma | 0.4590846 | 0.3015646 | 0.253564 | 0.15740599 | W15618_at | EST: zb05f07.r1 Soares fetal lung NbHL19W Homo sapiens cDNA clone 301189 5', mRNA sequence. (from Genbank) |
| 576 | Lymphoma | 0.4585275 | 0.3015617 | 0.253552 | 0.15732065 | N41987_at | EST: yw69b06.r1 Homo sapiens cDNA clone 257459 5'. (from Genbank) |
| 577 | Lymphoma | 0.4583989 | 0.3013871 | 0.253539 | 0.15720116 | U48263_at | Pre-pro-orphanin FQ (OFQ) mRNA |
| 578 | Lymphoma | 0.4583989 | 0.3013657 | 0.253271 | 0.15715349 | U48263_at-2 | Prepronociceptin |
| 579 | Lymphoma | 0.4582757 | 0.3012805 | 0.25323 | 0.15709794 | AA075599_a t | EST: zm88c03.r1 Stratagene ovarian cancer (#937219) Homo sapiens cDNA clone 544996 5' similar to SW:NI2M_BOVIN Q02369 NADH-UBIQUINONE OXIDOREDUCTASE B22 SUBUNIT :, mRNA sequence. (from Genbank) |
| 580 | Lymphoma | 0.4579643 | 0.3012222 | 0.253155 | 0.15700534 | AA047055_a t | EST: zf50g10.r1 Soares retina N2b4HR Homo sapiens cDNA clone 380418 5', mRNA sequence. (from Genbank) |
| 581 | Lymphoma | 0.4577725 | 0.3012019 | 0.253119 | 0.15694085 | M20902_at | APOC1 Apolipoprotein CI |
| 582 | Lymphoma | 0.4577502 | 0.3010995 | 0.253085 | 0.15688698 | FAS_at | No description for gene: FAS_at |
| 583 | Lymphoma | 0.4575031 | 0.3010762 | 0.253055 | 0.15682718 | RC_AA4657 19_at | EST: aa32i07.s1 NCI_CGAP_GCB1 Homo sapiens cDNA clone IMAGE:814981 3', mRNA sequence. (from Genbank) |
| 584 | Lymphoma | 0.4572826 | 0.3009313 | 0.252965 | 0.15676369 | RC_AA4500 40_s_at | ADP-ribosylation factor-like 2 |
| 585 | Lymphoma | 0.4566934 | 0.3006821 | 0.252884 | 0.15669736 | RC_AA0701 08_at | EST: zm69d06.s1 Stratagene neuroepithelium (#937231) Homo sapiens cDNA clone 530891 3', mRNA sequence. (from Genbank) |
| 586 | Lymphoma | 0.4565233 | 0.3006407 | 0.252845 | 0.1566089 | AA203548_a t | Homo sapiens F1F0-type ATPase subunit d mRNA, nuclear gene encoding mitochondrial protein, complete cds |
| 587 | Lymphoma | 0.4555549 | 0.3005857 | 0.252754 | 0.15649772 | R06629_at | Adducin 2 (beta) |
| 588 | Lymphoma | 0.4553219 | 0.3005146 | 0.252725 | 0.15638246 | RC_AA0593 86_at | EST: zf66c03.s1 Soares retina N2b4HR Homo sapiens cDNA clone 381892 3', mRNA sequence. (from Genbank) |
| 589 | Lymphoma | 0.454982 | 0.3004212 | 0.25272 | 0.15629982 | AFFX-HSAC07/X0 0351_3_at-2 | No info for gene |
| 590 | Lymphoma | 0.454982 | 0.3003941 | 0.252598 | 0.15623137 | AFFX-HSAC07/X0 0351_3_at | AFFX-HSAC07/X00351_3_at (endogenous control) |
| 591 | Lymphoma | 0.4547807 | 0.3003687 | 0.252461 | 0.15606539 | RC_AA2369 40_at | EST: zs01d07.s1 NCI_CGAP_GCB1 Homo sapiens cDNA clone IMAGE:683917 3', mRNA sequence. (from Genbank) |

FIG. 7G2

| | | | | | |
|---|---|---|---|---|---|
| 592 | Lymphoma | 0.4545412 | 0.300294 | 0.252402 | 0.15604697 | AA083339_a t | EST: zn31d10.r1 Stratagene endothelial cell 937223 Homo sapiens cDNA clone 549043 5', mRNA sequence. (from Genbank) |
| 593 | Lymphoma | 0.4541784 | 0.300242 | 0.252225 | 0.15596607 | RC_AA4890 74_at | EST: aa54g11.s1 NCI_CGAP_GCB1 Homo sapiens cDNA clone IMAGE:824804 3', mRNA sequence. (from Genbank) |
| 594 | Lymphoma | 0.454119 | 0.3001426 | 0.252159 | 0.15582645 | W80846_at | EST: zd83f05.r1 Soares fetal heart NbHH19W Homo sapiens cDNA clone 347265 5' similar to SW:SYB2_XENLA P47193 SYNAPTOBREVIN 2 .; mRNA sequence. (from Genbank) |
| 595 | Lymphoma | 0.4540041 | 0.3000544 | 0.252001 | 0.15579109 | N74749_at | EST: yv52a12.r1 Soares fetal liver spleen 1NFLS Homo sapiens cDNA clone 246334 5', mRNA sequence. (from Genbank) |
| 596 | Lymphoma | 0.4538769 | 0.3000216 | 0.251814 | 0.15573561 | W26989_at | EST: 19b2 Human retina cDNA randomly primed sublibrary Homo sapiens cDNA, mRNA sequence. (from Genbank) |
| 597 | Lymphoma | 0.4537107 | 0.3000007 | 0.251798 | 0.15569472 | R76066_at | EST: yi6f07.r1 Homo sapiens cDNA clone 143653 5'. (from Genbank) |
| 598 | Lymphoma | 0.4534683 | 0.2999614 | 0.251791 | 0.15562275 | J00214_f_at | Messenger RNA for human leukocyte (alpha) interferon. (from Genbank) |
| 599 | Lymphoma | 0.4533986 | 0.299957 | 0.251616 | 0.15556777 | RC_AA1369 40_at | EST: zn97h02.s1 Stratagene fetal retina 937202 Homo sapiens cDNA clone 566163 3', mRNA sequence. (from Genbank) |
| 600 | Lymphoma | 0.4533417 | 0.2999365 | 0.251604 | 0.15546615 | R11267_at | Homo sapiens chromosome 19, cosmid F22329 |
| 601 | Lymphoma | 0.4531421 | 0.2999177 | 0.251546 | 0.15536627 | AA460128_a t | Homo sapiens Dim1p homolog (hdim1+) mRNA, complete cds |
| 602 | Lymphoma | 0.4525061 | 0.2998219 | 0.251464 | 0.15531231 | D31184_at | EST: Human fetal-lung cDNA 5'-end sequence, mRNA sequence. (from Genbank) |
| 603 | Lymphoma | 0.4524671 | 0.2995821 | 0.251396 | 0.15523967 | RC_AA4529 13_at | KIAA0331 gene product |
| 604 | Lymphoma | 0.4523326 | 0.2995773 | 0.251394 | 0.15514946 | D89077_at | Src-like adapter protein mRNA |
| 605 | Lymphoma | 0.4522882 | 0.2995476 | 0.251307 | 0.15511785 | AA256771_a t | EST: zs22h09.r1 NCI_CGAP_GCB1 Homo sapiens cDNA clone IMAGE:685985 5', mRNA sequence. (from Genbank) |
| 606 | Lymphoma | 0.4520637 | 0.299465 | 0.251282 | 0.15504779 | W04732_at | EST: za76b09.r1 Soares fetal lung NbHL19W Homo sapiens cDNA clone 298457 5' similar to contains element MER22 repetitive element .; mRNA sequence. (from Genbank) |
| 607 | Lymphoma | 0.4518604 | 0.2994247 | 0.251256 | 0.15493405 | AA131127_a t | Cathepsin Z |
| 608 | Lymphoma | 0.45185O7 | 0.2993525 | 0.251252 | 0.15490547 | Y00816_s_at | Complement component (3b/4b) receptor 1, including Knops blood group system |
| 609 | Lymphoma | 0.4517575 | 0.2993226 | 0.25124 | 0.15486063 | AA410353_s _at | EST: zv11f02.r1 Soares NhHMPu S1 Homo sapiens cDNA clone 753339 5' similar to TR:G457883 G457883 ZINC FINGER PROTEIN. .; mRNA sequence. (from Genbank) |

FIG. 7H2

| | | | | | |
|---|---|---|---|---|---|
| 610 | Lymphoma | 0.4517442 | 0.2992886 | 0.251191 | 0.15479703 | RC_AA4559 21_at | EST: aa14f10.s1 Soares NhHMPu S1 Homo sapiens cDNA clone 813259 3', mRNA sequence. (from Genbank) |
| 611 | Lymphoma | 0.4516966 | 0.2991815 | 0.251131 | 0.1546873 | AA419464_a t | Zv01h10.r1 NCI_CGAP_GCB1 Homo sapiens cDNA clone IMAGE:746275 5' similar to gb:J04422 ISLET AMYLOID POLYPEPTIDE PRECURSOR (HUMAN);, mRNA sequence. (from Genbank) |
| 612 | Lymphoma | 0.4515642 | 0.2991568 | 0.251126 | 0.15462057 | U52682_at | IRF4 Interferon regulatory factor 4 |
| 613 | Lymphoma | 0.4510315 | 0.2990216 | 0.251114 | 0.15459685 | Y10260_at | EYA1A gene |
| 614 | Lymphoma | 0.4510014 | 0.2990108 | 0.251107 | 0.15447827 | RC_AA1264 29_at | Peroxisomal farnesylated protein |
| 615 | Lymphoma | 0.4509181 | 0.2989451 | 0.251094 | 0.15439142 | X74301_s_a t | MHC CLASS II TRANSACTIVATOR CIITA |
| 616 | Lymphoma | 0.4508372 | 0.2986669 | 0.250897 | 0.15434413 | RC_AA1761 64_r_at | EST: zp23h11.s1 Stratagene neuroepithelium (#937231) Homo sapiens cDNA clone 610341 3', mRNA sequence. (from Genbank) |
| 617 | Lymphoma | 0.4505091 | 0.2985756 | 0.250895 | 0.15431316 | M29877_at | FUCA1 Fucosidase, alpha-L-1, tissue |
| 618 | Lymphoma | 0.4504607 | 0.2985225 | 0.250874 | 0.15423946 | RC_AA4809 91_s_at | EST: aa28h02.s1 NCI_CGAP_GCB1 Homo sapiens cDNA clone IMAGE:814611 3', mRNA sequence. (from Genbank) |
| 619 | Lymphoma | 0.4502895 | 0.2984801 | 0.250818 | 0.15418112 | RC_AA1819 11_at | EST: zp63e07.s1 Stratagene endothelial cell 937223 Homo sapiens cDNA clone 624900 3', mRNA sequence. (from Genbank) |
| 620 | Lymphoma | 0.4499491 | 0.2984705 | 0.250762 | 0.15416263 | RC_AA2322 9_at | EST: zr75d08.s1 Soares NhHMPu S1 Homo sapiens cDNA clone 669231 3', mRNA sequence. (from Genbank) |
| 621 | Lymphoma | 0.4496515 | 0.2984419 | 0.250631 | 0.15409301 | W27603_at | 35a7 Human retina cDNA randomly primed sublibrary Homo sapiens cDNA, mRNA sequence. (from Genbank) |
| 622 | Lymphoma | 0.4494863 | 0.298413 | 0.25061 | 0.15401202 | R79255_at | EST: yi84a04.r1 Homo sapiens cDNA clone 145902 5' similar to contains Alu repetitive element;contains PTR7 repetitive element ;. (from Genbank) |
| 623 | Lymphoma | 0.4493459 | 0.2981668 | 0.250563 | 0.15398791 | RC_AA4963 47_at | EST: zv31e09.s1 Soares ovary tumor NbHOT Homo sapiens cDNA clone 755272 3', mRNA sequence. (from Genbank) |
| 624 | Lymphoma | 0.4490154 | 0.2980929 | 0.250494 | 0.1539272 8 | AA243523_a t | EST: zs15e03.r1 NCI_CGAP_GCB1 Homo sapiens cDNA clone IMAGE:685276 5', mRNA sequence. (from Genbank) |
| 625 | Lymphoma | 0.4489474 | 0.2980479 | 0.25044 | 0.15386732 | RC_AA6211 62_s_at | EST: af61g05.s1 Soares NhHMPu S1 Homo sapiens cDNA clone 1046552 3', mRNA sequence. (from Genbank) |
| 626 | Lymphoma | 0.4489304 | 0.2980459 | 0.250314 | 0.15379548 | RC_AA2793 37_at | EST: zs85b03.s1 NCI_CGAP_GCB1 Homo sapiens cDNA clone IMAGE:704237 3', mRNA sequence. (from Genbank) |

FIG. 712

| | | | | | |
|---|---|---|---|---|---|
| 627 | Lymphoma | 0.4485151 | 0.2979618 | 0.250266 | AA020927_a_t | EST: ze64e11.r1 Soares retina N2b4HR Homo sapiens cDNA clone 363788 5' similar to contains L1.l2 L1 repetitive element :, mRNA sequence. (from Genbank) |
| 628 | Lymphoma | 0.4482572 | 0.2979597 | 0.2501 | 0.15366735 W01881_at | Za35g05.r1 Soares fetal liver spleen 1NFLS Homo sapiens cDNA clone 294584 5', mRNA sequence. (from Genbank) |
| 629 | Lymphoma | 0.4477941 | 0.2978599 | 0.250099 | 0.15352747 RC_AA4865 79_at | EST: ab16f05.s1 Stratagene lung (#937210) Homo sapiens cDNA clone 840993 3', mRNA sequence. (from Genbank) |
| 630 | Lymphoma | 0.4477818 | 0.2977402 | 0.250083 | 0.15341356 RC_AA1303 49_at | EST: zo19g09.s1 Stratagene colon (#937204) Homo sapiens cDNA clone 587392 3', mRNA sequence. (from Genbank) |
| 631 | Lymphoma | 0.4476848 | 0.297669 | 0.250026 | 0.1532846 AA187579_a_t | EST: zp66d11.r1 Stratagene endothelial cell 937223 Homo sapiens cDNA clone 625173 5', mRNA sequence. (from Genbank) |
| 632 | Lymphoma | 0.4476775 | 0.2975923 | 0.249881 | 0.15321128 RC_D60438 _at | EST: Human fetal brain cDNA 3'-end GEN-108H04, mRNA sequence. (from Genbank) |
| 633 | Lymphoma | 0.4476775 | 0.2975807 | 0.249792 | 0.15314652 T75086_at | Cytochrome c oxidase subunit IV |
| 634 | Lymphoma | 0.4469234 | 0.297553 | 0.249556 | 0.15311949 RC_AA4031 16_at | Homo sapiens U-snRNP-associated cyclophilin (USA-CyP) mRNA, complete cds |
| 635 | Lymphoma | 0.4465935 | 0.2973303 | 0.249541 | 0.1530418 RC_AA0316 54_s_at | EST: zk14d05.s1 Soares pregnant uterus NbHPU Homo sapiens cDNA clone 470505 3' similar to contains Alu repetitive element;contains element PTR7 repetitive element :, mRNA sequence. (from Genbank) |
| 636 | Lymphoma | 0.4463517 | 0.2973099 | 0.249482 | 0.15298344 RC_AA4892 33_at | EST: aa57g04.s1 NCI_CGAP_GCB1 Homo sapiens cDNA clone IMAGE:825078 3', mRNA sequence. (from Genbank) |
| 637 | Lymphoma | 0.4462955 | 0.2972961 | 0.249387 | 0.15289684 U03397_s_a_t | Receptor protein 4-1BB mRNA |
| 638 | Lymphoma | 0.4461644 | 0.2972894 | 0.249364 | 0.15283406 RC_AA4172 65_s_at | EST: zu07h02.s1 Soares testis NHT Homo sapiens cDNA clone 731187 3', mRNA sequence. (from Genbank) |
| 639 | Lymphoma | 0.4459289 | 0.2972048 | 0.249278 | 0.15276879 AA458602_a_t | EST: aa12f12.r1 Soares NhHMPu S1 Homo sapiens cDNA clone 813071 5', mRNA sequence. (from Genbank) |
| 640 | Lymphoma | 0.4456292 | 0.2971727 | 0.249229 | 0.15269989 RC_AA4634 50_at | Homo sapiens gene for NBS1, complete cds |
| 641 | Lymphoma | 0.4456227 | 0.2971341 | 0.249193 | 0.15265991 AF014958_a t-2 | Chemokine receptor |
| 642 | Lymphoma | 0.4456227 | 0.2971186 | 0.249161 | 0.15261038 AF014958_a_t | Chemokine receptor X (CKRX) mRNA |
| 643 | Lymphoma | 0.4455442 | 0.2971025 | 0.248956 | 0.15253052 AA477288_a_t | EST: zu43f11.r1 Soares ovary tumor NbHOT Homo sapiens cDNA clone 740781 5', mRNA sequence. (from Genbank) |
| 644 | Lymphoma | 0.4453964 | 0.2969199 | 0.248956 | 0.15249592 RC_AA1802 08_at | EST: zp35f01.s1 Stratagene muscle 937209 Homo sapiens cDNA clone 611449 3', mRNA sequence. (from Genbank) |

FIG. 7J2

| | | | | | | |
|---|---|---|---|---|---|---|
| 645 | Lymphoma | 0.4452514 | 0.296896 | 0.248831 | 0.15242894 | RC_AA4575 28_at | EST: aa89e07.s1 Stratagene fetal retina 937202 Homo sapiens cDNA clone 838500 3', mRNA sequence. (from Genbank) |
| 646 | Lymphoma | 0.4452194 | 0.2968481 | 0.248751 | 0.15239221 | C15910_s_a t | NADH dehydrogenase (ubiquinone) 1 beta subcomplex, 1 (7kD, MNLL) |
| 647 | Lymphoma | 0.4451087 | 0.2968208 | 0.24875 | 0.15228991 | AA452724_a t | TFAR19 novel apoptosis-related gene |
| 648 | Lymphoma | 0.4449981 | 0.2967698 | 0.24866 | 0.15213473 | RC_AA2790 20_at | EST: zs83a12.s1 NCI_CGAP_GCB1 Homo sapiens cDNA clone IMAGE:704062 3', mRNA sequence. (from Genbank) |
| 649 | Lymphoma | 0.4442323 | 0.2967402 | 0.248507 | 0.15208687 | L44544_at | BUB3 (budding uninhibited by benzimidazoles 3, yeast) homolog |
| 650 | Lymphoma | 0.4439638 | 0.2967313 | 0.248433 | 0.15201409 | AF006084_a t | Arp2/3 protein complex subunit p41-Arc (ARC41) mRNA |
| 651 | Lymphoma | 0.4438327 | 0.2966866 | 0.248411 | 0.15197447 | AA095039_a t | Cp2534.seq.F Fetal heart, Lambda ZAP Express Homo sapiens cDNA 5', mRNA sequence. (from Genbank) |
| 652 | Lymphoma | 0.4436933 | 0.2965715 | 0.248346 | 0.15189724 | AA092376_a t | 15 kDa selenoprotein |
| 653 | Lymphoma | 0.4436805 | 0.2965468 | 0.248326 | 0.15187089 | RC_AA4117 96_at | Homo sapiens clone 24631 mRNA sequence |
| 654 | Lymphoma | 0.4433216 | 0.2965333 | 0.248185 | 0.15183495 | X01677_s_a t | Glyceraldehyde-3-phosphate dehydrogenase |
| 655 | Lymphoma | 0.4432945 | 0.2965299 | 0.248173 | 0.15168144 | AA059415_a t | EST: zl95a03.r1 Stratagene corneal stroma (#937222) Homo sapiens cDNA clone 512332 5' similar to contains Alu repetitive element;, mRNA sequence. (from Genbank) |
| 656 | Lymphoma | 0.4430245 | 0.2964172 | 0.248138 | 0.15165226 | RC_AA4307 38_at | EST: zw32c02.s1 Soares ovary tumor NbHOT Homo sapiens cDNA clone 770978 3', mRNA sequence. (from Genbank) |
| 657 | Lymphoma | 0.4426614 | 0.2963606 | 0.248062 | 0.15158977 | RC_AA4259 19_at | EST: zv48g04.s1 Soares ovary tumor NbHOT Homo sapiens cDNA clone 756918 3', mRNA sequence. (from Genbank) |
| 658 | Lymphoma | 0.4425106 | 0.2963586 | 0.248032 | 0.15151133 | RC_D60479 _at | EST: Human fetal brain cDNA 3'-end GEN-111H01, mRNA sequence. (from Genbank) |
| 659 | Lymphoma | 0.4423344 | 0.2963585 | 0.247897 | 0.1514648 | AA093977_a t | EST: cl1504.seq.F Fetal heart, Lambda ZAP Express Homo sapiens cDNA 5', mRNA sequence. (from Genbank) |
| 660 | Lymphoma | 0.4423284 | 0.2963068 | 0.247884 | 0.15137158 | L40395_at | (clone S20iii15) mRNA, 3' end of cds |
| 661 | Lymphoma | 0.4423284 | 0.2961477 | 0.247824 | 0.15133484 | L40395_at-2 | Homo sapiens clone 23689 mRNA, complete cds |
| 662 | Lymphoma | 0.4419232 | 0.2961083 | 0.247783 | 0.15126473 | RC_AA1026 52_at | EST: zn73b01.s1 Stratagene NT2 neuronal precursor 937230 Homo sapiens cDNA clone 5637853', mRNA sequence. (from Genbank) |
| 663 | Lymphoma | 0.4417889 | 0.2960556 | 0.24775 | 0.15120895 | RC_AA2927 58_at | EST: zl56a01.s1 Soares ovary tumor NbHOT Homo sapiens cDNA clone 726312 3', mRNA sequence. (from Genbank) |

FIG. 7K2

| | | | | | |
|---|---|---|---|---|---|
| 664 | Lymphoma | 0.4414763 | 0.2959104 | 0.247695 | 0.15109718 | R69700_at | EST: y45a03.r1 Homo sapiens cDNA clone 142156 5'. (from Genbank) |
| 665 | Lymphoma | 0.4407121 | 0.2959042 | 0.247579 | 0.15101692 | Z24459_rna1_at | H.sapiens MTCP1 gene, exons 2A to 7 (and joined mRNA)::H.sapiens MTCP1 gene, exons 2A to 7 (and joined mRNA) |
| 666 | Lymphoma | 0.44058550 | 0.2958241 | 0.247536 | 0.15099082 | RC_AA25617_at | EST: zr79g09.s1 Soares NhHMPu S1 Homo sapiens cDNA clone 681952 3', mRNA sequence. (from Genbank) |
| 667 | Lymphoma | 0.440322 | 0.2958203 | 0.247483 | 0.15095982 | X86032_at | Peroxisomal acyl-CoA thioesterase |
| 668 | Lymphoma | 0.43998550 | 0.2958139 | 0.247431 | 0.15087526 | H61002_at | EST: yr50b10.r1 Homo sapiens cDNA clone 208699 5'. (from Genbank) |
| 669 | Lymphoma | 0.43947190 | 0.2958035 | 0.247379 | 0.15084153 | RC_AA44422_at | EST: zv61g10.s1 Soares testis NHT Homo sapiens cDNA clone 758178 3', mRNA sequence. (from Genbank) |
| 670 | Lymphoma | 0.4394041 | 0.2957078 | 0.247261 | 0.15079863 | AA345469_s_at | EST: EST51569 Gall bladder II Homo sapiens cDNA 5' end, mRNA sequence. (from Genbank) |
| 671 | Lymphoma | 0.43894960 | 0.2955936 | 0.24719 | 0.15072393 | AA133244_at | EST: zl17g11.r1 Soares pregnant uterus NbHPU Homo sapiens cDNA clone 502244 5', mRNA sequence. (from Genbank) |
| 672 | Lymphoma | 0.43891980 | 0.2955197 | 0.247138 | 0.15069418 | L20773_at-2 | Homo sapiens mRNA in the region near the btk gene involved in a-gamma-globulinemia |
| 673 | Lymphoma | 0.4389198 | 0.295517 | 0.247079 | 0.15066328 | L20773_at | mRNA in the region near the btk gene involved in a-gamma-globulinemia |
| 674 | Lymphoma | 0.43875160 | 0.2954117 | 0.247033 | 0.15062588 | D60964_at | EST: Human fetal brain cDNA 5'-end GEN-143D03, mRNA sequence. (from Genbank) |
| 675 | Lymphoma | 0.43852560 | 0.2953101 | 0.246976 | 0.15059908 | RC_AA452004_a_at | EST: zv75e06.r1 Soares total fetus Nb2HF8 9w Homo sapiens cDNA clone 759490 5', mRNA sequence. (from Genbank) |
| 676 | Lymphoma | 0.43813410 | 0.2951872 | 0.24692 | 0.15049585 | RC_AA06466_at | Homo sapiens GTPase-activating protein (SIPA1) mRNA, complete cds |
| 677 | Lymphoma | 0.43768170 | 0.2950925 | 0.24686 | 0.15043089 | W95746_at | EST: ze07c05.r1 Soares fetal heart NbHH19W Homo sapiens cDNA clone 358280 5', mRNA sequence. (from Genbank) |
| 678 | Lymphoma | 0.43742240 | 0.2950745 | 0.246847 | 0.15033351 | AA285293_a_at | EST: PMY0799 KG1-a Lambda Zap Express cDNA library Homo sapiens cDNA 5', mRNA sequence. (from Genbank) |
| 679 | Lymphoma | 0.43731390 | 0.2950379 | 0.246751 | 0.15032057 | L23134_s_at | Homo sapiens metase (MET-1) mRNA, complete cds |
| 680 | Lymphoma | 0.43724220 | 0.2950192 | 0.246686 | 0.15028028 | AA424282_a_at | Polymyositis/scleroderma autoantigen 1 (75kD) |
| 681 | Lymphoma | 0.43721610 | 0.2950003 | 0.24658 | 0.15013526 | X66087_at | MYBL1 V-myb avian myeloblastosis viral oncogene homolog-like 1 |
| 682 | Lymphoma | 0.4371688 | 0.2949428 | 0.246528 | 0.15001209 | R50692_at | KIAA0476 gene product |

FIG. 7L2

| | | | | | |
|---|---|---|---|---|---|
| 683 | Lymphoma | 0.4371084 | 0.2949082 | 0.246478 | 0.14997393 | RC_AA4606 51_at | Eukaryotic translation initiation factor 2, subunit 3 (gamma, 52kD) |
| 684 | Lymphoma | 0.4368806 | 0.2948245 | 0.246472 | 0.14992474 | AA442400_a t | Homo sapiens hepatitis B virus X interacting protein (XIP) mRNA, complete cds |
| 685 | Lymphoma | 0.4363753 | 0.2946966 | 0.246402 | 0.1498426 | U19796_at-2 | Human melanoma antigen p15 mRNA, complete cds |
| 686 | Lymphoma | 0.4363753 | 0.2946158 | 0.246383 | 0.14976731 | U19796_at | Melanoma antigen p15 mRNA |
| 687 | Lymphoma | 0.4358464 | 0.2945809 | 0.24634 | 0.14972058 | RC_AA4257 53_at | EST: zw49d02.s1 Soares total fetus Nb2HF8 9w Homo sapiens cDNA clone 773379 3', mRNA sequence. (from Genbank) |
| 688 | Lymphoma | 0.4358135 | 0.2945532 | 0.246251 | 0.14963236 | AA431277_a t | EST: zw78h07.r1 Soares testis NHT Homo sapiens cDNA clone 782365 5', mRNA sequence. (from Genbank) |
| 689 | Lymphoma | 0.4356911 | 0.2944861 | 0.24621 | 0.14959077 | W26716_at | Non-histone chromosome protein 2 (S. cerevisiae)-like 1 |
| 690 | Lymphoma | 0.4352945 | 0.294481 | 0.246022 | 0.14951788 | RC_AA4592 77_at | EST: zx89a01.s1 Soares ovary tumor NbHOT Homo sapiens cDNA clone 810888 3', mRNA sequence. (from Genbank) |
| 691 | Lymphoma | 0.4351078 | 0.2943329 | 0.245988 | 0.14944656 | F15210_at | Hexosaminidase B (beta polypeptide) |
| 692 | Lymphoma | 0.4350218 | 0.2942882 | 0.245956 | 0.14940268 | RC_AA4522 80_s_at | EST: zx29g12.s1 Soares total fetus Nb2HF8 9w Homo sapiens cDNA clone 787942 3', mRNA sequence. (from Genbank) |
| 693 | Lymphoma | 0.4350001 | 0.2942882 | 0.245932 | 0.1493359 | AA215299_at | Homo sapiens chromosome 19, cosmid R30783 |
| 694 | Lymphoma | 0.4348142 | 0.2942571 | 0.245879 | 0.14927508 | RC_AA2528 _at | EST: zs27c02.s1 NCI_CGAP_GCB1 Homo sapiens cDNA clone IMAGE:686402 3', mRNA sequence. (from Genbank) |
| 695 | Lymphoma | 0.4347649 | 0.2942571 | 0.24579 | 0.14922553 | AA150364_a t | EST: zl07b03.r1 Soares pregnant uterus NbHPU Homo sapiens cDNA clone 491597 5', mRNA sequence. (from Genbank) |
| 696 | Lymphoma | 0.4346931 | 0.2941678 | 0.245703 | 0.14915347 | D42043_at | KIAA0084 gene, partial cds |
| 697 | Lymphoma | 0.4345636 | 0.2941446 | 0.245563 | 0.14901197 | RC_AA2527 62_at | EST: zs27c12.s1 NCI_CGAP_GCB1 Homo sapiens cDNA clone IMAGE:686422 3', mRNA sequence. (from Genbank) |
| 698 | Lymphoma | 0.4344814 | 0.294122 | 0.245556 | 0.14895856 | AA353903_s_at | EST: EST62091 Jurkat T-cells V Homo sapiens cDNA 5' end, mRNA sequence. (from Genbank) |
| 699 | Lymphoma | 0.4344083 | 0.2940624 | 0.245535 | 0.14893648 | AA255577_a t | EST: zs31b05.r1 NCI_CGAP_GCB1 Homo sapiens cDNA clone IMAGE:686769 5', mRNA sequence. (from Genbank) |
| 700 | Lymphoma | 0.4342016 | 0.2939774 | 0.245511 | 0.14883077 | W46245_at | Zc32a12.r1 Soares senescent fibroblasts NbHSF Homo sapiens cDNA clone 323998 5', mRNA sequence. (from Genbank) |
| 701 | Lymphoma | 0.4338027 | 0.2939622 | 0.245375 | 0.14881602 | AA236843_s_at | EST: zr76h09.r1 Soares NhHMPu S1 Homo sapiens cDNA clone 669377 5', mRNA sequence. (from Genbank) |
| 702 | Lymphoma | 0.4336802 | 0.2939196 | 0.245291 | 0.14881334 | RC_AA4499 14_at | Homo sapiens mRNA for glycoprotein-associated amino acid transporter y+LAT1 |

FIG. 7M2

| | | | | | |
|---|---|---|---|---|---|
| 703 | Lymphoma | 0.43362 | 0.293872 | 0.245223 | 0.14873835 | U53225_at | SNX1 Sorting nexin 1 |
| 704 | Lymphoma | 0.4333586 | 0.2938301 | 0.245159 | 0.1486321 | AA133359_a t | EST: zl17d12.r1 Soares pregnant uterus NbHPU Homo sapiens cDNA clone 502199 5', mRNA sequence. (from Genbank) |
| 705 | Lymphoma | 0.4332978 | 0.2937678 | 0.245135 | 0.14851177 | H66211_at | EST: yu16h09.r1 Homo sapiens cDNA clone 234017 5'. (from Genbank) |
| 706 | Lymphoma | 0.4332056 | 0.2937457 | 0.245033 | 0.14845335 | AA165234_a t | Immunoglobulin (CD79A) binding protein 1 |
| 707 | Lymphoma | 0.4331406 | 0.2937169 | 0.244939 | 0.14845173 | AA401547_a t | EST: zu62a05.r1 Soares testis NHT Homo sapiens cDNA clone 742544 5', mRNA sequence. (from Genbank) |
| 708 | Lymphoma | 0.432953 | 0.2936913 | 0.244912 | 0.14838 | AA085059_a t | Zn14b01.r1 Stratagene hNT neuron (#937233) Homo sapiens cDNA clone 547369 5' similar to gb:M26880 UBIQUITIN (HUMAN);. mRNA sequence. (from Genbank) |
| 709 | Lymphoma | 0.4329484 | 0.2936382 | 0.244832 | 0.14832777 | AA121287_a t | EST: zn76e04.r1 Stratagene NT2 neuronal precursor 937230 Homo sapiens cDNA clone 564126 5' similar to SW:PYRG_HUMAN P17812 CTP SYNTHASE ;. mRNA sequence. (from Genbank) |
| 710 | Lymphoma | 0.4327512 | 0.2936022 | 0.244781 | 0.14825161 | RC_AA5211 57_at | EST: aa73c10.s1 NCI_CGAP_GCB1 Homo sapiens cDNA clone IMAGE:826578 3', mRNA sequence. (from Genbank) |
| 711 | Lymphoma | 0.4320673 | 0.2935704 | 0.244676 | 0.14817566 | R90942_at | EST: yp92b03.r1 Homo sapiens cDNA clone 194861 5'. (from Genbank) |
| 712 | Lymphoma | 0.4320228 | 0.2935645 | 0.244651 | 0.14811444 | RC_AA4304 74_at | EST: zw23a12.s1 Soares ovary tumor NbHOT Homo sapiens cDNA clone 770110 3', mRNA sequence. (from Genbank) |
| 713 | Lymphoma | 0.4319933 | 0.2934007 | 0.244644 | 0.14804092 | S43646_at | KERATIN, TYPE II CYTOSKELETAL 2 EPIDERMAL |
| 714 | Lymphoma | 0.4319933 | 0.2933278 | 0.244586 | 0.14791767 | S43646_at-2 | Cytokeratin 2 [human, epidermis, mRNA, 2427 nt]. (from Genbank) |
| 715 | Lymphoma | 0.4317215 | 0.2932816 | 0.244568 | 0.1478633 | AA488505_a t | Human placenta (Diff33) mRNA, complete cds |
| 716 | Lymphoma | 0.4315046 | 0.2932765 | 0.244543 | 0.14783983 7 | RC_AA4564 37_at | EST: zx34h08.s1 Soares total fetus Nb2HF8.9w Homo sapiens cDNA clone 788415 3', mRNA sequence. (from Genbank) |
| 717 | Lymphoma | 0.4313668 | 0.2932565 | 0.244392 | 0.14781494 | W86706_at | EST: zh63d02.r1 Soares fetal liver spleen 1NFLS S1 Homo sapiens cDNA clone 416739 5', mRNA sequence. (from Genbank) |
| 718 | Lymphoma | 0.4312815 | 0.2930411 | 0.24433 | 0.14777303 | Z14982_ma 1_at | MHC-encoded proteasome subunit gene LAMP7-E1 gene (proteasome subunit LMP7) extracted from H.sapiens gene for major histocompatibility complex encoded proteasome subunit LMP7 |
| 719 | Lymphoma | 0.4311701 | 0.2928774 | 0.244297 | 0.14775419 | D49824_s_a t | HLA-B null allele mRNA |

FIG. 7N2

| | | | | | |
|---|---|---|---|---|---|
| 720 | Lymphoma | 0.4306343 | 0.292809 | 0.244247 | 0.14765108 | AA464043_s_at | EST: zx86c06.r1 Soares ovary tumor NbHOT Homo sapiens cDNA clone 810634 5', mRNA sequence. (from Genbank) |
| 721 | Lymphoma | 0.4304687 | 0.2927926 | 0.244222 | 0.14761382 | AA405278_a_t | EST: zu12b06.r1 Soares testis NHT Homo sapiens cDNA clone 731603 5', mRNA sequence. (from Genbank) |
| 722 | Lymphoma | 0.4304529 | 0.2927353 | 0.244198 | 0.14761147 | RC_AA2920 86_s_at | EST: zt46f03.s1 Soares ovary tumor NbHOT Homo sapiens cDNA clone 725405 3', mRNA sequence. (from Genbank) |
| 723 | Lymphoma | 0.4304477 | 0.2927232 | 0.244122 | 0.14752695 | H03686_i_at | Human GAP SH3 binding protein mRNA, complete cds |
| 724 | Lymphoma | 0.4304226 | 0.2927053 | 0.244118 | 0.14747022 | AA249538_a_t | EST: jj6896.seq.F Human fetal heart, Lambda ZAP Express Homo sapiens cDNA 5', mRNA sequence. (from Genbank) |
| 725 | Lymphoma | 0.4303733 | 0.2926831 | 0.244079 | 0.1473862 | AA471293_a_t | EST: PMY2391 KG1-a Lambda Zap Express cDNA library Homo sapiens cDNA 5', mRNA sequence. (from Genbank) |
| 726 | Lymphoma | 0.4302757 | 0.2926294 | 0.243975 | 0.14737943 | RC_AA2562 73_at | EST: zr81c12.s1 Soares NhHMPu S1 Homo sapiens cDNA clone 682102 3', mRNA sequence. (from Genbank) |
| 727 | Lymphoma | 0.4300166 | 0.292627 | 0.243972 | 0.14730097 | L13203_at-2 | Human HNF-3/fork-head homolog-3 HFH-3 mRNA, complete cds |
| 728 | Lymphoma | 0.4300166 | 0.2926255 | 0.243843 | 0.14712197 | L13203_at | HNF-3/fork-head homolog-3 HFH-3 mRNA |
| 729 | Lymphoma | 0.4298033 | 0.2925414 | 0.243794 | 0.14706735 | RC_AA0344 07_at | EST: zk20h10.s1 Soares pregnant uterus NbHPU Homo sapiens cDNA clone 471139 3', mRNA sequence. (from Genbank) |
| 730 | Lymphoma | 0.4296877 | 0.2923915 | 0.24379 | 0.14705315 | RC_AA0535 08_at | EST: zl73a02.s1 Stratagene colon (#937204) Homo sapiens cDNA clone 510218 3', mRNA sequence. (from Genbank) |
| 731 | Lymphoma | 0.4293944 | 0.2921976 | 0.243559 | 0.14695461 | U39817_at | BLM Bloom syndrome |
| 732 | Lymphoma | 0.4293805 | 0.2920614 | 0.243538 | 0.14686866 | W26845_at | Homo sapiens mRNA for KIAA0914 protein, complete cds |
| 733 | Lymphoma | 0.4290007 | 0.2919997 | 0.243504 | 0.14680415 | RC_AA4586 55_at | Carboxypeptidase D |
| 734 | Lymphoma | 0.4287318 | 0.2919738 | 0.243442 | 0.14672771 | RC_AA0559 92_at | EST: zf22b01.s1 Soares fetal heart NbHH19W Homo sapiens cDNA clone 377641 3', mRNA sequence. (from Genbank) |
| 735 | Lymphoma | 0.4285827 | 0.2919165 | 0.24338 | 0.14664954 | RC_AA4605 51_at | EST: zx68f11.s1 Soares total fetus Nb2HF8.9w Homo sapiens cDNA clone 796653 3', mRNA sequence. (from Genbank) |
| 736 | Lymphoma | 0.4284406 | 0.2918973 | 0.243291 | 0.14662546 | RC_AA4787 27_at | EST: zv14d10.s1 Soares NhHMPu S1 Homo sapiens cDNA clone 753619 3', mRNA sequence. (from Genbank) |
| 737 | Lymphoma | 0.4281119 | 0.2918845 | 0.243187 | 0.14659792 | AA430008_a_t | EST: zw65a08.r1 Soares testis NHT Homo sapiens cDNA clone 781046 5', mRNA sequence. (from Genbank) |
| 738 | Lymphoma | 0.4280496 | 0.2918436 | 0.243148 | 0.14652227 | RC_AA1820 01_r_at | EST: zp62f10.s1 Stratagene endothelial cell 937223 Homo sapiens cDNA clone 624811 3', mRNA sequence. (from Genbank) |

FIG. 7O2

| # | | | | | | | ID | Description |
|---|---|---|---|---|---|---|---|---|
| 739 | Lymphoma | 0.428009 | | 0.291746 | 0.243097 | 0.1464676 | RC_AA4486 32_at | EST: zx10b01.s1 Soares total fetus Nb2HF8 9w Homo sapiens cDNA clone 786025 3', mRNA sequence. (from Genbank) |
| 740 | Lymphoma | 0.427783 | | 0.2917074 | 0.243097 | 0.14639218 | W27069_at | Ribosomal protein L10 |
| 741 | Lymphoma | 0.4277492 | | 0.2916459 | 0.242974 | AA397529_a_at | Z187g06.r1 Soares testis NHT Homo sapiens cDNA clone 729370 5', mRNA sequence. (from Genbank) |
| 741 | Lymphoma | 0.4277492 | | 0.2916459 | 0.242974 | 0.14631101 | AA397529_a_at | Z187g06.r1 Soares testis NHT Homo sapiens cDNA clone 729370 5', mRNA sequence. (from Genbank) |
| 742 | Lymphoma | 0.4275969 | | 0.2916379 | 0.242949 | 0.14627075 | Z43703_at | Homo sapiens HRIHFB2157 mRNA, partial cds |
| 743 | Lymphoma | 0.4271707 | | 0.291633 | 0.242876 | 0.14623020 | RC_AA4007 60_at | EST: zt71b01.s1 Soares testis NHT Homo sapiens cDNA clone 727753 3', mRNA sequence. (from Genbank) |
| 744 | Lymphoma | 0.427011 | | 0.2916204 | 0.242862 | 0.14615493 | AFFX-HUMISGF3A /M97935_M A_at | AFFX-HUMISGF3A/M97935_MA_at (endogenous control) |
| 745 | Lymphoma | 0.427011 | | 0.2914937 | 0.24276 | 0.14607419 | AFFX-HUMISGF3A /M97935_M A_at-2 | No info for gene |
| 746 | Lymphoma | 0.4270021 | | 0.2914509 | 0.242673 | 0.14601389 | L31584_at | CMKBR7 Chemokine (C-C) receptor 7 |
| 747 | Lymphoma | 0.4269104 | | 0.2914418 | 0.242617 | 0.14599009 | AA314389_a_t | EST: EST186246 Colon carcinoma (HCC) cell line II Homo sapiens cDNA 5' end similar to similar to ADP-ribosylation factor-like gene 1, mRNA sequence. (from Genbank) |
| 748 | Lymphoma | 0.4263601 | | 0.291422 | 0.242585 | 0.14596522 | U14969_at | Ribosomal protein L28 mRNA |
| 749 | Lymphoma | 0.4263563 | | 0.2913748 | 0.242547 | 0.14581242 | AA252346_a_t | Zs12c08.r1 NCI_CGAP_GCB1 Homo sapiens cDNA clone IMAGE:684974 5', mRNA sequence. (from Genbank) |
| 750 | Lymphoma | 0.426326 | | 0.2912414 | 0.242532 | 0.14579228 | RC_AA4968 82_s_at | Eukaryotic translation initiation factor 3, subunit 4 (delta, 44kD) |
| 751 | Lymphoma | 0.4261841 | | 0.2911536 | 0.242448 | 0.14573523 | AA232774_a_t | EST: zr47a10.r1 Soares NhHMPu S1 Homo sapiens cDNA clone 666522 5', mRNA sequence. (from Genbank) |
| 752 | Lymphoma | 0.4259938 | | 0.2911263 | 0.242395 | 0.14564796 | RC_AA4299 04_at | EST: zw66d03.s1 Soares testis NHT Homo sapiens cDNA clone 781157 3', mRNA sequence. (from Genbank) |
| 753 | Lymphoma | 0.4259808 | | 0.2910357 | 0.242371 | 0.14559233 | RC_AA2801 05_s_at | Homo sapiens KIAA0409 mRNA, partial cds |
| 754 | Lymphoma | 0.4257785 | | 0.291008 | 0.242339 | 0.14555155 | N91071_s_a_t | EST: za17f10.r1 Soares fetal liver spleen 1NFLS Homo sapiens cDNA clone 292843 5', mRNA sequence. (from Genbank) |
| 755 | Lymphoma | 0.4256573 | | 0.2909321 | 0.242206 | 0.14547636 | RC_AA0016 11_at | EST: zh82e04.s1 Soares fetal liver spleen 1NFLS S1 Homo sapiens cDNA clone 427806 3', mRNA sequence. (from Genbank) |

FIG. 7P2

| # | | | | | | | |
|---|---|---|---|---|---|---|---|
| 756 | Lymphoma | 0.4256664 | 0.2908675 | 0.242114 | 0.145422771 | W67291_s_at | EST: zd43b10.r1 Soares fetal heart NbHH19W Homo sapiens cDNA clone 343387 5', mRNA sequence. (from Genbank) |
| 757 | Lymphoma | 0.4252334 | 0.2908505 | 0.242047 | 0.14537668 | U90546_at | Butyrophilin (BTF4) mRNA |
| 758 | Lymphoma | 0.4252334 | 0.2908505 | 0.242044 | 0.14533677 | U90546_at-2 | Human butyrophilin (BTF4) mRNA, complete cds |
| 759 | Lymphoma | 0.4251561 | 0.2908083 | 0.242003 | 0.14530474 | RC_AA405744_at | EST: zu66f10.s1 Soares testis NHT Homo sapiens cDNA clone 742987 3', mRNA sequence. (from Genbank) |
| 760 | Lymphoma | 0.4249699 | 0.2907927 | 0.241995 | 0.14520681 | AA248589_a_t | EST: csh0562.seq.F Human fetal heart, Lambda ZAP Express Homo sapiens cDNA 5', mRNA sequence. (from Genbank) |
| 761 | Lymphoma | 0.4248904 | 0.2907927 | 0.241982 | 0.14511361 | AC002306_a_t | Endothelial differentiation, lysophosphatidic acid G-protein-coupled receptor, 4 |
| 762 | Lymphoma | 0.424794 | 0.2907823 | 0.241956 | 0.14505336 | RC_AA063596_at | EST: ze87c06.s1 Soares fetal heart NbHH19W Homo sapiens cDNA clone 365962 3' similar to SW:NC5R_RAT P20070 NADH-CYTOCHROME B5 REDUCTASE ;, mRNA sequence. (from Genbank) |
| 763 | Lymphoma | 0.4246376 | 0.2906989 | 0.241774 | 0.14501981 | X16869_s_a_t | Eukaryotic translation elongation factor 1 alpha 1 |
| 764 | Lymphoma | 0.4244974 | 0.2906598 | 0.241689 | 0.14498104 | HG3549-HT3751_at | Wilm'S Tumor-Related Protein |
| 765 | Lymphoma | 0.424458 | 0.2906428 | 0.241644 | 0.1449409 | N71232_at | EST: yw36g09.r1 Homo sapiens cDNA clone 254368 5'. (from Genbank) |
| 766 | Lymphoma | 0.4244561 | 0.2906348 | 0.241643 | 0.14484346 | AA282978_a_t | EST: zt16c08.r1 NCI_CGAP_GCB1 Homo sapiens cDNA clone IMAGE:713294 5', mRNA sequence. (from Genbank) |
| 767 | Lymphoma | 0.424376 | 0.2905532 | 0.241643 | 0.14478923 | W67189_at | EST: zd43g04.r1 Soares fetal heart NbHH19W Homo sapiens cDNA clone 343446 5', mRNA sequence. (from Genbank) |
| 768 | Lymphoma | 0.4243576 | 0.2905335 | 0.24164 | 0.14476319 | RC_AA424129_at | EST: zv81a02.s1 Soares total fetus Nb2HF8 9w Homo sapiens cDNA clone 760010 3', mRNA sequence. (from Genbank) |
| 769 | Lymphoma | 0.424309 | 0.2905223 | 0.241635 | 0.14471485 | RC_AA406631_r_at | EST: zv15d12.s1 Soares NhHMPu S1 Homo sapiens cDNA clone 753719 3', mRNA sequence. (from Genbank) |
| 770 | Lymphoma | 0.4243012 | 0.2905117 | 0.241613 | 0.1446056 | M97936_at | SIGNAL TRANSDUCER AND ACTIVATOR OF TRANSCRIPTION 1-ALPHA/BETA |
| 771 | Lymphoma | 0.4239892 | 0.2905027 | 0.241569 | 0.14445581 | RC_AA005262_at | Homo sapiens DNA sequence from PAC 262D12 on chromosome 1q23.3-24.3. Contains a Tenascin (Hexabrachion, Cytotactin, Neuronectin, Myotendinous antigen)-LIKE gene and a mitochondrial/chloroplast 30S ribosomal protein S14-LIKE gene preceeded by a CpG island. Contains ESTs, genomic marker D1S2691 and STSs |
| 772 | Lymphoma | 0.4239311 | 0.290491 | 0.241561 | 0.14451359 | RC_AA459272_at | EST: aa27d08.s1 NCI_CGAP_GCB1 Homo sapiens cDNA clone IMAGE:814479 3', mRNA sequence. (from Genbank) |

FIG. 7Q2

| | | | | | | |
|---|---|---|---|---|---|---|
| 773 | Lymphoma | 0.4235869 | 0.2904481 | 0.241504 | 0.144428641 | X69908_rna1_at | P2 gene for c subunit of mitochondrial ATP synthase gene extracted from H.sapiens gene for mitochondrial ATP synthase c subunit (P2 form) |
| 774 | Lymphoma | 0.4235869 | 0.2903478 | 0.241283 | 0.144437862 | X69908_rna1_at-2 | ATP synthase, H+ transporting, mitochondrial F0 complex, subunit c (subunit 9), isoform 2 |
| 775 | Lymphoma | 0.422996 | 0.2903135 | 0.241242 | 0.144322272 | RC_AA412483_at | Homo sapiens clone 24448 unknown mRNA, partial cds |
| 776 | Lymphoma | 0.4228248 | 0.2902254 | 0.24122 | 0.144282323 | RC_AA599147_at | EST: ae52d08.s1 Stratagene lung carcinoma 937218 Homo sapiens cDNA clone 950511 3', mRNA sequence. (from Genbank) |
| 777 | Lymphoma | 0.4227898 | 0.2902139 | 0.241212 | 0.144224738 | RC_AA399587_at | EST: zi93d01.s1 Soares testis NHT Homo sapiens cDNA clone 729889 3', mRNA sequence. (from Genbank) |
| 778 | Lymphoma | 0.4226742 | 0.2901701 | 0.241167 | 0.144086978 | RC_AA459985_at | EST: zx66e07.s1 Soares total fetus Nb2HF8 9w Homo sapiens cDNA clone 796452 3', mRNA sequence. (from Genbank) |
| 779 | Lymphoma | 0.4226716 | 0.2901141 | 0.241148 | 0.144042372 | RC_D25755s_at | EST: Human colon 3'directed MboI cDNA, HUMGS04122, clone cm1358, mRNA sequence. (from Genbank) |
| 780 | Lymphoma | 0.4225621 | 0.290049 | 0.24114 | 0.143956272 | AA070671_at | Oxidase (cytochrome c) assembly 1-like |
| 781 | Lymphoma | 0.4225078 | 0.2896486 | 0.241115 | 0.143930782 | U10485_at | Lymphoid-restricted membrane protein (Jaw1) mRNA |
| 782 | Lymphoma | 0.4224639 | 0.2895004 | 0.241089 | 0.143890741 | AA316868_at | EST: EST188529 HCC cell line (metastasis to liver in mouse) II Homo sapiens cDNA 5' end, mRNA sequence. (from Genbank) |
| 783 | Lymphoma | 0.4223548 | 0.2894458 | 0.240873 | 0.143816641 | AA056171_at | EST: zk70c11.r1 Soares pregnant uterus NbHPU Homo sapiens cDNA clone 488180 5', mRNA sequence. (from Genbank) |
| 784 | Lymphoma | 0.4222235 | 0.2893836 | 0.240873 | 0.143756877 | RC_AA496357_at | Homo sapiens SKB1Hs mRNA, complete cds |
| 785 | Lymphoma | 0.4219461 | 0.2893681 | 0.240862 | 0.143713282 | AA215938_at | Human RNA polymerase III subunit (RPC62) mRNA, complete cds |
| 786 | Lymphoma | 0.4217372 | 0.2893335 | 0.2408 | 0.143647074 | RC_AA040394_at | EST: zf05h02.s1 Soares fetal heart NbHH19W Homo sapiens cDNA clone 376083 3', mRNA sequence. (from Genbank) |
| 787 | Lymphoma | 0.4213867 | 0.2892698 | 0.240652 | 0.143583122 | AA491617_at | Cell division cycle 2, G1 to S and G2 to M |
| 788 | Lymphoma | 0.421381 | 0.289134 | 0.240601 | 0.143543912 | RC_AA490825_at | EST: aa49g01.s1 NCI_CGAP_GCB1 Homo sapiens cDNA clone IMAGE:824304 3', mRNA sequence. (from Genbank) |
| 789 | Lymphoma | 0.4207785 | 0.289023 | 0.240551 | 0.143449815 | RC_AA452552_at | Acyl-Coenzyme A oxidase 3, pristanoyl |
| 790 | Lymphoma | 0.4207745 | 0.289023 | 0.240503 | 0.143337370 | U14970_at | RPS5 Ribosomal protein S5 |
| 791 | Lymphoma | 0.4206601 | 0.2889941 | 0.24044 | 0.143284314 | RC_AA599214_at | EST: ag34c05.s1 Jia bone marrow stroma Homo sapiens cDNA clone 1091432 3', mRNA sequence. (from Genbank) |

FIG. 7R2

| # | Class | | | | | | Description |
|---|---|---|---|---|---|---|---|
| 792 | Lymphoma | 0.4200393 | 0.2889794 | 0.240434 | 0.14325349 | W70167_at | EST: zd52b01.r1 Soares fetal heart NbHH19W Homo sapiens cDNA clone 344233 5', mRNA sequence. (from Genbank) |
| 793 | Lymphoma | 0.4198139 | 0.2889621 | 0.240425 | 0.14317684 | RC_AA6095 47_at | Homo sapiens mRNA for KIAA0625 protein, partial cds |
| 794 | Lymphoma | 0.4198082 | 0.2888152 | 0.24034 | 0.14310572 | AA085463_a t | Tropomyosin 4 |
| 795 | Lymphoma | 0.4196206 | 0.2887711 | 0.24034 | 0.14305925 | RC_AA4549 37_at | EST: aa30c07.s1 NCI_CGAP_GCB1 Homo sapiens cDNA clone IMAGE:814764 3', mRNA sequence. (from Genbank) |
| 796 | Lymphoma | 0.4195114 | 0.288769 | 0.240307 | 0.14296068 | AA306121_a t | EST: EST177101 Jurkat T-cells VI Homo sapiens cDNA 5' end, mRNA sequence. (from Genbank) |
| 797 | Lymphoma | 0.4194267 | 0.2887644 | 0.240294 | 0.14290671 | RC_AA4812 68_at | EST: aa35c04.s1 NCI_CGAP_GCB1 Homo sapiens cDNA clone IMAGE:815238 3', mRNA sequence. (from Genbank) |
| 798 | Lymphoma | 0.4194259 | 0.2887623 | 0.240249 | 0.14283907 | R78991_at | Lactate dehydrogenase B |
| 799 | Lymphoma | 0.4189566 | 0.2887376 | 0.240211 | 0.14280191 | RC_AA4002 59_at | EST: zu63a07.s1 Soares testis NHT Homo sapiens cDNA clone 742644 3', mRNA sequence. (from Genbank) |
| 800 | Lymphoma | 0.4187936 | 0.2887183 | 0.240117 | 0.14277191 | X89986_s_a t | NBK apoptotic inducer protein |
| 801 | Lymphoma | 0.4187437 | 0.2886976 | 0.240068 | 0.14270519 | AA460047_a t | EST: zx66b11.r1 Soares total fetus Nb2HF8 9w Homo sapiens cDNA clone 796413 5', mRNA sequence. (from Genbank) |
| 802 | Lymphoma | 0.4184738 | 0.2886471 | 0.240048 | 0.14267641 | AA418230_a t | EST: zy97h11.r1 Soares NhHMPu S1 Homo sapiens cDNA clone 767781 5', mRNA sequence. (from Genbank) |
| 803 | Lymphoma | 0.4178011 | 0.2885638 | 0.239937 | 0.14260337 | AA001296_s _at | EST: zh82b09.r1 Soares fetal liver spleen 1NFLS S1 Homo sapiens cDNA clone 427769 5', mRNA sequence. (from Genbank) |
| 804 | Lymphoma | 0.4177361 | 0.2885014 | 0.239797 | 0.1425292 | RC_AA2788 38_s_at | EST: zs80g10.s1 NCI_CGAP_GCB1 Homo sapiens cDNA clone IMAGE:703842 3', mRNA sequence. (from Genbank) |
| 805 | Lymphoma | 0.4176488 | 0.2885008 | 0.239785 | 0.14249793 | AA085232_a t | EST: zn12d03.r1 Stratagene hNT neuron (#937233) Homo sapiens cDNA clone 547205 5' similar to SW:ASF1_YEAST P32447 ANTI-SILENCING PROTEIN 1.; mRNA sequence. (from Genbank) |
| 806 | Lymphoma | 0.4174737 | 0.2884841 | 0.239723 | 0.14244393 | H60661_at | EST: yr13d05.r1 Homo sapiens cDNA clone 205161 5' similar to contains Alu repetitive element;contains L1 repetitive element.; (from Genbank) |
| 807 | Lymphoma | 0.4172906 | 0.2884431 | 0.239621 | 0.14242479 | RC_AA0455 96_at | EST: zi66d11.s1 Stratagene colon (#937204) Homo sapiens cDNA clone 509589 3' similar to gb:M25108 !!!! ALU CLASS F WARNING ENTRY !!!! (HUMAN);contains Alu repetitive element;, mRNA sequence. (from Genbank) |
| 808 | Lymphoma | 0.417079 | 0.2884104 | 0.239591 | 0.14236675 | W28953_at | EST: 54b7 Human retina cDNA randomly primed sublibrary Homo sapiens cDNA, mRNA sequence. (from Genbank) |

FIG. 7S2

| | | | | | |
|---|---|---|---|---|---|
| 809 | Lymphoma | 0.4168455 | 0.2882794 | 0.239568 | 0.142254444 | AA242923_a_t | EST: zr64g07.r1 Soares NhHMPu S1 Homo sapiens cDNA clone 668220 5', mRNA sequence. (from Genbank) |
| 810 | Lymphoma | 0.4167173 | 0.2882639 | 0.239508 | 0.142221868 | AA406000_a_t | EST: zu56g05.r1 Soares ovary tumor NbHOT Homo sapiens cDNA clone 742040 5', mRNA sequence. (from Genbank) |
| 811 | Lymphoma | 0.4165246 | 0.2881549 | 0.239393 | 0.142212856 | AA441970_a_t | KIAA0494 gene product |
| 812 | Lymphoma | 0.4164667 | 0.2880923 | 0.239345 | 0.14204984 5_at | RC_AA0226 | EST: ze71b02.s1 Soares fetal heart NbHH19W Homo sapiens cDNA clone 364395 3', mRNA sequence. (from Genbank) |
| 813 | Lymphoma | 0.4163246 | 0.2880853 | 0.239333 | 0.14196993 t | AA187045_a | EST: zp58a07.r1 Stratagene endothelial cell 937223 Homo sapiens cDNA clone 624372 5', mRNA sequence. (from Genbank) |
| 814 | Lymphoma | 0.4160707 | 0.2880386 | 0.239328 | 0.14192979 10_at | RC_AA2511 | EST: zs03g05.s1 NCI_CGAP_GCB1 Homo sapiens cDNA clone IMAGE:684152 3', mRNA sequence. (from Genbank) |
| 815 | Lymphoma | 0.4160548 | 0.2879706 | 0.239321 | 0.14188004 | D82558_at | Novel centrosomal protein RanBPM |
| 816 | Lymphoma | 0.4159915 | 0.2879281 | 0.239317 | 0.14184445 t | M36542_s_a | POU2F2 POU domain, class 2, transcription factor 2 |
| 817 | Lymphoma | 0.4157058 | 0.2877627 | 0.239255 | 0.14176275 | U29680_at | Bcl-2 related (Bfl-1) mRNA |
| 818 | Lymphoma | 0.4155923 | 0.2876655 | 0.239254 | 0.14171952 63_at | RC_AA0340 | EST: zf05g06.s1 Soares fetal liver spleen 1NFLS S1 Homo sapiens cDNA clone 429946 3', mRNA sequence. (from Genbank) |
| 819 | Lymphoma | 0.4155859 | 0.2876593 | 0.239213 | 0.14166424 | W88449_at | EST: zh69h03.r1 Soares fetal liver spleen 1NFLS S1 Homo sapiens cDNA clone 417365 5', mRNA sequence. (from Genbank) |
| 820 | Lymphoma | 0.4155579 | 0.2876409 | 0.239172 | 0.14160569 t | AA429706_a | Thioredoxin-like, 32kD |
| 821 | Lymphoma | 0.4155415 | 0.2876009 | 0.239045 | 0.14157908 | W74106_at | EST: zd03e05.r1 Soares Pancreatic Islet Homo sapiens cDNA clone 339584 5' similar to PIR:S52698 S52698 hypothetical protein YD9346.02c - yeast:, mRNA sequence. (from Genbank) |
| 822 | Lymphoma | 0.4154697 | 0.2874641 | 0.239017 | 0.14151977 | M28627_at | CD1C CD1c antigen (thymocyte antigen) |
| 823 | Lymphoma | 0.41528 | 0.2874085 | 0.238962 | 0.14146945 69_at | RC_AA4104 | EST: zv15g11.s1 Soares NhHMPu S1 Homo sapiens cDNA clone 753764 3', mRNA sequence. (from Genbank) |
| 824 | Lymphoma | 0.4151618 | 0.2873928 | 0.238954 | 0.14144704 at-2 | AFFX-HUMGAPDH /M33197_M_ | Glyceraldehyde-3-phosphate dehydrogenase |

FIG. 7T2

| | | | | AFFX-HUMGAPDH/M33197_M_at | |
|---|---|---|---|---|---|
| 825 | Lymphoma | 0.4151618 | 0.2873797 | 0.23875 | 0.14137994 | AFFX-HUMGAPDH/M33197_M_at (endogenous control) |
| 826 | Lymphoma | 0.4148818 | 0.2872924 | 0.238745 | 0.14131454 R60523_s_at | EST: yh13f11.r1 Homo sapiens cDNA clone 42955 5'. (from Genbank) |
| 827 | Lymphoma | 0.4146522 | 0.2872174 | 0.238696 | 0.14123037 RC_AA6090 08_at | EST: af05f06.s1 Soares testis NHT Homo sapiens cDNA clone 1030787 3', mRNA sequence. (from Genbank) |
| 828 | Lymphoma | 0.4145601 | 0.2871712 | 0.238668 | 0.14120658 AA227366_a t | EST: zr17h05.r1 Stratagene NT2 neuronal precursor 937230 Homo sapiens cDNA clone 663705 5', mRNA sequence. (from Genbank) |
| 829 | Lymphoma | 0.4144475 | 0.2870675 | 0.238628 | 0.1410762 W28968_at | EST: 54d6 Human retina cDNA randomly primed sublibrary Homo sapiens cDNA, mRNA sequence. (from Genbank) |
| 830 | Lymphoma | 0.4142996 | 0.2870529 | 0.238613 | 0.14102367 R36553_at | EST: yg35a04.r9 Homo sapiens cDNA clone 34269 5'. (from Genbank) |
| 831 | Lymphoma | 0.4141701 | 0.2869847 | 0.238547 | 0.14098641 AA096343_a t | EST: l9342.seq.F Fetal heart, Lambda ZAP Express Homo sapiens cDNA 5', mRNA sequence. (from Genbank) |
| 832 | Lymphoma | 0.4136955 | 0.2869802 | 0.23854 | 0.14097144 W79850_at | EST: zd75e07.r1 Soares fetal heart NbHH19W Homo sapiens cDNA clone 346500 5', mRNA sequence. (from Genbank) |
| 833 | Lymphoma | 0.4136472 | 0.2868038 | 0.238487 | 0.14093909 R39398_s_a t | EST: yh95d06.r1 Homo sapiens cDNA clone 137483 5'. (from Genbank) |
| 834 | Lymphoma | 0.4133438 | 0.2867934 | 0.238481 | 0.14088072 X83490_s_a t | Fas/Apo-1 (clone pCRTM11-Fasdelta(3,4)) |
| 835 | Lymphoma | 0.4132124 | 0.286692 | 0.238422 | 0.14081809 H71514_at | EST: ys11c12.r1 Homo sapiens cDNA clone 214486 5'. (from Genbank) |
| 836 | Lymphoma | 0.4131587 | 0.286541 | 0.23822 | 0.14072691 AB002378_a t | KIAA0380 gene product |
| 837 | Lymphoma | 0.4129566 | 0.2865333 | 0.238217 | 0.14069253 L42452_at | Pyruvate dehydrogenase kinase isoenzyme 3 (PDK3) mRNA |
| 838 | Lymphoma | 0.4129262 | 0.2864811 | 0.238165 | 0.14065503 AA084932_a t | Golgi SNAP receptor complex member 2 |
| 839 | Lymphoma | 0.4125276 | 0.2862485 | 0.238119 | 0.14055859 Z21206_at | EST: H. sapiens putatively transcribed partial sequence; UK-HGMP sequence ID AAADSOA; single read, mRNA sequence. (from Genbank) |
| 840 | Lymphoma | 0.4125085 | 0.2860758 | 0.238096 | 0.14054541 RC_AA4549 40_at | EST: aa30c12.s1 NCI_CGAP_GCB1 Homo sapiens cDNA clone IMAGE:814774 3', mRNA sequence. (from Genbank) |
| 841 | Lymphoma | 0.412377 | 0.2859515 | 0.238069 | 0.14034931 HG3928-HT4198_at | Surfactant Protein Sp-A1 Delta |
| 842 | Lymphoma | 0.4121418 | 0.28571 | 0.237991 | 0.14031689 RC_AA2807 96_at | EST: zs97b09.s1 NCI_CGAP_GCB1 Homo sapiens cDNA clone IMAGE:711545 3', mRNA sequence. (from Genbank) |

FIG. 7U2

| | | | | | |
|---|---|---|---|---|---|
| 843 | Lymphoma | 0.4120804 | 0.2855041 | 0.1403027 | RC_AA4516 72_s_at | EST: zx44a10.s1 Soares total fetus Nb2HF8 9w Homo sapiens cDNA clone 789306 3' similar to contains Alu repetitive element;, mRNA sequence. (from Genbank) |
| 844 | Lymphoma | 0.4120712 | 0.2854623 | 0.14025 | RC_AA4264 04_at | EST: zv05g05.s1 Soares NhHMPu S1 Homo sapiens cDNA clone 752792 3', mRNA sequence. (from Genbank) |
| 845 | Lymphoma | 0.4119494 | 0.2854359 | 0.14017548 | AA422159_a t | Homo sapiens chromosome 19, cosmid R26529 |
| 846 | Lymphoma | 0.41169 | 0.2854274 | 0.14016822 | AA313414_s at | EST: EST185312 Colon carcinoma (HCC) cell line Homo sapiens cDNA 5' end, mRNA sequence. (from Genbank) |
| 847 | Lymphoma | 0.4115815 | 0.2854227 | 0.14013141 | RC_AA4113 51_at | EST: 7v28c04.s1 Soares ovary tumor NbHOT Homo sapiens cDNA clone 754950 3', mRNA sequence. (from Genbank) |
| 848 | Lymphoma | 0.4112842 | 0.2853947 | 0.14008354 | RC_AA1433 29_at | EST: zo37h02.s1 Stratagene endothelial cell 937223 Homo sapiens cDNA clone 589107 3', mRNA sequence. (from Genbank) |
| 849 | Lymphoma | 0.4108565 | 0.2853418 | 0.1400208 | D14012_s_a t | HGF activator |
| 850 | Lymphoma | 0.4107183 | 0.2852789 | 0.13995393 | C00449_s_a t | EST: HUMGS0006582, Human Gene Signature, 3'-directed cDNA sequence, mRNA sequence. (from Genbank) |
| 851 | Lymphoma | 0.4104554 | 0.2852541 | 0.1399293 | AA496240_a t | EST: zx70g11.r1 Soares total fetus Nb2HF8 9w Homo sapiens cDNA clone 796868 5', mRNA sequence. (from Genbank) |
| 852 | Lymphoma | 0.4103429 | 0.2851472 | 0.13985819 | D79276_at | Eukaryotic translation elongation factor 1 delta (guanine nucleotide exchange protein) |
| 853 | Lymphoma | 0.4098373 | 0.2851324 | 0.13977322 | RC_AA4637 12_at | EST: aa07d06.s1 Soares NhHMPu S1 Homo sapiens cDNA clone 812555 3', mRNA sequence. (from Genbank) |
| 854 | Lymphoma | 0.4098248 | 0.2851318 | 0.13973069 | RC_AA4825 97_at | EST: zu98h10.s1 NCI_CGAP_GCB1 Homo sapiens cDNA clone IMAGE:746083 3', mRNA sequence. (from Genbank) |
| 855 | Lymphoma | 0.4097138 | 0.2851044 | 0.13968277 | U96769_rna 1_at-2 | Homo sapiens chondroadherin gene, 5'flanking region and |
| 856 | Lymphoma | 0.4097138 | 0.2850598 | 0.13961701 | U96769_rna 1_at | Chondroadherin gene, 5'flanking region and |
| 857 | Lymphoma | 0.4096688 | 0.2850225 | 0.13957484 | U69108_at | TNF receptor associated factor 5 mRNA, partial cds |
| 858 | Lymphoma | 0.4096688 | 0.2849141 | 0.1394939 | U69108_al-2 | TNF receptor-associated factor 5 |
| 859 | Lymphoma | 0.4096609 | 0.2848564 | 0.13941887 | W63699_s_ at | Homo sapiens RCL (Rcl) mRNA, complete cds |
| 860 | Lymphoma | 0.4095159 | 0.2847643 | 0.13940953 | T63174_s_at | KIAA0331 gene product |
| 861 | Lymphoma | 0.4094939 | 0.2846888 | 0.13934493 | R53779_at | EST: yi02f09.r1 Homo sapiens cDNA clone 136089 5'. (from Genbank) |

FIG. 7V2

| | | | | |
|---|---|---|---|---|
| 862 | Lymphoma | 0.4092678 | 0.2845846 | 0.237112 | 0.13928783 | W28610_at | EST: 49b12 Human retina cDNA randomly primed sublibrary Homo sapiens cDNA, mRNA sequence. (from Genbank) |
| 863 | Lymphoma | 0.4091986 | 0.2845556 | 0.237011 | 0.13925263 | AA384184_s_at | EST: EST97722 Thyroid Homo sapiens cDNA 5' end, mRNA sequence. (from Genbank) |
| 864 | Lymphoma | 0.4091433 | 0.2844135 | 0.236943 | 0.13917442 | AA203147_a_t | EST: zx57d05.r1 Soares fetal liver spleen 1NFLS S1 Homo sapiens cDNA clone 446601 5' similar to contains element MSR1 repetitive element:, mRNA sequence. (from Genbank) |
| 865 | Lymphoma | 0.4090335 | 0.2843816 | 0.236896 | 0.13907864 | RC_AA5999 5 | EST: ag24h03.s1 Jia bone marrow stroma Homo sapiens cDNA clone 1090517 3', mRNA sequence. (from Genbank) |
| 866 | Lymphoma | 0.4089425 | 0.2842468 | 0.236837 | 0.1390025 | T89072_at | EST: yd97g10.r1 Homo sapiens cDNA clone 116226 5'. (from Genbank) |
| 867 | Lymphoma | 0.4089276 | 0.2841432 | 0.23681 | 0.13899761 | L42243_cds1_at | IFNAR2 gene (interferon receptor) extracted from Homo sapiens (clone Q-2OD3) interferon receptor (IFNAR2) gene |
| 868 | Lymphoma | 0.4089276 | 0.2841425 | 0.236726 | 0.13891426 | L42243_cds1_at-2 | Interferon (alpha, beta and omega), receptor 2 |
| 869 | Lymphoma | 0.4089205 | 0.2838673 | 0.236676 | 0.13888681 | AA096465_a_t | EST: li9866.seq.F Fetal heart, Lambda ZAP Express Homo sapiens cDNA 5', mRNA sequence. (from Genbank) |
| 870 | Lymphoma | 0.4088943 | 0.2838481 | 0.236661 | 0.13886471 | AA179892_a_t | EST: zp14c07.r1 Stratagene fetal retina 937202 Homo sapiens cDNA clone 609420 5', mRNA sequence. (from Genbank) |
| 871 | Lymphoma | 0.4086964 | 0.2837812 | 0.236536 | 0.13886172 | U95822_at | Human putative transmembrane GTPase mRNA, partial cds |
| 872 | Lymphoma | 0.4086098 | 0.2837696 | 0.236506 | 0.13878341 | AA220220_a_t | EST: PMY0265 KG1-a Lambda Zap Express cDNA library Homo sapiens cDNA 5', mRNA sequence. (from Genbank) |
| 873 | Lymphoma | 0.4084718 | 0.2836947 | 0.236463 | 0.13873152 | AA136326_s_at | EST: zk93h01.r1 Soares pregnant uterus NbHPU Homo sapiens cDNA clone 490417 5', mRNA sequence. (from Genbank) |
| 874 | Lymphoma | 0.4082187 | 0.2836187 | 0.236443 | 0.13867393 | RC_AA2817 69_s_at | Human Hpast (HPAST) mRNA, complete cds |
| 875 | Lymphoma | 0.4081785 | 0.2835748 | 0.236342 | 0.13859299 | AA452705_a_t | EST: zx39c03.r1 Soares total fetus Nb2HF8 9w Homo sapiens cDNA clone 788836 5', mRNA sequence. (from Genbank) |
| 876 | Lymphoma | 0.4081028 | 0.2835184 | 0.236298 | 0.13856603 | U83236_s_a_t | Human DNA-PK interaction protein (KIP) mRNA, complete cds |
| 877 | Lymphoma | 0.4080448 | 0.2834147 | 0.236294 | 0.13854893 | RC_AA4966 85_s_at | Suppressor of variegation 3-9 (Drosophila) homolog |
| 878 | Lymphoma | 0.4080436 | 0.2834021 | 0.236233 | 0.1384677 | Y00062_at | PTPRC Protein tyrosine phosphatase, receptor type, c polypeptide |
| 879 | Lymphoma | 0.4076591 | 0.2833477 | 0.236232 | 0.13840868 | RC_AA4011 44_s_at | EST: zu52c05.s1 Soares ovary tumor NbHOT Homo sapiens cDNA clone 741608 3', mRNA sequence. (from Genbank) |
| 880 | Lymphoma | 0.4074731 | 0.2832753 | 0.236196 | 0.13839982 | RC_AA2326 86_s_at | EST: zr75d05.s1 Soares NhHMPu S1 Homo sapiens cDNA clone 669225 3', mRNA sequence. (from Genbank) |

FIG. 7W2

| | | | | | |
|---|---|---|---|---|---|
| 881 | Lymphoma | 0.4072835 | 0.2832347 | 0.236158 | 0.13830787 | RC_AA1914 54_at | FGF intracellular binding protein |
| 882 | Lymphoma | 0.4072093 | 0.2832301 | 0.236076 | 0.138218 | U91616_at | I kappa B epsilon (IkBe) mRNA |
| 883 | Lymphoma | 0.4071499 | 0.2832288 | 0.236045 | 0.13816349 49_at | RC_AA4362 | EST: zv24g07.s1 Soares NhHMPu S1 Homo sapiens cDNA clone 754620 3', mRNA sequence. (from Genbank) |
| 884 | Lymphoma | 0.4068977 | 0.283072 | 0.236033 | 0.13807723 81_at | RC_AA4602 | EST: zx51a04.s1 Soares testis NHT Homo sapiens cDNA clone 795726 3', mRNA sequence. (from Genbank) |
| 885 | Lymphoma | 0.4068012 | 0.283055 | 0.236003 | 0.13805269 | U31556_at | E2F5 E2F transcription factor 5, p130-binding |
| 886 | Lymphoma | 0.4067893 | 0.2830429 | 0.235995 | 0.13800958 34_at | RC_AA6100 | EST: af18f07.s1 Soares testis NHT Homo sapiens cDNA clone 1032037 3', mRNA sequence. (from Genbank) |
| 887 | Lymphoma | 0.406656 | 0.2829691 | 0.235986 | 0.13799176 | D82348_at-2 | Homo sapiens mRNA for 5-aminoimidazole-4-carboxamide-1-beta-D-ribon ucleotide transformylase/inosinicase, complete cds |
| 888 | Lymphoma | 0.406656 | 0.2829594 | 0.235956 | 0.13792677 | D82348_at | 5-aminoimidazole-4-carboxamide-1-beta-D-ribonucleoti de transformylase/inosinicase |
| 889 | Lymphoma | 0.4065511 | 0.2828924 | 0.235848 | 0.13782714 92_at | RC_AA0162 | EST: ze38c02.s1 Soares retina N2b4HR Homo sapiens cDNA clone 361250 3', mRNA sequence. (from Genbank) |
| 890 | Lymphoma | 0.4058655 | 0.2828535 | 0.235789 | 0.13779864 65_at | RC_AA4019 | Homo sapiens growth suppressor related (DOC-1R) mRNA, complete cds |
| 891 | Lymphoma | 0.4057701 | 0.28271 85 | 0.235711 | 0.13771069 | D42046_at-2 | DNA2 (DNA replication helicase, yeast, homolog)-like |
| 892 | Lymphoma | 0.4057701 | 0.2827081 | 0.235694 | 0.13767102 | D42046_at | KIAA0083 gene, partial cds |
| 893 | Lymphoma | 0.4057397 | 0.28266949 | 0.235647 | 0.137663493 | Z21081_at | EST: H. sapiens putatively transcribed partial sequence; UK-HGMP sequence ID AAADMBX; single read, mRNA sequence. (from Genbank) |
| 894 | Lymphoma | 0.4055338 | 0.28266 07 | 0.235589 | 0.13760754 96_at | RC_AA4358 | EST: zt80e12.s1 Soares testlis NHT Homo sapiens cDNA clone 728686 3', mRNA sequence. (from Genbank) |
| 895 | Lymphoma | 0.4052647 | 0.2826536 | 0.235563 | 0.13753949 75_at | RC_AA4546 | EST: zx76a07.s1 Soares ovary tumor NbHOT Homo sapiens cDNA clone 809652 3', mRNA sequence. (from Genbank) |
| 896 | Lymphoma | 0.4052604 | 0.2825769 | 0.235504 | 0.13747247 | AA216017_a t | EST: hp0234.seq.F Fetal heart, Lambda ZAP Express Homo sapiens cDNA 5', mRNA sequence. (from Genbank) |
| 897 | Lymphoma | 0.4051957 | 0.2825212 | 0.235426 | 0.13743249 | U14972_at | Ribosomal protein S10 mRNA |
| 898 | Lymphoma | 0.4050985 | 0.2824197 | 0.235419 | 0.137329 28 | AA147144_a t | Zo32c06.r1 Stratagene colon (#937204) Homo sapiens cDNA clone 588586 5' similar to WP:C14B1.4 CE00901 GUANINE NUCLEOTIDE BINDING PROTEIN.; mRNA sequence. (from Genbank) |

FIG. 7X2

| | | | | | |
|---|---|---|---|---|---|
| 899 | Lymphoma | 0.4050809 | 0.2835569 | 0.235391 | 0.13731675 | RC_AA4063 88_at | EST: zv10e03.s1 Soares NhHMPu S1 Homo sapiens cDNA clone 753244 3', mRNA sequence. (from Genbank) |
| 900 | Lymphoma | 0.4049054 | 0.2833419 | 0.235302 | 0.1372813 | RC_AA4598 97_at | Homo sapiens mRNA encoding rat C4.4-like protein |
| 901 | Lymphoma | 0.4048 | 0.282216 | 0.235297 | 0.137227795 | RC_AA0882 28_at | EST: zl82d04.s1 Stratagene colon (#937204) Homo sapiens cDNA clone 511111 3', mRNA sequence. (from Genbank) |
| 902 | Lymphoma | 0.404775 | 0.2822019 | 0.23524 | 0.13717978 | R97442_s_a t | EST: yq53b01.r1 Homo sapiens cDNA clone 199465 5'. (from Genbank) |
| 903 | Lymphoma | 0.4043019 | 0.2821743 | 0.235199 | 0.13716073 | AA307748_s _at | EST: EST17861 Aorta endothelial cells, TNF alpha-treated Homo sapiens cDNA 5' end similar to similar to M. musculus hypothetical protein (GB:L12982), mRNA sequence. (from Genbank) |
| 904 | Lymphoma | 0.4040363 | 0.2821442 | 0.235143 | 0.13710143 | AA234663_a t | EST: zs39a07.r1 Soares NhHMPu S1 Homo sapiens cDNA clone 687540 5', mRNA sequence. (from Genbank) |
| 905 | Lymphoma | 0.4037999 | 0.2821316 | 0.235105 | 0.13705318 | RC_AA4301 06_at | EST: zw61a09.s1 Soares total fetus Nb2HF8 9w Homo sapiens cDNA clone 774520 3', mRNA sequence. (from Genbank) |
| 906 | Lymphoma | 0.4037317 | 0.2820864 | 0.235092 | 0.13703439 | RC_AA3984 69_at | EST: zl62f06.s1 Soares testis NHT Homo sapiens cDNA clone 726947 3', mRNA sequence. (from Genbank) |
| 907 | Lymphoma | 0.4035078 | 0.2820782 | 0.234962 | 0.13696958 | W00799_at | Eukaryotic translation elongation factor 1 alpha 1 |
| 908 | Lymphoma | 0.4033656 | 0.282078 | 0.234912 | 0.13693401 | S78873_s_at 2 | RAB interacting factor |
| 909 | Lymphoma | 0.4033656 | 0.2818099 | 0.234879 | 0.1368451 | S78873_s_at | Guanine nucleotide exchange factor mss4 mRNA |
| 910 | Lymphoma | 0.4033484 | 0.2816954 | 0.234874 | 0.1368021 | AF001954_a t | Inhibitor of growth 1 |
| 911 | Lymphoma | 0.4032017 | 0.2816323 | 0.234822 | 0.13676618 | RC_AA0188 77_at | EST: ze58g08.s1 Soares retina N2b4HR Homo sapiens cDNA clone 363230 3', mRNA sequence. (from Genbank) |
| 912 | Lymphoma | 0.4029064 | 0.2815677 | 0.234802 | 0.13666014 | Z36714_at | CCNF Cyclin F |
| 913 | Lymphoma | 0.4027987 | 0.2815564 | 0.234685 | 0.13660644 | AA353516_a t | EST: EST61676 Activated T-cells XX Homo sapiens cDNA 5' end, mRNA sequence. (from Genbank) |
| 914 | Lymphoma | 0.4027576 | 0.2814837 | 0.234613 | 0.13655232 | RC_AA1654 00_at | EST: zo80h10.s1 Stratagene ovarian cancer (#937219) Homo sapiens cDNA clone 593251 3', mRNA sequence. (from Genbank) |
| 915 | Lymphoma | 0.4026642 | 0.2814697 | 0.234606 | 0.13649873 | AA251957_a t | EST: zs09f10.r1 NCI_CGAP_GCB1 Homo sapiens cDNA clone IMAGE:684715 5', mRNA sequence. (from Genbank) |
| 916 | Lymphoma | 0.4025022 | 0.2813993 | 0.234553 | 0.1364388 | U11292_at-2 | Human Ki nuclear autoantigen mRNA, complete cds |

FIG. 7Y2

| | | | | | |
|---|---|---|---|---|---|
| 917 | Lymphoma | 0.4025022 | 0.2813419 | 0.234455 | 0.136639612 | U11292_at | Ki nuclear autoantigen mRNA |
| 918 | Lymphoma | 0.4024472 | 0.2813035 | 0.234452 | 0.13637477 | C00032_at | EST: HUMGS0003377, Human Gene Signature, 3'-directed cDNA sequence, mRNA sequence. (from Genbank) |
| 919 | Lymphoma | 0.4023716 | 0.2812597 | 0.234396 | 0.13633724 | AA019475_a t | EST: ze57c01.r1 Soares retina N2b4HR Homo sapiens cDNA clone 363072 5', mRNA sequence. (from Genbank) |
| 920 | Lymphoma | 0.4022352 | 0.2812515 | 0.23436 | 0.13628450 5 | RC_AA2242 05_at | EST: zr15f03.s1 Stratagene NT2 neuronal precursor 937230 Homo sapiens cDNA clone 663485 3', mRNA sequence. (from Genbank) |
| 921 | Lymphoma | 0.4020522 | 0.2812256 | 0.23436 | 0.13624829 | AA012864_a t | Ze34d10.r1 Soares retina N2b4HR Homo sapiens cDNA clone 360883 5', mRNA sequence. (from Genbank) |
| 922 | Lymphoma | 0.401877 | 0.2811643 | 0.234357 | 0.13616103 62 | RC_AA4292 _at | EST: zv50a08.s1 Soares ovary tumor NbHOT Homo sapiens cDNA clone 757046 3', mRNA sequence. (from Genbank) |
| 923 | Lymphoma | 0.401781 | 0.2811466 | 0.234223 | 0.13610045 3 | RC_AA4634 _at | EST: zx98b12.s1 Soares NhHMPu S1 Homo sapiens cDNA clone 811775 3', mRNA sequence. (from Genbank) |
| 924 | Lymphoma | 0.4016997 | 0.2811163 | 0.234196 | 0.13606092 7 | U16811_s_a t | Bak protein mRNA |
| 925 | Lymphoma | 0.4016997 | 0.2810746 | 0.234146 | 0.13603964 | U16811_s_a t-2 | BCL2-antagonist/killer 1 |
| 926 | Lymphoma | 0.4014557 | 0.2810539 | 0.234146 | 0.13593347 | U89995_at | DNA binding protein FKHL 15 (FKHL15) mRNA |
| 927 | Lymphoma | 0.4014557 | 0.2809632 | 0.234122 | 0.13593347 | U89995_at-2 | Forkhead (Drosophila)-like 15 |
| 928 | Lymphoma | 0.4014535 | 0.2809392 | 0.234089 | 0.13585812 | W28839_at | KIAA0043 gene product |
| 929 | Lymphoma | 0.4014302 | 0.2808832 | 0.234022 | 0.13573688 | U77413_at | O-linked GlcNAc transferase mRNA |
| 930 | Lymphoma | 0.4011119 | 0.2808319 | 0.234011 | 0.13565734 | R50328_f_at | Homo sapiens mRNA for ADP ribosylation factor-like LAK, complete cds |
| 931 | Lymphoma | 0.4008947 | 0.280736 | 0.234011 | 0.13558364 | AA278286_a t | M-phase phosphoprotein 1 |
| 932 | Lymphoma | 0.4007486 | 0.2807001 | 0.233981 | 0.13553727 | AA232156_a t | Insulin-like growth factor 2 (somatomedin A) |
| 933 | Lymphoma | 0.4006888 | 0.2806735 | 0.233959 | 0.13552909 58 | RC_AA6001 _at | EST: ae50e09.s1 Stratagene lung carcinoma 937218 Homo sapiens cDNA clone 950344 3', mRNA sequence. (from Genbank) |
| 934 | Lymphoma | 0.4003771 | 0.2804357 | 0.233951 | 0.1354233 | X06617_at | RPS11 Ribosomal protein S11 |
| 935 | Lymphoma | 0.4003564 | 0.2804298 | 0.233859 | 0.13539194 77 | RC_AA4525 _at | EST: zx35h11.s1 Soares total fetus Nb2HF8 9w Homo sapiens cDNA clone 788517 3', mRNA sequence. (from Genbank) |

FIG. 7Z2

| | | | | | | |
|---|---|---|---|---|---|---|
| 936 | Lymphoma | 0.4002082 | 0.2804287 | 0.233838 | 0.13536817 | RC_AA4592 87_at | Myosin IXB |
| 937 | Lymphoma | 0.4001874 | 0.2803443 | 0.233835 | 0.13529858 | RC_AA5985 75_at | EST: ae35e11.s1 Gessler Wilms tumor Homo sapiens cDNA clone 897836 3', mRNA sequence. (from Genbank) |
| 938 | Lymphoma | 0.4000722 | 0.2803019 | 0.233791 | 0.1352478 | X16260_s_a t | ITIH3 Pre-alpha (globulin) inhibitor, H3 polypeptide |
| 939 | Lymphoma | 0.4000722 | 0.2802941 | 0.233791 | 0.135523708 | X16260_s_a t-2 | Inter-alpha (globulin) inhibitor, H1 polypeptide |
| 940 | Lymphoma | 0.4000463 | 0.2802793 | 0.233544 | 0.135517725 | U82979_at | Immunoglobulin-like transcript-3 mRNA |
| 941 | Lymphoma | 0.4000253 | 0.2802396 | 0.233499 | 0.135512638 | AA020941_a t | EST: ze64c11.r1 Soares retina N2b4HR Homo sapiens cDNA clone 363764 5', mRNA sequence. (from Genbank) |
| 942 | Lymphoma | 0.3998492 | 0.2801414 | 0.233363 | 0.135509157 | RC_AA5995 52_s_at | EST: ag08a06.s1 Gessler Wilms tumor Homo sapiens cDNA clone 1069714 3', mRNA sequence. (from Genbank) |
| 943 | Lymphoma | 0.3992499 | 0.2801414 | 0.233343 | 0.135508603 | U73514_at | Short-chain alcohol dehydrogenase (XH98G2) mRNA |
| 944 | Lymphoma | 0.3988138 | 0.2800792 | 0.233291 | 0.135505258 | RC_AA4600 24_at | Semaphorin W |
| 945 | Lymphoma | 0.3987513 | 0.2800788 | 0.233278 | 0.135502967 | RC_AA2788 24_at | EST: zs78f04.s1 NCI_CGAP_GCB1 Homo sapiens cDNA clone IMAGE:703615 3', mRNA sequence. (from Genbank) |
| 946 | Lymphoma | 0.3986904 | 0.2800648 | 0.233261 | 0.135502523 | H78550_at | EST: yu13g03.r1 Homo sapiens cDNA clone 233716 5'. (from Genbank) |
| 947 | Lymphoma | 0.3986233 | 0.2800198 | 0.233189 | 0.13494551 | AF004709_a t | Protein kinase mitogen- activated 13 |
| 948 | Lymphoma | 0.3980054 | 0.2799504 | 0.233178 | 0.134492592 | AA453130_a t | Homo sapiens mRNA for KIP2, complete cds |
| 949 | Lymphoma | 0.3978993 | 0.2798556 | 0.23311 | 0.134493009 | L12723_at | HSPA4 Heat shock 70kD protein 4 |
| 950 | Lymphoma | 0.3973691 | 0.2798534 | 0.233309 | 0.134746678 | U77735_at | Pim-2 protooncogene homolog pim-2h mRNA |
| 951 | Lymphoma | 0.3971289 | 0.2798316 | 0.233016 | 0.13471194 | M94891_s_a t | Pregnancy specific beta-1-glycoprotein 4 |
| 952 | Lymphoma | 0.3969451 | 0.2797855 | 0.233016 | 0.134675 | C00463_at | EST: HUMGS0007162, Human Gene Signature, 3'-directed cDNA sequence, mRNA sequence. (from Genbank) |
| 953 | Lymphoma | 0.3968857 | 0.2797609 | 0.232927 | 0.13462697 | AA214738_a t | EST: PMY0132 KG1-a Lambda Zap Express cDNA library Homo sapiens cDNA 5', mRNA sequence. (from Genbank) |
| 954 | Lymphoma | 0.3968269 | 0.2797566 | 0.232905 | 0.13462697 | AA092596_a t | Bone morphogenetic protein 6 |
| 955 | Lymphoma | 0.3963356 | 0.2797099 | 0.232849 | 0.13457035 | AA047791_a t | EST: zf49d06.r1 Soares retina N2b4HR Homo sapiens cDNA clone 380267 5', mRNA sequence. (from Genbank) |

FIG. 7A3

| | | | | |
|---|---|---|---|---|
| 956 | Lymphoma | 0.3962916 | 0.2796523 | 0.232846 | 0.13454406 | AA476639_a_t | EST: zw85e11.r1 Soares total fetus Nb2HF8 9w Homo sapiens cDNA clone 783788 5' similar to SW:KAD3_BOVIN P08760 GTP:AMP PHOSPHOTRANSFERASE MITOCHONDRIAL .; mRNA sequence. (from Genbank) |
| 957 | Lymphoma | 0.3959785 | 0.2796224 | 0.232833 | 0.13443808 | AFFX-HUMGAPDH/M33197_5_st | AFFX-HUMGAPDH/M33197_5_st (endogenous control) |
| 958 | Lymphoma | 0.3959785 | 0.279617 | 0.232737 | 0.13433419 | AFFX-HUMGAPDH/M33197_5_st-2 | Glyceraldehyde-3-phosphate dehydrogenase |
| 959 | Lymphoma | 0.3959328 | 0.2796168 | 0.232737 | 0.13429257 | RC_AA5984 29_at | EST: ae48d08.s1 Stratagene lung carcinoma 937218 Homo sapiens cDNA clone 950127 3', mRNA sequence. (from Genbank) |
| 960 | Lymphoma | 0.3956305 | 0.2794914 | 0.232718 | 0.13425575 | H57717_at | Homo sapiens clone DT1P1B6 mRNA, CAG repeat region |
| 961 | Lymphoma | 0.3956126 | 0.2794905 | 0.232561 | 0.13423847 | AA037199_a_t | Homo sapiens TRIAD1 type I mRNA, complete cds |
| 962 | Lymphoma | 0.3955412 | 0.2794116 | 0.23243 | 0.13418517 | RC_AA2238 74_at | Human BAC clone RG385F02 from 7p15 |
| 963 | Lymphoma | 0.3954591 | 0.2793925 | 0.232418 | 0.13408658 | U81787_at-2 | Human Wnt10B mRNA, complete cds |
| 964 | Lymphoma | 0.3954591 | 0.2793503 | 0.232416 | 0.13406663 | U81787_at | Wnt10B mRNA |
| 965 | Lymphoma | 0.3953896 | 0.2793139 | 0.232415 | 0.13402016 | RC_AA2828 03_at | EST: zs91d09.s1 NCI_CGAP_GCB1 Homo sapiens cDNA clone IMAGE:704849 3' similar to SW:DNA2_YEAST P38859 DNA REPLICATION HELICASE DNA2 .; mRNA sequence. (from Genbank) |
| 966 | Lymphoma | 0.3950799 | 0.2793093 | 0.232333 | 0.13400687 | AF005038_a_t | Secretory carrier membrane protein 2 |
| 967 | Lymphoma | 0.3947507 | 0.2792737 | 0.232291 | 0.13393493 | RC_AA4366 46_at | EST: zv57b03.s1 Soares testis NHT Homo sapiens cDNA clone 757709 3', mRNA sequence. (from Genbank) |
| 968 | Lymphoma | 0.3947169 | 0.278925 | 0.232183 | 0.13387349 | RC_AA2839 34_at | EST: zs47h12.s1 NCI_CGAP_GCB1 Homo sapiens cDNA clone IMAGE:706679 3', mRNA sequence. (from Genbank) |
| 969 | Lymphoma | 0.3947042 | 0.2788715 | 0.232046 | 0.13384195 | RC_AA4789 68_at | EST: zv18e04.s1 Soares NhHMPu S1 Homo sapiens cDNA clone 754014 3'; mRNA sequence. (from Genbank) |
| 970 | Lymphoma | 0.3946702 | 0.2788384 | 0.232021 | 0.13380262 | N36626_at | EST: yx88d07.r1 Homo sapiens cDNA clone 268813 5'. (from Genbank) |

FIG. 7B3

| | | | | | |
|---|---|---|---|---|---|
| 971 | Lymphoma | 0.3944314 | 0.2787418 | 0.231942 | 0.133765943 | RC_AA3510 31_i_at | Renal organic anion transporter 1 |
| 972 | Lymphoma | 0.3943266 | 0.2787197 | 0.23193 | | M17236_s_a t | HLA CLASS II HISTOCOMPATIBILITY ANTIGEN, DQ(2) ALPHA CHAIN PRECURSOR |
| 973 | Lymphoma | 0.3942747 | 0.2786675 | 0.231903 | 0.133701531 | W38687_at | SH3 binding protein |
| 974 | Lymphoma | 0.3942321 | 0.278616 | 0.231895 | 0.133362066 | AA307896_a t | Nuclear localization signal deleted in velocardiofacial syndrome |
| 975 | Lymphoma | 0.3939648 | 0.2785364 | 0.231856 | 0.133601552 | RC_AA416/ 6_s_at | EST: zu08a08.s1 Soares testis NHT Homo sapiens cDNA clone 731222 3', mRNA sequence. (from Genbank) |
| 976 | Lymphoma | 0.3938196 | 0.2785252 | 0.231786 | 0.133555236 | RC_AA4189 _s_at | Homo sapiens mRNA for KIAA0795 protein, partial cds |
| 977 | Lymphoma | 0.393611 | 0.2783257 | 0.231736 | 0.13350788 | U10493_s_a t | Mesenchyme homeo box 1 |
| 978 | Lymphoma | 0.3936067 | 0.2782948 | 0.231722 | 0.133473218 | U70660_at | Copper transport protein HAH1 (HAH1) mRNA |
| 979 | Lymphoma | 0.3933139 | 0.2782579 | 0.231692 | 0.133402854 | W28152_at | EST: 43f7 Human retina cDNA randomly primed sublibrary Homo sapiens cDNA, mRNA sequence. (from Genbank) |
| 980 | Lymphoma | 0.3932099 | 0.2782446 | 0.231635 | 0.133370881 | AA278547_a t | EST: zs76c04.r1 NCI_CGAP_GCB1 Homo sapiens cDNA clone IMAGE:703398 5', mRNA sequence. (from Genbank) |
| 981 | Lymphoma | 0.3928986 | 0.2782059 | 0.231623 | 0.133316311 | AA448946_r _at | EST: zx07a10.r1 Soares total fetus Nb2HF8 9w Homo sapiens cDNA clone 785754 5', mRNA sequence. (from Genbank) |
| 982 | Lymphoma | 0.3927018 | 0.2781959 | 0.231553 | 0.133327389 | J03019_s_at | Adrenergic, beta-1-, receptor |
| 983 | Lymphoma | 0.3926567 | 0.2781689 | 0.231539 | 0.133235564 | RC_AA2591 47_at | EST: zs30f01.s1 NCI_CGAP_GCB1 Homo sapiens cDNA clone IMAGE:686713 3', mRNA sequence. (from Genbank) |
| 984 | Lymphoma | 0.3925375 | 0.2781552 | 0.231509 | 0.13332259 | HG2259-HT2348_s_a t | Tubulin, Alpha 1, Isoform 44 |
| 985 | Lymphoma | 0.3924637 | 0.2781313 | 0.231384 | 0.133183461 | U59286_at-2 | Homo sapiens interferon stimulated T-cell alpha chemoattractant precursor, mRNA, complete cds |
| 986 | Lymphoma | 0.3924637 | 0.2780981 | 0.231371 | 0.133143325 | U59286_at | Beta-R1 mRNA, partial cds |
| 987 | Lymphoma | 0.3922967 | 0.2779997 | 0.231358 | 0.133102499 | RC_AA2521 1_at | Homo sapiens PAC clone DJ130H16 from 22q12.1-qter |
| 988 | Lymphoma | 0.3920615 | 0.2779722 | 0.231339 | 0.133058672 | X52222_at | Excision repair cross-complementing rodent repair deficiency, complementation group 2 (xeroderma pigmentosum D) |
| 989 | Lymphoma | 0.3916307 | 0.2779504 | 0.231328 | 0.133008152 | H72630_at | EST: yu05a11.r1 Homo sapiens cDNA clone 232892 5'. (from Genbank) |

FIG. 7C3

| | | | | |
|---|---|---|---|---|
| 990 | Lymphoma | 0.3913551 | 0.2779125 | 0.132980320 | RC_AA3982 05_at | EST: zl59b06.s1 Soares testis NHT Homo sapiens cDNA clone 726611 3', mRNA sequence. (from Genbank) |
| 991 | Lymphoma | 0.3909953 | 0.2778405 | 0.13286473 | AA405937_a t | EST: zu66a10.r1 Soares testis NHT Homo sapiens cDNA clone 742938 5', mRNA sequence. (from Genbank) |
| 992 | Lymphoma | 0.3907416 | 0.2778141 | 0.1328373 | M57888_ma 1_s_at | Granzyme B (granzyme 2, cytotoxic T-lymphocyte-associated serine esterase 1) |
| 993 | Lymphoma | 0.3905593 | 0.2777837 | 0.132796620 | RC_AA4276 _at | EST: zw30d02.s1 Soares ovary tumor NbHOT Homo sapiens cDNA clone 770787 3' similar to contains MER17.b1 MER17 repetitive element;, mRNA sequence. (from Genbank) |
| 994 | Lymphoma | 0.3904256 | 0.277604 | 0.1327928 | H43996_at | EST: yo70h10.r1 Homo sapiens cDNA clone 183331 5'. (from Genbank) |
| 995 | Lymphoma | 0.3901795 | 0.2775927 | 0.13273728 | R77159_at | EST: yi65a07.r1 Homo sapiens cDNA clone 144084 5'. (from Genbank) |
| 996 | Lymphoma | 0.3901083 | 0.2775575 | 0.13271026 | AA083797_s _at | Zm63c02.r1 Stratagene fibroblast (#937212) Homo sapiens cDNA clone 530306 5' similar to gb:X15822 CYTOCHROME C OXIDASE POLYPEPTIDE VIIA-LIVER PRECURSOR (HUMAN);, mRNA sequence. (from Genbank) |
| 997 | Lymphoma | 0.3900039 | 0.2775382 | 0.132617463 | RC_AA2819 4_at | EST: zf09b02.s1 NCI_CGAP_GCB1 Homo sapiens cDNA clone IMAGE:712587 3' similar to contains Alu repetitive element;, mRNA sequence. (from Genbank) |
| 998 | Lymphoma | 0.3897223 | 0.2775143 | 0.13258201 | AA057447_s _at | EST: zf56b01.r1 Soares retina N2b4HR Homo sapiens cDNA clone 380905 5' similar to contains Alu repetitive element;, mRNA sequence. (from Genbank) |
| 999 | Lymphoma | 0.3897168 | 0.2774331 | 0.13252158 | RC_AA2787 17_at | EST: zs77e04.s1 NCI_CGAP_GCB1 Homo sapiens cDNA clone IMAGE:703518 3', mRNA sequence. (from Genbank) |
| 1000 | Lymphoma | 0.3894596 | 0.2773911 | 0.1324749 | AA252436_a t | Homo sapiens lysophospholipase (LPL1) mRNA, complete cds |

FIG. 7D3

| | | | | |
|---|---|---|---|---|
| 1 Melanoma | 0.9608414 | 0.7808739 | 0.650197 | RC_AA1768 12_at | EST: zp32g12.s1 Stratagene neuroepithelium (#937231) Homo sapiens cDNA clone 611206 3' similar to contains Alu repetitive element;contains element THR repetitive element :, mRNA sequence. (from Genbank) |
| 2 Melanoma | 0.7282538 | 0.7080683 | 0.603304 | AA406087_s_at | TAL1 (SCL) interrupting locus |
| 3 Melanoma | 0.7215478 | 0.6774965 | 0.577166 | RC_AA0131 60_at | EST: ze35e10.s1 Soares retina N2b4HR Homo sapiens cDNA clone 361002 3' similar to contains Alu repetitive element; mRNA sequence. (from Genbank) |
| 4 Melanoma | 0.7208559 | 0.6629334 | 0.566053 | 0.42809093 U06452_at | MLANA Differentiation antigen melan-A |
| 5 Melanoma | 0.7199685 | 0.6520526 | 0.554953 | 0.4181803 W26392_at | EST: 30g3 Human retina cDNA randomly primed sublibrary Homo sapiens cDNA, mRNA sequence. (from Genbank) |

FIG. 8A

| | | | | | |
|---|---|---|---|---|---|
| 6 | Melanoma | 0.7067817 | 0.6412944 | 0.546567 | 0.41028038 | S73003_s_at | PMEL 17 PROTEIN PRECURSOR |
| 7 | Melanoma | 0.6579034 | 0.6341255 | 0.538004 | 0.4043727 | W39687_s_at | EST: zc21e08.r1 Soares senescent fibroblasts NbHSF Homo sapiens cDNA clone 322982 5', mRNA sequence. (from Genbank) |
| 8 | Melanoma | 0.655309 | 0.626457 | 0.534069 | 0.399452451 | X84707_rna1_at | MIA gene |
| 9 | Melanoma | 0.6420086 | 0.6221575 | 0.5285 | 0.39475552 | X96753_at | Melanoma-associated chondroitin sulfate proteoglycan (MCSP) |
| 10 | Melanoma | 0.6314878 | 0.616363 | 0.523382 | 0.390508176 | RC_AA4314 61_at | EST: zw70f11.s1 Soares testis NHT Homo sapiens cDNA clone 781581 3', mRNA sequence. (from Genbank) |
| 11 | Melanoma | 0.6251587 | 0.6129066 | 0.517861 | 0.38645318 | U58516_at | Breast epithelial antigen BA46 mRNA |
| 12 | Melanoma | 0.5877349 | 0.610369 | 0.515463 | 0.3833637 | Y07759_at | Myosin heavy chain 12 |
| 13 | Melanoma | 0.5693535 | 0.6066617 | 0.513179 | 0.38003224 | W26130_at | H.sapiens mRNA for ragB protein |
| 14 | Melanoma | 0.5553511 | 0.6044484 | 0.510592 | 0.3769805 | RC_AA4599 50_at | EST: zx66b03.s1 Soares total fetus Nb2HF8 9w Homo sapiens cDNA clone 796397 3', mRNA sequence. (from Genbank) |
| 15 | Melanoma | 0.5455789 | 0.6019571 | 0.506174 | 0.37361717 | X96381_rna1_at | Erm gene, exon 2,3,4,5 (and joined CDS) |
| 16 | Melanoma | 0.5353896 | 0.6005628 | 0.504058 | 0.37151223 | RC_AA4175 88_at | EST: zv04f10.s1 Soares NhHMPu S1 Homo sapiens cDNA clone 752683 3', mRNA sequence. (from Genbank) |
| 17 | Melanoma | 0.5332507 | 0.5986225 | 0.500591 | 0.36880952 | C01811_f_at | EST: HUMGS0003774, Human Gene Signature, 3'-directed cDNA sequence, mRNA sequence. (from Genbank) |
| 18 | Melanoma | 0.5239032 | 0.5962527 | 0.498758 | 0.366466 | W52706_at | EST: zc55g02.r1 Soares senescent fibroblasts NbHSF Homo sapiens cDNA clone 326258 5' similar to SW:INI7_HUMAN P40305 INTERFERON-ALPHA INDUCED 11.5 KD PROTEIN ;, mRNA sequence. (from Genbank) |
| 19 | Melanoma | 0.517573 | 0.5920323 | 0.497302 | 0.3646494 | RC_AA0373 57_at | EST: zc03c04.s1 Soares parathyroid tumor NbHPA Homo sapiens cDNA clone 321222 3' similar to contains Alu repetitive element;, mRNA sequence. (from Genbank) |
| 20 | Melanoma | 0.5169516 | 0.5900542 | 0.49433 | 0.36262759 | RC_AA4790 44_s_at | EST: zu36d09.s1 Soares ovary tumor NbHOT Homo sapiens cDNA clone 740081 3', mRNA sequence. (from Genbank) |
| 21 | Melanoma | 0.5163391 | 0.5876654 | 0.491902 | 0.3609353 | D45213_at | Homo sapiens mRNA for zinc finger protein, complete cds |
| 22 | Melanoma | 0.5158222 | 0.5862659 | 0.490266 | 0.3591987 | D81608_at | Polymerase (RNA) II (DNA directed) polypeptide L (7.6kD) |
| 23 | Melanoma | 0.5112641 | 0.5849024 | 0.488107 | 0.3570082 | RC_AA2438 70_at | EST: zr65d04.s1 Soares NhHMPu S1 Homo sapiens cDNA clone 668263 3' similar to WP:F59B2.3 CE00231 N-ACETYL-GLUCOSAMINE-6-PHOSPHATE DEACETYLASE ;, mRNA sequence. (from Genbank) |
| 24 | Melanoma | 0.5029985 | 0.5806069 | 0.487111 | 0.355449148 | 9_at | EST: zw04a08.s1 Soares NhHMPu S1 Homo sapiens cDNA clone 768278 3', mRNA sequence. (from Genbank) |
| 25 | Melanoma | 0.5026965 | 0.5788575 | 0.485787 | 0.35390604 | U61374_at | Sushi-repeat-containing protein precursor (SRPX) mRNA |
| 26 | Melanoma | 0.4985014 | 0.5788575 | 0.484349 | 0.35207295 | M27160_at | TYR Tyrosinase (oculocutaneous albinism IA) |

FIG. 8B

| # | Type | Val1 | Val2 | Val3 | ID1 | ID2 | Description |
|---|---|---|---|---|---|---|---|
| 27 | Melanoma | 0.492696 | 0.5777413 | 0.482515 | 0.35051897 | W26204_at | EST: 22c2 Human retina cDNA randomly primed sublibrary Homo sapiens cDNA, mRNA sequence. (from Genbank) |
| 28 | Melanoma | 0.4903655 | 0.5738001 | 0.48009 | | RC_AA4005 08_at | EST: zu70d02.s1 Soares testis NHT Homo sapiens cDNA clone 743331 3', mRNA sequence. (from Genbank) |
| 29 | Melanoma | 0.4883161 | 0.5734929 | 0.478928 | 0.3473155 | U46192_at | Human renal cell carcinoma antigen RAGE-1 mRNA, complete putative cds |
| 30 | Melanoma | 0.4866879 | 0.5715763 | 0.477293 | 0.34577134 | Z21384_at | EST: H. sapiens putatively transcribed partial sequence; UK-HGMP sequence ID AAAEBCK; single read, mRNA sequence. (from Genbank) |
| 31 | Melanoma | 0.4803894 | 0.5678329 | 0.476222 | 0.34444538 | RC_AA2791 68_at | EST: zs83a04.s1 NCI_CGAP_GCB1 Homo sapiens cDNA clone IMAGE:704046 3', mRNA sequence. (from Genbank) |
| 32 | Melanoma | 0.4782808 | 0.5665406 | 0.474667 | 0.34331143 | RC_AA0019 08_at | EST: zh83a05.s1 Soares fetal liver spleen 1NFLS S1 Homo sapiens cDNA clone 427856 3', mRNA sequence. (from Genbank) |
| 33 | Melanoma | 0.4765272 | 0.5645617 | 0.473651 | 0.34189883 | X93510_at | 37 kDa LIM domain protein |
| 34 | Melanoma | 0.4761572 | 0.5643998 | 0.47225 | 0.34045714 | RC_AA3502 68_at | EST: EST57664 Infant brain Homo sapiens cDNA 3' end, mRNA sequence. (from Genbank) |
| 35 | Melanoma | 0.4743735 | 0.5615582 | 0.471325 | 0.33946347 | N75618_at | EST: yw37c07.r1 Homo sapiens cDNA clone 254412 5'. (from Genbank) |
| 36 | Melanoma | 0.4734101 | 0.5597639 | 0.470184 | 0.33825866 | RC_AA1213 60_s_at | EST: zn77a05.s1 Stratagene NT2 neuronal precursor 937230 Homo sapiens cDNA clone 564176 3', mRNA sequence. (from Genbank) |
| 37 | Melanoma | 0.4712272 | 0.5579929 | 0.468796 | 0.33707577 | HG2465-HT4871_at | Dna-Binding Protein Ap-2, Alt. Splice 3 |
| 38 | Melanoma | 0.4681326 | 0.5578898 | 0.468016 | 0.3359151574_at | RC_AA0042 | EST: zh97f02.s1 Soares fetal liver spleen 1NFLS S1 Homo sapiens cDNA clone 429243 3' similar to contains element MER22 repetitive element.; mRNA sequence. (from Genbank) |
| 39 | Melanoma | 0.4675642 | 0.5571774 | 0.467047 | 0.33475953 | RC_AA3472 88_at | Growth arrest-specific 7 |
| 40 | Melanoma | 0.4670562 | 0.5569509 | 0.465969 | 0.33377916 | U28369_at | Semaphorin V mRNA |
| 41 | Melanoma | 0.459244 | 0.5551281 | 0.464208 | 0.33276048 | U62435_at | Cholinergic receptor, neuronal nicotinic, alpha polypeptide 6 |
| 42 | Melanoma | 0.4587679 | 0.5538403 | 0.463146 | 0.33199937 | D17547_at | DCT Dopachrome tautomerase (dopachrome delta-isomerase, tyrosine-related protein 2) |
| 43 | Melanoma | 0.4572299 | 0.5536631 | 0.462186 | 0.33097869 | J02611_at | APOD Apolipoprotein D |
| 44 | Melanoma | 0.4567213 | 0.5530116 | 0.461228 | 0.32997867 | W19089_s_at | EST: zb14f12.r1 Soares fetal lung NbHL19W Homo sapiens cDNA clone 302063 5', mRNA sequence. (from Genbank) |
| 45 | Melanoma | 0.4558684 | 0.5520168 | 0.46045 | 0.32907262 | RC_AA1570 01_at | EST: zl19f07.s1 Soares pregnant uterus NbHPU Homo sapiens cDNA clone 502405 3', mRNA sequence. (from Genbank) |
| 46 | Melanoma | 0.4514387 | 0.551138 | 0.459692 | 0.32787684 | X59812_at | CYP27 Cytochrome P450, subfamily XXVII (steroid 27-hydroxylase, cerebrotendinous xanthomatosis) |

FIG. 8C

| # | Type | | | | ID | Description |
|---|---|---|---|---|---|---|
| 47 | Melanoma | 0.4512526 | 0.5506679 | 0.458696 | 0.32703128 | S69231_s_at | DCT Dopachrome tautomerase (dopachrome delta-isomerase, tyrosine-related protein 2) |
| 48 | Melanoma | 0.4491101 | 0.549091 | 0.457926 | 0.32626364 | RC_AA4212 68_at | Homo sapiens putative tumor suppressor protein (101F6) mRNA, complete cds |
| 49 | Melanoma | 0.4486821 | 0.5477009 | 0.456482 | 0.32538444 | RC_AA4294 72_at | EST: zw34b09.s1 Soares ovary tumor NbHOT Homo sapiens cDNA clone 771161 3', mRNA sequence. (from Genbank) |
| 50 | Melanoma | 0.4465975 | 0.5468033 | 0.456439 | 0.32419178 | RC_AA0646 27_at | EST: zf72b06.s1 Soares pineal gland N3HPG Homo sapiens cDNA clone 382451 3', mRNA sequence. (from Genbank) |
| 51 | Melanoma | 0.4460179 | 0.5455118 | 0.455106 | 0.32350677 | AA130284_a t | EST: zi29d04.r1 Soares pregnant uterus NbHPU Homo sapiens cDNA clone 503335 5', mRNA sequence. (from Genbank) |
| 52 | Melanoma | 0.4442079 | 0.5452916 | 0.454662 | 0.32271257 | RC_AA4212 64_at | EST: zu06b02.s1 Soares testis NHT Homo sapiens cDNA clone 731019 3', mRNA sequence. (from Genbank) |
| 53 | Melanoma | 0.4440554 | 0.5449394 | 0.454417 | 0.32191643 | W26187_at | 22a6 Human retina cDNA randomly primed sublibrary Homo sapiens cDNA, mRNA sequence. (from Genbank) |
| 54 | Melanoma | 0.4438705 | 0.5436677 | 0.45371 | 0.32120335 | RC_AA2584 82_s_at | Homo sapiens mRNA for zinc finger protein, complete cds |
| 55 | Melanoma | 0.439707 | 0.5432443 | 0.452255 | 0.3203532 | U78310_at | Homo sapiens pescadillo mRNA, complete cds |
| 56 | Melanoma | 0.4386779 | 0.5425503 | 0.451433 | 0.31955892 | W02818_s_at | EST: za05g06.r1 Soares melanocyte 2NbHM Homo sapiens cDNA clone 291706 5' similar to contains Alu repetitive element;contains L1.b1 L1 repetitive element:, mRNA sequence. (from Genbank) |
| 57 | Melanoma | 0.4341292 | 0.5415173 | 0.451146 | 0.31882584 | T36219_s_at | EST: EST98661 Homo sapiens cDNA 5' end similar to EST containing Alu repeat. (from Genbank) |
| 58 | Melanoma | 0.4324835 | 0.5402542 | 0.450399 | 0.31818065 | X58079_at | S100 alpha protein |
| 59 | Melanoma | 0.4321239 | 0.5394698 | 0.449929 | 0.31730375 | RC_AA4017 45_at | EST: zt66e05.s1 Soares testis NHT Homo sapiens cDNA clone 727328 3', mRNA sequence. (from Genbank) |
| 60 | Melanoma | 0.4320263 | 0.5383166 | 0.449344 | 0.31660905 | D13168_at | EDNRB Endothelin receptor type B |
| 61 | Melanoma | 0.4308492 | 0.5380696 | 0.44784 | 0.3159954 | RC_AA2879 08_at | EST: zs55a11.s1 NCI_CGAP_GCB1 Homo sapiens cDNA clone IMAGE:701372 3' similar to contains element L1 repetitive element :, mRNA sequence. (from Genbank) |
| 62 | Melanoma | 0.4290593 | 0.5378286 | 0.447596 | 0.31534612 | RC_AA2561 31_at | Glycophosphatidylinositol anchor attachment 1 |
| 63 | Melanoma | 0.424973 | 0.5371596 | 0.447096 | 0.31482854 | RC_AA4428 47_at | RAN binding protein 3 |
| 64 | Melanoma | 0.4194453 | 0.535934 | 0.446662 | 0.31423962 | RC_AA4603 10_at | EST: zx51d03.s1 Soares testis NHT Homo sapiens cDNA clone 795749 3' similar to contains Alu repetitive element:, mRNA sequence. (from Genbank) |
| 65 | Melanoma | 0.4170016 | 0.5356467 | 0.445747 | 0.31372064 | RC_AA2352 95_at | EST: zs37c01.s1 Soares NhHMPu S1 Homo sapiens cDNA clone 687360 3', mRNA sequence. (from Genbank) |

FIG. 8D

| | | | | | |
|---|---|---|---|---|---|
| 66 | Melanoma | 0.4167444 | 0.5353056 | 0.445407 | 0.31324902 | RC_D51069_f_at | CELL SURFACE GLYCOPROTEIN MUC18 PRECURSOR |
| 67 | Melanoma | 0.4152276 | 0.5339204 | 0.44503 | 0.31253928 | D11428_at | PMP22 Peripheral myelin protein 22 |
| 68 | Melanoma | 0.4130476 | 0.5326095 | 0.443933 | 0.31203723 | RC_AA2353 03_at | EST: zs37e07.s1 Soares NhHMPu S1 Homo sapiens cDNA clone 687396 3', mRNA sequence. (from Genbank) |
| 69 | Melanoma | 0.4115631 | 0.5320333 | 0.442317 | 0.3112076 | AA458761_f_at | Transcription factor AP-2 alpha (activating enhancer-binding protein 2 alpha) |
| 70 | Melanoma | 0.410688 | 0.5319473 | 0.441587 | 0.31057757 | AA455001_s_at | EST: zx99g10.r1 Soares NhHMPu S1 Homo sapiens cDNA clone 811938 5', mRNA sequence. (from Genbank) |
| 71 | Melanoma | 0.409856 | 0.5312983 | 0.441312 | 0.31013402 | AA455860_s_at | EST: aa01a12.r1 Soares NhHMPu S1 Homo sapiens cDNA clone 811966 5' similar to WP:C05C12.3 CE02966 :, mRNA sequence. (from Genbank) |
| 72 | Melanoma | 0.4038689 | 0.5305765 | 0.440882 | 0.30957222 | AA421370_a_t | EST: zu06e06.r1 Soares testis NHT Homo sapiens cDNA clone 731074 5' similar to contains MER17.12 MER17 repetitive element :, mRNA sequence. (from Genbank) |
| 73 | Melanoma | 0.4036421 | 0.5296056 | 0.440133 | 0.30920815 | U09877_at | Helicase-like protein (HLP) mRNA |
| 74 | Melanoma | 0.4031294 | 0.5289932 | 0.439779 | 0.3083087 | AA426304_r_at | EST: zw11g07.r1 Soares NhHMPu S1 Homo sapiens cDNA clone 769020 5', mRNA sequence. (from Genbank) |
| 75 | Melanoma | 0.4026932 | 0.5285742 | 0.439047 | 0.3080181894_at | RC_AA4183 | EST: zv92e06.s1 Soares NhHMPu S1 Homo sapiens cDNA clone 767266 3', mRNA sequence. (from Genbank) |
| 76 | Melanoma | 0.401972 | 0.5283733 | 0.438637 | 0.30749956 | AA004987_a_t | Homo sapiens HRIHFB2017 mRNA, partial cds |
| 77 | Melanoma | 0.4010919 | 0.5280425 | 0.438043 | 0.30669998 | RC_AA0701 84_at | Homo sapiens mRNA for KIAA0890 protein, complete cds |
| 78 | Melanoma | 0.4009986 | 0.5276282 | 0.437495 | 0.30664283 | U94354_at | Lunatic fringe (Drosophila) homolog |
| 79 | Melanoma | 0.4001854 | 0.5273011 | 0.437197 | 0.30591923 | RC_AA2325 35_s_at | EST: zr24a12.s1 Stratagene NT2 neuronal precursor 937230 Homo sapiens cDNA clone 664318 3', mRNA sequence. (from Genbank) |
| 80 | Melanoma | 0.3999188 | 0.5264503 | 0.436371 | 0.30538633 | RC_AA4518 36_at | EST: zx12e02.s1 Soares total fetus Nb2HF8 9w Homo sapiens cDNA clone 786266 3', mRNA sequence. (from Genbank) |
| 81 | Melanoma | 0.3971598 | 0.5243206 | 0.435826 | 0.3050198 | RC_AA1523 35_at | EST: zo29h12.s1 Stratagene colon (#937204) Homo sapiens cDNA clone 588359 3', mRNA sequence. (from Genbank) |
| 82 | Melanoma | 0.3968127 | 0.5232914 | 0.435029 | 0.30452297 | RC_AA2531 75_at | EST: zr53d12.s1 Soares NhHMPu S1 Homo sapiens cDNA clone 667127 3', mRNA sequence. (from Genbank) |
| 83 | Melanoma | 0.3963689 | 0.523262 | 0.434706 | 0.3040379 | X04297_at | RPS13 RNA polymerase II polypeptide B (140 kD) |
| 84 | Melanoma | 0.3962359 | 0.5231977 | 0.434226 | 0.3035176 | J03060_at | GBA Glucosidase, beta; acid (includes glucosylceramidase) |
| 85 | Melanoma | 0.3955722 | 0.5231722 | 0.433638 | 0.3031395 | AA296994_s_at | Homo sapiens mRNA for putative seven transmembrane domain protein |
| 86 | Melanoma | 0.3953007 | 0.5220988 | 0.433017 | 0.30270478 | RC_AA2848 79_at | Homo sapiens incomplete cDNA for a mutated allele of a myosin class I, myh-1c |

FIG. 8E

| # | | | | | | |
|---|---|---|---|---|---|---|
| 87 | Melanoma | 0.3948215 | 0.5214791 | 0.432391 | 0.302297777 | X81832_s_a t | GIPR Gastric inhibitory polypeptide receptor |
| 88 | Melanoma | 0.3932553 | 0.5212368 | 0.432374 | | RC_AA1212 57_at | EST: zn30f10.s1 Stratagene neuroepithelium NT2RAMI 937234 Homo sapiens cDNA clone 548971 3', mRNA sequence. (from Genbank) |
| 89 | Melanoma | 0.392646 | 0.5210271 | 0.431914 | 0.301946 | RC_AA1797 87_at | Homo sapiens mRNA for JM26 protein, complete CDS (clone LLOXNC01U138D3 (Baylor College)) |
| 90 | Melanoma | 0.3925528 | 0.5210066 | 0.431179 | 0.301144435 | AA488122_a t | Pyruvate dehydrogenase kinase, isoenzyme 2 |
| 91 | Melanoma | 0.3912602 | 0.5205634 | 0.431019 | 0.300089706 | RC_AA1349 65_i_at | EST: zo23g05.s1 Stratagene colon (#937204) Homo sapiens cDNA clone 587768 3', mRNA sequence. (from Genbank) |
| 92 | Melanoma | 0.3908869 | 0.5201041 | 0.430854 | 0.30004101 2 | Y07868_s_at | Pirin |
| 93 | Melanoma | 0.3905791 | 0.5197888 | 0.430382 | 0.299985258 | RC_AA4238 20_at | EST: zv33f03.s1 Soares ovary tumor NbHOT Homo sapiens cDNA clone 755453 3', mRNA sequence. (from Genbank) |
| 94 | Melanoma | 0.3902303 | 0.5193771 | 0.429868 | 0.299664414 | AA004231_a t | EST: zv92a03.r1 Soares fetal liver spleen 1NFLS S1 Homo sapiens cDNA clone 428716 5', mRNA sequence. (from Genbank) |
| 95 | Melanoma | 0.3900459 | 0.5191097 | 0.429493 | 0.29934284 | Y07867_at | Pirin, isolate 1 |
| 96 | Melanoma | 0.3882048 | 0.519003 | 0.429153 | 0.2989236 | RC_AA4243 98_at | EST: zv82e01.s1 Soares total fetus Nb2HF8 9w Homo sapiens cDNA clone 760152 3', mRNA sequence. (from Genbank) |
| 97 | Melanoma | 0.3862614 | 0.5188314 | 0.428891 | 0.2984418 | RC_AA2837 86_at | EST: zt18f01.s1 Soares ovary tumor NbHOT Homo sapiens cDNA clone 713497 3', mRNA sequence. (from Genbank) |
| 98 | Melanoma | 0.3858051 | 0.5151219 | 0.428515 | 0.2980733 | D38293_at | Clathrin-like protein |
| 99 | Melanoma | 0.3832441 | 0.5144354 | 0.428413 | 0.2976946 | RC_AA4256 37_at | Homo sapiens mRNA, complete cds, similar to yeast pre-mRNA splicing factors, Prp1/Zer1 and Prp6 |
| 100 | Melanoma | 0.3827256 | 0.5143108 | 0.42706 | 0.2972991 | L43964_at | PSEN2 Presenilin 2 (Alzheimer disease 4) |
| 101 | Melanoma | 0.3805508 | 0.5139538 | 0.426749 | 0.2968471 6 | AA036900_a t | EST: zk29e11.r1 Soares pregnant uterus NbHPU Homo sapiens cDNA clone 471980 5', mRNA sequence. (from Genbank) |
| 102 | Melanoma | 0.3808003 | 0.5136665 | 0.426617 | 0.2964576 8 | RC_AA2370 37_at | Transmembrane 7 superfamily member 1 (upregulated in kidney) |
| 103 | Melanoma | 0.3805362 | 0.5136277 | 0.426378 | 0.29601356 | RC_AA4017 21_s_at | EST: zf66c01.s1 Soares testis NHT Homo sapiens cDNA clone 727296 3', mRNA sequence. (from Genbank) |
| 104 | Melanoma | 0.3780731 | 0.5133986 | 0.426033 | 0.29548684 | RC_AA4266 53_at | EST: zv47h02.s1 Soares ovary tumor NbHOT Homo sapiens cDNA clone 756819 3', mRNA sequence. (from Genbank) |
| 105 | Melanoma | 0.3776017 | 0.511921 | 0.425021 | 0.295124143 | M29277_at | CELL SURFACE GLYCOPROTEIN MUC18 PRECURSOR |
| 106 | Melanoma | 0.3775896 | 0.511921 | 0.424411 | 0.29473567 | AA004333_a t | EST: zh91a01.r1 Soares fetal liver spleen 1NFLS S1 Homo sapiens cDNA clone 428616 5', mRNA sequence. (from Genbank) |
| 107 | Melanoma | 0.3769374 | 0.5117986 | 0.424289 | 0.29441956 | L76687_at-2 | Growth factor receptor-bound protein 14 |
| | | | | | 0.29400867 | | |

FIG. 8F

| # | Type | | | | | Accession | Description |
|---|---|---|---|---|---|---|---|
| 108 | Melanoma | 0.3769374 | 0.5117167 | 0.424075 | 0.29359615 | L76687_at | Grb14 mRNA |
| 109 | Melanoma | 0.3753549 | 0.5109736 | 0.423988 | 0.2933038 | GMCSF_at | No description for gene: GMCSF_at |
| 110 | Melanoma | 0.3750506 | 0.5108213 | 0.42332 | 0.29296982 | RC_AA0105 30_at | Human BAC clone GS025M02 from 7q21-q22 |
| 111 | Melanoma | 0.3748601 | 0.5107618 | 0.422989 | 0.29251185 | RC_AA4814 20_at | EST: zv06d09.s1 Soares NhHMPu S1 Homo sapiens cDNA clone 752849 3', mRNA sequence. (from Genbank) |
| 112 | Melanoma | 0.3745289 | 0.5107177 | 0.422572 | 0.29222527 | RC_AA2838 48_at | EST: zt19h06.s1 Soares ovary tumor NbHOT Homo sapiens cDNA clone 713627 3', mRNA sequence. (from Genbank) |
| 113 | Melanoma | 0.374063 | 0.5100325 | 0.42237 | 0.2918496 | M59916_at | SMPD1 Sphingomyelin phosphodiesterase 1, acid lysosomal (acid sphingomyelinase) |
| 114 | Melanoma | 0.3723273 | 0.5100312 | 0.421678 | 0.29150435 | RC_AA5997 64_at | EST: ag33a04.s1 Jia bone marrow stroma Homo sapiens cDNA clone 1091310 3', mRNA sequence. (from Genbank) |
| 115 | Melanoma | 0.3722669 | 0.5099505 | 0.421409 | 0.29100713 | RC_AA4300 36_at | EST: zw65f10.s1 Soares testis NHT Homo sapiens cDNA clone 781099 3', mRNA sequence. (from Genbank) |
| 116 | Melanoma | 0.3718415 | 0.5097877 | 0.42089 | 0.29059976 | RC_AA4032 96_at | EST: zt44c06.s1 Soares ovary tumor NbHOT Homo sapiens cDNA clone 725194 3', mRNA sequence. (from Genbank) |
| 117 | Melanoma | 0.3716345 | 0.5081443 | 0.420311 | 0.29022896 | AA002245_a t | KIAA0663 gene product |
| 118 | Melanoma | 0.3713444 | 0.507693 | 0.420057 | 0.28997773 | D88667_at | Cerebroside sulfotransferase |
| 119 | Melanoma | 0.370407 | 0.5074483 | 0.419427 | 0.28977737 | R74226_at | Homo sapiens mRNA for ATP synthase subunit e, complete cds |
| 120 | Melanoma | 0.3677971 | 0.507306 | 0.419076 | 0.28926557 | RC_AA2274 48_at | Homo sapiens mRNA for KIAA0456 protein, partial cds |
| 121 | Melanoma | 0.3670363 | 0.5069388 | 0.418741 | 0.2889833 | RC_AA0858 51_at | Homo sapiens clone 24658 mRNA sequence |
| 122 | Melanoma | 0.3650442 | 0.5068746 | 0.418516 | 0.2885621 | X99920_at | S100 calcium-binding protein A13 |
| 123 | Melanoma | 0.3642675 | 0.505545 | 0.418327 | 0.28820908 | U87593_f_at | Endogenous retrovirus clone P1.8 polymerase mRNA, partial cds |
| 124 | Melanoma | 0.3638577 | 0.5047969 | 0.417886 | 0.28795332 | RC_AA2364 81_at | EST: zr75d02.s1 Soares NhHMPu S1 Homo sapiens cDNA clone 669219 3' similar to gb:t.276670 Human Landsteiner-Wiener blood group glycoprotein (HUMAN);contains Alu repetitive element;, mRNA sequence. (from Genbank) |
| 125 | Melanoma | 0.3634589 | 0.5044948 | 0.417541 | 0.28764743 | U79775_at | D21S2056E, novel nuclear protein 1 |
| 126 | Melanoma | 0.3617002 | 0.5039112 | 0.417234 | 0.28727781 | RC_AA4185 45_at | EST: zv93b06.s1 Soares NhHMPu S1 Homo sapiens cDNA clone 767315 3', mRNA sequence. (from Genbank) |
| 127 | Melanoma | 0.3602343 | 0.5038836 | 0.417061 | 0.2869366 | M12529_at | APOE Apolipoprotein E |
| 128 | Melanoma | 0.3602291 | 0.5033534 | 0.416498 | 0.28666443 | Z48804_at | mRNA (ocular albinism type 1 related) |
| 129 | Melanoma | 0.3588951 | 0.5017493 | 0.416196 | 0.28645402 | AA010324_a t | Zi09c03.r1 Soares fetal liver spleen 1NFLS S1 Homo sapiens cDNA clone 430276 5', mRNA sequence. (from Genbank) |
| 130 | Melanoma | 0.3577149 | 0.501243 | 0.415909 | 0.2860714 | RC_AA4775 61_at | EST: zu41f11.s1 Soares ovary tumor NbHOT Homo sapiens cDNA clone 740589 3', mRNA sequence. (from Genbank) |

FIG. 8G

| | | | | | |
|---|---|---|---|---|---|
| 131 | Melanoma | 0.35631 | 0.5008451 | 0.28580204 | U48807_at | Dual specific protein phosphatase mRNA |
| 132 | Melanoma | 0.355712 | 0.5005862 | 0.28546867 | D31417_at | EST: Human fetal-lung cDNA 5'-end sequence, mRNA sequence. (from Genbank) |
| 133 | Melanoma | 0.3543488 | 0.5003932 | 0.28526393 | RC_AA0558 09_at | EST: zi76c05.s1 Stratagene colon (#937204) Homo sapiens cDNA clone 510536 3', mRNA sequence. (from Genbank) |
| 134 | Melanoma | 0.3535736 | 0.5000116 | 0.2849233 | RC_AA2279 41_s_at | EST: zr56c12.s1 Soares NhHMPu S1 Homo sapiens cDNA clone 667414 3', mRNA sequence. (from Genbank) |
| 135 | Melanoma | 0.3522672 | 0.499754 | 0.2845885 | AA248169_a t | EST: csg1676.seq,F Human fetal heart, Lambda ZAP Express Homo sapiens cDNA 5', mRNA sequence. (from Genbank) |
| 136 | Melanoma | 0.3519219 | 0.4987215 | 0.28434095 | U23070_at | Putative transmembrane protein (nma) mRNA |
| 137 | Melanoma | 0.3471006 | 0.4983218 | 0.28407452 | M59488_at | S-100 PROTEIN, BETA CHAIN |
| 138 | Melanoma | 0.3471006 | 0.4980723 | 0.2837967 | M59488_at-2 | S-100 PROTEIN, BETA CHAIN |
| 139 | Melanoma | 0.3456042 | 0.4979875 | 0.28338763 | RC_AA4183 98_at | Neuropilin 2 |
| 140 | Melanoma | 0.3434531 | 0.4978204 | 0.28307116 | RC_AA4211 39_at | EST: zf79c09.s1 Soares testis NHT Homo sapiens cDNA clone 728560 3', mRNA sequence. (from Genbank) |
| 141 | Melanoma | 0.3433566 | 0.4976554 | 0.28286344 | RC_AA4774 59_at | EST: zu44c08.s1 Soares ovary tumor NbHOT Homo sapiens cDNA clone 740846 3', mRNA sequence. (from Genbank) |
| 142 | Melanoma | 0.3413 | 0.4966058 | 0.28236294 | RC_AA4192 00_at | KIAA0475 gene product |
| 143 | Melanoma | 0.3411124 | 0.49639 | 0.2820291 | RC_AA4431 90_s_at | EST: zo36a01.s1 Stratagene endothelial cell 937223 Homo sapiens cDNA clone 588936 3' similar to SW:YBF7_YEAST P34222 HYPOTHETICAL 23.1 KD PROTEIN IN SHP1-SEC17 INTERGENIC REGION ;, mRNA sequence. (from Genbank) |
| 144 | Melanoma | 0.3408222 | 0.4961314 | 0.28174967 | RC_AA4248 13_at | EST: zw04b04.s1 Soares NhHMPu S1 Homo sapiens cDNA clone 768271 3', mRNA sequence. (from Genbank) |
| 145 | Melanoma | 0.3405738 | 0.4953041 | 0.2815182 | L20859_at | Leukemia virus receptor 1 (GLVR1) mRNA |
| 146 | Melanoma | 0.3378144 | 0.4952997 | 0.28123853 | RC_AA1341 38_at | EST: zl29g04.s1 Soares pregnant uterus NbHPU Homo sapiens cDNA clone 503382 3' similar to TR:G971709 G971709 LEUCINE AMINOPEPTIDASE ;, mRNA sequence. (from Genbank) |
| 147 | Melanoma | 0.3355292 | 0.4938434 | 0.28104937 | X76534_at | NMB Neuromedin B |
| 148 | Melanoma | 0.3353969 | 0.4937563 | 0.28088385 | RC_AA4033 12_s_at | EST: zl44f05.s1 Soares ovary tumor NbHOT Homo sapiens cDNA clone 725217 3', mRNA sequence. (from Genbank) |
| 149 | Melanoma | 0.3341294 | 0.4932703 | 0.28067264 | RC_AA4165 51_at | EST: zu05e01.s1 Soares testis NHT Homo sapiens cDNA clone 730968 3', mRNA sequence. (from Genbank) |
| 150 | Melanoma | 0.333278 | 0.4931972 | 0.28035738 | RC_AA2359 85_at | EST: zs41g07.s1 Soares NhHMPu S1 Homo sapiens cDNA clone 687804 3', mRNA sequence. (from Genbank) |

FIG. 8H

| # | Tissue | | | | | | Description |
|---|---|---|---|---|---|---|---|
| 151 | Melanoma | 0.3317794 | 0.4931915 | 0.4097 | 0.28017464 | H29683_at | EST: ym61b06.r1 Homo sapiens cDNA clone 52750 5' similar to contains Alu repetitive element;contains KER repetitive element ;. (from Genbank) |
| 152 | Melanoma | 0.3313957 | 0.4927765 | 0.409468 | 0.27992666 | AA303745_s_at | TAP binding protein (tapasin) |
| 153 | Melanoma | 0.3313865 | 0.4919635 | 0.408626 | 0.27956122 | RC_AA1603_at | EST: zo56d04.s1 Stratagene pancreas (#937208) Homo sapiens cDNA clone 590887 3', mRNA sequence. (from Genbank) |
| 154 | Melanoma | 0.3308183 | 0.49153 | 0.408344 | 0.27936518 | X94628_rna1_s_at | MeCP-2 gene |
| 155 | Melanoma | 0.3296454 | 0.4911068 | 0.40788 | 0.2790183 | RC_AA4187_40_at | EST: zv98e10.s1 Soares NhHMPu S1 Homo sapiens cDNA clone 767850 3', mRNA sequence. (from Genbank) |
| 156 | Melanoma | 0.3287473 | 0.490314 | 0.40767 | 0.27885668 | RC_AA4565_3_s_at | Human PL6 protein (PL6) mRNA, complete cds |
| 157 | Melanoma | 0.3276548 | 0.4897965 | 0.407292 | 0.27859926 | RC_AA2365_16_at | 33 kDa transcriptional co-activator |
| 158 | Melanoma | 0.3271254 | 0.4895437 | 0.406972 | 0.27829015 | X97230_f_at | NK receptor, clone library 4M1#6 |
| 159 | Melanoma | 0.3266627 | 0.4894057 | 0.406562 | 0.2779128 | U65092_at | Melanocyte-specific gene 1 (msg1) mRNA |
| 160 | Melanoma | 0.3243132 | 0.4892736 | 0.406346 | 0.27751556 | H21601_at | EST: yl33e08.r1 Homo sapiens cDNA clone 160070 5'. (from Genbank) |
| 161 | Melanoma | 0.3239197 | 0.4891115 | 0.405955 | 0.27727428 | RC_AA5989_75_at | EST: ae40c09.s1 Gessler Wilms tumor Homo sapiens cDNA clone 898288 3', mRNA sequence. (from Genbank) |
| 162 | Melanoma | 0.3231382 | 0.48899 | 0.405499 | 0.2771026 | M58297_at | ZNF42 Zinc finger protein 42 (myeloid-specific retinoic acid-responsive) |
| 163 | Melanoma | 0.3230813 | 0.4888969 | 0.405458 | 0.27676967 | RC_AA2788_43_at | EST: zs80h04.s1 NCI_CGAP_GCB1 Homo sapiens cDNA clone IMAGE:703831 3', mRNA sequence. (from Genbank) |
| 164 | Melanoma | 0.3228191 | 0.4886015 | 0.405084 | 0.27630618 | N89563_s_at | EST: HFBEST-40 Human fetal brain QBoqin2 Homo sapiens cDNA, mRNA sequence. (from Genbank) |
| 165 | Melanoma | 0.3225167 | 0.4875982 | 0.404974 | 0.2760943 | X13589_at | CYP19 Cytochrome P450, subfamily XIX (aromatization of androgens) |
| 166 | Melanoma | 0.3222618 | 0.487021 | 0.404547 | 0.27590296 | RC_AA4783_00_at | CD39-like 2 |
| 167 | Melanoma | 0.3220997 | 0.4865582 | 0.404442 | 0.27572575 | U19147_s_at | GAGE4 G antigen 6 (GAGE-6) |
| 168 | Melanoma | 0.3219174 | 0.4859242 | 0.404396 | 0.2753855 | L03411_s_at | RD Radin blood group |
| 169 | Melanoma | 0.3211143 | 0.4854832 | 0.403627 | 0.27515632 | AA477018_s_at | EST: zu38a10.r1 Soares ovary tumor NbHOT Homo sapiens cDNA clone 740250 5', mRNA sequence. (from Genbank) |
| 170 | Melanoma | 0.3204015 | 0.4851222 | 0.403513 | 0.27489066 | M77348_rna1_s_at | Pmel 17 mRNA |

FIG. 8I

| # | Type | | | | | | Description |
|---|---|---|---|---|---|---|---|
| 171 | Melanoma | 0.3162881 | 0.4847945 | 0.403227 | 0.274610430 3_at | RC_AA1521 | Human Chromosome 16 BAC clone CIT987SK-A-735G6 |
| 172 | Melanoma | 0.3161022 | 0.4845065 | 0.402744 | 0.27437636 X51420_at | | TYRP1 Tyrosinase-related protein 1 |
| 173 | Melanoma | 0.3158724 | 0.4844235 | 0.402563 | 0.27414286 46_at | RC_AA6204 | RecQ protein-like 4 |
| 174 | Melanoma | 0.3158313 | 0.4843504 | 0.402373 | 0.27379596 M68520_at | | CDK2 Cyclin-dependent kinase 2 |
| 175 | Melanoma | 0.3154054 | 0.4843456 | 0.40202 | 0.27357447 U65011_at | | Preferentially expressed antigen of melanoma (PRAME) mRNA |
| 176 | Melanoma | 0.3137979 | 0.4842212 | 0.401845 | 0.27320093 R56678_at | | EST: yi04d08.r1 Homo sapiens cDNA clone 138255 5' similar to contains Alu repetitive element;. (from Genbank) |
| 177 | Melanoma | 0.3136749 | 0.48422 | 0.401509 | 0.27283943 60_r_at | RC_AA0555 | EST: zf21f02.s1 Soares fetal heart NbHH19W Homo sapiens cDNA clone 377595 3', mRNA sequence. (from Genbank) |
| 178 | Melanoma | 0.3130738 | 0.4840651 | 0.401045 | 0.27262697 | M17446_s_a t | FGF4 Fibroblast growth factor 4 (heparin secretory transforming protein 1, Kaposi sarcoma oncogene) |
| 179 | Melanoma | 0.3125835 | 0.4836405 | 0.400938 | 0.27246743 56_at | RC_AA4026 | EST: zu49e06.s1 Soares ovary tumor NbHOT Homo sapiens cDNA clone 741346 3', mRNA sequence. (from Genbank) |
| 180 | Melanoma | 0.3121697 | 0.4835044 | 0.4007 | 0.2721903 52_at | RC_AA4014 | EST: zu56e12.s1 Soares ovary tumor NbHOT Homo sapiens cDNA clone 742030 3', mRNA sequence. (from Genbank) |
| 181 | Melanoma | 0.3119107 | 0.4832527 | 0.4007 | 0.2720382 57_at | RC_AA4610 | Nuclear localization signal deleted in velocardiofacial syndrome |
| 182 | Melanoma | 0.3114898 | 0.4824477 | 0.400583 | 0.27179894 41_f_at | RC_AA4238 | Homo sapiens clone 23856 unknown mRNA, partial cds |
| 183 | Melanoma | 0.3114713 | 0.4821109 | 0.400356 | 0.27151352 N36588_at | | Ubiquitin-conjugating enzyme E2I (homologous to yeast UBC9) |
| 184 | Melanoma | 0.3112968 | 0.4813416 | 0.400297 | 0.27124965 t | AA293400_a | EST: zf53e06.r1 Soares ovary tumor NbHOT Homo sapiens cDNA clone 726082 5', mRNA sequence. (from Genbank) |
| 185 | Melanoma | 0.3109159 | 0.4810538 | 0.399981 | 0.27097747 79_at | RC_AA2531 | EST: zr53e08.s1 Soares NhHMPu S1 Homo sapiens cDNA clone 667142 3', mRNA sequence. (from Genbank) |
| 186 | Melanoma | 0.3106763 | 0.4807326 | 0.399862 | 0.27065808 D31120_at | | Clathrin adaptor complex 1, sigma 1B subunit |
| 187 | Melanoma | 0.3088199 | 0.4806334 | 0.39943 | 0.27043283 R13638_at | | EST: yf60d01.r1 Homo sapiens cDNA clone 26852 5'. (from Genbank) |
| 188 | Melanoma | 0.3087396 | 0.4803071 | 0.393364 | 0.27012375 Y12065_at | | Homo sapiens mRNA for nucleolar protein hNop56 |
| 189 | Melanoma | 0.308367 | 0.4802392 | 0.398812 | 0.26989028 U18009_at | | Chromosome 17q21 mRNA clone LF113 |
| 190 | Melanoma | 0.3083558 | 0.4802286 | 0.398628 | 0.2695829 U40380_at | | PSEN1 Presenilin 1 (Alzheimer disease 3) |
| 191 | Melanoma | 0.3079231 | 0.4800832 | 0.394436 | 0.26937652 18_at | RC_AA2794 | EST: zs85d07.s1 NCI_CGAP_GCB1 Homo sapiens cDNA clone IMAGE:704269 3', mRNA sequence. (from Genbank) |
| 192 | Melanoma | 0.3076862 | 0.4788971 | 0.398112 | 0.26913765 X04143_at | | BGLAP Bone gamma-carboxyglutamate (gla) protein (osteocalcin) |
| 193 | Melanoma | 0.3076298 | 0.4788971 | 0.397967 | 0.26890305 X72304_at | | CORTICOTROPIN RELEASING FACTOR RECEPTOR 1 PRECURSOR |
| 194 | Melanoma | 0.3063073 | 0.4778435 | 0.397748 | 0.26872072 HT4261_at | HG3991- | Cpg-Enriched Dna, Clone E18 |

FIG. 8J

| # | | | | | | |
|---|---|---|---|---|---|---|
| 195 | Melanoma | 0.3061732 | 0.4774236 | 0.397657 | 0.26828206 | M62895_s_a t | Annexin II (lipocortin II) pseudogene 2 |
| 196 | Melanoma | 0.3059957 | 0.4773791 | 0.397181 | 0.26794228 | M84349_at | CD59 CD59 antigen p18-20 (antigen identified by monoclonal antibodies 16.3A5, EJ16, EJ30, EL32 and G344) |
| 197 | Melanoma | 0.30579 | 0.4772935 | 0.396782 | 0.26770937 | RC_AA1518 82_at | Human DNA sequence from clone 149A16 on chromosome 22q12-13. Contains an IGLC (Immunoglobulin Lambda Chain C) pseudogene, the RFPL3 and RFPL3S genes for Ret finger protein-like 3 and Ret finger protein-like 3 antisense respectively, a gene for a novel Immunoglobulin Lambda Chain V family protein, a novel gene for a protein similar to mouse RGDS (RALGDS, RALGEF, Guanine Nucleotide Dissociation Stimulator A) and rabbit oncogene RSC, a novel gene for the human ortholog of worm F16A11.2 and bacterial and archea-bacterial predicted proteins, a novel gene for a protein similar to BPI (Bacterial Permeability-Increasing Protein) and rabbit LBP (Liposaccharide-Binding Protein), and a the 5' part of a novel gene. Contains ESTs, STSs, GSSs, genomic marker D22S1175, a ca repeat polymorphism and putative CpG islands |
| 198 | Melanoma | 0.303889 | 0.4772527 | 0.396745 | 0.26755148 | RC_AA4279 25_s_at | EST: zw50e01.s1 Soares total fetus Nb2HF8 9w Homo sapiens cDNA clone 773496 3', mRNA sequence. (from Genbank) |
| 199 | Melanoma | 0.3037446 | 0.4769441 | 0.396347 | 0.26733598 | AA449637_a t | EST: zx08f09.r1 Soares total fetus Nb2HF8 9w Homo sapiens cDNA clone 785897 5', mRNA sequence. (from Genbank) |
| 200 | Melanoma | 0.3023086 | 0.4766648 | 0.396134 | 0.2670427 | N98660_at | EST: yy66c03.r1 Homo sapiens cDNA clone 278500 5'. (from Genbank) |
| 201 | Melanoma | 0.3021154 | 0.4764675 | 0.396087 | 0.26681006 | U18934_at | TYRO3 Receptor protein-tyrosine kinase sky |
| 202 | Melanoma | 0.3018292 | 0.4759041 | 0.395747 | 0.26654088 | RC_AA4314 64_at | EST: zw70g08.s1 Soares testis NHT Homo sapiens cDNA clone 781598 3', mRNA sequence. (from Genbank) |
| 203 | Melanoma | 0.3017628 | 0.4759041 | 0.395466 | 0.2662759 | RC_AA4970 31_at | EST: ae32h12.s1 Gessler Wilms tumor Homo sapiens cDNA clone 897575 3', mRNA sequence. (from Genbank) |
| 204 | Melanoma | 0.3012943 | 0.4754742 | 0.395235 | 0.2659247 | M30625_s_a t | Dopamine D2 receptor, mRNA |
| 205 | Melanoma | 0.3006956 | 0.4754098 | 0.394916 | 0.26565508 | U19145_s_a t | G antigen 4 |
| 206 | Melanoma | 0.3002045 | 0.4754098 | 0.394844 | 0.2654657 | RC_AA0354 57_at | EST: zk27h06.s1 Soares pregnant uterus NbHPU Homo sapiens cDNA clone 471803 3', mRNA sequence. (from Genbank) |
| 207 | Melanoma | 0.2998828 | 0.4746822 | 0.394738 | 0.26525465 | AA009913_a t | Diptheria toxin resistance protein required for diphthamide biosynthesis (Saccharomyces)-like 2 |
| 208 | Melanoma | 0.2998321 | 0.4742857 | 0.394552 | 0.26504958 | RC_AA1350 95_at | Homo sapiens Sox-like transcriptional factor mRNA, complete cds |
| 209 | Melanoma | 0.2996786 | 0.4739449 | 0.394331 | 0.26484486 | U33822_at | Tax1-binding protein TXBP181 mRNA |

FIG. 8K

| # | Type | | | | ID | Gene | Description |
|---|---|---|---|---|---|---|---|---|
| 210 | Melanoma | 0.2994813 | 0.4736541 | 0.394032 | 0.26459083 | L06419_at | PLOD | Lysyl hydroxylase |
| 211 | Melanoma | 0.2973461 | 0.4731139 | 0.39329 | 0.2644364 | X53331_at | MGP | Matrix protein gla |
| 212 | Melanoma | 0.2971224 | 0.4728627 | 0.393024 | 0.26415023 | RC_AA4769 37_s_at | | EST: zu38d11.s1 Soares ovary tumor NbHOT Homo sapiens cDNA clone 740277 3', mRNA sequence. (from Genbank) |
| 213 | Melanoma | 0.296005 | 0.4726846 | 0.392945 | 0.2639375 | RC_AA2590 62_at | | EST: zs30h07.s1 NCI_CGAP_GCB1 Homo sapiens cDNA clone IMAGE:686749 3', mRNA sequence. (from Genbank) |
| 214 | Melanoma | 0.2957572 | 0.4724444 | 0.392807 | 0.26372978 | AA295819_s_at | | EST: EST101121 Thymus III Homo sapiens cDNA 5' end, mRNA sequence. (from Genbank) |
| 215 | Melanoma | 0.2953342 | 0.472102 | 0.392563 | 0.26352856 | AA482319_f_at | | EST: ab15c03.r1 Stratagene lung (#937210) Homo sapiens cDNA clone 840868 5', mRNA sequence. (from Genbank) |
| 216 | Melanoma | 0.2944885 | 0.4720918 | 0.39223 | 0.26317424 | RC_AA6095 92_at | | EST: af15d11.s1 Soares testis NHT Homo sapiens cDNA clone 1031733 3', mRNA sequence. (from Genbank) |
| 217 | Melanoma | 0.2933273 | 0.471941 | 0.39188 | 0.26305094 | L06845_at | CARS | Cysteinyl-tRNA synthetase |
| 218 | Melanoma | 0.2927195 | 0.4717935 | 0.391524 | 0.26281342 | W31698_at | | Zinc finger protein 42 (myeloid-specific retinoic acid-responsive) |
| 219 | Melanoma | 0.2920193 | 0.4717935 | 0.391505 | 0.26260287 | RC_AA4373 23_at | | EST: zv62f11.s1 Soares testis NHT Homo sapiens cDNA clone 758253 3', mRNA sequence. (from Genbank) |
| 220 | Melanoma | 0.2915961 | 0.471613 | 0.391455 | 0.26240373 | X82153_at | | CATHEPSIN K PRECURSOR |
| 221 | Melanoma | 0.2912415 | 0.471531 | 0.391322 | 0.26232177 | AA074897_a_t | | Zm85a05.r1 Stratagene ovarian cancer (#937219) Homo sapiens cDNA clone 544688 5' similar to SW:ANRE_MOUSE P15267 KIDNEY ANDROGEN-REGULATED PROTEIN PRECURSOR.; mRNA sequence. (from Genbank) |
| 222 | Melanoma | 0.2911212 | 0.4715292 | 0.391205 | 0.26217356 | RC_AA2851 62_at | | EST: zs48e06.s1 NCI_CGAP_GCB1 Homo sapiens cDNA clone IMAGE:700738 3', mRNA sequence. (from Genbank) |
| 223 | Melanoma | 0.2901944 | 0.4713063 | 0.391133 | 0.26193413 | D70830_at | Doc2 beta | |
| 224 | Melanoma | 0.2896082 | 0.4704381 | 0.390977 | 0.26165384 | D81308_s_at | | Homo sapiens mRNA expressed in placenta |
| 225 | Melanoma | 0.2889461 | 0.4703044 | 0.39075 | 0.2613345 | X99374_s_a_t | | Fertilin beta mRNA |
| 226 | Melanoma | 0.2887219 | 0.4702158 | 0.390451 | 0.26118717 | RC_AA4965 69_at | | EST: zv38h01.s1 Soares ovary tumor NbHOT Homo sapiens cDNA clone 755953 3', mRNA sequence. (from Genbank) |
| 227 | Melanoma | 0.2885264 | 0.4697903 | 0.390328 | 0.26097096 | RC_AA0252 at | | EST: ze74d01.s1 Soares fetal heart NbHH19W Homo sapiens cDNA clone 364705 3', mRNA sequence. (from Genbank) |
| 228 | Melanoma | 0.2877094 | 0.4693813 | 0.389878 | 0.26085648 | RC_AA2362 75_at | | EST: zr54e12.s1 Soares NhHMPu S1 Homo sapiens cDNA clone 667246 3', mRNA sequence. (from Genbank) |
| 229 | Melanoma | 0.2874858 | 0.4693238 | 0.389578 | 0.26062638 | S78569_at | LAMA4 | Laminin, alpha 4 |
| 230 | Melanoma | 0.2872049 | 0.4693238 | 0.389368 | 0.26041773 | RC_AA2348 99_at | | EST: zs36c07.s1 Soares NhHMPu S1 Homo sapiens cDNA clone 687276 3', mRNA sequence. (from Genbank) |
| 231 | Melanoma | 0.2871278 | 0.4683735 | 0.389188 | 0.26013744 | HG3104-HT3280_at | | Serine Protease Met1 |

FIG. 8L

| | | | | | | |
|---|---|---|---|---|---|---|
| 232 | Melanoma | 0.2867015 | 0.4683654 | 0.388866 | 0.25984997 | AA459542_s_at | Regulatory factor X-associated ankyrin-containing protein |
| 233 | Melanoma | 0.2866696 | 0.4683651 | 0.388669 | 0.25963005 | D50550_at | LLGL mRNA |
| 234 | Melanoma | 0.2853845 | 0.4681579 | 0.388501 | 0.25937495 | AA147543_a_t | Immunoglobulin superfamily, member 3 |
| 235 | Melanoma | 0.285368 | 0.4680657 | 0.388011 | 0.25924543 | W26116_s_at | Human DNA sequence from clone 149A16 on chromosome 22q12-13. Contains an IGLC (Immunoglobulin Lambda Chain C) pseudogene, the RFPL3 and RFPL3S genes for Ret finger protein-like 3 and Ret finger protein-like 3 antisense respectively, a gene for a novel Immunoglobulin Lambda Chain V family protein, a novel gene for a protein similar to mouse RGDS (RALGDS, RALGEF, Guanine Nucleotide Dissociation Stimulator A) and rabbit oncogene RSC, a novel gene for the human ortholog of worm F16A11.2 and bacterial and archea-bacterial predicted proteins, a novel gene for a protein similar to BPI (Bacterial Permeability-Increasing Protein) and rabbit LBP (Liposaccharide-Binding Protein), and a the 5' part of a novel gene. Contains ESTs, STSs, GSSs, genomic marker D22S1175, a ca repeat polymorphism and putative CpG islands |
| 236 | Melanoma | 0.2853295 | 0.467448 | 0.387737 | 0.25899255 | RC_AA4478 02_at | EST: aa20h07.s1 Soares NhHMPu S1 Homo sapiens cDNA clone 813853 3', mRNA sequence. (from Genbank) |
| 237 | Melanoma | 0.2845084 | 0.4671087 | 0.387638 | 0.25880787 | RC_AA0318 14_at | EST: zk17g04.s1 Soares pregnant uterus NbHPU Homo sapiens cDNA clone 470838 3', mRNA sequence. (from Genbank) |
| 238 | Melanoma | 0.2840831 | 0.4669968 | 0.387605 | 0.2586726 | AA306479_a_t | EST: EST177452 Jurkat T-cells VI Homo sapiens cDNA 5' end, mRNA sequence. (from Genbank) |
| 239 | Melanoma | 0.2838782 | 0.4667283 | 0.3876 | 0.25841814 | U80987_s_a_t | Transcription factor TBX5 mRNA |
| 240 | Melanoma | 0.2821052 | 0.4665916 | 0.387166 | 0.25813666 | AA455318_a_t | EST: aa30b07.r1 NCI_CGAP_GCB1 Homo sapiens cDNA clone IMAGE:814741 5', mRNA sequence. (from Genbank) |
| 241 | Melanoma | 0.281963 | 0.4660838 | 0.387008 | 0.25799898 | RC_AA4005 13_i_at | H.sapiens mRNA for GAR22 protein |
| 242 | Melanoma | 0.28163 | 0.466047 | 0.38668 | 0.25776437 | AA42274_a_t | EST: zv54a06.r1 Soares testis NHT Homo sapiens cDNA clone 757426 5', mRNA sequence. (from Genbank) |
| 243 | Melanoma | 0.28135241 | 0.4659845 | 0.386425 | 0.25757813 | HG4518-HT4921_at | Transcription Factor Btf3 Homolog (Gb:M90355) |
| 244 | Melanoma | 0.2810766 | 0.4653387 | 0.386154 | 0.25744718 | M21388_at | Unproductively rearranged Ig mu-chain mRNA V-region (VD), 5' end, clone mu-3A1A |
| 245 | Melanoma | 0.2805463 | 0.4653033 | 0.385898 | 0.25730935 | M60502_at | Filaggrin |
| 246 | Melanoma | 0.2797754 | 0.4651707 | 0.385693 | 0.25711423 | RC_AA5996 83_at | EST: ag10f09.s1 Gessler Wilms tumor Homo sapiens cDNA clone 1069961 3', mRNA sequence. (from Genbank) |

FIG. 8M

| | | | | | |
|---|---|---|---|---|---|
| 247 | Melanoma | 0.2797386 | 0.4651313 | 0.385388 | 0.25697386 | RC_AA4178 76_at | EST: zv05f04.s1 Soares NhHMPu S1 Homo sapiens cDNA clone 752767 3', mRNA sequence. (from Genbank) |
| 248 | Melanoma | 0.2792157 | 0.4649149 | 0.385264 | 0.2567826 | AA027760_a t | EST: HPLA_CCLEE_40f6ar HPLA CCLee Homo sapiens cDNA, mRNA sequence. (from Genbank) |
| 249 | Melanoma | 0.2789914 | 0.4647157 | 0.385119 | 0.25657552 | RC_AA4565 88_at | Homo sapiens BC-2 protein mRNA, complete cds |
| 250 | Melanoma | 0.2788058 | 0.4643362 | 0.385085 | 0.25627553 | X60955_s_a t | TYRP1 Tyrosinase-related protein 1 |
| 251 | Melanoma | 0.2780696 | 0.4642367 | 0.384821 | 0.2561592 | AA071223_a t | EST: zf79f10.r1 Soares pineal gland N3HPG Homo sapiens cDNA clone 383179 5', mRNA sequence. (from Genbank) |
| 252 | Melanoma | 0.2779724 | 0.464198 | 0.38462 | 0.25578913 | X69090_at | Skeletal muscle 190kD protein |
| 253 | Melanoma | 0.277904 | 0.4641301 | 0.384506 | 0.2555034 | AA458761_i_at | Transcription factor AP-2 alpha (activating enhancer-binding protein 2 alpha) |
| 254 | Melanoma | 0.277324 | 0.464048 | 0.384222 | 0.25534534 | U24153_at | P21-activated protein kinase (Pak2) gene |
| 255 | Melanoma | 0.2768664 | 0.4636004 | 0.384082 | 0.25520235 | RC_AA4344 41_at | Frizzled (Drosophila) homolog 7 |
| 256 | Melanoma | 0.2767919 | 0.4631521 | 0.383869 | 0.25498685 | HG415-HT415_at | Lectin, Galactoside-Binding, Soluble, 2 |
| 257 | Melanoma | 0.2767766 | 0.4628518 | 0.383559 | 0.25480798 | X78712_at | GKP2 Glycerol kinase 2 (testis specific) |
| 258 | Melanoma | 0.2766601 | 0.4626747 | 0.3833334 | 0.2546019 | RC_AA0293 56_at | EST: zk12d10.s1 Soares pregnant uterus NbHPU Homo sapiens cDNA clone 470323 3', mRNA sequence. (from Genbank) |
| 259 | Melanoma | 0.276047 | 0.4626548 | 0.383275 | 0.25424954 | RC_AA1310 84_at | Procollagen-lysine, 2-oxoglutarate 5-dioxygenase 3 |
| 260 | Melanoma | 0.2750642 | 0.4625938 | 0.383256 | 0.25412503 | X57206_at | ITPKB Inositol 1,4,5-trisphosphate 3-kinase B |
| 261 | Melanoma | 0.2745334 | 0.4623594 | 0.383076 | 0.2539976 | RC_AA4647 41_at | EST: zx86b07.s1 Soares ovary tumor NbHOT Homo sapiens cDNA clone 810613 3', mRNA sequence. (from Genbank) |
| 262 | Melanoma | 0.2743796 | 0.4622538 | 0.382908 | 0.25381115 | D10704_at | CHK Choline kinase |
| 263 | Melanoma | 0.2741447 | 0.4618519 | 0.3829901 | 0.25366384 | AB002303_a t | KIAA0305 gene product |
| 264 | Melanoma | 0.2741037 | 0.4617618 | 0.382635 | 0.25348043 | D50402_at | NRAMP1 Natural resistance-associated macrophage protein 1 (might include Leishmaniasis) |
| 265 | Melanoma | 0.2733528 | 0.4617061 | 0.382284 | 0.25333365 | RC_AA4355 39_at | Homo sapiens chromosome 19, cosmid F23858 |
| 266 | Melanoma | 0.273051 | 0.4612471 | 0.382142 | 0.25315657 | RC_AA2360 37_at | EST: zs05g08.s1 NCI_CGAP_GCB1 Homo sapiens cDNA clone IMAGE:684350 3', mRNA sequence. (from Genbank) |
| 267 | Melanoma | 0.2724566 | 0.4606605 | 0.382086 | 0.25293934 | AA036794_a t | EST: zk29a01.r1 Soares pregnant uterus NbHPU Homo sapiens cDNA clone 471912 5' similar to WP:T20B12.3 CE01409 ;, mRNA sequence. (from Genbank) |
| 268 | Melanoma | 0.2721901 | 0.4605867 | 0.38208 | 0.25271353 | X62654_rna 1_at | ME491 gene extracted from H.sapiens gene for Me491/CD63 antigen |

FIG. 8N

| | | | | | | |
|---|---|---|---|---|---|---|
| 269 | Melanoma | 0.27213322 | 0.46013590 | 0.381833 | 0.2526074 | U14550_at | Sialyltransferase SThM (sthm) mRNA |
| 270 | Melanoma | 0.27202240 | 0.46012150 | 0.38171 | 0.25244993 | RC_AA2937 19_at | EST: zt55h03.s1 Soares ovary tumor NbHOT Homo sapiens cDNA clone 726293 3', mRNA sequence. (from Genbank) |
| 271 | Melanoma | 0.27136780 | 0.46001590 | 0.381668 | 0.25221696 | W48808_s_at | EST: zc44h06.r1 Soares senescent fibroblasts NbHSF Homo sapiens cDNA clone 325211 5' similar to PIR:A55093 A55093 fatty acid transport protein precursor - mouse ;, mRNA sequence. (from Genbank) |
| 272 | Melanoma | 0.270191 | 0.45990430 | 0.381624 | 0.25203478 | RC_AA4888 5_at | EST: aa55f10.s1 NCI_CGAP_GCB1 Homo sapiens cDNA clone IMAGE:824875 3', mRNA sequence. (from Genbank) |
| 273 | Melanoma | 0.26989030 | 0.45987710 | 0.381368 | 0.25180337 | U44105_at | Rab9 expressed pseudogene mRNA |
| 274 | Melanoma | 0.26919140 | 0.45983 | 0.381324 | 0.25166315 | U62293_rna 1_s_at | LIMK1 gene (LIM-kinase1) extracted from Human LIM-kinase1 and alternatively spliced LIM-kinase1 (LIMK1) gene |
| 275 | Melanoma | 0.26877030 | 0.45971 | 0.381164 | 0.25139314 | RC_AA4516 80_at | Human DNA sequence from clone 1409 on chromosome Xp11.1-11.4. Contains a Inter-Alpha-Trypsin Inhibitor Heavy Chain LIKE gene, a alternatively spliced Melanoma-Associated Antigen MAGE LIKE gene and a 6-Phosphofructo-2-kinase (Fructose-2,6-bisphosphatase) LIKE pseudogene. Contains ESTs, STSs and genomic marker DXS8032 |
| 276 | Melanoma | 0.26692150 | 0.45964540 | 0.380814 | 0.25123549 | RC_AA4243 31_at | Homo sapiens ST15 mRNA, complete cds |
| 277 | Melanoma | 0.26677390 | 0.459614 | 0.380814 | 0.25109968 | RC_AA1560 97_s_at | EST: zo45d03.s1 Stratagene endothelial cell 937223 Homo sapiens cDNA clone 589829 3', mRNA sequence. (from Genbank) |
| 278 | Melanoma | 0.26646830 | 0.45944240 | 0.380406 | 0.25084763 | RC_AA3402 93_at | EST: EST45737 Fetal kidney III Homo sapiens cDNA 3' end, mRNA sequence. (from Genbank) |
| 279 | Melanoma | 0.26613120 | 0.45940320 | 0.380341 | 0.25071457 | W26928_at | Homo sapiens mRNA for ARPP-19 protein |
| 280 | Melanoma | 0.266076 | 0.45908680 | 0.380248 | 0.25044662 | RC_AA1428 49_at | EST: zl40h02.s1 Soares pregnant uterus NbHPU Homo sapiens cDNA clone 504435 3', mRNA sequence. (from Genbank) |
| 281 | Melanoma | 0.26546030 | 0.45888670 | 0.3800017 | 0.25038958 | U93867_at-2 | Human RNA polymerase III subunit (RPC62) mRNA, complete cds |
| 282 | Melanoma | 0.26546030 | 0.45878460 | 0.379651 | 0.25019650 | U93867_at | RNA polymerase III subunit (RPC62) mRNA |
| 283 | Melanoma | 0.264911 | 0.45861620 | 0.379577 | 0.25000017 | RC_AA4366 56_at | EST: zv57c04.s1 Soares testis NHT Homo sapiens cDNA clone 757734 3', mRNA sequence. (from Genbank) |
| 284 | Melanoma | 0.26441350 | 0.45822530 | 0.379454 | 0.24979512 | RC_AA4249 52_s_at | EST: zw03g12.s1 Soares NhHMPu S1 Homo sapiens cDNA clone 768262 3', mRNA sequence. (from Genbank) |
| 285 | Melanoma | 0.26426820 | 0.45812520 | 0.379378 | 0.24970591 | RC_AA5996 29_at | EST: ag10a01.s1 Gessler Wilms tumor Homo sapiens cDNA clone 1069896 3', mRNA sequence. (from Genbank) |
| 286 | Melanoma | 0.26342390 | 0.45801950 | 0.379125 | 0.24948074 | RC_AA4771 06_s_at | D21S2056E, novel nuclear protein 1 |
| 287 | Melanoma | 0.26332510 | 0.45785610 | 0.379039 | 0.24925558 | M33374_at | Cell adhesion protein (SQM1) mRNA |

FIG. 80

| # | | | | | | |
|---|---|---|---|---|---|---|
| 288 | Melanoma | 0.2618309 | 0.4577746 | 0.378884 | 0.24910279 | RC_AA4589 52_at | EST: zx88e03.s1 Soares ovary tumor NbHOT Homo sapiens cDNA clone 810844 3'; mRNA sequence. (from Genbank) |
| 289 | Melanoma | 0.260758 | 0.4576396 | 0.378808 | 0.24896085 | RC_AA4878 79_at | EST: ab12a04.s1 Stratagene lung (#937210) Homo sapiens cDNA clone 840558 3', mRNA sequence. (from Genbank) |
| 290 | Melanoma | 0.260383 | 0.4576065 | 0.378552 | 0.24870886 | L76927_rna1 _at | Galactokinase (GALK1) gene |
| 291 | Melanoma | 0.2601063 | 0.4574878 | 0.378338 | 0.24848868 | RC_AA0547 04_at | EST: zk69h02.s1 Soares pregnant uterus NbHPU Homo sapiens cDNA clone 488115 3', mRNA sequence. (from Genbank) |
| 292 | Melanoma | 0.2592943 | 0.4574501 | 0.37823 | 0.248392 | L44367_at | EST: Homo sapiens thymus mRNA (randomly primed, normalized), single-pass sequence, mRNA sequence. (from Genbank) |
| 293 | Melanoma | 0.2592537 | 0.4574042 | 0.377888 | 0.248202 | RC_AA2996 55_at | EST: EST12479 Uterus tumor I Homo sapiens cDNA 3' end, mRNA sequence. (from Genbank) |
| 294 | Melanoma | 0.2579902 | 0.457235 | 0.377747 | 0.24803293 | U47621_at | Nucleolar autoantigen No55 mRNA |
| 295 | Melanoma | 0.2570428 | 0.4571506 | 0.377521 | 0.24792519 | M31682_at | INHBB Inhibin, beta B (activin AB beta polypeptide) |
| 296 | Melanoma | 0.2569929 | 0.4570983 | 0.377435 | 0.2476867 | D61469_at | EST: Human fetal brain cDNA 5'-end GEN-405D05, mRNA sequence. (from Genbank) |
| 297 | Melanoma | 0.2558652 | 0.4569655 | 0.377335 | 0.2475044 | AA313977_s _at | Homo sapiens RNA polymerase II transcription factor SIII p18 subunit mRNA, complete cds |
| 298 | Melanoma | 0.255715 | 0.4568136 | 0.377172 | 0.24731573 | M96789_at | GJA4 Gap junction protein, alpha 4, 37kD (connexin 37) |
| 299 | Melanoma | 0.2544765 | 0.4565921 | 0.377066 | 0.24713327 | RC_AA4552 67_at | EST: zx80a02.s1 Soares ovary tumor NbHOT Homo sapiens cDNA clone 810026 3'; mRNA sequence. (from Genbank) |
| 300 | Melanoma | 0.2542394 | 0.456431 | 0.376631 | 0.24706388 | RC_AA2622 61_at | EST: zs25e01.s1 NCI_CGAP_GCB1 Homo sapiens cDNA clone IMAGE:686232 3' similar to WP:R05G6.4 CE07417 .; mRNA sequence. (from Genbank) |
| 301 | Melanoma | 0.2541125 | 0.4559673 | 0.375589 | 0.24697755 | Z29074_at | KRT9 Keratin 9 |
| 302 | Melanoma | 0.2537687 | 0.4559435 | 0.376429 | 0.24676791 | AA453369_a _t | EST: zx47c07.r1 Soares testis NHT Homo sapiens cDNA clone 795372 5', mRNA sequence. (from Genbank) |
| 303 | Melanoma | 0.253736 | 0.4559423 | 0.376283 | 0.2466273 | M19154_at | Transforming growth factor-beta-2 mRNA |
| 304 | Melanoma | 0.2536844 | 0.4558926 | 0.376064 | 0.24632998 | X63422_at-2 | ATP synthase, H+ transporting, mitochondrial F1 complex, delta subunit |
| 305 | Melanoma | 0.2536844 | 0.4558028 | 0.375672 | 0.24619456 | X63422_at | ATP5D ATP synthase, H+ transporting, mitochondrial F1 complex, delta subunit |
| 306 | Melanoma | 0.2532991 | 0.4557305 | 0.375549 | 0.24601288 | RC_AA2362 41_at | EST: zr51e07.s1 Soares NhHMPu S1 Homo sapiens cDNA clone 666948 3', mRNA sequence. (from Genbank) |
| 307 | Melanoma | 0.2524737 | 0.4555065 | 0.375048 | 0.24586938 | R33301_at | EST: yh81g01.r1 Homo sapiens cDNA clone 136176 5' similar to contains MSR1 repetitive element.; (from Genbank) |
| 308 | Melanoma | 0.2530058 | 0.4554679 | 0.375033 | 0.24574246 | AB002354_a _t | KIAA0356 gene product |

FIG. 8P

| # | Type | | | | ID | Description |
|---|---|---|---|---|---|---|
| 309 | Melanoma | 0.2522372 | 0.455388 | 0.374894 | 0.245510013 | RC_AA2435 62_at | EST: zs15h06.s1 NCI_CGAP_GCB1 Homo sapiens cDNA clone IMAGE:685307 3', mRNA sequence. (from Genbank) |
| 310 | Melanoma | 0.2520279 | 0.455204 | 0.374624 | 0.245394833 | AA028171_a t | EST: ze75h09.r1 Soares fetal heart NbHH19W Homo sapiens cDNA clone 364865 5' similar to contains element MER35 repetitive element ;, mRNA sequence. (from Genbank) |
| 311 | Melanoma | 0.2516953 | 0.4545035 | 0.374443 | 0.245143431 | L14595_at | SLC1A4 Solute carrier family 1 (glutamate/neutral amino acid transporter), member 4 |
| 312 | Melanoma | 0.2513504 | 0.4543545 | 0.374322 | 0.245017041 | U28249_at | MAT8 protein |
| 313 | Melanoma | 0.250055 | 0.4543239 | 0.374022 | 0.244848881 | RC_AA0467 04_at | EST: zk62b07.s1 Soares pregnant uterus NbHPU Homo sapiens cDNA clone 487381 3', mRNA sequence. (from Genbank) |
| 314 | Melanoma | 0.2505134 | 0.4537298 | 0.373988 | 0.244773213 | RC_AA2581 30_at | EST: zs35f03.s1 NCI_CGAP_GCB1 Homo sapiens cDNA clone IMAGE:687197 3', mRNA sequence. (from Genbank) |
| 315 | Melanoma | 0.2503504 | 0.4536887 | 0.373885 | 0.244528190 | X99897_s_a t | P/Q-type calcium channel alpha1 subunit |
| 316 | Melanoma | 0.2494522 | 0.4535285 | 0.373709 | 0.244253342 | RC_AA4636 24_at | EST: zx98g02.s1 Soares NhHMPu S1 Homo sapiens cDNA clone 811826 3', mRNA sequence. (from Genbank) |
| 317 | Melanoma | 0.2486976 | 0.4535079 | 0.373641 | 0.2441341 | AA374109_a t | EST: EST86231 HSC172 cells I Homo sapiens cDNA 5' end, mRNA sequence. (from Genbank) |
| 318 | Melanoma | 0.2485793 | 0.4533404 | 0.373337 | 0.2438887 | AA043157_a t | Zk48f06.r1 Soares pregnant uterus NbHPU Homo sapiens cDNA clone 486083 5', mRNA sequence. (from Genbank) |
| 319 | Melanoma | 0.2481357 | 0.4530735 | 0.373307 | 0.243879821 | RC_D58185 _at | EST: Human aorta cDNA 3'-end GEN-354C01, mRNA sequence. (from Genbank) |
| 320 | Melanoma | 0.2477354 | 0.4528528 | 0.373236 | 0.243706421 | RC_AA5209 96_at | EST: aa70c08.s1 NCI_CGAP_GCB1 Homo sapiens cDNA clone IMAGE:826286 3', mRNA sequence. (from Genbank) |
| 321 | Melanoma | 0.247037 | 0.4527831 | 0.37315 | 0.243519546 | RC_AA2509 8_s_at | Ran GTPase activating protein 1 |
| 322 | Melanoma | 0.2463604 | 0.452704 | 0.373064 | 0.243340271 | U91316_at | Acyl-CoA thioester hydrolase mRNA |
| 323 | Melanoma | 0.2461558 | 0.4526792 | 0.372944 | 0.243206921 | HG2171-HT2241_r_at | 12-Lipoxygenase |
| 324 | Melanoma | 0.2459892 | 0.4522368 | 0.372876 | 0.242983090 | RC_AA2824 05_at | EST: zs90e06.s1 NCI_CGAP_GCB1 Homo sapiens cDNA clone IMAGE:704770 3', mRNA sequence. (from Genbank) |
| 325 | Melanoma | 0.2456498 | 0.4518405 | 0.372866 | 0.244282981 | X71125_at | Glutamine cyclotransferase |
| 326 | Melanoma | 0.2455135 | 0.4515044 | 0.372842 | 0.244716281 | U84720_at | mRNA export protein Rae1 (RAE1) mRNA |
| 327 | Melanoma | 0.2453259 | 0.4513447 | 0.372836 | 0.242599821 | T92512_at | Ye24g11.r1 Homo sapiens cDNA clone 118724 5'. (from Genbank) |
| 328 | Melanoma | 0.2452174 | 0.4511167 | 0.372748 | 0.2423966 | AA094517_a t | Cp0694.seq.F Fetal heart, Lambda ZAP Express Homo sapiens cDNA 5', mRNA sequence. (from Genbank) |
| 329 | Melanoma | 0.2441149 | 0.4510652 | 0.372436 | 0.242193391 | AA005190_a t | Zh95d06.r1 Soares fetal liver spleen 1NFLS S1 Homo sapiens cDNA clone 429035 5', mRNA sequence. (from Genbank) |

FIG. 8Q

| # | Type | | | | | | Description |
|---|---|---|---|---|---|---|---|
| 330 | Melanoma | 0.2437409 | 0.4510483 | 0.372007 | 0.24208695 | HG544-HT544_at | Endothelial Cell Growth Factor 1 |
| 331 | Melanoma | 0.2436008 | 0.4509193 | 0.371949 | 0.24192439 | RC_AA4279 47_at | EST: zw50e09.s1 Soares total fetus Nb2HF8.9w Homo sapiens cDNA clone 773512 3', mRNA sequence. (from Genbank) |
| 332 | Melanoma | 0.2434131 | 0.4509096 | 0.371913 | 0.24184497 | T95377_at | EST: ye43c01.r1 Homo sapiens cDNA clone 120480 5'. (from Genbank) |
| 333 | Melanoma | 0.2428744 | 0.4507346 | 0.371838 | 0.24166644 | RC_AA4822 24_f_at | EST: ab15c03.s1 Stratagene lung (#937210) Homo sapiens cDNA clone 840868 3', mRNA sequence. (from Genbank) |
| 334 | Melanoma | 0.242527 | 0.450728 | 0.371691 | 0.24158628 | M93311_at | GIF |
| 335 | Melanoma | 0.2423358 | 0.4502693 | 0.37153 | 0.24127351 | AA482319_j_at | EST: ab15c03.r1 Stratagene lung (#937210) Homo sapiens cDNA clone 840868 5', mRNA sequence. (from Genbank) |
| 336 | Melanoma | 0.2420454 | 0.4502649 | 0.371334 | 0.24111953 | HG270-HT270_at | Lymphocyte Chemoattractant Factor |
| 337 | Melanoma | 0.2411593 | 0.4501162 | 0.37111 | 0.24096918 | AA314096_a_t | EST185947 Colon carcinoma (HCC) cell line II Homo sapiens cDNA 5' end, mRNA sequence. (from Genbank) |
| 338 | Melanoma | 0.2408172 | 0.4500458 | 0.370979 | 0.24075276 | RC_AA4214 87_at | EST: zu06g09.s1 Soares testis NHT Homo sapiens cDNA clone 731104 3', mRNA sequence. (from Genbank) |
| 339 | Melanoma | 0.2407118 | 0.450023 | 0.37085 | 0.24060452 | AA096094_s_at | EST: l8200.seq,F Fetal heart, Lambda ZAP Express Homo sapiens cDNA 5', mRNA sequence. (from Genbank) |
| 340 | Melanoma | 0.238808 | 0.4498797 | 0.370805 | 0.24042162 | N75215_s_a_t | EST: yw33h05.r1 Homo sapiens cDNA clone 254073 5'. (from Genbank) |
| 341 | Melanoma | 0.2386101 | 0.4498797 | 0.370645 | 0.24033217 | N24990_s_a_t | EST: yx16e10.r1 Homo sapiens cDNA clone 261930 5'. (from Genbank) |
| 342 | Melanoma | 0.2384981 | 0.4496641 | 0.370547 | 0.24018386 | L14927_at | LCN1 Lipocalin 1 (protein migrating faster than albumin, tear prealbumin) |
| 343 | Melanoma | 0.2380628 | 0.449582 | 0.370377 | 0.24006018 | AF001900_a_t | Secreted frizzled related protein 1 |
| 344 | Melanoma | 0.2378448 | 0.4493631 | 0.370141 | 0.23994544 | U30998_at | U30998 Homo sapiens 530 melanoma Homo sapiens cDNA clone nmd, mRNA sequence |
| 345 | Melanoma | 0.2376137 | 0.4492398 | 0.370023 | 0.23971084 | RC_AA4439 13_at | EST: zv46g06.s1 Soares ovary tumor NbHOT Homo sapiens cDNA clone 756730 3', mRNA sequence. (from Genbank) |
| 346 | Melanoma | 0.2364056 | 0.449043 | 0.369898 | 0.23960352 | RC_AA5214 16_at | EST: aa68d12.s1 NCI_CGAP_GCB1 Homo sapiens cDNA clone IMAGE:826103 3', mRNA sequence. (from Genbank) |
| 347 | Melanoma | 0.2363036 | 0.4488924 | 0.369807 | 0.23944761 | L18920_f_at | MELANOMA-ASSOCIATED ANTIGEN 2 |
| 348 | Melanoma | 0.2360517 | 0.4486598 | 0.369529 | 0.23933634 | RC_AA1133 87_at | EST: zn70g06.s1 Stratagene HeLa cell s3 937216 Homo sapiens cDNA clone 563578 3', mRNA sequence. (from Genbank) |
| 349 | Melanoma | 0.2359281 | 0.4486457 | 0.369297 | 0.23916377 | RC_AA4359 41_at | EST: zu01a11.s1 Soares testis NHT Homo sapiens cDNA clone 730556 3', mRNA sequence. (from Genbank) |
| 350 | Melanoma | 0.2355495 | 0.4485954 | 0.369214 | 0.23903833 | RC_AA4061 63_at | FSHD region gene 1 |

FIG. 8R

| | | | | | | |
|---|---|---|---|---|---|---|
| 351 | Melanoma | 0.2351726 | 0.448409 | 0.369091 | 0.2389092 | U84569_at-2 | Chromosome 21 open reading frame 2 |
| 352 | Melanoma | 0.2351726 | 0.447635 | 0.368958 | 0.23878157 | U84569_at | YF5 mRNA |
| 353 | Melanoma | 0.2350654 | 0.4474765 | 0.368883 | 0.23862992 | AA263056_a_t | EST: PMY0404 KG1-a Lambda Zap Express cDNA library Homo sapiens cDNA 5', mRNA sequence. (from Genbank) |
| 354 | Melanoma | 0.2345394 | 0.4473677 | 0.368485 | 0.238443 | AA422123_f_at | EST: zv26h12.r1 Soares NhHMPu S1 Homo sapiens cDNA clone 754823 5' similar to contains Alu repetitive element; mRNA sequence. (from Genbank) |
| 355 | Melanoma | 0.2341184 | 0.4473242 | 0.368443 | 0.23833175 | RC_AA2623 51_f_at | EST: zr44g03.s1 Soares NhHMPu S1 Homo sapiens cDNA clone 666292 3', mRNA sequence. (from Genbank) |
| 356 | Melanoma | 0.2336422 | 0.4469552 | 0.368284 | 0.23825628 | RC_AA4044 26_at | Homo sapiens snurportin1 mRNA, complete cds |
| 357 | Melanoma | 0.2331909 | 0.4468163 | 0.368236 | 0.23811057 | U79271_at | Clones 23920 and 23921 mRNA sequence |
| 358 | Melanoma | 0.2328122 | 0.4465261 | 0.368201 | 0.23789856 | R64412_at | EST: yi36b03.r1 Homo sapiens cDNA clone 141293 5'. (from Genbank) |
| 359 | Melanoma | 0.2312847 | 0.4463493 | 0.367966 | 0.23770474 | RC_AA4313 51_at | EST: zw72c12.s1 Soares testis NHT Homo sapiens cDNA clone 781750 3', mRNA sequence. (from Genbank) |
| 360 | Melanoma | 0.2312143 | 0.4463089 | 0.367887 | 0.23755601 | RC_AA4241 48_at | EST: zv81c03.s1 Soares total fetus Nb2HF8 9w Homo sapiens cDNA clone 760036 3', mRNA sequence. (from Genbank) |
| 361 | Melanoma | 0.2307322 | 0.4462811 | 0.367669 | 0.23735528 | J00117_f_at | Chorionic gonadotropin (hcg) beta subunit mRNA |
| 362 | Melanoma | 0.2306058 | 0.4462335 | 0.367622 | 0.23729226 | RC_AA1428 58_at | EST: zl40e04.s1 Soares pregnant uterus NbHPU Homo sapiens cDNA clone 504414 3', mRNA sequence. (from Genbank) |
| 363 | Melanoma | 0.2305651 | 0.4457164 | 0.367503 | 0.23714967 | RC_AA5992 14_at | EST: ag34c05.s1 Jia bone marrow stroma Homo sapiens cDNA clone 1091432 3', mRNA sequence. (from Genbank) |
| 364 | Melanoma | 0.2229695 | 0.4455922 | 0.36746 | 0.23701487 | T85532_f_at | EST: yd78g02.r1 Homo sapiens cDNA clone 114386 5' similar to contains Alu repetitive element;. (from Genbank) |
| 365 | Melanoma | 0.2293435 | 0.4453097 | 0.367369 | 0.236959934 | M94077_at | LOR Loricrin |
| 366 | Melanoma | 0.2287281 | 0.4452436 | 0.367187 | 0.23683812 | X90858_at | Uridine phosphorylase |
| 367 | Melanoma | 0.2285681 | 0.4449705 | 0.3671 | 0.23653269 | W73805_at | EST: zd50g02.r1 Soares fetal heart NbHH19W Homo sapiens cDNA clone 344114 5', mRNA sequence. (from Genbank) |
| 368 | Melanoma | 0.228322 | 0.4448954 | 0.3666932 | 0.23641627 | RC_AA4486 27_f_at | EST: zx10a05.s1 Soares total fetus Nb2HF8 9w Homo sapiens cDNA clone 786032 3' similar to contains Alu repetitive element;, mRNA sequence. (from Genbank) |
| 369 | Melanoma | 0.2281575 | 0.4446248 | 0.366899 | 0.23630421 | RC_AA2349 25_at | EST: zr78g10.s1 Soares NhHMPu S1 Homo sapiens cDNA clone 669570 3' similar to contains Alu repetitive element, mRNA sequence. (from Genbank) |
| 370 | Melanoma | 0.2275346 | 0.4444301 | 0.366758 | 0.23615283 | S67247_s_at | Smooth muscle myosin heavy chain isoform SMemb [human, umbilical cord, fetal aorta, mRNA Partial, 971 nt] |
| 371 | Melanoma | 0.2274068 | 0.4444104 | 0.366714 | 0.2359986 | X75593_at | Rab 13 |

FIG. 8S

| # | Type | | | | | Description |
|---|---|---|---|---|---|---|
| 372 | Melanoma | 0.226995 | 0.4443952 | 0.366297 | 0.23577452 | RC_AA2358 03_i_at | EST: zs42g06.s1 Soares NhHMPu S1 Homo sapiens cDNA clone 687898 3', mRNA sequence. (from Genbank) |
| 373 | Melanoma | 0.226912 | 0.4443952 | 0.366274 | 0.23561932 | RC_AA2435 82_at | Hemoglobin, gamma A |
| 374 | Melanoma | 0.2265553 | 0.4440478 | 0.36607 | 0.23547302 | M99564_at | P PROTEIN |
| 375 | Melanoma | 0.22258148 | 0.443518 | 0.365952 | 0.23536366 | HG4322-HT4592_at | Tubulin, Beta |
| 376 | Melanoma | 0.2257938 | 0.4433276 | 0.365733 | 0.23516381 | X51801_at | BMP7 Bone morphogenetic protein 7 (osteogenic protein 1) |
| 377 | Melanoma | 0.225499 | 0.4430509 | 0.365599 | 0.23498346 | AA456471_s_at | EST: zx74g11.r1 Soares ovary tumor NbHOT Homo sapiens cDNA clone 809540 5', mRNA sequence. (from Genbank) |
| 378 | Melanoma | 0.2243639 | 0.4429579 | 0.365487 | 0.23484543 | Y08682_rna 1_s_at | Carnitine palmitoyltransferase I type I |
| 379 | Melanoma | 0.2229818 | 0.4424886 | 0.365287 | 0.23471211 | RC_AA4771 32_at | EST: zu37f03.s1 Soares ovary tumor NbHOT Homo sapiens cDNA clone 740189 3', mRNA sequence. (from Genbank) |
| 380 | Melanoma | 0.2227774 | 0.4423669 | 0.365188 | 0.23463127 | N42272_s_a t | EST: yw85f08.r1 Homo sapiens cDNA clone 259047 5' similar to WP:T15H9.1 CE01664 DNAJ ;. (from Genbank) |
| 381 | Melanoma | 0.222104 | 0.44207 | 0.365105 | 0.23448561 | HG3985-HT4255_at | Cpg-Enriched Dna, Clone E04 |
| 382 | Melanoma | 0.2212297 | 0.4416662 | 0.364828 | 0.23428619 | RC_AA4014 01_f_at | PET112 (yeast homolog)-like |
| 383 | Melanoma | 0.2210947 | 0.4413311 | 0.364819 | 0.23421432 | RC_AA6203 61_at | EST: af07d11.s1 Soares testis NHT Homo sapiens cDNA clone 1030965 3', mRNA sequence. (from Genbank) |
| 384 | Melanoma | 0.2210868 | 0.4412695 | 0.364578 | 0.23402794 | RC_AA6099 88_at | EST: af18a06.s1 Soares testis NHT Homo sapiens cDNA clone 1031986 3', mRNA sequence. (from Genbank) |
| 385 | Melanoma | 0.2208166 | 0.4412347 | 0.364449 | 0.23386137 | RC_AA2523 95_at | EST: zs12g10.s1 NCI_CGAP_GCB1 Homo sapiens cDNA clone IMAGE:685026 3', mRNA sequence. (from Genbank) |
| 386 | Melanoma | 0.2207078 | 0.4410715 | 0.364382 | 0.23376092 | AA234651_a t | EST: zr75f06.r1 Soares NhHMPu S1 Homo sapiens cDNA clone 669251 5', mRNA sequence. (from Genbank) |
| 387 | Melanoma | 0.2205552 | 0.4409433 | 0.364255 | 0.23364411 | RC_AA6207 95_at | EST: af95b02.s1 Soares testis NHT Homo sapiens cDNA clone 1055499 3', mRNA sequence. (from Genbank) |
| 388 | Melanoma | 0.2201491 | 0.4408959 | 0.364213 | 0.23348783 | Y07909_at | B4B |
| 389 | Melanoma | 0.2201347 | 0.4406731 | 0.364174 | 0.23342176 | RC_AA1141 90_at | EST: zn76d01.s1 Stratagene NT2 neuronal precursor 937230 Homo sapiens cDNA clone 564097 3', mRNA sequence. (from Genbank) |
| 390 | Melanoma | 0.2198687 | 0.4406556 | 0.363888 | 0.23327684 | AA452428_a t | EST: zx15g01.r1 Soares total fetus Nb2HF8 9w Homo sapiens cDNA clone 786576 5', mRNA sequence. (from Genbank) |
| 391 | Melanoma | 0.2196641 | 0.4406005 | 0.363871 | 0.23317158 | RC_AA0183 46_at | EST: ze41d12.s1 Soares retina N2b4HR Homo sapiens cDNA clone 361559 3', mRNA sequence. (from Genbank) |
| 392 | Melanoma | 0.2195257 | 0.4405788 | 0.363752 | 0.23303775 | N42022_at | EST: yw69g06.r1 Homo sapiens cDNA clone 257530 5'. (from Genbank) |

FIG. 8T

| | | | | | | |
|---|---|---|---|---|---|---|
| 393 | Melanoma | 0.2192921 | 0.4405788 | 0.363716 | 0.23290403 | X14487_rna1_s_at | Keratin 10 (epidermolytic hyperkeratosis; keratosis palmaris et plantaris) |
| 394 | Melanoma | 0.2191667 | 0.4405689 | 0.363615 | 0.2327714 2_at | RC_AA4901 42_at | EST: ab05f07.s1 Stratagene fetal retina 937202 Homo sapiens cDNA clone 839941 3', mRNA sequence. (from Genbank) |
| 395 | Melanoma | 0.2190425 | 0.4405542 | 0.363578 | 0.23249954 | Z29678_at | MitF mRNA |
| 396 | Melanoma | 0.2181971 | 0.4405357 | 0.363407 | 0.23242291 | RC_AA4653 67_at | EST: aa23d09.s1 NCI_CGAP_GCB1 Homo sapiens cDNA clone IMAGE:814097 3', mRNA sequence. (from Genbank) |
| 397 | Melanoma | 0.217784 | 0.4405352 | 0.362978 | 0.2321932 | HG3565-HT3768_at | Zinc Finger Protein (Gb:M88357) |
| 398 | Melanoma | 0.2171904 | 0.4404236 | 0.362769 | 0.23211613 | RC_AA4594 12_at | EST: zx89h01.s1 Soares ovary tumor NbHOT Homo sapiens cDNA clone 810961 3', mRNA sequence. (from Genbank) |
| 399 | Melanoma | 0.217164 | 0.4403733 | 0.362695 | 0.23198104 | X63522_s_at | RETINOIC ACID RECEPTOR RXR-BETA |
| 400 | Melanoma | 0.21713 | 0.4403655 | 0.36264 | 0.23189938 | RC_AA4002 92_at | EST: zu63f03.s1 Soares testis NHT Homo sapiens cDNA clone 742685 3', mRNA sequence. (from Genbank) |
| 401 | Melanoma | 0.2167618 | 0.4403376 | 0.362486 | 0.23172878 | RC_AA1329 69_s_at | Homo sapiens metalloprotease 1 (MP1) mRNA, complete cds |
| 402 | Melanoma | 0.2165646 | 0.4402937 | 0.362423 | 0.23165119 | RC_AA1299 23_at | Ceroid-lipofuscinosis, neuronal 2, late infantile (Jansky-Bielschowsky disease) |
| 403 | Melanoma | 0.2159537 | 0.4402593 | 0.362363 | 0.23145026 | RC_AA1293 90_at | EST: zn85b02.s1 Stratagene lung carcinoma 937218 Homo sapiens cDNA clone 564939 3', mRNA sequence. (from Genbank) |
| 404 | Melanoma | 0.2159416 | 0.4401411 | 0.362304 | 0.23135072 | U73738_at | Calcium/calmodulin-dependent protein kinase II delta E mRNA, partial cds |
| 405 | Melanoma | 0.2157674 | 0.4400079 | 0.362258 | 0.23122585 | X60787_s_at | INTERLEUKIN ENHANCER-BINDING FACTOR |
| 406 | Melanoma | 0.2157221 | 0.4399687 | 0.362177 | 0.23109692 | RC_AA4859 45_at | EST: ab40g02.s1 Stratagene HeLa cell s3 937216 Homo sapiens cDNA clone 843314 3' similar to SW:SOH1_YEAST P38633 SOH1 PROTEIN. [1] .; mRNA sequence. (from Genbank) |
| 407 | Melanoma | 0.215441 | 0.4399644 | 0.361997 | 0.23099001 | RC_AA2521 91_at | Homo sapiens PAC clone DJ130H16 from 22q12.1-qter |
| 408 | Melanoma | 0.2149619 | 0.4396075 | 0.361931 | 0.23087378 | U06155_at | Chromosome 1q subtelomeric sequence D1S553 |
| 409 | Melanoma | 0.2148667 | 0.4395179 | 0.361885 | 0.23069708 | RC_AA2430 58_at | EST: zr24h08.s1 Stratagene NT2 neuronal precursor 937230 Homo sapiens cDNA clone 664383 3', mRNA sequence. (from Genbank) |
| 410 | Melanoma | 0.2147125 | 0.4394898 | 0.361795 | 0.23053299 | RC_AA4011 99_at | EST: zu52e12.s1 Soares ovary tumor NbHOT Homo sapiens cDNA clone 741646 3', mRNA sequence. (from Genbank) |
| 411 | Melanoma | 0.2143141 | 0.4389108 | 0.361721 | 0.23036164 | RC_AA0539 17_at | EST: ze75c02.s1 Soares fetal heart NbHH19W Homo sapiens cDNA clone 364802 3', mRNA sequence. (from Genbank) |

FIG. 8U

| | | | | |
|---|---|---|---|---|
| 412 | Melanoma | 0.2143084 | 0.4388792 | 0.361638 | 0.23033188 | AA424897_s_at | EST: zv47b09.r1 Soares ovary tumor NbHOT Homo sapiens cDNA clone 756761 5', mRNA sequence. (from Genbank) |
| 413 | Melanoma | 0.214153 | 0.4387619 | 0.361385 | 0.23000069308_at | RC_AA4521 | Transcription factor AP-2 alpha (activating enhancer-binding protein 2 alpha) |
| 414 | Melanoma | 0.2133391 | 0.4387061 | 0.361271 | 0.2299282439_at | RC_AA4560 | EST: aa03d01.s1 Soares NhHMPu S1 Homo sapiens cDNA clone 812161 3', mRNA sequence. (from Genbank) |
| 415 | Melanoma | 0.2129301 | 0.4384987 | 0.361135 | 0.22985701 | C02053_at | EST: HUMGS0005644, Human Gene Signature, 3'-directed cDNA sequence, mRNA sequence. (from Genbank) |
| 416 | Melanoma | 0.2122679 | 0.4381451 | 0.360984 | 0.22976142 | AA082668_a_t | ADP-ribosylation factor 1 |
| 417 | Melanoma | 0.2120888 | 0.4380468 | 0.360918 | 0.2296199 | AA316686_s_at | EST: EST188361 HCC cell line (matastasis to liver in mouse) II Homo sapiens cDNA 5' end, mRNA sequence. (from Genbank) |
| 418 | Melanoma | 0.2116727 | 0.4380354 | 0.360867 | 0.2295157 05_at | RC_AA4599 | EST: zx73f07.s1 Soares ovary tumor NbHOT Homo sapiens cDNA clone 809413 3', mRNA sequence. (from Genbank) |
| 419 | Melanoma | 0.2115293 | 0.4379143 | 0.360725 | 0.22935697 | AA043223_a_t | Homo sapiens clone 486790 diphosphoinositol polyphosphate phosphohydrolase mRNA, complete cds |
| 420 | Melanoma | 0.2113843 | 0.4378288 | 0.360649 | 0.22921386 | X93921_at-2 | Dual specificity phosphatase 7 |
| 421 | Melanoma | 0.2113843 | 0.4377695 | 0.360465 | 0.22902337 | X93921_at | Protein-tyrosine-phosphatase (tissue type: testis) |
| 422 | Melanoma | 0.2112357 | 0.4377505 | 0.360426 | 0.22885567 | H81241_at | EST: yu73c07.r1 Homo sapiens cDNA clone 239436 5' similar to SP:S35643 S35643 BTEB2 PROTEIN -.; (from Genbank) |
| 423 | Melanoma | 0.2112098 | 0.4374024 | 0.360203 | 0.22877741 78_at | RC_AA4321 | EST: zw71g02.s1 Soares testis NHT Homo sapiens cDNA clone 781682 3', mRNA sequence. (from Genbank) |
| 424 | Melanoma | 0.2110319 | 0.4373793 | 0.360155 | 0.22860296 43_at | RC_AA2530 | EST: zr52h12.s1 Soares NhHMPu S1 Homo sapiens cDNA clone 667007 3', mRNA sequence. (from Genbank) |
| 425 | Melanoma | 0.2110153 | 0.4373013 | 0.360062 | 0.22853592 74_at | RC_AA3986 | EST: zi70d05.s1 Soares testis NHT Homo sapiens cDNA clone 727689 3' similar to SW:YKU7_YEAST P36039 HYPOTHETICAL 29.4 KD PROTEIN IN STE6-LOS1 INTERGENIC REGION. ;; mRNA sequence. (from Genbank) |
| 426 | Melanoma | 0.2107318 | 0.4369316 | 0.360013 | 0.22837286 | H49499_s_a_t | Homo sapiens chromosome 19, cosmid F23149 |
| 427 | Melanoma | 0.2105456 | 0.4369161 | 0.359867 | 0.22815207 | M63962_rna1_at | Gastric H,K-ATPase catalytic subunit gene |
| 428 | Melanoma | 0.2102353 | 0.43688807 | 0.359746 | 0.22809754 40_at | RC_AA4282 | EST: zw51d04.s1 Soares total felus Nb2HF8 9w Homo sapiens cDNA clone 773575 3', mRNA sequence. (from Genbank) |
| 429 | Melanoma | 0.2095892 | 0.436777 | 0.359458 | 0.22797056 | AA012885_a_t | EST: zo27f07.r1 Soares retina N2b4HR Homo sapiens cDNA clone 360229 5', mRNA sequence. (from Genbank) |
| 430 | Melanoma | 0.2095192 | 0.4367441 | 0.359368 | 0.22785403 | D61596_at | Human fetal brain cDNA 5'-end GEN-421F03, mRNA sequence. (from Genbank) |

FIG. 8V

| | | | | | |
|---|---|---|---|---|---|
| 431 | Melanoma | 0.2092282 | 0.4367388 | 0.359142 | 0.227709998 | RC_AA4602 93_at | EST: zx51b08.s1 Soares testis NHT Homo sapiens cDNA clone 795735 3' similar to TR:G1196644 G1196644 BAT-4.:, mRNA sequence. (from Genbank) |
| 432 | Melanoma | 0.2092453 | 0.4367388 | 0.359133 | 0.22760746 | D31389_at | Homo sapiens clone 633 unknown mRNA, complete sequence |
| 433 | Melanoma | 0.2092362 | 0.4367304 | 0.359099 | 0.22774584 | X98405_at | Myelin associated glycoprotein |
| 434 | Melanoma | 0.2083055 | 0.436706 | 0.358958 | 0.22736652 | L26339_at | Autoantigen mRNA |
| 435 | Melanoma | 0.2081056 | 0.4366873 | 0.358909 | 0.22723185 | RC_AA4055 43_at | EST: zw39c01.s1 Soares total fetus Nb2HF8 9w Homo sapiens cDNA clone 772416 3', mRNA sequence. (from Genbank) |
| 436 | Melanoma | 0.208016 | 0.4364752 | 0.358909 | 0.22712642 | AD000092_c ds7_s_at | RAD23A gene (human RAD23A homolog) extracted from Homo sapiens DNA from chromosome 19p13.2 cosmids R31240, R30272 and R28549 containing the EKLF, GCDH, CRTC, and RAD23A genes, genomic sequence |
| 437 | Melanoma | 0.2078692 | 0.436435 | 0.358782 | 0.22699864 | U75370_at | Mitochondrial RNA polymerase mRNA, nuclear gene encoding mitochondrial protein |
| 438 | Melanoma | 0.2074884 | 0.4364017 | 0.358729 | 0.22679035 | N98666_at | Homo sapiens metaxin 2 (MTX2) mRNA, nuclear gene encoding mitochondrial protein, complete cds |
| 439 | Melanoma | 0.207364 | 0.4363637 | 0.358713 | 0.22663519 | S81914_at | IEX-1 |
| 440 | Melanoma | 0.2073615 | 0.4361584 | 0.358576 | 0.22660254 | RC_AA4534 31_at | EST: zx32g10.s1 Soares total fetus Nb2HF8 9w Homo sapiens cDNA clone 788226 3', mRNA sequence. (from Genbank) |
| 441 | Melanoma | 0.2061277 | 0.4359535 | 0.358478 | 0.22638807 | RC_AA4762 35_at | EST: zw35h03.s1 Soares ovary tumor NbHOT Homo sapiens cDNA clone 771317 3', mRNA sequence. (from Genbank) |
| 442 | Melanoma | 0.2059628 | 0.4358276 | 0.3584 | 0.22626669 | RC_AA4030 41_at | Cellular retinoic acid-binding protein 1 |
| 443 | Melanoma | 0.2057747 | 0.4357776 | 0.358092 | 0.22616643 | J04444_at | CYC1 Cytochrome c-1 |
| 444 | Melanoma | 0.2050022 | 0.4357337 | 0.358052 | 0.22610559 | AA328993_s _at | EST: EST32546 Embryo, 12 week 1 Homo sapiens cDNA 5' end, mRNA sequence. (from Genbank) |
| 445 | Melanoma | 0.2047467 | 0.4356204 | 0.357899 | 0.22600846 | RC_AA4787 78_at | EST: zv20b06.s1 Soares NhHMPu S1 Homo sapiens cDNA clone 754163 3', mRNA sequence. (from Genbank) |
| 446 | Melanoma | 0.2042919 | 0.4354142 | 0.357772 | 0.22585885 | RC_AA4243 46_at | Human sialyltransferase SThM (sthm) mRNA, complete cds |
| 447 | Melanoma | 0.2034747 | 0.4354035 | 0.357759 | 0.22578618 | RC_AA2917 71_at | EST: zl45g06.s1 Soares ovary tumor NbHOT Homo sapiens cDNA clone 725338 3', mRNA sequence. (from Genbank) |
| 448 | Melanoma | 0.2027902 | 0.4353237 | 0.357607 | 0.22568338 | RC_AA4785 87_at | Homo sapiens mRNA for leukemia associated gene 1 |
| 449 | Melanoma | 0.2023935 | 0.4351651 | 0.357516 | 0.22551976 | X05855_at | EEF1G Translation elongation factor 1 gamma |
| 450 | Melanoma | 0.2023352 | 0.4350275 | 0.357417 | 0.22532429 | X04602_s_a t | IL6 Interleukin 6 (B cell stimulatory factor 2) |
| 451 | Melanoma | 0.2023352 | 0.4344044 | 0.357413 | 0.2251814 | X04602_s_a t-2 | Interleukin 6 (interferon, beta 2) |

FIG. 8W

| # | | | | | | Description |
|---|---|---|---|---|---|---|
| 452 | Melanoma | 0.2022497 | 0.4343902 | 0.357402 | 0.225503994 | U05572_s_a t | MANB Mannosidase alpha-B (lysosomal) |
| 453 | Melanoma | 0.2014993 | 0.4342621 | 0.357231 | 0.22486462 | RC_AA0262 80_at | EST: ze91d10.s1 Soares fetal heart NbHH19W Homo sapiens cDNA clone 366355 3', mRNA sequence. (from Genbank) |
| 454 | Melanoma | 0.2011292 | 0.4342141 | 0.356987 | 0.22477579 | R22673_at | EST: yg08a04.r1 Homo sapiens cDNA clone 31308 5'. (from Genbank) |
| 455 | Melanoma | 0.2009812 | 0.4342006 | 0.356903 | 0.22459036 | RC_AA0531 39_at | EST: zi73e05.s1 Stratagene colon (#937204) Homo sapiens cDNA clone 510272 3' similar to TR:E243948 E243948 CHROMOSOME VII READING FRAME ORF YGL054C :, mRNA sequence. (from Genbank) |
| 456 | Melanoma | 0.2003417 | 0.4341824 | 0.356819 | 0.22449128 | RC_AA3987 08_at | Cell division cycle 10 (homologous to CDC10 of S. cerevisiae) |
| 457 | Melanoma | 0.2000301 | 0.4333594 | 0.356711 | 0.22437325 | RC_AA2534 32_at | EST: zr77f04.s1 Soares NhHMPu S1 Homo sapiens cDNA clone 669439 3', mRNA sequence. (from Genbank) |
| 458 | Melanoma | 0.1996321 | 0.4333543 | 0.356661 | 0.22418156 | RC_AA6209 98_at | EST: ag03a06.s1 Soares testis NHT Homo sapiens cDNA clone 1056178 3' similar to WP:C16A3.1 CE04002 HELICASES OF SNF2/RAD54 FAMILY ;, mRNA sequence. (from Genbank) |
| 459 | Melanoma | 0.1995644 | 0.4333488 | 0.356562 | 0.22412516 | L12350_at | THBS2 Thrombospondin 2 |
| 460 | Melanoma | 0.1993956 | 0.4326458 | 0.356424 | 0.22388084 | U76421_at | DsRNA adenosine deaminase DRADA2b (DRADA2b) mRNA |
| 461 | Melanoma | 0.1992854 | 0.4324863 | 0.356307 | 0.22371888 | RC_AA2848 36_at | EST: zf22a05.s1 Soares ovary tumor NbHOT Homo sapiens cDNA clone 713840 3', mRNA sequence. (from Genbank) |
| 462 | Melanoma | 0.1992078 | 0.432301 | 0.356221 | 0.22368261 | HG3570-HT3773_at | Protein Phosphatase Inhibitor Homolog |
| 463 | Melanoma | 0.1990525 | 0.4322276 | 0.356193 | 0.22351474 | RC_AA2919 27_at | EST: zr58g09.s1 Soares NhHMPu S1 Homo sapiens cDNA clone 667648 3', mRNA sequence. (from Genbank) |
| 464 | Melanoma | 0.1989889 | 0.4322276 | 0.355945 | 0.2233952 | RC_AA4320 83_at | EST: zw89c10.s1 Soares total fetus Nb2HF8 9w Homo sapiens cDNA clone 784146 3', mRNA sequence. (from Genbank) |
| 465 | Melanoma | 0.1989587 | 0.4315779 | 0.355893 | 0.22320239 | RC_AA4492 38_s_at | EST: zx04b11.s1 Soares total fetus Nb2HF8 9w Homo sapiens cDNA clone 785469 3', mRNA sequence. (from Genbank) |
| 466 | Melanoma | 0.198394 | 0.4314396 | 0.357751 | 0.22313479 | U10685_at | MAGE-10 antigen (MAGE10) gene |
| 467 | Melanoma | 0.198394 | 0.4313746 | 0.355653 | 0.22304982 | U10685_at-2 | Melanoma antigen, family A, 10 |
| 468 | Melanoma | 0.1982618 | 0.43111813 | 0.355544 | 0.22298507 | D14533_at | XPA Xeroderma pigmentosum, complementation group A |
| 469 | Melanoma | 0.1979379 | 0.4308189 | 0.355437 | 0.22287999 | RC_AA1943 09_s_at | Reticulon 2 |
| 470 | Melanoma | 0.1977596 | 0.4306039 | 0.35542 | 0.22282349 | AA428025_a t | Transforming growth factor beta-stimulated protein TSC-22 |
| 471 | Melanoma | 0.1976767 | 0.430593 | 0.355384 | 0.22268313 | M55621_at | MGAT1 N-acetylglucosaminyltransferase I |
| 472 | Melanoma | 0.197651 | 0.4305851 | 0.3553319 | 0.22255063 | M29277_s_a t | CELL SURFACE GLYCOPROTEIN MUC18 PRECURSOR |

FIG. 8X

| | | | | | | |
|---|---|---|---|---|---|---|
| 473 | Melanoma | 0.1966506 | 0.4304506 | 0.355276 | RC_AA2532 16_at | EST: zr53g08.s1 Soares NhHMPu S1 Homo sapiens cDNA clone 667166 3', mRNA sequence. (from Genbank) |
| 474 | Melanoma | 0.1963065 | 0.4304157 | 0.355053 | 0.222313315 | AVPR1B Arginine vasopressin receptor 1B |
| 475 | Melanoma | 0.195943 | 0.4301827 | 0.354949 | 0.222217534 D87942_at D31833_s_a t | Fucosyltransferase 2 (secretor status included) |
| 476 | Melanoma | 0.1959128 | 0.430105 | 0.354889 | 0.222216122 M77481_rna 1_f_at | Antigen (MAGE-1) gene |
| 477 | Melanoma | 0.195543 | 0.4298595 | 0.354873 | 0.221943481 AA313990_a t | EST: EST186070 Colon carcinoma (HCC) cell line II Homo sapiens cDNA 5' end similar to similar to C. elegans hypothetical protein, cosmid C30A5.3, mRNA sequence. (from Genbank) |
| 478 | Melanoma | 0.19553 | 0.4297839 | 0.354757 | 0.221861141 RC_AA0558 at | EST: zf20c08.s1 Soares fetal heart NbHH19W Homo sapiens cDNA clone 377486 3', mRNA sequence. (from Genbank) |
| 479 | Melanoma | 0.1946821 | 0.4296794 | 0.354652 | 0.221769023 RC_AA0259 30_at | EST: ze84a02.s1 Soares fetal heart NbHH19W Homo sapiens cDNA clone 365642 3' similar to contains element L1 repetitive element ;, mRNA sequence. (from Genbank) |
| 480 | Melanoma | 0.1944419 | 0.4295352 | 0.354545 | 0.221529269 RC_AA4010 98_f_at | EST: zu50g01.s1 Soares ovary tumor NbHOT Homo sapiens cDNA clone 741456 3' similar to contains Alu repetitive element;contains element THR repetitive element ;, mRNA sequence. (from Genbank) |
| 481 | Melanoma | 0.1944125 | 0.4292206 | 0.354436 | 0.221402731 AA074407_a t | EST: zm15c08.r1 Stratagene pancreas (#937208) Homo sapiens cDNA clone 525710 5', mRNA sequence. (from Genbank) |
| 482 | Melanoma | 0.1939223 | 0.4288764 | 0.354415 | 0.221288110 M80563_at | PLACENTAL CALCIUM-BINDING PROTEIN |
| 483 | Melanoma | 0.1938383 | 0.4288454 | 0.354047 | 0.221200404 M91493_at | EST: HUMRTPGEAL Homo sapiens cDNA. (from Genbank) |
| 484 | Melanoma | 0.1936976 | 0.4285816 | 0.353799 | 0.221137510 U90546_at | Butyrophilin (BTF4) mRNA |
| 485 | Melanoma | 0.1935041 | 0.4282132 | 0.353705 | 0.221102640 U90546_at-2 | Human butyrophilin (BTF4) mRNA, complete cds |
| 486 | Melanoma | 0.1933889 | 0.4281569 | 0.353628 | 0.220975070 RC_AA4055 01_at | EST: zw36d10.s1 Soares total fetus Nb2HF8 9w Homo sapiens cDNA clone 772147 3', mRNA sequence. (from Genbank) |
| 487 | Melanoma | 0.1933889 | 0.4279993 | 0.353451 | 0.220875146 RC_AA2566 4_at | EST: zr82g12.s1 Soares NhHMPu S1 Homo sapiens cDNA clone 682246 3' similar to contains Alu repetitive element;contains element MSR1 repetitive element ;, mRNA sequence. (from Genbank) |
| 488 | Melanoma | 0.1925444 | 0.4279454 | 0.353442 | 0.220721021 AA197134_a t | EST: zq11b11.r1 Stratagene muscle 937209 Homo sapiens cDNA clone 629373 5', mRNA sequence. (from Genbank) |
| 489 | Melanoma | 0.1919538 | 0.4277693 | 0.353185 | 0.220601221 HG3731-HT4001_r_at | Immunoglobulin Heavy Chain, Vdjrc Regions (Gb:L23566) |
| 490 | Melanoma | 0.1916102 | 0.4275903 | 0.353042 | 0.220445681 X52611_s_a t-2 | Transcription factor AP-2 alpha (activating enhancer-binding protein 2 alpha) |

FIG. 8Y

| # | Type | | | | Accession | Description |
|---|---|---|---|---|---|---|
| 491 | Melanoma | 0.1916102 | 0.4274349 | 0.353042 | X52611_s_a t | TRANSCRIPTION FACTOR AP-2 |
| 492 | Melanoma | 0.1913768 | 0.4274195 | 0.353041 | RC_AA4646 0.220175640 6_at | EST: aa11g01.s1 Soares NhHMPu S1 Homo sapiens cDNA clone 812976 3', mRNA sequence. (from Genbank) |
| 493 | Melanoma | 0.1908572 | 0.427271 | 0.352942 | HG67-HT67_f_at 0.220032870 | Zinc Finger Protein (Gb:X61870) |
| 494 | Melanoma | 0.1904382 | 0.4271973 | 0.35278 | R29077_at 0.219882220 | EST: F1-110D 22 week old human fetal liver cDNA library Homo sapiens cDNA clone F1-110D 5', mRNA sequence. (from Genbank) |
| 495 | Melanoma | 0.18921101 | 0.4271949 | 0.352757 | M32304_s_a t 0.219823960 | TIMP2 Tissue inhibitor of metalloproteinase 2 |
| 496 | Melanoma | 0.1892043 | 0.426892 | 0.352574 | J00231_f_at 0.219706040 | Immunoglobulin gamma 3 (Gm marker) |
| 497 | Melanoma | 0.1890262 | 0.4267497 | 0.35253 | RC_AA4497 0.219552160 72_at | EST: zx07h06.s1 Soares total fetus Nb2HF8 9w Homo sapiens cDNA clone 785819 3', mRNA sequence. (from Genbank) |
| 498 | Melanoma | 0.1879698 | 0.4267349 | 0.352435 | R14545_at 0.219389720 | EST: yf84f08.r1 Homo sapiens cDNA clone 292219 5'. (from Genbank) |
| 499 | Melanoma | 0.18751105 | 0.4267203 | 0.3523368 | AA055916_s _at 0.219362270 | Homo sapiens mRNA from chromosome 5q31-33 region |
| 500 | Melanoma | 0.1874958 | 0.4266153 | 0.352143 | L13210_at 0.219191340 | Mac-2 binding protein mRNA |
| 501 | Melanoma | 0.1874263 | 0.4263006 | 0.352138 | RC_AA4210 0.219049330 46_at | EST: zu09i09.s1 Soares testis NHT Homo sapiens cDNA clone 731369 3', mRNA sequence. (from Genbank) |
| 502 | Melanoma | 0.1871408 | 0.4262551 | 0.351984 | AA081209_a t 0.218876990 | Regulator of G-protein signalling 5 |
| 503 | Melanoma | 0.1869301 | 0.4262493 | 0.351956 | AA027766_a t 0.2187628 | EST: HPLA_CCLEE_69a10u HPLA CCLee Homo sapiens cDNA, mRNA sequence. (from Genbank) |
| 504 | Melanoma | 0.1869133 | 0.4261301 | 0.351948 | RC_AA1259 0.218688280 69_at | EST: zj85c04.s1 Stratagene colon (#937204) Homo sapiens cDNA clone 511398 3', mRNA sequence. (from Genbank) |
| 505 | Melanoma | 0.1865781 | 0.4260473 | 0.351918 | AA027765_a t 0.218634590 | EST: HPLA_CCLEE_65h7r HPLA CCLee Homo sapiens cDNA, mRNA sequence. (from Genbank) |
| 506 | Melanoma | 0.1864684 | 0.4256356 | 0.351782 | U35340_at 0.218469990 | CRYBB1 Crystallin beta-B1 |
| 507 | Melanoma | 0.1859926 | 0.425513 | 0.351727 | U72514_at 0.218392150 | C2f mRNA |
| 508 | Melanoma | 0.1857141 | 0.4247508 | 0.351632 | R53717_at 0.218288330 | EST: yi02e03.r1 Homo sapiens cDNA clone 138076 5'. (from Genbank) |
| 509 | Melanoma | 0.1852936 | 0.424706 | 0.351439 | J00277_at 0.218226240 | (genomic clones lambda-[SK2-T2, HS5781]; cDNA clones RS-[3,4, 6]) c-Ha-ras1 proto-oncogene, complete coding sequence |
| 510 | Melanoma | 0.1847509 | 0.4246754 | 0.351433 | AA007583_a t 0.218090635 | Homo sapiens DNA sequence from Fosmid 27C3 on chromosome 22q11.2-qter. Contains two possibly alternatively spliced unknown genes, one with homology to a worm protein. Contains ESTs |

FIG. 8Z

| | | | | | |
|---|---|---|---|---|---|
| 511 | Melanoma | 0.1846325 | 0.4244558 | 0.351433 | 0.218004408 17_at | RC_AA4780 | Homo sapiens alpha 1,2-mannosidase IB mRNA, complete cds |
| 512 | Melanoma | 0.1845188 | 0.4242718 | 0.351369 | 0.217819667 6_at | RC_AA1608 | H.sapiens hGDS mRNA for smg GDS |
| 513 | Melanoma | 0.1839874 | 0.4242469 | 0.351264 | 0.217634176 3_at | RC_AA2274 | Homo sapiens mRNA for KIAA0859 protein, complete cds |
| 514 | Melanoma | 0.1837206 | 0.4241274 | 0.35112 | 0.217620496 3_at | RC_AA4169 | EST: zl69h05.s1 Soares testis NHT Homo sapiens cDNA clone 727641 3' similar to gb:X14850_cds1 HISTONE H2A.X (HUMAN).; mRNA sequence. (from Genbank) |
| 515 | Melanoma | 0.1835473 | 0.424098 | 0.351081 | 0.217474755 | U22662_at | Nuclear orphan receptor LXR-alpha mRNA |
| 516 | Melanoma | 0.1834348 | 0.424037 | 0.351061 | 0.217267572 8_at | RC_AA1509 | EST: zl47e06.s1 Soares pregnant uterus NbHPU Homo sapiens cDNA clone 505090 3', mRNA sequence. (from Genbank) |
| 517 | Melanoma | 0.1830188 | 0.4238995 | 0.350885 | 0.217229251 | M20777_at | , alpha-2 (VI) collagen |
| 518 | Melanoma | 0.1825981 | 0.4238286 | 0.350783 | 0.21719977 6_at | RC_AA4614 | EST: zx68g01.s1 Soares total fetus Nb2HF8 9w Homo sapiens cDNA clone 796656 3' similar to TR:G577189 G577189 SIMILAR TO DEAD BOX RNA HELICASES.; mRNA sequence. (from Genbank) |
| 519 | Melanoma | 0.182339 | 0.4237262 | 0.350783 | 0.217041896 _at | RC_AA2817 | Mannose-P-dolichol utilization defect 1 |
| 520 | Melanoma | 0.1822734 | 0.4237137 | 0.350589 | 0.216998174 4_at | RC_AA4421 | EST: zw56h03.s1 Soares total fetus Nb2HF8 9w Homo sapiens cDNA clone 774101 3', mRNA sequence. (from Genbank) |
| 521 | Melanoma | 0.1822424 | 0.4237042 | 0.350588 | 0.216888382 1_at | RC_AA2825 | Platelet-activating factor acetylhydrolase, isoform Ib, alpha subunit (45kD) |
| 522 | Melanoma | 0.1821363 | 0.4230932 | 0.350534 | 0.21680659 | U50330_at | BMP1 Bone morphogenetic protein 1 |
| 523 | Melanoma | 0.1818144 | 0.4227979 | 0.350458 | 0.216735844 6_at | RC_AA3211 | EST: EST23600 Frontal lobe Homo sapiens cDNA 3' end similar to EST containing Alu repeat, mRNA sequence. (from Genbank) |
| 524 | Melanoma | 0.1810391 | 0.4227945 | 0.350324 | 0.216603471 | D31628_s_a t | 4-HYDROXYPHENYLPYRUVATE DIOXYGENASE |
| 525 | Melanoma | 0.1809776 | 0.4227658 | 0.350138 | 0.216477441 | M23234_s_a t | PGY3 P glycoprotein 3/multiple drug resistance 3 |
| 526 | Melanoma | 0.1808598 | 0.4227137 | 0.350031 | 0.216382477 4_at | RC_AA4306 | EST: zw26d12.s1 Soares ovary tumor NbHOT Homo sapiens cDNA clone 770423 3', mRNA sequence. (from Genbank) |
| 527 | Melanoma | 0.1806435 | 0.422467 | 0.349852 | 0.216355045 7_at | RC_AA2332 | Transforming growth factor beta 1 induced transcript 1 |
| 528 | Melanoma | 0.1806164 | 0.4223196 | 0.349725 | 0.216182663 0_at | RC_AA4528 | EST: zx36d04.s1 Soares total fetus Nb2HF8 9w Homo sapiens cDNA clone 788551 3' similar to TR:G595950 G595950 PROTEIN N-TERMINAL ASPARAGINE AMIDOHYDROLASE.; mRNA sequence. (from Genbank) |
| 529 | Melanoma | 0.1799611 | 0.4221661 | 0.349615 | 0.216137595 8_at | RC_AA0397 | EST: zk40g10.s1 Soares pregnant uterus NbHPU Homo sapiens cDNA clone 485346 3', mRNA sequence. (from Genbank) |

FIG. 8A2

| # | Type | | | | | | Description |
|---|---|---|---|---|---|---|---|
| 530 | Melanoma | 0.1799459 | 0.4221318 | 0.349279 | 0.21604268 | RC_AA4022 72_at | EST: zu48b11.s1 Soares ovary tumor NbHOT Homo sapiens cDNA clone 741213 3', mRNA sequence. (from Genbank) |
| 531 | Melanoma | 0.1798918 | 0.4219402 | 0.349164 | 0.21593903 | U49928_at | TAK1 binding protein 1 (TAB1) mRNA |
| 532 | Melanoma | 0.1795847 | 0.4217333 | 0.349121 | 0.21579422 | RC_AA3218 33_at | EST: EST24395 Cerebellum II Homo sapiens cDNA 3' end, mRNA sequence. (from Genbank) |
| 533 | Melanoma | 0.1795117 | 0.4216305 | 0.349116 | 0.21560128 | D30954_at | EST: Human fetal-lung cDNA 5'-end sequence, mRNA sequence. (from Genbank) |
| 534 | Melanoma | 0.1791461 | 0.4216085 | 0.349113 | 0.21553794 | RC_AA6096 16_at | EST: af15g02.s1 Soares testis NHT Homo sapiens cDNA clone 1031762 3', mRNA sequence. (from Genbank) |
| 535 | Melanoma | 0.1789497 | 0.4215317 | 0.349103 | 0.21540767 | N75611_s_a t | EST: yw37b04.r1 Homo sapiens cDNA clone 254383 5'. (from Genbank) |
| 536 | Melanoma | 0.1788928 | 0.421485 | 0.348997 | 0.21533713 | S78187_at | M-PHASE INDUCER PHOSPHATASE 2 |
| 537 | Melanoma | 0.1785964 | 0.4214769 | 0.348988 | 0.21529533 | AA174173_a t | EST: PTH156 HTCDL1 Homo sapiens cDNA 5'/3', mRNA sequence. (from Genbank) |
| 538 | Melanoma | 0.1783743 | 0.421444 | 0.348814 | 0.21517867 | D31286_at | Homo sapiens mRNA for smallest subunit of ubiquinol-cytochrome c reductase, complete cds |
| 539 | Melanoma | 0.1776384 | 0.4213603 | 0.348732 | 0.21498258 | D13640_at | HLA-C Major histocompatibility complex, class I, C |
| 540 | Melanoma | 0.1771608 | 0.4212545 | 0.34867 | 0.2148057 | AA292745_a t | EST: zt55h02.r1 Soares ovary tumor NbHOT Homo sapiens cDNA clone 726291 5' similar to TR:G984317 G984317 TRYPSIN-RELATED PROTEIN.; mRNA sequence. (from Genbank) |
| 541 | Melanoma | 0.1767132 | 0.4212402 | 0.348464 | 0.21475953 | RC_AA6213 40_a | EST: af85c04.s1 Soares testis NHT Homo sapiens cDNA clone 1048806 3' similar to SW:YK61_YEAST P36160 HYPOTHETICAL 39.6 KD PROTEIN IN MTD1-NUP133 INTERGENIC REGION.; mRNA sequence. (from Genbank) |
| 542 | Melanoma | 0.1764979 | 0.421196 | 0.348367 | 0.21470709 | AA382383_f _at | EST: EST95583 Testis I Homo sapiens cDNA 5' end, mRNA sequence. (from Genbank) |
| 543 | Melanoma | 0.1763369 | 0.421051 | 0.348321 | 0.21461616 | M11313_s_a t | A2M Alpha-2-macroglobulin |
| 544 | Melanoma | 0.1761146 | 0.4210094 | 0.348195 | 0.21451747 | RC_AA4500 10_at | EST: zx33f04.s1 Soares total fetus Nb2HF8 9w Homo sapiens cDNA clone 788287 3', mRNA sequence. (from Genbank) |
| 545 | Melanoma | 0.1757035 | 0.4208742 | 0.348036 | 0.21441372 | AD000092_c ds2_at | Hypothetical human protein R31240_2 gene extracted from Homo sapiens DNA from chromosome 19p13.2 cosmids R31240, R30272 and R28549 containing the EKLF, GCDH, CRTC, and RAD23A genes, genomic sequence |
| 546 | Melanoma | 0.1755118 | 0.42087 | 0.34789 | 0.21432891 | U49785_at | DCT Dopachrome tautomerase (dopachrome delta-isomerase, tyrosine-related protein 2) |
| 547 | Melanoma | 0.1752885 | 0.4208263 | 0.347805 | 0.21419992 | L04751_at | CYP4A11 Cytochrome P450, subfamily IVA, polypeptide 11 |
| 548 | Melanoma | 0.1749978 | 0.4207246 | 0.347629 | 0.21413423 | RC_AA2335 45_at | EST: zr30h12.s1 Stratagene NT2 neuronal precursor 937230 Homo sapiens cDNA clone 664967 3', mRNA sequence. (from Genbank) |

FIG. 8B2

| | | | | | | |
|---|---|---|---|---|---|---|
| 549 | Melanoma | 0.1746173 | 0.4203002 | 0.34762 | RC_AA3994 14_at | EST: zt50e07.s1 Soares ovary tumor NbHOT Homo sapiens cDNA clone 725796 3', mRNA sequence. (from Genbank) |
| 550 | Melanoma | 0.174472 | 0.4202484 | 0.347565 | 0.21401525 U79258_at | Clone 23732 mRNA, partial cds |
| 551 | Melanoma | 0.1742542 | 0.4200515 | 0.347502 | 0.21393442 YEL019c/M MS21_at | No info for gene |
| 552 | Melanoma | 0.1740017 | 0.4198775 | 0.347477 | RC_AA4285 0.21381629 67_at | EST: zw74b07.s1 Soares testis NHT Homo sapiens cDNA clone 781909 3', mRNA sequence. (from Genbank) |
| 553 | Melanoma | 0.1739702 | 0.4197269 | 0.347206 | 0.21370651 AA315930_a t | EST: EST187807 Colon carcinoma (HCC) cell line II Homo sapiens cDNA 5' end, mRNA sequence. (from Genbank) |
| 554 | Melanoma | 0.1736185 | 0.4195799 | 0.347203 | 0.21359609 R29548_f_at | Proteasome (prosome, macropain) subunit, beta type, 7 |
| 555 | Melanoma | 0.1730741 | 0.4195797 | 0.347187 | RC_AA4432 0.2135655 12_at | EST: aa14d01.s1 Soares NhHMPu S1 Homo sapiens cDNA clone 813217 3', mRNA sequence. (from Genbank) |
| 556 | Melanoma | 0.1730713 | 0.4194993 | 0.347141 | 0.21342245 X54936_at | PGF Placental growth factor, vascular endothelial growth factor-related protein |
| 557 | Melanoma | 0.1730232 | 0.4193354 | 0.347092 | RC_AA2356 0.2131477 04_at | EST: zt36b07.s1 Soares ovary tumor NbHOT Homo sapiens cDNA clone 724405 3', mRNA sequence. (from Genbank) |
| 558 | Melanoma | 0.1728407 | 0.4192781 | 0.347068 | RC_AA4256 0.2130221 36_at | Potassium intermediate/small conductance calcium-activated channel, subfamily N, member 4 |
| 559 | Melanoma | 0.1728082 | 0.4192761 | 0.346734 | 0.21298885 R12538_at | EST: yf56b10.r1 Homo sapiens cDNA clone 26221 5'. (from Genbank) |
| 560 | Melanoma | 0.1726556 | 0.4192098 | 0.346644 | RC_AA4364 0.21287689 71_at | EST: zv08e05.s1 Soares NhHMPu S1 Homo sapiens cDNA clone 753056 3', mRNA sequence. (from Genbank) |
| 561 | Melanoma | 0.1726251 | 0.4191891 | 0.346516 | 0.21277319 X76040_at | HLON ATP-dependent protease mRNA, nuclear gene encoding mitochondrial protein |
| 562 | Melanoma | 0.1723469 | 0.4191715 | 0.346282 | 0.2126996 AA422029_a t | EST: zv26g08.r1 Soares NhHMPu S1 Homo sapiens cDNA clone 754814 5', mRNA sequence. (from Genbank) |
| 563 | Melanoma | 0.1722348 | 0.4191453 | 0.346185 | RC_AA4323 0.21264328 62_at | Homo sapiens mRNA for KIAA0678 protein, partial cds |
| 564 | Melanoma | 0.1720402 | 0.4190887 | 0.346129 | RC_AA0853 0.21259494 99_at | Homo sapiens mRNA for JM4 protein, complete CDS (clone IMAGE 546750 and LLNLc110F1857Q7 (RZPD Berlin)) |
| 565 | Melanoma | 0.1716323 | 0.4189315 | 0.346018 | 0.21249521 R54918_at | EST: yf78h06.r1 Homo sapiens cDNA clone 154907 5'. (from Genbank) |
| 566 | Melanoma | 0.1714507 | 0.4188944 | 0.345902 | 0.21228649 D26561_cds 3_at | ORF for E7 protein gene extracted from Human papillomavirus 5b genome integrated into human carcinoma DNA |
| 567 | Melanoma | 0.1710486 | 0.4188809 | 0.345889 | 0.2122844 C01766_s_a t | EST: HUMGS0003714, Human Gene Signature, 3'-directed cDNA sequence, mRNA sequence. (from Genbank) |
| 568 | Melanoma | 0.1700993 | 0.4185803 | 0.345773 | 0.21220465 M60299_at | Alpha-1 collagen type II gene, exons 1, 2 and 3 |
| 569 | Melanoma | 0.1700562 | 0.4184842 | 0.345638 | RC_AA4471 0.21206182 53_at | EST: zw93h05.s1 Soares total fetus Nb2HF8 9w Homo sapiens cDNA clone 784569 3', mRNA sequence. (from Genbank) |
| 570 | Melanoma | 0.1700185 | 0.4183255 | 0.345604 | 0.21201916 IL2_at | No info for gene |

FIG. 8C2

| # | Type | | | | | Description |
|---|---|---|---|---|---|---|
| 571 | Melanoma | 0.169941 | 0.4183255 | 0.345583 | 0.21197927 U57094_at | Small GTP-binding protein mRNA |
| 572 | Melanoma | 0.1698767 | 0.417914 | 0.345577 | 0.21189353 M98528_at | BRAIN NEURON CYTOPLASMIC PROTEIN 1 |
| 573 | Melanoma | 0.1698465 | 0.4176918 | 0.345471 | 0.21173748 RC_AA477432_s_at | EST: zu42f03.s1 Soares ovary tumor NbHOT Homo sapiens cDNA clone 740669 3', mRNA sequence. (from Genbank) |
| 574 | Melanoma | 0.1697034 | 0.4175581 | 0.345457 | 0.21155561 RC_AA426403_at | EST: zv05g04.s1 Soares NhHMPu S1 Homo sapiens cDNA clone 752790 3', mRNA sequence. (from Genbank) |
| 575 | Melanoma | 0.1692975 | 0.4174145 | 0.345434 | 0.21151495 RC_AA029455_at | Homo sapiens myosin-IXb splice variant (Myo9b) mRNA, partial cds |
| 576 | Melanoma | 0.1691612 | 0.4173892 | 0.345403 | 0.21130994 AA043111_s_at | EST: zk48b08.r1 Soares pregnant uterus NbHPU Homo sapiens cDNA clone 486039 5', mRNA sequence. (from Genbank) |
| 577 | Melanoma | 0.1688578 | 0.417167 | 0.345358 | 0.21121506 U62317_rna7_at | Hypothetical protein 384D8_7 gene extracted from Chromosome 22q13 BAC Clone CIT987SK-384D8 complete sequence |
| 578 | Melanoma | 0.1687387 | 0.4169852 | 0.345307 | 0.21111076 C00125_s_at | EST: HUMGS0005758, Human Gene Signature, 3'-directed cDNA sequence, mRNA sequence. (from Genbank) |
| 579 | Melanoma | 0.1685409 | 0.4168473 | 0.345115 | 0.21097471 D87002_cds2_at | POM121-like 1 gene extracted from Human (lambda) DNA for immunoglobin light chain |
| 580 | Melanoma | 0.1679878 | 0.4166603 | 0.34507 | 0.21091464 RC_AA191512_at | EST: zp81g01.s1 Stratagene HeLa cell s3 937216 Homo sapiens cDNA clone 626640 3', mRNA sequence. (from Genbank) |
| 581 | Melanoma | 0.1677827 | 0.4166479 | 0.344923 | 0.21083865 RC_AA620395_at | EST: ae57c05.s1 Stratagene lung carcinoma 937218 Homo sapiens cDNA clone 950984 3', mRNA sequence. (from Genbank) |
| 582 | Melanoma | 0.1677489 | 0.4165682 | 0.344823 | 0.21077015 M63959_at | LRPAP1 Low density lipoprotein-related protein-associated protein 1 (alpha-2-macroglobulin receptor-associated protein 1 |
| 583 | Melanoma | 0.167699 | 0.4161298 | 0.344816 | 0.21066098 RC_AA476352_at | EST: zw99e08.s1 Soares total fetus Nb2HF8 9w Homo sapiens cDNA clone 785126 3', mRNA sequence. (from Genbank) |
| 584 | Melanoma | 0.1676976 | 0.4161204 | 0.344571 | 0.21048081 RC_AA486183_at | EST: ab35a02.s1 Stratagene HeLa cell s3 937216 Homo sapiens cDNA clone 842762 3', mRNA sequence. (from Genbank) |
| 585 | Melanoma | 0.1666581 | 0.4160848 | 0.344571 | 0.21045741 X05345_at | HARS Histidyl-tRNA synthetase |
| 586 | Melanoma | 0.1663773 | 0.4158745 | 0.344385 | 0.21031791 W77943_at | Apolipoprotein E |
| 587 | Melanoma | 0.1663605 | 0.4158723 | 0.344316 | 0.21018654 RC_AA447123_at | EST: zw93c01.s1 Soares total fetus Nb2HF8 9w Homo sapiens cDNA clone 784512 3', mRNA sequence. (from Genbank) |
| 588 | Melanoma | 0.1658524 | 0.4157987 | 0.344164 | 0.21010713 RC_AA282196_at | Homo sapiens PKY protein kinase mRNA, complete cds |
| 589 | Melanoma | 0.1657034 | 0.4156921 | 0.344051 | 0.20998488 W02342_at | Homo sapiens putative transmembrane protein (CLN5) mRNA, complete cds |
| 590 | Melanoma | 0.1651086 | 0.4156921 | 0.344043 | 0.20988046 M23533_at | Alpha 2 adrenergic receptor gene |
| 591 | Melanoma | 0.1650042 | 0.4155925 | 0.343897 | 0.20974827 AA033766_s_at | EST: zk19b12.r1 Soares pregnant uterus NbHPU Homo sapiens cDNA clone 470975 5', mRNA sequence. (from Genbank) |
| 592 | Melanoma | 0.164975 | 0.4153034 | 0.343593 | 0.20967725 M36205_at | SYNAPTOBREVIN 2 |

FIG. 8D2

| # | Type | | | | | Accession | Description |
|---|---|---|---|---|---|---|---|
| 593 | Melanoma | 0.1647443 | 0.4153034 | 0.343503 | 0.2095669921 | U08198_rna1_at | Complement C8 gamma subunit precursor (C8G) gene |
| 594 | Melanoma | 0.1646106 | 0.4151892 | 0.343479 | 0.209520772 | RC_AA4818 | EST: zv41b12.s1 Soares ovary tumor NbHOT Homo sapiens cDNA clone 756191 3', mRNA sequence. (from Genbank) |
| 595 | Melanoma | 0.1644774 | 0.4150965 | 0.343294 | 0.20947394 | L32976_at-2 | Mixed lineage kinase 3 |
| 596 | Melanoma | 0.1644774 | 0.4150607 | 0.343279 | 0.20939918 | L32976_at | Protein kinase (MLK-3) mRNA |
| 597 | Melanoma | 0.1643526 | 0.4148867 | 0.34326 | 0.20933764 | RC_AA6209 65_at | EST: af88f01.s1 Soares testis NHT Homo sapiens cDNA clone 1049113 3' similar to SW:PUA1_MOUSE P28650 ADENYLOSUCCINATE SYNTHETASE, MUSCLE ISOZYME ;contains Alu repetitive element;, mRNA sequence. (from Genbank) |
| 598 | Melanoma | 0.1641523 | 0.4147874 | 0.343244 | 0.20926857 | U96922_at | Inositol polyphosphate 4-phosphatase type II-alpha mRNA |
| 599 | Melanoma | 0.1640507 | 0.4147636 | 0.343143 | 0.20895597 | RC_AA4243 43_at | EST: zv82c10.s1 Soares total fetus Nb2HF8 9w Homo sapiens cDNA clone 760146 3', mRNA sequence. (from Genbank) |
| 600 | Melanoma | 0.1638886 | 0.4146904 | 0.343084 | 0.20890443 | RC_AA2522 09_at | EST: zr63g05.s1 Soares NbHMPu S1 Homo sapiens cDNA clone 668120 3', mRNA sequence. (from Genbank) |
| 601 | Melanoma | 0.1633869 | 0.4146731 | 0.343052 | 0.20889341 | D79985_at | A cell surface protein |
| 602 | Melanoma | 0.1632321 | 0.4143687 | 0.34296 | 0.20884775 | RC_AA3995 92_s_at | Homo sapiens Dim1p homolog (hdim1+) mRNA, complete cds |
| 603 | Melanoma | 0.1632116 | 0.4143323 | 0.342917 | 0.2087036 | RC_AA0402 70_at | EST: zf05e04.s1 Soares fetal heart NbHH19W Homo sapiens cDNA clone 376062 3', mRNA sequence. (from Genbank) |
| 604 | Melanoma | 0.163021 | 0.4143316 | 0.342914 | 0.2085798 | AF008442_a t | RNA polymerase I subunit |
| 605 | Melanoma | 0.1629673 | 0.4139958 | 0.342763 | 0.20850164 | RC_AA4170 34_at | EST: zu04f10.s1 Soares testis NHT Homo sapiens cDNA clone 730891 3', mRNA sequence. (from Genbank) |
| 606 | Melanoma | 0.1627408 | 0.4137412 | 0.342582 | 0.20836495 | AA009826_a t | EST: ze82h02.r1 Soares fetal heart NbHH19W Homo sapiens cDNA clone 365451 5', mRNA sequence. (from Genbank) |
| 607 | Melanoma | 0.1624795 | 0.4132887 | 0.342514 | 0.20828451 | L39060_at | Transcription factor SL1 mRNA |
| 608 | Melanoma | 0.1624795 | 0.4128082 | 0.342383 | 0.20816506 | L39060_at-2 | Homo sapiens transcription factor SL1 mRNA, complete cds |
| 609 | Melanoma | 0.1623464 | 0.4126639 | 0.342291 | 0.20805807 | AF000545_a t | Putative purinergic receptor P2Y10 gene |
| 610 | Melanoma | 0.1623273 | 0.4125285 | 0.342262 | 0.20793438 | X04325_at | GJB1 Gap junction protein, beta 1, 32kD (connexin 32, Charcot-Marie-Tooth neuropathy, X-linked) |
| 611 | Melanoma | 0.1622748 | 0.4125083 | 0.341841 | 0.20775728 | RC_AA6091 85_at | EST: af12c06.s1 Soares testis NHT Homo sapiens cDNA clone 1031434 3' similar to SW:INO1_SPIPO P42803 MYO-INOSITOL-1-PHOSPHATE SYNTHASE ;, mRNA sequence. (from Genbank) |
| 612 | Melanoma | 0.1620027 | 0.4124818 | 0.341782 | 0.2077292 | H19570_s_a t | EST: yn59b03.r1 Homo sapiens cDNA clone 172685 5' similar to contains Alu repetitive element;contains PTR5 repetitive element :, (from Genbank) |
| 613 | Melanoma | 0.1617696 | 0.4124554 | 0.341514 | 0.20765826 | M73077_at | Glucocorticoid receptor repression factor 1 (GRF-1) mRNA |

FIG. 8E2

| | | | | | | |
|---|---|---|---|---|---|---|
| 614 | Melanoma | 0.1617623 | 0.4124381 | 0.341331 | 0.20761944 | RC_AA4777 39_at | EST: zu34a07.s1 Soares ovary tumor NbHOT Homo sapiens cDNA clone 739860 3', mRNA sequence. (from Genbank) |
| 615 | Melanoma | 0.1617525 | 0.4123822 | 0.341248 | 0.20745352 | L33799_at | PCOLCE Procollagen C-endopeptidase enhancer |
| 616 | Melanoma | 0.16108 | 0.4121076 | 0.341213 | 0.20731756 | RC_AA0373 57_j_at | EST: zc03c04.s1 Soares parathyroid tumor NbHPA Homo sapiens cDNA clone 321222 3' similar to contains Alu repetitive element;, mRNA sequence. (from Genbank) |
| 617 | Melanoma | 0.1609976 | 0.4120706 | 0.341036 | 0.20722262 | X84746_at | Histo-blood group AB0 gene, exon 1 |
| 618 | Melanoma | 0.1609453 | 0.4118742 | 0.341016 | 0.20713113 | Z21507_at | EEF1D Eukaryotic translation elongation factor 1 delta (guanine nucleotide exchange protein) |
| 619 | Melanoma | 0.1609122 | 0.4118393 | 0.340939 | 0.20709316 | U08998_at | TAR RNA binding protein (TRBP) mRNA |
| 620 | Melanoma | 0.1606792 | 0.4118208 | 0.340871 | 0.20705383 | RC_AA0629 15_at | Endothelin converting enzyme 1 |
| 621 | Melanoma | 0.1592472 | 0.4116835 | 0.340782 | 0.20687534 | J05070_at | MMP2 Matrix metalloproteinase 2 (gelatinase A; collagenase type IV) |
| 622 | Melanoma | 0.1591439 | 0.4115713 | 0.340664 | 0.20678422 | HG862-HT862_s_at | Transition Protein 2 |
| 623 | Melanoma | 0.1589046 | 0.4115148 | 0.340657 | 0.20670292 | N72380_s_a t | EST: yw38f12.r1 Soares fetal liver spleen 1NFLS Homo sapiens cDNA clone 245039 5', mRNA sequence. (from Genbank) |
| 624 | Melanoma | 0.1587699 | 0.4113918 | 0.340523 | 0.20651266 | AB000584_a _a | Prostate differentiation factor mRNA |
| 625 | Melanoma | 0.1587646 | 0.4113701 | 0.340451 | 0.20646665 | HG2171-HT2241_at | 12-Lipoxygenase |
| 626 | Melanoma | 0.1583884 | 0.4113576 | 0.340412 | 0.20635054 | X00038_at | H4 histone gene |
| 627 | Melanoma | 0.1576769 | 0.4111387 | 0.340374 | 0.20623243 | RC_AA5051 41_at | EST: aa65e04.s1 NCI_CGAP_GCB1 Homo sapiens cDNA clone IMAGE:825822 3', mRNA sequence. (from Genbank) |
| 628 | Melanoma | 0.1576515 | 0.4111219 | 0.340267 | 0.20620953 | RC_AA0741 57_at | EST: zm76b01.s1 Stratagene neuroepithelium (#937231) Homo sapiens cDNA clone 531529 3', mRNA sequence. (from Genbank) |
| 629 | Melanoma | 0.1573105 | 0.4111149 | 0.34025 | 0.20612557 | RC_AA2232 09_at | EST: zr06c11.s1 Stratagene NT2 neuronal precursor 937230 Homo sapiens cDNA clone 650708 3', mRNA sequence. (from Genbank) |
| 630 | Melanoma | 0.1572623 | 0.4109894 | 0.340224 | 0.20606777 | X68733_rna 1_at | Alpha1-antichymotrypsin, exon 1 |
| 631 | Melanoma | 0.1569663 | 0.4109894 | 0.34021 | 0.20599413 | RC_AA4968 82_s_at | Eukaryotic translation initiation factor 3, subunit 4 (delta, 44kD) |
| 632 | Melanoma | 0.156695 | 0.4109779 | 0.340111 | 0.20581071 | M68864_at | ORF mRNA |
| 633 | Melanoma | 0.1555559 | 0.4109672 | 0.34008 | 0.2057663 | RC_AA4479 94_at | EST: zw82g03.s1 Soares testis NHT Homo sapiens cDNA clone 782740 3', mRNA sequence. (from Genbank) |
| 634 | Melanoma | 0.1553542 | 0.4109068 | 0.34006 | 0.2056065 | RC_AA4534 58_at | EST: zx45b04.s1 Soares testis NHT Homo sapiens cDNA clone 795151 3', mRNA sequence. (from Genbank) |

FIG. 8F2

| | | | | | | |
|---|---|---|---|---|---|---|
| 635 | Melanoma | 0.1552873 | 0.4108117 | 0.340005 | 0.205531886 3_at | RC_AA4653 | EST: aa23d02.s1 NCI_CGAP_GCB1 Homo sapiens cDNA clone IMAGE:814083 3', mRNA sequence. (from Genbank) |
| 636 | Melanoma | 0.1547989 | 0.4105207 | 0.33995 | 0.20548458 t | AB002365_a | KIAA0367 gene, partial cds |
| 637 | Melanoma | 0.1543463 | 0.4103411 | 0.339807 | 0.20540215 | W70167_at | EST: zd52b01.r1 Soares fetal heart NbHH19W Homo sapiens cDNA clone 344233 5', mRNA sequence. (from Genbank) |
| 638 | Melanoma | 0.154187 | 0.410048 | 0.339741 | 0.20537351 14_f_at | RC_AA4107 | EST: zv35h07.s1 Soares ovary tumor NbHOT Homo sapiens cDNA clone 755677 3' similar to contains element MSR1 repetitive element ., mRNA sequence. (from Genbank) |
| 639 | Melanoma | 0.1540165 | 0.4099736 | 0.339573 | 0.20514625 72_s_at | RC_AA3823 | EST: EST95571 Testis I Homo sapiens cDNA 3' end, mRNA sequence. (from Genbank) |
| 640 | Melanoma | 0.1540105 | 0.4099084 | 0.339345 | 0.20514336 t | AA129547_a | EST: zn83f01.r1 Stratagene lung carcinoma 937218 Homo sapiens cDNA clone 564793 5', mRNA sequence. (from Genbank) |
| 641 | Melanoma | 0.1539971 | 0.4097418 | 0.33934 | 0.2049741 57_at | RC_AA0993 | EST: zk85c01.s1 Soares pregnant uterus NbHPU Homo sapiens cDNA clone 489600 3', mRNA sequence. (from Genbank) |
| 642 | Melanoma | 0.1539887 | 0.4096412 | 0.339228 | 0.2049223 89_at | RC_AA0341 | EST: zi06h12.s1 Soares fetal liver spleen 1NFLS S1 Homo sapiens cDNA clone 430055 3', mRNA sequence. (from Genbank) |
| 643 | Melanoma | 0.1537932 | 0.4095921 | 0.33915 | 0.20484224 | M54927_at | PLP Proteolipid protein (Pelizaeus-Merzbacher disease, spastic paraplegia 2, uncomplicated) |
| 644 | Melanoma | 0.1535034 | 0.4095879 | 0.339068 | 0.20469436 22_at | RC_AA4530 | Homo sapiens clone 638 unknown mRNA, complete sequence |
| 645 | Melanoma | 0.1534117 | 0.4094783 | 0.338861 | 0.20461649 | U91616_at | I kappa B epsilon (IkBe) mRNA |
| 646 | Melanoma | 0.1533542 | 0.4093291 | 0.338812 | 0.20455588 | U09587_at | GARS Glycyl-tRNA synthetase |
| 647 | Melanoma | 0.1527722 | 0.4092308 | 0.338722 | 0.20444237 69_s_at | RC_AA1372 | EST: zn94d01.s1 Stratagene lung carcinoma 937218 Homo sapiens cDNA clone 565825 3', mRNA sequence. (from Genbank) |
| 648 | Melanoma | 0.1525199 | 0.4090834 | 0.338556 | 0.20441602 75_at | RC_AA0710 | EST: zm58d10.s1 Stratagene fibroblast (#937212) Homo sapiens cDNA clone 529843 3', mRNA sequence. (from Genbank) |
| 649 | Melanoma | 0.152433 | 0.4089777 | 0.338542 | 0.2043104 43_at | RC_AA4888 | EST: aa55a10.s1 NCI_CGAP_GCB1 Homo sapiens cDNA clone IMAGE:824826 3', mRNA sequence. (from Genbank) |
| 650 | Melanoma | 0.1524173 | 0.4088474 | 0.338509 | 0.20423162 32_at | RC_AA0789 | EST: zm95f07.s1 Stratagene colon HT29 (#937221) Homo sapiens cDNA clone 545701 3', mRNA sequence. (from Genbank) |
| 651 | Melanoma | 0.1523878 | 0.408763 | 0.338479 | 0.204171 | D83767_at | Clone N9 Rep-8 mRNA |
| 652 | Melanoma | 0.152278 | 0.4086798 | 0.338396 | 0.20403653 t | AF006084_a | Arp2/3 protein complex subunit p41-Arc (ARC41) mRNA |

FIG. 8G2

| | | | | | | |
|---|---|---|---|---|---|---|
| 653 | Melanoma | 0.1518822 | 0.4085639 | 0.338295 | 0.20395334 | HG2260-HT2349_s_a t | Duchenne Muscular Dystrophy Protein (Dmd) |
| 654 | Melanoma | 0.1514909 | 0.408477 | 0.338285 | 0.20381165 | U43368_at | Vascular endothelial growth factor B |
| 655 | Melanoma | 0.1511821 | 0.4084748 | 0.338251 | 0.203758 | AA490685_a t | EST: aa45b03.r1 Soares Nh-HMPu S1 Homo sapiens cDNA clone 823853 5', mRNA sequence. (from Genbank) |
| 656 | Melanoma | 0.1510878 | 0.4083822 | 0.338197 | 0.20361517 | RC_AA5999 91_at | EST: ag28h10.s1 Jia bone marrow stroma Homo sapiens cDNA clone 1090915 3', mRNA sequence. (from Genbank) |
| 657 | Melanoma | 0.1510479 | 0.4083098 | 0.338146 | 0.20346221 | RC_AA1328 74_at | EST: zo19e03.s1 Stratagene colon (#937204) Homo sapiens cDNA clone 587356 3', mRNA sequence. (from Genbank) |
| 658 | Melanoma | 0.1508188 | 0.4082077 | 0.337873 | 0.20339692 | Y08374_rna 1_at | GP-39 cartilage protein gene extracted from H.sapiens gene encoding cartilage GP-39 protein, exon 1 and 2 (and joined CDS) |
| 659 | Melanoma | 0.1507824 | 0.4081267 | 0.337746 | 0.203314 | AA094752_a t | Protein phosphatase 3 (formerly 2B), catalytic subunit, beta isoform (calcineurin A beta) |
| 660 | Melanoma | 0.1507763 | 0.4080437 | 0.337705 | 0.20326771 | U32907_at | P37NB mRNA |
| 661 | Melanoma | 0.1502544 | 0.4080264 | 0.337628 | 0.20314482 | X02956_f_at | Interferon, alpha 5 |
| 662 | Melanoma | 0.1497564 | 0.4080111 | 0.337543 | 0.20310876 | R71205_at | EST: yi53g09.r1 Homo sapiens cDNA clone 143008 5' similar to gb:M15182 BETA-GLUCURONIDASE PRECURSOR (HUMAN); (from Genbank) |
| 663 | Melanoma | 0.1496204 | 0.4079685 | 0.337524 | 0.20306845 | M27826_at | Endogenous retroviral protease mRNA |
| 664 | Melanoma | 0.1495073 | 0.4079287 | 0.337434 | 0.20297052 | RC_AA0046 37_at | EST: zh92b04.s1 Soares fetal liver spleen 1NFLS S1 Homo sapiens cDNA clone 428719 3', mRNA sequence. (from Genbank) |
| 665 | Melanoma | 0.1492769 | 0.4079234 | 0.337403 | 0.2028724 | U51003_s_a t | DLX-2 (DLX-2) gene |
| 666 | Melanoma | 0.1488662 | 0.4079145 | 0.33738 | 0.20282988 | X83301_s_a t | SMA5 mRNA |
| 667 | Melanoma | 0.148714 | 0.4078824 | 0.337323 | 0.20273574 | RC_AA4259 21_at | Homo sapiens I-1 receptor candidate protein mRNA, complete cds |
| 668 | Melanoma | 0.1486256 | 0.4078138 | 0.337294 | 0.20268215 | U29953_rna 1_at | Pigment epithelium-derived factor gene |
| 669 | Melanoma | 0.1485013 | 0.4077911 | 0.337225 | 0.20255241 | M17236_s_a t | HLA CLASS II HISTOCOMPATIBILITY ANTIGEN, DQ(2) ALPHA CHAIN PRECURSOR |
| 670 | Melanoma | 0.1484353 | 0.4077572 | 0.337045 | 0.20247227 | HG491-HT491_at | Fc Receptor IIb3 For Igg, Low Affinity |
| 671 | Melanoma | 0.1484263 | 0.4076456 | 0.337014 | 0.20233943 | RC_AA2232 84_at | EST: zr08c04.s1 Stratagene NT2 neuronal precursor 937230 Homo sapiens cDNA clone 650886 3', mRNA sequence. (from Genbank) |
| 672 | Melanoma | 0.1484085 | 0.4076387 | 0.336911 | 0.20226167 | AA389673_a t | EST: M164 Fetal heart, Lambda ZAP Express Homo sapiens cDNA 5', mRNA sequence. (from Genbank) |

FIG. 8H2

| # | Type | | | | | | Description |
|---|---|---|---|---|---|---|---|
| 673 | Melanoma | 0.1478715 | 0.4076189 | 0.336833 | 0.20217139 | RC_AA2796 32_at | Homo sapiens chromosome 11, BAC CIT-HSP-311e8 (BC269730) containing the hFEN1 gene |
| 674 | Melanoma | 0.1478334 | 0.4076123 | 0.336633 | 0.20211749 | U52682_at | IRF4 Interferon regulatory factor 4 |
| 675 | Melanoma | 0.1476832 | 0.4075528 | 0.33649 | 0.20209406 | M91368_s_a t | Na+/Ca+ exchanger (CNC) mRNA |
| 676 | Melanoma | 0.1473922 | 0.4074754 | 0.336459 | 0.20196345 | D79998_at | KIAA0176 gene, partial cds |
| 677 | Melanoma | 0.1473374 | 0.4074722 | 0.336459 | 0.20180266 | D50914_at | KIAA0124 gene, partial cds |
| 678 | Melanoma | 0.1472847 | 0.4074695 | 0.336384 | 0.20174090 | U48263_at-2 | Prepronociceptin |
| 679 | Melanoma | 0.1472847 | 0.4074688 | 0.33634 | 0.20163990 | U48263_at | Pre-pro-orphanin FQ (OFQ) mRNA |
| 680 | Melanoma | 0.1469678 | 0.4073905 | 0.336294 | 0.20150504 | W26785_i_a t | EST: 15d6 Human retina cDNA randomly primed sublibrary Homo sapiens cDNA, mRNA sequence. (from Genbank) |
| 681 | Melanoma | 0.1468993 | 0.4073892 | 0.336226 | 0.20146188 | W26649_at | Zinc finger protein 140 (clone pHZ-39) |
| 682 | Melanoma | 0.1464878 | 0.4073837 | 0.336218 | 0.20139492 | M26657_s_a t | DCP1 Dipeptidyl carboxypeptidase 1 (angiotensin I converting enzyme) |
| 683 | Melanoma | 0.1459135 | 0.4071904 | 0.336085 | 0.20130838 | X87871_s_a t | HEPATOCYTE NUCLEAR FACTOR 4 |
| 684 | Melanoma | 0.145714 | 0.4070824 | 0.335956 | 0.20123917 | RC_AA4856 97_at | EST: ab10e09.s1 Stratagene lung (#937210) Homo sapiens cDNA clone 840424 3', mRNA sequence. (from Genbank) |
| 685 | Melanoma | 0.145382 | 0.4069882 | 0.335821 | 0.20112543 | D21163_at | KIAA0031 gene |
| 686 | Melanoma | 0.1452742 | 0.4069247 | 0.335812 | 0.20097478 | AA282300_a t | SET binding factor 1 |
| 687 | Melanoma | 0.1451272 | 0.4069037 | 0.33571 | 0.20092842 | RC_AA1672 73_at | KIAA0468 gene product |
| 688 | Melanoma | 0.1438857 | 0.4067208 | 0.335663 | 0.20086873 | RC_AA1222 17_at | EST: zn83a11.s1 Stratagene lung carcinoma 937218 Homo sapiens cDNA clone 564764 3', mRNA sequence. (from Genbank) |
| 689 | Melanoma | 0.1438632 | 0.4066826 | 0.335424 | 0.20080958 | RC_AA2830 74_at | Homo sapiens mRNA for KIAA0819 protein, partial cds |
| 690 | Melanoma | 0.1437447 | 0.4066334 | 0.335398 | 0.20070097 | R22260_at | EST: yh26c06.r1 Homo sapiens cDNA clone 130858 5'. (from Genbank) |
| 691 | Melanoma | 0.1434109 | 0.4065459 | 0.335242 | 0.20068964 | X87838_at | CTNNB1 Catenin (cadherin-associated protein), beta 1 (88kD) |
| 692 | Melanoma | 0.1428416 | 0.406521 | 0.335207 | 0.20061766 | RC_D59354 _i_at | EST: Human fetal brain cDNA 3'-end GEN-020E05, mRNA sequence. (from Genbank) |
| 693 | Melanoma | 0.1427493 | 0.4064244 | 0.334989 | 0.20051530 1_f_at | RC_AA4910 | EST: aa52g12.s1 NCI_CGAP_GCB1 Homo sapiens cDNA clone IMAGE:824614 3' similar to TR:G1293732 G1293732 O3625P.; mRNA sequence. (from Genbank) |
| 694 | Melanoma | 0.1425003 | 0.4064232 | 0.334703 | 0.20040062 47_at | RC_AA2823 | EST: zf12g11.s1 NCI_CGAP_GCB1 Homo sapiens cDNA clone IMAGE:712964 3', mRNA sequence. (from Genbank) |

FIG. 8I2

| | | | | | |
|---|---|---|---|---|---|
| 695 | Melanoma | 0.1420614 | 0.4064048 | 0.334687 | 0.200333479 | RC_AA4588 90_at | EST: zx88c06.s1 Soares ovary tumor NbHOT Homo sapiens cDNA clone 810826 3', mRNA sequence. (from Genbank) |
| 696 | Melanoma | 0.1418886 | 0.4063966 | 0.334643 | 0.200028089 | W29077_at | EST: 56a9 Human retina cDNA randomly primed sublibrary Homo sapiens cDNA, mRNA sequence. (from Genbank) |
| 697 | Melanoma | 0.1418705 | 0.4062741 | 0.334624 | 0.20019725 | U21090_at | DNA polymerase delta small subunit mRNA |
| 698 | Melanoma | 0.141763 | 0.4062607 | 0.334575 | 0.200095151521_at | RC_AA0530 | SCO1 (yeast homolog) cytochrome oxidase deficient 1 |
| 699 | Melanoma | 0.1415603 | 0.4062389 | 0.334357 | 0.19998854928_s_at | RC_AA4280 | EST: zw54g08.s1 Soares total fetus Nb2HF8 9w Homo sapiens cDNA clone 773918 3', mRNA sequence. (from Genbank) |
| 700 | Melanoma | 0.1415497 | 0.4061989 | 0.334299 | 0.19985531 | X82068_at | GLUTAMATE RECEPTOR 3 PRECURSOR |
| 701 | Melanoma | 0.1415497 | 0.4060484 | 0.334247 | 0.19978759 | X82068_at-2 | Glutamate receptor, ionotrophic, AMPA 3 |
| 702 | Melanoma | 0.1415045 | 0.4058664 | 0.334091 | 0.19970787 | AA249119_a t | EcO276.seq.F Human fetal heart, Lambda ZAP Express Homo sapiens cDNA 5', mRNA sequence. (from Genbank) |
| 703 | Melanoma | 0.1413478 | 0.4056143 | 0.334043 | 0.19962983 | RC_AA4790 40_at | EST: zu36b12.s1 Soares ovary tumor NbHOT Homo sapiens cDNA clone 740063 3', mRNA sequence. (from Genbank) |
| 704 | Melanoma | 0.141247 | 0.4056049 | 0.334009 | 0.19952247 | M62782_s_a t | IGFBP5 Insulin-like growth factor binding protein 5 |
| 705 | Melanoma | 0.1412253 | 0.4055601 | 0.333869 | 0.19936337 | X65633_at | ACTH-R gene for adrenocorticotropic hormone receptor |
| 706 | Melanoma | 0.1409109 | 0.4054221 | 0.333742 | 0.19927162 | D25216_at-2 | KIAA0014 gene product |
| 707 | Melanoma | 0.1409109 | 0.4051966 | 0.333664 | 0.19921839 | D25216_at | KIAA0014 gene |
| 708 | Melanoma | 0.140788 | 0.4049565 | 0.333527 | 0.19914496 | U82987_at-2 | Human Bcl-2 binding component 3 (bbc3) mRNA, partial cds |
| 709 | Melanoma | 0.140788 | 0.4049431 | 0.333491 | 0.19906245 | U82987_at | Bcl-2 binding component 3 (bbc3) mRNA, partial cds |
| 710 | Melanoma | 0.1407813 | 0.4048721 | 0.333482 | 0.19902317 | U69126_s_a t | FUSE binding protein 2 (FBP2) mRNA, partial cds |
| 711 | Melanoma | 0.1407781 | 0.4045708 | 0.333367 | 0.19881782 | S74720_at | DAX-1 |
| 712 | Melanoma | 0.1397577 | 0.4044474 | 0.333314 | 0.19881162 | RC_AA1499 40_at | GLUT1 C-terminal binding protein |
| 713 | Melanoma | 0.1396766 | 0.4043399 | 0.333239 | 0.19864906 | AA380393_a t | EST: EST93352 Supt cells Homo sapiens cDNA 5' end, mRNA sequence. (from Genbank) |
| 714 | Melanoma | 0.1395071 | 0.4041789 | 0.333196 | 0.19858003 | RC_AA4190 26_a | EST: zv34e11.s1 Soares ovary tumor NbHOT Homo sapiens cDNA clone 755564 3' similar to SW:PTN2_RAT P35233 PROTEIN-TYROSINE PHOSPHATASE PTP-S ;, mRNA sequence. (from Genbank) |
| 715 | Melanoma | 0.1394334 | 0.4041316 | 0.333169 | 0.19847952 | AA151565_a t | EST: zl39g07.r1 Soares pregnant uterus NbHPU Homo sapiens cDNA clone 504348 5', mRNA sequence. (from Genbank) |
| 716 | Melanoma | 0.1393092 | 0.404078 | 0.332925 | 0.19839214 | L08904_at-2 | Homo sapiens mRNA for H-2K binding factor-2, complete cds |
| 717 | Melanoma | 0.1393092 | 0.4040715 | 0.332891 | 0.19835356 | L08904_at | H2K binding factor 2 (KBF2) mRNA |
| 718 | Melanoma | 0.1389471 | 0.4039998 | 0.332886 | 0.19828278 | U24169_at | JTV-1 (JTV-1) mRNA |

FIG. 8J2

| | | | | | |
|---|---|---|---|---|---|
| 719 | Melanoma | 0.1389367 | 0.4039849 | 0.332814 | 0.19818299 | S79281_at | Pancreatic ribonuclease [human, mRNA Recombinant Partial, 491 nt] |
| 720 | Melanoma | 0.1388918 | 0.4039556 | 0.332785 | 0.19809368 | RC_AA2165 89_at | EST: zq94e07.s1 Stratagene NT2 neuronal precursor 937230 Homo sapiens cDNA clone 649668 3', mRNA sequence. (from Genbank) |
| 721 | Melanoma | 0.1385533 | 0.403673 | 0.332781 | 0.19797772 | AB002319_a t | Human mRNA for KIAA0321 gene, partial cds. (from Genbank) |
| 722 | Melanoma | 0.1385215 | 0.4034226 | 0.332677 | 0.19790241 | D61391_at | Phosphoribosylpyrophosphate synthetase-associated protein 39 |
| 723 | Melanoma | 0.1383693 | 0.4033905 | 0.332582 | 0.1977957 | HG273-HT273_at | Lymphocyte Antigen Hla-G3 |
| 724 | Melanoma | 0.1383447 | 0.4033891 | 0.332252 | 0.19775091 | M91490_s_a t | EST: HUMRTPGEAI Homo sapiens cDNA. (from Genbank) |
| 725 | Melanoma | 0.1383432 | 0.4032182 | 0.332065 | 0.19764198 | RC_AA2364 55_at | EST: zr75g02.s1 Soares NhHMPu S1 Homo sapiens cDNA clone 669266 3', mRNA sequence. (from Genbank) |
| 726 | Melanoma | 0.1382845 | 0.4031147 | 0.332032 | 0.19562274 | AA156838_a t | Human tumor susceptibility protein (TSG101) mRNA, complete cds |
| 727 | Melanoma | 0.1381723 | 0.4029766 | 0.331914 | 0.19750789 | RC_AA2817 69_s_at | Human Hpast (HPAST) mRNA, complete cds |
| 728 | Melanoma | 0.1377631 | 0.4029068 | 0.33181 | 0.19745281 | RC_AA4221 46_at | EST: zv29g12.s1 Soares ovary tumor NbHOT Homo sapiens cDNA clone 755014 3', mRNA sequence. (from Genbank) |
| 729 | Melanoma | 0.1370225 | 0.4028711 | 0.331769 | 0.19739631 | X51985_at | LAG3 Lymphocyte-activation gene 3 |
| 730 | Melanoma | 0.1368334 | 0.4026319 | 0.331713 | 0.19722208 | U80034_at | Mitochondrial intermediate peptidase precursor (MIPEP) mRNA, mitochondrial gene encoding mitochondrial protein |
| 731 | Melanoma | 0.1367962 | 0.4022857 | 0.331674 | 0.19718078 | S69369_at | PAX3 Paired box homeotic gene 3 (Waardenburg syndrome 1)(alternative products)] |
| 732 | Melanoma | 0.1365472 | 0.4022635 | 0.331506 | 0.19710423 | R36221_at | EST: yh91b09.r1 Homo sapiens cDNA clone 137081 5'. (from Genbank) |
| 733 | Melanoma | 0.1363534 | 0.4022262 | 0.331477 | 0.19701219 | RC_AA1612 92_s_at | Interferon, alpha-inducible protein 27 |
| 734 | Melanoma | 0.1361048 | 0.4021548 | 0.331383 | 0.1969097 | L11931_at | SHMT1 Serine hydroxymethyltransferase 1 (soluble) |
| 735 | Melanoma | 0.1359024 | 0.4021312 | 0.331206 | 0.19679315 | RC_AA4167 23_at | KIAA0446 gene product |
| 736 | Melanoma | 0.1357039 | 0.4020033 | 0.331204 | 0.1967593 | RC_AA4217 81_at | Homo sapiens NADH:ubiquinone dehydrogenase 51 kDa subunit (NDUFV1) mRNA, nuclear gene encoding mitochondrial protein, complete cds |
| 737 | Melanoma | 0.1352835 | 0.4019288 | 0.331166 | 0.19663438 | X66358_at | mRNA KKIALRE for serine/threonine protein kinase |
| 738 | Melanoma | 0.135255 | 0.4019068 | 0.330972 | 0.19660686 | RC_AA4551 81_at | EST: aa15g04.s1 Soares NhHMPu S1 Homo sapiens cDNA clone 813366 3', mRNA sequence. (from Genbank) |
| 739 | Melanoma | 0.135093 | 0.4017475 | 0.330933 | 0.19646664 | RC_AA4900 69_at | EST: ab05d09.s1 Stratagene fetal retina 937202 Homo sapiens cDNA clone 839921 3', mRNA sequence. (from Genbank) |

FIG. 8K2

| | | | | | |
|---|---|---|---|---|---|
| 740 | Melanoma | 0.1349085 | 0.4016933 | 0.330922 | 0.19633192 | H47955_s_at | Homo sapiens mRNA for cartilage-associated protein (CASP) |
| 741 | Melanoma | 0.1348517 | 0.4016911 | 0.330821 | 0.19629982 | RC_AA2849 76_at | Human ets domain protein ERF mRNA, complete cds |
| 742 | Melanoma | 0.1342228 | 0.4015278 | 0.3308 | 0.19622768 | RC_AA2517 65_at | EST: zs09a08.s1 NCI_CGAP_GCB1 Homo sapiens cDNA clone IMAGE:684662 3', mRNA sequence. (from Genbank) |
| 743 | Melanoma | 0.1340681 | 0.4014157 | 0.330766 | 0.1961769 | Z69923_at | HEPATOCYTE GROWTH FACTOR ACTIVATOR PRECURSOR |
| 744 | Melanoma | 0.13392 | 0.4013308 | 0.33063 | 0.19610956 | RC_AA4879 07_at | EST: ab12d06.s1 Stratagene lung (#937210) Homo sapiens cDNA clone 840587 3', mRNA sequence. (from Genbank) |
| 745 | Melanoma | 0.1337962 | 0.4012294 | 0.330411 | 0.19597074 | RC_AA4791 14_at | EST: zv17h04.s1 Soares NhHMPu S1 Homo sapiens cDNA clone 753943 3', mRNA sequence. (from Genbank) |
| 746 | Melanoma | 0.1337654 | 0.401193 | 0.330357 | 0.19594654 | M95929_at | Homeobox protein (PHOX1) mRNA, 3' end |
| 747 | Melanoma | 0.1335841 | 0.4010455 | 0.330256 | 0.19588678 | AA452625_a t | Iduronate 2-sulfatase (Hunter syndrome) |
| 748 | Melanoma | 0.1335778 | 0.4009734 | 0.330244 | 0.19576679 | RC_AA4649 62_at | EST: zx80f06.s1 Soares ovary tumor NbHOT Homo sapiens cDNA clone 810083 3', mRNA sequence. (from Genbank) |
| 749 | Melanoma | 0.1331834 | 0.400778 | 0.330075 | 0.19566491 | M99438_at | Transducin-like enhancer protein (TLE3) mRNA |
| 750 | Melanoma | 0.1330449 | 0.4007738 | 0.330066 | 0.19558439 | X98833_rna 1_at | Zinc finger protein, Hsal1 |
| 751 | Melanoma | 0.132348 | 0.4006806 | 0.330021 | 0.19548663 | M57710_at | LGALS3 Lectin, galactoside-binding, soluble, 3 (galectin 3) (NOTE: redefinition of symbol) |
| 752 | Melanoma | 0.13200432 | 0.4006806 | 0.3299222 | 0.19545133 | AA262132_a t | EST: zs23b10.r1 NCI_CGAP_GCB1 Homo sapiens cDNA clone IMAGE:686011 5' similar to SW:YHH6_YEAST P32793 HYPOTHETICAL 41.8 KD PROTEIN IN SPO13-ARG4 INTERGENIC REGION. ;, mRNA sequence. (from Genbank) |
| 753 | Melanoma | 0.1320193 | 0.4005162 | 0.329832 | 0.195391 | L38503_at | GSTT2 Glutathione S-transferase theta 2 |
| 754 | Melanoma | 0.1318512 | 0.4004496 | 0.329732 | 0.1953472 | U00928_at | RNA-BINDING PROTEIN FUS/TLS |
| 755 | Melanoma | 0.1317899 | 0.4004144 | 0.329702 | 0.1952117 | RC_AA0749 19_at | EST: zn82b10.s1 Stratagene ovarian cancer (#937219) Homo sapiens cDNA clone 544411 3', mRNA sequence. (from Genbank) |
| 756 | Melanoma | 0.1317374 | 0.4004084 | 0.329624 | 0.19505751 | RC_AA0349 25_at | EST: zk25e01.s1 Soares pregnant uterus NbHPU Homo sapiens cDNA clone 471576 3', mRNA sequence. (from Genbank) |
| 757 | Melanoma | 0.1307086 | 0.4003678 | 0.329508 | 0.19491097 | X53414_at | AGXT Alanine-glyoxylate aminotransferase (oxalosis I; hyperoxaluria I; glycolicaciduria; serine-pyruvate aminotransferase) |
| 758 | Melanoma | 0.1302885 | 0.4003058 | 0.329483 | 0.19486497 | N27054_at | EST: yx19f02.r1 Homo sapiens cDNA clone 262203 5'. (from Genbank) |
| 759 | Melanoma | 0.1298051 | 0.4003029 | 0.329294 | 0.19481339 | T30851_i_at | Homo sapiens clone 24775 mRNA sequence |
| 760 | Melanoma | 0.1297829 | 0.399908 | 0.329245 | 0.19468595 | D57823_at | H.sapiens mRNA for Sec23A isoform, 2748bp |
| 761 | Melanoma | 0.1297366 | 0.3998798 | 0.32904 | 0.19465022 | L04270_at | LYMPHOTOXIN-BETA RECEPTOR PRECURSOR |

FIG. 8L2

| # | Type | | | | | Description |
|---|------|---|---|---|---|---|
| 762 | Melanoma | 0.1296622 | 0.3997881 | 0.328998 | 0.19458172 | RC_AA1286 17_at | EST: zl15d10.s1 Soares pregnant uterus NbHPU Homo sapiens cDNA clone 502003 3', mRNA sequence. (from Genbank) |
| 763 | Melanoma | 0.1295995 | 0.3997402 | 0.32898 | 0.19442078 | X58288_at | PTPRM Protein tyrosine phosphatase, receptor type, mu polypeptide |
| 764 | Melanoma | 0.1293769 | 0.3996834 | 0.328919 | 0.19433254 | C00627_at | EST: HUMGS0008169, Human Gene Signature, 3'-directed cDNA sequence, mRNA sequence. (from Genbank) |
| 765 | Melanoma | 0.1290219 | 0.3995092 | 0.328745 | 0.19422564 | RC_AA5986 95_at | EST: ae49b03.s1 Stratagene lung carcinoma 937218 Homo sapiens cDNA clone 950189 3', mRNA sequence. (from Genbank) |
| 766 | Melanoma | 0.128814 | 0.399299 | 0.328637 | 0.19409238 | AA431505_a t | Homo sapiens mRNA for putative Sqv-7-like protein, partial |
| 767 | Melanoma | 0.1286864 | 0.399214 | 0.328586 | 0.19403484 | U18235_at | ATP-binding cassette protein (ABC2) mRNA HFBCD04 clone, partial cds |
| 768 | Melanoma | 0.1285017 | 0.3991802 | 0.328516 | 0.19392638 | HG2724-HT2820_at | Oncogene Tls/Chop, Fusion Activated |
| 769 | Melanoma | 0.1281797 | 0.3990843 | 0.328442 | 0.19384022 | M94547_at | HUMMLC2At; Homo sapiens; ; 593 base-pairs |
| 770 | Melanoma | 0.1280772 | 0.3988671 | 0.328427 | 0.19378556 | AA478194_a t | Murine leukemia viral (bmi-1) oncogene homolog |
| 771 | Melanoma | 0.1279452 | 0.398865 | 0.328336 | 0.19373389 | AA454908_s at | EST: zx79c12.r1 Soares ovary tumor NbHOT Homo sapiens cDNA clone 809974 5', mRNA sequence. (from Genbank) |
| 772 | Melanoma | 0.1279317 | 0.3988339 | 0.328332 | 0.19370347 | RC_AA4648 47_at | EST: zx44g07.s1 Soares total fetus Nb2HF8 9w Homo sapiens cDNA clone 789372 3', mRNA sequence. (from Genbank) |
| 773 | Melanoma | 0.1278742 | 0.3987913 | 0.328254 | 0.1935958 | RC_AA2808 40_at | Homo sapiens casein kinase I gamma 2 mRNA, complete cds |
| 774 | Melanoma | 0.1277539 | 0.3987612 | 0.328226 | 0.19354512 | AA401510_s at | EST: zu63c08.r1 Soares testis NHT Homo sapiens cDNA clone 742670 5', mRNA sequence. (from Genbank) |
| 775 | Melanoma | 0.1275922 | 0.3987287 | 0.32818 | 0.19347076 | RC_AA1948 81_at | TAL1 (SCL) interrupting locus |
| 776 | Melanoma | 0.127352 | 0.3986388 | 0.328031 | 0.1933746 | RC_AA2830 66_at | EST: zs91h04.s1 NCI_CGAP_GCB1 Homo sapiens cDNA clone IMAGE:704887 3', mRNA sequence. (from Genbank) |
| 777 | Melanoma | 0.1270126 | 0.3985798 | 0.328001 | 0.19328494 | RC_AA5213 54_at | EST: aa68h12.s1 NCI_CGAP_GCB1 Homo sapiens cDNA clone IMAGE:826151 3', mRNA sequence. (from Genbank) |
| 778 | Melanoma | 0.1268752 | 0.3985745 | 0.32782 | 0.19322516 | RC_AA2334 59_at | EST: zr30c03.s1 Stratagene NT2 neuronal precursor 937230 Homo sapiens cDNA clone 664900 3', mRNA sequence. (from Genbank) |
| 779 | Melanoma | 0.1268664 | 0.3985241 | 0.327724 | 0.19316153 | U07882_at | OPRD1 Opioid receptor, delta 1 |
| 780 | Melanoma | 0.1262611 | 0.3984626 | 0.327698 | 0.19307594 | RC_AA4339 30_at | EST: zw52e11.s1 Soares total fetus Nb2HF8 9w Homo sapiens cDNA clone 773708 3' similar to contains Alu repetitive element;, mRNA sequence. (from Genbank) |

FIG. 8M2

| | | | | | |
|---|---|---|---|---|---|
| 781 | Melanoma | 0.1257661 | 0.3984493 | 0.327644 | 0.19303386 | R57419_s_a t | EST: F3059 Fetal heart Homo sapiens cDNA clone F3059 5' end, mRNA sequence. (from Genbank) |
| 782 | Melanoma | 0.1257356 | 0.3983665 | 0.327541 | 0.19296196 | RC_AA4656 94_r_at | Homo sapiens mRNA for C17orf1 protein |
| 783 | Melanoma | 0.1255551 | 0.3982446 | 0.327472 | 0.19288833 | RC_AA2434 97_at | Human DNA sequence from clone 30M3 on chromosome 6p22.1-22.3. Contains three novel genes, one similar to C. elegans Y63D3A.4 and one similar to (predicted) plant, worm, yeast and archaea bacterial genes, and the first exon of the KIAA0319 gene. Contains ESTs, GSSs and putative CpG islands |
| 784 | Melanoma | 0.1254365 | 0.3982427 | 0.327435 | 0.19276989 | RC_AA1761 64_i_at | EST: zp23h11.s1 Stratagene neuroepithelium (#937231) Homo sapiens cDNA clone 610341 3', mRNA sequence. (from Genbank) |
| 785 | Melanoma | 0.1251098 | 0.3981143 | 0.327393 | 0.19271116 | RC_AA4593 10_f_at | EST: zx89d06.s1 Soares ovary tumor NbHOT Homo sapiens cDNA clone 810923 3', mRNA sequence. (from Genbank) |
| 786 | Melanoma | 0.1247954 | 0.3980862 | 0.327347 | 0.19260463 | L19686_rna1 _at | Macrophage migration inhibitory factor (MIF) gene |
| 787 | Melanoma | 0.1247241 | 0.3979709 | 0.327339 | 0.19255554 | M77810_at | GATA2 GATA-binding protein 2 |
| 788 | Melanoma | 0.1247123 | 0.3979473 | 0.327233 | 0.19243136 | M20030_f_at | Small proline rich protein (sprII) mRNA, clone 930 |
| 789 | Melanoma | 0.1244471 | 0.3979058 | 0.326952 | 0.19236399 | X99268_at | B-HLH DNA binding protein |
| 790 | Melanoma | 0.1243374 | 0.3978472 | 0.326801 | 0.19225538 | K03430_at | C1QB Complement component 1, q subcomponent, beta polypeptide |
| 791 | Melanoma | 0.1241899 | 0.3977416 | 0.326696 | 0.18215532 | RC_AA2813 37_at | EST: zs94g02.s1 NCI_CGAP_GCB1 Homo sapiens cDNA clone IMAGE:705170 3', mRNA sequence. (from Genbank) |
| 792 | Melanoma | 0.1236242 | 0.3977305 | 0.326522 | 0.19209646 | HG1067-HT1067_r_at | Mucin (Gb:M22406) |
| 793 | Melanoma | 0.1234471 | 0.3976594 | 0.326434 | 0.1920443 | RC_AA4114 00_at | EST: zv28f01.s1 Soares ovary tumor NbHOT Homo sapiens cDNA clone 754969 3', mRNA sequence. (from Genbank) |
| 794 | Melanoma | 0.123365 | 0.3975432 | 0.326375 | 0.19201964 | RC_AA4103 04_at | EST: zv23b12.s1 Soares NhHMPu S1 Homo sapiens cDNA clone 754463 3', mRNA sequence. (from Genbank) |
| 795 | Melanoma | 0.1233082 | 0.3974744 | 0.326341 | 0.19192186 | IL12_P40_at | No info for gene |
| 796 | Melanoma | 0.1224675 | 0.3974658 | 0.326321 | 0.19189802 | R22345_at | Yh26h11.r1 Homo sapiens cDNA clone 130917 5'. (from Genbank) |
| 797 | Melanoma | 0.1219996 | 0.3973614 | 0.326193 | 0.19174205 | X92762_at | Tafazzins protein |
| 798 | Melanoma | 0.121729 | 0.3972339 | 0.326192 | 0.19157267 | M34516_r_at | Omega light chain protein 14.1 (Ig lambda chain related) gene, exon 3 |
| 799 | Melanoma | 0.1213728 | 0.397211 | 0.326176 | 0.19155142 | RC_AA6211 31_at | EST: af61a05.s1 Soares NhHMPu S1 Homo sapiens cDNA clone 1046480 3', mRNA sequence. (from Genbank) |

FIG. 8N2

| # | Type | | | | ID | Description |
|---|---|---|---|---|---|---|
| 800 | Melanoma | 0.1212943 | 0.3972036 | 0.326107 | 0.19150853 | RC_AA2370_17_at | EST: zs01c10.s1 NCI_CGAP_GCB1 Homo sapiens cDNA clone IMAGE:683922 3', mRNA sequence. (from Genbank) |
| 801 | Melanoma | 0.1210167 | 0.3969826 | 0.326036 | 0.19125849 | RC_AA1561_18_at | KIAA0469 gene product |
| 802 | Melanoma | 0.1209745 | 0.3969459 | 0.32602 | 0.19119929 | X81788_at | DS-1 mRNA |
| 803 | Melanoma | 0.1206663 | 0.3968384 | 0.325959 | 0.19109996 | W26054_at | EST: 18d8 Human retina cDNA randomly primed sublibrary Homo sapiens cDNA, mRNA sequence. (from Genbank) |
| 804 | Melanoma | 0.1204253 | 0.3967301 | 0.325929 | 0.19103418 | RC_AA0018_86_at | EST: zh81d12.s1 Soares fetal liver spleen 1NFLS S1 Homo sapiens cDNA clone 427703 3' similar to contains Alu repetitive element,, mRNA sequence. (from Genbank) |
| 805 | Melanoma | 0.1203127 | 0.3965745 | 0.325604 | 0.19096377 | U18932_at | HSST Heparan sulfate-N-deacetylase/N-sulfotransferase |
| 806 | Melanoma | 0.1195421 | 0.3964731 | 0.325445 | 0.19090624 | K03021_at | PLAT Plasminogen activator, tissue type (t-PA) |
| 807 | Melanoma | 0.1194001 | 0.3964352 | 0.325411 | 0.19078447 | D38128_at | PTGIR Prostaglandin I2 (prostacyclin) receptor (IP) |
| 808 | Melanoma | 0.1191858 | 0.3964336 | 0.325351 | 0.19074327 | RC_AA6096_72_at | Dual-specificity tyrosine-(Y)-phosphorylation regulated kinase 3 |
| 809 | Melanoma | 0.1191147 | 0.3963173 | 0.325331 | 0.19061303 | RC_AA0102_11_at | EST: zi08f07.s1 Soares fetal liver spleen 1NFLS S1 Homo sapiens cDNA clone 430213 3', mRNA sequence. (from Genbank) |
| 810 | Melanoma | 0.1190739 | 0.3962691 | 0.325195 | 0.19055262 | RC_AA4959_50_at | EST: zw06a06.s1 Soares NhHMPu S1 Homo sapiens cDNA clone 768466 3', mRNA sequence. (from Genbank) |
| 811 | Melanoma | 0.1189652 | 0.3961387 | 0.325159 | 0.19045714 | M65066_at | PRKAR1B Protein kinase, cAMP-dependent, regulatory, type I, beta |
| 812 | Melanoma | 0.1185296 | 0.3961369 | 0.325065 | 0.19049014 | M34516_at | Omega light chain protein 14.1 (Ig lambda chain related) gene, exon 3 |
| 813 | Melanoma | 0.1184965 | 0.3960993 | 0.324961 | 0.19032753 | RC_AA4165_38_at | EST: zu05b09.s1 Soares testis NHT Homo sapiens cDNA clone 730937 3', mRNA sequence. (from Genbank) |
| 814 | Melanoma | 0.1184959 | 0.3960033 | 0.32494 | 0.19026989 | AA059327_i_at | EST: zf65e11.r1 Soares retina N2b4HR Homo sapiens cDNA clone 381836 5', mRNA sequence. (from Genbank) |
| 815 | Melanoma | 0.1179602 | 0.3958509 | 0.324906 | 0.19017744 | U74324_at | Guanine nucleotide exchange factor mss4 mRNA |
| 816 | Melanoma | 0.1177455 | 0.3958509 | 0.324834 | 0.19004424 | Z35278_at | PEBP2aC1 acute myeloid leukaemia mRNA |
| 817 | Melanoma | 0.1172975 | 0.3956665 | 0.324689 | 0.18987063 | U04810_at | DbpB-like protein mRNA |
| 818 | Melanoma | 0.1160099 | 0.3955402 | 0.324684 | 0.18981868 | HG2591-HT2687_s_at | Transcription Factor Itf-1 |
| 819 | Melanoma | 0.1153999 | 0.3953739 | 0.324663 | 0.1896937 | RC_AA2629_69_f_at | EST: zr71c02.s1 Soares NhHMPu S1 Homo sapiens cDNA clone 668834 3' similar to TR:G969170 G969170 PX19.;, mRNA sequence. (from Genbank) |
| 820 | Melanoma | 0.1150892 | 0.3952682 | 0.324602 | 0.18957858 | H58818_at | EST: yr36a04.r1 Homo sapiens cDNA clone 207342 5' similar to contains Alu repetitive element,, mRNA sequence. (from Genbank) |
| 821 | Melanoma | 0.1146236 | 0.3952252 | 0.324567 | 0.1895497 | U35139_at | NECDIN related protein mRNA |

FIG. 8O2

| # | Tissue | | | | Description |
|---|---|---|---|---|---|
| 822 | Melanoma | 0.1141343 | 0.395089 | 0.32453 | 0.18949603 | RC_AA2326 86_i_at | EST: z75d05.s1 Soares NhHMPu S1 Homo sapiens cDNA clone 669225 3', mRNA sequence. (from Genbank) |
| 823 | Melanoma | 0.1140791 | 0.3950616 | 0.324448 | 0.18944205 | U89336_cds 7_at | Unknown gene extracted from Human HLA class III region containing NOTCH4 gene, partial sequence, homeobox PBX2 (HPBX) gene, receptor for advanced glycosylation end products (RAGE) gene, and 6 unidentified cds, complete sequence |
| 824 | Melanoma | 0.1139379 | 0.3950544 | 0.32444 | 0.18937255 | RC_AA5041 46_at | EST: aa59e06.s1 NCI_CGAP_GCB1 Homo sapiens cDNA clone IMAGE:825250 3', mRNA sequence. (from Genbank) |
| 825 | Melanoma | 0.1134549 | 0.3949163 | 0.32436 | 0.1893278 | RC_AA3985 96_at | EST: zi70a05.s1 Soares testis NHT Homo sapiens cDNA clone 727664 3', mRNA sequence. (from Genbank) |
| 826 | Melanoma | 0.113358 | 0.3949138 | 0.3243 | 0.18927787 | R08723_at | EST: yf24f04.r1 Homo sapiens cDNA clone 127807 5'. (from Genbank) |
| 827 | Melanoma | 0.1132343 | 0.3949101 | 0.32426 | 0.18921457 | RC_AA2794 67_at | EST: zs85g09.s1 NCI_CGAP_GCB1 Homo sapiens cDNA clone IMAGE:704320 3', mRNA sequence. (from Genbank) |
| 828 | Melanoma | 0.1131499 | 0.3948787 | 0.324224 | 0.18918161 | AA485038_a t | Aa41g01.r1 NCI_CGAP_GCB1 Homo sapiens cDNA clone IMAGE:815856 5', mRNA sequence. (from Genbank) |
| 829 | Melanoma | 0.1124555 | 0.3948531 | 0.324123 | 0.18911679 | RC_AA1005 21_at | EST: zn46g09.s1 Stratagene HeLa cell s3 937216 Homo sapiens cDNA clone 550528 3', mRNA sequence. (from Genbank) |
| 830 | Melanoma | 0.1123063 | 0.3948292 | 0.324123 | 0.18906522 | RC_AA4872 18_at | EST: ab19g10.s1 Stratagene lung (#937210) Homo sapiens cDNA clone 841314 3', mRNA sequence. (from Genbank) |
| 831 | Melanoma | 0.1122078 | 0.3948292 | 0.324104 | 0.18899734 00_at | RC_AA6215 | EST: af62h11.s1 Soares NhHMPu S1 Homo sapiens cDNA clone 1046661 3', mRNA sequence. (from Genbank) |
| 832 | Melanoma | 0.1120003 | 0.3948282 | 0.324036 | 0.18892995 t | AA047045_a | EST: zf50d12.r1 Soares retina N2b4HR Homo sapiens cDNA clone 380375 5' similar to contains Alu repetitive element;, mRNA sequence. (from Genbank) |
| 833 | Melanoma | 0.11142 | 0.3946242 | 0.323892 | 0.18882604 | RC_AA4440 54_at | EST: zv45f09.s1 Soares ovary tumor NbHOT Homo sapiens cDNA clone 756617 3', mRNA sequence. (from Genbank) |
| 834 | Melanoma | 0.1111291 | 0.3944597 | 0.323837 | 0.18870665 | R76185_s_a t | EST: yi71h07.r1 Homo sapiens cDNA clone 144733 5'. (from Genbank) |
| 835 | Melanoma | 0.1110274 | 0.3943892 | 0.323805 | 0.18864472 | RC_AA4061 42_at | Homo sapiens mRNA for dTDP-D-glucose 4,6-dehydratase |
| 836 | Melanoma | 0.1106474 | 0.3942312 | 0.323711 | 0.1885513 | M19888_at | SPRR1B Small proline-rich protein 1B (cornifin) |
| 837 | Melanoma | 0.1106379 | 0.3941664 | 0.323658 | 0.18845952 | U77845_at-2 | Human hTRIP (hTRIP) mRNA, complete cds |
| 838 | Melanoma | 0.1106379 | 0.3937046 | 0.323536 | 0.18834326 | U77845_at | HTRIP (hTRIP) mRNA |
| 839 | Melanoma | 0.1104998 | 0.3937046 | 0.32347 | 0.18826395 | K03183_f_at | Chorionic gonadotropin beta subunit gene |
| 840 | Melanoma | 0.1104912 | 0.3936746 | 0.323387 | 0.18815212 | X52773_at | RXRA Retinoid X receptor, alpha |
| 841 | Melanoma | 0.1104912 | 0.3935966 | 0.323368 | 0.18806313 | X52773_at-2 | Retinoid X receptor, alpha |

FIG. 8P2

| | | | | | |
|---|---|---|---|---|---|
| 842 | Melanoma | 0.1100458 | 0.393548 | 0.323281 | 0.18797132 | W60965_at | EST: zd30c02.r1 Soares fetal heart NbHH19W Homo sapiens cDNA clone 342146 5', mRNA sequence. (from Genbank) |
| 843 | Melanoma | 0.1099631 | 0.3935442 | 0.32324 | 0.18790708 | RC_AA3989 37_at | EST: zt86e06.s1 Soares testis NHT Homo sapiens cDNA clone 729250 3', mRNA sequence. (from Genbank) |
| 844 | Melanoma | 0.1095692 | 0.3935015 | 0.3233217 | 0.18778257 | N45402_at | EST: yw97f08.r1 Homo sapiens cDNA clone 260199 5'. (from Genbank) |
| 845 | Melanoma | 0.1095227 | 0.3935015 | 0.3233119 | 0.18767127 | RC_AA4045 43_at | EST: zw37h03.s1 Soares total fetus Nb2HF8 9w Homo sapiens cDNA clone 772277 3', mRNA sequence. (from Genbank) |
| 846 | Melanoma | 0.109249 | 0.3934807 | 0.323081 | 0.1876313 | RC_AA0095 27_at | EST: ze83a02.s1 Soares fetal heart NbHH19W Homo sapiens cDNA clone 365546 3', mRNA sequence. (from Genbank) |
| 847 | Melanoma | 0.1091305 | 0.3933812 | 0.3233067 | 0.18754692 | U95301_at | Phospholipase A2, group X |
| 848 | Melanoma | 0.1087535 | 0.3933455 | 0.3222965 | 0.18749177 | L27671_s_at | Intercellular adhesion molecule 4, Landsteiner-Wiener blood group |
| 849 | Melanoma | 0.1081799 | 0.3933285 | 0.3222935 | 0.1874309 | RC_AA0195 28_at | EST: ze55b02.s1 Soares retina N2b4HR Homo sapiens cDNA clone 362859 3', mRNA sequence. (from Genbank) |
| 850 | Melanoma | 0.1079254 | 0.3932181 | 0.322896 | 0.1873654 | RC_AA5986 84_s_at | EST: ae49a02.s1 Stratagene lung carcinoma 937218 Homo sapiens cDNA clone 950186 3', mRNA sequence. (from Genbank) |
| 851 | Melanoma | 0.1078999 | 0.393106 | 0.3222888 | 0.18722086 | RC_AA2358 03_f_at | EST: zs42g06.s1 Soares NhHMPu S1 Homo sapiens cDNA clone 687898 3', mRNA sequence. (from Genbank) |
| 852 | Melanoma | 0.1074504 | 0.3929525 | 0.3222833 | 0.18719555 | X52599_at | NGFB Nerve growth factor beta |
| 853 | Melanoma | 0.1074084 | 0.3929499 | 0.3222806 | 0.18708922 | U73377_at | SKI V-ski avian sarcoma viral oncogene homolog |
| 854 | Melanoma | 0.1073041 | 0.3928169 | 0.322746 | 0.18701448 | RC_AA2922 28_at | STAT induced STAT inhibitor 3 |
| 855 | Melanoma | 0.1071516 | 0.3925747 | 0.322718 | 0.18690909 | RC_AA4276 38_at | EST: zw30e10.s1 Soares ovary tumor NbHOT Homo sapiens cDNA clone 770826 3', mRNA sequence. (from Genbank) |
| 856 | Melanoma | 0.1068336 | 0.3925746 | 0.3226692 | 0.18684049 | HG2271-HT2367_at | Profilaggrin |
| 857 | Melanoma | 0.1060727 | 0.3925106 | 0.3222583 | 0.18675248 | AA136369_a t | EST: zk93d06.r1 Soares pregnant uterus NbHPU Homo sapiens cDNA clone 490379 5', mRNA sequence. (from Genbank) |
| 858 | Melanoma | 0.1060166 | 0.3924542 | 0.3224425 | 0.18670306 | U20758_rna 1_at | Osteopontin gene |
| 859 | Melanoma | 0.1057976 | 0.3923574 | 0.3222393 | 0.18663722 | Z78285_f_at | Z78285 Homo sapiens brain fetus Homo sapiens cDNA clone 1A7, mRNA sequence |
| 860 | Melanoma | 0.1057677 | 0.3923568 | 0.3222365 | 0.18658338 | X59798_at | CCND1 Cyclin D1 (PRAD1; parathyroid adenomatosis 1) |
| 861 | Melanoma | 0.1052273 | 0.3921631 | 0.3222365 | 0.18652064 | X59303_s_a t | VALYL-TRNA SYNTHETASE |
| 862 | Melanoma | 0.1050115 | 0.3920976 | 0.3222244 | 0.1864017 | D28124_at | Unknown product |
| 863 | Melanoma | 0.1046773 | 0.3920807 | 0.3221145 | 0.1863747 | U48707_at | Protein phosphatase-1 inhibitor mRNA |

FIG. 8Q2

| | | | | | | |
|---|---|---|---|---|---|---|
| 864 | Melanoma | 0.1046509 | 0.392052 | 0.322141 | 0.18628754 | RC_AA4113 51_at | EST: zv28c04.s1 Soares ovary tumor NbHOT Homo sapiens cDNA clone 754950 3', mRNA sequence. (from Genbank) |
| 865 | Melanoma | 0.1042421 | 0.3918513 | 0.322061 | 0.18625675 | RC_AA6090 43_at | Eukaryotic translation initiation factor 4 gamma, 3 |
| 866 | Melanoma | 0.1041958 | 0.3917824 | 0.322009 | 0.18618384 | L48546_at-2 | Tuberous sclerosis 2 |
| 867 | Melanoma | 0.1041958 | 0.3917522 | 0.321912 | 0.18605064 | L48546_at | TSC2 Tuberin |
| 868 | Melanoma | 0.1041752 | 0.3917522 | 0.321866 | 0.18601082 | RC_AA4122 50_at | EST: zu10a06.s1 Soares testis NHT Homo sapiens cDNA clone 731410 3', mRNA sequence. (from Genbank) |
| 869 | Melanoma | 0.1041631 | 0.3916954 | 0.321847 | 0.18591599 | AA095045_s _at | EST: cp2563.seq,F Fetal heart, Lambda ZAP Express Homo sapiens cDNA 5', mRNA sequence. (from Genbank) |
| 870 | Melanoma | 0.1034102 | 0.3916188 | 0.321705 | 0.18581009 | RC_AA6210 41_at | EST: ag03c04.s1 Soares testis NHT Homo sapiens cDNA clone 1056222 3', mRNA sequence. (from Genbank) |
| 871 | Melanoma | 0.1028432 | 0.3915756 | 0.321646 | 0.18574595 | RC_AA4358 99_at | Homo sapiens mRNA for KIAA0462 protein, partial cds |
| 872 | Melanoma | 0.1027382 | 0.3913935 | 0.321416 | 0.18574013 | RC_AA4051 99_at | EST: zu52h04.s1 Soares ovary tumor NbHOT Homo sapiens cDNA clone 741655 3', mRNA sequence. (from Genbank) |
| 873 | Melanoma | 0.1026259 | 0.3913217 | 0.321408 | 0.18557717 | AA091231_a t | EST: cchn2158.seq,F Fetal heart, Lambda ZAP Express Homo sapiens cDNA 5', mRNA sequence. (from Genbank) |
| 874 | Melanoma | 0.1023213 | 0.391227 | 0.321295 | 0.18553251 | AA367473_ at | Crystallin, beta B2 |
| 875 | Melanoma | 0.1019788 | 0.39122212 | 0.32121 | 0.18546972 | M80647_at | THROMBOXANE-A SYNTHASE |
| 876 | Melanoma | 0.1015902 | 0.3912096 | 0.321165 | 0.18537652 | RC_AA4870 54_at | EST: ab18e01.s1 Stratagene lung (#937210) Homo sapiens cDNA clone 841176 3', mRNA sequence. (from Genbank) |
| 877 | Melanoma | 0.1013599 | 0.3910843 | 0.321017 | 0.18530053 | U87460_at | Putative endothelin receptor type B-like protein mRNA |
| 878 | Melanoma | 0.1013224 | 0.3908899 | 0.320926 | 0.18524969 | RC_AA2357 37_at | EST: zt32c03.s1 Soares ovary tumor NbHOT Homo sapiens cDNA clone 724060 3' similar to TR:G1199669 G1199669 PROTEIN KINASE C-BINDING PROTEIN BETA 15.;, mRNA sequence. (from Genbank) |
| 879 | Melanoma | 0.1012426 | 0.3908723 | 0.320864 | 0.18522058 | X56677_at | MYOD1 Myogenic factor 3 |
| 880 | Melanoma | 0.1007926 | 0.3908723 | 0.32077 | 0.18515226 | AA092290_f _at | EST: ll6470.seq,F Fetal heart, Lambda ZAP Express Homo sapiens cDNA 5', mRNA sequence. (from Genbank) |
| 881 | Melanoma | 0.1007301 | 0.3907448 | 0.320075 | 0.18505064 | RC_AA4433 42_s_at | EST: zw94h05.s1 Soares total fetus Nb2HF8 9w Homo sapiens cDNA clone 784466 5 3', mRNA sequence. (from Genbank) |
| 882 | Melanoma | 0.1005677 | 0.3907435 | 0.320748 | 0.18497916 | M14338_at | PROS1 Plasma protein S |
| 883 | Melanoma | 0.1004886 | 0.3907372 | 0.320704 | 0.18488216 | RC_AA2924 27_s_at | EST: zt28g07.s1 Soares ovary tumor NbHOT Homo sapiens cDNA clone 714492 3' similar to TR:E91187 E91187 NMDA RECEPTOR GLUTAMATE-BINDING SUBUNIT.;, mRNA sequence. (from Genbank) |
| 884 | Melanoma | 0.1004353 | 0.3906381 | 0.320623 | 0.18483162 | RC_AA0225 90_at | EST: ze72c10.s1 Soares fetal heart NbHH19W Homo sapiens cDNA clone 364530 3', mRNA sequence. (from Genbank) |

FIG. 8R2

| # | Type | | | | Accession | Description |
|---|---|---|---|---|---|---|
| 885 | Melanoma | 0.1003836 | 0.3905987 | 0.320549 | 0.18471456 | RC_AA1523 72_at | EST: zo07c04.s1 Stratagene endothelial cell 937223 Homo sapiens cDNA clone 566982 3', mRNA sequence. (from Genbank) |
| 886 | Melanoma | 0.1002404 | 0.3905306 | 0.320431 | 0.18463658 | HG417-HT417_s_at | Cathepsin B |
| 887 | Melanoma | 0.1002299 | 0.3903944 | 0.320332 | 0.18457657 | M86752_at | TRANSFORMATION-SENSITIVE PROTEIN IEF SSP 3521 |
| 888 | Melanoma | 0.0998752 | 0.3903006 | 0.320327 | 0.18453667 | HG1153-HT1153_at | Nucleoside Diphosphate Kinase Nm23-H2s |
| 889 | Melanoma | 0.0997796 | 0.3901956 | 0.320312 | 0.18444451 | D86961_at | KIAA0206 gene, partial cds |
| 890 | Melanoma | 0.0997444 | 0.3901956 | 0.320252 | 0.18438782 | M29335_at | MHC class II DO-alpha mRNA, partial cds |
| 891 | Melanoma | 0.0997242 | 0.3900967 | 0.320094 | 0.18427648 | AF006609_a_t | RGS3 mRNA, 5' UTR |
| 892 | Melanoma | 0.0992877 | 0.3900816 | 0.320054 | 0.18421733 | U03735_f_at | MAGE-3 antigen (MAGE-3) gene |
| 893 | Melanoma | 0.0987119 | 0.3900546 | 0.320027 | 0.18412265 | X79200_at | Homo spaiens mRNA for SYT-SSX protein |
| 894 | Melanoma | 0.0986034 | 0.3900199 | 0.320019 | 0.18407716 | X04011_at | CYBB Chronic granulomatous disease |
| 895 | Melanoma | 0.0986034 | 0.3900199 | 0.319995 | 0.1840112 | X04011_at-2 | Cytochrome b-245, beta polypeptide (chronic granulomatous disease) |
| 896 | Melanoma | 0.0985939 | 0.3899832 | 0.319846 | 0.183946 | U43328_at | CRTL1 Cartilage linking protein 1 |
| 897 | Melanoma | 0.0982294 | 0.3899099 | 0.319821 | 0.18387742 | RC_AA2321 28_at | Sarcoglycan, epsilon |
| 898 | Melanoma | 0.0981448 | 0.3898684 | 0.319781 | 0.18379147 | RC_AA3984 23_at | EST: zf62a05.s1 Soares testis NHT Homo sapiens cDNA clone 726896 3', mRNA sequence. (from Genbank) |
| 899 | Melanoma | 0.0981261 | 0.38986 | 0.319781 | 0.18370776 | RC_AA4244 06_at | EST: zv82g01.s1 Soares total fetus Nb2HF8 9w Homo sapiens cDNA clone 760176 3', mRNA sequence. (from Genbank) |
| 900 | Melanoma | 0.0980848 | 0.3898141 | 0.319658 | 0.18361829 | RC_AA6000 12_at | EST: ag29h10.s1 Jia bone marrow stroma Homo sapiens cDNA clone 1091011 3', mRNA sequence. (from Genbank) |
| 901 | Melanoma | 0.0979518 | 0.3897422 | 0.319547 | 0.1835669 | RC_AA1792 98_at | Homo sapiens chromosome 9, P1 clone 11659 |
| 902 | Melanoma | 0.0977802 | 0.3895993 | 0.319532 | 0.18351091 | N27587_s_a t | Homo sapiens mRNA for KIAA0851 protein, complete cds |
| 903 | Melanoma | 0.0977496 | 0.3895966 | 0.319361 | 0.18345913 | U94703_at | Homo sapiens mitochondrial DNA polymerase accessory subunit precursor (MtPolB) mRNA, nuclear gene encoding mitochondrial protein, complete cds |
| 904 | Melanoma | 0.0975498 | 0.3895849 | 0.319346 | 0.1833842 | X92896_at | ITBA2 protein |
| 905 | Melanoma | 0.0973293 | 0.3895712 | 0.319312 | 0.18335311 | M20471_at | CLTA Clathrin light chain A |
| 906 | Melanoma | 0.0971652 | 0.389535 | 0.319111 | 0.1832331 | C00810_s_a t | Homo sapiens clone 24733 mRNA sequence |
| 907 | Melanoma | 0.0965471 | 0.3895115 | 0.319029 | 0.18316567 | AA464368_s _at | EST: zx81c11.r1 Soares ovary tumor NbHOT Homo sapiens cDNA clone 810164 5', mRNA sequence. (from Genbank) |

FIG. 8S2

| | | | | | | |
|---|---|---|---|---|---|---|
| 908 | Melanoma | 0.0964824 | 0.3892891 | 0.319029 | 0.18313889 | L01406_at | GHRHR Growth hormone-releasing hormone receptor |
| 909 | Melanoma | 0.0964487 | 0.3891713 | 0.318898 | 0.18307947 | RC_AA2566 68_at | EST: zr82h02.s1 Soares NhHMPu S1 Homo sapiens cDNA clone 682227 3', mRNA sequence. (from Genbank) |
| 910 | Melanoma | 0.0952727 | 0.3890674 | 0.318809 | 0.18292217 | U66468_at | Cell growth regulator CGR11 mRNA |
| 911 | Melanoma | 0.0960448 | 0.389056 | 0.318794 | 0.18287022 | RC_AA1668 10_at | EST: zo87a05.s1 Stratagene ovarian cancer (#937219) Homo sapiens cDNA clone 593840 3', mRNA sequence. (from Genbank) |
| 912 | Melanoma | 0.0960059 | 0.3889403 | 0.318793 | 0.18279134 | AA479567_a t | EST: zu42b02.r1 Soares ovary tumor NbHOT Homo sapiens cDNA clone 740619 5', mRNA sequence. (from Genbank) |
| 913 | Melanoma | 0.0959051 | 0.389918 | 0.318612 | 0.18273012 | X95463_s_a t | FMR2 Fragile X mental retartation 2 |
| 914 | Melanoma | 0.0958561 | 0.3888968 | 0.318588 | 0.18263909 | RC_AA5048 14_at | Ribosomal protein L14 |
| 915 | Melanoma | 0.0956575 | 0.3888289 | 0.318529 | 0.18253863 | RC_AA2517 72_at | H.sapiens mRNA for HES1 protein |
| 916 | Melanoma | 0.0956069 | 0.3888728 | 0.318501 | 0.18237096 | RC_AA4472 06_at | Homo sapiens mRNA for KIAA0538 protein, partial cds |
| 917 | Melanoma | 0.0954152 | 0.3886916 | 0.318382 | 0.1823179 | AA210757_a t | Transcription factor 3 (E2A immunoglobulin enhancer binding factors E12/E47) |
| 918 | Melanoma | 0.0949926 | 0.3886501 | 0.318344 | 0.18223679 | C01803_s_a t | EST: HUMGS0003762, Human Gene Signature, 3'-directed cDNA sequence, mRNA sequence. (from Genbank) |
| 919 | Melanoma | 0.0949657 | 0.3886199 | 0.318255 | 0.18217865 | N57359_at | EST: yw86f09.r1 Homo sapiens cDNA clone 259145 5' similar to contains Alu repetitive element;contains element MSR1 repetitive element :. (from Genbank) |
| 920 | Melanoma | 0.0949553 | 0.3886012 | 0.318175 | 0.18210067 | X74801_at | T-COMPLEX PROTEIN 1, GAMMA SUBUNIT |
| 921 | Melanoma | 0.0946426 | 0.3885637 | 0.318154 | 0.18202373 | RC_AA5984 12_at | EST: ae48b08.s1 Stratagene lung carcinoma 937218 Homo sapiens cDNA clone 950103 3', mRNA sequence. (from Genbank) |
| 922 | Melanoma | 0.0942835 | 0.3883481 | 0.318112 | 0.18197712 | RC_AA5990 32_at | EST: ae41h03.s1 Gessler Wilms tumor Homo sapiens cDNA clone 898421 3', mRNA sequence. (from Genbank) |
| 923 | Melanoma | 0.0941602 | 0.3882537 | 0.318043 | 0.18187974 | RC_AA2566 04_at | EST: zr86g02.s1 Soares NhHMPu S1 Homo sapiens cDNA clone 682610 3', mRNA sequence. (from Genbank) |
| 924 | Melanoma | 0.0941322 | 0.3881894 | 0.318031 | 0.18174182 | X78342_at | (clone PK2J) CDC2-related protein kinase (PISSLRE) mRNA |
| 925 | Melanoma | 0.0940312 | 0.3881287 | 0.317904 | 0.18169144 | RC_AA2801 04_s_at | EST: zt05h09.s1 NCI_CGAP_GCB1 Homo sapiens cDNA clone IMAGE:712289 3', mRNA sequence. (from Genbank) |
| 926 | Melanoma | 0.0938226 | 0.3880296 | 0.317847 | 0.18159491 | RC_AA0259 05_f_at | Homo sapiens TNF-inducible protein CG12-1 mRNA, complete cds |
| 927 | Melanoma | 0.0937703 | 0.3880194 | 0.317702 | 0.18155839 | RC_AA2333 17_at | EST: zr69h02.s1 Soares NhHMPu S1 Homo sapiens cDNA clone 668691 3', mRNA sequence. (from Genbank) |

FIG. 8T2

| | | | | | | |
|---|---|---|---|---|---|---|
| 928 | Melanoma | 0.0933541 | 0.3879547 | 0.317565 | 0.18151687 | RC_AA4105_10_at | EST: zv16g03.s1 Soares NhHMPu S1 Homo sapiens cDNA clone 753844 3', mRNA sequence. (from Genbank) |
| 929 | Melanoma | 0.0932733 | 0.3879547 | 0.317407 | 0.18137814 | HG2566-HT4792_r_at | Microtubule-Associated Protein Tau, Alt. Splice 3, Exon 8 |
| 930 | Melanoma | 0.0929806 | 0.3879485 | 0.317344 | 0.18126793 | W25933_at | EST: 15b2 Human retina cDNA randomly primed sublibrary Homo sapiens cDNA, mRNA sequence. (from Genbank) |
| 931 | Melanoma | 0.0926989 | 0.3879154 | 0.317221 | 0.18121965 | RC_AA2629_43_at | EST: zr71a09.s1 Soares NhHMPu S1 Homo sapiens cDNA clone 668824 3', mRNA sequence. (from Genbank) |
| 932 | Melanoma | 0.0926205 | 0.3878732 | 0.317189 | 0.18113133 | M63835_at | HIGH AFFINITY IMMUNOGLOBULIN GAMMA FC RECEPTOR I "A FORM" PRECURSOR |
| 933 | Melanoma | 0.0926039 | 0.3878423 | 0.317161 | 0.18109566 | RC_AA2820_69_at | KIAA0603 gene product |
| 934 | Melanoma | 0.0924361 | 0.3876936 | 0.317156 | 0.18109117 | RC_AA4280_69_at | EST: zw57b01.s1 Soares total fetus Nb2HF8 9w Homo sapiens cDNA clone 774121 3', mRNA sequence. (from Genbank) |
| 935 | Melanoma | 0.092388 | 0.387603 | 0.317136 | 0.18100832 | RC_AA2561_57_at | EST: zr79b01.s1 Soares NhHMPu S1 Homo sapiens cDNA clone 681865 3', mRNA sequence. (from Genbank) |
| 936 | Melanoma | 0.0920761 | 0.3873778 | 0.31707 | 0.18091042 | C00358_at | EST: HUMGS0003384, Human Gene Signature, 3'-directed cDNA sequence, mRNA sequence. (from Genbank) |
| 937 | Melanoma | 0.09154411 | 0.3873482 | 0.316937 | 0.18088587 | AA017283_a_t | EST: ze52b01.r1 Soares retina N2b4HR Homo sapiens cDNA clone 362569 5', mRNA sequence. (from Genbank) |
| 938 | Melanoma | 0.0913049 | 0.3873269 | 0.316873 | 0.1807297 | X95191_at | Delta-sarcoglycan |
| 939 | Melanoma | 0.0911804 | 0.3872909 | 0.316873 | 0.18070118 | RC_AA4274_42_at | Guanine nucleotide regulatory factor |
| 940 | Melanoma | 0.0905795 | 0.3872227 | 0.316858 | 0.18065019 | AA082546_a_t | EST: ze88h10.r1 Soares fetal heart NbHH19W Homo sapiens cDNA clone 366115 5', mRNA sequence. (from Genbank) |
| 941 | Melanoma | 0.09033393 | 0.3872016 | 0.316817 | 0.18057401 | RC_AA4525_38_at | EST: zx35e05.s1 Soares total fetus Nb2HF8 9w Homo sapiens cDNA clone 788480 3', mRNA sequence. (from Genbank) |
| 942 | Melanoma | 0.09024495 | 0.3871875 | 0.316772 | 0.18051295 | W23913_at | EST: zb47b02.r1 Soares fetal lung NbHL19W Homo sapiens cDNA clone 306699 5', mRNA sequence. (from Genbank) |
| 943 | Melanoma | 0.0897958 | 0.3869011 | 0.316734 | 0.1804641 | D80002_at-2 | Human mRNA for KIAA0180 gene, partial cds. (from Genbank) |
| 944 | Melanoma | 0.0897958 | 0.3868024 | 0.316547 | 0.18038586 | D80002_at | KIAA0180 gene, partial cds |
| 945 | Melanoma | 0.0894883 | 0.3867989 | 0.316535 | 0.18030895 | M97936_at | SIGNAL TRANSDUCER AND ACTIVATOR OF TRANSCRIPTION 1-ALPHA/BETA |
| 946 | Melanoma | 0.0893936 | 0.3867657 | 0.316531 | 0.18025132 | X95876_at | G-protein coupled receptor |
| 947 | Melanoma | 0.0891839 | 0.3866815 | 0.316466 | 0.18017781 | U26591_at | ICA1 Islet cell autoantigen 1 (69kD) |
| 948 | Melanoma | 0.0891555 | 0.3866746 | 0.31637 | 0.18012705 | RC_AA4592_69_at | EST: aa27d04.s1 NCI_CGAP_GCB1 Homo sapiens cDNA clone IMAGE:814471 3', mRNA sequence. (from Genbank) |

FIG. 8U2

| | | | | | | |
|---|---|---|---|---|---|---|
| 949 | Melanoma | 0.0888772 | 0.3866697 | 0.316333 | 0.18009418 | RC_AA1495 30_at | Interferon regulatory factor 3 |
| 950 | Melanoma | 0.0888387 | 0.3865062 | 0.31616 | 0.18001218 | L77701_at | COX17 mRNA |
| 951 | Melanoma | 0.0887662 | 0.3864703 | 0.31616 | 0.1799261 | RC_AA2368 93_at | EST: zs43a08.s1 Soares NhHMPu S1 Homo sapiens cDNA clone 687926 3', mRNA sequence. (from Genbank) |
| 952 | Melanoma | 0.0886884 | 0.3863932 | 0.316049 | 0.17988726 | RC_AA3981 24_s_at | Growth factor receptor-bound protein 14 |
| 953 | Melanoma | 0.0884562 | 0.3863059 | 0.316029 | 0.17981195 | D50923_at | KIAA0133 gene |
| 954 | Melanoma | 0.0881556 | 0.386303 | 0.316021 | 0.17971534 | W68097_at | EST: zd41b11.r1 Soares fetal heart NbHH19W Homo sapiens cDNA clone 343197 5', mRNA sequence. (from Genbank) |
| 955 | Melanoma | 0.0879364 | 0.3862831 | 0.315927 | 0.17964177 | C15910_s_a t | NADH dehydrogenase (ubiquinone) 1 beta subcomplex, 1 (7kD, MNLL) |
| 956 | Melanoma | 0.0877927 | 0.3861978 | 0.315902 | 0.17955232 | AA070545_a t | EST: Zm70c03.r1 Stratagene neuroepithelium (#937231) Homo sapiens cDNA clone 530980 5', mRNA sequence. (from Genbank) |
| 957 | Melanoma | 0.0876146 | 0.3860516 | 0.315902 | 0.1794887 | AA386297_a t | EST: EST185039 Brain IV Homo sapiens cDNA, mRNA sequence. (from Genbank) |
| 958 | Melanoma | 0.0873856 | 0.3860243 | 0.315832 | 0.17940362 | X13766_s_a | CSN2 Beta-casein |
| 959 | Melanoma | 0.0873313 | 0.3859452 | 0.315712 | 0.17934053 | D88153_at | Homo sapiens mRNA for HYA22, complete cds |
| 960 | Melanoma | 0.0871529 | 0.3859246 | 0.315686 | 0.17927803 | AA486144_a t | EST: ab14c10.r1 Stratagene lung (#937210) Homo sapiens cDNA clone 840786 5', mRNA sequence. (from Genbank) |
| 961 | Melanoma | 0.087082 | 0.3859092 | 0.315593 | 0.17923926 | RC_AA0019 36_at | EST: zh86b04.s1 Soares fetal liver spleen 1NFLS S1 Homo sapiens cDNA clone 428143 3', mRNA sequence. (from Genbank) |
| 962 | Melanoma | 0.0870151 | 0.3857962 | 0.315522 | 0.1791759 | Z34820_s_at | Calcium channel, voltage-dependent, L type, alpha 1C subunit |
| 963 | Melanoma | 0.0863522 | 0.385725 | 0.315522 | 0.179089896 | RC_D60475 _at | EST: Human fetal brain cDNA 3'-end GEN-111F09, mRNA sequence. (from Genbank) |
| 964 | Melanoma | 0.0862478 | 0.3857182 | 0.315436 | 0.17900999 | RC_AA4122 84_s_at | Human poliovirus receptor mRNA, clone H20A |
| 965 | Melanoma | 0.0862031 | 0.385542 | 0.315356 | 0.17893206 | AA156215_a t | EST: zo48h03.r1 Stratagene endothelial cell 937223 Homo sapiens cDNA clone 590165 5' similar to contains element LTR8 repetitive element ;, mRNA sequence. (from Genbank) |
| 966 | Melanoma | 0.085889 | 0.3852078 | 0.315344 | 0.17883709 | RC_AA2331 78_at | Homo sapiens mRNA for KIAA0831 protein, complete cds |
| 967 | Melanoma | 0.0858335 | 0.3851854 | 0.315284 | 0.17876199 | RC_AA0740 90_at | EST: zm75f02.s1 Stratagene neuroepithelium (#937231) Homo sapiens cDNA clone 531483 3', mRNA sequence. (from Genbank) |
| 968 | Melanoma | 0.0850627 | 0.3851712 | 0.315166 | 0.1787029 | AA033703_a t | EST: zf01d10.r1 Soares fetal heart NbHH19W Homo sapiens cDNA clone 375667 5', mRNA sequence. (from Genbank) |

FIG. 8V2

| # | Type | | | | | Description |
|---|---|---|---|---|---|---|
| 969 | Melanoma | 0.0849712 | 0.3851475 | 0.315104 | 0.17861678 RC_AA0226 32_at | EST: ze73a01.s1 Soares fetal heart NbHH19W Homo sapiens cDNA clone 364584 3', mRNA sequence. (from Genbank) |
| 970 | Melanoma | 0.0847323 | 0.3850874 | 0.315063 | 0.17851534 Y09912_rna 1_at | AP-2 beta gene |
| 971 | Melanoma | 0.0844758 | 0.3848748 | 0.315013 | 0.1784022 U41060_at | Breast cancer, estrogen regulated LIV-1 protein (LIV-1) mRNA, partial cds |
| 972 | Melanoma | 0.084397 | 0.3848319 | 0.314762 | 0.17835619 RC_AA1949 8_at | Homo sapiens purinergic receptor P2Y5 mRNA, complete cds |
| 973 | Melanoma | 0.0841837 | 0.3846905 | 0.314741 | 0.17833209 Y09022_at | Not56-like protein |
| 974 | Melanoma | 0.0839795 | 0.3845742 | 0.314721 | 0.17821473 U38480_at | Retinoid X receptor-gamma mRNA |
| 975 | Melanoma | 0.0838402 | 0.3845255 | 0.314689 | 0.17813747 D85429_at | DNAJ PROTEIN HOMOLOG 1 |
| 976 | Melanoma | 0.0837794 | 0.3844882 | 0.314605 | 0.17810053 RC_AA4787 26_at | EST: zv14d09.s1 Soares NhHMPu S1 Homo sapiens cDNA clone 753617 3', mRNA sequence. (from Genbank) |
| 977 | Melanoma | 0.083725 | 0.3844882 | 0.31454 | 0.17804712 S67156_at | ASPA Aspartoacylase (aminoacylase 2, Canavan disease) |
| 978 | Melanoma | 0.0836926 | 0.384462 | 0.314432 | 0.17794101 D87012_at | Immunoglobulin lambda gene locus DNA, clone:61D6 |
| 979 | Melanoma | 0.083654 | 0.3844456 | 0.314242 | 0.17792843 RC_AA4311 93_at | Homo sapiens mRNA for KIAA0544 protein, partial cds |
| 980 | Melanoma | 0.0836 | 0.3843976 | 0.314223 | 0.17786537 M95925_at | Leucine zipper on the D14S46E locus mRNA |
| 981 | Melanoma | 0.0834826 | 0.3843418 | 0.314181 | 0.17783083 RC_AA4890 09_at | EST: aa54d11.s1 NCI_CGAP_GCB1 Homo sapiens cDNA clone IMAGE:824757 3', mRNA sequence. (from Genbank) |
| 982 | Melanoma | 0.0833386 | 0.3841745 | 0.314112 | 0.17760456 RC_AA4881 91_at | EST: ad08e05.s1 Soares NbHFB Homo sapiens cDNA clone 877664 3', mRNA sequence. (from Genbank) |
| 983 | Melanoma | 0.0832802 | 0.3841633 | 0.314061 | 0.17752959 RC_AA0273 17_at | EST: ze97d11.s1 Soares fetal heart NbHH19W Homo sapiens cDNA clone 366933 3' similar to contains Alu repetitive element.; mRNA sequence. (from Genbank) |
| 984 | Melanoma | 0.0831597 | 0.3841532 | 0.314041 | 0.17743386 RC_AA1502 84_at | EST: zl07h04.s1 Soares pregnant uterus NbHPU Homo sapiens cDNA clone 491671 3', mRNA sequence. (from Genbank) |
| 985 | Melanoma | 0.0831503 | 0.3841532 | 0.313964 | 0.1774302 AFFX-HUMGAPDH /M33197_3_ st-2 | Glyceraldehyde-3-phosphate dehydrogenase |
| 986 | Melanoma | 0.0831503 | 0.3841521 | 0.313922 | 0.17741387 AFFX-HUMGAPDH /M33197_3_ st | |
| 987 | Melanoma | 0.0831186 | 0.3840401 | 0.313834 | 0.17733847 T92791_at | EST: ye23a04.r1 Homo sapiens cDNA clone 118542 5'. (from Genbank) |
| 988 | Melanoma | 0.0829896 | 0.3839553 | 0.313796 | 0.17733108 RC_AA4787 40_at | EST: zv14g12.s1 Soares NhHMPu S1 Homo sapiens cDNA clone 753670 3', mRNA sequence. (from Genbank) |

FIG. 8W2

| # | Category | | | | ID | Description |
|---|---|---|---|---|---|---|
| 989 | Melanoma | 0.0829753 | 0.3839081 | 0.3137211 | RC_AA1971 80_at | EST: zq11a05.s1 Stratagene muscle 937209 Homo sapiens cDNA clone 629360 3', mRNA sequence. (from Genbank) |
| 990 | Melanoma | 0.0822569 | 0.3838808 | 0.313621 | 0.17719446 D13645_at | KIAA0020 gene |
| 991 | Melanoma | 0.0818772 | 0.3838668 | 0.313557 | 0.17710419 U62531_at | SLC4A2 Solute carrier family 4, anion exchanger, member 2 (erythrocyte membrane protein band 3-like 1) |
| 992 | Melanoma | 0.0817362 | 0.3838567 | 0.31351 | 0.17699933 L38025_at | CNTFR Ciliary neurotrophic factor receptor |
| 993 | Melanoma | 0.081425 | 0.3838294 | 0.313457 | 0.17699103 L38517_at | Indian hedgehog protein (IHH) mRNA, 5' end |
| 994 | Melanoma | 0.0814158 | 0.3834817 | 0.313452 | 0.17693147 AA284709_a t | Kallikrein 3, (prostate specific antigen) |
| 995 | Melanoma | 0.0813572 | 0.3834803 | 0.313435 | 0.17682509 RC_AA2054 37_at | EST: zq66b06.s1 Stratagene neuroepithelium (#937231) Homo sapiens cDNA clone 646547 3', mRNA sequence. (from Genbank) |
| 996 | Melanoma | 0.0812518 | 0.3832463 | 0.313343 | 0.17674197 RC_AA0261 11_at | EST: ze94c06.s1 Soares fetal heart NbHH19W Homo sapiens cDNA clone 366634 3', mRNA sequence. (from Genbank) |
| 997 | Melanoma | 0.0810807 | 0.383213 | 0.313267 | 0.17671172 RC_AA0260 54_at | EST: ze86b05.s1 Soares fetal heart NbHH19W Homo sapiens cDNA clone 365841 3', mRNA sequence. (from Genbank) |
| 998 | Melanoma | 0.0807698 | 0.3832115 | 0.313262 | 0.17665395 L35594_at | Autotaxin mRNA |
| 999 | Melanoma | 0.0806223 | 0.3832029 | 0.313012 | 0.1766273 AA324364_a t | EST: EST27175 Cerebellum II Homo sapiens cDNA 5' end similar to EST containing Alu repeat, mRNA sequence. (from Genbank) |
| 1000 | Melanoma | 0.0806181 | 0.383182 | 0.313 | 0.17657281 U68135_s_a t | U68135 Human cell line PCI-O6B Homo sapiens cDNA clone SCC-S1c, mRNA sequence |

FIG. 8X2

| | | | | |
|---|---|---|---|---|
| Mesothelioma 1 | 1.0591416 | 0.6999174 | 0.47049877 | AFFX-M27830_M_at-2 | Human 28S ribosomal RNA gene, complete cds. (from Genbank) |
| Mesothelioma 2 | 1.0591416 | 0.6458688 | 0.43784672 | AFFX-M27830_M_at | AFFX-M27830_M_at (endogenous control) |
| Mesothelioma 3 | 1.0539508 | 0.6269065 | 0.4221624 | X16662_at | ANX8 Annexin VIII |
| Mesothelioma 4 | 0.992618 | 0.612074 | 0.4113423 | RC_AA4196 09_at | EST: zv04p06.s1 Soares NhHMPu S1 Homo sapiens cDNA clone 752627 3', mRNA sequence. (from Genbank) |
| Mesothelioma 5 | 0.8888267 | 0.5970459 | 0.40285575 | RC_AA2937 96_at | EST: zt56g08.s1 Soares ovary tumor NbHOT Homo sapiens cDNA clone 726398 3', mRNA sequence. (from Genbank) |
| Mesothelioma 6 | 0.8654811 | 0.5931432 | 0.5227774 | N71503_s_a t | EST: yw32b10.r1 Homo sapiens cDNA clone 253915 5'. (from Genbank) |
| Mesothelioma 7 | 0.8612852 | 0.5855894 | 0.39051464 | RC_AA0378 03_at | Glutamine-fructose-6-phosphate transaminase 2 |
| Mesothelioma 8 | 0.8443461 | 0.5781475 | 0.512088 0.38488322 | RC_AA4550 78_at | EST: aa04d11.s1 Soares NhHMPu S1 Homo sapiens cDNA clone 812277 3', mRNA sequence. (from Genbank) |

FIG. 9A

| | | | | |
|---|---|---|---|---|
| Mesothelioma 9 | 0.8403058 | 0.5759057 | 0.380811115 | RC_AA4062 18_at | EST: zu65e08.s1 Soares testis NHT Homo sapiens cDNA clone 742886 3', mRNA sequence. (from Genbank) |
| Mesothelioma 10 | 0.8332273 | 0.5695669 | 0.501049 | 0.376639734 | RC_AA1502 10_at | EST: zl04g08.s1 Soares pregnant uterus NbHPU Homo sapiens cDNA clone 491390 3', mRNA sequence. (from Genbank) |
| Mesothelioma 11 | 0.8295968 | 0.5643299 | 0.497722 | 0.372266138 | K02765_at | COMPLEMENT C3 PRECURSOR |
| Mesothelioma 12 | 0.827219 | 0.5607175 | 0.49555 | 0.369189445 | V00594_s_at | Metallothionein isoform 2 |
| Mesothelioma 13 | 0.82658 | 0.5570877 | 0.492473 | 0.36661324 | RC_AA1956 56_at | EST: zr33f05.s1 Soares NhHMPu S1 Homo sapiens cDNA clone 665217 3', mRNA sequence. (from Genbank) |
| Mesothelioma 14 | 0.8225429 | 0.5529053 | 0.489945 | 0.36331722 | RC_AA1956 60_at | EST: zr33f10.s1 Soares NhHMPu S1 Homo sapiens cDNA clone 665227 3', mRNA sequence. (from Genbank) |
| Mesothelioma 15 | 0.7978091 | 0.5509036 | 0.487753 | 0.3606286 | C01833_at | EST: HUMGS0003801, Human Gene Signature, 3'-directed cDNA sequence, mRNA sequence. (from Genbank) |
| Mesothelioma 16 | 0.7942148 | 0.5479719 | 0.484985 | 0.3579962 | L33799_at | PCOLCE Procollagen C-endopeptidase enhancer |
| Mesothelioma 17 | 0.7825837 | 0.5463682 | 0.482761 | 0.35580337 | M62895_s_a t | Annexin II (lipocortin II) pseudogene 2 |
| Mesothelioma 18 | 0.7629534 | 0.5449515 | 0.480798 | 0.35362204 | RC_AA2916 44_at | EST: zt37a11.s1 Soares ovary tumor NbHOT Homo sapiens cDNA clone 724508 3' similar to contains Alu repetitive element;contains element MER25 repetitive element ;, mRNA sequence. (from Genbank) |
| Mesothelioma 19 | 0.7571154 | 0.5421202 | 0.478808 | 0.351162205 | J04080_at | C1S Complement component 1, s subcomponent |
| Mesothelioma 20 | 0.7431973 | 0.5402978 | 0.477441 | 0.349785165 | U27185_at | RAR-responsive (TIG1) mRNA |
| Mesothelioma 21 | 0.7386388 | 0.5377274 | 0.47298 | 0.3476147 | RC_AA2341 90_at | EST: zr54f06.s1 Soares NhHMPu S1 Homo sapiens cDNA clone 667235 3', mRNA sequence. (from Genbank) |
| Mesothelioma 22 | 0.7328405 | 0.536799 | 0.471744 | 0.3454912 | U63824_at-2 | TEA domain family member 4 |
| Mesothelioma 23 | 0.7328405 | 0.5349843 | 0.471154 | 0.3438294 | U63824_at | Transcription factor RTEF-1 (RTEF1) mRNA |
| Mesothelioma 24 | 0.7216471 | 0.534914 | 0.468383 | 0.3425291 | AA156897_s _at | EST: zl20b07.r1 Soares pregnant uterus NbHPU Homo sapiens cDNA clone 502453 5', mRNA sequence. (from Genbank) |
| Mesothelioma 25 | 0.7209008 | 0.5338743 | 0.466288 | 0.34100002 | X15882_at | COL6A2 Collagen, type VI, alpha 2 |
| Mesothelioma 26 | 0.7201456 | 0.5310615 | 0.464752 | 0.33956483 | U08021_at | Nicotinamide N-methyltransferase (NNMT) mRNA |
| Mesothelioma 27 | 0.7165751 | 0.5294145 | 0.463369 | 0.33806699 | M14058_at | C1R Complement component C1r |

FIG. 9B

| | | | | | |
|---|---|---|---|---|---|
| Mesothelioma 28 | 0.6926372 | 0.5285939 | 0.462431 | 0.33655077 | AA115572_s_at | EST: zl05d11.r1 Soares pregnant uterus NbHPU Homo sapiens cDNA clone 491445 5' similar to TR:G895845 G895845 PUTATIVE P64 CLCP PROTEIN. ;, mRNA sequence. (from Genbank) |
| Mesothelioma 29 | 0.6917406 | 0.5273998 | 0.461138 | 0.33555776 | M55998_s_at | Alpha-1 collagen type I gene, 3' end |
| Mesothelioma 30 | 0.6893457 | 0.5247737 | 0.459714 | 0.33412012 | M62402_at | IGFBP6 Insulin-like growth factor binding protein 6 |
| Mesothelioma 31 | 0.6727957 | 0.5238205 | 0.45833 | 0.33274401 | M77349_at | Transforming growth factor-beta induced gene product (BIGH3) mRNA |
| Mesothelioma 32 | 0.6682161 | 0.5225286 | 0.457361 | 0.33140004 | X74929_s_at | KRT8 Keratin 8 |
| Mesothelioma 33 | 0.6650274 | 0.5218657 | 0.456506 | 0.33014134 | X56667_at | CALB2 Calbindin 2, (29kD, calretinin) |
| Mesothelioma 34 | 0.6600438 | 0.5208061 | 0.454849 | 0.32891425 | M38591_at | S100A10 S100 calcium-binding protein A10 (annexin II ligand, calpactin I, light polypeptide (p11)) |
| Mesothelioma 35 | 0.6511369 | 0.5193346 | 0.453717 | 0.32773528 | R79356_at | EST: yi83a11.r1 Homo sapiens cDNA clone 145820 5'. (from Genbank) |
| Mesothelioma 36 | 0.6490868 | 0.5186078 | 0.452831 | 0.32669944 | U77594_at | Tazarotene-induced gene 2 (TIG2) mRNA |
| Mesothelioma 37 | 0.6456585 | 0.5181995 | 0.451232 | 0.3253647 | X12876_s_at | KRT18 Keratin 18 |
| Mesothelioma 38 | 0.6436112 | 0.5175271 | 0.449982 | 0.32408893 | RC_AA4789 71_s_at | Disabled (Drosophila) homolog 2 (mitogen-responsive phosphoprotein) |
| Mesothelioma 39 | 0.6390519 | 0.5152585 | 0.448872 | 0.32326820 | M11718_at | COL5A2 Collagen, type V, alpha |
| Mesothelioma 40 | 0.6375759 | 0.515186 | 0.447571 | 0.32227367 | R33735_at | EST: yh82a08.r1 Homo sapiens cDNA clone 136214 5'. (from Genbank) |
| Mesothelioma 41 | 0.6253181 | 0.5146735 | 0.446496 | 0.32155768 | RC_AA4239 87_at | EST: zv79g03.s1 Soares total fetus Nb2HF8 9w Homo sapiens cDNA clone 759892 3', mRNA sequence. (from Genbank) |
| Mesothelioma 42 | 0.6253093 | 0.5128632 | 0.446151 | 0.32042876 | RC_AA4914 63_at | EST: ab01df2.s1 Stratagene fetal retina 937202 Homo sapiens cDNA clone 839543 3', mRNA sequence. (from Genbank) |
| Mesothelioma 43 | 0.6244977 | 0.5115336 | 0.444976 | 0.31952454 | V00594_at | Metallothionein isoform 2 |
| Mesothelioma 44 | 0.6022893 | 0.5113515 | 0.444402 | 0.31864456 | U03877_at | HEAT SHOCK 70 KD PROTEIN 1 |
| Mesothelioma 45 | 0.5995887 | 0.5111262 | 0.44345 | 0.31794432 | RC_AA4294 73_at | CD63 antigen (melanoma 1 antigen) |
| Mesothelioma 46 | 0.5993412 | 0.5102298 | 0.442973 | 0.31701964 | RC_AA4051 99_at | EST: zu52h04.s1 Soares ovary tumor NbHOT Homo sapiens cDNA clone 741655 3', mRNA sequence. (from Genbank) |

FIG. 9C

| | | | | | |
|---|---|---|---|---|---|
| Mesothelioma 47 | 0.5948009 | 0.5094348 | 0.441091 | 0.31625485 | RC_AA2106 95_at | EST: zr88b05.s1 NCI_CGAP_GCB1 Homo sapiens cDNA clone IMAGE:682737 3', mRNA sequence. (from Genbank) |
| Mesothelioma 48 | 0.5877 | 0.5091056 | 0.440596 | 0.31535986 | RC_AA4105 23_at | EST: zv16h06.s1 Soares NhHMPu S1 Homo sapiens cDNA clone 753851 3', mRNA sequence. (from Genbank) |
| Mesothelioma 49 | 0.5824053 | 0.5080108 | 0.439732 | 0.31431034 | T47256_s_at | Growth arrest-specific 6 |
| Mesothelioma 50 | 0.5815163 | 0.5078136 | 0.438868 | 0.31348523 | AFFX-HUMRGE/M 10098_M_at | AFFX-HUMRGE/M10098_M_at (endogenous control) |
| Mesothelioma 51 | 0.5815163 | 0.507282 | 0.437575 | 0.3127073 | AFFX-HUMRGE/M 10098_M_at-2 | Human 18S rRNA gene, complete. (from Genbank) |
| Mesothelioma 52 | 0.5735108 | 0.5070326 | 0.436988 | 0.31167787 | X15880_at | COL6A1 Collagen, type VI, alpha 1 |
| Mesothelioma 53 | 0.5714307 | 0.5060708 | 0.436353 | 0.31103255 | RC_AA2279 56_at | Homo sapiens follistatin-related protein FLRG (FLRG) mRNA, complete cds |
| Mesothelioma 54 | 0.6654825 | 0.5059533 | 0.436017 | 0.31040466 | Z83821_cds 1_at | Keratin 8 |
| Mesothelioma 55 | 0.5641878 | 0.5051439 | 0.434903 | 0.30962515 | D84424_at | Fetal brain mRNA for hyaluronan synthase |
| Mesothelioma 56 | 0.562882 | 0.5050014 | 0.434625 | 0.30891085 | U24488_s_a t | CYP21 Cytochrome P450, subfamily XXI (steroid 21-hydroxylase, congenital adrenal hyperplasia) |
| Mesothelioma 57 | 0.5626015 | 0.504792 | 0.433541 | 0.30838344 | AA479826_a t | Solute carrier family 16 (monocarboxylic acid transporters), member 3 |
| Mesothelioma 58 | 0.562515 | 0.5041066 | 0.432483 | 0.30750188 | L13720_at | Growth-arrest-specific protein (gas) mRNA |
| Mesothelioma 59 | 0.5606002 | 0.5020004 | 0.43202 | 0.3067724 | RC_AA4175 58_at | EST: zv04d02.s1 Soares NhHMPu S1 Homo sapiens cDNA clone 752643 3', mRNA sequence. (from Genbank) |
| Mesothelioma 60 | 0.5600552 | 0.5016353 | 0.430666 | 0.30611625 | L15702_at | BF B-factor, properdin |
| Mesothelioma 61 | 0.5580165 | 0.5003334 | 0.430132 | 0.30547282 | M62896_i_at | Human lipocortin (LIP) 2 pseudogene mRNA, complete cds-like region. (from Genbank) |
| Mesothelioma 62 | 0.5565792 | 0.5002633 | 0.428992 | 0.30475378 | U84573_at | Lysyl hydroxylase isoform 2 (PLOD2) mRNA |
| Mesothelioma 63 | 0.552521 | 0.49959 | 0.42858 | 0.3042281 | RC_AA4194 61_at | EST: zu99d05.s1 NCI_CGAP_GCB1 Homo sapiens cDNA clone IMAGE:746121 3', mRNA sequence. (from Genbank) |
| Mesothelioma 64 | 0.5410206 | 0.498832 | 0.428373 | 0.30358905 | X53587_at | ITGB4 Integrin beta-4 subunit |

FIG. 9D

| | | | | |
|---|---|---|---|---|
| Mesothelio ma 65 | 0.5389456 | 0.4987521 | 0.427308 | 0.303033353 | RC_AA0374 15_at | EST: zk33a09.s1 Soares pregnant uterus NbHPU Homo sapiens cDNA clone 484600 3', mRNA sequence. (from Genbank) |
| Mesothelio ma 66 | 0.5375664 | 0.4984164 | 0.42658 | 0.30241174 | RC_AA0042 74_at | EST: zh97f02.s1 Soares fetal liver spleen 1NFLS S1 Homo sapiens cDNA clone 429243 3' similar to contains element MER22 repetitive element.; mRNA sequence. (from Genbank) |
| Mesothelio ma 67 | 0.5290971 | 0.4983387 | 0.426241 | 0.30173755 34_at | RC_AA1215 | Ribosomal protein L24 |
| Mesothelio ma 68 | 0.5285683 | 0.496771 | 0.425882 | 0.3010942 | Y00503_at | KRT19 Keratin 19 |
| Mesothelio ma 69 | 0.5278923 | 0.4963656 | 0.425264 | 0.3007496 | X76029_at | NEUROMEDIN U-25 PRECURSOR |
| Mesothelio ma 70 | 0.5227398 | 0.4955348 | 0.424915 | 0.3001268 | AB000220_a t | Semaphorin E |
| Mesothelio ma 71 | 0.5193663 | 0.4954979 | 0.424008 | 0.2994847 | D00017_at | ANX2 Annexin II (lipocortin II) |
| Mesothelio ma 72 | 0.5178543 | 0.4953613 | 0.423249 | 0.29888615 02_at | RC_AA4872 | EST: ab19f04.s1 Stratagene lung (#937210) Homo sapiens cDNA clone 841279 3', mRNA sequence. (from Genbank) |
| Mesothelio ma 73 | 0.5129159 | 0.4952377 | 0.423076 | 0.29839018 | R73982_at | EST: yi56e02.r1 Homo sapiens cDNA clone 143258 5' (from Genbank) |
| Mesothelio ma 74 | 0.5123816 | 0.4942474 | 0.421875 | 0.29777405 | AA443499_f _at | Keratin 8 |
| Mesothelio ma 75 | 0.5096717 | 0.4936403 | 0.421006 | 0.2974624 84_at | RC_AA4238 | Homo sapiens mRNA for KIAA0287 gene, partial cds |
| Mesothelio ma 76 | 0.5087988 | 0.4932602 | 0.42067 | 0.29684785 66_at | RC_AA1131 | EST: zm27e01.s1 Stratagene pancreas (#937208) Homo sapiens cDNA clone 526872 3', mRNA sequence. (from Genbank) |
| Mesothelio ma 77 | 0.5079263 | 0.4924502 | 0.420124 | 0.2963723 5_t | AA292153_a | Growth arrest-specific 1 |
| Mesothelio ma 78 | 0.506678 | 0.4922077 | 0.419533 | 0.29579991 4_t | AA381902_a | EST: EST95112 Activated T-cells I Homo sapiens cDNA 5' end, mRNA sequence. (from Genbank) |
| Mesothelio ma 79 | 0.5061134 | 0.4911891 | 0.418903 | 0.29550776 04_at | RC_AA4475 | EST: zw90n07.s1 Soares total fetus Nb2HF8.9w Homo sapiens cDNA clone 784285 3', mRNA sequence. (from Genbank) |
| Mesothelio ma 80 | 0.5039741 | 0.4904096 | 0.418557 | 0.2950375 7_t | AA046840_a | CCAAT/enhancer binding protein (C/EBP), delta |
| Mesothelio ma 81 | 0.5032339 | 0.49010 18 | 0.417974 | 0.2944168 4_63_at | RC_AA2337 | EST: zr44a07.s1 Soares NhHMPu S1 Homo sapiens cDNA clone 666228 3', mRNA sequence. (from Genbank) |
| Mesothelio ma 82 | 0.5032095 | 0.4899276 | 0.417707 | 0.2940374 | D62965_at | EST: Human aorta cDNA 5'-end GEN-345B11, mRNA sequence. (from Genbank) |
| Mesothelio ma 83 | 0.5031133 | 0.4893804 | 0.417361 | 0.29366824 | M21389_at | KRT5 Keratin 5 (epidermolysis bullosa simplex, Dowling-Meara/Kobner/Weber-Cockayne types) |

FIG. 9E

| | | | | | |
|---|---|---|---|---|---|
| Mesothelioma 84 | 0.5016016 | 0.4893059 | 0.416528 | 0.2931924 | AFFX-HUMRGE/M10098_3_at-2 | Human 18S rRNA gene, complete. (from Genbank) |
| Mesothelioma 85 | 0.5016016 | 0.4874221 | 0.416227 | 0.29273582 | AFFX-HUMRGE/M10098_3_at | AFFX-HUMRGE/M10098_3_at (endogenous control) |
| Mesothelioma 86 | 0.4985302 | 0.4866997 | 0.416095 | 0.29224983 | M90657_at | TUMOR-ASSOCIATED ANTIGEN L6 |
| Mesothelioma 87 | 0.4983092 | 0.4866791 | 0.415768 | 0.29178137 | L13923_at | FBN1 Fibrillin 1 (Marfan syndrome) |
| Mesothelioma 88 | 0.4912033 | 0.4857902 | 0.415072 | 0.29146454 | RC_AA4436 67_at | EST: zw86b07.s1 Soares total fetus Nb2HF8 9w Homo sapiens cDNA clone 783829 3', mRNA sequence. (from Genbank) |
| Mesothelioma 89 | 0.4899468 | 0.4850152 | 0.414634 | 0.2910173 | L13698_at | GAS1 Growth arrest-specific 1 |
| Mesothelioma 90 | 0.4878193 | 0.4849082 | 0.414287 | 0.2906958 | AA477978_s_at | Short-chain dehydrogenase/reductase 1 |
| Mesothelioma 91 | 0.4872159 | 0.4832644 | 0.413671 | 0.29027018 | U77643_at-2 | Secreted and transmembrane 1 |
| Mesothelioma 92 | 0.4872159 | 0.4822632 | 0.413579 | 0.28975877 | U77643_at | K12 protein precursor mRNA |
| Mesothelioma 93 | 0.4836731 | 0.4818311 | 0.413071 | 0.289421 | RC_AA6091 85_at | EST: af12c06.s1 Soares testis NHT Homo sapiens cDNA clone 1031434 3' similar to SW:INO1_SPIPO P42803 MYO-INOSITOL-1-PHOSPHATE SYNTHASE .; mRNA sequence. (from Genbank) |
| Mesothelioma 94 | 0.4835745 | 0.4812809 | 0.412609 | 0.28914264 | U40434_at | Pre-pro-megakaryocyte potentiating factor |
| Mesothelioma 95 | 0.4810574 | 0.4805446 | 0.411895 | 0.28857827 | X79982_at | Lrp mRNA |
| Mesothelioma 96 | 0.4808653 | 0.4804767 | 0.411201 | 0.28802437 | M58286_s_at | TNFR1 Tumor necrosis factor receptor 1 (55kD) |
| Mesothelioma 97 | 0.4793426 | 0.478838 | 0.410784 | 0.28769788 | U50330_at | BMP1 Bone morphogenetic protein 1 |
| Mesothelioma 98 | 0.4774815 | 0.478525 | 0.410118 | 0.2873057 | L35545_at | Endothelial cell protein C/APC receptor (EPCR) mRNA |
| Mesothelioma 99 | 0.4763861 | 0.4778755 | 0.409964 | 0.26685072 | J03464_s_at | Collagen, type I, alpha 2 |
| Mesothelioma 100 | 0.4737621 | 0.4774978 | 0.409577 | 0.26651568 | M65292_s_at | HFL1 H factor (complement)-like 1 |

FIG. 9F

| # | Tissue | | | | Description |
|---|---|---|---|---|---|
| 101 | Mesothelioma | 0.4714901 | 0.4774398 | 0.40913 | 0.286142 | U70136_at | THPO Thrombopoietin (myeloproliferative leukemia virus oncogene ligand, megakaryocyte growth and development factor) |
| 102 | Mesothelioma | 0.4702461 | 0.4769206 | 0.408089 | 0.28585374 | M13955_at | Mesothelial keratin K7 (type II) mRNA, 3' end |
| 103 | Mesothelioma | 0.4690899 | 0.4765172 | 0.40777 | 0.28563184 | RC_AA4959 94_at | EST: zw06e06.s1 Soares NhHMPu S1 Homo sapiens cDNA clone 768514 3', mRNA sequence. (from Genbank) |
| 104 | Mesothelioma | 0.4660687 | 0.4756764 | 0.40759 | 0.2851871 | RC_AA0373 57_i_at | EST: zc03c04.s1 Soares parathyroid tumor NbHPA Homo sapiens cDNA clone 321222 3' similar to contains Alu repetitive element;, mRNA sequence. (from Genbank) |
| 105 | Mesothelioma | 0.4624333 | 0.47552229 | 0.407197 | 0.28481406 | RC_AA4500 06_s_at | Sulfotransferase, estrogen-preferring |
| 106 | Mesothelioma | 0.4621536 | 0.4752841 | 0.406856 | 0.28464383 | RC_AA3983 86_at | EST: zt62d05.s1 Soares testis NHT Homo sapiens cDNA clone 726921 3' similar to gb:M65290 INTERLEUKIN-12 BETA CHAIN PRECURSOR (HUMAN);, mRNA sequence. (from Genbank) |
| 107 | Mesothelioma | 0.4613135 | 0.4752674 | 0.406525 | 0.28434384 | D62584_at | Osteoglycin (osteoinductive factor) |
| 108 | Mesothelioma | 0.4612729 | 0.4748662 | 0.405754 | 0.2839068 | Z74615_at | COL1A1 Collagen, type I, alpha 1 |
| 109 | Mesothelioma | 0.4606631 | 0.4747266 | 0.405528 | 0.28351343 | L12350_at | THBS2 Thrombospondin 2 |
| 110 | Mesothelioma | 0.4594612 | 0.4745681 | 0.405044 | 0.28319076 | RC_AA2783 99_at | EST: zt08d05.s1 NCI_CGAP_GCB1 Homo sapiens cDNA clone IMAGE:712521 3', mRNA sequence. (from Genbank) |
| 111 | Mesothelioma | 0.45913 | 0.4741481 | 0.404472 | 0.28281102 | RC_AA4656 87_at | RNA binding motif, single stranded interacting protein 1 |
| 112 | Mesothelioma | 0.4583692 | 0.4740085 | 0.404313 | 0.2824474 | U51010_s_a t | Nicotinamide N-methyltransferase gene, exon 1 and 5' flanking region |
| 113 | Mesothelioma | 0.4579493 | 0.4739832 | 0.403959 | 0.28218293 | RC_AA4061 63_at | FSHD region gene 1 |
| 114 | Mesothelioma | 0.4559823 | 0.4736125 | 0.403626 | 0.28172773 | RC_AA1355 54_at | EST: zl09g08.s1 Soares pregnant uterus NbHPU Homo sapiens cDNA clone 501470 3', mRNA sequence. (from Genbank) |
| 115 | Mesothelioma | 0.455856 | 0.4718037 | 0.403307 | 0.28141677 | RC_AA1906 76_at | EST: zp89g09.s1 Stratagene HeLa cell s3 937216 Homo sapiens cDNA clone 627424 3', mRNA sequence. (from Genbank) |
| 116 | Mesothelioma | 0.4552911 | 0.4713191 | 0.402801 | 0.28103325 | RC_AA4002 92_at | EST: zu63f03.s1 Soares testis NHT Homo sapiens cDNA clone 742685 3', mRNA sequence. (from Genbank) |
| 117 | Mesothelioma | 0.4528318 | 0.4711553 | 0.402516 | 0.28071174 | W58057_s_ at | Periplakin |
| 118 | Mesothelioma | 0.4506959 | 0.4708276 | 0.402449 | 0.28039315 | RC_AA4969 80_at | KIAA0331 gene product |
| 119 | Mesothelioma | 0.4487174 | 0.4703919 | 0.402328 | 0.28007892 | H12674_at | RNA binding motif, single stranded interacting protein 1 |

FIG. 9G

| | | | | | |
|---|---|---|---|---|---|
| 120 | Mesothelioma | 0.4486 | 0.4702272 | 0.401804 | 0.29980366 | D37965_at | PDGF receptor beta-like tumor suppressor (PRLTS) |
| 121 | Mesothelioma | 0.4482785 | 0.4698058 | 0.401566 | 0.2793671 | AA490685_a_t | EST: aa45b03.r1 Soares NhHMPu S1 Homo sapiens cDNA clone 823853 5', mRNA sequence. (from Genbank) |
| 122 | Mesothelioma | 0.4478299 | 0.4697229 | 0.400739 | 0.27912572 | RC_AA5999 91_at | EST: ag28h10.s1 Jia bone marrow stroma Homo sapiens cDNA clone 1090915 3', mRNA sequence. (from Genbank) |
| 123 | Mesothelioma | 0.4469251 | 0.4688821 | 0.400611 | 0.2788366 | H47955_s_a t | Homo sapiens mRNA for cartilage-associated protein (CASP) |
| 124 | Mesothelioma | 0.4427893 | 0.4687813 | 0.400237 | 0.27847564 | AFFX-HUMGAPDH /M33197_3_st | AFFX-HUMGAPDH/M33197_3_st (endogenous control) |
| 125 | Mesothelioma | 0.4427893 | 0.4686248 | 0.399759 | 0.27780949 | AFFX-HUMGAPDH /M33197_3_st-2 | Glyceraldehyde-3-phosphate dehydrogenase |
| 126 | Mesothelioma | 0.4424716 | 0.4685089 | 0.399613 | 0.2777363 | M59815_at | C4A Complement component 4A |
| 127 | Mesothelioma | 0.4407809 | 0.4675502 | 0.39909 | 0.27749163 2 | AFFX-HUMRGE/M 10098_5_at- | Human 18S rRNA gene, complete. (from Genbank) |
| 128 | Mesothelioma | 0.4407809 | 0.4674844 | 0.398778 | 0.27716902 | AFFX-HUMRGE/M 10098_5_at | AFFX-HUMRGE/M10098_5_at (endogenous control) |
| 129 | Mesothelioma | 0.4398573 | 0.4674425 | 0.39874 | 0.27682126 | RC_AA1478 84_at | EST: zl50b04.s1 Soares pregnant uterus NbHPU Homo sapiens cDNA clone 505327 3', mRNA sequence. (from Genbank) |
| 130 | Mesothelioma | 0.439275 | 0.4671778 | 0.398498 | 0.27652305 | AA402971_s _at | Homo sapiens mRNA for serine protease (TLSP), complete cds |
| 131 | Mesothelioma | 0.4373124 | 0.4669934 | 0.398209 | 0.2761791 | X13334_at | CD14 CD14 antigen |
| 132 | Mesothelioma | 0.4372183 | 0.4668276 | 0.398136 | 0.27757815 | R22139_at | EST: yh25b11.r1 Homo sapiens cDNA clone 130749 5'. (from Genbank) |
| 133 | Mesothelioma | 0.4347976 | 0.466678 | 0.397539 | 0.275471 | J03764_at | PAI1 Plasminogen activator inhibitor, type I |
| 134 | Mesothelioma | 0.4337199 | 0.4665658 | 0.397285 | 0.27523434 | RC_AA4301 54_at | EST: zw59h08.s1 Soares total fetus Nb2HF8 9w Homo sapiens cDNA clone 774399 3', mRNA sequence. (from Genbank) |
| 135 | Mesothelioma | 0.43283 | 0.4664007 | 0.396849 | 0.27479455 | RC_AA2364 60_at | EST: zr75h04.s1 Soares NhHMPu S1 Homo sapiens cDNA clone 669271 3', mRNA sequence. (from Genbank) |

FIG. 9H

| | | | | | |
|---|---|---|---|---|---|
| 136 | Mesothelioma | 0.4277421 | 0.4656811 | 0.396524 | 0.27458873 | K03430_at | C1QB Complement component 1, q subcomponent, beta polypeptide |
| 137 | Mesothelioma | 0.4233997 | 0.4654488 | 0.396135 | 0.27432048 | M13690_s_a t | C1NH Complement component 1 inhibitor (angioedema, hereditary) |
| 138 | Mesothelioma | 0.4216149 | 0.4654255 | 0.395989 | 0.2740517 | M98447_rna 1_at | Keratinocyte transglutaminase gene |
| 139 | Mesothelioma | 0.4204468 | 0.4652267 | 0.395796 | 0.27387062 | RC_AA4499 14_at | Homo sapiens mRNA for glycoprotein-associated amino acid transporter y+LAT1 |
| 140 | Mesothelioma | 0.418851 | 0.4645197 | 0.39544 | 0.2736085 | RC_AA6217 14_at | EST: af54e12.s1 Soares total fetus Nb2HF8 9w Homo sapiens cDNA clone 1035502 3', mRNA sequence. (from Genbank) |
| 141 | Mesothelioma | 0.4183705 | 0.4624448 | 0.395152 | 0.27318463 | AA479567_a t | EST: zu42b02.r1 Soares ovary tumor NbHOT Homo sapiens cDNA clone 740619 5', mRNA sequence. (from Genbank) |
| 142 | Mesothelioma | 0.4182154 | 0.4618441 | 0.394914 | 0.27290955 | U53446_at | Mitogen-responsive phosphoprotein (DOC-2) mRNA |
| 143 | Mesothelioma | 0.4175313 | 0.4616772 | 0.39463 | 0.27259552 | RC_AA2523 95_at | EST: zs12g10.s1 NCI_CGAP_GCB1 Homo sapiens cDNA clone IMAGE:685026 3', mRNA sequence. (from Genbank) |
| 144 | Mesothelioma | 0.414622 | 0.4614214 | 0.394423 | 0.27232054 | HG2614-HT2710_at | Collagen, Type Viii, Alpha 1 |
| 145 | Mesothelioma | 0.4145766 | 0.4612699 | 0.394323 | 0.27210695 | M62403_s_a t | IGFBP4 Insulin-like growth factor-binding protein 4 |
| 146 | Mesothelioma | 0.4141904 | 0.4604793 | 0.394092 | 0.2719206 | RC_AA1820 01_i_at | EST: zp62f10.s1 Stratagene endothelial cell 937223 Homo sapiens cDNA clone 624811 3', mRNA sequence. (from Genbank) |
| 147 | Mesothelioma | 0.4124289 | 0.4600243 | 0.393741 | 0.27168834 | U66075_at | Transcription factor hGATA-6 mRNA |
| 148 | Mesothelioma | 0.411295 | 0.4596118 | 0.393425 | 0.27147886 | RC_AA0538 15_at | EST: ze25h09.s1 Soares fetal heart NbHH19W Homo sapiens cDNA clone 360065 3', mRNA sequence. (from Genbank) |
| 149 | Mesothelioma | 0.4109646 | 0.4594492 | 0.393041 | 0.27117264 | RC_AA1370 73_at | EST: zi02g02.s1 Soares pregnant uterus NbHPU Homo sapiens cDNA clone 491186 3', mRNA sequence. (from Genbank) |
| 150 | Mesothelioma | 0.4106963 | 0.4590646 | 0.392806 | 0.27085504 | H90124_at | EST: yu83h04.r1 Homo sapiens cDNA clone 240439 5'. (from Genbank) |
| 151 | Mesothelioma | 0.4101897 | 0.4589709 | 0.392596 | 0.27060622 | T30851_i_at | Homo sapiens clone 24775 mRNA sequence |
| 152 | Mesothelioma | 0.4100129 | 0.458912 | 0.392312 | 0.27025464 | AA157623_s _at | KIAA0750 gene product |
| 153 | Mesothelioma | 0.4089626 | 0.4584708 | 0.391809 | 0.27006364 | L13210_at | Mac-2 binding protein mRNA |
| 154 | Mesothelioma | 0.4057352 | 0.4580235 | 0.391417 | 0.26973784 | D83174_s_a t | CBP1 Collagen-binding protein 1 |

FIG. 9I

| | | | | | |
|---|---|---|---|---|---|
| 155 | Mesothelioma | 0.4054766 | 0.4578699 | 0.391138 | 0.2694268856_at | RC_AA2625 | EST: z522b09.s1 NCI_CGAP_GCB1 Homo sapiens cDNA clone IMAGE:685913 3', mRNA sequence. (from Genbank) |
| 156 | Mesothelioma | 0.4047325 | 0.4575348 | 0.391059 | 0.26906043 U90913_at | Clone 23665 mRNA sequence |
| 157 | Mesothelioma | 0.4040333 | 0.4573097 | 0.390543 | 0.26897198 | AFFX-HSAC07/X00351_3_st | AFFX-HSAC07/X00351_3_st (endogenous control) |
| 158 | Mesothelioma | 0.4040333 | 0.4566076 | 0.3904404 | 0.2688685 | AFFX-HSAC07/X00351_3_st-2 | No info for gene |
| 159 | Mesothelioma | 0.4007604 | 0.4565281 | 0.390192 | 0.2684282 | RC_AA609576_at | KIAA0331 gene product |
| 160 | Mesothelioma | 0.3997216 | 0.4563727 | 0.389836 | 0.2683481 | RC_AA621169_at | EST: af61h05.s1 Soares NhHMPu S1 Homo sapiens cDNA clone 1046553 3', mRNA sequence. (from Genbank) |
| 161 | Mesothelioma | 0.3992522 | 0.4562641 | 0.389698 | 0.26807234 | RC_AA281465_at | EST: zt04c07.s1 NCI_CGAP_GCB1 Homo sapiens cDNA clone IMAGE:712140 3', mRNA sequence. (from Genbank) |
| 162 | Mesothelioma | 0.3990413 | 0.4562237 | 0.389546 | 0.26789218 | RC_AA236542_at | EST: zr75g11.s1 Soares NhHMPu S1 Homo sapiens cDNA clone 669284 3', mRNA sequence. (from Genbank) |
| 163 | Mesothelioma | 0.398028 | 0.4560871 | 0.389379 | 0.267438 | AA281694_at | EST: zt03d07.r1 NCI_CGAP_GCB1 Homo sapiens cDNA clone IMAGE:712045 5' similar to TR:G409466 G409466 CG1 PROTEIN PRECURSOR. [2] TR:G296164 ;, mRNA sequence. (from Genbank) |
| 164 | Mesothelioma | 0.3975346 | 0.4558353 | 0.388906 | 0.26728898 | U89942_at | Lysyl oxidase-related protein (WS9-14) mRNA |
| 165 | Mesothelioma | 0.3964796 | 0.4555971 | 0.388827 | 0.26700023 | AFFX-M27830_5_at | AFFX-M27830_5_at (endogenous control) |
| 166 | Mesothelioma | 0.3964796 | 0.4549846 | 0.388596 | 0.26667702 | AFFX-M27830_5_at-2 | Human 28S ribosomal RNA gene, complete cds. (from Genbank) |
| 167 | Mesothelioma | 0.3962999 | 0.454874 | 0.388293 | 0.26649773 | RC_AA435769_s_at | EST: zl79h07.s1 Soares testis NHT Homo sapiens cDNA clone 728605 3', mRNA sequence. (from Genbank) |
| 168 | Mesothelioma | 0.3939805 | 0.4548523 | 0.387803 | 0.26626006 | AA418478_at | EST: zv92d05.r1 Soares NhHMPu S1 Homo sapiens cDNA clone 767241 5' similar to TR:E213399 E213399 TISSUE CARBOXYPEPTIDASE INHIBITOR. ;, mRNA sequence. (from Genbank) |
| 169 | Mesothelioma | 0.3938985 | 0.4547785 | 0.387513 | 0.26606774 | U24389_s_at | Lysyl oxidase-like protein gene |
| 170 | Mesothelioma | 0.3936696 | 0.4545196 | 0.387249 | 0.2658143 | U41518_at | AQP1 Aquaporin 1 (channel-forming integral protein, 28kD) |

FIG. 9J

| # | | | | | | |
|---|---|---|---|---|---|---|
| 171 | Mesothelioma | 0.3933392 | 0.4539185 | 0.386935 | 0.2655198 | RC_AA1364 74_at | Meis (mouse) homolog 2 |
| 172 | Mesothelioma | 0.3915184 | 0.4537064 | 0.386729 | 0.265315181 | RC_AA2554 32_at | EST: zr85f08.s1 Soares NhHMPu S1 Homo sapiens cDNA clone 682503 3', mRNA sequence. (from Genbank) |
| 173 | Mesothelioma | 0.3911737 | 0.4534501 | 0.386458 | 0.2650505 | AB002364_a t | Human mRNA for KIAA0366 gene, partial cds |
| 174 | Mesothelioma | 0.3908614 | 0.4529941 | 0.386238 | 0.2646919 | D31294_at | EST: Human fetal-lung cDNA 5'-end sequence, mRNA sequence. (from Genbank) |
| 175 | Mesothelioma | 0.3903879 | 0.4527878 | 0.386039 | 0.26459667 | H42262_at | EST: yo63a04.r1 Homo sapiens cDNA clone 182574 5'. (from Genbank) |
| 176 | Mesothelioma | 0.3902266 | 0.4526013 | 0.385761 | 0.26431003 | X57351_s_a t | RPS3 Ribosomal protein S3 |
| 177 | Mesothelioma | 0.3898825 | 0.4521105 | 0.385573 | 0.2640921 | AA203274_a t | EST: zx55h09.r1 Soares fetal liver spleen 1NFLS S1 Homo sapiens cDNA clone 446465 5' similar to contains element MER27 repetitive element ;, mRNA sequence. (from Genbank) |
| 178 | Mesothelioma | 0.3867889 | 0.4517249 | 0.385237 | 0.2639344 | D21254_s_a t | Cadherin 11 (OB-cadherin, osteoblast) |
| 179 | Mesothelioma | 0.3865562 | 0.4516666 | 0.385119 | 0.26351938 | L37882_at | Frizzled gene product mRNA |
| 180 | Mesothelioma | 0.3860667 | 0.4516502 | 0.385014 | 0.26335284 | U37283_at | Microfibril-associated glycoprotein-2 MAGP-2 mRNA |
| 181 | Mesothelioma | 0.3859107 | 0.4508272 | 0.384864 | 0.263146 | X02761_s_a t | FN1 Fibronectin 1 |
| 182 | Mesothelioma | 0.3850843 | 0.4505113 | 0.384726 | 0.26282948 | RC_AA6211 59_at | EST: af61g01.s1 Soares NhHMPu S1 Homo sapiens cDNA clone 1046544 3', mRNA sequence. (from Genbank) |
| 183 | Mesothelioma | 0.3828769 | 0.4502988 | 0.384253 | 0.2626094 | L25081_at | ARH9 Aplysia ras-related homolog 9 |
| 184 | Mesothelioma | 0.3811958 | 0.4500729 | 0.384044 | 0.26247543 | RC_AA3978 25_at | EST: zf47g02.s1 Soares ovary tumor NbHOT Homo sapiens cDNA clone 725522 3', mRNA sequence. (from Genbank) |
| 185 | Mesothelioma | 0.3804112 | 0.4497275 | 0.383866 | 0.26229405 | AA059327_i at | EST: zf65e11.r1 Soares retina N2b4HR Homo sapiens cDNA clone 381836 5', mRNA sequence. (from Genbank) |
| 186 | Mesothelioma | 0.3794902 | 0.4493083 | 0.383752 | 0.26205167 | RC_AA6003 63_at | Endocytic receptor (macrophage mannose receptor family) |
| 187 | Mesothelioma | 0.3791049 | 0.448932 | 0.3835 | 0.26184973 | U73377_at | SKI V-ski avian sarcoma viral oncogene homolog |
| 188 | Mesothelioma | 0.3785763 | 0.4486814 | 0.383025 | 0.26169628 | D57823_at | H.sapiens mRNA for Sec23A isoform, 2748bp |
| 189 | Mesothelioma | 0.3774908 | 0.4485579 | 0.382896 | 0.26139084 | S71018_at-2 | Peptidylprolyl isomerase C (cyclophilin C) |

FIG. 9K

| | | | | | |
|---|---|---|---|---|---|
| 190 | Mesothelio ma | 0.3774908 | 0.4485042 | 0.382475 | 0.26129478 | S71018_at | Cyclophilin C [human, kidney, mRNA, 883 nt] |
| 191 | Mesothelio ma | 0.3765168 | 0.4484175 | 0.382411 | 0.26107258 | RC_AA1612 92_s_at | Interferon, alpha-inducible protein 27 |
| 192 | Mesothelio ma | 0.3753303 | 0.4482835 | 0.382331 | 0.26083657 | RC_AA4875 57_at | EST: ab20h12.s1 Stratagene lung (#937210) Homo sapiens cDNA clone 841415 3', mRNA sequence. (from Genbank) |
| 193 | Mesothelio ma | 0.373353 | 0.4482321 | 0.382306 | 0.26060086 | RC_AA4103 37_at | EST: zv16e01.s1 Soares NhHMPu S1 Homo sapiens cDNA clone 753816 3', mRNA sequence. (from Genbank) |
| 194 | Mesothelio ma | 0.3705493 | 0.4481449 | 0.38173 | 0.26035422 | RC_AA4282 40_at | EST: zw51d04.s1 Soares total fetus Nb2HF8 9w Homo sapiens cDNA clone 773575 3', mRNA sequence. (from Genbank) |
| 195 | Mesothelio ma | 0.3699757 | 0.4475755 | 0.38142 | 0.2600308 | AA156670_r_at | Homo sapiens agrin precursor mRNA, partial cds |
| 196 | Mesothelio ma | 0.3692148 | 0.4473875 | 0.38125 | 0.25979215 | W38778_s_at | EST: zb27g04.r1 Soares parathyroid tumor NbHPA Homo sapiens cDNA clone 304854 5', mRNA sequence. (from Genbank) |
| 197 | Mesothelio ma | 0.3680646 | 0.4467453 | 0.381135 | 0.2594731 | HG2743-HT2846_s_a t | Caldesmon 1, Alt. Splice 4, Non-Muscle |
| 198 | Mesothelio ma | 0.3676729 | 0.4467193 | 0.380682 | 0.259308 | X06700_s_a t | COL3A1 Alpha-1 type 3 collagen |
| 199 | Mesothelio ma | 0.3667775 | 0.4459901 | 0.380444 | 0.25922918 | AA147510_s_at | EST: zl50c12.r1 Soares pregnant uterus NbHPU Homo sapiens cDNA clone 505366 5', mRNA sequence. (from Genbank) |
| 200 | Mesothelio ma | 0.366183 | 0.4458225 | 0.380323 | 0.25888658 | AA393089_a t | EST: zt69b10.r1 Soares testis NHT Homo sapiens cDNA clone 727579 5', mRNA sequence. (from Genbank) |
| 201 | Mesothelio ma | 0.3658275 | 0.4454646 | 0.380123 | 0.25863868 | X51441_s_a t | SERUM AMYLOID A PROTEIN PRECURSOR |
| 202 | Mesothelio ma | 0.3656358 | 0.4448871 | 0.379825 | 0.25832933 | RC_AA4005 28_at | EST: zu70f09.s1 Soares testis NHT Homo sapiens cDNA clone 743369 3', mRNA sequence. (from Genbank) |
| 203 | Mesothelio ma | 0.3641193 | 0.444782 | 0.379658 | 0.2581616 | RC_AA2269 68_at | EST: zr18g03.s1 Stratagene NT2 neuronal precursor 937230 Homo sapiens cDNA clone 663796 3', mRNA sequence. (from Genbank) |
| 204 | Mesothelio ma | 0.3624646 | 0.444782 | 0.379348 | 0.25793135 | L36033_at | SDF1 Stromal cell-derived factor 1 |
| 205 | Mesothelio ma | 0.3613996 | 0.4444318 | 0.379111 | 0.2577622 | U28369_at | Semaphorin V mRNA |
| 206 | Mesothelio ma | 0.3599863 | 0.4434809 | 0.378983 | 0.2573951 | R77200_at | EST: yi65g05.r1 Homo sapiens cDNA clone 144152 5'. (from Genbank) |
| 207 | Mesothelio ma | 0.35968864 | 0.4430622 | 0.378786 | 0.25721616 | HG2797-HT2906_s_a t | Clathrin, Light Polypeptide B, Alt. Splice 2 |

FIG. 9L

| | | | | | |
|---|---|---|---|---|---|
| 208 | Mesothelio ma | 0.3595741 | 0.4426197 | 0.378631 | 0.25707701 | Z23090_at | HSPB1 Heat shock 27kD protein 1 |
| 209 | Mesothelio ma | 0.359108 | 0.4422325 | 0.37818 | 0.25694147 | AA465016_a t | EST: zx80d02.r1 Soares ovary tumor NbHOT Homo sapiens cDNA clone 810051 5' similar to TR:G1020091 G1020091 NEUROPSIN. ;contains element LTR3 repetitive element ;, mRNA sequence. (from Genbank) |
| 210 | Mesothelio ma | 0.3590687 | 0.4419912 | 0.37789 | 0.25659284 | M63835_at | HIGH AFFINITY IMMUNOGLOBULIN GAMMA FC RECEPTOR I "A FORM" PRECURSOR |
| 211 | Mesothelio ma | 0.3584483 | 0.4419668 | 0.377562 | 0.25640056 | AA094507_s _at | EST: cp0543.seq.F Fetal heart, Lambda ZAP Express Homo sapiens cDNA 5', mRNA sequence. (from Genbank) |
| 212 | Mesothelio ma | 0.3573782 | 0.4410614 | 0.377264 | 0.256252 | W49521_at | Procollagen-proline, 2-oxoglutarate 4-dioxygenase (proline 4-hydroxylase), alpha polypeptide II |
| 213 | Mesothelio ma | 0.3536399 | 0.4407468 | 0.376993 | 0.25602996 | AFFX-HSAC07/X0 0351_3_at-2 | No info for gene |
| 214 | Mesothelio ma | 0.3536399 | 0.4405411 | 0.376849 | 0.25570235 | AFFX-HSAC07/X0 0351_3_at | AFFX-HSAC07/X00351_3_at (endogenous control) |
| 215 | Mesothelio ma | 0.3528539 | 0.4402399 | 0.376497 | 0.25554204 | C01721_at | Homo sapiens PNG pseudogene, complete sequence |
| 216 | Mesothelio ma | 0.3497838 | 0.4397745 | 0.376335 | 0.2551188 | RC_AA1668 10_at | EST: zo87a05.s1 Stratagene ovarian cancer (#937219) Homo sapiens cDNA clone 593840 3', mRNA sequence. (from Genbank) |
| 217 | Mesothelio ma | 0.3496834 | 0.439612 | 0.376185 | 0.25492033 | M14949_at | RAS-RELATED PROTEIN R-RAS |
| 218 | Mesothelio ma | 0.3495798 | 0.4394777 | 0.375819 | 0.25478593 | M63573_at | PPIB Peptidylprolyl isomerase B (cyclophilin B) |
| 219 | Mesothelio ma | 0.3468566 | 0.4391219 | 0.375668 | 0.25463685 | RC_AA2358 03_f_at | EST: zs42g06.s1 Soares NhHMPu S1 Homo sapiens cDNA clone 687898 3', mRNA sequence. (from Genbank) |
| 220 | Mesothelio ma | 0.3462601 | 0.4391219 | 0.375647 | 0.25448275 | RC_AA4210 51_at | Homo sapiens serum-inducible kinase mRNA, complete cds |
| 221 | Mesothelio ma | 0.346117 | 0.4384002 | 0.375443 | 0.25418022 | D14838_at | FGF9 Fibroblast growth factor 9 (glia-activating factor) |
| 222 | Mesothelio ma | 0.3446173 | 0.4382553 | 0.375166 | 0.25397906 | U59877_s_a t | Low-Mr GTP-binding protein (RAB31) mRNA |
| 223 | Mesothelio ma | 0.3441015 | 0.4379733 | 0.374856 | 0.2537038 | RC_AA1016 01_at | Homo sapiens herpesvirus entry protein B (HVEB) mRNA, complete cds |
| 224 | Mesothelio ma | | | | | RC_AA1258 61_at | Homo sapiens clone 24742 mRNA sequence |

FIG. 9M

| | | | | | |
|---|---|---|---|---|---|
| 225 | Mesothelioma | 0.3438057 | 0.4373981 | 0.374545 | 0.253462177 | RC_AA4295 71_at | EST: zw75d12.s1 Soares testis NHT Homo sapiens cDNA clone 782039 3' similar to contains element PTR7 repetitive element ;, mRNA sequence. (from Genbank) |
| 226 | Mesothelioma | 0.34354434 | 0.4373783 | 0.37439 | 0.253161341 | AA446512_a t | EST: zw67d05.r1 Soares testis NHT Homo sapiens cDNA clone 781257 5', mRNA sequence. (from Genbank) |
| 227 | Mesothelioma | 0.343192 | 0.4372861 | 0.374084 | 0.253004482 | HG544-HT544_at | Endothelial Cell Growth Factor 1 |
| 228 | Mesothelioma | 0.3416644 | 0.4371724 | 0.373831 | 0.252826485 9_at | RC_AA4615 | Chromogranin A (parathyroid secretory protein 1) |
| 229 | Mesothelioma | 0.340757 | 0.436476 | 0.373435 | 0.252585577 | D62633_f_at | EST: Human aorta cDNA 5'-end GEN-308H02, mRNA sequence. (from Genbank) |
| 230 | Mesothelioma | 0.3392169 | 0.4364047 | 0.373303 | 0.252402721 01_r_at | RC_AA1820 | EST: zp62f10.s1 Stratagene endothelial cell 937223 Homo sapiens cDNA clone 624811 3', mRNA sequence. (from Genbank) |
| 231 | Mesothelioma | 0.3391393 | 0.4361565 | 0.373245 | 0.252276845 4_at | RC_AA2338 | EST: zr47a02.s1 Stratagene NbHMPu S1 Homo sapiens cDNA clone 666506 3', mRNA sequence. (from Genbank) |
| 232 | Mesothelioma | 0.3385454 | 0.4361417 | 0.3728 | 0.251996374 6_at | RC_AA0183 | EST: ze41d12.s1 Soares retina N2b4HR Homo sapiens cDNA clone 361559 3', mRNA sequence. (from Genbank) |
| 233 | Mesothelioma | 0.3370938 | 0.4360204 | 0.372671 | 0.251824917 | HG3494-HT3688_at | Nuclear Factor NF-Il6 |
| 234 | Mesothelioma | 0.3361548 | 0.4355957 | 0.372566 | 0.251570084 5_at | RC_AA2335 | EST: zr30h12.s1 Stratagene NT2 neuronal precursor 937230 Homo sapiens cDNA clone 664967 3', mRNA sequence. (from Genbank) |
| 235 | Mesothelioma | 0.3359577 | 0.4354698 | 0.37239 | 0.251322191_at | RC_AA4598 | EST: zx73e01.s1 Soares ovary tumor NbHOT Homo sapiens cDNA clone 809400 3', mRNA sequence. (from Genbank) |
| 236 | Mesothelioma | 0.3351829 | 0.4351678 | 0.372306 | 0.251193823 L41939_at-2 | L41939_at | EphB2 |
| 237 | Mesothelioma | 0.3351829 | 0.4350362 | 0.3711858 | 0.251031431 | L41939_at | Receptor protein-tyrosine kinase (HEK5) mRNA, 3' end |
| 238 | Mesothelioma | 0.3350738 | 0.4346767 | 0.3714476 | 0.2506894 | AA159673_a t | EST: zo80a02.r1 Stratagene ovarian cancer (#937219) Homo sapiens cDNA clone 593162 5', mRNA sequence. (from Genbank) |
| 239 | Mesothelioma | 0.33344775 | 0.43459059 | 0.3711373 | 0.250478740 9_at | RC_AA4302 | Homo sapiens LIM protein mRNA, complete cds |
| 240 | Mesothelioma | 0.3326101 | 0.4344939 | 0.371108 | 0.250352252 | D31417_at | EST: Human fetal-lung cDNA 5'-end sequence, mRNA sequence. (from Genbank) |
| 241 | Mesothelioma | 0.3312918 | 0.4343924 | 0.3370959 | 0.250150477 9_at | RC_AA2923 | EST: zt51h09.s1 Soares ovary tumor NbHOT Homo sapiens cDNA clone 725921 3', mRNA sequence. (from Genbank) |
| 242 | Mesothelioma | 0.3308044 | 0.4342115 | 0.370559 | 0.2500489 | AA380393_a t | EST: EST93352 Sup1 cells Homo sapiens cDNA 5' end, mRNA sequence. (from Genbank) |

FIG. 9N

| | | | | | |
|---|---|---|---|---|---|
| 243 | Mesothelioma | 0.3307214 | 0.434191 | 0.37051 | RC_AA4177<br>61_at | Homo sapiens clone 24416 mRNA sequence |
| 244 | Mesothelioma | 0.3255457 | 0.4341651 | 0.370429 | AA120886_a<br>t | EST: zk99g11.r1 Soares pregnant uterus NbHPU Homo sapiens cDNA clone 491012 5', mRNA sequence. (from Genbank) |
| 245 | Mesothelioma | 0.3250185 | 0.4339003 | 0.370208 | RC_AA6096<br>16_at | EST: af15g02.s1 Soares testis NHT Homo sapiens cDNA clone 1031762 3', mRNA sequence. (from Genbank) |
| 246 | Mesothelioma | 0.3236072 | 0.4336375 | 0.370053 | 0.24916016 U57099_at | APEG-1 mRNA |
| 247 | Mesothelioma | 0.3234938 | 0.4335405 | 0.369922 | 0.24899484 X13916_at | LDL-receptor related protein |
| 248 | Mesothelioma | 0.3232438 | 0.4334988 | 0.369864 | RC_AA6090<br>60_at | EST: af10g04.s1 Soares testis NHT Homo sapiens cDNA clone 1031286 3', mRNA sequence. (from Genbank) |
| 249 | Mesothelioma | 0.3231517 | 0.4334652 | 0.369814 | RC_AA4475<br>49_at | UDP-N-acetylglucosamine pyrophosphorylase 1; Sperm associated antigen 2 |
| 250 | Mesothelioma | 0.3229977 | 0.4334141 | 0.369812 | 0.24830554 M94893_at | TSPY Testis specific protein, Y-linked |
| 251 | Mesothelioma | 0.3226399 | 0.4334072 | 0.369423 | 0.24812084 M97675_at | Protein tyrosine kinase t-Ror1 (Ror1) mRNA |
| 252 | Mesothelioma | 0.3217647 | 0.4330064 | 0.369396 | HG162-<br>HT3165_at | Tyrosine Kinase, Receptor Axl, Alt. Splice 2 |
| 253 | Mesothelioma | 0.3216868 | 0.4329847 | 0.369252 | RC_AA1762<br>33_at | EST: zp08d05.s1 Stratagene ovarian cancer (#937219) Homo sapiens cDNA clone 595785 3', mRNA sequence. (from Genbank) |
| 254 | Mesothelioma | 0.3178299 | 0.4328803 | 0.36904 | 0.24759671 L20591_at | ANX3 Annexin III (lipocortin III) |
| 255 | Mesothelioma | 0.3175295 | 0.4327803 | 0.368648 | 0.24744944 Z74616_s_at | COL1A2 Collagen, type I, alpha-2 |
| 256 | Mesothelioma | 0.3172893 | 0.432263 | 0.368564 | Z25821_rna<br>1_s_at | Dodecenoyl-Coenzyme A delta isomerase (3.2 trans-enoyl-Coenzyme A isomerase) |
| 257 | Mesothelioma | 0.3145921 | 0.4321356 | 0.368308 | RC_AA3389<br>60_at | EST: EST44060 Fetal brain I Homo sapiens cDNA 3' end, mRNA sequence. (from Genbank) |
| 258 | Mesothelioma | 0.3130382 | 0.4320917 | 0.368208 | 0.24677531 HT862_s_at | Transition Protein 2 |
| 259 | Mesothelioma | 0.3121178 | 0.4319926 | 0.368095 | AA303745_s<br>_at | TAP binding protein (tapasin) |
| 260 | Mesothelioma | 0.3111942 | 0.4318494 | 0.368035 | RC_AA1490<br>44_at | EST: zl45d09.s1 Soares pregnant uterus NbHPU Homo sapiens cDNA clone 504881 3', mRNA sequence. (from Genbank) |
| 261 | Mesothelioma | 0.3110852 | 0.4317474 | 0.367852 | 0.2462237 D12485_at | Plasma cell membrane glycoprotein (PC-1) mRNA |

FIG. 9O

| | | | | | |
|---|---|---|---|---|---|
| 262 | Mesothelioma | 0.3106881 | 0.43166411 | 0.36783 | 0.24611571 | RC_AA5883 97_at | EST: ae40d12.s1 Gessler Wilms tumor Homo sapiens cDNA clone 898295 3', mRNA sequence. (from Genbank) |
| 263 | Mesothelioma | 0.3089063 | 0.4315382 | 0.367609 | 0.24600083 | RC_AA6093 06_at | EST: af13g03.s1 Soares testis NHT Homo sapiens cDNA clone 1031572 3' similar to contains Alu repetitive element;, mRNA sequence. (from Genbank) |
| 264 | Mesothelioma | 0.3080049 | 0.4314415 | 0.367396 | 0.2458277 | W28414_at | EST: 46g7 Human retina cDNA randomly primed sublibrary Homo sapiens cDNA, mRNA sequence. (from Genbank) |
| 265 | Mesothelioma | 0.3077215 | 0.4312745 | 0.367349 | 0.24565282 | C01409_s_a t | EST: HUMGS0008391, Human Gene Signature, 3'-directed cDNA sequence, mRNA sequence. (from Genbank) |
| 266 | Mesothelioma | 0.3076487 | 0.4308608 | 0.367075 | 0.2454651 | RC_AA4814 40_at | EST: zv45a05.s1 Soares ovary tumor NbHOT Homo sapiens cDNA clone 756560 3', mRNA sequence. (from Genbank) |
| 267 | Mesothelioma | 0.3061175 | 0.4305389 | 0.366964 | 0.245164 | RC_AA6207 95_at | EST: af95b02.s1 Soares testis NHT Homo sapiens cDNA clone 1055499 3', mRNA sequence. (from Genbank) |
| 268 | Mesothelioma | 0.3055421 | 0.4305275 | 0.366865 | 0.24489594 | U09770_at | Cysteine-rich heart protein (hCRHP) mRNA |
| 269 | Mesothelioma | 0.3054353 | 0.4300905 | 0.367761 | 0.24475668 | X69910_at | P63 mRNA for transmembrane protein |
| 270 | Mesothelioma | 0.3033843 | 0.4299874 | 0.366548 | 0.24456517 | X03350_at | ADH2 Alcohol dehydrogenase 2 (class I), beta polypeptide |
| 271 | Mesothelioma | 0.3031211 | 0.4299009 | 0.366409 | 0.24445161 | RC_AA4588 99_at | EST: zx88d07.s1 Soares ovary tumor NbHOT Homo sapiens cDNA clone 810829 3', mRNA sequence. (from Genbank) |
| 272 | Mesothelioma | 0.3027946 | 0.4297488 | 0.366333 | 0.24419366 | U28694_s_a t | Chemokine (C-C motif) receptor 3 |
| 273 | Mesothelioma | 0.3027324 | 0.4297168 | 0.366194 | 0.24407129 | AA129547_a t | EST: zn83f01.r1 Stratagene lung carcinoma 937218 Homo sapiens cDNA clone 564793 5', mRNA sequence. (from Genbank) |
| 274 | Mesothelioma | 0.3018513 | 0.4297033 | 0.366055 | 0.24401702 | X51441_at | SERUM AMYLOID A PROTEIN PRECURSOR |
| 275 | Mesothelioma | 0.3018349 | 0.4294328 | 0.366008 | 0.24376348 | D21255_at | CDH11 Cadherin 11 (OB-cadherin) |
| 276 | Mesothelioma | 0.3016914 | 0.4293107 | 0.365826 | 0.24356075 | AA247685_a t | Desmoplakin (DPI, DPII) |
| 277 | Mesothelioma | 0.3013536 | 0.4292366 | 0.365614 | 0.24352042 | RC_AA4050 49_at | EST: zu19g04.s1 Soares NhHMPu S1 Homo sapiens cDNA clone 738486 3', mRNA sequence. (from Genbank) |
| 278 | Mesothelioma | 0.3000722 | 0.4291593 | 0.365541 | 0.24333526 | RC_AA2916 24_s_at | EST: zt45e11.s1 Soares ovary tumor NbHOT Homo sapiens cDNA clone 725324 3', mRNA sequence. (from Genbank) |
| 279 | Mesothelioma | 0.2996498 | 0.4290913 | 0.365257 | 0.24327342 | RC_AA0270 50_at | EST: zk02g01.s1 Soares pregnant uterus NbHPU Homo sapiens cDNA clone 469392 3', mRNA sequence. (from Genbank) |
| 280 | Mesothelioma | 0.2995715 | 0.4284799 | 0.365113 | 0.24310869 | Y00815_at | PTPRF Protein tyrosine phosphatase, receptor type, f polypeptide |

FIG. 9P

| # | | | | | | |
|---|---|---|---|---|---|---|
| 281 | Mesothelioma | 0.2993168 | 0.4283962 | 0.3649948 | 0.24270055 | HG2755-HT2862_at | T-Plastin |
| 282 | Mesothelioma | 0.2988851 | 0.428394 | 0.364857 | 0.24244279 | RC_AA4528 55_at | Human mannose-specific lectin (MR60) mRNA, complete cds |
| 283 | Mesothelioma | 0.2977975 | 0.428258 | 0.364746 | 0.2423502 | X60673_s_a t | Adenylate kinase 3 |
| 284 | Mesothelioma | 0.2977417 | 0.428211 | 0.364509 | 0.24218814 | M94065_s_a t | Dihydroorotate dehydrogenase |
| 285 | Mesothelioma | 0.2976749 | 0.4280612 | 0.364124 | 0.24208091 | J03040_at | SPARC SPARC/osteonectin |
| 286 | Mesothelioma | 0.2968232 | 0.4278942 | 0.364015 | 0.24190435 | RC_AA6095 97_s_at | H.sapiens mRNA for galectin-8 |
| 287 | Mesothelioma | 0.2961833 | 0.4276793 | 0.363967 | 0.2417727 | RC_AA6001 38_at | Ribosomal protein S20 |
| 288 | Mesothelioma | 0.2957991 | 0.4276401 | 0.363836 | 0.24150997 | R64459_at | OX-2 MEMBRANE GLYCOPROTEIN PRECURSOR |
| 289 | Mesothelioma | 0.2954979 | 0.4273034 | 0.363687 | 0.2414491600 | RC_AA4613 _at | EST: zx65a08.s1 Soares total fetus Nb2HF8.9w Homo sapiens cDNA clone 796310 3', mRNA sequence. (from Genbank) |
| 290 | Mesothelioma | 0.2951317 | 0.4272735 | 0.363419 | 0.24130782 | Z48482_at | MMP2 Matrix metalloproteinase 2 |
| 291 | Mesothelioma | 0.2943574 | 0.4272735 | 0.363102 | 0.24115908 | RC_AA4044 26_at | Homo sapiens snuportin1 mRNA, complete cds |
| 292 | Mesothelioma | 0.2942408 | 0.4272478 | 0.363017 | 0.24086666 | AA495758_s _at | EST: zw04d05.r1 Soares NhHMPu S1 Homo sapiens cDNA clone 768297 5', mRNA sequence. (from Genbank) |
| 293 | Mesothelioma | 0.2938848 | 0.4270558 | 0.362996 | 0.2408116274 | RC_AA2837 _at | EST: zl18d04.s1 Soares ovary tumor NbHOT Homo sapiens cDNA clone 713479 3', mRNA sequence. (from Genbank) |
| 294 | Mesothelioma | 0.2937915 | 0.4269194 | 0.362802 | 0.24062264 | N81162_at | EST: yw36d01.r1 Homo sapiens cDNA clone 254305 5'. (from Genbank) |
| 295 | Mesothelioma | 0.2937113 | 0.4262981 | 0.36248 | 0.24039601 | RC_AA2358 03_i_at | EST: zs42g06.s1 Soares NhHMPu S1 Homo sapiens cDNA clone 687898 3', mRNA sequence. (from Genbank) |
| 296 | Mesothelioma | 0.2933489 | 0.4259831 | 0.362187 | 0.24020358 | RC_AA2584 82_s_at | Homo sapiens mRNA for zinc finger protein, complete cds |
| 297 | Mesothelioma | 0.292262 | 0.4255233 | 0.362161 | 0.24014857 | U14407_at | IL15 Interleukin 15 |
| 298 | Mesothelioma | 0.292262 | 0.4253293 | 0.361853 | 0.23989204 | U14407_at-2 | Interleukin 15 |
| 299 | Mesothelioma | 0.2911484 | 0.425132 | 0.361777 | 0.23972273 | M58509_cds 1_s_at | FDXR gene (adrenodoxin reductase) extracted from Human adrenodoxin reductase gene |
| 300 | Mesothelioma | 0.2908772 | 0.4249571 | 0.361405 | 0.23955049 | RC_AA2554 80_at | EST: zr83c09.s1 Soares NhHMPu S1 Homo sapiens cDNA clone 682288 3', mRNA sequence. (from Genbank) |

FIG. 9Q

| | | | | | |
|---|---|---|---|---|---|
| 301 | Mesothelioma | 0.2904261 | 0.4248895 | 0.361357 | 0.23939008 | RC_AA2165 89_at | EST: zq94e07.s1 Stratagene NT2 neuronal precursor 937230 Homo sapiens cDNA clone 649668 3', mRNA sequence. (from Genbank) |
| 302 | Mesothelioma | 0.2900542 | 0.4248895 | 0.361357 | 0.23922196 | RC_D60272 i_at | EST: Human fetal brain cDNA 3'-end GEN-095A07, mRNA sequence. (from Genbank) |
| 303 | Mesothelioma | 0.2899059 | 0.4248767 | 0.361203 | 0.23908468 | M86933_at | AMELY Amelogenin (chromosome Y encoded) |
| 304 | Mesothelioma | 0.2895241 | 0.4248321 | 0.361068 | 0.23890056 | RC_AA4784 11_at | Homo sapiens SH3-containing adaptor molecule-1 mRNA, complete cds |
| 305 | Mesothelioma | 0.289039 | 0.4247147 | 0.360984 | 0.23857582 | AA174185_a t | Solute carrier family 9 (sodium/hydrogen exchanger), isoform 3 regulatory factor 1 |
| 306 | Mesothelioma | 0.2880138 | 0.4246508 | 0.360765 | 0.23843938 | M69023_at | Globin gene |
| 307 | Mesothelioma | 0.2878855 | 0.4238956 | 0.360589 | 0.2381562 | RC_AA4500 45_at | Homo sapiens cargo selection protein TIP47 (TIP47) mRNA, complete cds |
| 308 | Mesothelioma | 0.287489 | 0.4238037 | 0.360492 | 0.23806638 | U35139_at | NECDIN related protein mRNA |
| 309 | Mesothelioma | 0.2870542 | 0.4237463 | 0.360457 | 0.23803474 | RC_AA4192 00_at | KIAA0475 gene product |
| 310 | Mesothelioma | 0.2870087 | 0.4237195 | 0.36015 | 0.23781359 | RC_AA4361 74_at | EST: zv22d06.s1 Soares NhHMPu S1 Homo sapiens cDNA clone 754379 3' similar to contains Alu repetitive element;contains L1.13 L1 repetitive element;, mRNA sequence. (from Genbank) |
| 311 | Mesothelioma | 0.2865384 | 0.4234672 | 0.36001 | 0.23762485 | M16474_s_a t | Butyrylcholinesterase, mRNA |
| 312 | Mesothelioma | 0.2851837 | 0.4234127 | 0.359979 | 0.23761922 | M24283_at | ICAM1 Intercellular adhesion molecule 1 (CD54), human rhinovirus receptor |
| 313 | Mesothelioma | 0.284964 | 0.4223645 | 0.359705 | 0.23733614 | RC_AA4476 50_at | EST: zw97g03.s1 Soares total fetus Nb2HF8 9w Homo sapiens cDNA clone 784948 3', mRNA sequence. (from Genbank) |
| 314 | Mesothelioma | 0.2849332 | 0.4222865 | 0.359699 | 0.23726723 | W38597_s_ at | EST: zb20c11.r1 Soares fetal lung NbHL19W Homo sapiens cDNA clone 302612 5', mRNA sequence. (from Genbank) |
| 315 | Mesothelioma | 0.2843717 | 0.4222146 | 0.359447 | 0.23711482 | Y11709_at | Extracellular matrix protein collagen type XIV, N-terminus |
| 316 | Mesothelioma | 0.2841564 | 0.4220865 | 0.359292 | 0.23703521 | D78011_at | Dihydropyrimidinase |
| 317 | Mesothelioma | 0.2830383 | 0.4219773 | 0.3592 | 0.23688203 | W67899_at | KIAA0405 gene product |
| 318 | Mesothelioma | 0.2829634 | 0.4217566 | 0.359142 | 0.23675115 | J02783_at | P4HB Procollagen-proline, 2-oxoglutarate 4-dioxygenase (proline 4-hydroxylase), beta polypeptide (protein disulfide isomerase; thyroid hormone binding protein p55) |

FIG. 9R

| | | | | | |
|---|---|---|---|---|---|
| 319 | Mesothelioma | 0.282797 | 0.421396 | 0.358936 | 0.23653317 | C15160_at | Keratin 8 |
| 320 | Mesothelioma | 0.2825536 | 0.4213612 | 0.358914 | 0.23646818 | HG2788-HT2896_at | Calcyclin |
| 321 | Mesothelioma | 0.2824925 | 0.4212976 | 0.358765 | 0.2363912 | AA320369_s_at | GLUT1 C-terminal binding protein |
| 322 | Mesothelioma | 0.2823211 | 0.4208453 | 0.358605 | 0.23622328 | RC_AA004637_at | EST: zh92b04.s1 Soares fetal liver spleen 1NFLS S1 Homo sapiens cDNA clone 428719 3', mRNA sequence. (from Genbank) |
| 323 | Mesothelioma | 0.2814243 | 0.4207469 | 0.35844 | 0.23589112 | N44757_at | EST: yy38c10.r1 Homo sapiens cDNA clone 273522 5'. (from Genbank) |
| 324 | Mesothelioma | 0.2811649 | 0.4206722 | 0.358427 | 0.2356065 | AFFX-HUMGAPDH/M33197_3_at | AFFX-HUMGAPDH/M33197_3_at (endogenous control) |
| 325 | Mesothelioma | 0.2811649 | 0.4205172 | 0.358021 | 0.23548514 | AFFX-HUMGAPDH/M33197_3_at-2 | Glyceraldehyde-3-phosphate dehydrogenase |
| 326 | Mesothelioma | 0.2796657 | 0.4203257 | 0.357875 | 0.23530777 | RC_AA448627_f_at | EST: zx10a05.s1 Soares total fetus Nb2HF8 9w Homo sapiens cDNA clone 786032 3' similar to contains Alu repetitive element;, mRNA sequence. (from Genbank) |
| 327 | Mesothelioma | 0.2794736 | 0.4200859 | 0.357723 | 0.23518856 | RC_AA428069_at | EST: zw57b01.s1 Soares total fetus Nb2HF8 9w Homo sapiens cDNA clone 774121 3', mRNA sequence. (from Genbank) |
| 328 | Mesothelioma | 0.2790166 | 0.4199543 | 0.357607 | 0.23511584 | RC_AA284721_s_at | EST: zt24a09.s1 Soares ovary tumor NbHOT Homo sapiens cDNA clone 714040 3', mRNA sequence. (from Genbank) |
| 329 | Mesothelioma | 0.2790019 | 0.4198158 | 0.357442 | 0.23497021 | M12963_s_at | ADH1 Alcohol dehydrogenase 1 (class I), alpha polypeptide |
| 330 | Mesothelioma | 0.2789257 | 0.4198058 | 0.357342 | 0.23492737 | RC_AA621601_at | EST: af47g08.s1 Soares total fetus Nb2HF8 9w Homo sapiens cDNA clone 1034846 3' similar to TR:G240986 G240986 LMW G-PROTEIN.; mRNA sequence. (from Genbank) |
| 331 | Mesothelioma | 0.2787233 | 0.4196574 | 0.35723 | 0.23479421 | D62504_s_at | EST: Human aorta cDNA 5'-end GEN-292H10, mRNA sequence. (from Genbank) |
| 332 | Mesothelioma | 0.2784993 | 0.4191384 | 0.357153 | 0.23463072 | RC_AA284082_at | EST: zs49b09.s1 NCI_CGAP_GCB1 Homo sapiens cDNA clone IMAGE:700793 3', mRNA sequence. (from Genbank) |
| 333 | Mesothelioma | 0.2780942 | 0.4188893 | 0.357132 | 0.23457842 | AA399338_a_t | EST: zf49d10.r1 Soares ovary tumor NbHOT Homo sapiens cDNA clone 725683 5', mRNA sequence. (from Genbank) |
| 334 | Mesothelioma | 0.2779906 | 0.4188823 | 0.357114 | 0.23441109 | D79819_at | EST: Human aorta cDNA 5'-end GEN-331C09, mRNA sequence. (from Genbank) |

FIG. 9S

| | | | | | |
|---|---|---|---|---|---|
| 335 | Mesothelioma | 0.277864 | 0.418596 | 0.356924 | 0.23436195 | AA431876_a_t | EST: zw51h07.r1 Soares total fetus Nb2HF8 9w Homo sapiens cDNA clone 773629 5', mRNA sequence. (from Genbank) |
| 336 | Mesothelioma | 0.27773225 | 0.4185888 | 0.356664 | 0.23414975 | RC_AA2562 68_at | EST: zw80c01.s1 Soares NhHMPu S1 Homo sapiens cDNA clone 681984 3', mRNA sequence. (from Genbank) |
| 337 | Mesothelioma | 0.2767816 | 0.4184786 | 0.356579 | 0.23399428 | W76492_at | EST: zd67d01.r1 Soares fetal heart NbHH19W Homo sapiens cDNA clone 345697 5', mRNA sequence. (from Genbank) |
| 338 | Mesothelioma | 0.2764948 | 0.418467 | 0.356322 | 0.23378077 | RC_AA4469 68_at | EST: zw85f08.s1 Soares total fetus Nb2HF8 9w Homo sapiens cDNA clone 783783 3', mRNA sequence. (from Genbank) |
| 339 | Mesothelioma | 0.27600193 | 0.4183464 | 0.356215 | 0.23365131 | AA478194_a_t | Murine leukemia viral (bmi-1) oncogene homolog |
| 340 | Mesothelioma | 0.27753549 | 0.4179443 | 0.356111 | 0.2334893 | X51521_at | VIL2 Villin 2 (ezrin) |
| 341 | Mesothelioma | 0.27751349 | 0.4177954 | 0.355983 | 0.23332065 | T50262_at | Human ribosomal protein L35 mRNA, complete cds |
| 342 | Mesothelioma | 0.2744901 | 0.417682 | 0.355905 | 0.23313068 | RC_AA4248 13_at | EST: zw04b04.s1 Soares NhHMPu S1 Homo sapiens cDNA clone 768271 3', mRNA sequence. (from Genbank) |
| 343 | Mesothelioma | 0.27535335 | 0.4176089 | 0.355783 | 0.2300342 | RC_AA2517 72_at | H.sapiens mRNA for HES1 protein |
| 344 | Mesothelioma | 0.2734388 | 0.4174465 | 0.35544 | 0.23292561 | M55210_at | LAMC1 Laminin, gamma 1 (formerly LAMB2) |
| 345 | Mesothelioma | 0.27311738 | 0.4174359 | 0.355271 | 0.23270084 | RC_AA4320 74_at | EST: zw84128 3', mRNA sequence. (from Genbank) |
| 346 | Mesothelioma | 0.27229727 | 0.4172877 | 0.355165 | 0.2325193 | M11433_at | RBP1 Cellular retinol-binding protein |
| 347 | Mesothelioma | 0.27224803 | 0.4170156 | 0.355145 | 0.23242276 | M69197_xpt 42_s_at | HPR from Human haptoglobin and haptoglobin-related protein (HP and HPR) genes./ntype=DNA /annot=mRNA |
| 348 | Mesothelioma | 0.27241 | 0.4169379 | 0.355086 | 0.23223045 | RC_AA4109 54_at | EST: zv39g09.s1 Soares ovary tumor NbHOT Homo sapiens cDNA clone 756064 3', mRNA sequence. (from Genbank) |
| 349 | Mesothelioma | 0.27222752 | 0.4167611 | 0.354783 | 0.23212373 | AB002373_a_t | KIAA0375 gene product |
| 350 | Mesothelioma | 0.27219807 | 0.4167071 | 0.354577 | 0.23202516 | RC_AA1366 60_f_at | EST: zk99a04.s1 Soares pregnant uterus NbHPU Homo sapiens cDNA clone 490926 3', mRNA sequence. (from Genbank) |
| 351 | Mesothelioma | 0.27717615 | 0.4166851 | 0.354459 | 0.23187621 | HG998-HT998_s_at | Sulfotransferase, Phenol-Preferring |
| 352 | Mesothelioma | 0.27714625 | 0.4166542 | 0.354303 | 0.2317313 | X64177_f_at | Metallothionein |
| 353 | Mesothelioma | 0.27711764 | 0.4166268 | 0.35413 | 0.2316397 | N89563_s_a_t | EST: HFBEST-40 Human fetal brain QBoqin2 Homo sapiens cDNA, mRNA sequence. (from Genbank) |
| 354 | Mesothelioma | 0.27711233 | 0.4165609 | 0.35406 | 0.23149377 | RC_AA2810 90_at | Homo sapiens mRNA for KIAA0524 protein, partial cds |

FIG. 9T

| | | | | | |
|---|---|---|---|---|---|
| 355 | Mesothelioma | 0.2705316 | 0.4163262 | 0.354054 | 0.23132135 | D31117_at | Ribosome binding protein 1 (dog 180kD homolog) |
| 356 | Mesothelioma | 0.2698444 | 0.4163151 | 0.353716 | | AA292234_a_t | EST: zt50h06.r1 Soares ovary tumor NbHOT Homo sapiens cDNA clone 725819 5', mRNA sequence. (from Genbank) |
| 357 | Mesothelioma | 0.2696341 | 0.4163128 | 0.353684 | 0.23121814 | X53002_s_at | ITGB5 Integrin beta-5 subunit |
| 358 | Mesothelioma | 0.2695124 | 0.416113 | 0.353393 | 0.23109083 | D78014_at | Dihydropyrimidinase related protein-3 |
| 359 | Mesothelioma | 0.2692829 | 0.415942 | 0.353259 | 0.23097472 | HG3227-HT3404_at | Guanine Nucleotide-Binding Protein Hsr1 |
| 360 | Mesothelioma | 0.2692072 | 0.4158708 | 0.353233 | 0.23085128 | U33837_at | Glycoprotein receptor gp330 precursor, mRNA |
| 361 | Mesothelioma | 0.2691709 | 0.415728 | 0.353207 | 0.23066181 | W48808_s_at | EST: zc44h06.r1 Soares senescent fibroblasts NbHSF Homo sapiens cDNA clone 325211 5' similar to PIR:A55093 A55093 fatty acid transport protein precursor - mouse ;, mRNA sequence. (from Genbank) |
| 362 | Mesothelioma | 0.2688853 | 0.4155587 | 0.353138 | 0.23060541 | RC_AA234925_at | EST: zr78g10.s1 Soares NhHMPu S1 Homo sapiens cDNA clone 669570 3' similar to contains Alu repetitive element;, mRNA sequence. (from Genbank) |
| 363 | Mesothelioma | 0.2679166 | 0.4155543 | 0.353038 | 0.2304331 | RC_AA279913_at | EST: zs88b05.s1 NCI_CGAP_GCB1 Homo sapiens cDNA clone IMAGE:704529 3', mRNA sequence. (from Genbank) |
| 364 | Mesothelioma | 0.2674819 | 0.4153965 | 0.353038 | 0.23023693 | K03431_cds1_at | HPR gene (haptoglobin-related protein) extracted from Human haptoglobin gene (alpha-2 allele) |
| 365 | Mesothelioma | 0.2669676 | 0.4153308 | 0.352677 | 0.23004094 | RC_AA457707_at | EST: zx87c05.s1 Soares ovary tumor NbHOT Homo sapiens cDNA clone 810728 3', mRNA sequence. (from Genbank) |
| 366 | Mesothelioma | 0.2659099 | 0.4149956 | 0.352549 | 0.22978924 | L33881_at | PRKCI Protein kinase C, iota |
| 367 | Mesothelioma | 0.2658401 | 0.4149952 | 0.352473 | 0.22971031 | W38597_i_at | EST: zb20c11.r1 Soares fetal lung NbHL19W Homo sapiens cDNA clone 302612 5', mRNA sequence. (from Genbank) |
| 368 | Mesothelioma | 0.2654928 | 0.4147382 | 0.352361 | 0.22962393 | AA405548_a_t | EST: zw39f01.r1 Soares total fetus Nb2HF8.9w Homo sapiens cDNA clone 772441 5', mRNA sequence. (from Genbank) |
| 369 | Mesothelioma | 0.2654812 | 0.4147237 | 0.35229 | 0.2294616 | AA292158_s_at | EST: zt46c03.r1 Soares ovary tumor NbHOT Homo sapiens cDNA clone 725380 5', mRNA sequence. (from Genbank) |
| 370 | Mesothelioma | 0.2646896 | 0.4146949 | 0.352265 | 0.22931917 | RC_AA234061_at | EST: zr74b02.s1 Soares NhHMPu S1 Homo sapiens cDNA clone 669099 3', mRNA sequence. (from Genbank) |
| 371 | Mesothelioma | 0.2645322 | 0.4146686 | 0.352208 | 0.2292628 | RC_AA228020_at | Splicing factor (CC1.3) |
| 372 | Mesothelioma | 0.2644391 | 0.4146319 | 0.352189 | 0.22898363 | AA092182_a_t | EST: ll6255.seq.F Fetal heart, Lambda ZAP Express Homo sapiens cDNA 5', mRNA sequence. (from Genbank) |

FIG. 9U

| | | | | | |
|---|---|---|---|---|---|
| 373 | Mesothelioma | 0.2639977 | 0.4145599 | 0.352117 | 0.22876163 | HG3945-HT4215_at | Phospholipid Transfer Protein |
| 374 | Mesothelioma | 0.2638247 | 0.4142842 | 0.352091 | 0.22865224 | RC_AA4026_37_at | EST: zu49e02.s1 Soares ovary tumor NbHOT Homo sapiens cDNA clone 741338 3', mRNA sequence. (from Genbank) |
| 375 | Mesothelioma | 0.263732 | 0.4142569 | 0.351852 | 0.22840008 | RC_AA0404_65_at | EST: zk46h09.s1 Soares pregnant uterus NbHPU Homo sapiens cDNA clone 485921 3', mRNA sequence. (from Genbank) |
| 376 | Mesothelioma | 0.2622728 | 0.4141102 | 0.351821 | 0.2283448 | RC_AA4365_60_at | EST: zv08e10.s1 Soares NhHMPu S1 Homo sapiens cDNA clone 753066 3', mRNA sequence. (from Genbank) |
| 377 | Mesothelioma | 0.2620748 | 0.4140485 | 0.35164 | 0.22818822 | RC_AA4546_54_at | EST: zx99f06.s1 Soares NhHMPu S1 Homo sapiens cDNA clone 811907 3', mRNA sequence. (from Genbank) |
| 378 | Mesothelioma | 0.2608421 | 0.4138808 | 0.351371 | 0.22810231 | L11005_at | ALDEHYDE OXIDASE |
| 379 | Mesothelioma | 0.2602913 | 0.4134417 | 0.351323 | 0.22787218 | D82226_s_at | EST: similar to TAT-binding protein-2, mRNA sequence. (from Genbank) |
| 380 | Mesothelioma | 0.259976 | 0.4132258 | 0.351218 | 0.22782445 | AA412620_s_at | EST: zt97b10.r1 Soares testis NHT Homo sapiens cDNA clone 730267 5', mRNA sequence. (from Genbank) |
| 381 | Mesothelioma | 0.2597271 | 0.4131955 | 0.351182 | 0.22762097 | D78611_at | MEST Mesoderm specific transcript (mouse) homolog |
| 382 | Mesothelioma | 0.2587902 | 0.4131866 | 0.351129 | 0.22741862 | M62486_at | C4BPA Complement component 4-binding protein, alpha |
| 383 | Mesothelioma | 0.2579113 | 0.4130346 | 0.350854 | 0.22732015 | RC_AA6211_62_s_at | EST: af61g05.s1 Soares NhHMPu S1 Homo sapiens cDNA clone 1046552 3', mRNA sequence. (from Genbank) |
| 384 | Mesothelioma | 0.2577417 | 0.4128937 | 0.350851 | 0.22721846 | RC_AA4428_83_at | EST: zv60g03.s1 Soares testis NHT Homo sapiens cDNA clone 758068 3', mRNA sequence. (from Genbank) |
| 385 | Mesothelioma | 0.2572492 | 0.4128761 | 0.350594 | 0.22701173 | RC_AA3938_03_at | EST: zv64c05.s1 Soares total fetus Nb2HF8 9w Homo sapiens cDNA clone 758408 3', mRNA sequence. (from Genbank) |
| 386 | Mesothelioma | 0.2571623 | 0.4128408 | 0.350497 | 0.2268388 | AA247966_a_at | EST: k1064.seq.F Human fetal heart, Lambda ZAP Express Homo sapiens cDNA 5', mRNA sequence. (from Genbank) |
| 387 | Mesothelioma | 0.2563624 | 0.4128379 | 0.350494 | 0.22669156 | AA043021_a_t | UDP-Gal:betaGlcNAc beta 1,4-galactosyltransferase, polypeptide 4 |
| 388 | Mesothelioma | 0.2561876 | 0.4128003 | 0.350492 | 0.22664171 | RC_AA4314_54_at | EST: zw70f01.s1 Soares testis NHT Homo sapiens cDNA clone 781561 3', mRNA sequence. (from Genbank) |
| 389 | Mesothelioma | 0.2561725 | 0.412762 | 0.350424 | 0.22647038 | RC_AA4822_24_f_at | EST: ab15c03.s1 Stratagene lung (#937210) Homo sapiens cDNA clone 840868 3', mRNA sequence. (from Genbank) |
| 390 | Mesothelioma | 0.255707 | 0.4127204 | 0.350346 | 0.2263404 | RC_AA4468_99_at | EST: zw90e07.s1 Soares total fetus Nb2HF8 9w Homo sapiens cDNA clone 784260 3', mRNA sequence. (from Genbank) |
| 391 | Mesothelioma | 0.255569 | 0.4123099 | 0.350298 | 0.22612622 | R50008_s_a_t | 7-dehydrocholesterol reductase |
| 392 | Mesothelioma | 0.2540791 | 0.4123089 | 0.350177 | 0.22603863 | RC_AA2561_62_at | EST: zr79b07.s1 Soares NhHMPu S1 Homo sapiens cDNA clone 681877 3', mRNA sequence. (from Genbank) |

FIG. 9V

| | | | | |
|---|---|---|---|---|
| Mesothelioma 393 | 0.2539966 | 0.4119516 | 0.22599895 | U62531_at | SLC4A2 Solute carrier family 4, anion exchanger, member 2 (erythrocyte membrane protein band 3-like 1) |
| Mesothelioma 394 | 0.2536245 | 0.4117795 | 0.350086 | AA389673_a t | EST: M164 Fetal heart, Lambda ZAP Express Homo sapiens cDNA 5', mRNA sequence. (from Genbank) |
| Mesothelioma 395 | 0.2526417 | 0.4112976 | 0.349921 | X16869_s_a t | Eukaryotic translation elongation factor 1 alpha 1 |
| Mesothelioma 396 | 0.2523231 | 0.4111635 | 0.349691 | RC_AA4321 86_at | EST: zw71g10.s1 Soares testis NHT Homo sapiens cDNA clone 781698 3', mRNA sequence. (from Genbank) |
| Mesothelioma 397 | 0.2522436 | 0.4111333 | 0.349443 | HG3431-HT3616_s_a t | Decorin, Alt. Splice 1 |
| Mesothelioma 398 | 0.2520875 | 0.4111212 | 0.3494 | AA399299_a t | EST: zt52e09.r1 Soares ovary tumor NbHOT Homo sapiens cDNA clone 725992 5' similar to contains element PTR5 repetitive element :, mRNA sequence. (from Genbank) |
| Mesothelioma 399 | 0.251916 | 0.4106347 | 0.349393 | X75342_at | SHB SH B adaptor protein (a Src homology 2 protein) |
| Mesothelioma 400 | 0.2516347 | 0.4106028 | 0.349298 | X04011_at-2 | Cytochrome b-245, beta polypeptide (chronic granulomatous disease) |
| Mesothelioma 401 | 0.2516347 | 0.4105609 | 0.349045 | X04011_at | CYBB Chronic granulomatous disease |
| Mesothelioma 402 | 0.2512981 | 0.4105581 | 0.348728 | RC_AA1361 30_at | VAMP (vesicle-associated membrane protein)-associated protein A (33kD) |
| Mesothelioma 403 | 0.2511897 | 0.4100671 | 0.348501 | M37435_at | CSF1 Colony-stimulating factor 1 (M-CSF) |
| Mesothelioma 404 | 0.2507062 | 0.4098586 | 0.348415 | RC_AA2332 57_at | Transforming growth factor beta 1 induced transcript 1 |
| Mesothelioma 405 | 0.2503646 | 0.4098494 | 0.348254 | RC_AA4901 42_at | EST: ab05f07.s1 Stratagene fetal retina 937202 Homo sapiens cDNA clone 839941 3', mRNA sequence. (from Genbank) |
| Mesothelioma 406 | 0.2501709 | 0.4096539 | 0.348087 | Y00318_at | IF I factor (complement) |
| Mesothelioma 407 | 0.2499502 | 0.4093384 | 0.347538 | RC_AA4908 28_at | GLYCERALDEHYDE 3-PHOSPHATE DEHYDROGENASE, LIVER |
| Mesothelioma 408 | 0.2496551 | 0.4092615 | 0.347529 | S77410_at | AGTR1 Angiotensin receptor 1 |
| Mesothelioma 409 | 0.2492012 | 0.4089173 | 0.347515 | RC_AA4795 33_at | EST: zu36h10.s1 Soares ovary tumor NbHOT Homo sapiens cDNA clone 740131 3', mRNA sequence. (from Genbank) |
| Mesothelioma 410 | 0.2491543 | 0.4089043 | 0.34739 | RC_AA5991 44_at | Myosin phosphatase, target subunit 1 |
| Mesothelioma 411 | 0.2490323 | 0.4086484 | 0.347381 | AA156670_s _at | Homo sapiens agrin precursor mRNA, partial cds |
|  |  |  | 0.2238495 |  |  |

FIG. 9W

| | | | | | |
|---|---|---|---|---|---|
| Mesothelioma 412 | 0.2489954 | 0.4085035 | 0.347076 | 0.22380021 | RC_AA4577 18_at | EST: zx87d04.s1 Soares ovary tumor NbHOT Homo sapiens cDNA clone 810727 3', mRNA sequence. (from Genbank) |
| Mesothelioma 413 | 0.2482034 | 0.4084218 | 0.347049 | 0.22367676 | X14885_rna 1_s_at | Transforming growth factor-beta 3 (TGF-beta 3) exon 1 (and joined CDS) |
| Mesothelioma 414 | 0.2480238 | 0.4081271 | 0.347048 | 0.22361214 | RC_AA1207 83_at | Eukaryotic translation initiation factor 2, subunit 3 (gamma, 52kD) |
| Mesothelioma 415 | 0.2477716 | 0.4080536 | 0.346969 | 0.22338553 | D53639_at | Ribosomal protein S26 |
| Mesothelioma 416 | 0.2477203 | 0.4078318 | 0.346805 | 0.2233027 | RC_AA4118 09_at | EST: zt67a06.s1 Soares testis NHT Homo sapiens cDNA clone 727378 3', mRNA sequence. (from Genbank) |
| Mesothelioma 417 | 0.2476606 | 0.4076881 | 0.346688 | 0.22317707 | RC_AA2510 14_at | EST: zs02g08.s1 NCI_CGAP_GCB1 Homo sapiens cDNA clone IMAGE:684062 3' similar to contains element CER repetitive element ;, mRNA sequence. (from Genbank) |
| Mesothelioma 418 | 0.2475363 | 0.4075764 | 0.346504 | 0.22301116 | L04270_at | LYMPHOTOXIN-BETA RECEPTOR PRECURSOR |
| Mesothelioma 419 | 0.2474755 | 0.4073702 | 0.346401 | 0.22287212 | Z29083_at | 5T4 gene for 5T4 Oncofetal antigen |
| Mesothelioma 420 | 0.2471586 | 0.4072858 | 0.346311 | 0.22264346 | C06271_at | EST: similar to none, mRNA sequence. (from Genbank) |
| Mesothelioma 421 | 0.2463169 | 0.407275 | 0.346096 | 0.22253941 | X54936_at | PGF Placental growth factor, vascular endothelial growth factor-related protein |
| Mesothelioma 422 | 0.2450352 | 0.4072544 | 0.346001 | 0.22233939 | U03057_at | Actin bundling protein mRNA |
| Mesothelioma 423 | 0.2445143 | 0.4071796 | 0.345941 | 0.22221208 | RC_AA4969 14_at | Homo sapiens short form transcription factor C-MAF (c-maf) mRNA, complete cds |
| Mesothelioma 424 | 0.2442416 | 0.4068076 | 0.345919 | 0.22221232 | Z71389_at | Skin-antimicrobial-peptide 1 (SAP1) |
| Mesothelioma 425 | 0.2441866 | 0.4067788 | 0.345833 | 0.22194098 | D87258_at | Cancellous bone osteoblast mRNA for serin protease with IGF-binding motif |
| Mesothelioma 426 | 0.2436549 | 0.4067064 | 0.345551 | 0.22187173 | RC_AA4497 49_at | EST: zx07e10.s1 Soares total fetus Nb2HF8 9w Homo sapiens cDNA clone 785802 3', mRNA sequence. (from Genbank) |
| Mesothelioma 427 | 0.2434348 | 0.4064515 | 0.345485 | 0.22170399 | AA448101_a t | EST: zw82c11.r1 Soares testis NHT Homo sapiens cDNA clone 782708 5' similar to SW:A412_PLAFA P15847 41-2 PROTEIN ANTIGEN PRECURSOR. ;, mRNA sequence. (from Genbank) |
| Mesothelioma 428 | 0.2423227 | 0.4064489 | 0.345308 | 0.22164738 | AA247903_a t | EST: j5812.seq.F Human fetal heart, Lambda ZAP Express Homo sapiens cDNA 5', mRNA sequence. (from Genbank) |
| Mesothelioma 429 | 0.2423147 | 0.4064195 | 0.345274 | 0.22157875 | W26231_at | H.sapiens mRNA for NRD1 convertase |
| Mesothelioma 430 | 0.2422528 | 0.4063329 | 0.345094 | 0.22149576 | U43328_at | CRTL1 Cartilage linking protein 1 |

FIG. 9X

| | | | | | |
|---|---|---|---|---|---|
| 431 | Mesothelioma | 0.24210410 | 0.4063158 | 0.344922 | 0.22134243 | J03241_s_at | TGFB3 Transforming growth factor, beta 3 |
| 432 | Mesothelioma | 0.241955 | 0.4063049 | 0.344886 | | RC_AA4466 50_at | EST: zw89g02.s1 Soares total fetus Nb2HF8 9w Homo sapiens cDNA clone 784178 3', mRNA sequence. (from Genbank) |
| 433 | Mesothelioma | 0.2413752 | 0.4062403 | 0.344814 | 0.22118278 | D50840_at-2 | UDP-glucose ceramide glucosyltransferase |
| 434 | Mesothelioma | 0.2413752 | 0.4061826 | 0.344564 | 0.22111838 | D50840_at | Ceramide glucosyltransferase |
| 435 | Mesothelioma | 0.2410928 | 0.4061479 | 0.344559 | 0.22093682 | J04177_at | COL11A1 Collagen, type XI, alpha 1 |
| 436 | Mesothelioma | 0.2407925 | 0.4061341 | 0.344522 | 0.22075522 | D86961_at | KIAA0206 gene, partial cds |
| 437 | Mesothelioma | 0.2404071 | 0.4060069 | 0.344313 | 0.2207041 | RC_AA4856 55_at | Human low-Mr GTP-binding protein (RAB31) mRNA, complete cds |
| 438 | Mesothelioma | 0.2403573 | 0.4057519 | 0.344154 | 0.22062474 | AA234634_f_at | CCAAT/enhancer binding protein (C/EBP), delta |
| 439 | Mesothelioma | 0.2401941 | 0.4057243 | 0.344011 | 0.22045289 | M83667_ma 1_s_at | NF-IL6-beta protein mRNA |
| 440 | Mesothelioma | 0.2398953 | 0.4056556 | 0.344005 | 0.22026935 | RC_AA4259 06_at | EST: zw17h06.s1 Soares ovary tumor NbHOT Homo sapiens cDNA clone 769595 3', mRNA sequence. (from Genbank) |
| 441 | Mesothelioma | 0.2397178 | 0.4055153 | 0.343983 | 0.22015002 | RC_AA2357 37_at | EST: zt32e03.s1 Soares ovary tumor NbHOT Homo sapiens cDNA clone 724060 3' similar to TR:G1199669 G1199669 PROTEIN KINASE C-BINDING PROTEIN BETA 15. ; mRNA sequence. (from Genbank) |
| 442 | Mesothelioma | 0.2396792 | 0.4053633 | 0.343776 | 0.22002147 | AA504595_a_t | EST: aa60g12.r1 NCI_CGAP_GCB1 Homo sapiens cDNA clone IMAGE:825382 5', mRNA sequence. (from Genbank) |
| 443 | Mesothelioma | 0.2383773 | 0.4051912 | 0.343764 | 0.21994853 | U89606_at | Pyridoxal kinase mRNA |
| 444 | Mesothelioma | 0.2378864 | 0.4049136 | 0.343732 | 0.21983626 | RC_AA2561 53_s_at | EST: zr79a09.s1 Soares NhHMPu S1 Homo sapiens cDNA clone 681880 3', mRNA sequence. (from Genbank) |
| 445 | Mesothelioma | 0.2364085 | 0.4046356 | 0.343486 | 0.21976471 | RC_AA3862 64_at | EST: EST07569 Fetal brain Homo sapiens cDNA 3' end, mRNA sequence. (from Genbank) |
| 446 | Mesothelioma | 0.2363854 | 0.4043772 | 0.343235 | 0.21971491 | AA410325_a_t | EST: zv11e04.r1 Soares NhHMPu S1 Homo sapiens cDNA clone 753342 5', mRNA sequence. (from Genbank) |
| 447 | Mesothelioma | 0.2357366 | 0.4039094 | 0.343106 | 0.21957351 | RC_AA6202 89_at | Homo sapiens clone 23887 mRNA sequence |
| 448 | Mesothelioma | 0.2346154 | 0.4038987 | 0.342923 | 0.21950486 | U76189_at | EXTL2 (EXTL2) mRNA, partial cds |
| 449 | Mesothelioma | 0.2342033 | 0.4037402 | 0.342911 | 0.21945164 | RC_AA2817 69_s_at | Human Hpast (HPAST) mRNA, complete cds |

FIG. 9Y

| | | | | | |
|---|---|---|---|---|---|
| 450 | Mesothelioma | 0.2336829 | 0.4037049 | 0.342818 | 0.21939255 | X06256_at | ITGA5 Integrin, alpha 5 (fibronectin receptor, alpha polypeptide) |
| 451 | Mesothelioma | 0.2336102 | 0.4036565 | 0.342695 | 0.21919474 | RC_AA4494 42_at | EST: zx05d07.s1 Soares total fetus Nb2HF8 9w Homo sapiens cDNA clone 785581 3', mRNA sequence. (from Genbank) |
| 452 | Mesothelioma | 0.2329444 | 0.4036079 | 0.342587 | 0.21908201 | U33202_s_a t | Mdm2-D (mdm2) mRNA |
| 453 | Mesothelioma | 0.2321748 | 0.4036035 | 0.342412 | 0.21891865 | U05291_at | FMOD Fibromodulin |
| 454 | Mesothelioma | 0.2319844 | 0.4035982 | 0.342316 | 0.21871565 | RC_AA0318 14_at | EST: zk17g04.s1 Soares pregnant uterus NbHPU Homo sapiens cDNA clone 470838 3', mRNA sequence. (from Genbank) |
| 455 | Mesothelioma | 0.2319695 | 0.4035739 | 0.34231 | 0.21859495 | M97639_at | Transmembrane receptor (ror2) mRNA |
| 456 | Mesothelioma | 0.2314104 | 0.403105 | 0.342241 | 0.21853642 | AA027765_a t | EST: HPLA_CCLEE_65h7r HPLA CCLee Homo sapiens cDNA, mRNA sequence. (from Genbank) |
| 457 | Mesothelioma | 0.2311485 | 0.4031004 | 0.342118 | 0.21836177 | M12272_s_a t | Alcohol dehydrogenase 3 (class I), gamma polypeptide |
| 458 | Mesothelioma | 0.2310899 | 0.4026878 | 0.342 | 0.21827297 | RC_AA4551 81_at | EST: aa15g04.s1 Soares NhHMPu S1 Homo sapiens cDNA clone 813366 3', mRNA sequence. (from Genbank) |
| 459 | Mesothelioma | 0.2310309 | 0.4020965 | 0.341792 | 0.21812743 | HG1153-HT1153_at | Nucleoside Diphosphate Kinase Nm23-H2s |
| 460 | Mesothelioma | 0.2307408 | 0.4020499 | 0.341577 | 0.2180665 | AA214658_a t | H beta 58 homolog |
| 461 | Mesothelioma | 0.230499 | 0.401907 | 0.341572 | 0.21788551 | L09708_at | C2 Complement component C2 |
| 462 | Mesothelioma | 0.2301794 | 0.4018511 | 0.341387 | 0.21783352 | N75870_s_a t | Dual specificity phosphatase 1 |
| 463 | Mesothelioma | 0.2296507 | 0.4017795 | 0.341305 | 0.21767801 | AA2789546_a t | EST: zs86b06.r1 NCI_CGAP_GCB1 Homo sapiens cDNA clone IMAGE:704339 5', mRNA sequence. (from Genbank) |
| 464 | Mesothelioma | 0.2293372 | 0.4017411 | 0.341303 | 0.21742909 | X04470_s_a t | RPL32 Ribosomal protein L32 |
| 465 | Mesothelioma | 0.2291974 | 0.4016492 | 0.341281 | 0.21733332 | RC_AA4615 05_at | EST: zx60b05.s1 Soares testis NHT Homo sapiens cDNA clone 795825 3', mRNA sequence. (from Genbank) |
| 466 | Mesothelioma | 0.2288922 | 0.4016431 | 0.341244 | 0.2172764 | AA422123_f at | EST: zv26h12.r1 Soares NhHMPu S1 Homo sapiens cDNA clone 754823 5' similar to contains Alu repetitive element; mRNA sequence. (from Genbank) |
| 467 | Mesothelioma | 0.2285914 | 0.4015709 | 0.340908 | 0.21708141 | D63475_at | KIAA0109 gene |
| 468 | Mesothelioma | 0.2284748 | 0.4013893 | 0.340908 | 0.21694946 | RC_AA2530 43_at | EST: zr52b12.s1 Soares NhHMPu S1 Homo sapiens cDNA clone 667007 3', mRNA sequence. (from Genbank) |

FIG. 9Z

| | | | | | |
|---|---|---|---|---|---|
| 469 | Mesothelioma | 0.2283897 | 0.4013639 | 0.340857 | 0.21685775 | RC_AA0565 88_at | EST: zi66a02.s1 Stratagene colon (#937204) Homo sapiens cDNA clone 509546 3', mRNA sequence. (from Genbank) |
| 470 | Mesothelioma | 0.2283637 | 0.40135630 | 0.340729 | 0.21672162 | AA458761_i_at | Transcription factor AP-2 alpha (activating enhancer-binding protein 2 alpha) |
| 471 | Mesothelioma | 0.2282104 | 0.4013358 | 0.3407 | 0.21651788 | U09278_at | Fibroblast activation protein mRNA |
| 472 | Mesothelioma | 0.2277899 | 0.4013133 | 0.340642 | 0.21640705 | RC_AA4577 30_at | Homo sapiens clone 23851 mRNA sequence |
| 473 | Mesothelioma | 0.2274588 | 0.4011942 | 0.340563 | 0.21628280 | U19718_at | MFAP2 Microfibrillar-associated protein 2 |
| 474 | Mesothelioma | 0.227407 | 0.40091590 | 0.340445 | 0.21620809 | RC_AA2783 29_f_at | EST: zs80f03.s1 NCI_CGAP_GCB1 Homo sapiens cDNA clone IMAGE:703805 3', mRNA sequence. (from Genbank) |
| 475 | Mesothelioma | 0.2272256 | 0.4008453 | 0.340368 | 0.2161225 | X04741_at | UBIQUITIN CARBOXYL-TERMINAL HYDROLASE ISOZYME L1 |
| 476 | Mesothelioma | 0.2271608 | 0.4008043 | 0.340186 | 0.21593271 | D90224_at | TXGP1 Tax-transcriptionally activated glycoprotein 1 (34kD) |
| 477 | Mesothelioma | 0.227099 | 0.4007765 | 0.34001 | 0.21587294 | RC_AA0749 19_at | EST: zm82b10.s1 Stratagene ovarian cancer (#937219) Homo sapiens cDNA clone 544411 3', mRNA sequence. (from Genbank) |
| 478 | Mesothelioma | 0.2266117 | 0.4006988 | 0.34 | 0.21583039 | RC_AA4315 71_at | EST: zw79e12.s1 Soares testis NHT Homo sapiens cDNA clone 782446 3', mRNA sequence. (from Genbank) |
| 479 | Mesothelioma | 0.2265718 | 0.4006097 | 0.339973 | 0.21567237 | W39573_at | EST: zc20b05.r1 Soares senescent fibroblasts NbHSF Homo sapiens cDNA clone 322833 5', mRNA sequence. (from Genbank) |
| 480 | Mesothelioma | 0.2265282 | 0.4005969 | 0.339935 | 0.21547976 | RC_AA2821 40_at | EST: zl02b01.s1 NCI_CGAP_GCB1 Homo sapiens cDNA clone IMAGE:711913 3', mRNA sequence. (from Genbank) |
| 481 | Mesothelioma | 0.2260045 | 0.40044966 | 0.339869 | 0.21533905 | W26649_at | Zinc finger protein 140 (clone pHZ-39) |
| 482 | Mesothelioma | 0.2255955 | 0.400438 | 0.339705 | 0.21529225 | RC_AA4126 89_at | EST: zu12e03.s1 Soares testis NHT Homo sapiens cDNA clone 731644 3', mRNA sequence. (from Genbank) |
| 483 | Mesothelioma | 0.2254329 | 0.4003266 | 0.339406 | 0.21497512 | J05633_at | ITGB5 Integrin beta-5 subunit |
| 484 | Mesothelioma | 0.2241578 | 0.4002476 | 0.339405 | 0.21492091 | RC_D59894 _at | EST: Human fetal brain cDNA 3'-end GEN-073B05, mRNA sequence. (from Genbank) |
| 485 | Mesothelioma | 0.2237888 | 0.4001212 | 0.339354 | 0.21484278 | RC_AA2629 43_at | EST: zr71a09.s1 Soares NhHMPu S1 Homo sapiens cDNA clone 668824 3', mRNA sequence. (from Genbank) |
| 486 | Mesothelioma | 0.2236281 | 0.4000667 | 0.339313 | 0.21466696 | U27655_at | RGP3 mRNA |
| 487 | Mesothelioma | 0.2227389 | 0.3998457 | 0.339278 | 0.21457149 | RC_AA3996 34_at | EST: zt93e08.s1 Soares testis NHT Homo sapiens cDNA clone 729926 3', mRNA sequence. (from Genbank) |

FIG. 9A2

| # | Type | Val1 | Val2 | Val3 | ID1 | ID2 | Description |
|---|---|---|---|---|---|---|---|
| 488 | Mesothelioma | 0.2220808 | 0.3997865 | 0.339144 | 0.21446584 | RC_AA2363 65_s_at | Homo sapiens 3-phosphoglycerate dehydrogenase mRNA, complete cds |
| 489 | Mesothelioma | 0.2218874 | 0.3997648 | 0.338991 | 0.21440908 | AA456471_s_at | EST: zx74g11.r1 Soares ovary tumor NbHOT Homo sapiens cDNA clone 809540 5'. mRNA sequence. (from Genbank) |
| 490 | Mesothelioma | 0.2217476 | 0.3996199 | 0.338851 | 0.21436471 | U55853_at | 130 kD Golgi-localized phosphoprotein (GPP130) mRNA |
| 491 | Mesothelioma | 0.2217476 | 0.3994732 | 0.33884 | 0.21142572 | U55853_at-2 | Homo sapiens 130 kD Golgi-localized phosphoprotein (GPP130) mRNA, complete cds |
| 492 | Mesothelioma | 0.2216582 | 0.3992892 | 0.338791 | 0.21410935 | AA357394_a_t | EST: EST66127 Kidney IX Homo sapiens cDNA 5' end, mRNA sequence. (from Genbank) |
| 493 | Mesothelioma | 0.2215727 | 0.3992518 | 0.338639 | 0.21399806 | Y09022_at | Not56-like protein |
| 494 | Mesothelioma | 0.2203614 | 0.3991641 | 0.338591 | 0.2138821 | M23892_s_a_t | ALOX15 Arachidonate 15-lipoxygenase |
| 495 | Mesothelioma | 0.2203567 | 0.3985607 | 0.338348 | 0.21379384 | RC_AA4179 70_at | EST: zv97c03.s1 Soares NhHMPu S1 Homo sapiens cDNA clone 767716 3'. mRNA sequence. (from Genbank) |
| 496 | Mesothelioma | 0.2201312 | 0.3985315 | 0.338226 | 0.21372181 | M19309_s_a_t | TNNT1 Troponin T1, skeletal, slow |
| 497 | Mesothelioma | 0.2195137 | 0.3981684 | 0.338199 | 0.2134969 | X79683_s_a_t | LAMB2 Laminin, beta 2 (laminin S) |
| 498 | Mesothelioma | 0.2189459 | 0.3980964 | 0.338072 | 0.21342461 | AA216017_a_t | EST: hp0234.seq.F Fetal heart, Lambda ZAP Express Homo sapiens cDNA 5'. mRNA sequence. (from Genbank) |
| 499 | Mesothelioma | 0.2186447 | 0.3980737 | 0.338057 | 0.21333252 | W52431_at | EST: zc45b12.r1 Soares senescent fibroblasts NbHSF Homo sapiens cDNA clone 325247 5' similar to SW:WDNM_RAT P14730 WDNM1 PROTEIN. [2] PIR:S07807 ;. mRNA sequence. (from Genbank) |
| 500 | Mesothelioma | 0.2184503 | 0.3978872 | 0.337763 | 0.21330836 | RC_AA4852 49_at | Homo sapiens chromosome 19, cosmid R33729 |
| 501 | Mesothelioma | 0.2181622 | 0.3978508 | 0.337742 | 0.21131824 | D49950_at-2 | Interleukin 18 (interferon-gamma-inducing factor) |
| 502 | Mesothelioma | 0.2181622 | 0.3975223 | 0.337737 | 0.21215591 | D49950_at | Liver mRNA for interferon-gamma inducing factor(IGIF) |
| 503 | Mesothelioma | 0.2179292 | 0.3974858 | 0.337643 | 0.21298145 | R93659_at | Homo sapiens mRNA for KIAA0871 protein, complete cds |
| 504 | Mesothelioma | 0.2177952 | 0.3967421 | 0.337613 | 0.21286994 | R94662_at | EST: yq42d12.r1 Homo sapiens cDNA clone 198455 5'. (from Genbank) |
| 505 | Mesothelioma | 0.2177161 | 0.3963943 | 0.33742 | 0.21272859 | R66239_at | EST: yi34d06.r1 Homo sapiens cDNA clone 141131 5'. (from Genbank) |
| 506 | Mesothelioma | 0.2176677 | 0.3961885 | 0.337368 | 0.2125208 | R21443_at | Human pre-B cell enhancing factor (PBEF) mRNA, complete cds |

FIG. 9B2

| | | | | | |
|---|---|---|---|---|---|
| 507 | Mesothelio ma | 0.2174594 | 0.3961577 | 0.337204 | 0.21240178 | C00225_s_a t | EST: HUMGS0005889, Human Gene Signature, 3'-directed cDNA sequence, mRNA sequence. (from Genbank) |
| 508 | Mesothelio ma | 0.2170233 | 0.3958407 | 0.337034 | 0.21230745 | AA033703_a t | EST: zf01d10.r1 Soares fetal heart NbHH19W Homo sapiens cDNA clone 375667 5', mRNA sequence. (from Genbank) |
| 509 | Mesothelio ma | 0.2161591 | 0.3958302 | 0.336945 | 0.21222252983_s_at | RC_AA4565 | Human PL6 protein (PL6) mRNA, complete cds |
| 510 | Mesothelio ma | 0.2157186 | 0.3957498 | 0.336935 | 0.21208715 | U40572_at | Beta2-syntrophin (SNT B2) mRNA |
| 511 | Mesothelio ma | 0.2153397 | 0.3957498 | 0.336914 | 0.21207146 | M23161_at-2 | Human transposon-like element mRNA |
| 512 | Mesothelio ma | 0.2153397 | 0.3956994 | 0.336914 | 0.21193664 | M23161_at | Transposon-like element mRNA |
| 513 | Mesothelio ma | 0.215177 | 0.3956912 | 0.336877 | 0.2118418 | L37868_s_at | POU-domain transcription factor (N-Oct-3) |
| 514 | Mesothelio ma | 0.2150646 | 0.3953228 | 0.336802 | 0.21173024 | M20030_f_at | Small proline rich protein (sprll) mRNA, clone 930 |
| 515 | Mesothelio ma | 0.214339 | 0.3949409 | 0.336794 | 0.2116793 | HG3044-HT3742_s_a t | Fibronectin, Alt. Splice 1 |
| 516 | Mesothelio ma | 0.2142871 | 0.3947811 | 0.336638 | 0.21148464 | N95507_at | EST: yy62b11.r1 Homo sapiens cDNA clone 278109 5'. (from Genbank) |
| 517 | Mesothelio ma | 0.2136581 | 0.3942333 | 0.336604 | 0.21138994 | RC_AA2274 48_at | Homo sapiens mRNA for KIAA0456 protein, partial cds |
| 518 | Mesothelio ma | 0.2135595 | 0.3941188 | 0.336591 | 0.2112771 | X07438_s_a t | DNA for cellular retinol binding protein (CRBP) exons 3 and 4 |
| 519 | Mesothelio ma | 0.2133301 | 0.3939915 | 0.336587 | 0.21115571 | RC_AA4440 54_at | EST: zv45f09.s1 Soares ovary tumor NbHOT Homo sapiens cDNA clone 756617 3', mRNA sequence. (from Genbank) |
| 520 | Mesothelio ma | 0.213175 | 0.3938974 | 0.336563 | 0.21102558 | RC_AA1499 40_at | GLUT1 C-terminal binding protein |
| 521 | Mesothelio ma | 0.2128176 | 0.3934979 | 0.336474 | 0.21088155 | RC_AA1668 38_at | EST: zq39h04.s1 Stratagene hNT neuron (#937233) Homo sapiens cDNA clone 632119 3' similar to contains Alu repetitive element;contains element MSR1 repetitive element ;, mRNA sequence. (from Genbank) |
| 522 | Mesothelio ma | 0.2122943 | 0.3934718 | 0.336363 | 0.21079014 | RC_AA0562 | EST: zf62g04.s1 Soares retina N2b4HR Homo sapiens cDNA clone 381558 3', mRNA sequence. (from Genbank) |
| 523 | Mesothelio ma | 0.2117215 | 0.3934179 | 0.336189 | 0.21069182 | U28811_at | Cysteine-rich fibroblast growth factor receptor (CFR-1) mRNA |
| 524 | Mesothelio ma | 0.2114994 | 0.3932855 | 0.336152 | 0.21059765 | D14822_at | Chimeric mRNA derived from AML1 gene and MTG8(ETO) gene, partial sequence |

FIG. 9C2

| | | | | | |
|---|---|---|---|---|---|
| 525 | Mesothelioma | 0.2114889 | 0.3932436 | 0.33608 | 0.21049662 | RC_AA4890 12_at | Human pre-B cell enhancing factor (PBEF) mRNA, complete cds |
| 526 | Mesothelioma | 0.2114278 | 0.3931314 | 0.335977 | 0.2103492 | RC_AA4820 10_at | Homo sapiens mRNA for KIAA0747 protein, partial cds |
| 527 | Mesothelioma | 0.2109894 | 0.3929205 | 0.335861 | 0.21016462 | RC_AA2621 11_at | EST: zs21f07.s1 NCI_CGAP_GCB1 Homo sapiens cDNA clone IMAGE:685861 3' similar to SW:YB9B_YEAST P38334 HYPOTHETICAL 19.7 KD PROTEIN IN SRB6-RIB5 INTERGENIC REGION. ;, mRNA sequence. (from Genbank) |
| 528 | Mesothelioma | 0.2108305 | 0.3928882 | 0.335856 | 0.21014549 | X66945_at | FGFR1 Basic fibroblast growth factor (bFGF) receptor (shorter form) |
| 529 | Mesothelioma | 0.2106664 | 0.3925149 | 0.335753 | 0.20998912 | RC_AA2349 45_at | EST: zr78h09.s1 Soares NhHMPu S1 Homo sapiens cDNA clone 669569 3', mRNA sequence. (from Genbank) |
| 530 | Mesothelioma | 0.2100579 | 0.3925138 | 0.335667 | 0.20994061 | AA401047_a t | Homo sapiens mRNA for neuropsin, complete cds |
| 531 | Mesothelioma | 0.2099166 | 0.3924354 | 0.335613 | 0.20980108 | RC_AA4875 76_at | EST: ab23g01.s1 Stratagene lung (#937210) Homo sapiens cDNA clone 841680 3', mRNA sequence. (from Genbank) |
| 532 | Mesothelioma | 0.2098505 | 0.3923666 | 0.335597 | 0.20973511 | U46751_at | Phosphotyrosine independent ligand p62 for the Lck SH2 domain mRNA |
| 533 | Mesothelioma | 0.2088933 | 0.3922677 | 0.335511 | 0.20962076 | D87465_at | KIAA0275 gene |
| 534 | Mesothelioma | 0.2088825 | 0.3921462 | 0.335393 | 0.20957813 | AF006088_a t | Arp2/3 protein complex subunit p16 |
| 535 | Mesothelioma | 0.208203 | 0.3921398 | 0.33539 | 0.20944118 | L37347_at | NRAMP2 Natural resistance-associated macrophage protein 2 |
| 536 | Mesothelioma | 0.2078574 | 0.3919636 | 0.335345 | 0.20935881 | J04164_at | RPS3 Ribosomal protein S3 |
| 537 | Mesothelioma | 0.2077247 | 0.3917378 | 0.33529 | 0.20916462 | M32053_at | H19 RNA gene |
| 538 | Mesothelioma | 0.2075718 | 0.3916083 | 0.335238 | 0.20905395 | AA397724_a t | Ash2 (absent, small, or homeotic, Drosophila, homolog)-like |
| 539 | Mesothelioma | 0.2074651 | 0.3915875 | 0.335168 | 0.20895852 | D16532_at | VLDLR Very low density lipoprotein receptor |
| 540 | Mesothelioma | 0.2074577 | 0.3913639 | 0.335117 | 0.20882647 | RC_AA4117 71_at | KIAA0671 gene product |
| 541 | Mesothelioma | 0.2063453 | 0.3910105 | 0.335019 | 0.20875412 | Z50022_at | Surface glycoprotein |
| 542 | Mesothelioma | 0.206067 | 0.3909571 | 0.335006 | 0.20866536 | U01062_at | ITPR3 Inositol 1,4,5-triphosphate receptor, type 3 |
| 543 | Mesothelioma | 0.2057923 | 0.3908807 | 0.334948 | 0.20857204 | AA351461_a t | EST: EST59216 Infant brain Homo sapiens cDNA 5' end similar to similar to perforin, mRNA sequence. (from Genbank) |

FIG. 9D2

| | | | | | |
|---|---|---|---|---|---|
| 544 | Mesothelioma | 0.2054123 | 0.3908607 | 0.334815 | 0.20848213 | RC_AA4122 84_s_at | Human poliovirus receptor mRNA, clone H20A |
| 545 | Mesothelioma | 0.2053218 | 0.3908163 | 0.334677 | 0.20841846 t | AA296821_a_at | EST:EST112387 Aorta endothelial cells Homo sapiens cDNA 5' end, mRNA sequence. (from Genbank) |
| 546 | Mesothelioma | 0.2041049 | 0.3908101 | 0.33461 | 0.20833330 29_at | RC_AA4528 | EST: zx36d03.s1 Soares total fetus Nb2HF8.9w Homo sapiens cDNA clone 788549 3', mRNA sequence. (from Genbank) |
| 547 | Mesothelioma | 0.2036573 | 0.390066 | 0.334605 | 0.20831555 | M64082_at | FMO1 Flavin-containing monooxygenase 1 |
| 548 | Mesothelioma | 0.2036435 | 0.3906317 | 0.334285 | 0.20816615 17_at | RC_AA0539 | EST: ze75c02.s1 Soares fetal heart NbHH19W Homo sapiens cDNA clone 364802 3', mRNA sequence. (from Genbank) |
| 549 | Mesothelioma | 0.2032492 | 0.3906317 | 0.33422 | 0.20814091 | X89066_at | TRPC1 Transient receptor potential channel 1 |
| 550 | Mesothelioma | 0.2031317 | 0.3902877 | 0.334201 | 0.20799284 39_at | RC_AA0531 | EST: zl73e05.s1 Stratagene colon (#937204) Homo sapiens cDNA clone 510272 3' similar to TR:E243948 E243948 CHROMOSOME VII READING FRAME ORF YGL054C.; mRNA sequence. (from Genbank) |
| 551 | Mesothelioma | 0.201605 | 0.390279 | 0.334157 | 0.20782875 04_at | RC_AA4050 | EST: zt06e03.s1 NCI_CGAP_GCB1 Homo sapiens cDNA clone IMAGE:712348 3', mRNA sequence. (from Genbank) |
| 552 | Mesothelioma | 0.2015334 | 0.3902004 | 0.334137 | 0.20773098 t | AA464468_a | EST: zx84d05.r1 Soares ovary tumor NbHOT Homo sapiens cDNA clone 810441 5', mRNA sequence. (from Genbank) |
| 553 | Mesothelioma | 0.2007246 | 0.3901786 | 0.334108 | 0.20764877 t | AA233231_a | EST: zr69c12.r1 Soares NhHMPu S1 Homo sapiens cDNA clone 668662 5', mRNA sequence. (from Genbank) |
| 554 | Mesothelioma | 0.1999803 | 0.3899444 | 0.33408 | 0.20761088 t | U57843_s_a | Human phosphatidylinositol 3-kinase delta catalytic subunit mRNA, complete cds |
| 555 | Mesothelioma | 0.1998984 | 0.3898961 | 0.334006 | 0.20747742 | J03077_s_at | PSAP Sulfated glycoprotein 1 |
| 556 | Mesothelioma | 0.1991575 | 0.3897548 | 0.333888 | 0.20743416 t | AA236610_a | Zr99c11.r1 NCI_CGAP_GCB1 Homo sapiens cDNA clone IMAGE:683828 5', mRNA sequence. (from Genbank) |
| 557 | Mesothelioma | 0.1988742 | 0.3897381 | 0.333658 | 0.20724596 0_at | RC_AA0131 | EST: ze35e10.s1 Soares retina N2b4HR Homo sapiens cDNA clone 361002 3' similar to contains Alu repetitive element; mRNA sequence. (from Genbank) |
| 558 | Mesothelioma | 0.1988557 | 0.3896993 | 0.333617 | 0.20715865 | Z21217_at | KIAA0008 gene product |
| 559 | Mesothelioma | 0.198782 | 0.3896819 | 0.333428 | 0.20708343 65_at | RC_AA2848 | EST: zt23a03.s1 Soares ovary tumor NbHOT Homo sapiens cDNA clone 713932 3', mRNA sequence. (from Genbank) |
| 560 | Mesothelioma | 0.1986974 | 0.3896152 | 0.333328 | 0.20690812 t | AA151544_a | Matrix metalloproteinase 21 |
| 561 | Mesothelioma | 0.1986462 | 0.3896053 | 0.333328 | 0.20676218 t | N52656_s_a | EST: yz06a09.r1 Homo sapiens cDNA clone 282232 5'. (from Genbank) |

FIG. 9E2

| | | | | | |
|---|---|---|---|---|---|
| 562 | Mesothelioma | 0.1983917 | 0.3895016 | 0.333283 | 0.206720001 | M35410_s_a t | Insulin-like growth factor binding protein 2 (36kD) |
| 563 | Mesothelioma | 0.1980007 | 0.3894578 | 0.333217 | 0.20664987 | H52836_at | Yo22e10.r1 Homo sapiens cDNA clone 178698 5'. (from Genbank) |
| 564 | Mesothelioma | 0.1978949 | 0.3892011 | 0.332941 | 0.2065955_at | RC_D51370 | EST: Human fetal brain cDNA 3'-end GEN-031A12, mRNA sequence. (from Genbank) |
| 565 | Mesothelioma | 0.1977138 | 0.3890399 | 0.332792 | 0.20655228 | H86648_at | EST: yt02a04.r1 Homo sapiens cDNA clone 223086 5'. (from Genbank) |
| 566 | Mesothelioma | 0.1977069 | 0.3889526 | 0.332741 | 0.20650889 | RC_AA2332 58_at | EST: zr48d01.s1 Soares NhHMPu S1 Homo sapiens cDNA clone 666625 3', mRNA sequence. (from Genbank) |
| 567 | Mesothelioma | 0.1974199 | 0.3883913 | 0.332594 | 0.20632608 | RC_AA4486 88_at | EST: zx11g04.s1 Soares total fetus Nb2HF8 9w Homo sapiens cDNA clone 786198 3', mRNA sequence. (from Genbank) |
| 568 | Mesothelioma | 0.1973655 | 0.3883345 | 0.332457 | 0.20618044 | J04456_at | LGALS1 Ubiquinol-cytochrome c reductase core protein II |
| 569 | Mesothelioma | 0.1968024 | 0.3882178 | 0.332368 | 0.2060999 | L32976_at | Protein kinase (MLK-3) mRNA |
| 570 | Mesothelioma | 0.1968024 | 0.3880515 | 0.332365 | 0.20598094 | L32976_at-2 | Mixed lineage kinase 3 |
| 571 | Mesothelioma | 0.1967201 | 0.3878915 | 0.332349 | 0.2058916 | X51630_at | WT1 Wilms tumor 1 |
| 572 | Mesothelioma | 0.1962218 | 0.3874916 | 0.332244 | 0.20574267 | L16895_at | LOX Lysyl oxidase |
| 573 | Mesothelioma | 0.1957652 | 0.3874026 | 0.332045 | 0.20566025 | M61916_at | LAMB1 Laminin B1 chain |
| 574 | Mesothelioma | 0.195733 | 0.3873881 | 0.331748 | 0.2055847_a t | AA478129_a | EST: zu42c09.r1 Soares ovary tumor NbHOT Homo sapiens cDNA clone 740656 5' similar to SW:BI3_MOUSE P28662 BRAIN PROTEIN I3 ; mRNA sequence. (from Genbank) |
| 575 | Mesothelioma | 0.195714 | 0.3873186 | 0.331626 | 0.20550896_t | D45917_s_a | TIMP-3, partial cds (C-terminus region) |
| 576 | Mesothelioma | 0.1953356 | 0.3873185 | 0.331391 | 0.20540448 6_at | RC_AA6100 | EST: af08h02.s1 Soares testis NHT Homo sapiens cDNA clone 1031091 3', mRNA sequence. (from Genbank) |
| 577 | Mesothelioma | 0.1952033 | 0.387284 | 0.331359 | 0.20528395 | W24957_at | EST: zb65h10.r1 Soares fetal lung NbHL19W Homo sapiens cDNA clone 308515 5', mRNA sequence. (from Genbank) |
| 578 | Mesothelioma | 0.1939937 | 0.3872666 | 0.331327 | 0.2052298 | U97519_at | Podocalyxin-like |
| 579 | Mesothelioma | 0.193278 | 0.3872604 | 0.33131 | 0.20502394 | X64878_at | OXTR Oxytocin receptor |
| 580 | Mesothelioma | 0.1932006 | 0.3872537 | 0.331248 | 0.20490564 | RC_AA4521 08_at | Transcription factor AP-2 alpha (activating enhancer-binding protein 2 alpha) |

FIG. 9F2

| | | | | | | |
|---|---|---|---|---|---|---|
| 581 | Mesothelioma | 0.1931225 | 0.3872353 | 0.331201 | 0.20485955 | RC_AA0252 96_at | EST: ze74d01.s1 Soares fetal heart NbHH19W Homo sapiens cDNA clone 364705 3', mRNA sequence. (from Genbank) |
| 582 | Mesothelioma | 0.1928806 | 0.3872264 | 0.3311 | 0.2048273 | D87433_at | KIAA0246 gene, partial cds |
| 583 | Mesothelioma | 0.1925956 | 0.3870134 | 0.33101 | 0.20471369 | M24398_at | PTMS Parathymosin |
| 584 | Mesothelioma | 0.1918052 | 0.3869906 | 0.330973 | 0.20464611 | C02053_at | EST: HUMGS0005644, Human Gene Signature, 3'-directed cDNA sequence, mRNA sequence. (from Genbank) |
| 585 | Mesothelioma | 0.1916117 | 0.3869688 | 0.330898 | 0.20451282 | M55593_at | MMP2 Matrix metalloproteinase 2 (gelatinase A, 72kD gelatinase, 72kD type IV collagenase) |
| 586 | Mesothelioma | 0.1914123 | 0.3868948 | 0.330751 | 0.20439922 | RC_AA1890 15_at | Homo sapiens mRNA for cytochrome b5, partial cds |
| 587 | Mesothelioma | 0.1913175 | 0.3868339 | 0.330681 | 0.20424563 | RC_AA4968 91_at | EST: ae33c05.s1 Gessler Wilms tumor Homo sapiens cDNA clone 897608 3' similar to WP:F10G7.4 CE02628 DNA DOUBLE-STRAND BREAK REPAIR .;, mRNA sequence. (from Genbank) |
| 588 | Mesothelioma | 0.1908514 | 0.3866944 | 0.330608 | 0.20421125 | D78676_at | EST: Human placenta cDNA 5'-end GEN-502F04, mRNA sequence. (from Genbank) |
| 589 | Mesothelioma | 0.1908042 | 0.3865404 | 0.330595 | 0.20407999 | HG4310-HT4580_at | Cellular Retinol Binding Protein Ii |
| 590 | Mesothelioma | 0.1905037 | 0.3865145 | 0.330539 | 0.20407383 | D13814_s_a t | AGTR1 Angiotensin receptor 1 |
| 591 | Mesothelioma | 0.1900148 | 0.3864979 | 0.330513 | 0.20395282 | AA096094_s _at | EST: lb200.seq,F Fetal heart, Lambda ZAP Express Homo sapiens cDNA 5', mRNA sequence. (from Genbank) |
| 592 | Mesothelioma | 0.1896491 | 0.3864979 | 0.330389 | 0.20386317 | RC_AA1366 60_i_at | EST: zk99a04.s1 Soares pregnant uterus NbHPU Homo sapiens cDNA clone 490926 3', mRNA sequence. (from Genbank) |
| 593 | Mesothelioma | 0.1890415 | 0.3864113 | 0.330352 | 0.2037366 | S37730_s_at | Insulin-like growth factor binding protein-2 [human, placenta, Genomic, 1342 nt, segment 4 of 4] |
| 594 | Mesothelioma | 0.1883227 | 0.3863119 | 0.330274 | 0.20359865 | L78132_at | Prostate carcinoma tumor antigen (pcta-1) mRNA |
| 595 | Mesothelioma | 0.1881342 | 0.3862024 | 0.330255 | 0.20351024 | RC_AA2906 79_at | Selenium binding protein 1 |
| 596 | Mesothelioma | 0.188134 | 0.386116 | 0.330076 | 0.20340508 | RC_AA4782 98_s_at | Human apM2 mRNA for GS2374 (unknown product specific to adipose tissue), complete cds |
| 597 | Mesothelioma | 0.1879949 | 0.3858351 | 0.330015 | 0.2033644 | C01782_at | EST: HUMGS0003737, Human Gene Signature, 3'-directed cDNA sequence, mRNA sequence. (from Genbank) |
| 598 | Mesothelioma | 0.1878685 | 0.3857179 | 0.329949 | 0.20324661 | M10942_at | Metallothionein-Ie gene (hMT-Ie) |
| 599 | Mesothelioma | 0.1874569 | 0.3853968 | 0.329909 | 0.20319045 | L33075_at | Ras GTPase-activating-like protein (IQGAP1) mRNA |

FIG. 9G2

| | | | | | |
|---|---|---|---|---|---|
| 600 | Mesothelioma | 0.1873512 | 0.3853352 | 0.329886 | 0.203079983 | S78569_at | LAMA4 Laminin, alpha 4 |
| 601 | Mesothelioma | 0.1869947 | 0.3852638 | 0.32968 | 0.20297918 | W27325_at | Homo sapiens mRNA for GCP170, complete cds |
| 602 | Mesothelioma | 0.1869064 | 0.385242 | 0.329593 | 0.20280015 | J03474_at | SERUM AMYLOID A PROTEIN PRECURSOR |
| 603 | Mesothelioma | 0.1868855 | 0.3850896 | 0.329423 | 0.20276515 | U85773_at | Phosphomannomutase 2 |
| 604 | Mesothelioma | 0.1867134 | 0.3849286 | 0.329416 | 0.20264563 | RC_AA2356 04_at | EST: zt36b07.s1 Soares ovary tumor NbHOT Homo sapiens cDNA clone 724405 3', mRNA sequence. (from Genbank) |
| 605 | Mesothelioma | 0.1858333 | 0.3849052 | 0.329401 | 0.2025336 | RC_AA0373 57_f_at | EST: zc03c04.s1 Soares parathyroid tumor NbHPA Homo sapiens cDNA clone 321222 3' similar to contains Alu repetitive element;, mRNA sequence. (from Genbank) |
| 606 | Mesothelioma | 0.1856962 | 0.3846811 | 0.329306 | 0.20247835 | RC_AA6090 45_at | EST: af10e04.s1 Soares testis NHT Homo sapiens cDNA clone 1031262 3', mRNA sequence. (from Genbank) |
| 607 | Mesothelioma | 0.1856397 | 0.3844618 | 0.329289 | 0.20236593 | RC_AA2912 93_at | EST: zs18d11.s1 NCI_CGAP_GCB1 Homo sapiens cDNA clone IMAGE:685557 3', mRNA sequence. (from Genbank) |
| 608 | Mesothelioma | 0.1852401 | 0.3844458 | 0.328857 | 0.20223911 | RC_AA6099 88_at | EST: af18a06.s1 Soares testis NHT Homo sapiens cDNA clone 1031986 3', mRNA sequence. (from Genbank) |
| 609 | Mesothelioma | 0.1850165 | 0.3844308 | 0.328761 | 0.20221132 | J02854_at | 20-kDa myosin light chain (MLC-2) mRNA |
| 610 | Mesothelioma | 0.184947 | 0.3842261 | 0.328747 | 0.20207407 | R67128_at | KIAA0331 gene product |
| 611 | Mesothelioma | 0.1845868 | 0.3841472 | 0.328726 | 0.20191963 | HG417-HT417_s_at | Cathepsin B |
| 612 | Mesothelioma | 0.1842545 | 0.3841435 | 0.328629 | 0.20187184 | C01714_at | Homo sapiens serum-inducible kinase mRNA, complete cds |
| 613 | Mesothelioma | 0.1841733 | 0.3840794 | 0.328555 | 0.2018431 | X16323_at | HGF Hepatocyte growth factor (hepapoietin A; scatter factor) |
| 614 | Mesothelioma | 0.1836578 | 0.3838438 | 0.328521 | 0.20177379 | AA036900_a t | EST: zk29e11.r1 Soares pregnant uterus NbHPU Homo sapiens cDNA clone 471980 5', mRNA sequence. (from Genbank) |
| 615 | Mesothelioma | 0.1836305 | 0.3834631 | 0.328487 | 0.20164914 | U66711_rna 1_s_at | Ly-6-related protein (9804) gene |
| 616 | Mesothelioma | 0.1835091 | 0.3829757 | 0.328288 | 0.20160782 | D42073_at | Reticulocalbin |
| 617 | Mesothelioma | 0.1829329 | 0.3828857 | 0.328148 | 0.20156088 | AA293544_a t | D component of complement (adipsin) |
| 618 | Mesothelioma | 0.1828559 | 0.3828296 | 0.328092 | 0.20144865 | M91556_s_a t-2 | Sodium channel, voltage-gated, type VI, alpha polypeptide |

FIG. 9H2

| | | | | | |
|---|---|---|---|---|---|
| 619 | Mesothelioma | 0.1828559 | 0.3828063 | 0.328067 | 0.201136723_t | M91556_s_a | SCN6A Sodium channel, voltage-gated, type VI, alpha polypeptide |
| 620 | Mesothelioma | 0.182582 | 0.3827744 | 0.32797 | 0.201129631_at | RC_AA4561 47_at | General transcription factor IIIA |
| 621 | Mesothelioma | 0.1825701 | 0.3827287 | 0.327925 | 0.201188957 7_at | RC_AA4518 | EST: zx16e06.s1 Soares total fetus Nb2HF8 9w Homo sapiens cDNA clone 786658 3', mRNA sequence. (from Genbank) |
| 622 | Mesothelioma | 0.1824623 | 0.3826162 | 0.327896 | 0.201016757 2_at | RC_AA2050 | ATPase, Ca++ transporting, plasma membrane 1 |
| 623 | Mesothelioma | 0.1820259 | 0.3826037 | 0.327689 | 0.20099492 51_f_at | RC_AA2623 | EST: zr44g03.s1 Soares NhHMPu S1 Homo sapiens cDNA clone 666292 3', mRNA sequence. (from Genbank) |
| 624 | Mesothelioma | 0.1817187 | 0.3825004 | 0.327652 | 0.200906566 1_at | RC_AA4912 | Homo sapiens clone 23923 mRNA sequence |
| 625 | Mesothelioma | 0.1812172 | 0.3824107 | 0.327616 | 0.20085259 28_at | RC_AA1509 | EST: zl47e06.s1 Soares pregnant uterus NbHPU Homo sapiens cDNA clone 505090 3', mRNA sequence. (from Genbank) |
| 626 | Mesothelioma | 0.180924 | 0.3823892 | 0.327543 | 0.200750682 02_at | RC_AA1289 | EST: zn90a05.s1 Stratagene lung carcinoma 937218 Homo sapiens cDNA clone 565424 3', mRNA sequence. (from Genbank) |
| 627 | Mesothelioma | 0.1809178 | 0.3823841 | 0.327461 | 0.200701137 t | M28213_s_a | RAB2 RAB2, member RAS oncogene family |
| 628 | Mesothelioma | 0.1805072 | 0.3822286 | 0.327332 | 0.200609998 | AA328993_s_at | EST: EST32546 Embryo, 12 week I Homo sapiens cDNA 5' end, mRNA sequence. (from Genbank) |
| 629 | Mesothelioma | 0.1803827 | 0.3821041 | 0.327331 | 0.200571366 9_f_at | RC_AA2629 | EST: zr71c02.s1 Soares NhHMPu S1 Homo sapiens cDNA clone 668834 3' similar to TR:G969170 G969170 PX19. .;. mRNA sequence. (from Genbank) |
| 630 | Mesothelioma | 0.1798011 | 0.3820793 | 0.327218 | 0.200517312 6_s_at | RC_AA4469 | UDP-Gal:betaGlcNAc beta 1,4- galactosyltransferase, polypeptide 4 |
| 631 | Mesothelioma | 0.1793241 | 0.3817459 | 0.327103 | 0.200395911 | M63896_at | Transcriptional enhancer factor (TEF1) DNA |
| 632 | Mesothelioma | 0.1793036 | 0.3815177 | 0.327043 | 0.200262563 | L34155_at-2 | Laminin, alpha 3 (nicein (150kD), kalinin (165kD), BM600 (150kD), epilegrin) |
| 633 | Mesothelioma | 0.1793036 | 0.3815156 | 0.327026 | 0.200156673 | L34155_at | Laminin-related protein (LamA3) mRNA |
| 634 | Mesothelioma | 0.1780946 | 0.3813306 | 0.327018 | 0.200118699 2_at | RC_AA1316 | EST: zl34i04.s1 Soares pregnant uterus NbHPU Homo sapiens cDNA clone 503839 3', mRNA sequence. (from Genbank) |
| 635 | Mesothelioma | 0.1780903 | 0.3812982 | 0.32691 | 0.199991031 | S77393_at | Transcript ch138 [human, RF1, RF48 stomach cancer cell lines, mRNA, 235 nt] |
| 636 | Mesothelioma | 0.1774533 | 0.3811724 | 0.326891 | 0.199918377 | U20499_at | Estrogen sulfotransferase mRNA |
| 637 | Mesothelioma | 0.1774391 | 0.3807287 | 0.326891 | 0.199830231 t | N91071_s_a | EST: za17f10.r1 Soares fetal liver spleen 1NFLS Homo sapiens cDNA clone 292843 5', mRNA sequence. (from Genbank) |

FIG. 9I2

| | | | | |
|---|---|---|---|---|
| 638 | Mesothelio ma | 0.1770483 | 0.3806177 | 0.32688 | 0.199736711 M19311_at | CALM1 Calmodulin 1 (phosphorylase kinase, delta) |
| 639 | Mesothelio ma | 0.176779 | 0.380611 | 0.326799 | 0.19965887 RC_AA6094 62_at | EST: zu72g10.s1 Soares testis NHT Homo sapiens cDNA clone 7435863' similar to SW:JANA_DROME P20348 SEX-REGULATED PROTEIN JANUS-A PRECURSOR.; mRNA sequence. (from Genbank) |
| 640 | Mesothelio ma | 0.1766856 | 0.3804237 | 0.326705 | 0.19960706 RC_AA4323 62_at | Homo sapiens mRNA for KIAA0678 protein, partial cds |
| 641 | Mesothelio ma | 0.1765347 | 0.3802867 | 0.326462 | 0.19950008 RC_AA4908 99_at | EST: aa52b01.s1 NCI_CGAP_GCB1 Homo sapiens cDNA clone IMAGE:824521 3', mRNA sequence. (from Genbank) |
| 642 | Mesothelio ma | 0.176487 | 0.3801666 | 0.326386 | 0.19944473 L35240_at-2 | Enigma (LIM domain protein) |
| 643 | Mesothelio ma | 0.176487 | 0.3801205 | 0.32615 | 0.19931161 L35240_at | Enigma gene |
| 644 | Mesothelio ma | 0.1764312 | 0.3801171 | 0.326073 | 0.19925913 RC_AA5212 90_at | EST: aa79e03.s1 NCI_CGAP_GCB1 Homo sapiens cDNA clone IMAGE:827164 3', mRNA sequence. (from Genbank) |
| 645 | Mesothelio ma | 0.1761882 | 0.3800408 | 0.326033 | 0.19916373 RC_AA1556 33_at | Insulin-like growth factor 1 receptor |
| 646 | Mesothelio ma | 0.1761463 | 0.3800141 | 0.326018 | 0.19910164 L32137_at | COMP Cartilage oligomeric matrix protein |
| 647 | Mesothelio ma | 0.1760845 | 0.3799084 | 0.325951 | 0.19899285 RC_AA4173 73_at | EST: zr21b01.s1 Stratagene NT2 neuronal precursor 937230 Homo sapiens cDNA clone 664009 3', mRNA sequence. (from Genbank) |
| 648 | Mesothelio ma | 0.1758694 | 0.3798092 | 0.325725 | 0.19897059 RC_AA2269 22_at | EST: zr21b01.s1 Stratagene NT2 neuronal precursor 937230 Homo sapiens cDNA clone 664009 3', mRNA sequence. (from Genbank) |
| 649 | Mesothelio ma | 0.1755718 | 0.3797453 | 0.325681 | 0.19882444 AA095022_a t | EST: cp2494.seq.F Fetal heart, Lambda ZAP Express Homo sapiens cDNA 5', mRNA sequence. (from Genbank) |
| 650 | Mesothelio ma | 0.1755296 | 0.3797176 | 0.32544 | 0.19874278 RC_AA4427 68_i_at | Homo sapiens inner mitochondrial membrane translocase Tim23 (TIM23) mRNA, nuclear gene encoding mitochondrial protein, complete cds |
| 651 | Mesothelio ma | 0.1753673 | 0.3796374 | 0.325407 | 0.19861484 D31762_at | KIAA0057 gene |
| 652 | Mesothelio ma | 0.1753 | 0.3795107 | 0.325312 | 0.19854918 X53331_at | MGP Matrix protein gla |
| 653 | Mesothelio ma | 0.1750296 | 0.3793477 | 0.32522 | 0.19837253 N72380_s_a t | EST: yv38f12.r1 Soares fetal liver spleen 1NFLS Homo sapiens cDNA clone 245039 5', mRNA sequence. (from Genbank) |
| 654 | Mesothelio ma | 0.1750197 | 0.3792232 | 0.325195 | 0.19834757 RC_AA4609 69_at | Transforming growth factor beta-activated kinase 1 |

FIG. 9J2

| | | | | | |
|---|---|---|---|---|---|
| Mesothelio ma | 655 | 0.174399 | 0.3791791 | 0.325056 | 0.19818458 | RC_AA2583 83_at | Ash2 (absent, small, or homeotic, Drosophila, homolog)-like |
| Mesothelio ma | 656 | 0.1743555 | 0.3790249 | 0.324918 | 0.198128131 | U95626_ma 1_at | Ccr2 gene (ccr2a) extracted from Homo sapiens ccr2b (ccr2), ccr2a (ccr2), ccr5 (ccr5) and ccr6 (ccr6) genes, and lactoferrin (lactoferrin) gene, partial cds, complete sequence |
| Mesothelio ma | 657 | 0.1734003 | 0.3789631 | 0.324858 | 0.19800977 | J00277_at | (genomic clones lambda-[SK2-T2, HS578T]; cDNA clones RS-[3,4, 6]) c-Ha-ras1 proto-oncogene, complete coding sequence |
| Mesothelio ma | 658 | 0.1730158 | 0.3787981 | 0.324854 | 0.197943661 | X01677_s_a t | Glyceraldehyde-3-phosphate dehydrogenase |
| Mesothelio ma | 659 | 0.172954 | 0.3786646 | 0.32485 | 0.19782118 | L34774_s_at | Opioid-binding protein/cell adhesion molecule-like |
| Mesothelio ma | 660 | 0.1728227 | 0.3785189 | 0.324726 | 0.19775367 | RC_AA4364 77_at | EST: zv08f05.s1 Soares NhHMPu S1 Homo sapiens cDNA clone 753057 3', mRNA sequence. (from Genbank) |
| Mesothelio ma | 661 | 0.1726466 | 0.3784561 | 0.324724 | 0.19763532 | X77744_at | F11 mRNA |
| Mesothelio ma | 662 | 0.1725055 | 0.3784482 | 0.324681 | 0.19758083 | RC_AA4109 86_at | EST: zv03a05.s1 Soares NhHMPu S1 Homo sapiens cDNA clone 752528 3' similar to TR:G642072 G642072 FIBRILLIN-1 .; mRNA sequence. (from Genbank) |
| Mesothelio ma | 663 | 0.1722005 | 0.3783309 | 0.324679 | 0.19740883 | RC_AA3982 43_at | EST: zt59f03.s1 Soares testis NHT Homo sapiens cDNA clone 726653 3', mRNA sequence. (from Genbank) |
| Mesothelio ma | 664 | 0.1721294 | 0.3781903 | 0.324465 | 0.19735311 | RC_AA0446 01_at | EST: zk55d05.s1 Soares pregnant uterus NbHPU Homo sapiens cDNA clone 486729 3', mRNA sequence. (from Genbank) |
| Mesothelio ma | 665 | 0.1719806 | 0.3781803 | 0.324394 | 0.19732334 | RC_AA0858 51_at | Homo sapiens clone 24658 mRNA sequence |
| Mesothelio ma | 666 | 0.1719037 | 0.3779434 | 0.324271 | 0.19729023 | X00949_at | Prepro-relaxin H1 |
| Mesothelio ma | 667 | 0.171875 | 0.3779163 | 0.324155 | 0.19712195 | RC_AA3938 25_at | Homo sapiens mRNA for leptin receptor gene-related protein |
| Mesothelio ma | 668 | 0.1717139 | 0.3779119 | 0.324137 | 0.19704229 | L07515_at-2 | Human heterochromatin protein homologue (HP1) mRNA, complete cds. (from Genbank) |
| Mesothelio ma | 669 | 0.1717139 | 0.3777939 | 0.324052 | 0.19698034 | L07515_at | HETEROCHROMATIN PROTEIN 1 HOMOLOG |
| Mesothelio ma | 670 | 0.1714479 | 0.3776662 | 0.323953 | 0.196867961 | AA402538_a t | Homo sapiens chromosome 19, cosmid R26445 |
| Mesothelio ma | 671 | 0.1713939 | 0.377657 | 0.323953 | 0.19671832 | X01630_at | ASS Argininosuccinate synthetase |
| Mesothelio ma | 672 | 0.1713457 | 0.3775536 | 0.323945 | 0.19668762 | RC_AA4211 39_at | EST: zf79c09.s1 Soares testis NHT Homo sapiens cDNA clone 728560 3', mRNA sequence. (from Genbank) |
| Mesothelio ma | 673 | 0.1710866 | 0.3773328 | 0.323858 | 0.19651799 | RC_AA4299 98_at | EST: zw65e01.s1 Soares testis NHT Homo sapiens cDNA clone 781080 3', mRNA sequence. (from Genbank) |

FIG. 9K2

| | | | | | |
|---|---|---|---|---|---|
| 674 | Mesothelioma | 0.1710471 | 0.3772689 | 0.323795 | 0.19646917 | M11749_at | THY-1 MEMBRANE GLYCOPROTEIN PRECURSOR |
| 675 | Mesothelioma | 0.1701795 | 0.3772266 | 0.323793 | 0.1963923 | AB002337_a_t | KIAA0339 gene product |
| 676 | Mesothelioma | 0.1700468 | 0.3771604 | 0.323609 | 0.19624177 | RC_AA4765 82_at | EST: zx03b04.s1 Soares total fetus Nb2HF8 9w Homo sapiens cDNA clone 785359 3', mRNA sequence. (from Genbank) |
| 677 | Mesothelioma | 0.169847 | 0.3770596 | 0.323553 | 0.19616893 | R69417_at | EST: yj83f12.r1 Homo sapiens cDNA clone 155375 5'. (from Genbank) |
| 678 | Mesothelioma | 0.169529 | 0.3769505 | 0.323353 | 0.19607806 | RC_AA4821 27_at | Homo sapiens mRNA for PAK4 protein |
| 679 | Mesothelioma | 0.1690904 | 0.3768851 | 0.323512 | 0.19595851 | RC_AA2922 28_at | STAT induced STAT inhibitor 3 |
| 680 | Mesothelioma | 0.1690471 | 0.3768125 | 0.323385 | 0.19589542 | RC_AA1303 49_at | EST: zo19g09.s1 Stratagene colon (#937204) Homo sapiens cDNA clone 587392 3', mRNA sequence. (from Genbank) |
| 681 | Mesothelioma | 0.1688984 | 0.3767556 | 0.323307 | 0.19584116 | AA242923_a_t | EST: zr64g07.r1 Soares NhHMPu S1 Homo sapiens cDNA clone 668220 5', mRNA sequence. (from Genbank) |
| 682 | Mesothelioma | 0.1688756 | 0.3767038 | 0.323221 | 0.19575141 | T68246_at | EST: yc40f01.r1 Homo sapiens cDNA clone 83161 5' similar to contains PTR5 repetitive element.; (from Genbank) |
| 683 | Mesothelioma | 0.1687327 | 0.3764948 | 0.323149 | 0.19559388 | RC_AA4914 65_at | EST: ab04a05.s1 Stratagene fetal retina 937202 Homo sapiens cDNA clone 839792 3', mRNA sequence. (from Genbank) |
| 684 | Mesothelioma | 0.1688777 | 0.3764604 | 0.323131 | 0.19551757 | RC_AA2923 28_at | EST: zt51f09.s1 Soares ovary tumor NbHOT Homo sapiens cDNA clone 725897 3' similar to SW:ATF4_MOUSE Q06507 CYCLIC-AMP-DEPENDENT TRANSCRIPTION FACTOR ATF-4 ;contains Alu repetitive element;contains element MER22 repetitive element ;, mRNA sequence. (from Genbank) |
| 685 | Mesothelioma | 0.1684962 | 0.3763945 | 0.323126 | 0.19535476 | RC_AA4767 20_at | EST: zw92g06.s1 Soares total fetus Nb2HF8 9w Homo sapiens cDNA clone 784474 3', mRNA sequence. (from Genbank) |
| 686 | Mesothelioma | 0.1683016 | 0.3763241 | 0.323097 | 0.19520125 | Z18951_at | CAV Caveolin, caveolae protein, 22kD |
| 687 | Mesothelioma | 0.1676102 | 0.3761976 | 0.323042 | 0.19514242 | D28124_at | Unknown product |
| 688 | Mesothelioma | 0.1675837 | 0.3760434 | 0.32303 | 0.19506693 | AA443230_a_t | Casein kinase 2, alpha 1 polypeptide |
| 689 | Mesothelioma | 0.1674299 | 0.3757714 | 0.322895 | 0.19493578 | RC_AA4339 30_at | EST: zw52e11.s1 Soares total fetus Nb2HF8 9w Homo sapiens cDNA clone 773708 3' similar to contains Alu repetitive element;, mRNA sequence. (from Genbank) |
| 690 | Mesothelioma | 0.1670877 | 0.3756686 | 0.32279 | 0.19483002 | AB002301_a_t | Human mRNA for KIAA0303 gene, partial cds |
| 691 | Mesothelioma | 0.1663516 | 0.375599 | 0.322638 | 0.19477801 | AA482319_f_at | EST: ab15c03.r1 Stratagene lung (#937210) Homo sapiens cDNA clone 840868 5', mRNA sequence. (from Genbank) |

FIG. 9L2

| | | | | | | |
|---|---|---|---|---|---|---|
| Mesothelio ma | 692 | 0.1662612 | 0.3755322 | 0.322569 | 0.19466743 | U83411_at | Carboxypeptidase Z precursor, mRNA |
| Mesothelio ma | 693 | 0.1659816 | 0.3754666 | 0.322499 | 0.19462407 | RC_AA2345 61_at | EST: zr66c06.s1 Soares NhHMPu S1 Homo sapiens cDNA clone 668362 3', mRNA sequence. (from Genbank) |
| Mesothelio ma | 694 | 0.1657323 | 0.3753299 | 0.322489 | 0.19457056 | C02099_s_a t | EST: HUMGS0006419, Human Gene Signature, 3'-directed cDNA sequence, mRNA sequence. (from Genbank) |
| Mesothelio ma | 695 | 0.1655708 | 0.3752501 | 0.322383 | 0.19453711 | RC_AA1355 39_at | EST: zl09h04.s1 Soares pregnant uterus NbHPU Homo sapiens cDNA clone 501463 3', mRNA sequence. (from Genbank) |
| Mesothelio ma | 696 | 0.1653273 | 0.3751435 | 0.322347 | 0.19444753 | RC_AA2927 17_at | EST: zs59e08.s1 NCI_CGAP_GCB1 Homo sapiens cDNA clone IMAGE:701798 3', mRNA sequence. (from Genbank) |
| Mesothelio ma | 697 | 0.1652006 | 0.37509570 | 0.322295 | 0.19431947 | X67698_at | Tissue specific mRNA |
| Mesothelio ma | 698 | 0.1647305 | 0.3750265 | 0.322185 | 0.19426782 | U20758_rna 1_at | Osteopontin gene |
| Mesothelio ma | 699 | 0.1646477 | 0.37501380 | 0.322051 | 0.19418511 | RC_AA5996 79_s_at | Homo sapiens clone 23584 mRNA sequence |
| Mesothelio ma | 700 | 0.1643827 | 0.3749325 | 0.321858 | 0.19408143 | RC_AA5996 53_s_at | Homo sapiens TCFL5 mRNA for transcription factor-like 5, complete cds |
| Mesothelio ma | 701 | 0.1642591 | 0.37488670 | 0.321831 | 0.19395018 | RC_AA4116 21_at | EST: zv23i05.s1 Soares NhHMPu S1 Homo sapiens cDNA clone 754497 3', mRNA sequence. (from Genbank) |
| Mesothelio ma | 702 | 0.1632671 | 0.3748223 | 0.321809 | 0.19389415 | L09260_at | (chromosome 3p25) membrane protein mRNA |
| Mesothelio ma | 703 | 0.1631031 | 0.37471990 | 0.321784 | | RC_AA1341 38_at | EST: zl29g04.s1 Soares pregnant uterus NbHPU Homo sapiens cDNA clone 503382 3' similar to TR:G971709 G971709 LEUCINE AMINOPEPTIDASE ;, mRNA sequence. (from Genbank) |
| Mesothelio ma | 704 | 0.1627993 | 0.3747064 | 0.321751 | 0.19370669 | U07919_at | ALDH6 Aldehyde dehydrogenase 6 |
| Mesothelio ma | 705 | 0.1627977 | 0.37470110 | 0.321657 | | AA427379_a t | EST: zw52h08.r1 Soares total fetus Nb2HF8 9w Homo sapiens cDNA clone 773727 5', mRNA sequence. (from Genbank) |
| Mesothelio ma | 706 | 0.1627709 | 0.37436430 | 0.321369 | 0.19344762 | RC_AA0253 51_at | EST: ze74h03.s1 Soares fetal heart NbHH19W Homo sapiens cDNA clone 364757 3' similar to contains OFR.t1 OFR repetitive element ;, mRNA sequence. (from Genbank) |
| Mesothelio ma | 707 | 0.1617806 | 0.3738854 | 0.321329 | 0.19334777 | RC_AA4127 22_s_at | Homo sapiens putative cyclin G1 interacting protein mRNA, complete cds |
| Mesothelio ma | 708 | 0.1616822 | 0.37388230 | 0.321326 | 0.19333446 | RC_AA4826 13_at | EST: zl34e11.s1 Soares ovary tumor NbHOT Homo sapiens cDNA clone 724268 3', mRNA sequence. (from Genbank) |
| Mesothelio ma | 709 | 0.1615035 | 0.3738562 | 0.321175 | 0.19330108 | AA405288_a t | EST: zt37f09.r1 Soares ovary tumor NbHOT Homo sapiens cDNA clone 724553 5' similar to contains Alu rupetitive element;contains element LTR5 repetitive element ;, mRNA sequence. (from Genbank) |

FIG. 9M2

| | | | | | |
|---|---|---|---|---|---|
| 710 | Mesothelioma | 0.160909 | 0.3738555 | 0.321168 | 0.19323151 | RC_AA4013 45_s_at | EST: zu62d03.s1 Soares testis NHT Homo sapiens cDNA clone 742565 3' similar to SW:YEY6_YEAST P40093 HYPOTHETICAL 38.2 KD PROTEIN IN BEM2-SPT2 INTERGENIC REGION. ;, mRNA sequence. (from Genbank) |
| 711 | Mesothelioma | 0.1608695 | 0.3738073 | 0.321153 | 0.19314803 | RC_C20974_at | Vanin 1 |
| 712 | Mesothelioma | 0.1608506 | 0.3736539 | 0.321123 | 0.19307591 | RC_AA4432 12_at | EST: aa14d01.s1 Soares NhHMPu S1 Homo sapiens cDNA clone 813217 3', mRNA sequence. (from Genbank) |
| 713 | Mesothelioma | 0.1607781 | 0.3735802 | 0.321092 | 0.19305487 | AA252929_a_t | H2A histone family, member X |
| 714 | Mesothelioma | 0.1607056 | 0.3735255 | 0.32105 | 0.19291717 | C01877_at | EST: HUMGS0003856, Human Gene Signature, 3'-directed cDNA sequence, mRNA sequence. (from Genbank) |
| 715 | Mesothelioma | 0.1606276 | 0.373473 | 0.321047 | 0.19289306 | RC_AA4864 18_at | EST: ab36c09.s1 Stratagene HeLa cell s3 937216 Homo sapiens cDNA clone 842896 3' similar to SW:DYHC_ANTCR P39057 DYNEIN BETA CHAIN, CILIARY. ;, mRNA sequence. (from Genbank) |
| 716 | Mesothelioma | 0.1605957 | 0.3734498 | 0.321008 | 0.19283643 | AA059213_a_t | EST: zf64g11.r1 Soares retina N2b4HR Homo sapiens cDNA clone 381764 5', mRNA sequence. (from Genbank) |
| 717 | Mesothelioma | 0.1603726 | 0.3734496 | 0.320939 | 0.19267048 | RC_AA6088 50_at | EIF4E-like cap-binding protein |
| 718 | Mesothelioma | 0.1600236 | 0.3732539 | 0.320913 | 0.19252278 | AA328684_a_t | EST: EST32211 Embryo, 12 week I Homo sapiens cDNA 5' end, mRNA sequence. (from Genbank) |
| 719 | Mesothelioma | 0.1599198 | 0.3732411 | 0.320662 | 0.19247916 | M13452_s_a_t | LMNA Lamin A |
| 720 | Mesothelioma | 0.1596973 | 0.3731312 | 0.320526 | 0.19243203 | H89551_s_a_t | EST: yw28e07.r1 Homo sapiens cDNA clone 253572 5'. (from Genbank) |
| 721 | Mesothelioma | 0.1593922 | 0.3730203 | 0.320457 | 0.19233853 | RC_D20297_at | EST: Human HL60 3'directed MboI cDNA, HUMGS01271, clone pm2o24, mRNA sequence. (from Genbank) |
| 722 | Mesothelioma | 0.1591617 | 0.37299 | 0.320448 | 0.19226988 | RC_AA6001 40_at | Deleted in oral cancer-1 |
| 723 | Mesothelioma | 0.1589988 | 0.372941 | 0.320427 | 0.19216892 | RC_AA4606 59_at | EST: zx64b12.s1 Soares total fetus Nb2HF8 9w Homo sapiens cDNA clone 796223 3', mRNA sequence. (from Genbank) |
| 724 | Mesothelioma | 0.1587076 | 0.3728561 | 0.320349 | 0.1921416 | AA482319_i_at | EST: ab15c03.r1 Stratagene lung (#937210) Homo sapiens cDNA clone 840868 5', mRNA sequence. (from Genbank) |
| 725 | Mesothelioma | 0.1583093 | 0.3728167 | 0.320073 | 0.19204576 | L08096_s_at | CD70 CD70 antigen (CD27 ligand) |
| 726 | Mesothelioma | 0.1583093 | 0.3727327 | 0.320006 | 0.19198087 | L08096_s_at | Tumor necrosis factor (ligand) superfamily, member 7 |

FIG. 9N2

| | | | | | |
|---|---|---|---|---|---|
| 727 | Mesothelioma | 0.1583065 | 0.3726967 | 0.320006 | 0.1917944430_at RC_AA4528 | EST: zx36d04.s1 Soares total fetus Nb2HF8 9w Homo sapiens cDNA clone 788551 3' similar to TR:G595950 G595950 PROTEIN N-TERMINAL ASPARAGINE AMIDOHYDROLASE.; mRNA sequence. (from Genbank) |
| 728 | Mesothelioma | 0.1576646 | 0.3722281 | 0.319961 | 0.1917312166_at RC_AA4466 | EST: zw89h10.s1 Soares total fetus Nb2HF8 9w Homo sapiens cDNA clone 784195 3'; mRNA sequence. (from Genbank) |
| 729 | Mesothelioma | 0.1576219 | 0.3722671 | 0.319946 | 0.191634631_s_at U22970_rna | 6-16 gene (interferon-inducible peptide precursor) extracted from Human interferon-inducible peptide (6-16) gene |
| 730 | Mesothelioma | 0.1575477 | 0.3722461 | 0.319918 | 0.19150676 U61262_at | NEO1 Neogenin (chicken) homolog 1 |
| 731 | Mesothelioma | 0.1573079 | 0.3721707 | 0.319754 | 0.19142288 Z21081_at | EST: H. sapiens putatively transcribed partial sequence; UK-HGMP sequence ID AAADMBX; single read, mRNA sequence. (from Genbank) |
| 732 | Mesothelioma | 0.1571627 | 0.3721646 | 0.319649 | 0.19136856 L10844_at | CDC42 Cell division cycle 42 (GTP-binding protein, 25kD) |
| 733 | Mesothelioma | 0.156899 | 0.3720034 | 0.319635 | 0.1912990417_at RC_AA4780 | Homo sapiens alpha 1,2-mannosidase IB mRNA, complete cds |
| 734 | Mesothelioma | 0.1565195 | 0.3718828 | 0.319561 | 0.1911915293_at RC_AA3402 | EST: EST45737 Fetal kidney III Homo sapiens cDNA 3' end, mRNA sequence. (from Genbank) |
| 735 | Mesothelioma | 0.1561409 | 0.3717813 | 0.319359 | 0.1911037698_at RC_AA1020 | EST: zi79f12.s1 Stratagene colon (#937204) Homo sapiens cDNA clone 510863 3'; mRNA sequence. (from Genbank) |
| 736 | Mesothelioma | 0.1560452 | 0.3716324 | 0.319217 | 0.19106494 AA477031_a_t | EST: zu38c01.r1 Soares ovary tumor NbHOT Homo sapiens cDNA clone 740256 5'; mRNA sequence. (from Genbank) |
| 737 | Mesothelioma | 0.1553954 | 0.371482 | 0.319086 | 0.19095929 X06614_at | Receptor of retinoic acid |
| 738 | Mesothelioma | 0.1551423 | 0.3714087 | 0.318994 | 0.1908723418_at RC_AA3983 | KIAA0331 gene product |
| 739 | Mesothelioma | 0.155034 | 0.37128795 | 0.318924 | 0.19075368 AFFX-HSAC07/X00351_M_st | AFFX-HSAC07/X00351_M_st (endogenous control) |
| 740 | Mesothelioma | 0.155034 | 0.3712511 | 0.318891 | 0.19072299 AFFX-HSAC07/X00351_M_st-2 | No info for gene |
| 741 | Mesothelioma | 0.1546977 | 0.3710883 | 0.31884 | 0.19063099 T50576_at | EST: yb76c11.r1 Homo sapiens cDNA clone 77108 5' similar to SP:VE85_LAMBD P03755 EA8.5 GENE. (from Genbank) |
| 742 | Mesothelioma | 0.1546808 | 0.370976 | 0.318681 | 0.19056338 RC_AA4516 76_at | EST: zx44b03.s1 Soares total fetus Nb2HF8 9w Homo sapiens cDNA clone 789293 3'; mRNA sequence. (from Genbank) |
| 743 | Mesothelioma | 0.1546719 | 0.3709493 | 0.318648 | 0.1905262362_at RC_AA6217 | EST: af06d05.s1 Soares testis NHT Homo sapiens cDNA clone 1030857 3'; mRNA sequence. (from Genbank) |

FIG. 9O2

| | | | | | |
|---|---|---|---|---|---|
| 744 | Mesothelioma | 0.1545339 | 0.3708064 | 0.318621 | 0.19048376 | M12125_at | Skeletal beta-tropomyosin |
| 745 | Mesothelioma | 0.1541821 | 0.370778 | 0.318591 | 0.19046527 | L22548_at | COL18A1 Collagen, type XVIII, alpha 1 |
| 746 | Mesothelioma | 0.1539157 | 0.3706593 | 0.318505 | 0.19025284 | M27492_at | INTERLEUKIN-1 RECEPTOR, TYPE I PRECURSOR |
| 747 | Mesothelioma | 0.1538554 | 0.3706252 | 0.3184 | 0.19022676 | D88153_at | Homo sapiens mRNA for HYA22, complete cds |
| 748 | Mesothelioma | 0.1534408 | 0.3705863 | 0.318399 | 0.19016187 | X07979_at | ITGB1 Integrin, beta 1 (fibronectin receptor, beta polypeptide, antigen CD29 includes MDF2, MSK12) |
| 749 | Mesothelioma | 0.1533933 | 0.3705222 | 0.318289 | 0.19005607 | RC_AA456588_at | Homo sapiens BC-2 protein mRNA, complete cds |
| 750 | Mesothelioma | 0.1532873 | 0.3704566 | 0.318209 | 0.19001427 | D84239_at | IgG Fc binding protein |
| 751 | Mesothelioma | 0.1532873 | 0.3704194 | 0.318161 | 0.18984726 | D84239_at-2 | IgG Fc binding protein |
| 752 | Mesothelioma | 0.1531884 | 0.3703296 | 0.318111 | 0.18982284 | D31286_at | Homo sapiens mRNA for smallest subunit of ubiquinol-cytochrome c reductase, complete cds |
| 753 | Mesothelioma | 0.1531226 | 0.3702906 | 0.318039 | 0.18976784 | Z37976_at | LTBP2 Latent transforming growth factor beta binding protein 2 |
| 754 | Mesothelioma | 0.1528485 | 0.3702906 | 0.317893 | 0.18972875 | RC_AA100026_at | EST: zi79c09.s1 Stratagene colon (#937204) Homo sapiens cDNA clone 510832 3', mRNA sequence. (from Genbank) |
| 755 | Mesothelioma | 0.1528481 | 0.3702314 | 0.317798 | 0.18969578 | X73478_at | HPTPA mRNA |
| 756 | Mesothelioma | 0.1520649 | 0.3700841 | 0.317688 | 0.18966319 | RC_AA034925_at | EST: zk25e01.s1 Soares pregnant uterus NbHPU Homo sapiens cDNA clone 471576 3', mRNA sequence. (from Genbank) |
| 757 | Mesothelioma | 0.1518661 | 0.3700409 | 0.317639 | 0.18951707 | U77845_at-2 | Human hTRIP (hTRIP) mRNA, complete cds |
| 758 | Mesothelioma | 0.1518661 | 0.3700409 | 0.317511 | 0.18939087 | U77845_at | HTRIP (hTRIP) mRNA |
| 759 | Mesothelioma | 0.1517683 | 0.3700068 | 0.317475 | 0.18935347 | U92074_at | RAD51 (S. cerevisiae)-like 1 |
| 760 | Mesothelioma | 0.1509183 | 0.3699558 | 0.317415 | 0.18926412 | RC_AA113387_at | EST: zn70g06.s1 Stratagene HeLa cell s3 937216 Homo sapiens cDNA clone 563578 3', mRNA sequence. (from Genbank) |
| 761 | Mesothelioma | 0.1507523 | 0.3697926 | 0.317383 | 0.18918574 | M11717_rna1_at | Heat shock protein (hsp 70) gene |
| 762 | Mesothelioma | 0.1503657 | 0.3696068 | 0.317227 | 0.1891194 | AA043160_at | EST: zk48g01.r1 Soares pregnant uterus NbHPU Homo sapiens cDNA clone 486096 5', mRNA sequence. (from Genbank) |

FIG. 9P2

| # | Type | | | | Description |
|---|---|---|---|---|---|
| 763 | Mesothelioma | 0.1502544 | 0.3696044 | 0.317218 | RC_AA4872 97_at | EST: aa94h04.s1 Stratagene fetal retina 937202 Homo sapiens cDNA clone 838999 3' similar to contains Alu repetitive element;contains element L1 L1 repetitive element .;, mRNA sequence. (from Genbank) |
| 764 | Mesothelioma | 0.1498383 | 0.3695536 | 0.317179 | 0.18891975 U69114_at | EST: Human Down syndrome region, YAC 152F7, mRNA sequence. (from Genbank) |
| 765 | Mesothelioma | 0.1497865 | 0.3693851 | 0.317112 | RC_AA5994 34_at | EST: ag23d09.s1 Jia bone marrow stroma Homo sapiens cDNA clone 1071185 3', mRNA sequence. (from Genbank) |
| 766 | Mesothelioma | 0.1497794 | 0.3693826 | 0.317056 | AA386297_a t | EST: EST185039 Brain IV Homo sapiens cDNA, mRNA sequence. (from Genbank) |
| 767 | Mesothelioma | 0.1497228 | 0.3693816 | 0.317004 | AA285290_a t | Pinin, desmosome associated protein |
| 768 | Mesothelioma | 0.1484581 | 0.3693137 | 0.316981 | 0.18854679 L05188_f_at | Small proline-rich protein 2 (SPRR2B) gene |
| 769 | Mesothelioma | 0.1484308 | 0.3690531 | 0.316793 | 0.18842697 M19154_at | Transforming growth factor-beta-2 mRNA |
| 770 | Mesothelioma | 0.1482684 | 0.3689131 | 0.316694 | RC_AA4814 14_at | Golgi SNAP receptor complex member 1 |
| 771 | Mesothelioma | 0.1481842 | 0.368808 | 0.316631 | AA011479_a 0.18834558 t | EST: zi01b10.r1 Soares fetal liver spleen 1NFLS S1 Homo sapiens cDNA clone 429499 5', mRNA sequence. (from Genbank) |
| 772 | Mesothelioma | 0.1481102 | 0.3684657 | 0.316577 | 0.1883156 D45333_at | Prefoldin 1 |
| 773 | Mesothelioma | 0.1480379 | 0.3684416 | 0.316437 | AA400333_a 0.18824713 t | Homo sapiens clone 24619 mRNA sequence |
| 774 | Mesothelioma | 0.1479324 | 0.3683705 | 0.316411 | AF009674_a 0.18810296 t | Axin (AXIN) mRNA, partial cds |
| 775 | Mesothelioma | 0.1479324 | 0.3683169 | 0.316404 | AF009674_a 0.18808661 t-2 | Axin |
| 776 | Mesothelioma | 0.1477969 | 0.3682683 | 0.31637 | RC_AA6100 52_at | EST: af18h05.s1 Soares testis NHT Homo sapiens cDNA clone 1032057 3' similar to TR:G168081 G168081 UNIDENTIFIED GENE .;; mRNA sequence. (from Genbank) |
| 777 | Mesothelioma | 0.1477346 | 0.3681783 | 0.31637 | RC_AA4010 0.18781441 98_f_at | EST: zu50g01.s1 Soares ovary tumor NbHOT Homo sapiens cDNA clone 741456 3' similar to contains Alu repetitive element;contains element THR repetitive element .;, mRNA sequence. (from Genbank) |
| 778 | Mesothelioma | 0.1476634 | 0.3681735 | 0.316299 | AFFX-HUMGAPDH /M33197_M_ 0.18769458 st-2 | Glyceraldehyde-3-phosphate dehydrogenase |

FIG. 9Q2

| | | | | AFFX-HUMGAPDH/M33197_M_st | |
|---|---|---|---|---|---|
| 779 | Mesothelioma | 0.1476634 | 0.3880417 | 0.316258 | 0.18759729 | AFFX-HUMGAPDH/M33197_M_st (endogenous control) |
| 780 | Mesothelioma | 0.1473678 | 0.3679475 | 0.316246 | 0.18752535 | RC_AA0194 98_at | EST: ze58g01.s1 Soares retina N2b4HR Homo sapiens cDNA clone 363216 3', mRNA sequence. (from Genbank) |
| 781 | Mesothelioma | 0.1472232 | 0.3679125 | 0.316225 | 0.18750322 | Y00281_at | RPN1 Ribophorin I |
| 782 | Mesothelioma | 0.1471884 | 0.3678747 | 0.315958 | 0.18736114 | RC_AA4360 05_at | EST: zu03c01.s1 Soares testis NHT Homo sapiens cDNA clone 730752 3', mRNA sequence. (from Genbank) |
| 783 | Mesothelioma | 0.1469105 | 0.3678747 | 0.315917 | 0.18729561 | RC_AA4969 61_at | EST: aa42f08.s1 Soares NhHMPu S1 Homo sapiens cDNA clone 823623 3', mRNA sequence. (from Genbank) |
| 784 | Mesothelioma | 0.1468581 | 0.3678202 | 0.3159 | 0.18722205 | RC_AA4438 28_at | EST: zw88e11.s1 Soares total fetus Nb2HF8 9w Homo sapiens cDNA clone 784076 3', mRNA sequence. (from Genbank) |
| 785 | Mesothelioma | 0.1466967 | 0.3677664 | 0.315844 | 0.18717499 | RC_AA4960 30_s_at | EST: zv72c09.s1 Soares total fetus Nb2HF8 9w Homo sapiens cDNA clone 759184 3', mRNA sequence. (from Genbank) |
| 786 | Mesothelioma | 0.1464503 | 0.3677286 | 0.315727 | 0.1870555 | AA485585_a_t | EST: zx90e01.r1 Soares ovary tumor NbHOT Homo sapiens cDNA clone 811032 5', mRNA sequence. (from Genbank) |
| 787 | Mesothelioma | 0.1464263 | 0.3677156 | 0.315715 | 0.18704283 | RC_AA0554 75_at | EST: zf21b01.s1 Soares fetal heart NbHH19W Homo sapiens cDNA clone 377545 3' similar to SW:V1P_RAT P80144 MYOTROPHIN.; mRNA sequence. (from Genbank) |
| 788 | Mesothelioma | 0.1464106 | 0.367512 | 0.31569 | 0.18698433 | RC_AA1025 81_at | EST: zn42d02.s1 Stratagene endothelial cell 937223 Homo sapiens cDNA clone 550083 3', mRNA sequence. (from Genbank) |
| 789 | Mesothelioma | 0.1462587 | 0.3674645 | 0.315682 | 0.18683857 | RC_AA2912 69_at | Homo sapiens mRNA for KIAA0776 protein, partial cds |
| 790 | Mesothelioma | 0.1459198 | 0.3674036 | 0.315666 | 0.18679723 | AA451640_a_t | EST: zx43d06.r1 Soares total fetus Nb2HF8 9w Homo sapiens cDNA clone 789227 5', mRNA sequence. (from Genbank) |
| 791 | Mesothelioma | 0.1455774 | 0.3673827 | 0.315628 | 0.18678425 | N71232_at | EST: yw36g09.r1 Homo sapiens cDNA clone 254368 5'. (from Genbank) |
| 792 | Mesothelioma | 0.1455075 | 0.3673371 | 0.315513 | 0.18671526 | RC_AA2331 70_at | Interleukin 13 receptor, alpha 1 |
| 793 | Mesothelioma | 0.1454725 | 0.3672379 | 0.31546 | 0.18654309 | J04162_at | FCGR3 Fc fragment of IgG, low affinity IIIa, receptor for (CD16) |
| 794 | Mesothelioma | 0.1454179 | 0.3672225 | 0.315427 | 0.18653782 | IL10_at | No info for gene |
| 795 | Mesothelioma | 0.1453689 | 0.3670139 | 0.315347 | 0.18641892 | AA148581_a_t | Human mariner-like element-containing mRNA, clone pcHMT1 |
| 796 | Mesothelioma | 0.1453478 | 0.3669868 | 0.315273 | 0.18631609 | RC_AA2629 17_at | EST: zs26e11.s1 NCI_CGAP_GCB1 Homo sapiens cDNA clone IMAGE:686348 3', mRNA sequence. (from Genbank) |

FIG. 9R2

| | | | | | |
|---|---|---|---|---|---|
| 797 | Mesothelioma | 0.1451573 | 0.3669825 | 0.315266 | 0.18629725 | U90546_at-2 | Human butyrophilin (BTF4) mRNA, complete cds |
| 798 | Mesothelioma | 0.1451573 | 0.3668467 | 0.315224 | 0.18623957 | U90546_at | Butyrophilin (BTF4) mRNA |
| 799 | Mesothelioma | 0.1445275 | 0.3668164 | 0.315051 | 0.18619058 | Z26317_at | DSG2 Desmoglein 2 |
| 800 | Mesothelioma | 0.1444851 | 0.366618 | 0.314938 | 0.18611446_at | AA296994_s_at | Homo sapiens mRNA for putative seven transmembrane domain protein |
| 801 | Mesothelioma | 0.1438183 | 0.3665991 | 0.314911 | 0.18603478 | RC_AA4875 58_at | EST: ab23e01.s1 Stratagene lung (#937210) Homo sapiens cDNA clone 841656 3', mRNA sequence. (from Genbank) |
| 802 | Mesothelioma | 0.1434477 | 0.366464 | 0.314905 | 0.18598638 | RC_AA6091 95_at | EST: af12d09.s1 Soares testis NHT Homo sapiens cDNA clone 1031441 3' similar to TR:G988221 G988221 TBC1.; mRNA sequence. (from Genbank) |
| 803 | Mesothelioma | 0.1430161 | 0.366379 | 0.314704 | 0.18590131 | AA053853_a t | EST: zf52d01.r1 Soares retina N2b4HR Homo sapiens cDNA clone 380545 5', mRNA sequence. (from Genbank) |
| 804 | Mesothelioma | 0.1429838 | 0.3663466 | 0.314658 | 0.18586475 | RC_AA2916 29_at | EST: zt45f05.s1 Soares ovary tumor NbHOT Homo sapiens cDNA clone 725313 3', mRNA sequence. (from Genbank) |
| 805 | Mesothelioma | 0.1426572 | 0.366249 | 0.314334 | 0.18575393 | RC_AA5987 25_at | Endothelial differentiation-related factor 1 |
| 806 | Mesothelioma | 0.1422785 | 0.3661376 | 0.31431 | 0.18571821 | W49745_at | Homo sapiens FK506-binding protein (FKBP63) mRNA, partial cds |
| 807 | Mesothelioma | 0.1420904 | 0.3658996 | 0.31426 | 0.18568048 | RC_AA4777 29_at | EST: zu44g09.s1 Soares ovary tumor NbHOT Homo sapiens cDNA clone 740896 3', mRNA sequence. (from Genbank) |
| 808 | Mesothelioma | 0.1420582 | 0.3658615 | 0.31426 | 0.18556799 | T30851_s_at | Homo sapiens clone 24775 mRNA sequence |
| 809 | Mesothelioma | 0.1420529 | 0.3658107 | 0.314221 | 0.18545656 | R74226_at | Homo sapiens mRNA for ATP synthase subunit e, complete cds |
| 810 | Mesothelioma | 0.1418984 | 0.3657485 | 0.314168 | 0.18536109 | U94353_at | Radical fringe (Drosophila) homolog |
| 811 | Mesothelioma | 0.1416609 | 0.3656623 | 0.314074 | 0.18534394 | RC_D51235 f_at | Tumor rejection antigen (gp96) 1 |
| 812 | Mesothelioma | 0.1413069 | 0.3655205 | 0.314035 | 0.18529645 | M59911_at | ITGA3 Integrin alpha-3 subunit |
| 813 | Mesothelioma | 0.1412658 | 0.3654581 | 0.313913 | 0.18517862 | RC_AA0652 17_at | EST: zm51f01.s1 Stratagene fibroblast (#937212) Homo sapiens cDNA clone 529177 3', mRNA sequence. (from Genbank) |
| 814 | Mesothelioma | 0.1411568 | 0.3654521 | 0.313885 | 0.1850962 | U19495_s_a t | Intercrine-alpha (hIRH) mRNA |
| 815 | Mesothelioma | 0.1410309 | 0.365438 | 0.313669 | 0.18497877 | RC_AA4647 22_s_at | EST: zx82d05.s1 Soares ovary tumor NbHOT Homo sapiens cDNA clone 810249 3', mRNA sequence. (from Genbank) |

FIG. 9S2

| | | | | | |
|---|---|---|---|---|---|
| 816 | Mesothelioma | 0.14099987 | 0.3654273 | 0.313565 | 0.18486263 | RC_AA3991 64_at | EST: zl57a02.s1 Soares testis NHT Homo sapiens cDNA clone 726410 3', mRNA sequence. (from Genbank) |
| 817 | Mesothelioma | 0.14097840 | 0.3652456 | 0.313491 | 0.18484572 | U57847_s_a t | Ribosomal protein S27 (metallopanstimulin 1) |
| 818 | Mesothelioma | 0.14095450 | 0.3649857 | 0.313453 | 0.18482298 | AA313977_s_at | Homo sapiens RNA polymerase II transcription factor SIII p18 subunit mRNA, complete cds |
| 819 | Mesothelioma | 0.14060660 | 0.3649317 | 0.313408 | 0.18473002 | W26054_at | EST: 18d8 Human retina cDNA randomly primed sublibrary Homo sapiens cDNA, mRNA sequence. (from Genbank) |
| 820 | Mesothelioma | 0.14060140 | 0.3648743 | 0.313358 | 0.18472590 | W73751_at | EST: zd52c12.r1 Soares fetal heart NbHH19W Homo sapiens cDNA clone 344278 5', mRNA sequence. (from Genbank) |
| 821 | Mesothelioma | 0.14042190 | 0.3647515 | 0.313243 | 0.18466003 | X66785_f_at | Dihydrolipoamide branched chain transacylase (E2 component of branched chain keto acid dehydrogenase complex; maple syrup urine disease) |
| 822 | Mesothelioma | 0.14019710 | 0.3647273 | 0.313196 | 0.18464224 | D64109_at | Tob family |
| 823 | Mesothelioma | 0.14002130 | 0.3646845 | 0.313031 | 0.18451874 | AA480073_a t | EST: zv42a08.r1 Soares ovary tumor NbHOT Homo sapiens cDNA clone 756278 5', mRNA sequence. (from Genbank) |
| 824 | Mesothelioma | 0.14001930 | 0.3646337 | 0.312817 | 0.18447679 6_at | RC_AA4477 | EST: aa20g11.s1 Soares NhHMPu S1 Homo sapiens cDNA clone 813860 3', mRNA sequence. (from Genbank) |
| 825 | Mesothelioma | 0.13978430 | 0.3645709 | 0.312782 | 0.18446559 62_at | RC_AA2590 | EST: zs30h07.s1 NCI_CGAP_GCB1 Homo sapiens cDNA clone IMAGE:6886749 3', mRNA sequence. (from Genbank) |
| 826 | Mesothelioma | 0.13958580 | 0.3645709 | 0.312723 | 0.18433616 | RC_AA1325 54_at | EST: zo20g08.s1 Stratagene colon (#937204) Homo sapiens cDNA clone 587486 3' similar to SW:MDCE_MOUSE P21271 MYOSIN-LIKE PROTEIN.;, mRNA sequence. (from Genbank) |
| 827 | Mesothelioma | 0.13954840 | 0.3644692 | 0.312657 | 0.18423387 99_at | RC_AA0853 | Homo sapiens mRNA for JM4 protein, complete CDS (clone IMAGE 546750 and LLNLc110F1857Q7 (RZPD Berlin)) |
| 828 | Mesothelioma | 0.13949300 | 0.3642390 | 0.312490 | 0.18416665 | Z24727_at | TPM1 Tropomyosin alpha chain (skeletal muscle) |
| 829 | Mesothelioma | 0.13939760 | 0.3642100 | 0.312483 | 0.18405384 | C01750_at | EST: HUMGS00036883, Human Gene Signature, 3'-directed cDNA sequence, mRNA sequence. (from Genbank) |
| 830 | Mesothelioma | 0.13934510 | 0.3639538 | 0.312433 | 0.18404976 | L33801_at | Protein kinase mRNA |
| 831 | Mesothelioma | 0.13906740 | 0.3638888 | 0.312413 | 0.18397096 68_at | RC_AA4651 | EST: aa33d06.s1 NCI_CGAP_GCB1 Homo sapiens cDNA clone IMAGE:815051 3', mRNA sequence. (from Genbank) |
| 832 | Mesothelioma | 0.13904340 | 0.3638184 | 0.312221 | 0.18386336 | D14660_at | PUTATIVE 60S RIBOSOMAL PROTEIN |
| 833 | Mesothelioma | 0.13877890 | 0.3637702 | 0.312188 | 0.18374841 | U20648_at | ZNF154 Zinc finger protein 154 (pHZ-92) |
| 834 | Mesothelioma | 0.13874720 | 0.3637558 | 0.312167 | 0.18373337 | M12529_at | APOE Apolipoprotein E |

FIG. 9T2

| | | | | | |
|---|---|---|---|---|---|
| 835 | Mesothelioma | 0.1385799 | 0.3636716 | 0.312115 | 0.18373168 | RC_AA0395 95_at | EST: zf08d12.s1 Soares fetal heart NbHH19W Homo sapiens cDNA clone 376343 3', mRNA sequence. (from Genbank) |
| 836 | Mesothelioma | 0.1385695 | 0.3635986 | 0.312085 | 0.18365657 | RC_AA4165 51_at | EST: zu05e01.s1 Soares testis NHT Homo sapiens cDNA clone 730963 3', mRNA sequence. (from Genbank) |
| 837 | Mesothelioma | 0.1385294 | 0.3635841 | 0.312041 | 0.18362677 | RC_AA2812 45_at | EST: zs94d07.s1 NCI_CGAP_GCB1 Homo sapiens cDNA clone IMAGE:705133 3', mRNA sequence. (from Genbank) |
| 838 | Mesothelioma | 0.1381553 | 0.3633605 | 0.312027 | 0.18351926 | RC_AA0170 83_at | EST: ze33e11.s1 Soares retina N2b4HR Homo sapiens cDNA clone 360812 3' similar to contains Alu repetitive element;, mRNA sequence. (from Genbank) |
| 839 | Mesothelioma | 0.1381341 | 0.3633239 | 0.312027 | 0.18344453 | RC_AA0019 08_at | EST: zh83a05.s1 Soares fetal liver spleen 1NFLS S1 Homo sapiens cDNA clone 427856 3', mRNA sequence. (from Genbank) |
| 840 | Mesothelioma | 0.1377126 | 0.3629965 | 0.312019 | 0.18343467 | RC_AA0841 04_at | EST: zn17h01.s1 Stratagene neuroepithelium NT2RAMI 937234 Homo sapiens cDNA clone 547729 3', mRNA sequence. (from Genbank) |
| 841 | Mesothelioma | 0.1374714 | 0.3629862 | 0.311751 | 0.18312952 | RC_AA2839 07_at | Homo sapiens clone 23837 mRNA sequence |
| 842 | Mesothelioma | 0.1374435 | 0.3627804 | 0.311641 | 0.18309907 | RC_AA1914 54_at | FGF intracellular binding protein |
| 843 | Mesothelioma | 0.1371823 | 0.3626934 | 0.311622 | 0.18299173 | X03168_at | VTN Vitronectin (serum spreading factor, somatomedin B, complement S-protein) |
| 844 | Mesothelioma | 0.1366761 | 0.3625163 | 0.311564 | 0.18294007 | L14637_at | TJP1 Tight junction protein 1 (zona occludens 1) |
| 845 | Mesothelioma | 0.1365293 | 0.3625107 | 0.311499 | 0.18280005 | U95006_at | D9 splice variant A mRNA |
| 846 | Mesothelioma | 0.136349 | 0.3624749 | 0.311474 | 0.18274887 | RC_AA0322 50_at | EST: zk19f06.s1 Soares pregnant uterus NbHPU Homo sapiens cDNA clone 471011 3', mRNA sequence. (from Genbank) |
| 847 | Mesothelioma | 0.1362507 | 0.3624749 | 0.311464 | 0.18263337 | RC_AA6211 79_at | Homo sapiens clone 23899 mRNA sequence |
| 848 | Mesothelioma | 0.1360817 | 0.3624114 | 0.311369 | 0.18258612 | Z95636_at | H.sapiens mRNA for laminin alpha 5 chain |
| 849 | Mesothelioma | 0.1360424 | 0.3624096 | 0.311263 | 0.18253212 | RC_AA4307 38_at | EST: zw32c02.s1 Soares ovary tumor NbHOT Homo sapiens cDNA clone 770978 3', mRNA sequence. (from Genbank) |
| 850 | Mesothelioma | 0.1358195 | 0.3623553 | 0.31115 | 0.18236065 | RC_AA0246 22_at | Solute carrier family 22 (organic cation transporter), member 5 |
| 851 | Mesothelioma | 0.1355915 | 0.3623509 | 0.311125 | 0.18231326 | M77235_at | Cardiac tetrodotoxin-insensitive voltage-dependent sodium channel alpha subunit (hH1) mRNA |
| 852 | Mesothelioma | 0.135088 | 0.3623033 | 0.311122 | 0.18221447 | T83444_at | Homo sapiens mRNA for KIAA0887 protein, partial cds |

FIG. 9U2

| | | | | | |
|---|---|---|---|---|---|
| 853 | Mesothelio ma | 0.1349272 | 0.3622848 | 0.311086 | 0.18214425 | AB004066_a t | Differentiated Embryo Chondrocyte expressed gene 1 |
| 854 | Mesothelio ma | 0.1348272 | 0.362282 | 0.311035 | 0.18212922 | RC_AA6090 43_at | Eukaryotic translation initiation factor 4 gamma, 3 |
| 855 | Mesothelio ma | 0.1347467 | 0.3622463 | 0.311098 | 0.18206054 | N57397_at | EST: yw82a03.r1 Homo sapiens cDNA clone 258700 5' similar to contains Alu repetitive element. (from Genbank) |
| 856 | Mesothelio ma | 0.1347012 | 0.3621258 | 0.310985 | 0.18191877 | AA458761_f at | Transcription factor AP-2 alpha (activating enhancer-binding protein 2 alpha) |
| 857 | Mesothelio ma | 0.1346761 | 0.3621259 | 0.310842 | 0.18187337 | RC_AA1219 20_at | EST: zn97h10.s1 Stratagene fetal retina 937202 Homo sapiens cDNA clone 566179 3', mRNA sequence. (from Genbank) |
| 858 | Mesothelio ma | 0.1341703 | 0.362096 | 0.310738 | 0.1817629 | M95787_at | 22kDa smooth muscle protein (SM22) mRNA |
| 859 | Mesothelio ma | 0.1339089 | 0.3620649 | 0.310729 | 0.18170764 | N48010_at | EST: yy23a03.r1 Homo sapiens cDNA clone 272044 5'. (from Genbank) |
| 860 | Mesothelio ma | 0.1331933 | 0.3620499 | 0.310727 | 0.1816921 | RC_AA1279 64_at | EST: zl13g07.s1 Soares pregnant uterus NbHPU Homo sapiens cDNA clone 501852 3', mRNA sequence. (from Genbank) |
| 861 | Mesothelio ma | 0.1329128 | 0.3620183 | 0.310656 | 0.1815934 | RC_AA4970 15_at | Homo sapiens mRNA for Epsilon COP |
| 862 | Mesothelio ma | 0.1327154 | 0.3619411 | 0.310644 | 0.18145964 | RC_AA2343 71_at | EST: zr72f12.s1 Soares NhHMPu S1 Homo sapiens cDNA clone 668975 3', mRNA sequence. (from Genbank) |
| 863 | Mesothelio ma | 0.1324424 | 0.3618533 | 0.310644 | 0.18144707 | X95735_at | Zyxin |
| 864 | Mesothelio ma | 0.1323123 | 0.3618313 | 0.310603 | 0.18136661 | RC_AA4602 64_at | KIAA0677 gene product |
| 865 | Mesothelio ma | 0.1309748 | 0.3617846 | 0.310552 | 0.18122612 | RC_AA1521 03_at | Human Chromosome 16 BAC clone CIT987SK-A-735G6 |
| 866 | Mesothelio ma | 0.1309566 | 0.361748 | 0.310453 | 0.18113305 | RC_AA4486 63_at | EST: zx10e03.s1 Soares total fetus Nb2HF8 9w Homo sapiens cDNA clone 786076 3', mRNA sequence. (from Genbank) |
| 867 | Mesothelio ma | 0.1306207 | 0.3617436 | 0.31037 | 0.18102998 | RC_AA4056 98_at | EST: zu66e10.s1 Soares testis NHT Homo sapiens cDNA clone 742986 3', mRNA sequence. (from Genbank) |
| 868 | Mesothelio ma | 0.1301341 | 0.3617042 | 0.310321 | 0.18094808 | D38305_at | Tob |
| 869 | Mesothelio ma | 0.1297913 | 0.3617042 | 0.310193 | 0.18086627 | X76105_at | DAP-1 mRNA |
| 870 | Mesothelio ma | 0.1297482 | 0.3616875 | 0.310183 | 0.18078786 | RC_AA6096 35_at | EST: af15h11.s1 Soares testis NHT Homo sapiens cDNA clone 1031781 3', mRNA sequence. (from Genbank) |
| 871 | Mesothelio ma | 0.1296342 | 0.3616667 | 0.310117 | 0.1807498 | L41919_rna1 _at | HIC-1 gene fragment |
| 872 | Mesothelio ma | 0.1294733 | 0.3616667 | 0.309979 | 0.18069968 | RC_AA4602 34_at | EST: zx67b04.s1 Soares total fetus Nb2HF8 9w Homo sapiens cDNA clone 796495 3', mRNA sequence. (from Genbank) |

FIG. 9V2

| | | | | | |
|---|---|---|---|---|---|
| 873 | Mesothelioma | 0.1293987 | 0.3616236 | 0.309932 | RC_AA2624 | EST: zs17g03.s1 NCI_CGAP_GCB1 Homo sapiens cDNA clone IMAGE:685492 3', mRNA sequence. (from Genbank) |
| 874 | Mesothelioma | 0.1292872 | 0.3615972 | 0.309993 | 0.18065564 72_at | EST: yz94g12.r1 Soares melanocyte 2NbHM Homo sapiens cDNA clone 290758 5', mRNA sequence. (from Genbank) |
| 875 | Mesothelioma | 0.1291995 | 0.361521 | 0.309884 | 0.18060285 W01296_at | Calcium channel, voltage-dependent, L type, alpha 1C subunit |
| 876 | Mesothelioma | 0.1286409 | 0.3615159 | 0.309726 | 0.18055838 Z34820_s_at | MaTu MN mRNA for p54/58N protein |
| 877 | Mesothelioma | 0.1286174 | 0.3612731 | 0.30972 | 0.18047541 X66839_at | NADH dehydrogenase (ubiquinone) 1 beta subcomplex, 4 (15kD, B15) |
| 878 | Mesothelioma | 0.1283925 | 0.3612652 | 0.309704 | 0.18038265 W15482_at | EST: Human fetal-lung cDNA 5'-end sequence, mRNA sequence. (from Genbank) |
| 879 | Mesothelioma | 0.1282987 | 0.3612469 | 0.309673 | 0.18035804 D31161_s_a t | EST: zo23g08.s1 Stratagene colon (#937204) Homo sapiens cDNA clone 587774 3', mRNA sequence. (from Genbank) |
| 880 | Mesothelioma | 0.1282456 | 0.361207 | 0.309601 | 0.18030137 RC_AA1349 68_at | EST: zs85d07.s1 NCI_CGAP_GCB1 Homo sapiens cDNA clone IMAGE:704269 3', mRNA sequence. (from Genbank) |
| 881 | Mesothelioma | 0.1281267 | 0.3611771 | 0.309541 | 0.18026473 RC_AA2794 18_at | Homo sapiens chromosome 1 atrophin-1 related protein (DRPLA) mRNA, complete cds |
| 882 | Mesothelioma | 0.1279139 | 0.3610486 | 0.309501 | 0.18015584 RC_AA2841 43_at | EST: ze41a07.s1 Soares retina N2b4HR Homo sapiens cDNA clone 361524 3' similar to contains element PTR7 repetitive element ;, mRNA sequence. (from Genbank) |
| 883 | Mesothelioma | 0.1278893 | 0.3609966 | 0.309345 | 0.18007254 RC_AA0171 6_at | EST: zw90b07.r1 Soares total fetus Nb2HF8 9w Homo sapiens cDNA clone 784213 5', mRNA sequence. (from Genbank) |
| 884 | Mesothelioma | 0.1278207 | 0.3609622 | 0.30933 | 0.18005331 AAA46990_a t | EST: zo36a01.s1 Stratagene endothelial cell 937223 Homo sapiens cDNA clone 588936 3' similar to SW:YBF7_YEAST P34222 HYPOTHETICAL 23.1 KD PROTEIN IN SHP1-SEC17 INTERGENIC REGION. ;, mRNA sequence. (from Genbank) |
| 885 | Mesothelioma | 0.1274802 | 0.3609615 | 0.309231 | 0.17998809 RC_AA1431 90_s_at | EST: ag29h10.s1 Jia bone marrow stroma Homo sapiens cDNA clone 1091011 3', mRNA sequence. (from Genbank) |
| 886 | Mesothelioma | 0.1273314 | 0.3609431 | 0.309144 | 0.17994206 RC_AA6000 12_at | TYRO protein tyrosine kinase binding protein |
| 887 | Mesothelioma | 0.1272465 | 0.3606437 | 0.309042 | 0.17978294 T555959_s_at | Vesicle trafficking protein sec22b |
| 888 | Mesothelioma | 0.127244 | 0.3606011 | 0.308988 | 0.17974265 W23469_at | Homo sapiens signal peptidase complex 18 kDa subunit mRNA, partial cds |
| 889 | Mesothelioma | 0.1270613 | 0.3604923 | 0.308902 | 0.17968704 AA151795_s_at | Nuclear orphan receptor ROR-beta |
| 890 | Mesothelioma | 0.1270314 | 0.3604904 | 0.308818 | 0.17960605 Y08639_at | EST: zi74a08.s1 Soares testis NHT Homo sapiens cDNA clone 728054 3', mRNA sequence. (from Genbank) |
| | | | | | 0.17954895 RC_AA3986 06_at | |

FIG. 9W2

| | | | | |
|---|---|---|---|---|
| 891 | Mesothelioma | 0.1267453 | 0.3601458 | 0.1795266 | L44367_at | EST: Homo sapiens thymus mRNA (randomly primed, normalized), single-pass sequence, mRNA sequence. (from Genbank) |
| 892 | Mesothelioma | 0.126685 | 0.3599991 | 0.17942157 | L39060_at | Transcription factor SL1 mRNA |
| 893 | Mesothelioma | 0.126685 | 0.3599644 | 0.17939046 | L39060_at-2 | Homo sapiens transcription factor SL1 mRNA, complete cds |
| 894 | Mesothelioma | 0.1262371 | 0.3599457 | 0.17931265 | S78187_at | M-PHASE INDUCER PHOSPHATASE 2 |
| 895 | Mesothelioma | 0.1261937 | 0.3599069 | 0.17919485 | U12595_at | Tumor necrosis factor type 1 receptor associated protein (TRAP1) mRNA, partial cds |
| 896 | Mesothelioma | 0.125905 | 0.3597957 | 0.17913784 | RC_AA053021_at | SCO1 (yeast homolog) cytochrome oxidase deficient 1 |
| 897 | Mesothelioma | 0.1256268 | 0.3596991 | 0.17900568 | U47621_at | Nucleolar autoantigen No55 mRNA |
| 898 | Mesothelioma | 0.1253305 | 0.3594312 | 0.17898133 | W27873_at | Human skeletal muscle 1.3 kb mRNA for tropomyosin |
| 899 | Mesothelioma | 0.1251713 | 0.3593925 | 0.17888178 | RC_AA293719_at | EST: zt55h03.s1 Soares ovary tumor NbHOT Homo sapiens cDNA clone 720293 3', mRNA sequence. (from Genbank) |
| 900 | Mesothelioma | 0.1248676 | 0.3593658 | 0.17877924 | RC_AA258203_at | EST: zs35g04.s1 NCI_CGAP_GCB1 Homo sapiens cDNA clone IMAGE:687222 3', mRNA sequence. (from Genbank) |
| 901 | Mesothelioma | 0.1247353 | 0.3593054 | 0.1787499 | AA402298_s_at | Actinin, alpha 4 |
| 902 | Mesothelioma | 0.1247023 | 0.3593051 | 0.17864318 | RC_AA448282_at | EST: zw83h07.s1 Soares testis NHT Homo sapiens cDNA clone 782845 3', mRNA sequence. (from Genbank) |
| 903 | Mesothelioma | 0.1244502 | 0.3591977 | 0.1786131 | M77144_rna1_at | 3-beta-hydroxysteroid dehydrogenase gene extracted from Human type II 3-beta hydroxysteroid dehydrogenase/ 5-delta - 4-delta isomerase gene |
| 904 | Mesothelioma | 0.1240703 | 0.3590309 | 0.17853925 | RC_AA243497_at | Human DNA sequence from clone 30M3 on chromosome 6p22.1.-22.3. Contains three novel genes, one similar to C. elegans Y63D3A.4 and one similar to (predicted) plant, worm, yeast and archaea bacterial genes, and the first exon of the KIAA0319 gene. Contains ESTs, GSSs and putative CpG islands |
| 905 | Mesothelioma | 0.1240644 | 0.3589746 | 0.17850018 | RC_AA393766_at | EST: zv64f06.s1 Soares total fetus Nb2HF8 9w Homo sapiens cDNA clone 758435 3', mRNA sequence. (from Genbank) |
| 906 | Mesothelioma | 0.1236625 | 0.3588665 | 0.17842485 | M83088_at | PGM1 Phosphoglucomutase 1 |
| 907 | Mesothelioma | 0.1235042 | 0.3588092 | 0.17831104 | R39394_at | Homo sapiens mRNA for E1B-55kDa-associated protein |

FIG. 9X2

| # | Tissue | | | | ID | Description |
|---|---|---|---|---|---|---|
| 908 | Mesothelioma | 0.1234809 | 0.3587831 | 0.307886 | AA464013_a t | EST: zx82d05.r1 Soares ovary tumor NbHOT Homo sapiens cDNA clone 810249 5', mRNA sequence. (from Genbank) |
| 909 | Mesothelioma | 0.1234238 | 0.3587174 | 0.307844 | 0.17825784 | RNA polymerase II subunit (hsRPB10) mRNA |
| 910 | Mesothelioma | 0.1232986 | 0.3587139 | 0.307749 | 0.178111759 M97815_at | CRABP2 Cellular retinoic acid-binding protein 2 |
| 911 | Mesothelioma | 0.1229773 | 0.3587134 | 0.30773 | 0.17779859 HT174_ HG174- at | Desmoplakin I |
| 912 | Mesothelioma | 0.1226119 | 0.3586837 | 0.307628 | 0.17790654 RC_AA2274 63_at | Homo sapiens mRNA for KIAA0859 protein, complete cds |
| 913 | Mesothelioma | 0.1224362 | 0.3586761 | 0.307569 | 0.17786632 U28386_at | RCH1 RAG (recombination activating gene) cohort 1 |
| 914 | Mesothelioma | 0.122195 | 0.35865 | 0.307477 | 0.17778982 RC_AA6098 85_at | EST: af08d11.s1 Soares testis NHT Homo sapiens cDNA clone 1031061 3', mRNA sequence. (from Genbank) |
| 915 | Mesothelioma | 0.1220511 | 0.3586392 | 0.307347 | 0.17779456 RC_AA4888 43_at | EST: aa55a10.s1 NCI_CGAP_GCB1 Homo sapiens cDNA clone IMAGE:824826 3', mRNA sequence. (from Genbank) |
| 916 | Mesothelioma | 0.1215292 | 0.3586242 | 0.307231 | 0.1777433 RC_AA2783 91_at | EST: zt08c05.s1 NCI_CGAP_GCB1 Homo sapiens cDNA clone IMAGE:712520 3', mRNA sequence. (from Genbank) |
| 917 | Mesothelioma | 0.1214902 | 0.3585805 | 0.307114 | 0.17763695 RC_AA1470 67_at | EST: zo32a02.s1 Stratagene colon (#937204) Homo sapiens cDNA clone 588554 3', mRNA sequence. (from Genbank) |
| 918 | Mesothelioma | 0.1212508 | 0.3585594 | 0.307005 | 0.17756614 RC_AA0215 92_at | EST: ze67c01.s1 Soares retina N2b4HR Homo sapiens cDNA clone 364032 3', mRNA sequence. (from Genbank) |
| 919 | Mesothelioma | 0.121142 | 0.3585175 | 0.306978 | 0.17747997 RC_AA4476 17_at | EST: zw97a02.s1 Soares total fetus Nb2HF8 9w Homo sapiens cDNA clone 784874 3', mRNA sequence. (from Genbank) |
| 920 | Mesothelioma | 0.1211297 | 0.3584479 | 0.306971 | 0.17742203 RC_AA0248 66_at | EST: ze79b09.s1 Soares fetal heart NbHH19W Homo sapiens cDNA clone 365177 3', mRNA sequence. (from Genbank) |
| 921 | Mesothelioma | 0.1206806 | 0.3584403 | 0.30689 | 0.17735139 RC_AA1483 18_s_at | Human mRNA for KIAA0069 gene, partial cds |
| 922 | Mesothelioma | 0.1200143 | 0.3583807 | 0.306671 | 0.1772684 H53657_s_a t | Homo sapiens mRNA for KIAA0511 protein, partial cds |
| 923 | Mesothelioma | 0.119891 | 0.3583632 | 0.306669 | 0.17771784 M59216_s_a 1 t | GABRB1 Gamma-aminobutyric acid (GABA) A receptor, beta 1 |
| 924 | Mesothelioma | 0.1197425 | 0.3583282 | 0.306668 | 0.17710753 RC_AA4114 62_at | EST: zv30g03.s1 Soares ovary tumor NbHOT Homo sapiens cDNA clone 755188 3', mRNA sequence. (from Genbank) |
| 925 | Mesothelioma | 0.1196871 | 0.3582468 | 0.306555 | 0.17701708 AA011243_s at | EST: ze19d03.r1 Soares fetal heart NbHH19W Homo sapiens cDNA clone 359429 5', mRNA sequence. (from Genbank) |
| 926 | Mesothelioma | 0.1195219 | 0.3582159 | 0.306384 | 0.16699331 D38449_at | G protein-coupled receptor |
| 927 | Mesothelioma | 0.1192552 | 0.358186 | 0.306384 | 0.1769431 X93510_at | 37 kDa LIM domain protein |

FIG. 9Y2

| | | | | | |
|---|---|---|---|---|---|
| 928 | Mesothelioma | 0.1192548 | 0.358097 | 0.306246 | 0.1768503 W37660_at | EST: zc12e07.r1 Soares parathyroid tumor NbHPA Homo sapiens cDNA clone 322116 5' similar to contains Alu repetitive element;, mRNA sequence. (from Genbank) |
| 929 | Mesothelioma | 0.1188443 | 0.3580616 | 0.30622 | 0.17678544 S57235_at-2 | CD68 antigen |
| 930 | Mesothelioma | 0.1188443 | 0.3580124 | 0.306215 | 0.17672476 S57235_at | CD68 CD68 antigen |
| 931 | Mesothelioma | 0.1187804 | 0.3578187 | 0.306186 | 0.17665581 W79496_at | EST: zd78h06.r1 Soares fetal heart NbHH19W Homo sapiens cDNA clone 346811 5', mRNA sequence. (from Genbank) |
| 932 | Mesothelioma | 0.1187195 | 0.3577879 | 0.306076 | 0.17651887 L44497_at | Small inducible cytokine A5 (RANTES) |
| 933 | Mesothelioma | 0.1186495 | 0.3577812 | 0.306061 | 0.17646107 RC_AA4479 94_at | EST: zw82g03.s1 Soares testis NHT Homo sapiens cDNA clone 782740 3', mRNA sequence. (from Genbank) |
| 934 | Mesothelioma | 0.1184462 | 0.3576656 | 0.305854 | 0.17638555 L42621_at | Ly-9 mRNA |
| 935 | Mesothelioma | 0.1184462 | 0.357582 | 0.305843 | 0.17635528 L42621_at-2 | Lymphocyte antigen 9 |
| 936 | Mesothelioma | 0.1184227 | 0.3575677 | 0.305755 | 0.17627822 RC_AA4569 81_at | EST: aa90h11.s1 Stratagene fetal retina 937202 Homo sapiens cDNA clone 838629 3' similar to contains Alu repetitive element;, mRNA sequence. (from Genbank) |
| 937 | Mesothelioma | 0.1183584 | 0.3575545 | 0.305717 | 0.17623325 RC_AA2812 60_at | EST: zs94f04.s1 NCI_CGAP_GCB1 Homo sapiens cDNA clone IMAGE:705151 3', mRNA sequence. (from Genbank) |
| 938 | Mesothelioma | 0.1179122 | 0.3575407 | 0.305648 | 0.17621173 U53831_s_a t | Homo sapiens interferon regulatory factor 7B mRNA, complete cds |
| 939 | Mesothelioma | 0.1177467 | 0.3574895 | 0.305626 | 0.17613311 RC_AA3984 23_at | EST: zt62a05.s1 Soares testis NHT Homo sapiens cDNA clone 726896 3', mRNA sequence. (from Genbank) |
| 940 | Mesothelioma | 0.1176955 | 0.357475 | 0.305526 | 0.17611235 U52840_at | Cri-du-chat region mRNA, clone CSA1 |
| 941 | Mesothelioma | 0.117556 | 0.3574715 | 0.305503 | 0.1760122 RC_AA5041 45_at | Human Chromosome 16 BAC clone CIT987SK-A-635H12 |
| 942 | Mesothelioma | 0.1175122 | 0.3574573 | 0.305498 | 0.1758089 D17516_at | PACAP receptor |
| 943 | Mesothelioma | 0.1174797 | 0.357405 | 0.305441 | 0.1757365 8 M55682_s_a t | CRTM Cartilage matrix protein |
| 944 | Mesothelioma | 0.1174023 | 0.3573946 | 0.305438 | 0.17572148 W27435_at | EST: 3118 Human retina cDNA randomly primed sublibrary Homo sapiens cDNA, mRNA sequence. (from Genbank) |
| 945 | Mesothelioma | 0.1173181 | 0.3573315 | 0.305418 | 0.1756895 RC_AA2876 81_s_at | EST: zs53f07.s1 NCI_CGAP_GCB1 Homo sapiens cDNA clone IMAGE:701221 3', mRNA sequence. (from Genbank) |
| 946 | Mesothelioma | 0.1172893 | 0.3572818 | 0.305364 | 0.1755497 X90857_at | -14 gene, containing globin regulatory element |

FIG. 9Z2

| | | | | |
|---|---|---|---|---|
| 947 | Mesothelioma | 0.1172746 | 0.3572787 | 0.3051 | M16973_at | C8B Complement component 8, beta polypeptide |
| 948 | Mesothelioma | 0.1172237 | 0.3572785 | 0.305047 | AA316686_s_at | EST: EST183361 HCC cell line (matastasis to liver in mouse) II Homo sapiens cDNA 5' end, mRNA sequence. (from Genbank) |
| 949 | Mesothelioma | 0.1170895 | 0.3572647 | 0.305047 | U28368_at | ID4 Inhibitor of DNA binding 4, dominant negative helix-loop-helix protein |
| 950 | Mesothelioma | 0.116983 | 0.3572566 | 0.304943 | L32866_at | Effector cell protease receptor-1 (EPR-1) gene, partial cds |
| 951 | Mesothelioma | 0.1168641 | 0.3572474 | 0.30494 | RC_AA429478_at | EST: zw34c05.s1 Soares ovary tumor NbHOT Homo sapiens cDNA clone 771176 3', mRNA sequence. (from Genbank) |
| 952 | Mesothelioma | 0.1164243 | 0.3570024 | 0.304918 | W16804_at | NCK adaptor protein 1 |
| 953 | Mesothelioma | 0.1158706 | 0.3569776 | 0.304862 | U72882_s_at | Interferon-induced leucine zipper protein (IFP35) mRNA, partial cds |
| 954 | Mesothelioma | 0.1158272 | 0.3569629 | 0.30477 | M13994_s_at | BCL2 B-cell CLL/lymphoma 2 |
| 955 | Mesothelioma | 0.1155963 | 0.3569373 | 0.304748 | D84454_at | UDP-galactose translocator |
| 956 | Mesothelioma | 0.1154589 | 0.3568518 | 0.304526 | X76534_at | NMB Neuromedin B |
| 957 | Mesothelioma | 0.1154283 | 0.356781 | 0.304526 | U03115_cds10_at | Human V beta T-cell receptor (TCRBV) gene locus |
| 958 | Mesothelioma | 0.1153941 | 0.3567528 | 0.304378 | W27327_at | EST: 27e5 Human retina cDNA randomly primed sublibrary Homo sapiens cDNA, mRNA sequence. (from Genbank) |
| 959 | Mesothelioma | 0.1152854 | 0.3567329 | 0.304354 | RC_AA280810_at | EST: zs99b05.s1 NCI_CGAP_GCB1 Homo sapiens cDNA clone IMAGE:711729 3' similar to SW:L10K_RAT Q05310 LEYDIG CELL TUMOR 10 KD PROTEIN.; mRNA sequence. (from Genbank) |
| 960 | Mesothelioma | 0.115184 | 0.3566887 | 0.30434 | RC_AA113165_at | EST: zm27d08.s1 Stratagene pancreas (#937208) Homo sapiens cDNA clone 526863 3', mRNA sequence. (from Genbank) |
| 961 | Mesothelioma | 0.1151825 | 0.356628 | 0.304268 | RC_AA291272_at | EST: zs18d06.s1 NCI_CGAP_GCB1 Homo sapiens cDNA clone IMAGE:685547 3', mRNA sequence. (from Genbank) |
| 962 | Mesothelioma | 0.1146084 | 0.3565882 | 0.304211 | AA292171_a_at | EST: zt50d08.r1 Soares ovary tumor NbHOT Homo sapiens cDNA clone 725775 5', mRNA sequence. (from Genbank) |
| 963 | Mesothelioma | 0.1145436 | 0.3565616 | 0.304105 | RC_AA454651_at | EST: zx99f01.s1 Soares NhHMPu S1 Homo sapiens cDNA clone 811897 3', mRNA sequence. (from Genbank) |
| 964 | Mesothelioma | 0.1143449 | 0.3562443 | 0.304056 | U62800_at | CST6 Cystatin M |
| 965 | Mesothelioma | 0.1142265 | 0.3559554 | 0.304054 | AA055019_a_at | EST: zf16g06.r1 Soares fetal heart NbHH19W Homo sapiens cDNA clone 377146 5', mRNA sequence. (from Genbank) |

FIG. 9A3

| | | | | | |
|---|---|---|---|---|---|
| 966 | Mesothelio ma | 0.1141428 | 0.3559169 | 0.304024 | 0.174305811 | RC_AA2851 62_at | EST: zs48e06.s1 NCI_CGAP_GCB1 Homo sapiens cDNA clone IMAGE:700738 3', mRNA sequence. (from Genbank) |
| 967 | Mesothelio ma | 0.1139822 | 0.3556997 | 0.303989 | 0.174269121 | RC_AA0547 04_at | EST: zk69h02.s1 Soares pregnant uterus NbHPU Homo sapiens cDNA clone 488115 3', mRNA sequence. (from Genbank) |
| 968 | Mesothelio ma | 0.1139767 | 0.3556572 | 0.303974 | 0.174232236 | L05148_at-2 | Zeta-chain (TCR) associated protein kinase (70 kD) |
| 969 | Mesothelio ma | 0.1139767 | 0.3555978 | 0.303946 | 0.174183521 | L05148_at | Protein tyrosine kinase related mRNA sequence |
| 970 | Mesothelio ma | 0.113762 | 0.3555742 | 0.303828 | 0.174123561 | W26257_at | KIAA0735 gene product |
| 971 | Mesothelio ma | 0.1136964 | 0.3554648 | 0.303822 | 0.174010991 | U87460_at | Putative endothelin receptor type B-like protein mRNA |
| 972 | Mesothelio ma | 0.1135905 | 0.3553256 | 0.303599 | 0.173960361 | M83738_at | PTPN9 Protein tyrosine phosphatase, non-receptor type 9 |
| 973 | Mesothelio ma | 0.1134531 | 0.355229 | 0.303591 | 0.173900571 | H58818_at | EST: yr36a04.r1 Homo sapiens cDNA clone 207342 5' similar to contains Alu repetitive element;. (from Genbank) |
| 974 | Mesothelio ma | 0.113278 | 0.3552262 | 0.303512 | 0.1738147 | AA092290_f_at | EST: ll6470.seq.F Fetal heart, Lambda ZAP Express Homo sapiens cDNA 5', mRNA sequence. (from Genbank) |
| 975 | Mesothelio ma | 0.1132218 | 0.3550117 | 0.303492 | 0.173743551 | D79052_s_a t | EST: Human placenta cDNA 5'-end GEN-530B11, mRNA sequence. (from Genbank) |
| 976 | Mesothelio ma | 0.1128792 | 0.3548782 | 0.303411 | 0.173696581 | AA480838_s_at | EST: zx87e06.r1 Soares ovary tumor NbHOT Homo sapiens cDNA clone 810754 5', mRNA sequence. (from Genbank) |
| 977 | Mesothelio ma | 0.1127837 | 0.3548776 | 0.303388 | 0.173606911 | U10492_at | MEOX1 Homeobox protein mox1 |
| 978 | Mesothelio ma | 0.1123052 | 0.3547699 | 0.303326 | 0.173525231 | W29077_at | EST: 56a9 Human retina cDNA randomly primed sublibrary Homo sapiens cDNA, mRNA sequence. (from Genbank) |
| 979 | Mesothelio ma | 0.1122921 | 0.3547059 | 0.3032621 | 0.173499031 | X02874_at | OIAS (2'-5') oligoadenylate synthetase |
| 980 | Mesothelio ma | 0.1122151 | 0.3545501 | 0.303166 | 0.173447191 | M10277_s_a | ACTB Actin, beta |
| 981 | Mesothelio ma | 0.1121894 | 0.3542998 | 0.303102 | 0.173368571 | D31628_s_a | 4-HYDROXYPHENYLPYRUVATE DIOXYGENASE |
| 982 | Mesothelio ma | 0.1121843 | 0.3542716 | 0.303055 | 0.173363631 | AA247475_a_t | EST: csg2940.seq.F Human fetal heart, Lambda ZAP Express Homo sapiens cDNA 5', mRNA sequence. (from Genbank) |
| 983 | Mesothelio ma | 0.1120748 | 0.3542278 | 0.302891 | 0.173283951 | T30341_s_at | Human Chromosome 16 BAC clone CIT987SK-A-211C6 |
| 984 | Mesothelio ma | 0.1117274 | 0.3541208 | 0.30288 | 0.173202471 | J00231_f_at | Immunoglobulin gamma 3 (Gm marker) |
| 985 | Mesothelio ma | 0.1117074 | 0.3540888 | 0.302844 | 0.173089221 | RC_AA4314 62_at | EST: zw70g01.s1 Soares testis NHT Homo sapiens cDNA clone 781584 3', mRNA sequence. (from Genbank) |

FIG. 9B3

| | | | | | |
|---|---|---|---|---|---|
| Mesothelio 986 ma | 0.1115528 | 0.353954 | 0.302769 | 0.173015270 RC_AA4777 1_at | Homo sapiens mRNA for p27, complete cds |
| Mesothelio 987 ma | 0.1109471 | 0.3539161 | 0.302728 | 0.17301151 AA400177_a t | EST: zu69e07.r1 Soares testis NHT Homo sapiens cDNA clone 743268 5', mRNA sequence. (from Genbank) |
| Mesothelio 988 ma | 0.1109444 | 0.3537544 | 0.302728 | 0.17293644 RC_AA4471 23_at | EST: zw93c01.s1 Soares total fetus Nb2HF8 9w Homo sapiens cDNA clone 784512 3', mRNA sequence. (from Genbank) |
| Mesothelio 989 ma | 0.1108445 | 0.353748 | 0.302706 | 0.17283714 RC_AA4373 23_at | EST: zv62f11.s1 Soares testis NHT Homo sapiens cDNA clone 758253 3', mRNA sequence. (from Genbank) |
| Mesothelio 990 ma | 0.110785 | 0.3535135 | 0.302702 | 0.1727591 D14823_at | Chimeric mRNA derived from AML1 gene and MTG8(ETO) gene, partial sequence |
| Mesothelio 991 ma | 0.1107583 | 0.3534746 | 0.302617 | 0.1726766 RC_AA2362 49_s_at | EST: zr51f04.s1 Soares NhHMPu S1 Homo sapiens cDNA clone 666943 3', mRNA sequence. (from Genbank) |
| Mesothelio 992 ma | 0.1106295 | 0.3534361 | 0.302595 | 0.17258398 X56494_at | PKM2 Pyruvate kinase, muscle |
| Mesothelio 993 ma | 0.1105758 | 0.3533171 | 0.30251 | 0.17256624 AA053052_a t | EST: zi71a06.r1 Stratagene colon (#937204) Homo sapiens cDNA clone 510034 5', mRNA sequence. (from Genbank) |
| Mesothelio 994 ma | 0.1103812 | 0.3531734 | 0.302484 | 0.17250869 X81636_at | Clathrin light chain a gene |
| Mesothelio 995 ma | 0.1101894 | 0.3531734 | 0.302247 | 0.17241189 Y09836_at | 3'UTR of unknown protein |
| Mesothelio 996 ma | 0.1101144 | 0.3529702 | 0.302388 | 0.17232104 RC_AA1674 36_i_at | EST: zp08f09.s1 Stratagene ovarian cancer (#937219) Homo sapiens cDNA clone 595817 3', mRNA sequence. (from Genbank) |
| Mesothelio 997 ma | 0.1098023 | 0.3529194 | 0.302281 | 0.17225125 RC_AA6210 41_at | EST: ag03e04.s1 Soares testis NHT Homo sapiens cDNA clone 1056222 3', mRNA sequence. (from Genbank) |
| Mesothelio 998 ma | 0.10945 | 0.3528121 | 0.302192 | 0.1722164 AA364267_a t | EST: EST74873 Pineal gland II Homo sapiens cDNA 5' end, mRNA sequence. (from Genbank) |
| Mesothelio 999 ma | 0.1089872 | 0.3527307 | 0.302169 | 0.17214063 RC_AA4436 83_at | EST: zw86c12.s1 Soares total fetus Nb2HF8 9w Homo sapiens cDNA clone 783862 3' similar to WP:B0303.15 CE00004 RIBOSOMAL PROTEIN L11 .; mRNA sequence. (from Genbank) |
| Mesothelio 1000 ma | 0.1088465 | 0.3527138 | 0.302085 | 0.17197074 R51809_at | EST: yg77g09.r1 Homo sapiens cDNA clone 39567 5'. (from Genbank) |

FIG. 9C3

| | | | | |
|---|---|---|---|---|
| 1 | Ovary | 0.8510338 | 0.7160559 | 0.620598 | 0.46732655 | L02321_at | GSTM5 Glutathione S-transferase M5 |
| 2 | Ovary | 0.7569259 | 0.6572545 | 0.574083 | 0.43466276 | M74093_at | G1/S-SPECIFIC CYCLIN E |
| 3 | Ovary | 0.6046355 | 0.6343286 | 0.555416 | 0.4186588 | M64936_at | Retinoic acid-inducible endogenous retroviral DNA |
| 4 | Ovary | 0.5680414 | 0.6189399 | 0.541685 | 0.40732542 | L00389_f_at | Cytochrome P-450 4 gene |
| 5 | Ovary | 0.5276701 | 0.6066929 | 0.533466 | 0.39899954 | RC_AA4560 55_at | EST: aa03f02.s1 Soares NhHMPu S1 Homo sapiens cDNA clone 812187 3', mRNA sequence. (from Genbank) |
| 6 | Ovary | 0.522472 | 0.5995995 | 0.526755 | 0.39146128 | S81294_at | DCC=deleted in colorectal cancer {alternatively spliced, exon 1A} [human, brain tumor, tumor no. 245, mRNA Partial, 216 nt] |

FIG. 10A

| | | | | | |
|---|---|---|---|---|---|
| 7 | Ovary | 0.5195484 | 0.5954214 | 0.52132 | 0.38639146 | U78793_at | Folate receptor alpha (hFR) mRNA, partial cds |
| 8 | Ovary | 0.5137958 | 0.5912506 | 0.515128 | 0.3810037 | RC_AA3043 44_f_at | EST: EST17092 Aorta endothelial cells, TNF alpha-treated Homo sapiens cDNA 3' end similar to EST containing Alu repeat, mRNA sequence. (from Genbank) |
| 9 | Ovary | 0.4945446 | 0.584052 | 0.510391 | 0.37765996 | HG3236-HT3413_f_at | Neurofibromatosis 2 Tumor Suppressor (Gb:L27065) |
| 10 | Ovary | 0.4869052 | 0.5789442 | 0.505045 | 0.37242782 | M11973_cds 1_at | Gamma-B-crystallin gene (gamma 1-2) |
| 11 | Ovary | 0.4853579 | 0.5760211 | 0.501902 | 0.36822984 | HG3987-HT4257_at | Cpg-Enriched Dna, Clone E06 |
| 12 | Ovary | 0.4831111 | 0.5726396 | 0.499049 | 0.3651814 | RC_AA1906 76_at | EST: zp89g09.s1 Stratagene HeLa cell s3 937216 Homo sapiens cDNA clone 627424 3', mRNA sequence. (from Genbank) |
| 13 | Ovary | 0.4823868 | 0.5684215 | 0.495929 | 0.3626741 | U14910_at | RPE-retinal G protein-coupled receptor (rgr) mRNA |
| 14 | Ovary | 0.48102 | 0.5659592 | 0.493198 | 0.35952345 | S72503_s_at | HRK1 |
| 15 | Ovary | 0.4806888 | 0.5639328 | 0.490725 | 0.3566498 | S74445_at | Cellular retinoic acid-binding protein [human, skin, mRNA, 735 nt] |
| 16 | Ovary | 0.4796256 | 0.5606981 | 0.488236 | 0.35449806 | D87023_cds 2_at | J1 gene extracted from Human (lambda) DNA for immunoglobulin light chain |
| 17 | Ovary | 0.476544 | 0.5564995 | 0.485709 | 0.35224438 | RC_AA1648 51_at | EST: zp02c11.s1 Stratagene ovarian cancer (#937219) Homo sapiens cDNA clone 595220 3', mRNA sequence. (from Genbank) |
| 18 | Ovary | 0.4756043 | 0.5564252 | 0.483583 | 0.34994422 | U10690_f_at | MAGE-5a antigen (MAGE5a) gene |
| 19 | Ovary | 0.4742535 | 0.5535537 | 0.481697 | 0.34787157 | M31667_f_at | CYTOCHROME P450 IA2 |
| 20 | Ovary | 0.4741597 | 0.5519682 | 0.479513 | 0.34592605 | T89571_f_at | EST: ye04h07.r1 Homo sapiens cDNA clone 116797 5' similar to contains Alu repetitive element;. (from Genbank) |
| 21 | Ovary | 0.4701093 | 0.5498317 | 0.479994 | 0.3441474 | S77415_at | Melanocortin-4 receptor [human, Genomic, 1671 nt] |
| 22 | Ovary | 0.4676537 | 0.5481562 | 0.47624 | 0.34225956 | M19159_at | ALPP Alkaline phosphatase, placental (Regan isozyme) |
| 23 | Ovary | 0.4644734 | 0.545431 | 0.474711 | 0.3405618 | D78129_at | Squalene epoxidase, partial cds |
| 24 | Ovary | 0.4605246 | 0.5448023 | 0.473484 | 0.33923305 | Z49825_s_at | HEPATOCYTE NUCLEAR FACTOR 4 |
| 25 | Ovary | 0.458623 | 0.5438333 | 0.471184 | 0.33755607 | S58733_at | Pp52 |
| 26 | Ovary | 0.4584377 | 0.5427226 | 0.470246 | 0.33613613 | M13699_at | CP Ceruloplasmin (ferroxidase) |
| 27 | Ovary | 0.4572116 | 0.5400738 | 0.469214 | 0.33507967 | U28413_at | Cockayne syndrome complementation group A CSA protein (CSA) mRNA |
| 28 | Ovary | 0.4538827 | 0.5378203 | 0.468239 | 0.33353886 | D13644_at | 40S RIBOSOMAL PROTEIN S17 |
| 29 | Ovary | 0.4525212 | 0.535572 | 0.466516 | 0.33212996 | M14091_at | THYROXINE-BINDING GLOBULIN PRECURSOR |

FIG. 10B

| | | | | | | |
|---|---|---|---|---|---|---|
| 30 | Ovary | 0.4525142 | 0.5345969 | 0.465137 | 0.3305585 | S79781_at | WT1 (antisense promoter, intron 1) [human, kidney, Genomic, 780 nt] |
| 31 | Ovary | 0.451627 | 0.5328317 | 0.464586 | 0.329938924 | AJ000099_s_at | Lysosomal hyaluronidase |
| 32 | Ovary | 0.4504809 | 0.5299715 | 0.462596 | 0.328371132 | L22548_at | COL18A1 Collagen, type XVIII, alpha 1 |
| 33 | Ovary | 0.4487543 | 0.5297619 | 0.461529 | 0.32713124 | U49974_f_at | Mariner2 transposable element, complete consensus sequence |
| 34 | Ovary | 0.4478474 | 0.5288946 | 0.46037 | 0.326207558 | X83425_at | LU gene for Lutheran blood group glycoprotein |
| 35 | Ovary | 0.4461511 | 0.5282426 | 0.459307 | 0.324471213 | X89059_at | Unknown protein expressed in macrophages |
| 36 | Ovary | 0.4444712 | 0.5270001 | 0.458142 | 0.322353207 | AA422123_i_at | EST: zv26h12.r1 Soares NhHMPu S1 Homo sapiens cDNA clone 754823 5' similar to contains Alu repetitive element;, mRNA sequence. (from Genbank) |
| 37 | Ovary | 0.4438221 | 0.5255702 | 0.457301 | 0.32265148 | M14565_at | CYP11A Cytochrome P450, subfamily XIA (cholesterol side chain cleavage) |
| 38 | Ovary | 0.4435201 | 0.5253384 | 0.45566 | 0.321399966 | L16782_at | Putative M phase phosphoprotein 1 (MPP1) mRNA, partial cds |
| 39 | Ovary | 0.4430219 | 0.5235044 | 0.454693 | 0.32021856 | D78367_at | K12 keratin |
| 40 | Ovary | 0.4409986 | 0.5229932 | 0.453046 | 0.31930768 | M10943_at | Metallothionein-If gene (hMT-If) |
| 41 | Ovary | 0.4405581 | 0.522803 | 0.45159 | 0.3183145 | HG3125-HT3301_s_a_t | Estrogen Receptor (Gb:S67777) |
| 42 | Ovary | 0.4386855 | 0.5218499 | 0.451101 | 0.3175664 | X69699_at | Pax8 mRNA |
| 43 | Ovary | 0.4384039 | 0.5191208 | 0.450069 | 0.31629783_at | M14123_xpt | Gag 2 protein from Human endogenous retrovirus HERV-K10./ntype=DNA./annot=CDS |
| 44 | Ovary | 0.4366822 | 0.5190125 | 0.448641 | 0.315301950 | HG4749-HT5197_at | Carnitine Calcium-Binding Protein, Mitochondrial |
| 45 | Ovary | 0.4349622 | 0.5188058 | 0.448021 | 0.314574480 | S79854_at | Type 3 Iodothyronine deiodinase |
| 46 | Ovary | 0.4349622 | 0.5174404 | 0.446937 | 0.313643870 | S79854_at-2 | Deiodinase, iodothyronine, type III |
| 47 | Ovary | 0.4295164 | 0.516957 | 0.446696 | 0.31302225 | M31776_s_a_t | BRAIN NATRIURETIC PEPTIDE PRECURSOR |
| 48 | Ovary | 0.4290302 | 0.5168963 | 0.445974 | 0.312221905 | U82303_at | Unknown protein mRNA, partial cds |
| 49 | Ovary | 0.4272335 | 0.5166276 | 0.445373 | 0.311406050 | U79301_at-2 | Human clone 23842 mRNA sequence |
| 50 | Ovary | 0.4272335 | 0.5158307 | 0.443361 | 0.310599980 | U79301_at | Clone 23842 mRNA sequence |
| 51 | Ovary | 0.4256684 | 0.5157086 | 0.442638 | 0.30954327 | X04470_s_a_t | RPL32 Ribosomal protein L32 |
| 52 | Ovary | 0.4254899 | 0.5148147 | 0.442335 | 0.308628920 | S79639_at | EXT1 Exostoses (multiple) 1 |
| 53 | Ovary | 0.4231078 | 0.5140933 | 0.441541 | 0.307851820 | U82532_at | GDI-dissociation inhibitor RhoGDIgamma mRNA |
| 54 | Ovary | 0.4211866 | 0.5129408 | 0.441305 | 0.306968721 | X07438_s_a_t | DNA for cellular retinol binding protein (CRBP) exons 3 and 4 |

FIG. 10C

| | | | | | | |
|---|---|---|---|---|---|---|
| 55 | Ovary | 0.4199884 | 0.51225253 | 0.440456 | 0.30648792 | S82472_at | Beta -pol=DNA polymerase beta (exon alpha to exon VII region) [human, Genomic, 124 nt, segment 1 of 2] |
| 56 | Ovary | 0.4181991 | 0.510801 | 0.439134 | 0.30575787 | Y10506_at | CD110 protein |
| 57 | Ovary | 0.417632 | 0.5104915 | 0.438371 | 0.30515698 | X77909_at | IKBL mRNA |
| 58 | Ovary | 0.4154039 | 0.5097205 | 0.437848 | 0.30438116 | L15309_at | ZNF141 Zinc finger protein 141 (clone pHZ-44) |
| 59 | Ovary | 0.4152832 | 0.5085704 | 0.437338 | 0.30353743 | D49410_at | IL3RA Interleukin 3 receptor, alpha (low affinity) |
| 60 | Ovary | 0.4146924 | 0.5076208 | 0.436682 | 0.30305088 | D83767_at | Clone N9 Rep-8 mRNA |
| 61 | Ovary | 0.4145735 | 0.5071911 | 0.436345 | 0.30218625 | U12779_at | MAP KINASE-ACTIVATED PROTEIN KINASE 2 |
| 62 | Ovary | 0.4145672 | 0.5060761 | 0.434477 | 0.301170184 | HG3492-HT3686_at | Uncoupling Protein Ucp |
| 63 | Ovary | 0.4142466 | 0.505459 | 0.434213 | 0.301103585 | M32598_at | RPS11 Ribosomal protein S11 |
| 64 | Ovary | 0.4141421 | 0.5047199 | 0.4336661 | 0.300553598 | R11710_at | Transcobalamin I (vitamin B12 binding protein, R binder family) |
| 65 | Ovary | 0.4131945 | 0.5046203 | 0.432994 | 0.29996446 | L20815_at | S protein mRNA |
| 66 | Ovary | 0.412573 | 0.50339035 | 0.432471 | 0.29994829 | Z74616_s_at | COL1A2 Collagen, type I, alpha-2 |
| 67 | Ovary | 0.4112487 | 0.50335855 | 0.431944 | 0.29893354 | Z74615_at | COL1A1 Collagen, type I, alpha 1 |
| 68 | Ovary | 0.4099566 | 0.50293368 | 0.431724 | 0.29830384 | Z29331_at | UBE2H Ubiquitin-conjugating enzyme E2H (homologous to yeast UBC8) |
| 69 | Ovary | 0.4095814 | 0.50253941 | 0.431376 | 0.2978331 | L01406_at | GHRHR Growth hormone-releasing hormone receptor |
| 70 | Ovary | 0.4092859 | 0.50066956 | 0.430838 | 0.2971351 | L35269_at | ZINC FINGER PROTEIN 35 |
| 71 | Ovary | 0.4084033 | 0.4988408 | 0.430237 | 0.29651558 | U62437_at | Neuronal nicotinic acetylcholine receptor beta-2 subunit |
| 72 | Ovary | 0.4080739 | 0.4987781 | 0.429871 | 0.29609123 | D38024_at | Facioscapulohumeral muscular dystrophy (FSHD) gene region, D4Z4 tandem repeat unit |
| 73 | Ovary | 0.4074743 | 0.4984912 | 0.429478 | 0.295597 | M55998_s_a_t | Alpha-1 collagen type I gene, 3' end |
| 74 | Ovary | 0.4068982 | 0.4981076 | 0.428569 | 0.29510810 | L11238_s_at | GP5 Glycoprotein V (platelet) |
| 75 | Ovary | 0.4063406 | 0.4976544 | 0.427979 | 0.29459664 | D87024_at | Immunoglobulin lambda gene locus DNA, clone:92H4 |
| 76 | Ovary | 0.4057267 | 0.4976192 | 0.427583 | 0.29416174 | S73840_at | Type IIx myosin heavy chain (3' region) [human, skeletal muscle, mRNA Partial, 827 nt] |
| 77 | Ovary | 0.4049314 | 0.497051 | 0.427454 | 0.293832 | D31765_at | KIAA0061 gene, partial cds |
| 78 | Ovary | 0.4046499 | 0.4965777 | 0.426667 | 0.29341102 | M77836_at | PYCR1 Pyrroline-5-carboxylate reductase 1 |
| 79 | Ovary | 0.403001 | 0.4959625 | 0.426381 | 0.293110068 | HG3432-HT3621_at | Fibroblast Growth Factor Receptor K-Sam, Alt. Splice 4, K-Sam Iv |
| 80 | Ovary | 0.401601 | 0.49556725 | 0.425764 | 0.292334478 | AA434329_a_t | EST: zw24g07.r1 Soares ovary tumor NbHOT Homo sapiens cDNA clone 770268 5' similar to contains element TAR1 repetitive element:, mRNA sequence. (from Genbank) |
| 81 | Ovary | 0.4010463 | 0.4948143 | 0.425352 | 0.29194021 | X96924_rna1_at | Gene encoding mitochondrial citrate transport protein |

FIG. 10D

| | | | | | | |
|---|---|---|---|---|---|---|
| 82 | Ovary | 0.4007482 | 0.4940607 | 0.424348 | 0.291151362_1_at | ADH4 gene for class II alcohol dehydrogenase (pi subunit), exon 1 |
| 83 | Ovary | 0.4002867 | 0.4934896 | 0.424144 | 0.291148884 Z15005_at | CENPE Centromere protein E (312kD) |
| 84 | Ovary | 0.3983925 | 0.492963 | 0.42353 | 0.29070893 M55420_at | IgE chain, last 2 exons |
| 85 | Ovary | 0.3983288 | 0.4928631 | 0.423063 | 0.2903554 HG4058-HT4328_at | Oncogene Aml1-Evi-1, Fusion Activated |
| 86 | Ovary | 0.3973214 | 0.4915406 | 0.422256 | 0.2899093 RC_AA4534 51_at | EST: zx45a09.s1 Soares testis NHT Homo sapiens cDNA clone 795160 3', mRNA sequence. (from Genbank) |
| 87 | Ovary | 0.3964302 | 0.4915406 | 0.422067 | 0.2896022 RC_AA6091 31_at | EST: aff1f03.s1 Soares testis NHT Homo sapiens cDNA clone 1031357 3', mRNA sequence. (from Genbank) |
| 88 | Ovary | 0.3957653 | 0.4909155 | 0.421357 | 0.28913614 D87258_at | Cancellous bone osteoblast mRNA for serin protease with IGF-binding motif |
| 89 | Ovary | 0.3951776 | 0.4908244 | 0.420984 | 0.2884789 X74764_at | Receptor protein tyrosine kinase |
| 90 | Ovary | 0.3948695 | 0.4893472 | 0.420621 | 0.28808346 L06419_at | PLOD Lysyl hydroxylase |
| 91 | Ovary | 0.3931691 | 0.48894 | 0.420116 | 0.28766322 L13197_at | PAPPA Pregnancy-associated plasma protein A |
| 92 | Ovary | 0.3931588 | 0.4889143 | 0.419797 | 0.28737557 M55268_at | CSNK2A2 Casein kinase 2, alpha prime polypeptide |
| 93 | Ovary | 0.392731 | 0.4872286 | 0.419466 | 0.2868552 U18018_at | ETV4 Ets variant gene 4 (E1A enhancer-binding protein, E1AF) |
| 94 | Ovary | 0.3922851 | 0.486495 | 0.419272 | 0.2863664 L37199_at | (clone cD24-1) Huntington's disease candidate region mRNA fragment |
| 95 | Ovary | 0.3917779 | 0.4861869 | 0.418956 | 0.28598052 M17236_at | HLA CLASS II HISTOCOMPATIBILITY ANTIGEN, DQ(2) ALPHA CHAIN PRECURSOR |
| 96 | Ovary | 0.3917357 | 0.4859612 | 0.41828 | 0.28550702 L32164_at | Zinc finger protein mRNA, 3' end |
| 97 | Ovary | 0.3904399 | 0.4858529 | 0.417434 | 0.28500661 S79219_s_at | PCCA Propionyl-coA carboxylase alpha chain |
| 98 | Ovary | 0.3877922 | 0.4853906 | 0.417191 | 0.28476134 HG4272-HT4542_at | Hepatocyte Growth Factor Receptor |
| 99 | Ovary | 0.3874707 | 0.4853081 | 0.416784 | 0.28440332 M94547_at | HUMMLC2At; Homo sapiens; ; 593 base-pairs |
| 100 | Ovary | 0.3863349 | 0.4849725 | 0.41667 | 0.2840003 M68840_at | MAOA Monoamine oxidase A |
| 101 | Ovary | 0.3855568 | 0.4838219 | 0.416284 | 0.2837835 HG2480-HT2576_at | Fmlp-Related Receptor I |
| 102 | Ovary | 0.3843816 | 0.4836282 | 0.415891 | 0.283424 M19309_s_a t | TNNT1 Troponin T1, skeletal, slow |
| 103 | Ovary | 0.3839634 | 0.4833496 | 0.415752 | 0.28316036 L10377_s_at | (clone CTG-B37) mRNA sequence |
| 104 | Ovary | 0.3837733 | 0.4828865 | 0.414906 | 0.2826997 U20428_at | SNC19 mRNA sequence |
| 105 | Ovary | 0.3830413 | 0.4827887 | 0.414661 | 0.2823038 HG3740-HT4010_at | Basic Transcription Factor 2, 34 Kda Subunit |
| 106 | Ovary | 0.3825671 | 0.4823815 | 0.414504 | 0.28198874 D86425_at | Osteoblast mRNA for osteonidogen |
| 107 | Ovary | 0.3817932 | 0.4821015 | 0.414059 | 0.28149918 D14827_at | Tax helper protein 1 |
| 108 | Ovary | 0.3806244 | 0.4810468 | 0.413609 | 0.28116593 D79995_at | KIAA0173 gene |

FIG. 10E

| # | Tissue | | | | | Description |
|---|---|---|---|---|---|---|
| 109 | Ovary | 0.3802058 | 0.4808693 | 0.413232 | 0.28078696 | U36501_at | SP-100 Nuclear antigen Sp100 |
| 110 | Ovary | 0.3781182 | 0.4804787 | 0.412926 | 0.2803331 | HG1155-HT4822_at | Colony-Stimulating Factor 1, Macrophage, Alt. Splice 3 |
| 111 | Ovary | 0.3773591 | 0.4797828 | 0.412516 | 0.2799939 | M13485_at | Metallothionein I-B gene |
| 112 | Ovary | 0.3767476 | 0.4796143 | 0.412243 | 0.27974236 | D63877_at | KIAA0241 gene, partial cds |
| 113 | Ovary | 0.376534 | 0.4789506 | 0.411868 | 0.27941853 | U09850_at | ZNF143 Zinc finger protein 143 (clone pHZ-1) |
| 114 | Ovary | 0.376534 | 0.4784158 | 0.411302 | 0.27895638 | U09850_at-2 | Zinc finger protein 143 (clone pHZ-1) |
| 115 | Ovary | 0.3764934 | 0.4779274 | 0.410862 | 0.278606552 | AA465016_a_t | EST: zx80d02.r1 Soares ovary tumor NbHOT Homo sapiens cDNA clone 810051 5' similar to TR:G1020091 G1020091 NEUROPSIN. ;contains element LTR3 repetitive element ;, mRNA sequence. (from Genbank) |
| 116 | Ovary | 0.3740737 | 0.4776643 | 0.410488 | 0.2782667 | M68941_at | Protein-tyrosine phosphatase mRNA |
| 117 | Ovary | 0.3739618 | 0.4770488 | 0.410383 | 0.2779299 | K03021_at | PLAT Plasminogen activator, tissue type (t-PA) |
| 118 | Ovary | 0.3706565 | 0.4761932 | 0.409845 | 0.2775942 | Y00318_at | IF I factor (complement) |
| 119 | Ovary | 0.3697582 | 0.475856 | 0.409553 | 0.2773474 | M92449_at | LTR mRNA, 3' end of coding region and 3' flank |
| 120 | Ovary | 0.3692319 | 0.4756043 | 0.409207 | 0.27719274 | X04707_at | C-erb-A mRNA for thyroid hormone receptor |
| 121 | Ovary | 0.3691303 | 0.4754246 | 0.408837 | 0.27662453 | RC_AA194257_r_at | Human DNA sequence from clone 522J7 on chromosome 22q13.3. Contains part of a 60S Ribosomal protein L5 pseudogene and a Peregrin (BR140) LIKE gene downstream of a putative CpG island. Contains ESTs, STSs and GSSs |
| 122 | Ovary | 0.3689959 | 0.4751352 | 0.408431 | 0.27626103 | X52011_at | MYF6 Muscle determination factor |
| 123 | Ovary | 0.3686954 | 0.4749398 | 0.408172 | 0.27587326 | Z34897_at | HRH1 Histamine receptor H1 |
| 124 | Ovary | 0.3686464 | 0.4733662 | 0.407906 | 0.2755622 | X63755_at | High-sulphur keratin |
| 125 | Ovary | 0.3682404 | 0.4732527 | 0.407587 | 0.27531594 | X15880_at | COL6A1 Collagen, type VI, alpha 1 |
| 126 | Ovary | 0.3678046 | 0.4730955 | 0.407097 | 0.27489182 | X74039_at | Variant urokinase plasminogen activator receptor (uPAR2) mRNA, partial cds |
| 127 | Ovary | 0.3676732 | 0.4729119 | 0.406807 | 0.2746096 | Z22533_s_at | Activin A receptor type II-like 1 |
| 128 | Ovary | 0.3672675 | 0.4725936 | 0.406409 | 0.27424642 | U70370_at | Hindlimb expressed homeobox protein backfoot (Bft) mRNA |
| 129 | Ovary | 0.3672675 | 0.472568 | 0.405583 | 0.27397794 | U70370_at-2 | Human hindlimb expressed homeobox protein backfoot (Bft) mRNA, complete cds |
| 130 | Ovary | 0.3666754 | 0.4720468 | 0.405287 | 0.27370065 | M95740_at | IDUA Iduronidase, alpha-L- |
| 131 | Ovary | 0.3656579 | 0.4718669 | 0.404672 | 0.27331546 | U20530_at | Bone phosphoprotein spp-24 precursor mRNA |
| 132 | Ovary | 0.365128 | 0.4718661 | 0.404403 | 0.2729669 | D00632_at | GPX3 Glutathione peroxidase 3 (plasma) |
| 133 | Ovary | 0.364676 | 0.4715564 | 0.404318 | 0.27266794 | L16464_at | ETS-RELATED PROTEIN PE-1 |
| 134 | Ovary | 0.3642536 | 0.4713914 | 0.404228 | 0.27240065 | HG4099-HT4369_s_a_t | Adrenergic Receptor, Alpha 1b |

FIG. 10F

| | | | | | | |
|---|---|---|---|---|---|---|
| 135 | Ovary | 0.3635305 | 0.4710352 | 0.404057 | 0.272111183 RC_AA4304 96_r_at | Ferritin, light polypeptide |
| 136 | Ovary | 0.3630706 | 0.4709762 | 0.403538 | 0.2718631 AA401047_a_t | Homo sapiens mRNA for neuropsin, complete cds |
| 137 | Ovary | 0.3614486 | 0.4699248 | 0.403429 | 0.2715823 M99063_at | KERATIN, TYPE II CYTOSKELETAL 2 ORAL |
| 138 | Ovary | 0.3609935 | 0.4695281 | 0.402471 | 0.271122495 RC_AA2365 33_s_at | Ecotropic viral integration site 1 |
| 139 | Ovary | 0.3604792 | 0.4691197 | 0.402362 | 0.2708809 RC_AA1133 87_at | EST: zn70g06.s1 Stratagene HeLa cell s3 937216 Homo sapiens cDNA clone 563578 3', mRNA sequence. (from Genbank) |
| 140 | Ovary | 0.3602834 | 0.4690814 | 0.402032 | 0.27066174 U78095_at | Placental bikunin mRNA |
| 141 | Ovary | 0.3602108 | 0.4688845 | 0.401946 | 0.2702911 Z80345_rna s_at | SCAD gene, exon 1 and joining features |
| 142 | Ovary | 0.3601319 | 0.4687942 | 0.401438 | 0.27014562 U49973_xpt _at | ORF2: function unknown from Human Tigger1 transposable element, complete consensus sequence./ntype=DNA /annot=CDS |
| 143 | Ovary | 0.3597421 | 0.4686669 | 0.409986 | 0.2697907 M64930_at | Protein phosphatase 2A beta subunit mRNA |
| 144 | Ovary | 0.3590123 | 0.4685938 | 0.400711 | 0.26961127 M64497_at | APOLIPOPROTEIN AI REGULATORY PROTEIN-1 |
| 145 | Ovary | 0.3589212 | 0.4685489 | 0.400617 | 0.26917824 M62628_s_a t | Alpha-1 Ig germline C-region membrane-coding region, 3' end |
| 146 | Ovary | 0.3589044 | 0.4681783 | 0.400056 | 0.26680133 L47125_s_at | EEF1A1 Translation elongation factor 1-alpha-1 |
| 147 | Ovary | 0.3586063 | 0.4681377 | 0.399781 | 0.2685907 U07223_at | Beta2-chimaerin mRNA |
| 148 | Ovary | 0.3584908 | 0.4678547 | 0.399623 | 0.26831234 M27826_at | Endogenous retroviral protease mRNA |
| 149 | Ovary | 0.3577883 | 0.4677807 | 0.399517 | 0.268112 L77563_at | DGS-F partial mRNA |
| 150 | Ovary | 0.3572949 | 0.4673126 | 0.39897 | 0.26777637 D49490_at | Protein disulfide Isomerase-related protein (PDIR) |
| 151 | Ovary | 0.3572133 | 0.4671712 | 0.398723 | 0.26740307 RC_AA4046 09_s_at | EST: zl43h04.s1 Soares ovary tumor NbHOT Homo sapiens cDNA clone 725143 3', mRNA sequence. (from Genbank) |
| 152 | Ovary | 0.3571547 | 0.4665582 | 0.398685 | 0.26711863 D50495_at | Transcription elongation factor S-II, hS-II-T1 |
| 153 | Ovary | 0.3568475 | 0.4657049 | 0.398354 | 0.26594195 U05291_at | FMOD Fibromodulin |
| 154 | Ovary | 0.3558626 | 0.465421 | 0.397805 | 0.26553154 M86546_at | PBX1 PBX1a and PBX1b |
| 155 | Ovary | 0.3556008 | 0.4651786 | 0.397473 | 0.2664457 U73499_at | Hepatic nuclear factor 1-alpha (TCF-1-alpha) gene, promoter region and partial cds |
| 156 | Ovary | 0.3554865 | 0.4647488 | 0.397251 | 0.26618755 X02956_at | IFNA5 Interferon, alpha 5 |
| 157 | Ovary | 0.3532516 | 0.4646909 | 0.396984 | 0.26594195 U17280_at | STAR Steroidogenic acute regulatory protein |
| 158 | Ovary | 0.353161 | 0.4644649 | 0.396861 | 0.26553154 X78262_f_at | H.sapiens mRNA for TRE5 |
| 159 | Ovary | 0.3530989 | 0.4644649 | 0.396277 | 0.26535395 AA167824_a t | Cell division cycle 27 |
| 160 | Ovary | 0.3529449 | 0.4641308 | 0.396244 | 0.26501605 X97675_rna 1_at | Plakophilin 2a gene extracted from H.sapiens mRNA for plakophilin 2a and b |
| 161 | Ovary | 0.3519212 | 0.4641308 | 0.396071 | 0.264767 L02648_at | TCN2 Transcobalamin II |

FIG. 10G

| # | Tissue | | | | ID | Description |
|---|---|---|---|---|---|---|
| 162 | Ovary | 0.3519083 | 0.4639741 | 0.395921 | 0.264401140 1_at | RC_AA6216 EST: af47g08.s1 Soares total fetus Nb2HF8 9w Homo sapiens cDNA clone 1034846 3' similar to TR:G240986 G240986 LMW G-PROTEIN.; mRNA sequence. (from Genbank) |
| 163 | Ovary | 0.3511486 | 0.4632016 | 0.395162 | 0.2641507 | D32001_at HuSAA1g gene for serum amyloid A1 gamma, exon 3 and intron 3 |
| 164 | Ovary | 0.3505362 | 0.4630316 | 0.395036 | 0.26385072 | U82321_at Clone 14.9B mRNA sequence |
| 165 | Ovary | 0.3499089 | 0.4621575 | 0.394608 | 0.26370892 | X77307_at 5-HYDROXYTRYPTAMINE 2B RECEPTOR |
| 166 | Ovary | 0.3490718 | 0.4621525 | 0.394232 | 0.2634417 | M11433_at RBP1 Cellular retinol-binding protein |
| 167 | Ovary | 0.3475946 | 0.4619069 | 0.394048 | 0.26312995 | M80482_at PACE4 Paired basic amino acid cleaving system 4 |
| 168 | Ovary | 0.3475035 | 0.4616751 | 0.393895 | 0.26288402 | Z33642_at V7 mRNA for leukocyte surface protein |
| 169 | Ovary | 0.3467984 | 0.4615618 | 0.393185 | 0.26259285 | S90469_at Cytochrome P450 reductase [human, placenta, mRNA Partial, 2403 nt] |
| 170 | Ovary | 0.3458812 | 0.4612084 | 0.393098 | 0.26224127 | D83699_at Brain 3'UTR of mRNA for neuronal death protein, partial sequence |
| 171 | Ovary | 0.3455918 | 0.4611816 | 0.39284 | 0.26195264 | U20758_ma 1_at Osteopontin gene |
| 172 | Ovary | 0.3453621 | 0.4607912 | 0.392259 | 0.26181865 | RC_AA1557 63_at EST: z052g12.s1 Stratagene pancreas (#937208) Homo sapiens cDNA clone 590566 3'; mRNA sequence. (from Genbank) |
| 173 | Ovary | 0.3453137 | 0.4607093 | 0.39249 | 0.26162684 | U51127_at IRF5 Interferon regulatory factor 5 |
| 174 | Ovary | 0.3438769 | 0.4606453 | 0.392429 | 0.26140743 | RC_AA1583 86_at EST: z066c01.s1 Stratagene pancreas (#937208) Homo sapiens cDNA clone 591840 3'; mRNA sequence. (from Genbank) |
| 175 | Ovary | 0.3438713 | 0.4605341 | 0.392272 | 0.26117808 | U13220_at Forkhead protein FREAC-2 mRNA, partial cds |
| 176 | Ovary | 0.3438034 | 0.4603596 | 0.392271 | 0.26105964 | HG3355-HT3532_at Peroxisome Proliferator Activated Receptor (Gb:Z30972) |
| 177 | Ovary | 0.3437833 | 0.4603063 | 0.391927 | 0.26081172 | M20137_at Interleukin 3 (IL-3) mRNA |
| 178 | Ovary | 0.3436563 | 0.460271 | 0.391749 | 0.26052493 | U28281_at SCTR Secretin receptor |
| 179 | Ovary | 0.343484 | 0.4591674 | 0.391135 | 0.26030207 | U49973_xpt 1_at ORF-1; MER37; putative transposase similar to pogo element from Human Tigger1 transposable element, complete consensus sequence./ntype=DNA /annot=CDS |
| 180 | Ovary | 0.3430626 | 0.4591604 | 0.390845 | 0.2601607 | U51587_at Golgi complex autoantigen golgin-97 mRNA |
| 181 | Ovary | 0.3429836 | 0.4589919 | 0.390492 | 0.2598922 | X99920_at S100 calcium-binding protein A13 |
| 182 | Ovary | 0.3426471 | 0.4583454 | 0.39033 | 0.2595495 | HG3570-HT3773_at Protein Phosphatase Inhibitor Homolog |
| 183 | Ovary | 0.3422476 | 0.4583454 | 0.390084 | 0.25928584 | RC_AA2522 89_at EST: zr29d01.s1 Stratagene NT2 neuronal precursor 937230 Homo sapiens cDNA clone 664801 3' similar to TR:G1060907 G1060907 QPRTASE.; mRNA sequence. (from Genbank) |
| 184 | Ovary | 0.3417338 | 0.4583368 | 0.389755 | 0.25912726 | X59770_at INTERLEUKIN-1 RECEPTOR, TYPE II PRECURSOR |
| 185 | Ovary | 0.3416281 | 0.4583199 | 0.389721 | 0.25896212 | F15197_at EST: H. sapiens partial cDNA sequence. mRNA sequence. (from Genbank) |
| 186 | Ovary | 0.3414222 | 0.458183 | 0.389451 | 0.25052475 | HG3934-HT4204_at G1 Phase-Specific Gene |

FIG. 10H

| | | | | | |
|---|---|---|---|---|---|
| 187 | Ovary | 0.3413274 | 0.4580171 | 0.389399 | 0.25831652 | RC_AA0554 04_f_at | EST: zl74e11.s1 Stratagene colon (#937204) Homo sapiens cDNA clone 510380 3' similar to contains Alu repetitive element;, mRNA sequence. (from Genbank) |
| 188 | Ovary | 0.3409599 | 0.457955 | 0.388898 | 0.25806504 | U11872_at | Interleukin-8 receptor type B (IL8RB) mRNA, splice variant IL8RB1, partial cds |
| 189 | Ovary | 0.3406475 | 0.457388 | 0.388815 | 0.25793046 | U53442_at | P38Beta MAP kinase mRNA |
| 190 | Ovary | 0.340593 | 0.4573231 | 0.388576 | 0.25769994 | M13903_at | Involucrin gene, exon 2 |
| 191 | Ovary | 0.3402839 | 0.4570587 | 0.388246 | 0.25754994 | X69910_at | P63 mRNA for transmembrane protein |
| 192 | Ovary | 0.339761 | 0.4569697 | 0.388047 | 0.25725085 | L18877_f_at | MELANOMA-ASSOCIATED ANTIGEN 12 |
| 193 | Ovary | 0.3396801 | 0.4561032 | 0.387903 | 0.2569487 | U89606_at | Pyridoxal kinase mRNA |
| 194 | Ovary | 0.3395448 | 0.4555301 | 0.387711 | 0.256757 | Z22536_at | SERINE/THREONINE-PROTEIN KINASE RECEPTOR R2 PRECURSOR |
| 195 | Ovary | 0.3384668 | 0.4552065 | 0.387684 | 0.2565639 | U08049_at | Peripheral myelin protein-22 (PMP22) gene, non-coding exon 1A |
| 196 | Ovary | 0.3383509 | 0.4548742 | 0.387421 | 0.25635135 | D17525_at | CRARF C4/C2 activating component of Ra-reactive factor |
| 197 | Ovary | 0.3381242 | 0.4547932 | 0.386991 | 0.2561573 | X63359_at | UDP-GLUCURONOSYLTRANSFERASE 2B10 PRECURSOR, MICROSOMAL |
| 198 | Ovary | 0.3380196 | 0.4547619 | 0.386978 | 0.25594023 | S79267_at | CD4 CD4 antigen (p55) |
| 199 | Ovary | 0.3379935 | 0.4547222 | 0.386926 | 0.25571144 | U90336_at | PEG3 mRNA, partial cds |
| 200 | Ovary | 0.3377791 | 0.4544876 | 0.386665 | 0.255556 | Z17240_at | HMG2 High-mobility group (nonhistone chromosomal) protein 2 |
| 201 | Ovary | 0.3376427 | 0.453914 | 0.386597 | 0.25532442 | L11370_at | Protocadherin 42 mRNA for abbreviated PC42 |
| 202 | Ovary | 0.3376159 | 0.453831 | 0.386409 | 0.2550344 | U53786_at | EVPL Envoplakin |
| 203 | Ovary | 0.337601 | 0.4536987 | 0.385996 | 0.25485766 | U85658_at | Transcription factor ERF-1 mRNA |
| 204 | Ovary | 0.3375918 | 0.4536511 | 0.385611 | 0.25462577 | U28055_at | MST1 Macrophage stimulating 1 (hepatocyte growth factor-like) |
| 205 | Ovary | 0.3374082 | 0.4536158 | 0.385451 | 0.25447085 | U18914_at | 19.8 kDa protein mRNA |
| 206 | Ovary | 0.3372495 | 0.4533797 | 0.385156 | 0.25425944 | HG742-HT742_at | Latent Membrane Protein Lmp1 |
| 207 | Ovary | 0.3370855 | 0.4532545 | 0.384975 | 0.25440849 | L36644_at | Receptor protein-tyrosine kinase (HEK7) mRNA, 3' end |
| 208 | Ovary | 0.3370002 | 0.4531988 | 0.384794 | 0.25390726 | X78416_s_at | CSN1 Casein, alpha S1 |
| 209 | Ovary | 0.3360256 | 0.4529272 | 0.384738 | 0.25370634 | AC000061_cds2_at | WUGSC:H_133K23.1c gene extracted from Human BAC clone 133K23 from 7q31.2 |
| 210 | Ovary | 0.3356686 | 0.4527278 | 0.384636 | 0.25341874 | RC_AA4958 11_at | EST: zw05c08.s1 Soares NhHMPu S1 Homo sapiens cDNA clone 768398 3', mRNA sequence. (from Genbank) |
| 211 | Ovary | 0.3355818 | 0.45268373 | 0.384422 | 0.2531499 | X97198_at | Receptor protein tyrosine phosphatase hPTP-J precursor, mRNA |
| 212 | Ovary | 0.335531 | 0.4526272 | 0.384402 | 0.25298935 | U58675_cds2_at | OR17-40 gene extracted from Human olfactory receptor gene cluster on chromosome 17, OR17-228 and OR17-40, and OR17-24 and OR17-25 pseudogenes |
| 213 | Ovary | 0.3352304 | 0.4523008 | 0.384103 | 0.2528791 | HG1148-HT1148_at | Llipopolysaccharide-Binding Protein |

FIG. 10I

| # | Tissue | | | | Accession | Description |
|---|---|---|---|---|---|---|
| 214 | Ovary | 0.3348942 | 0.4522636 | 0.383862 | 0.25257525 W25945_at | EST: 17c5 Human retina cDNA randomly primed sublibrary Homo sapiens cDNA, mRNA sequence. (from Genbank) |
| 215 | Ovary | 0.3334721 | 0.4520645 | 0.383773 | 0.2523241 HT3647_at HG3454- | Zinc Finger Protein 20 |
| 216 | Ovary | 0.3333991 | 0.4519715 | 0.383731 | 0.25216863 U60116_at | Skeletal muscle LIM-protein SLIM2 mRNA, partial cds |
| 217 | Ovary | 0.3331086 | 0.4513786 | 0.383329 | 0.25193855 HT45113_at HG4243- | Zinc Finger Protein Znf155 |
| 218 | Ovary | 0.3324413 | 0.4504939 | 0.382929 | 0.25163853 M61176_at | BDNF Brain-derived neurotrophic factor |
| 219 | Ovary | 0.3323246 | 0.4504926 | 0.382833 | 0.25137806 M82783_at | NAGA N-acetylgalactosaminidase, alpha- |
| 220 | Ovary | 0.3317945 | 0.4502795 | 0.38323 | 0.25126776 D63483_at | KIAA0149 gene |
| 221 | Ovary | 0.3312594 | 0.4501259 | 0.382237 | 0.25102973 J03507_at | C7 Complement component 7 |
| | | | | | | TFAP4 Transcription factor AP-4 (activating enhancer-binding protein 4) |
| 222 | Ovary | 0.3302882 | 0.450061 | 0.382089 | 0.25088960 S73885_s_at | |
| 223 | Ovary | 0.3302741 | 0.4500556 | 0.381631 | 0.25060543 L49054_at | T(3;5)(q25.1;p34) fusion gene NPM-MLF1 mRNA |
| 224 | Ovary | 0.3300763 | 0.4500448 | 0.381519 | 0.2504044 M93143_at | PLGL Plasminogen-like protein |
| 225 | Ovary | 0.3291991 | 0.4498737 | 0.381372 | 0.2503395 U04520_at | COL4A5 Collagen, type IV, alpha 5 (Alport syndrome) |
| 226 | Ovary | 0.3290296 | 0.4497706 | 0.3813 | 0.25016794 U58516_at | Breast epithelial antigen BA46 mRNA |
| 227 | Ovary | 0.3285824 | 0.4492782 | 0.381233 | 0.24989246 J05582_s_at U10667_s_a | MUC1 Mucin 1, transmembrane |
| 228 | Ovary | 0.3285583 | 0.4488469 | 0.381188 | 0.24965535 t | MAGE-4a antigen (MAGE4a) gene |
| | | | | | | Heterogeneous nuclear ribonucleoprotein D (hnRNP D), partial cds, clone ctx4 |
| 229 | Ovary | 0.3284228 | 0.4485668 | 0.380986 | 0.24938098 U02019_at X87871_s_a | |
| 230 | Ovary | 0.3282152 | 0.4485668 | 0.38078 | 0.24931112 t | HEPATOCYTE NUCLEAR FACTOR 4 |
| 231 | Ovary | 0.3277755 | 0.4478116 | 0.380602 | 0.2491276 U76010_at | Putative zinc transporter ZnT-3 (ZnT-3) mRNA |
| 232 | Ovary | 0.3276983 | 0.4470856 | 0.380353 | 0.24907762 Z48511_at | XG mRNA (clone PEP11) |
| 233 | Ovary | 0.3275667 | 0.4470595 | 0.379805 | 0.24880347 U02632_at | Calcium-activated potassium channel mRNA, partial cds |
| | | | | | | EST: zr82h02.s1 Soares NhHMPu S1 Homo sapiens cDNA clone 682227 3', mRNA sequence. (from Genbank) |
| 234 | Ovary | 0.327109 | 0.4468249 | 0.379314 | 0.2486329768 RC_AA2566 | |
| 235 | Ovary | 0.327092 | 0.4467199 | 0.379079 | 0.24842624 U39487_at | XDH Xanthine dehydrogenase |
| 236 | Ovary | 0.3268701 | 0.4465624 | 0.379028 | 0.24830648 D42073_at HG4533- | Reticulocalbin |
| 237 | Ovary | 0.3265834 | 0.446451 | 0.378525 | 0.24812 HT49938_at | Kallistatin, Protease Inhibitor 4 |
| 238 | Ovary | 0.3263997 | 0.4461886 | 0.378508 | 0.24797988 J05682_at | ATP6D ATPase, H+ transporting, lysosomal (vacuolar proton pump) 42kD |
| 239 | Ovary | 0.3263054 | 0.4461799 | 0.378473 | 0.24777484 L20861_at | WNT5A Wingless-type MMTV integration site 5A, human homolog |
| 240 | Ovary | 0.3255011 | 0.4460755 | 0.378191 | 0.24744873 J04164_at | RPS3 Ribosomal protein S3 |

FIG. 10J

| # | Tissue | | | | Accession | Description |
|---|---|---|---|---|---|---|
| 241 | Ovary | 0.3252869 | 0.4458446 | 0.378008 | 0.247259130_07_at | EST: zx87c05.s1 Soares ovary tumor NbHOT Homo sapiens cDNA clone 810728 3', mRNA sequence. (from Genbank) |
| 242 | Ovary | 0.3250082 | 0.4456842 | 0.377766 | 0.247007190 U72512_at | B-cell receptor associated protein (hBAP) alternatively spliced mRNA, partial 3'UTR |
| 243 | Ovary | 0.3244113 | 0.4454906 | 0.377583 | 0.246845360 Y10512_at | CD282 protein |
| 244 | Ovary | 0.3241328 | 0.4453909 | 0.377294 | 0.246717840 U12139_at | Alpha1(XI) collagen (COL11A1) gene, 5' region and exon 1 |
| 245 | Ovary | 0.3239564 | 0.4452778 | 0.377194 | 0.246473920 M24248_at | MYL3 Myosin, light polypeptide 3, alkali; ventricular, skeletal, slow |
| 246 | Ovary | 0.3235721 | 0.4452037 | 0.376603 | 0.246259760 S65583_rna | SP-10=intra-acrosomal protein [alternatively spliced] [human, liver, Genomic, 2339 nt 4 segments] |
| | | | | | 1_at L00137_cds | GHrF gene (growth hormone releasing factor) extracted from Human |
| 247 | Ovary | 0.3228675 | 0.4447861 | 0.376429 | 0.246115490 1_at | growth hormone-releasing factor (GHF) gene, exon 1 ( |
| 248 | Ovary | 0.321914 | 0.4445459 | 0.376367 | 0.245828120 L13042_at | VITAMIN D-DEPENDENT CALCIUM-BINDING PROTEIN |
| | | | | | HG4113-HT4383_s_a | |
| 249 | Ovary | 0.3206765 | 0.4444298 | 0.376233 | 0.245719210 t | Olfactory Receptor Or17-201 |
| 250 | Ovary | 0.320379 | 0.444367 | 0.375944 | 0.245553804 W28734_at | EST: 51a1l Human retina cDNA randomly primed sublibrary Homo sapiens cDNA, mRNA sequence. (from Genbank) |
| 251 | Ovary | 0.3195731 | 0.4443653 | 0.375714 | 0.245144770 RC_AA4306 74_at | EST: zw26d12.s1 Soares ovary tumor NbHOT Homo sapiens cDNA clone 770423 3', mRNA sequence. (from Genbank) |
| 252 | Ovary | 0.3183776 | 0.4441814 | 0.375474 | 0.245004370 D83542_at | Cadherin-15 |
| | | | | | RC_AA0046 | EST: zh92b04.s1 Soares fetal liver spleen 1NFLS S1 Homo sapiens |
| 253 | Ovary | 0.3187421 | 0.4438948 | 0.375311 | 0.244882380 37_at | cDNA clone 428719 3', mRNA sequence. (from Genbank) |
| 254 | Ovary | 0.3183998 | 0.4437257 | 0.375202 | 0.244618060 U80457_at | Transcription factor SIM2 long form mRNA |
| | | | | | HG1723- | |
| 255 | Ovary | 0.3183529 | 0.4437001 | 0.374968 | 0.244433330 HT1729_at | Macrophage Scavenger Receptor, Alt. Splice 2 |
| 256 | Ovary | 0.3181185 | 0.4435859 | 0.374935 | 0.244350240 X51630_at | WT1 Wilms tumor 1 |
| 257 | Ovary | 0.3176007 | 0.4435591 | 0.374511 | 0.244075830 U58130_at | Bumetanide-sensitive Na-K-2Cl cotransporter (NKCC2) mRNA |
| | | | | | X59842_rna | |
| 258 | Ovary | 0.3170546 | 0.4430474 | 0.374257 | 0.243906041 s_at | PBX2 mRNA |
| 259 | Ovary | 0.3168788 | 0.4423561 | 0.374224 | 0.243750530 X14766_at | GABRA1 Gamma-aminobutyric acid (GABA) A receptor, alpha 1 |
| 260 | Ovary | 0.3168087 | 0.442224 | 0.373952 | 0.243592620 D13643_at | KIAA0018 gene |
| | | | | | MB1780_cds | SMPD1 gene (acid sphingomyelinase) extracted from Homo sapiens |
| 261 | Ovary | 0.3161633 | 0.4417891 | 0.373813 | 0.243292285_at | acid sphingomyelinase (SMPD1) gene, ORF's 1-3's |
| | | | | | HG3995- | |
| 262 | Ovary | 0.3159532 | 0.4416606 | 0.373813 | 0.243112770 HT4265_at | Cpg-Enriched Dna, Clone S19 |
| 263 | Ovary | 0.3158379 | 0.4416436 | 0.373691 | 0.242957710 U28369_at | Semaphorin V mRNA |
| 264 | Ovary | 0.3154985 | 0.4409589 | 0.373489 | 0.242480720 U14550_at | Sialyltransferase SThM (sthm) mRNA |
| 265 | Ovary | 0.315418 | 0.4409183 | 0.37329 | 0.242517040 U83192_at | Post-synaptic density protein 95 (PSD95) mRNA |

FIG. 10K

| | | | | | |
|---|---|---|---|---|---|
| 266 | Ovary | 0.315358 | 0.4408466 | 0.372938 | 0.24244083 | X81836_s_at | Dents Disease candidate gene |
| 267 | Ovary | 0.3152581 | 0.440784 | 0.372877 | 0.24219371 | U43753_cds2_at | Frataxin (FRDA) gene, promoter region and |
| 268 | Ovary | 0.3143329 | 0.4405132 | 0.37271 | 0.2420173 | M32053_at | H19 RNA gene |
| 269 | Ovary | 0.3141116 | 0.4393335 | 0.37271 | 0.24192733 | AC002398_cds4_at | Human DNA from chromosome 19-specific cosmid F25965, genomic sequence::Human DNA from chromosome 19-specific cosmid F25965, genomic sequence::Human DNA from chromosome 19-specific cosmid F25965, genomic sequence |
| 270 | Ovary | 0.313858 | 0.4392479 | 0.372627 | 0.24169725 | D49487_s_at | LEP Leptin (murine obesity homolog) |
| 271 | Ovary | 0.3138369 | 0.4392319 | 0.372348 | 0.24149735 | X59434_at | TST Thiosulfate sulfurtransferase (rhodanese) |
| 272 | Ovary | 0.3138215 | 0.4391035 | 0.37204 | 0.24139927 | AD000684_cds1_at | LISCH7 gene (liver-specific bHLH-Zip transcription factor) extracted from Homo sapiens DNA from chromosome 19-cosmid R30879 containing USF2, genomic sequence |
| 273 | Ovary | 0.3136735 | 0.4388695 | 0.371979 | 0.24130292 | C00476_at | EST: HUMGS0007866, Human Gene Signature, 3'-directed cDNA sequence, mRNA sequence. (from Genbank) |
| 274 | Ovary | 0.3136552 | 0.4386366 | 0.371193 | 0.24106702 | RC_AA4602 57_at | EST: zx67d07.s1 Soares total fetus Nb2HF8.9w Homo sapiens cDNA clone 796525 3', mRNA sequence. (from Genbank) |
| 275 | Ovary | 0.3134788 | 0.438628 | 0.371822 | 0.24082136 | X52005_at | MYL4 Myosin, light polypeptide 4, alkali; atrial, embryonic |
| 276 | Ovary | 0.3134194 | 0.4384591 | 0.371751 | 0.24064212 | N75646_at | EST: yv29a08.r1 Homo sapiens cDNA clone 244118 5'. (from Genbank) |
| 277 | Ovary | 0.3133209 | 0.4382579 | 0.371643 | 0.2405207 | L13436_at | Guanylate cyclase mRNA, complete mature peptide |
| 278 | Ovary | 0.3131231 | 0.4378072 | 0.371128 | 0.24030808 | D50911_at | KIAA0121 gene |
| 279 | Ovary | 0.313045 | 0.4376422 | 0.371261 | 0.24015269 | X89267_at | UROD Uroporphyrinogen decarboxylase |
| 280 | Ovary | 0.3129973 | 0.4373537 | 0.371089 | 0.2398905 | HG2148-HT2218_f_at | Mucin 3, Intestinal (Gb:M55406) |
| 281 | Ovary | 0.3125866 | 0.437321 | 0.3709 | 0.23970832 | L02950_at | CRYM Crystallin Mu |
| 282 | Ovary | 0.3122273 | 0.4373119 | 0.370796 | 0.23944938 | J03756_at | SOMATOTROPIN PRECURSOR |
| 283 | Ovary | 0.3121966 | 0.4373119 | 0.370324 | 0.23923942 | L34355_at | (clone p4) 50 kD dystrophin-associated glycoprotein mRNA |
| 284 | Ovary | 0.3116051 | 0.4372887 | 0.370259 | 0.23916294 | U00930_at | Clone CE29 8.1 (CAC)n/(GTG)n repeat-containing mRNA |
| 285 | Ovary | 0.3109543 | 0.437277 | 0.370071 | 0.23897909 | HG759-HT759_s_at | Adrenergic Receptor, Beta 1 |
| 286 | Ovary | 0.3109146 | 0.4370823 | 0.370071 | 0.23880526 | D90276_at | CGM7 Carcinoembryonic antigen gene family member 7 |
| 287 | Ovary | 0.3108355 | 0.4364497 | 0.369504 | 0.23868537 | L17330_at | Pre-T/NK cell associated protein (6H9A) mRNA |
| 288 | Ovary | 0.3104795 | 0.4364195 | 0.369475 | 0.23850334 | X80878_at | R kappa B mRNA |
| 289 | Ovary | 0.3104476 | 0.4362122 | 0.369455 | 0.23842709 | X66436_at | POSSIBLE GTP-BINDING PROTEIN HSR1 |

FIG. 10L

| # | Tissue | Val1 | Val2 | Val3 | ID | Accession | Description |
|---|---|---|---|---|---|---|---|
| 290 | Ovary | 0.3100228 | 0.4361731 | 0.369239 | 0.23822524 | N88827_at | EST: K5685F Fetal heart, Lambda ZAP Express Homo sapiens cDNA clone K5685 5' similar to EST(YI03A03.R1), mRNA sequence. (from Genbank) |
| 291 | Ovary | 0.3098479 | 0.4360671 | 0.369015 | 0.23805574 | HT831-HG831-HT831_at | Potassium Channel (Gb:L02752) |
| 292 | Ovary | 0.3097896 | 0.4359309 | 0.368798 | 0.23791076 | L77567_s_at | RPS11 Ribosomal protein S11 |
| 293 | Ovary | 0.3093366 | 0.4357427 | 0.368711 | 0.23770911 | HG2987-HT3136_s_a t | Vasoactive Intestinal Peptide |
| 294 | Ovary | 0.3089089 | 0.4356483 | 0.368693 | 0.23762587 | M60092_at | AMP DEAMINASE 1 |
| 295 | Ovary | 0.308522 | 0.4355986 | 0.368597 | 0.2375019 | M55153_at | PROTEIN-GLUTAMINE GAMMA-GLUTAMYL TRANSFERASE |
| 296 | Ovary | 0.3079246 | 0.4354538 | 0.368593 | 0.23741032 | U25771_at | ARF4L ADP-ribosylation factor 4-like |
| 297 | Ovary | 0.3070011 | 0.4354359 | 0.368269 | 0.23732395 | RC_AA4213 28_at | EST: zu27d04.s1 Soares ovary tumor NbHOT Homo sapiens cDNA clone 739207 3', mRNA sequence. (from Genbank) |
| 298 | Ovary | 0.3065926 | 0.4353176 | 0.368121 | 0.23716921 | RC_AA4577 18_at | EST: zx87d04.s1 Soares ovary tumor NbHOT Homo sapiens cDNA clone 810727 3', mRNA sequence. (from Genbank) |
| 299 | Ovary | 0.3059326 | 0.4349396 | 0.367913 | 0.23688458 | M74587_rna 1_s_at | Insulin-like growth factor binding protein (hIGFBP1) gene |
| 300 | Ovary | 0.3056498 | 0.4349167 | 0.367899 | 0.23680103 | J03133_at | SP1 Sp1 transcription factor |
| 301 | Ovary | 0.3053604 | 0.4349098 | 0.367662 | 0.23667708 | S81419_at | Dystrophin, dystrophin (Purkinje promoter, alternatively spliced) [human, cortical brain and adult heart, mRNA Partial, 377 nt] |
| 302 | Ovary | 0.3053014 | 0.4348318 | 0.367598 | 0.23656616 | HT2416_at HG2320-HG4234- | Integrin, Beta 3 Subunit |
| 303 | Ovary | 0.3051694 | 0.4346883 | 0.367539 | 0.23636462 | HT4504_at | Methylenetetrahydrofolate Reductase |
| 304 | Ovary | 0.3051249 | 0.4346043 | 0.367285 | 0.23607734 | X05615_at | Thyroglobulin |
| 305 | Ovary | 0.3050338 | 0.4344032 | 0.367263 | 0.23583615 | L13720_at | Growth-arrest-specific protein (gas) mRNA |
| 306 | Ovary | 0.3047769 | 0.4342573 | 0.367185 | 0.23563027 | U79302_at | Clone 23855 mRNA, partial cds |
| 307 | Ovary | 0.3046756 | 0.4341425 | 0.367072 | 0.23553297 | L25119_at | OPRM1 Opioid receptor, mu 1 |
| 308 | Ovary | 0.3040958 | 0.4340047 | 0.366745 | 0.23539943 | M59829_at | MHC class III HSP70-HOM gene (HLA) |
| 309 | Ovary | 0.3040667 | 0.4339595 | 0.366676 | 0.23525032 | Y14140_at | G protein gene encoding beta 3 subunit exon 1 and promoter |
| 310 | Ovary | 0.3038235 | 0.4337996 | 0.366388 | 0.235093821 | AA280228_a t | EST: zf04c11.r1 NCI_CGAP_GCB1 Homo sapiens cDNA clone IMAGE:712148 5', mRNA sequence. (from Genbank) |
| 311 | Ovary | 0.3037371 | 0.4337436 | 0.366339 | 0.23491555 | M87770_at | FGFR2 Fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 312 | Ovary | 0.3035098 | 0.4336832 | 0.366152 | 0.2348209 | M55210_at | LAMC1 Laminin, gamma 1 (formerly LAMB2) |
| 313 | Ovary | 0.3032565 | 0.4336724 | 0.366085 | 0.23461284 | M37075_at | MYL4 Myosin, light polypeptide 4, alkali; atrial; embryonic |

FIG. 10M

| # | Tissue | V1 | V2 | V3 | ID | Description |
|---|---|---|---|---|---|---|
| 314 | Ovary | 0.3031955 | 0.4333319 | 0.366029 | 0.23444179 L08488_at | INPP1 Inositol polyphosphate-1-phosphatase |
| 315 | Ovary | 0.3031398 | 0.433214 | 0.365609 | 0.23430899 M93036_at | MAJOR GASTROINTESTINAL TUMOR-ASSOCIATED PROTEIN GA733-2 PRECURSOR |
| 316 | Ovary | 0.3029516 | 0.4329197 | 0.365475 | 0.23417956 D87292_at | Rhodanese |
| 317 | Ovary | 0.3027791 | 0.4329096 | 0.365359 | 0.2340593 X14085_s_a t | GGTB2 Glycoprotein-4-beta-galactosyltransferase 2 |
| 318 | Ovary | 0.302771 | 0.4327172 | 0.36522 | 0.2338703 X91117_rna 1_at | HG NET gene exon 1 |
| 319 | Ovary | 0.302668 | 0.4326317 | 0.364835 | 0.2337195 U43292_at | MDS1B (MDS1) mRNA |
| 320 | Ovary | 0.3023225 | 0.4324317 | 0.364823 | 0.23363064 RC_AA0589 51_at | EST: zl96f07.s1 Stratagene corneal stroma (#937222) Homo sapiens cDNA clone 512485 3', mRNA sequence. (from Genbank) |
| 321 | Ovary | 0.3008312 | 0.4322963 | 0.364615 | 0.23348193 X72790_at | Endogenous retrovirus mRNA for ORF |
| 322 | Ovary | 0.3006096 | 0.4321942 | 0.364214 | 0.23329866 X51954_at | UCP gene for uncoupling protein exon 5 |
| 323 | Ovary | 0.3005936 | 0.4321432 | 0.363897 | 0.23317431 U25128_at | PTH2 parathyroid hormone receptor mRNA |
| 324 | Ovary | 0.2996019 | 0.4319474 | 0.363784 | 0.23300894 S69189_at | Peroxisomal acyl-coenzyme A oxidase [human, liver, mRNA, 3086 nt] |
| 325 | Ovary | 0.2993978 | 0.4319191 | 0.363499 | 0.23281892 U88063_at | Agouti (mouse) related protein |
| 326 | Ovary | 0.298642 | 0.4317655 | 0.363417 | 0.23270716 X01630_at | ASS Argininosuccinate synthetase |
| 327 | Ovary | 0.2986266 | 0.4316864 | 0.363316 | 0.23266083 U67934_at | 44.9 kDa protein C18B11 homolog gene, partial cds |
| 328 | Ovary | 0.298249 | 0.4316292 | 0.363211 | 0.23249696 Y11897_at | Brx gene 3'UTR |
| 329 | Ovary | 0.2980638 | 0.4312482 | 0.363091 | 0.23240772 L40157_at | P162 mRNA |
| 330 | Ovary | 0.2977973 | 0.4312281 | 0.362982 | 0.23223758 L33404_at | Stratum corneum chymotryptic enzyme mRNA |
| 331 | Ovary | 0.2977416 | 0.4311388 | 0.362896 | 0.23200443 D16350_at | SA mRNA for SA gene product |
| 332 | Ovary | 0.2976578 | 0.4310868 | 0.362844 | 0.23183209 X06268_at | COL2A1 Collagen, type II, alpha 1 (primary osteoarthritis, spondyloepiphyseal dysplasia, congenital) |
| 333 | Ovary | 0.2973583 | 0.4308829 | 0.362724 | 0.23157568 X87344_cds 10_r_at | DMA gene extracted from H.sapiens DMA, DMB, HLA-Z1, IPP2, LMP2, TAP1, LMP7, TAP2, DOB, DQB2 and RING8, 9, 13 and 14 genes |
| 334 | Ovary | 0.2973435 | 0.43010039 | 0.362447 | 0.23145604 M59979_at | PTGS1 Prostaglandin-endoperoxide synthase 1 (prostaglandin G/H synthase and cyclooxygenase) |
| 335 | Ovary | 0.2971261 | 0.4298395 | 0.362432 | 0.23133469 H42106_at | Integrin, alpha 6 |
| 336 | Ovary | 0.2969471 | 0.4291033 | 0.362424 | 0.2311644 U82311_at | Unknown protein mRNA, partial cds |
| 337 | Ovary | 0.2969405 | 0.4290307 | 0.362398 | 0.23105912 X12492_at | CCAAT BOX-BINDING TRANSCRIPTION FACTOR 1 |
| 338 | Ovary | 0.2962611 | 0.4290212 | 0.362163 | 0.23098865 L24559_at | POLA DNA polymerase alpha subunit |
| 339 | Ovary | 0.2959635 | 0.4289011 | 0.361954 | 0.23082802 Z37987_s_at | EEF1A1 Translation elongation factor 1-alpha-1 |
| 340 | Ovary | 0.2958476 | 0.42873 | 0.361728 | 0.23073515 M19169_at | Cystatin SN |
| 341 | Ovary | 0.2957599 | 0.4286155 | 0.361652 | 0.2305297 AA092261_a t | Secreted frizzled-related protein 1 |

FIG. 10N

| # | Tissue | | | | ID | Description |
|---|---|---|---|---|---|---|
| 342 | Ovary | 0.2956987 | 0.4283781 | 0.361518 | 0.23048693 U88902_cds 1_f_at | Integrase gene extracted from Human endogenous retrovirus H clone g10.34 integrase and putative envelope protein genes, partial cds |
| 343 | Ovary | 0.2955886 | 0.4281563 | 0.361164 | 0.23041068 X58079_at | S100 alpha protein |
| 344 | Ovary | 0.2954217 | 0.4278579 | 0.361133 | 0.23019546 AA393164_s_at | Mammaglobin 2 |
| 345 | Ovary | 0.2954149 | 0.4277857 | 0.360758 | 0.23000894 K01900_at | IFNA8 Interferon, alpha 8 |
| 346 | Ovary | 0.2946013 | 0.4276598 | 0.360738 | 0.22971661 S37730_s_at | Insulin-like growth factor binding protein-2 [human, placenta, Genomic, 1342 nt, segment 4 of 4] |
| 347 | Ovary | 0.293713 | 0.4275924 | 0.360667 | 0.22961067 J03915_s_at | CHGA Chromogranin A |
| 348 | Ovary | 0.2936141 | 0.4274464 | 0.360601 | 0.22947325 W67675_at | EST: zd37c12.r1 Soares fetal heart NbHH19W Homo sapiens cDNA clone 342838 5', mRNA sequence. (from Genbank) |
| 349 | Ovary | 0.2933178 | 0.4273311 | 0.360455 | 0.22929354 N73185_at | EST: yv46a09.r1 Homo sapiens cDNA clone 245752 5'. (from Genbank) |
| 350 | Ovary | 0.2933112 | 0.4273259 | 0.360337 | 0.22920062 U59228_at | EDA Ectodermal dysplasia protein |
| 351 | Ovary | 0.2921804 | 0.4272642 | 0.360107 | 0.22906823 Z73677_at | Gene encoding plakophilin 1b |
| 352 | Ovary | 0.2918409 | 0.4271641 | 0.360081 | 0.22898206 U32659_at | CTLA8 Cytotoxic T lymphocyte-associated serine esterase 8 |
| 353 | Ovary | 0.2914525 | 0.4271562 | 0.359842 | 0.22881638 X99140_at | Hair keratin, hHb5 |
| 354 | Ovary | 0.2914246 | 0.4269381 | 0.359765 | 0.22886694 L25286_s_at RC_AA4539 | COL15A1 Collagen, type XV, alpha 1 |
| 355 | Ovary | 0.291405 | 0.4269082 | 0.359653 | 0.22851677 88_at | EST: zx46a03.s1 Soares testis NHT Homo sapiens cDNA clone 795244 3', mRNA sequence. (from Genbank) |
| 356 | Ovary | 0.2913615 | 0.4268948 | 0.359592 | 0.2283418 U70981_at | IL13 receptor |
| 357 | Ovary | 0.291014 | 0.4268904 | 0.359579 | 0.22822042 AA478835_at | EST: zu43g02.r1 Soares ovary tumor NbHOT Homo sapiens cDNA clone 740786 5' similar to TR:G1001232 G1001232 HYPOTHETICAL 21.5 KD PROTEIN_; mRNA sequence. (from Genbank) |
| 358 | Ovary | 0.2908981 | 0.4265733 | 0.359224 | 0.22809975 AA410617_s_at | EST: zf29h04.r1 Soares ovary tumor NbHOT Homo sapiens cDNA clone 723799 5', mRNA sequence. (from Genbank) |
| 359 | Ovary | 0.2907844 | 0.4265711 | 0.35906 | 0.22784252 HG3517-HT3711_at | Alpha-1-Antitrypsin, 5' End |
| 360 | Ovary | 0.2907384 | 0.4265699 | 0.358976 | 0.22776932 U66711_ma 1_s_at | Ly-6-related protein (9804) gene |
| 361 | Ovary | 0.2906261 | 0.4264962 | 0.358718 | 0.22767004 D49394_at | H1R3 5-hydroxytryptamine (serotonin) receptor 3 |
| 362 | Ovary | 0.2897787 | 0.4263888 | 0.358709 | 0.22759067 H42262_at | EST: yo63a04.r1 Homo sapiens cDNA clone 182574 5'. (from Genbank) |
| 363 | Ovary | 0.289736 | 0.426195 | 0.358487 | 0.2274408 X63187_at | HE4 mRNA for extracellular proteinase inhibitor homologue |
| 364 | Ovary | 0.2895342 | 0.4261453 | 0.358302 | 0.22731112 RC_AA4865 79_at | EST: ab16f05.s1 Stratagene lung (#937210) Homo sapiens cDNA clone 840993 3', mRNA sequence. (from Genbank) |

FIG. 10O

| | | | | | | |
|---|---|---|---|---|---|---|
| 365 | Ovary | 0.2889626 | 0.4259148 | 0.358075 | 0.22714211 | D14520_at | GC-Box binding protein BTEB2 |
| | | | | | X54667_s_a | | |
| 366 | Ovary | 0.2888683 | 0.4256082 | 0.358058 | 0.22701569 | t | CST4 Cystatin S |
| 367 | Ovary | 0.2886474 | 0.4253817 | 0.358006 | 0.22686821 | X67325_at | INTERFERON-ALPHA INDUCED 11.5 KD PROTEIN |
| 368 | Ovary | 0.2886202 | 0.4253469 | 0.357974 | 0.22672059 | U26424_at | Stress responsive serine/threonine protein kinase Krs-1 mRNA |
| 369 | Ovary | 0.2883739 | 0.4253242 | 0.357898 | 0.22655448 | X52022_at | RNA for type VI collagen alpha3 chain |
| 370 | Ovary | 0.2883459 | 0.4251092 | 0.357682 | 0.22650806 | M28983_at | IL1A interleukin 1, alpha |
| 371 | Ovary | 0.2882215 | 0.4251061 | 0.357628 | 0.22635423 | D25248_at | Randomly sequenced mRNA |
| 372 | Ovary | 0.2880521 | 0.4248702 | 0.357552 | 0.22626412 | S77812_at | FLT1 Fms-related tyrosine kinase 1 (vascular endothelial growth factor/vascular permeability factor receptor) |
| 373 | Ovary | 0.2877684 | 0.4242862 | 0.357377 | 0.22598389 | U09609_at | NFKB2 Nuclear factor of kappa light polypeptide gene enhancer in B-cells 2 (p49/p100) |
| 374 | Ovary | 0.2876712 | 0.4240072 | 0.357257 | 0.22579683 | M91083_at | DNA-binding protein (HRC1) mRNA |
| 375 | Ovary | 0.2873843 | 0.4239157 | 0.357165 | 0.22561815 | RC_AA4125 05_at | EST: zt97b09.s1 Soares testis NHT Homo sapiens cDNA clone 730265 3', mRNA sequence. (from Genbank) |
| 376 | Ovary | 0.287114 | 0.4238419 | 0.356904 | 0.22547539 | Y08134_at-2 | H.sapiens mRNA for ASM-like phosphodiesterase 3b |
| 377 | Ovary | 0.287114 | 0.4238222 | 0.356564 | 0.22538858 | Y08134_at | ASM-like phosphodiesterase 3b |
| 378 | Ovary | 0.2866591 | 0.423739 | 0.356299 | 0.22525188 | J04152_rna1 s_at | M1S1 gene extracted from Human gastrointestinal tumor-associated antigen GA733-1 protein gene, clone 05516 |
| 379 | Ovary | 0.2865467 | 0.4235776 | 0.356221 | 0.22509935 | D31889_at | KIAA0072 gene, partial cds |
| 380 | Ovary | 0.2864013 | 0.4235012 | 0.356174 | 0.22501242 | M57506_rna 1_at | SCYA1 gene (secreted protein I-309) extracted from Human secreted protein (I-309) gene |
| 381 | Ovary | 0.2860443 | 0.4233095 | 0.356154 | 0.22491688 | RC_AA4266 40_at | EST: zv47h07.s1 Soares ovary tumor NbHOT Homo sapiens cDNA clone 756829 3', mRNA sequence. (from Genbank) |
| 382 | Ovary | 0.2860022 | 0.4233008 | 0.355837 | 0.22474885 | X68994_at | CREB gene, exon Y |
| 383 | Ovary | 0.2853175 | 0.4231295 | 0.355707 | 0.22464982 | U34380_rna 1_s_at | TEC gene extracted from Human protein tyrosine kinase TEC (tec) gene, partial cds, and tyrosine kinase TXK (txk) gene |
| 384 | Ovary | 0.2852303 | 0.4227576 | 0.355449 | 0.22454898 | M60828_at | FGF7 Fibroblast growth factor 7 (keratinocyte growth factor) |
| 385 | Ovary | 0.2847958 | 0.4227187 | 0.355266 | 0.22443832 | D28137_at | RPS11 Ribosomal protein S11 |
| 386 | Ovary | 0.2846023 | 0.4227178 | 0.35523 | 0.22441494 | HG3998-HT4268_at | L-Glycerol-3-Phosphate:Nad+ Oxidoreductase |
| 387 | Ovary | 0.2845584 | 0.4226161 | 0.355099 | 0.22407779 | X13930_f_at | CYTOCHROME P450 IIA6 |
| 388 | Ovary | 0.2845058 | 0.4223986 | 0.354692 | 0.22399472 | RC_AA4613 00_at | EST: zx65a08.s1 Soares total fetus Nb2HF8.9w Homo sapiens cDNA clone 796310 3', mRNA sequence. (from Genbank) |
| | | | | | X57351_s_a | | |
| 389 | Ovary | 0.2842396 | 0.4219515 | 0.354627 | 0.22388555 | t | RPS3 Ribosomal protein S3 |
| 390 | Ovary | 0.283926 | 0.4219432 | 0.354536 | 0.22375253 | U07664_at | HB9 homeobox gene |
| 391 | Ovary | 0.2837994 | 0.4219196 | 0.354363 | 0.22355713 | Y09912_rna 1_at | AP-2 beta gene |

FIG. 10P

| | | | | | |
|---|---|---|---|---|---|
| 392 | Ovary | 0.2837583 | 0.4218976 | 0.354064 | 0.2233342 | U14528_at | DTD Diastrophic dysplasia (sulfate transporter) |
| 393 | Ovary | 0.2835562 | 0.4218059 | 0.354032 | 0.22326332 | M24470_at | G6PD Glucose-6-phosphate dehydrogenase |
| 394 | Ovary | 0.2834089 | 0.4217534 | 0.353982 | 0.22313873 | X99142_at | Hair keratin, hHb6 |
| 395 | Ovary | 0.2831879 | 0.4216939 | 0.3538 | 0.22303075 | U90910_at-2 | Human clone 23564 mRNA sequence |
| 396 | Ovary | 0.2831879 | 0.4215317 | 0.353616 | 0.22290865 | U90910_at | Clone 23564 mRNA sequence |
| 397 | Ovary | 0.2830176 | 0.4215039 | 0.353524 | 0.2227879 | HG4704-HT5146_at | Glial Growth Factor 2 |
| 398 | Ovary | 0.2829984 | 0.4214258 | 0.35319 | 0.22263035 | AFFX-BioDn-5_st | AFFX-BioDn-5_st (endogenous control) |
| 399 | Ovary | 0.2829984 | 0.4213758 | 0.352988 | 0.22252668 | AFFX-BioDn-5_st-2 | AFFX-BioDn-5_st (miscellaneous control - 11k chips) |
| 400 | Ovary | 0.2829951 | 0.4213321 | 0.352858 | 0.22237244 | RC_AA39996 33_at | EST: zj93e07.s1 Soares testis NHT Homo sapiens cDNA clone 729924 3', mRNA sequence. (from Genbank) |
| 401 | Ovary | 0.282854 | 0.4212547 | 0.352814 | 0.22226556 | M64231_rna 1_at | Spermidine synthase gene |
| 402 | Ovary | 0.2826962 | 0.4210324 | 0.352545 | 0.2220912 | U89916_at | Putative OSP like protein mRNA, partial cds |
| 403 | Ovary | 0.2825628 | 0.4209334 | 0.352474 | 0.22199528 | M54914_s_a t | FOLLITROPIN BETA CHAIN PRECURSOR |
| 404 | Ovary | 0.2820657 | 0.4209192 | 0.352473 | 0.22189172 | D38535_at | PK-120 |
| 405 | Ovary | 0.282002 | 0.4207298 | 0.352153 | 0.22175573 | U72517_at | Alternatively spliced variant C7f (C3f) mRNA, partial 3'UTR |
| 406 | Ovary | 0.2812738 | 0.4207082 | 0.352058 | 0.22154498 | M61916_at | LAMB1 Laminin B1 chain |
| 407 | Ovary | 0.2811636 | 0.4205895 | 0.351965 | 0.22145319 | L32179_at | Arylacetamide deacetylase mRNA |
| 408 | Ovary | 0.2809862 | 0.4199428 | 0.351854 | 0.22126916 | L27943_at | CDA Cytidine deaminase |
| 409 | Ovary | 0.2801471 | 0.4198133 | 0.351516 | 0.22116962 | HG2668-HT2764_at | Bradykinin Receptor |
| 410 | Ovary | 0.2799327 | 0.4196879 | 0.351427 | 0.2210543 | U67674_at | SLC15A2 Solute carrier family 15 (H+/peptide transporter), member 2 |
| 411 | Ovary | 0.2792108 | 0.4196585 | 0.351291 | 0.22100516 | HG3231-HT3408_at | Protease Receptor-1, Effector Cell |
| 412 | Ovary | 0.2788408 | 0.4193187 | 0.35129 | 0.2208674 | X55005_rna 1_at | C-erbA-1 mRNA for thyroid hormone receptor alpha |
| 413 | Ovary | 0.2784462 | 0.4192111 | 0.35129 | 0.2207376 | U66578_at | Purinergic receptor P2Y9 mRNA |
| 414 | Ovary | 0.2783903 | 0.419054 | 0.351271 | 0.22054425 | M87284_at | 69971 KD |
| 415 | Ovary | 0.2772172 | 0.4189279 | 0.351197 | 0.22046967 | X67697_at | SPERM ANTIGEN HE2 PRECURSOR |
| 416 | Ovary | 0.2767097 | 0.4187665 | 0.350903 | 0.2202613 | M88163_at | SNF2L1 SNF2 (sucrose nonfermenting, yeast, homolog)-like 1 |
| 417 | Ovary | 0.2766607 | 0.4187465 | 0.350744 | 0.22012547 | U28758_s_a | NMDA receptor subtype 2B subunit (GRIN2B) mRNA, partial cds |
| 418 | Ovary | 0.2753914 | 0.4184718 | 0.350728 | 0.21995997 | H52378_at | Spectrin, alpha, erythrocytic 1 (elliptocytosis 2) |
| 419 | Ovary | 0.2751567 | 0.418268 | 0.350681 | 0.21987474 | U07695_at | HTK Hepatoma transmembrane kinase |

FIG. 10Q

| # | Tissue | | | | | Description |
|---|---|---|---|---|---|---|
| 420 | Ovary | 0.2750188 | 0.4181652 | 0.350208 | 0.21978685 | X52001_at | EDN3 Endothelin 3 |
| 421 | Ovary | 0.2748964 | 0.4181488 | 0.350177 | 0.21967626 | X80915_rna1_at | Gdf5 gene |
| 422 | Ovary | 0.2746596 | 0.4181164 | 0.350161 | 0.2195222 | M57892_at | CA6 Carbonic anhydrase VI |
| 423 | Ovary | 0.274656 | 0.4181044 | 0.349742 | 0.21937796 | U31903_s_at | CREB-RP (creb-rp) mRNA |
| 424 | Ovary | 0.2743574 | 0.4180789 | 0.349615 | 0.21914612 | D88532_at | P55pik |
| 425 | Ovary | 0.2742131 | 0.4178208 | 0.349531 | 0.21911949 | M31651_at | SHBG Sex hormone-binding globulin |
| 426 | Ovary | 0.2741422 | 0.4177589 | 0.349496 | 0.21893924 | W01059_at | EST: za55e09.r1 Soares fetal liver spleen 1NFLS Homo sapiens cDNA clone 296488 5', mRNA sequence. (from Genbank) |
| 427 | Ovary | 0.2741136 | 0.4176905 | 0.349296 | 0.2189072 | U23430_s_at | CCKAR Cholecystokinin A receptor |
| 428 | Ovary | 0.2737004 | 0.4176888 | 0.34927 | 0.21882677 | L42379_at | Quiescin (Q6) mRNA, partial cds |
| 429 | Ovary | 0.2733313 | 0.4176083 | 0.349171 | 0.21867739 | X98253_at | ZNF183 gene |
| 430 | Ovary | 0.273136 | 0.4174984 | 0.349166 | 0.21854211 | L36475_at | Olfactory receptor-like gene |
| 431 | Ovary | 0.2729535 | 0.4172265 | 0.349072 | 0.21845086 | U65011_at | Preferentially expressed antigen of melanoma (PRAME) mRNA |
| 432 | Ovary | 0.2727675 | 0.4168316 | 0.349072 | 0.21834032 | M38258_at | RARG Retinoic acid receptor, gamma 1 |
| 433 | Ovary | 0.2725751 | 0.4167488 | 0.349056 | 0.21828201 | X72475_at | GLUL Glutamate-ammonia ligase (glutamine synthase) |
| 434 | Ovary | 0.272344 | 0.4162361 | 0.348809 | 0.21812978 | L33881_at | PRKCI Protein kinase C, iota |
| 435 | Ovary | 0.272269 | 0.4160873 | 0.348564 | 0.2180722 | RC_AA3985733_at | EST: zt73b05.s1 Soares testis NHT Homo sapiens cDNA clone 727953 3', mRNA sequence. (from Genbank) |
| 436 | Ovary | 0.2721697 | 0.4160379 | 0.348491 | 0.2178827 | AC000099_at | Metabotropic glutamate receptor 8 mRNA |
| 437 | Ovary | 0.2718494 | 0.4158911 | 0.348257 | 0.21782205 | AA292466_s_at | Claudin 3 |
| 438 | Ovary | 0.2715959 | 0.4155899 | 0.34823 | 0.21763584 | W31287_at | EST: zb92a04.r1 Soares parathyroid tumor NbHPA Homo sapiens cDNA clone 320238 5', mRNA sequence. (from Genbank) |
| 439 | Ovary | 0.2713278 | 0.4154755 | 0.348108 | 0.2175184 | S71018_at | Cyclophilin C [human, kidney, mRNA, 883 nt] |
| 440 | Ovary | 0.2713278 | 0.4153767 | 0.347962 | 0.21740979 | S71018_at-2 | Peptidylprolyl isomerase C (cyclophilin C) |
| 441 | Ovary | 0.271245 | 0.41521 | 0.347832 | 0.21732847 | U20860_at | Angiotensin II type 2 receptor mRNA |
| 442 | Ovary | 0.2709535 | 0.4151868 | 0.347574 | 0.21723093 | M97815_at | CRABP2 Cellular retinoic acid-binding protein 2 |
| 443 | Ovary | 0.2705047 | 0.4151128 | 0.347446 | 0.21712686 | X52730_rna1_at | Phenylethanolamine n-methyltransferase gene extracted from Human gene for phenylethanolamine N-methylase (PNMT) (EC 2.1.1.28) |
| 444 | Ovary | 0.2703179 | 0.4149669 | 0.347257 | 0.21703608 | RC_AA227146_at | EST: zr22c03.s1 Stratagene NT2 neuronal precursor 937230 Homo sapiens cDNA clone 664132 3', mRNA sequence. (from Genbank) |
| 445 | Ovary | 0.2702496 | 0.4149245 | 0.347136 | 0.21695489 | U51586_at | Siah binding protein 1 (SiahBP1) mRNA, partial cds |

FIG. 10R

| # | Tissue | | | | | Description |
|---|---|---|---|---|---|---|
| 446 | Ovary | 0.2699719 | 0.4148539 | 0.347037 | 0.21679743 | M96739_at | NSCL-1 mRNA sequence |
| 447 | Ovary | 0.269469 | 0.4147767 | 0.346839 | AA292809_a t | | Xeroderma pigmentosum, complementation group F |
| 448 | Ovary | 0.2690276 | 0.4147117 | 0.346732 | 0.21669935 | U37219_at | Cyclophilin-like protein CyP-60 mRNA |
| 449 | Ovary | 0.2689862 | 0.4145296 | 0.346677 | 0.21647656 | M14764_at | NGFR Nerve growth factor receptor |
| 450 | Ovary | 0.2687894 | 0.4145218 | 0.346563 | 0.21638729 | M74509_s_a t | Endogenous retrovirus type C oncovirus sequence |
| 451 | Ovary | 0.2686271 | 0.4144711 | 0.346482 | 0.21618497 | U43177_at | Mpv17 protein (MPV17) gene, partial cds; and urocortin gene |
| 452 | Ovary | 0.2685032 | 0.4144135 | 0.346429 | 0.21612753 | S85963_at | Insulin receptor substrate-1 [human, skeletal muscle, mRNA, 5828 nt] |
| 453 | Ovary | 0.2682308 | 0.4143538 | 0.346429 | 0.21598002 | D31883_at | KIAA0059 gene |
| 454 | Ovary | 0.2681149 | 0.4142139 | 0.346415 | 0.21583405 | X96969_at | Urea transporter |
| 455 | Ovary | 0.2679211 | 0.4141609 | 0.346362 | 0.21579473 | N40774_at | EST: yw81e10.r1 Homo sapiens cDNA clone 258666 5'. (from Genbank) |
| 456 | Ovary | 0.2678742 | 0.4140211 | 0.346282 | 0.21570365 | L25081_at | ARH9 Aplysia ras-related homolog 9 |
| 457 | Ovary | 0.2678328 | 0.4139188 | 0.34627 | 0.21558635 | U01102_at | UGB Uteroglobin |
| 458 | Ovary | 0.26775 | 0.4138277 | 0.346122 | AA393299_a t | | EST: zt52e09.r1 Soares ovary tumor NbHOT Homo sapiens cDNA clone 725992 5' similar to contains element PTR5 repetitive element ;, mRNA sequence. (from Genbank) |
| 459 | Ovary | 0.2677144 | 0.413375 | 0.345743 | 0.21521002 | D63481_at | KIAA0147 gene, partial cds |
| 460 | Ovary | 0.2676709 | 0.4136404 | 0.345712 | 0.21518531 | M21494_at | CKM Creatine kinase, muscle |
| 461 | Ovary | 0.2672732 | 0.4135974 | 0.345535 | 0.21503061 | M36634_at | VIP Vasoactive intestinal peptide |
| 462 | Ovary | 0.2672488 | 0.413538 | 0.345373 | 0.21490474 | U93553_at-2 | Fetoprotein-alpha 1 (AFP) transcription factor |
| 463 | Ovary | 0.2672488 | 0.4133633 | 0.345338 | 0.21474656 | U93553_at | Alpha1-fetoprotein transcription factor (hFTF) mRNA |
| 464 | Ovary | 0.2672114 | 0.4132712 | 0.345161 | 0.21470048 | AA304829_a t | EST176060 Colon carcinoma (Caco-2) cell line II Homo sapiens cDNA 5' end, mRNA sequence. (from Genbank) |
| 465 | Ovary | 0.2667795 | 0.4132262 | 0.345111 | 0.21462113 | M57609_at | GLI3 PROTEIN |
| 466 | Ovary | 0.2666887 | 0.4131307 | 0.344933 | 0.21443458 | D80011_at | KIAA0189 gene |
| 467 | Ovary | 0.2666887 | 0.4129319 | 0.344926 | 0.21433756 | D80011_at-2 | KIAA0189 gene product |
| 468 | Ovary | 0.2665639 | 0.4127077 | 0.34488 | 0.21412256 | U82310_at | Unknown protein mRNA, partial cds |
| 469 | Ovary | 0.2665055 | 0.4125737 | 0.344428 | 0.21412256 | H78886_at | EST: yu11a03.r1 Homo sapiens cDNA clone 233452 5'. (from Genbank) |
| 470 | Ovary | 0.2663021 | 0.4124796 | 0.344228 | 0.21376312 | HG2175-HT2245_s_a t | Myosin, Heavy Polypeptide 10, Non-Muscle |
| 471 | Ovary | 0.2659546 | 0.4123149 | 0.344219 | 0.21367392 | U66406_at | EPLG8 Eph-related receptor tyrosine kinase ligand 8 |
| 472 | Ovary | 0.2659378 | 0.4122962 | 0.344192 | 0.21355115 | U11870_rna 1_at | Interleukin-8 receptor type A (IL8RBA) gene, promoter and complete cds |

FIG. 10S

| # | Tissue | | | | | | Description |
|---|---|---|---|---|---|---|---|
| 473 | Ovary | 0.2657849 | 0.4121736 | 0.344092 | 0.21327704 | L77730_at | ADORA3 Adenosine receptor A3 |
| 474 | Ovary | 0.2657564 | 0.4120143 | 0.343891 | 0.213158 | D38145_at | Prostacyclin synthase |
| 475 | Ovary | 0.2657276 | 0.4120076 | 0.343813 | 0.21310914 | HG908-HT908_at | Mg61 Protein (Gb:L08239) |
| 476 | Ovary | 0.265711 | 0.411983 | 0.343755 | 0.21302736 | HG3884-HT4154_at | Homeotic Protein Hpx-42 |
| 477 | Ovary | 0.2656896 | 0.41183 | 0.343676 | 0.2129512 | HG371-HT26388_s_at | Mucin 1, Epithelial, Alt. Splice 9 |
| 478 | Ovary | 0.2655256 | 0.4118093 | 0.343528 | 0.21284524 | X57348_s_a t | SFN Stratifiin |
| 479 | Ovary | 0.2652213 | 0.4117406 | 0.343528 | 0.2127327 | X82634_at | Partial mRNA for hair keratin acidic 3-II |
| 480 | Ovary | 0.2651835 | 0.4117106 | 0.343505 | 0.21265955 | X96698_at | D1075-like gene |
| 481 | Ovary | 0.264683 | 0.4116855 | 0.343401 | 0.21251659 | Y08564_at | GalNAc-T4 gene |
| 482 | Ovary | 0.2646747 | 0.4115379 | 0.343283 | 0.21232747 | M59911_at | ITGA3 Integrin alpha-3 subunit |
| 483 | Ovary | 0.2645927 | 0.4114965 | 0.343152 | 0.21222517 | U54804_at | Has2 mRNA |
| 484 | Ovary | 0.2644429 | 0.4112892 | 0.34296 | 0.21219595 | Y10209_at | CD30L protein |
| 485 | Ovary | 0.264427 | 0.4110016 | 0.342949 | 0.21210513 | S81957_at | BMP-5-bone morphogenic protein-5 {promoter} [human, Genomic, 1116 nt] |
| 486 | Ovary | 0.2644258 | 0.4107987 | 0.342839 | 0.21205978 | RC_AA3720 18_at | EST: EST83940 Parathyroid gland tumor I Homo sapiens cDNA 3' end, mRNA sequence. (from Genbank) |
| 487 | Ovary | 0.264282 | 0.4107699 | 0.342835 | 0.21204166 | RC_AA2117 77_at | EST: zn57d02.s1 Stratagene muscle 937209 Homo sapiens cDNA clone 562275 3', mRNA sequence. (from Genbank) |
| 488 | Ovary | 0.2639894 | 0.4107074 | 0.342768 | 0.21178684 | RC_AA1612 92_s_at | Interferon, alpha-inducible protein 27 |
| 489 | Ovary | 0.2638342 | 0.4103184 | 0.342618 | 0.21167074 | M86849_at | Connexin 26 (GJB2) mRNA |
| 490 | Ovary | 0.2637067 | 0.4102355 | 0.34243 | 0.21147881 | X54667_at | CST4 Cystatin S |
| 491 | Ovary | 0.2635544 | 0.4100462 | 0.342324 | 0.2113911 | X65962_s_a t | CYP2C17 Cytochrome P450, subfamily IIC (mephenytoin 4-hydroxylase), polypeptide 17 |
| 492 | Ovary | 0.2634786 | 0.4100315 | 0.342284 | 0.21120098 | Y00477_at | Bone marrow serine protease gene (medullasin) (leukocyte neutrophil elastase gene) |
| 493 | Ovary | 0.263438 | 0.409926 | 0.342233 | 0.21114148 | X60483_at | H4/d gene for H4 histone |
| 494 | Ovary | 0.2629789 | 0.4098917 | 0.342184 | 0.21093363 | U17579_rna 1_at | Growth hormone-releasing hormone receptor form b gene extracted from Human growth hormone-releasing hormone receptor gene, alternatively spliced forms a, b, and c, partial cds |
| 495 | Ovary | 0.2628802 | 0.4097485 | 0.342069 | 0.21084823 | U16720_rna 1_s_at | Interleukin 10 (IL10) gene |
| 496 | Ovary | 0.2627642 | 0.4097359 | 0.341919 | 0.21071276 | X17360_rna 1_at | HOX 5.1 gene for HOX 5.1 protein |
| 497 | Ovary | 0.2621831 | 0.4096476 | 0.341842 | 0.21056288 | Z38026_at | CAP-18 protein |

FIG. 10T

| | | | | | |
|---|---|---|---|---|---|
| 498 | Ovary | 0.2615432 | 0.4094477 | 0.34175 | 0.21051963 | M81830_at | Somatostatin receptor isoform 2 (SSTR2) gene |
| 499 | Ovary | 0.2614543 | 0.4093441 | 0.341669 | 0.21044078 | RC_AA0013 99_at | EST: ze45b05.s1 Soares retina N2b4HR Homo sapiens cDNA clone 361905 3', mRNA sequence. (from Genbank) |
| 500 | Ovary | 0.2613242 | 0.4092804 | 0.341611 | 0.21028979 | Z35402_rna 1_s_at | Gene encoding E-cadherin, exon 3 and joined CDS |
| 501 | Ovary | 0.261281 | 0.409172 | 0.341594 | 0.21018983 | HG25930-HT26386_at | Estradiol 17-beta dehydrogenase 1 |
| 502 | Ovary | 0.2610615 | 0.4091594 | 0.341536 | 0.2101366 | D79206_s_a t | SDC4 Syndecan 4 (amphiglycan, ryudocan) |
| 503 | Ovary | 0.26083 | 0.409025 | 0.34151 | 0.21005002 | D38462_at | A1 chain of type XIX collagen, exon +3' |
| 504 | Ovary | 0.260621 | 0.4089933 | 0.344487 | 0.20982467 | F15201_at | EST: H. sapiens partial cDNA sequence, mRNA sequence. (from Genbank) |
| 505 | Ovary | 0.2600528 | 0.408914 | 0.341324 | 0.20964968 | L17128_at | GGCX Gamma-glutamyl carboxylase |
| 506 | Ovary | 0.2598971 | 0.4087319 | 0.341269 | 0.20958297 | W52493_at | EST: zc54a05.r1 Soares senescent fibroblasts NbHSF Homo sapiens cDNA clone 326096 5' similar to contains element MER6 repetitive element:, mRNA sequence. (from Genbank) |
| 507 | Ovary | 0.2598472 | 0.4086904 | 0.341202 | 0.2095407 | RC_AA2331 26_at | EST: zr69b08.s1 Soares NhHMPu S1 Homo sapiens cDNA clone 668631 3', mRNA sequence. (from Genbank) |
| 508 | Ovary | 0.2596304 | 0.4086684 | 0.341108 | 0.20944946 | M19888_at | SPRR1B Small proline-rich protein 1B (cornifin) |
| 509 | Ovary | 0.2592468 | 0.4083718 | 0.341084 | 0.2093381 | HG1751-HT1768_at | Chorionic Somatomammotropin Hormone Cs-5 |
| 510 | Ovary | 0.2591555 | 0.4081817 | 0.34103 | 0.20921104 | U04343_at | CD86 CD86 antigen (CD28 antigen ligand 2, B7-2 antigen) |
| 511 | Ovary | 0.2580365 | 0.4081394 | 0.340961 | 0.20915589 | U66828_s_a t | Carnitine palmitoyltransferase I (CPT1) mRNA |
| 512 | Ovary | 0.2578356 | 0.4079959 | 0.340949 | 0.20901753 | RC_AA4821 26_at | Claudin 3 |
| 513 | Ovary | 0.2575471 | 0.4079853 | 0.340887 | 0.20893502 | HG3893-HT4163_at | Phosphoglucomutase 1, Alt. Splice |
| 514 | Ovary | 0.2573818 | 0.4079454 | 0.34044 | 0.20877808 | M93107_at | D-BETA-HYDROXYBUTYRATE DEHYDROGENASE PRECURSOR |
| 515 | Ovary | 0.2573291 | 0.4078276 | 0.340212 | 0.20862111 | U32499_s_a t | D3 dopamine receptor mRNA |
| 516 | Ovary | 0.2573051 | 0.407768 | 0.339996 | 0.2085401 | L13258_at | SLC17A2 Solute carrier family 17 (sodium phosphate), member 2 |
| 517 | Ovary | 0.2566785 | 0.4075463 | 0.33993 | 0.20844713 | RC_AA4357 20_i_at | Homo sapiens (clone ch13lambda7) alpha-tubulin mRNA, complete cds |
| 518 | Ovary | 0.2563115 | 0.4074981 | 0.339551 | 0.20836873 | hum_alu_at-hum_alu_at- | hum_alu_at (miscellaneous control) |
| 519 | Ovary | 0.2563115 | 0.4074932 | 0.339657 | 0.20830174 | 2 | No description for gene: hum_alu_at |
| 520 | Ovary | 0.2561358 | 0.4074622 | 0.339591 | 0.20807372 | M85164_at | ELK4 SRF accessory protein 1B (SAP-1) |
| 521 | Ovary | 0.2560056 | 0.4073862 | 0.339552 | 0.20799507 | X58255_at | Flg-2 gene for fibroblast growth factor receptor |

FIG. 10U

| | | | | | |
|---|---|---|---|---|---|
| 522 | Ovary | 0.25559532 | 0.4073812 | 0.399329 | 0.207899853 | RC_AA3982 76_at | EST: zt60c07.s1 Soares testis NHT Homo sapiens cDNA clone 726732 3', mRNA sequence. (from Genbank) |
| 523 | Ovary | 0.2558202 | 0.4072704 | 0.339237 | 0.20779629 | HG1098-HT1098_at | Cystatin D |
| 524 | Ovary | 0.2557321 | 0.4068154 | 0.339164 | 0.207726 | AB002339_a_t | Human mRNA for KIAA0341 gene, partial cds |
| 525 | Ovary | 0.2555668 | 0.4066967 | 0.33887 | 0.20759502 | AB002293_a_t | Human mRNA for KIAA0295 gene, partial cds |
| 526 | Ovary | 0.2553219 | 0.4066631 | 0.338761 | 0.20744364 | U85625_at | Ribonuclease 6 precursor |
| 527 | Ovary | 0.2551437 | 0.4066447 | 0.338742 | 0.20737857 | U62432_at-2 | Cholinergic receptor, nicotinic, alpha polypeptide 3 |
| 528 | Ovary | 0.2551437 | 0.4066334 | 0.338646 | 0.20710474 | U62432_at | CHRNA3 Cholinergic receptor, nicotinic, alpha polypeptide 3 |
| 529 | Ovary | 0.2550468 | 0.4063708 | 0.338603 | 0.20709254 | RC_AA4787 40_at | EST: zv14g12.s1 Soares NhHMPu S1 Homo sapiens cDNA clone 753670 3', mRNA sequence. (from Genbank) |
| 530 | Ovary | 0.2550132 | 0.4061648 | 0.338562 | 0.20700388 | AA046737_a t | EST: zf48a10.r1 Soares retina N2b4HR Homo sapiens cDNA clone 380154 5' similar to contains Alu repetitive element;, mRNA sequence. (from Genbank) |
| 531 | Ovary | 0.2549136 | 0.4061568 | 0.338454 | 0.20695385 | L19493_s_at | FRAGILE X MENTAL RETARDATION 1 PROTEIN |
| 532 | Ovary | 0.2548626 | 0.405966 | 0.338421 | 0.20687246 | M94250_at | MDK Midkine (neurite growth-promoting factor 2) |
| 533 | Ovary | 0.2548583 | 0.4058723 | 0.338317 | 0.20677233 | AF012270_a_t | Peropsin (Rrh) mRNA |
| 534 | Ovary | 0.2548583 | 0.4058106 | 0.338288 | 0.20669466 | AF012270_a_t-2 | Homo sapiens visual pigment-like receptor peropsin (Rrh) mRNA, complete cds |
| 535 | Ovary | 0.2548117 | 0.4054902 | 0.338262 | 0.20655999 | H50398_at | Human multidrug resistance-associated protein homolog (MRP5) mRNA, partial cds |
| 536 | Ovary | 0.2545832 | 0.4054203 | 0.338179 | 0.2065201 | M37245_s_a t | Ig superfamily cytotoxic T-lymphocyte-associated protein (CTLA-4) gene, last exon |
| 537 | Ovary | 0.2543919 | 0.4052288 | 0.338094 | 0.2064347 | M31774_s_a t | TSHR Thyroid stimulating hormone receptor |
| 538 | Ovary | 0.2535895 | 0.4050861 | 0.337897 | 0.20629858 | AD001527_c ds1_at | Comment for location 3447-3655: BLASTX gi\|103290\|pir\|S16356 ovo protein - fruit fly (Drosophila melanogaster), PVal= 3.8e-47 gene extracted from Homo sapiens DNA from chromosome 19-cosmid f24590 containing CAPNS and POL2RI, genomic sequence |
| 539 | Ovary | 0.2535449 | 0.405033 | 0.337847 | 0.20620194 | L10123_at | Surfactant protein A mRNA |
| 540 | Ovary | 0.2534203 | 0.404902 | 0.337765 | 0.20609696 | U39905_at | SLC18A1 Solute carrier family 18 (vesicular monoamine), member 1 |

FIG. 10V

| # | Tissue | | | | | Description |
|---|---|---|---|---|---|---|
| 541 | Ovary | 0.2533096 | 0.4043981 | 0.337599 | 0.20952223 | W92242_s_at | EST: ze14b12.r1 Soares fetal heart NbHH19W Homo sapiens cDNA clone 358943 5' similar to PIR:A49128 A49128 cell-fate determining gene Notch2 product:; mRNA sequence. (from Genbank) |
| 542 | Ovary | 0.2532285 | 0.4043856 | 0.337578 | 0.20591557 | Z83838_at | Human DNA sequence from PAC 127B20 on chromosome 22q11.2-qter, contains gene for GTPase-activating protein similar to rhoGAP protein, ribosomal protein L6 pseudogene, ESTs and CA repeat |
| 543 | Ovary | 0.2531765 | 0.4043479 | 0.337528 | 0.20576685 | D21337_at | COL4A6 Collagen, type IV, alpha 6 |
| 544 | Ovary | 0.2529089 | 0.404157 | 0.337442 | 0.20571235 | U66661_at | GABA-A receptor epsilon subunit mRNA |
| 545 | Ovary | 0.2527888 | 0.4039888 | 0.337292 | 0.20555034 | U97698_at | Homo sapiens secretory mucin MUC6 (MUC6) mRNA, partial cds |
| 546 | Ovary | 0.2527282 | 0.4039433 | 0.337215 | 0.20538808 | HG3945-HT4215_at | Phospholipid Transfer Protein |
| 547 | Ovary | 0.2526975 | 0.4038402 | 0.337188 | 0.20532483 | V01515_cds1_at | Unnamed protein product gene extracted from Human gene encoding preproglucagon. Glucagon is a 29-amino acid pancreatic hormone which counteracts the blood glucose-lowering action of insulin by stimulating hepatic glycogenolysis and gluconeogenesis. Also included in the proglucagon sequence are two regions (GLP-1 and GLP-2) which are homologous to glucagon itself but not identical |
| 548 | Ovary | 0.2526632 | 0.4038066 | 0.337137 | 0.20524211 | RC_AA191647_at | Ceruloplasmin (ferroxidase) |
| 549 | Ovary | 0.2526164 | 0.4037749 | 0.337126 | 0.20519333 | RC_AA398423_at | EST: zt62a05.s1 Soares testis NHT Homo sapiens cDNA clone 726896 3'; mRNA sequence. (from Genbank) |
| 550 | Ovary | 0.252471 | 0.4037693 | 0.33703 | 0.20512982 | X55448_cds2_at | 2-19 gene (2-19 protein) extracted from H.sapiens G6PD gene for glucose-6-phosphate dehydrogenase |
| 551 | Ovary | 0.2523131 | 0.403747 | 0.337011 | 0.20507078 | M55131_at | CFTR Cystic fibrosis conductance regulator |
| 552 | Ovary | 0.252227 | 0.403634 | 0.336935 | 0.20503685 | RC_AA130089_at | EST: zl33f12.s1 Soares pregnant uterus NbHPU Homo sapiens cDNA clone 503759 3'; mRNA sequence. (from Genbank) |
| 553 | Ovary | 0.2516393 | 0.4034919 | 0.336905 | 0.20482620 | S83366_cds3_at | Description: orf3 gene extracted from region centromeric to t(12;17) brakepoint: orf1/unknown 43 amino acid transcript...orf3/unknown 50 amino acid transcript [human, testis, acampomelic campomelic dysplasia and sex reversal patient, Genomic, 3 genes, 3414 nt] |
| 554 | Ovary | 0.2516153 | 0.4032913 | 0.336805 | 0.20476466 | X87160_at | Kidney epithelial sodium channel gamma subunit (gamma hENaC) mRNA |
| 555 | Ovary | 0.2514882 | 0.403023 | 0.336756 | 0.2046211 | X76059_at | YRRM1 |
| 556 | Ovary | 0.2509307 | 0.4028296 | 0.336521 | 0.20449257 | Z31357_at | CDO1 Cysteine dioxygenase, type 1 |
| 557 | Ovary | 0.2508515 | 0.4027182 | 0.336514 | 0.20444589 | Y10936_at | Hypothetical protein downstream of DMPK and DMAHP |

FIG. 10W

| | | | | | |
|---|---|---|---|---|---|
| 558 | Ovary | 0.2508087 | 0.4026777 | 0.336329 | 0.204363396 | M77348_rna1_s_at | Pmel 17 mRNA |
| 559 | Ovary | 0.2506595 | 0.4026501 | 0.336178 | 0.20425196 | D55640_at | Monocyte PABL (pseudoautosomal boundary-like sequence) mRNA, clone Mo2 |
| 560 | Ovary | 0.2505702 | 0.4026042 | 0.336157 | 0.204192258 | Z19675_at | EST: H. sapiens putatively transcribed partial sequence; UK-HGMP sequence ID AAAGNB; single read, mRNA sequence. (from Genbank) |
| 561 | Ovary | 0.2503649 | 0.4024495 | 0.33606 | 0.204110079 | D49387_at | NADP dependent leukotriene b4 12-hydroxydehydrogenase, partial cds |
| 562 | Ovary | 0.2500466 | 0.4023899 | 0.335887 | 0.203966836 | U26914_at | Ras-responsive element binding protein (RREB-1) mRNA |
| 563 | Ovary | 0.2499296 | 0.4023601 | 0.335878 | 0.203886107 | X17622_at | KCNA6 Potassium voltage-gated channel, shaker-related subfamily, member 6 |
| 564 | Ovary | 0.2499203 | 0.402204 | 0.335661 | 0.20374103 | M60614_at | WT1 Wilms tumor 1 |
| 565 | Ovary | 0.2499082 | 0.4021704 | 0.335404 | 0.203361574 | X13255_at | DBH Dopamine beta-hydroxylase (dopamine beta-monooxygenase) |
| 566 | Ovary | 0.2497903 | 0.4020307 | 0.335277 | 0.203598892 | RC_AA459389_at | Tyrosylprotein sulfotransferase 2 |
| 567 | Ovary | 0.2496847 | 0.4019973 | 0.335245 | 0.203353478 | M24351_cds3_s_at | PTHLH gene (parathyroid hormone-like protein A) extracted from Human parathyroid hormone-like protein (PLP) gene |
| 568 | Ovary | 0.249279 | 0.4018865 | 0.335212 | 0.2033138 | L15702_at | BF B-factor, properdin |
| 569 | Ovary | 0.2492415 | 0.4018194 | 0.335155 | 0.203253316 | M13207_at | CSF2 Colony-stimulating factor 2 (GM-CSF) |
| 570 | Ovary | 0.2492151 | 0.4018015 | 0.335105 | 0.20316797 | U20908_at | Clone 350/2 melanoma ubiquitous mutated protein (MUM-1) gene, partial cds |
| 571 | Ovary | 0.24917 | 0.4017427 | 0.334959 | 0.202923385 | AF009368_a_t | Lumen mRNA |
| 572 | Ovary | 0.24912 | 0.4016173 | 0.33478 | 0.202289564 | L13977_at | LYSOSOMAL PRO-X CARBOXYPEPTIDASE PRECURSOR |
| 573 | Ovary | 0.2489907 | 0.4015809 | 0.334777 | 0.202281175 | D29805_at | GGTB2 Glycoprotein-4-beta-galactosyltransferase 2 |
| 574 | Ovary | 0.2489894 | 0.4013782 | 0.334565 | 0.202679866 | U65258_at | HBRAVO/Nr-CAM precursor (hBRAVO/Nr-CAM) gene |
| 575 | Ovary | 0.2480893 | 0.4013435 | 0.334376 | 0.202258774 | U10362_at | GP36b glycoprotein mRNA |
| 576 | Ovary | 0.2479471 | 0.4013435 | 0.334376 | 0.202254685 | HG2715-HT2811_at | Tyrosine Kinase (Gb:725437) |
| 577 | Ovary | 0.2479209 | 0.4013175 | 0.334272 | 0.202245755 | D86966_at | KIAA0211 gene |
| 578 | Ovary | 0.2478948 | 0.4011774 | 0.334406 | 0.202241871 | U20391_rna6_at | Folate receptor (FOLR1) gene |
| 579 | Ovary | 0.2478382 | 0.4010236 | 0.333983 | 0.202229219 | X07024_at | TRANSCRIPTION INITIATION FACTOR TFIID 250 KD SUBUNIT |
| 580 | Ovary | 0.2477879 | 0.4009556 | 0.33393 | 0.20223966 | X81637_at | CLTB Clathrin, light polypeptide (Lcb) |
| 581 | Ovary | 0.2477336 | 0.4009417 | 0.333898 | 0.20222239 | RC_AA491001_f_at | EST: aa52g12.s1 NCI_CGAP_GCB1 Homo sapiens cDNA clone IMAGE:824614 3' similar to TR:G1293732 G1293732 O3625P.;. mRNA sequence. (from Genbank) |
| 582 | Ovary | 0.2474372 | 0.4007636 | 0.33389 | 0.202115479 | U38276_at | Semaphorin III family homolog mRNA |

FIG. 10X

| # | Tissue | | | | ID | Description |
|---|---|---|---|---|---|---|
| 583 | Ovary | 0.2471709 | 0.400761 | 0.333736 | 0.20197856 J03474_at | SERUM AMYLOID A PROTEIN PRECURSOR |
| 584 | Ovary | 0.2471177 | 0.400758 | 0.333728 | 0.20187068 X78706_at | CRAT Carnitine acetyltransferase |
| 585 | Ovary | 0.247063 | 0.4005463 | 0.333717 | 0.20176512 D45906_at | LIMK-2 |
| 586 | Ovary | 0.2470482 | 0.4005349 | 0.336695 | 0.20169307 X83127_at | K+ channel beta 1a subunit mRNA, alternatively spliced |
| 587 | Ovary | 0.2470227 | 0.4004628 | 0.333615 | 0.20166042 X80923_at | Nov gene |
| 588 | Ovary | 0.246805 | 0.4004031 | 0.33339 | 0.20148031 D38305_at | Tob |
| 589 | Ovary | 0.2467307 | 0.4002866 | 0.333314 | 0.20141147 L17328_at | Pre-T/NK cell associated protein (3Cl) mRNA |
| 590 | Ovary | 0.2466294 | 0.4001569 | 0.333281 | 0.20124652 Z21966_at | POU6F1 POU homeobox protein |
| 591 | Ovary | 0.2464729 | 0.4001063 | 0.333254 | 0.20116653 U03270_at | Centrin mRNA |
| 592 | Ovary | 0.2462271 | 0.4000655 | 0.333243 | 0.20110865 N48927_at | EST: yy75e09.r1 Homo sapiens cDNA clone 279400 5'. (from Genbank) |
| 593 | Ovary | 0.2460588 | 0.3999787 | 0.33297 | 0.20103784 U46569_at | Aquaporin-5 (AQP5) gene |
| 594 | Ovary | 0.2459124 | 0.3999254 | 0.332862 | 0.20091069 RC_AA2358 34_s_at | EST: zs41a10.s1 Soares NhHMPu S1 Homo sapiens cDNA clone 687738 3', mRNA sequence. (from Genbank) |
| 595 | Ovary | 0.2456928 | 0.3998796 | 0.332828 | 0.20062262 U89942_at | Lysyl oxidase-related protein (WS9-14) mRNA |
| 596 | Ovary | 0.245507 | 0.399838 | 0.332657 | 0.20060207 L38500_at | Na+/myo-inositol cotransporter (SLC5A3) gene |
| 597 | Ovary | 0.2454886 | 0.3996636 | 0.332516 | 0.20050538 RC_AA4314 79_at | EST: zw72f05.s1 Soares testis NHT Homo sapiens cDNA clone 781761 3', mRNA sequence. (from Genbank) |
| 598 | Ovary | 0.2452701 | 0.3995775 | 0.332393 | 0.20043796 AA292609_a t | EST: zs57g01.r1 NCI_CGAP_GCB1 Homo sapiens cDNA clone IMAGE:701616 5' similar to contains L1.11 L1 repetitive element.; mRNA sequence. (from Genbank) |
| 599 | Ovary | 0.2451796 | 0.3992013 | 0.332368 | 0.20032588 X51441_at | SERUM AMYLOID A PROTEIN PRECURSOR |
| 600 | Ovary | 0.2451349 | 0.3991809 | 0.332226 | 0.2002477 HG2280-HT2376_at | D-Amino-Acid Oxidase |
| 601 | Ovary | 0.2450647 | 0.3991486 | 0.332219 | 0.20016891 RC_AA4889 79_at | Homo sapiens cell cycle-regulated factor p78 mRNA, complete cds |
| 602 | Ovary | 0.2449481 | 0.3991421 | 0.332093 | 0.20000227 HT3924_at | Spermidine/Spermine N1-Acetyltransferase, Alt. Splice 2 |
| 603 | Ovary | 0.2447337 | 0.3990979 | 0.332067 | 0.19998762 X59892_at | TRYPTOPHANYL-TRNA SYNTHETASE |
| 604 | Ovary | 0.2446139 | 0.3990898 | 0.332053 | 0.19980809 HG919-HT919_at | Dna Polymerase, Epsilon, Catalytic Subunit |
| 605 | Ovary | 0.2445739 | 0.3990673 | 0.331969 | 0.19976458 RC_AA4007 68_at | EST: zi71c01.s1 Soares testis NHT Homo sapiens cDNA clone 727776 3', mRNA sequence. (from Genbank) |
| 606 | Ovary | 0.2445341 | 0.3989032 | 0.331947 | 0.19964974 L10615_s_at | CSN2 Beta-casein |
| 607 | Ovary | 0.2441043 | 0.3988426 | 0.331898 | 0.19958155 RC_AA0312 74_at | EST: zk15a10.s1 Soares pregnant uterus NbHPU Homo sapiens cDNA clone 470536 3', mRNA sequence. (from Genbank) |
| 608 | Ovary | 0.2440666 | 0.3988044 | 0.331799 | 0.19954087 X52A79_at | PRkCA Protein kinase C, alpha |
| 609 | Ovary | 0.2438923 | 0.3987324 | 0.331619 | 0.19948214 HG363-HT363_at | Epidermal Growth Factor Receptor-Related Protein |

FIG. 10Y

| | | | | | |
|---|---|---|---|---|---|
| 610 | Ovary | 0.2438448 | 0.3986809 | 0.331495 | 0.19938543 | L24203_at | Ataxia-telangiectasia group D-associated protein mRNA |
| 611 | Ovary | 0.2435269 | 0.3984745 | 0.331429 | 0.19933096 | RC_AA3981 24_s_at | Growth factor receptor-bound protein 14 |
| 612 | Ovary | 0.2435159 | 0.3983022 | 0.331299 | 0.1990926 | X98176_at | MACH-alpha-2 protein |
| 613 | Ovary | 0.2430712 | 0.39820059 | 0.331242 | 0.19904166 | M69263_at | Matrilin-2 precursor mRNA, partial cds |
| 614 | Ovary | 0.2428666 | 0.398203 | 0.3331239 | 0.1982269 | HG3107-HT3283_s_a t | Plasma Membrane Calcium Pump Hpmca2a |
| 615 | Ovary | 0.2428224 | 0.3981988 | 0.331192 | 0.1987493 | U25182_at | Antioxidant enzyme AOE37-2 mRNA |
| 616 | Ovary | 0.2426744 | 0.398058 | 0.331106 | 0.19867557 | U28749_s_a t | High-mobility group phosphoprotein isoform I-C (HMGIC) mRNA |
| 617 | Ovary | 0.2426077 | 0.3980478 | 0.33103 | 0.19867557 | HG3288-HT3465_at | Xanthine Dehydrogenase (Gb:U06117) |
| 618 | Ovary | 0.2422744 | 0.3978426 | 0.330952 | 0.19864419 | HG2290-HT2386_at | Calcitonin |
| 619 | Ovary | 0.2422255 | 0.3978349 | 0.330876 | 0.19851272 | D43642_at | YL-1 mRNA for YL-1 protein (nuclear protein with DNA-binding ability) |
| 620 | Ovary | 0.2421735 | 0.3978189 | 0.330752 | 0.19849677 | D86096_cds 1_s_at | EP3-IV gene extracted from Human DNA for prostaglandin E receptor EP3 subtype |
| 621 | Ovary | 0.2421258 | 0.397801 | 0.330716 | 0.1983327 | M85085_at | CSTF2 Cleavage stimulation factor, 3' pre-RNA, subunit 2, 64kD |
| 622 | Ovary | 0.2418219 | 0.3977831 | 0.330456 | 0.19824454 | X02544_at | ORM1 Orosomucoid 1 |
| 623 | Ovary | 0.2416403 | 0.3977028 | 0.330376 | 0.19821772 | M55593_at | MMP2 Matrix metalloproteinase 2 (gelatinase A, 72kD gelatinase, 72kD type IV collagenase) |
| 624 | Ovary | 0.2414672 | 0.3976994 | 0.330341 | 0.19814219 | L19711_at | Dystroglycan (DAG1) mRNA |
| 625 | Ovary | 0.2411349 | 0.3975974 | 0.330334 | 0.19798787 | HG2460-HT2556_at | Integrin Beta 1 (Gb:M34189) |
| 626 | Ovary | 0.2409652 | 0.397554 | 0.330293 | 0.19784574 | X04325_at | GJB1 Gap junction protein, beta 1, 32kD (connexin 32, Charcot-Marie-Tooth neuropathy, X-linked) |
| 627 | Ovary | 0.2408217 | 0.397472 | 0.330215 | 0.19776194 | U65932_at | Extracellular matrix protein 1 (ECM1) mRNA |
| 628 | Ovary | 0.2408072 | 0.3974669 | 0.330197 | 0.19771169 | L14269_at | SLC18A2 Solute carrier family 18 (vesicular monoamine), member 2 |
| 629 | Ovary | 0.240689 | 0.3974335 | 0.330111 | 0.19754815 | U79251_at | OPCML Opioid-binding cell adhesion molecule |
| 630 | Ovary | 0.2404317 | 0.3970117 | 0.330029 | 0.19750503 | U47931_at | G-protein beta-3 subunit alternatively spliced form mRNA sequence |
| 631 | Ovary | 0.2403633 | 0.3969821 | 0.329919 | 0.1974592 | M86808_at | Pyruvate dehydrogenase complex (PDHA2) gene |
| 632 | Ovary | 0.2401766 | 0.3969784 | 0.3299 | 0.1972791 | U82467_at | Tub homolog (TUB) mRNA |
| 633 | Ovary | 0.2400923 | 0.3965403 | 0.3299 | 0.1971084 | L22524_s_at | MATRILYSIN PRECURSOR |
| 634 | Ovary | 0.2400444 | 0.3964808 | 0.329758 | 0.19710705 | RC_D58185_ at | EST: Human aorta cDNA 3'-end GEN-354C01, mRNA sequence. (from Genbank) |

FIG. 10Z

| | | | | | |
|---|---|---|---|---|---|
| 635 | Ovary | 0.2399658 | 0.3964537 | 0.329738 | 0.19703965 | S71129_at | Acetylcholinesterase {[4-E5 domain} [human, tumor cell lines, Genomic, 847 nt] |
| 636 | Ovary | 0.2399486 | 0.3964308 | 0.329653 | 0.19694088 | U90905_at | Clone 23574 mRNA sequence |
| 637 | Ovary | 0.2397565 | 0.3963174 | 0.329652 | 0.196811 | U54617_at | PDK4 Pyruvate dehydrogenase kinase, isoenzyme 4 |
| 638 | Ovary | 0.2395354 | 0.3962031 | 0.329584 | 0.19664232 | U03272_at | FBN2 Fibrillin 2 |
| 639 | Ovary | 0.2394803 | 0.3960701 | 0.329419 | 0.1955813 | U81523_at | Endometrial bleeding associated factor mRNA |
| 640 | Ovary | 0.2388746 | 0.3960078 | 0.329395 | 0.19644605 | HG4036-HT4306_at | Retinoblastoma 1 |
| 641 | Ovary | 0.2381233 | 0.3959744 | 0.329368 | 0.19636932 | U30930_at | CGT UDP-galactose ceramide galactosyl transferase |
| 642 | Ovary | 0.2378548 | 0.3957806 | 0.323354 | 0.19628023 | L03785_at | MYL5 Myosin, light polypeptide 5, regulatory |
| 643 | Ovary | 0.2377848 | 0.3956446 | 0.329278 | 0.19623984 | J03464_s_at | Collagen, type I, alpha 2 |
| 644 | Ovary | 0.2377693 | 0.3955021 | 0.329175 | 0.19618486 | RC_AA4778 26_at | EST: zu39g07.s1 Soares ovary tumor NbHOT Homo sapiens cDNA clone 740412 3', mRNA sequence. (from Genbank) |
| 645 | Ovary | 0.2376645 | 0.3954524 | 0.3290599 | 0.1959321 | U83303_cds 2_at | GCP-2 gene (granulocyte chemotactic protein-2) extracted from Human line-1 reverse transcriptase gene, partial cds, and granulocyte chemotactic protein-2 (GCP-2) gene |
| 646 | Ovary | 0.2371658 | 0.3953841 | 0.328969 | 0.19579662 | X96849_at | 5' mRNA of PECAM-1 molecule |
| 647 | Ovary | 0.2371214 | 0.3953473 | 0.328813 | 0.19577729 | L43579_at | L43579 Soares fetal liver spleen 1NFLS Homo sapiens cDNA clone 110298, mRNA sequence |
| 648 | Ovary | 0.2370138 | 0.3953266 | 0.328789 | 0.19564402 | U71207_at | Eyes absent homolog (Eab1) mRNA |
| 649 | Ovary | 0.2369099 | 0.3953043 | 0.328735 | 0.19561632 | D56495_at | Reg-related sequence derived peptide-1 |
| 650 | Ovary | 0.2366379 | 0.3951756 | 0.328543 | 0.19552177 | U15131_at | HTS1 |
| 651 | Ovary | 0.2363132 | 0.3951675 | 0.328402 | 0.19546023 | U52100_at | XMP mRNA |
| 652 | Ovary | 0.2360786 | 0.3950028 | 0.328471 | 0.1953924 | HG4185-HT4455_at | Estrogen Sulfotransferase, Ste |
| 653 | Ovary | 0.2360169 | 0.394968 | 0.328375 | 0.19535156 | M98343_at | Anaplaxin (EMS1) mRNA |
| 654 | Ovary | 0.2358758 | 0.3947818 | 0.328192 | 0.1952818 | AA459545_f_at | EST: zx89d12.r1 Soares ovary tumor NbHOT Homo sapiens cDNA clone 8110935 5', mRNA sequence. (from Genbank) |
| 655 | Ovary | 0.2358091 | 0.3946359 | 0.328174 | 0.19509967 | M82809_at | ANX4 Annexin IV (placental anticoagulant protein II) |
| 656 | Ovary | 0.2356793 | 0.3945908 | 0.328116 | 0.19508412 | H89896_s_a t | EST: yw29e12.r1 Homo sapiens cDNA clone 253678 5'. (from Genbank) |
| 657 | Ovary | 0.2356619 | 0.3945717 | 0.328112 | 0.19490215 | H24127_at | EST: ym50f03.r1 Homo sapiens cDNA clone 51827 5'. (from Genbank) |
| 658 | Ovary | 0.2354938 | 0.3945151 | 0.32792 | 0.19484152 | U26727_at | CDKN2A Cyclin-dependent kinase inhibitor 2A (melanoma, p16, inhibits CDK4) |
| 659 | Ovary | 0.2352029 | 0.3943844 | 0.3276 | 0.19473664 | U64197_at | CC chemokine LARC precursor |
| 660 | Ovary | 0.2347788 | 0.3943701 | 0.327544 | 0.19462222 | D80008_at | KIAA0186 gene |
| 661 | Ovary | 0.2346284 | 0.3943402 | 0.327505 | 0.19458441 | L42176_at | (clone 35.3) DRAL mRNA |

FIG. 10A2

| | | | | | | |
|---|---|---|---|---|---|---|
| 662 | Ovary | 0.234362 | 0.3942555 | 0.327322 | 0.19453587 | AA358888_a t | EST: EST67818 Fetal lung II Homo sapiens cDNA 5' end, mRNA sequence. (from Genbank) |
| 663 | Ovary | 0.2343044 | 0.394174 | 0.327253 | 0.19446646 | HG2442-HT2538_at | Tropomyosin, Alpha, Muscle, Alt. Splice 2, Skeletal Muscle (Fibroblast) |
| 664 | Ovary | 0.2334933 | 0.3940778 | 0.3272 | 0.19442731 | D88797_at | Cadherin, partial cds |
| 665 | Ovary | 0.2332717 | 0.3940532 | 0.327167 | 0.1942794 | HG1827-HT1856_s_a t | Cytochrome P450, Subfamily IIc, Alt. Splice Form 2 |
| 666 | Ovary | 0.2330434 | 0.3940191 | 0.327152 | 0.1941689 | Z18859_rna 1_at | Cone transducin alpha subunit gene extracted from H.sapiens gene for cone transducin alpha subunit |
| 667 | Ovary | 0.2330377 | 0.3939594 | 0.327096 | 0.1940721 | Y08999_at | Sop2p-like protein |
| 668 | Ovary | 0.2329765 | 0.3938775 | 0.326952 | 0.19404262 | Z21488_at | CNTN1 Contactin 1 |
| 669 | Ovary | 0.2327799 | 0.3938316 | 0.326909 | 0.19401522 | L42563_at | ATP1AL1 ATP-driven ion pump |
| 670 | Ovary | 0.2327498 | 0.3936808 | 0.326899 | 0.19392665 | S68874_s_at | PTGER3 Prostaglandin E receptor 3 (subtype EP3) (alternative products) |
| 671 | Ovary | 0.2325117 | 0.3935646 | 0.326848 | 0.1938264 | M25164_at | THYROTROPIN BETA CHAIN PRECURSOR |
| 672 | Ovary | 0.2324094 | 0.3934652 | 0.326816 | 0.193794 | M35410_s_a t | Insulin-like growth factor binding protein 2 (36kD) |
| 673 | Ovary | 0.2322222 | 0.3932697 | 0.326717 | 0.1937344 | U40434_at | Pre-pro-megakaryocyte potentiating factor |
| 674 | Ovary | 0.2316186 | 0.3931069 | 0.326616 | 0.19363283 | X90763_at | Type I keratin, hHa5 |
| 675 | Ovary | 0.2314556 | 0.3929695 | 0.326579 | 0.19348839 | U83600_at | Death domain receptor 3 (DDR3) mRNA, alternatively spliced form 2, partial cds |
| 676 | Ovary | 0.2314241 | 0.3928176 | 0.326579 | 0.19337085 | HG880-HT880_at | Mucin 6, Gastric (Gb:L07517) |
| 677 | Ovary | 0.2313847 | 0.3927828 | 0.326553 | 0.19333906 | RC_AA4764 15_at | EST: zx02a09.s1 Soares total fetus Nb2HF8 9w Homo sapiens cDNA clone 785272 3', mRNA sequence. (from Genbank) |
| 678 | Ovary | 0.2307315 | 0.39276 | 0.326489 | 0.19320577 | X68486_at | ADENOSINE A2A RECEPTOR |
| 679 | Ovary | 0.2306292 | 0.3926652 | 0.326468 | 0.19311209 | D13634_at | KIAA0009 gene |
| 680 | Ovary | 0.2305704 | 0.3925849 | 0.326234 | 0.1930455 | J03068_at | APEH N-acylaminoacyl-peptide hydrolase |
| 681 | Ovary | 0.2304064 | 0.3924752 | 0.326201 | 0.19288935 | L16883_s_at | Homo sapiens cytochrome P4502C9 (CYP2C9) gene, exon 9. (from Genbank) |
| 682 | Ovary | 0.2300964 | 0.3923346 | 0.326141 | 0.19278567 | U35005_s_a t | STRESS-ACTIVATED PROTEIN KINASE JNK1 |
| 683 | Ovary | 0.2300749 | 0.3923096 | 0.326109 | 0.19267742 | RC_AA3985 98_at | EST: zi70a07.s1 Soares testis NHT Homo sapiens cDNA clone 727668 3', mRNA sequence. (from Genbank) |
| 684 | Ovary | 0.2300397 | 0.3922575 | 0.325983 | 0.192559 | U51704_at | EST: Human mRNA sequence containing Alu repetitive elements. (from Genbank) |
| 685 | Ovary | 0.2297734 | 0.3922218 | 0.325716 | 0.192559 | O32202_at | ADRA1C Adrenergic, alpha-1C, receptor |
| 686 | Ovary | 0.2296775 | 0.3921641 | 0.325702 | 0.19250238 | T09468_at | Homo sapiens TACC1 (TACC1) mRNA, complete cds |

FIG. 10B2

| | | | | | |
|---|---|---|---|---|---|
| 687 | Ovary | 0.2293986 | 0.3921191 | 0.325598 | 0.19239146 | M19720_rna1_at | L-myc gene (L-myc protein) extracted from Human L-myc protein gene |
| 688 | Ovary | 0.2290153 | 0.3920947 | 0.325402 | 0.19232488 | X92518_s_at | HMGI-C |
| 689 | Ovary | 0.2290026 | 0.3920568 | 0.325362 | 0.19228831 | M87434_at | 69/71 KD |
| 690 | Ovary | 0.2289286 | 0.3919165 | 0.325305 | 0.19216312 | J05158_at | CARBOXYPEPTIDASE N 83 KD CHAIN |
| 691 | Ovary | 0.2286594 | 0.3918904 | 0.325249 | 0.19206144 | J03161_at | SRF Serum response factor (c-fos serum response element-binding transcription factor) |
| 692 | Ovary | 0.2281737 | 0.391555 | 0.325153 | 0.1920031 | HG4332-HT4602_at | Zinc Finger Protein Znfpt1 |
| 693 | Ovary | 0.227524 | 0.3915486 | 0.325119 | 0.19195436 | X99141_at | Hair keratin, hHb3 |
| 694 | Ovary | 0.2270346 | 0.39145 | 0.325069 | 0.19179772 | X66403_at | CHRNE Cholinergic receptor, nicotinic, epsilon polypeptide |
| 695 | Ovary | 0.2268547 | 0.3911955 | 0.325069 | 0.19176559 | AB002382_at | KIAA0384 gene |
| 696 | Ovary | 0.2267593 | 0.3911682 | 0.325002 | 0.1917211 | Z86000_at | DNA sequence from clone RP1-151B14 on chromosome 22 Contains SSTR3 (somatostatin receptor 3) gene, pseudogene similar to ribosomal protein L39, RAC2 (ras-related C3 botulinum toxin substrate 2 (rho family, small GTP binding protein Rac2)) gene, ESTs, STSs, GSSs and CpG islands, complete sequence |
| 697 | Ovary | 0.2266369 | 0.3911057 | 0.324888 | 0.19162359 | RC_AA418398_at | Neuropilin 2 |
| 698 | Ovary | 0.2264652 | 0.3911035 | 0.324843 | 0.19158219 | X78549_at | Brk mRNA for tyrosine kinase |
| 699 | Ovary | 0.2262559 | 0.3906581 | 0.324605 | 0.19153577 | X02404_at | CALCB Calcitonin-related polypeptide, beta |
| 700 | Ovary | 0.2259493 | 0.3905812 | 0.32456 | 0.19145368 | M13666_at | MYB Proto-oncogene c-myb (alternative products) |
| 701 | Ovary | 0.2256623 | 0.3902359 | 0.324478 | 0.19137146 | RC_AA464603_at | EST: aa11f10.s1 Soares NhHMPu S1 Homo sapiens cDNA clone 812971 3', mRNA sequence. (from Genbank) |
| 702 | Ovary | 0.2254506 | 0.390088 | 0.324425 | 0.19129649 | M59941_at | CSF2RB Colony stimulating factor 2 receptor, beta, low-affinity (granulocyte-macrophage) |
| 703 | Ovary | 0.2251173 | 0.3899641 | 0.324384 | 0.19110961 | Z37976_at | LTBP2 Latent transforming growth factor beta binding protein 2 |
| 704 | Ovary | 0.2250925 | 0.3899183 | 0.324283 | 0.1910619 | AB006190_at | Aquaporin 6 |
| 705 | Ovary | 0.2250637 | 0.3898705 | 0.324006 | 0.19105485 | U78722_at | Zinc finger gene |
| 706 | Ovary | 0.2247989 | 0.3897544 | 0.323969 | 0.19083706 | X99133_at | NGAL gene |
| 707 | Ovary | 0.2247052 | 0.3895951 | 0.323937 | 0.19076073 | U02082_at | Guanine nucleotide regulatory protein (tim1) mRNA |
| 708 | Ovary | 0.2245486 | 0.3895175 | 0.32392 | 0.19074714 | U82169_at-2 | Frizzled (Drosophila) homolog 9 |
| 709 | Ovary | 0.2245486 | 0.389423 | 0.323812 | 0.1906824 | U82169_at | Frizzled homolog (FZD3) mRNA |
| 710 | Ovary | 0.2241699 | 0.3893352 | 0.323755 | 0.19064657 | L41351_at | Prostasin mRNA |
| 711 | Ovary | 0.2239232 | 0.3893337 | 0.323704 | 0.19058192 | X99688_at | mRNA from TYL gene |

FIG. 10C2

| | | | | | |
|---|---|---|---|---|---|
| 712 | Ovary | 0.2234368 | 0.389288 | 0.323504 | 0.19056508 | Z21507_at | EEF1D Eukaryotic translation elongation factor 1 delta (guanine nucleotide exchange protein) |
| 713 | Ovary | 0.223324 | 0.3892518 | 0.323535 | 0.19044599 | D84110_at | RBP-MS/type 1 |
| 714 | Ovary | 0.2231025 | 0.3891506 | 0.323528 | 0.19035226 | U60521_at | Cysteine protease ICE-LAP6 mRNA |
| 715 | Ovary | 0.2230733 | 0.3890696 | 0.323485 | 0.19027635 | M91467_at | HTR1E 5-hydroxytryptamine (serotonin) receptor 1E |
| 716 | Ovary | 0.2228691 | 0.3889066 | 0.323365 | 0.19018038 | W27857_at | EST: 39c2 Human retina cDNA randomly primed sublibrary Homo sapiens cDNA, mRNA sequence. (from Genbank) |
| 717 | Ovary | 0.2227874 | 0.3887913 | 0.32331 | 0.19008285 | X62515_s_at | HSPG2 Heparan sulfate proteoglycan |
| 718 | Ovary | 0.2223649 | 0.3887279 | 0.323249 | 0.19000892 | U68488_at | HTR7 5-hydroxytryptamine (serotonin) receptor 7 (adenylate cyclase-coupled) |
| 719 | Ovary | 0.2223529 | 0.3886375 | 0.322944 | RC_AA4289 X90780_rna 90_at | EST: zw19c12.s1 Soares ovary tumor NbHOT Homo sapiens cDNA clone 769750 3' similar to contains element MER22 repetitive element :. mRNA sequence. (from Genbank) |
| 720 | Ovary | 0.2220772 | 0.3886029 | 0.322821 | 0.18982892 | 1_at | Cardiac troponin I gene, exons 1 to 5 |
| 721 | Ovary | 0.2216803 | 0.3885098 | 0.322761 | 0.18978372 | Z18954_at | S100A5 S100 calcium-binding protein A5 (formerly S100D) |
| 722 | Ovary | 0.2216221 | 0.388467 | 0.32271 | 0.18966484 | L10378_at | (clone CTG-B43a) mRNA sequence |
| 723 | Ovary | 0.2213966 | 0.388462 | 0.322677 | 0.1896279 | W27873_at | Human skeletal muscle 1.3 kb mRNA for tropomyosin |
| 724 | Ovary | 0.2212793 | 0.3884361 | 0.322625 | 0.18950622 | X83863_at | PTGER3 Prostaglandin E receptor 3 (subtype EP3) (alternative products) |
| 725 | Ovary | 0.2212671 | 0.3884253 | 0.322576 | 0.18936893 | AA427468_s_at | Claudin 4 |
| 726 | Ovary | 0.2212168 | 0.3881708 | 0.322359 | 0.1893564 | U30894_at | N-sulphoglucosamine sulphohydrolase mRNA |
| 727 | Ovary | 0.2211196 | 0.3880746 | 0.322208 | 0.18924423 | S70609_at | Glycine transporter type 1b [human, substantia nigra, mRNA, 2364 nt] |
| 728 | Ovary | 0.2206905 | 0.3878066 | 0.322193 | 0.18916713 | L76224_at | NMDA receptor mRNA |
| 729 | Ovary | 0.2203375 | 0.3876561 | 0.322168 | AA182909_a_t | EST: zp51d08.r1 Stratagene HeLa cell s3 937216 Homo sapiens cDNA clone 612975 5', mRNA sequence. (from Genbank) |
| 730 | Ovary | 0.220168 | 0.3876159 | 0.322168 | 0.1890672 | | 5T4 gene for 5T4 Oncofetal antigen |
| 731 | Ovary | 0.2201077 | 0.3875642 | 0.322086 | 0.18901655 | Z29083_at | EST: zr63g05.s1 Soares NhHMPu S1 Homo sapiens cDNA clone 668120 3', mRNA sequence. (from Genbank) |
| 732 | Ovary | 0.2198882 | 0.387551 | 0.322018 | 0.18893233 | RC_AA2522 09_at | M5 muscarinic acetylcholine receptor gene |
| 733 | Ovary | 0.2196115 | 0.3875038 | 0.321938 | 0.18880351 | M80333_at | MEST Mesoderm specific transcript (mouse) homolog |
| | | | | | 0.18872634 | D78611_at | |
| 734 | Ovary | 0.219519 | 0.3874264 | 0.321868 | 0.18866165 | RC_AA2335 32_at | EST: zr30g08.s1 Stratagene NT2 neuronal precursor 937230 Homo sapiens cDNA clone 664958 3', mRNA sequence. (from Genbank) |
| 735 | Ovary | 0.2190676 | 0.387377 | 0.321785 | 0.18447336 | D16593_at | HPCA Hippocalcin |
| 736 | Ovary | 0.2190574 | 0.3872845 | 0.321654 | 0.18843888 | M26041_s_at | HLA-DQA1 MHC class II DQ alpha |

FIG. 10D2

| | | | | | |
|---|---|---|---|---|---|
| 737 | Ovary | 0.2189261 | 0.3870583 | 0.3221625 | 0.18831177 | X89211_at | DNA for endogenous retroviral like element |
| 738 | Ovary | 0.2186424 | 0.387041 | 0.321564 | 0.18825033 | D38496_s_a t | LZTR-1 |
| 739 | Ovary | 0.2186417 | 0.3868621 | 0.321533 | 0.18805781 | D26067_at | KIAA0033 gene, partial cds |
| 740 | Ovary | 0.2186181 | 0.3867657 | 0.321503 | 0.18796907 | J00116_s_at | COL2A1 Collagen, type II, alpha 1 (primary osteoarthritis, spondyloepiphyseal dysplasia, congenital) |
| 741 | Ovary | 0.218522 | 0.3865779 | 0.321439 | 0.18787229 | M20747_s_a t | SLC2A4 Solute carrier family 2 (facilitated glucose transporter), member 4 |
| 742 | Ovary | 0.218484 | 0.3864823 | 0.321364 | 0.18777655 | M15517_cds 3_s_at | TTR gene extracted from Human mutant prealbumin gene directly linked to familial amyloidotic polyneuropathy (FAP) |
| 743 | Ovary | 0.2179969 | 0.3863682 | 0.321336 | 0.18765055 | S76067_at | CNG2=cyclic nucleotide-gated cation channel [human, peripheral leucocytes, Genomic, 784 nt] |
| 744 | Ovary | 0.2178555 | 0.3863513 | 0.321234 | 0.18764892 | M37712_at | CDC2L1 Cell division cycle 2-like 1 (PITSLRE proteins) |
| 745 | Ovary | 0.2177287 | 0.3863513 | 0.321059 | 0.18756416 | D38449_at | G protein-coupled receptor |
| 746 | Ovary | 0.2176923 | 0.3863173 | 0.320925 | 0.1875377 | RC_AA2806 70_at | EST: zs97a07.s1 NCI_CGAP_GCB1 Homo sapiens cDNA clone IMAGE:711540 3', mRNA sequence. (from Genbank) |
| 747 | Ovary | 0.2175772 | 0.3863161 | 0.320826 | 0.18750414 | D63879_at | KIAA0156 gene |
| 748 | Ovary | 0.2175709 | 0.3862604 | 0.320796 | 0.18746865 | RC_AA2434 42_at | Homo sapiens clone 192 Rer1 mRNA, complete cds |
| 749 | Ovary | 0.217467 | 0.3862357 | 0.320772 | 0.18739155 | X14813_at | ACAA Acetyl-Coenzyme A acyltransferase (peroxisomal 3-oxoacyl-Coenzyme A thiolase) |
| 750 | Ovary | 0.2173896 | 0.3861036 | 0.320639 | 0.18729836 | D63477_at | KIAA0143 gene, partial cds |
| 751 | Ovary | 0.2173405 | 0.3860097 | 0.320485 | 0.18718186 | M74447_at | TAP2 Transporter 2, ABC (ATP binding cassette) |
| 752 | Ovary | 0.2170995 | 0.3860021 | 0.320457 | 0.18716078 | RC_AA0529 59_at | EST: zi70b07.s1 Stratagene colon (#937204) Homo sapiens cDNA clone 509941 3' similar to TR:G762826 G762826 PHOSPHOLIPASE C BETA 4. ;, mRNA sequence. (from Genbank) |
| 753 | Ovary | 0.2170971 | 0.386 | 0.320385 | 0.18706916 | RC_AA0265 97_at | EST: ze92h11.s1 Soares fetal heart NbHH19W Homo sapiens cDNA clone 366501 3', mRNA sequence. (from Genbank) |
| 754 | Ovary | 0.2169062 | 0.3858313 | 0.320383 | 0.1869126 | L23852_at | (clone Z146) retinal mRNA, 3' end and repeat region |
| 755 | Ovary | 0.216648 | 0.3857361 | 0.320348 | 0.18686944 | Z29572_at | Antisense mRNA for BCMA peptide |
| 756 | Ovary | 0.2165398 | 0.3856614 | 0.320348 | 0.18678357 | U26710_at | Cbl-b mRNA |
| 757 | Ovary | 0.2165143 | 0.3856599 | 0.320283 | 0.18671958 | HG3039-HT3200_at | Adp-Ribosylation-Like Factor |
| 758 | Ovary | 0.2163815 | 0.3855888 | 0.320237 | 0.18661875 | U37221_at | Cyclophilin-like protein mRNA, partial cds |
| 759 | Ovary | 0.2162752 | 0.385539 | 0.32 | 0.18653804 | RC_AA0244 82_at | EST: ze76a01.s1 Soares fetal heart NbHH19W Homo sapiens cDNA clone 364872 3', mRNA sequence. (from Genbank) |
| 760 | Ovary | 0.2162493 | 0.3855353 | 0.319836 | 0.18639429 | T35656_at | EST: EST88663 Homo sapiens cDNA 5' end similar to None. (from Genbank) |
| 761 | Ovary | 0.2158947 | 0.3855033 | 0.319794 | 0.18635087 | X69636_at | mRNA sequence (15q11-13) |

FIG. 10E2

| | | | | | |
|---|---|---|---|---|---|
| 762 | Ovary | 0.2157192 | 0.3854658 | 0.319782 | RC_AA2514 | EST: zs09g11.s1 NCI_CGAP_GCB1 Homo sapiens cDNA clone IMAGE:684740 3', mRNA sequence. (from Genbank) |
| 763 | Ovary | 0.2156471 | 0.3854393 | 0.319677 | 0.18628952 0_at AF015910_a t | Unknown protein mRNA, partial cds |
| 764 | Ovary | 0.2156437 | 0.3854275 | 0.319667 | 0.186254464 | Unknown protein mRNA, partial cds |
| 765 | Ovary | 0.2153332 | 0.3853348 | 0.319662 | 0.186120033 T47256_s_at | Growth arrest-specific 6 |
| 766 | Ovary | 0.2150727 | 0.3852523 | 0.319635 | 0.186003130313 J02871_s_at RC_AA1214 33_s_at | CYP4B1 Cytochrome P450 IVB1 Axin |
| 767 | Ovary | 0.2148703 | 0.3850054 | 0.319493 | 0.185871162 68_at RC_AA2570 | EST: zr82b05.s1 Soares NhI-IMPu S1 Homo sapiens cDNA clone 682161 3', mRNA sequence. (from Genbank) |
| 768 | Ovary | 0.2148693 | 0.3849889 | 0.319487 | 0.185744933 AA476704_a t | EST: zw87h02.r1 Soares total fetus Nb2HF8 9w Homo sapiens cDNA clone 783987 5', mRNA sequence. (from Genbank) |
| 769 | Ovary | 0.2147891 | 0.3849504 | 0.319358 | 0.185647777 D60964_at | EST: Human fetal brain cDNA 5'-end GEN-143D03, mRNA sequence. (from Genbank) |
| 770 | Ovary | 0.2146678 | 0.3848469 | 0.31931 | 0.185539908 D10995_at | Serotonin 1B receptor |
| 771 | Ovary | 0.2144604 | 0.3846716 | 0.319198 | 0.185478644 M22348_s_a t | UQCRB Ubiquinol-cytochrome c reductase binding protein |
| 772 | Ovary | 0.2143412 | 0.3846225 | 0.319198 | 0.185340033 S77576_at | ERV9 reverse transcriptase homolog [clone RT18] [human, multiple sclerosis, brain plaques, mRNA Partial, 84 nt] |
| 773 | Ovary | 0.2142831 | 0.3844945 | 0.319196 | 0.1852607 U65533_s_a t | KIAA0221 gene |
| 774 | Ovary | 0.2142806 | 0.3844911 | 0.319024 | 0.185234011 M64936_f_at | Homo sapiens retinoic acid-inducible endogenous retroviral DNA |
| 775 | Ovary | 0.2135843 | 0.3844189 | 0.319018 | 0.185171715 X85786_at | BINDING REGULATORY FACTOR |
| 776 | Ovary | 0.2134746 | 0.3843627 | 0.318913 | 0.185117511 M35128_at | Muscarinic acetylcholine receptor gene |
| 777 | Ovary | 0.2131993 | 0.3842661 | 0.318863 | 0.185033377 X64994_at | HGMP07I gene for olfactory receptor |
| 778 | Ovary | 0.213095 | 0.384203 | 0.318795 | 0.184932844 X79683_s_a t | LAMB2 Laminin, beta 2 (laminin S) |
| 779 | Ovary | 0.213039 | 0.3840847 | 0.318693 | 0.184738887 U44754_at | PSE-binding factor PTF gamma subunit mRNA |
| 780 | Ovary | 0.2129948 | 0.3840422 | 0.318683 | 0.184716544 D87449_at | KIAA0260 gene, partial cds |
| 781 | Ovary | 0.2125735 | 0.3836422 | 0.318574 | 0.184681161 M11119_at | Endogenous retrovirus envelope region mRNA (PL1) |
| 782 | Ovary | 0.2125442 | 0.3835498 | 0.318523 | 0.184588166 U02310_at | FKHR Homolog 1 of Drosophila forkhead (rhabdomyosarcoma) |
| 783 | Ovary | 0.2121771 | 0.3835224 | 0.31824 | 0.184563341 AA004333_a t | EST: zh91a01.r1 Soares fetal liver spleen 1NFLS S1 Homo sapiens cDNA clone 428616 5', mRNA sequence. (from Genbank) |
| 784 | Ovary | 0.2119414 | 0.383513 | 0.318199 | 0.184487522 U77601_at | Microsomal glutathione S-transferase (GST-II) mRNA |
| 785 | Ovary | 0.2118475 | 0.3835011 | 0.318155 | 0.184380288 U22816_at | LAR-interacting protein 1b mRNA |

FIG. 10F2

| | | | | | |
|---|---|---|---|---|---|
| 786 | Ovary | 0.2114469 | 0.3833741 | 0.318097 | 0.18432036_t | M96738_s_a | Somatostatin receptor subtype 3 (SSTR3) gene |
| 787 | Ovary | 0.2112345 | 0.3833125 | 0.318094 | 0.18424696 | D79997_at | KIAA0175 gene |
| 788 | Ovary | 0.2110709 | 0.3832769 | 0.31794 | 0.18417068 | HG2566-HT4867_at | Microtubule-Associated Protein Tau, Alt. Splice 5, Exon 4a |
| 789 | Ovary | 0.2108621 | 0.3832431 | 0.317908 | 0.184129177 | M90299_at | GCK Glucokinase (hexokinase 4, maturity onset diabetes of the young 2) |
| 790 | Ovary | 0.2101338 | 0.3831612 | 0.317908 | 0.18412505 | HT2324_at | Potassium Channel Protein (Gb:Z11585) |
| 791 | Ovary | 0.2100628 | 0.383081 | 0.317834 | 0.18400887 | Z78289_at | Z78289 Homo sapiens brain fetus Homo sapiens cDNA clone 1D2, mRNA sequence |
| 792 | Ovary | 0.2099933 | 0.3830184 | 0.317827 | 0.18397938 | U59914_at | Chromosome 15 Mad homolog Smad6 mRNA |
| 793 | Ovary | 0.2099743 | 0.3829334 | 0.317726 | 0.18338685 | D37965_at | PDGF receptor beta-like tumor suppressor (PRLTS) |
| 794 | Ovary | 0.2099292 | 0.3828823 | 0.317663 | 0.18383309 | D42123_at | ESP1/CRP2 |
| 795 | Ovary | 0.2098618 | 0.382842 | 0.317647 | 0.18378854_t | U40152_s_a | Origin recognition complex 1 (HsORC1) mRNA |
| 796 | Ovary | 0.2097012 | 0.3828374 | 0.317639 | 0.18370338_t | D49372_s_a | SCYA11 Small inducible cytokine A11 (eotaxin) |
| 797 | Ovary | 0.2093392 | 0.3827462 | 0.317623 | 0.18367413 | C00038_s_a | EST: HUMGS0003443, Human Gene Signature, 3'-directed cDNA sequence, mRNA sequence. (from Genbank) |
| 798 | Ovary | 0.2092109 | 0.3826993 | 0.317613 | 0.18362753 | U56418_at | Lysophosphatidic acid acyltransferase-beta mRNA |
| 799 | Ovary | 0.2091021 | 0.3826528 | 0.317601 | 0.18353024 | HG1078-HT1078_at | Lamin-Like Protein (Gb:M24732) |
| 800 | Ovary | 0.2089959 | 0.3825613 | 0.317572 | 0.18335396 | S34389_at | HMOX2 Heme oxygenase (decycling) 2 |
| 801 | Ovary | 0.2089027 | 0.3825159 | 0.317476 | 0.18327694 | M28439_at | KERATIN, TYPE I CYTOSKELETAL 17 |
| 802 | Ovary | 0.2088515 | 0.3824928 | 0.317368 | 0.18321551 | H55437_at | EST: CHR220376 Homo sapiens genomic clone C22_491 5'. (from Genbank) |
| 803 | Ovary | 0.2087314 | 0.3824579 | 0.317308 | 0.18319185 | S72493_s_at | KERATIN, TYPE I CYTOSKELETAL 17 |
| 804 | Ovary | 0.2084796 | 0.3824425 | 0.317109 | 0.18310583 | HG3936-HT4206_at | Interleukin 9 Receptor (Gb:S71404) |
| 805 | Ovary | 0.2081756 | 0.3824143 | 0.317 | 0.18306648 | RC_AA449475_at | EST: zx08f10.s1 Soares total fetus Nb2HF8 9w Homo sapiens cDNA clone 785899 3' similar to contains Alu repetitive element;contains element MER22 repetitive element .; mRNA sequence. (from Genbank) |
| 806 | Ovary | 0.2081726 | 0.3824058 | 0.316918 | 0.18295516 | X00129_at | PLASMA RETINOL-BINDING PROTEIN PRECURSOR |
| 807 | Ovary | 0.2078704 | 0.3823701 | 0.316911 | 0.18283588_t | D89377_s_a | Msh (Drosophila) homeo box homolog 2 |
| 808 | Ovary | 0.2078704 | 0.382341 | 0.316714 | 0.1828001_t | D89377_s_a | Adult tooth pulp of third molar fibroblast mRNA for MSX-2 |

FIG. 10G2

| | | | | | |
|---|---|---|---|---|---|
| 809 | Ovary | 0.2078197 | 0.3823199 | 0.316621 | 0.18274665 | M18391_s_a t | TYROSINE-PROTEIN KINASE RECEPTOR EPH PRECURSOR |
| 810 | Ovary | 0.2077808 | 0.3821313 | 0.316527 | 0.18263741 | L40992_at | (clone PEBP2aA1) core-binding factor, runt domain, alpha subunit 1 (CBFA1) mRNA, 3' end of cds |
| 811 | Ovary | 0.2077745 | 0.3821238 | 0.316493 | 0.18259025 | RC_AA0547 15_at | EST: zk68a03.s1 Soares pregnant uterus NbHPU Homo sapiens cDNA clone 487948 3' similar to WP:R04E5.6 CE04798 ; mRNA sequence. (from Genbank) |
| 812 | Ovary | 0.2077466 | 0.3819745 | 0.316348 | 0.18250951 | RC_AA1490_at | EST: zl46b12.s1 Soares pregnant uterus NbHPU Homo sapiens cDNA clone 504959 3', mRNA sequence. (from Genbank) |
| 813 | Ovary | 0.2075722 | 0.3819158 | 0.316244 | 0.18245599 | U76189_at | EXTL2 (EXTL2) mRNA, partial cds |
| 814 | Ovary | 0.2073383 | 0.3817716 | 0.316209 | 0.18238774 | L38517_at | Indian hedgehog protein (IHH) mRNA, 5' end |
| 815 | Ovary | 0.2071717 | 0.3817098 | 0.316178 | 0.18235284 | HG1496-HT1496_s_a t | Adrenal-Specific Protein Pg2 |
| 816 | Ovary | 0.2069506 | 0.3815561 | 0.316122 | 0.18214336 | S78569_at | LAMA4 Laminin, alpha 4 |
| 817 | Ovary | 0.2064033 | 0.3813432 | 0.316109 | 0.1820708 | U45880_at | X-linked inhibitor of apoptosis protein XIAP mRNA |
| 818 | Ovary | 0.2058696 | 0.3813363 | 0.316064 | 0.18204506 | M74525_at | UBE2B Ubiquitin-conjugating enzyme E2B (RAD6 homolog) |
| 819 | Ovary | 0.2055314 | 0.3812586 | 0.31605 | 0.18197961 | X95238_s_a t | H.sapiens mRNA for cysteine-rich secretory protein-1 delta |
| 820 | Ovary | 0.2053392 | 0.3812457 | 0.31604 | 0.18189794 | HG4333-HT4603_at | Zinc Finger Protein Znfpl7 |
| 821 | Ovary | 0.2052299 | 0.3812123 | 0.315992 | 0.18172874 | HG4194-HT4464_at | Sodium/Hydrogen Exchanger 5 |
| 822 | Ovary | 0.2051002 | 0.3812068 | 0.315874 | 0.18171063 | Z11559_at | IREB1 Iron-responsive element binding protein 1 |
| 823 | Ovary | 0.2050945 | 0.3812057 | 0.315859 | 0.18166459 | D63485_at | KIAA0151 gene |
| 824 | Ovary | 0.2049917 | 0.3811966 | 0.315785 | 0.181595312 | U60269_cds | Putative envelope protein; orf similar to env of Type A and Type B retroviruses and to class II HERVs gene extracted from Human endogenous retrovirus HERV-K(HML6) proviral clone HML6.17 putative polymerase and envelope genes, partial cds, and 3'LTR |
| 825 | Ovary | 0.2049604 | 0.3810985 | 0.315769 | 0.1815839 | HG2264-HT2360_at | Atpase, Ca2+ Transporting, Plasma Membrane 1, Alt. Splice 6 |
| 826 | Ovary | 0.2042984 | 0.3810538 | 0.31573 | 0.18145345 | AA191072_a t | EST: zq43c11.r1 Stratagene hNT neuron (#937233) Homo sapiens cDNA clone 632468 5', mRNA sequence. (from Genbank) |
| 827 | Ovary | 0.2041318 | 0.3810325 | 0.315719 | 0.18139854 | U11090_at | Hydroxyindole-O-methyltransferase promoter B-derived (HIOMT) mRNA |
| 828 | Ovary | 0.2035693 | 0.3810171 | 0.315693 | 0.18136963 | D50924_at | KIAA0134 gene |
| 829 | Ovary | 0.2034448 | 0.3808361 | 0.315683 | 0.18131539 | HG982-HT982_s_at | Pre-T/Nk-Cell-Associated Protein 1f6 |

FIG. 10H2

| | | | | | | |
|---|---|---|---|---|---|---|
| 830 | Ovary | 0.2030279 | 0.3807914 | 0.315563 | 0.18124525 HG4114-HT4384_at | Olfactory Receptor Or17-209 |
| 831 | Ovary | 0.2029247 | 0.3804281 | 0.315547 | 0.18114795 Z48512_at | XG mRNA (clone PEP6) |
| 832 | Ovary | 0.2025874 | 0.3803895 | 0.315522 | 0.18112515 RC_AA2338 99_at | EST: zr49c02.s1 Soares NhHMPu S1 Homo sapiens cDNA clone 666/22 3' similar to TR:G469478 G469478 SM-20.; mRNA sequence. (from Genbank) |
| 833 | Ovary | 0.2024833 | 0.3803838 | 0.315441 | 0.18100642 RC_AA0442 77_at | EST: zk54h07.s1 Soares pregnant uterus NbHPU Homo sapiens cDNA clone 486685 3', mRNA sequence. (from Genbank) |
| 834 | Ovary | 0.2022828 | 0.3802317 | 0.315419 | 0.18089731 U65416_rna 1_s_at | MHC class I molecule (MICB) gene |
| 835 | Ovary | 0.2021611 | 0.3801235 | 0.315187 | 0.18077508 X69920_s_a t | CALCR Calcitonin receptor |
| 836 | Ovary | 0.2018699 | 0.3801059 | 0.315102 | 0.18077508 L46353_at | High-mobility group phosphoprotein (HMGI-C) gene, exons 1-3 |
| 837 | Ovary | 0.2017007 | 0.3800293 | 0.315077 | 0.18073854 S83513_s_at | ADCYAP1 Adenylate cyclase activating polypeptide 1 (pituitary) |
| 838 | Ovary | 0.2016619 | 0.3798647 | 0.314984 | 0.1806245 W26635_at | Core-binding factor, runt domain, alpha subunit 2; translocated to, 2 |
| 839 | Ovary | 0.2016012 | 0.3797779 | 0.314983 | 0.18054736 D87953_at | RTP |
| 840 | Ovary | 0.2015148 | 0.3797651 | 0.314942 | 0.1804437 X68742_at | Integrin, alpha subunit |
| 841 | Ovary | 0.2010873 | 0.3797258 | 0.314823 | 0.18038128 M25322_at | SELP Selectin P (granule membrane protein 140kD, antigen CD62) |
| 842 | Ovary | 0.2010492 | 0.3796482 | 0.314676 | 0.18030246 RC_AA4043 81_f_at | EST: zw37a04.s1 Soares total fetus Nb2HF8 9w Homo sapiens cDNA clone 772206 3', mRNA sequence. (from Genbank) |
| 843 | Ovary | 0.2010197 | 0.379615 | 0.3146 | 0.18024704 U32674_s_a t | Orphan receptor GPR9 (GPR9) gene, partial cds |
| 844 | Ovary | 0.2009825 | 0.3795275 | 0.314587 | 0.18014386 S75256_s_at | LNI.=neutrophil lipocalin [human, ovarian cancer cell line OC6, mRNA Partial, 534 nt] |
| 845 | Ovary | 0.2009288 | 0.3794918 | 0.314529 | 0.18005228 X16105_at | RD Radin blood group |
| 846 | Ovary | 0.2008977 | 0.3794338 | 0.314423 | 0.17996652 AA488505_a t | Human placenta (Diff33) mRNA, complete cds |
| 847 | Ovary | 0.2007899 | 0.3791668 | 0.314416 | 0.17986195 RC_AA1258 08_at | EST: zi29e12.s1 Soares pregnant uterus NbHPU Homo sapiens cDNA clone 503374 3', mRNA sequence. (from Genbank) |
| 848 | Ovary | 0.2007868 | 0.3790296 | 0.314414 | 0.17985153 AB000895_a t | Cadherin FIB1, partial cds |
| 849 | Ovary | 0.2005977 | 0.3790249 | 0.314404 | 0.17976114 X86570_at | Acidic hair keratin 1 |
| 850 | Ovary | 0.2004578 | 0.3789289 | 0.3144 | 0.17971715 M88468_at | MVK Mevalonate kinase |
| 851 | Ovary | 0.2003512 | 0.3788907 | 0.314362 | 0.17967772 U43923_at | Transcription factor SUPT4H mRNA |
| 852 | Ovary | 0.2000227 | 0.3788375 | 0.314302 | 0.1795528 Y13153_at | Kynurenine 3-monooxygenase |
| 853 | Ovary | 0.1998798 | 0.3788328 | 0.314245 | 0.17947468 L09717_at | LAMP2 Lysosome-associated membrane protein 2 (alternative products) |

FIG. 10I2

| # | Tissue | | | | | | Description |
|---|---|---|---|---|---|---|---|
| 854 | Ovary | 0.1997251 | 0.3788036 | 0.314226 | 0.1793820G | U43148_at | PTCH Patched (Drosophila) homolog |
| 855 | Ovary | 0.1989991 | 0.3787949 | 0.314199 | 0.17933722 | U13706_at | ELAV-like neuronal protein 1 isoform Hel-N2 (Hel-N1) mRNA, partial cds |
| 856 | Ovary | 0.1988059 | 0.3787683 | 0.314192 | 0.17926261 | L14565_at | PERIPHERIN |
| 857 | Ovary | 0.1987526 | 0.3787781 | 0.314065 | 0.17909911 | U43030_at | Cardiotrophin-1 (CTF-1) mRNA |
| 858 | Ovary | 0.1987522 | 0.3787632 | 0.313982 | 0.1789784 | M64936_i_at | Homo sapiens retinoic acid-inducible endogenous retroviral DNA |
| 859 | Ovary | 0.1985444 | 0.3787413 | 0.313888 | 0.17895679 | L21893_at | SLC10A1 Na/taurocholate cotransporting polypeptide |
| 860 | Ovary | 0.1982387 | 0.3786836 | 0.313382 | 0.17885178 | RC_AA4546 75_at | EST: zx76a07.s1 Soares ovary tumor NbHOT Homo sapiens cDNA clone 809652 3', mRNA sequence. (from Genbank) |
| 861 | Ovary | 0.1982161 | 0.3786035 | 0.313787 | 0.17874955 | X63629_at | CDH3 Cadherin 3 (P-cadherin) |
| 862 | Ovary | 0.1980929 | 0.3785956 | 0.31376 | 0.17867254 | X05610_at | COL4A2 Collagen, type IV, alpha 2 |
| 863 | Ovary | 0.1979989 | 0.3785528 | 0.3137599 | 0.17862225 | HG862-HT862_s_at | Transition Protein 2 |
| 864 | Ovary | 0.1978848 | 0.3785414 | 0.313739 | 0.17861186 | RC_AA2814 51_at | EST: zt02g06.s1 NCI_CGAP_GCB1 Homo sapiens cDNA clone IMAGE:711994 3', mRNA sequence. (from Genbank) |
| 865 | Ovary | 0.1977714 | 0.3784512 | 0.313369 | 0.17850742 | X13444_at | T-CELL SURFACE GLYCOPROTEIN CD8 BETA.3 CHAIN PRECURSOR |
| 866 | Ovary | 0.1974371 | 0.3784433 | 0.313681 | 0.17848812 | M16282_at | Fragile X locus M2C containing an unidentified open reading frame, 3' end |
| 867 | Ovary | 0.197321 | 0.378344 | 0.313671 | 0.178437 | M73489_at | Heat-stable enterotoxin receptor mRNA |
| 868 | Ovary | 0.1972371 | 0.3782725 | 0.313624 | 0.1783249 | AA206625_a_t | EST: zq56d06.r1 Stratagene neuroepithelium (#937231) Homo sapiens cDNA clone 645611 5', mRNA sequence. (from Genbank) |
| 869 | Ovary | 0.1971943 | 0.3782334 | 0.313624 | 0.17825852 | HG3994-HT4264_at | Cpg-Enriched Dna, Clone S16 |
| 870 | Ovary | 0.1971036 | 0.3781698 | 0.313624 | 0.17821059 | H79230_at | EST: yu27e05.r1 Homo sapiens cDNA clone 235040 5'. (from Genbank) |
| 871 | Ovary | 0.1969368 | 0.3780294 | 0.313487 | 0.17808999 | T83397_at | Homo sapiens peroxisomal phytanoyl-CoA alpha-hydroxylase (PAHX) mRNA, complete cds |
| 872 | Ovary | 0.1966432 | 0.3779567 | 0.313437 | 0.17807156 | M57710_at | LGALS3 Lectin, galactoside-binding, soluble, 3 (galectin 3) (NOTE: redefinition of symbol) |
| 873 | Ovary | 0.1965922 | 0.3779428 | 0.313348 | 0.17794518 | HG2197-HT2267_s_a t | Collage, Type VII, Alpha 1 |
| 874 | Ovary | 0.1965641 | 0.3777723 | 0.313284 | 0.17785382 | J00146_at | DHFRP1 Dihydrofolate reductase pseudogene 1 |
| 875 | Ovary | 0.1964848 | 0.3777543 | 0.31328 | 0.17782108 | C16161_s_a t | EST: Human aorta cDNA 5'-end GEN-234B03, mRNA sequence. (from Genbank) |
| 876 | Ovary | 0.1963598 | 0.3776805 | 0.313262 | 0.17770942 | HG174-HT174_at | Desmoplakin I |

FIG. 10J2

| # | Tissue | | | | | Accession | Description |
|---|---|---|---|---|---|---|---|
| 877 | Ovary | 0.1962343 | 0.3776398 | 0.313242 | 0.17761466 | X99393_s_a | CMKBR5 gene, non-functional mutant |
| 878 | Ovary | 0.1961761 | 0.3775093 | 0.313099 | 0.17759982 | AA076003_a t | Zm89c09.r1 Stratagene ovarian cancer (#937219) Homo sapiens cDNA clone 545104 5', mRNA sequence. (from Genbank) |
| 879 | Ovary | 0.1961386 | 0.3774971 | 0.313096 | 0.17754743 | Z28339_at | Delta 4-3-oxosteroid 5 beta-reductase |
| 880 | Ovary | 0.1956929 | 0.3774835 | 0.312813 | 0.17737551_s_at | X52150_rna | Arylsulfatase A |
| 881 | Ovary | 0.1956315 | 0.3772636 | 0.312769 | 0.17732102_t | X16609_s_a | ANK1 Ankyrin 1, erythrocytic |
| 882 | Ovary | 0.1955971 | 0.3772588 | 0.31268 | 0.1772554 | D83779_at | KIAA0195 gene |
| 883 | Ovary | 0.1955952 | 0.3770583 | 0.312657 | 0.17720369_75_at | RC_AA5989 | EST: ae40c09.s1 Gessler Wilms tumor Homo sapiens cDNA clone 898288 3', mRNA sequence. (from Genbank) |
| 884 | Ovary | 0.1952489 | 0.3769278 | 0.312598 | 0.17714316 | D83778_at | KIAA0194 gene, partial cds |
| 885 | Ovary | 0.195103 | 0.3769049 | 0.312571 | 0.1770328 | HG4167-HT4437_al | Nuclear Factor 1, A Type |
| 886 | Ovary | 0.1947902 | 0.3768638 | 0.312467 | 0.17698736 | RC_AA4062 33_at | EST: zv10e07.s1 Soares NhHMPu S1 Homo sapiens cDNA clone 753252 3', mRNA sequence. (from Genbank) |
| 887 | Ovary | 0.1947533 | 0.3768362 | 0.312342 | 0.17690822 | U07151_at | GTP binding protein (ARL3) mRNA |
| 888 | Ovary | 0.1946614 | 0.3765677 | 0.312274 | 0.176884171 | HG3412-HT3593_s_a | Blue Cone Photoreceptor Pigment |
| 889 | Ovary | 0.1946374 | 0.3765479 | 0.3121821 | 0.17677781 | M31932_at | FCGR2A Fc fragment of IgG, low affinity IIa, receptor for (CD32) |
| 890 | Ovary | 0.1945941 | 0.3764178 | 0.312151 | 0.1767181t | AA262132_a | EST: zs23b10.r1 NCI_CGAP_GCB1 Homo sapiens cDNA clone IMAGE:686011 5' similar to SW:YHH6_YEAST P32793 HYPOTHETICAL 41.8 KD PROTEIN IN SPO13-ARG4 INTERGENIC REGION. ;; mRNA sequence. (from Genbank) |
| 891 | Ovary | 0.1943887 | 0.376358 | 0.312022 | 0.17657585 | Y00815_at | PTPRF Protein tyrosine phosphatase, receptor type, f polypeptide |
| 892 | Ovary | 0.1943494 | 0.3763244 | 0.311752 | 0.17652713 | X81892_at | HE6 Tm7 receptor |
| 893 | Ovary | 0.1941002 | 0.376241 | 0.311736 | 0.17650083 | AA252752_a t | EST: zs26b10.r1 NCI_CGAP_GCB1 Homo sapiens cDNA clone IMAGE:686299 5', mRNA sequence. (from Genbank) |
| 894 | Ovary | 0.1940012 | 0.3762325 | 0.311662 | 0.17634219 | J03258_at | VDR Vitamin D (1,25-dihydroxyvitamin D3) receptor |
| 895 | Ovary | 0.1939615 | 0.3722209 | 0.311659 | 0.17627579 | V00535_rna 2_s_at | Interferon beta 1 gene extracted from Gene for human fibroblast interferon beta 1 |
| 896 | Ovary | 0.1935352 | 0.3761881 | 0.311643 | 0.17620535 | X85106_at | Ribosomal S6 kinase |
| 897 | Ovary | 0.1932634 | 0.3757755 | 0.311151 | 0.17616215 | U62325_at | FE65-like protein (hFE65L) mRNA, partial cds |
| 898 | Ovary | 0.193139 | 0.3754952 | 0.311083 | 0.17610224 | L41607_at | GCNT2 Glucosaminyl (N-acetyl) transferase 2, I-branching enzyme |
| 899 | Ovary | 0.1930834 | 0.3754535 | 0.310993 | 0.17605074 | U46023_at | Xq28 mRNA |
| 900 | Ovary | 0.1929601 | 0.3753222 | 0.310989 | 0.17593881 | Y13620_at | BCL9 gene |

FIG. 10K2

| # | Tissue | Col3 | Col4 | Col5 | Col6 | Col7 | Description |
|---|---|---|---|---|---|---|---|
| 901 | Ovary | 0.1926704 | 0.3753078 | 0.310983 | 0.17590858 | U09303_at | Placenta LERK-2 (EPLG2) mRNA |
| 902 | Ovary | 0.1925829 | 0.3752275 | 0.310757 | | M68516_rna1_at | PCI gene (plasminogen activator inhibitor 3) extracted from Human protein C inhibitor gene |
| 903 | Ovary | 0.1923133 | 0.3762243 | 0.310733 | 0.17572318 | M57730_at | EPH-RELATED RECEPTOR TYROSINE KINASE LIGAND 1 PRECURSOR |
| 904 | Ovary | 0.1923027 | 0.3751989 | 0.310709 | 0.17563832 | X03635_at | ESR Estrogen receptor |
| 905 | Ovary | 0.1921478 | 0.3751304 | 0.310638 | 0.17561139 | D38548_at | KIAA0076 gene |
| 906 | Ovary | 0.1921162 | 0.3749445 | 0.310588 | 0.17551304 | X72964_at | CALT Callractin (20kD calcium-binding protein) |
| 907 | Ovary | 0.1920067 | 0.3749433 | 0.310403 | 0.17545338 | L05188_f_at | Small proline-rich protein 2 (SPRR2B) gene |
| 908 | Ovary | 0.1917377 | 0.3749367 | 0.310385 | 0.17530051 | X82279_s_at | Fas, Apo-1 gene (promoter and exon 1) |
| 909 | Ovary | 0.1917295 | 0.3748834 | 0.310373 | 0.1752377 | L11369_at | Protocadherin 42 mRNA, 3' end of cds for alternative splicing PC42-8 |
| 910 | Ovary | 0.1914227 | 0.3748066 | 0.310298 | 0.17521891 | RC_AA013231_at | EST: ze28h05.s1 Soares retina N2b4HR Homo sapiens cDNA clone 360345 3', mRNA sequence. (from Genbank) |
| 911 | Ovary | 0.1913304 | 0.3747638 | 0.310269 | 0.17518118 | X69878_at | FLT4 Fms-related tyrosine kinase 4 |
| 912 | Ovary | 0.1913173 | 0.3746395 | 0.310087 | 0.17513362 | M21305_at | Alpha satellite and satellite 3 junction DNA sequence |
| 913 | Ovary | 0.1910931 | 0.3745894 | 0.31002 | 0.1750784 | U66083_at | MAGE-9 antigen (MAGE9) gene |
| 914 | Ovary | 0.1907415 | 0.3745084 | 0.309991 | 0.17494902 | M37190_at | Ras inhibitor mRNA, 3' end |
| 915 | Ovary | 0.1907338 | 0.3743423 | 0.309921 | 0.17490327 | U15642_s_at | E2F5 E2F transcription factor 5, p130-binding |
| 916 | Ovary | 0.1906841 | 0.374249 | 0.309797 | 0.17484218 | HG3731-HT4001_at | Immunoglobulin Heavy Chain, Vdjrc Regions (Gb:L23566) |
| 917 | Ovary | 0.1906285 | 0.3741354 | 0.309763 | 0.17475237 | D31766_at | PUTATIVE GLUCOSAMINE-6-PHOSPHATE ISOMERASE |
| 918 | Ovary | 0.190567 | 0.3740816 | 0.309617 | 0.17469741 | RC_AA290745_at | EST: zt22h02.s1 Soares ovary tumor NbHOT Homo sapiens cDNA clone 713907 3' similar to TR:G520469 G520469 NA+/GLUCOSE COTRANSPORTER-RELATED PROTEIN ;, mRNA sequence. (from Genbank) |
| 919 | Ovary | 0.190565 | 0.3739551 | 0.309561 | 0.17465876 | D26129_at | RNS1 Ribonuclease A (pancreatic) |
| 920 | Ovary | 0.1904499 | 0.3738669 | 0.309505 | 0.17461519 | M17754_at | BN51T BN51 (BHK21) temperature sensitivity complementing |
| 921 | Ovary | 0.1904486 | 0.373741 | 0.309338 | 0.17453624 | K00629_f_at | Human kpni repeat mrna (cdna clone pcd-kpni-4), 3' end |
| 922 | Ovary | 0.1901666 | 0.373658 | 0.309334 | 0.17444245 | HG3566-HT3769_at | Zinc Finger Protein (Gb:M88359) |
| 923 | Ovary | 0.190132 | 0.3735214 | 0.309205 | 0.17437154 | X95191_at | Delta-sarcoglycan |
| 924 | Ovary | 0.1901048 | 0.3734771 | 0.309075 | 0.17433326 | U06088_at | N-ACETYLGALACTOSAMINE-6-SULFATASE PRECURSOR |
| 925 | Ovary | 0.1900652 | 0.3734525 | 0.309058 | 0.17425455 | U79242_at | Clone 23560 mRNA sequence |
| 926 | Ovary | 0.1896956 | 0.3734359 | 0.309031 | 0.17418864 | X90568_at | TTN Titin |

FIG. 10L2

| # | Tissue | | | | ID | Description |
|---|---|---|---|---|---|---|
| 927 | Ovary | 0.1896563 | 0.373349 | 0.309003 | M77144_rna1_at | 3-beta-hydroxysteroid dehydrogenase gene extracted from Human type II 3-beta hydroxysteroid dehydrogenase/ 5-delta - 4-delta isomerase gene |
| 928 | Ovary | 0.1896153 | 0.3733118 | 0.308968 | X14008_rna1_f_at | Lysozyme gene (EC 3.2.1.17) |
| 929 | Ovary | 0.1895359 | 0.3731683 | 0.308892 | L27080_at | Melanocortin 5 receptor (MC5R) gene |
| 930 | Ovary | 0.1895244 | 0.3731147 | 0.308891 | RC_AA430026_at | EST: zw65e11.s1 Soares testis NHT Homo sapiens cDNA clone 781100 3', mRNA sequence. (from Genbank) |
| 931 | Ovary | 0.189448 | 0.3730601 | 0.308862 | M85165_at | ELK4 ELK4, ETS-domain protein (SRF accessory protein 1) NOTE: Symbol and name provisional |
| 932 | Ovary | 0.1893279 | 0.3729532 | 0.308752 | M95585_s_at | HLF Hepatic leukemia factor |
| 933 | Ovary | 0.1893212 | 0.3729438 | 0.308701 | U41515_at | Deleted in split hand/split foot 1 (DSS1) mRNA |
| 934 | Ovary | 0.1889277 | 0.3729428 | 0.308527 | U31120_rna1_at | Interleukin-13 (IL-13) precursor gene |
| 935 | Ovary | 0.1887721 | 0.3729209 | 0.308491 | U72209_at | YY1-associated factor 2 (YAF2) mRNA |
| 936 | Ovary | 0.1884949 | 0.3728914 | 0.308382 | X06700_s_at | COL3A1 Alpha-1 type 3 collagen |
| 937 | Ovary | 0.1884324 | 0.3728731 | 0.308356 | U21049_at | DD96 mRNA |
| 938 | Ovary | 0.1883637 | 0.3727579 | 0.308327 | L13210_at | Mac-2 binding protein mRNA |
| 939 | Ovary | 0.1883624 | 0.3727554 | 0.308248 | RC_AA290599_at | EST: zs45c01.s1 NCI_CGAP_GCB1 Homo sapiens cDNA clone IMAGE:700416 3', mRNA sequence. (from Genbank) |
| 940 | Ovary | 0.188347 | 0.372631 | 0.308168 | HG1140-HT4817_s_at | Collagen, Type Vi, Alpha 2, Alt. Splice 2 |
| 941 | Ovary | 0.1833355 | 0.3726174 | 0.308155 | AA402971_s_at | Homo sapiens mRNA for serine protease (TLSP), complete cds |
| 942 | Ovary | 0.1882888 | 0.3723436 | 0.308014 | D13720_s_at | TYROSINE-PROTEIN KINASE ITK/TSK |
| 943 | Ovary | 0.1882583 | 0.3721747 | 0.307962 | U30313_at | Diadenosine tetraphosphatase mRNA |
| 944 | Ovary | 0.1882418 | 0.3720534 | 0.30796 | U17894_at | Alpha(1,2)fucosyltransferase |
| 945 | Ovary | 0.1880472 | 0.3720158 | 0.307657 | AF004709_a_at | Protein kinase mitogen- activated 13 |
| 946 | Ovary | 0.1879802 | 0.3719988 | 0.307498 | U34976_at | Gamma-sarcoglycan mRNA |
| 947 | Ovary | 0.1876881 | 0.3719514 | 0.307498 | U46461_at | Dishevelled homolog (DVL) mRNA |

| | | | | | | |
|---|---|---|---|---|---|---|
| 948 | Ovary | 0.1876494 | 0.3719071 | 0.30737 | 0.172708963_at | U52111_rna | ALD gene (adrenoleukodystrophy protein) extracted from Human Xq28 genomic DNA in the region of the ALD locus containing the genes for creatine transporter (SLC6A8), CDM, adrenoleukodystrophy (ALD), Na+-isocitrate dehydrogenase gamma subunit (IDH), and translocon-associated protein delta (TRAP) genes, plexin related protein (PLEXR) and serine kinase (SK) genes, partial cds, Xq28lu1 gene and cytochrome C (CCp) pseudogene |
| 949 | Ovary | 0.187404 | 0.3717812 | 0.307353 | 0.1726645 | X92744_at | BETA-DEFENSIN 1 PRECURSOR |
| 950 | Ovary | 0.1873567 | 0.3716532 | 0.307284 | 0.172614 | M27749_r_at | Immunoglobulin-related 14.1 protein mRNA |
| 951 | Ovary | 0.1873296 | 0.3715813 | 0.307164 | 0.172253736 | U33839_at | No description available for U33839 |
| 952 | Ovary | 0.1872688 | 0.3715774 | 0.307103 | 0.1725215 | D14874_at | ADM Adrenomedullin |
| 953 | Ovary | 0.1872684 | 0.3715721 | 0.307056 | 0.17249201 | D90084_at | PDHA1 Pyruvate dehydrogenase (lipoamide) alpha 1 |
| 954 | Ovary | 0.1872599 | 0.3715013 | 0.306941 | 0.17243743 | X58298_s_at | IL6R Interleukin 6 receptor |
| 955 | Ovary | 0.1870949 | 0.3712805 | 0.306941 | 0.172410059 | RC_AA4029 68_at | EST: zu54b12.s1 Soares ovary tumor NbHOT Homo sapiens cDNA clone 741791 3', mRNA sequence. (from Genbank) |
| 956 | Ovary | 0.1869254 | 0.3712608 | 0.306883 | 0.17231303 | C02170_at X12876_s_a | EST: HUMGS0006510, Human Gene Signature, 3'-directed cDNA sequence, mRNA sequence. (from Genbank) |
| 957 | Ovary | 0.1868315 | 0.3712539 | 0.306867 | 0.17223693 | t | KRT18 Keratin 18 |
| 958 | Ovary | 0.1867321 | 0.3712421 | 0.306864 | 0.172129214 | L19314_at | HRY gene |
| 959 | Ovary | 0.1867098 | 0.3712182 | 0.306856 | 0.17200824 | RC_AA4183 94_at | EST: zv92e06.s1 Soares NhHMPu S1 Homo sapiens cDNA clone 767266 3', mRNA sequence. (from Genbank) |
| 960 | Ovary | 0.1866799 | 0.3711844 | 0.306856 | 0.17192397 | U19557_s_a t | Squamous cell carcinoma antigen 2 (SCCA2) mRNA |
| 961 | Ovary | 0.1866336 | 0.3711673 | 0.30685 | 0.171892541_at | U46692_rna | Cystatin B gene |
| 962 | Ovary | 0.1865829 | 0.3710637 | 0.306752 | 0.1718061 | U75968_at | CHL1 protein |
| 963 | Ovary | 0.1864663 | 0.3710224 | 0.306614 | 0.171755181 | AA479266_ t | EST: zv17h06.r1 Soares NhHMPu S1 Homo sapiens cDNA clone 753947 5', mRNA sequence. (from Genbank) |
| 964 | Ovary | 0.186417 | 0.3709579 | 0.306575 | 0.17172752 | Y10505_at | CD104 protein |
| 965 | Ovary | 0.1863659 | 0.3709482 | 0.306569 | 0.17169054 | D63487_at | KIAA0153 gene, partial cds |
| 966 | Ovary | 0.1861701 | 0.370808 | 0.306565 | 0.17164125 | X63717_at | APT1 Apoptosis (APO-1) antigen 1 |
| 967 | Ovary | 0.1860835 | 0.3707033 | 0.306491 | 0.17153943 | M25629_at | Kallikrein mRNA, clone clone phKK25 |
| 968 | Ovary | 0.185776 | 0.3706603 | 0.306488 | 0.17144233 | RC_AA4295 71_at | EST: zw75d12.s1 Soares testis NHT Homo sapiens cDNA clone 782039 3' similar to contains element PTR7 repetitive element; mRNA sequence. (from Genbank) |

| | | | | | | |
|---|---|---|---|---|---|---|
| 969 | Ovary | 0.1857371 | 0.3706249 | 0.306371 | 0.1713900158 | RC_AA2430 | EST: zr24h08.s1 Stratagene NT2 neuronal precursor 937230 Homo sapiens cDNA clone 664383 3', mRNA sequence. (from Genbank) |
| 970 | Ovary | 0.1857223 | 0.370395 | 0.306204 | 0.1713776 | W26652_at | EST: 34c6 Human retina cDNA randomly primed sublibrary Homo sapiens cDNA, mRNA sequence. (from Genbank) |
| 971 | Ovary | 0.1856695 | 0.3703745 | 0.30618 | 0.171280985_at | RC_AA1351 | EST: zo27a05.s1 Stratagene colon (#937204) Homo sapiens cDNA clone 588080 3', mRNA sequence. (from Genbank) |
| 972 | Ovary | 0.1856064 | 0.3703034 | 0.305967 | 0.17122948 | U11701_at | LIM-homeobox domain protein (hLH-2) mRNA |
| 973 | Ovary | 0.1854401 | 0.3702684 | 0.305955 | 0.17115727 | U75362_at | Isopeptidase T-3 (ISOT-3) mRNA |
| 974 | Ovary | 0.1853963 | 0.370245 | 0.30566 | 0.17109703t | HG4063-HT4333_s_a | Transcription Factor Hbf-2 |
| 975 | Ovary | 0.1853801 | 0.3701545 | 0.305493 | 0.17100959 | D16469_at | ORF, Xq terminal portion |
| 976 | Ovary | 0.1853302 | 0.3701243 | 0.305478 | 0.17096443t | AF006265_a | Estrogen receptor-binding fragment-associated gene 9 |
| 977 | Ovary | 0.1853019 | 0.3699972 | 0.30547 | 0.17094505 | U79277_at | Clone 23548 mRNA sequence |
| 978 | Ovary | 0.1852112 | 0.3699404 | 0.305441 | 0.17087772t | HG2850-HT4814_s_a | Biliary Glycoprotein, Alt. Splice 5, A |
| 979 | Ovary | 0.1851208 | 0.3698106 | 0.305434 | 0.17083211 | X12453_at | S-ARRESTIN |
| 980 | Ovary | 0.1850885 | 0.3698041 | 0.305344 | 0.17076683 | R10770_at | EST: yf36a08.r1 Homo sapiens cDNA clone 128918 5'. (from Genbank) |
| 981 | Ovary | 0.1850545 | 0.3697596 | 0.305238 | 0.17066713 | M74297_at | HOXA4 Homeo box A4 |
| 982 | Ovary | 0.1849343 | 0.369603 | 0.305179 | 0.17061892t | X51441_s_a | SERUM AMYLOID A PROTEIN PRECURSOR |
| 983 | Ovary | 0.1848842 | 0.3696023 | 0.305136 | 0.17054844 | C15401_at | Human fetal brain cDNA 5'-end GEN-140D09, mRNA sequence. (from Genbank) |
| 984 | Ovary | 0.1848446 | 0.3694861 | 0.305114 | 0.17051065 | J03634_at | INHBA Inhibin, beta A (activin A, activin AB alpha polypeptide) |
| 985 | Ovary | 0.1848191 | 0.3694773 | 0.305052 | 0.1704397453_at | RC_AA6090 | EST: aff0f08.s1 Soares testis NHT Homo sapiens cDNA clone 1031271 3', mRNA sequence. (from Genbank) |
| 986 | Ovary | 0.1846284 | 0.3694176 | 0.305007 | 0.17036076 | U25750_at | Chromosome 17q21 mRNA clone 1046:1-1 |
| 987 | Ovary | 0.1845811 | 0.3694044 | 0.304967 | 0.17033893 | X64643_at | C6.1A PROTEIN |
| 988 | Ovary | 0.1845043 | 0.3693574 | 0.304959 | 0.17028628 | X06825_at | Skeletal beta-tropomyosin |
| 989 | Ovary | 0.184469 | 0.3692072 | 0.30493 | 0.17022148 | M87338_at | RFC2 Replication factor C (activator 1) 2, 40kD subunit |
| 990 | Ovary | 0.1843618 | 0.3691933 | 0.304866 | 0.17016836 | L14812_at | RBL1 Retinoblastoma-like 1 (p107) |
| 991 | Ovary | 0.1843207 | 0.369055 | 0.30481 | 0.17003818 | X54489_ma1_at | Melanoma growth stimulatory activity (MGSA) |
| 992 | Ovary | 0.1842822 | 0.3689825 | 0.304772 | 0.16992377 | D10656_at | CRK V-crk avian sarcoma virus CT10 oncogene homolog |
| 993 | Ovary | 0.1841096 | 0.368921 | 0.304749 | 0.16984268 | D28364_at | Annexin II, 5'UTR (sequence from the 5'cap to the start codon) |

FIG. 1002

| | | | | |
|---|---|---|---|---|
| 994 | Ovary | 0.1840693 | 0.3688842 | 0.304749 | 0.1697481 | AA504384_a | EST: aa59c02.r1 NCI_CGAP_GCB1 Homo sapiens cDNA clone IMAGE:825218 5' similar to contains element MIR repetitive element.; mRNA sequence. (from Genbank) |
| 995 | Ovary | 0.1839207 | 0.3688733 | 0.304582 | 0.16971926 | U45982_at | G protein-coupled receptor GPR-9-6 gene |
| 996 | Ovary | 0.1838374 | 0.3687535 | 0.304525 | 0.16964038 | X70811_at | ADRB3 Adrenergic, beta-3-, receptor |
| 997 | Ovary | 0.1837558 | 0.3687232 | 0.304496 | 0.1696318 | M58583_at | CEREBELLIN 1 PRECURSOR |
| 998 | Ovary | 0.1837549 | 0.3686511 | 0.304458 | 0.16958816 | X72841_at | Retinoblastoma-binding protein (RbAp46) mRNA |
| 999 | Ovary | 0.1836975 | 0.3686487 | 0.304438 | 0.1695004 | S82592_at | Evi-1 |
| 1000 | Ovary | 0.1834772 | 0.3686337 | 0.304397 | 0.16941014 | U64315_s_a t | XPF Xeroderma pigmentosum, complementation group F |

FIG. 10P2

| | | | | |
|---|---|---|---|---|
| 1 | Pancreas | 0.9278966 | 0.7129607 | 0.625972 | X51698_s_a t | 0.46571717 | SPASMOLYTIC POLYPEPTIDE PRECURSOR |
| 2 | Pancreas | 0.7787252 | 0.6661443 | 0.579693 | 0.4348104 | J00268_s_at | INS Insulin |
| 3 | Pancreas | 0.6587432 | 0.6388133 | 0.556793 | 0.41948733 | J05412_at | REG1A Regenerating islet-derived 1 alpha (pancreatic stone protein, pancreatic thread protein) |
| 4 | Pancreas | 0.6290712 | 0.6197183 | 0.543397 | 0.40783224 | X52003_at | TFF1 Trefoil factor 1 (breast cancer, estrogen-inducible sequence expressed in) |
| 5 | Pancreas | 0.6248099 | 0.6119224 | 0.534312 | 0.39945528 | Z48314_s_at | MUC5B Mucin 5, subtype B, tracheobronchial |
| 6 | Pancreas | 0.5983197 | 0.6003079 | 0.528163 | 0.3925389 | U31449_at | Intestinal and liver tetraspan membrane protein (il-TMP) mRNA |
| 7 | Pancreas | 0.5959305 | 0.5949147 | 0.521431 | 0.3871077 | J05036_s_at | CTSE Cathepsin E |
| 8 | Pancreas | 0.5958913 | 0.5919794 | 0.514464 | 0.38182062 | M84424_at | CATHEPSIN E PRECURSOR |
| 9 | Pancreas | 0.5700184 | 0.5832725 | 0.509603 | 0.37752536 | AA372630_s_at | Homo sapiens GW112 protein (GW112) mRNA, complete cds |
| 10 | Pancreas | 0.5665532 | 0.5786274 | 0.505425 | 0.37383676 | J04813_s_at | Cytochrome P450, subfamily IIIA (niphedipine oxidase), polypeptide 5 |
| 11 | Pancreas | 0.5406267 | 0.5773224 | 0.501868 | 0.3697819 | RC_AA2623 51_f_at | EST: zr44g03.s1 Soares NhHMPu S1 Homo sapiens cDNA clone 666292 3', mRNA sequence. (from Genbank) |
| 12 | Pancreas | 0.5383231 | 0.5728496 | 0.50052 | 0.36606857 | AB006781_s_at | Galectin-4 |
| 13 | Pancreas | 0.5372187 | 0.5711106 | 0.49599 | 0.363105 | L08010_at | Regenerating protein I beta |
| 14 | Pancreas | 0.5348939 | 0.5670255 | 0.492834 | 0.36071837 | M24400_at | CTRB1 Chymotrypsinogen B1 |
| 15 | Pancreas | 0.5152407 | 0.5668822 | 0.49035 | 0.35809212 | U31201_cds_s_at | Laminin gamma2 chain gene (LAMC2) |
| 16 | Pancreas | 0.5134798 | 0.5623378 | 0.487834 | 0.35570014 | D83847_f_at | ELASTASE IIIB PRECURSOR |
| 17 | Pancreas | 0.5104177 | 0.5595179 | 0.485651 | 0.35347328 | M22612_f_at | PRSS1 Protease, serine, 1 (trypsin 1) |

FIG. 11A

| | | | | | |
|---|---|---|---|---|---|
| 18 | Pancreas | 0.5086832 | 0.5594127 | 0.481914 | 0.35122478 | K01396_at | PI Protease inhibitor 1 (anti-elastase), alpha-1-antitrypsin |
| 19 | Pancreas | 0.5085123 | 0.5581134 | 0.480139 | 0.34485228 | M27602_f_at | Protease, serine, 2 (trypsin 2) |
| 20 | Pancreas | 0.5063022 | 0.5550363 | 0.478336 | 0.3466433 | M16653_at | Pancreatic elastase IIB mRNA |
| 21 | Pancreas | 0.5047094 | 0.5535021 | 0.47632 | 0.34488845 | M54994_f_at | Carboxyl ester lipase (bile salt-stimulated lipase) |
| 22 | Pancreas | 0.5045138 | 0.5502149 | 0.474429 | 0.3431327 | L32137_at | COMP Cartilage oligomeric matrix protein |
| 23 | Pancreas | 0.5037171 | 0.5494857 | 0.473367 | 0.3414517 | M64099_at | GAMMA-GLUTAMYLTRANSPEPTIDASE 5 PRECURSOR |
| 24 | Pancreas | 0.5036094 | 0.5476162 | 0.471479 | 0.33992696 | HG2797-HT2906_s_a t | Clathrin, Light Polypeptide B, Alt. Splice 2 |
| 25 | Pancreas | 0.5034949 | 0.5466424 | 0.469193 | 0.33800283 | J05125_at | PNLIP Pancreatic lipase |
| 26 | Pancreas | 0.497818 | 0.5450661 | 0.467477 | 0.3362076 | X54457_s_a t | CEL Carboxyl ester lipase (bile salt-stimulated lipase) |
| 27 | Pancreas | 0.4964372 | 0.5427789 | 0.465752 | 0.33502817 | U21128_at | LUM Lumican |
| 28 | Pancreas | 0.4941935 | 0.54114159 | 0.465018 | 0.33354896 | M21054_s_a t | Phospholipase A2, group IB (pancreas) |
| 29 | Pancreas | 0.4880559 | 0.5404347 | 0.463772 | 0.3323119 | L15533_rna1_at | Pancreatits-associated protein (PAP) gene |
| 30 | Pancreas | 0.485838 | 0.5398616 | 0.462766 | 0.33064112 | X67318_at | CPA1 Carboxypeptidase A1 |
| 31 | Pancreas | 0.4848106 | 0.5381253 | 0.461915 | 0.32895386 | M21056_at | Lung phospholipase A-2 (PLA-2) mRNA, clone lung-1(hcDNA) |
| 32 | Pancreas | 0.4799522 | 0.5300885 | 0.460993 | 0.32767808 | M18728_at | NCA Non-specific cross reacting antigen |
| 33 | Pancreas | 0.4793133 | 0.5371567 | 0.459889 | 0.326587 | J04040_at | GCG Glucagon |
| 34 | Pancreas | 0.4768606 | 0.5359932 | 0.45902 | 0.32553014 | M18700_s_a t | ELASTASE IIIA PRECURSOR |
| 35 | Pancreas | 0.4708147 | 0.5328612 | 0.45802 | 0.32453454 | L22524_s_at | MATRILYSIN PRECURSOR |
| 36 | Pancreas | 0.4680343 | 0.5319334 | 0.455965 | 0.323309172 | X90579_s_a t | H.sapiens DNA for cyp related pseudogene |
| 37 | Pancreas | 0.4678389 | 0.531292 | 0.455625 | 0.32220298 | X99133_at | NGAL gene |
| 38 | Pancreas | 0.4635845 | 0.5302596 | 0.453677 | 0.32110864 | HG3431-HT3616_s_a t | Decorin, Alt. Splice 1 |
| 39 | Pancreas | 0.4605548 | 0.5292271 | 0.45318 | 0.31988648 | J02883_at | CLPS Colipase, pancreatic |
| 40 | Pancreas | 0.4553431 | 0.5274373 | 0.452509 | 0.3191138 | RC_AA4357 69_s_at | EST: zf79h07.s1 Soares testis NHT Homo sapiens cDNA clone 728605 3', mRNA sequence. (from Genbank) |
| 41 | Pancreas | 0.451547 | 0.5254321 | 0.45119 | 0.318234 | Z71389_at | Skin-antimicrobial-peptide 1 (SAP1) |
| 42 | Pancreas | 0.451321 | 0.5250532 | 0.450535 | 0.31721777 | J05068_at | TCN1 Transcobalamin I |
| 43 | Pancreas | 0.4501483 | 0.5236372 | 0.449284 | 0.3164184 | S75256_s_at | HNL=neutrophil lipocalin [human, ovarian cancer cell line OC6, mRNA Partial, 534 nt] |

FIG. 11B

| | | | | | | |
|---|---|---|---|---|---|---|
| 44 | Pancreas | 0.4495522 | 0.5234609 | 0.448033 | 0.315403671 J03507_at | C7 Complement component 7 |
| 45 | Pancreas | 0.448858 | 0.5204639 | 0.447189 | 0.31452382 M34057_at | LTBP1 Latent transforming growth factor beta binding protein 1 |
| 46 | Pancreas | 0.4431819 | 0.5185894 | 0.446309 | 0.3138691 X71345_f_at | PRSS3 Protease, serine, 3 (trypsin 3) |
| 47 | Pancreas | 0.4355238 | 0.5182232 | 0.445197 | 0.31310672 Y00757_at | SGNE1 Secretory granule, neuroendocrine protein 1 (7B2 protein) |
| 48 | Pancreas | 0.4347078 | 0.5168417 | 0.444231 | 0.31222358 RC_AA4497 49_at | EST: zx07e10.s1 Soares total fetus Nb2HF8 9w Homo sapiens cDNA clone 785802 3', mRNA sequence. (from Genbank) |
| 49 | Pancreas | 0.4306283 | 0.5161458 | 0.443862 | 0.31143254 RC_AA4547 33_s_at | EST: zx77c10.s1 Soares ovary tumor NbHOT Homo sapiens cDNA clone 809778 3', mRNA sequence. (from Genbank) |
| 50 | Pancreas | 0.4301526 | 0.5160719 | 0.443338 | 0.31104864 M62403_s_a t | IGFBP4 Insulin-like growth factor-binding protein 4 |
| 51 | Pancreas | 0.4244237 | 0.515964 | 0.442747 | 0.3097386 L24203_at | Ataxia-telangiectasia group D-associated protein mRNA |
| 52 | Pancreas | 0.4240417 | 0.5150696 | 0.441664 | 0.3088449 X52022_at | RNA for type VI collagen alpha3 chain |
| 53 | Pancreas | 0.4239698 | 0.5145325 | 0.44059 | 0.30840855 D00408_s_a 2t | CYP3A7 Cytochrome P450 IIIA7 (P450-HFLa) |
| 54 | Pancreas | 0.4231774 | 0.5124851 | 0.439691 | 0.3075618 M16652_s_a t | ELA1 Elastase 1, pancreatic (elastase IIA) |
| 55 | Pancreas | 0.421436 | 0.5121627 | 0.438925 | 0.30695662 W20514_at | EST: zb26f06.r1 Soares fetal lung NbHL19W Homo sapiens cDNA clone 303203 5', mRNA sequence. (from Genbank) |
| 56 | Pancreas | 0.4210104 | 0.5115693 | 0.438508 | 0.3063722 AA314779_a t | EST: EST186601 Colon carcinoma (HCC) cell line II Homo sapiens cDNA 5' end, mRNA sequence. (from Genbank) |
| 57 | Pancreas | 0.4162491 | 0.5108511 | 0.438022 | 0.30575418 U17760_rna 1_at | Laminin S B3 chain (LAMB3) gene |
| 58 | Pancreas | 0.4079636 | 0.5105087 | 0.437687 | 0.30490136 J00306_at | Somatostatin I gene and flanks |
| 59 | Pancreas | 0.4036738 | 0.5101459 | 0.437068 | 0.30435598 Y00705_at | SPINK1 Serine protease inhibitor, Kazal type 1 |
| 60 | Pancreas | 0.4026848 | 0.5096456 | 0.436298 | 0.30365527 RC_AA1349 85_at | EST: zo26h05.s1 Stratagene colon (#937204) Homo sapiens cDNA clone 588057 3', mRNA sequence. (from Genbank) |
| 61 | Pancreas | 0.3999345 | 0.5091632 | 0.435287 | 0.3030284 U17077_at | BENE mRNA, partial cds |
| 62 | Pancreas | 0.3993665 | 0.5087592 | 0.434922 | 0.3023357 U06711_s_a t | Mucin 5, subtype B, tracheobronchial |
| 63 | Pancreas | 0.3954412 | 0.5084084 | 0.434372 | 0.30164677 U04313_at | PI5 Protease inhibitor 5 (maspin) |
| 64 | Pancreas | 0.3902982 | 0.507421 | 0.433536 | 0.30094382 M93284_at | Pancreatic lipase related protein 2 (PLRP2) mRNA |
| 65 | Pancreas | 0.3893445 | 0.5065737 | 0.432771 | 0.30048516 RC_AA1567 92_at | EST: zl18n06.s1 Soares pregnant uterus NbHPU Homo sapiens cDNA clone 502331 3', mRNA sequence. (from Genbank) |

FIG. 11C

| # | Tissue | Val1 | Val2 | Val3 | ID | Description |
|---|---|---|---|---|---|---|
| 66 | Pancreas | 0.3875845 | 0.5065606 | 0.431797 | 0.30009714 U66061_cds 3_at | TRY8 gene (trypsinogen E) extracted from Human germline T-cell receptor beta chain TCRBV17S1A1T, TCRBV2S1, TCRBV10S1P, TCRBV29S1P, TCRBV19S1P, TCRBV15S1, TCRBV11S1A1T, HVB relic, TCRBV28S1P, TCRBV34S1, TCRBV14S1, TCRBV3S1, TCRBV4S1A1T, TRY4, TRY5, TRY6, TRY7, TRY8, TCRBD1, TCRBJ1S1, TCRBJ1S2, TCRBJ1S3, TCRBJ1S4, TCRBJ1S5, TCRBJ1S6, TCRBC1, TCRBD2, TCRBJ2S1, TCRBJ2S2, TCRBJ2S3, TCRBJ2S4, TCRBJ2S5, TCRBJ2S6, TCRBJ2S7, TCRBC2, TCRBV20S1A1N2 genes from bases 452324 to 684973 (section 3 of 3) |
| 67 | Pancreas | 0.3849158 | 0.5060208 | 0.431333 | 0.29950368 L11708_at | HSD17B2 17 beta hydroxysteroid dehydrogenase, type 2 |
| 68 | Pancreas | 0.3846538 | 0.5055683 | 0.430483 | 0.2988619 M16652_at | ELA1 Elastase 1, pancreatic (elastase IIA) |
| 69 | Pancreas | 0.3835028 | 0.5052698 | 0.43013 | 0.29827955 HG371-HT26388_s_at | Mucin 1, Epithelial, Alt. Splice 9 |
| 70 | Pancreas | 0.3828116 | 0.504387 | 0.429693 | 0.29767913 RC_AA1007 19_s_at | Non-specific cross reacting antigen |
| 71 | Pancreas | 0.3811176 | 0.5033779 | 0.428787 | 0.29708844 D90097_at | ALPHA-AMYLASE 2B PRECURSOR |
| 72 | Pancreas | 0.380816 | 0.5026341 | 0.428532 | 0.29656819 S71043_rna 1_s_at | Ig alpha 2=immunoglobulin A heavy chain allotype 2 (constant region, germ line) [human, peripheral blood neutrophils, Genomic, 1799 nt] |
| 73 | Pancreas | 0.3807718 | 0.5024124 | 0.427945 | 0.29608276 M11718_at | COL5A2 Collagen, type V, alpha |
| 74 | Pancreas | 0.3780765 | 0.5023708 | 0.427088 | 0.2956553 M14949_at | RAS-RELATED PROTEIN R-RAS |
| 75 | Pancreas | 0.3758304 | 0.5020343 | 0.426697 | 0.29510015 M11321_at | GC Group-specific component (vitamin D binding protein) |
| 76 | Pancreas | 0.3743256 | 0.5015573 | 0.426078 | 0.2946248 U27333_s_a t | Alpha-1,3 fucosyltransferase 6 (FCT3A) mRNA |
| 77 | Pancreas | 0.3729319 | 0.5015123 | 0.42574 | 0.29379228 RC_AA4283 68_at | EST: zw51f07.s1 Soares total fetus Nb2HF8 9w Homo sapiens cDNA clone 773605 3', mRNA sequence. (from Genbank) |
| 78 | Pancreas | 0.3725418 | 0.5002543 | 0.424768 | 0.2933036 X06700_s_a t | COL3A1 Alpha-1 type 3 collagen |
| 79 | Pancreas | 0.3715697 | 0.5002543 | 0.424517 | 0.2930601 Z24680_at | Garp gene mRNA |
| 80 | Pancreas | 0.3690722 | 0.4999781 | 0.424136 | 0.29250193 X72012_at | ENG Endoglin (Osler-Rendu-Weber syndrome 1) |
| 81 | Pancreas | 0.3669019 | 0.4997639 | 0.4241 | 0.2921337 L27560_at | Insulin-like growth factor binding protein 5 (IGFBP5) mRNA |
| 82 | Pancreas | 0.3668293 | 0.4991988 | 0.423788 | 0.29161403 M35252_at | TUMOR-ASSOCIATED ANTIGEN CO-029 |
| 83 | Pancreas | 0.3665817 | 0.497894 | 0.42304 | 0.29106683 X60382_rna 1_at | COL10A1 gene for collagen (alpha-1 type X) |
| 84 | Pancreas | 0.3663838 | 0.497385 | 0.422691 | 0.29063255 J02611_at | APOD Apolipoprotein D |
| 85 | Pancreas | 0.3642896 | 0.4976251 | 0.422397 | 0.29017088 M55998_s_a t | Alpha-1 collagen type I gene, 3' end |
| 86 | Pancreas | 0.3641634 | 0.4971929 | 0.422094 | 0.2898828 X82153_at | CATHEPSIN K PRECURSOR |

FIG. 11D

| # | Tissue | | | | Accession | Description |
|---|---|---|---|---|---|---|
| 87 | Pancreas | 0.3633644 | 0.4971874 | 0.421636 | 0.289339676 | RC_AA1513 33_at | EST: zl41c12.s1 Soares pregnant uterus NbHPU Homo sapiens cDNA clone 504502 3', mRNA sequence. (from Genbank) |
| 88 | Pancreas | 0.3590803 | 0.4970192 | 0.420811 | 0.28880373 | K03021_at | PLAT Plasminogen activator, tissue type (t-PA) |
| 89 | Pancreas | 0.3562413 | 0.4963301 | 0.42053 | 0.28827852 | X68314_at | GPX2 Glutathione peroxidase 2, gastrointestinal |
| 90 | Pancreas | 0.3562031 | 0.4957914 | 0.419768 | 0.28785974 | U78556_at | Cisplatin resistance associated alpha protein (hCRA alpha) mRNA |
| 91 | Pancreas | 0.3551772 | 0.4946986 | 0.419392 | 0.28751352 | AD000684_c ds1_at | LISCH7 gene (liver-specific bHLH-Zip transcription factor) extracted from Homo sapiens DNA from chromosome 19-cosmid R30879 containing USF2, genomic sequence |
| 92 | Pancreas | 0.3548342 | 0.493108 | 0.419061 | 0.2870863 | M34516_at | Omega light chain protein 14.1 (Ig lambda chain related) gene, exon 3 |
| 93 | Pancreas | 0.3528661 | 0.4926478 | 0.418758 | 0.28664374 | X54925_at | MMP1 Matrix metalloproteinase 1 (interstitial collagenase) |
| 94 | Pancreas | 0.3524107 | 0.492324 | 0.418444 | 0.28630418 | U19977_at | Preprocarboxypeptidase A2 (proCPA2) mRNA |
| 95 | Pancreas | 0.3520485 | 0.4923139 | 0.418102 | 0.28595534 | M81057_at | CPB1 Carboxypeptidase B1 (tissue) |
| 96 | Pancreas | 0.3520236 | 0.4922782 | 0.417717 | 0.28537646 | L01406_at | GHRHR Growth hormone-releasing hormone receptor |
| 97 | Pancreas | 0.3478723 | 0.4920433 | 0.417254 | 0.284984 | M15517_cds 5_at | TTR gene (prealbumin) extracted from Human mutant prealbumin gene directly linked to familial amyloidotic polyneuropathy (FAP) |
| 98 | Pancreas | 0.3429684 | 0.4910463 | 0.41665 | 0.28457248 | X04412_at | GSN Gelsolin (amyloidosis, Finnish type) |
| 99 | Pancreas | 0.3424987 | 0.4906896 | 0.416391 | 0.28418133 | U73843_at | Epithelial-specific transcription factor ESE-1b (ESE-1) mRNA |
| 100 | Pancreas | 0.3411254 | 0.4902216 | 0.415502 | 0.28387678 | RC_AA4518 77_at | EST: zx16e06.s1 Soares total fetus Nb2HF8 9w 1 homo sapiens cDNA clone 786658 3', mRNA sequence. (from Genbank) |
| 101 | Pancreas | 0.340963 | 0.4894419 | 0.415252 | 0.28369093 | AA465016_a 3t | EST: zx80d02.r1 Soares ovary tumor NbHOT Homo sapiens cDNA clone 810051 5' similar to TR:G1020091 G1020091 NEUROPSIN. ;contains element LTR3 repetitive element :, mRNA sequence. (from Genbank) |
| 102 | Pancreas | 0.3405969 | 0.4893701 | 0.415035 | 0.28314155 | J03278_at | PDGFRB Platelet-derived growth factor receptor, beta polypeptide |
| 103 | Pancreas | 0.3387594 | 0.4893091 | 0.414265 | 0.28276925 | M85289_at | HSPG2 Heparan sulfate proteoglycan |
| 104 | Pancreas | 0.3348676 | 0.4888622 | 0.414209 | 0.2823444 | U66674_at | Canicular multispecific organic anion transporter |
| 105 | Pancreas | 0.3339839 | 0.4887695 | 0.413839 | 0.28193548 | U29953_rna 1_at | Pigment epithelium-derived factor gene |
| 106 | Pancreas | 0.3288856 | 0.4885137 | 0.412887 | 0.28170332 | J05582_s_at | MUC1 Mucin 1, transmembrane |
| 107 | Pancreas | 0.328445 | 0.4881949 | 0.412794 | 0.2811877 | X53331_at | MGP Matrix protein gla |
| 108 | Pancreas | 0.3279358 | 0.4879515 | 0.412556 | 0.28087282 | S82198_at | Caldecrin |
| 109 | Pancreas | 0.3278747 | 0.4877526 | 0.412163 | 0.28060302 | M61853_at | CYP2C18 Cytochrome P450, subfamily IIC (mephenytoin 4-hydroxylase), polypeptide 18 |
| 110 | Pancreas | 0.3276188 | 0.4876936 | 0.412086 | 0.280084 | V00565_s_at 2 | Insulin |
| 111 | Pancreas | 0.3276188 | 0.4871563 | 0.411174 | 0.279966347 | V00565_s_at | INS Insulin |

FIG. 11E

| # | Tissue | | | | ID | Description |
|---|---|---|---|---|---|---|
| 112 | Pancreas | 0.3274485 | 0.4861364 | 0.419985 | X79882_at | Lrp mRNA |
| 113 | Pancreas | 0.3261286 | 0.4857553 | 0.410523 | 0.29942872 0.27907494 D31294_at | EST: Human fetal-lung cDNA 5'-end sequence, mRNA sequence. (from Genbank) |
| 114 | Pancreas | 0.322083 | 0.4853031 | 0.410112 | 0.27870932 U78551_at-2 | Homo sapiens gallbladder mucin MUC5B mRNA, partial cds |
| 115 | Pancreas | 0.322083 | 0.4849784 | 0.409909 | 0.2782639 U78551_at | Gallbladder mucin MUC5B mRNA, partial cds |
| 116 | Pancreas | 0.3215038 | 0.48393324 | 0.40957 | 0.2780548 M88338_at | SERUM PROTEIN MSE55 |
| 117 | Pancreas | 0.3203934 | 0.4838944 | 0.40953 | 0.27776566 AF001294_a_t | IPL (IPL) mRNA |
| 118 | Pancreas | 0.3198348 | 0.4838789 | 0.409257 | 0.27745736 AA059327_i_at | EST: zf65e11.r1 Soares retina N2b4HR Homo sapiens cDNA clone 381836 5', mRNA sequence. (from Genbank) |
| 119 | Pancreas | 0.3197726 | 0.48354 | 0.408635 | 0.27699953 U59877_s_a_t | Low-Mr GTP-binding protein (RAB31) mRNA |
| 120 | Pancreas | 0.3194833 | 0.482961 | 0.408297 | 0.27659935 M14058_at | C1R Complement component C1r |
| 121 | Pancreas | 0.3193275 | 0.4826955 | 0.407868 | 0.27633497 C01409_s_a_t | EST: HUMGS0008391, Human Gene Signature, 3'-directed cDNA sequence, mRNA sequence. (from Genbank) |
| 122 | Pancreas | 0.316809 | 0.4823362 | 0.407673 | 0.2757695 Z74616_s_at | COL1A2 Collagen, type I, alpha-2 |
| 123 | Pancreas | 0.314764 | 0.4809273 | 0.407351 | 0.2755098 M16967_at | F5 Coagulation factor V |
| 124 | Pancreas | 0.3121455 | 0.4805009 | 0.406636 | 0.27523875 X53587_at | ITGB4 Integrin beta-4 subunit |
| 125 | Pancreas | 0.3120098 | 0.4799707 | 0.406607 | 0.27504593 Z19585_at | THBS4 Thrombospondin 4 |
| 126 | Pancreas | 0.3118338 | 0.4794049 | 0.406177 | 0.27472496 U20362_at | Tg737 mRNA |
| 127 | Pancreas | 0.311305 | 0.4789395 | 0.405915 | 0.27444765 L12350_at | THBS2 Thrombospondin 2 |
| 128 | Pancreas | 0.3112249 | 0.4785829 | 0.40554 | 0.27424577 U27655_at | RGP3 mRNA |
| 129 | Pancreas | 0.3101831 | 0.4781972 | 0.405457 | 0.27397862 U16799_s_a_t | Na,K-ATPase beta-1 subunit mRNA |
| 130 | Pancreas | 0.3087581 | 0.4779261 | 0.40506 | 0.27374766 X82494_at | FBLN2 Fibulin 2 |
| 131 | Pancreas | 0.3084479 | 0.4776994 | 0.404705 | 0.2733133 D38128_at | PTGIR Prostaglandin I2 (prostacyclin) receptor (IP) |
| 132 | Pancreas | 0.3067206 | 0.4776905 | 0.404395 | 0.27296965 M34516_r_at | Omega light chain protein 14.1 (Ig lambda chain related) gene, exon 3 |
| 133 | Pancreas | 0.3059252 | 0.477582 | 0.403966 | 0.27250776 J04080_at | C1S Complement component 1, s subcomponent |
| 134 | Pancreas | 0.3053519 | 0.4769051 | 0.403724 | 0.27216664 M12963_s_a_t | ADH1 Alcohol dehydrogenase 1 (class I), alpha polypeptide |
| 135 | Pancreas | 0.3050191 | 0.4764769 | 0.403486 | 0.27198407 L27559_s_at | IGFBP5 Insulin-like growth factor binding protein 5 |
| 136 | Pancreas | 0.2889849 | 0.4763989 | 0.402715 | 0.27167347 U41344_at | PRELP Proline arginine-rich end leucine-rich repeat protein |
| 137 | Pancreas | 0.2967506 | 0.4755846 | 0.402501 | 0.2713921 U89916_at | Putative OSP like protein mRNA, partial cds |
| 138 | Pancreas | 0.2932977 | 0.4755001 | 0.402063 | 0.27114147 U32989_at | Tryptophan oxygenase (TDO) mRNA |
| 139 | Pancreas | 0.2928493 | 0.4748476 | 0.401165 | 0.27083558 U97698_at | Homo sapiens secretory mucin MUC6 (MUC6) mRNA, partial cds |

FIG. 11F

| # | Tissue | | | | | Description |
|---|---|---|---|---|---|---|
| 140 | Pancreas | 0.2924698 | 0.4747597 | 0.401627 | 0.2706232 | HG987-HT987_at | Mac25 |
| 141 | Pancreas | 0.2916048 | 0.474475 | 0.401411 | 0.27024934 | RC_AA4771_32_at | EST: zu37f03.s1 Soares ovary tumor NbHOT Homo sapiens cDNA clone 740189 3', mRNA sequence. (from Genbank) |
| 142 | Pancreas | 0.2915885 | 0.4739853 | 0.401142 | 0.26979876 | D13666_s_a_t | Osteoblast specific factor 2 (OSF-2os) |
| 143 | Pancreas | 0.2911396 | 0.4737241 | 0.400938 | 0.26950166 | HG1034-HT1034_f_at | Atpase, Na+/K+ Transporting, Alpha 1 Polypeptide |
| 144 | Pancreas | 0.2906164 | 0.4728 | 0.400722 | 0.26922756 | M11726_at | PPY Pancreatic polypeptide |
| 145 | Pancreas | 0.2905367 | 0.472558 | 0.400221 | 0.2689106 | U11862_s_a_t | ABP1 Amiloride binding protein 1 (amine oxidase (copper-containing)) |
| 146 | Pancreas | 0.2894171 | 0.4724881 | 0.399998 | 0.28873595 | D31762_at | KIAA0057 gene |
| 147 | Pancreas | 0.2884169 | 0.472351 | 0.399564 | 0.2685563 | HG880-HT880_s_at | Mucin 6, Gastric (Gb:L07517) |
| 148 | Pancreas | 0.2878242 | 0.4721525 | 0.399341 | 0.26816157 | U62800_at | CST6 Cystatin M |
| 149 | Pancreas | 0.2848009 | 0.4717545 | 0.398909 | 0.2679188 | S68287_at | CHDR Chlordecone reductase |
| 150 | Pancreas | 0.2842883 | 0.4717306 | 0.398898 | 0.2675533 | M63438_s_a_t | GLUL Glutamate-ammonia ligase (glutamine synthase) |
| 151 | Pancreas | 0.2831808 | 0.4710011 | 0.398177 | 0.26740058 | RC_AA4914_65_at | EST: ab04a05.s1 Stratagene fetal retina 937202 Homo sapiens cDNA clone 839792 3', mRNA sequence. (from Genbank) |
| 152 | Pancreas | 0.2823113 | 0.4707929 | 0.398047 | 0.26711547 | L40379_at | Thyroid receptor interactor (TRIP10) mRNA, 3' end of cds |
| 153 | Pancreas | 0.2820395 | 0.4705439 | 0.397251 | 0.2670215 | X84707_ma_1_at | MIA gene |
| 154 | Pancreas | 0.2817896 | 0.4700401 | 0.397065 | 0.26654932 | X74929_s_a_t | KRT8 Keratin 8 |
| 155 | Pancreas | 0.2807249 | 0.4699358 | 0.397045 | 0.26635092 | J03934_s_at | NMOR1 NAD(P)H:menadione oxidoreductase |
| 156 | Pancreas | 0.2788769 | 0.4695598 | 0.396816 | 0.26615363 | AA452428_a_t | EST: zx15g01.r1 Soares total fetus Nb2HF8 9w Homo sapiens cDNA clone 786576 5', mRNA sequence. (from Genbank) |
| 157 | Pancreas | 0.277946 | 0.4691865 | 0.396795 | 0.26582745 | U66036_at | Sulfotransferase mRNA |
| 158 | Pancreas | 0.2773519 | 0.4690745 | 0.396443 | 0.26561254 | X03168_at | VTN Vitronectin (serum spreading factor, somatomedin B, complement S-protein) |
| 159 | Pancreas | 0.2771673 | 0.4689885 | 0.395874 | 0.26531574 | U33632_at | Two P-domain K+ channel TWIK-1 mRNA |
| 160 | Pancreas | 0.275548 | 0.468899 | 0.395492 | 0.26494673 | M28249_at | ITGA2 Integrin, alpha 2 (CD49B, alpha 2 subunit of VLA-2 receptor) |
| 161 | Pancreas | 0.2753103 | 0.468315 | 0.395207 | 0.26479402 | HG2689-HT2785_at | Mucin 5b, Tracheobronchial (Gb:X74955) |
| 162 | Pancreas | 0.2747399 | 0.4680592 | 0.39496 | 0.26449436 | L13923_at | FBN1 Fibrillin 1 (Marfan syndrome) |
| 163 | Pancreas | 0.274682 | 0.4677942 | 0.394631 | 0.26430032 | X97261_r_at | Metallothionein isoform 1R |

FIG. 11G

| # | Tissue | | | ID | Description |
|---|---|---|---|---|---|
| 164 | Pancreas | 0.2743028 | 0.4676946 | 0.394423 | 0.26387852 | L07594_at | TGFBR3 Transforming growth factor, beta receptor III (betaglycan, 300kD)) |
| 165 | Pancreas | 0.2730731 | 0.4676102 | 0.394142 | 0.26363352 | X13916_at | LDL-receptor related protein |
| 166 | Pancreas | 0.2728557 | 0.4670301 | 0.394016 | 0.26332533 | D38583_at | Calgizzarin |
| 167 | Pancreas | 0.2720528 | 0.4669901 | 0.393935 | 0.26314235 | X57766_at | PSG11 Pregnancy-specific beta-1 glycoprotein 11 |
| 168 | Pancreas | 0.2719561 | 0.4661515 | 0.393646 | 0.26282045 | D87012_at | Immunoglobulin lambda gene locus DNA, clone:61D6 |
| 169 | Pancreas | 0.2707795 | 0.4656936 | 0.393127 | 0.26253322 | J29433_at | COAGULATION FACTOR X PRECURSOR |
| 170 | Pancreas | 0.2693385 | 0.4654318 | 0.392992 | 0.26223975 | L42176_at | (clone 35.3) DRAL mRNA |
| 171 | Pancreas | 0.2689302 | 0.4650724 | 0.392674 | 0.26197657 | M82809_at | ANX4 Annexin IV (placental anticoagulant protein II) |
| 172 | Pancreas | 0.2683395 | 0.4650724 | 0.392517 | 0.26173648 | L13720_at | Growth-arrest-specific protein (gas) mRNA |
| 173 | Pancreas | 0.2674237 | 0.464959 | 0.392372 | 0.26142424 | L34155_at | Laminin-related protein (LamA3) mRNA |
| 174 | Pancreas | 0.2674237 | 0.4648172 | 0.392069 | 0.26105756 | L34155_at-2 | Laminin, alpha 3 (nicein (150kD), kalinin (165kD), BM600 (150kD), epilegrin) |
| 175 | Pancreas | 0.2674176 | 0.464741 | 0.391972 | 0.26080438 | HG2788-HT2896_at | Calcyclin |
| 176 | Pancreas | 0.2671013 | 0.4644892 | 0.391845 | 0.26062673 | L20591_at | ANX3 Annexin III (lipocortin III) |
| 177 | Pancreas | 0.2660541 | 0.4641811 | 0.391238 | 0.26037118 | U01062_at | ITPR3 Inositol 1,4,5-triphosphate receptor, type 3 |
| 178 | Pancreas | 0.2654402 | 0.464153 | 0.391109 | 0.26004875 | U36221_at | Pancreatic zymogen granule membrane protein GP-2 mRNA |
| 179 | Pancreas | 0.2652055 | 0.4641528 | 0.391001 | 0.25991356 | U42408_at | Ladinin (LAD) mRNA |
| 180 | Pancreas | 0.265055 | 0.463795 | 0.390767 | 0.25955158 | HG2743-HT2846_s_at | Caldesmon 1, Alt. Splice 4, Non-Muscle |
| 181 | Pancreas | 0.2646077 | 0.463795 | 0.390317 | 0.259351 | U51010_s_at | Nicotinamide N-methyltransferase gene, exon 1 and 5' flanking region |
| 182 | Pancreas | 0.2645448 | 0.4637207 | 0.390182 | 0.2590681 | U79293_at | Clone 23948 mRNA sequence |
| 183 | Pancreas | 0.2635272 | 0.4624023 | 0.389677 | 0.25895628 | M31516_s_at | DAF Decay accelerating factor for complement (CD55, Cromer blood group system) |
| 184 | Pancreas | 0.2631126 | 0.4623061 | 0.389545 | 0.2586853 | D11428_at | PMP22 Peripheral myelin protein 22 |
| 185 | Pancreas | 0.2629194 | 0.462205 | 0.389476 | 0.25830814 | U75272_s_at | PGC Gastricsin (pepsinogen C) |
| 186 | Pancreas | 0.262751 | 0.4620446 | 0.389285 | 0.2581156 | HG1067-HT1067_r_at | Mucin (GbM22406) |
| 187 | Pancreas | 0.2625998 | 0.4616099 | 0.389171 | 0.25783736 | M14338_at | PROS1 Plasma protein S |
| 188 | Pancreas | 0.260711 | 0.4613836 | 0.388803 | 0.25762293 | X68742_at | Integrin, alpha subunit |
| 189 | Pancreas | 0.2606377 | 0.4613482 | 0.388368 | 0.25740916 | K02765_at | COMPLEMENT C3 PRECURSOR |
| 190 | Pancreas | 0.259076 | 0.4612887 | 0.388247 | 0.25710133 | X66357_s_at | Cyclin-dependent kinase 3 |
| 191 | Pancreas | 0.258786 | 0.4610257 | 0.388037 | 0.25685441 | X03350_at | ADH2 Alcohol dehydrogenase 2 (class I), beta polypeptide |

FIG. 11H

| | | | | | | |
|---|---|---|---|---|---|---|
| 192 | Pancreas | 0.2587432 | 0.4608453 | 0.388037 | 0.25675175 RC_AA0374 09_at | EST: zc03h03.s1 Soares parathyroid tumor NbHPA Homo sapiens cDNA clone 321269 3', mRNA sequence. (from Genbank) |
| 193 | Pancreas | 0.25742 | 0.4601225 | 0.387539 | 0.2564938 U10550_at | Gem GTPase (gem) mRNA |
| 194 | Pancreas | 0.256658 | 0.4599291 | 0.387413 | 0.25624022 X66839_at | MaTu MN mRNA for p54/58N protein |
| 195 | Pancreas | 0.2562678 | 0.4596589 | 0.387269 | 0.25608438 X14008_rna 1_f_at | Lysozyme gene (EC 3.2.1.17) |
| 196 | Pancreas | 0.2557063 | 0.4594903 | 0.387189 | 0.25586015 X57348_s_a t | SFN Stratifin |
| 197 | Pancreas | 0.2556424 | 0.4586637 | 0.387067 | 0.25564355 X53002_s_a t | ITGB5 Integrin beta-5 subunit |
| 198 | Pancreas | 0.2547337 | 0.4585979 | 0.386753 | 0.25527582 L08488_at | INPP1 Inositol polyphosphate-1-phosphatase |
| 199 | Pancreas | 0.2519156 | 0.458411 | 0.386604 | 0.2550488 L00352_at | LOW-DENSITY LIPOPROTEIN RECEPTOR PRECURSOR |
| 200 | Pancreas | 0.2513616 | 0.4577566 | 0.386122 | 0.25489885 J05633_at | ITGB5 Integrin beta-5 subunit |
| 201 | Pancreas | 0.2504257 | 0.457121 | 0.386102 | 0.25470585 AA009826_a t | EST: ze82b02.r1 Soares fetal heart NbHH19W Homo sapiens cDNA clone 365451 5', mRNA sequence. (from Genbank) |
| 202 | Pancreas | 0.2493664 | 0.4571194 | 0.38599 | 0.2545078 Y00503_at | KRT19 Keratin 19 |
| 203 | Pancreas | 0.2483454 | 0.4571194 | 0.385709 | 0.25408345 Z46632_at | PDE4C Phosphodiesterase 4C, cAMP-specific (dunce (Drosophila)-homolog phosphodiesterase E1) |
| 204 | Pancreas | 0.2480411 | 0.4570982 | 0.385664 | 0.25396025 HG4310-HT4580_at | Cellular Retinol Binding Protein Ii |
| 205 | Pancreas | 0.2469718 | 0.4562626 | 0.385538 | 0.25373492 D50683_at | TGFBR2 Transforming growth factor, beta receptor II (70-80kD) |
| 206 | Pancreas | 0.2463778 | 0.4555808 | 0.385377 | 0.25356093 M25756_at | SECRETOGRANIN II PRECURSOR |
| 207 | Pancreas | 0.2452414 | 0.4551576 | 0.385324 | 0.2533396 X67325_at | INTERFERON-ALPHA INDUCED 11.5 KD PROTEIN |
| 208 | Pancreas | 0.2451037 | 0.4550618 | 0.385152 | 0.2530935 AA147510_s _at | EST: zl50c12.r1 Soares pregnant uterus NbHPU Homo sapiens cDNA clone 505366 5', mRNA sequence. (from Genbank) |
| 209 | Pancreas | 0.2445737 | 0.4550605 | 0.384839 | 0.25282523 J05481_s_at | Endoglin (Osler-Rendu-Weber syndrome 1) |
| 210 | Pancreas | 0.2435489 | 0.4549896 | 0.384735 | 0.25253943 M31994_at | ALDH1 Aldehyde dehydrogenase 1, soluble |
| 211 | Pancreas | 0.2431813 | 0.454711 | 0.384353 | 0.25235546 M21574_at | PDGFRA Platelet-derived growth factor receptor, alpha polypeptide |
| 212 | Pancreas | 0.240173 | 0.4545118 | 0.384215 | 0.2520813 M59371_at | TYROSINE-PROTEIN KINASE RECEPTOR ECK PRECURSOR |
| 213 | Pancreas | 0.2399713 | 0.4544923 | 0.383889 | 0.25183654 D00017_at | ANX2 Annexin II (lipocortin II) |
| 214 | Pancreas | 0.2394403 | 0.4543074 | 0.383456 | 0.25164106 M37721_at | PAM Peptidylglycine alpha-amidating monooxygenase |
| 215 | Pancreas | 0.238449 | 0.454164 | 0.383426 | 0.25114285 Z74615_at | COL1A1 Collagen, type I, alpha 1 |
| 216 | Pancreas | 0.2384211 | 0.4541328 | 0.383383 | 0.25118315 M20530_at | SPINK1 Serine protease inhibitor, Kazal type 1 |
| 217 | Pancreas | 0.237254 | 0.4541205 | 0.383042 | 0.25094923 U66077_at | DAZ Deleted in azoospermia |
| 218 | Pancreas | 0.2365542 | 0.4540057 | 0.383009 | 0.2506271 D14520_at | GC-Box binding protein BTEB2 |
| 219 | Pancreas | 0.2359637 | 0.4539793 | 0.382752 | 0.2504809 X01038_rna 1_s_at | Fetal gene for apolipoprotein AI precursor |

FIG. 11I

| | | | | | |
|---|---|---|---|---|---|
| 220 | Pancreas | 0.2347494 | 0.4539002 | 0.25029945 | M11749_at | THY-1 MEMBRANE GLYCOPROTEIN PRECURSOR |
| 221 | Pancreas | 0.2344722 | 0.4538841 | 0.2500699 | K03204_f_at | PRB1 locus salivary proline-rich protein mRNA, clone cP3 |
| 222 | Pancreas | 0.2340556 | 0.4537915 | 0.24984193 | M95929_at | Homeobox protein (PHOX1) mRNA, 3' end |
| 223 | Pancreas | 0.2337428 | 0.4533325 | 0.24966602 | D49742_at | HGF activator like protein |
| 224 | Pancreas | 0.2318988 | 0.4533138 | 0.24941944 | L41668_rna1_at | UDP-Galactose 4 epimerase (GALE) gene |
| 225 | Pancreas | 0.231032 | 0.453293 | 0.24923486 | X93036_at | MAT8 protein |
| 226 | Pancreas | 0.2305552 | 0.4531743 | 0.24911986 | X57809_s_at | IGL@ Immunoglobulin lambda light chain |
| 227 | Pancreas | 0.2301815 | 0.4530017 | 0.24898967 | M29540_at | CARCINOEMBRYONIC ANTIGEN PRECURSOR |
| 228 | Pancreas | 0.2301014 | 0.4528688 | 0.24872367 | U61374_at | Sushi-repeat-containing protein precursor (SRPX) mRNA |
| 229 | Pancreas | 0.228501 | 0.4528638 | 0.24853861 | J00117_f_at | Chorionic gonadotropin (hcg) beta subunit mRNA |
| 230 | Pancreas | 0.2283772 | 0.4527063 | 0.24833627 | Z11502_at | ANNEXIN XIII |
| 231 | Pancreas | 0.2274223 | 0.4525733 | 0.24818288 | U21049_at | DD96 mRNA |
| 232 | Pancreas | 0.2267079 | 0.4525674 | 0.24791834 | U20760_at | CASR Calcium-sensing receptor (hypocalciuric hypercalcemia 1 severe neonatal hyperparathyroidism) |
| 233 | Pancreas | 0.2264592 | 0.4524208 | 0.24770606 | X15882_at | COL6A2 Collagen, type VI, alpha 2 |
| 234 | Pancreas | 0.2257574 | 0.4522184 | 0.24765816 | L25081_at | ARH9 Aplysia ras-related homolog 9 |
| 235 | Pancreas | 0.2246593 | 0.4521857 | 0.2474238 | X56692_at | CRP C-reactive protein |
| 236 | Pancreas | 0.2244831 | 0.4517563 | 0.24717562 | M87789_s_at | (hybridoma H210) anti-hepatitis A IgG variable region, constant region, complementarity-determining regions mRNA |
| 237 | Pancreas | 0.2232518 | 0.4517563 | 0.24702367 | L06147_at | (clone SY11) golgin-95 mRNA |
| 238 | Pancreas | 0.2222428 | 0.4515882 | 0.24682315 | S66896_at | SCCA1 Squamous cell carcinoma antigen 1 |
| 239 | Pancreas | 0.2218647 | 0.4515482 | 0.24666798 | D87942_at | Fucosyltransferase 2 (secretor status included) |
| 240 | Pancreas | 0.2198549 | 0.4514823 | 0.24646409 | RC_AA132453_at | EST: zo20b01.s1 Stratagene colon (#937204) Homo sapiens cDNA clone 587401 3', mRNA sequence. (from Genbank) |
| 241 | Pancreas | 0.2195458 | 0.4510178 | 0.24626474 | D15049_at | PTPRH Protein tyrosine phosphatase |
| 242 | Pancreas | 0.219455 | 0.4509698 | 0.2461846 | U90913_at | Clone 23665 mRNA sequence |
| 243 | Pancreas | 0.2193557 | 0.4509153 | 0.24598858 | M27891_at | CST3 Cystatin C (amyloid angiopathy and cerebral hemorrhage) |
| 244 | Pancreas | 0.2191868 | 0.450439 | 0.24570969 | M35878_at | INSULIN-LIKE GROWTH FACTOR BINDING PROTEIN 3 PRECURSOR |
| 245 | Pancreas | 0.2191834 | 0.4503764 | 0.24539942 | RC_C20974 HG2614-HT2710_at | Vanin 1 |
| 246 | Pancreas | 0.2186853 | 0.4503687 | 0.24523824 | HT2710_at | Collagen, Type Viii, Alpha 1 |
| 247 | Pancreas | 0.2180892 | 0.4503357 | 0.24503675 | L77886_at | Protein tyrosine phosphatase mRNA |
| 248 | Pancreas | 0.2176803 | 0.4502353 | 0.24476923 | U53204_at | Plectin (PLEC1) mRNA |
| 249 | Pancreas | 0.2169857 | 0.4500107 | 0.24457306 | AA156897_s_at | EST: zl20b07.r1 Soares pregnant uterus NbHPU Homo sapiens cDNA clone 502453 5', mRNA sequence. (from Genbank) |

FIG. 11J

| # | Tissue | | | ID | Description |
|---|---|---|---|---|---|
| 250 | Pancreas | 0.2160575 | 0.449934 | 0.375965 | X02761_s_at FN1 Fibronectin 1 |
| 251 | Pancreas | 0.2150459 | 0.449934 | 0.375694 | D79206_s_at SDC4 Syndecan 4 (amphiglycan, ryudocan) |
| 252 | Pancreas | 0.2139522 | 0.4497347 | 0.3755545 | RC_AA4479 782740 3', mRNA sequence. (from Genbank) |
| 253 | Pancreas | 0.2136497 | 0.4496954 | 0.375449 | RC_AA2279 EST: zr57d06.s1 Soares NhHMPu S1 Homo sapiens cDNA clone 667499 3', mRNA sequence. (from Genbank) |
| 254 | Pancreas | 0.2134282 | 0.4494686 | 0.375202 | 0.243487734 J03464_s_at Collagen, type I, alpha 2 |
| 255 | Pancreas | 0.2116019 | 0.4494176 | 0.374616 | AB002354_a_t KIAA0356 gene product |
| 256 | Pancreas | 0.210531 | 0.4493226 | 0.374585 | 0.243141104 M38591_at S100A10 S100 calcium-binding protein A10 (annexin II ligand, calpactin I, light polypeptide (p11)) |
| 257 | Pancreas | 0.2100283 | 0.4485026 | 0.374204 | 0.242886538 M13690_s_at C1NH Complement component 1 inhibitor (angioedema, hereditary) |
| 258 | Pancreas | 0.2099217 | 0.4483339 | 0.373941 | 0.242736568 D86479_at Non-lens beta gamma-crystallin like protein (AIM1) mRNA, partial cds |
| 259 | Pancreas | 0.2098654 | 0.4475095 | 0.373782 | 0.242578578 L03840_s_at FGFR4 Fibroblast growth factor receptor 4 |
| 260 | Pancreas | 0.2094783 | 0.4474704 | 0.373604 | 0.242381086 L36983_at Dynamin (DNM) mRNA |
| 261 | Pancreas | 0.2089765 | 0.447446 | 0.373414 | 0.242133339 M90657_at TUMOR-ASSOCIATED ANTIGEN L6 |
| 262 | Pancreas | 0.2082431 | 0.4472224 | 0.373285 | 0.241923996 M57710_at LGALS3 Lectin, galactoside-binding, soluble, 3 (galectin 3) (NOTE: redefinition of symbol) |
| 263 | Pancreas | 0.2076829 | 0.447086 | 0.373057 | RC_AA2554 32_at EST: zr85f08.s1 Soares NhHMPu S1 Homo sapiens cDNA clone 682503 3', mRNA sequence. (from Genbank) |
| 264 | Pancreas | 0.2074831 | 0.4470066 | 0.372981 | 0.241656186 U28811_at Cysteine-rich fibroblast growth factor receptor (CFR-1) mRNA |
| 265 | Pancreas | 0.2068356 | 0.4469305 | 0.37281 | 0.241393663 U66075_at Transcription factor hGATA-6 mRNA |
| 266 | Pancreas | 0.2067316 | 0.4469159 | 0.372722 | 0.241192918 W27099_at EST: 20c4 Human retina cDNA randomly primed sublibrary Homo sapiens cDNA, mRNA sequence. (from Genbank) |
| 267 | Pancreas | 0.2066826 | 0.4468707 | 0.372488 | 0.241218958 D28124_at Unknown product |
| 268 | Pancreas | 0.20614 | 0.4467433 | 0.372304 | 0.241000743 X79483_at ERK6 mRNA for extracellular signal regulated kinase |
| 269 | Pancreas | 0.2054201 | 0.446303 | 0.372189 | 0.240711746 L25286_s_at COL15A1 Collagen, type XV, alpha 1 |
| 270 | Pancreas | 0.204237 | 0.4462716 | 0.371703 | RC_AA1478 0.240589168 4_at EST: zl50b04.s1 Soares pregnant uterus NbHPU Homo sapiens cDNA clone 505327 3', mRNA sequence. (from Genbank) |
| 271 | Pancreas | 0.2028583 | 0.4460846 | 0.371602 | 0.240287086 U14394_at METALLOPROTEINASE INHIBITOR 3 PRECURSOR |
| 272 | Pancreas | 0.2027239 | 0.4457809 | 0.371431 | RC_AA4475 0.240075230 4_at EST: zw90h07.s1 Soares total fetus Nb2HF8 9w Homo sapiens cDNA clone 784285 3', mRNA sequence. (from Genbank) |
| 273 | Pancreas | 0.2026614 | 0.4455964 | 0.371253 | 0.239866627 M95787_at 22kDa smooth muscle protein (SM22) mRNA |

FIG. 11K

| # | Tissue | | | | | Accession | Description |
|---|---|---|---|---|---|---|---|
| 274 | Pancreas | | 0.20253 | 0.4455964 | 0.371253 | 0.23974404 | L15388_at | G PROTEIN-COUPLED RECEPTOR KINASE GRK5 |
| 275 | Pancreas | 0.2023137 | 0.4455882 | 0.370798 | 0.2395318 | J05428_at | UDP-GLUCURONOSYLTRANSFERASE 2B7 PRECURSOR, MICROSOMAL |
| 276 | Pancreas | 0.2020412 | 0.4455882 | 0.370697 | 0.2392989 | D42045_at | KIAA0086 gene |
| 277 | Pancreas | 0.2017758 | 0.4451509 | 0.370685 | 0.23918618 | M15656_at | ALDOB Aldolase B, fructose-bisphosphate |
| 278 | Pancreas | 0.2013191 | 0.4450379 | 0.370592 | 0.23889017 | D21255_at | CDH11 Cadherin 11 (OB-cadherin) |
| 279 | Pancreas | 0.2012664 | 0.445013 | 0.370514 | 0.23876333 | AA489716_a t | EST: aa43a01.r1 Soares NhHMPu S1 Homo sapiens cDNA clone 823656 5' similar to contains element MER22 repetitive element ;. mRNA sequence. (from Genbank) |
| 280 | Pancreas | 0.2006551 | 0.4449511 | 0.370491 | 0.23868455 | Y11306_rna 1_at | HTcf-4 gene extracted from H.sapiens mRNA for beta catenin/TCF-4 |
| 281 | Pancreas | 0.200424 | 0.444548 | 0.370094 | 0.23854801 | X86163_at | BDKRB2 Bradykinin receptor B2 |
| 282 | Pancreas | 0.2004194 | 0.4444534 | 0.3699925 | 0.23831032 | X71877_at | CTRL Chymotrypsin-like |
| 283 | Pancreas | 0.1985597 | 0.4444445 | 0.3699925 | 0.23805958 | M27436_s_a t | F3 Coagulation factor III (thromboplastin, tissue factor) |
| 284 | Pancreas | 0.1979547 | 0.4444399 | 0.369979 | 0.23789924 | C01766_r_at | EST: HUMGS0003714, Human Gene Signature, 3'-directed cDNA sequence, mRNA sequence. (from Genbank) |
| 285 | Pancreas | 0.1971832 | 0.444424 | 0.369687 | 0.23781882 | Z24727_at | TPM1 Tropomyosin alpha chain (skeletal muscle) |
| 286 | Pancreas | 0.1968961 | 0.4443879 | 0.369444 | 0.2375083 | M76180_at | DDC Dopa decarboxylase (aromatic L-amino acid decarboxylase) |
| 287 | Pancreas | 0.1965919 | 0.4442333 | 0.369292 | 0.23730977 | J04177_at | COL11A1 Collagen, type XI, alpha 1 |
| 288 | Pancreas | 0.1964797 | 0.4441634 | 0.369253 | 0.23720081 | U09278_at | Fibroblast activation protein mRNA |
| 289 | Pancreas | 0.1964206 | 0.4439878 | 0.369187 | 0.23699033 | Y09267_at | Flavin-containing monooxygenase 2 |
| 290 | Pancreas | 0.1960992 | 0.4439692 | 0.368869 | 0.23684187 | J03801_f_at | LYZ Lysozyme |
| 291 | Pancreas | 0.1960305 | 0.4438405 | 0.368687 | 0.23672394 | RC_AA0019 08_at | EST: zh83a05.s1 Soares fetal liver spleen 1NFLS S1 Homo sapiens cDNA clone 427856 3'; mRNA sequence. (from Genbank) |
| 292 | Pancreas | 0.1951598 | 0.4436182 | 0.368492 | 0.23660825 | U40223_at | Uridine nucleotide receptor (UNR) gene |
| 293 | Pancreas | 0.1944396 | 0.443327 | 0.368444 | 0.23645079 | X05409_at | ALDH2 Aldehyde dehydrogenase 2, mitochondrial |
| 294 | Pancreas | 0.1943116 | 0.4432485 | 0.368382 | 0.23626012 | Z37976_at | LTBP2 Latent transforming growth factor beta binding protein 2 |
| 295 | Pancreas | 0.1939876 | 0.4428038 | 0.368219 | 0.23617645 | X56677_at | MYOD1 Myogenic factor 3 |
| 296 | Pancreas | 0.1922783 | 0.4427584 | 0.368084 | 0.2360612 | U08021_at | Nicotinamide N-methyltransferase (NNMT) mRNA |
| 297 | Pancreas | 0.1908299 | 0.4424619 | 0.367897 | 0.2358742 | M92934_at | CTGF Connective tissue growth factor |
| 298 | Pancreas | 0.190257 | 0.4422684 | 0.367837 | 0.23571731 | M65292_s_a t | HFL1 H factor (complement)-like 1 |
| 299 | Pancreas | 0.1896515 | 0.4419518 | 0.367772 | 0.23557775 | RC_AA4282 40_at | EST: zw51d04.s1 Soares total fetus Nb2HF8 9w Homo sapiens cDNA clone 773575 3'; mRNA sequence. (from Genbank) |
| 300 | Pancreas | 0.1892472 | 0.4418405 | 0.367758 | 0.23537093 | D87292_at | Rhodanese |
| 301 | Pancreas | 0.188899 | 0.4417597 | 0.367744 | 0.23517503 | TNFa_at | No description for gene: TNFa_at |
| 302 | Pancreas | 0.1885506 | 0.4417055 | 0.367401 | 0.23503572 | hum_alu_at-2 | No description for gene: hum_alu_at |

FIG. 11L

| | | | | | |
|---|---|---|---|---|---|
| 303 | Pancreas | 0.1885506 | 0.4415661 | 0.2348528 | hum_alu_at | hum_alu_at (miscellaneous control) |
| 304 | Pancreas | 0.1879477 | 0.4413022 | 0.234665607 | D12485_at | Plasma cell membrane glycoprotein (PC-1) mRNA |
| 305 | Pancreas | 0.1877398 | 0.44122 | 0.23456301 | AA151544_a_t | Matrix metalloproteinase 21 |
| 306 | Pancreas | 0.1874823 | 0.4412107 | 0.23436244 | X54667_at | CST4 Cystatin S |
| 307 | Pancreas | 0.186752 | 0.440699 | 0.234292258 | RC_AA4546 54_at | EST: zx99f06.s1 Soares NhHMPu S1 Homo sapiens cDNA clone 811907 3', mRNA sequence. (from Genbank) |
| 308 | Pancreas | 0.1863556 | 0.4406077 | 0.234412889 | L10343_at | Pl3 Protease inhibitor 3, skin-derived (SKALP) |
| 309 | Pancreas | 0.1861374 | 0.4404019 | 0.2338312 | HG2239-HT2324_at | Potassium Channel Protein (Gb:Z11585) |
| 310 | Pancreas | 0.1855841 | 0.4403467 | 0.233369552 | U24389_s_a t | Lysyl oxidase-like protein gene |
| 311 | Pancreas | 0.1849923 | 0.4402908 | 0.23360941 | Z48199_at | SDC1 Syndecan 1 |
| 312 | Pancreas | 0.1847203 | 0.4402893 | 0.23338372 | RC_AA4790 44_s_at | EST: zu36d09.s1 Soares ovary tumor NbHOT Homo sapiens cDNA clone 740081 3', mRNA sequence. (from Genbank) |
| 313 | Pancreas | 0.1841381 | 0.4402766 | 0.23330152 | M61855_at | CYP2C9 Cytochrome P450, subfamily IIC (mephenytoin 4-hydroxylase), polypeptide 9 |
| 314 | Pancreas | 0.1829358 | 0.4399118 | 0.23315011 | AA053052_a t | EST: zl71a06.r1 Stratagene colon (#937204) Homo sapiens cDNA clone 510034 5', mRNA sequence. (from Genbank) |
| 315 | Pancreas | 0.18191 | 0.4397945 | 0.2329875 | M63391_rna 1_at | Desmin gene |
| 316 | Pancreas | 0.1810602 | 0.4395127 | 0.23279957 | X07979_at | ITGB1 Integrin, beta 1 (fibronectin receptor, beta polypeptide, antigen CD29 includes MDF2, MSK12) |
| 317 | Pancreas | 0.1806336 | 0.4395041 | 0.23256098 | M19045_f_at | LYZ Lysozyme |
| 318 | Pancreas | 0.180214 | 0.4394699 | 0.23249878 | RC_AA4969 80_at | KIAA0331 gene product |
| 319 | Pancreas | 0.1797838 | 0.4393834 | 0.232238738 | X63131_s_a t | PML Probable transcription factor PML [alternative products] |
| 320 | Pancreas | 0.1786759 | 0.4392951 | 0.232225546 | U32331_at | RIG mRNA, complete sequence |
| 321 | Pancreas | 0.1784829 | 0.4391857 | 0.23197828 | HG2167-HT2237_at | Protein Kinase Ht31, Camp-Dependent |
| 322 | Pancreas | 0.1784077 | 0.4388098 | 0.2318316 | U67963_at | Lysophospholipase homolog (HU-K5) mRNA |
| 323 | Pancreas | 0.1783882 | 0.4384459 | 0.2316843 | HG162-HT3165_at | Tyrosine Kinase, Receptor Axl, Alt. Splice 2 |
| 324 | Pancreas | 0.1782384 | 0.4384019 | 0.23155992 | L02326_f_at | (clone Hu lambda-17) lambda-like gene |
| 325 | Pancreas | 0.1781566 | 0.4383445 | 0.23138705 | D86957_at | KIAA0202 gene, partial cds |
| 326 | Pancreas | 0.177194 | 0.4381441 | 0.23120856 | HG491-HT491_at | Fc Receptor Iib3 For Igg, Low Affinity |

FIG. 11M

| | | | | | |
|---|---|---|---|---|---|
| 327 | Pancreas | 0.1765499 | 0.4377639 | 0.363297 | 0.2310578 | U41766_s_at | Metalloprotease/disintegrin/cysteine-rich protein precursor (MDC9) mRNA |
| 328 | Pancreas | 0.1753717 | 0.4376566 | 0.363239 | 0.23086834 | U80184_rna1_at | FLI1 gene |
| 329 | Pancreas | 0.1740268 | 0.4375736 | 0.363182 | 0.23070936 | U15131_at | IITS1 |
| 330 | Pancreas | 0.1739228 | 0.4372805 | 0.362984 | 0.2306095 | X68733_rna1_at | Alpha1-antichymotrypsin, exon 1 |
| 331 | Pancreas | 0.173609 | 0.4371579 | 0.362964 | 0.23040158 | X57579_s_at | Activin beta-A subunit (exon 2) |
| 332 | Pancreas | 0.1733888 | 0.437153 | 0.362743 | 0.23032051 | D45917_s_at | TIMP-3, partial cds (C-terminus region) |
| 333 | Pancreas | 0.171895 | 0.43707 | 0.362719 | 0.2302363 | RC_AA1131 66_at | EST: zm27e01.s1 Stratagene pancreas (#937208) Homo sapiens cDNA clone 526872 3', mRNA sequence. (from Genbank) |
| 334 | Pancreas | 0.1718943 | 0.4368998 | 0.362514 | 0.23009038 | U27326_s_at | FUT3 Alpha (1,3/1,4) fucosyltransferase |
| 335 | Pancreas | 0.1717693 | 0.4367237 | 0.362326 | 0.2299985 | HG2994-HT4850_s_at | Elastin, Alt. Splice 2 |
| 336 | Pancreas | 0.1706867 | 0.4366488 | 0.362181 | 0.2297499 | L36645_at | Receptor protein-tyrosine kinase (HEK8) mRNA |
| 337 | Pancreas | 0.1698695 | 0.435845 | 0.362181 | 0.22960057 | M93036_at | MAJOR GASTROINTESTINAL TUMOR-ASSOCIATED PROTEIN GA733-2 PRECURSOR |
| 338 | Pancreas | 0.1696099 | 0.4358323 | 0.362061 | 0.22946241 | U27333_at | Alpha-1,3 fucosyltransferase 6 (FCT3A) mRNA |
| 339 | Pancreas | 0.1695393 | 0.4357249 | 0.361712 | 0.22942427 | D00003_s_at | CYP3A3 Cytochrome P450 IIIA3 (nifedipine oxidase chain 3) |
| 340 | Pancreas | 0.1694579 | 0.4356631 | 0.361691 | 0.22932297 | D87071_at | KIAA0233 gene |
| 341 | Pancreas | 0.1693031 | 0.4356532 | 0.361642 | 0.22915365 | M19267_s_at | TPM1 Tropomyosin alpha chain (skeletal muscle) |
| 342 | Pancreas | 0.1690814 | 0.4355716 | 0.361459 | 0.22902328 | RC_AA1906 76_at | EST: zp89g09.s1 Stratagene HeLa cell s3 937216 Homo sapiens cDNA clone 627424 3', mRNA sequence. (from Genbank) |
| 343 | Pancreas | 0.1689974 | 0.4349706 | 0.361145 | 0.22888122 | D50532_at | Macrophage lectin 2 |
| 344 | Pancreas | 0.1689202 | 0.4347507 | 0.361065 | 0.22877204 | L04270_at | LYMPHOTOXIN-BETA RECEPTOR PRECURSOR |
| 345 | Pancreas | 0.1688594 | 0.4344482 | 0.361012 | 0.22861604 | M26629_at | Kallikrein mRNA, clone phKK25 |
| 346 | Pancreas | 0.1688129 | 0.4337712 | 0.360701 | 0.22852479 | RC_AA0789 32_at | EST: zm95f07.s1 Stratagene colon HT29 (#937221) Homo sapiens cDNA clone 545701 3', mRNA sequence. (from Genbank) |
| 347 | Pancreas | 0.1686712 | 0.4337262 | 0.360543 | 0.22840263 | X75342_at | SHB SHB adaptor protein (a Src homology 2 protein) |
| 348 | Pancreas | 0.1684651 | 0.4334429 | 0.360504 | 0.22816657 | C00476_at | EST: HUMGS0007866, Human Gene Signature, 3'-directed cDNA sequence, mRNA sequence. (from Genbank) |
| 349 | Pancreas | 0.1681121 | 0.4331623 | 0.360444 | 0.227799188 | M11313_s_at | A2M Alpha-2-macroglobulin |

FIG. 11N

| | | | | | | |
|---|---|---|---|---|---|---|
| 350 | Pancreas | 0.1679768 | 0.4330843 | 0.360311 | 0.22782744 | U28249_at | MAT8 protein |
| 351 | Pancreas | 0.1676114 | 0.4330517 | 0.360228 | 0.22765163 | U03056_at | Hyaluronoglucosaminidase 1 (HYAL1) mRNA |
| 352 | Pancreas | 0.1675607 | 0.4329445 | 0.360063 | 0.22761236 | J00231_f_at | Immunoglobulin gamma 3 (Gm marker) |
| 353 | Pancreas | 0.1668353 | 0.4327779 | 0.360023 | 0.22748797 | D11151_at | EDNRA Endothelin receptor type A |
| 354 | Pancreas | 0.1665658 | 0.4324268 | 0.359929 | 0.22731425 | D17793_at | DDH1 Dihydrodiol dehydrogenase |
| 355 | Pancreas | 0.1665002 | 0.4322735 | 0.359594 | 0.22722998 | U67849_at | Beta-galactoside alpha2,6-sialyltransferase (SIAT1) mRNA, exon W |
| 356 | Pancreas | 0.1663914 | 0.432159 | 0.359256 | 0.22706501 | L20826_at | I-plastin mRNA |
| 357 | Pancreas | 0.1662391 | 0.4321106 | 0.359233 | 0.22684869 | RC_AA454978_at | EST: zx99d10.s1 Soares NhHMPu S1 Homo sapiens cDNA clone 8118913', mRNA sequence. (from Genbank) |
| 358 | Pancreas | 0.1660601 | 0.4320543 | 0.359153 | 0.22679117 | U16306_at | CSPG2 Chondroitin sulfate proteoglycan 2 (versican) |
| 359 | Pancreas | 0.1651519 | 0.4318324 | 0.359128 | 0.22654821 | W31097_at | Homo sapiens COX4AL mRNA, complete cds |
| 360 | Pancreas | 0.1648087 | 0.4315773 | 0.35897 | 0.22643818 | X81420_at | MLN137 mRNA |
| 361 | Pancreas | 0.1644733 | 0.4314531 | 0.35853 | 0.2263567 | U03688_at | CYP1B1 Cytochrome P450 IB1 (dioxin-inducible) |
| 362 | Pancreas | 0.1634512 | 0.4311937 | 0.358367 | 0.22618711 | U48707_at | Protein phosphatase-1 inhibitor mRNA |
| 363 | Pancreas | 0.1633332 | 0.4307453 | 0.358285 | 0.22612299 | Y07829_xpl3_at | Exon A1 from H.sapiens gene encoding RING finger protein./ntype=DNA /annot=exon |
| 364 | Pancreas | 0.1620863 | 0.4306892 | 0.358064 | 0.22601184 | M34309_at | ERBB3 V-erb-b2 avian erythroblastic leukemia viral oncogene homolog 3 {alternative products} |
| 365 | Pancreas | 0.1619619 | 0.4306732 | 0.358035 | 0.22583023 | RC_AA0440465_at | EST: zk46h09.s1 Soares pregnant uterus NbHPU Homo sapiens cDNA clone 485921 3', mRNA sequence. (from Genbank) |
| 366 | Pancreas | 0.1619335 | 0.4304644 | 0.35787 | 0.22574383 | L04733_at | KINESIN LIGHT CHAIN |
| 367 | Pancreas | 0.1616663 | 0.4302097 | 0.357694 | 0.22562861 | Z19574_rna1_at | Cytokeratin 17 |
| 368 | Pancreas | 0.161317 | 0.4300522 | 0.357533 | 0.2254944 | M69023_at | Globin gene |
| 369 | Pancreas | 0.160555 | 0.4300077 | 0.357501 | 0.22531718 | AA455860_s_at | EST: aa01a12.r1 Soares NhHMPu S1 Homo sapiens cDNA clone 811966 5' similar to WP:C05C12.3 CE02966 :, mRNA sequence. (from Genbank) |
| 370 | Pancreas | 0.1598018 | 0.4298748 | 0.357331 | 0.22518858 | HG3494-HT3688_at | Nuclear Factor Nf-Il6 |
| 371 | Pancreas | 0.1596494 | 0.4298276 | 0.357304 | 0.22508019 | D26129_at | RNS1 Ribonuclease A (pancreatic) |
| 372 | Pancreas | 0.1592098 | 0.4298215 | 0.357159 | 0.22489779 | X76105_at | DAP-1 mRNA |
| 373 | Pancreas | 0.1592042 | 0.4297251 | 0.357082 | 0.22475794 | RC_AA134968_at | EST: zo23g08.s1 Stratagene colon (#937204) Homo sapiens cDNA clone 5877743', mRNA sequence. (from Genbank) |
| 374 | Pancreas | 0.1588987 | 0.429719 | 0.356935 | 0.22472617 | M61916_at | LAMB1 Laminin B1 chain |
| 375 | Pancreas | 0.1587369 | 0.4296986 | 0.356819 | 0.22448462 | J02758_s_at | APOLIPOPROTEIN A-IV PRECURSOR |
| 376 | Pancreas | 0.1585681 | 0.4296492 | 0.356803 | 0.22438303 | HG1098-HT1098_at | Cystatin D |
| 377 | Pancreas | 0.1582393 | 0.4295513 | 0.35655 | 0.2243046 | U49260_at | Mevalonate pyrophosphate decarboxylase (MPD) mRNA |

FIG. 11O

| # | Tissue | | | | | Description |
|---|---|---|---|---|---|---|
| 378 | Pancreas | 0.1580268 | 0.4292826 | 0.356427 | 0.22409247 U55054_at | K-Cl cotransporter (hKCC1) mRNA |
| 379 | Pancreas | 0.1578262 | 0.429173 | 0.356332 | 0.22395745 X65614_at | S100P S100 calcium-binding protein P |
| 380 | Pancreas | 0.1577343 | 0.4291019 | 0.356317 | 0.22383262 X57809_at | IGL@ immunoglobulin lambda light chain |
| 381 | Pancreas | 0.157375 | 0.4290769 | 0.356179 | 0.22376604 M76665_at | CORTICOSTEROID 11-BETA-DEHYDROGENASE, ISOZYME 1 |
| 382 | Pancreas | 0.1562685 | 0.4290619 | 0.356117 | 0.22364071 AA477978_s_at | Short-chain dehydrogenase/reductase 1 |
| 383 | Pancreas | 0.156221 | 0.4289388 | 0.355984 | 0.22350217 R33301_at | EST: yh81g01.r1 Homo sapiens cDNA clone 136176 5' similar to contains MSR1 repetitive element :. (from Genbank) |
| 384 | Pancreas | 0.1561164 | 0.4289348 | 0.355923 | 0.22338259 M62402_at | IGFBP6 Insulin-like growth factor binding protein 6 |
| 385 | Pancreas | 0.1549851 | 0.4289142 | 0.355735 | 0.22329882 RC_AA4266 40_at | EST: zv47h07.s1 Soares ovary tumor NbHOT Homo sapiens cDNA clone 756829 3', mRNA sequence. (from Genbank) |
| 386 | Pancreas | 0.154768 | 0.4288451 | 0.355595 | 0.2231326 D85418_at | Phosphatidylinositol-glycan-class C (PIG-C) |
| 387 | Pancreas | 0.1546832 | 0.4286616 | 0.35554 | 0.22305468 AA156215_a_t | EST: zo48h03.r1 Stratagene endothelial cell 937223 Homo sapiens cDNA clone 590165 5' similar to contains element LTR8 repetitive element :. mRNA sequence. (from Genbank) |
| 388 | Pancreas | 0.1534232 | 0.4286403 | 0.355096 | 0.22295855 AA314587_a_t | EST: EST186420 Colon carcinoma (HCC) cell line II Homo sapiens cDNA 5' end, mRNA sequence. (from Genbank) |
| 389 | Pancreas | 0.1528883 | 0.4281668 | 0.354846 | 0.22288442 M57730_at | EPH-RELATED RECEPTOR TYROSINE KINASE LIGAND 1 PRECURSOR |
| 390 | Pancreas | 0.1526794 | 0.4278888 | 0.354781 | 0.22270949 HG3570-HT3773_at | Protein Phosphatase Inhibitor Homolog |
| 391 | Pancreas | 0.1519917 | 0.4276867 | 0.354647 | 0.22262543 AFFX-LysX-M_at | AFFX-LysX-M_at (endogenous control) |
| 392 | Pancreas | 0.1519917 | 0.4276668 | 0.354553 | 0.22257286 AFFX-LysX-M_at-2 | AFFX-LysX-M_at (miscellaneous control - 11k chips) |
| 393 | Pancreas | 0.1518772 | 0.4274579 | 0.354484 | 0.22234379 M84349_at | CD59 CD59 antigen p18-20 (antigen identified by monoclonal antibodies 16.3A5, EJ16, EJ30, EL32 and G344) |
| 394 | Pancreas | 0.1516642 | 0.4272135 | 0.354436 | 0.22224523 J05252_s_at | PCSK2 Proprotein convertase subtilisin/kexin type 2 |
| 395 | Pancreas | 0.1507802 | 0.426927 | 0.354431 | 0.2220705 RC_AA1612 92_s_at | Interferon, alpha-inducible protein 27 |
| 396 | Pancreas | 0.1506744 | 0.4262222 | 0.354307 | 0.22192991 U83600_at | Death domain receptor 3 (DDR3) mRNA, alternatively spliced form 2, partial cds |
| 397 | Pancreas | 0.1504689 | 0.4261222 | 0.354128 | 0.22182258 M95178_at | ALPHA-ACTININ 1, CYTOSKELETAL ISOFORM |
| 398 | Pancreas | 0.1494065 | 0.4261217 | 0.354066 | 0.22162929 RC_AA2279 56_at | Homo sapiens follistatin-related protein FLRG (FLRG) mRNA, complete cds |
| 399 | Pancreas | 0.1487714 | 0.4257195 | 0.354059 | 0.22146438 AA071223_a_t | EST: zl79l10.r1 Soares pineal gland N3HPG Homo sapiens cDNA clone 383179 5', mRNA sequence. (from Genbank) |
| 400 | Pancreas | 0.1482132 | 0.4257063 | 0.353944 | 0.22135113 J02854_at | 20-kDa myosin light chain (MLC-2) mRNA |
| 401 | Pancreas | 0.1466654 | 0.4255509 | 0.353582 | 0.22124396 L13210_at | Mac-2 binding protein mRNA |

FIG. 11P

| | | | | | | |
|---|---|---|---|---|---|---|
| 402 | Pancreas | 0.1465931 | 0.4254811 | 0.353412 | 0.22108869 | L40371_at | Thyroid receptor interactor (TRIP4) mRNA, 3' end of cds |
| 403 | Pancreas | 0.1465808 | 0.4253718 | 0.353263 | 0.22101992 | D16154_at | Cytochrome P-450c11, exon 3-9 |
| 404 | Pancreas | 0.1465383 | 0.4251455 | 0.353122 | 0.22078371 | HG4115-HT4385_at | Olfactory Receptor Or17-210 |
| 405 | Pancreas | 0.1448025 | 0.425101 | 0.353001 | 0.22063361 | M14218_at | ASL Argininosuccinate lyase |
| 406 | Pancreas | 0.1447358 | 0.425075 | 0.352915 | 0.22054137 | RC_AA4906 70_at | EST: zv99f10.s1 Soares total fetus Nb2HF8 9w Homo sapiens cDNA clone 785131 3', mRNA sequence. (from Genbank) |
| 407 | Pancreas | 0.1446189 | 0.4249286 | 0.352885 | 0.22036909 | J03764_at | PAI1 Plasminogen activator inhibitor, type I |
| 408 | Pancreas | 0.1445339 | 0.4249265 | 0.352817 | 0.22028802 | D55696_at | Cysteine protease |
| 409 | Pancreas | 0.1440039 | 0.4248809 | 0.352547 | 0.22010562 | X92814_at | Rat HREV107-like protein |
| 410 | Pancreas | 0.1432172 | 0.4247118 | 0.352419 | 0.2200262 | RC_AA4550 78_at | EST: aa04d11.s1 Soares NhHMPu S1 Homo sapiens cDNA clone 812277 3', mRNA sequence. (from Genbank) |
| 411 | Pancreas | 0.1431273 | 0.4246844 | 0.352225 | 0.21986967 | V00563_at | Immunoglobulin mu, part of exon 8 |
| 412 | Pancreas | 0.1426979 | 0.4245849 | 0.352015 | 0.21982433 | AA456471_s_at | EST: zx74g11.r1 Soares ovary tumor NbHOT Homo sapiens cDNA clone 809540 5', mRNA sequence. (from Genbank) |
| 413 | Pancreas | 0.142507 | 0.4245292 | 0.351879 | 0.21961014 | D45213_at | Homo sapiens mRNA for zinc finger protein, complete cds |
| 414 | Pancreas | 0.1420584 | 0.4245271 | 0.351839 | 0.2195332 | U01317_cds 1_at | Epsilon-globin gene extracted from Human beta globin region on chromosome 11 |
| 415 | Pancreas | 0.1416256 | 0.4243606 | 0.351757 | 0.21943115 | HG880-HT880_at | Mucin 6, Gastric (Gb:L07517) |
| 416 | Pancreas | 0.1397498 | 0.4243606 | 0.351622 | 0.21926348 | U72882_s_at | Interferon-induced leucine zipper protein (IFP35) mRNA, partial cds |
| 417 | Pancreas | 0.1392388 | 0.4243341 | 0.351565 | 0.21919066 | S57132_s_at | COL16A1 Alpha-1 type XVI collagen |
| 418 | Pancreas | 0.1388932 | 0.4242676 | 0.35154 | 0.21911976 | RC_AA4167 42_at | EST: zu09g03.s1 Soares testis NHT Homo sapiens cDNA clone 731380 3', mRNA sequence. (from Genbank) |
| 419 | Pancreas | 0.1387572 | 0.424144 | 0.351491 | 0.21902552 | M16707_ma 1_at | Histone H4 gene, clone FO108 |
| 420 | Pancreas | 0.1383305 | 0.4239167 | 0.35143 | 0.21890402 | L08044_s_at 2 | Trefoil factor 3 (intestinal) |
| 421 | Pancreas | 0.1383305 | 0.4238932 | 0.35141 | 0.21876638 | L08044_s_at | TFF3 Trefoil factor 3 (intestinal) |
| 422 | Pancreas | 0.1377552 | 0.4238139 | 0.351393 | 0.2186529 | L38487_at | Estrogen receptor-related protein (hERRa1) mRNA, 3' end, partial cds |
| 423 | Pancreas | 0.1371543 | 0.4230788 | 0.351355 | 0.21842928 | L33799_at | PCOLCE Procollagen C-endopeptidase enhancer |
| 424 | Pancreas | 0.1371511 | 0.4230616 | 0.351351 | 0.21838579 | D31883_at | KIAA0059 gene |
| 425 | Pancreas | 0.1371464 | 0.423006 | 0.351201 | 0.21824138 | M80359_at | PUTATIVE SERINE/THREONINE-PROTEIN KINASE P78 |
| 426 | Pancreas | 0.1370405 | 0.423003 | 0.351173 | 0.21815978 | M86849_at | Connexin 26 (GJB2) mRNA |
| 427 | Pancreas | 0.1366365 | 0.4229905 | 0.351012 | 0.21808575 | RC_AA4062 18_at | EST: zu65e08.s1 Soares testis NHT Homo sapiens cDNA clone 742886 3', mRNA sequence. (from Genbank) |

FIG. 11Q

| | | | | | |
|---|---|---|---|---|---|
| 428 | Pancreas | 0.1364298 | 0.4229495 | 0.350966 | 0.21794756 | U68019_at | Mad protein homolog (hMAD-3) mRNA |
| 429 | Pancreas | 0.1363869 | 0.4229094 | 0.350932 | 0.21772872 | X05610_at | COL4A2 Collagen, type IV, alpha 2 |
| 430 | Pancreas | 0.1360926 | 0.4228163 | 0.350798 | 0.21767052 | RC_AA4299 98_at | EST: zw65e01.s1 Soares testis NHT Homo sapiens cDNA clone 781080 3', mRNA sequence. (from Genbank) |
| 431 | Pancreas | 0.1359602 | 0.422373 | 0.350561 | 0.21754344 | AA156838_a t | Human tumor susceptibility protein (TSG101) mRNA, complete cds |
| 432 | Pancreas | 0.1351346 | 0.4222394 | 0.350338 | 0.21735202 | S68805_at | L-arginine:glycine amidinotransferase [human, kidney carcinoma cells, mRNA, 2330 nt] |
| 433 | Pancreas | 0.1345958 | 0.4221798 | 0.350296 | 0.21723673 | Z26317_at | DSG2 Desmoglein 2 |
| 434 | Pancreas | 0.1336637 | 0.4220383 | 0.350171 | 0.21711375 | M97639_at | Transmembrane receptor (ror2) mRNA |
| 435 | Pancreas | 0.1331809 | 0.4218547 | 0.349997 | 0.21705256 | Z80777_at | H2A/k gene |
| 436 | Pancreas | 0.1330381 | 0.4215976 | 0.349303 | 0.21685627 | U60669_rna 1_s_at | Human 1 alpha,25-dihydroxyvitamin D3 24-hydroxylase (CYP24) gene, promoter region and partial CDS. (from Genbank) |
| 437 | Pancreas | 0.1319078 | 0.4215976 | 0.349303 | 0.21667595 | X98311_at | Carcinoembryonic antigen family member 2, CGM2 |
| 438 | Pancreas | 0.1319019 | 0.4215236 | 0.348979 | 0.21665491 | M93283_at | Pancreatic lipase related protein 1 (PLRP1) mRNA |
| 439 | Pancreas | 0.1318878 | 0.4213508 | 0.348765 | 0.216568 | Z49989_at | Smoothellin |
| 440 | Pancreas | 0.1317985 | 0.4210648 | 0.348756 | 0.21641165 | M55593_at | MMP2 Matrix metalloproteinase 2 (gelatinase A, 72kD gelatinase, 72kD type IV collagenase) |
| 441 | Pancreas | 0.1313918 | 0.4209068 | 0.348707 | 0.21627662 | AA043160_a t | EST: zk48g01.r1 Soares pregnant uterus NbHPU Homo sapiens cDNA clone 486096 5', mRNA sequence. (from Genbank) |
| 442 | Pancreas | 0.1305154 | 0.4208304 | 0.348676 | 0.21615298 | U90065_s_a t | Potassium channel KCNQ1 mRNA |
| 443 | Pancreas | 0.1300213 | 0.4208304 | 0.348663 | 0.21607332 | X04297_at | RPS13 RNA polymerase II polypeptide B (140 kD) |
| 444 | Pancreas | 0.1294292 | 0.4204094 | 0.348629 | 0.21590476 | RC_AA1466 19_at | EST: zo71b06.s1 Stratagene pancreas (#937208) Homo sapiens cDNA clone 592307 3', mRNA sequence. (from Genbank) |
| 445 | Pancreas | 0.1286612 | 0.4204049 | 0.348285 | 0.21579467 | U82108_s_a t | SIP-1 mRNA |
| 446 | Pancreas | 0.1286612 | 0.4203105 | 0.348154 | 0.21564145 | U82108_s_a t-2 | Solute carrier family 9 (sodium/hydrogen exchanger), isoform 3 regulatory factor 2 |
| 447 | Pancreas | 0.1286392 | 0.4203105 | 0.348057 | 0.21556382 | D43767_at | Chemokine |
| 448 | Pancreas | 0.1277934 | 0.4202434 | 0.347994 | 0.21546201 | L40393_at | (clone S171) mRNA |
| 449 | Pancreas | 0.1276084 | 0.42024 | 0.34797 | 0.21538307 | U77594_at | Tazarotene-induced gene 2 (TIG2) mRNA |
| 450 | Pancreas | 0.1268105 | 0.4201832 | 0.347913 | 0.21522285 | HG3884-HT4154_at | Homeotic Protein Hpx-42 |
| 451 | Pancreas | 0.1261273 | 0.4199822 | 0.347852 | 0.21510401 | X53586_rna 1_at | Integrin alpha 6 (or alpha E) protein gene extracted from Human mRNA for integrin alpha 6 |
| 452 | Pancreas | 0.1256997 | 0.4199315 | 0.347754 | 0.21499509 | RC_AA1370 73_at | EST: zl02g02.s1 Soares pregnant uterus NbHPU Homo sapiens cDNA clone 491186 3', mRNA sequence. (from Genbank) |
| 453 | Pancreas | 0.1256432 | 0.4199202 | 0.347708 | 0.21487539 | M23533_at | Alpha 2 adrenergic receptor gene |

FIG. 11R

| | | | | | |
|---|---|---|---|---|---|
| 454 | Pancreas | 0.1252295 | 0.419746 | 0.347654 | 0.21469477 | RC_AA4599 49_at | EST: zx6b02.s1 Soares total fetus Nb2HF8 9w Homo sapiens cDNA clone 796395 3', mRNA sequence. (from Genbank) |
| 455 | Pancreas | 0.1254913 | 0.41962 | 0.347641 | 0.21453787 | AA443499_f_at | Keratin 8 |
| 456 | Pancreas | 0.1247778 | 0.41962 | 0.347318 | 0.21448666 | L37347_at | NRAMP2 Natural resistance-associated macrophage protein 2 |
| 457 | Pancreas | 0.1242701 | 0.4195918 | 0.347231 | 0.21438734 | J03258_at | VDR Vitamin D (1,25- dihydroxyvitamin D3) receptor |
| 458 | Pancreas | 0.1238554 | 0.4194851 | 0.347217 | 0.21424824 | L19872_at | AHR AH-receptor |
| 459 | Pancreas | 0.1237912 | 0.4194425 | 0.347054 | 0.21408753 | L23116_at | GALC Galactocerebrosidase |
| 460 | Pancreas | 0.1236062 | 0.4194204 | 0.346948 | 0.2139876 | M33493_s_a t | Tryptase-III mRNA, 3' end |
| 461 | Pancreas | 0.1222131 | 0.4190792 | 0.346641 | 0.21383649 | AA156670_r_at | Homo sapiens agrin precursor mRNA, partial cds |
| 462 | Pancreas | 0.1220419 | 0.4188728 | 0.3465 | 0.21376938 | U40370_at | 3',5' cyclic nucleotide phosphodiesterase (HSPDE1A3A) mRNA |
| 463 | Pancreas | 0.1217272 | 0.4187281 | 0.346456 | 0.21369001 | D89016_at | Neuroblastoma |
| 464 | Pancreas | 0.1214543 | 0.4187148 | 0.346368 | 0.21347573 | U70867_at | Prostaglandin transporter hPGT mRNA |
| 465 | Pancreas | 0.1210791 | 0.4186941 | 0.34619 | 0.21340513 | M23254_at | CAPN2 Calpain, large polypeptide L2 |
| 466 | Pancreas | 0.1201572 | 0.4186941 | 0.346087 | 0.21328305 | D83174_s_a t | CBP1 Collagen-binding protein 1 |
| 467 | Pancreas | 0.1204439 | 0.4185918 | 0.346038 | 0.21320248 | RC_AA4890 63_at | EST: aa54f09.s1 NCI_CGAP_GCB1 Homo sapiens cDNA clone IMAGE:824777 3', mRNA sequence. (from Genbank) |
| 468 | Pancreas | 0.1197977 | 0.4185861 | 0.345924 | 0.21292841 | J05200_s_at | Ryanodine receptor 1 (skeletal) |
| 469 | Pancreas | 0.1196643 | 0.418361 | 0.345881 | 0.2129455 | L27080_at | Melanocortin 5 receptor (MC5R) gene |
| 470 | Pancreas | 0.11923 | 0.4182988 | 0.345665 | 0.2128496 | AA252581_a t | KIAA0336 gene product |
| 471 | Pancreas | 0.1191973 | 0.4182084 | 0.345622 | 0.21272261 | RC_D59847 _at | EST: Human fetal brain cDNA 3'-end GEN-070G07, mRNA sequence. (from Genbank) |
| 472 | Pancreas | 0.1183518 | 0.4181297 | 0.345532 | 0.21260984 | L11369_at | Protocadherin 42 mRNA, 3' end of cds for alternative splicing PC42-8 |
| 473 | Pancreas | 0.1180387 | 0.4179826 | 0.345332 | 0.21233512 | AA491376_a t | EST: aa65e11.r1 NCI_CGAP_GCB1 Homo sapiens cDNA clone IMAGE:825836 5', mRNA sequence. (from Genbank) |
| 474 | Pancreas | 0.11794 | 0.4179387 | 0.345241 | 0.2122144 | U77846_rna 1_s_at | Elastin gene, partial cds and partial 3'UTR |
| 475 | Pancreas | 0.1178205 | 0.4178039 | 0.345226 | 0.21217644 | D76444_at | Hkl-1 mRNA |
| 476 | Pancreas | 0.1177303 | 0.4175842 | 0.34513 | 0.21216248 | R39374_at | EST: yh95a06.r1 Homo sapiens cDNA clone 137458 5' similar to gb:M55542 INTERFERON-INDUCED GUANYLATE-BINDING PROTEIN 1 (HUMAN);. (from Genbank) |
| 477 | Pancreas | 0.1172372 | 0.4175842 | 0.345098 | 0.21203023 | W27435_at | EST: 31f8 Human retina cDNA randomly primed sublibrary Homo sapiens cDNA, mRNA sequence. (from Genbank) |
| 478 | Pancreas | 0.1168284 | 0.4175636 | 0.345067 | 0.21198222 | X69090_at | Skeletal muscle 190kD protein |

FIG. 11S

| # | Tissue | | | | ID | Gene |
|---|---|---|---|---|---|---|
| 479 | Pancreas | 0.1164274 | 0.4174888 | 0.3345037 | 0.211186382 X77567_s_at | InsP3 5-phosphatase |
| 480 | Pancreas | 0.1159584 | 0.4174105 | 0.345007 | 0.21179631 X63629_at | CDH3 Cadherin 3 (P-cadherin) |
| 481 | Pancreas | 0.1158195 | 0.4173543 | 0.344777 | 0.211594413 U49928_at | TAK1 binding protein 1 (TAB1) mRNA |
| 482 | Pancreas | 0.1155414 | 0.4171035 | 0.344776 | 0.211153237 X79204_at | SCA1 Ataxin 1 |
| 483 | Pancreas | 0.1155159 | 0.4170411 | 0.344638 | 0.211145776 Z49269_at | Chemokine HCC-1 |
| 484 | Pancreas | 0.1148278 | 0.4170252 | 0.344147 | 0.211138282 X04898_rna1_at | Apolipoprotein AII |
| 485 | Pancreas | 0.1144981 | 0.4169194 | 0.344047 | 0.211127579 AA381902_at | EST: EST95112 Activated T-cells I Homo sapiens cDNA 5' end, mRNA sequence. (from Genbank) |
| 486 | Pancreas | 0.1142331 | 0.4168361 | 0.343907 | 0.211108493 D87120_at | Cancellous bone osteoblast mRNA for GS3786 |
| 487 | Pancreas | 0.1140519 | 0.4168026 | 0.343736 | 0.21093573 HG3044-HT3742_s_at | Fibronectin, Alt. Splice 1 |
| 488 | Pancreas | 0.1138885 | 0.4167035 | 0.343648 | 0.2108611 U37055_rna1_s_at | Hepatocyte growth factor-like protein gene |
| 489 | Pancreas | 0.1134855 | 0.416477 | 0.343567 | 0.21069598 S73591_at | Brain-expressed HHCPA78 homolog [human, HL-60 acute promyelocytic leukemia cells, mRNA, 2704 nt] |
| 490 | Pancreas | 0.1130875 | 0.4163693 | 0.343451 | 0.21063247 RC_AA463861_at | EST: zx97c05.s1 Soares NhHMPu S1 Homo sapiens cDNA clone 811688 3' similar to SW:RB25_RABIT P46629 RAS-RELATED PROTEIN RAB-25.;, mRNA sequence. (from Genbank) |
| 491 | Pancreas | 0.1126792 | 0.4163249 | 0.343245 | 0.21060526 AF000561_at | Homo sapiens HIV-1 inducer of short transcripts binding protein (FBIt) mRNA, complete cds |
| 492 | Pancreas | 0.1126343 | 0.4162713 | 0.343123 | 0.21038824 HG3227-HT3404_at | Guanine Nucleotide-Binding Protein Hsr1 |
| 493 | Pancreas | 0.1115712 | 0.4162294 | 0.343 | 0.210183955 U83411_at | Carboxypeptidase Z precursor, mRNA |
| 494 | Pancreas | 0.1114354 | 0.4162073 | 0.343 | 0.21005812 M93221_at | M6PR Mannose receptor |
| 495 | Pancreas | 0.1114248 | 0.4160898 | 0.342879 | 0.21000981 J04599_at | BGN Biglycan |
| 496 | Pancreas | 0.1113904 | 0.415869 | 0.342873 | 0.2099505 J03040_at | SPARC SPARC/osteonectin |
| 497 | Pancreas | 0.1103433 | 0.4158028 | 0.342857 | 0.20980817 U40992_at | Heat shock protein hsp40 homolog mRNA |
| 498 | Pancreas | 0.1100771 | 0.415697 | 0.342696 | 0.20964763 D64109_at | Tob family |
| 499 | Pancreas | 0.1100137 | 0.4154531 | 0.342587 | 0.2095504 M60052_at | HRC Histidine-rich calcium binding protein |
| 500 | Pancreas | 0.1098329 | 0.4154259 | 0.342578 | 0.209495355 AF000959_at | Transmembrane protein mRNA |
| 501 | Pancreas | 0.1098121 | 0.4154259 | 0.342447 | 0.20939425 U24576_at | Breast tumor autoantigen mRNA, complete sequence |
| 502 | Pancreas | 0.1095284 | 0.415381 | 0.342434 | 0.20929237 RC_AA1568_at | EST: zi20h08.s1 Soares pregnant uterus NbHPU Homo sapiens cDNA clone 502527 3', mRNA sequence. (from Genbank) |
| 503 | Pancreas | 0.1093876 | 0.4152254 | 0.342279 | 0.2095202 X79683_s_at | LAMB2 Laminin, beta 2 (laminin S) |

FIG. 11T

| | | | | | | |
|---|---|---|---|---|---|---|
| 504 | Pancreas | 0.1092651 | 0.4150834 | 0.34225 | 0.209035141 | C00038_s_at | EST: HUMGS0003443, Human Gene Signature, 3'-directed cDNA sequence, mRNA sequence. (from Genbank) |
| 505 | Pancreas | 0.1090078 | 0.41497 | 0.342206 | 0.208949911 | X51757_at-2 | Heat shock 70kD protein 6 (HSP70B') |
| 506 | Pancreas | 0.1090078 | 0.4148919 | 0.342032 | 0.208857211 | X51757_at | HSPA6 Heat shock 70kD protein 6 (HSP70B') |
| 507 | Pancreas | 0.1089873 | 0.4147652 | 0.341945 | 0.208739981 | U33317_rna1_at | Defensin 6 (HD-6) gene |
| 508 | Pancreas | 0.1084821 | 0.4147107 | 0.341941 | 0.208662688 | RC_AA4461 at | EST: zw66b09.s1 Soares testis NHT Homo sapiens cDNA clone 781145 3', mRNA sequence. (from Genbank) |
| 509 | Pancreas | 0.1082371 | 0.4146037 | 0.341869 | 0.208526091 | M55621_at | MGAT1 N-acetylglucosaminyltransferase I |
| 510 | Pancreas | 0.108202 | 0.4145249 | 0.3418 | 0.208489761 | U73936_at | Soluble protein Jagged mRNA, partial cds |
| 511 | Pancreas | 0.1079309 | 0.4144937 | 0.341769 | 0.208369021 | X13839_at | LCAT Lecithin-cholesterol acyltransferase |
| 512 | Pancreas | 0.107587 | 0.4144106 | 0.341633 | 0.208275961 | L04076_at | EGR2 Early growth response 2 (Krox-20 (Drosophila) homolog) |
| 513 | Pancreas | 0.1074948 | 0.4142174 | 0.341491 | 0.2080612 | U95740_ma_at | 362G6.2 gene extracted from Human chromosome 16p13.1 BAC clone CIT987SK-362G6 complete sequence |
| 514 | Pancreas | 0.106733 | 0.4141842 | 0.341477 | 0.207951131 | H61361_s_at | Immunoglobulin superfamily containing leucine-rich repeat |
| 515 | Pancreas | 0.1062176 | 0.4140984 | 0.341352 | 0.207906251-2 | X16666_at | Homeo box B1 |
| 516 | Pancreas | 0.1062176 | 0.4140593 | 0.341202 | 0.207854821 | X16666_s_at | HOXB1 Homeo box B1 |
| 517 | Pancreas | 0.1061217 | 0.4139687 | 0.341039 | 0.207724941 | U58496_s_at | Dual-specificity tyrosine-(Y)-phosphorylation regulated kinase 1 |
| 518 | Pancreas | 0.1051414 | 0.413943 | 0.341039 | 0.207658131 | M27492_at | INTERLEUKIN-1 RECEPTOR, TYPE I PRECURSOR |
| 519 | Pancreas | 0.1046546 | 0.4138496 | 0.340988 | 0.207535601 | N78437_at | EST: yz76d04.r1 Homo sapiens cDNA clone 288967 5' similar to contains L1.t3 L1 repetitive element.; (from Genbank) |
| 520 | Pancreas | 0.1042106 | 0.4137324 | 0.340714 | 0.2073522 | K03008_cds at | Gamma-G2-psi gene extracted from Human gamma-C-crystallin (gamma-3) gene |
| 521 | Pancreas | 0.1036883 | 0.4136788 | 0.340706 | 0.207217471 | X59812_at | CYP27 Cytochrome P450, subfamily XXVII (steroid 27-hydroxylase, cerebrotendinous xanthomatosis) |
| 522 | Pancreas | 0.1034349 | 0.4134644 | 0.340614 | 0.207111951 | RC_AA4539 97_at | EST: zx46a12.s1 Soares testis NHT Homo sapiens cDNA clone 795262 3', mRNA sequence. (from Genbank) |
| 523 | Pancreas | 0.1031755 | 0.4134043 | 0.340577 | 0.207022281 | X70040_at | MST1R Protein-tyrosine kinase RON |
| 524 | Pancreas | 0.1030601 | 0.4133453 | 0.340516 | 0.207017851 | U19718_at | MFAP2 Microfibrillar-associated protein 2 |
| 525 | Pancreas | 0.1027545 | 0.4132289 | 0.340514 | 0.206812291 | S62539_at | Insulin receptor substrate-1 [human, skeletal muscle, mRNA, 5828 nt] |
| 526 | Pancreas | 0.1020946 | 0.4132258 | 0.340281 | 0.206712341 | L32866_at | Effector cell protease receptor-1 (EPR-1) gene, partial cds |
| 527 | Pancreas | 0.1018125 | 0.4129247 | 0.340139 | 0.2066905 | AA081209_a t | Regulator of G-protein signalling 5 |
| 528 | Pancreas | 0.1018037 | 0.4127833 | 0.340118 | 0.206542751 | U32114_at | Caveolin-2 mRNA |

FIG. 11U

| | | | | | |
|---|---|---|---|---|---|
| 529 | Pancreas | 0.1013078 | 0.4126998 | 0.339877 | 0.20648128 | M55682_s_at | CRTM Cartilage matrix protein |
| 530 | Pancreas | 0.1011229 | 0.4126075 | 0.33985 | 0.20635456 | M98343_at | Amplaxin (EMS1) mRNA |
| 531 | Pancreas | 0.1008726 | 0.4123334 | 0.339715 | 0.20623834 | X17651_at | MYOG Myogenin (myogenic factor 4) |
| 532 | Pancreas | 0.1006438 | 0.4121501 | 0.339641 | 0.20615427 | U53445_at | Ovarian cancer downregulated myosin heavy chain homolog (Doc1) mRNA |
| 533 | Pancreas | 0.1005173 | 0.4119512 | 0.339417 | 0.20601691 | J00098_cds1_s_at | Apolipoprotein C-III::apolipoprotein A-I |
| 534 | Pancreas | 0.1004105 | 0.4119156 | 0.339038 | 0.20600589 | J04469_at | Mitochondrial creatine kinase (CKMT) gene |
| 535 | Pancreas | 0.1002531 | 0.4118582 | 0.338911 | 0.20595379 | RC_AA406640_s_at | EST: zv15e12.s1 Soares NhHMPu S1 Homo sapiens cDNA clone 753742 3', mRNA sequence. (from Genbank) |
| 536 | Pancreas | 0.0996175 | 0.411843 | 0.338754 | 0.20582399 | U11313_at | SCP2 Sterol carrier protein 2 |
| 537 | Pancreas | 0.0995893 | 0.4117179 | 0.338747 | 0.20572168 | AA496215_at | EST: zx70c12.r1 Soares total fetus Nb2HF8 9w Homo sapiens cDNA clone 796822 5', mRNA sequence. (from Genbank) |
| 538 | Pancreas | 0.0993346 | 0.4117013 | 0.338688 | 0.20554462 | RC_AA142849_at | EST: zl40h02.s1 Soares pregnant uterus NbHPU Homo sapiens cDNA clone 504435 3', mRNA sequence. (from Genbank) |
| 539 | Pancreas | 0.0993295 | 0.4117005 | 0.338631 | 0.20548584 | X83228_at | LI-cadherin |
| 540 | Pancreas | 0.0993019 | 0.4116893 | 0.338562 | 0.20533413 | X04325_at | GJB1 Gap junction protein, beta 1, 32kD (connexin 32, Charcot-Marie-Tooth neuropathy, X-linked) |
| 541 | Pancreas | 0.0990149 | 0.4116114 | 0.338365 | 0.20528915 | RC_AA03f02.s1_at | EST: aa03f02.s1 Soares NhHMPu S1 Homo sapiens cDNA clone 812187 3', mRNA sequence. (from Genbank) |
| 542 | Pancreas | 0.0988109 | 0.4114097 | 0.338358 | 0.20512081 | M86406_at | ACTN2 Actinin alpha 2 |
| 543 | Pancreas | 0.0986825 | 0.4111492 | 0.338004 | 0.20502268 | U53446_at | Mitogen-responsive phosphoprotein (DOC-2) mRNA |
| 544 | Pancreas | 0.0981786 | 0.411137 | 0.337974 | 0.20494626 | U33267_at | Glycine receptor beta subunit (GLRB) mRNA |
| 545 | Pancreas | 0.098084 | 0.4110865 | 0.337969 | 0.20482378 | D38305_at | Tob |
| 546 | Pancreas | 0.0976737 | 0.4107786 | 0.337796 | 0.20468907 | RC_AA495994_at | EST: zw06e06.s1 Soares NhHMPu S1 Homo sapiens cDNA clone 768514 3', mRNA sequence. (from Genbank) |
| 547 | Pancreas | 0.0976723 | 0.4106137 | 0.337952 | 0.20452134 | X76534_at | NMB Neuromedin B |
| 548 | Pancreas | 0.0975629 | 0.4106137 | 0.337931 | 0.20445386 | AA232837_at | EST: zr44g03.r1 Soares NhHMPu S1 Homo sapiens cDNA clone 666292 5', mRNA sequence. (from Genbank) |
| 549 | Pancreas | 0.0972004 | 0.4105976 | 0.337667 | 0.20435306 | RC_AA495926_at | EST: zw05h01.s1 Soares NhHMPu S1 Homo sapiens cDNA clone 768433 3', mRNA sequence. (from Genbank) |
| 550 | Pancreas | 0.0971799 | 0.4104979 | 0.337565 | 0.2041196 | U62317_rna | Hypothetical protein 384D8_7 gene extracted from Chromosome 22q13 BAC Clone CIT987SK-384D8 complete sequence |
| 551 | Pancreas | 0.096436 | 0.4104713 | 0.337517 | 0.20405622 | X79440_at | NADP+-dependent malic enzyme |
| 552 | Pancreas | 0.0959474 | 0.4103843 | 0.337513 | 0.20399094 | RC_AA393803_at | EST: zv64c05.s1 Soares total fetus Nb2HF8 9w Homo sapiens cDNA clone 758408 3', mRNA sequence. (from Genbank) |
| 553 | Pancreas | 0.0958099 | 0.4101951 | 0.337424 | 0.20388122 | X66945_at | FGFR1 Basic fibroblast growth factor (bFGF) receptor (shorter form) |

FIG. 11V

| # | Tissue | | | | | | Description |
|---|---|---|---|---|---|---|---|
| 554 | Pancreas | 0.0957991 | 0.40987 | 0.337334 | 0.203861346 | RC_AA4700 66_at | EST: zt98b05.s1 Soares testis NHT Homo sapiens cDNA clone 730353 3' similar to SW:SAST_RAT P08635 S-ACYL FATTY ACID SYNTHASE THIOESTERASE, MEDIUM CHAIN ;, mRNA sequence. (from Genbank) |
| 555 | Pancreas | 0.0952122 | 0.409845 | 0.337307 | 0.203369741 | Y00318_at | IF I factor (complement) |
| 556 | Pancreas | 0.0950644 | 0.4098233 | 0.337061 | 0.20362344 | AA203274_a t | EST: zx55h09.r1 Soares fetal liver spleen 1NFLS S1 Homo sapiens cDNA clone 446465 5' similar to contains element MER27 repetitive element ;, mRNA sequence. (from Genbank) |
| 557 | Pancreas | 0.09493 | 0.4097378 | 0.336981 | 0.20350453 | U25997_at | Stanniocalcin precursor (STC) mRNA |
| 558 | Pancreas | 0.0943425 | 0.4097345 | 0.336918 | 0.20337877 | N48927_at | EST: yy75e09.r1 Homo sapiens cDNA clone 279400 5'. (from Genbank) |
| 559 | Pancreas | 0.0941559 | 0.4096106 | 0.336917 | 0.20332345 | AA306051_a t | KIAA0683 gene product |
| 560 | Pancreas | 0.0939614 | 0.4094395 | 0.336865 | 0.203152786 | RC_AA4280 69_at | EST: zw57b01.s1 Soares total fetus Nb2HF8 9w Homo sapiens cDNA clone 774121 3', mRNA sequence. (from Genbank) |
| 561 | Pancreas | 0.093534 | 0.4092763 | 0.336722 | 0.203111129 | HG4679-HT5104_at | Oncogene Ret/Ptc, Fusion Activated |
| 562 | Pancreas | 0.093391 | 0.4092578 | 0.336275 | 0.203033391 | X54667_s_a t | EST: yx52e01.r1 Homo sapiens cDNA clone 265368 5'. (from Genbank) |
| 563 | Pancreas | 0.0926611 | 0.4092093 | 0.336223 | 0.20292598 | N31127_at | Myosin-IC mRNA |
| 564 | Pancreas | 0.0922383 | 0.4089408 | 0.335995 | 0.20288192 | U14391_at | Inward rectifier K channel |
| 565 | Pancreas | 0.0921624 | 0.4088525 | 0.335978 | 0.20269935 | D50582_at | KIAA0206 gene, partial cds |
| 566 | Pancreas | 0.09214418 | 0.408699 | 0.335913 | 0.20259373 | D86961_at | Protein immuno-reactive with anti-PTH polyclonal antibodies mRNA, partial cds |
| 567 | Pancreas | 0.0916047 | 0.4085547 | 0.335878 | 0.20248578 | U28831_at | Gene encoding E-cadherin, exon 3 and joined CDS |
| 568 | Pancreas | 0.0915589 | 0.4084188 | 0.335718 | 0.20236084 | Z35402_rna 1_s_at | EST: ae49e10.s1 Stratagene lung carcinoma 937218 Homo sapiens cDNA clone 950250 3', mRNA sequence. (from Genbank) |
| 569 | Pancreas | 0.0911742 | 0.4082805 | 0.335573 | 0.20220631 | RC_AA5987 23_at | Lipid-activated, protein kinase PRK2 mRNA |
| 570 | Pancreas | 0.0909908 | 0.4082049 | 0.335512 | 0.202213962 | U33052_s_a t | E2F4 E2F transcription factor 4, p107/p130-binding |
| 571 | Pancreas | 0.0909893 | 0.4079372 | 0.335474 | 0.2020836 | S75174_at | ETO mRNA |
| 572 | Pancreas | 0.09089435 | 0.4078955 | 0.335391 | 0.20178682 | D43638_at | PUTATIVE MUCIN CORE PROTEIN PRECURSOR 24 |
| 573 | Pancreas | 0.09035513 | 0.4075186 | 0.335297 | 0.2017477 | D14043_at | UDP-galactose translocator |
| 574 | Pancreas | 0.0902054 | 0.407365 | 0.335112 | 0.20164298 | D84454_at | |
| 575 | Pancreas | 0.089557 | 0.4073069 | 0.335074 | 0.20161234 | RC_AA4632 34_at | KIAA0792 gene product |
| 576 | Pancreas | 0.089489 | 0.407287 | 0.335063 | 0.20157944 | U66033_at | Glypican-5 (GPC5) mRNA |

FIG. 11W

| # | Tissue | | | | | Accession | Description |
|---|---|---|---|---|---|---|---|
| 577 | Pancreas | 0.0893297 | 0.4072731 | 0.335019 | 0.20135632 | X00129_at | PLASMA RETINOL-BINDING PROTEIN PRECURSOR |
| 578 | Pancreas | 0.0892999 | 0.4072643 | 0.334981 | 0.20130648 | RC_AA6211 69_at | EST: af61h05.s1 Soares NhHMPu S1 Homo sapiens cDNA clone 1046553 3', mRNA sequence. (from Genbank) |
| 579 | Pancreas | 0.0887913 | 0.4071906 | 0.344909 | 0.20127305 | X06256_at | ITGA5 Integrin, alpha 5 (fibronectin receptor, alpha polypeptide) |
| 580 | Pancreas | 0.0886179 | 0.4071283 | 0.334789 | 0.20122279 | Z84718_cds 1_at | GSTT1 gene extracted from Human DNA sequence from BAC 322B1 on chromosome 22q11.2-qter contains GSTT1, GSTT2 glutathione transferases 4E-binding protein 1 pseudogene, D-dopachrome tautomerase pseudogene ESTs and polymorphic CA repeat |
| 581 | Pancreas | 0.0881335 | 0.4070313 | 0.334747 | 0.20110972 | L04751_at | CYP4A11 Cytochrome P450, subfamily IVA, polypeptide 11 |
| 582 | Pancreas | 0.0878883 | 0.4070194 | 0.334637 | 0.20098080 | RC_AA1956 60_at | EST: zr33f10.s1 Soares NhHMPu S1 Homo sapiens cDNA clone 665227 3', mRNA sequence. (from Genbank) |
| 583 | Pancreas | 0.0872879 | 0.4068774 | 0.334548 | 0.20090043 | Z23090_at | HSPB1 Heat shock 27kD protein 1 |
| 584 | Pancreas | 0.0870695 | 0.4068527 | 0.334395 | 0.20083475 | U61262_at | NEO1 Neogenin (chicken) homolog 1 |
| 585 | Pancreas | 0.0870118 | 0.4068477 | 0.334381 | 0.20073375 | RC_AA2332 57_at | Transforming growth factor beta 1 induced transcript 1 |
| 586 | Pancreas | 0.0868659 | 0.406768 | 0.334322 | 0.20066239 | HG2259-HT2348_s_a t | Tubulin, Alpha 1, Isoform 44 |
| 587 | Pancreas | 0.0866208 | 0.40676 | 0.334287 | 0.20050982 | RC_AA3992 26_at | Homo sapiens chromosome 19, cosmid R28784 |
| 588 | Pancreas | 0.0862912 | 0.4066867 | 0.33417 | 0.20045422 | X64177_f_at | Metallothionein |
| 589 | Pancreas | 0.0856267 | 0.4066675 | 0.333931 | 0.20034033 | X12876_s_a t | KRT18 Keratin 18 |
| 590 | Pancreas | 0.0854019 | 0.40646 | 0.33384 | 0.20026898 | L11695_at | SERINE/THREONINE-PROTEIN KINASE RECEPTOR R4 PRECURSOR |
| 591 | Pancreas | 0.084338 | 0.4063246 | 0.333775 | 0.20018150 | K01160_s_at | HLA-DQA1 MHC class II DQ alpha |
| 592 | Pancreas | 0.0842467 | 0.4062246 | 0.33361 | 0.20014293 | K02054_at | GRP Gastrin-releasing peptide |
| 593 | Pancreas | 0.08422 | 0.4060774 | 0.333588 | 0.19999817 | AJ001421_at | Rer1 protein |
| 594 | Pancreas | 0.0833995 | 0.4060424 | 0.333355 | 0.19993936 | U47025_s_a t | |
| 595 | Pancreas | 0.0837941 | 0.4060392 | 0.333462 | 0.19987467 | AB002382_a t | PYGB Glycogen phosphorylase B (brain form) |
| 596 | Pancreas | 0.0832928 | 0.406034 | 0.333397 | 0.19980462 | X16354_at | KIAA0384 gene |
| 597 | Pancreas | 0.0831747 | 0.4059914 | 0.333395 | 0.19965303 | RC_AA4342 45_r_at | BGP Biliary glycoprotein (alternative products) EST: zw24g05.s1 Soares ovary tumor NbHOT Homo sapiens cDNA clone 770264 3', mRNA sequence. (from Genbank) |
| 598 | Pancreas | 0.0828352 | 0.4059157 | 0.333395 | 0.19950363 | U39487_at | XDH Xanthine dehydrogenase |

FIG. 11X

| # | Tissue | Col3 | Col4 | Col5 | ID | Description |
|---|---|---|---|---|---|---|
| 599 | Pancreas | 0.0827454 | 0.405914 | 0.1994687 | L33930_s_at | CD24 signal transducer mRNA and 3' region |
| 600 | Pancreas | 0.0836639 | 0.4058448 | 0.199432339 | RC_AA2340 66_at | EST: zr74b07.s1 Soares NhHMPu S1 Homo sapiens cDNA clone 669109 3', mRNA sequence. (from Genbank) |
| 601 | Pancreas | 0.08231 | 0.4058345 | 0.19932204 | L37792_at | Syntaxin 1A mRNA |
| 602 | Pancreas | 0.082285 | 0.4057868 | 0.19916914 | L77701_at | COX17 mRNA |
| 603 | Pancreas | 0.0819284 | 0.4057504 | 0.19913451 | U63455_at | SUR Sulfonylurea receptor (hyperinsulinemia) |
| 604 | Pancreas | 0.0818573 | 0.4056875 | 0.19902349 | X65633_at | ACTH-R gene for adrenocorticotropic hormone receptor |
| 605 | Pancreas | 0.0818389 | 0.4056812 | 0.19895706 | J05257_at | DPEP1 Dipeptidase 1 (renal) |
| 606 | Pancreas | 0.0818003 | 0.4056769 | 0.19891724 | D87258_at | Cancellous bone osteoblast mRNA for serin protease with IGF-binding motif |
| 607 | Pancreas | 0.0810012 | 0.4055005 | 0.19881985 | Y00064_at | CHGB Chromogranin B (secretogranin 1) |
| 608 | Pancreas | 0.0805052 | 0.4054101 | 0.1987502 | U04898_at | RORA RAR-related orphan receptor A |
| 609 | Pancreas | 0.0803671 | 0.4051523 | 0.19864947 | RC_AA2783 73_at | Homo sapiens mRNA for KIAA0746 protein, partial cds |
| 610 | Pancreas | 0.079641 | 0.4049811 | 0.19859292 | AA306264_a t | EST: EST177232 Jurkat T-cells VI Homo sapiens cDNA 5' end, mRNA sequence. (from Genbank) |
| 611 | Pancreas | 0.0794707 | 0.4049687 | 0.19839124 | U60808_s_a t | CDP-diacylglycerol synthase (CDS) mRNA |
| 612 | Pancreas | 0.0789514 | 0.4048894 | 0.19836743 | Y09561_at | P2X7 receptor |
| 613 | Pancreas | 0.0787257 | 0.4048343 | 0.19828215 | AB0023l6_a t | Human mRNA for KIAA0318 gene, partial cds. (from Genbank) |
| 614 | Pancreas | 0.0785069 | 0.4048207 | 0.19814326 | M97675_at | Protein tyrosine kinase t-Ror1 (Ror1) mRNA |
| 615 | Pancreas | 0.078423 | 0.4047233 | 0.197988 | U56998_at | Putative serine/threonine protein kinase PRK (prk) mRNA |
| 616 | Pancreas | 0.0776481 | 0.4046421 | 0.19791195 | M58286_s_a t | TNFR1 Tumor necrosis factor receptor 1 (55kD) |
| 617 | Pancreas | 0.0776421 | 0.4044043 | 0.19782032 | M65199_at | EDN2 Endothelin 2 |
| 618 | Pancreas | 0.0775303 | 0.4043191 | 0.19777517 | RC_AA2628 87_at | EST: zs26b12.s1 NCI_CGAP_GCB1 Homo sapiens cDNA clone IMAGE:686303 3' similar to contains Alu repetitive element; mRNA sequence. (from Genbank) |
| 619 | Pancreas | 0.0757827 | 0.4042187 | 0.19763578 | L41351_at | Prostasin mRNA |
| 620 | Pancreas | 0.0756736 | 0.4041202 | 0.19755837 | U05291_at | FMOD Fibromodulin |
| 621 | Pancreas | 0.0755747 | 0.4040855 | 0.19745106 | U22028_r_at | Cytochrome P450 (CYP2A13) gene |
| 622 | Pancreas | 0.0752706 | 0.4040651 | 0.19739838 | M37435_at | CSF1 Colony-stimulating factor 1 (M-CSF) |
| 623 | Pancreas | 0.0751096 | 0.4040651 | 0.19732223 | X12901_at | VILLIN |
| 624 | Pancreas | 0.0750878 | 0.4039925 | 0.19723009 | L41919_rna1 _at | HIC-1 gene fragment |
| 625 | Pancreas | 0.0749503 | 0.4035203 | 0.19717816 | HG2604- HT2700_at | Pan-2 |

FIG. 11Y

| # | Tissue | | | | ID | Description |
|---|---|---|---|---|---|---|
| 626 | Pancreas | 0.0745711 | 0.4034933 | 0.330394 | 0.19707073 | RC_AA2165 89_at | EST: zq94e07.s1 Stratagene NT2 neuronal precursor 937230 Homo sapiens cDNA clone 649668 3', mRNA sequence. (from Genbank) |
| 627 | Pancreas | 0.0745633 | 0.4034843 | 0.330286 | 0.19697988 | M81182_s_at | PXMP1 Peroxisomal membrane protein 1 (70kD, Zellweger syndrome) |
| 628 | Pancreas | 0.0743295 | 0.4033777 | 0.330238 | 0.19690345 | M83186_at | COX7A1 Cytochrome c oxidase subunit VIIa polypeptide 1 (muscle) |
| 629 | Pancreas | 0.0742191 | 0.4033226 | 0.330163 | 0.19684352 | U43944_at | MALATE OXIDOREDUCTASE |
| 630 | Pancreas | 0.0740601 | 0.4033165 | 0.330163 | 0.19679824 | U56418_at | Lysophosphatidic acid acyltransferase-beta mRNA |
| 631 | Pancreas | 0.0736893 | 0.4033131 | 0.330064 | 0.1967322 | RC_AA4436 67_at | EST: zw86b07.s1 Soares total fetus Nb2HF8 9w Homo sapiens cDNA clone 783829 3', mRNA sequence. (from Genbank) |
| 632 | Pancreas | 0.0731634 | 0.4032323 | 0.329905 | 0.19662224 | D87438_at | KIAA0251 gene, partial cds |
| 633 | Pancreas | 0.0728746 | 0.4031362 | 0.329892 | 0.19652843 | M18079_at | FATTY ACID-BINDING PROTEIN, INTESTINAL |
| 634 | Pancreas | 0.0727107 | 0.4030623 | 0.329783 | 0.19641562 | D64053_at | Protein-tyrosine phosphatase |
| 635 | Pancreas | 0.0724607 | 0.402816 | 0.329601 | 0.19622745 | U01691_s_a t | Annexin V (ANX5) gene, 5'-untranslated region |
| 636 | Pancreas | 0.0724527 | 0.4024667 | 0.329559 | 0.19612709 | Y12670_at | LEPR Leptin receptor |
| 637 | Pancreas | 0.0722438 | 0.4022011 | 0.329464 | 0.19607201 | S69272_s_at | Cytoplasmic antiproteinase |
| 638 | Pancreas | 0.0718779 | 0.4020826 | 0.32939 | 0.19601893 | M62895_s_a t | Annexin II (lipocortin II) pseudogene 2 |
| 639 | Pancreas | 0.0713764 | 0.402037 | 0.329371 | 0.19587103 | D88154_at | Homo sapiens mRNA for villin-like protein, complete cds. (from Genbank) |
| 640 | Pancreas | 0.0711892 | 0.4018884 | 0.329325 | 0.19573468 | RC_AA3996 33_at | EST: zt93e07.s1 Soares testis NHT Homo sapiens cDNA clone 729924 3', mRNA sequence. (from Genbank) |
| 641 | Pancreas | 0.0709684 | 0.4018324 | 0.329191 | 0.19555256 | L42379_at | Quiescin (Q6) mRNA, partial cds |
| 642 | Pancreas | 0.0708247 | 0.4017611 | 0.329091 | 0.1955421 | D82347_at | NEUROD1 Neurogenic differentiation 1 |
| 643 | Pancreas | 0.0707143 | 0.4016902 | 0.329025 | 0.1954168 | J00277_at | (genomic clones lambda-[SK2-T2, HS578T]; cDNA clones RS-[3,4, 6]) c-Ha-ras1 proto-oncogene, complete coding sequence |
| 644 | Pancreas | 0.070359 | 0.4016834 | 0.328989 | 0.1953942 | Z16411_s_at | 1-PHOSPHATIDYLINOSITOL-4,5-BISPHOSPHATE PHOSPHODIESTERASE BETA 3 |
| 645 | Pancreas | 0.07026 | 0.4015907 | 0.328876 | 0.19527598 | S81914_at | IEX-1 |
| 646 | Pancreas | 0.0699539 | 0.4012235 | 0.328857 | 0.19513087 | U35637_s_a t | Nebulin mRNA, partial cds |
| 647 | Pancreas | 0.0697996 | 0.4012144 | 0.328832 | 0.19511808 | U78095_at | Placental bikunin mRNA |
| 648 | Pancreas | 0.0694097 | 0.4011256 | 0.328782 | 0.19501936 | HG4052-HT4322_at | Glutamate Ionotropic Receptor 1 |
| 649 | Pancreas | 0.069198 | 0.4010988 | 0.32872 | 0.19494246 | U46569_at | Aquaporin-5 (AQP5) gene |
| 650 | Pancreas | 0.0686109 | 0.4007911 | 0.328578 | 0.19486268 | U84569_at | YF5 mRNA |

FIG. 11Z

| # | Tissue | Col3 | Col4 | Col5 | Col6 | Col7 | Description |
|---|---|---|---|---|---|---|---|
| 651 | Pancreas | 0.0686109 | 0.4007261 | 0.328456 | 0.19478604 | U84569_at-2 | Chromosome 21 open reading frame 2 |
| 652 | Pancreas | 0.0678274 | 0.4006982 | 0.328266 | 0.19463858 | J04152_rna1 s_at | M1S1 gene extracted from Human gastrointestinal tumor-associated antigen GA733-1 protein gene, clone 05516 |
| 653 | Pancreas | 0.0674938 | 0.4004478 | 0.328124 | 0.1946017 | U21931_at | FBP1 Fructose-bisphosphatase 1 |
| 654 | Pancreas | 0.0667722 | 0.4003499 | 0.327991 | 0.19451174 | U95367_at | Human GABA-A receptor pi subunit mRNA, complete cds |
| 655 | Pancreas | 0.0667504 | 0.4003232 | 0.327877 | 0.19440651 | X95876_at | G-protein coupled receptor |
| 656 | Pancreas | 0.06666562 | 0.4003226 | 0.327844 | 0.19435789 | D85429_at | DNAJ PROTEIN HOMOLOG 1 |
| 657 | Pancreas | 0.0665032 | 0.4002916 | 0.327819 | 0.19429946 | M31013_at | MYH9 Myosin, heavy polypeptide 9, non-muscle |
| 658 | Pancreas | 0.06597 | 0.4002819 | 0.3278 | 0.19415566 | M73720_at | CPA3 Carboxypeptidase A3 (mast cell) |
| 659 | Pancreas | 0.0657443 | 0.3999901 | 0.327781 | 0.19409369 | AB002380_a t | KIAA0382 gene, partial cds |
| 660 | Pancreas | 0.0656389 | 0.3999532 | 0.327731 | 0.19402985 | X55019_s_a t | CHRND Cholinergic receptor, nicotinic, delta polypeptide |
| 661 | Pancreas | 0.0656389 | 0.3998774 | 0.327577 | 0.19394241 | X55019_s_a t-2 | Cholinergic receptor, nicotinic, delta polypeptide |
| 662 | Pancreas | 0.0656329 | 0.3998449 | 0.327484 | 0.19378129 | U73682_at | Meningioma-expressed antigen 6 (MEA6) mRNA |
| 663 | Pancreas | 0.065575 | 0.3998072 | 0.327479 | 0.19375148 | RC_AA1714 88_at | Homo sapiens clone 24778 unknown mRNA |
| 664 | Pancreas | 0.0654741 | 0.3997836 | 0.327478 | 0.19369625 | S79854_at-2 | Deiodinase, iodothyronine, type III |
| 665 | Pancreas | 0.0654741 | 0.3996081 | 0.327453 | 0.19362615 | S79854_at | Type 3 iodothyronine deiodinase |
| 666 | Pancreas | 0.0650274 | 0.3992822 | 0.327346 | 0.19352014 | L17128_at | GGCX Gamma-glutamyl carboxylase |
| 667 | Pancreas | 0.0649902 | 0.3992768 | 0.327227 | 0.19337107 | M64788_at | RAP1GA1 RAP1, GTPase activating protein 1 |
| 668 | Pancreas | 0.0648868 | 0.3991098 | 0.327027 | 0.19328368 | Z26653_at | LAMA2 Laminin, alpha 2 (merosin, congenital muscular dystrophy) |
| 669 | Pancreas | 0.0647603 | 0.3990901 | 0.326945 | 0.19325253 | X89066_at | TRPC1 Transient receptor potential channel 1 |
| 670 | Pancreas | 0.0647027 | 0.3989755 | 0.326941 | 0.19318736 | RC_AA1325 54_at | EST: zo20g08.s1 Stratagene colon (#937204) Homo sapiens cDNA clone 587486 3' similar to SW:MDCE_MOUSE P21271 MYOSIN-LIKE PROTEIN. ; mRNA sequence. (from Genbank) |
| 671 | Pancreas | 0.0644335 | 0.3989382 | 0.326722 | 0.19307046 | RC_AA4020 00_at | EST: zu55b03.s1 Soares ovary tumor NbHOT Homo sapiens cDNA clone 741869 3' similar to TR:G452270 G452270 2-19 PROTEIN PRECURSOR. ; mRNA sequence. (from Genbank) |
| 672 | Pancreas | 0.0643771 | 0.3985494 | 0.326635 | 0.19302645 | RC_AA4559 67_at | Neuronal PAS domain protein 2 |
| 673 | Pancreas | 0.0641495 | 0.3985007 | 0.32661 | 0.19286697 | RC_AA3484 66_s_at | Regulator of G-protein signalling 5 |
| 674 | Pancreas | 0.0630208 | 0.398468 | 0.326483 | 0.19278526 | AA303711_a t | Ephrin-B1 |

FIG. 11A2

| # | Tissue | | | | ID | Description |
|---|---|---|---|---|---|---|
| 675 | Pancreas | 0.0627377 | 0.3982904 | 0.326399 | 0.19263771 | AA295819_s_at | EST: EST101121 Thymus III Homo sapiens cDNA 5' end, mRNA sequence. (from Genbank) |
| 676 | Pancreas | 0.0619927 | 0.3981885 | 0.326291 | 0.19251992 | D83735_at | Adult heart mRNA for neutral calponin |
| 677 | Pancreas | 0.0617258 | 0.3981172 | 0.326291 | 0.1924785 | X05615_at | Thyroglobulin |
| 678 | Pancreas | 0.0615823 | 0.3981042 | 0.326217 | 0.19238625 | AA487015_s_at | EST: ab24f09.r1 Stratagene lung (#937210) Homo sapiens cDNA clone 841769 5', mRNA sequence. (from Genbank) |
| 679 | Pancreas | 0.0612557 | 0.3979692 | 0.326199 | 0.19225594 | M59499_at | TISSUE FACTOR PATHWAY INHIBITOR PRECURSOR |
| 680 | Pancreas | 0.06124 | 0.3979077 | 0.32618 | 0.19214974 | L13391_at | REGULATOR OF G-PROTEIN SIGNALLING 2 |
| 681 | Pancreas | 0.0610174 | 0.3978736 | 0.326137 | 0.19206993 | AA426304_r_at | EST: zw11g07.r1 Soares NhHMPu S1 Homo sapiens cDNA clone 769020 5', mRNA sequence. (from Genbank) |
| 682 | Pancreas | 0.0603275 | 0.3977551 | 0.32605 | 0.19201934 | AB000897_a_t | Cadherin FIB3, partial cds |
| 683 | Pancreas | 0.060263 | 0.3975529 | 0.326006 | 0.19197464 | D82675_at | EST: similar to none, mRNA sequence. (from Genbank) |
| 684 | Pancreas | 0.0601004 | 0.3974492 | 0.325751 | 0.19189379 | X54162_at | 64 KD AUTOANTIGEN D1 |
| 685 | Pancreas | 0.0600266 | 0.3974408 | 0.325682 | 0.19177243 | M17466_at | F12 Coagulation factor XII (Hageman factor) |
| 686 | Pancreas | 0.0592057 | 0.3974216 | 0.325567 | 0.19171983 | Y00317_at-2 | UDP-GLUCURONOSYLTRANSFERASE 2B4 PRECURSOR, MICROSOMAL |
| 687 | Pancreas | 0.0592057 | 0.3974179 | 0.325533 | 0.1916082 | Y00317_at | UDP-GLUCURONOSYLTRANSFERASE 2B4 PRECURSOR, MICROSOMAL |
| 688 | Pancreas | 0.0587257 | 0.3973526 | 0.325521 | 0.19148682 | AA095600_a_t | L5079.seq.F Fetal heart, Lambda ZAP Express Homo sapiens cDNA 5', mRNA sequence. (from Genbank) |
| 689 | Pancreas | 0.0584491 | 0.3972171 | 0.325489 | 0.19141361 | U05875_at | Clone pSK1 interferon gamma receptor accessory factor-1 (AF-1) mRNA |
| 690 | Pancreas | 0.0583136 | 0.3971216 | 0.325449 | 0.19129473 | AA122302_a_t | EST: zk97d12.r1 Soares pregnant uterus NbHPU Homo sapiens cDNA clone 490775 5' similar to gb:L32179 Human arylacetamide deacetylase mRNA, complete cds. (HUMAN);, mRNA sequence. (from Genbank) |
| 691 | Pancreas | 0.0578924 | 0.3971093 | 0.32542 | 0.19123964 | M24122_s_at | MYL3 Myosin, light polypeptide 3, alkali; ventricular, skeletal, slow |
| 692 | Pancreas | 0.05765 | 0.3970932 | 0.325414 | 0.1911619 | L48513_at | Paraoxonase (PON2) mRNA |
| 693 | Pancreas | 0.0575461 | 0.3970162 | 0.325373 | 0.19105273 | U79258_at | Clone 23732 mRNA, partial cds |
| 694 | Pancreas | 0.0570444 | 0.3969659 | 0.32527 | 0.19090556 | U64871_at | G protein-coupled receptor GPR-NGA gene |
| 695 | Pancreas | 0.056731 | 0.3968439 | 0.325195 | 0.19087186 | RC_AA423884_at | Homo sapiens mRNA for KIAA0287 gene, partial cds |
| 696 | Pancreas | 0.0566979 | 0.3968068 | 0.325079 | 0.19085953 | D50855_s_at | CASR Calcium-sensing receptor (hypocalciuric hypercalcemia 1, severe neonatal hyperparathyroidism) |
| 697 | Pancreas | 0.0566699 | 0.3967628 | 0.325048 | 0.1906883 | M22960_at | PPGB Protective protein for beta-galactosidase (galactosialidosis) |
| 698 | Pancreas | 0.0561367 | 0.3966727 | 0.324969 | 0.19067462 | AC002077_a_t | GUANINE NUCLEOTIDE-BINDING PROTEIN G(T), ALPHA-1 SUBUNIT |

FIG. 11B2

| # | Tissue | | | | | | Description |
|---|---|---|---|---|---|---|---|
| 699 | Pancreas | 0.0560136 | 0.3966568 | 0.324911 | 0.19056943 | U20758_rna1_at | Osteopontin gene |
| 700 | Pancreas | 0.0558856 | 0.3963859 | 0.324878 | 0.19051494 | R60605_at | Yh14b06.r1 Homo sapiens cDNA clone 37738 5'. (from Genbank) |
| 701 | Pancreas | 0.0552527 | 0.3961977 | 0.324813 | 0.19041143 | U53786_at | EVPL Envoplakin |
| 702 | Pancreas | 0.0551515 | 0.396041 | 0.324686 | 0.19033171 | S71018_at-2 | Peptidylprolyl isomerase C (cyclophilin C) |
| 703 | Pancreas | 0.0551515 | 0.3960319 | 0.324561 | 0.19022691 | S71018_at | Cyclophilin C [human, kidney, mRNA, 883 nt] |
| 704 | Pancreas | 0.0551309 | 0.3959803 | 0.324547 | 0.19017349 | U12471_cds1_at | Thrombospondin-p50 gene extracted from Human thrombospondin-1 gene, partial cds |
| 705 | Pancreas | 0.0547465 | 0.3958941 | 0.32451 | 0.19006127 | X13766_s_at | CSN2 Beta-casein |
| 706 | Pancreas | 0.0546628 | 0.3956415 | 0.32451 | 0.18998659 | S34389_at | HMOX2 Heme oxygenase (decycling) 2 |
| 707 | Pancreas | 0.0546542 | 0.3954517 | 0.324502 | 0.18989405 | A358888_at | EST: EST67818 Fetal lung II Homo sapiens cDNA 5' end, mRNA sequence. (from Genbank) |
| 708 | Pancreas | 0.0545703 | 0.3954237 | 0.324455 | 0.18981382 | M12125_at | Skeletal beta-tropomyosin |
| 709 | Pancreas | 0.054416 | 0.3953139 | 0.324428 | 0.18977097 | AA033703_at | EST: zf01d10.r1 Soares fetal heart NbHH19W Homo sapiens cDNA clone 375667 5', mRNA sequence. (from Genbank) |
| 710 | Pancreas | 0.0542019 | 0.395284 | 0.324403 | 0.1896241 | U28281_at | SCTR Secretin receptor |
| 711 | Pancreas | 0.0541305 | 0.3952656 | 0.324391 | 0.18953659 | U49188_at | Placenta (Diff33) mRNA |
| 712 | Pancreas | 0.0539464 | 0.3952472 | 0.324258 | 0.18949248 | M91083_at | DNA-binding protein (HRC1) mRNA |
| 713 | Pancreas | 0.0535458 | 0.3952055 | 0.324239 | 0.18942979 | Y08136_at | ASM-like phosphodiesterase 3a |
| 714 | Pancreas | 0.0535063 | 0.3951488 | 0.324234 | 0.18934222 | U78313_at | Myogenic repressor I-mf (MDFI) mRNA |
| 715 | Pancreas | 0.0533906 | 0.3950844 | 0.324161 | 0.18930747 | RC_AA404487_at | EST: zw38a06.s1 Soares total fetus Nb2HF8 9w Homo sapiens cDNA clone 772306 3', mRNA sequence. (from Genbank) |
| 716 | Pancreas | 0.0529316 | 0.3950577 | 0.3241 | 0.18924192 | U09860_at | PRSS7 Protease, serine, 7 (enterokinase) |
| 717 | Pancreas | 0.052749 | 0.3949802 | 0.32409 | 0.18909808 | M21302_at | Small proline rich protein (sprI) mRNA, clone 174N |
| 718 | Pancreas | 0.0525981 | 0.3949701 | 0.324059 | 0.18900725 | M91368_s_at | Na+/Ca+ exchanger (CNC) mRNA |
| 719 | Pancreas | 0.0518923 | 0.3949174 | 0.323985 | 0.18896532 | AB002296_at | KIAA0298 gene product |
| 720 | Pancreas | 0.0518132 | 0.394871 | 0.323713 | 0.18883476 | X02419_rna1_s_at | UPA gene |
| 721 | Pancreas | 0.0517804 | 0.3946853 | 0.323598 | 0.1886775 | RC_AA398533_at | EST: zt73b05.s1 Soares testis NHT Homo sapiens cDNA clone 727953 3', mRNA sequence. (from Genbank) |
| 722 | Pancreas | 0.0517782 | 0.3946745 | 0.323564 | 0.18861987 | X64810_at | PCSK1 Proprotein convertase subtilisin/kexin type 1 |
| 723 | Pancreas | 0.0508785 | 0.3944626 | 0.323531 | 0.18853721 | W27650_at | EST: 36e12 Human retina cDNA randomly primed sublibrary Homo sapiens cDNA, mRNA sequence. (from Genbank) |
| 724 | Pancreas | 0.0508736 | 0.3943932 | 0.323531 | 0.18846573 | HG3236-HT3413_f_at | Neurofibromatosis 2 Tumor Suppressor (Gb:L27065) |

FIG. 11C2

| # | Tissue | | | | Accession | Description |
|---|---|---|---|---|---|---|
| 725 | Pancreas | 0.0508008 | 0.3943844 | 0.323519 | HG3517-HT3711_at | Alpha-1-Antitrypsin, 5' End |
| 726 | Pancreas | 0.0505374 | 0.3943604 | 0.323492 | 0.18830512 M59911_at | ITGA3 Integrin alpha-3 subunit |
| 727 | Pancreas | 0.0505132 | 0.394157 | 0.323478 | 0.18823019 M96789_at | GJA4 Gap junction protein, alpha 4, 37kD (connexin 37) |
| 728 | Pancreas | 0.0502943 | 0.394157 | 0.323405 | 0.18816702 X93510_at | 37 kDa LIM domain protein |
| 729 | Pancreas | 0.0498247 | 0.3938775 | 0.323309 | 0.18809421 U45878_s_at | Inhibitor of apoptosis protein 1 mRNA |
| 730 | Pancreas | 0.0493286 | 0.3937683 | 0.323305 | 0.18798196 M96132_at | MHC class II HLA-DR-beta-1*09012 (HLA-DRB1*09012) gene, 3'end cds |
| 731 | Pancreas | 0.0491917 | 0.3937386 | 0.323068 | 0.18782736 V00574_s_at | (genomic clones lambda-[SK2-T2, HS578T]; cDNA clones RS-[3,4, 6]) c-Ha-ras1 proto-oncogene, complete coding sequence |
| 732 | Pancreas | 0.0491057 | 0.3936019 | 0.323064 | 0.18776813 AA418143_a_t | EST: zv97b09.r1 Soares NhHMPu S1 Homo sapiens cDNA clone 767705 5', mRNA sequence. (from Genbank) |
| 733 | Pancreas | 0.048753 | 0.3935812 | 0.32264 | 0.18768327 X97058_at | P2Y6 receptor, short splice variant mRNA |
| 734 | Pancreas | 0.0487488 | 0.3935328 | 0.322351 | 0.18765172 X60673_rna1_at | AK3 mRNA for adenylate kinase 3 |
| 735 | Pancreas | 0.048641 | 0.3934996 | 0.322332 | HG2755-HT2862_at | T-Plastin |
| 736 | Pancreas | 0.0485113 | 0.3934173 | 0.322328 | 0.18757421 AD000092_cds2_at | Hypothetical human protein R31240_2 gene extracted from Homo sapiens DNA from chromosome 19p13.2 cosmids R31240, R30272 and R28549 containing the EKLF, GCDH, CRTC, and RAD23A genes, genomic sequence |
| 737 | Pancreas | 0.0484873 | 0.3933761 | 0.322276 | 0.18735895_at AA464051_s_at | EST: zx86d04.r1 Soares ovary tumor NbHOT Homo sapiens cDNA clone 810631 5', mRNA sequence. (from Genbank) |
| 738 | Pancreas | 0.0484705 | 0.3932881 | 0.322081 | 0.18726256 L36033_at | SDF1 Stromal cell-derived factor 1 |
| 739 | Pancreas | 0.0483683 | 0.3932245 | 0.321989 | 0.18721056 X78706_at | CRAT Carnitine acetyltransferase |
| 740 | Pancreas | 0.0481097 | 0.3930922 | 0.321475 | 0.18712951 AF001548_rna1_at | 815A9.1 gene (myosin heavy chain) extracted from Homo sapiens chromosome 16 BAC clone CIT987SK-815A9 complete sequence |
| 741 | Pancreas | 0.0480806 | 0.3930864 | 0.321413 | 0.18705058 RC_D25942_r_at | EST: Human colon 3'directed MboI cDNA, HUMGS06716, clone cm2781, mRNA sequence. (from Genbank) |
| 742 | Pancreas | 0.0478097 | 0.3930864 | 0.3214 | 0.18695353 D28137_at | RPS11 Ribosomal protein S11 |
| 743 | Pancreas | 0.0478048 | 0.3929904 | 0.321345 | 0.18681973 U73377_at | SKI V-ski avian sarcoma viral oncogene homolog |
| 744 | Pancreas | 0.0474275 | 0.3928776 | 0.321279 | 0.18671212 U90905_at | Clone 23574 mRNA sequence |
| 745 | Pancreas | 0.0471585 | 0.3928713 | 0.3212 | 0.18668373 RC_AA4914 63_at | EST: ab01d12.s1 Stratagene fetal retina 937202 Homo sapiens cDNA clone 8339543 3', mRNA sequence. (from Genbank) |
| 746 | Pancreas | 0.046876 | 0.3928489 | 0.321177 | 0.18656825 D31887_at | KIAA0062 gene, partial cds |
| 747 | Pancreas | 0.0467393 | 0.3927784 | 0.321175 | 0.18653668 D43968_at | CBFA2 Proto-oncogene AML1 (alternative products) |
| 748 | Pancreas | 0.0458387 | 0.3926974 | 0.321026 | 0.18644363 M27749_r_at | Immunoglobulin-related 14.1 protein mRNA |

FIG. 11D2

| # | Tissue | | | | | | |
|---|---|---|---|---|---|---|---|
| 749 | Pancreas | 0.0454475 | 0.3926883 | 0.320905 | 0.18636368 | X53416_at | FLN1 Filamin 1 (actin-binding protein-280) |
| 750 | Pancreas | 0.0454158 | 0.3925128 | 0.320852 | 0.1863169 | U07664_at | HR9 homeobox gene |
| 751 | Pancreas | 0.0447514 | 0.3924449 | 0.320764 | 0.186256951 | X61755_rna_s_at | HOX3D gene for homeoprotein HOX3D |
| 752 | Pancreas | 0.0446037 | 0.3924094 | 0.320726 | 0.18619926 | M90696_at | CTSS Cathepsin S |
| 753 | Pancreas | 0.0441947 | 0.3923088 | 0.32069 | 0.18607153 | X58298_s_at | IL6R Interleukin 6 receptor |
| 754 | Pancreas | 0.0441815 | 0.392295 | 0.320522 | 0.18603428 | RC_AA496366_at | EST: zv37c09.s1 Soares ovary tumor NbHOT Homo sapiens cDNA clone 755824 3', mRNA sequence. (from Genbank) |
| 755 | Pancreas | 0.0438538 | 0.392151 | 0.320457 | 0.18595268 | L02648_at | TCN2 Transcobalamin II |
| 756 | Pancreas | 0.0433454 | 0.3920745 | 0.320356 | 0.18583295 | X72308_at-2 | Small inducible cytokine A7 (monocyte chemotactic protein 3) |
| 757 | Pancreas | 0.0433454 | 0.3920402 | 0.320237 | 0.18578789 | X72308_at | MONOCYTE CHEMOTACTIC PROTEIN 3 PRECURSOR |
| 758 | Pancreas | 0.0422934 | 0.3918841 | 0.320117 | 0.18572955 | D84110_at | RBP-MS/type 1 |
| 759 | Pancreas | 0.0422398 | 0.3918409 | 0.319911 | 0.1856809 | HG2724-HT2820_at | Oncogene Tls/Chop, Fusion Activated |
| 760 | Pancreas | 0.0421554 | 0.3916346 | 0.319902 | 0.18563306 | RC_AA430036_at | EST: zw65f10.s1 Soares testis NHT Homo sapiens cDNA clone 781099 3', mRNA sequence. (from Genbank) |
| 761 | Pancreas | 0.041823 | 0.3916287 | 0.319841 | 0.18554859 | X79200_at | Homo sapiens mRNA for SYT-SSX protein |
| 762 | Pancreas | 0.0416487 | 0.3916132 | 0.319733 | 0.185405725_at | J00220_cds | IGHA1 gene extracted from Human Ig germline H-chain G-E-A region A: gamma-3 5' flank |
| 763 | Pancreas | 0.0415134 | 0.3914889 | 0.319603 | 0.18531708 | HG3415-HT3598_at | Poliovirus Receptor |
| 764 | Pancreas | 0.0414927 | 0.3914706 | 0.319581 | 0.18530028 | RC_AA487558_at | EST: ab23e01.s1 Stratagene lung (#937210) Homo sapiens cDNA clone 841656 3', mRNA sequence. (from Genbank) |
| 765 | Pancreas | 0.0414651 | 0.3914217 | 0.31938 | 0.18522041 | L22548_at | COL18A1 Collagen, type XVIII, alpha 1 |
| 766 | Pancreas | 0.0414315 | 0.3913104 | 0.31929 | 0.1852084 | U12535_at | Epidermal growth factor receptor kinase substrate (Eps8) mRNA |
| 767 | Pancreas | 0.0413034 | 0.3912281 | 0.319285 | 0.18515123 | AF015950_at | Telomerase reverse transcriptase (hTRT) mRNA |
| 768 | Pancreas | 0.0412396 | 0.3911472 | 0.319167 | 0.18502258 | D25274_at | Randomly sequenced mRNA |
| 769 | Pancreas | 0.0411955 | 0.3911472 | 0.319141 | 0.184944 | M77349_at | Transforming growth factor-beta induced gene product (BIGH3) mRNA |
| 770 | Pancreas | 0.0411105 | 0.3910776 | 0.31913 | 0.18483837 | M85220_at | Germline Ig alpha mutant chain gene C-alpha-3 region of the secreted protein, 3' end |
| 771 | Pancreas | 0.0410391 | 0.3910221 | 0.319023 | 0.18472582 | X71125_at | Glutamine cyclotransferase |
| 772 | Pancreas | 0.0409171 | 0.39009954 | 0.318967 | 0.1846892 | U77180_at | EBI1-ligand chemokine |
| 773 | Pancreas | 0.0407 | 0.39099498 | 0.318924 | 0.18460506 | D87434_at | KIAA0247 gene |
| 774 | Pancreas | 0.0406888 | 0.3907001 | 0.318829 | 0.18451984 | M97925_rna1_at | Defensin 5 gene |
| 775 | Pancreas | 0.0401114 | 0.3903465 | 0.318764 | 0.18444623 | U09210_at | SLC18A3 Solute carrier family 18 (vesicular acetylcholine), member 3 |

FIG. 11E2

| # | Tissue | | | | | Description |
|---|---|---|---|---|---|---|
| 776 | Pancreas | 0.0398312 | 0.3902517 | 0.318744 | 0.18440726 | U45285_at | Specific 116-kDa vacuolar proton pump subunit (OC-116KDa) mRNA |
| 777 | Pancreas | 0.0397135 | 0.3901192 | 0.318743 | 0.18431243 | U40380_at | PSEN1 Presenilin 1 (Alzheimer disease 3) |
| 778 | Pancreas | 0.0387971 | 0.3901587 | 0.318565 | 0.18415372 | RC_AA4194 61_at | EST: zu99d05.s1 NCI_CGAP_GCB1 Homo sapiens cDNA clone IMAGE:746121 3', mRNA sequence. (from Genbank) |
| 779 | Pancreas | 0.0385597 | 0.3901347 | 0.318405 | 0.1841216 | AA287749_a at | Zs51b11.r1 NCI_CGAP_GCB1 Homo sapiens cDNA clone IMAGE:7009899 5', mRNA sequence. (from Genbank) |
| 780 | Pancreas | 0.0377284 | 0.3901133 | 0.318386 | 0.18406631 | M36803_at | HPX Hemopexin |
| 781 | Pancreas | 0.0373459 | 0.3900852 | 0.31831 | 0.18403506 | U52100_at | XMP mRNA |
| 782 | Pancreas | 0.0369694 | 0.3900309 | 0.318169 | 0.18396205 | U68135_s_a t | U68135 Human cell line PCI-O6B Homo sapiens cDNA clone SCC-S1c, mRNA sequence |
| 783 | Pancreas | 0.0365574 | 0.3899592 | 0.318104 | 0.18377244 | U48705_rna 1_s_at | Receptor tyrosine kinase DDR gene |
| 784 | Pancreas | 0.035841 | 0.3895468 | 0.318052 | 0.18372366 | Z68228_s_at | JUP Junction plakoglobin |
| 785 | Pancreas | 0.0352118 | 0.3894484 | 0.317833 | 0.18364914 | RC_AA4781 12_at | EST: zt89e03.s1 Soares testis NHT Homo sapiens cDNA clone 729532 3', mRNA sequence. (from Genbank) |
| 786 | Pancreas | 0.0346144 | 0.3893405 | 0.31782 | 0.18356068 | AA320369_s at | GLUT1 C-terminal binding protein |
| 787 | Pancreas | 0.0344629 | 0.3892617 | 0.31782 | 0.18353364 | Z24725_at | Mitogen inducible gene mig-2 |
| 788 | Pancreas | 0.0344202 | 0.3892587 | 0.317811 | 0.18341781 | W259945_at | EST: 17c5 Human retina cDNA randomly primed sublibrary Homo sapiens cDNA, mRNA sequence. (from Genbank) |
| 789 | Pancreas | 0.0343859 | 0.389198 | 0.317742 | 0.18335396 | AB0023259_a t | KIAA0327 gene product |
| 790 | Pancreas | 0.0337823 | 0.3891447 | 0.317701 | 0.18327224 | U39447_at | Placenta copper monamine oxidase mRNA |
| 791 | Pancreas | 0.0334188 | 0.3891069 | 0.317633 | 0.18315534 | RC_AA2341 12_at | EST: zr74a05.s1 Soares NhHMPu S1 Homo sapiens cDNA clone 669104 3', mRNA sequence. (from Genbank) |
| 792 | Pancreas | 0.0333544 | 0.3890183 | 0.317568 | 0.1830357 | U40434_at | Pre-pro-megakaryocyte potentiating factor |
| 793 | Pancreas | 0.0333063 | 0.3888591 | 0.317526 | 0.18297827 | HG429-HT429_at | B-Cell Growth Factor 1 |
| 794 | Pancreas | 0.0330798 | 0.3888443 | 0.31746 | 0.18290998 | U02556_at | RP3 mRNA |
| 795 | Pancreas | 0.0329533 | 0.3887434 | 0.317316 | 0.18282567 | Y08639_at | Nuclear orphan receptor ROR-beta |
| 796 | Pancreas | 0.0328809 | 0.3886541 | 0.317273 | 0.18273741 | U67171_at | Selenoprotein W (selW) mRNA |
| 797 | Pancreas | 0.032871 | 0.3884676 | 0.317206 | 0.18266168 | U91903_at | Frezzled (fre) mRNA |
| 798 | Pancreas | 0.0326147 | 0.388227 | 0.317117 | 0.1825429 | AB0023329_a t | KIAA0334 gene |
| 799 | Pancreas | 0.0326079 | 0.3880671 | 0.31704 | 0.18254118 | M13452_s_a t | LMNA Lamin A |
| 800 | Pancreas | 0.0324061 | 0.3879441 | 0.316879 | 0.18245973 | D14823_at | Chimeric mRNA derived from AML1 gene and MTG8(ETO) gene, partial sequence |

FIG. 11F2

| # | Tissue | | | | | Description |
|---|---|---|---|---|---|---|
| 801 | Pancreas | 0.0323881 | 0.3877875 | 0.316801 | 0.18235482 | U37283_at | Microfibril-associated glycoprotein-2 MAGP-2 mRNA |
| 802 | Pancreas | 0.0323168 | 0.3877806 | 0.316766 | 0.1823015 | U82130_at | Tumor susceptibility protein (TSG101) mRNA |
| 803 | Pancreas | 0.0322793 | 0.3877108 | 0.316723 | 0.1821918 | U81607_at | GRAVIN |
| 804 | Pancreas | 0.0322522 | 0.3875997 | 0.31667 | 0.18216777 | RC_AA0402 44_at | EST: zk44d12.s1 Soares pregnant uterus NbHPU Homo sapiens cDNA clone 485687 3', mRNA sequence. (from Genbank) |
| 805 | Pancreas | 0.0318007 | 0.3875524 | 0.316633 | 0.18211982 | RC_AA4302 09_at | Homo sapiens LIM protein mRNA, complete cds |
| 806 | Pancreas | 0.0317025 | 0.3875092 | 0.316579 | 0.18203923 | M59815_at | C4A Complement component 4A |
| 807 | Pancreas | 0.0315603 | 0.3874682 | 0.316511 | 0.18193968 | RC_AA2919 27_at | EST: zr58g09.s1 Soares NhHMPu S1 Homo sapiens cDNA clone 667648 3', mRNA sequence. (from Genbank) |
| 808 | Pancreas | 0.0311749 | 0.3874079 | 0.316493 | 0.18188252 | M57732_at | TCF1 Transcription factor 1, hepatic; LF-B1, hepatic nuclear factor (HNF1), albumin proximal factor |
| 809 | Pancreas | 0.0310991 | 0.387293 | 0.316379 | 0.18175524 | HG3242-HT3419_s_a t | Calcium Channel, Voltage-Gated, Alpha 1e Subunit, Alt. Splice 2 |
| 810 | Pancreas | 0.0309182 | 0.3872835 | 0.316287 | 0.18171705 | Z80345_rna 1_s_at | SCAD gene, exon 1 and joining features |
| 811 | Pancreas | 0.0308594 | 0.3872346 | 0.316168 | 0.18165159 | AA251636_a t | EST: zs10b09.r1 NCI_CGAP_GCB1 Homo sapiens cDNA clone IMAGE:684761 5', mRNA sequence. (from Genbank) |
| 812 | Pancreas | 0.0307786 | 0.3871786 | 0.316114 | 0.18153405 | U10493_s_a t | Mesenchyme homeo box 1 |
| 813 | Pancreas | 0.0306988 | 0.3870966 | 0.316011 | 0.18145765 | X04366_at | CALPAIN 1, LARGE |
| 814 | Pancreas | 0.0306647 | 0.3870095 | 0.315996 | 0.1814266 | D16217_at | CAST Calpastatin |
| 815 | Pancreas | 0.0305153 | 0.3869424 | 0.315944 | 0.18138085 | HG4126-HT4396_at | Zinc Finger Protein Hzf4 |
| 816 | Pancreas | 0.0304767 | 0.3868362 | 0.315753 | 0.18132313 | X78342_at | (clone PK2J) CDC2-related protein kinase (PISSLRE) mRNA |
| 817 | Pancreas | 0.0302488 | 0.3866913 | 0.315748 | 0.18123081 | RC_AA3218 33_at | EST: EST24395 Cerebellum II Homo sapiens cDNA 3' end, mRNA sequence. (from Genbank) |
| 818 | Pancreas | 0.0302483 | 0.3866816 | 0.315711 | 0.18111803 | RC_AA4875 57_at | EST: ab20h12.s1 Stratagene lung (#937210) Homo sapiens cDNA clone 841415 3', mRNA sequence. (from Genbank) |
| 819 | Pancreas | 0.0297827 | 0.3866339 | 0.315711 | 0.18104862 | L11370_at | Protocadherin 42 mRNA for abbreviated PC42 |
| 820 | Pancreas | 0.0293067 | 0.3866109 | 0.315648 | 0.18094556 | L00389_f_at | Cytochrome P-450 4 gene |
| 821 | Pancreas | 0.0291889 | 0.3866008 | 0.315566 | 0.18087313 | RC_AA3938 76_s_at | APOLIPOPROTEIN AI REGULATORY PROTEIN-1 |
| 822 | Pancreas | 0.0289653 | 0.3866008 | 0.315535 | 0.18078643 | HG2936-HT3080_at | Immunoglobulin Heavy Chain, Enhancer Element |
| 823 | Pancreas | 0.0286998 | 0.3865607 | 0.315492 | 0.1806871 | J04093_s_at | UDP-GLUCURONOSYLTRANSFERASE 1F PRECURSOR, MICROSOMAL |
| 824 | Pancreas | 0.0285771 | 0.3861924 | 0.31548 | 0.18059951 | RC_AA4245 15_at | EST: zv90f02.s1 Soares NhHMPu S1 Homo sapiens cDNA clone 767067 3', mRNA sequence. (from Genbank) |

FIG. 11G2

| | | | | | | |
|---|---|---|---|---|---|---|
| 825 | Pancreas | 0.0283829 | 0.3861498 | 0.315454 | 0.18040824 | M11717_rna1_at | Heat shock protein (hsp 70) gene |
| 826 | Pancreas | 0.0283379 | 0.3861168 | 0.315412 | 0.18039578 | D13969_at | DNA-BINDING PROTEIN MEL-18 |
| 827 | Pancreas | 0.0282287 | 0.386032 | 0.31539 | 0.18039241 | RC_AA4361 74_at | EST: zv22d06.s1 Soares NhHMPu S1 Homo sapiens cDNA clone 754379 3' similar to contains Alu repetitive element;contains L1.t3 L1 repetitive element:, mRNA sequence. (from Genbank) |
| 828 | Pancreas | 0.0281155 | 0.3860165 | 0.315325 | 0.18027721 | RC_AA3941 _at | EST: zt52g05.s1 Soares ovary tumor NbHOT Homo sapiens cDNA clone 726008 3', mRNA sequence. (from Genbank) |
| 829 | Pancreas | 0.0279444 | 0.385967 | 0.315258 | 0.18022232 | U79241_at | Clone 23759 mRNA, partial cds |
| 830 | Pancreas | 0.0277871 | 0.3859116 | 0.315228 | 0.18013038 | L02785_at | DRA Down-regulated in adenoma |
| 831 | Pancreas | 0.0277547 | 0.385909 | 0.315013 | 0.18004806 | RC_AA4320 74_at | EST: zw89c01.s1 Soares total fetus Nb2HF8 9w Homo sapiens cDNA clone 784128 3', mRNA sequence. (from Genbank) |
| 832 | Pancreas | 0.0276283 | 0.3857677 | 0.314943 | 0.17994042 | M91392_at | EST: HUMRTPGEM Homo sapiens cDNA. (from Genbank) |
| 833 | Pancreas | 0.0275305 | 0.3857462 | 0.314932 | 0.17992336 | U53506_at | Type II iodothyronine deiodinase mRNA |
| 834 | Pancreas | 0.0270495 | 0.3857426 | 0.314897 | 0.17951602 | RC_AA2435 62_at | EST: zs15h06.s1 NCI_CGAP_GCB1 Homo sapiens cDNA clone IMAGE:605307 3', mRNA sequence. (from Genbank) |
| 835 | Pancreas | 0.02702 | 0.3857287 | 0.314814 | 0.17971656 | M13955_at | Mesothelial keratin K7 (type II) mRNA, 3' end |
| 836 | Pancreas | 0.0269895 | 0.3857287 | 0.31476 | 0.17968687 | AA427468_s _at | Claudin 4 |
| 837 | Pancreas | 0.026901 | 0.3857121 | 0.314752 | 0.17963299 | X58822_rna 1_s_at | IFN-omega 1 gene for interferon-omega 1 |
| 838 | Pancreas | 0.0268838 | 0.3856923 | 0.314725 | 0.17960931 | AC002450_a _t | BAC clone GS244B22 from 7q21-q22, complete sequence |
| 839 | Pancreas | 0.0266984 | 0.3856869 | 0.314653 | 0.17951602 | M83667_rna 1_s_at | NF-IL6-beta protein mRNA |
| 840 | Pancreas | 0.0266384 | 0.3856348 | 0.314628 | 0.17942718 | X72304_s_a t | Corticotropin releasing hormone receptor 1 |
| 841 | Pancreas | 0.0266116 | 0.385612 | 0.31453 | 0.17935938 | L19711_at | Dystroglycan (DAG1) mRNA |
| 842 | Pancreas | 0.026571 | 0.385607 | 0.314416 | 0.17935938 | HG3995-HT4265_at | Cpg-Enriched Dna, Clone S19 |
| 843 | Pancreas | 0.0264226 | 0.385607 | 0.314377 | 0.1792777 | X03363_s_a t | ERBB2 V-erb-b2 avian erythroblastic leukemia viral oncogene homolog 2 (neuro/glioblastoma derived oncogene homolog) |
| 844 | Pancreas | 0.026225 | 0.3854704 | 0.314314 | 0.17913444 | HG4683-HT5108_s_a t | Tumor Necrosis Factor Receptor 2 Associated Protein Trap3 |
| 845 | Pancreas | 0.0262104 | 0.3854447 | 0.314192 | 0.17907988 | V00594_at | Metallothionein isoform 2 |
| 846 | Pancreas | 0.0258902 | 0.3854392 | 0.314158 | 0.17906326 | M16505_at | STS Steroid sulfatase (microsomal) |
| 847 | Pancreas | 0.0255124 | 0.3854319 | 0.314108 | 0.17900291 | RC_AA6217 14_at | EST: af54e12.s1 Soares total fetus Nb2HF8 9w Homo sapiens cDNA clone 1035502 3', mRNA sequence. (from Genbank) |

FIG. 11H2

| | | | | | |
|---|---|---|---|---|---|
| 848 | Pancreas | 0.0251997 | 0.3854319 | 0.314049 | 0.178926205 | RC_AA2783 29_f_at | EST: zs80f03.s1 NCI_CGAP_GCB1 Homo sapiens cDNA clone IMAGE:703805 3', mRNA sequence. (from Genbank) |
| 849 | Pancreas | 0.0249567 | 0.3854254 | 0.313868 | 0.178887783 | RC_AA0244 82_at | EST: ze76a01.s1 Soares fetal heart NbHH19W Homo sapiens cDNA clone 364872 3', mRNA sequence. (from Genbank) |
| 850 | Pancreas | 0.0248002 | 0.3854228 | 0.313847 | 0.178807170 | AA011479_a t | EST: zi01b10.r1 Soares fetal liver spleen 1NFLS S1 Homo sapiens cDNA clone 429499 5', mRNA sequence. (from Genbank) |
| 851 | Pancreas | 0.0246769 | 0.3853476 | 0.313719 | 0.17877142t | HG2564-HT2660_s_a | Gamma-Aminobutyric Acid (Gaba) A Receptor, Alpha Subunit |
| 852 | Pancreas | 0.0246648 | 0.385281 | 0.313719 | 0.178663908 | RC_AA4880 74_at | Cell division cycle 42 (GTP-binding protein, 25kD) |
| 853 | Pancreas | 0.0243452 | 0.385217 | 0.313663 | 0.178558819 | HG4058-HT4328_at | Oncogene Aml1-Evi-1, Fusion Activated |
| 854 | Pancreas | 0.024243 | 0.3851121 | 0.313562 | 0.178842634 | M93425_at | PTPN12 Protein tyrosine phosphatase, non-receptor type 12 |
| 855 | Pancreas | 0.0239828 | 0.3849711 | 0.313442 | 0.178398518 | RC_D20171 _at | EST: Human HL60 3'directed MboI cDNA, HUMGS01145, clone pm2260, mRNA sequence. (from Genbank) |
| 856 | Pancreas | 0.0238274 | 0.3846764 | 0.313357 | 0.1783034 | U10492_at | MEOX1 Homeobox protein mox1 |
| 857 | Pancreas | 0.0237864 | 0.384407 | 0.313292 | 0.178233067 | U07969_s_a t | Intestinal peptide-associated transporter HPT-1 mRNA |
| 858 | Pancreas | 0.023641 | 0.3842898 | 0.313274 | 0.178200074 | Z46629_at | SOX9 SRY (sex-determining region Y)-box 9 (campomelic dysplasia, autosomal sex-reversal) |
| 859 | Pancreas | 0.0228214 | 0.3842488 | 0.313216 | 0.178112856t | AA431505_a t | Homo sapiens mRNA for putative Sqv-7-like protein, partial |
| 860 | Pancreas | 0.0228041 | 0.3840572 | 0.313124 | 0.178080755 | M64497_at | APOLIPOPROTEIN AI REGULATORY PROTEIN-1 |
| 861 | Pancreas | 0.0224255 | 0.3840372 | 0.313117 | 0.178048883 | M91493_at | EST: HUMRTPGEAL Homo sapiens cDNA. (from Genbank) |
| 862 | Pancreas | 0.0223697 | 0.3840275 | 0.313024 | 0.1780225 | U03100_at | CTNNA1 Catenin (cadherin-associated protein), alpha 1 (102kD) |
| 863 | Pancreas | 0.0223422 | 0.3839934 | 0.312934 | 0.177959952 | U67156_at | Mitogen-activated kinase kinase kinase 5 (MAPKKK5) mRNA |
| 864 | Pancreas | 0.0221932 | 0.3839398 | 0.312916 | 0.177782331 | U51003_s_a t | DLX-2 (DLX-2) gene |
| 865 | Pancreas | 0.0220404 | 0.383853 | 0.312887 | 0.177771026 | M19169_at | Cystatin SN |
| 866 | Pancreas | 0.021531 | 0.3838234 | 0.312863 | 0.177770809 | U85611_at | Snk interacting protein 2-28 mRNA |
| 867 | Pancreas | 0.0215241 | 0.3837043 | 0.312822 | 0.177762850 | C01811_f_al | EST: HUMGS0003774, Human Gene Signature, 3'-directed cDNA sequence, mRNA sequence. (from Genbank) |
| 868 | Pancreas | 0.0214896 | 0.3836268 | 0.31269 | 0.177754743 | M96684_at | Pur (pur-alpha) mRNA |
| 869 | Pancreas | 0.0212778 | 0.3835089 | 0.312684 | 0.177749256 | K03195_at | (HepG2) glucose transporter gene mRNA |
| 870 | Pancreas | 0.0210133 | 0.3834915 | 0.312584 | 0.177746082 | D10495_at | PRKCD Protein kinase C, delta |
| 871 | Pancreas | 0.0207598 | 0.3834124 | 0.312511 | 0.177387835_at | AFFX-LysX-5_at | AFFX-LysX-5_at (endogenous control) |

FIG. 11I2

| # | Tissue | | | | ID1 | ID2 | Description |
|---|---|---|---|---|---|---|---|
| 872 | Pancreas | 0.0207598 | 0.3833924 | 0.177373935 | AFFX-LysX-_at-2 | AFFX-LysX-5_at | (miscellaneous control - 11k chips) |
| 873 | Pancreas | 0.0202174 | 0.3833924 | 0.17734972 | U41804_at | | Putative T1/ST2 receptor binding protein precursor mRNA |
| 874 | Pancreas | 0.0201764 | 0.3832988 | 0.17719974 | X73029_at | | Nitric oxide synthase 2A (inducible, hepatocytes) |
| 875 | Pancreas | 0.0200009 | 0.3832488 | 0.17711325 | X89986_s_a t | | NBK apoptotic inducer protein |
| 876 | Pancreas | 0.0193584 | 0.3832371 | 0.177019 | M33308_at | | VCL Vinculin |
| 877 | Pancreas | 0.0192371 | 0.3831261 | 0.17700893 | M37763_at | | Neurotrophin-3 (NT-3) gene |
| 878 | Pancreas | 0.0190351 | 0.3829823 | 0.17697026 | RC_AA0376 51_at | | EST: zk34e10.s1 Soares pregnant uterus NbHPU Homo sapiens cDNA clone 484746 3' similar to PIR:S18878 S18878 irlB protein - human .; mRNA sequence. (from Genbank) |
| 879 | Pancreas | 0.0189054 | 0.3829823 | 0.17692587 | HG3548-HT3749_at | | Ccaat Displacement Protein, Cut Homolog, Alt. Splice 1 |
| 880 | Pancreas | 0.0188678 | 0.3829767 | 0.17681041 | N56451_at | | Human zinc-finger domain-containing protein mRNA, partial cds |
| 881 | Pancreas | 0.0186373 | 0.3828223 | 0.17667513 | RC_AA1913 23_at | | EST: zp83b09.s1 Stratagene HeLa cell s3 937216 Homo sapiens cDNA clone 626777 3', mRNA sequence. (from Genbank) |
| 882 | Pancreas | 0.018227 | 0.38281 | 0.17663309 | X51405_at | | CPE Carboxypeptidase E |
| 883 | Pancreas | 0.0180159 | 0.3827739 | 0.176546 | RC_AA4341 13_at | | EST: zw24b11.s1 Soares ovary tumor NbHOT Homo sapiens cDNA clone 770205 3' similar to contains element TAR1 repetitive element .; mRNA sequence. (from Genbank) |
| 884 | Pancreas | 0.0179569 | 0.3827105 | 0.17650795 | HG2157-HT2227_at | | Mucin 4, Tracheobronchial |
| 885 | Pancreas | 0.0177274 | 0.3826726 | 0.17638993 | X98534_s_a t | | VASP gene, exons 4 to 13 |
| 886 | Pancreas | 0.0176302 | 0.3825615 | 0.17629634 | HG174-HT174_at | | Desmoplakin I |
| 887 | Pancreas | 0.017617 | 0.382545 | 0.17625247 | GMCSF_at | | No description for gene: GMCSF |
| 888 | Pancreas | 0.0174386 | 0.3823973 | 0.17621383 | S65738_at | | Actin depolymerizing factor [human, fetal brain, mRNA, 1452 nt] |
| 889 | Pancreas | 0.0173534 | 0.3823854 | 0.17608044 | Y00815_at | | PTPRF Protein tyrosine phosphatase, receptor type, f polypeptide |
| 890 | Pancreas | 0.0171226 | 0.3823151 | 0.17604436 | U37146_at | | Silencing mediator of retinoid and thyroid hormone action (SMRT) mRNA |
| 891 | Pancreas | 0.0170954 | 0.382247 | 0.17594041 | N75215_s_a t | | EST: yw33h05.r1 Homo sapiens cDNA clone 254073 5'. (from Genbank) |
| 892 | Pancreas | 0.0170875 | 0.3822207 | 0.1759003 | HG1783-HT1803_s_a t | | Islet Amyloid Polypeptide |
| 893 | Pancreas | 0.0170757 | 0.3821062 | 0.17577389 | X95191_at | | Delta-sarcoglycan |
| 894 | Pancreas | 0.0169598 | 0.3820921 | 0.17574449 | X00038_at | | H4 histone gene |
| 895 | Pancreas | 0.0169261 | 0.3820739 | 0.17568327 | S80343_at | | RARS Arginyl-tRNA synthetase |

FIG. 11J2

| | | | | | |
|---|---|---|---|---|---|
| 896 | Pancreas | 0.0168983 | 0.3819385 | 0.311085 | 0.175622294 | D87463_at | KIAA0273 gene |
| 897 | Pancreas | 0.0166389 | 0.3818834 | 0.310858 | 0.175570068 | M94250_at | MDK Midkine (neurite growth-promoting factor 2) |
| 898 | Pancreas | 0.0163755 | 0.381864 | 0.310845 | 0.175411833 | U78166_at | Human Ras-like small GTPase RIBA mRNA, alternatively spliced, complete cds |
| 899 | Pancreas | 0.0162663 | 0.3818345 | 0.310769 | 0.175373308 | HG1496-HT1496_s_a_t | Adrenal-Specific Protein Pg2 |
| 900 | Pancreas | 0.0160273 | 0.3817584 | 0.310672 | 0.17535571 | T57140_s_at | Paraoxonase 3 |
| 901 | Pancreas | 0.0159504 | 0.381728 | 0.31065 | 0.175284461 | D86960_at | KIAA0205 gene |
| 902 | Pancreas | 0.0159152 | 0.3816479 | 0.310649 | 0.17524263 | AA429793_a | EST: zw57d06.r1 Soares total fetus Nb2HF8 9w Homo sapiens cDNA clone 774155 5', mRNA sequence. (from Genbank) |
| 903 | Pancreas | 0.0158731 | 0.3816283 | 0.310602 | 0.175089241 | X17098_at | PSG6 Pregnancy-specific beta-1 glycoprotein 6 |
| 904 | Pancreas | 0.0157441 | 0.3814851 | 0.310531 | 0.174999995 | M28713_at | NADH-CYTOCHROME B5 REDUCTASE |
| 905 | Pancreas | 0.0156694 | 0.3814664 | 0.310539 | 0.1749758 | D17570_s_a_t-2 | Human mRNA for zona-pellucida-binding protein (sp38), complete cds |
| 906 | Pancreas | 0.0156694 | 0.3813849 | 0.310486 | 0.17489211 | D17570_s_a_t | Zona-pellucida-binding protein (sp38) |
| 907 | Pancreas | 0.0155905 | 0.3813748 | 0.310355 | 0.174813551 | HG273-HT273_at | Lymphocyte Antigen Hla-G3 |
| 908 | Pancreas | 0.0154867 | 0.3811627 | 0.310261 | 0.174734371 | U73191_at | Inward rectifier potassium channel (Kir1.3) |
| 909 | Pancreas | 0.0154498 | 0.3811541 | 0.310248 | 0.174669881 | X99920_at | S100 calcium-binding protein A13 |
| 910 | Pancreas | 0.0153782 | 0.3811277 | 0.310218 | 0.174587091 | L21954_at | PERIPHERAL-TYPE BENZODIAZEPINE RECEPTOR |
| 911 | Pancreas | 0.0150023 | 0.3811205 | 0.310195 | 0.174503711 | M63603_at | PLN Phospholamban |
| 912 | Pancreas | 0.0147481 | 0.3810508 | 0.310139 | 0.174440295 | RC_AA424006_at | EST: zv79h09.s1 Soares total fetus Nb2HF8 9w Homo sapiens cDNA clone 759905 3' similar to WP:B0024.13 CE05157 :, mRNA sequence. (from Genbank) |
| 913 | Pancreas | 0.0147269 | 0.3810111 | 0.309995 | 0.174342741 | U48959_at | Myosin light chain kinase (MLCK) mRNA |
| 914 | Pancreas | 0.0146187 | 0.3809514 | 0.309951 | 0.1742641 | AA251078_a_t | EST: zs01b12.r1 NCI_CGAP_GCB1 Homo sapiens cDNA clone IMAGE:6839003 5', mRNA sequence. (from Genbank) |
| 915 | Pancreas | 0.0145964 | 0.3809514 | 0.309853 | 0.174197581 | U08854_s_a | UDP glucuronosyltransferase precursor (UGT2B15) mRNA |
| 916 | Pancreas | 0.0145888 | 0.38093 | 0.309845 | 0.174133911_s_at | U50822_rna | Neurogenic helix-loop-helix protein NEUROD (neurod) gene |
| 917 | Pancreas | 0.0144809 | 0.3809081 | 0.309826 | 0.174028221 | X86693_at | High endothelial venule |
| 918 | Pancreas | 0.0142442 | 0.3808982 | 0.309783 | 0.173965891 | L13278_at | CRYZ Crystallin zeta (quinone reductase) |
| 919 | Pancreas | 0.0141174 | 0.3808469 | 0.309747 | 0.173901331 | C14915_at | Homo sapiens Chromosome 16 BAC clone CIT987SK-A-69G12 |
| 920 | Pancreas | 0.0140228 | 0.3800843 | 0.309709 | 0.173878461 | M63138_at | CTSD Cathepsin D (lysosomal aspartyl protease) |
| 921 | Pancreas | 0.0137339 | 0.3808041 | 0.309676 | 0.173795011 | M55210_at | LAMC1 Laminin, gamma 1 (formerly LAMB2) |
| 922 | Pancreas | 0.0136758 | 0.3807679 | 0.309562 | 0.173737711 | U89942_at | Lysyl oxidase-related protein (WS9-14) mRNA |

FIG. 11K2

| # | Tissue | | | | | Description |
|---|---|---|---|---|---|---|
| 923 | Pancreas | 0.0136356 | 0.3807412 | 0.309509 | 0.17360435 | RC_AA3982 90_at | EST: zt60f12.s1 Soares testis NHT Homo sapiens cDNA clone 726767 3' similar to contains MER13.b3 MER13 repetitive element ;, mRNA sequence. (from Genbank) |
| 924 | Pancreas | 0.0134755 | 0.3806644 | 0.309458 | 0.17354436 | X81372_at | Biphenyl hydrolase-related protein |
| 925 | Pancreas | 0.0132196 | 0.3805783 | 0.309445 | 0.17354208 | M23294_at | HEXB Hexosaminidase B (beta polypeptide) |
| 926 | Pancreas | 0.013061 | 0.3804676 | 0.309434 | 0.17342241 | M63256_at | CDR2 Cerebellar degeneration-related protein (62kD) |
| 927 | Pancreas | 0.0126659 | 0.3803845 | 0.309358 | 0.17340198 | RC_AA4774 32_s_at | EST: zu42f03.s1 Soares ovary tumor NbHOT Homo sapiens cDNA clone 740669 3'; mRNA sequence. (from Genbank) |
| 928 | Pancreas | 0.0125107 | 0.3803458 | 0.309228 | 0.17324902 | D28364_at | Annexin II, 5'UTR (sequence from the 5'cap to the start codon) |
| 929 | Pancreas | 0.0122572 | 0.3802981 | 0.309211 | 0.1731849 | M20778_s_a_t | Homo sapien, alpha-3 (VI) collagen |
| 930 | Pancreas | 0.012046 | 0.3801141 | 0.309168 | 0.17312045 | W26360_at | Chromogranin B (secretogranin 1) |
| 931 | Pancreas | 0.0120275 | 0.3801066 | 0.309105 | 0.1730738 | U58516_at | Breast epithelial antigen BA46 mRNA |
| 932 | Pancreas | 0.0119055 | 0.3800434 | 0.30906 | 0.1730264 | AA478129_a_t | EST: zu42c09.r1 Soares ovary tumor NbHOT Homo sapiens cDNA clone 740656 5' similar to SW:BI3_MOUSE P28662 BRAIN PROTEIN I3 ;, mRNA sequence. (from Genbank) |
| 933 | Pancreas | 0.0118301 | 0.3799817 | 0.309027 | 0.17297786 | D17516_at | PACAP receptor |
| 934 | Pancreas | 0.0114276 | 0.3798537 | 0.309026 | 0.17295383 | U69114_at | EST: Human Down syndrome region, YAC 152F7, mRNA sequence. (from Genbank) |
| 935 | Pancreas | 0.0112642 | 0.3798404 | 0.308992 | 0.17289628 | RC_AA1871 33_at | EST: zp62b01.s1 Stratagene endothelial cell 937223 Homo sapiens cDNA clone 624745 3', mRNA sequence. (from Genbank) |
| 936 | Pancreas | 0.0112601 | 0.3798097 | 0.308919 | 0.17287809 | Z35307_at | ECE1 Endothelin converting enzyme 1 |
| 937 | Pancreas | 0.0109491 | 0.3797908 | 0.308815 | 0.17278089 | L34219_at | RLBP1 Cellular retinaldehyde-binding protein |
| 938 | Pancreas | 0.0109036 | 0.3797874 | 0.308753 | 0.17263697 | RC_AA4365 53_at | EST: zv08c11.s1 Soares NhHMPu S1 Homo sapiens cDNA clone 753044 3', mRNA sequence. (from Genbank) |
| 939 | Pancreas | 0.0110878 | 0.3796868 | 0.308742 | 0.17257673 | X77307_at | 5-HYDROXYTRYPTAMINE 2B RECEPTOR |
| 940 | Pancreas | 0.0098719 | 0.3795845 | 0.308719 | 0.17251839 | U90552_at | Butyrophilin (BTF5) mRNA |
| 941 | Pancreas | 0.0098491 | 0.3795497 | 0.308682 | 0.17246318 | Z24459_xpt5_at | Exon2A from H.sapiens MTCP1 gene, exons 2A to 7 (and joined mRNA)./n\ype=DNA /annot=exon |
| 942 | Pancreas | 0.009683 | 0.3794782 | 0.308563 | 0.17239702 | RC_AA2814 82_at | EST: zt03e10.s1 NCI_CGAP_GCB1 Homo sapiens cDNA clone IMAGE:712074 3', mRNA sequence. (from Genbank) |
| 943 | Pancreas | 0.0095531 | 0.3791548 | 0.308551 | 0.17237099 | M26041_s_a_t | HLA-DQA1 MHC class II DQ alpha |
| 944 | Pancreas | 0.0094053 | 0.379135 | 0.308511 | 0.17224282 | M99438_at | Transducin-like enhancer protein (TLE3) mRNA |
| 945 | Pancreas | 0.0093573 | 0.3791104 | 0.308503 | 0.1722058 | M29277_s_a | CELL SURFACE GLYCOPROTEIN MUC18 PRECURSOR |
| 946 | Pancreas | 0.0093008 | 0.3791104 | 0.308444 | 0.17220096 | HG3893-HT4163_at | Phosphoglucomutase 1, Alt. Splice |
| 947 | Pancreas | 0.0092136 | 0.378905 | 0.308444 | 0.17205693 | U49278_at | Putative DNA-binding protein mRNA, partial cds |

FIG. 11L2

| | | | | | |
|---|---|---|---|---|---|
| 948 | Pancreas | 0.009138 | 0.3788716 | 0.1719559 | U90914_at | Clone 23587 mRNA sequence |
| 949 | Pancreas | 0.0090597 | 0.3786599 | 0.1718823 | X62320_at | GRN Granulin |
| 950 | Pancreas | 0.0089913 | 0.3785595 | 0.1718628 | X06956_at | TUBULIN ALPHA-4 CHAIN |
| 951 | Pancreas | 0.0088865 | 0.3781415 | 0.1717525 | U09770_at | Cysteine-rich heart protein (hCRHP) mRNA |
| 952 | Pancreas | 0.008879 | 0.3780962 | 0.1716952 | M11433_at | RBP1 Cellular retinol-binding protein |
| 953 | Pancreas | 0.0087769 | 0.3780586 | 0.1716574 | L20859_at | Leukemia virus receptor 1 (GLVR1) mRNA |
| 954 | Pancreas | 0.0083901 | 0.3779708 | 0.1716017 | M11844_at | Transthyretin (prealbumin, amyloidosis type I) |
| 955 | Pancreas | 0.0083634 | 0.3779382 | 0.1714249 | RC_AA5042 70_at | EST: aa61c10.s1 NCI_CGAP_GCB1 Homo sapiens cDNA clone IMAGE:825426 3', mRNA sequence. (from Genbank) |
| 956 | Pancreas | 0.0082552 | 0.3778285 | 0.1714213 | X58288_at | PTPRM Protein tyrosine phosphatase, receptor type, mu polypeptide |
| 957 | Pancreas | 0.0081863 | 0.3778197 | 0.1713812 | D10202_at | PTAFR Platelet activating factor receptor |
| 958 | Pancreas | 0.0081535 | 0.3777149 | 0.1712919 | RC_AA4656 94_r_at | Homo sapiens mRNA for C17orf1 protein |
| 959 | Pancreas | 0.0080825 | 0.3776925 | 0.1712792 | W19984_at | EST: zb38d11.r1 Soares parathyroid tumor NbHPA Homo sapiens cDNA clone 305877 5', mRNA sequence. (from Genbank) |
| 960 | Pancreas | 0.0080685 | 0.3776852 | 0.1712133 | K02215_at | ANGIOTENSINOGEN PRECURSOR |
| 961 | Pancreas | 0.0078111 | 0.3775716 | 0.1711911 | D49357_at | S-ADENOSYLMETHIONINE SYNTHETASE ALPHA AND BETA FORMS |
| 962 | Pancreas | 0.0077751 | 0.3775214 | 0.1711449 | Y13492_s_at | Homo sapiens mRNA for smoothelin. (from Genbank) |
| 963 | Pancreas | 0.0076494 | 0.3772996 | 0.1711181 | RC_AA4187 40_at | EST: zv98e10.s1 Soares NhHMPu S1 Homo sapiens cDNA clone 767850 3', mRNA sequence. (from Genbank) |
| 964 | Pancreas | 0.0076052 | 0.3772263 | 0.1710263 | M35296_at | Tyrosine kinase arg gene mRNA |
| 965 | Pancreas | 0.0074967 | 0.3771517 | 0.1708519 | RC_AA4196 09_at | EST: zv04b06.s1 Soares NhHMPu S1 Homo sapiens cDNA clone 752627 3', mRNA sequence. (from Genbank) |
| 966 | Pancreas | 0.0073405 | 0.3770905 | 0.1708481 | M19154_at | Transforming growth factor-beta-2 mRNA |
| 967 | Pancreas | 0.0071212 | 0.3769288 | 0.1708013 | U13369_at | Ribosomal DNA complete repeating unit |
| 968 | Pancreas | 0.0070183 | 0.37686 | 0.1706657 | D17400_at | PTS 6-pyruvoyltetrahydropterin synthase |
| 969 | Pancreas | 0.0067312 | 0.3767347 | 0.1706657 | D10523_at | OGDH Oxoglutarate dehydrogenase (lipoamide) |
| 970 | Pancreas | 0.0066718 | 0.3764095 | 0.1706243 | X16665_at | HOXB2 Homeo box B2 |
| 971 | Pancreas | 0.0063001 | 0.3763723 | 0.1705804 | RC_AA1868 97_at | EST: zp74c05.s1 Stratagene HeLa cell s3 937216 Homo sapiens cDNA clone 625928 3', mRNA sequence. (from Genbank) |
| 972 | Pancreas | 0.0062173 | 0.3763551 | 0.1704482 | D63487_at | KIAA0153 gene, partial cds |
| 973 | Pancreas | 0.0062023 | 0.3762989 | 0.1704323 | RC_AA3500 30_at | EST: EST57075 Infant brain Homo sapiens cDNA 3' end, mRNA sequence. (from Genbank) |
| 974 | Pancreas | 0.0061597 | 0.3761855 | 0.1703570 | RC_AA0373 57_i_at | EST: zc03c04.s1 Soares parathyroid tumor NbHPA Homo sapiens cDNA clone 321222 3' similar to contains Alu repetitive element;, mRNA sequence. (from Genbank) |

FIG. 11M2

| | | | | | |
|---|---|---|---|---|---|
| 975 | Pancreas | 0.0061341 | 0.3759746 | 0.306664 | 0.1701967 | L19267_at | 59 protein mRNA, 3' end |
| 976 | Pancreas | 0.0053417 | 0.3758259 | 0.306659 | 0.1701876 | U26710_at | Cbl-b mRNA |
| 977 | Pancreas | 0.0051793 | 0.3755874 | 0.306571 | 0.1701371 | M16447_at | QDPR Dihydropteridine reductase |
| 978 | Pancreas | 0.0051524 | 0.3755744 | 0.306554 | 0.1700522 | Z29083_at | 5T4 gene for 5T4 Oncofetal antigen |
| 979 | Pancreas | 0.005104 | 0.375461 | 0.306551 | 0.16996583 | J02947_s_at | SOD3 Superoxide dismutase 3, extracellular |
| 980 | Pancreas | 0.0049885 | 0.3753988 | 0.306468 | 0.16986897 | H09058_at | EST: yl96f11.r1 Homo sapiens cDNA clone 45943 5'. (from Genbank) |
| 981 | Pancreas | 0.0048985 | 0.3752322 | 0.306435 | 0.16984868 | RC_AA0856 76_at | EST: zn53e03.s1 Stratagene muscle 937209 Homo sapiens cDNA clone 561916 3'; mRNA sequence. (from Genbank) |
| 982 | Pancreas | 0.0047371 | 0.3751638 | 0.306426 | 0.16975155 | RC_AA4902 62_at | EST: aa44c09.s1 Soares NhHMPu S1 Homo sapiens cDNA clone 823792 3', mRNA sequence. (from Genbank) |
| 983 | Pancreas | 0.0046622 | 0.3751578 | 0.306318 | 0.16968475 | RC_AA2996 5_at | EST: EST12479 Uterus tumor I Homo sapiens cDNA 3' end, mRNA sequence. (from Genbank) |
| 984 | Pancreas | 0.004536 | 0.3751535 | 0.306315 | 0.16956673 | RC_AA5048 90_at | EST: ab03d12.s1 Stratagene fetal retina 937202 Homo sapiens cDNA clone 839735 3', mRNA sequence. (from Genbank) |
| 985 | Pancreas | 0.0044392 | 0.375113 | 0.306297 | 0.16953933 | L14787_at | DNA-binding protein mRNA, 3'end |
| 986 | Pancreas | 0.0042782 | 0.3749534 | 0.306218 | 0.16950552 | U67784_at | Orphan G protein-coupled receptor (RDC1) mRNA, partial cds |
| 987 | Pancreas | 0.0039998 | 0.3749511 | 0.30619 | 0.16945219 | Z15108_at | PRKCZ Protein kinase C, zeta |
| 988 | Pancreas | 0.0039818 | 0.3748851 | 0.306075 | 0.16932535 | R80351_at | EST: yi96e02.r1 Homo sapiens cDNA clone 147098 5'. (from Genbank) |
| 989 | Pancreas | 0.0039155 | 0.3748787 | 0.306028 | 0.16930793 | RC_AA4593 89_at | Tyrosylprotein sulfotransferase 2 |
| 990 | Pancreas | 0.0038674 | 0.3748153 | 0.305968 | 0.16923661 | D86331_s_a t | MMP2 Matrix metalloproteinase 2 |
| 991 | Pancreas | 0.0035995 | 0.3747873 | 0.305908 | 0.1691872 | U64197_at | CC chemokine LARC precursor |
| 992 | Pancreas | 0.0035149 | 0.3747445 | 0.305808 | 0.16909090 | RC_AA4545 97_s_at | EST: zx96a12.s1 Soares ovary tumor NbHOT Homo sapiens cDNA clone 811582 3', mRNA sequence. (from Genbank) |
| 993 | Pancreas | 0.0034695 | 0.374696 | 0.305805 | 0.16905203 | HG2602-HT2698_at | Succinate Dehydrogenase, Flavoprotein Subunit |
| 994 | Pancreas | 0.0033017 | 0.3746279 | 0.305801 | 0.16900474 | W26187_at | EST: l1uman retina cDNA randomly primed sublibrary Homo sapiens 22a6 cDNA, mRNA sequence. (from Genbank) |
| 995 | Pancreas | 0.0027846 | 0.3745216 | 0.305771 | 0.16891864 | U36922_at | Fork head domain protein (FKHR) mRNA, 3' end |
| 996 | Pancreas | 0.0025467 | 0.3745115 | 0.305718 | 0.16878948 | M88458_at | ELP-1 mRNA sequence |
| 997 | Pancreas | 0.0025293 | 0.3745095 | 0.305711 | 0.16874222 | RC_AA0536 60_at | EST: zf74e07.s1 Stratagene colon (#937204) Homo sapiens cDNA clone 510372 3' similar to contains Alu repetitive element; mRNA sequence. (from Genbank) |
| 998 | Pancreas | 0.0021767 | 0.3745001 | 0.305665 | 0.16867444 | J02973_ma1_at | THBD gene extracted from Human thrombomodulin gene |

FIG. 11N2

| | | | | | |
|---|---|---|---|---|---|
| 999 | Pancreas | 0.0020229 | 0.3745001 | 0.305637 | 0.16860674 | X62515_s_a t | HSPG2 Heparan sulfate proteoglycan |
| 1000 | Pancreas | 0.0016461 | 0.3744899 | 0.305616 | 0.16851833 | W56463_at | EST: zc57h06.r1 Soares parathyroid tumor NbHPA Homo sapiens cDNA clone 326459 5', mRNA sequence. (from Genbank) |

FIG. 11O2

| # | Tissue | | | | ID | Description |
|---|---|---|---|---|---|---|
| 1 | Prostate | 1.2056562 | 0.7462531 | 0.651255 | 0.49000722 | RC_AA1769 75_s_at | Human prostatic secretory protein 57 mRNA, complete cds |
| 2 | Prostate | 1.150031 | 0.6942502 | 0.603854 | 0.4573873 | X07730_at | APS Prostate specific antigen |
| 3 | Prostate | 1.1072491 | 0.6685929 | 0.582254 | 0.4402699 | M34376_s_a t | MSMB Beta-microseminoprotein (prostate secreted) |
| 4 | Prostate | 1.0564668 | 0.6536669 | 0.566208 | 0.4287084 | RC_AA4169 63_at | EST: zt69h05.s1 Soares testis NHT Homo sapiens cDNA clone 7276413' similar to gb:X14850_cds1 HISTONE H2A.X (HUMAN);, mRNA sequence. (from Genbank) |
| 5 | Prostate | 1.0498478 | 0.6413899 | 0.555247 | 0.419234575 | U22178_s_a t | MSMB Beta-microseminoprotein (prostate secreted) |
| 6 | Prostate | 1.0272197 | 0.6314022 | 0.546222 | 0.41171598 | M24902_at | ACPP Acid phosphatase, prostate |
| 7 | Prostate | 1.0131627 | 0.6237198 | 0.540418 | 0.40537417 | RC_AA1956 26_at | EST: zr38h09.s1 Soares NbHMPu S1 Homo sapiens cDNA clone 6657293', mRNA sequence. (from Genbank) |
| 8 | Prostate | 1.0064116 | 0.617686 | 0.53471 | 0.39937273 | HG2261-HT2351_s_a t | Antigen, Prostate Specific, Alt. Splice Form 2 |
| 9 | Prostate | 0.9983715 | 0.6117601 | 0.530192 | 0.39433932 | AA099391_s _at | EST: zk85e12.r1 Soares pregnant uterus NbHPU Homo sapiens cDNA clone 489646 5', mRNA sequence. (from Genbank) |
| 10 | Prostate | 0.9497854 | 0.6091605 | 0.525377 | 0.39051536 | RC_AA0472 90_at | EST: zk74f05.s1 Soares pregnant uterus NbHPU Homo sapiens cDNA clone 488577 3', mRNA sequence. (from Genbank) |
| 11 | Prostate | 0.9145066 | 0.6044182 | 0.52174 | 0.38678116 | C01409_s_a t | EST: HUMGS0008391, Human Gene Signature, 3'-directed cDNA sequence, mRNA sequence. (from Genbank) |
| 12 | Prostate | 0.8882394 | 0.6030476 | 0.517905 | 0.3831058 | AA234665_a t | Supervillin |
| 13 | Prostate | 0.8852299 | 0.5962434 | 0.514562 | 0.379996072 | RC_AA0171 46_at | EST: ze41a07.s1 Soares retina N2b4HR Homo sapiens cDNA clone 361524 3' similar to contains element PTR7 repetitive element ;, mRNA sequence. (from Genbank) |
| 14 | Prostate | 0.8648246 | 0.5930536 | 0.512382 | 0.37685722 | X59766_at | AZGP1 Zinc-alpha-2-glycoprotein 1 |
| 15 | Prostate | 0.8643197 | 0.5876886 | 0.509529 | 0.37419074 | RC_AA0263 49_r_at | EST: zj99f01.s1 Soares pregnant uterus NbHPU Homo sapiens cDNA clone 4691773', mRNA sequence. (from Genbank) |
| 16 | Prostate | 0.861838 | 0.5842731 | 0.507509 | 0.37194743 | RC_AA4058 32_at | EST: zu57g11.s1 Soares ovary tumor NbHOT Homo sapiens cDNA clone 742148 3' similar to TR:G780241 G780241 AU-BINDING PROTEIN/ENOYL-COA HYDRATASE.;, mRNA sequence. (from Genbank) |

FIG. 12A

| # | Tissue | | | | | Description |
|---|---|---|---|---|---|---|
| 17 | Prostate | 0.8583609 | 0.5810913 | 0.504399 | 0.3697102 W26769_at | EST: 12g3 Human retina cDNA randomly primed sublibrary Homo sapiens cDNA, mRNA sequence. (from Genbank) |
| 18 | Prostate | 0.8567439 | 0.5788426 | 0.500787 | 0.36733624 S39329_at | KLK1 Kallikrein 1 (renal/pancreas/salivary) {alternative products} |
| 19 | Prostate | 0.8544304 | 0.5758644 | 0.499316 | 0.3650193 RC_AA4561 35_at | EST: zx65e12.s1 Soares total fetus Nb2HF8 9w Homo sapiens cDNA clone 796366 3', mRNA sequence. (from Genbank) |
| 20 | Prostate | 0.8508199 | 0.5740604 | 0.497976 | 0.36277044 RC_AA4299 98_at | EST: zw65e01.s1 Soares testis NHT Homo sapiens cDNA clone 781080 3', mRNA sequence. (from Genbank) |
| 21 | Prostate | 0.8503591 | 0.5721853 | 0.496438 | 0.36110395 AF001548_r na1_at | 815A9.1 gene (myosin heavy chain) extracted from Homo sapiens chromosome 16 BAC clone CIT987SK-815A9 complete sequence |
| 22 | Prostate | 0.8487131 | 0.5697741 | 0.493364 | 0.3594728 AB002351_a t | Human mRNA for KIAA0353 gene, partial cds |
| 23 | Prostate | 0.8481424 | 0.5683232 | 0.49259 | 0.357773683 RC_AA4878 79_at | EST: ab12a04.s1 Stratagene lung (#937210) Homo sapiens cDNA clone 840558 3', mRNA sequence. (from Genbank) |
| 24 | Prostate | 0.8479604 | 0.566691 | 0.490684 | 0.3558713 D00654_at | Enteric smooth muscle gamma-actin gene, 5' flank and |
| 25 | Prostate | 0.8473496 | 0.5634838 | 0.489226 | 0.35401163 RC_AA1871 3_at | EST: zp62b01.s1 Stratagene endothelial cell 937223 Homo sapiens cDNA clone 624745 3', mRNA sequence. (from Genbank) |
| 26 | Prostate | 0.8106132 | 0.5619771 | 0.488052 | 0.35228416 X15306_rna 1_at | NF-H gene, exon 1 (and joined CDS) |
| 27 | Prostate | 0.7970863 | 0.5601654 | 0.485825 | 0.35091248 RC_AA4565 98_at | EST: zx75a05.s1 Soares ovary tumor NbHOT Homo sapiens cDNA clone 809552 3' similar to contains MER16.b3 MER16 repetitive element:, mRNA sequence. (from Genbank) |
| 28 | Prostate | 0.7859255 | 0.559049 | 0.484755 | 0.34926105 RC_AA1289 97_at | Phosphodiesterase 9A |
| 29 | Prostate | 0.7857197 | 0.5563237 | 0.483382 | 0.3481089 D10667_s_a t | MYH11 Myosin, heavy polypeptide 11, smooth muscle |
| 30 | Prostate | 0.7834053 | 0.5544608 | 0.48175 | 0.34659663 U00943_at | Clone A9A2BRB2 (CAC)n/(GTG)n repeat-containing mRNA |
| 31 | Prostate | 0.7834053 | 0.5540588 | 0.480478 | 0.34514582 U00943_at-2 | Human clone A9A2BRB2 (CAC)n/(GTG)n repeat-containing mRNA |
| 32 | Prostate | 0.7809461 | 0.5535718 | 0.479351 | 0.34363896 U52969_at | BRAIN SPECIFIC POLYPEPTIDE PEP-19 |
| 33 | Prostate | 0.7801142 | 0.5517426 | 0.477309 | 0.34231102 RC_AA6091 13_at | Homo sapiens mRNA, chromosome 1 specific transcript KIAA0503 |
| 34 | Prostate | 0.7770838 | 0.5491698 | 0.47656 | 0.34123212 RC_AA4115 32_at | EST: zv27d12.s1 Soares ovary tumor NbHOT Homo sapiens cDNA clone 754871 3', mRNA sequence. (from Genbank) |
| 35 | Prostate | 0.7764195 | 0.5484343 | 0.475776 | 0.34006175 RC_AA4300 47_at | EST: zw65g09.s1 Soares testis NHT Homo sapiens cDNA clone 781120 3', mRNA sequence. (from Genbank) |
| 36 | Prostate | 0.7761946 | 0.5469251 | 0.474368 | 0.3387454 RC_AA4963 66_at | EST: zv37c09.s1 Soares ovary tumor NbHOT Homo sapiens cDNA clone 755824 3', mRNA sequence. (from Genbank) |

FIG. 12B

| | | | | | |
|---|---|---|---|---|---|
| 37 | Prostate | 0.7723309 | 0.5450091 | 0.473031 | RC_AA4610 86_at | EST: zx63e10.s1 Soares total fetus Nb2HF8 9w Homo sapiens cDNA clone 796170 3', mRNA sequence. (from Genbank) |
| 38 | Prostate | 0.768858 | 0.5419448 | 0.471731 | RC_D59971 s_at | EST: Human fetal brain cDNA 3'-end GEN-078E12, mRNA sequence. (from Genbank) |
| 39 | Prostate | 0.765341 | 0.5411084 | 0.470842 | HG2261-HT2352_at | Antigen, Prostate Specific, Alt. Splice Form 3 |
| 40 | Prostate | 0.7642014 | 0.5397279 | 0.469657 | AA047151_a t | EST: zk74i05.r1 Soares pregnant uterus NbHPU Homo sapiens cDNA clone 488577 5', mRNA sequence. (from Genbank) |
| 41 | Prostate | 0.7641559 | 0.5385019 | 0.46851 | U48959_at | Myosin light chain kinase (MLCK) mRNA |
| 42 | Prostate | 0.7630378 | 0.5383377 | 0.467798 | AA037316_a t | EST: zc52h08.r1 Soares senescent fibroblasts NbHSF Homo sapiens cDNA clone 325983 5', mRNA sequence. (from Genbank) |
| 43 | Prostate | 0.7613946 | 0.538004 | 0.4664 | M99487_at | PROSTATE-SPECIFIC MEMBRANE ANTIGEN |
| 44 | Prostate | 0.7604477 | 0.5369695 | 0.465384 | RC_AA4180 20_at | EST: zv94n02.s1 Soares NhHMPu S1 Homo sapiens cDNA clone 767475 3', mRNA sequence. (from Genbank) |
| 45 | Prostate | 0.7590286 | 0.5345332 | 0.464409 | X91868_at | SIX1 protein |
| 46 | Prostate | 0.7572511 | 0.5332657 | 0.463036 | N40141_at | Homo sapiens mRNA for JM27 protein, complete CDS (clone IMAGE 145745 and IMAGE 257878) |
| 47 | Prostate | 0.7556858 | 0.5329203 | 0.462426 | RC_AA4357 48_at | EST: zt79e05.s1 Soares testis NHT Homo sapiens cDNA clone 728576 3', mRNA sequence. (from Genbank) |
| 48 | Prostate | 0.749978 | 0.5324418 | 0.461185 | U39840_at | Hepatocyte nuclear factor-3 alpha (HNF-3 alpha) mRNA |
| 49 | Prostate | 0.7490042 | 0.5324418 | 0.460694 | M22430_at | PLA2G2A Phospholipase A2, group IIA (platelets, synovial fluid) |
| 50 | Prostate | 0.747659 | 0.5315405 | 0.460338 | M12125_at | Skeletal beta-tropomyosin |
| 51 | Prostate | 0.7473589 | 0.5308155 | 0.459396 | D17408_s_a t | Calponin |
| 52 | Prostate | 0.7391968 | 0.5299506 | 0.458432 | RC_AA2933 27_at | Homo sapiens NADP-dependent isocitrate dehydrogenase (IDH) mRNA, complete cds |
| 53 | Prostate | 0.7329932 | 0.5290732 | 0.457546 | RC_AA1284 86_at | EST: zm24e06.s1 Stratagene pancreas (#937208) Homo sapiens cDNA clone 526594 3', mRNA sequence. (from Genbank) |
| 54 | Prostate | 0.7308882 | 0.5286248 | 0.457037 | RC_AA2358 03_i_at | EST: zs42g06.s1 Soares NhHMPu S1 Homo sapiens cDNA clone 687898 3', mRNA sequence. (from Genbank) |
| 55 | Prostate | 0.7307606 | 0.5281515 | 0.456172 | U92314_s_a t | Hydroxysteroid sulfotransferase SULT2B1a (HSST2) mRNA |
| 56 | Prostate | 0.7307606 | 0.5270093 | 0.455333 | U92314_s_a t-2 | Sulfotransferase family 2B, member 1 |
| 57 | Prostate | 0.7303116 | 0.5263293 | 0.454279 | RC_AA4302 09_at | Homo sapiens LIM protein mRNA, complete cds |
| 58 | Prostate | 0.7290818 | 0.5244746 | 0.453399 | AA033766_s _at | EST: zk19b12.r1 Soares pregnant uterus NbHPU Homo sapiens cDNA clone 470975 5', mRNA sequence. (from Genbank) |

FIG. 12C

| | | | | | |
|---|---|---|---|---|---|
| 59 | Prostate | 0.7266153 | 0.5233697 | 0.452613 | 0.318262204 | RC_AA0846 02_at | EST: zn19g04.s1 Stratagene neuroepithelium NT2RAMI 937234 Homo sapiens cDNA clone 547926 3', mRNA sequence. (from Genbank) |
| 60 | Prostate | 0.7226381 | 0.5228489 | 0.452064 | 0.317501285 | RC_AA2332 57_at | Transforming growth factor beta 1 induced transcript 1 |
| 61 | Prostate | 0.7212004 | 0.5227233 | 0.451636 | 0.317034244 | L40399_at | (clone S240ii17/zap112) mRNA |
| 62 | Prostate | 0.7208732 | 0.5217126 | 0.450765 | 0.316481616 | D85181_at | Thymosin beta-4 mRNA |
| 63 | Prostate | 0.7149324 | 0.5215629 | 0.450357 | 0.31577867 | AA082546_a t | EST: ze88h10.r1 Soares fetal heart NbHH19W Homo sapiens cDNA clone 366115 5', mRNA sequence. (from Genbank) |
| 64 | Prostate | 0.7100186 | 0.5208399 | 0.449244 | 0.315167 | RC_AA4790 96_at | EST: zv17e07.s1 Soares NhHMPu S1 Homo sapiens cDNA clone 753924 3', mRNA sequence. (from Genbank) |
| 65 | Prostate | 0.7076368 | 0.5197024 | 0.448685 | 0.31441122 | AA402971_s _at | Homo sapiens mRNA for serine protease (TLSP), complete cds |
| 66 | Prostate | 0.706525 | 0.5193453 | 0.447742 | 0.313825555 | AA429793_a t | EST: zw57d06.r1 Soares total fetus Nb2HF8 9w Homo sapiens cDNA clone 774155 5', mRNA sequence. (from Genbank) |
| 67 | Prostate | 0.7024102 | 0.5182234 | 0.447323 | 0.313319913 | T48536_at | EST: hbc3204 Homo sapiens cDNA clone hbc3204 5'end. (from Genbank) |
| 68 | Prostate | 0.7023528 | 0.5180734 | 0.446659 | 0.312340143 | RC_AA6216 34_at | EST: af48c08.s1 Soares total fetus Nb2HF8 9w Homo sapiens cDNA clone 1034894 3', mRNA sequence. (from Genbank) |
| 69 | Prostate | 0.7015156 | 0.5167005 | 0.445428 | 0.311966657 | RC_AA2911 59_r_at | EST: zs46d03.s1 NCI_CGAP_GCB1 Homo sapiens cDNA clone IMAGE:700517 3', mRNA sequence. (from Genbank) |
| 70 | Prostate | 0.7011182 | 0.515649 | 0.445371 | 0.311194424 | RC_AA2057 24_at | EST: zq69c06.s1 Stratagene neuroepithelium (#937231) Homo sapiens cDNA clone 646858 3', mRNA sequence. (from Genbank) |
| 71 | Prostate | 0.700474 | 0.5152378 | 0.445083 | 0.310620358 | RC_AA4436 58_at | Transmembrane 7 superfamily member 2 |
| 72 | Prostate | 0.6951623 | 0.5144462 | 0.44436 | 0.31021988 | AB002345_a t | PERIOD, DROSOPHILA, HOMOLOG OF, 2 |
| 73 | Prostate | 0.6941831 | 0.5143696 | 0.443158 | 0.309446462 | RC_AA1279 64_at | EST: zf13g07.s1 Soares pregnant uterus NbHPU Homo sapiens cDNA clone 501852 3', mRNA sequence. (from Genbank) |
| 74 | Prostate | 0.6929858 | 0.5136402 | 0.443123 | 0.308916645 | C00358_at | EST: HUMGS0003384, Human Gene Signature, 3'-directed cDNA sequence, mRNA sequence. (from Genbank) |
| 75 | Prostate | 0.691104 | 0.513193 | 0.441924 | 0.30823631 | RC_AA3720 18_at | EST: EST83940 Parathyroid gland tumor I Homo sapiens cDNA 3' end, mRNA sequence. (from Genbank) |
| 76 | Prostate | 0.6906615 | 0.5126681 | 0.4414 | 0.307805035 | RC_AA4372 58_at | EST: zv54f03.s1 Soares testis NHT Homo sapiens cDNA clone 757469 3', mRNA sequence. (from Genbank) |
| 77 | Prostate | 0.690201 | 0.5116948 | 0.411004 | 0.307287482 | RC_AA1264 72_at | EST: zn85a12.s1 Stratagene lung carcinoma 937218 Homo sapiens cDNA clone 564958 3', mRNA sequence. (from Genbank) |

FIG. 12D

| | | | | | | |
|---|---|---|---|---|---|---|
| 78 | Prostate | 0.6893996 | 0.5107673 | 0.440284 | 0.30680072 | RC_AA1323 66_at | EST: zo28d09.s1 Stratagene colon (#937204) Homo sapiens cDNA clone 588209 3', mRNA sequence. (from Genbank) |
| 79 | Prostate | 0.6883029 | 0.5101306 | 0.439416 | 0.3064534 | N75870_s_a t | Dual specificity phosphatase 1 |
| 80 | Prostate | 0.6862451 | 0.5096272 | 0.439234 | 0.3059563 | RC_AA1565 32_at | Homo sapiens interferon regulatory factor 6 (IRF6) mRNA, complete cds |
| 81 | Prostate | 0.6836953 | 0.509364 | 0.438744 | 0.30535868 | RC_AA2911 59_f_at | EST: zs46d03.s1 NCI_CGAP_GCB1 Homo sapiens cDNA clone IMAGE:700517 3', mRNA sequence. (from Genbank) |
| 82 | Prostate | 0.6822293 | 0.509044 | 0.438305 | 0.30486175 | T68510_at | EST: yc42e04.r1 Homo sapiens cDNA clone 83358 5'. (from Genbank) |
| 83 | Prostate | 0.6807238 | 0.5083146 | 0.438027 | 0.304442053 | D79791_s_a t | EST: Human aorta cDNA 5'-end GEN-327F09, mRNA sequence. (from Genbank) |
| 84 | Prostate | 0.6762923 | 0.5075067 | 0.437799 | 0.30414927 | J02854_at | 20-kDa myosin light chain (MLC-2) mRNA |
| 85 | Prostate | 0.6741846 | 0.5067304 | 0.437174 | 0.30356243 | L29008_at | SORD Sorbitol dehydrogenase |
| 86 | Prostate | 0.6713697 | 0.5059861 | 0.436605 | 0.30308852 | D14695_at | APOA2 Apolipoprotein A-II |
| 87 | Prostate | 0.6699484 | 0.5055976 | 0.435889 | 0.30238143 | W63793_at | S-adenosylmethionine decarboxylase 1 |
| 88 | Prostate | 0.6693808 | 0.5050273 | 0.435253 | 0.30199936 | RC_AA2564 85_at | EST: zf81e12.s1 Soares NhHMPu S1 Homo sapiens cDNA clone 682126 3', mRNA sequence. (from Genbank) |
| 89 | Prostate | 0.6684371 | 0.5044967 | 0.434721 | 0.30170682 | RC_AA4357 40_at | EST: zf79d05.s1 Soares testis NHT Homo sapiens cDNA clone 728553 3' similar to TR:G452276 G452276 NPDCF-1.;, mRNA sequence. (from Genbank) |
| 90 | Prostate | 0.6664848 | 0.5042999 | 0.434469 | 0.30115393 | RC_AA4516 80_at | Human DNA sequence from clone 14O9 on chromosome Xp11.1-11.4. Contains a Inter-Alpha-Trypsin Inhibitor Heavy Chain LIKE gene, a alternatively spliced Melanoma-Associated Antigen MAGE LIKE gene and a 6-Phosphofructo-2-kinase (Fructose-2,6-bisphosphatase) LIKE pseudogene. Contains ESTs, STSs and genomic marker DXS8032 |
| 91 | Prostate | 0.6636378 | 0.5031441 | 0.433818 | 0.30045217 | RC_AA4339 46_at | EST: zw52g09.s1 Soares total fetus Nb2HF8 9w Homo sapiens cDNA clone 773728 3' similar to WP:R11D1.11 CE06316 MOUSE ADIPOCYTE P27 PROTEIN LIKE .;, mRNA sequence. (from Genbank) |
| 92 | Prostate | 0.663594 | 0.5030469 | 0.433587 | 0.3001968 | RC_AA2363 56_at | Zf54a11.s1 Soares_NhHMPu_S1 Homo sapiens cDNA clone IMAGE:667196 3', mRNA sequence |
| 93 | Prostate | 0.6632475 | 0.5021772 | 0.432832 | 0.29985258 | RC_AA4056 63_at | EST: zu19b03.s1 Soares NhHMPu S1 Homo sapiens cDNA clone 738413 3', mRNA sequence. (from Genbank) |
| 94 | Prostate | 0.6616011 | 0.5017547 | 0.432422 | 0.29953346 | L19783_at | GPI-H mRNA |
| 95 | Prostate | 0.6614391 | 0.5010664 | 0.431851 | 0.2890152 | L13740_at | HMR Hormone receptor (growth factor-inducible nuclear protein N10) |
| 96 | Prostate | 0.6586252 | 0.5005027 | 0.431508 | 0.28976097 | RC_AA3992 71_at | EST: zt57h04.s1 Soares testis NHT Homo sapiens cDNA clone 726487 3', mRNA sequence. (from Genbank) |

FIG. 12E

| | | | | | |
|---|---|---|---|---|---|
| 97 | Prostate | 0.6583689 | 0.5002668 | 0.430452 | 0.29841784 | RC_AA6095 76_at | KIAA0331 gene product |
| 98 | Prostate | 0.6579552 | 0.4991493 | 0.43029 | 0.29797372 | RC_AA4194 61_at | EST: zu99d05.s1 NCI_CGAP_GCB1 Homo sapiens cDNA clone IMAGE:746121 3', mRNA sequence. (from Genbank) |
| 99 | Prostate | 0.6575186 | 0.498833 | 0.429985 | 0.29760277 | AA479266_a t | EST: zv17h06.r1 Soares NhHMPu S1 Homo sapiens cDNA clone 753947 5', mRNA sequence. (from Genbank) |
| 100 | Prostate | 0.6570579 | 0.4985224 | 0.429647 | 0.29716057 | N71513_s_a t | EST: yw32h09.r1 Homo sapiens cDNA clone 253985 5'. (from Genbank) |
| 101 | Prostate | 0.6568294 | 0.4984954 | 0.429326 | 0.29676324 | Z31695_at | 43 kDa inositol polyphosphate 5-phosphatase |
| 102 | Prostate | 0.6558126 | 0.4982454 | 0.428744 | 0.29643303 | RC_AA4260 11_at | EST: zw49f01.s1 Soares total fetus Nb2HF8 9w Homo sapiens cDNA clone 773401 3', mRNA sequence. (from Genbank) |
| 103 | Prostate | 0.6517711 | 0.4981883 | 0.428364 | 0.29582968 | M69225_at | Bullous pemphigoid antigen (BPAG1) mRNA |
| 104 | Prostate | 0.6512691 | 0.4980562 | 0.427941 | 0.29556254 | RC_AA4029 68_at | EST: zu54b12.s1 Soares ovary tumor NbHOT Homo sapiens cDNA clone 741791 3', mRNA sequence. (from Genbank) |
| 105 | Prostate | 0.6510165 | 0.4978114 | 0.427915 | 0.29507384 | RC_AA2364 55_s_at | EST: zr75g02.s1 Soares NhHMPu S1 Homo sapiens cDNA clone 669266 3', mRNA sequence. (from Genbank) |
| 106 | Prostate | 0.6506759 | 0.4976958 | 0.42732 | 0.2947822 | U81599_at | Homeodomain protein HOXB13 mRNA |
| 107 | Prostate | 0.6493998 | 0.4973906 | 0.427263 | 0.29438636 | RC_AA2345 61_at | EST: zr66c06.s1 Soares NhHMPu S1 Homo sapiens cDNA clone 668362 3', mRNA sequence. (from Genbank) |
| 108 | Prostate | 0.6493228 | 0.4971947 | 0.42685 | 0.29403 78 | RC_AA2821 38_at | EST: zt02a10.s1 NCI_CGAP_GCB1 Homo sapiens cDNA clone IMAGE:711930 3', mRNA sequence. (from Genbank) |
| 109 | Prostate | 0.6493036 | 0.4966466 | 0.426709 | 0.29365513 | M27492_at | INTERLEUKIN-1 RECEPTOR, TYPE I PRECURSOR |
| 110 | Prostate | 0.6492758 | 0.4951832 | 0.426277 | 0.29314995 | RC_AA4103 11_at | EST: zv23c07.s1 Soares NhHMPu S1 Homo sapiens cDNA clone 754476 3', mRNA sequence. (from Genbank) |
| 111 | Prostate | 0.6485527 | 0.4951832 | 0.425904 | 0.29278666 | RC_AA4782 98_s_at | Human apM2 mRNA for GS2374 (unknown product specific to adipose tissue), complete cds |
| 112 | Prostate | 0.6480391 | 0.4946998 | 0.425431 | 0.29245773 | X13839_at | LCAT Lecithin-cholesterol acyltransferase |
| 113 | Prostate | 0.6479582 | 0.4943146 | 0.425074 | 0.29199937 | RC_AA0111 76_at | EST: ze22b07.s1 Soares fetal heart NbHH19W Homo sapiens cDNA clone 359701 3', mRNA sequence. (from Genbank) |
| 114 | Prostate | 0.6474449 | 0.4931663 | 0.424772 | 0.2917363 | X00371_at | Myoglobin gene (exon 1) (and joined CDS) |
| 115 | Prostate | 0.6465631 | 0.492733 | 0.424629 | 0.2912448 | RC_AA0290 46_s_at | EST: zk09g09.s1 Soares pregnant uterus NbHPU Homo sapiens cDNA clone 470080 3', mRNA sequence. (from Genbank) |
| 116 | Prostate | 0.6465359 | 0.4922514 | 0.423876 | 0.29083043 | RC_AA2534 32_at | EST: zr77f04.s1 Soares NhHMPu S1 Homo sapiens cDNA clone 669439 3', mRNA sequence. (from Genbank) |
| 117 | Prostate | 0.6457118 | 0.4916819 | 0.423369 | 0.29052582 | Z35402_ma 1_s_at | Gene encoding E-cadherin, exon 3 and joined CDS |
| 118 | Prostate | 0.6452014 | 0.4913182 | 0.423151 | 0.29019535 | RC_AA4969 80_at | KIAA0331 gene product |

FIG. 12F

| | | | | |
|---|---|---|---|---|
| 119 | Prostate | 0.6445446 | 0.4908056 | 0.422795 | 0.28996736 | U41060_at | Breast cancer, estrogen regulated LIV-1 protein (LIV-1) mRNA, partial cds |
| 120 | Prostate | 0.6445197 | 0.4904437 | 0.422433 | 0.28952515 | X60708_at | DPP4 Dipeptidylpeptidase IV (CD26, adenosine deaminase complexing protein 2) |
| 121 | Prostate | 0.6435612 | 0.4899734 | 0.421749 | 0.28934842 | RC_AA1016 01_at | Homo sapiens herpesvirus entry protein B (HVEB) mRNA, complete cds |
| 122 | Prostate | 0.643281 | 0.4895182 | 0.421642 | 0.28889202 | RC_AA4016 33_at | EST: zx65b11.s1 Soares total fetus Nb2HF8 9w Homo sapiens cDNA clone 758493 3', mRNA sequence. (from Genbank) |
| 123 | Prostate | 0.6428337 | 0.4895182 | 0.421487 | 0.28858697 | X99977_at | H.sapiens ARS gene, component B |
| 124 | Prostate | 0.6420888 | 0.4892011 | 0.421402 | 0.28822535 | RC_AA4496 77_at | EST: zx07b04.s1 Soares total fetus Nb2HF8 9w Homo sapiens cDNA clone 785743 3', mRNA sequence. (from Genbank) |
| 125 | Prostate | 0.6412803 | 0.4889637 | 0.421105 | 0.28796474 | RC_AA0352 84_at | EST: zk25b02.s1 Soares pregnant uterus NbHPU Homo sapiens cDNA clone 471531 3', mRNA sequence. (from Genbank) |
| 126 | Prostate | 0.641219 | 0.4888274 | 0.420925 | 0.28778097 | RC_AA4301 08_at | EST: zw61a11.s1 Soares total fetus Nb2HF8 9w Homo sapiens cDNA clone 774524 3', mRNA sequence. (from Genbank) |
| 127 | Prostate | 0.641183 | 0.488632 | 0.420512 | 0.28726017 | RC_AA4221 46_at | EST: zv28g12.s1 Soares ovary tumor NbHOT Homo sapiens cDNA clone 755014 3', mRNA sequence. (from Genbank) |
| 128 | Prostate | 0.6407533 | 0.4886051 | 0.420041 | 0.2871002 | M95787_at | 22kDa smooth muscle protein (SM22) mRNA |
| 129 | Prostate | 0.6382334 | 0.4882474 | 0.419724 | 0.28677955 | M76378_at | FN1 Fibronectin 1 |
| 130 | Prostate | 0.6376609 | 0.4878603 | 0.419416 | 0.28645197 | AA447410_s_at | EST: zw93c10.r1 Soares total fetus Nb2HF8 9w Homo sapiens cDNA clone 784530 5', mRNA sequence. (from Genbank) |
| 131 | Prostate | 0.637006 | 0.4875477 | 0.419131 | 0.2861282 | M62994_at | Thyroid autoantigen (truncated actin-binding protein) mRNA |
| 132 | Prostate | 0.6360824 | 0.4872048 | 0.418772 | 0.2858967 | RC_AA2812 45_at | EST: zs94d07.s1 NCI_CGAP_GCB1 Homo sapiens cDNA clone IMAGE:705133 3', mRNA sequence. (from Genbank) |
| 133 | Prostate | 0.6349918 | 0.4870953 | 0.418674 | 0.285586615 | N34737_s_a t | EST: yx82f11.r1 Homo sapiens cDNA clone 268269 5'. (from Genbank) |
| 134 | Prostate | 0.6348161 | 0.4868452 | 0.418453 | 0.28511065 | W23474_at | EST: zb33d08.r1 Soares parathyroid tumor NbHPA Homo sapiens cDNA clone 305391 5', mRNA sequence. (from Genbank) |
| 135 | Prostate | 0.6342157 | 0.4865417 | 0.417681 | 0.2847816 | RC_AA4890 12_at | Human pre-B cell enhancing factor (PBEF) mRNA, complete cds |
| 136 | Prostate | 0.6344179 | 0.4864672 | 0.417429 | 0.2843933 | J04152_rna1 _s_at | M1S1 gene extracted from Human gastrointestinal tumor-associated antigen GA733-1 protein gene, clone 05516 |
| 137 | Prostate | 0.6332777 | 0.4861375 | 0.417344 | 0.2841175 | D58115_s_a t | EST: Human aorta cDNA 5'-end GEN-347F12, mRNA sequence. (from Genbank) |
| 138 | Prostate | 0.6312944 | 0.4858992 | 0.416728 | 0.28381932 | RC_AA6097 23_at | EST: af17b03.s1 Soares testis NHT Homo sapiens cDNA clone 1031885 3', mRNA sequence. (from Genbank) |
| 139 | Prostate | 0.6298189 | 0.4857845 | 0.416619 | 0.28362876 | RC_AA6088 02_at | EST: af04e03.s1 Soares testis NHT Homo sapiens cDNA clone 1030684 3', mRNA sequence. (from Genbank) |

FIG. 12G

| # | Tissue | | | | ID | Description |
|---|---|---|---|---|---|---|
| 140 | Prostate | 0.6290444 | 0.485503 | 0.28323716 | RC_AA2927 17_at | EST: zs59e08.s1 NCI_CGAP_GCB1 Homo sapiens cDNA clone IMAGE:701798 3', mRNA sequence. (from Genbank) |
| 141 | Prostate | 0.6290371 | 0.4850179 | 0.2830048 | M22324_at | ANPEP Alanyl (membrane) aminopeptidase (aminopeptidase N, aminopeptidase M, microsomal aminopeptidase, CD13) |
| 142 | Prostate | 0.6268249 | 0.4847548 | 0.2826026 | RC_AA0184 53_at | EST: ze50c06.s1 Soares retina N2b4HR Homo sapiens cDNA clone 362410 3', mRNA sequence. (from Genbank) |
| 143 | Prostate | 0.6262843 | 0.4846771 | 0.28226548 | RC_AA0629 15_at | Endothelin converting enzyme 1 |
| 144 | Prostate | 0.6256754 | 0.4840952 | 0.28197953 | U83115_at | Non-lens beta gamma-crystallin like protein (AIM1) mRNA, partial cds |
| 145 | Prostate | 0.6255443 | 0.4838995 | 0.28164443 | RC_AA6090 53_at | EST: af10f08.s1 Soares testis NHT Homo sapiens cDNA clone 1031271 3', mRNA sequence. (from Genbank) |
| 146 | Prostate | 0.6249026 | 0.4838116 | 0.28139332 | M97639_at | Transmembrane receptor (ror2) mRNA |
| 147 | Prostate | 0.6219987 | 0.4832098 | 0.28120813 | C16248_at | NADH dehydrogenase (ubiquinone) 1, subcomplex unknown, 1 (6kD, KFYI) |
| 148 | Prostate | 0.6209018 | 0.4828006 | 0.28098103 | U82535_at | Fatty acid amide hydrolase mRNA |
| 149 | Prostate | 0.6194904 | 0.4827782 | 0.28062576 | RC_AA0215 92_at | EST: ze67c01.s1 Soares retina N2b4HR Homo sapiens cDNA clone 364032 3', mRNA sequence. (from Genbank) |
| 150 | Prostate | 0.6190519 | 0.481953 | 0.28045684 | U07919_at | ALDH6 Aldehyde dehydrogenase 6 |
| 151 | Prostate | 0.6172585 | 0.4817271 | 0.28027204 | AA427468_s_at | Claudin 4 |
| 152 | Prostate | 0.6155099 | 0.4817121 | 0.27995634 | AA393432_s_at | EST: zf71a04.r1 Soares testis NHT Homo sapiens cDNA clone 727758 5', mRNA sequence. (from Genbank) |
| 153 | Prostate | 0.6150956 | 0.4815701 | 0.27961266 | RC_AA2338 56_at | EST: zr47a06.s1 Soares NhHMPu S1 Homo sapiens cDNA clone 666514 3', mRNA sequence. (from Genbank) |
| 154 | Prostate | 0.6147652 | 0.4811368 | 0.27928016 | RC_AA4022 24_at | Homo sapiens growth arrest and DNA-damage-inducible protein GADD45gamma mRNA, complete cds |
| 155 | Prostate | 0.6142747 | 0.4809717 | 0.27890116 | RC_AA4814 14_at | Golgi SNAP receptor complex member 1 |
| 156 | Prostate | 0.6133595 | 0.4806446 | 0.27865797 | RC_AA4044 87_at | EST: zw38a06.s1 Soares total fetus Nb2HF8 9w Homo sapiens cDNA clone 772306 3', mRNA sequence. (from Genbank) |
| 157 | Prostate | 0.6123323 | 0.4801837 | 0.27839088 | AA028171_a_t | EST: ze75h09.r1 Soares fetal heart NbHH19W Homo sapiens cDNA clone 364865 5' similar to contains element MER35 repetitive element ; mRNA sequence. (from Genbank) |
| 158 | Prostate | 0.6116102 | 0.4800968 | 0.41086 0.2779724 | X66785_f_at | Dihydrolipoamide branched chain transacylase (E2 component of branched chain keto acid dehydrogenase complex; maple syrup urine disease) |
| 159 | Prostate | 0.6112962 | 0.4799881 | 0.277805 27 | RC_AA4494 55_at | EST: zx05e10.s1 Soares total fetus Nb2HF8 9w Homo sapiens cDNA clone 785610 3' similar to contains Alu repetitive element;, mRNA sequence. (from Genbank) |

FIG. 12H

| # | Tissue | | | | ID | Description |
|---|---|---|---|---|---|---|
| 160 | Prostate | 0.6112632 | 0.4795347 | 0.410558 | 0.27747253 | RC_AA4900 69_at | EST: ab05d09.s1 Stratagene fetal retina 937202 Homo sapiens cDNA clone 833921 3', mRNA sequence. (from Genbank) |
| 161 | Prostate | 0.6104791 | 0.4793637 | 0.41026 | 0.27723765 | RC_AA2358 03_f_at | EST: zs42g06.s1 Soares NhHMPu S1 Homo sapiens cDNA clone 687898 3', mRNA sequence. (from Genbank) |
| 162 | Prostate | 0.6094204 | 0.4792782 | 0.410004 | 0.27700478 | D13643_at | KIAA0018 gene |
| 163 | Prostate | 0.6090662 | 0.4785797 | 0.409971 | 0.2766968 | U29463_s_a t | Cytochrome b561 gene |
| 164 | Prostate | 0.6063626 | 0.4776153 | 0.409727 | 0.2763642 | RC_AA4499 90_at | EST: zx38a01.s1 Soares total fetus Nb2HF8 9w Homo sapiens cDNA clone 788712 3', mRNA sequence. (from Genbank) |
| 165 | Prostate | 0.6060374 | 0.4773963 | 0.40943 | 0.2761838 | L02870_s_at | Collagen, type VII, alpha 1 (epidermolysis bullosa, dystrophic, dominant and recessive) |
| 166 | Prostate | 0.6038646 | 0.4771512 | 0.409049 | 0.27594388 | RC_AA4343 90_at | EST: zx31a06.s1 Soares ovary tumor NbHOT Homo sapiens cDNA clone 770866 3', mRNA sequence. (from Genbank) |
| 167 | Prostate | 0.602949 | 0.4770647 | 0.408604 | 0.27569866 | RC_AA0265 97_at | EST: ze92h11.s1 Soares fetal heart NbHH19W Homo sapiens cDNA clone 366501 3', mRNA sequence. (from Genbank) |
| 168 | Prostate | 0.6025259 | 0.4767934 | 0.408603 | 0.2754560_r_at | RC_AA0555 | EST: zf21f02.s1 Soares fetal heart NbHH19W Homo sapiens cDNA clone 377595 3', mRNA sequence. (from Genbank) |
| 169 | Prostate | 0.6009183 | 0.4765101 | 0.408317 | 0.27517274 | RC_AA0106 65_at | EST: ze19f06.s1 Soares fetal heart NbHH19W Homo sapiens cDNA clone 359459 3', mRNA sequence. (from Genbank) |
| 170 | Prostate | 0.6004708 | 0.4761858 | 0.408066 | 0.2749901 | X51405_at | CPE Carboxypeptidase E |
| 171 | Prostate | 0.6001433 | 0.4760726 | 0.407598 | 0.27468523 | U25138_at | MaxiK potassium channel beta subunit mRNA |
| 172 | Prostate | 0.5984812 | 0.4759167 | 0.407427 | 0.27451712 | RC_AA4420 71_at | EST: zw63b06.s1 Soares total fetus Nb2HF8 9w Homo sapiens cDNA clone 774707 3', mRNA sequence. (from Genbank) |
| 173 | Prostate | 0.5978817 | 0.475613 | 0.407415 | 0.27425542 | AA418921_a t | EST: zw01b03.r1 Soares NhHMPu S1 Homo sapiens cDNA clone 767981 5', mRNA sequence. (from Genbank) |
| 174 | Prostate | 0.5978021 | 0.475487 | 0.406835 | 0.27402558 | RC_AA4565 84_at | EST: zx73c09.s1 Soares ovary tumor NbHOT Homo sapiens cDNA clone 809392 3', mRNA sequence. (from Genbank) |
| 175 | Prostate | 0.5970512 | 0.4753977 | 0.406686 | 0.27367917 | AA114949_a t | UDP-N-acteylglucosamine pyrophosphorylase 1; Sperm associated antigen 2 |
| 176 | Prostate | 0.5970486 | 0.4741243 | 0.406428 | 0.27338088 | RC_AA4460 05_at | EST: zw64f03.s1 Soares testis NHT Homo sapiens cDNA clone 780989 3', mRNA sequence. (from Genbank) |
| 177 | Prostate | 0.5966892 | 0.4736542 | 0.405812 | 0.27317977 | RC_AA1868 97_at | EST: zp74c05.s1 Stratagene HeLa cell s3 937216 Homo sapiens cDNA clone 625928 3', mRNA sequence. (from Genbank) |
| 178 | Prostate | 0.5957331 | 0.4734552 | 0.405712 | 0.27297464 | Y13492_s_at | Homo sapiens mRNA for smoothelin. (from Genbank) |
| 179 | Prostate | 0.5947304 | 0.4730634 | 0.405282 | 0.2725586 | RC_AA0404 65_at | EST: zk46h09.s1 Soares pregnant uterus NbHPU Homo sapiens cDNA clone 485921 3', mRNA sequence. (from Genbank) |
| 180 | Prostate | 0.5943906 | 0.4730365 | 0.405038 | 0.27237383 | L20591_at | ANX3 Annexin III (lipocortin III) |
| 181 | Prostate | 0.5934044 | 0.4728706 | 0.404844 | 0.27214924 | RC_AA410529_s_at | EST: zv23a01.r1 Soares NhHMPu S1 Homo sapiens cDNA clone 754440 5', mRNA sequence. (from Genbank) |

FIG. 12I

| # | Tissue | | | | | ID | Description |
|---|---|---|---|---|---|---|---|
| 182 | Prostate | 0.5925654 | 0.4723791 | 0.404601 | 0.27184728 | N77716_s_at | Homo sapiens mRNA for low molecular mass ubiquinone-binding protein, complete cds |
| 183 | Prostate | 0.5913555 | 0.4722694 | 0.404173 | 0.27162698 | RC_AA621485_at | KIAA0575 gene product |
| 184 | Prostate | 0.5913445 | 0.4721748 | 0.404031 | 0.27139384 | RC_AA155633_at | Insulin-like growth factor 1 receptor |
| 185 | Prostate | 0.5913063 | 0.4715289 | 0.403658 | 0.27109021 | L09717_at | LAMP2 Lysosome-associated membrane protein 2 {alternative products} |
| 186 | Prostate | 0.5910223 | 0.4715125 | 0.403521 | 0.27084655 | AA447439_s_at | EST: zw93g09.r1 Soares total fetus Nb2HF8 9w Homo sapiens cDNA clone 784576 5', mRNA sequence. (from Genbank) |
| 187 | Prostate | 0.5909669 | 0.4712761 | 0.403023 | 0.27078071 | Y00815_at | PTPRF Protein tyrosine phosphatase, receptor type, f polypeptide |
| 188 | Prostate | 0.589317 | 0.4710031 | 0.402745 | 0.27036641 | U35048_at | TSC-22 protein mRNA |
| 189 | Prostate | 0.5885118 | 0.4709901 | 0.402465 | 0.27015834 | RC_AA598444_at | Homo sapiens clone 486790 diphosphoinositol polyphosphate phosphohydrolase mRNA, complete cds |
| 190 | Prostate | 0.5884084 | 0.4707774 | 0.402335 | 0.26995188 | Z83806_at | Axonemal dynein heavy chain (partial, ID hdhc9) |
| 191 | Prostate | 0.588371 | 0.4706789 | 0.4019 | 0.26968554 | K01911_at | NPY Neuropeptide Y |
| 192 | Prostate | 0.5882217 | 0.4706759 | 0.401643 | 0.26952174 | AA194815_s_at | EST: zr35f03.r1 Soares NhHMPu S1 Homo sapiens cDNA clone 665405 5', mRNA sequence. (from Genbank) |
| 193 | Prostate | 0.588086 | 0.4704573 | 0.401376 | 0.26922711 | RC_AA148539_at | EST: zl06e05.s1 Soares pregnant uterus NbHPU Homo sapiens cDNA clone 491552 3', mRNA sequence. (from Genbank) |
| 194 | Prostate | 0.5879937 | 0.470377 | 0.401128 | 0.26905355 | U12778_at | ACADSB Acyl-coA dehydrogenase |
| 195 | Prostate | 0.5875179 | 0.4702776 | 0.401128 | 0.26879364 | RC_AA057839_at | EST: zi95d07.s1 Stratagene corneal stroma (#937222) Homo sapiens cDNA clone 512365 3', mRNA sequence. (from Genbank) |
| 196 | Prostate | 0.5871372 | 0.4700534 | 0.40102 | 0.26854077 | U04636_rna1_at-2 | Prostaglandin-endoperoxide synthase 2 (prostaglandin G/H synthase and cyclooxygenase) |
| 197 | Prostate | 0.5871372 | 0.4700235 | 0.400654 | 0.26829576 | U04636_rna1_at | Cyclooxygenase-2 (hCox-2) gene |
| 198 | Prostate | 0.586886 | 0.4698977 | 0.400569 | 0.2680042 | C00038_s_at | EST: HUMGS0003443, Human Gene Signature, 3'-directed cDNA sequence, mRNA sequence. (from Genbank) |
| 199 | Prostate | 0.5864977 | 0.4694937 | 0.400314 | 0.26781183 | X66276_s_at | MYBPC1 Myosin-binding protein C, slow-type |
| 200 | Prostate | 0.5863636 | 0.4688512 | 0.400104 | 0.26758297 | RC_AA453997_at | EST: zx46a12.s1 Soares testis NHT Homo sapiens cDNA clone 795262 3', mRNA sequence. (from Genbank) |
| 201 | Prostate | 0.5855955 | 0.4685086 | 0.39981 | 0.26732737 | RC_AA505141_at | EST: aa65e04.s1 NCI_CGAP_GCB1 Homo sapiens cDNA clone IMAGE:825822 3', mRNA sequence. (from Genbank) |
| 202 | Prostate | 0.5841315 | 0.4682981 | 0.39967 | 0.26711115 | RC_AA191323_at | EST: zp83b09.s1 Stratagene HeLa cell s3 937216 Homo sapiens cDNA clone 626777 3', mRNA sequence. (from Genbank) |

FIG. 12J

| # | Tissue | | | | Accession | Description |
|---|---|---|---|---|---|---|
| 203 | Prostate | 0.5838199 | 0.4679814 | 0.399317 | 0.26696646 | RC_AA4853 08_at | EST: ab09a07.s1 Stratagene lung (#937210) Homo sapiens cDNA clone 840276 3', mRNA sequence. (from Genbank) |
| 204 | Prostate | 0.5827327 | 0.4673873 | 0.399067 | 0.26659372 | D76444_at | Hkf-1 mRNA |
| 205 | Prostate | 0.5814714 | 0.4664888 | 0.398938 | 0.26646683 | X97335_at | Kinase A anchor protein |
| 206 | Prostate | 0.5814693 | 0.4663544 | 0.3984 | 0.26632953 | M19267_s_at | TPM1 Tropomyosin alpha chain (skeletal muscle) |
| 207 | Prostate | 0.5790319 | 0.4662611 | 0.398168 | 0.2659507 | RC_AA4762 35_at | EST: zw35h03.s1 Soares ovary tumor NbHOT Homo sapiens cDNA clone 771317 3', mRNA sequence. (from Genbank) |
| 208 | Prostate | 0.5790135 | 0.4660753 | 0.397856 | 0.26579258 | RC_AA3703 53_at | EST: EST82247 Prostate gland I Homo sapiens cDNA 3' end, mRNA sequence. (from Genbank) |
| 209 | Prostate | 0.5781454 | 0.4658954 | 0.397822 | 0.26557875 | AF000573_r na1_at | Homogentisate 1,2-dioxygenase gene |
| 210 | Prostate | 0.5780271 | 0.4658386 | 0.397777 | 0.2654417 | X51345_at | JUNB Jun B proto-oncogene |
| 211 | Prostate | 0.5775183 | 0.465359 | 0.397631 | 0.26520842 | C01397_at | EST: HUMGS0008379, Human Gene Signature, 3'-directed cDNA sequence, mRNA sequence. (from Genbank) |
| 212 | Prostate | 0.5771865 | 0.4653239 | 0.396751 | 0.26501727 | RC_AA4020 00_at | EST: zu55b03.s1 Soares ovary tumor NbHOT Homo sapiens cDNA clone 741869 3' similar to TR:G452270 G452270 2-19 PROTEIN PRECURSOR.; mRNA sequence. (from Genbank) |
| 213 | Prostate | 0.57686 | 0.4651363 | 0.396495 | 0.26469582 | D87742_at | KIAA0268 gene, partial cds |
| 214 | Prostate | 0.576651 | 0.4650046 | 0.396269 | 0.26459795 | U82613_at-2 | Human DNA-binding protein ABP/ZF mRNA, complete cds |
| 215 | Prostate | 0.576651 | 0.4647957 | 0.396173 | 0.26439974 | U82613_at | DNA-binding protein ABP/ZF mRNA |
| 216 | Prostate | 0.5764993 | 0.4647071 | 0.395851 | 0.2641381 | X59405_at | MCP Membrane cofactor protein (CD46, trophoblast-lymphocyte cross-reactive antigen) |
| 217 | Prostate | 0.5757962 | 0.4646206 | 0.39568 | 0.26393047 | AA477978_s_at | Short-chain dehydrogenase/reductase 1 |
| 218 | Prostate | 0.5751578 | 0.4643598 | 0.395397 | 0.26372898 | S65738_at | Actin depolymerizing factor [human, fetal brain, mRNA, 1452 nt] |
| 219 | Prostate | 0.574474 | 0.4641366 | 0.39522 | 0.26355585 | RC_AA1965 12_at | Human DNA sequence from clone 431H6 on chromosome 16. Contains a novel gene with some homology to mouse HN1 (Hematological and Neurological expressed sequence 1) downstream of a putative CpG island. Contains ESTs and GSSs |
| 220 | Prostate | 0.574224 | 0.4639533 | 0.39512 | 0.26337394 | HG2383-HT4824_s_at | Cystathionine Beta Synthase, Alt. Splice 3 |
| 221 | Prostate | 0.5742155 | 0.4638831 | 0.395119 | 0.26302627 | RC_AA3435 14_at | EST: EST49299 Gall bladder I Homo sapiens cDNA 3' end, mRNA sequence. (from Genbank) |
| 222 | Prostate | 0.5736166 | 0.463758 | 0.395103 | 0.26286376 | D14662_at | KIAA0106 gene |
| 223 | Prostate | 0.572737 | 0.4636937 | 0.394641 | 0.26249048 | RC_AA2912 69_at | Homo sapiens mRNA for KIAA0776 protein, partial cds |

FIG. 12K

| | | | | | |
|---|---|---|---|---|---|
| 224 | Prostate | 0.5726978 | 0.463195 | 0.2622721 | RC_D20888 at | EST: Human HL60 3'directed MboI cDNA, HUMGS01869, clone mp0836, mRNA sequence. (from Genbank) |
| 225 | Prostate | 0.5719746 | 0.4629356 | 0.394534 | U31383_at | G protein gamma-10 subunit mRNA |
| 226 | Prostate | 0.5715209 | 0.4628296 | 0.26213694 | RC_AA4119 44_at | Coagulation factor C (Limulus polyphemus) homology |
| 227 | Prostate | 0.5712687 | 0.4626799 | 0.26199704_s AA195179_s at | EST: zr35h11.r1 Soares NhHMPu S1 Homo sapiens cDNA clone 665445 5', mRNA sequence. (from Genbank) |
| 228 | Prostate | 0.5709884 | 0.4623777 | 0.26142707 | RC_AA5984 53_s_at | H.sapiens mRNA for retrotransposon |
| 229 | Prostate | 0.5708897 | 0.462335 | 0.26123214 | RC_AA4286 07_at | EST: zw69c08.s1 Soares testis NHT Homo sapiens cDNA clone 781454 3', mRNA sequence. (from Genbank) |
| 230 | Prostate | 0.5703667 | 0.4620423 | 0.261094 | RC_AA4180 46_at | EST: zv97f10.s1 Soares NhHMPu S1 Homo sapiens cDNA clone 767755 3', mRNA sequence. (from Genbank) |
| 231 | Prostate | 0.5702447 | 0.4617716 | 0.392632 | RC_AA4814 40_at | EST: zv45a05.s1 Soares ovary tumor NbHOT Homo sapiens cDNA clone 756560 3', mRNA sequence. (from Genbank) |
| 232 | Prostate | 0.5701376 | 0.461212 | 0.392415 | X75756_at | PRKCM Protein kinase C, mu |
| 233 | Prostate | 0.5695193 | 0.4606413 | 0.392186 | Z24727_at | TPM1 Tropomyosin alpha chain (skeletal muscle) |
| 234 | Prostate | 0.5692244 | 0.46061 | 0.391931 | Z49989_at | Smoothelin |
| 235 | Prostate | 0.5691826 | 0.460608 | 0.391747 | D14533_at | XPA Xeroderma pigmentosum, complementation group A |
| 236 | Prostate | 0.5689654 | 0.4604097 | 0.39148 | RC_AA0322 50_at | EST: zk19f06.s1 Soares pregnant uterus NbHPU Homo sapiens cDNA clone 471011 3', mRNA sequence. (from Genbank) |
| 237 | Prostate | 0.5687566 | 0.4600774 | 0.391363 | AA247685_a t | Desmoplakin (DPI, DPII) |
| 238 | Prostate | 0.5687344 | 0.4600278 | 0.391127 | R66239_at | EST: yi34d06.r1 Homo sapiens cDNA clone 141131 5'. (from Genbank) |
| 239 | Prostate | 0.5682151 | 0.4599342 | 0.25900626 | RC_AA1952 60_at | EST: zr36g02.s1 Soares NhHMPu S1 Homo sapiens cDNA clone 665522 3', mRNA sequence. (from Genbank) |
| 240 | Prostate | 0.5665769 | 0.4597729 | 0.390709 | W02027_s_ at | EST: za57c08.r1 Soares fetal liver spleen 1NFLS Homo sapiens cDNA clone 296654 5', mRNA sequence. (from Genbank) |
| 241 | Prostate | 0.5652082 | 0.4597072 | 0.25870547 | RC_AA3981 97_at | EST: zt59a08.s1 Soares testis NHT Homo sapiens cDNA clone 726614 3', mRNA sequence. (from Genbank) |
| 242 | Prostate | 0.564452 | 0.4596437 | 0.390347 | RC_AA0349 25_at | EST: zk25e01.s1 Soares pregnant uterus NbHPU Homo sapiens cDNA clone 471576 3', mRNA sequence. (from Genbank) |
| 243 | Prostate | 0.5641075 | 0.4596017 | 0.390108 | D13315_at | GLO1 Glyoxalase I |
| 244 | Prostate | 0.5630525 | 0.4594392 | 0.389974 | W31738_s_ at | EST: zb93b06.r1 Soares parathyroid tumor NbHPA Homo sapiens cDNA clone 320339 5' similar to contains Alu repetitive element;, mRNA sequence. (from Genbank) |
| 245 | Prostate | 0.5619864 | 0.459054 | 0.38981 | M57730_at | EPH-RELATED RECEPTOR TYROSINE KINASE LIGAND 1 PRECURSOR |
| 246 | Prostate | 0.5617257 | 0.4587861 | 0.389758 | X83425_at | LU gene for Lutheran blood group glycoprotein |

FIG. 12L

| # | Tissue | | | | Accession | Description |
|---|---|---|---|---|---|---|
| 247 | Prostate | 0.5613579 | 0.4581961 | 0.389617 | 0.257464408 | D78134_at | YWHAZ Tyrosine 3-monooxygenase/tryptophan 5-monooxygenase activation protein, zeta polypeptide |
| 248 | Prostate | 0.5611047 | 0.4581895 | 0.38943 | 0.25730734 6_at | RC_AA1279 | EST: zl13d08.s1 Soares pregnant uterus NbHPU Homo sapiens cDNA clone 501807 3'; mRNA sequence. (from Genbank) |
| 249 | Prostate | 0.5599628 | 0.4579037 | 0.389205 | 0.25708506 07_at | RC_AA4180 | EST: zv94f11.s1 Soares NhHMPu S1 Homo sapiens cDNA clone 767469 3'; mRNA sequence. (from Genbank) |
| 250 | Prostate | 0.5597033 | 0.457627 | 0.388934 | 0.25569068 77_i_at | RC_AA4063 | EST: zv10d03.s1 Soares NhHMPu S1 Homo sapiens cDNA clone 753221 3'; mRNA sequence. (from Genbank) |
| 251 | Prostate | 0.5594444 | 0.4575253 | 0.388517 | 0.25666118 | U02082_at | Guanine nucleotide regulatory protein (tim1) mRNA |
| 252 | Prostate | 0.5588209 | 0.4575253 | 0.388232 | 0.25642875 | U79272_at | Clone 23720 mRNA sequence |
| 253 | Prostate | 0.5586749 | 0.4569283 | 0.388198 | 0.256335585 | HG2743-HT2845_at | Caldesmon 1, All_Splice 3, Non-Muscle |
| 254 | Prostate | 0.5583576 | 0.4567877 | 0.388144 | 0.25600607 | U24266_at | Pyrroline-5-carboxylate dehydrogenase (P5CDh) mRNA, long form |
| 255 | Prostate | 0.5578245 | 0.4564635 | 0.388125 | 0.2559091 | R73299_at | Tissue inhibitor of metalloproteinase 3 (Sorsby fundus dystrophy, pseudoinflammatory) |
| 256 | Prostate | 0.5565282 | 0.4564447 | 0.388071 | 0.25576164 3_at | RC_AA4852 | EST: aa41e07.s1 NCI_CGAP_GCB1 Homo sapiens cDNA clone IMAGE:815844 3', mRNA sequence. (from Genbank) |
| 257 | Prostate | 0.5561669 | 0.4562562 | 0.387841 | 0.25553864 | U41740_at | Golgin-245 mRNA |
| 258 | Prostate | 0.5560176 | 0.456138 | 0.387831 | 0.25529474 | D30756_at | KIAA0108 gene |
| 259 | Prostate | 0.5543262 | 0.4559726 | 0.387701 | 0.255215857 | D84294_at | TPRD |
| 260 | Prostate | 0.5541329 | 0.4559328 | 0.387136 | 0.25493225 | L27479_at | X123 mRNA, 3' end |
| 261 | Prostate | 0.553995 | 0.4556782 | 0.387136 | 0.25469186 692216 3' | RC_AA2364 76_at | EST: zr75c01.s1 Soares NhHMPu S1 Homo sapiens cDNA clone 692216 3' similar to TR:G755466 G755466 TRANSMEMBRANE PROTEIN PRECURSOR. ;. mRNA sequence. (from Genbank) |
| 262 | Prostate | 0.5538735 | 0.4552889 | 0.386688 | 0.25450677 | M90516_at | GFPT Glutamine-fructose-6-phosphate transaminase |
| 263 | Prostate | 0.5529212 | 0.4551171 | 0.386585 | 0.25442073 88_at | RC_AA4045 | Homo sapiens herpesvirus entry protein B (HVEB) mRNA, complete cds |
| 264 | Prostate | 0.5515243 | 0.4549871 | 0.386423 | 0.25415593 86_at | RC_AA4476 | EST: aa18c12.s1 Soares NhHMPu S1 Homo sapiens cDNA clone 813622 3'; mRNA sequence. (from Genbank) |
| 265 | Prostate | 0.5503541 | 0.4549871 | 0.386397 | 0.25393826 | U49957_s_at | LIM protein (LPP) mRNA, partial cds |
| 266 | Prostate | 0.5500592 | 0.4549741 | 0.386294 | 0.25376058 93_at | RC_AA3473 | EST: EST53685 Fetal heart II Homo sapiens cDNA 3' end, mRNA sequence. (from Genbank) |
| 267 | Prostate | 0.5496034 | 0.4548665 | 0.386055 | 0.253581 | S80437_s_at | Fatty acid synthase (3' region) [human, breast and HepG2 cells, mRNA Partial, 2237 nt] |
| 268 | Prostate | 0.5494102 | 0.4548655 | 0.385553 | 0.25333914 07_at | RC_AA2619 | EST: zs17d04.s1 NCI_CGAP_GCB1 Homo sapiens cDNA clone IMAGE:685447 3'; mRNA sequence. (from Genbank) |
| 269 | Prostate | 0.5493456 | 0.4546997 | 0.385537 | 0.25316197 24_f_at | RC_AA4822 | EST: ab15c03.s1 Stratagene lung (#937210) Homo sapiens cDNA clone 840868 3'; mRNA sequence. (from Genbank) |

FIG. 12M

| | | | | | |
|---|---|---|---|---|---|
| 270 | Prostate | 0.5492716 | 0.4545837 | 0.385476 | 0.2529523 | M24736_s_at | SELE Selectin E (endothelial adhesion molecule 1) |
| 271 | Prostate | 0.5487302 | 0.4542674 | 0.384923 | 0.2527982696_at | RC_AA4117 | Homo sapiens clone 24631 mRNA sequence |
| 272 | Prostate | 0.5484247 | 0.4542443 | 0.384876 | 0.252651726_at | U72518_s_a | Human destrin-2 pseudogene mRNA, complete cds |
| 273 | Prostate | 0.547724 | 0.4541701 | 0.38473 | 0.2524418515_at | RC_AA1332 | Homo sapiens mRNA encoding RAMP1 |
| 274 | Prostate | 0.5470277 | 0.4539807 | 0.384725 | 0.2522324351_at | RC_AA4969 | EST: aa42e08.s1 Soares NhHMPu S1 Homo sapiens cDNA clone 823622 3', mRNA sequence. (from Genbank) |
| 275 | Prostate | 0.5469666 | 0.4534964 | 0.384629 | 0.2520308888_at | D11151_at | EDNRA Endothelin receptor type A |
| 276 | Prostate | 0.5465493 | 0.4534719 | 0.384534 | 0.25176066t | M83216_s_a | CALD1 Caldesmon |
| 277 | Prostate | 0.5463292 | 0.4532066 | 0.38444 | 0.251573404_at | RC_AA4533 | EST: zx32b10.s1 Soares total fetus Nb2HF8 9w Homo sapiens cDNA clone 7881155 3', mRNA sequence. (from Genbank) |
| 278 | Prostate | 0.5463022 | 0.4528663 | 0.384035 | 0.2513391_s_at | M83667_rna | NF-IL6-beta protein mRNA |
| 279 | Prostate | 0.5456138 | 0.452676 | 0.383755 | 0.251220956_at | RC_AA4258 | Homo sapiens mRNA for KIAA0908 protein, partial cds |
| 280 | Prostate | 0.5454785 | 0.4526494 | 0.383675 | 0.25106984 | M83822_at | Beige-like protein (BGL) mRNA, partial cds |
| 281 | Prostate | 0.545441 | 0.4525109 | 0.383386 | 0.2508398663_at | RC_AA4914 | EST: ab01d12.s1 Stratagene fetal retina 937202 Homo sapiens cDNA clone 839543 3', mRNA sequence. (from Genbank) |
| 282 | Prostate | 0.5447523 | 0.4524036 | 0.383371 | 0.2506934 | U51711_at | DESMOCOLLIN 2A/BB PRECURSOR |
| 283 | Prostate | 0.5445942 | 0.4522296 | 0.383243 | 0.2505571849_at | RC_AA4050 | EST: zu19g04.s1 Soares NhHMPu S1 Homo sapiens cDNA clone 738486 3', mRNA sequence. (from Genbank) |
| 284 | Prostate | 0.5440533 | 0.4520229 | 0.383186 | 0.2503373600_at | RC_AA4783 | CD39-like 2 |
| 285 | Prostate | 0.5437453 | 0.4518799 | 0.382972 | 0.2500083470_at | RC_AA2817 | Seven in absentia (Drosophila) homolog 1 |
| 286 | Prostate | 0.5436813 | 0.4515054 | 0.382823 | 0.24995187 | AA485585_a | EST: zx90e01.r1 Soares ovary tumor NbHOT Homo sapiens cDNA clone 811032 5', mRNA sequence. (from Genbank) |
| 287 | Prostate | 0.5436299 | 0.4514624 | 0.382561 | 0.2498199 | U88871_at | Peroxisome targeting signal 2 receptor (Pex7) mRNA |
| 288 | Prostate | 0.5430307 | 0.4513028 | 0.382257 | 0.2496602 | M33690_at | CD9 CD9 antigen |
| 289 | Prostate | 0.5430216 | 0.4505165 | 0.382019 | 0.2494660340_s_at | RC_AA2534 | EST: zr76h03.s1 Soares NhHMPu S1 Homo sapiens cDNA clone 669365 3', mRNA sequence. (from Genbank) |
| 290 | Prostate | 0.5429966 | 0.4500143 | 0.381532 | 0.2492514662_at | RC_AA2561 | EST: zr79b07.s1 Soares NhHMPu S1 Homo sapiens cDNA clone 681877 3', mRNA sequence. (from Genbank) |
| 291 | Prostate | 0.5424957 | 0.4498984 | 0.381334 | 0.2491652898_at | RC_AA4056 | EST: zu66e10.s1 Soares testis NHT Homo sapiens cDNA clone 742986 3', mRNA sequence. (from Genbank) |

FIG. 12N

| # | Tissue | Val1 | Val2 | Val3 | Val4 | ID | Description |
|---|---|---|---|---|---|---|---|
| 292 | Prostate | 0.5423896 | 0.4498854 | 0.381322 | 0.24902043 | W28151_at | EST: 4315 Human retina cDNA randomly primed sublibrary Homo sapiens cDNA, mRNA sequence. (from Genbank) |
| 293 | Prostate | 0.5421512 | 0.4498085 | 0.381211 | 0.24885654 | U80456_at | Transcription factor SIM2 long form mRNA |
| 294 | Prostate | 0.5414596 | 0.4497663 | 0.381009 | 0.24857931 | X83618_at | Clone HSH1 HMG CoA synthase mRNA, partial cds |
| 295 | Prostate | 0.5412862 | 0.4497064 | 0.380775 | 0.24848191 | RC_AA424849_at | EST: zw03b06.s1 Soares NhHMPu S1 Homo sapiens cDNA clone 768179 3', mRNA sequence. (from Genbank) |
| 296 | Prostate | 0.5410488 | 0.4496755 | 0.380684 | 0.24836177 | C01803_s_at | EST: HUMGS0003762, Human Gene Signature, 3'-directed cDNA sequence, mRNA sequence. (from Genbank) |
| 297 | Prostate | 0.5404763 | 0.4494449 | 0.380576 | 0.24817023 | AA488793_a_t | Aa54d11.r1 NCI_CGAP_GCB1 Homo sapiens cDNA clone IMAGE:824757 5', mRNA sequence. (from Genbank) |
| 298 | Prostate | 0.5401263 | 0.448764 | 0.380523 | 0.24798755 | U49928_at | TAK1 binding protein 1 (TAB1) mRNA |
| 299 | Prostate | 0.5400038 | 0.4484839 | 0.38039 | 0.24773268 | RC_AA461057_at | Nuclear localization signal deleted in velocardiofacial syndrome |
| 300 | Prostate | 0.5399782 | 0.4483686 | 0.380343 | 0.24776032 | D87438_at | KIAA0251 gene, partial cds |
| 301 | Prostate | 0.5396916 | 0.4482804 | 0.380235 | 0.24748597 | R53717_at | EST: yi02e03.r1 Homo sapiens cDNA clone 138076 5'. (from Genbank) |
| 302 | Prostate | 0.5390546 | 0.4481291 | 0.380078 | 0.24737182 | RC_AA450294_s_at | EST: zx43g04.s1 Soares total fetus Nb2HF8 9w Homo sapiens cDNA clone 789270 3', mRNA sequence. (from Genbank) |
| 303 | Prostate | 0.5387057 | 0.448094 | 0.379942 | 0.24703121 | RC_AA446944_at | EST: zw85c11.s1 Soares total fetus Nb2HF8 9w Homo sapiens cDNA clone 783764 3', mRNA sequence. (from Genbank) |
| 304 | Prostate | 0.5385253 | 0.4480678 | 0.379802 | 0.24697034 | RC_AA130089_at | EST: zl33f12.s1 Soares pregnant uterus NbHPU Homo sapiens cDNA clone 503759 3', mRNA sequence. (from Genbank) |
| 305 | Prostate | 0.5383057 | 0.4480511 | 0.379388 | 0.24675086 | U84011_s_at | AGL Amylo-1,6-glucosidase, 4-alpha-glucanotransferase (glycogen debranching enzyme, glycogen storage disease type III) |
| 306 | Prostate | 0.5376237 | 0.4479351 | 0.379236 | 0.24657524 | M35851_s_at | AR Androgen receptor (dihydrotestosterone receptor; testicular feminization; spinal and bulbar muscular atrophy; Kennedy disease) |
| 307 | Prostate | 0.536918 | 0.4477828 | 0.37903 | 0.24638523 | RC_AA449475_at | EST: zx08f10.s1 Soares total fetus Nb2HF8 9w Homo sapiens cDNA clone 785899 3' similar to contains Alu repetitive element;contains element MER22 repetitive element :, mRNA sequence. (from Genbank) |
| 308 | Prostate | 0.5368192 | 0.4477741 | 0.378904 | 0.24615584 | U39447_at | Placenta copper monoamine oxidase mRNA |
| 309 | Prostate | 0.5367519 | 0.4477734 | 0.378589 | 0.24608794 | U11313_at | SCP2 Sterol carrier protein 2 |
| 310 | Prostate | 0.5364852 | 0.4473016 | 0.378548 | 0.24588968 | RC_AA340539_at | EST: EST45795 Fetal kidney I Homo sapiens cDNA 3' end, mRNA sequence. (from Genbank) |
| 311 | Prostate | 0.5361521 | 0.4472838 | 0.378178 | 0.24556942 | RC_AA135850_at | EST: zn93h01.s1 Stratagene lung carcinoma 9372218 Homo sapiens cDNA clone 565777 3', mRNA sequence. (from Genbank) |

FIG. 12O

| # | Tissue | | | | | Description |
|---|---|---|---|---|---|---|
| 312 | Prostate | 0.5358225 | 0.4464575 | 0.37787 | 0.245434941 | RC_AA6209 65_at | EST: af88f01.s1 Soares testis NHT Homo sapiens cDNA clone 1049113 3' similar to SW:PUA1_MOUSE P28650 ADENYLOSUCCINATE SYNTHETASE, MUSCLE ISOZYME ;contains Alu repetitive element;, mRNA sequence. (from Genbank) |
| 313 | Prostate | 0.5357221 | 0.4461213 | 0.377733 | 0.245252052 | RC_AA4795 33_at | EST: zu36h10.s1 Soares ovary tumor NbHOT Homo sapiens cDNA clone 740131 3', mRNA sequence. (from Genbank) |
| 314 | Prostate | 0.5356431 | 0.4461089 | 0.377698 | 0.245092293 | D38305_at | Tob |
| 315 | Prostate | 0.5356014 | 0.4460386 | 0.37763 | 0.244925204 | X63741_s_a t | Pilot mRNA |
| 316 | Prostate | 0.5354915 | 0.4460049 | 0.377602 | 0.244793586 | S77393_at | Transcript ch138 [human, RF1,RF48 stomach cancer cell lines, mRNA, 235 nt] |
| 317 | Prostate | 0.5353308 | 0.4459347 | 0.377323 | 0.244575631 | AF004709_a t | Protein kinase mitogen- activated 13 |
| 318 | Prostate | 0.5351836 | 0.445543 | 0.377206 | 0.244485578 | RC_AA4585 78_at | Homo sapiens KIAA0439 mRNA, partial cds |
| 319 | Prostate | 0.5350846 | 0.4454449 | 0.377109 | 0.244278311 | M63391_rna _at | Desmin gene |
| 320 | Prostate | 0.5346963 | 0.4453443 | 0.376906 | 0.244408878 | RC_AA2321 87_at | EST: zr25c10.s1 Stratagene NT2 neuronal precursor 937230 Homo sapiens cDNA clone 664434 3', mRNA sequence. (from Genbank) |
| 321 | Prostate | 0.5341402 | 0.4451794 | 0.376712 | 0.244034770 | U60205_at | Methyl sterol oxidase (ERG25) mRNA |
| 322 | Prostate | 0.5341062 | 0.4451002 | 0.376646 | 0.243853180 | M34309_at | ERBB3 V-erb-b2 avian erythroblastic leukemia viral oncogene homolog 3 (alternative products) |
| 323 | Prostate | 0.5330498 | 0.4448044 | 0.376522 | 0.243611258 | AA292234_a t | EST: zt50h06.r1 Soares ovary tumor NbHOT Homo sapiens cDNA clone 725819 5', mRNA sequence. (from Genbank) |
| 324 | Prostate | 0.5328742 | 0.4447177 | 0.37647 | 0.243458692 | RC_AA2554 32_at | RTP |
| 325 | Prostate | 0.5327897 | 0.4444883 | 0.376452 | 0.243412392 | U40572_at | EST: zr85f08.s1 Soares NhHMPu S1 Homo sapiens cDNA clone 682503 3', mRNA sequence. (from Genbank) |
| 326 | Prostate | 0.5320264 | 0.4441834 | 0.376366 | 0.243121515 | U40572_at | Beta2-syntrophin (SNT B2) mRNA |
| 327 | Prostate | 0.5319198 | 0.4438101 | 0.376285 | 0.242971510 | D88153_at | Homo sapiens mRNA for HYA22, complete cds |
| 328 | Prostate | 0.5312803 | 0.4433218 | 0.376 | 0.242874808 | D28124_at | Unknown product |
| 329 | Prostate | 0.5305515 | 0.4432703 | 0.375707 | 0.242729780 | RC_AA4594 02_s_at | EST: zx89g02.s1 Soares ovary tumor NbHOT Homo sapiens cDNA clone 810962 3' similar to SW:MV10_MOUSE P23249 PUTATIVE GTP-BINDING PROTEIN MOV10.;, mRNA sequence. (from Genbank) |
| 330 | Prostate | 0.5302557 | 0.4430404 | 0.375513 | 0.242252342 | RC_AA4490 76_at | EST: zx06a12.s1 Soares total fetus Nb2HF8 9w Homo sapiens cDNA clone 785662 3' similar to contains Alu repetitive element;contains element MER22 repetitive element ;, mRNA sequence. (from Genbank) |

FIG. 12P

| # | Tissue | | | | | Description |
|---|---|---|---|---|---|---|
| 331 | Prostate | 0.5299988 | 0.4426315 | 0.375476 | 0.242437796 | RC_AA6214 40_at | EST: af35g10.s1 Soares total fetus Nb2HF8 9w Homo sapiens cDNA clone 1033698 3', mRNA sequence. (from Genbank) |
| 332 | Prostate | 0.5290062 | 0.4422808 | 0.375072 | 0.242322268 | R694417_at | EST: yl83f12.r1 Homo sapiens cDNA clone 155375 5'. (from Genbank) |
| 333 | Prostate | 0.5289936 | 0.4422798 | 0.374495 | 0.242222267 | X07696_at | KRT15 Keratin 15 |
| 334 | Prostate | 0.5285142 | 0.4419763 | 0.374859 | 0.242011627 | RC_AA4500 10_at | EST: zx33f04.s1 Soares total fetus Nb2HF8 9w Homo sapiens cDNA clone 788287 3', mRNA sequence. (from Genbank) |
| 335 | Prostate | 0.5277329 | 0.4419254 | 0.374727 | 0.24168041 | L14778_s_at | PPP3CA Protein phosphatase 3 (formerly 2B), catalytic subunit, alpha isoform (calcineurin A alpha)(alternative products) |
| 336 | Prostate | 0.5275849 | 0.4418683 | 0.374591 | 0.24150343 | U90552_at | Butyrophilin (BTF5) mRNA |
| 337 | Prostate | 0.5271085 | 0.4416855 | 0.374561 | 0.24132104 | AA279359_a_at | EST: zs84d01.r1 NCI_CGAP_GCB1 Homo sapiens cDNA clone IMAGE:704161 5', mRNA sequence. (from Genbank) |
| 338 | Prostate | 0.5265877 | 0.4416533 | 0.374539 | 0.24113257 | W38226_s_at | No info for gene |
| 339 | Prostate | 0.5263924 | 0.4414782 | 0.3745 | 0.24084426 | U78294_at | Arachidonate 15-lipoxygenase, second type |
| 340 | Prostate | 0.5263754 | 0.4414145 | 0.373733 | 0.24076356 | N75646_at | EST: yv29a08.r1 Homo sapiens cDNA clone 244118 5'. (from Genbank) |
| 341 | Prostate | 0.5258607 | 0.4413914 | 0.37373 | 0.2406929 | M63509_s_a t | Glutathione S-transferase M2 (muscle) |
| 342 | Prostate | 0.5257589 | 0.4409685 | 0.373571 | 0.24063863 | R78309_at | EST: yl82b05.r1 Homo sapiens cDNA clone 145713 5'. (from Genbank) |
| 343 | Prostate | 0.5255864 | 0.440687 | 0.373414 | 0.24049558 | M21154_at | AMD1 S-adenosylmethionine decarboxylase 1 |
| 344 | Prostate | 0.5245456 | 0.4406291 | 0.373311 | 0.24041334 | L40401_at | (clone zap128) mRNA, 3' end of cds |
| 345 | Prostate | 0.5245456 | 0.4405527 | 0.373268 | 0.2401133 | L40401_at-2 | Homo sapiens (clone zap128) mRNA, 3' end of cds |
| 346 | Prostate | 0.5245253 | 0.4405329 | 0.373224 | 0.24004823 | RC_AA4775 61_at | EST: zu41f11.s1 Soares ovary tumor NbHOT Homo sapiens cDNA clone 740589 3', mRNA sequence. (from Genbank) |
| 347 | Prostate | 0.5241652 | 0.4404768 | 0.373169 | 0.23978539 | AA037192_a t | Dual specificity phosphatase 3 (vaccinia virus phosphatase VH1-related) |
| 348 | Prostate | 0.5241537 | 0.4404557 | 0.372968 | 0.23958275 | RC_AA2583 79_at | Angiotensin receptor-like 2 |
| 349 | Prostate | 0.5227521 | 0.4404486 | 0.372967 | 0.23941249 | AA477891_a_at | EST: zu34e12.r1 Soares ovary tumor NbHOT Homo sapiens cDNA clone 739918 5', mRNA sequence. (from Genbank) |
| 350 | Prostate | 0.5227351 | 0.4403846 | 0.372269 | 0.23931338 | RC_AA1207 83_at | Eukaryotic translation initiation factor 2, subunit 3 (gamma, 52kD) |
| 351 | Prostate | 0.5223597 | 0.440243 | 0.372668 | 0.23929104 | M11717_rna 1_at | Heat shock protein (hsp 70) gene |
| 352 | Prostate | 0.5220991 | 0.4400503 | 0.372568 | 0.23914976 | RC_AA0545 61_at | EST: zk83h03.s1 Soares pregnant uterus NbHPU Homo sapiens cDNA clone 489461 3', mRNA sequence. (from Genbank) |
| 353 | Prostate | 0.5220723 | 0.4398834 | 0.372379 | 0.23903655 | AA227621_a t | EST: zr57e11.r1 Soares NhHMPu S1 Homo sapiens cDNA clone 667532 5', mRNA sequence. (from Genbank) |

FIG. 12Q

| # | Tissue | | | | ID | Description |
|---|---|---|---|---|---|---|
| 354 | Prostate | 0.521638 | 0.4399368 | 0.372151 | 0.238892976 U37518_at | TNF-related apoptosis inducing ligand TRAIL mRNA |
| 355 | Prostate | 0.5215861 | 0.4399333 | 0.372003 | 0.238731119 RC_AA4615 59_at | Chromogranin A (parathyroid secretory protein 1) |
| 356 | Prostate | 0.5214881 | 0.4398906 | 0.371846 | 0.238854685 HG4126-HT4396_at | Zinc Finger Protein Hzf4 |
| 357 | Prostate | 0.5212281 | 0.4398903 | 0.371757 | 0.238392319 RC_AA2930 6_at | EST: zt55b05.s1 Soares ovary tumor NbHOT Homo sapiens cDNA clone 726225 3', mRNA sequence. (from Genbank) |
| 358 | Prostate | 0.5201612 | 0.4395452 | 0.371582 | 0.238161113 RC_AA0565 57_at | EST: zk81d06.s1 Soares pregnant uterus NbHPU Homo sapiens cDNA clone 489227 3', mRNA sequence. (from Genbank) |
| 359 | Prostate | 0.5201383 | 0.4394583 | 0.371549 | 0.237980928 RC_AA4303 8_at | EST: zw23c04.s1 Soares ovary tumor NbHOT Homo sapiens cDNA clone 770118 3' similar to TR:E243387 E243387 ORF YGR038W.; mRNA sequence. (from Genbank) |
| 360 | Prostate | 0.5193806 | 0.439154 | 0.371245 | 0.237862 M96843_at | ID2 Inhibitor of DNA binding 2, dominant negative helix-loop-helix protein |
| 361 | Prostate | 0.5193806 | 0.438893 | 0.371117 | 0.237776511 M96843_at-2 | Human striated muscle contraction regulatory protein (Id2B) mRNA, complete cds |
| 362 | Prostate | 0.5182194 | 0.4388778 | 0.37087 | 0.237604259 RC_AA4860 2_at | EST: ab14d08.s1 Stratagene lung (#937210) Homo sapiens cDNA clone 840783 3' similar to TR:G603951 G603951 MRNA.; mRNA sequence. (from Genbank) |
| 363 | Prostate | 0.5179917 | 0.4380459 | 0.370719 | 0.237493638 W07142_at | EST: za92c10.r1 Soares fetal lung NbHL19W Homo sapiens cDNA clone 300018 5', mRNA sequence. (from Genbank) |
| 364 | Prostate | 0.5179279 | 0.4380455 | 0.370419 | 0.237333936 X66534_at | GUANYLATE CYCLASE SOLUBLE, ALPHA-3 CHAIN |
| 365 | Prostate | 0.5174235 | 0.4379379 | 0.370259 | 0.237164411 U26424_at | Stress responsive serine/threonine protein kinase Krs-1 mRNA |
| 366 | Prostate | 0.5173146 | 0.4378173 | 0.370191 | 0.237054054 RC_AA4614 4_at | EST: zx68b01.s1 Soares total fetus Nb2HF8_9w Homo sapiens cDNA clone 796585 3', mRNA sequence. (from Genbank) |
| 367 | Prostate | 0.5171329 | 0.4374064 | 0.370077 | 0.23692276 AA075427_a t | EST: zm87a05.r1 Stratagene ovarian cancer (#937219) Homo sapiens cDNA clone 544880 5', mRNA sequence. (from Genbank) |
| 368 | Prostate | 0.5165435 | 0.4372525 | 0.370068 | 0.236722333 C00337_at | EST: HUMGS0002430, Human Gene Signature, 3'-directed cDNA sequence, mRNA sequence. (from Genbank) |
| 369 | Prostate | 0.5165025 | 0.4367335 | 0.369981 | 0.236627717 RC_AA4313 17_at | EST: zw70d08.s1 Soares testis NHT Homo sapiens cDNA clone 781551 3' similar to TR:E243579 E243579 CHROMOSOME VII READING FRAME ORF YGR255C.; mRNA sequence. (from Genbank) |
| 370 | Prostate | 0.5161634 | 0.4366573 | 0.369967 | 0.236574162 RC_AA4014 52_at | EST: zu56e12.s1 Soares ovary tumor NbHOT Homo sapiens cDNA clone 742030 3', mRNA sequence. (from Genbank) |
| 371 | Prostate | 0.5155192 | 0.4365458 | 0.369517 | 0.236327936 RC_AA0248 66_at | EST: ze79b09.s1 Soares fetal heart NbHH19W Homo sapiens cDNA clone 365177 3', mRNA sequence. (from Genbank) |
| 372 | Prostate | 0.514276 | 0.4362349 | 0.369404 | 0.236293762 S76978_s_at | Prostate-specific membrane antigen {alternatively spliced} [human, primary prostatic tissues, mRNA Partial, 251 nt] |

FIG. 12R

| | | | | | | |
|---|---|---|---|---|---|---|
| 373 | Prostate | 0.5141313 | 0.436129 | 0.369276 | 0.23602082 | M27436_s_at | F3 Coagulation factor III (thromboplastin, tissue factor) |
| 374 | Prostate | 0.513948 | 0.4360542 | 0.369176 | 0.23577218 | AB002344_a_t | Human mRNA for KIAA0346 gene, partial cds |
| 375 | Prostate | 0.513438 | 0.4359814 | 0.36898 | 0.23565511 | RC_AA4477 18_at | EST: aa20c10.s1 Soares NhHMPu S1 Homo sapiens cDNA clone 813810 3', mRNA sequence. (from Genbank) |
| 376 | Prostate | 0.5129824 | 0.4358728 | 0.368935 | 0.23548256 | X04434_at | IGF1R Insulin-like growth factor 1 receptor |
| 377 | Prostate | 0.5129111 | 0.4358144 | 0.368877 | 0.23545301 | RC_AA4599 44_at | EST: zx66a08.s1 Soares total fetus Nb2HF8 9w Homo sapiens cDNA clone 796406 3', mRNA sequence. (from Genbank) |
| 378 | Prostate | 0.5126345 | 0.4357514 | 0.368752 | 0.23536316 | RC_AA2528 93_at | EST: zr76e01.s1 Soares NhHMPu S1 Homo sapiens cDNA clone 669336 3', mRNA sequence. (from Genbank) |
| 379 | Prostate | 0.5122163 | 0.4357111 | 0.36872 | 0.23513953 | R77200_at | EST: yl65g05.r1 Homo sapiens cDNA clone 144152 5'. (from Genbank) |
| 380 | Prostate | 0.512036 | 0.4356674 | 0.368693 | 0.23487738 | RC_AA4339 30_at | EST: zw52e11.s1 Soares total fetus Nb2HF8 9w Homo sapiens cDNA clone 773708 3' similar to contains Alu repetitive element;, mRNA sequence. (from Genbank) |
| 381 | Prostate | 0.5119253 | 0.435622 | 0.368138 | 0.23476673 | RC_AA2325 35_s_at | EST: zr24a12.s1 Stratagene NT2 neuronal precursor 937230 Homo sapiens cDNA clone 664318 3', mRNA sequence. (from Genbank) |
| 382 | Prostate | 0.5118731 | 0.4355272 | 0.368047 | 0.23471372 | H26326_f_at | Ribosomal protein S20 |
| 383 | Prostate | 0.5118585 | 0.4355272 | 0.367978 | 0.23456888 | W45259_at | EST: zc24e10.r1 Soares senescent fibroblasts NbHSF Homo sapiens cDNA clone 323274 5', mRNA sequence. (from Genbank) |
| 384 | Prostate | 0.5117744 | 0.4354133 | 0.367793 | 0.23435543 | RC_AA1910 14_at | EST: zp85g03.s1 Stratagene HeLa cell s3 937216 Homo sapiens cDNA clone 627028 3', mRNA sequence. (from Genbank) |
| 385 | Prostate | 0.5115058 | 0.43518819 | 0.367526 | 0.23426354 | S74728_at | Antiquitin |
| 386 | Prostate | 0.5112071 | 0.4351701 | 0.36745 | 0.23409894 | RC_AA4821 27_at | Homo sapiens mRNA for PAK4 protein |
| 387 | Prostate | 0.5103671 | 0.4351701 | 0.367215 | 0.23400894 | D82344_at | NBPhox |
| 388 | Prostate | 0.5103671 | 0.4351673 | 0.367211 | 0.23384629 | D82344_at-2 | Paired mesoderm homeobox 2b |
| 389 | Prostate | 0.5097561 | 0.4350255 | 0.367121 | 0.23378049 | U44111_at | Histamine N-methyltransferase |
| 390 | Prostate | 0.5088751 | 0.4349452 | 0.366978 | 0.2336974 | U33921_at | HSU33921 Clontech adult lung cDNA library (HL1158a) Homo sapiens cDNA clone L1-204, mRNA sequence |
| 391 | Prostate | 0.5087709 | 0.4347852 | 0.366966 | 0.23364335 | AA249437_a_t | EST: j3966.seq.F Human fetal heart, Lambda ZAP Express Homo sapiens cDNA 5', mRNA sequence. (from Genbank) |
| 392 | Prostate | 0.5086383 | 0.4345133 | 0.366412 | 0.23348135 | RC_AA0273 17_at | EST: ze97d11.s1 Soares fetal heart NbHH19W Homo sapiens cDNA clone 366033 3' similar to contains Alu repetitive element;, mRNA sequence. (from Genbank) |

FIG. 12S

| # | Tissue | Val1 | Val2 | Val3 | ID1 | ID2 | Description |
|---|---|---|---|---|---|---|---|
| 393 | Prostate | 0.5084479 | 0.434114 | 0.366371 | 0.233340301 | AA234141_s_at | Homo sapiens katanin p80 subunit mRNA, complete cds |
| 394 | Prostate | 0.507778 | 0.433728 | 0.36621 | 0.233328044 | RC_AA0562 47_at | Homo sapiens clone 24511 mRNA sequence |
| 395 | Prostate | 0.5074742 | 0.4334349 | 0.366182 | 0.233319981 | RC_AA5999 91_at | EST: ag28h10.s1 Jia bone marrow stroma Homo sapiens cDNA clone 1090915 3', mRNA sequence. (from Genbank) |
| 396 | Prostate | 0.5061113 | 0.4333497 | 0.365948 | 0.233315383 | U42359_at | N33 protein form 1 (N33) gene, exon 10 and complete cds |
| 397 | Prostate | 0.5060412 | 0.433254 | 0.365916 | 0.233307365 | RC_AA6204 46_at | RecQ protein-like 4 |
| 398 | Prostate | 0.5058664 | 0.4329896 | 0.365734 | 0.233275709 | RC_AA6207 95_at | EST: af95b02.s1 Soares testis NHT Homo sapiens cDNA clone 1055499 3', mRNA sequence. (from Genbank) |
| 399 | Prostate | 0.5058322 | 0.4329538 | 0.365642 | 0.233263827 | AA365742_s_at | EST: EST76593 Pineal gland II Homo sapiens cDNA 5' end, mRNA sequence. (from Genbank) |
| 400 | Prostate | 0.5056704 | 0.4327875 | 0.365454 | 0.232244311 | RC_AA1428 58_at | EST: zi40e04.s1 Soares pregnant uterus NbHPU Homo sapiens cDNA clone 504414 3', mRNA sequence. (from Genbank) |
| 401 | Prostate | 0.50539 | 0.432649 | 0.365414 | 0.232237228 | RC_AA4475 49_at | UDP-N-acetylglucosamine pyrophosphorylase 1; Sperm associated antigen 2 |
| 402 | Prostate | 0.5051856 | 0.4325792 | 0.365358 | 0.232225614 | D79601_f_at | EST: Human aorta cDNA 5'-end GEN-286G10, mRNA sequence. (from Genbank) |
| 403 | Prostate | 0.5051112 | 0.4325317 | 0.365193 | 0.232214176 | RC_AA4460 27_s_at | Early growth response 2 (Krox-20 (Drosophila) homolog) |
| 404 | Prostate | 0.5050933 | 0.4323327 | 0.365033 | 0.23185767 | RC_AA5984 61_at | EST: ae48h01.s1 Stratagene lung carcinoma 937218 Homo sapiens cDNA clone 950161 3', mRNA sequence. (from Genbank) |
| 405 | Prostate | 0.5045458 | 0.432308 | 0.364953 | 0.23177072 | RC_AA5991 44_at | Myosin phosphatase, target subunit 1 |
| 406 | Prostate | 0.5045164 | 0.4320883 | 0.364724 | 0.23158269 | U67156_at | Mitogen-activated kinase kinase kinase 5 (MAPKKK5) mRNA |
| 407 | Prostate | 0.5041468 | 0.4319305 | 0.364624 | 0.2314845 | RC_D25718_at | EST: Human colon 3'directed MboI cDNA, HUMGS04084, clone cm1380, mRNA sequence. (from Genbank) |
| 408 | Prostate | 0.5040523 | 0.4319247 | 0.36458 | 0.231140244 | U30313_at | Diadenosine tetraphosphatase mRNA |
| 409 | Prostate | 0.5039243 | 0.4319012 | 0.364411 | 0.2313318 | N42196_at | Homo sapiens clone 486790 diphosphoinositol polyphosphate phosphohydrolase mRNA, complete cds |
| 410 | Prostate | 0.5037817 | 0.4318748 | 0.36426 | 0.23119189 | W37398_at | EST: zc11a10.r1 Soares parathyroid tumor NbHPA Homo sapiens cDNA clone 321978 5', mRNA sequence. (from Genbank) |
| 411 | Prostate | 0.5033535 | 0.4316391 | 0.364181 | 0.231117846 | RC_AA3941 62_at | EST: zt52c08.s1 Soares ovary tumor NbHOT Homo sapiens cDNA clone 725966 3', mRNA sequence. (from Genbank) |
| 412 | Prostate | 0.5030174 | 0.4316218 | 0.363993 | 0.2308602 | N75889_f_at | EST: yw32h06.r1 Homo sapiens cDNA clone 253979 5'. (from Genbank) |

FIG. 12T

| # | Tissue | | | | Description |
|---|---|---|---|---|---|
| 413 | Prostate | 0.5025252 | 0.4315696 | 0.363954 | 0.23076434 J02783_at | P4HB Procollagen-proline, 2-oxoglutarate 4-dioxygenase (proline 4-hydroxylase), beta polypeptide (protein disulfide isomerase; thyroid hormone binding protein p55) |
| 414 | Prostate | 0.5021772 | 0.4315063 | 0.363944 | 0.23065019 S49953_s_at | N-cym |
| 415 | Prostate | 0.5020724 | 0.4314967 | 0.363845 | 0.23051204 D57737_at | EST: Human aorta cDNA 5'-end GEN-323G06, mRNA sequence. (from Genbank) |
| 416 | Prostate | 0.5019936 | 0.4313687 | 0.363671 | 0.23036776 X66785_i_at | Dihydrolipoamide branched chain transacylase (E2 component of branched chain keto acid dehydrogenase complex; maple syrup urine disease) |
| 417 | Prostate | 0.5018032 | 0.431357 | 0.363346 | RC_AA4960 0.23029144 37_at | EST: zv72d08.s1 Soares total fetus Nb2HF8 9w Homo sapiens cDNA clone 759183 3', mRNA sequence. (from Genbank) |
| 418 | Prostate | 0.5017911 | 0.4312735 | 0.36321 | 0.23011512 L36531_at-2 | Integrin, alpha 8 |
| 419 | Prostate | 0.5017911 | 0.4312611 | 0.363195 | 0.2297981 L36531_at | Integrin alpha 8 subunit mRNA, 3' end |
| 420 | Prostate | 0.5014889 | 0.4309902 | 0.363073 | RC_AA4545 0.22967741 97_s_at | EST: zx96a12.s1 Soares ovary tumor NbHOT Homo sapiens cDNA clone 811582 3', mRNA sequence. (from Genbank) |
| 421 | Prostate | 0.5013135 | 0.4309738 | 0.362968 | 0.22950125 D31763_at | KIAA0065 gene, partial cds |
| 422 | Prostate | 0.5007668 | 0.4309557 | 0.362946 | RC_AA0294 0.22949994 62_at | EST: ze96g03.s1 Soares fetal heart NbHH19W Homo sapiens cDNA clone 366868 3', mRNA sequence. (from Genbank) |
| 423 | Prostate | 0.5003974 | 0.4307732 | 0.362933 | 0.22294932 18_s_at | EST: aa51c06.s1 NCI_CGAP_GCB1 Homo sapiens cDNA clone IMAGE:824458 3', mRNA sequence. (from Genbank) |
| 424 | Prostate | 0.5003853 | 0.4307364 | 0.362748 | 0.22936775 X93036_at | MAT8 protein |
| 425 | Prostate | 0.5002678 | 0.4307352 | 0.362639 | H89551_s_a 0.22924876 t | EST: yw28e07.r1 Homo sapiens cDNA clone 253572 5'. (from Genbank) |
| 426 | Prostate | 0.4997987 | 0.4307112 | 0.362483 | AF001900_a 0.22911148 t | Secreted frizzled-related protein 1 |
| 427 | Prostate | 0.4997084 | 0.4307112 | 0.362483 | AA285284_a 0.228931159 t | Homo sapiens NADP-dependent isocitrate dehydrogenase (IDH) mRNA, complete cds |
| 428 | Prostate | 0.4994963 | 0.4306861 | 0.362167 | 0.22289285 T28246_at | Hepsin (transmembrane protease, serine 1) |
| 429 | Prostate | 0.4993705 | 0.4306297 | 0.362144 | RC_AA4769 0.22859085 22_at | EST: zu38c05.s1 Soares ovary tumor NbHOT Homo sapiens cDNA clone 740264 3', mRNA sequence. (from Genbank) |
| 430 | Prostate | 0.4989584 | 0.4302877 | 0.362113 | RC_AA4317 0.22854143 99_at | EST: zw80h06.s1 Soares testis NHT Homo sapiens cDNA clone 782555 3', mRNA sequence. (from Genbank) |
| 431 | Prostate | 0.4989091 | 0.4299843 | 0.36206 | 0.22837944 L39833_at | K+ channel beta 1a subunit mRNA, alternatively spliced |
| 432 | Prostate | 0.4988997 | 0.429983 | 0.361745 | 0.2282243 AB002308_a t | KIAA0310 gene product |
| 433 | Prostate | 0.4986846 | 0.4299813 | 0.361609 | 0.22813979 D00723_at | GCSH Glycine cleavage system protein H (aminomethyl carrier) |
| 434 | Prostate | 0.4986771 | 0.4298061 | 0.361478 | 0.2280336 D45370_at | ApM2 mRNA for GS2374 (unknown product specific to adipose tissue) |

FIG. 12U

| | | | | | | |
|---|---|---|---|---|---|---|
| 435 | Prostate | 0.4983941 | 0.4297482 | 0.361461 | 0.227818888 39_at | RC_AA4777 | EST: zu34a07.s1 Soares ovary tumor NbHOT Homo sapiens cDNA clone 739860 3', mRNA sequence. (from Genbank) |
| 436 | Prostate | 0.4983423 | 0.4296413 | 0.361444 | 0.227758767 | D49387_at | NADP dependent leukotriene b4 12-hydroxydehydrogenase, partial cds |
| 437 | Prostate | 0.4981293 | 0.4295896 | 0.361072 | 0.2275285 27_s_at | RC_AA2924 | EST: zt28g07.s1 Soares ovary tumor NbHOT Homo sapiens cDNA clone 714492 3' similar to TR:E91187 E91187 NMDA RECEPTOR GLUTAMATE-BINDING SUBUNIT. ;, mRNA sequence. (from Genbank) |
| 438 | Prostate | 0.4976596 | 0.429543 | 0.360954 | 0.22744726 | U30894_at | N-sulphoglucosamine sulphohydrolase mRNA |
| 439 | Prostate | 0.4975875 | 0.4292265 | 0.360909 | 0.227331124 7_at | RC_AA4339 | EST: zw52g10.s1 Soares total fetus Nb2HF8 9w Homo sapiens cDNA clone 773730 3', mRNA sequence. (from Genbank) |
| 440 | Prostate | 0.4973697 | 0.4291074 | 0.360864 | 0.227722267 55_at | RC_AA4528 | Human mannose-specific lectin (MR60) mRNA, complete cds |
| 441 | Prostate | 0.4973115 | 0.4290175 | 0.360665 | 0.227113325 | S62539_at | Insulin receptor substrate-1 [human, skeletal muscle, mRNA, 5828 nt] |
| 442 | Prostate | 0.497174 | 0.4290175 | 0.360505 | 0.227704089 77_s_at | RC_AA4479 | EST: zw82e09.s1 Soares testis NHT Homo sapiens cDNA clone 782728 3', mRNA sequence. (from Genbank) |
| 443 | Prostate | 0.4970815 | 0.4289598 | 0.360425 | 0.226988799 | L04270_at | LYMPHOTOXIN-BETA RECEPTOR PRECURSOR |
| 444 | Prostate | 0.4967847 | 0.4289326 | 0.360265 | 0.226745 1 | AA137153_a t | EST: zv61b01.r1 Soares testis NHT Homo sapiens cDNA clone 758089 5', mRNA sequence. (from Genbank) |
| 445 | Prostate | 0.4966342 | 0.4288378 | 0.360156 | 0.226664878 04_at | RC_AA4045 | EST: zw38b09.s1 Soares total fetus Nb2HF8 9w Homo sapiens cDNA clone 772313 3', mRNA sequence. (from Genbank) |
| 446 | Prostate | 0.4960628 | 0.4288147 | 0.359983 | 0.226576886 28_at | RC_AA1509 | EST: zl47e06.s1 Soares pregnant uterus NbHPU Homo sapiens cDNA clone 505090 3', mRNA sequence. (from Genbank) |
| 447 | Prostate | 0.4958171 | 0.4287976 | 0.359918 | 0.226441 19_at | RC_AA0432 | EST: zk55g09.s1 Soares pregnant uterus NbHPU Homo sapiens cDNA clone 486784 3' similar to contains Alu repetitive element;contains element MER27 repetitive element.;, mRNA sequence. (from Genbank) |
| 448 | Prostate | 0.4952663 | 0.4287861 | 0.359822 | 0.226328281 93_at | RC_AA2812 | EST: zt02h12.s1 NCI_CGAP_GCB1 Homo sapiens cDNA clone IMAGE:712007 3' similar to SW:IPYR_BOVIN P37980 INORGANIC PYROPHOSPHATASE .;, mRNA sequence. (from Genbank) |
| 449 | Prostate | 0.4952615 | 0.4287541 | 0.359787 | 0.226068356 3_at | RC_AA4120 | EST: zu10b08.s1 Soares testis NHT Homo sapiens cDNA clone 731415 3', mRNA sequence. (from Genbank) |
| 450 | Prostate | 0.4951125 | 0.4287541 | 0.359637 | 0.226026426 | AA405288_a t | EST: zt37f09.r1 Soares ovary tumor NbHOT Homo sapiens cDNA clone 724553 5' similar to contains Alu repetitive element;contains element LTR5 repetitive element.;, mRNA sequence. (from Genbank) |
| 451 | Prostate | 0.4945203 | 0.4280362 | 0.359528 | 0.225849171_at | RC_AA1364 | EST: zl01e08.s1 Soares pregnant uterus NbHPU Homo sapiens cDNA clone 491078 3', mRNA sequence. (from Genbank) |

FIG. 12V

| | | | | | |
|---|---|---|---|---|---|
| 452 | Prostate | 0.4943693 | 0.4279348 | 0.359308 | 0.2257586 | D79998_at | KIAA0176 gene, partial cds |
| 453 | Prostate | 0.4940013 | 0.4277588 | 0.359284 | RC_AA2932 66_at | EST: zt28b08.s1 Soares ovary tumor NbHOT Homo sapiens cDNA clone 714423 3', mRNA sequence. (from Genbank) |
| 454 | Prostate | 0.4931679 | 0.4277523 | 0.359066 | 0.22562273 | W68097_at | EST: zd41b11.r1 Soares fetal heart NbHH19W Homo sapiens cDNA clone 343197 5', mRNA sequence. (from Genbank) |
| 455 | Prostate | 0.4929107 | 0.4276916 | 0.35891 | 0.22553377 | U94831_at | Multispanning membrane protein mRNA |
| 456 | Prostate | 0.4929107 | 0.4276341 | 0.358744 | 0.22534484 | U94831_at-2 | Homo sapiens multispanning membrane protein mRNA, complete cds |
| 457 | Prostate | 0.49254 | 0.4273988 | 0.358661 | 0.22523685 | U01833_at | Nucleotide-binding protein mRNA |
| 458 | Prostate | 0.4921792 | 0.427328 | 0.358592 | 0.22501433 | D79601_i_at | EST: Human aorta cDNA 5'-end GEN-286G10, mRNA sequence. (from Genbank) |
| 459 | Prostate | 0.4918219 | 0.4272743 | 0.358471 | 0.22495238 | W27827_at | Homo sapiens KIAA0439 mRNA, partial cds |
| 460 | Prostate | 0.4899189 | 0.4271086 | 0.358294 | AA461426_r_at | EST: zx63h02.r1 Soares total fetus Nb2HF8 9w Homo sapiens cDNA clone 796179 5', mRNA sequence. (from Genbank) |
| 461 | Prostate | 0.4896146 | 0.4269415 | 0.358184 | RC_AA0561 93_at | EST: zl65e03.s1 Stratagene colon (#937204) Homo sapiens cDNA clone 509500 3' similar to TR:G809573 G809573 GLUTAREDOXIN.; mRNA sequence. (from Genbank) |
| 462 | Prostate | 0.4892179 | 0.4265257 | 0.358165 | 0.2246568 | X54162_at | 64 KD AUTOANTIGEN D1 |
| 463 | Prostate | 0.4891504 | 0.4265034 | 0.357963 | RC_AA0766 72_at | EST: zm20g08.s1 Stratagene pancreas (#937208) Homo sapiens cDNA clone 526238 3', mRNA sequence. (from Genbank) |
| 464 | Prostate | 0.4885833 | 0.4261915 | 0.357701 | 0.22340072 | L44367_at | EST: Homo sapiens thymus mRNA (randomly primed, normalized), single-pass sequence, mRNA sequence. (from Genbank) |
| 465 | Prostate | 0.4881712 | 0.4258363 | 0.357693 | RC_AA4550 87_at | EST: aa04e08.s1 Soares NhHMPu S1 Homo sapiens cDNA clone 812294 3', mRNA sequence. (from Genbank) |
| 466 | Prostate | 0.4879358 | 0.4258225 | 0.357538 | 0.22414841 | R73982_at | EST: yi56e02.r1 Homo sapiens cDNA clone 143258 5'. (from Genbank) |
| 467 | Prostate | 0.487839 | 0.4257926 | 0.357456 | RC_AA4763 52_at | EST: zw99e08.s1 Soares total fetus Nb2HF8 9w Homo sapiens cDNA clone 785126 3', mRNA sequence. (from Genbank) |
| 468 | Prostate | 0.4878324 | 0.425725 | 0.357397 | 0.22383511 | M98343_at | Amplaxin (EMS1) mRNA |
| 469 | Prostate | 0.4870774 | 0.425725 | 0.357278 | 0.22368766 | U03608_at | CYP1B1 Cytochrome P450 IB1 (dioxin-inducible) |
| 470 | Prostate | 0.4870743 | 0.4257187 | 0.357069 | RC_AA1668 10_at | EST: zo87a05.s1 Stratagene ovarian cancer (#937219) Homo sapiens cDNA clone 593840 3', mRNA sequence. (from Genbank) |
| 471 | Prostate | 0.4869723 | 0.4257183 | 0.357045 | RC_AA2362 41_at | EST: zr51e07.s1 Soares NhHMPu S1 Homo sapiens cDNA clone 666948 3', mRNA sequence. (from Genbank) |
| 472 | Prostate | 0.4674469 | 0.4256854 | 0.356695 | 0.22333422 | RC_AA5987 25_at | Endothelial differentiation-related factor 1 |
| 473 | Prostate | 0.4867377 | 0.425673 | 0.356906 | 0.22316931 | M18533_at | DMD Dystrophin (muscular dystrophy, Duchenne and Becker types) |

FIG. 12W

| # | Tissue | | | | ID | Description |
|---|---|---|---|---|---|---|
| 474 | Prostate | 0.4866144 | 0.4255597 | 0.2230886 | RC_AA024622_at | Solute carrier family 22 (organic cation transporter), member 5 |
| 475 | Prostate | 0.4865256 | 0.4254746 | 0.2229704 | RC_AA255617_at | EST: zs31b05.s1 NCI_CGAP_GCB1 Homo sapiens cDNA clone IMAGE:6867769 3', mRNA sequence. (from Genbank) |
| 476 | Prostate | 0.4864205 | 0.4252388 | 0.22286671 | D10040_at | FACL1 Long chain fatty acid acyl-coA ligase |
| 477 | Prostate | 0.4863043 | 0.4251491 | 0.22274701 | R29657_at | Eukaryotic translation elongation factor 1 delta (guanine nucleotide exchange protein) |
| 478 | Prostate | 0.4854397 | 0.4249058 | 0.22263481 | M14200_ma_at | Diazepam binding inhibitor (DBI) mRNA |
| 479 | Prostate | 0.4852038 | 0.4247776 | 0.22256811 | AA046840_a_at | CCAAT/enhancer binding protein (C/EBP), delta |
| 480 | Prostate | 0.4851553 | 0.4243332 | 0.22244516 | M31627_at | X BOX BINDING PROTEIN-1 |
| 481 | Prostate | 0.4850763 | 0.4242047 | 0.22232372 | AA428006_a_at | H.sapiens gene from PAC 295C6, similar to rat PO44 |
| 482 | Prostate | 0.4841552 | 0.4241798 | 0.22222532 | RC_AA489091_at | EST: aa56g08.s1 NCI_CGAP_GCB1 Homo sapiens cDNA clone IMAGE:824990 3', mRNA sequence. (from Genbank) |
| 483 | Prostate | 0.4831136 | 0.4241585 | 0.22216727 | D50063_at | Proteasome subunit p40 / Mov34 protein |
| 484 | Prostate | 0.4831136 | 0.4241585 | 0.22220622 | D50063_at-2 | Proteasome (prosome, macropain) 26S subunit, non-ATPase, 7 (Mov34 homolog) |
| 485 | Prostate | 0.4828214 | 0.4238142 | 0.22195727 | D82060_at | Kidney mRNA for putative membrane protein with histidine rich charge clusters |
| 486 | Prostate | 0.4827728 | 0.4236276 | 0.22181395 | RC_AA449435_at | EST: zx05c11.s1 Soares total fetus Nb2HF8 9w Homo sapiens cDNA clone 785588 3', mRNA sequence. (from Genbank) |
| 487 | Prostate | 0.4823512 | 0.4235345 | 0.22179504 | AA228148_s_at | EST: zr58d07.r1 Soares NhHMPu S1 Homo sapiens cDNA clone 667597 5', mRNA sequence. (from Genbank) |
| 488 | Prostate | 0.4823498 | 0.4234478 | 0.22165026 | AA233231_t | EST: zr69c12.r1 Soares NhHMPu S1 Homo sapiens cDNA clone 668662 5', mRNA sequence. (from Genbank) |
| 489 | Prostate | 0.4822123 | 0.4232519 | 0.2214981 | AA173998_a_at | Homo sapiens katanin p80 subunit mRNA, complete cds |
| 490 | Prostate | 0.4819391 | 0.4230056 | 0.22142391 | D16469_at | ORF, Xq terminal portion |
| 491 | Prostate | 0.4818828 | 0.4228583 | 0.22124158 | L04510_at | Nucleotide binding protein mRNA |
| 492 | Prostate | 0.4813539 | 0.4228233 | 0.22114493 | RC_AA1568_73_t | EST: zl20h08.s1 Soares pregnant uterus NbHPU Homo sapiens cDNA clone 502527 3', mRNA sequence. (from Genbank) |
| 493 | Prostate | 0.4813514 | 0.422763 | 0.22105758 | AA045870_a_t | EST: zk75a04.r1 Soares pregnant uterus NbHPU Homo sapiens cDNA clone 488622 5', mRNA sequence. (from Genbank) |
| 494 | Prostate | 0.4812442 | 0.4227255 | 0.2209206 | X78706_at | CRAT Carnitine acetyltransferase |
| 495 | Prostate | 0.4812403 | 0.4225861 | 0.2208542 | RC_AA232208_at | EST: zr45e02.s1 Soares NhHMPu S1 Homo sapiens cDNA clone 666362 3' similar to contains Alu repetitive element;contains PTR7 repetitive element :, mRNA sequence. (from Genbank) |

FIG. 12X

| | | | | | | |
|---|---|---|---|---|---|---|
| 496 | Prostate | 0.481186 | 0.4221488 | 0.354702 | 0.22080989 | RC_AA2513 30_at | EST: zs04g12.s1 NCI_CGAP_GCB1 Homo sapiens cDNA clone IMAGE:684262 3', mRNA sequence. (from Genbank) |
| 497 | Prostate | 0.481183 | 0.4220813 | 0.35467 | 0.22073023 | RC_AA4890 09_at | EST: aa54d11.s1 NCI_CGAP_GCB1 Homo sapiens cDNA clone IMAGE:824757 3', mRNA sequence. (from Genbank) |
| 498 | Prostate | 0.4811459 | 0.4220557 | 0.354497 | 0.22046477 | AA206983_a t | EST: zq50h02.r1 Stratagene neuroepithelium (#937231) Homo sapiens cDNA clone 645075 5' similar to contains Alu repetitive element;contains element MER22 repetitive element ;. mRNA sequence. (from Genbank) |
| 499 | Prostate | 0.4809305 | 0.421865 | 0.354449 | 0.22043318 | RC_AA4854 24_at | EST: zx90e04.s1 Soares ovary tumor NbHOT Homo sapiens cDNA clone 811038 3', mRNA sequence. (from Genbank) |
| 500 | Prostate | 0.480412 | 0.4218177 | 0.354073 | 0.22032848 | RC_AA4432 77_at | Peroxisomal biogenesis factor 11A |
| 501 | Prostate | 0.4803762 | 0.4217586 | 0.353912 | 0.21999514 | X61755_rna 1_s_at | HOX3D gene for homeoprotein HOX3D |
| 502 | Prostate | 0.4802926 | 0.4216798 | 0.353867 | 0.21993512 | RC_AA4294 78_at | EST: zw34c05.s1 Soares ovary tumor NbHOT Homo sapiens cDNA clone 771176 3', mRNA sequence. (from Genbank) |
| 503 | Prostate | 0.4802088 | 0.421679 | 0.353592 | 0.21988717 | U78095_at | Placental bikunin mRNA |
| 504 | Prostate | 0.4799088 | 0.4216203 | 0.353571 | 0.21978256 | RC_AA4177 61_at | Homo sapiens clone 24416 mRNA sequence |
| 505 | Prostate | 0.4798356 | 0.4216003 | 0.353392 | 0.21974431 | RC_AA4322 70_at | EST: zw78f04.s1 Soares testis NHT Homo sapiens cDNA clone 782335 3', mRNA sequence. (from Genbank) |
| 506 | Prostate | 0.4797888 | 0.4216003 | 0.353392 | 0.21964496 | RC_AA0263 88_at | EST: ze92c03.s1 Soares fetal heart NbHH19W Homo sapiens cDNA clone 366436 3', mRNA sequence. (from Genbank) |
| 507 | Prostate | 0.4792092 | 0.4214622 | 0.353334 | 0.2195449 | M30894_at | TCRG T cell receptor gamma chain |
| 508 | Prostate | 0.4790092 | 0.4212152 | 0.353201 | 0.21933801 | RC_AA4417 98_at | EST: zw62c11.s1 Soares total fetus Nb2HF8 9w Homo sapiens cDNA clone 774644 3' similar to TR:G207250 G207250 RAT GROWTH AND TRANSFORMATION-DEPENDENT ;. mRNA sequence. (from Genbank) |
| 509 | Prostate | 0.4789818 | 0.4211292 | 0.353141 | 0.21928045 | RC_AA4436 76_at | EST: zw86c05.s1 Soares total fetus Nb2HF8 9w Homo sapiens cDNA clone 783848 3', mRNA sequence. (from Genbank) |
| 510 | Prostate | 0.4787184 | 0.4210449 | 0.35311 | 0.21916084 | C01782_at | EST: HUMGS0003737, Human Gene Signature, 3'-directed cDNA sequence, mRNA sequence. (from Genbank) |
| 511 | Prostate | 0.4786262 | 0.4209897 | 0.352866 | 0.21903756 | M16364_s_a t | CKB Creatine kinase B |
| 512 | Prostate | 0.4782155 | 0.4208801 | 0.352788 | 0.21891852 | RC_AA2906 79_at | Selenium binding protein 1 |
| 513 | Prostate | 0.4781523 | 0.4207286 | 0.352571 | 0.21888942 | RC_AA2825 18_at | EST: zs90b04.s1 NCI_CGAP_GCB1 Homo sapiens cDNA clone IMAGE:704719 3', mRNA sequence. (from Genbank) |
| 514 | Prostate | 0.4773699 | 0.4207286 | 0.352469 | 0.21872292 | RC_AA4551 08_at | Homo sapiens mRNA for GEF-2 protein |

FIG. 12Y

| | | | | | |
|---|---|---|---|---|---|
| 515 | Prostate | 0.4768436 | 0.4205802 | 0.352194 | 0.21862721 | D10704_at | CHK Choline kinase |
| 516 | Prostate | 0.4764953 | 0.4205383 | 0.352097 | 0.21852232 | L00354_at | PROCHOLECYSTOKININ PRECURSOR |
| 517 | Prostate | 0.4763672 | 0.4205153 | 0.352063 | 0.21843252 | U46499_at | GLUTATHIONE S-TRANSFERASE, MICROSOMAL |
| 518 | Prostate | 0.476211 | 0.4202813 | 0.351986 | 0.21837524 | H51340_at | EST: yo30c06.r1 Homo sapiens cDNA clone 179434 5'. (from Genbank) |
| 519 | Prostate | 0.4761674 | 0.4202813 | 0.351861 | 0.21828333 | RC_AA2436 95_at | Deoxynucleotidyltransferase, terminal |
| 520 | Prostate | 0.4760428 | 0.4201604 | 0.351799 | 0.21801597 | RC_AA4894 78_f_at | Ribosomal protein L33-like |
| 521 | Prostate | 0.475884 | 0.4199514 | 0.351773 | 0.21790563 | X76057_at | MPI Mannose phosphate isomerase |
| 522 | Prostate | 0.4758772 | 0.4198275 | 0.351739 | 0.21784933 | AA482319_f_at | EST: ab15c03.r1 Stratagene lung (#937210) Homo sapiens cDNA clone 840868 5', mRNA sequence. (from Genbank) |
| 523 | Prostate | 0.475772 | 0.4198064 | 0.351663 | 0.21773437 | R97442_s_at | EST: yq53b01.r1 Homo sapiens cDNA clone 199465 5'. (from Genbank) |
| 524 | Prostate | 0.4753561 | 0.4197453 | 0.351588 | 0.21755999 | AB004066_a_at | Differentiated Embryo Chondrocyte expressed gene 1 |
| 525 | Prostate | 0.475234 | 0.4197453 | 0.351401 | 0.21755995 | RC_AA4361 74_at | EST: zv22d06.r1 Soares NhHMPu S1 Homo sapiens cDNA clone 754379 3' similar to contains Alu repetitive element;contains L1.t3 L1 repetitive element.; mRNA sequence. (from Genbank) |
| 526 | Prostate | 0.4750778 | 0.4195409 | 0.351396 | 0.21744862 | RC_AA0567 35_at | KIAA0755 gene product |
| 527 | Prostate | 0.4748892 | 0.4194762 | 0.35135 | 0.21739009 | AA173597_a_t | EST: zp03c08.r1 Stratagene ovarian cancer (#937219) Homo sapiens cDNA clone 595310 5', mRNA sequence. (from Genbank) |
| 528 | Prostate | 0.4748345 | 0.4192931 | 0.351324 | 0.21717148 | RC_AA1739 81_at | EST: zp03e05.r1 Stratagene ovarian cancer (#937219) Homo sapiens cDNA clone 595328 3', mRNA sequence. (from Genbank) |
| 529 | Prostate | 0.4745788 | 0.4192803 | 0.351137 | 0.21705941 | RC_AA0446 01_at | EST: zk55d05.s1 Soares pregnant uterus NbHPU Homo sapiens cDNA clone 486729 3', mRNA sequence. (from Genbank) |
| 530 | Prostate | 0.4744635 | 0.4191549 | 0.351101 | 0.21696733 | RC_AA4471 23_at | EST: zw93c01.s1 Soares total fetus Nb2HF8 9w Homo sapiens cDNA clone 784512 3', mRNA sequence. (from Genbank) |
| 531 | Prostate | 0.4741087 | 0.4189834 | 0.351053 | 0.21684709 | HG2743-HT2846_s_at | Caldesmon 1, Alt. Splice 4, Non-Muscle |
| 532 | Prostate | 0.473874 | 0.4186851 | 0.350898 | 0.21673721 | D87969_at | CMP-sialic acid transporter |
| 533 | Prostate | 0.4734711 | 0.4185752 | 0.350805 | 0.21658084 | X87176_at | 17-beta-hydroxysteroid dehydrogenase |
| 534 | Prostate | 0.4734324 | 0.4185299 | 0.350727 | 0.21650496 | T30341_s_at | Human Chromosome 16 BAC clone CIT987SK-A-211C6 |
| 535 | Prostate | 0.4733933 | 0.418521 | 0.350727 | 0.2164181 | X76061_at | P130 mRNA for 130K protein |
| 536 | Prostate | 0.4733506 | 0.4183221 | 0.350716 | 0.21631354 | D55696_at | Cysteine protease |

FIG. 12Z

| | | | | | |
|---|---|---|---|---|---|
| 537 | Prostate | 0.4733381 | 0.4180539 | 0.350697 | 0.2161799 | M23294_at | HEXB Hexosaminidase B (beta polypeptide) |
| 538 | Prostate | 0.4731357 | 0.4180054 | 0.350641 | 0.21603681 | HG1067-HT1067_r_at | Mucin (Gb:M22406) |
| 539 | Prostate | 0.4729984 | 0.4179926 | 0.350379 | 0.21597473 | D45906_at | LIMK-2 |
| 540 | Prostate | 0.4721035 | 0.417973 | 0.350323 | 0.2158746 | RC_AA055829_at | EST: zf21d10.s1 Soares fetal heart NbHH19W Homo sapiens cDNA clone 377587 3' similar to contains Alu repetitive element;, mRNA sequence. (from Genbank) |
| 541 | Prostate | 0.4720426 | 0.4179134 | 0.350138 | 0.21556876 | RC_AA147067_at | EST: zo32a02.s1 Stratagene colon (#937204) Homo sapiens cDNA clone 588554 3', mRNA sequence. (from Genbank) |
| 542 | Prostate | 0.4718402 | 0.4178899 | 0.350048 | 0.21560808 | U17989_at | Nuclear autoantigen GS2NA mRNA |
| 543 | Prostate | 0.4713742 | 0.4175566 | 0.349994 | 0.21535192 | X77366_at | TCF11 Transcription factor 11 (basic leucine zipper type) |
| 544 | Prostate | 0.4709698 | 0.4175141 | 0.349889 | 0.21527556 | N78005_at | Homo sapiens SRp46 splicing factor retropseudogene mRNA |
| 545 | Prostate | 0.4709955 | 0.4174214 | 0.349677 | 0.215255861 | X14885_rna1_s_at | Transforming growth factor-beta 3 (TGF-beta 3) exon 1 (and joined CDS) |
| 546 | Prostate | 0.4708366 | 0.4172009 | 0.349609 | 0.21514435 | RC_AA397779_at | EST: zt72d01.s1 Soares testis NHT Homo sapiens cDNA clone 727873 3', mRNA sequence. (from Genbank) |
| 547 | Prostate | 0.4705275 | 0.4171824 | 0.349549 | 0.21513969 | AA465601_at | EST: aa24h10.r1 NCI_CGAP_GCB1 Homo sapiens cDNA clone IMAGE:814243 5', mRNA sequence. (from Genbank) |
| 548 | Prostate | 0.4703622 | 0.4170886 | 0.34942 | 0.21497187 | D87127_at | Translocation protein-1 |
| 549 | Prostate | 0.4700913 | 0.4168933 | 0.349251 | 0.21484044 | M28713_at | NADH-CYTOCHROME B5 REDUCTASE |
| 550 | Prostate | 0.470028 | 0.4168479 | 0.349171 | 0.21475515 | D81608_at | Polymerase (RNA) II (DNA directed) polypeptide L (7.6kD) |
| 551 | Prostate | 0.469882 | 0.4167889 | 0.348713 | 0.21462978 | AF000234_at | P2x purinoceptor mRNA |
| 552 | Prostate | 0.4698817 | 0.4164996 | 0.348495 | 0.21451737 | U52100_at | XMP mRNA |
| 553 | Prostate | 0.4696866 | 0.4163142 | 0.348487 | 0.21440569 | RC_AA256067_at | EST: zs29e03.s1 NCI_CGAP_GCB1 Homo sapiens cDNA clone IMAGE:686620 3' similar to TR:G529430 G529430 GUANINE NUCLEOTIDE EXCHANGE FACTOR, EIF-2B, DELTA SUBUNIT. [1]; mRNA sequence. (from Genbank) |
| 554 | Prostate | 0.4694013 | 0.4163142 | 0.348367 | 0.21437782 | RC_AA431462_at | EST: zw70g01.s1 Soares testis NHT Homo sapiens cDNA clone 781584 3', mRNA sequence. (from Genbank) |
| 555 | Prostate | 0.469375 | 0.4163111 | 0.348321 | 0.21433653 | D14658_at | KIAA0102 gene |
| 556 | Prostate | 0.4687887 | 0.4161404 | 0.348149 | 0.21426697 | RC_AA137034_at | EST: zl02c01.s1 Soares pregnant uterus NbHPU Homo sapiens cDNA clone 491136 3' similar to contains element THR repetitive element;, mRNA sequence. (from Genbank) |
| 557 | Prostate | 0.4684328 | 0.4161023 | 0.348095 | 0.21415664 | RC_AA236455_r_at | EST: zr75g02.s1 Soares NhHMPu S1 Homo sapiens cDNA clone 669266 3', mRNA sequence. (from Genbank) |
| 558 | Prostate | 0.4681656 | 0.415963 | 0.34796 | 0.21408698 | L00352_at | LOW-DENSITY LIPOPROTEIN RECEPTOR PRECURSOR |
| 559 | Prostate | 0.4678988 | 0.4159472 | 0.347952 | 0.21389228 | RC_AA459278_s_at | Homo sapiens connector enhancer of KSR-like protein CNK1 mRNA, complete cds |

FIG. 12A2

| # | Tissue | | | | | Description |
|---|---|---|---|---|---|---|
| 560 | Prostate | 0.4677499 | 0.4157948 | 0.347635 | 0.21382812 | RC_AA6099 43_at | EST: af09d11.s1 Soares testis NHT Homo sapiens cDNA clone 1031157 3', mRNA sequence. (from Genbank) |
| 561 | Prostate | 0.4674173 | 0.4154708 | 0.347635 | 0.21364091 | U07559_at | ISL1 ISL1 transcription factor, LIM/homeodomain, (islet-1) |
| 562 | Prostate | 0.4672241 | 0.4154708 | 0.347622 | 0.2135868 | RC_AA4599 50_at | EST: zx66b03.s1 Soares total fetus Nb2HF8 9w Homo sapiens cDNA clone 796397 3', mRNA sequence. (from Genbank) |
| 563 | Prostate | 0.4670945 | 0.4153872 | 0.347544 | 0.21348487 | RC_AA2274 28_at | EST: zr03g08.s1 Stratagene NT2 neuronal precursor 937230 Homo sapiens cDNA clone 650462 3', mRNA sequence. (from Genbank) |
| 564 | Prostate | 0.4670173 | 0.4152984 | 0.347289 | 0.21337622 | RC_AA4238 54_at | EST: zv79c03.s1 Soares total fetus Nb2HF8 9w Homo sapiens cDNA clone 759844 3', mRNA sequence. (from Genbank) |
| 565 | Prostate | 0.465954 | 0.415282 | 0.347281 | 0.21328649 | AA490758_a t | No info for gene |
| 566 | Prostate | 0.4654475 | 0.4150982 | 0.347106 | 0.21309635 | X53331_at | MGP Matrix protein gla |
| 567 | Prostate | 0.4652272 | 0.415092 | 0.346917 | 0.21299706 | HG4069-HT4339_s_a t | Monocyte Chemotactic Protein 1 |
| 568 | Prostate | 0.4652084 | 0.4147359 | 0.346812 | 0.21292007 | AA316686_s _at | EST: EST188361 HCC cell line (matastasis to liver in mouse) II Homo sapiens cDNA 5' end, mRNA sequence. (from Genbank) |
| 569 | Prostate | 0.4648758 | 0.4144529 | 0.346496 | 0.21281216 | RC_AA4762 51_at | EST: zw44g01.s1 Soares total fetus Nb2HF8 9w Homo sapiens cDNA clone 772944 3', mRNA sequence. (from Genbank) |
| 570 | Prostate | 0.4638747 | 0.4144386 | 0.346328 | 0.21276914 | AA376468_a t | EST: EST88890 HSC172 cells II Homo sapiens cDNA 5' end, mRNA sequence. (from Genbank) |
| 571 | Prostate | 0.4638384 | 0.4143752 | 0.346215 | 0.21261276 | U72263_s_a t | EXT2 Exostoses (multiple) 2 |
| 572 | Prostate | 0.4636175 | 0.4144346 | 0.346168 | 0.21258208 | U33317_rna 1_at | Defensin 6 (HD-6) gene |
| 573 | Prostate | 0.463445 | 0.4141929 | 0.346137 | 0.21242008 | L13391_at | REGULATOR OF G-PROTEIN SIGNALLING 2 |
| 574 | Prostate | 0.4633997 | 0.4141748 | 0.346122 | 0.2123822 | D79994_at | KIAA0172 gene, partial cds |
| 575 | Prostate | 0.4624637 | 0.4140586 | 0.346092 | 0.21235679 | RC_AA6210 32_at | KIAA0660 gene product |
| 576 | Prostate | 0.4623283 | 0.4140204 | 0.345975 | 0.21219398 | RC_AA4356 06_at | EST: zt74a11.s1 Soares testis NHT Homo sapiens cDNA clone 728060 3', mRNA sequence. (from Genbank) |
| 577 | Prostate | 0.4620402 | 0.4139726 | 0.345747 | 0.21211095 | U77845_at-2 | Human hTRIP (hTRIP) mRNA, complete cds |
| 578 | Prostate | 0.4620402 | 0.4138997 | 0.345553 | 0.21198465 | U77845_at | HTRIP (hTRIP) mRNA |
| 579 | Prostate | 0.4619762 | 0.4137215 | 0.345544 | 0.21188074 | RC_AA6205 82_at | EST: ae60g01.s1 Stratagene lung carcinoma 937218 Homo sapiens cDNA clone 951312 3', mRNA sequence. (from Genbank) |

FIG. 12B2

| # | Tissue | | | | Probe ID | Description |
|---|---|---|---|---|---|---|
| 580 | Prostate | 0.4619107 | 0.4137022 | 0.345497 | 0.2117148 | HG3187-HT3366_s_at Tyrosine Phosphatase 1, Non-Receptor, Alt. Splice 3 |
| 581 | Prostate | 0.461554 | 0.4136694 | 0.345438 | 0.21170902 | RC_AA5214 68_at EST: ae69f08.s1 NCI_CGAP_GCB1 Homo sapiens cDNA clone IMAGE:826215 3', mRNA sequence. (from Genbank) |
| 582 | Prostate | 0.4615535 | 0.4135719 | 0.345344 | 0.21155502 | RC_D20171 _at EST: Human HL60 3'directed MboI cDNA, HUMGS01145, clone pm2260, mRNA sequence. (from Genbank) |
| 583 | Prostate | 0.4612748 | 0.413527 | 0.345223 | 0.21147132 | RC_AA4969 14_at Homo sapiens short form transcription factor C-MAF (c-maf) mRNA, complete cds |
| 584 | Prostate | 0.4611512 | 0.4134147 | 0.345104 | 0.21146244 | U85773_at Phosphomannomutase 2 |
| 585 | Prostate | 0.4607839 | 0.4133673 | 0.345036 | 0.21111792 | RC_AA0020 64_at EST: zh85b03.s1 Soares fetal liver spleen 1NFLS S1 Homo sapiens cDNA clone 428045 3', mRNA sequence. (from Genbank) |
| 586 | Prostate | 0.4606392 | 0.4133565 | 0.34489 | 0.21116512 | RC_AA4170 46_at Fatty-acid-Coenzyme A ligase, very long-chain 1 |
| 587 | Prostate | 0.4605568 | 0.4132011 | 0.344873 | 0.21109723 | RC_AA4872 28_at EST: ab19h12.s1 Stratagene lung (#937210) Homo sapiens cDNA clone 841319 3', mRNA sequence. (from Genbank) |
| 588 | Prostate | 0.4604807 | 0.4131632 | 0.344844 | 0.21105784 | RC_AA1956 57_at EST: zr33f06.s1 Soares NhHMPu S1 Homo sapiens cDNA clone 665219 3', mRNA sequence. (from Genbank) |
| 589 | Prostate | 0.4602445 | 0.4131423 | 0.344698 | 0.21097907 | D79276_at Eukaryotic translation elongation factor 1 delta (guanine nucleotide exchange protein) |
| 590 | Prostate | 0.4600363 | 0.4130001 | 0.344602 | 0.2107887 | HG3510-HT3704_at V-Erba Related Ear-3 Protein |
| 591 | Prostate | 0.4597544 | 0.4129914 | 0.344564 | 0.21072008 | J02947_s_at SOD3 Superoxide dismutase 3, extracellular |
| 592 | Prostate | 0.4596662 | 0.4129583 | 0.344472 | 0.21062452 | RC_AA2923 05_s_at EST: zt51f07.s1 Soares ovary tumor NbHOT Homo sapiens cDNA clone 725893 3', mRNA sequence. (from Genbank) |
| 593 | Prostate | 0.4591857 | 0.4129244 | 0.344441 | 0.21051039 | RC_AA4371 18_at EST: zv53d04.s1 Soares testis NHT Homo sapiens cDNA clone 757351 3', mRNA sequence. (from Genbank) |
| 594 | Prostate | 0.4589096 | 0.4128578 | 0.344392 | 0.21043542 | RC_AA1507 76_at Homo sapiens clone 24405 mRNA sequence |
| 595 | Prostate | 0.4586531 | 0.4128389 | 0.344222 | 0.21025772 | X87838_at CTNNB1 Catenin (cadherin-associated protein), beta 1 (88kD) |
| 596 | Prostate | 0.4586371 | 0.4128299 | 0.344157 | 0.21013573 | AA377492_a_t EST: EST190100 Synovial membrane Homo sapiens cDNA 5' end similar to similar to ATPase, Ca2+ transporting, mRNA sequence. (from Genbank) |
| 597 | Prostate | 0.4586249 | 0.4127669 | 0.344134 | 0.21007369 | RC_AA4273 98_at Acetylserotonin N-methyltransferase-like |
| 598 | Prostate | 0.4585702 | 0.4127511 | 0.344108 | 0.20990688 | AB000220_a_t Semaphorin E |

FIG. 12C2

| | | | | | | |
|---|---|---|---|---|---|---|
| 599 | Prostate | 0.4583125 | 0.412744 | 0.34408 | 0.20984566 | D81932_at | Human fetal brain cDNA 5'-end GEN-424C05, mRNA sequence. (from Genbank) |
| 600 | Prostate | 0.458282 | 0.4127009 | 0.344045 | 0.20971763 | RC_AA3465 51_at | EST: EST52717 Fetal heart II Homo sapiens cDNA 3' end, mRNA sequence. (from Genbank) |
| 601 | Prostate | 0.4580848 | 0.4126431 | 0.343986 | 0.20965916 | RC_AA4875 57_at | EST: ab20h12.s1 Stratagene lung (#937210) Homo sapiens cDNA clone 841415 3', mRNA sequence. (from Genbank) |
| 602 | Prostate | 0.4580222 | 0.4125036 | 0.34387 | 0.20963615 | U34252_at | ALDH7 Aldehyde dehydrogenase 7 (NOTE: redefinition of symbol) |
| 603 | Prostate | 0.4577188 | 0.4124649 | 0.343855 | 0.20940739 | U84487_at | CX3C chemokine precursor, mRNA, alternatively spliced |
| 604 | Prostate | 0.4576982 | 0.4122647 | 0.343745 | 0.20932516 | RC_AA4793 50_at | EST: zv17d09.s1 Soares NhHMPu S1 Homo sapiens cDNA clone 753905 3' similar to contains element TAR1 TAR1 repetitive element :, mRNA sequence. (from Genbank) |
| 605 | Prostate | 0.4576055 | 0.412229 | 0.34366 | 0.20926428 | U76421_at | DsRNA adenosine deaminase DRADA2b (DRADA2b) mRNA |
| 606 | Prostate | 0.4574566 | 0.4121933 | 0.343571 | 0.20905165 | RC_AA4210 11_at | EST: zu09a12.s1 Soares testis NHT Homo sapiens cDNA clone 731326 3', mRNA sequence. (from Genbank) |
| 607 | Prostate | 0.4571891 | 0.4121902 | 0.343557 | 0.20899865 | J04982_at | ANT1 Adenine nucleotide translocator 1 (skeletal muscle) |
| 608 | Prostate | 0.457174 | 0.4120575 | 0.343484 | 0.20887363 | RC_AA2333 22_at | EST: zr69h06.s1 Soares NhHMPu S1 Homo sapiens cDNA clone 668699 3', mRNA sequence. (from Genbank) |
| 609 | Prostate | 0.4570489 | 0.4120112 | 0.343393 | 0.20884766 | Z50749_at | Sds22-like mRNA |
| 610 | Prostate | 0.4568037 | 0.4119704 | 0.343364 | 0.20873824 | J04615_at | SNRPN Small nuclear ribonucleoprotein polypeptide N |
| 611 | Prostate | 0.4564337 | 0.4119704 | 0.343306 | 0.20862147 | S69272_s_at | Cytoplasmic antiproteinase |
| 612 | Prostate | 0.4558826 | 0.4118694 | 0.342973 | 0.20855764 | RC_AA5989 02_at | EST: ae41a12.s1 Gessler Wilms tumor Homo sapiens cDNA clone 898366 3' similar to contains L1.t1 L1 repetitive element :, mRNA sequence. (from Genbank) |
| 613 | Prostate | 0.4553488 | 0.4117642 | 0.342719 | 0.20851274 | RC_AA5985 71_at | EST: ae35e03.s1 Gessler Wilms tumor Homo sapiens cDNA clone 897820 3' similar to contains Alu repetitive element, mRNA sequence. (from Genbank) |
| 614 | Prostate | 0.4550474 | 0.4115278 | 0.342592 | 0.20839316 | RC_AA2582 03_at | EST: zs35g04.s1 NCI_CGAP_GCB1 Homo sapiens cDNA clone IMAGE:687222 3', mRNA sequence. (from Genbank) |
| 615 | Prostate | 0.4550388 | 0.4115041 | 0.342514 | 0.20829849 | RC_AA4610 97_at | Human 150 kDa oxygen-regulated protein ORP150 mRNA, complete cds |
| 616 | Prostate | 0.4549998 | 0.4113391 | 0.342509 | 0.20823423 | M64098_at | High density lipoprotein binding protein (HBP) mRNA |
| 617 | Prostate | 0.4547598 | 0.4112002 | 0.342403 | 0.20813042 | RC_AA4248 f_at | Tumor rejection antigen (gp96) 1 |
| 618 | Prostate | 0.4547398 | 0.4111493 | 0.342366 | 0.20803371 81_at | | EST: zw03c10.s1 Soares NhHMPu S1 Homo sapiens cDNA clone 768210 3', mRNA sequence. (from Genbank) |
| 619 | Prostate | 0.4546146 | 0.4111002 | 0.342353 | 0.20791109 | M29927_at | OAT Ornithine aminotransferase (gyrate atrophy) |
| 620 | Prostate | 0.4544917 | 0.411093 | 0.342257 | 0.20778951 | D42047_at | KIAA0089 gene, partial cds |
| 621 | Prostate | 0.4543607 | 0.4110116 | 0.342201 | 0.20773074 | T85532_f_at | EST: yd78g02.r1 Homo sapiens cDNA clone 114386 5' similar to contains Alu repetitive element;. (from Genbank) |

FIG. 12D2

| | | | | | |
|---|---|---|---|---|---|
| 622 | Prostate | 0.4534678 | 0.4109512 | 0.342154 | 0.20762148 | AA504595_a t | EST: aa60g12.r1 NCI_CGAP_GCB1 Homo sapiens cDNA clone IMAGE:825382 5', mRNA sequence. (from Genbank) |
| 623 | Prostate | 0.4533294 | 0.4109497 | 0.342111 | 0.20750062 | AA384503_s at | EST: EST98057 Thyroid Homo sapiens cDNA 5' end, mRNA sequence. (from Genbank) |
| 624 | Prostate | 0.4530057 | 0.4109297 | 0.342071 | 0.20733081 | U01160_at | Transmembrane 4 superfamily protein (SAS) mRNA |
| 625 | Prostate | 0.4528284 | 0.410875 | 0.341914 | 0.20718566 | RC_AA6098 88_at | EST: af19a02.s1 Soares total fetus Nb2HF8 9w Homo sapiens cDNA clone 1032074 3', mRNA sequence. (from Genbank) |
| 626 | Prostate | 0.4525233 | 0.410849 | 0.341907 | 0.2070667 | L19314_at | HRY gene |
| 627 | Prostate | 0.4523786 | 0.4107423 | 0.341815 | 0.20693469 | R22139_at | EST: yh25b11.r1 Homo sapiens cDNA clone 130749 5'. (from Genbank) |
| 628 | Prostate | 0.4521277 | 0.4107401 | 0.3417 | 0.20688249 | RC_AA4362 39_at | Cryptochrome 2 (photolyase-like) |
| 629 | Prostate | 0.451974 | 0.4105443 | 0.341618 | 0.20678183 | AA282640_a t | EST: zs90d09.r1 NCI_CGAP_GCB1 Homo sapiens cDNA clone IMAGE:704753 5', mRNA sequence. (from Genbank) |
| 630 | Prostate | 0.451787 | 0.4104579 | 0.341556 | 0.20671822 | RC_AA4565 88_at | Homo sapiens BC-2 protein mRNA, complete cds |
| 631 | Prostate | 0.45123 | 0.4103386 | 0.341497 | 0.20665486 | RC_AA4313 99_at | Homo sapiens chromosome 1 atrophin-1 related protein (DRPLA) mRNA, complete cds |
| 632 | Prostate | 0.4510981 | 0.4102477 | 0.341258 | 0.20658553 | W37319_at | EST: zc11l08.r1 Soares parathyroid tumor NbHPA Homo sapiens cDNA clone 322023 5', mRNA sequence. (from Genbank) |
| 633 | Prostate | 0.4510467 | 0.4102229 | 0.341103 | 0.20650682 | RC_D60272 i_at | EST: Human fetal brain cDNA 3'-end GEN-095A07, mRNA sequence. (from Genbank) |
| 634 | Prostate | 0.4510176 | 0.4100752 | 0.341044 | 0.2064547 | RC_AA4010 98_f_at | EST: zu50g01.s1 Soares ovary tumor NbHOT Homo sapiens cDNA clone 741456 3' similar to contains Alu repetitive element;contains element THR repetitive element :. mRNA sequence. (from Genbank) |
| 635 | Prostate | 0.4510124 | 0.4100483 | 0.340941 | 0.20635265 | D83913_at | Genethonin 1 |
| 636 | Prostate | 0.4510018 | 0.4099484 | 0.340918 | 0.20617178 | RC_AA4656 57_at | EST: aa31b01.s1 NCI_CGAP_GCB1 Homo sapiens cDNA clone IMAGE:814825 3', mRNA sequence. (from Genbank) |
| 637 | Prostate | 0.4507329 | 0.4098405 | 0.340686 | 0.20605376 | RC_AA2847 20_at | EST: zt24a08.s1 Soares ovary tumor NbHOT Homo sapiens cDNA clone 714038 3', mRNA sequence. (from Genbank) |
| 638 | Prostate | 0.4506903 | 0.4097191 | 0.340639 | 0.20601654 | RC_AA6090 45_at | EST: af10e04.s1 Soares testis NHT Homo sapiens cDNA clone 1031262 3', mRNA sequence. (from Genbank) |
| 639 | Prostate | 0.4506204 | 0.4095034 | 0.340608 | 0.20596814 | RC_AA1259 69_at | EST: zl85c04.s1 Stratagene colon (#937204) Homo sapiens cDNA clone 511398 3', mRNA sequence. (from Genbank) |
| 640 | Prostate | 0.4504725 | 0.4095034 | 0.340513 | 0.20586215 | U79258_at | Clone 23732 mRNA, partial cds |
| 641 | Prostate | 0.4504251 | 0.4093716 | 0.340414 | 0.20585093 | RC_AA4241 57_at | EST: zv81d01.s1 Soares total fetus Nb2HF8 9w Homo sapiens cDNA clone 760033 3', mRNA sequence. (from Genbank) |
| 642 | Prostate | 0.4501839 | 0.4093559 | 0.340324 | 0.20581944 | AA376875_a t | Monoamine oxidase A |

FIG. 12E2

| # | Tissue | | | | | Description |
|---|---|---|---|---|---|---|
| 643 | Prostate | 0.4498132 | 0.4093312 | 0.340293 | 0.20568494 | AA149560_a t | EST: zo29d07.r1 Stratagene colon (#937204) Homo sapiens cDNA clone 588301 5', mRNA sequence. (from Genbank) |
| 644 | Prostate | 0.4498003 | 0.4093231 | 0.340226 | 0.20550168 | R21443_at | Human pre-B cell enhancing factor (PBEF) mRNA, complete cds |
| 645 | Prostate | 0.4496872 | 0.4088535 | 0.340038 | 0.20541993 | RC_AA4364 71_at | EST: zv08e05.s1 Soares NhHMPu S1 Homo sapiens cDNA clone 753056 3', mRNA sequence. (from Genbank) |
| 646 | Prostate | 0.4496679 | 0.408794 | 0.340033 | 0.20524056 | M28213_s_a t | RAB2, member RAS oncogene family |
| 647 | Prostate | 0.4492113 | 0.4086928 | 0.339773 | 0.20521215 | L29433_at | COAGULATION FACTOR X PRECURSOR |
| 648 | Prostate | 0.4492019 | 0.4086669 | 0.339719 | 0.20509459 | X52541_at | EGR1 Early growth response protein 1 |
| 649 | Prostate | 0.4491784 | 0.4086669 | 0.339705 | 0.20499219 | RC_AA6217 14_at | EST: af54e12.s1 Soares total fetus Nb2HF8 9w Homo sapiens cDNA clone 1035502 3', mRNA sequence. (from Genbank) |
| 650 | Prostate | 0.4489568 | 0.4085876 | 0.3396 | 0.20487808 | RC_AA2554 73_at | EST: zr83b12.s1 Soares NhHMPu S1 Homo sapiens cDNA clone 682271 3', mRNA sequence. (from Genbank) |
| 651 | Prostate | 0.4488983 | 0.4085564 | 0.339595 | 0.20482288 | RC_AA1499 87_at | Homo sapiens thymus specific serine peptidase mRNA, complete cds |
| 652 | Prostate | 0.4486919 | 0.4084703 | 0.339543 | 0.20468791 | RC_AA4281 50_at | EST: zw57c05.s1 Soares total fetus Nb2HF8 9w Homo sapiens cDNA clone 774152 3', mRNA sequence. (from Genbank) |
| 653 | Prostate | 0.448645 | 0.4083979 | 0.339365 | 0.20455398 | RC_AA2871 31_at | Human NAD+-specific isocitrate dehydrogenase beta subunit precursor, mRNA, nuclear gene encoding mitochondrial protein, complete cds |
| 654 | Prostate | 0.4484783 | 0.408326 | 0.339329 | 0.20452226 | RC_AA1212 66_at | EST: zk91c02.s1 Soares pregnant uterus NbHPU Homo sapiens cDNA clone 490178 3', mRNA sequence. (from Genbank) |
| 655 | Prostate | 0.4484256 | 0.4082827 | 0.339166 | 0.20450250 | D50495_at | Transcription elongation factor S-II, hS-II-T1 |
| 656 | Prostate | 0.4482389 | 0.4082586 | 0.339137 | 0.20441054 | RC_AA4795 15_at | EST: zv21f11.s1 Soares NhHMPu S1 Homo sapiens cDNA clone 754317 3', mRNA sequence. (from Genbank) |
| 657 | Prostate | 0.4480494 | 0.4080672 | 0.339099 | 0.20433152 | RC_AA2274 63_at | Homo sapiens mRNA for KIAA0859 protein, complete cds |
| 658 | Prostate | 0.4475973 | 0.408043 | 0.338996 | 0.20426917 | RC_AA1575 68_at | EST: zo68h02.s1 Stratagene pancreas (#937208) Homo sapiens cDNA clone 592083 3', mRNA sequence. (from Genbank) |
| 659 | Prostate | 0.4474273 | 0.4080304 | 0.338951 | 0.2041825 | RC_AA6001 50_at | EST: ae50d12.s1 Stratagene lung carcinoma 937218 Homo sapiens cDNA clone 950327 3', mRNA sequence. (from Genbank) |
| 660 | Prostate | 0.4471706 | 0.4080052 | 0.338797 | 0.2041678 | AB000464_a 9 | mRNA, clone RES4-24A, exon 1, 2, 3, 4 |
| 661 | Prostate | 0.4471706 | 0.408003 | 0.338699 | 0.20410322 | AB000464_a t-2 | Homo sapiens mRNA, exon 1, 2, 3, 4, clone:RES4-24A |
| 662 | Prostate | 0.446917 | 0.4079745 | 0.338653 | 0.20380314 | AA215938_a t | Human RNA polymerase III subunit (RPC62) mRNA, complete cds |
| 663 | Prostate | 0.4466961 | 0.4079468 | 0.33854 | 0.20371406 | C02053_at | EST: HUMGS0005644, Human Gene Signature, 3'-directed cDNA sequence, mRNA sequence. (from Genbank) |

FIG. 12F2

| # | Tissue | | | | | Description |
|---|---|---|---|---|---|---|
| 664 | Prostate | 0.4463672 | 0.4077636 | 0.338437 | 0.20362942 | M58459_at | RPS4Y Ribosomal protein S4, Y-linked |
| 665 | Prostate | 0.4462358 | 0.4077579 | 0.338394 | 0.20358667 | U24577_at | LDL-phospholipase A2 mRNA |
| 666 | Prostate | 0.4459783 | 0.407492 | 0.338292 | 0.20350587 | RC_AA2851 62_at | EST: zs48e06.s1 NCI_CGAP_GCB1 Homo sapiens cDNA clone IMAGE:700738 3', mRNA sequence. (from Genbank) |
| 667 | Prostate | 0.4459188 | 0.4073233 | 0.338171 | 0.20343268 | RC_AA4365 68_at | EST: zv08g11.s1 Soares NhHMPu S1 Homo sapiens cDNA clone 753092 3', mRNA sequence. (from Genbank) |
| 668 | Prostate | 0.4458916 | 0.4072642 | 0.33804 | 0.20340994 | RC_AA4367 00_at | EST: zv59c02.s1 Soares testis NHT Homo sapiens cDNA clone 757922 3', mRNA sequence. (from Genbank) |
| 669 | Prostate | 0.4455394 | 0.407167 | 0.33794 | 0.20331459 | RC_AA1349 68_at | EST: zo23g08.s1 Stratagene colon (#937204) Homo sapiens cDNA clone 587774 3', mRNA sequence. (from Genbank) |
| 670 | Prostate | 0.4453411 | 0.4070605 | 0.337881 | 0.2033 | RC_AA0704 37_at | Human smoothened mRNA, complete cds |
| 671 | Prostate | 0.4451298 | 0.4070396 | 0.337833 | 0.203141 | RC_AA0694 25_at | EST: zf73g10.s1 Soares pineal gland N3HPG Homo sapiens cDNA clone 382626 3', mRNA sequence. (from Genbank) |
| 672 | Prostate | 0.4451118 | 0.4069111 | 0.337796 | 0.20308977 | AA133029_a t | Homo sapiens TACC2 protein (TACC2) mRNA, partial cds |
| 673 | Prostate | 0.4450391 | 0.4068884 | 0.33776 | 0.20304814 | AB002309_a t | A-kinase anchor protein 100 |
| 674 | Prostate | 0.4445111 | 0.4067781 | 0.337675 | 0.20303649 | D88154_at | Homo sapiens mRNA for villin-like protein, complete cds. (from Genbank) |
| 675 | Prostate | 0.4444396 | 0.4067443 | 0.337619 | 0.20282245 | RC_AA4031 59_at | EST: zv65c07.s1 Soares total fetus Nb2HF8 9w Homo sapiens cDNA clone 758508 3', mRNA sequence. (from Genbank) |
| 676 | Prostate | 0.4441059 | 0.4067166 | 0.337591 | 0.2027383 | RC_AA4960 40_at | Homo sapiens mRNA for tob family, complete cds |
| 677 | Prostate | 0.4438286 | 0.4065543 | 0.337411 | 0.20263897 | L19871_at | ATF3 Activating transcription factor 3 |
| 678 | Prostate | 0.443666 | 0.406448 | 0.337364 | 0.20259309 | AB002380_a t | KIAA0382 gene, partial cds |
| 679 | Prostate | 0.4432063 | 0.406448 | 0.337149 | 0.20248236 | AA203501_a t | EST: zx59a01.r1 Soares fetal liver spleen 1NFLS S1 Homo sapiens cDNA clone 446760 5', mRNA sequence. (from Genbank) |
| 680 | Prostate | 0.4431706 | 0.4063713 | 0.337104 | 0.20236038 | L05779_at | EPHX2 Epoxide hydrolase 2, cytoplasmic |
| 681 | Prostate | 0.4431396 | 0.4063621 | 0.336751 | 0.20230192 | RC_AA2561 53_i_at | EST: zr79a09.s1 Soares NhHMPu S1 Homo sapiens cDNA clone 681880 3', mRNA sequence. (from Genbank) |
| 682 | Prostate | 0.4426568 | 0.4062735 | 0.336729 | 0.2022666 | RC_AA2566 16_at | EST: zr86h05.s1 Soares NhHMPu S1 Homo sapiens cDNA clone 682617 3', mRNA sequence. (from Genbank) |
| 683 | Prostate | 0.441923 | 0.4061262 | 0.336646 | 0.20212989 | Z29067_at | Nek3 mRNA for protein kinase |
| 684 | Prostate | 0.4418305 | 0.4061262 | 0.336329 | 0.20203097 | RC_AA1646 33_at | EST: zo93d04.s1 Stratagene ovarian cancer (#937219) Homo sapiens cDNA clone 594439 3', mRNA sequence. (from Genbank) |
| 685 | Prostate | 0.4417298 | 0.406093 | 0.336094 | 0.20197883 | M98528_at | BRAIN NEURON CYTOPLASMIC PROTEIN 1 |

FIG. 12G2

| # | Tissue | | | | ID | Description |
|---|---|---|---|---|---|---|
| 686 | Prostate | 0.4415572 | 0.4053367 | 0.336089 | RC_AA1004 37_at | EST: zn59e02.s1 Stratagene muscle 937209 Homo sapiens cDNA clone 562490 3', mRNA sequence. (from Genbank) |
| 687 | Prostate | 0.4412361 | 0.4058255 | 0.335966 | X57985_rna 2_at | GL105 gene (histone H2B) extracted from H.sapiens genes for histones H2B.1 and H2A |
| 688 | Prostate | 0.4412261 | 0.4058056 | 0.335909 | AA418098_a t | CAMP responsive element binding protein-like 2 |
| 689 | Prostate | 0.4412253 | 0.4057108 | 0.335833 | RC_AA0351 59_at | EST: zk27b12.s1 Soares pregnant uterus NbHPU Homo sapiens cDNA clone 471743 3', mRNA sequence. (from Genbank) |
| 690 | Prostate | 0.4408905 | 0.4055765 | 0.335683 | HG3111-HT3287_at | Autoantigen (Gb:S67069) |
| 691 | Prostate | 0.4407939 | 0.4055374 | 0.335672 | RC_AA2848 44_at | EST: zt22d02.s1 Soares ovary tumor NbHOT Homo sapiens cDNA clone 713859 3', mRNA sequence. (from Genbank) |
| 692 | Prostate | 0.4407404 | 0.4055374 | 0.335548 | T47256_s_at | Growth arrest-specific 6 |
| 693 | Prostate | 0.4406497 | 0.4055138 | 0.335306 | U83460_s_a t | Solute carrier family 31 (copper transporters), member 1 |
| 694 | Prostate | 0.4405653 | 0.4054483 | 0.335265 | HG2442-HT2538_at | Tropomyosin, Alpha, Muscle, Alt. Splice 2, Skeletal Muscle (Fibroblast) |
| 695 | Prostate | 0.4403343 | 0.4053973 | 0.335265 | RC_AA0200 05_at | EST: ze62e11.s1 Soares retina N2b4HR Homo sapiens cDNA clone 363596 3', mRNA sequence. (from Genbank) |
| 696 | Prostate | 0.4401454 | 0.4053914 | 0.335233 | RC_AA4055 01_at | EST: zw36f10.s1 Soares total fetus Nb2HF8 9w Homo sapiens cDNA clone 772147 3', mRNA sequence. (from Genbank) |
| 697 | Prostate | 0.440049 | 0.4053361 | 0.335517 | U85658_at | Transcription factor ERF-1 mRNA |
| 698 | Prostate | 0.4399736 | 0.4052946 | 0.335026 | AB002365_a t | KIAA0367 gene, partial cds |
| 699 | Prostate | 0.4398666 | 0.4050439 | 0.334969 | L10910_at | Splicing factor (CC1.3) mRNA |
| 700 | Prostate | 0.4396864 | 0.4050439 | 0.334963 | RC_AA4188 24_at | EST: zw01b03.s1 Soares NhHMPu S1 Homo sapiens cDNA clone 767981 3', mRNA sequence. (from Genbank) |
| 701 | Prostate | 0.4396553 | 0.4049802 | 0.334855 | RC_AA4282 40_at | EST: zw51d04.s1 Soares total fetus Nb2HF8 9w Homo sapiens cDNA clone 773575 3', mRNA sequence. (from Genbank) |
| 702 | Prostate | 0.439581 | 0.4049227 | 0.334851 | AA416829_a t | EST: zu08e03.r1 Soares testis NHT Homo sapiens cDNA clone 731260 5', mRNA sequence. (from Genbank) |
| 703 | Prostate | 0.4395618 | 0.4047621 | 0.334813 | D82373_at | Squamous cell carcinoma antigen recognised by T cells |
| 704 | Prostate | 0.4392845 | 0.4046469 | 0.334798 | RC_AA2912 71_at | EST: zs18d05.s1 NCI_CGAP_GCB1 Homo sapiens cDNA clone IMAGE:685545 3' similar to contains Alu repetitive element; mRNA sequence. (from Genbank) |
| 705 | Prostate | 0.4391167 | 0.4046248 | 0.334762 | M92843_s_a t | ZFP36 Zinc finger protein homologous to Zfp-36 in mouse |
| 706 | Prostate | 0.4389651 | 0.4045189 | 0.334755 | RC_AA4175 58_at | EST: zv04d02.s1 Soares NhHMPu S1 Homo sapiens cDNA clone 752643 3', mRNA sequence. (from Genbank) |

FIG. 12H2

| # | Tissue | | | | Accession | Description |
|---|---|---|---|---|---|---|
| 707 | Prostate | 0.4385174 | 0.4044705 | 0.200050984 | RC_AA2560 42_at | EST: zs29d04.s1 NCI_CGAP_GCB1 Homo sapiens cDNA clone IMAGE:686599 3', mRNA sequence. (from Genbank) |
| 708 | Prostate | 0.4384335 | 0.4044085 | 0.199970020 | RC_AA4854 09_at | EST: ab09g07.s1 Stratagene lung (#937210) Homo sapiens cDNA clone 840348 3', mRNA sequence. (from Genbank) |
| 709 | Prostate | 0.4384063 | 0.404278 | 0.199793593 | RC_AA2269 90_at | EST: zr18h05.s1 Stratagene NT2 neuronal precursor 937230 Homo sapiens cDNA clone 663801 3', mRNA sequence. (from Genbank) |
| 710 | Prostate | 0.4383704 | 0.4042311 | 0.19977663 | AA464334_s_at | EST: zx78f01.r1 Soares ovary tumor NbHOT Homo sapiens cDNA clone 809881 5', mRNA sequence. (from Genbank) |
| 711 | Prostate | 0.4383659 | 0.4041654 | 0.1997443 | D54358_at | KIAA0336 gene product |
| 712 | Prostate | 0.4381131 | 0.4041195 | 0.19953504 | U95367_at | Human GABA-A receptor pi subunit mRNA, complete cds |
| 713 | Prostate | 0.4380261 | 0.4040963 | 0.19950843 | D61391_at | Phosphoribosylpyrophosphate synthetase-associated protein 39 |
| 714 | Prostate | 0.4379628 | 0.4040305 | 0.19935721 | AA093748_a_t | EST: cl0752.seq.F Fetal heart, Lambda ZAP Express Homo sapiens cDNA 5', mRNA sequence. (from Genbank) |
| 715 | Prostate | 0.4379367 | 0.4039871 | 0.19934022 | RC_AA2520 33_at | EST: zx64h01.s1 Soares NhHMPu S1 Homo sapiens cDNA clone 668209 3' similar to contains Alu repetitive element;, mRNA sequence. (from Genbank) |
| 716 | Prostate | 0.4379017 | 0.4039317 | 0.19927722 | H81492_at | EST: yu61d04.r1 Homo sapiens cDNA clone 230599 5'. (from Genbank) |
| 717 | Prostate | 0.4377557 | 0.4038667 | 0.19907656 | AA209290_a_t | EST: zq85c01.r1 Stratagene hNT neuron (#937233) Homo sapiens cDNA clone 648384 5' similar to contains element MER22 repetitive element:, mRNA sequence. (from Genbank) |
| 718 | Prostate | 0.4376873 | 0.40376 | 0.1989719 | RC_AA4588 99_at | EST: zx88d07.s1 Soares ovary tumor NbHOT Homo sapiens cDNA clone 810829 3', mRNA sequence. (from Genbank) |
| 719 | Prostate | 0.4375426 | 0.403583 | 0.1989674 | RC_AA4571 40_at | EST: zx84f04.s1 Soares ovary tumor NbHOT Homo sapiens cDNA clone 810463 3', mRNA sequence. (from Genbank) |
| 720 | Prostate | 0.4375037 | 0.403507 | 0.19895968 | RC_AA2563 76_s_at | Homo sapiens metaxin 2 (MTX2) mRNA, nuclear gene encoding mitochondrial protein, complete cds |
| 721 | Prostate | 0.4374536 | 0.403507 | 0.19872452 | X07732_at | HPN Hepsin |
| 722 | Prostate | 0.4374207 | 0.4032191 | 0.1987123 | RC_AA4609 16_at | EST: zx61a12.s1 Soares total fetus Nb2HF8 9w Homo sapiens cDNA clone 795934 3', mRNA sequence. (from Genbank) |
| 723 | Prostate | 0.4372653 | 0.4031832 | 0.19858259 | RC_AA0171 61_at | EST: ze36a01.s1 Soares retina N2b4HR Homo sapiens cDNA clone 361032 3', mRNA sequence. (from Genbank) |
| 724 | Prostate | 0.4370687 | 0.4031622 | 0.19850706 | RC_D19672_at | EST: Human HL60 3'directed MboI cDNA, HUMGS00627, clone mm2330, mRNA sequence. (from Genbank) |
| 725 | Prostate | 0.4369998 | 0.4031599 | 0.1984888 | R36553_at | EST: yg35a04.r9 Homo sapiens cDNA clone 34269 5'. (from Genbank) |
| 726 | Prostate | 0.4367928 | 0.4030821 | 0.19844672 | M24470_at | G6PD Glucose-6-phosphate dehydrogenase |
| 727 | Prostate | 0.4367324 | 0.4030568 | 0.1983133 | M68891_at | GATA2 GATA-binding protein 2 |

FIG. 12I2

| | | | | HG3395-HT3573_s_a | |
|---|---|---|---|---|---|
| 728 | Prostate | 0.4366635 | 0.402983 | 0.19823146 t | Dnaj Homolog (Gb:X63368), Alt. Splice Form 2 |
| 729 | Prostate | 0.4366095 | 0.4027703 | 0.19815956 L21934_at | SOAT Sterol O-acyltransferase (acyl-Coenzyme A: cholesterol acyltransferase) |
| 730 | Prostate | 0.4365448 | 0.4028299 | 0.19810496 RC_AA4789 60_at | EST: zv18d03.s1 Soares NhHMPu S1 Homo sapiens cDNA clone 753989 3', mRNA sequence. (from Genbank) |
| 731 | Prostate | 0.4365364 | 0.4025403 | 0.19802769 U09646_at | Carnitine palmitoyltransferase (CPT1) mRNA |
| 732 | Prostate | 0.4365064 | 0.4024445 | 0.1979474 RC_AA2788 16_f_at | EST: zs78d05.s1 NCI_CGAP_GCB1 Homo sapiens cDNA clone IMAGE:703593 3', mRNA sequence. (from Genbank) |
| 733 | Prostate | 0.4362698 | 0.4023952 | 0.19789223 RC_AA2618 58_at | EST: zs18g11.s1 NCI_CGAP_GCB1 Homo sapiens cDNA clone IMAGE:685604 3', mRNA sequence. (from Genbank) |
| 734 | Prostate | 0.4362235 | 0.4023664 | 0.19781542 AA374109_a t | EST: EST86231 HSC172 cells I Homo sapiens cDNA 5' end, mRNA sequence. (from Genbank) |
| 735 | Prostate | 0.4358467 | 0.4023311 | 0.19773218 R63545_at | EST: yi09a01.r1 Homo sapiens cDNA clone 138696 5'. (from Genbank) |
| 736 | Prostate | 0.4358108 | 0.4023311 | 0.19764638 RC_AA4592 93_at | EST: zx89b07.s1 Soares ovary tumor NbHOT Homo sapiens cDNA clone 810901 3', mRNA sequence. (from Genbank) |
| 737 | Prostate | 0.4354711 | 0.4022841 | 0.19753803 RC_AA1956 56_at | EST: zr33f05.s1 Soares NhHMPu S1 Homo sapiens cDNA clone 665217 3', mRNA sequence. (from Genbank) |
| 738 | Prostate | 0.4354708 | 0.4022616 | 0.19738871 D17400_at | PTS 6-pyruvoyltetrahydropterin synthase |
| 739 | Prostate | 0.4350477 | 0.4021196 | 0.19737059 RC_AA6214 71_at | EST: af92d09.s1 Soares total fetus Nb2HF8 9w Homo sapiens cDNA clone 1055249 3', mRNA sequence. (from Genbank) |
| 740 | Prostate | 0.4345098 | 0.4020691 | 0.19728471 RC_AA4549 67_at | EST: zx99b12.s1 Soares NhHMPu S1 Homo sapiens cDNA clone 811871 3', mRNA sequence. (from Genbank) |
| 741 | Prostate | 0.4344536 | 0.4020049 | 0.19714217 Z24725_at | Mitogen inducible gene mig-2 |
| 742 | Prostate | 0.4339835 | 0.4019191 | 0.19705033 RC_AA1917 08_at | EST: zp82d10.s1 Stratagene HeLa cell s3 937216 Homo sapiens cDNA clone 626707 3', mRNA sequence. (from Genbank) |
| 743 | Prostate | 0.4338846 | 0.4015465 | 0.19701813 RC_AA4170 79_at | EST: zu13c03.s1 Soares testis NHT Homo sapiens cDNA clone 731716 3', mRNA sequence. (from Genbank) |
| 744 | Prostate | 0.4337904 | 0.4014925 | 0.19697765 AA292440_s _at | Homo sapiens negative growth-regulatory protein MyD118 (MYD118) mRNA, complete cds |
| 745 | Prostate | 0.4330917 | 0.4010649 | 0.19694628 RC_AA1472 18_s_at | EST: zo64g03.s1 Stratagene pancreas (#937208) Homo sapiens cDNA clone 591700 3', mRNA sequence. (from Genbank) |
| 746 | Prostate | 0.4329 | 0.4010241 | 0.19686767 AA195136_a t | Zr34d05.r1 Soares NhHMPu S1 Homo sapiens cDNA clone 665289 5', mRNA sequence. (from Genbank) |
| 747 | Prostate | 0.4328548 | 0.4009121 | 0.19681153 AA071256_a t | EST: zo64g03.r1 Stratagene neuroepithelium (#937231) Homo sapiens cDNA clone 531265 5', mRNA sequence. (from Genbank) |
| 748 | Prostate | 0.4328035 | 0.4008208 | 0.19673526 X63629_at | CDH3 Cadherin 3 (P-cadherin) |

FIG. 12J2

| | | | | | | |
|---|---|---|---|---|---|---|
| 749 | Prostate | 0.4327704 | 0.4008161 | 0.331143 | 0.19653058 | RC_AA6099 52_at | Homo sapiens mRNA for KIAA0293 gene, partial cds |
| 750 | Prostate | 0.4326661 | 0.4008137 | 0.331106 | 0.19652055 | RC_AA0016 48_at | EST: zh82g08.s1 Soares fetal liver spleen 1NFLS S1 Homo sapiens cDNA clone 427838 3' similar to contains Alu repetitive element;contains MER15.b2 MER15 repetitive element :, mRNA sequence. (from Genbank) |
| 751 | Prostate | 0.4320492 | 0.4006029 | 0.331056 | 0.19637837 | RC_AA2534 59_at | EST: zs06f01.s1 NCI_CGAP_GCB1 Homo sapiens cDNA clone IMAGE:684409 3', mRNA sequence. (from Genbank) |
| 752 | Prostate | 0.432012 | 0.4003765 | 0.331033 | 0.19624431 | D63486_at | KIAA0152 gene |
| 753 | Prostate | 0.431336 | 0.40024 | 0.331013 | 0.19617972 | RC_AA4634 45_at | Homo sapiens KIAA0439 mRNA, partial cds |
| 754 | Prostate | 0.4313242 | 0.4000148 | 0.330099 | 0.19613698 | RC_AA2436 92_at | EST: zr68e05.s1 Soares NhHMPu S1 Homo sapiens cDNA clone 668576 3', mRNA sequence. (from Genbank) |
| 755 | Prostate | 0.4312824 | 0.3996762 | 0.330718 | 0.19601087 | M20867_s_a t | GLUD1 Glutamate dehydrogenase |
| 756 | Prostate | 0.4311726 | 0.3996258 | 0.330627 | 0.19600748 | RC_AA4469 64_at | Homo sapiens prostate stem cell antigen (PSCA) mRNA, complete cds |
| 757 | Prostate | 0.431136 | 0.3995624 | 0.330574 | 0.19592664 | RC_AA2337 90_at | EST: zr44c08.s1 Soares NhHMPu S1 Homo sapiens cDNA clone 666254 3', mRNA sequence. (from Genbank) |
| 758 | Prostate | 0.4304979 | 0.3995085 | 0.33054 | 0.19588415 | RC_AA4780 17_at | Homo sapiens alpha 1,2-mannosidase IB mRNA, complete cds |
| 759 | Prostate | 0.4302453 | 0.3994539 | 0.33052 | 0.19577092 | RC_AA4498 18_s_at | Human modulator recognition factor I (MRF-1) mRNA, 3' end |
| 760 | Prostate | 0.4301287 | 0.3993386 | 0.330486 | 0.19564317 | RC_AA4210 50_at | EST: zu09g09.s1 Soares testis NHT Homo sapiens cDNA clone 731392 3', mRNA sequence. (from Genbank) |
| 761 | Prostate | 0.430074 | 0.3992576 | 0.330481 | 0.19554058 | U62015_at | Cyr61 mRNA |
| 762 | Prostate | 0.4300156 | 0.3990995 | 0.330303 | 0.19551383 | AA312994_a t | EST: EST183781 Bone VII Homo sapiens cDNA 5' end, mRNA sequence. (from Genbank) |
| 763 | Prostate | 0.4298206 | 0.3990897 | 0.330193 | 0.1954222 | D50916_at | KIAA0126 gene |
| 764 | Prostate | 0.4297597 | 0.3987017 | 0.330111 | 0.19539207 | AA464029_a t | Myosin, light polypeptide 5, regulatory |
| 765 | Prostate | 0.4296312 | 0.3986723 | 0.330055 | 0.1952798 | RC_AA2876 81_s_at | EST: zs53f07.s1 NCI_CGAP_GCB1 Homo sapiens cDNA clone IMAGE:701221 3', mRNA sequence. (from Genbank) |
| 766 | Prostate | 0.4295986 | 0.3986723 | 0.329762 | 0.19512317 | AA425563_a t | EST: zw46e06.r1 Soares total fetus Nb2HF8 9w Homo sapiens cDNA clone 773122 5', mRNA sequence. (from Genbank) |
| 767 | Prostate | 0.4295588 | 0.398567 | 0.329731 | 0.1949569 | U23942_at | CYP51 Cytochrome P450, 51 (lanosterol 14-alpha-demethylase) |
| 768 | Prostate | 0.4294392 | 0.3983211 | 0.329664 | 0.19491456 | RC_AA6100 86_at | EST: af08h02.s1 Soares testis NHT Homo sapiens cDNA clone 1031091 3', mRNA sequence. (from Genbank) |
| 769 | Prostate | 0.4292552 | 0.3982899 | 0.329651 | 0.19482696 | RC_AA4852 49_at | Homo sapiens chromosome 19, cosmid R33729 |

FIG. 12K2

| # | Tissue | | | | ID | Description |
|---|---|---|---|---|---|---|
| 770 | Prostate | 0.4290439 | 0.3981572 | 0.32965 | M29037_s_at | 17 beta-hydroxysteroid dehydrogenase (17BHSDI) gene, exons 1-5 |
| 771 | Prostate | 0.4289562 | 0.3981506 | 0.329578 | RC_AA4904 61_at | EST: aa45a12.s1 Soares NhHMPu S1 Homo sapiens cDNA clone 823870 3', mRNA sequence. (from Genbank) |
| 772 | Prostate | 0.4289091 | 0.3980968 | 0.329483 | RC_AA2926 31_at | EST: zs58g01.s1 NCI_CGAP_GCB1 Homo sapiens cDNA clone IMAGE:701712 3', mRNA sequence. (from Genbank) |
| 773 | Prostate | 0.4288587 | 0.3979822 | 0.329429 | AA287308_a_t | EST: zs52f04.r1 NCI_CGAP_GCB1 Homo sapiens cDNA clone IMAGE:701119 5' similar to contains Alu repetitive element;contains element MER1 repetitive element.; mRNA sequence. (from Genbank) |
| 774 | Prostate | 0.4288124 | 0.3977624 | 0.329365 | U35735_at | RACH1 (RACH1) mRNA |
| 775 | Prostate | 0.428749 | 0.3977339 | 0.329342 | RC_AA1558 03_at | EST: zo48h01.s1 Stratagene endothelial cell 937223 Homo sapiens cDNA clone 590161 3', mRNA sequence. (from Genbank) |
| 776 | Prostate | 0.4286153 | 0.3976284 | 0.329261 | D12620_s_a t-2 | Cytochrome P450, subfamily IVF, polypeptide 3 (leukotriene B4 omega hydroxylase) |
| 777 | Prostate | 0.4286153 | 0.3975871 | 0.329198 | D12620_s_a t | LTB4H Leukotriene B4 omega hydroxylase (cytochrome P450, subfamily IVF) |
| 778 | Prostate | 0.4284203 | 0.3975263 | 0.329153 | RC_AA1148 66_s_at | Homo sapiens homeobox A11 (HOXA11) gene, complete cds |
| 779 | Prostate | 0.4283599 | 0.3974879 | 0.329076 | U28249_at | MAT8 protein |
| 780 | Prostate | 0.4280409 | 0.397439 | 0.329048 | AA364267_a_t | EST: EST74873 Pineal gland II Homo sapiens cDNA clone 5' end, mRNA sequence. (from Genbank) |
| 781 | Prostate | 0.4280153 | 0.39742 | 0.328819 | R78838_a_t | EST: yi90d06.r1 Homo sapiens cDNA clone 146507 5' similar to contains Alu repetitive element.. (from Genbank) |
| 782 | Prostate | 0.4275732 | 0.3974145 | 0.328684 | X89066_at | TRPC1 Transient receptor potential channel 1 |
| 783 | Prostate | 0.4273481 | 0.3973976 | 0.32857 | X75593_at | Rab 13 |
| 784 | Prostate | 0.4272367 | 0.3973084 | 0.328541 | H66367_at | EST: yu14a06.r1 Homo sapiens cDNA clone 233746 5' similar to contains Alu repetitive element.. (from Genbank) |
| 785 | Prostate | 0.4271023 | 0.3972519 | 0.328424 | RC_AA0116 54_at | EST: zl03c05.s1 Soares fetal liver spleen 1NFLS S1 Homo sapiens cDNA clone 429704 3', mRNA sequence. (from Genbank) |
| 786 | Prostate | 0.4266099 | 0.3971175 | 0.328401 | RC_AA4482 38_at | Homo sapiens mRNA for KIAA0915 protein, complete cds |
| 787 | Prostate | 0.4264824 | 0.3970003 | 0.328393 | D31286_at | Homo sapiens mRNA for smallest subunit of ubiquinol-cytochrome c reductase, complete cds |
| 788 | Prostate | 0.4264698 | 0.3969697 | 0.328372 | V01512_rna 1_at | Cellular oncogene c-fos (complete sequence) |
| 789 | Prostate | 0.4259252 | 0.3969217 | 0.328302 | RC_AA5044 67_at | HEAT SHOCK 70 KD PROTEIN 1 |

FIG. 12L2

| | | | | | |
|---|---|---|---|---|---|
| 790 | Prostate | 0.4258873 | 0.3968504 | 0.328216 | 0.19292852 | W25821_at | EST: 14e10 Human retina cDNA randomly primed sublibrary Homo sapiens cDNA, mRNA sequence. (from Genbank) |
| 791 | Prostate | 0.425848 | 0.3968504 | 0.32808 | 0.19285561 | Z11793_at | Selenoprotein P |
| 792 | Prostate | 0.4257871 | 0.396773 | 0.32808 | 0.19284156 | L40397_at | (clone S31I125) mRNA, 3' end of cds |
| 793 | Prostate | 0.4256406 | 0.396744 | 0.328071 | 0.19274718 | M28211_at | RAS-RELATED PROTEIN RAB-4A |
| 794 | Prostate | 0.4255692 | 0.3967108 | 0.328042 | 0.19261345 | HG2604-HT2700_at | Pan-2 |
| 795 | Prostate | 0.4244045 | 0.3967068 | 0.327961 | 0.19256182 | T09468_at | Homo sapiens TACC1 (TACC1) mRNA, complete cds |
| 796 | Prostate | 0.4242599 | 0.3963889 | 0.327955 | 0.19251592 | RC_AA4365 53_at | EST: zv08c11.s1 Soares NhHMPu S1 Homo sapiens cDNA clone 753044 3', mRNA sequence. (from Genbank) |
| 797 | Prostate | 0.4241512 | 0.3963723 | 0.327924 | 0.1923873 | RC_AA0538 83_at | EST: ze75b02.s1 Soares fetal heart NbHH19W Homo sapiens cDNA clone 364779 3', mRNA sequence. (from Genbank) |
| 798 | Prostate | 0.4233569 | 0.3963343 | 0.327646 | 0.19229203 | D63480_at | KIAA0146 gene, partial cds |
| 799 | Prostate | 0.4231926 | 0.3962487 | 0.327592 | 0.1922502 | L33881_at | PRKCI Protein kinase C, iota |
| 800 | Prostate | 0.4230956 | 0.3962155 | 0.327572 | 0.19221573 | M13231_s_a t | T-cell receptor, gamma cluster |
| 801 | Prostate | 0.4225114 | 0.396173 | 0.327745 | 0.19207254 | D10216_s_a t | POU domain, class 1, transcription factor 1 (Pit1, growth hormone factor 1) |
| 802 | Prostate | 0.4223507 | 0.3960989 | 0.327436 | 0.19199635 | U72649_at | BTG2 (BTG2) mRNA |
| 803 | Prostate | 0.4221884 | 0.3960874 | 0.327397 | 0.1919021 | D31313_s_a t | EST: Human fetal-lung cDNA 5'-end sequence, mRNA sequence. (from Genbank) |
| 804 | Prostate | 0.4219862 | 0.3959613 | 0.327324 | 0.19179529 | U35139_at | NECDIN related protein mRNA |
| 805 | Prostate | 0.4219184 | 0.3959597 | 0.327321 | 0.19167933 | U39226_at-2 | Myosin VIIA (Usher syndrome 1B (autosomal recessive, severe)) |
| 806 | Prostate | 0.4219184 | 0.3957888 | 0.327297 | 0.19165356 | U39226_at | Myosin VIIA (USH1B) mRNA |
| 807 | Prostate | 0.4216776 | 0.3955513 | 0.327297 | 0.19154319 | AB000584_a t | Prostate differentiation factor mRNA |
| 808 | Prostate | 0.4216431 | 0.3952626 | 0.327146 | 0.19147629 | AA228127_a t | EST: zr58c05.r1 Soares NhHMPu S1 Homo sapiens cDNA clone 667592 5', mRNA sequence. (from Genbank) |
| 809 | Prostate | 0.4215747 | 0.3952517 | 0.327093 | 0.19137256 | X17025_at | Homolog of yeast IPP isomerase |
| 810 | Prostate | 0.4213993 | 0.3952054 | 0.327026 | 0.1913152 | D79985_at | A cell surface protein |
| 811 | Prostate | 0.4213829 | 0.3951472 | 0.327016 | 0.19127809 | D13641_at | KIAA0016 gene |
| 812 | Prostate | 0.4212766 | 0.3950817 | 0.326997 | 0.19115831 | RC_AA2581 58_at | EST: zs35b02.s1 NCI_CGAP_GCB1 Homo sapiens cDNA clone IMAGE:687147 3', mRNA sequence. (from Genbank) |
| 813 | Prostate | 0.4211496 | 0.3947606 | 0.326972 | 0.19109187 | RC_AA4239 74_at | EST: zv62h04.s1 Soares testis NHT Homo sapiens cDNA clone 758263 3', mRNA sequence. (from Genbank) |
| 814 | Prostate | 0.4208253 | 0.3946797 | 0.326918 | 0.19093364 | D57823_at | H.sapiens mRNA for Sec23A isoform, 2748bp |
| 815 | Prostate | 0.4208242 | 0.3945882 | 0.326519 | 0.19090173 | X74331_at | PRIM2A DNA primase polypeptide 2A (58kD) |
| 816 | Prostate | 0.4207758 | 0.3945707 | 0.326519 | 0.190734 | H46074_at | EST: yo13f07.r1 Homo sapiens cDNA clone 177829 5'. (from Genbank) |

FIG. 12M2

| | | | | | |
|---|---|---|---|---|---|
| 817 | Prostate | 0.4203761 | 0.394561 | 0.326425 | 0.19070965 | N94146_at | EST: za25b12.r1 Homo sapiens cDNA clone 293567 5'. (from Genbank) |
| 818 | Prostate | 0.4202022 | 0.3945041 | 0.326325 | 0.19066928 | U85193_at | Nuclear factor I-B2 (NFIB2) mRNA |
| 819 | Prostate | 0.4201458 | 0.3943B3 | 0.326229 | 0.19055944 | M75126_at | HK1 Hexokinase 1 |
| 820 | Prostate | 0.4200172 | 0.3943754 | 0.326057 | 0.19053781 | D86960_at | KIAA0205 gene |
| 821 | Prostate | 0.4198446 | 0.3943699 | 0.326029 | 0.19042568 | RC_AA4613 00_at | EST: zx65a08.s1 Soares total fetus Nb2HF8 9w Homo sapiens cDNA clone 796310 3', mRNA sequence. (from Genbank) |
| 822 | Prostate | 0.4198187 | 0.3943579 | 0.326026 | 0.19034584 | RC_D60607 _at | EST: Human fetal brain cDNA 3'-end GEN-120A01, mRNA sequence. (from Genbank) |
| 823 | Prostate | 0.4196816 | 0.3943393 | 0.325899 | 0.19028157 | M73547_at | POLYPOSIS LOCUS PROTEIN 1 |
| 824 | Prostate | 0.4195609 | 0.3941727 | 0.325899 | 0.19016132 | AA203649_a t | EST: zx6e12.r1 Soares fetal liver spleen 1NFLS S1 Homo sapiens cDNA clone 446734 5', mRNA sequence. (from Genbank) |
| 825 | Prostate | 0.4193544 | 0.3940995 | 0.325716 | 0.19008482 | AF001294_a t | IPL (IPL) mRNA |
| 826 | Prostate | 0.4192291 | 0.3940621 | 0.325711 | 0.19001427 | RC_AA4521 16_at | EST: zx15c02.s1 Soares total fetus Nb2HF8 9w Homo sapiens cDNA clone 786530 3', mRNA sequence. (from Genbank) |
| 827 | Prostate | 0.4190343 | 0.3940621 | 0.325698 | 0.18993546 | RC_AA1478 91_at | EST: zo43f05.s1 Stratagene endothelial cell 937223 Homo sapiens cDNA clone 589665 3', mRNA sequence. (from Genbank) |
| 828 | Prostate | 0.4186913 | 0.3939539 | 0.325662 | 0.18986106 | RC_AA4313 18_at | EST: zw70d09.s1 Soares testis NHT Homo sapiens cDNA clone 781553 3', mRNA sequence. (from Genbank) |
| 829 | Prostate | 0.4182051 | 0.3938967 | 0.325649 | 0.189856 | U02680_at | Protein tyrosine kinase mRNA |
| 830 | Prostate | 0.4181297 | 0.3938662 | 0.32557 | 0.1897782 | RC_AA0763 26_at | Ribosomal protein L32 |
| 831 | Prostate | 0.4180297 | 0.3938533 | 0.325276 | 0.18972114 | RC_AA2819 51_at | EST: zs89e04.s1 NCI_CGAP_GCB1 Homo sapiens cDNA clone IMAGE:704670 3', mRNA sequence. (from Genbank) |
| 832 | Prostate | 0.4179683 | 0.3936731 | 0.325269 | 0.18966519 | RC_AA0402 70_at | EST: zf05e04.s1 Soares fetal heart NbHH19W Homo sapiens cDNA clone 376062 3', mRNA sequence. (from Genbank) |
| 833 | Prostate | 0.4176296 | 0.3935787 | 0.32521 | 0.1895263 | AA454462_a t | EST: zw28f11.r1 Soares ovary tumor NbHOT Homo sapiens cDNA clone 770637 5', mRNA sequence. (from Genbank) |
| 834 | Prostate | 0.41752 | 0.3935441 | 0.325193 | 0.18934787 | S80562_at | CNN3 Calponin 3, acidic |
| 835 | Prostate | 0.4174088 | 0.3935312 | 0.325131 | 0.18944083 | M34192_at | IVD Isovaleryl Coenzyme A dehydrogenase |
| 836 | Prostate | 0.416987 | 0.3935105 | 0.325126 | 0.18934672 | X17094_at | PACE Paired basic amino acid cleaving enzyme (furin, membrane associated receptor protein) |
| 837 | Prostate | 0.4169661 | 0.393083 | 0.325037 | 0.18925475 | RC_AA4431 14_at | EST: zx74c07.s1 Soares ovary tumor NbHOT Homo sapiens cDNA clone 809484 3', mRNA sequence. (from Genbank) |
| 838 | Prostate | 0.4167318 | 0.3929958 | 0.324971 | 0.18922225 | U06631_at | IEF SSP 9502 mRNA |
| 839 | Prostate | 0.4166757 | 0.3928948 | 0.324886 | 0.18916391 | RC_AA4812 68_at | EST: aa35c04.s1 NCI_CGAP_GCB1 Homo sapiens cDNA clone IMAGE:815238 3', mRNA sequence. (from Genbank) |

FIG. 12N2

| | | | | | |
|---|---|---|---|---|---|
| 840 | Prostate | 0.4165961 | 0.3928434 | 0.324862 | 0.18900887 | RC_AA4486 27_f_at | EST: zx10a05.s1 Soares total fetus Nb2HF8 9w Homo sapiens cDNA clone 786032 3' similar to contains Alu repetitive element;, mRNA sequence. (from Genbank) |
| 841 | Prostate | 0.4164773 | 0.3927999 | 0.324827 | 0.18906832 | AA328993_s_at | EST: EST32546 Embryo, 12 week I Homo sapiens cDNA 5' end, mRNA sequence. (from Genbank) |
| 842 | Prostate | 0.4157123 | 0.3927659 | 0.324731 | 0.18895558 | C01833_at | EST: HUMGS0003801, Human Gene Signature, 3'-directed cDNA sequence, mRNA sequence. (from Genbank) |
| 843 | Prostate | 0.4151094 | 0.3927232 | 0.32464 | 0.18894494 | RC_AA4909 30_at | EST: aa46e04.s1 NCI_CGAP_GCB1 Homo sapiens cDNA clone IMAGE:823998 3', mRNA sequence. (from Genbank) |
| 844 | Prostate | 0.41506 | 0.3926233 | 0.324537 | 0.18883753 | RC_AA4501 14_at | EST: zx42e04.s1 Soares total fetus Nb2HF8 9w Homo sapiens cDNA clone 789150 3' similar to TR:G641819 G641819 HHEB HALOHYDRIN EPOXIDASE B. ;, mRNA sequence. (from Genbank) |
| 845 | Prostate | 0.4150477 | 0.3925594 | 0.324401 | 0.18867612 | RC_AA4361 92_at | EST: zv22f01.s1 Soares NhHMPu S1 Homo sapiens cDNA clone 754393 3', mRNA sequence. (from Genbank) |
| 846 | Prostate | 0.4149323 | 0.3925212 | 0.324332 | 0.18862917 | RC_AA2367 15_at | EST: zt29c10.s1 Soares ovary tumor NbHOT Homo sapiens cDNA clone 723762 3', mRNA sequence. (from Genbank) |
| 847 | Prostate | 0.4143633 | 0.3924784 | 0.324112 | 0.18850122 | L07594_at | TGFBR3 Transforming growth factor, beta receptor III (betaglycan, 300kD)) |
| 848 | Prostate | 0.4141221 | 0.3924667 | 0.324086 | 0.18841319 | RC_AA2868 73_at | EST: zs55g07.s1 NCI_CGAP_GCB1 Homo sapiens cDNA clone IMAGE:701436 3', mRNA sequence. (from Genbank) |
| 849 | Prostate | 0.4136635 | 0.3924512 | 0.324082 | 0.18830906 | M57888_rna 1_s_at | Granzyme B (granzyme 2, cytotoxic T-lymphocyte-associated serine esterase 1) |
| 850 | Prostate | 0.4135426 | 0.3924359 | 0.323952 | 0.18817572 | L40391_at | (clone s153) mRNA fragment |
| 851 | Prostate | 0.4134507 | 0.3923549 | 0.323952 | 0.18817572 | M85289_at | HSPG2 Heparan sulfate proteoglycan |
| 852 | Prostate | 0.4132956 | 0.3922624 | 0.323928 | 0.18813461 | D63477_at | KIAA0143 gene, partial cds |
| 853 | Prostate | 0.412986 | 0.3922581 | 0.323817 | 0.18808953 | T69384_at | Period (Drosophila) homolog |
| 854 | Prostate | 0.412788 | 0.3921701 | 0.323808 | 0.18799576 | R76363_at | Homo sapiens Chromosome 16 BAC clone CIT987SK-44M2 |
| 855 | Prostate | 0.4126909 | 0.3921285 | 0.323808 | 0.18794096 | RC_AA4125 05_at | EST: zt97b09.s1 Soares testis NHT Homo sapiens cDNA clone 730265 3', mRNA sequence. (from Genbank) |
| 856 | Prostate | 0.4125964 | 0.391906 | 0.323744 | 0.1879026 | N31668_at | Novel centrosomal protein RanBPM |
| 857 | Prostate | 0.4119702 | 0.3918923 | 0.32358 | 0.18779713 | RC_AA4888 44_f_at | EST: aa55a11.s1 NCI_CGAP_GCB1 Homo sapiens cDNA clone IMAGE:824828 3', mRNA sequence. (from Genbank) |
| 858 | Prostate | 0.4117664 | 0.3918372 | 0.323479 | 0.18776494 | RC_AA4469 26_s_at | UDP-Gal:betaGlcNAc beta 1,4- galactosyltransferase, polypeptide 4 |
| 859 | Prostate | 0.4117362 | 0.391823 | 0.323428 | 0.18767688 | RC_AA4787 94_at | EST: zv20e01.s1 Soares NhHMPu S1 Homo sapiens cDNA clone 754200 3', mRNA sequence. (from Genbank) |
| 860 | Prostate | 0.411589 | 0.391754 | 0.323344 | 0.18758014 | RC_D25786_at | Myosin, heavy polypeptide-like (110kD) |

FIG. 12O2

| | | | | | |
|---|---|---|---|---|---|
| 861 | Prostate | 0.4114483 | 0.3916954 | 0.32329 | 0.187436685 | RC_AA2587 38_at | UBIQUITIN |
| 862 | Prostate | 0.4112792 | 0.3916414 | 0.323216 | 0.187391188 | RC_AA4536 14_i_at | Homo sapiens mRNA for KIAA0776 protein, partial cds |
| 863 | Prostate | 0.4110654 | 0.3915603 | 0.323144 | 0.187353394 | Z48633_at | Retrotransposon |
| 864 | Prostate | 0.4109948 | 0.3914363 | 0.323111 | 0.18734684 | RC_AA0750 48_at | EST: zm85c11.s1 Stratagene ovarian cancer (#937219) Homo sapiens cDNA clone 544724 3'; mRNA sequence. (from Genbank) |
| 865 | Prostate | 0.4107381 | 0.3914286 | 0.323058 | 0.187251148 | M34057_at | LTBP1 Latent transforming growth factor beta binding protein 1 |
| 866 | Prostate | 0.4107137 | 0.3913721 | 0.323048 | 0.187133385 | RC_AA1949 98_at | Homo sapiens purinergic receptor P2Y5 mRNA, complete cds |
| 867 | Prostate | 0.4105425 | 0.3913721 | 0.322957 | 0.18704987 | RC_AA4304 96_r_at | Ferritin, light polypeptide |
| 868 | Prostate | 0.4105303 | 0.3912928 | 0.322952 | 0.18695141 | RC_AA4638 61_at | EST: zx97c05.s1 Soares NhHMPu S1 Homo sapiens cDNA clone 811688 3' similar to SW:RB25_RABIT P46629 RAS-RELATED PROTEIN RAB-25. ; mRNA sequence. (from Genbank) |
| 869 | Prostate | 0.4102131 | 0.3910668 | 0.322869 | 0.186827366 | RC_AA4120 19_at | EST: zt68b12.s1 Soares testis NHT Homo sapiens cDNA clone 727487 3', mRNA sequence. (from Genbank) |
| 870 | Prostate | 0.4102112 | 0.3909649 | 0.322837 | 0.187244450 | D50926_at | KIAA0136 gene, partial cds |
| 871 | Prostate | 0.4102056 | 0.3909392 | 0.322602 | 0.186682911 | RC_AA1017 67_at | EST: zk96d09.s1 Soares pregnant uterus NbHPU Homo sapiens cDNA clone 490673 3', mRNA sequence. (from Genbank) |
| 872 | Prostate | 0.4101055 | 0.39092 | 0.322548 | 0.186596547 | RC_AA5986 79_at | EST: ae40b06.s1 Gessler Wilms tumor Homo sapiens cDNA clone 898259 3' similar to contains Alu repetitive element;, mRNA sequence. (from Genbank) |
| 873 | Prostate | 0.4100795 | 0.3908784 | 0.322543 | 0.186496348 | RC_AA2781 34_at | EST: zt08f12.s1 NCI_CGAP_GCB1 Homo sapiens cDNA clone IMAGE:712559 3', mRNA sequence. (from Genbank) |
| 874 | Prostate | 0.4099734 | 0.3907792 | 0.322519 | 0.186376537 | D87447_at | KIAA0258 gene |
| 875 | Prostate | 0.4098536 | 0.3907502 | 0.322485 | 0.186340420 | RC_AA1558 20_at | Transmembrane 4 superfamily member 6 |
| 876 | Prostate | 0.4095132 | 0.3907459 | 0.322468 | 0.186290019 | W27721_at | Homo sapiens KIAA0424 mRNA, partial cds |
| 877 | Prostate | 0.4092820 | 0.3907272 | 0.322308 | 0.186204368 | L07592_at-2 | Human peroxisome proliferator activated receptor mRNA, complete cds |
| 878 | Prostate | 0.409282 | 0.3906829 | 0.322195 | 0.186142585 | L07592_at | Peroxisome proliferator activated receptor mRNA |
| 879 | Prostate | 0.4092353 | 0.3906716 | 0.322177 | 0.186084264 | U37547_at | IAP homolog B (MIHB) mRNA |
| 880 | Prostate | 0.4090486 | 0.3906173 | 0.322125 | 0.186046536 | RC_AA4007 66_at | Homo sapiens mRNA for KIAA0556 protein, partial cds |
| 881 | Prostate | 0.4087048 | 0.39057 | 0.322088 | 0.186008931 | U63973_at | Rhodopsin kinase |
| 882 | Prostate | 0.408646 | 0.3903907 | 0.32207 | 0.185929821 | M90391_s_a_t | Putative IL-16 protein precursor, mRNA |

FIG. 12P2

| | | | | | |
|---|---|---|---|---|---|
| 883 | Prostate | 0.408646 | 0.3903125 | 0.321921 | 0.18583238 | M90391_s_a t-2 | Interleukin 16 (lymphocyte chemoattractant factor) |
| 884 | Prostate | 0.407977 | 0.3902375 | 0.321856 | 0.18579483 | U41766_s_a t | Metalloprotease/disintegrin/cysteine-rich protein precursor (MDC9) mRNA |
| 885 | Prostate | 0.4079583 | 0.3901998 | 0.321782 | 0.18570139 | AA128724_a t | Homo sapiens mRNA for KIAA0684 protein, partial cds |
| 886 | Prostate | 0.4078014 | 0.3901773 | 0.321711 | 0.18559916 | RC_AA5213 54_at | EST: aa68h12.s1 NCI_CGAP_GCB1 Homo sapiens cDNA clone IMAGE:826151 3', mRNA sequence. (from Genbank) |
| 887 | Prostate | 0.4076878 | 0.3901469 | 0.321576 | 0.18551043 | RC_AA4521 08_at | Transcription factor AP-2 alpha (activating enhancer-binding protein 2 alpha) |
| 888 | Prostate | 0.4074649 | 0.3901374 | 0.321401 | 0.18541263 | U49785_at | DCT Dopachrome tautomerase (dopachrome delta-isomerase, tyrosine-related protein 2) |
| 889 | Prostate | 0.4074521 | 0.390047 | 0.321314 | 0.18530278 | J00123_at | PROENKEPHALIN A PRECURSOR |
| 890 | Prostate | 0.4072436 | 0.3900428 | 0.321264 | 0.1852362 | M15169_at | ADRB2 Adrenergic, beta-2-, receptor, surface |
| 891 | Prostate | 0.4070797 | 0.3899363 | 0.32126 | 0.18517093 | AA227813_a t | EST: zr56d01.r1 Soares NhHMPu S1 Homo sapiens cDNA clone 667393 5', mRNA sequence. (from Genbank) |
| 892 | Prostate | 0.4065349 | 0.3899047 | 0.321174 | 0.18513048 | RC_AA4178 76_at | EST: zv05f04.s1 Soares NhHMPu S1 Homo sapiens cDNA clone 752767 3', mRNA sequence. (from Genbank) |
| 893 | Prostate | 0.4064272 | 0.3896814 | 0.321159 | 0.18508972 | RC_AA1431 90_s_at | EST: zo36a01.s1 Stratagene endothelial cell 937223 Homo sapiens cDNA clone 588936 3' similar to SW:YBF7_YEAST P34222 HYPOTHETICAL 23.1 KD PROTEIN IN SHP1-SEC17 INTERGENIC REGION. ; mRNA sequence. (from Genbank) |
| 894 | Prostate | 0.4062292 | 0.3896766 | 0.321052 | 0.18505378 | AFFX-BioDn-3_st | AFFX-BioDn-3_st (endogenous control) |
| 895 | Prostate | 0.4062292 | 0.3896471 | 0.321052 | 0.18497527 | AFFX-BioDn-3_st-2 | AFFX-BioDn-3_st (miscellaneous control - 11k chips) |
| 896 | Prostate | 0.4061936 | 0.3896192 | 0.320988 | 0.18481416 | D87440_at | KIAA0252 gene, partial cds |
| 897 | Prostate | 0.4061287 | 0.3895537 | 0.320953 | 0.18473566 | D87461_at | KIAA0271 gene |
| 898 | Prostate | 0.4059938 | 0.3894101 | 0.320852 | 0.18465701 | RC_AA0318 14_at | EST: zk17g04.s1 Soares pregnant uterus NbHPU Homo sapiens cDNA clone 470838 3', mRNA sequence. (from Genbank) |
| 899 | Prostate | 0.4059903 | 0.3893094 | 0.3208 | 0.1845848 | M36341_at | ARF4 ADP-ribosylation factor 4 |
| 900 | Prostate | 0.4058068 | 0.3891715 | 0.320793 | 0.18448263 | RC_AA6101 16_i_at | EST: af19g10.s1 Soares total fetus Nb2HF8 9w Homo sapiens cDNA clone 1032162 3', mRNA sequence. (from Genbank) |
| 901 | Prostate | 0.4057325 | 0.3891715 | 0.320708 | 0.18444683 | AA234634_f _at | CCAAT/enhancer binding protein (C/EBP), delta |

FIG. 12Q2

| # | Tissue | | | | | ID | Description |
|---|---|---|---|---|---|---|---|
| 902 | Prostate | 0.4053121 | 0.3891494 | | 0.320708 | 0.18434486 | RC_AA2877_35_at | Human DNA sequence from clone 1169B24 on chromosome Xq25-26.3. Contains NADH-Ubiquinone Oxidoreductase MLRQ subunit (EC 1.6.5.3, EC 1.6.99.3, CI-MLRQ), Tubulin Beta and Proto-oncogene Tyrosine-protein Kinase FER (EC 2.7.1.112, P94-FER, C-FER, TYK3) pseudogenes, and part of a novel gene similar to hypothetical proteins S. pombe C22F3.14C and C. elegans C16A3.8. Contains ESTs and GSSs |
| 903 | Prostate | 0.405306 | 0.3891183 | | 0.320583 | 0.18429292 | RC_AA2847_55_at | CDW52 antigen (CAMPATH-1 antigen) |
| 904 | Prostate | 0.4052855 | 0.3890992 | | 0.320499 | 0.18420975 | RC_AA4890_74_at | EST: aa54g11.s1 NCI_CGAP_GCB1 Homo sapiens cDNA clone IMAGE:824804 3', mRNA sequence. (from Genbank) |
| 905 | Prostate | 0.4052009 | 0.389085 | | 0.320491 | 0.18411641 | D80005_at | KIAA0183 gene, partial cds |
| 906 | Prostate | 0.4052003 | 0.3890787 | | 0.320253 | 0.18411295 | RC_AA4283_25_at | EST: zw18e01.s1 Soares ovary tumor NbHOT Homo sapiens cDNA clone 769656 3', mRNA sequence. (from Genbank) |
| 907 | Prostate | 0.4051893 | 0.3890466 | | 0.320226 | 0.18409792 | AA486511_a_t | EST: ab38g04.r1 Stratagene HeLa cell s3 937216 Homo sapiens cDNA clone 843126 5' similar to TR:G728657 G728657 HYPOTHETICAL 20.9 KD PROTEIN.; mRNA sequence. (from Genbank) |
| 908 | Prostate | 0.4051694 | 0.3889134 | | 0.320196 | 0.18399018 | RC_AA4897_07_at | EST: aa50f01.s1 NCI_CGAP_GCB1 Homo sapiens cDNA clone IMAGE:824377 3', mRNA sequence. (from Genbank) |
| 909 | Prostate | 0.4043695 | 0.388903 | | 0.32013 | 0.18385305 | AF009301_a_t | TEB4 protein mRNA |
| 910 | Prostate | 0.4042842 | 0.3887318 | | 0.319992 | 0.18377991 | RC_AA1932_04_at | Arg/Abl-interacting protein ArgBP2 |
| 911 | Prostate | 0.4041726 | 0.3886707 | | 0.319973 | 0.18372235 | L20492_s_at | Gamma-glutamyltransferase 1 |
| 912 | Prostate | 0.4040466 | 0.3885544 | | 0.319967 | 0.18365577 | RC_AA4537_90_at | EST: aa19i01.s1 Soares NhHMPu S1 Homo sapiens cDNA clone 813721 3', mRNA sequence. (from Genbank) |
| 913 | Prostate | 0.4039669 | 0.3883877 | | 0.319938 | 0.18362539 | Z84718_cds1_at | GSTT1 gene extracted from Human DNA sequence from BAC 322B1 on chromosome 22q11.2-qter contains GSTT1, GSTT2 glutathione transferases 4E-binding protein 1 pseudogene, D-dopachrome tautomerase pseudogene ESTs and polymorphic CA repeat |
| 914 | Prostate | 0.4039596 | 0.3883841 | | 0.319982 | 0.18336846 | RC_AA0888_51_s_at | S-adenosylmethionine decarboxylase 1 |
| 915 | Prostate | 0.4037938 | 0.3883561 | | 0.319803 | 0.18333037 | AA477274_s_at | EST: zu43d11.r1 Soares ovary tumor NbHOT Homo sapiens cDNA clone 740757 5', mRNA sequence. (from Genbank) |
| 916 | Prostate | 0.4037715 | 0.3883128 | | 0.319733 | 0.18321554 | RC_AA4569_81_at | EST: aa90h11.s1 Stratagene fetal retina 937202 Homo sapiens cDNA clone 838629 3' similar to contains Alu repetitive element;, mRNA sequence. (from Genbank) |

FIG. 12R2

| # | Tissue | | | | | Description |
|---|---|---|---|---|---|---|
| 917 | Prostate | 0.4037338 | 0.3882999 | 0.319733 | 0.18319468 | D21851_at | KIAA0028 gene, partial cds |
| 918 | Prostate | 0.403671 | 0.3882406 | 0.319717 | 0.18316568 | RC_AA4033 05_at | EST: zt44e03.s1 Soares ovary tumor NbHOT Homo sapiens cDNA clone 725212 3', mRNA sequence. (from Genbank) |
| 919 | Prostate | 0.4034759 | 0.3882097 | 0.319717 | 0.18312657 | RC_AA4902 62_at | EST: aa44c09.s1 Soares NhHMPu S1 Homo sapiens cDNA clone 823792 3', mRNA sequence. (from Genbank) |
| 920 | Prostate | 0.4031337 | 0.3882001 | 0.319676 | 0.183018 | H41895_at | EST: yo07h11.r1 Homo sapiens cDNA clone 177285 5'. (from Genbank) |
| 921 | Prostate | 0.402958 | 0.3881559 | 0.319644 | 0.18299669 | RC_AA2563 23_at | EST: zr80f05.s1 Soares NhHMPu S1 Homo sapiens cDNA clone 682017 3', mRNA sequence. (from Genbank) |
| 922 | Prostate | 0.4026491 | 0.3881149 | 0.319419 | 0.18294485 | RC_AA0019 28_at | EST: zh83f05.s1 Soares fetal liver spleen 1NFLS S1 Homo sapiens cDNA clone 427905 3', mRNA sequence. (from Genbank) |
| 923 | Prostate | 0.4026029 | 0.3881457 | 0.319412 | 0.18285854 | D50927_at | KIAA0137 gene |
| 924 | Prostate | 0.4025732 | 0.3881173 | 0.31927 | 0.18276237 | RC_AA2512 97_at | EST: zs10a10.s1 NCI_CGAP_GCB1 Homo sapiens cDNA clone IMAGE:684762 3', mRNA sequence. (from Genbank) |
| 925 | Prostate | 0.4025597 | 0.3880583 | 0.319168 | 0.18269958 | AA216094_s at | EST: hp0453.seq.F Fetal heart, Lambda ZAP Express Homo sapiens cDNA 5', mRNA sequence. (from Genbank) |
| 926 | Prostate | 0.4024883 | 0.388041 | 0.319148 | 0.18259564 | M88163_at | SNF2L1 SNF2 (sucrose nonfermenting, yeast, homolog)-like 1 |
| 927 | Prostate | 0.4024381 | 0.3880153 | 0.319134 | 0.1825456 | RC_AA4868 68_s_at | Slit (Drosophila) homolog 2 |
| 928 | Prostate | 0.4022618 | 0.3879926 | 0.319085 | 0.18242222 | RC_AA4427 68_i_at | Homo sapiens inner mitochondrial membrane translocase Tim23 (TIM23) mRNA, nuclear gene encoding mitochondrial protein, complete cds |
| 929 | Prostate | 0.4021527 | 0.3879268 | 0.318983 | 0.18235163 | M33680_at | 26-kDa cell surface protein TAPA-1 mRNA |
| 930 | Prostate | 0.4020408 | 0.3878605 | 0.318944 | 0.18229832 | RC_AA4771 10_at | EST: zu37a08.s1 Soares ovary tumor NbHOT Homo sapiens cDNA clone 740150 3', mRNA sequence. (from Genbank) |
| 931 | Prostate | 0.4019333 | 0.3875953 | 0.318822 | 0.18218704 | AA011479_a t | EST: zi01b10.r1 Soares fetal liver spleen 1NFLS S1 Homo sapiens cDNA clone 429499 5', mRNA sequence. (from Genbank) |
| 932 | Prostate | 0.4014008 | 0.3876688 | 0.318811 | 0.1821415 | U69114_at | EST: Human Down syndrome region, YAC 152F7, mRNA sequence. (from Genbank) |
| 933 | Prostate | 0.4012037 | 0.387523 | 0.318685 | 0.18209605 | RC_AA1590 25_at | EST: zo57h03.s1 Stratagene pancreas (#937208) Homo sapiens cDNA clone 591029 3', mRNA sequence. (from Genbank) |
| 934 | Prostate | 0.4008134 | 0.3875125 | 0.318656 | 0.18197335 | RC_AA4912 95_at | Homo sapiens mRNA for KIAA0787 protein, partial cds |
| 935 | Prostate | 0.4007025 | 0.3874985 | 0.318547 | 0.18193193 | D80009_at | KIAA0187 gene |
| 936 | Prostate | 0.4003674 | 0.3873945 | 0.318527 | 0.18185376 | IL4_at | No info for gene |
| 937 | Prostate | 0.4000988 | 0.3873667 | 0.318484 | 0.18174767 | X79888_at | AUH mRNA |
| 938 | Prostate | 0.3998589 | 0.3873302 | 0.318458 | 0.18161681 | U47025_s_a t | PYGB Glycogen phosphorylase B (brain form) |

FIG. 12S2

| | | | | | |
|---|---|---|---|---|---|
| 939 | Prostate | 0.3993242 | 0.3873293 | 0.318361 | 0.18161076 | RC_AA4572 42_at | Etoposide-induced mRNA |
| 940 | Prostate | 0.3990546 | 0.3873209 | 0.318225 | 0.18154973 | RC_AA1803 21_at | Homo sapiens (clone S164) mRNA, 3' end of cds |
| 941 | Prostate | 0.3988855 | 0.3872608 | 0.318175 | 0.18145733 | U90716_at | Cell surface protein HCAR mRNA |
| 942 | Prostate | 0.3985443 | 0.3871708 | 0.318057 | 0.1813474 | U72507_at-2 | Human 40871 mRNA partial sequence. (from Genbank) |
| 943 | Prostate | 0.3985443 | 0.3871149 | 0.318019 | 0.18131801 | U72507_at | 40871 mRNA partial sequence |
| 944 | Prostate | 0.3984186 | 0.3871095 | 0.317891 | 0.18130562 | RC_AA4192 17_at | EST: zv34h10.s1 Soares ovary tumor NbHOT Homo sapiens cDNA clone 755587 3', mRNA sequence. (from Genbank) |
| 945 | Prostate | 0.3982768 | 0.3870637 | 0.317826 | 0.1812315 | H66279_at | Yr72b07.r1 Homo sapiens cDNA clone 210805 5'. (from Genbank) |
| 946 | Prostate | 0.3979961 | 0.3869908 | 0.317794 | 0.1810997 | AA410565_a t | EST: zv23d06.r1 Soares NhHMPu S1 Homo sapiens cDNA clone 754475 5', mRNA sequence. (from Genbank) |
| 947 | Prostate | 0.3979238 | 0.3868783 | 0.317794 | 0.18106246 | RC_AA2533 97_at | Homo sapiens clone 24659 mRNA sequence |
| 948 | Prostate | 0.3979104 | 0.3868615 | 0.317695 | 0.1810318 | Y09858_at | Unknown protein |
| 949 | Prostate | 0.3979104 | 0.3868431 | 0.317675 | 0.18094458 | Y09858_at-2 | H.sapiens mRNA for unknown protein. (from Genbank) |
| 950 | Prostate | 0.3977601 | 0.3868421 | 0.317573 | 0.18091044 | M25077_at | 60-kdal ribonucleoprotein (Ro) mRNA |
| 951 | Prostate | 0.3977529 | 0.3868181 | 0.317535 | 0.1807694 | W58057_s_ at | Periplakin |
| 952 | Prostate | 0.3977314 | 0.3867126 | 0.317512 | 0.18073604 | X70476_at | COATOMER BETA' SUBUNIT |
| 953 | Prostate | 0.3974473 | 0.3866468 | 0.317392 | 0.18062319 | L43964_at | PSEN2 Presenilin 2 (Alzheimer disease 4) |
| 954 | Prostate | 0.397377 | 0.3865768 | 0.317239 | 0.18061261 | RC_AA2810 92_at | EST: zt01f01.s1 NCI_CGAP_GCB1 Homo sapiens cDNA clone IMAGE:711865 3' similar to contains Alu repetitive element;, mRNA sequence. (from Genbank) |
| 955 | Prostate | 0.3973098 | 0.3865537 | 0.317235 | 0.18055633 | U77396_at | LPS-Induced TNF-Alpha Factor (LITAF) mRNA |
| 956 | Prostate | 0.3970723 | 0.386523 | 0.317171 | 0.18048686 | AA017469_a t | EST: ze38f11.r1 Soares retina N2b4HR Homo sapiens cDNA clone 361293 5', mRNA sequence. (from Genbank) |
| 957 | Prostate | 0.3967476 | 0.3864747 | 0.317098 | 0.18048686 | D58019_s_a t | EST: Human aorta cDNA 5'-end GEN-341A10, mRNA sequence. (from Genbank) |
| 958 | Prostate | 0.3966605 | 0.3861831 | 0.317047 | 0.1804609 | V00594_s_at | Metallothionein isoform 2 |
| 959 | Prostate | 0.3966207 | 0.3861783 | 0.31697 | 0.18037982 | RC_AA2362 80_at | EST: zr51f08.s1 Soares NhHMPu S1 Homo sapiens cDNA clone 666951 3', mRNA sequence. (from Genbank) |
| 960 | Prostate | 0.3965805 | 0.3861576 | 0.316922 | 0.18022922 | RC_AA0183 46_at | EST: ze41d12.s1 Soares retina N2b4HR Homo sapiens cDNA clone 361559 3', mRNA sequence. (from Genbank) |
| 961 | Prostate | 0.3965654 | 0.3861554 | 0.31688 | 0.18017419 | D31161_s_a t | EST: Human fetal-lung cDNA 5'-end sequence, mRNA sequence. (from Genbank) |

FIG. 12T2

| | | | | | | |
|---|---|---|---|---|---|---|
| 962 | Prostate | 0.3962975 | 0.3861492 | 0.316859 | 0.18015334 | RC_AA3427 80_at | EST: EST48360 Fetal spleen Homo sapiens cDNA 3' end, mRNA sequence. (from Genbank) |
| 963 | Prostate | 0.3962705 | 0.386134 | 0.316828 | 0.18009858 | U52522_at | Arfaptin 2, putative target protein of ADP-ribosylation factor, mRNA |
| 964 | Prostate | 0.3960956 | 0.3861249 | 0.316665 | 0.18001568 | R15917_at | Homo sapiens clone 24629 mRNA sequence |
| 965 | Prostate | 0.3960561 | 0.3860441 | 0.316647 | 0.18001218 | H49499_s_a t | Homo sapiens chromosome 19, cosmid F23149 |
| 966 | Prostate | 0.3960558 | 0.3859657 | 0.316636 | 0.17996643 | D16350_at | SA mRNA for SA gene product |
| 967 | Prostate | 0.3957903 | 0.3859039 | 0.316556 | 0.17980534 | AA091278_a t | EST: cctin24o4.seq.F Fetal heart, Lambda ZAP Express Homo sapiens cDNA 5', mRNA sequence. (from Genbank) |
| 968 | Prostate | 0.3956522 | 0.3857664 | 0.316549 | 0.17979702 | RC_AA2590 62_at | EST: zs30h07.s1 NCI_CGAP_GCB1 Homo sapiens cDNA clone IMAGE:686749 3', mRNA sequence. (from Genbank) |
| 969 | Prostate | 0.3956273 | 0.3857104 | 0.316481 | 0.17969652 | AA402121_a t | EST: zf67e02.r1 Soares testis NHT Homo sapiens cDNA clone 727418 5', mRNA sequence. (from Genbank) |
| 970 | Prostate | 0.3955916 | 0.3857104 | 0.316414 | 0.17964965 | HG2810-HT2921_at | Homeotic Protein PI2 |
| 971 | Prostate | 0.3952883 | 0.3856884 | 0.316407 | 0.17957145 | RC_AA1583 86_at | EST: zo66c01.s1 Stratagene pancreas (#937208) Homo sapiens cDNA clone 591840 3', mRNA sequence. (from Genbank) |
| 972 | Prostate | 0.3952823 | 0.3856613 | 0.316385 | 0.17946391 | RC_AA3985 21_at | EST: zf47d09.s1 Soares ovary tumor NbHOT Homo sapiens cDNA clone 725489 3', mRNA sequence. (from Genbank) |
| 973 | Prostate | 0.3951265 | 0.3856427 | 0.316295 | 0.17944537 | L41816_at | Cam kinase I mRNA |
| 974 | Prostate | 0.3949496 | 0.3854027 | 0.316245 | 0.17941353 | U72515_at | C3f mRNA |
| 975 | Prostate | 0.3942614 | 0.3853829 | 0.316106 | 0.17933471 | RC_AA1570 13_at | EST: zl21b03.s1 Soares pregnant uterus NbHPU Homo sapiens cDNA clone 502541 3', mRNA sequence. (from Genbank) |
| 976 | Prostate | 0.3942431 | 0.3852371 | 0.316089 | 0.17925505 | RC_AA2522 42_at | EST: zr64g04.s1 Soares NhHMPu S1 Homo sapiens cDNA clone 668214 3', mRNA sequence. (from Genbank) |
| 977 | Prostate | 0.394226 | 0.3851859 | 0.315979 | 0.17925505 | W27176_s_a t | EST: 23c2 Human retina cDNA randomly primed sublibrary Homo sapiens cDNA, mRNA sequence. (from Genbank) |
| 978 | Prostate | 0.3940985 | 0.385127 | 0.315818 | 0.17922665 | X89986_s_a t | NBK apoptotic inducer protein |
| 979 | Prostate | 0.3933957 | 0.3850906 | 0.315818 | 0.1791471 | AA442274_a t | EST: zv54a06.r1 Soares testis NHT Homo sapiens cDNA clone 757426 5', mRNA sequence. (from Genbank) |
| 980 | Prostate | 0.3933111 | 0.3850804 | 0.315774 | 0.17896011 | R06629_at | Adducin 2 (beta) |
| 981 | Prostate | 0.3930253 | 0.3850281 | 0.315638 | 0.17887908 | X56807_at-2 | Desmocollin 2 |
| 982 | Prostate | 0.3930253 | 0.3850281 | 0.315581 | 0.17879327 | X56807_at | DESMOCOLLIN 2A/BB PRECURSOR |
| 983 | Prostate | 0.3929346 | 0.3849988 | 0.315558 | 0.17875476 | RC_D58894 _at | EST: Human fetal brain cDNA 3'-end GEN-073B05, mRNA sequence. (from Genbank) |
| 984 | Prostate | 0.3928745 | 0.3849641 | 0.315552 | 0.17870230 | L42176_at | (clone 35.3) DRAL mRNA |
| 985 | Prostate | 0.39284 | 0.3849206 | 0.315516 | 0.17862254 | RC_AA2530 43_at | EST: zr52b12.s1 Soares NhHMPu S1 Homo sapiens cDNA clone 667007 3', mRNA sequence. (from Genbank) |

FIG. 12U2

| | | | | | |
|---|---|---|---|---|---|
| 986 | Prostate | 0.392768 | 0.3848803 | 0.17860498 | AA340065_s_at | Homo sapiens hHa4 gene, complete CDS |
| 987 | Prostate | 0.3927505 | 0.384696 | 0.17839946 | RC_AA2532 20_at | EST: zr53g12.s1 Soares NhHMPu S1 Homo sapiens cDNA clone 667174 3', mRNA sequence. (from Genbank) |
| 988 | Prostate | 0.3922151 | 0.384696 | 0.17835936 | X67098_at | RTS beta protein |
| 989 | Prostate | 0.392006 | 0.3846896 | 0.17830187 | RC_AA4062 18_at | EST: zu65e08.s1 Soares testis NHT Homo sapiens cDNA clone 742886 3', mRNA sequence. (from Genbank) |
| 990 | Prostate | 0.3914417 | 0.3845063 | 0.17825313 | RC_AA0529 47_i_at | EST: zl70d10.s1 Stratagene colon (#937204) Homo sapiens cDNA clone 509971 3', mRNA sequence. (from Genbank) |
| 991 | Prostate | 0.3914041 | 0.3844245 | 0.17821486 | S62539_s_at | Insulin receptor substrate 1 |
| 992 | Prostate | 0.3913986 | 0.384361 | 0.17804605 | D13630_at | KIAA0005 gene |
| 993 | Prostate | 0.3913282 | 0.3843182 | 0.17794557 | AA150333_a t | Homo sapiens thyroid hormone receptor activator molecule (TRAM-1) mRNA, complete cds |
| 994 | Prostate | 0.3912189 | 0.3842264 | 0.17793225 | U20908_at | Clone 350/2 melanoma ubiquitous mutated protein (MUM-1) gene, partial cds |
| 995 | Prostate | 0.3911457 | 0.3841692 | 0.1778919 | W27770_at | EST: 3779 Human retina cDNA randomly primed sublibrary Homo sapiens cDNA, mRNA sequence. (from Genbank) |
| 996 | Prostate | 0.3909054 | 0.3840391 | 0.1778893 | U33286_at | Chromosome segregation gene homolog CAS mRNA |
| 997 | Prostate | 0.3908841 | 0.3839263 | 0.17776524 | U41515_at | Deleted in split hand/split foot 1 (DSS1) mRNA |
| 998 | Prostate | 0.3904275 | 0.3838315 | 0.17763752 | H88035_s_a t | Homo sapiens mRNA for KIAA0776 protein, partial cds |
| 999 | Prostate | 0.3904215 | 0.3838297 | 0.17775948 | RC_AA2338 41_at | EST: zr49a12.s1 Soares NhHMPu S1 Homo sapiens cDNA clone 666718 3', mRNA sequence. (from Genbank) |
| 1000 | Prostate | 0.3903119 | 0.3837899 | 0.17753293 | RC_AA2806 87_at | EST: zs95h08.s1 NCI_CGAP_GCB1 Homo sapiens cDNA clone IMAGE:705279 3', mRNA sequence. (from Genbank) |

FIG. 12V2

| | | | | |
|---|---|---|---|---|
| 1 Renal | 0.7236232 | 0.7189214 | 0.623652 | 0.46917585 | U66036_at | Sulfotransferase mRNA |
| 2 Renal | 0.7142936 | 0.6679657 | 0.579002 | 0.43806225 | U14588_at | Paxillin mRNA |
| 3 Renal | 0.7051538 | 0.6428464 | 0.557459 | 0.420653853 | RC_AA4342 45_r_at | EST: zw24g05.s1 Soares ovary tumor NbHOT Homo sapiens cDNA clone 770264 3', mRNA sequence. (from Genbank) |
| 4 Renal | 0.6645773 | 0.6222867 | 0.542078 | 0.410399953 | X91117_rna 1_at | HG NET gene exon 1 |
| 5 Renal | 0.659478 | 0.6137351 | 0.533008 | 0.40186924 | M32373_at | ARSB Arylsulfatase B |
| 6 Renal | 0.6550589 | 0.6054473 | 0.524504 | 0.39495236 | D13897_rna 2_at | Peptide YY precursor gene extracted from Human DNA for peptide YY |
| 7 Renal | 0.6428379 | 0.5974814 | 0.519016 | 0.3887878 | R25253_at | Seven in absentia (Drosophila) homolog 2 |
| 8 Renal | 0.6412759 | 0.5927476 | 0.514072 | 0.38363478 | L05144_at | PCK1 Phosphoenolpyruvate carboxykinase 1 (soluble) |
| 9 Renal | 0.632971 | 0.5899819 | 0.509061 | 0.37931246 | M64082_at | FMO1 Flavin-containing monooxygenase 1 |
| 10 Renal | 0.6279231 | 0.5835127 | 0.504413 | 0.37547505 | M31994_at | ALDH1 Aldehyde dehydrogenase 1, soluble |

FIG. 13A

| # | Type | | | | | Description |
|---|---|---|---|---|---|---|
| 11 | Renal | 0.6124989 | 0.5762743 | 0.500571 | 0.371892967_at | U73167_cds H_LUCA14.6 gene extracted from Human cosmid LUCA14 |
| 12 | Renal | 0.6097494 | 0.5751283 | 0.496931 | 0.3688056 M27318_f_at | INTERFERON ALPHA-4 PRECURSOR |
| 13 | Renal | 0.6088486 | 0.5700821 | 0.493593 | 0.3654079 U92015_at | Clone 143789 defective mariner transposon Hsmar2 mRNA sequence |
| 14 | Renal | 0.6077709 | 0.5665063 | 0.490415 | 0.36294618 U31384_at | G protein gamma-11 subunit mRNA |
| 15 | Renal | 0.6037929 | 0.5646834 | 0.487563 | 0.36004543 D42039_at | KIAA0081 gene, partial cds |
| 16 | Renal | 0.6037357 | 0.5617836 | 0.485499 | AA452353_i_at | Protein phosphatase 2 (formerly 2A), regulatory subunit B" (PR 72), alpha isoform and (PR 130), beta isoform |
| 17 | Renal | 0.6029763 | 0.5587423 | 0.483813 | 0.3552889 X66436_at | POSSIBLE GTP-BINDING PROTEIN HSR1 |
| 18 | Renal | 0.5986047 | 0.5530478 | 0.481411 | 0.35289082 U32114_at | Caveolin-2 mRNA |
| 19 | Renal | 0.5976415 | 0.5524086 | 0.47945 | 0.35053915 M28439_at | KERATIN, TYPE I CYTOSKELETAL 17 |
| 20 | Renal | 0.5975566 | 0.5500898 | 0.476969 | 0.34884948 X99393_s_a_t | CMKBR5 gene, non-functional mutant |
| 21 | Renal | 0.5973349 | 0.5481755 | 0.475213 | J00207_rna2_at | IFNA gene (interferon alpha-a) extracted from Human leukocyte interferon (leif) alpha-a gene |
| 22 | Renal | 0.5881828 | 0.5460957 | 0.473502 | 0.34502512 D86962_at | KIAA0207 gene |
| 23 | Renal | 0.5817567 | 0.5451021 | 0.471977 | 0.3431942 S81916_at | Phosphoglycerate kinase (alternatively spliced) [human, phosphoglycerate kinase deficient patient with episodes of muscl, mRNA Partial Mutant, 307 nt] |
| 24 | Renal | 0.5785691 | 0.5442907 | 0.469703 | 0.34171772 U03735_f_at | MAGE-3 antigen (MAGE-3) gene |
| 25 | Renal | 0.578142 | 0.5409883 | 0.468094 | 0.340043 J05428_at | UDP-GLUCURONOSYLTRANSFERASE 2B7 PRECURSOR, MICROSOMAL |
| 26 | Renal | 0.5774897 | 0.540307 | 0.46676 | 0.3384387 M31659_at | GT mitochondrial solute carrier protein homologue mRNA |
| 27 | Renal | 0.577166 | 0.5386123 | 0.465425 | 0.336952151 Z80345_rna1_s_at | SCAD gene, exon 1 and joining features |
| 28 | Renal | 0.5763867 | 0.53668555 | 0.463855 | 0.335575952 AA314587_a_t | EST: EST186420 Colon carcinoma (HCC) cell line II Homo sapiens cDNA 5' end, mRNA sequence. (from Genbank) |
| 29 | Renal | 0.5733975 | 0.5360127 | 0.462335 | 0.33346012864_at RC_AA4573 | EST: aa86a02.s1 Stratagene fetal retina 937202 Homo sapiens cDNA clone 838154 3', mRNA sequence. (from Genbank) |
| 30 | Renal | 0.5735829 | 0.5352877 | 0.461339 | 0.3333448 HT4268_at HG3998- | L-Glycerol-3-Phosphate:Nad+ Oxidoreductase |
| 31 | Renal | 0.5712965 | 0.5323939 | 0.459847 | 0.33201018 M96944_at | PAIRED BOX PROTEIN PAX-5 |
| 32 | Renal | 0.5710069 | 0.5318915 | 0.458679 | 0.33062482 83_s_a RC_AA4565 | Human PL6 protein (PL6) mRNA, complete cds |
| 33 | Renal | 0.5704181 | 0.5305039 | 0.457928 | 0.32922646 L07590_at | PPP2R3 Protein phosphatase 2 (formerly 2A), regulatory subunit B" (PR 72), alpha isoform and (PR 130), beta isoform |
| 34 | Renal | 0.5699427 | 0.5284476 | 0.45722 | 0.327758245 L36644_at | Receptor protein-tyrosine kinase (HEK7) mRNA, 3' end |

FIG. 13B

| # | Tissue | | | | Description |
|---|---|---|---|---|---|
| 35 | Renal | 0.5692905 | 0.527718 | 0.455012 | 0.32679015 | T80685_at | EST: yd23a06.r1 Homo sapiens cDNA clone 109042 5' (from Genbank) |
| 36 | Renal | 0.5681835 | 0.5256051 | 0.454189 | 0.32595423 | X13100_s_at | MYH3 Myosin, heavy polypeptide 3, skeletal muscle, embryonic |
| 37 | Renal | 0.5606657 | 0.5253213 | 0.4534 | 0.32484365 | X69920_s_at | CALCR Calcitonin receptor |
| 38 | Renal | 0.5633689 | 0.5245482 | 0.452031 | 0.32380253 | D14827_at | Tax helper protein 1 |
| 39 | Renal | 0.5615135 | 0.5219296 | 0.45112 | 0.32258534 | U58675_cds2_at | OR17-40 gene extracted from Human olfactory receptor gene cluster on chromosome 17, OR17-228 and OR17-40, and OR17-24 and OR17-25 pseudogenes |
| 40 | Renal | 0.5604476 | 0.5213687 | 0.450483 | 0.32169798 | D88155_s_at | Steroidogenic factor 1 mRNA |
| 41 | Renal | 0.5596337 | 0.5206158 | 0.450309 | 0.32051897 | X81892_at | HE6 Tm7 receptor |
| 42 | Renal | 0.5582625 | 0.5196485 | 0.448726 | 0.31971857 | M61853_at | CYP2C18 Cytochrome P450, subfamily IIC (mephenytoin 4-hydroxylase), polypeptide 18 |
| 43 | Renal | 0.5569618 | 0.5173948 | 0.44789 | 0.3185993 | X92814_at | Rat HREV107-like protein |
| 44 | Renal | 0.5561226 | 0.5159215 | 0.44739 | 0.31764483 | HT4513_at | Zinc Finger Protein Znf155 |
| 45 | Renal | 0.5551963 | 0.5158634 | 0.446623 | 0.31692484 | HG4243-HT4290_s_at | GPI anchored molecule like protein |
| 46 | Renal | 0.5529269 | 0.5152429 | 0.445734 | 0.31592748 | RC_AA401341_at | EST: zu62c02.s1 Soares testis NHT Homo sapiens cDNA clone 742562 3', mRNA sequence. (from Genbank) |
| 47 | Renal | 0.5519459 | 0.5147941 | 0.444671 | 0.31505772 | M21539_at | Small proline rich protein (sprII) mRNA, clone 1292 |
| 48 | Renal | 0.5514525 | 0.5136164 | 0.44371 | 0.31407627 | M14091_at | THYROXINE-BINDING GLOBULIN PRECURSOR |
| 49 | Renal | 0.5510593 | 0.5132961 | 0.442931 | 0.3132262 | U57623_s_at | FATTY ACID-BINDING PROTEIN, HEART |
| 50 | Renal | 0.5503163 | 0.5128887 | 0.442024 | 0.3125271 | M30257_s_at | VCAM1 Vascular cell adhesion molecule 1 |
| 51 | Renal | 0.5473999 | 0.511822 | 0.441733 | 0.31178474 | M16594_at | GSTA1 Glutathione S-transferase A2 |
| 52 | Renal | 0.5459741 | 0.5104736 | 0.440548 | 0.31079242 | M60614_at | WT1 Wilms tumor 1 |
| 53 | Renal | 0.5439452 | 0.5100777 | 0.439719 | 0.31003334 | D38024_at | Facioscapulohumeral muscular dystrophy (FSHD) gene region, D4Z4 tandem repeat unit |
| 54 | Renal | 0.5437236 | 0.5093127 | 0.439292 | 0.30965507 | X69699_at | Pax8 mRNA |
| 55 | Renal | 0.5421976 | 0.5092225 | 0.438973 | 0.30897507 | M59499_at | TISSUE FACTOR PATHWAY INHIBITOR PRECURSOR |
| 56 | Renal | 0.5420483 | 0.5086933 | 0.438347 | 0.30835576 | J03810_at | SLC2A2 Solute carrier family 2 (facilitated glucose transporter), member 2 |
| 57 | Renal | 0.5417423 | 0.5075871 | 0.437618 | 0.307894 | M26901_s_at | RENIN PRECURSOR, RENAL |
| 58 | Renal | 0.5415649 | 0.5070452 | 0.436881 | 0.3068828 | X04707_at | C-erb-A mRNA for thyroid hormone receptor |
| 59 | Renal | 0.5382758 | 0.5065996 | 0.436354 | 0.30625692 | X59798_at | CCND1 Cyclin D1 (PRAD1; parathyroid adenomatosis 1) |

FIG. 13C

| # | Tissue | Val1 | Val2 | Val3 | Accession | Description |
|---|---|---|---|---|---|---|
| 60 | Renal | 0.5369051 | 0.5057533 | 0.435823 | 0.30566636 | RC_AA5984 10_at | EST: ae48b06.s1 Stratagene lung carcinoma 937218 Homo sapiens cDNA clone 950099 3', mRNA sequence. (from Genbank) |
| 61 | Renal | 0.5364182 | 0.5054519 | 0.435343 | 0.30474308 | RC_AA4486 88_at | EST: zx11g04.s1 Soares total fetus Nb2HF8 9w Homo sapiens cDNA clone 786198 3', mRNA sequence. (from Genbank) |
| 62 | Renal | 0.5363359 | 0.505252 | 0.434117 | 0.30419895 | D49488_at | TTPA Tocopherol (alpha) transfer protein (ataxia (Friedreich-like) with vitamin E deficiency) |
| 63 | Renal | 0.5360441 | 0.5038647 | 0.43365 | 0.30332038 | X82279_s_a t | Fas, Apo-1 gene (promoter and exon I) |
| 64 | Renal | 0.5355861 | 0.5035169 | 0.432658 | 0.3027145 | U17579_rna 1_at | Growth hormone-releasing hormone receptor form b gene extracted from Human growth hormone-releasing hormone receptor gene, alternatively spliced forms a, b, and c, partial cds |
| 65 | Renal | 0.5350391 | 0.5032614 | 0.431951 | 0.30180454 | U50743_at | Na,K-ATPase gamma subunit mRNA |
| 66 | Renal | 0.5347237 | 0.5031233 | 0.430822 | 0.3012688 | HG3412-HT3593_s_a t | Blue Cone Photoreceptor Pigment |
| 67 | Renal | 0.5345752 | 0.5024473 | 0.430411 | 0.30080283 | HG3502-HT3696_at | Homeotic Protein Hox5.4 |
| 68 | Renal | 0.534575 | 0.5021753 | 0.429907 | 0.30020672 | U38480_at | Retinoid X receptor-gamma mRNA |
| 69 | Renal | 0.5336061 | 0.5020564 | 0.429471 | 0.29952967 | Z49826_at | Hepatocyte nuclear factor 4, gamma |
| 70 | Renal | 0.5330759 | 0.5019126 | 0.42844 | 0.29922056 | HG4749-HT5197_at | Calmitine Calcium-Binding Protein, Mitochondrial |
| 71 | Renal | 0.5312939 | 0.5009093 | 0.427667 | 0.29866818 | L21893_at | SLC10A1 Na/taurocholate cotransporting polypeptide |
| 72 | Renal | 0.5293385 | 0.5004296 | 0.427014 | 0.29830635 | X56692_at | CRP C-reactive protein |
| 73 | Renal | 0.5284635 | 0.5002533 | 0.426675 | 0.29758814 | M17863_s_a t | IGF2 Insulin-like growth factor 2 (somatomedin A) |
| 74 | Renal | 0.5284146 | 0.499681 | 0.425717 | 0.29714543 | W26257_at | KIAA0735 gene product |
| 75 | Renal | 0.5280957 | 0.4990851 | 0.424726 | 0.29654333 | RC_AA4043 81_f_at | EST: zw37a04.s1 Soares total fetus Nb2HF8 9w Homo sapiens cDNA clone 772206 3', mRNA sequence. (from Genbank) |
| 76 | Renal | 0.5275608 | 0.4978843 | 0.424352 | 0.2959705 | HG3543-HT3739_at | Insulin-Like Growth Factor 2 |
| 77 | Renal | 0.5268567 | 0.4975213 | 0.423614 | 0.2955634 | X02958_at | Interferon alpha gene IFN-alpha 6 |
| 78 | Renal | 0.5267267 | 0.4973052 | 0.422879 | 0.29503918 | X98253_at | ZNF183 gene |
| 79 | Renal | 0.5266106 | 0.4960711 | 0.422853 | 0.29457882 | X00368_xpt 2_at | Exon 1 from Human prolactin gene 5' region./ntype=DNA /annot=mRNA |
| 80 | Renal | 0.5253429 | 0.4958387 | 0.422436 | 0.29426545 | S83366_cds 3_at | Description: orf3 gene extracted from region centromeric to t(12;17) brakepoint: orf1/unknown 43 amino acid transcript...orf3/unknown 50 amino acid transcript [human, testis, acampomelic campomelic dysplasia and sex reversal patient, Genomic, 3 genes, 3414 nt] |

FIG. 13D

| | | | | | | |
|---|---|---|---|---|---|---|
| 81 | Renal | 0.5251769 | 0.4950556 | 0.421732 | 0.2938592 | HG1071-HT1071_at | Bone Morphogenetic Protein 3 |
| 82 | Renal | 0.524478 | 0.4940273 | 0.421019 | 0.29338193 | X98307_at | UV-B repressed sequence, HUR 7 |
| 83 | Renal | 0.524478 | 0.4935573 | 0.420435 | 0.2928866 | X98307_at-2 | H.sapiens mRNA for UV-B repressed sequence, HUR 7 |
| 84 | Renal | 0.5228156 | 0.4934258 | 0.419967 | 0.29243842 | S81294_at | DCC=deleted in colorectal cancer {alternatively spliced, exon 1A} [human, brain tumor, tumor no. 245, mRNA Partial, 216 nt] |
| 85 | Renal | 0.5226573 | 0.493371 | 0.41961 | 0.2919467 | X07618_s_at-2 | Human mRNA for cytochrome P450 db1 variant a. (from Genbank) |
| 86 | Renal | 0.5226573 | 0.4932461 | 0.419199 | 0.29154822 | X07618_s_at | Cytochrome P450 db1 variant a |
| 87 | Renal | 0.5217367 | 0.4930835 | 0.418993 | 0.29116666 | HG3638-HT3993_s_a t | Amyloid Beta (A4) Precursor Protein, Alt. Splice 4 |
| 88 | Renal | 0.5215014 | 0.4926982 | 0.418571 | 0.29069647 | M36634_at | VIP Vasoactive intestinal peptide |
| 89 | Renal | 0.5208378 | 0.4921912 | 0.418088 | 0.29025248 | M24248_at | MYL3 Myosin, light polypeptide 3, alkali; ventricular, skeletal, slow |
| 90 | Renal | 0.5200136 | 0.4905491 | 0.417268 | 0.28987566 | M62628_s_a t | Alpha-1 Ig germline C-region membrane-coding region, 3' end |
| 91 | Renal | 0.519979 | 0.4903485 | 0.416472 | 0.289555 | M13207_at | CSF2 Colony-stimulating factor 2 (GM-CSF) |
| 92 | Renal | 0.5192758 | 0.4902283 | 0.416108 | 0.28915972 | HG3231-HT3408_at | Protease Receptor-1, Effector Cell |
| 93 | Renal | 0.5173352 | 0.4888274 | 0.415593 | 0.2886322 | RC_AA4466 50_at | EST: zw89g02.s1 Soares total fetus Nb2HF8 9w Homo sapiens cDNA clone 784178 3', mRNA sequence. (from Genbank) |
| 94 | Renal | 0.5172132 | 0.487926 | 0.414892 | 0.28830683 | HG2841-HT2968_s_a t | Albumin, Alt. Splice 1 |
| 95 | Renal | 0.5166175 | 0.4877747 | 0.414549 | 0.28777137 | S77812_at | FLT1 Fms-related tyrosine kinase 1 (vascular endothelial growth factor/vascular permeability factor receptor) |
| 96 | Renal | 0.5148366 | 0.4877535 | 0.414251 | 0.28745458 | HG3432-HT3621_at | Fibroblast Growth Factor Receptor K-Sam, Alt. Splice 4, K-Sam Iv |
| 97 | Renal | 0.5138602 | 0.4875854 | 0.414004 | 0.28705877 | S67798_at | HYALURONIDASE PRECURSOR |
| 98 | Renal | 0.5122757 | 0.4865042 | 0.413662 | 0.2665816 | U64197_at | CC chemokine LARC precursor |
| 99 | Renal | 0.5120382 | 0.486361 | 0.412998 | 0.2861182 | U14910_at | RPE-retinal G protein-coupled receptor (rgr) mRNA |
| 100 | Renal | 0.5119239 | 0.4852832 | 0.412591 | 0.28576726 | D17357_at | Activin beta-A gene, regulatory sequence of 5'upstream region |
| 101 | Renal | 0.5110655 | 0.4849925 | 0.411791 | 0.28543746 | M15169_at | ADRB2 Adrenergic, beta-2-, receptor, surface |
| 102 | Renal | 0.5106257 | 0.4846978 | 0.41168 | 0.2851244 | HG3987-HT4257_at | Cpg-Enriched Dna, Clone E06 |
| 103 | Renal | 0.5101805 | 0.4842634 | 0.411618 | 0.28348569 | HG3236-HT3413_f_at | Neurofibromatosis 2 Tumor Suppressor (Gb:L27065) |

FIG. 13E

| | | | | |
|---|---|---|---|---|
| 104 | Renal | 0.5096447 | 0.4840603 | 0.28438586_1_at | U11870_rna | Interleukin-8 receptor type A (IL8RBA) gene, promoter and complete cds |
| 105 | Renal | 0.5091612 | 0.48401 | 0.28411022 | X63359_at | UDP-GLUCURONOSYLTRANSFERASE 2B10 PRECURSOR, MICROSOMAL |
| 106 | Renal | 0.5086218 | 0.483975 | 0.283777 | D45370_at | ApM2 mRNA for GS2374 (unknown product specific to adipose tissue) |
| 107 | Renal | 0.5078191 | 0.4836609 | 0.28329715 | M28585_f_at | IFNA16 Interferon, alpha 16 |
| 108 | Renal | 0.5074842 | 0.482684 | 0.2830076 | S79267_at | CD4 CD4 antigen (p55) |
| 109 | Renal | 0.5063532 | 0.4825053 | 0.28262782 | M99701_at | (pp21) mRNA |
| 110 | Renal | 0.505725 | 0.4816677 | 0.2822789 | M31667_f_at | CYTOCHROME P450 IA2 |
| 111 | Renal | 0.5055621 | 0.4814259 | 0.28184566 | RC_AA3484 66_s_at | Regulator of G-protein signalling 5 |
| 112 | Renal | 0.5054359 | 0.4805757 | 0.28154778 | U07664_at | HB9 homeobox gene |
| 113 | Renal | 0.5022615 | 0.4800084 | 0.2810928 | HG3286-HT3463_at | Crystallin, Alpha A |
| 114 | Renal | 0.5005578 | 0.4790703 | 0.28074247 | U32659_at | CTLA8 Cytotoxic T lymphocyte-associated serine esterase 8 |
| 115 | Renal | 0.5004692 | 0.4786463 | 0.28037712 | L78833_cds 4_at | Ifp35 gene extracted from Human BRCA1, Rho7 and vatI genes, and ipf35 gene, partial cds |
| 116 | Renal | 0.4999971 | 0.4783976 | 0.2800195 | Z29572_at | Antisense mRNA for BCMA peptide |
| 117 | Renal | 0.4996918 | 0.478174 | 0.2796258 | U51587_at | Golgi complex autoantigen golgin-97 mRNA |
| 118 | Renal | 0.4984784 | 0.4776675 | 0.27941263 | AA424381_s_at | EST: zv90g12.r1 Soares NhHMPu S1 Homo sapiens cDNA clone 767110 5', mRNA sequence. (from Genbank) |
| 119 | Renal | 0.4980153 | 0.4772277 | 0.27907494 | U03886_at | GS2 mRNA |
| 120 | Renal | 0.4972384 | 0.4770812 | | RC_AA2335 32_at | EST: zr30g08.s1 Stratagene NT2 neuronal precursor 937230 Homo sapiens cDNA clone 664958 3', mRNA sequence. (from Genbank) |
| 121 | Renal | 0.4966165 | 0.4769793 | 0.278763 | D31797_at | CD40LG CD40 antigen ligand (hyper IgM syndrome) |
| 122 | Renal | 0.4963382 | 0.4766741 | 0.27805278 | M32598_at | RPS11 Ribosomal protein S11 |
| 123 | Renal | 0.4961634 | 0.4763677 | 0.27781078 | HG2148-HT2218_f_at | Mucin 3, Intestinal (Gb:M55406) |
| 124 | Renal | 0.4960195 | 0.4763326 | 0.27753037 | M88579_at | Zinc finger protein (SRE-ZBP) mRNA, 3' end |
| 125 | Renal | 0.4957403 | 0.4758397 | 0.27719319 | RC_AA4560 3_at | EST: aa17d05.s1 Soares NhHMPu S1 Homo sapiens cDNA clone 813513 3', mRNA sequence. (from Genbank) |
| 126 | Renal | 0.4946911 | 0.4758215 | 0.2768464 | D31784_at | Cadherin-6 |
| 127 | Renal | 0.4938916 | 0.4758109 | 0.2764690 | AA211295_a_t | EST: zq87g01.r1 Stratagene hNT neuron (#937233) Homo sapiens cDNA clone 649008 5', mRNA sequence. (from Genbank) |

FIG. 13F

| # | Tissue | | | | | Description |
|---|---|---|---|---|---|---|
| 128 | Renal | 0.4935767 | 0.4752962 | 0.402372 | 0.27614656 L07615_at | Neuropeptide Y receptor Y1 (NPYY1) mRNA, exon 2-3 and complete cds |
| 129 | Renal | 0.4933341 | 0.4746762 | 0.402161 | 0.27563456 X52005_at | MYL4 Myosin, light polypeptide 4, alkali; atrial, embryonic |
| 130 | Renal | 0.4932557 | 0.4742239 | 0.401802 | 0.275551705 W24962_at | EST: zb65a09.r1 Soares fetal lung NbHL19W Homo sapiens cDNA clone 308440 5' similar to contains Alu repetitive element;, mRNA sequence. (from Genbank) |
| 131 | Renal | 0.4931884 | 0.474179 | 0.401269 | 0.275533743 X98176_at | MACH-alpha-2 protein |
| 132 | Renal | 0.4930548 | 0.4739016 | 0.401252 | 0.275502114 T89571_f_at | EST: ye04h07.r1 Homo sapiens cDNA clone 116797 5' similar to contains Alu repetitive element;. (from Genbank) |
| 133 | Renal | 0.4930302 | 0.4734512 | 0.400817 | 0.27474076 U04343_at | CD86 CD86 antigen (CD28 antigen ligand 2, B7-2 antigen) |
| 134 | Renal | 0.4922877 | 0.4732334 | 0.400708 | 0.27437055 RC_AA2057 24_at | EST: zq69c06.s1 Stratagene neuroepithelium (#937231) Homo sapiens cDNA clone 646858 3', mRNA sequence. (from Genbank) |
| 135 | Renal | 0.4919962 | 0.4730649 | 0.40020 | 0.273997922 M21305_at | Alpha satellite and satellite 3 junction DNA sequence |
| 136 | Renal | 0.4918339 | 0.4728741 | 0.400173 | 0.27736989 X64877_at | HFL1 H factor (complement)-like 1 |
| 137 | Renal | 0.4911411 | 0.472578 | 0.399609 | 0.273740713 U12140_at | Tyrosine kinase receptor p145TRK-B (TRK-B) mRNA |
| 138 | Renal | 0.4910342 | 0.4724754 | 0.399065 | 0.2731371 X82324_at | POU3F4 POU domain, class 3, transcription factor 4 |
| 139 | Renal | 0.4902448 | 0.4721566 | 0.398813 | 0.2728986 Y07512_at | CGMP-DEPENDENT PROTEIN KINASE, BETA ISOZYME |
| 140 | Renal | 0.4898108 | 0.471933 | 0.398434 | 0.2725721 K02100_at | OTC Ornithine carbamoyltransferase |
| 141 | Renal | 0.4891868 | 0.4716626 | 0.393313 | 0.27209738 HT2435_at | Nuclear Factor 1, Variant Hepatic |
| 142 | Renal | 0.4874343 | 0.4714976 | 0.39818 | 0.2718957 U53446_at | Mitogen-responsive phosphoprotein (DOC-2) mRNA |
| 143 | Renal | 0.4870393 | 0.4704 | 0.398002 | 0.2717699 S78723_rna 2_at | 5-HT2A=serotonin 5-HT2A receptor {promoter} [human, Genomic, 1678 nt] |
| 144 | Renal | 0.4862061 | 0.4702396 | 0.397754 | 0.2712601 M24364_at | HLA-DQB1 Major histocompatibility complex, class II, DQ beta 1 |
| 145 | Renal | 0.4859688 | 0.4701102 | 0.397521 | 0.2710308 D83407_at | ZAKI-4 mRNA in human skin fibroblast |
| 146 | Renal | 0.4858132 | 0.4695216 | 0.397186 | 0.27085215 L10123_at | Surfactant protein A mRNA |
| 147 | Renal | 0.4856626 | 0.4694558 | 0.396955 | 0.270505076 RC_AA1557 63_at | EST: zo52g12.s1 Stratagene pancreas (#937208) Homo sapiens cDNA clone 590566 3', mRNA sequence. (from Genbank) |
| 148 | Renal | 0.4854891 | 0.4691881 | 0.396744 | 0.2702475 X72177_rna 1_at | C6 gene, exon 1 |
| 149 | Renal | 0.4845726 | 0.4689745 | 0.396652 | 0.2700087 U83303_cds 2_at | GCP-2 gene (granulocyte chemotactic protein-2) extracted from Human line-1 reverse transcriptase gene, partial cds, and granulocyte chemotactic protein-2 (GCP-2) gene |
| 150 | Renal | 0.4840626 | 0.4687249 | 0.396368 | 0.269737784 Z18859_rna 1_at | Cone transducin alpha subunit gene extracted from H.sapiens gene for cone transducin alpha subunit |
| 151 | Renal | 0.4837237 | 0.4681715 | 0.396619 | 0.26947364 M93143_at | PLGL Plasminogen-like protein |
| 152 | Renal | 0.482527 | 0.4679957 | 0.395694 | 0.26922822 Z83745_at | DNA sequence from PAC 453A3 contains EST and STS |
| 153 | Renal | 0.48205 | 0.4678475 | 0.395353 | 0.26905018 Y10505_at | CD104 protein |

FIG. 13G

| | | | | | |
|---|---|---|---|---|---|
| 154 | Renal | 0.4817508 | 0.4676682 | 0.395116 | 0.2687374 | X90579_s_a t | H.sapiens DNA for cyp related pseudogene |
| 155 | Renal | 0.4805055 | 0.4673708 | 0.395016 | 0.268403621 | X56411_rna 1_at | ADH4 gene for class II alcohol dehydrogenase (pi subunit), exon 1 |
| 156 | Renal | 0.4797793 | 0.466339 | 0.394861 | 0.268022448 | U40215_at | SYN2 Synapsin IIb |
| 157 | Renal | 0.4790477 | 0.4661244 | 0.39441 | 0.267935371 3_at | RC_AA2275 | EST: zr18d09.s1 Stratagene NT2 neuronal precursor 937230 Homo sapiens cDNA clone 663761 3', mRNA sequence. (from Genbank) |
| 158 | Renal | 0.479015 | 0.4653074 | 0.394147 | 0.267753780 | U03270_at | Centrin mRNA |
| 159 | Renal | 0.4789934 | 0.4651112 | 0.394025 | 0.267454955 | U66083_at | MAGE-9 antigen (MAGE9) gene |
| 160 | Renal | 0.4776748 | 0.4649223 | 0.39387 | 0.2671558 | X52479_at | PRKCA Protein kinase C, alpha |
| 161 | Renal | 0.477149 | 0.4646435 | 0.393353 | 0.2669536 | U16799_s_a t | Na,K-ATPase beta-1 subunit mRNA |
| 162 | Renal | 0.4789938 | 0.4644854 | 0.39316 | 0.2666773 | HG2987-HT3136_s_a t | Vasoactive Intestinal Peptide |
| 163 | Renal | 0.4764756 | 0.4643896 | 0.393009 | 0.266481341 | J03242_s_at | IGF2 Insulin-like growth factor 2 (somatomedin A) |
| 164 | Renal | 0.476325 | 0.4641056 | 0.392718 | 0.2662302 | R11267_at | Homo sapiens chromosome 19, cosmid F22329 |
| 165 | Renal | 0.4760614 | 0.4640841 | 0.392558 | 0.265983555 | M76180_at | DDC Dopa decarboxylase (aromatic L-amino acid decarboxylase) |
| 166 | Renal | 0.4758192 | 0.4640458 | 0.392183 | 0.265750440 | L27080_at | Melanocortin 5 receptor (MC5R) gene |
| 167 | Renal | 0.4753879 | 0.4639266 | 0.392036 | 0.2654998 | M94065_at | DHODH Dihydroorotate dehydrogenase |
| 168 | Renal | 0.4740228 | 0.4639256 | 0.391747 | 0.2653588 7 | U08049_at | Peripheral myelin protein-22 (PMP22) gene, non-coding exon 1A |
| 169 | Renal | 0.4738825 | 0.4638733 | 0.391343 | 0.2650604 2 | U04520_at | COL4A5 Collagen, type IV, alpha 5 (Alport syndrome) |
| 170 | Renal | 0.4738723 | 0.4638542 | 0.391133 | 0.2648271 6 | H93249_at | Angiotensin receptor-like 2 |
| 171 | Renal | 0.4736692 | 0.4637421 | 0.391007 | 0.264476931 | Z17240_at | HMG2 High-mobility group (nonhistone chromosomal) protein 2 |
| 172 | Renal | 0.4730158 | 0.4635257 | 0.390675 | 0.264195050 | L18877_f_at | MELANOMA-ASSOCIATED ANTIGEN 12 |
| 173 | Renal | 0.4729687 | 0.4633065 | 0.390658 | 0.26389384 | X96969_at | Urea transporter |
| 174 | Renal | 0.4726276 | 0.463132 | 0.390375 | 0.2635611 6 | U21936_at | Peptide transporter (HPEPT1) mRNA |
| 175 | Renal | 0.4725176 | 0.4621524 | 0.389689 | 0.263415960 | M25322_at | SELP Selectin P (granule membrane protein 140kD, antigen CD62) |
| 176 | Renal | 0.4725164 | 0.4618957 | 0.389681 | 0.2630577 | U43030_at | Cardiotrophin-1 (CTF1) mRNA |
| 177 | Renal | 0.4723269 | 0.4615095 | 0.389289 | 0.262851275 | U62438_at | CHRNB3 Cholinergic receptor, nicotinic, beta polypeptide 3 |
| 178 | Renal | 0.4723269 | 0.461395 | 0.389223 | 0.262560736 | U62438_at-2 | Cholinergic receptor, nicotinic, beta polypeptide 3 |
| 179 | Renal | 0.4716551 | 0.461187 | 0.388704 | 0.262384361 | U88902_cds 1_f_at | Integrase gene extracted from Human endogenous retrovirus H clone g10.34 integrase and putative envelope protein genes, partial cds |
| 180 | Renal | 0.4711404 | 0.4609575 | 0.388277 | 0.261197 | U02019_at | Heterogeneous nuclear ribonucleoprotein D (hnRNP D), partial cds, clone cDx4 |

FIG. 13H

| | | | | | | |
|---|---|---|---|---|---|---|
| 181 | Renal | 0.4706616 | 0.4608661 | 0.38827 | 0.26174766 | X99142_at | Hair keratin, hHb6 |
| 182 | Renal | 0.4704123 | 0.4605599 | 0.387993 | 0.26157203 | U51334_at | Putative RNA binding protein (RBP56) mRNA |
| 183 | Renal | 0.470077 | 0.4604487 | 0.387886 | 0.26128706 | D10511_at | ACAT1 Acetyl-Coenzyme A acetyltransferase 2 (acetoacetyl Coenzyme A thiolase) |
| 184 | Renal | 0.4691925 | 0.4604487 | 0.387271 | 0.26097825 | M13485_at | Metallothionein I-B gene |
| 185 | Renal | 0.468209 | 0.460412 | 0.386938 | 0.26090252 | U00930_at | Clone CE29 8.1 (CACn/(GTG)n repeat-containing mRNA |
| 186 | Renal | 0.4673617 | 0.4604045 | 0.386815 | 0.2605903 | X04571_at | EGF Epidermal growth factor |
| 187 | Renal | 0.4670265 | 0.4597874 | 0.386445 | 0.26031488 | K01900_at | IFNA8 Interferon, alpha 8 |
| 188 | Renal | 0.4663361 | 0.4597704 | 0.386286 | 0.26004514 | U59914_at | Chromosome 15 Mad homolog Smad6 mRNA |
| 189 | Renal | 0.4663277 | 0.4596564 | 0.386261 | 0.25991943 | U58130_at | Bumetanide-sensitive Na-K-2Cl cotransporter (NKCC2) mRNA |
| 190 | Renal | 0.4659388 | 0.4595583 | 0.386247 | 0.2596626 | D45371_at | ApM1 mRNA for GS3109 (novel adipose specific collagen-like factor) |
| 191 | Renal | 0.4647116 | 0.4594835 | 0.385977 | 0.2593686 | U13220_at | Forkhead protein FREAC-2 mRNA, partial cds |
| 192 | Renal | 0.4646249 | 0.4593631 | 0.385722 | 0.25916377 | X99886_s_a t | MCP-2 gene |
| 193 | Renal | 0.4637511 | 0.4592623 | 0.385384 | 0.25895628 | Y11897_at | Bix gene 3'UTR |
| 194 | Renal | 0.4636717 | 0.4588284 | 0.385218 | 0.2586058 | M13149_at | HRG Histidine-rich glycoprotein |
| 195 | Renal | 0.463173 | 0.458656 | 0.385097 | 0.2582481 | D87002_cds 2_at | POM121-like 1 gene extracted from Human (lambda) DNA for immunoglobin light chain |
| 196 | Renal | 0.4616602 | 0.4576354 | 0.384807 | 0.2580935 | U09609_at | NFKB2 Nuclear factor of kappa light polypeptide gene enhancer in B-cells 2 (p49/p100) |
| 197 | Renal | 0.4615954 | 0.4576304 | 0.384481 | 0.25796086 | M27533_s_a t | Ig rearranged B7 protein mRNA VC1-region |
| 198 | Renal | 0.4605679 | 0.4575374 | 0.3844 | 0.25768372 | D25248_at | Randomly sequenced mRNA |
| 199 | Renal | 0.4594386 | 0.4571116 | 0.384316 | 0.25741625 | U38276_at | Semaphorin III family homolog mRNA |
| 200 | Renal | 0.459354 | 0.4568678 | 0.383994 | 0.25720614 | RC_AA4179 35_at | EST: zv94c08.s1 Soares NhHMPu S1 Homo sapiens cDNA clone 767438 3', mRNA sequence. (from Genbank) |
| 201 | Renal | 0.4591454 | 0.4567329 | 0.383674 | 0.25699124 | X89960_at | Mitochondrial capsule selenoprotein |
| 202 | Renal | 0.4585022 | 0.4565887 | 0.383325 | 0.25678307 | U83598_s_a t | Death domain receptor 3 soluble form (DDR3) mRNA, partial cds |
| 203 | Renal | 0.4584846 | 0.4563644 | 0.383208 | 0.25673687 | X83127_at | K+ channel beta 1a subunit mRNA, alternatively spliced |
| 204 | Renal | 0.4579437 | 0.4561909 | 0.38304 | 0.25642866 | L11238_s_at | GP5 Glycoprotein V (platelet) |
| 205 | Renal | 0.457156 | 0.4559228 | 0.382502 | 0.25621232 | Y08417_s_at | CHRNB3 Cholinergic receptor, nicotinic, beta polypeptide 3 |
| 206 | Renal | 0.4556969 | 0.4556257 | 0.382427 | 0.25609115 | D90359_at | TRANSCRIPTION INITIATION FACTOR TFIID 250 KD SUBUNIT |
| 207 | Renal | 0.4561397 | 0.4556257 | 0.382219 | 0.25586684 | U79242_at | Clone 23560 mRNA sequence |
| 208 | Renal | 0.4558845 | 0.4553845 | 0.382173 | 0.25558877 | D16626_at-2 | Histidine ammonia-lyase |
| 209 | Renal | 0.4558845 | 0.4547038 | 0.381992 | 0.25537455 | D16626_at | HAL Histidine ammonia-lyase |

FIG. 131

| # | Tissue | | | | | Accession | Description |
|---|---|---|---|---|---|---|---|
| 210 | Renal | 0.4556653 | 0.4539073 | 0.38184 | 0.255114 | X80923_at | Nov gene |
| 211 | Renal | 0.455609 | 0.4533153 | 0.381558 | 0.25493976 | U66726_s_a t | Testis specific RNA binding protein (SPGYLA) mRNA |
| 212 | Renal | 0.4550555 | 0.4529456 | 0.381105 | 0.25475857 | HG1827-HT1856_s_a t | Cytochrome P450, Subfamily IIc, Alt. Splice Form 2 |
| 213 | Renal | 0.4544807 | 0.4525909 | 0.380692 | 0.25450525 | X92744_at | BETA-DEFENSIN 1 PRECURSOR |
| 214 | Renal | 0.4540066 | 0.4523014 | 0.380351 | 0.25425166 | X07024_at | TRANSCRIPTION INITIATION FACTOR TFIID 250 KD SUBUNIT |
| 215 | Renal | 0.4539972 | 0.4518955 | 0.380307 | 0.25394082 | L11708_at | HSD17B2 17 beta hydroxysteroid dehydrogenase, type 2 |
| 216 | Renal | 0.453534 | 0.4517961 | 0.380255 | 0.25374186 | M73547_at | POLYPOSIS LOCUS PROTEIN 1 |
| 217 | Renal | 0.4533644 | 0.4515377 | 0.379691 | 0.25352407 | U01824_at | Glutamate transporter |
| 218 | Renal | 0.4531839 | 0.4515265 | 0.379595 | 0.25329667 | M86546_at | PBX1 PBX1a and PBX1b |
| 219 | Renal | 0.4531534 | 0.4510225 | 0.379564 | 0.2531539 | U14383_at | MUC8 Mucin 8, tracheobronchial |
| 220 | Renal | 0.4528641 | 0.450989 | 0.379391 | 0.25290683 | U01337_at | ARAF1 V-raf murine sarcoma 3611 viral oncogene homolog 1 |
| 221 | Renal | 0.4527474 | 0.4509457 | 0.379088 | 0.25268885 | X80915_rna 1_at | Gdf5 gene |
| 222 | Renal | 0.4524092 | 0.4508876 | 0.378764 | 0.25248748 | L16464_at | ETS-RELATED PROTEIN PE-1 |
| 223 | Renal | 0.4521114 | 0.4506054 | 0.378693 | 0.25229758 | M34344_at | ITGA2B Integrin, alpha 2b (platelet glycoprotein IIb of IIb/IIIa complex, antigen CD41B) |
| 224 | Renal | 0.4519019 | 0.4500148 | 0.378165 | 0.25215918 | M64930_at | Protein phosphatase 2A beta subunit mRNA |
| 225 | Renal | 0.4512746 | 0.4496061 | 0.377777 | 0.25192854 | X53065_f_at | SPRR2A gene encoding small proline rich protein |
| 226 | Renal | 0.450934 | 0.4496032 | 0.377337 | 0.25168833 | M16938_s_a t | Homeo box c8 protein, mRNA |
| 227 | Renal | 0.4508805 | 0.449519 | 0.377324 | 0.25147906 | HG4593-HT4998_at | Sodium Channel 1 |
| 228 | Renal | 0.4503698 | 0.4495043 | 0.377192 | 0.2512481 | M88468_at | MVK Mevalonate kinase |
| 229 | Renal | 0.4497153 | 0.4486896 | 0.37704 | 0.25112978 | AA253330_s_at | EST: zr72g02.r1 Soares NhHMPu S1 Homo sapiens cDNA clone 668978 5', mRNA sequence. (from Genbank) |
| 230 | Renal | 0.4492177 | 0.4484296 | 0.377021 | 0.2509351 | U80457_at | Transcription factor SIM2 long form mRNA |
| 231 | Renal | 0.4491665 | 0.4483455 | 0.376633 | 0.25078318 | X82634_at | Partial mRNA for hair keratin acidic 3-II |
| 232 | Renal | 0.4486195 | 0.4479919 | 0.376129 | 0.25058961 5 | RC_AA0547 | EST: zk68a03.s1 Soares pregnant uterus NbHPU Homo sapiens cDNA clone 487948 3' similar to WP:R04E5.6 CE04798 ; mRNA sequence. (from Genbank) |
| 233 | Renal | 0.4484495 | 0.4476027 | 0.375817 | 0.25037545 | W28931_at | EST: 56f3 Human retina cDNA randomly primed sublibrary Homo sapiens cDNA, mRNA sequence. (from Genbank) |
| 234 | Renal | 0.4475988 | 0.4468683 | 0.375758 | 0.25022826 | L07077_at | EHHADH Enyol-coA: hydralase 3-hydroxyacyl-coA dehydrogenase |
| 235 | Renal | 0.4474518 | 0.4468131 | 0.375729 | 0.25001648 | U40371_at | 3',5' cyclic nucleotide phosphodiesterase (HSPDE1C1A) mRNA |
| 236 | Renal | 0.4462721 | 0.4468131 | 0.375661 | 0.24987371 | Z38133_s_at | Myosin |

FIG. 13J

| | | | | | |
|---|---|---|---|---|---|
| 237 | Renal | 0.4462324 | 0.4467959 | 0.375657 | 0.24962375 | N88827_at | EST: K5685F Fetal heart, Lambda ZAP Express Homo sapiens cDNA clone K5685 5' similar to EST(YI03A03.R1), mRNA sequence. (from Genbank) |
| 238 | Renal | 0.446096 | 0.4466362 | 0.375339 | 0.24951465 | L12760_s_at | PHOSPHOENOLPYRUVATE CARBOXYKINASE, CYTOSOLIC |
| 239 | Renal | 0.4459003 | 0.4465057 | 0.375159 | 0.24928167 | HG2460-HT2556_at | Integrin Beta 1 (Gb:M34189) |
| 240 | Renal | 0.4457481 | 0.4464997 | 0.375086 | 0.24917136 | Z29077_xpt1_at | Un-named-transcript-1 from H.sapiens cdc25 gene promoter region./ntype=DNA /annot=mRNA |
| 241 | Renal | 0.4453765 | 0.4457137 | 0.374688 | 0.248915 | M84349_at | CD59 CD59 antigen p18-20 (antigen identified by monoclonal antibodies 16.3A5, EJ16, EJ30, EL32 and G344) |
| 242 | Renal | 0.4446758 | 0.445549 | 0.374284 | 0.24878845 | U78793_at | Folate receptor alpha (hFR) mRNA, partial cds |
| 243 | Renal | 0.4446306 | 0.4455332 | 0.373955 | 0.24855393 | HG4113-HT4383_s_at | Olfactory Receptor Or17-201 |
| 244 | Renal | 0.4430218 | 0.4450903 | 0.373909 | 0.24838038 | HG2290-HT2386_at | Calcitonin |
| 245 | Renal | 0.4426053 | 0.4449075 | 0.373515 | 0.24816786 | M54914_s_at | FOLLITROPIN BETA CHAIN PRECURSOR |
| 246 | Renal | 0.4424292 | 0.4448434 | 0.373394 | 0.24782759 | X79888_at | AUH mRNA |
| 247 | Renal | 0.4423468 | 0.4446103 | 0.373283 | 0.24764816 | X86401_s_a_t | L-arginine:glycine amidinotransferase |
| 248 | Renal | 0.4417665 | 0.4445456 | 0.373206 | 0.24753561 | X16609_s_a_t | ANK1 Ankyrin 1, erythrocytic |
| 249 | Renal | 0.4411078 | 0.4444898 | 0.373042 | 0.24740592 | D49490_at | Protein disulfide isomerase-related protein (PDIR) |
| 250 | Renal | 0.4410874 | 0.4444415 | 0.372689 | 0.24716543 | U47334_at | Gamma aminobutyric acid receptor beta4 subunit-like mRNA, partial cds |
| 251 | Renal | 0.4409656 | 0.4442276 | 0.372679 | 0.24701273 | RC_AA035514_at | EST: zk26b02.s1 Soares pregnant uterus NbHPU Homo sapiens cDNA clone 471627 3', mRNA sequence. (from Genbank) |
| 252 | Renal | 0.44086041 | 0.444168 | 0.372377 | 0.24694474 | HG3566-HT3769_at | Zinc Finger Protein (Gb:M88359) |
| 253 | Renal | 0.4405067 | 0.4438285 | 0.37236 | 0.24664462 | X65962_s_at | CYP2C17 Cytochrome P450, subfamily IIC (mephenytoin 4-hydroxylase), polypeptide 17 |
| 254 | Renal | 0.4402601 | 0.4433534 | 0.372222 | 0.24664867 | U52154_at | Clone KGP G-protein coupled inwardly rectifying potassium channel mRNA |
| 255 | Renal | 0.4401465 | 0.4432873 | 0.371862 | 0.24632388 | M16801_at | MLR Mineralocorticoid receptor (aldosterone receptor) |
| 256 | Renal | 0.439692 | 0.4428797 | 0.371646 | 0.2462302 | X83543_at | APXL Apical protein (Xenopus laevis-like) |
| 257 | Renal | 0.4391957 | 0.4428474 | 0.371526 | 0.24606343 | X13444_at | T-CELL SURFACE GLYCOPROTEIN CD8 BETA.3 CHAIN PRECURSOR |
| 258 | Renal | 0.4390288 | 0.44274 | 0.371439 | 0.24586682 | M65085_at | FSHR Follicle stimulating hormone receptor |

FIG. 13K

| | | | | | |
|---|---|---|---|---|---|
| 259 | Renal | 0.4390196 | 0.4422293 | 0.371045 | 0.2455607 | D86969_at | KIAA0215 gene |
| 260 | Renal | 0.4385335 | 0.442189 | 0.3709 | 0.2454285 | X91220_at | Na-Cl electroneutral thiazide-sensitive cotransporter |
| 261 | Renal | 0.4385155 | 0.4421747 | 0.370767 | 0.2452792 | HG315-HT315_at | Beta-1-Glycoprotein 11, Pregnancy-Specific |
| 262 | Renal | 0.4378127 | 0.4421202 | 0.37073 | 0.2451073 | S70609_at | Glycine transporter type 1b [human, substantia nigra, mRNA, 2364 nt] |
| 263 | Renal | 0.4378035 | 0.4419343 | 0.370586 | 0.2450234 | U67674_at | SLC15A2 Solute carrier family 15 (H+/peptide transporter), member 2 |
| 264 | Renal | 0.4374701 | 0.4417766 | 0.370535 | 0.2447719 | M85165_at | ELK4 ELK4, ETS-domain protein (SRF accessory protein 1) NOTE: Symbol and name provisional |
| 265 | Renal | 0.4372114 | 0.4413635 | 0.370452 | 0.2445257 | L00389_f_at | Cytochrome P-450 4 gene |
| 266 | Renal | 0.4371215 | 0.4412714 | 0.370148 | 0.2444037 | U26914_at | Ras-responsive element binding protein (RREB-1) mRNA |
| 267 | Renal | 0.4367936 | 0.4411529 | 0.369851 | 0.2442389 | X92110_at | HcgVIII protein |
| 268 | Renal | 0.4365993 | 0.4411415 | 0.369823 | 0.2440436 | L00972_at | CBS Cystathionine-beta-synthase |
| 269 | Renal | 0.4358992 | 0.4405547 | 0.369753 | 0.2439142 | L12468_at | ENPEP Glutamyl aminopeptidase (aminopeptidase A) |
| 270 | Renal | 0.4354511 | 0.4403466 | 0.369627 | 0.2437361 | M55131_at | CFTR Cystic fibrosis conductance regulator |
| 271 | Renal | 0.4348126 | 0.4401135 | 0.369541 | 0.243513 | L17328_at | Pre-T/NK cell associated protein (3CI) mRNA |
| 272 | Renal | 0.434758 | 0.4400542 | 0.369359 | 0.2434026 | U01157_at | GLP1R Glucagon-like peptide 1 receptor |
| 273 | Renal | 0.4344039 | 0.4399711 | 0.369185 | 0.2432245 | M95167_at | SLC6A3 Solute carrier family 6 (neurotransmitter transporter, dopamine), member 3 |
| 274 | Renal | 0.4343543 | 0.4398235 | 0.369094 | 0.2431146 | U18467_at | PSG7 Pregnancy-specific beta 1-glycoprotein 7 |
| 275 | Renal | 0.4342729 | 0.4397599 | 0.369027 | 0.2428800 | D00003_s_at | CYP3A3 Cytochrome P450 IIIA3 (nifedipine oxidase chain 3) |
| 276 | Renal | 0.4342702 | 0.4396057 | 0.3689 | 0.2427627 | RC_AA2533 31_at | EST: zr72g02.s1 Soares NhHMPu S1 Homo sapiens cDNA clone 668978 3', mRNA sequence. (from Genbank) |
| 277 | Renal | 0.4338369 | 0.4394375 | 0.368833 | 0.2425696 | L33930_s_at | CD24 signal transducer mRNA and 3' region |
| 278 | Renal | 0.4326671 | 0.4394273 | 0.368577 | 0.2424220 | X77753_at | M1S1 Membrane component, chromosome 1, surface marker 1 (40kD glycoprotein, identified by monoclonal antibody GA733) |
| 279 | Renal | 0.4326013 | 0.4393339 | 0.368431 | 0.2422896 | M96739_at | NSCL-1 mRNA sequence |
| 280 | Renal | 0.4320322 | 0.4392824 | 0.368291 | 0.2421603 | U46023_at | Xq28 mRNA |
| 281 | Renal | 0.4319125 | 0.4390194 | 0.368248 | 0.2419921 | RC_AA4782 98_s_at | Human apM2 mRNA for GS2374 (unknown product specific to adipose tissue), complete cds |
| 282 | Renal | 0.4317016 | 0.4388118 | 0.368025 | 0.2418339 | D88797_at | Cadherin, partial cds |
| 283 | Renal | 0.4313663 | 0.4386233 | 0.367965 | 0.2416326 | S45630_at | CRYAB Crystallin alpha-B |
| 284 | Renal | 0.4309753 | 0.4379709 | 0.367914 | 0.2415208 | Y10205_at | CD88 protein |
| 285 | Renal | 0.4308858 | 0.4377607 | 0.367432 | 0.2413546 | HG3125-HT3301_s_at | Estrogen Receptor (Gb:S67777) |
| 286 | Renal | 0.4308232 | 0.4376942 | 0.367314 | 0.2410595 | U87408_at | Clone IMAGE:30008 unknown protein mRNA, partial cds |

FIG. 13L

| # | Tissue | Val1 | Val2 | Val3 | ID | Description |
|---|---|---|---|---|---|---|
| 287 | Renal | 0.4304842 | 0.4376725 | 0.367198 | 0.240843866 S81419_at | Dystrophin, dystrophin (Purkinje promoter, alternatively spliced) [human, cortical brain and adult heart, mRNA Partial, 377 nt] |
| 288 | Renal | 0.4299807 | 0.4374535 | 0.366822 | 0.24070808 X01059_at | GNRH Gonadotropin-releasing hormone (leutinizing-releasing hormone) |
| 289 | Renal | 0.4298089 | 0.4372046 | 0.366627 | 0.24051054 X78687_at | G9 gene encoding sialidase |
| 290 | Renal | 0.4293836 | 0.4371876 | 0.36642 | 0.24034225 U89336_cds8_at | Unknown gene extracted from Human HLA class III region containing NOTCH4 gene, partial sequence, homeobox PBX2 (HPBX) gene, receptor for advanced glycosylation end products (RAGE) gene, and 6 unidentified cds, complete sequence |
| 291 | Renal | 0.4289232 | 0.4370761 | 0.366145 | 0.24016605 J02888_at | NMOR2 Quinone oxidoreductase (NQO2) |
| 292 | Renal | 0.428873 | 0.4370709 | 0.365989 | 0.24000885 RC_AA4475 04_at | EST: zw90h07.s1 Soares total fetus Nb2HF8 9w Homo sapiens cDNA clone 784285 3', mRNA sequence. (from Genbank) |
| 293 | Renal | 0.4286834 | 0.436872 | 0.365005 | 0.23977031 M59911_at | ITGA3 Integrin alpha-3 subunit |
| 294 | Renal | 0.4286338 | 0.4367907 | 0.365789 | 0.23964794 S77415_at | Melanocortin-4 receptor [human, Genomic, 1671 nt] |
| 295 | Renal | 0.4285545 | 0.4366997 | 0.365686 | 0.23956911 U78556_at | Cisplatin resistance associated alpha protein (hCRA alpha) mRNA |
| 296 | Renal | 0.4284764 | 0.4366091 | 0.365596 | 0.23937702 Z15005_at | CENPE Centromere protein E (312kD) |
| 297 | Renal | 0.4280776 | 0.4365664 | 0.365487 | 0.23918616 M31651_at | SHBG Sex hormone-binding globulin |
| 298 | Renal | 0.4277073 | 0.4364947 | 0.365361 | 0.23901333 M88163_at | SNF2L1 SNF2 (sucrose nonfermenting, yeast, homolog)-like 1 |
| 299 | Renal | 0.4276336 | 0.4361454 | 0.36528 | 0.2388741 X17622_at | KCNA6 Potassium voltage-gated channel, shaker-related subfamily, member 6 |
| 300 | Renal | 0.4276045 | 0.4359124 | 0.365017 | 0.23875788 M20530_at | SPINK1 Serine protease inhibitor, Kazal type 1 |
| 301 | Renal | 0.4275243 | 0.4354979 | 0.364873 | 0.23849778 U53442_at | P38Beta MAP kinase mRNA |
| 302 | Renal | 0.4274338 | 0.434961 | 0.364775 | 0.23837191 HG4332-HT4602_at | Zinc Finger Protein Znfpt1 |
| 303 | Renal | 0.4270585 | 0.4347154 | 0.364641 | 0.23810951 U13706_at | ELAV-like neuronal protein 1 isoform Hel-N2 (Hel-N1) mRNA, partial cds |
| 304 | Renal | 0.4268817 | 0.4347154 | 0.364484 | 0.23794194 RC_D58185_at | EST: Human aorta cDNA 3'-end GEN-354C01, mRNA sequence. (from Genbank) |
| 305 | Renal | 0.4268105 | 0.434706 | 0.364295 | 0.23784144 L07033_at | HMGCL 3-hydroxymethyl-3-methylglutaryl-Coenzyme A lyase (hydroxymethylglutaricaciduria) |
| 306 | Renal | 0.4265924 | 0.4346966 | 0.36361 | 0.2376996 YEL024w/RI P1_at | No info for gene |
| 307 | Renal | 0.4254589 | 0.434591 | 0.363352 | 0.23763552 L20861_at | WNT5A Wingless-type MMTV integration site 5A, human homolog |
| 308 | Renal | 0.4253571 | 0.4344069 | 0.363341 | 0.23741938 RC_AA3043 44_f_at | EST: EST17092 Aorta endothelial cells, TNF alpha-treated Homo sapiens cDNA 3' end similar to EST containing Alu repeat, mRNA sequence. (from Genbank) |

FIG. 13M

| | | | | |
|---|---|---|---|---|
| 309 | Renal | 0.425243 | 0.4342575 | 0.23732324 | M27093_s_a t | DBT Dihydrolipoamide branched chain transacylase (E2 component of branched chain keto acid dehydrogenase complex; maple syrup urine disease) |
| 310 | Renal | 0.4251254 | 0.4340541 | 0.363115 | RC_AA4503 | EST: zx05n06.s1 Soares total fetus Nb2HF8 9w Homo sapiens cDNA clone 785627 3', mRNA sequence. (from Genbank) |
| 311 | Renal | 0.4249124 | 0.4339815 | 0.363114 | 0.23717207 73_at | HBRAVO/Nr-CAM precursor (hBRAVO/Nr-CAM) gene |
| 312 | Renal | 0.4238513 | 0.4338114 | 0.363113 | 0.23701248 | U55258_at | CYB5 Cytochrome b-5 |
| | | | | 0.362572 | 0.23687395 | M22976_at | |
| 313 | Renal | 0.42377619 | 0.4337421 | 0.362406 | M14123_xpt 3_at | Gag 2 protein from Human endogenous retrovirus HERV-K10./ntype=DNA/annot=CDS |
| 314 | Renal | 0.4236083 | 0.4334933 | 0.36237 | 0.23675115 | | |
| | | | | | 0.23656695 | M64347_at | FGFR3 Fibroblast growth factor receptor 3 (achondroplasia, thanatophoric dwarfism) |
| 315 | Renal | 0.4231577 | 0.4334756 | 0.362171 | 0.23628488 | L16782_at | Putative M phase phosphoprotein 1 (MPP1) mRNA, partial cds |
| 316 | Renal | 0.4227037 | 0.4334409 | 0.362205 | X80763_s_a t | HTR2C 5-hydroxytryptamine (serotonin) receptor 2C |
| 317 | Renal | 0.4225365 | 0.4326023 | 0.36205 | 0.23621109 | | |
| | | | | | 0.2360774 | X90908_at | Ileal lipid binding protein mRNA |
| 318 | Renal | 0.422017 | 0.4322593 | 0.361773 | 0.23597923 | U69961_at | RIEG Rieger syndrome (solurshin) |
| 319 | Renal | 0.422017 | 0.4322593 | 0.361736 | 0.23584041 | U69961_at-2 | Paired-like homeodomain transcription factor 2 |
| 320 | Renal | 0.4216357 | 0.4319465 | 0.3615535 | U43753_cds 2_at | Frataxin (FRDA) gene, promoter region and |
| 321 | Renal | 0.4216345 | 0.4317624 | 0.36138 | 0.25560219 | | |
| | | | | | 0.23545852 | L10405_at | DNA binding protein for surfactant protein B mRNA |
| 322 | Renal | 0.4213863 | 0.4317512 | 0.361026 | 0.23534898 | M80333_at | M5 muscarinic acetylcholine receptor gene |
| 323 | Renal | 0.4213459 | 0.4316221 | 0.36101 | 0.23514846 | M14758_at | MULTIDRUG RESISTANCE PROTEIN 1 |
| 324 | Renal | 0.4212861 | 0.4314864 | 0.360883 | RC_AA0043 53_at | EST: zh91h05.s1 Soares fetal liver spleen 1NFLS S1 Homo sapiens cDNA clone 428697 3' similar to contains Alu repetitive element;. mRNA sequence. (from Genbank) |
| 325 | Renal | 0.4208609 | 0.4313865 | 0.360712 | 0.23489729 | | |
| | | | | | 0.23475614 | L34219_at | RLBP1 Cellular retinaldehyde-binding protein |
| 326 | Renal | 0.4204913 | 0.431221 | 0.360665 | 0.2346112 | U70426_at | A28-RGS14p mRNA |
| 327 | Renal | 0.4203819 | 0.4308143 | 0.360289 | 0.23454165 | D90276_at | CGM7 Carcinoembryonic antigen gene family member 7 |
| 328 | Renal | 0.4200121 | 0.4302467 | 0.360201 | 0.2343712 | U18937_at | Histidyl-tRNA synthetase homolog (HO3) mRNA |
| 329 | Renal | 0.4200087 | 0.4301441 | 0.360027 | 0.23418541 | U12779_at | MAP KINASE-ACTIVATED PROTEIN KINASE 2 |
| 330 | Renal | 0.4200085 | 0.4300801 | 0.359976 | 0.2340767 | Z86000_at | DNA sequence from clone RP1-151B14 on chromosome 22 Contains SSTR3 (somatostatin receptor 3) gene, pseudogene similar to ribosomal protein L39, RAC2 (ras-related C3 botulinum toxin substrate 2 (rho family, small GTP binding protein Rac2)) gene, ESTs, STSs, GSSs and CpG islands, complete sequence |
| 331 | Renal | 0.4199946 | 0.4300267 | 0.359802 | 0.23394343 | M21985_at | ORPHAN RECEPTOR TR2 |
| 332 | Renal | 0.4199186 | 0.4299301 | 0.359756 | 0.23368876 | X83425_at | LU gene for Lutheran blood group glycoprotein |
| 333 | Renal | 0.4196365 | 0.4298415 | 0.359537 | 0.2336179 | Y11710_rna 1_at | Extracellular matrix protein collagen type XIV, C-terminus |

FIG. 13N

| | | | | | | |
|---|---|---|---|---|---|---|
| 334 | Renal | 0.4196039 | 0.4297887 | 0.2332813 | RC_AA4521 30_at | EST: zx15d05.s1 Soares total fetus Nb2HF8.9w Homo sapiens cDNA clone 786537 3', mRNA sequence. (from Genbank) |
| 335 | Renal | 0.4194522 | 0.4297887 | 0.23314606 70_at | RC_AA0071 | EST: 13cDNA84-3.seq Soares fetal liver spleen 1NFLS Homo sapiens cDNA clone HY30-cDNA12 3', mRNA sequence. (from Genbank) |
| 336 | Renal | 0.4190468 | 0.4295895 | 0.359164 | 0.23300155 | U49974_f_at | Mariner2 transposable element, complete consensus sequence |
| 337 | Renal | 0.4188597 | 0.4295651 | 0.358991 | 0.23291014 | M26393_s_a t | Acyl-Coenzyme A dehydrogenase, C-2 to C-3 short chain |
| 338 | Renal | 0.4188416 | 0.4295132 | 0.358707 | 0.23282695 | U12387_s_a t | TPMT Thiopurine S-methyltransferase |
| 339 | Renal | 0.4185665 | 0.4293802 | 0.358614 | 0.2325892 | U44848_at | Nuclear respiratory factor 1 (NRF-1) mRNA, 3' UTR |
| 340 | Renal | 0.418561 | 0.4292367 | 0.358562 | 0.2325325 | U13666_at | G protein-coupled receptor (GPR1) gene |
| 341 | Renal | 0.4181312 | 0.4291975 | 0.358489 | 0.23242423 | L02950_at | CRYM Crystallin Mu |
| 342 | Renal | 0.4179115 | 0.4291949 | 0.356279 | 0.23222579 | M25164_at | THYROTROPIN BETA CHAIN PRECURSOR |
| 343 | Renal | 0.4178161 | 0.4291683 | 0.358178 | 0.23215204 | HG1155-HT4822_at | Colony-Stimulating Factor 1, Macrophage, Alt. Splice 3 |
| 344 | Renal | 0.4173721 | 0.4290789 | 0.358082 | 0.2320245 | D86519_at | Truncated pancreatic polypeptide receptor PP2 mRNA |
| 345 | Renal | 0.4169045 | 0.4287652 | 0.357736 | 0.23181531 | AA182909_a t | EST: zp51d08.r1 Stratagene HeLa cell s3 937216 Homo sapiens cDNA clone 612975 5', mRNA sequence. (from Genbank) |
| 346 | Renal | 0.4166946 | 0.4287064 | 0.357673 | 0.23169628 | Z63336_at | HH2B/d gene |
| 347 | Renal | 0.4162298 | 0.4286731 | 0.357449 | 0.23159422 | L40933_at | Phosphoglucomutase-related protein (PGMRP) gene |
| 348 | Renal | 0.4162298 | 0.4286258 | 0.357166 | 0.23140834 | L40933_at-2 | Homo sapiens phosphoglucomutase-related protein (PGMRP) gene, complete cds |
| 349 | Renal | 0.4159051 | 0.4285968 | 0.357012 | 0.23129977 | M18391_s_a t | TYROSINE-PROTEIN KINASE RECEPTOR EPH PRECURSOR |
| 350 | Renal | 0.4155744 | 0.4280471 | 0.356817 | 0.2311/651 | U11872_at | Interleukin-8 receptor type B (IL8RB) mRNA, splice variant IL8RB1, partial cds |
| 351 | Renal | 0.4150478 | 0.4280306 | 0.356727 | 0.23110898 | X52011_at | MYF6 Muscle determination factor |
| 352 | Renal | 0.41491 | 0.4279622 | 0.365569 | 0.23094295 | D87024_at | Immunoglobulin lambda gene locus DNA, clone:92H4 |
| 353 | Renal | 0.4146766 | 0.4275723 | 0.356394 | 0.23081186 | U19906_at | VASOPRESSIN V1A RECEPTOR |
| 354 | Renal | 0.4146203 | 0.4274197 | 0.356307 | 0.23066366 | M24900_at | V-ERBA RELATED PROTEIN EAR-1 |
| 355 | Renal | 0.4144927 | 0.4273355 | 0.356286 | 0.23052967 | J00212_f_at | IFNA21 Interferon, alpha 21 |
| 356 | Renal | 0.4140909 | 0.4273262 | 0.356144 | 0.23035994 | U09411_at | ZNF132 Zinc finger protein 132 (clone pHZ-12) |
| 357 | Renal | 0.4140842 | 0.4272097 | 0.355899 | 0.23021741 | Z22536_at | SERINE/THREONINE-PROTEIN KINASE RECEPTOR R2 PRECURSOR |
| 358 | Renal | 0.4138938 | 0.4272065 | 0.355806 | 0.23009057 | U82303_at | Unknown protein mRNA, partial cds |
| 359 | Renal | 0.4138169 | 0.4270621 | 0.355705 | 0.22998436 | M76482_at | DSG3 Desmoglein 3 (pemphigus vulgaris antigen) |
| 360 | Renal | 0.4136464 | 0.4269424 | 0.355531 | 0.22983654 | X83857_s_a t | PTGER3 Prostaglandin E receptor 3 (subtype EP3) [alternative products] |

FIG. 13O

| # | Tissue | Col3 | Col4 | Col5 | ID1 | ID2 | Description |
|---|---|---|---|---|---|---|---|
| 361 | Renal | 0.4131471 | 0.426882 | 0.355399 | 0.22960745 | U28055_at | MST1 Macrophage stimulating 1 (hepatocyte growth factor-like) |
| 362 | Renal | 0.4130569 | 0.426745 | 0.355382 | 0.2294616 | X86570_at | Acidic hair keratin 1 |
| 363 | Renal | 0.4122247 | 0.4264519 | 0.355283 | 0.22931892 | X68994_at | CREB gene, exon Y |
| 364 | Renal | 0.4117986 | 0.4262722 | 0.355227 | 0.22924946 | X70340_at | TGFA Transforming growth factor, alpha |
| 365 | Renal | 0.4116842 | 0.4261806 | 0.355068 | 0.22905804 | J03027_at | HLA-G MHC class I protein HLA-G |
| 366 | Renal | 0.4111903 | 0.4260974 | 0.354908 | 0.22893767 | M85164_at | ELK4 SRF accessory protein 1B (SAP-1) |
| 367 | Renal | 0.4110927 | 0.4260954 | 0.354781 | 0.22879517 | X69115_at / U31903_s_a t | ZNF37A Zinc finger protein 37a (KOX 21) |
| 368 | Renal | 0.4109768 | 0.4259909 | 0.35461 | 0.22862218 | | CREB-RP (creb-rp) mRNA |
| 369 | Renal | 0.4108892 | 0.4256344 | 0.354498 | 0.22885062 | X80878_at | R kappa B mRNA |
| 370 | Renal | 0.410046 | 0.4254816 | 0.354367 | 0.22839436 | U25128_at | PTH2 parathyroid hormone receptor mRNA |
| 371 | Renal | 0.4099722 | 0.4252286 | 0.354271 | 0.2282706 | S68805_at | L-arginine:glycine amidinotransferase [human, kidney carcinoma cells, mRNA, 2330 nt] |
| 372 | Renal | 0.4098469 | 0.4249915 | 0.354164 | 0.22818829 | X59842_rna 1_s_at | PBX2 mRNA |
| 373 | Renal | 0.4097792 | 0.4249467 | 0.354005 | 0.2280433 | HG3355-HT3532_at | Peroxisome Proliferator Activated Receptor (Gb:Z30972) |
| 374 | Renal | 0.4086786 | 0.4247629 | 0.3539919 | 0.22787397 | X79981_at | CDH5 Cadherin 5, VE-cadherin (vascular epithelium) |
| 375 | Renal | 0.4084653 | 0.4246295 | 0.353761 | 0.22775418 | L32164_at | Zinc finger protein mRNA, 3' end |
| 376 | Renal | 0.4082082 | 0.4242346 | 0.353406 | 0.22760104 | M59829_at | MHC class III HSP70-HOM gene (HLA) |
| 377 | Renal | 0.408042 | 0.4240703 | 0.353157 | 0.22744492 | S71824_at | NEURAL CELL ADHESION MOLECULE, PHOSPHATIDYLINOSITOL LINKED ISOFORM PRECURSOR |
| 378 | Renal | 0.4079479 | 0.4240014 | 0.353138 | 0.22731654 | M13666_at | MYB Proto-oncogene c-myb [alternative products] |
| 379 | Renal | 0.4079266 | 0.4238806 | 0.353114 | 0.22708957 | U82310_at | Unknown protein mRNA, partial cds |
| 380 | Renal | 0.4073801 | 0.4235334 | 0.352954 | 0.22704422 | S83366_cds 1_at | Description: orf1 gene extracted from region centromeric to t(12;17) brakepoint: orf1/unknown 43 amino acid transcript...orf3/unknown 50 amino acid transcript [human, testis, acampomelic campomelic dysplasia and sex reversal patient, Genomic, 3 genes, 3414 nt] |
| 381 | Renal | 0.4069284 | 0.4233476 | 0.3529925 | 0.22678313 | RC_AA2628 80_at | EST: zs26b02.s1 NCI_CGAP_GCB1 Homo sapiens cDNA clone IMAGE:686283 3', mRNA sequence. (from Genbank) |
| 382 | Renal | 0.4065524 | 0.4232457 | 0.35283 | 0.2267272 | L11370_at | Protocadherin 42 mRNA for abbreviated PC42 |
| 383 | Renal | 0.406537 | 0.4232417 | 0.352664 | 0.22622409 | M14158_cds 4_at | T-cell receptor beta-chain J1.3 gene extracted from Human T-cell receptor germline beta-chain D1.1 and J1.1 to J1.6 genes |
| 384 | Renal | 0.4060856 | 0.4232099 | 0.352574 | 0.22644052 | U67614_at | No description available for U67614 |
| 385 | Renal | 0.4054925 | 0.4231928 | 0.3525543 | 0.22626273 | U10690_f_at | MAGE-5a antigen (MAGE5a) gene |
| 386 | Renal | 0.405372 | 0.422649 | 0.352249 | 0.22613432 | M16405_at | MUSCARINIC ACETYLCHOLINE RECEPTOR M4 |
| 387 | Renal | 0.4052052 | 0.4226379 | 0.352114 | 0.22608586 | J04093_s_at | UDP-GLUCURONOSYLTRANSFERASE 1F PRECURSOR, MICROSOMAL |

FIG. 13P

| # | Type | | | | | Description |
|---|---|---|---|---|---|---|
| 388 | Renal | 0.4050798 | 0.4225664 | 0.352014 | 0.22589439 H79230_at | EST: yu27e05.r1 Homo sapiens cDNA clone 235040 5'. (from Genbank) |
| 389 | Renal | 0.4048739 | 0.4222954 | 0.351855 | 0.22570261 M16282_at | Fragile X locus M2C containing an unidentified open reading frame, 3' end |
| 390 | Renal | 0.4043465 | 0.4222593 | 0.351659 | 0.22557326 S77582_at | HERVK10/HUMMTV reverse transcriptase homolog (clone RT240) [human, multiple sclerosis, brain plaques, mRNA Partial, 89 nt] |
| 391 | Renal | 0.404346 | 0.4221785 | 0.351482 | 0.22548026 S73885_s_at | TFAP4 Transcription factor AP-4 (activating enhancer-binding protein 4) |
| 392 | Renal | 0.4041498 | 0.4221757 | 0.351478 | 0.22530912 J05556_at | MMP8 Matrix metalloproteinase 8 (neutrophil collagenase) |
| 393 | Renal | 0.4036514 | 0.4220168 | 0.351261 | 0.22520922 U28043_at | Plasma membrane Na+/H+ exchanger isoform 3 (NHE3) mRNA |
| 394 | Renal | 0.4036282 | 0.4217885 | 0.350982 | 0.22509372 X52228_at | MUC1 Mucin 1, transmembrane |
| 395 | Renal | 0.4033422 | 0.4217146 | 0.350956 | 0.22499554 H89551_s_a t | EST: yw28e07.r1 Homo sapiens cDNA clone 253572 5'. (from Genbank) |
| 396 | Renal | 0.4032672 | 0.4216479 | 0.350825 | 0.22484872 S68874_s_at | PTGER3 Prostaglandin E receptor 3 (subtype EP3) (alternative products) |
| 397 | Renal | 0.4031481 | 0.4214196 | 0.350825 | 0.22473663 HG2538-HT2634_at | Heterogeneous Nuclear Ribonucleoprotein C |
| 398 | Renal | 0.4028293 | 0.4213535 | 0.350788 | 0.2245758 M37245_at | Ig superfamily cytotoxic T-lymphocyte-associated protein (CTLA-4) gene, last exon |
| 399 | Renal | 0.4027892 | 0.4213373 | 0.350076 | 0.2244271 Z48511_at | XG mRNA (clone PEP11) |
| 400 | Renal | 0.4026902 | 0.4210858 | 0.350675 | 0.22435418 M31165_at | TUMOR NECROSIS FACTOR-INDUCIBLE PROTEIN TSG-6 PRECURSOR |
| 401 | Renal | 0.4024642 | 0.4209718 | 0.350566 | 0.22420274 U31176_at | HERV1 mRNA |
| 402 | Renal | 0.4023454 | 0.4209531 | 0.350273 | 0.22409862 S73840_at | Type IIx myosin heavy chain {3' region} [human, skeletal muscle, mRNA Partial, 827 nt] |
| 403 | Renal | 0.4014818 | 0.4206194 | 0.350273 | 0.22399996 L11931_at | SHMT1 Serine hydroxymethyltransferase 1 (soluble) |
| 404 | Renal | 0.4013373 | 0.4203845 | 0.35011 | 0.22382079 M89473_at | NEUROMEDIN K RECEPTOR |
| 405 | Renal | 0.4012959 | 0.4203489 | 0.349798 | 0.22365946 X97198_at | Receptor protein tyrosine phosphatase hPTP-J precursor, mRNA |
| 406 | Renal | 0.4012114 | 0.4202897 | 0.349585 | 0.22353107 R73982_at | EST: yi56e02.r1 Homo sapiens cDNA clone 143258 5'. (from Genbank) |
| 407 | Renal | 0.40121 | 0.420178 | 0.34949 | 0.22350426 X91653_s_a t | DNA for exon encoding for N-acetylglucosaminyltransferase V (340 bp) |
| 408 | Renal | 0.4009431 | 0.4199558 | 0.349366 | 0.22328146 U02632_at | Calcium-activated potassium channel mRNA, partial cds |
| 409 | Renal | 0.4007365 | 0.4198668 | 0.349201 | 0.22310607 U82311_at | Unknown protein mRNA, partial cds |
| 410 | Renal | 0.3997416 | 0.4195454 | 0.34916 | 0.22298881 M77144_ma 1_at | 3-beta-hydroxysteroid dehydrogenase gene extracted from Human type II 3-beta hydroxysteroid dehydrogenase/ 5-delta - 4-delta isomerase gene |
| 411 | Renal | 0.3993855 | 0.4194925 | 0.349004 | 0.22284803 L21715_at | TNNI2 Troponin I (skeletal fast) |

FIG. 13Q

| # | Tissue | Val1 | Val2 | Val3 | ID1 | ID2 | Description |
|---|---|---|---|---|---|---|---|
| 412 | Renal | 0.3990949 | 0.419488 | 0.348942 | 0.222274947 | AA134488_a t | Zc26f12.r1 Stratagene colon (#937204) Homo sapiens cDNA clone 588047 5', mRNA sequence. (from Genbank) |
| 413 | Renal | 0.3990306 | 0.4194454 | 0.348771 | 0.22257294 | D88613_at | HGCMa |
| 414 | Renal | 0.3990282 | 0.4192733 | 0.348708 | 0.22248846 | X81333_at | PPH beta subunit protein |
| 415 | Renal | 0.3989536 | 0.41924 | 0.348601 | 0.22240154 | U10686_at | MAGE-11 antigen (MAGE11) gene |
| 416 | Renal | 0.3987506 | 0.4192145 | 0.348564 | 0.22224782 | M73489_at | Heat-stable enterotoxin receptor mRNA |
| 417 | Renal | 0.3986234 | 0.419084 | 0.34844 | 0.22213174 | X51602_at | VASCULAR ENDOTHELIAL GROWTH FACTOR RECEPTOR 1 PRECURSOR |
| 418 | Renal | 0.3984112 | 0.4190419 | 0.348378 | 0.221975971 | U95626_rna 1_at | Ccr2 gene (ccr2a) extracted from Homo sapiens ccr2b (ccr2), ccr2a (ccr2), ccr5 (ccr5) and ccr6 (ccr6) genes, and lactoferrin (lactoferrin) gene, partial cds, complete sequence |
| 419 | Renal | 0.3981755 | 0.4189785 | 0.348166 | 0.22219515 | HG4533-HT4938_at | Kallistatin, Protease Inhibitor 4 |
| 420 | Renal | 0.3977778 | 0.4188449 | 0.348134 | 0.22188286 | X91348_at | Predicted non coding cDNA (DGCR5) |
| 421 | Renal | 0.3977778 | 0.4186541 | 0.348104 | 0.2218123 | X91348_at-2 | H.sapiens predicted non coding cDNA (DGCR5) |
| 422 | Renal | 0.3976371 | 0.4185515 | 0.348092 | 0.22175573 | U87972_at | NAD+-isocitrate dehydrogenase mRNA, partial cds |
| 423 | Renal | 0.3974625 | 0.418485 | 0.348022 | 0.22165784 | M26880_at | UBA52 Ubiquitin A-52 residue ribosomal protein fusion product 1 |
| 424 | Renal | 0.3973343 | 0.418357 | 0.347952 | 0.22149038 | U19142_at | GAGE1 G antigen 1 (GAGE-1) |
| 425 | Renal | 0.3970754 | 0.418179 | 0.347765 | 0.22124243 | M23668_at | ADRENODOXIN PRECURSOR |
| 426 | Renal | 0.3970079 | 0.4180574 | 0.347519 | 0.22119683 | Z11559_at | IREB1 Iron-responsive element binding protein 1 |
| 427 | Renal | 0.3961533 | 0.4178814 | 0.347417 | 0.22104162 | U66578_at | Purinergic receptor P2Y9 mRNA |
| 428 | Renal | 0.396008 | 0.417601 | 0.347395 | 0.22084461 | U50929_at | Betaine:homocysteine methyltransferase mRNA |
| 429 | Renal | 0.3958074 | 0.41749 | 0.347223 | 0.22071193 | U72209_at | YY1-associated factor 2 (YAF2) mRNA |
| 430 | Renal | 0.3956077 | 0.417376 | 0.347085 | 0.22063436 | M10943_at | Metallothionein-If gene (hMT-If) |
| 431 | Renal | 0.3954826 | 0.4173618 | 0.346899 | 0.2205449 | X99141_at | Hair keratin, hHb3 |
| 432 | Renal | 0.3954071 | 0.4172122 | 0.346863 | 0.2203038 | U87964_at | Putative G-protein (GP-1) mRNA |
| 433 | Renal | 0.3953168 | 0.4169845 | 0.346603 | 0.22025992 | M74297_at | HOXA4 Homeo box A4 |
| 434 | Renal | 0.3952664 | 0.4167714 | 0.346601 | 0.22015975 | U13395_at | Oxidoreductase (HHCMA56) mRNA |
| 435 | Renal | | 0.4165319 | 0.346198 | 0.22009698 | RC_AA0554 04_f_at | EST: zl74e11.s1 Stratagene colon (#937204) Homo sapiens cDNA clone 510380 3' similar to contains Alu repetitive element;, mRNA sequence. (from Genbank) |
| 436 | Renal | 0.39496 01 | 0.4164842 | 0.346186 | 0.21993133 | S80905_f_at | PRB2 locus salivary proline-rich protein mRNA, clone cP7 |
| 437 | Renal | 0.3944329 | 0.4163989 | 0.346137 | 0.21981794 | U30998_at | U30998 Homo sapiens 530 melanoma Homo sapiens cDNA clone nmd, mRNA sequence |
| 438 | Renal | 0.3941328 | 0.4163486 | 0.345869 | 0.219783 | Z29678_at | MitF mRNA |
| 439 | Renal | 0.3938225 | 0.4163345 | 0.345671 | 0.21968207 | X02176_s_a t | C9 Complement component C9 |
| 440 | Renal | 0.3936858 | 0.4162787 | 0.345615 | 0.21949068 | U28281_at | SCTR Secretin receptor |

FIG. 13R

| # | Tissue | | | | ID | Description |
|---|---|---|---|---|---|---|
| 441 | Renal | 0.3934735 | 0.4162787 | 0.345563 | AA480838_s_at | EST: zx87e06.r1 Soares ovary tumor NbHOT Homo sapiens cDNA clone 810754 5', mRNA sequence. (from Genbank) |
| 442 | Renal | 0.3933882 | 0.4160348 | 0.34556 | 0.219940257 | EST: Homo sapiens mRNA; expressed sequence tag; clone DKFZphsnu1_1b16, 5' read, mRNA sequence. (from Genbank) |
| 443 | Renal | 0.3931437 | 0.4159394 | 0.345526 | 0.219292209 Z98497_at | BMP-5=bone morphogenic protein-5 {promoter} [human, Genomic, 1116 nt] |
| 444 | Renal | 0.3929899 | 0.4158582 | 0.345264 | 0.219168859 S81957_at | CD39 CD39 antigen |
| 445 | Renal | 0.392935 | 0.4158127 | 0.345205 | 0.219900862 S73813_at RC_AA4355 | EST: zt85g06.s1 Soares testis NHT Homo sapiens cDNA clone 729178 3', mRNA sequence. (from Genbank) |
| 446 | Renal | 0.3927434 | 0.4156061 | 0.345099 | 0.218838597_at L78440_at | STAT4 Signal transducer and activator of transcription 4 |
| 447 | Renal | 0.3922619 | 0.4155586 | 0.344835 | 0.218774421 U32674_s_a t | Orphan receptor GPR9 (GPR9) gene, partial cds |
| 448 | Renal | 0.3922592 | 0.4155227 | 0.344716 | 0.218546297 X06985_at | HMOX1 Heme oxygenase (decycling) 1 |
| 449 | Renal | 0.3920944 | 0.4155054 | 0.34456 | 0.218318953_s_at M15517_cds | TTR gene extracted from Human mutant prealbumin gene directly linked to familial amyloidotic polyneuropathy (FAP) |
| 450 | Renal | 0.3920615 | 0.41533 | 0.344512 | 0.218186785 M20137_at | Interleukin 3 (IL-3) mRNA |
| 451 | Renal | 0.3919278 | 0.4150119 | 0.344261 | 0.218127987 M22348_s_a t | UQCRB Ubiquinol-cytochrome c reductase binding protein |
| 452 | Renal | 0.3913983 | 0.4148741 | 0.344114 | 0.218032578 X58255_at | Flg-2 gene for fibroblast growth factor receptor |
| 453 | Renal | 0.391211 | 0.4145787 | 0.343984 | 0.217895229 HT4241_at HG3971- | Transcription Factor (Gb:L32162) |
| 454 | Renal | 0.3909785 | 0.4145568 | 0.343888 | 0.217774079 U59228_at | EDA Ectodermal dysplasia protein |
| 455 | Renal | 0.3909106 | 0.4145226 | 0.343849 | 0.217572553 X02875_s_a t | OIAS (2'-5') oligoadenylate synthetase |
| 456 | Renal | 0.3908465 | 0.4143627 | 0.343503 | 0.217466715_at M81780_cds | SMPD1 gene (acid sphingomyelinase) extracted from Homo sapiens acid sphingomyelinase (SMPD1) gene, ORF's 1-3's |
| 457 | Renal | 0.390837 | 0.4143391 | 0.343497 | 0.217353699 X95384_at | Unknown 14kDa protein |
| 458 | Renal | 0.3903177 | 0.4142064 | 0.343429 | 0.217233846 RC_AA4880 74_at | Cell division cycle 42 (GTP-binding protein, 25kD) |
| 459 | Renal | 0.39021 | 0.4141249 | 0.343381 | 0.217131734 L35475_at | Olfactory receptor-like gene |
| 460 | Renal | 0.3901584 | 0.4140622 | 0.343285 | 0.216938478 U28150_at | Adrenoleukodystrophy related protein (hALDR) gene, partial cds |
| 461 | Renal | 0.3900426 | 0.4140292 | 0.34323 | 0.2168348 X86371_s_a t | Tumour suppressor protein, HUGL |
| 462 | Renal | 0.3898647 | 0.4135601 | 0.343146 | 0.216670319 D17525_at | CRARF C4/C2 activating component of Ra-reactive factor |
| 463 | Renal | 0.3897955 | 0.41327 | 0.342896 | 0.216596662 U13680_at-2 | Lactate dehydrogenase C |
| 464 | Renal | 0.3897955 | 0.4128727 | 0.342699 | 0.216434454 U13680_at | LDHC Lactate dehydrogenase C |
| 465 | Renal | 0.3897939 | 0.4127775 | 0.342612 | 0.216332424 X83378_at | Putative chloride channel |
| 466 | Renal | 0.3894637 | 0.4126578 | 0.342516 | 0.216212210 RC_AA2338 7_at | EST: zr44f10.s1 Soares NhHMPu S1 Homo sapiens cDNA clone 666283 3', mRNA sequence. (from Genbank) |

FIG. 13S

| # | Tissue | | | | Description |
|---|---|---|---|---|---|
| 467 | Renal | 0.3892597 | 0.4124726 | 0.342467 | 0.21608788 Y08136_at | ASM-like phosphodiesterase 3a |
| 468 | Renal | 0.3887051 | 0.4124129 | 0.342407 | 0.21601352 D14686_at | AMT Glycine cleavage system protein T (aminomethyltransferase) |
| 469 | Renal | 0.3886014 | 0.4123459 | 0.342203 | 0.21586327 D50924_at | KIAA0134 gene |
| 470 | Renal | 0.3882052 | 0.4123277 | 0.342171 | 0.21572451 M28713_at | NADH-CYTOCHROME B5 REDUCTASE |
| 471 | Renal | 0.3873729 | 0.4121672 | 0.342129 | 0.21560512 X52889_at | MYH7 Myosin, heavy polypeptide 7, cardiac muscle, beta |
| 472 | Renal | 0.3871222 | 0.4120859 | 0.342051 | 0.21549097 RC_AA025351_at | EST: ze74h03.s1 Soares fetal heart NbHH19W Homo sapiens cDNA clone 364757 3' similar to contains OFR.t1 OFR repetitive element :, mRNA sequence. (from Genbank) |
| 473 | Renal | 0.386937 | 0.4119662 | 0.341679 | 0.21544583 S81264_s_at | Hs-TBX2=T-box gene {T-box region} [human, fetal kidney, mRNA Partial, 283 nt] |
| 474 | Renal | 0.3868803 | 0.411963 | 0.341484 | 0.21535738 U01120_at | G6PT Glucose-6-phosphatase |
| 475 | Renal | 0.3868523 | 0.4118257 | 0.341468 | 0.21522906 U97018_at | Echinoderm microtubule-associated protein homolog HuEMAP mRNA |
| 476 | Renal | 0.3867081 | 0.4116475 | 0.341433 | 0.2150264 Y00264_at | APP Amyloid A4 protein of Alzheimer's disease |
| 477 | Renal | 0.3866564 | 0.4116346 | 0.34143 | 0.21497259 RC_D59362_at | EST: Human fetal brain cDNA 3'-end GEN-023A02, mRNA sequence. (from Genbank) |
| 478 | Renal | 0.3864065 | 0.4115213 | 0.341306 | 0.21489744 U58658_at | Unknown protein mRNA within the p53 intron 1 |
| 479 | Renal | 0.3859122 | 0.4114434 | 0.341269 | 0.21479595 L19314_at | HRY gene |
| 480 | Renal | 0.3855977 | 0.4113829 | 0.341213 | 0.2146994 X02956_at | IFNA5 Interferon, alpha 5 |
| 481 | Renal | 0.3855954 | 0.4113756 | 0.34112 | 0.21459176 U12622_at | Beaded intermediate filament protein CP115 mRNA, partial cds |
| 482 | Renal | 0.3855891 | 0.4112196 | 0.340794 | 0.21441936 U08989_at | Glutamate transporter mRNA |
| 483 | Renal | 0.3854718 | 0.4111506 | 0.340542 | 0.21434422 U70867_at | Prostaglandin transporter hPGT mRNA |
| 484 | Renal | 0.3852766 | 0.4110371 | 0.340518 | 0.21418306 RC_AA005196_at | EST: zh95g08.s1 Soares fetal liver spleen 1NFLS S1 Homo sapiens cDNA clone 429086 3', mRNA sequence. (from Genbank) |
| 485 | Renal | 0.3844384 | 0.41083 | 0.340421 | 0.21406052 U29943_s_at | ELAV-like neuronal protein-2 Hel-N2 mRNA |
| 486 | Renal | 0.3844263 | 0.4106331 | 0.34037 | 0.21391034 D31765_at | KIAA0061 gene, partial cds |
| 487 | Renal | 0.3842909 | 0.4105851 | 0.340358 | 0.21389607 U16282_at | ELL mRNA |
| 488 | Renal | 0.3842713 | 0.4105597 | 0.34032 | 0.21368133 L37199_at | (clone cD24-1) Huntington's disease candidate region mRNA fragment |
| 489 | Renal | 0.3838697 | 0.4104933 | 0.340307 | 0.21358728 M74096_at | ACADL Acyl-Coenzyme A dehydrogenase, long chain |
| 490 | Renal | 0.3837603 | 0.4102729 | 0.340248 | 0.21342765 HG3454-HT3647_at | Zinc Finger Protein 20 |
| 491 | Renal | 0.3835089 | 0.4102442 | 0.340127 | 0.21334514 L06133_at | ATP7A ATPase, Cu++ transporting, alpha polypeptide (Menkes syndrome) |
| 492 | Renal | 0.3834429 | 0.4101942 | 0.340005 | 0.21326189 X83492_s_at | Fas/Apo-1 (clone pCRTM11-Fasdelta(4,7)) |
| 493 | Renal | 0.3833537 | 0.4101942 | 0.339902 | 0.21311911 U31248_at | ZNF174 Zinc finger protein 174 |

FIG. 13T

| | | | | | | |
|---|---|---|---|---|---|---|
| 494 | Renal | 0.3831945 | 0.4101698 | 0.339868 | 0.21297929 | X63717_at | APT1 Apoptosis (APO-1) antigen 1 |
| 495 | Renal | 0.3831752 | 0.4101422 | 0.339764 | 0.2128441 | X06948_at | FCER1A High affinity IgE receptor alpha-subunit (FcERI) |
| 496 | Renal | 0.3829342 | 0.4101422 | 0.339427 | 0.21276782 | X92521_at | Clone rasi-1 matrix metalloproteinase RASI-1 mRNA |
| 497 | Renal | 0.3828145 | 0.4096177 | 0.339375 | 0.21265146 | U20350_at | CMKRL1 Chemokine receptor-like 1 |
| 498 | Renal | 0.38241 | 0.4094276 | 0.33919 | 0.2125849 | X67697_at | SPERM ANTIGEN HE2 PRECURSOR |
| 499 | Renal | 0.3823005 | 0.4092183 | 0.339052 | 0.21245904 | U76010_at | Putative zinc transporter ZnT-3 (ZnT-3) mRNA |
| 500 | Renal | 0.3808028 | 0.4091129 | 0.338987 | 0.21238157 | Y08976_at | FEV protein |
| 501 | Renal | 0.3807296 | 0.4091128 | 0.338931 | 0.21220458 | U19251_s_at | SMA5 mRNA |
| 502 | Renal | 0.3806546 | 0.4090794 | 0.338908 | 0.212103 | U31501_at | Fragile X mental retardation syndrome related protein (FXR2) mRNA |
| 503 | Renal | 0.3804053 | 0.409059 | 0.338764 | 0.212069121 | AA437346_a_at | EST: zw30c06.r1 Soares ovary tumor NbHOT Homo sapiens cDNA clone 770794 5' similar to TR:G406738 G406738 SHB MRNA.; mRNA sequence. (from Genbank) |
| 504 | Renal | 0.3799121 | 0.4090375 | 0.338764 | 0.21188968 | M61855_at | CYP2C9 Cytochrome P450, subfamily IIC (mephenytoin 4-hydroxylase), polypeptide 9 |
| 505 | Renal | 0.3799048 | 0.408982 | 0.33865 | 0.21184519 | U39905_at | SLC18A1 Solute carrier family 18 (vesicular monoamine), member 1 |
| 506 | Renal | 0.3793142 | 0.4089387 | 0.338636 | 0.21175718 | L13761_rna1_at | Dihydrolipoamide dehydrogenase gene, exon 14 |
| 507 | Renal | 0.3789361 | 0.4088156 | 0.338417 | 0.21161208 | U37143_at | CYP2J2 Cytochrome P450, subfamily IIJ (arachidonic acid epoxygenase) polypeptide 2 |
| 508 | Renal | 0.378836 | 0.4087991 | 0.33839 | 0.21150245 | L19058_at | Glutamate receptor (GLUR5) mRNA |
| 509 | Renal | 0.3786276 | 0.4086725 | 0.338269 | 0.21131727 | L21936_at | SDH2 Succinate dehydrogenase 2, flavoprotein (Fp) subunit |
| 510 | Renal | 0.378587 | 0.4086427 | 0.338169 | 0.21127494 | D16294_at | 3-KETOACYL-COA THIOLASE MITOCHONDRIAL |
| 511 | Renal | 0.3782788 | 0.4085008 | 0.338097 | 0.21119153 | RC_AA4958 27_s_at | EST: zw05e08.s1 Soares NhHMPu S1 Homo sapiens cDNA clone 768422 3' similar to contains Alu repetitive element; mRNA sequence. (from Genbank) |
| 512 | Renal | 0.3780057 | 0.4083075 | 0.338 | 0.21098797 | D63483_at | KIAA0149 gene |
| 513 | Renal | 0.3778997 | 0.4082763 | 0.337888 | 0.21088673 | M15881_at | UMOD Uromodulin (uromucoid, Tamm-Horsfall glycoprotein) |
| 514 | Renal | 0.3776736 | 0.4082113 | 0.337844 | 0.21080297 | U77975_at | Hepatocyte nuclear factor 6 (HNF-6) mRNA, partial cds |
| 515 | Renal | 0.3773 | 0.4081832 | 0.337798 | 0.21076393 | HG721-HT4827_s_at | Placental Protein 14, Endometrial Alpha 2 Globulin, Alt. Splice 2 |
| 516 | Renal | 0.3771043 | 0.4081209 | 0.337629 | 0.21066396 | X16105_at | RD Radin blood group |
| 517 | Renal | 0.3770738 | 0.4080607 | 0.337605 | 0.21060382 | M64934_at | XK Kell blood group precursor (McLeod phenotype) |
| 518 | Renal | 0.3769071 | 0.4078405 | 0.337517 | 0.2105385 | X97671_at | EPOR Erythropoietin receptor |
| 519 | Renal | 0.3768947 | 0.4077682 | 0.337399 | 0.2104809 | D31766_at | PUTATIVE GLUCOSAMINE-6-PHOSPHATE ISOMERASE |
| 520 | Renal | 0.3766561 | 0.4075239 | 0.33738 | 0.21040672 | U47101_at | NifU-like protein (hNifU) mRNA, partial cds |
| 521 | Renal | 0.3765176 | 0.4074901 | 0.337306 | 0.21029882 | D31815_at | SMP-30 (senescence marker protein-30) |

FIG. 13U

| # | Type | | | | | Description |
|---|---|---|---|---|---|---|
| 522 | Renal | 0.3763641 | 0.4070943 | 0.3372 | 0.21022041 U49250_at | Putative cerebral cortex transcriptional regulator T-Brain-1 (Tbr-1) mRNA |
| 523 | Renal | 0.376022 | 0.4069965 | 0.337155 | 0.21013334 M14113_at | F8C Coagulation factor VIIIc (hemophilia A) |
| 524 | Renal | 0.3757579 | 0.4069413 | 0.336983 | 0.210093450 RC_AA0576 40_at | Neuropilin 2 |
| 525 | Renal | 0.3750456 | 0.4068812 | 0.336898 | 0.20991942 L24774_s_at | DCI Dodecenoyl-Coenzyme A delta isomerase (3,2 trans-enoyl-Coenzyme A isomerase) |
| 526 | Renal | 0.374915 | 0.4067298 | 0.336742 | 0.20990273 M17236_at | HLA CLASS II HISTOCOMPATIBILITY ANTIGEN, DQ(2) ALPHA CHAIN PRECURSOR |
| 527 | Renal | 0.3746587 | 0.4067225 | 0.33668 | 0.20982628 R81768_at | Homo sapiens mRNA for KIAA0890 protein, complete cds |
| 528 | Renal | 0.3746503 | 0.4063532 | 0.336656 | 0.20978773 U03486_at | Connexin40 gene |
| 529 | Renal | 0.3744914 | 0.4062526 | 0.336401 | 0.20969816 U63541_at | mRNA expressed in HC/HCC livers and MolT-4 proliferating cells, partial sequence |
| 530 | Renal | 0.3744638 | 0.4062274 | 0.336361 | 0.20962615 RC_AA2623 51_f_at | EST: zr44g03.s1 Soares NhHMPu S1 Homo sapiens cDNA clone 666292 3', mRNA sequence. (from Genbank) |
| 531 | Renal | 0.3743906 | 0.406089 | 0.336337 | 0.20956138 M60092_at | AMP DEAMINASE 1 |
| 532 | Renal | 0.3743085 | 0.4059748 | 0.336256 | 0.20937243 D49387_at | NADP dependent leukotriene b4 12-hydroxydehydrogenase, partial cds |
| 533 | Renal | 0.3742258 | 0.405899 | 0.336152 | 0.20929945 L17128_at | GGCX Gamma-glutamyl carboxylase |
| 534 | Renal | 0.374256 | 0.405873 | 0.336015 | 0.20918402 HG3994-HT4264_at | Cpg-Enriched Dna, Clone S16 |
| 535 | Renal | 0.3740803 | 0.405873 | 0.335833 | 0.20914286 U89336_cds 3_at | RAGE gene (receptor for advanced glycosylation end products) extracted from Human HLA class III region containing NOTCH4 gene, partial sequence, homeobox PBX2 (HPBX) gene, receptor for advanced glycosylation end products (RAGE) gene, and 6 unidentified cds, complete sequence |
| 536 | Renal | 0.37343550 | 0.4057755 | 0.335805 | 0.20907441 M87770_at | FGFR2 Fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 537 | Renal | 0.3730355 | 0.4057663 | 0.335648 | 0.20888889 U24266_at | Pyrroline-5-carboxylate dehydrogenase (P5CDh) mRNA, long form |
| 538 | Renal | 0.3726522 | 0.4056656 | 0.335541 | 0.20880626 M11437_cds 2_at | KNG gene (kininogen) extracted from Human kininogen gene |
| 539 | Renal | 0.37259 | 0.4054915 | 0.335468 | 0.20857964 M95585_s_a t | HLF Hepatic leukemia factor |
| 540 | Renal | 0.3725378 | 0.405445 | 0.335366 | 0.20850569 J03756_at | SOMATOTROPIN PRECURSOR |
| 541 | Renal | 0.3725201 | 0.4053759 | 0.335121 | 0.2084435 AA282769_a t | EST: zt15c05.r1 NCI_CGAP_GCB1 Homo sapiens cDNA clone IMAGE:713192 5', mRNA sequence. (from Genbank) |
| 542 | Renal | 0.3722635 | 0.4053047 | 0.335045 | 0.2082695 D42047_at | KIAA0089 gene, partial cds |

FIG. 13V

| # | Tissue | | | | ID | Description |
|---|---|---|---|---|---|---|
| 543 | Renal | 0.3721954 | 0.4051834 | 0.334832 | 0.2082486 | HG2850-HT4814_s_at Biliary Glycoprotein, Alt. Splice 5, A |
| 544 | Renal | 0.3721655 | 0.405041 | 0.334695 | 0.20811312 | L49054_at T(3;5)(q25.1;p34) fusion gene NPM-MLF1 mRNA |
| 545 | Renal | 0.3720413 | 0.4050139 | 0.333458 | 0.20791422 | Y09615_at Mitochondrial transcription termination factor |
| 546 | Renal | 0.3717674 | 0.4049185 | 0.334506 | 0.20786637 | RC_AA151674_at Carbonic anhydrase XII |
| 547 | Renal | 0.3713738 | 0.4048333 | 0.334488 | 0.20780845 | U34877_at Biliverdin-IXalpha reductase mRNA |
| 548 | Renal | 0.3713234 | 0.404668 | 0.334399 | 0.2076894 | L77213_at Phosphomevalonate kinase mRNA |
| 549 | Renal | 0.3712392 | 0.4043476 | 0.334339 | 0.2076744 | D63877_at KIAA0241 gene, partial cds |
| 550 | Renal | 0.3712028 | 0.4042949 | 0.334237 | 0.20744576 | T61992_at EST: yb96h08.r1 Homo sapiens cDNA clone 79071 5'. (from Genbank) |
| 551 | Renal | 0.3711499 | 0.4038581 | 0.334102 | 0.20738308 | M83088_at PGM1 Phosphoglucomutase 1 |
| 552 | Renal | 0.3711476 | 0.4036543 | 0.334087 | 0.20734066 | D38535_at PK-120 |
| 553 | Renal | 0.370813 | 0.4035873 | 0.333797 | 0.20717373 | U89335_cds2_at NOTCH4 gene (notch4) extracted from Human HLA class III region containing notch4 (NOTCH4) gene, complete sequence |
| 554 | Renal | 0.3705376 | 0.4034331 | 0.333756 | 0.20711143 | L42354_at (clone 48ES4) mRNA fragment |
| 555 | Renal | 0.3704077 | 0.4033913 | 0.333635 | 0.20697162 | L02932_at PPARA Peroxisome proliferative activated receptor, alpha |
| 556 | Renal | 0.3704044 | 0.4032013 | 0.333611 | 0.20676987 | HG2264-HT2360_at Atpase, Ca2+ Transporting, Plasma Membrane 1, Alt. Splice 6 |
| 557 | Renal | 0.3703476 | 0.4029535 | 0.333584 | 0.20668733 | X61615_at LIFR Leukemia inhibitory factor receptor |
| 558 | Renal | 0.3700893 | 0.4027599 | 0.333456 | 0.20658544 | U09002_at N-methyl-D-aspartate receptor modulatory subunit 2A (hNR2A) mRNA |
| 559 | Renal | 0.3693424 | 0.4023378 | 0.333217 | 0.20655525 | U15172_at Nip1 (NIP1) mRNA |
| 560 | Renal | 0.3692714 | 0.4022266 | 0.333147 | 0.20645323 | X62515_s_at HSPG2 Heparan sulfate proteoglycan |
| 561 | Renal | 0.3685216 | 0.4021958 | 0.333113 | 0.20631331 | RC_AA281426_at Natural resistance-associated macrophage protein 1 (might include Leishmaniasis) |
| 562 | Renal | 0.3684205 | 0.402086 | 0.333045 | 0.20622149 | L17075_s_at SERINE/THREONINE-PROTEIN KINASE RECEPTOR R3 PRECURSOR |
| 563 | Renal | 0.3674965 | 0.4019934 | 0.333025 | 0.20611528 | J03133_at SP1 Sp1 transcription factor |
| 564 | Renal | 0.3672717 | 0.4019609 | 0.332862 | 0.20597196 | HG3492-HT3686_at Uncoupling Protein Ucp |
| 565 | Renal | 0.3669781 | 0.4019541 | 0.332518 | 0.20593803 | HG2320-HT2416_at Integrin, Beta 3 Subunit |
| 566 | Renal | 0.3668887 | 0.4017842 | 0.332428 | 0.20581642 | RC_AA013160_at EST: ze35e10.s1 Soares retina N2b4HR Homo sapiens cDNA clone 361002 3' similar to contains Alu repetitive element., mRNA sequence. (from Genbank) |
| 567 | Renal | 0.3667753 | 0.4017219 | 0.332379 | 0.2056499 | X14766_at GABRA1 Gamma-aminobutyric acid (GABA) A receptor, alpha 1 |

FIG. 13W

| # | Tissue | | | | | | Description |
|---|---|---|---|---|---|---|---|
| 568 | Renal | 0.3666224 | 0.4016691 | 0.332295 | 0.205577608 | M73255_rna1_s_at | Vascular cell adhesion molecule 1 |
| 569 | Renal | 0.3661323 | 0.4016309 | 0.332198 | 0.205545489 | X52426_s_a_t | KRT13 Keratin 13 |
| 570 | Renal | 0.3660792 | 0.4016249 | 0.332154 | 0.205540152 | L77730_at | ADORA3 Adenosine receptor A3 |
| 571 | Renal | 0.3659006 | 0.4015688 | 0.332139 | 0.205274448 | M14745_at | BCL2 B cell lymphoma protein 2 |
| 572 | Renal | 0.3656499 | 0.4015611 | 0.332136 | 0.2051995 | M32053_at | H19 RNA gene |
| 573 | Renal | 0.3656006 | 0.4013943 | 0.332124 | 0.205077771 | X66403_at | CHRNE Cholinergic receptor, nicotinic, epsilon polypeptide |
| 574 | Renal | 0.3650194 | 0.401306 | 0.332113 | 0.20494086 | AA454191_a_t | EST: zx48b10.r1 Soares testis NHT Homo sapiens cDNA clone 795451 5', mRNA sequence. (from Genbank) |
| 575 | Renal | 0.3649092 | 0.4012667 | 0.33192 | 0.2048647 | L17330_at | Pre-T/NK cell associated protein (6H9A) mRNA |
| 576 | Renal | 0.3638829 | 0.4012012 | 0.331745 | 0.20473251 | M62958_at | RDS Retinal degeneration slow |
| 577 | Renal | 0.3638237 | 0.4011016 | 0.331693 | 0.204694511 | HG1747-HT1764_s_a_t | Proto-Oncogene Met, Alt. Splice Form 2 |
| 578 | Renal | 0.3636029 | 0.4010126 | 0.33154 | 0.20468138 | L23852_at | (clone Z146) retinal mRNA, 3' end and repeat region |
| 579 | Renal | 0.3634948 | 0.4008013 | 0.331383 | 0.2045977 | D42108_at | Phospholipase C |
| 580 | Renal | 0.3634436 | 0.4007189 | 0.331135 | 0.20454402 | L15309_at | ZNF-141 Zinc finger protein 141 (clone pHZ-44) |
| 581 | Renal | 0.3634397 | 0.4005471 | 0.331289 | 0.20450142 | L02321_at | GSTM5 Glutathione S-transferase M5 |
| 582 | Renal | 0.3634004 | 0.4004182 | 0.330963 | 0.20435885 | M28819_at | GRANZYME B PRECURSOR |
| 583 | Renal | 0.3631155 | 0.4003435 | 0.330962 | 0.2042858 | X64269_at | TCF6L1 Transcription factor 6-like 1 (mitochondrial transcription factor 1-like) |
| 584 | Renal | 0.3629541 | 0.4003039 | 0.330807 | 0.20422466 | M83712_s_a_t | CHRNA5 Cholinergic receptor, nicotinic, alpha polypeptide 5 |
| 585 | Renal | 0.3624992 | 0.4001426 | 0.330794 | 0.20413674 | U62433_at | CHRNA4 Cholinergic receptor, nicotinic, alpha polypeptide 4 |
| 586 | Renal | 0.3621728 | 0.4000062 | 0.33061 | 0.20401943 | HG3242-HT3419_s_a_t | Calcium Channel, Voltage-Gated, Alpha 1e Subunit, Alt. Splice 2 |
| 587 | Renal | 0.3621294 | 0.3999776 | 0.33061 | 0.20391245 | M31774_s_a_t | TSHR Thyroid stimulating hormone receptor |
| 588 | Renal | 0.3612174 | 0.3999643 | 0.330514 | 0.20387268 | HG3976-HT4246_at | Pou-Domain Dna Binding Factor Pit1, Pituitary-Specific |
| 589 | Renal | 0.3611723 | 0.3998818 | 0.330514 | 0.20374495 | U76369_at | Cationic amino acid transporter-2B (ATRC2) mRNA, partial cds |
| 590 | Renal | 0.3604267 | 0.3995867 | 0.330468 | 0.20367342 | M87860_at | GALECTIN-2 |
| 591 | Renal | 0.3602555 | 0.3995598 | 0.330407 | 0.20353624 | U01160_at | Transmembrane 4 superfamily protein (SAS) mRNA |
| 592 | Renal | 0.3599847 | 0.399408 | 0.330393 | 0.20342363 | L43366_at | (clone jj1b) cadherin mRNA fragment |
| 593 | Renal | 0.3593457 | 0.3993884 | 0.33037 | 0.20338346 | X89426_at | ESM-1 protein |
| 594 | Renal | 0.3591742 | 0.3992048 | 0.33023 | 0.20327507 | M55150_at | FAH Fumarylacetoacetate |
| 595 | Renal | 0.3590226 | 0.3989284 | 0.330119 | 0.2031748 | U44059_at | Thyrotroph embryonic factor (TEF) mRNA |
| 596 | Renal | 0.3589031 | 0.3989205 | 0.330097 | 0.20306428 | X89267_at | UROD Uroporphyrinogen decarboxylase |

FIG. 13X

| | | | | | |
|---|---|---|---|---|---|
| 597 | Renal | 0.3588903 | 0.3989023 | 0.33008 | 0.20298326 | M26665_at | HISTATIN 3 PRECURSOR |
| 598 | Renal | 0.3588768 | 0.3988683 | 0.329961 | 0.20275915 | U11090_at | Hydroxyindole-O-methyltransferase promoter B-derived (HIOMT) mRNA |
| 599 | Renal | 0.3588289 | 0.3987047 | 0.329933 | 0.20271072 | J00129_at | FIBRINOGEN BETA CHAIN PRECURSOR |
| 600 | Renal | 0.358696 | 0.3986954 | 0.329891 | 0.20266162 | M14338_at | PROS1 Plasma protein S |
| 601 | Renal | 0.3586696 | 0.3984921 | 0.329794 | 0.20251815 | S82592_at | Evi-1 |
| 602 | Renal | 0.3581415 | 0.3983944 | 0.329775 | 0.20250145 | J04501_at | GYS1 Glycogen synthase 1 (muscle) |
| 603 | Renal | 0.3580428 | 0.3981897 | 0.329743 | 0.20243107 | X14085_s_at | GGTB2 Glycoprotein-4-beta-galactosyltransferase 2 |
| 604 | Renal | 0.3580149 | 0.3980464 | 0.329671 | 0.20233926 | S81893_at | MESI3/15=extracellular matrix induced gene [human, endometrial adenocarcinoma cells HEC1B(L), mRNA Partial, 453 nt] |
| 605 | Renal | 0.3579947 | 0.397913 | 0.329643 | 0.20233478 | M26061_at | CGMP phosphodiesterase alpha subunit (CGPR-A) mRNA |
| 606 | Renal | 0.3577042 | 0.3977703 | 0.329609 | 0.20226664 | RC_AA477252_at | Homo sapiens mRNA for KIAA0664 protein, partial cds |
| 607 | Renal | 0.3576125 | 0.3976313 | 0.329528 | 0.20220138 | X69878_at | FLT4 Fms-related tyrosine kinase 4 |
| 608 | Renal | 0.3574897 | 0.3976313 | 0.329367 | 0.20209628 | U90550_at | Butyrophilin (BTF2) mRNA |
| 609 | Renal | 0.3574897 | 0.3975459 | 0.3293 | 0.20193954 | U90550_at-2 | Human butyrophilin (BTF2) mRNA, complete cds |
| 610 | Renal | 0.3573702 | 0.3974564 | 0.329231 | 0.20190722 | S73149_at | Insulin-like growth factor II [intron 7] [human, Genomic, 1702 nt] |
| 611 | Renal | 0.3572469 | 0.3972337 | 0.329148 | 0.20171547 | AA446139_at | EST: zw64a03.r1 Soares testis NHT Homo sapiens cDNA clone 780940 5', mRNA sequence. (from Genbank) |
| 612 | Renal | 0.3571375 | 0.3972125 | 0.32911 | 0.20157892 | L03785_at | MYL5 Myosin, light polypeptide 5, regulatory |
| 613 | Renal | 0.3571369 | 0.3971468 | 0.329077 | 0.20137623 | AFFX-CreX-3_at-2 | AFFX-CreX-3_at (miscellaneous control - 11k chips) |
| 614 | Renal | 0.3571369 | 0.3969357 | 0.328872 | 0.20132859 | AFFX-CreX-3_at | AFFX-CreX-3_at (endogenous control) |
| 615 | Renal | 0.3570361 | 0.3969184 | 0.32868 | 0.20124388 | U35005_s_at | STRESS-ACTIVATED PROTEIN KINASE JNK1 |
| 616 | Renal | 0.3569427 | 0.3967667 | 0.32866 | 0.20116995 | M37400_at | GOT1 Glutamic-oxaloacetic transaminase 1, soluble (aspartate aminotransferase 1) |
| 617 | Renal | 0.3568608 | 0.3966655 | 0.32866 | 0.20114276 | M36653_s_at | POU2F2 POU domain, class 2, transcription factor 2 |
| 618 | Renal | 0.3567165 | 0.3965512 | 0.328526 | 0.20104828 | AA478688_at | EST: zv09a02.r1 Soares NhHMPu S1 Homo sapiens cDNA clone 753098 5', mRNA sequence. (from Genbank) |
| 619 | Renal | 0.3565405 | 0.3964182 | 0.328512 | 0.20096345 | HG2730-HT2827_s_at | Fibrinogen, A Alpha Polypeptide, Alt. Splice 2, E |
| 620 | Renal | 0.3564823 | 0.3963827 | 0.328417 | 0.20066801 | M69177_at | MAOB Monoamine oxidase B |
| 621 | Renal | 0.3563189 | 0.3963134 | 0.328382 | 0.20059875 | U72512_at | B-cell receptor associated protein (hBAP) alternatively spliced mRNA, partial 3'UTR |

FIG. 13Y

| # | Tissue | | | | | | Description |
|---|---|---|---|---|---|---|---|
| 622 | Renal | 0.3557967 | 0.3962861 | 0.328277 | 0.20050707 | D79995_at | KIAA0173 gene |
| 623 | Renal | 0.3557048 | 0.3962824 | 0.328149 | 0.20045382 | X80026_at | B-cam mRNA |
| 624 | Renal | 0.3553119 | 0.3962611 | 0.328052 | 0.20040374 | U32499_s_at | D3 dopamine receptor mRNA |
| 625 | Renal | 0.3552127 | 0.3962386 | 0.327427 | 0.2003607 | J02947_s_at | SOD3 Superoxide dismutase 3, extracellular |
| 626 | Renal | 0.3551889 | 0.3962371 | 0.327396 | 0.20027341 | L37112_at | AVPR1B Arginine vasopressin receptor 1B |
| 627 | Renal | 0.3551028 | 0.3961571 | 0.327379 | 0.20026898 | U45982_at | G protein-coupled receptor GPR-9-6 gene |
| 628 | Renal | 0.3548034 | 0.3961118 | 0.327235 | 0.20024565 | Z49825_s_at | HEPATOCYTE NUCLEAR FACTOR 4 |
| 629 | Renal | 0.3547591 | 0.3960826 | 0.327111 | 0.20015876 | X78416_s_a_t | CSN1 Casein, alpha S1 |
| 630 | Renal | 0.3545881 | 0.395968 | 0.327056 | 0.20005926 | X51954_at | UCP gene for uncoupling protein exon 5 |
| 631 | Renal | 0.3544369 | 0.395944 | 0.327046 | 0.19995838 | HT5146_at HG4704- | Glial Growth Factor 2 |
| 632 | Renal | 0.354406 | 0.3958628 | 0.327038 | 0.19984716 | X81636_at | Clathrin light chain a gene |
| 633 | Renal | 0.3543758 | 0.3956588 | 0.327038 | 0.19973393 | M18737_rna_1_at | GJA1P1 gene extracted from Human Hanukah factor serine protease (HuHF) mRNA |
| 634 | Renal | 0.3542035 | 0.3956152 | 0.327017 | 0.19958307 | U31875_at-2 | Human Hep27 protein mRNA, complete cds |
| 635 | Renal | 0.3542035 | 0.395514 | 0.327006 | 0.19957952 | U31875_at | Hep27 protein mRNA |
| 636 | Renal | 0.3540561 | 0.3954646 | 0.326827 | 0.19943224 | D21241_xpt_s_at | Ovary- and prostate-specific exon 1 from Human cytochrome P-450 aromatase gene, multiple exons 1 and exon 2./ntype=DNA /annot=exon |
| 637 | Renal | 0.3540553 | 0.3954081 | 0.326755 | 0.19931318 | L32179_at | Arylacetamide deacetylase mRNA |
| 638 | Renal | 0.3539787 | 0.3952312 | 0.326631 | 0.19928361 | M13143_at | KLK3 Plasma prekallikrein |
| 639 | Renal | 0.3535397 | 0.3950702 | 0.326619 | 0.19922282 | M35878_at | INSULIN-LIKE GROWTH FACTOR BINDING PROTEIN 3 PRECURSOR |
| 640 | Renal | 0.3534947 | 0.3950038 | 0.326144 | 0.19930067 | L42373_at | Protein phosphatase 2A B56-alpha mRNA |
| 641 | Renal | 0.3531952 | 0.3949249 | 0.326123 | 0.19896884 | HT1729_at HG1723- | Macrophage Scavenger Receptor, Alt. Splice 2 |
| 642 | Renal | 0.3531679 | 0.3948891 | 0.326054 | 0.1989163 | L16862_at | GPRK6 G protein-coupled receptor kinase 6 |
| 643 | Renal | 0.352989 | 0.3948552 | 0.325907 | 0.19874288 | AA459155_a_t | EST: aa26h04.r1 NCI_CGAP_GCB1 Homo sapiens cDNA clone IMAGE:814423 5', mRNA sequence. (from Genbank) |
| 644 | Renal | 0.3526775 | 0.39469 | 0.325862 | 0.198712 | AA335018_a_t | EST: EST39611 Epididymus Homo sapiens cDNA 5' end, mRNA sequence. (from Genbank) |
| 645 | Renal | 0.3523508 | 0.3946898 | 0.325859 | 0.19862176 | AB006190_a_t | Aquaporin 6 |
| 646 | Renal | 0.3520599 | 0.3946385 | 0.325713 | 0.19858225 | D63135_at | ETS-like 30 kDa protein |
| 647 | Renal | 0.3520218 | 0.3945831 | 0.325697 | 0.19854018 | L18920_f_at | MELANOMA-ASSOCIATED ANTIGEN 2 |

FIG. 13Z

| # | Tissue | | | | | ID | Description |
|---|---|---|---|---|---|---|---|
| 648 | Renal | 0.3516439 | 0.3945081 | 0.325657 | 0.19848417 | D00408_s_at | CYP3A7 Cytochrome P450 IIIA7 (P450-HFLa) |
| 649 | Renal | 0.3515484 | 0.3944737 | 0.325448 | 0.19842924_at | U89336_cds1 | Unknown gene extracted from Human HLA class III region containing NOTCH4 gene, partial sequence, homeobox PBX2 (HPBX) gene, receptor for advanced glycosylation end products (RAGE) gene, and 6 unidentified cds, complete sequence |
| 650 | Renal | 0.3505727 | 0.3944271 | 0.32544 | 0.19823736 | S65921_at | Anti-colorectal carcinoma light chain |
| 651 | Renal | 0.3505555 | 0.3943587 | 0.3254103 | 0.19818567 | M64231_rna1_at | Spermidine synthase gene |
| 652 | Renal | 0.35503852 | 0.3941846 | 0.325397 | 0.1981264 | M55420_at | IgE chain, last 2 exons |
| 653 | Renal | 0.3499542 | 0.3940334 | 0.3251159 | 0.19806585 | U29615_at | Chitotriosidase precursor mRNA |
| 654 | Renal | 0.3498043 | 0.3939528 | 0.3251133 | 0.19791447 | M11119_at | Endogenous retrovirus envelope region mRNA (PL1) |
| 655 | Renal | 0.3497235 | 0.3938099 | 0.3251121 | 0.19781208 | X87871_s_at | HEPATOCYTE NUCLEAR FACTOR 4 |
| 656 | Renal | 0.34924 | 0.3938069 | 0.324741 | 0.19773096 | X02404_at | CALCB Calcitonin-related polypeptide, beta |
| 657 | Renal | 0.3489599 | 0.3936937 | 0.3246658 | 0.19767737 | J00073_at | Alpha-cardiac actin gene, 5' flank and |
| 658 | Renal | 0.348807 | 0.3936736 | 0.3245583 | 0.19754806 | M31932_at | FCGR2A Fc fragment of IgG, low affinity IIa, receptor for (CD32) |
| 659 | Renal | 0.3486592 | 0.3935997 | 0.3245583 | 0.19740452 | U64315_s_at | XPF Xeroderma pigmentosum, complementation group F |
| 660 | Renal | 0.3486265 | 0.3935698 | 0.3245502 | 0.19737563 | M96789_at | GJA4 Gap junction protein, alpha 4, 37kD (connexin 37) |
| 661 | Renal | 0.348592 | 0.3935035 | 0.324341 | 0.19722337 | H04627_at | EST: yf49f04.r1 Homo sapiens cDNA clone 152095 5'. (from Genbank) |
| 662 | Renal | 0.3483137 | 0.3933162 | 0.324341 | 0.19712573 | X61755_rna1_s_at | HOX3D gene for homeoprotein HOX3D |
| 663 | Renal | 0.3481135 | 0.3932594 | 0.3244278 | 0.19699985 | W86690_at | Zh63b01.r1 Soares fetal liver spleen 1NFLS S1 Homo sapiens cDNA clone 416713 5' similar to SW:ENV1_HUMAN P10267 RETROVIRUS-RELATED ENV POLYPROTEIN, [1] ;contains Alu repetitive element;. mRNA sequence. (from Genbank) |
| 664 | Renal | 0.3481256 | 0.3932548 | 0.3244255 | 0.1969025 | X81637_at | CLTB Clathrin, light polypeptide (Lcb) |
| 665 | Renal | 0.3481196 | 0.3930719 | 0.3244244 | 0.19680189 | AA422123_i_at | EST: zv26h12.r1 Soares NhHMPu S1 Homo sapiens cDNA clone 754823 5' similar to contains Alu repetitive element;. mRNA sequence. (from Genbank) |
| 666 | Renal | 0.3477797 | 0.3929515 | 0.324423 | 0.1967391 | M55268_at | CSNK2A2 Casein kinase 2, alpha prime polypeptide |
| 667 | Renal | 0.3476794 | 0.3928977 | 0.3244112 | 0.19671062 | L12060_s_at | RARG Retinoic acid receptor, gamma 1 |
| 668 | Renal | 0.3474272 | 0.3928819 | 0.324092 | 0.19660585 | AA095600_a_at | L5079.seq.F Fetal heart, Lambda ZAP Express Homo sapiens cDNA 5', mRNA sequence. (from Genbank) |
| 669 | Renal | 0.3472509 | 0.3928621 | 0.324042 | 0.19650031 | J02963_at | ITGA2B Integrin, alpha 2b (platelet glycoprotein IIb of IIb/IIIa complex, antigen CD41B) |

FIG. 13A2

| | | | | | | |
|---|---|---|---|---|---|---|
| 670 | Renal | 0.3471251 | 0.3928243 | 0.324028 | 0.19637915 | HG3342-HT3519_s_at | Id1 |
| 671 | Renal | 0.3467232 | 0.392773 | 0.323926 | 0.19626933 | U96115_at | WW domain-containing protein WWP3 mRNA, partial cds |
| 672 | Renal | 0.346529 | 0.3927681 | 0.323926 | 0.19623083 | L46353_at | High-mobility group phosphoprotein (HMGI-C) gene, exons 1-3 |
| 673 | Renal | 0.346446 | 0.3924998 | 0.323909 | 0.19620797 | HG4114-HT4384_at | Olfactory Receptor Or17-209 |
| 674 | Renal | 0.3464454 | 0.3924695 | 0.323754 | 0.19616012 | X65357_at | HGMP07E gene for olfactory receptor |
| 675 | Renal | 0.3457331 | 0.3924381 | 0.323582 | 0.19611828 | Z48199_at | SDC1 Syndecan 1 |
| 676 | Renal | 0.34569 | 0.39241 | 0.3234409 | 0.19593845 | M24439_at | ALPL Alkaline phosphatase, liver/bone/kidney |
| 677 | Renal | 0.3456682 | 0.3923555 | 0.3234 | 0.19585276 | RC_AA4541 44_at | Homo sapiens Chromosome 16 BAC clone CIT987SK-44M2 |
| 678 | Renal | 0.3454686 | 0.3923453 | 0.323368 | 0.19582383 | L03840_s_at | FGFR4 Fibroblast growth factor receptor 4 |
| 679 | Renal | 0.3453525 | 0.3923306 | 0.32327 | 0.19573395 | U57450_at | PEDF Pigment epithelium-derived factor |
| 680 | Renal | 0.345311 | 0.3922194 | 0.323137 | 0.19565634 | U70064_s_a t | Lysosomal trafficking regulator (LYST) mRNA, partial cds |
| 681 | Renal | 0.3450503 | 0.3917247 | 0.32311 | 0.19540915 | D29675_at | Inducible nitric oxide synthase gene, promoter and exon 1 |
| 682 | Renal | 0.3448924 | 0.3916361 | 0.323106 | 0.19528644 | D90086_at | PDHB Pyruvate dehydrogenase (lipoamide) beta |
| 683 | Renal | 0.3448676 | 0.3915019 | 0.323004 | 0.19511889 | HT4910_at | Fk506-Binding Protein, Alt. Splice 2 |
| 684 | Renal | 0.3446094 | 0.3914001 | 0.322997 | 0.19509153 | HG3085-HT3254_s_a t | Phosphodiesterase |
| 685 | Renal | 0.3442414 | 0.3910697 | 0.322905 | 0.19497009 | S72503_s_at | HRK1 |
| 686 | Renal | 0.3442323 | 0.3909295 | 0.322778 | 0.19490562 | X97302_at | Ptg-1 protein |
| 687 | Renal | 0.3439733 | 0.3909109 | 0.32263 | 0.19481704 | D56495_at | Reg-related sequence derived peptide-1 |
| 688 | Renal | 0.3435934 | 0.3909003 | 0.322406 | 0.19476211 | U94585_at | Requiem homolog (hsReq) mRNA |
| 689 | Renal | 0.3433878 | 0.3908764 | 0.322337 | 0.19461392 | AA247989_a t | K8033.seq.F Human fetal heart, Lambda ZAP Express Homo sapiens cDNA 5', mRNA sequence. (from Genbank) |
| 690 | Renal | 0.3430464 | 0.3905971 | 0.322333 | 0.19449466 | X68487_at | ADORA2B Adenosine A2b receptor |
| 691 | Renal | 0.3429397 | 0.3905893 | 0.322085 | 0.19445929 | M99063_at | KERATIN, TYPE II CYTOSKELETAL 2 ORAL |
| 692 | Renal | 0.3428729 | 0.3905438 | 0.322073 | 0.19432255 | J04621_at | SDC2 Syndecan 2 (heparan sulfate proteoglycan 1, cell surface-associated, fibroglycan) |
| 693 | Renal | 0.342853 | 0.3904676 | 0.321955 | 0.19418946 | X15525_rna 1_at | Lysosomal acid phosphatase gene (EC 3.1.3.2) Exon 1 (and joined CDS) |
| 694 | Renal | 0.3427598 | 0.3903585 | 0.321746 | 0.19417049 | HG2280-HT2376_at | D-Amino-Acid Oxidase |
| 695 | Renal | 0.3427282 | 0.3902644 | 0.321655 | 0.19412436 | Y07566_at | Rit mRNA |

FIG. 13B2

| # | Tissue | | | | | Description |
|---|---|---|---|---|---|---|
| 696 | Renal | 0.3425638 | 0.390189 | 0.321645 | 0.19407158 U88898_at | Endogenous retroviral H protease/integrase-derived ORF1 mRNA, and putative envelope protein mRNA, partial cds |
| 697 | Renal | 0.3425187 | 0.3900869 | 0.321632 | 0.19397607 X95876_at | G-protein coupled receptor |
| 698 | Renal | 0.3424706 | 0.3899632 | 0.321627 | 0.19389954 L40904_at-2 | Peroxisome proliferative activated receptor, gamma |
| 699 | Renal | 0.3424706 | 0.3898534 | 0.321566 | 0.19378711 L40904_at | LGALS1 Ubiquinol-cytochrome c reductase core protein II |
| 700 | Renal | 0.3423106 | 0.3898434 | 0.321459 | 0.19366889 S67156_at | ASPA Aspartoacylase (aminoacylase 2, Canavan disease) |
| 701 | Renal | 0.3417245 | 0.3898053 | 0.321422 | 0.19355892 D13634_at | KIAA0009 gene |
| 702 | Renal | 0.3416438 | 0.3897854 | 0.321419 | 0.19356117 L05568_at | SLC6A4 Solute carrier family 6 (neurotransmitter transporter, serotonin), member 4 |
| 703 | Renal | 0.3415645 | 0.3897193 | 0.321329 | 0.19342928 U45975_at | Phosphatidylinositol (4,5)bisphosphate 5-phosphatase homolog mRNA, partial cds |
| 704 | Renal | 0.341493 | 0.3896901 | 0.321254 | 0.19333288 U28049_at | TBX2 (TXB2) mRNA |
| 705 | Renal | 0.3414096 | 0.3896388 | 0.321122 | 0.19331224 Z34897_at | HRH1 Histamine receptor H1 |
| 706 | Renal | 0.3410736 | 0.3895244 | 0.32105 | 0.19311282 X96924_rna1_at | Gene encoding mitochondrial citrate transport protein |
| 707 | Renal | 0.3408606 | 0.3893557 | 0.321008 | 0.19301993 RC_AA410337_at | EST: zv16e01.s1 Soares NhHMPu S1 Homo sapiens cDNA clone 753816 3', mRNA sequence. (from Genbank) |
| 708 | Renal | 0.3408184 | 0.3892041 | 0.320894 | 0.19296043 M62783_at | NAGA N-acetylgalactosaminidase, alpha- |
| 709 | Renal | 0.3406851 | 0.3889227 | 0.320891 | 0.19285224 X63755_at | High-sulphur keratin |
| 710 | Renal | 0.3405662 | 0.3889072 | 0.320834 | 0.19272797 Y00477_at | Bone marrow serine protease gene (medullasin) (leukocyte neutrophil elastase gene) |
| 711 | Renal | 0.3405135 | 0.3887257 | 0.320752 | 0.192658331 AA292609_a_at | EST: zs57g01.r1 NCI_CGAP_GCB1 Homo sapiens cDNA clone IMAGE:701616 5' similar to contains L1.11 L1 repetitive element :; mRNA sequence. (from Genbank) |
| 712 | Renal | 0.3403084 | 0.3885924 | 0.320702 | 0.19255373 U94332_at | Osteoprotegerin (OPG) mRNA |
| 713 | Renal | 0.3401754 | 0.3884881 | 0.320585 | 0.19249742 X89211_at | DNA for endogenous retroviral like element |
| 714 | Renal | 0.3401473 | 0.3883623 | 0.320577 | 0.19236046 L41268_f_at | Nkal2b mRNA |
| 715 | Renal | 0.3396228 | 0.3882358 | 0.320564 | 0.19235238 M19888_at | 62 kDa paraneoplastic antigen mRNA, 3' end |
| 716 | Renal | 0.3394282 | 0.3882287 | 0.320545 | 0.192280351 M82967_s_at | Acrosomal vesicle protein 1 |
| 717 | Renal | 0.3394173 | 0.3882212 | 0.32052 | 0.19221435 J04982_at | ANT1 Adenine nucleotide translocator 1 (skeletal muscle) |
| 718 | Renal | 0.3392756 | 0.3881142 | 0.32047 | 0.19204263 U32376_at | Channel associated protein of synapse (chapsyn-110) mRNA |
| 719 | Renal | 0.3392274 | 0.3880983 | 0.32047 | 0.19199556 L02867_at | 62 kDa paraneoplastic antigen mRNA, 3' end |
| 720 | Renal | 0.3391443 | 0.387876 | 0.320259 | 0.19194852 U02310_at | FKHR Homolog 1 of Drosophila forkhead (rhabdomyosarcoma) |
| 721 | Renal | 0.3390824 | 0.3877849 | 0.320218 | 0.19181135 R74226_at | Homo sapiens mRNA for ATP synthase subunit e, complete cds |
| 722 | Renal | 0.3389169 | 0.3877172 | 0.320203 | 0.1917885 D37931_at | RNS4 Ribonuclease 4 (2',5'-oligoisoadenylate synthetase-dependent) |
| 723 | Renal | 0.3385291 | 0.3874441 | 0.320132 | 0.19169824 L22214_at | ADORA1 Adenosine receptor A1 |
| 724 | Renal | 0.3384832 | 0.3875274 | 0.320112 | 0.19161275 M90299_at | GCK Glucokinase (hexokinase 4, maturity onset diabetes of the young 2) |

FIG. 13C2

| | | | | | | |
|---|---|---|---|---|---|---|
| 725 | Renal | 0.3381861 | 0.387516 | 0.320109 | 0.19156706 | M31776_s_at | BRAIN NATRIURETIC PEPTIDE PRECURSOR |
| 726 | Renal | 0.3381411 | 0.387474 | 0.319641 | 0.19149089 | D50495_at | Transcription elongation factor S-II, hS-II-T1 |
| 727 | Renal | 0.3376066 | 0.3873493 | 0.319621 | 0.19142161 | X00540_at | PRL Prolactin |
| 728 | Renal | 0.3375934 | 0.3872063 | 0.319383 | 0.1913378 | D30036_at | PHOSPHATIDYLINOSITOL |
| 729 | Renal | 0.3374308 | 0.3871664 | 0.319278 | 0.19129066 | AA170806_a t | EST: ATH322 HTCDL1 Homo sapiens cDNA 5'/3', mRNA sequence. (from Genbank) |
| 730 | Renal | 0.3373368 | 0.3871574 | 0.319259 | 0.19126253 | M33987_at | CA1 Carbonic anhydrase I |
| 731 | Renal | 0.3370994 | 0.3871062 | 0.319255 | 0.19114996 | HG987-HT987_at | Mac25 |
| 732 | Renal | 0.3368902 | 0.3869556 | 0.319213 | 0.19104853 | Y10936_at | Hypothetical protein downstream of DMPK and DMAHP |
| 733 | Renal | 0.336607 | 0.3868908 | 0.319066 | 0.19091788 | M60828_at | FGF7 Fibroblast growth factor 7 (keratinocyte growth factor) |
| 734 | Renal | 0.3363716 | 0.3868537 | 0.31895 | 0.19084176 | AJ000099_s_at | Lysosomal hyaluronidase |
| 735 | Renal | 0.3363614 | 0.3868427 | 0.318748 | 0.19077009 | D87464_at | KIAA0274 gene |
| 736 | Renal | 0.3363575 | 0.3868076 | 0.318737 | 0.19065401 | U79275_at | Clone 23947 mRNA, partial cds |
| 737 | Renal | 0.3362269 | 0.3866982 | 0.318688 | 0.19051167 | D28532_at | Renal Na+-dependent phosphate cotransporter |
| 738 | Renal | 0.3362221 | 0.3866249 | 0.318597 | 0.19044842 | Z18954_at | S100A5 S100 calcium-binding protein A5 (formerly S100D) |
| 739 | Renal | 0.3361335 | 0.386557 | 0.318548 | 0.19039601 | W25869_at | EST: 14c3 Human retina cDNA randomly primed sublibrary Homo sapiens cDNA, mRNA sequence. (from Genbank) |
| 740 | Renal | 0.3359634 | 0.386476 | 0.318464 | 0.19033145 | M37190_at | Ras inhibitor mRNA, 3' end |
| 741 | Renal | 0.3357193 | 0.3864346 | 0.318395 | 0.19029394 | M13903_at | Involucrin gene, exon 2 |
| 742 | Renal | 0.3355545 | 0.3862293 | 0.318357 | 0.19005889 | X98311_at | Carcinoembryonic antigen family member 2, CGM2 |
| 743 | Renal | 0.3354717 | 0.3862266 | 0.318192 | 0.19000942 | M91217_at | EST: HUMRTPGEB Homo sapiens cDNA. (from Genbank) |
| 744 | Renal | 0.3353689 | 0.3861983 | 0.318034 | 0.18990159 | M21064_at | S100A9 S100 calcium-binding protein A9 (calgranulin B) |
| 745 | Renal | 0.3353222 | 0.3861059 | 0.317884 | 0.18987103 | RC_AA4179 15_at | EST: zv94a08.s1 Soares NhHMPu S1 Homo sapiens cDNA clone 767414 3', mRNA sequence. (from Genbank) |
| 746 | Renal | 0.3350031 | 0.3859556 | 0.317837 | 0.18973076 | M83186_at | COX7A1 Cytochrome c oxidase subunit VIIa polypeptide 1 (muscle) |
| 747 | Renal | 0.3351668 | 0.3858636 | 0.317822 | 0.18961442 | U03056_at | Hyaluronoglucosaminidase 1 (HYAL1) mRNA |
| 748 | Renal | 0.3350747 | 0.3858386 | 0.317774 | 0.1895815 | C16652_at | KIAA0575 gene product |
| 749 | Renal | 0.3348722 | 0.3857617 | 0.317663 | 0.18946299 | U21049_at | DD96 mRNA |
| 750 | Renal | 0.334522 | 0.3857487 | 0.317626 | 0.18937667 | L13278_at | CRYZ Crystallin zeta (quinone reductase) |
| 751 | Renal | 0.3344249 | 0.38567 | 0.317616 | 0.18932723 | D85939_at | P97 homologous protein |
| 752 | Renal | 0.3343292 | 0.3852831 | 0.317545 | 0.18931971 | S83513_s_at | ADCYAP1 Adenylate cyclase activating polypeptide 1 (pituitary) |
| 753 | Renal | 0.3338736 | 0.3852434 | 0.317515 | 0.18918636 | M15990_at | C-yes-1 mRNA |
| 754 | Renal | 0.333722 | 0.3851345 | 0.317512 | 0.18913867 | X52520_at | TAT Tyrosine aminotransferase |
| 755 | Renal | 0.3336839 | 0.3850431 | 0.317498 | 0.1890185 | M95549_at | SLC5A2 Solute carrier family 5 (sodium/glucose cotransporter), member 2 |

FIG. 13D2

| | | | | | | |
|---|---|---|---|---|---|---|
| 756 | Renal | 0.3335902 | 0.3850208 | 0.317466 | 0.18891267 | D38145_at | Prostacyclin synthase |
| 757 | Renal | 0.3334494 | 0.384498 | 0.317462 | 0.18880822 | X66894_s_a t | FACC Fanconi anemia complementation group C |
| 758 | Renal | 0.3333639 | 0.3848212 | 0.317398 | 0.1888451 | M74525_at | UBE2B Ubiquitin-conjugating enzyme E2B (RAD6 homolog) |
| 759 | Renal | 0.3333602 | 0.3847713 | 0.317358 | 0.18872614 | M55422_at | Krueppel-related zinc finger protein (H-plk) mRNA |
| 760 | Renal | 0.3333305 | 0.3846266 | 0.317264 | 0.18866096 | X91249_at | WHITE PROTEIN HOMOLOG |
| 761 | Renal | 0.3333274 | 0.3845261 | 0.317235 | 0.18854165 | W28252_at | EST: 44b5 Human retina cDNA randomly primed sublibrary Homo sapiens cDNA, mRNA sequence. (from Genbank) |
| 762 | Renal | 0.3332911 | 0.3845105 | 0.317066 | 0.18840943 | X17360_rna 1_at | HOX 5.1 gene for HOX 5.1 protein |
| 763 | Renal | 0.3329465 | 0.3842048 | 0.316985 | 0.18836315 | RC_AA0246 22_at | Solute carrier family 22 (organic cation transporter), member 5 |
| 764 | Renal | 0.3328454 | 0.3841692 | 0.316884 | 0.18835384 | HG4185-HT4455_at | Estrogen Sulfotransferase, Ste |
| 765 | Renal | 0.3327761 | 0.3841619 | 0.316813 | 0.18828923 | L43576_at | (clone EST02946) mRNA |
| 766 | Renal | 0.3326327 | 0.3840097 | 0.316785 | 0.18804356 | U13616_at | ANK3 Ankyrin G |
| 767 | Renal | 0.3324762 | 0.3839233 | 0.316779 | 0.1880141 | M13955_at | Mesothelial keratin K7 (type II) mRNA, 3' end |
| 768 | Renal | 0.3323973 | 0.3837909 | 0.316596 | 0.18791753 | Y13153_at | Kynurenine 3-monooxygenase |
| 769 | Renal | 0.332176 | 0.3837041 | 0.316586 | 0.18783362 | RC_AA2566 68_at | EST: zr82h02.s1 Soares NhHMPu S1 Homo sapiens cDNA clone 682227 3', mRNA sequence. (from Genbank) |
| 770 | Renal | 0.3316922 | 0.3835922 | 0.316562 | 0.1877799 | RC_AA1214 33_s_at | Axin |
| 771 | Renal | 0.3316832 | 0.3835675 | 0.316531 | 0.18770248 | U61276_s_a t | Transmembrane protein Jagged 1 (HJ1) mRNA |
| 772 | Renal | 0.3316751 | 0.3833942 | 0.316503 | 0.1876624 | X13930_f_at | CYTOCHROME P450 IIA6 |
| 773 | Renal | 0.3316169 | 0.3832688 | 0.316367 | 0.18760407 | Z11793_at | Selenoprotein P |
| 774 | Renal | 0.3315574 | 0.3830946 | 0.316266 | 0.18745396 | U08316_at | Insulin-stimulated protein kinase 1 (ISPK-1) mRNA |
| 775 | Renal | 0.3313074 | 0.3830572 | 0.316254 | 0.18742038 | U83461_at | Putative copper uptake protein (hCTR2) mRNA |
| 776 | Renal | 0.3310696 | 0.382894 | 0.316215 | 0.18730733 | D78367_at | K12 keratin |
| 777 | Renal | 0.3305893 | 0.382755 | 0.316039 | 0.18724056 | L20826_at | I-plastin mRNA |
| 778 | Renal | 0.3305432 | 0.3826832 | 0.315968 | 0.187147347 | RC_AA0457 75_at | EST: zk75f06.s1 Soares pregnant uterus NbHPU Homo sapiens cDNA clone 488675 3', mRNA sequence. (from Genbank) |
| 779 | Renal | 0.3302904 | 0.3826714 | 0.315744 | 0.18708047 | U05861_at | DDH1 Dihydrodiol dehydrogenase |
| 780 | Renal | 0.3302496 | 0.3825672 | 0.315628 | 0.18703298 | X74764_at | Receptor protein tyrosine kinase |
| 781 | Renal | 0.3301779 | 0.3825566 | 0.315586 | 0.18696555 | X87344_cds 10_r_at | DMA gene extracted from H.sapiens DMA, DMB, HLA-Z1, IPP2, LMP2, TAP1, LMP7, TAP2, DOB, DQB2 and RING6, 9, 13 and 14 genes |
| 782 | Renal | 0.3295049 | 0.3825398 | 0.315556 | 0.18686375 | R66239_at | EST: yi34d06.r1 Homo sapiens cDNA clone 141131 5'. (from Genbank) |
| 783 | Renal | 0.3293637 | 0.382411 | 0.315533 | 0.1867733 | X52332_at | Homo sapiens mRNA for zinc finger protein 10 |

FIG. 13E2

| | | | | | |
|---|---|---|---|---|---|
| 784 | Renal | 0.3292254 | 0.3822895 | 0.315511 | 0.18674085 | X74819_at | TNNT2 Troponin T2 (cardiac) |
| 785 | Renal | 0.3291726 | 0.3820478 | 0.315507 | 0.18666981 | U46570_at | Tetratricopeptide repeat protein (tpr1) mRNA |
| 786 | Renal | 0.3286105 | 0.3819696 | 0.315421 | 0.18658648 | M61176_at | BDNF Brain-derived neurotrophic factor |
| 787 | Renal | 0.3284702 | 0.381963 | 0.315366 | 0.186528 | D43638_at | ETO mRNA |
| 788 | Renal | 0.3283326 | 0.3817953 | 0.315296 | 0.186487591 | AA197134_a_t | EST: zq11b11.r1 Stratagene muscle 937209 Homo sapiens cDNA clone 629373 5', mRNA sequence. (from Genbank) |
| 789 | Renal | 0.3282912 | 0.381772 | 0.315254 | 0.186273781 | X85116_rna1_s_at | Epb72 gene exon 1 |
| 790 | Renal | 0.3279557 | 0.3815335 | 0.315159 | 0.186200646 | U66052_at | Clone W2-6 mRNA from chromosome X |
| 791 | Renal | 0.3278849 | 0.3815141 | 0.315046 | 0.18610956 | RC_AA4357 69_s_at | EST: zf79h07.s1 Soares testis NHT Homo sapiens cDNA clone 728605 3', mRNA sequence. (from Genbank) |
| 792 | Renal | 0.327816 | 0.3814159 | 0.314869 | 0.180051745 | RC_AA4541 59_at | EST: zx46f10.s1 Soares testis NHT Homo sapiens cDNA clone 795307 3', mRNA sequence. (from Genbank) |
| 793 | Renal | 0.3278085 | 0.3813825 | 0.314777 | 0.18598215 | X71135_at | Sox3 gene |
| 794 | Renal | 0.3277835 | 0.3812118 | 0.314749 | 0.185900507 | R29657_at | Eukaryotic translation elongation factor 1 delta (guanine nucleotide exchange protein) |
| 795 | Renal | 0.3276572 | 0.3811337 | 0.314742 | 0.18586591 | RC_AA0374 15_at | EST: zk33a09.s1 Soares pregnant uterus NbHPU Homo sapiens cDNA clone 484600 3', mRNA sequence. (from Genbank) |
| 796 | Renal | 0.3275357 | 0.381116 | 0.314681 | 0.18572412 | U62739_at | Branched-chain amino acid aminotransferase (ECA40) mRNA |
| 797 | Renal | 0.3273712 | 0.3810949 | 0.314591 | 0.18566713 | X78549_at | Brk mRNA for tyrosine kinase |
| 798 | Renal | 0.327243 | 0.3809758 | 0.314567 | 0.1855873 | X92518_s_a_t | HMGI-C |
| 799 | Renal | 0.3271439 | 0.3809617 | 0.314531 | 0.18547701 | X64994_at | HGMP071 gene for olfactory receptor |
| 800 | Renal | 0.3271374 | 0.3809617 | 0.314436 | 0.18544142 | D87683_at | KIAA0243 gene, partial cds |
| 801 | Renal | 0.3271317 | 0.3808968 | 0.314411 | 0.18537605 | D31889_at | KIAA0072 gene, partial cds |
| 802 | Renal | 0.326995 | 0.3808344 | 0.314322 | 0.18526094 | D87023_cds2_at | J1 gene extracted from Human (lambda) DNA for immunoglobin light chain |
| 803 | Renal | 0.3269932 | 0.380799 | 0.314248 | 0.18517825 | U79725_at | A33 antigen precursor mRNA |
| 804 | Renal | 0.3268255 | 0.3807083 | 0.31422 | 0.18509927 | U80226_s_a_t | Gamma-aminobutyric acid transaminase mRNA, partial cds |
| 805 | Renal | 0.3267257 | 0.3806604 | 0.314102 | 0.18504494 | U03494_at | Transcription factor LSF mRNA |
| 806 | Renal | 0.326581 | 0.3805684 | 0.31402 | 0.18494351 | L05779_at | EPHX2 Epoxide hydrolase 2, cytoplasmic |
| 807 | Renal | 0.3264266 | 0.3804789 | 0.313928 | 0.18486823 | D14874_at | ADM Adrenomedullin |
| 808 | Renal | 0.3261631 | 0.3804607 | 0.313858 | 0.1847823 | AA284709_a_t | Kallikrein 3, (prostate specific antigen) |
| 809 | Renal | 0.3261541 | 0.3804076 | 0.313803 | 0.18476222 | D83646_at | Metalloproteinase |
| 810 | Renal | 0.3261262 | 0.3803524 | 0.313803 | 0.18466152 | H50398_at | Human multidrug resistance-associated protein homolog (MRP5) mRNA, partial cds |
| 811 | Renal | 0.3260465 | 0.3800457 | 0.313797 | 0.18463066 | U66879_at | Bcl-2 binding component 6 (bbc6) mRNA |

FIG. 13F2

| | | | | | |
|---|---|---|---|---|---|
| 812 | Renal | 0.3258425 | 0.3800103 | 0.313731 | 0.18452291 | D83838_at | EST: similar to protein Nterminal asparagine amidohydrolase, mRNA sequence. (from Genbank) |
| 813 | Renal | 0.3254609 | 0.3799576 | 0.313718 | 0.18445426 | X05309_at | CR1 Complement component (3b/4b) receptor 1, including Knops blood group system |
| 814 | Renal | 0.3252286 | 0.3799559 | 0.313853 | 0.18436936 | D90042_at | AAC2 Arylamine N-acetyltransferase, liver |
| 815 | Renal | 0.3250527 | 0.3798692 | 0.313572 | 0.18427728 | RC_AA4251 28_at | EST: zw07e04.s1 Soares NhHMPu S1 Homo sapiens cDNA clone 768606 3', mRNA sequence. (from Genbank) |
| 816 | Renal | 0.3249222 | 0.3795579 | 0.313508 | 0.18423028 | RC_AA2588 19_s_at | EST: zs32f05.s1 NCI_CGAP_GCB1 Homo sapiens cDNA clone IMAGE:686913 3', mRNA sequence. (from Genbank) |
| 817 | Renal | | | | | U66059_cds 17_at | TCRBV1S1A1N1 gene extracted from Human germline T-cell receptor beta chain Dopamine-beta-hydroxylase-like, TRY1, TRY2, TRY3, TCRBV27S1P, TCRBV22S1A2N1T, TCRBV9S1A1T, TCRBV7S1A1N2T, TCRBV5S1A1T, TCRBV13S3, TCRBV6S7P, TCRBV7S3A2T, TCRBV13S2A1T, TCRBV9S2A2PT, TCRBV7S2A1N4T, TCRBV13S9/13S2A1T, TCRBV6S5A1N1, TCRBV30S1P, TCRBV31S1, TCRBV13S5, TCRBV6S1A1N1, TCRBV32S1P, TCRBV5S5P, TCRBV1S1A1N1, TCRBV12S2A1T, TCRBV21S1, TCRBV8S4P, TCRBV12S3, TCRBV21S3A2N2T, TCRBV8S5P, TCRBV13S1 genes from bases 1 to 267156 (section 1 of 3) |
| 817 | Renal | 0.3248884 | 0.379554 | 0.313481 | 0.18418561 | | |
| 818 | Renal | 0.3245713 | 0.379505 | 0.3133392 | 0.18405467 | M93107_at | D-BETA-HYDROXYBUTYRATE DEHYDROGENASE PRECURSOR |
| 819 | Renal | 0.3245355 | 0.3794232 | 0.313332 | 0.18399994 | RC_AA4002 92_at | EST: zu63i03.s1 Soares testis NHT Homo sapiens cDNA clone 742685 3', mRNA sequence. (from Genbank) |
| 820 | Renal | 0.3244972 | 0.3793763 | 0.313294 | 0.18394764 | U02082_at | Guanine nucleotide regulatory protein (tim1) mRNA |
| 821 | Renal | 0.324093 | 0.3792895 | 0.313181 | 0.18392056 | X98178_s_a t | MACH-beta-4 protein |
| 822 | Renal | 0.324023 | 0.3792115 | 0.31314 | 0.18386295 | AA129547_a t | EST: zn83f01.r1 Stratagene lung carcinoma 937218 Homo sapiens cDNA clone 564793 5', mRNA sequence. (from Genbank) |
| 823 | Renal | 0.3239605 | 0.3791415 | 0.313056 | 0.18378769 | HG721-HT4828_s_a t | Placental Protein 14, Endometrial Alpha 2 Globulin, Alt. Splice 3 |
| 824 | Renal | 0.3239071 | 0.3791073 | 0.312905 | 0.18371966 | U17418_at | PARATHYROID HORMONE/PARATHYROID HORMONE-RELATED PEPTIDE RECEPTOR PRECURSOR |
| 825 | Renal | 0.3238674 | 0.3791 | 0.312847 | 0.18365976 | U66048_at | Clone 161455 breast expressed mRNA from chromosome X |
| 826 | Renal | 0.3237765 | 0.3789435 | 0.312821 | 0.18360248 | RC_AA2347 65_at | Homo sapiens mRNA for KIAA0779 protein, partial cds |
| 827 | Renal | 0.3237325 | 0.3788541 | 0.312772 | 0.18353726 | M57506_rna 1_at | SCYA1 gene (secreted protein I-309) extracted from Human secreted protein (I-309) gene |

FIG. 13G2

| | | | | | |
|---|---|---|---|---|---|
| 828 | Renal | 0.3235096 | 0.3788064 | 0.31276 | 0.18346485 | S52028_s_at | CTH Cystathionase (cystathionine gamma-lyase) |
| 829 | Renal | 0.3234691 | 0.3787721 | 0.312727 | 0.18336569 | J04168_at | SPN Sialophorin (gpL115, leukosialin, CD43) |
| 830 | Renal | 0.3234051 | 0.3786811 | 0.312723 | 0.18331559 | U66559_at | NPM1 Nucleophosmin (nucleolar phosphoprotein B23, numatrin) |
| 831 | Renal | 0.3231022 | 0.3786236 | 0.312607 | 0.18322831 | M80482_at | PACE4 Paired basic amino acid cleaving system 4 |
| 832 | Renal | 0.3231017 | 0.3782547 | 0.31234 | 0.18317835 | RC_AA2438 42_at | EST: zr68a03.s1 Soares NhHMPu S1 Homo sapiens cDNA clone 668524 3', mRNA sequence. (from Genbank) |
| 833 | Renal | 0.3230941 | 0.3781152 | 0.312329 | 0.183041 | U68233_at | Farnesol receptor HRR-1 (HRR-1) mRNA |
| 834 | Renal | 0.323053 | 0.3779843 | 0.312322 | 0.18300988 | M16961_at | AHSG Alpha-2-HS-glycoprotein alpha and beta chain |
| 835 | Renal | 0.3230498 | 0.3778628 | 0.3123 | 0.18290968 | HG4234-HT4504_at | Methylenetetrahydrofolate Reductase |
| 836 | Renal | 0.3229353 | 0.3777469 | 0.312254 | 0.18280931 | X16665_at | HOXB2 Homeo box B2 |
| 837 | Renal | 0.3228123 | 0.3776012 | 0.312187 | 0.18267765 | RC_AA2522 09_at | EST: zr63g05.s1 Soares NhHMPu S1 Homo sapiens cDNA clone 668120 3', mRNA sequence. (from Genbank) |
| 838 | Renal | 0.3224518 | 0.3775809 | 0.311937 | 0.18263504 | Y10512_at | CD282 protein |
| 839 | Renal | 0.3223818 | 0.3775608 | 0.311927 | 0.18255305 | L27476_at | X104 mRNA |
| 840 | Renal | 0.3223707 | 0.3774489 | 0.311881 | 0.18250666 | U04325_cds 3_at | PSG11 gene (pregnancy-specific beta-1-glycoprotein 11 C-A domain) extracted from Human pregnancy-specific beta-1-glycoprotein alternatively spliced C-R, C-S, C-B, and C-A domains (PSG11) gene, partial cds |
| 841 | Renal | 0.3221953 | 0.3773829 | 0.311878 | 0.18247168 | L31573_at | Sulfite oxidase mRNA |
| 842 | Renal | 0.3220803 | 0.3773496 | 0.311782 | 0.18232067 | D79206_s_a t | SDC4 Syndecan 4 (amphiglycan, ryudocan) |
| 843 | Renal | 0.3220578 | 0.3772926 | 0.311689 | 0.18225133 | Z24680_at | Garp gene mRNA |
| 844 | Renal | 0.3220269 | 0.3771383 | 0.311517 | 0.18218234 | U82010_rna 1_at | Heme A: farnesyltransferase (COX10) gene promoter region and B12 protein mRNA |
| 845 | Renal | 0.3220007 | 0.3769856 | 0.311471 | 0.18209842 | M80783_at | OPRM1 Opioid receptor, mu 1 |
| 846 | Renal | 0.3219165 | 0.3768717 | 0.311434 | 0.18203145 | L25119_at | EDN1 Endothelin 1 (alternative products) |
| 847 | Renal | 0.3216748 | 0.3768414 | 0.31141 | 0.18196511 | J05008_at | KCNA4 Potassium voltage-gated channel, shaker-related subfamily, member 4 |
| 848 | Renal | 0.3216395 | 0.3768202 | 0.311403 | 0.18189396 | M60450_s_a t | SPTB Spectrin, beta, erythrocytic (includes sperocytosis, clinical type 1) |
| 849 | Renal | 0.3215899 | 0.3768117 | 0.311391 | 0.18177405 | J05500_at | GOT2 Glutamic-oxaloacetic transaminase 2, mitochondrial (aspartate aminotransferase 2) |
| 850 | Renal | 0.3215417 | 0.3767574 | 0.311389 | 0.18174458 | M22632_at | |
| 851 | Renal | 0.3215307 | 0.3767109 | 0.311351 | 0.18164527 | U90545_at | Human sodium phosphate transporter (NPT4) mRNA, complete cds |
| 852 | Renal | 0.321485 | 0.3767016 | 0.31127 | 0.18156762 | H42106_at | Integrin, alpha 6 |
| 853 | Renal | 0.32148 | 0.3765091 | 0.311136 | 0.18152207 | T39897_s_at | EST: ya13a11.r1 Homo sapiens cDNA clone 61340 5'. (from Genbank) |

FIG. 13H2

| | | | | | |
|---|---|---|---|---|---|
| 854 | Renal | 0.3213351 | 0.376478 | 0.311073 | 0.18145415 | U23430_s_a_t | CCKAR Cholecystokinin A receptor |
| 855 | Renal | 0.3207556 | 0.3764677 | 0.310871 | 0.18131775 | HG4272-HT4272_at | Hepatocyte Growth Factor Receptor |
| 856 | Renal | 0.3206912 | 0.3763979 | 0.310844 | 0.18121792 | U40279_at | Beta-2 integrin alphaD subunit (ITGAD) gene, exons 25-30, and partial cds |
| 857 | Renal | 0.3206495 | 0.3763746 | 0.310834 | 0.18118303 | D83542_at | Cadherin-15 |
| 858 | Renal | 0.3206473 | 0.376322 | 0.310725 | 0.18107681 | D42138_at | PIG-B |
| 859 | Renal | 0.3204515 | 0.3761867 | 0.310612 | 0.18101196 | M86934_at | GS1 PROTEIN |
| 860 | Renal | 0.3203024 | 0.37609 | 0.310594 | 0.1809933 | HG759-HT759_s_at | Adrenergic Receptor, Beta 1 |
| 861 | Renal | 0.3200921 | 0.3760622 | 0.310562 | 0.18090326 | U14391_at | Myosin-IC mRNA |
| 862 | Renal | 0.3197577 | 0.376054 | 0.310536 | 0.18078479 | X78342_at | (clone PK2J) CDC2-related protein kinase (PISSLRE) mRNA |
| 863 | Renal | 0.3195469 | 0.3760118 | 0.310392 | 0.18077844 | RC_AA485945_at | EST: ab40g02.s1 Stratagene HeLa cell s3 937216 Homo sapiens cDNA clone 843314 3' similar to SW:SOH1_YEAST P38633 SOH1 PROTEIN. [1];, mRNA sequence. (from Genbank) |
| 864 | Renal | 0.3195258 | 0.3759757 | 0.310318 | 0.1806422 | X65727_s_at | GSTalpha locus gene (glutathione S-transferase) extracted from H.sapiens GSTalpha gene for glutathione S-tranferase exon 2 |
| 865 | Renal | 0.319335 | 0.3757326 | 0.310294 | 0.18062116 | RC_AA446864_at | EST: zw90a07.s1 Soares total fetus Nb2HF8 9w Homo sapiens cDNA clone 784212 3', mRNA sequence. (from Genbank) |
| 866 | Renal | 0.3192502 | 0.3756543 | 0.310293 | 0.18054211 | U89942_at | Lysyl oxidase-related protein (WS9-14) mRNA |
| 867 | Renal | 0.3190333 | 0.3756371 | 0.31022 | 0.18050478 | D63813_at | Rod photoreceptor protein |
| 868 | Renal | 0.3187402 | 0.3755995 | 0.310181 | 0.18043761 | W67867_at | KIAA0685 gene product |
| 869 | Renal | 0.3187189 | 0.3755743 | 0.310084 | 0.18032438 | RC_AA455988_at | Butyrobetaine (gamma), 2-oxoglutarate dioxygenase (gamma-butyrobetaine hydroxylase) |
| 870 | Renal | 0.3186964 | 0.3755262 | 0.31005 | 0.18025285 | RC_AA018877_at | EST: ze58g08.s1 Soares retina N2b4HR Homo sapiens cDNA clone 363230 3', mRNA sequence. (from Genbank) |
| 871 | Renal | 0.3186063 | 0.3753666 | 0.310019 | 0.18025124 | RC_AA446204_at | EST: zw66d10.s1 Soares testis NHT Homo sapiens cDNA clone 781171 3', mRNA sequence. (from Genbank) |
| 872 | Renal | 0.3184134 | 0.3752924 | 0.309877 | 0.18014196 | U41635_at | OS-9 precurosor mRNA |
| 873 | Renal | 0.3181113 | 0.3751264 | 0.309848 | 0.18005013 | L47726_at | PAH Phenylalanine hydroxylase |
| 874 | Renal | 0.3180274 | 0.3750943 | 0.309787 | 0.17992719 | U47931_at | G-protein beta-3 subunit alternatively spliced form mRNA sequence |
| 875 | Renal | 0.3177788 | 0.3749907 | 0.309735 | 0.17982854 | HG4683-HT5108_s_a_t | Tumor Necrosis Factor Receptor 2 Associated Protein Trap3 |
| 876 | Renal | 0.317491 | 0.3749606 | 0.309705 | 0.17982295 | D28588_at | SP2 Sp2 transcription factor |
| 877 | Renal | 0.3174391 | 0.3749298 | 0.309616 | 0.17972697 | Z69923_at | HEPATOCYTE GROWTH FACTOR ACTIVATOR PRECURSOR |
| 878 | Renal | 0.3173252 | 0.3748428 | 0.309553 | 0.17972697 | D87467_at | KIAA0277 gene |

FIG. 131 2

| # | Tissue | | | | Accession | Description |
|---|---|---|---|---|---|---|
| 879 | Renal | 0.3172932 | 0.3746559 | 0.30948 | 0.17957157 | RC_AA0197 12_at | KIAA0735 gene product |
| 880 | Renal | 0.317229 | 0.3745456 | 0.309462 | 0.17953223 | X75593_at | Rab 13 |
| 881 | Renal | 0.3170421 | 0.3745335 | 0.309452 | 0.17948665 | Y08836_at | HRX-like protein |
| 882 | Renal | 0.3167754 | 0.3744883 | 0.3094 | 0.17935655 | S65583_rna1_at | SP-10=intra-acrosomal protein [alternatively spliced] [human, liver, Genomic, 2339 nt 4 segments] |
| 883 | Renal | 0.3167454 | 0.3744513 | 0.309376 | 0.17929961 | U19147_s_at | GAGE4 G antigen 6 (GAGE-6) |
| 884 | Renal | 0.3165341 | 0.3744192 | 0.309313 | 0.17923063 | U60269_cds2_at | Putative envelope protein; orf similar to env of Type A and Type B retroviruses and to class II HERVs gene extracted from Human endogenous retrovirus HERV-K(HML6) proviral clone HML6.17 putative polymerase and envelope genes, partial cds, and 3'LTR |
| 885 | Renal | 0.316432 | 0.3743021 | 0.309042 | 0.17915723 | AA496083_a_at | EST: zu67c08.r1 Soares testis NHT Homo sapiens cDNA clone 743054 5', mRNA sequence. (from Genbank) |
| 886 | Renal | 0.3163941 | 0.3742907 | 0.309029 | 0.1791224 | U20582_at | Actin-like peptide mRNA, partial cds |
| 887 | Renal | 0.3163636 | 0.3742464 | 0.309026 | 0.17904094 | AF004709_a_at | Protein kinase mitogen- activated 13 |
| 888 | Renal | 0.3160904 | 0.3742063 | 0.308991 | 0.17893082 | L43821_at | Enhancer of filamentation (HEF1) mRNA |
| 889 | Renal | 0.3157753 | 0.3740406 | 0.308974 | 0.1788627 | U73682_at | Meningioma-expressed antigen 6 (MEA6) mRNA |
| 890 | Renal | 0.3157056 | 0.3739548 | 0.308877 | 0.17881872 | U29700_at | Anti-mullerian hormone type II receptor precursor gene |
| 891 | Renal | 0.3156739 | 0.3739328 | 0.308862 | 0.17870833 | RC_AA0195 28_at | EST: ze55b02.s1 Soares retina N2b4HR Homo sapiens cDNA clone 362859 3', mRNA sequence. (from Genbank) |
| 892 | Renal | 0.3156673 | 0.3739106 | 0.308773 | 0.17860527 | M29550_at | SERINE/THREONINE PROTEIN PHOSPHATASE 2B CATALYTIC SUBUNIT, BETA ISOFORM |
| 893 | Renal | 0.3156299 | 0.3737858 | 0.30861 | 0.17856164 | L27479_at | X123 mRNA, 3' end |
| 894 | Renal | 0.3156226 | 0.3737568 | 0.308551 | 0.17851286 | D13305_at | CCKBR Cholecystokinin B receptor |
| 895 | Renal | 0.3155973 | 0.3737403 | 0.308387 | 0.17843656 | X15414_at | ALDR1 Aldehyde reductase 1 (low Km aldose reductase) |
| 896 | Renal | 0.3154658 | 0.3737167 | 0.308318 | 0.17839879 | Y10514_s_at | CD152 protein |
| 897 | Renal | 0.31527 | 0.3736674 | 0.308138 | 0.17832921 | RC_AA4781 09_at | EST: zt89d04.s1 Soares testis NHT Homo sapiens cDNA clone 729511 3', mRNA sequence. (from Genbank) |
| 898 | Renal | 0.3147596 | 0.3734426 | 0.308056 | 0.17826791 | RC_AA3986 17_at | EST: zt74c07.s1 Soares testis NHT Homo sapiens cDNA clone 728076 3', mRNA sequence. (from Genbank) |
| 899 | Renal | 0.3147498 | 0.3734426 | 0.308001 | 0.17817846 | RC_AA4213 28_at | EST: zu27d04.s1 Soares ovary tumor NbHOT Homo sapiens cDNA clone 739207 3', mRNA sequence. (from Genbank) |
| 900 | Renal | 0.3146823 | 0.3731026 | 0.307969 | 0.17811115 | S81243_s_at | Mitogen induced nuclear orphan receptor (MINOR) mRNA |
| 901 | Renal | 0.314565 | 0.3730821 | 0.307931 | 0.17804714 | X74295_at | ITGA7 Integrin, alpha 7B |
| 902 | Renal | 0.3145042 | 0.3728358 | 0.307893 | 0.17800939 | L07548_at | ACY1 Aminoacylase 1 |

FIG. 13J2

| | | | | | | |
|---|---|---|---|---|---|---|
| 903 | Renal | 0.3144387 | 0.3727079 | 0.30776 | 0.17796813 | AA486144_a t | EST: ab14c10.r1 Stratagene lung (#937210) Homo sapiens cDNA clone 840786 5', mRNA sequence. (from Genbank) |
| 904 | Renal | 0.3143961 | 0.3726792 | 0.307709 | 0.17787024 | U43408_at | Tyrosine kinase (Tnk1) mRNA |
| 905 | Renal | 0.3142912 | 0.37026561 | 0.307692 | 0.17775387 | D13644_at | 40S RIBOSOMAL PROTEIN S17 |
| 906 | Renal | 0.3141209 | 0.3724626 | 0.307577 | 0.17770758 | X06562_at | GHR Growth hormone receptor |
| 907 | Renal | 0.3138284 | 0.372343 | 0.307536 | 0.17767093 | M62397_at | MCC Mutated in colorectal cancers |
| 908 | Renal | 0.3137688 | 0.3722902 | 0.307505 | 0.1776357 | M19989_cds 1_at | Platelet-derived growth factor (PDGFA) A chain gene |
| 909 | Renal | 0.3137447 | 0.3722901 | 0.307468 | 0.17746572 | X81889_at | P0071 protein |
| 910 | Renal | 0.3136922 | 0.3722629 | 0.307432 | 0.17741957 | X00129_at | PLASMA RETINOL-BINDING PROTEIN PRECURSOR |
| 911 | Renal | 0.3135428 | 0.3721944 | 0.307384 | 0.17737001 | HG3105-HT3281_s_a t | Atpase, Cu2+ Transporting |
| 912 | Renal | 0.3134645 | 0.3721453 | 0.307282 | 0.1773265 | HG2810-HT2921_at | Homeotic Protein Pl2 |
| 913 | Renal | 0.3131843 | 0.3720278 | 0.307193 | 0.17725606 | D13705_s_a t | Fatty acids omega-hydroxylase (cytochrome P-450HKV) |
| 914 | Renal | 0.3131683 | 0.3719966 | 0.307193 | 0.17715439 | D13720_s_a t | TYROSINE-PROTEIN KINASE ITK/TSK |
| 915 | Renal | 0.3129149 | 0.3719544 | 0.307193 | 0.1771518 | AF010126_a t | Synuclein, gamma (breast cancer-specific protein 1) |
| 916 | Renal | 0.3128205 | 0.3718598 | 0.307105 | 0.17706026 | U33203_s_a t | Mdm2-E (mdm2) mRNA |
| 917 | Renal | 0.3126757 | 0.3716984 | 0.307095 | 0.17701097 | U82321_at | Clone 14.9B mRNA sequence |
| 918 | Renal | 0.3124899 | -0.3716931 | 0.307017 | 0.17700393 | D13435_at | PIGF Phosphatidylinositol glycan, class F |
| 919 | Renal | 0.3123357 | 0.3716208 | 0.307014 | 0.17689146 | M29581_at | ZNF8 Zinc finger protein 8 (clone HF.18) |
| 920 | Renal | 0.3120605 | 0.3715673 | 0.306986 | 0.17685159 | AB002382_a t | KIAA0384 gene |
| 921 | Renal | 0.3116437 | 0.3715609 | 0.306944 | 0.17681238 | U17894_at | Alpha(1,2)fucosyltransferase |
| 922 | Renal | 0.3116399 | 0.3714059 | 0.306935 | 0.17667205 | U12775_at | AGOUTI SWITCH PROTEIN PRECURSOR |
| 923 | Renal | 0.3116071 | 0.3713586 | 0.306906 | 0.17661725 | M83181_at | Serotonin receptor gene |
| 924 | Renal | 0.311444 | 0.3712415 | 0.306854 | 0.1765033 | L11066_at | MITOCHONDRIAL STRESS-70 PROTEIN PRECURSOR |
| 925 | Renal | 0.3111227 | 0.3712336 | 0.306793 | 0.17647257 | Y13896_at | Skeletal muscle alternate 5'end of gene Kir4.2 5'UTR |
| 926 | Renal | 0.3110628 | 0.3709673 | 0.306776 | 0.17641173 | HG4099-HT4369_s_a t | Adrenergic Receptor, Alpha 1b |
| 927 | Renal | 0.3109215 | 0.3708851 | 0.306665 | 0.17631018 | D26067_at | KIAA0033 gene, partial cds |
| 928 | Renal | 0.3107315 | 0.3708629 | 0.30662 | 0.1762679 | D25278_at-2 | KIAA0036 gene product |
| 929 | Renal | 0.3107315 | 0.3708255 | 0.306515 | 0.17618574 | D25278_at | KIAA0036 gene |

FIG. 13K2

| | | | | | | |
|---|---|---|---|---|---|---|
| 930 | Renal | 0.3105735 | 0.3707206 | 0.306423 | 0.17611796 | M29194_at | LIPC Lipase, hepatic |
| 931 | Renal | 0.3105734 | 0.3707047 | 0.306356 | 0.17603756 | M68840_at | MAOA Monoamine oxidase A |
| 932 | Renal | 0.3105623 | 0.3706407 | 0.306172 | 0.17597857 | RC_AA0051 35_at | EST: zh95e02.s1 Soares fetal liver spleen 1NFLS S1 Homo sapiens cDNA clone 429050 3' similar to contains MER10.t3 MER10 repetitive element:, mRNA sequence. (from Genbank) |
| 933 | Renal | 0.3104093 | 0.3705502 | 0.306064 | 0.17592363 | HG908-HT908_at | Mg61 Protein (Gb:L08239) |
| 934 | Renal | 0.3103851 | 0.3704681 | 0.306034 | 0.17580864 | L44140_cds 4_s_at | DNL1L gene extracted from Homo sapiens chromosome X region from filamin (FLN) gene to glucose-6-phosphate dehydrogenase (G6PD) gene's |
| 935 | Renal | 0.3103216 | 0.3704635 | 0.305884 | 0.17577613 | L28957_at | CHOLINEPHOSPHATE CYTIDYLYLTRANSFERASE |
| 936 | Renal | 0.3101899 | 0.3704542 | 0.30585 | 0.17563617 | U54617_at | PDK4 Pyruvate dehydrogenase kinase, isoenzyme 4 |
| 937 | Renal | 0.3101041 | 0.3702519 | 0.305746 | 0.17555682 | M14764_at | NGFR Nerve growth factor receptor |
| 938 | Renal | 0.3098607 | 0.3701085 | 0.305717 | 0.17551242 | HG34b35-HT4940_s_a t | Dematin |
| 939 | Renal | 0.3098414 | 0.3700652 | 0.305888 | 0.1754223 | X07876_at | WNT2 Wingless-type MMTV integration site 2, human homolog |
| 940 | Renal | 0.3095872 | 0.3700644 | 0.305665 | 0.17539027 | X69111_at | ID3 Inhibitor of DNA binding 3, dominant negative helix-loop-helix protein |
| 941 | Renal | 0.3093972 | 0.3700363 | 0.305595 | 0.17534581 | W25607_at | EST: zc64c06.r1 Soares fetal heart NbHH19W Homo sapiens cDNA clone 327082 5', mRNA sequence. (from Genbank) |
| 942 | Renal | 0.3093758 | 0.3700361 | 0.305508 | 0.1753104 | R81217_at | Yj03b09.r1 Homo sapiens cDNA clone 147641 5' similar to gb:X54156_rna1 CELLULAR TUMOR ANTIGEN P53 (HUMAN);contains Alu repetitive element:. (from Genbank) |
| 943 | Renal | 0.3091755 | 0.3699523 | 0.30549 | 0.17527272 | W27857_at | EST: 39e2 Human retina cDNA randomly primed sublibrary Homo sapiens cDNA, mRNA sequence. (from Genbank) |
| 944 | Renal | 0.3090769 | 0.3698397 | 0.305422 | 0.17520563 | RC_AA2438 75_at | EST: zr65f01.s1 Soares NhHMPu S1 Homo sapiens cDNA clone 668281 3', mRNA sequence. (from Genbank) |
| 945 | Renal | 0.3089404 | 0.369783 | 0.305378 | 0.17514792 | U75968_at | CHL1 protein |
| 946 | Renal | 0.3088788 | 0.3696925 | 0.305351 | 0.17510456 | X55005_rna 1_at | C-erbA-1 mRNA for thyroid hormone receptor alpha |
| 947 | Renal | 0.3087453 | 0.3696863 | 0.305342 | 0.17500173 | M10051_s_a t | INSR Insulin receptor |
| 948 | Renal | 0.3086598 | 0.3695467 | 0.305278 | 0.17494278 | L37036_s_at | NEUTROPHIL ACTIVATING PROTEIN ENA-78 PRECURSOR |
| 949 | Renal | 0.3085495 | 0.3694697 | 0.305209 | 0.17480225 | U40990_at | Putative voltage-gated potassium channel (KVLQT1) mRNA, partial cds |
| 950 | Renal | 0.3085351 | 0.3693803 | 0.30509 | 0.17485693 | U03851_at | Capping protein alpha mRNA, partial cds |
| 951 | Renal | 0.3084908 | 0.3693143 | 0.304915 | 0.17478639 | RC_AA4195 47_at | EST: zv04a05.s1 Soares NhHMPu S1 Homo sapiens cDNA clone 752624 3', mRNA sequence. (from Genbank) |

FIG. 13L2

| | | | | | |
|---|---|---|---|---|---|
| 952 | Renal | 0.3082287 | 0.3692446 | 0.304905 | 0.17471132 | M21494_at | CKM Creatine kinase, muscle |
| 953 | Renal | 0.307682 | 0.3691434 | 0.304856 | 0.1746515 | L77563_at | DGS-F partial mRNA |
| 954 | Renal | 0.3076601 | 0.3691195 | 0.304651 | 0.17457531 | AA481218_a t | EST: aa34e09.r1 NCI_CGAP_GCB1 Homo sapiens cDNA clone IMAGE:815176 5', mRNA sequence. (from Genbank) |
| 955 | Renal | 0.3076124 | 0.3690145 | 0.304627 | 0.17452455 | U15782_at | CSTF3 Cleavage stimulation factor, 3' pre-RNA, subunit 3, 77kD |
| 956 | Renal | 0.3072781 | 0.3690038 | 0.304543 | 0.17444416 | RC_AA2338 99_at | EST: zr49c02.s1 Soares NhHMPu S1 Homo sapiens cDNA clone 666722 3' similar to TR:G469478 G469478 SM-20. ; mRNA sequence. (from Genbank) |
| 957 | Renal | 0.3071813 | 0.368816 | 0.304388 | 0.17440307 | U47054_at | Putative mono-ADP-ribosyltransferase (htMART) mRNA |
| 958 | Renal | 0.3068606 | 0.3687052 | 0.304354 | 0.17432237 | X58288_at | PTPRM Protein tyrosine phosphatase, receptor type, mu polypeptide |
| 959 | Renal | 0.3066514 | 0.3686282 | 0.304293 | 0.17432237 | U27699_at | SODIUM- AND CHLORIDE-DEPENDENT BETAINE TRANSPORTER |
| 960 | Renal | 0.3065192 | 0.3684268 | 0.304155 | 0.1742837 | M14777_s_a t | Glutathione S-transferase A2 |
| 961 | Renal | 0.306422 | 0.3683979 | 0.304003 | 0.17423628 | D29963_at | Platelet-endothelial tetraspan antigen 3 mRNA |
| 962 | Renal | 0.3063225 | 0.3683672 | 0.303971 | 0.17409466 | U64573_s_a t | Connexin43 gap junction protein (connexin43) gene, exon 1 and promoter region |
| 963 | Renal | 0.3062556 | 0.3681825 | 0.303945 | 0.1740359 | H30778_at | EST: yo79e01.r1 Homo sapiens cDNA clone 184152 5'. (from Genbank) |
| 964 | Renal | 0.3058928 | 0.3680337 | 0.303914 | 0.17400722 | D25539_at | KIAA0040 gene |
| 965 | Renal | 0.3058895 | 0.3680263 | 0.303869 | 0.17388469 | L34820_at | NAD+-dependent succinate-semialdehyde dehydrogenase (SSADH) mRNA, 3' end |
| 966 | Renal | 0.3058102 | 0.3679665 | 0.303842 | 0.17375073 | HG2442-HT2538_at | Tropomyosin, Alpha, Muscle, Alt. Splice 2, Skeletal Muscle (Fibroblast) |
| 967 | Renal | 0.3057534 | 0.3677768 | 0.303838 | 0.17372268 | U31986_at | Cartilage-specific homeodomain protein Cart-1 mRNA |
| 968 | Renal | 0.3056674 | 0.3677692 | 0.303777 | 0.17363551 | X91196_s_a t | E14 and A-T proteins |
| 969 | Renal | 0.3056506 | 0.367559 | 0.303699 | 0.17353642 | X13967_at | LIF Leukemia inhibitory factor (cholinergic differentiation factor) |
| 970 | Renal | 0.3056201 | 0.3675534 | 0.30344 | 0.17350143 | D90084_at | PDHA1 Pyruvate dehydrogenase (lipoamide) alpha 1 |
| 971 | Renal | 0.3055057 | 0.3674869 | 0.303412 | 0.17344938 | X66417_at | KAPPA CASEIN PRECURSOR |
| 972 | Renal | 0.3052165 | 0.3674226 | 0.303397 | 0.17336708 | U17714_at | Putative tumor suppressor (SNC6) mRNA |
| 973 | Renal | 0.3051603 | 0.3673614 | 0.303223 | 0.17330551 | M35198_at | Integrin B-6 mRNA |
| 974 | Renal | 0.3050692 | 0.3672248 | 0.303078 | 0.17319436 | RC_AA3581 47_at | EST: EST66987 Fetal lung III Homo sapiens cDNA 3' end, mRNA sequence. (from Genbank) |
| 975 | Renal | 0.3050264 | 0.3672186 | 0.303039 | 0.17315984 | D13969_at | DNA-BINDING PROTEIN MEL-18 |
| 976 | Renal | 0.3049942 | 0.3671365 | 0.302964 | 0.17313407 | X79439_at | Notch 3 DNA sequence |
| 977 | Renal | 0.3049178 | 0.3669319 | 0.302936 | 0.17330334 | M25629_at | Kallikrein mRNA, clone phKK25 |
| 978 | Renal | 0.3049066 | 0.366839 | 0.302917 | 0.17294593 | J04809_rna1 _at | Cytosolic adenylate kinase (AK1) gene |

FIG. 13M2

| # | Tissue | | | | | Description |
|---|---|---|---|---|---|---|
| 979 | Renal | 0.3046137 | 0.3667952 | 0.302917 | 0.17289947 HG4668-HT5083_s_a_t | Transcription Factor Mef2, Alt. Splice 2 |
| 980 | Renal | 0.304464 | 0.3667437 | 0.302887 | 0.17287736 U84388_at | Death domain containing protein CRADD mRNA |
| 981 | Renal | 0.3043042 | 0.3664827 | 0.302865 | 0.17278095 U61263_at | Acetolactate synthase homolog mRNA |
| 982 | Renal | 0.3042852 | 0.3664717 | 0.302772 | 0.17272903 M65131_rna1_at | Methylmalonyl-CoA mutase (MCM) mRNA |
| 983 | Renal | 0.3042667 | 0.3663333 | 0.302751 | 0.17265637 X77909_at | IKBL mRNA |
| 984 | Renal | 0.3041199 | 0.3662105 | 0.302667 | 0.17256646 M85247_at | Dopamine D1A receptor gene, complete exon 1, and exon 2, 5' end |
| 985 | Renal | 0.3041064 | 0.3662094 | 0.302625 | 0.17252102 U89336_cds7_at | Unknown gene extracted from Human HLA class III region containing NOTCH4 gene, partial sequence, homeobox PBX2 (HPBX) gene, receptor for advanced glycosylation end products (RAGE) gene, and 6 unidentified cds, complete sequence |
| 986 | Renal | 0.3037222 | 0.3660864 | 0.302574 | 0.17247929 U37251_at | ZNF177 KRAB zinc finger protein (alternative products) |
| 987 | Renal | 0.303679 | 0.3660156 | 0.302574 | 0.17238969 X63578_rna1_at | Parvalbumin |
| 988 | Renal | 0.303647 | 0.3659922 | 0.302536 | 0.17231564 Z50053_at | GUC1A2 Guanylate cyclase 1, soluble, alpha 2 |
| 989 | Renal | 0.3035386 | 0.3658622 | 0.302376 | 0.17225973 U51704_at | EST: Human mRNA sequence containing Alu repetitive elements. (from Genbank) |
| 990 | Renal | 0.3033458 | 0.3657061 | 0.302317 | 0.17224173 U70321_at | Herpesvirus entry mediator mRNA |
| 991 | Renal | 0.3032986 | 0.3656631 | 0.302309 | 0.17213383 L19401_at | MYO5A Myosin VA (heavy polypeptide 12, myoxin) |
| 992 | Renal | 0.3030077 | 0.3655565 | 0.302209 | 0.1721126 U43292_at | MDS1B (MDS1) mRNA |
| 993 | Renal | 0.3030002 | 0.3654885 | 0.302098 | 0.17206554 M20747_s_a_t | SLC2A4 Solute carrier family 2 (facilitated glucose transporter), member 4 |
| 994 | Renal | 0.3029182 | 0.3654729 | 0.301988 | 0.17202441 U13044_at | GABPA GA-binding protein transcription factor, alpha subunit (60kD) |
| 995 | Renal | 0.3029045 | 0.3654238 | 0.301944 | 0.17192478 X00237_at | F variable segment 5' to antithrombin III gene (AT III) |
| 996 | Renal | 0.3028929 | 0.3653984 | 0.301922 | 0.17177361 W28229_at | EST: 43h11 Human retina cDNA randomly primed sublibrary Homo sapiens cDNA, mRNA sequence. (from Genbank) |
| 997 | Renal | 0.3026291 | 0.3653928 | 0.301869 | 0.1717327 M63379_at | CLU Clusterin (complement lysis inhibitor; testosterone-repressed prostate message 2; apolipoprotein J) |
| 998 | Renal | 0.3025326 | 0.3653437 | 0.301818 | 0.17169896 U19557_s_a_t | Squamous cell carcinoma antigen 2 (SCCA2) mRNA |
| 999 | Renal | 0.3019649 | 0.3653304 | 0.301776 | 0.17163287 M28882_s_a_t | CELL SURFACE GLYCOPROTEIN MUC18 PRECURSOR |
| 1000 | Renal | 0.3019368 | 0.3653186 | 0.301723 | 0.17160499 X12492_at | CCAAT BOX-BINDING TRANSCRIPTION FACTOR 1 |

FIG. 13N2

| Uterus_A | 0.0014274 | 0.7546642 | 0.655026 | 0.4906163 | X07438_s_a | DNA for cellular retinol binding protein (CRBP) exons 3 and 4 |
|---|---|---|---|---|---|---|
| 1 dena | | | | | | |

FIG. 14A

| | | | | | |
|---|---|---|---|---|---|
| Uterus_A 2 deno | 0.7885609 | 0.7049133 | 0.609112 | 0.45793012 | X63187_at | HE4 mRNA for extracellular proteinase inhibitor homologue |
| Uterus_A 3 deno | 0.7596874 | 0.6836953 | 0.58733 | 0.4409759 | U19718_at | MFAP2 Microfibrillar-associated protein 2 |
| Uterus_A 4 deno | 0.7034049 | 0.6724176 | 0.569706 | 0.4280845 | HG2815-HT4023_s_a t | Myosin, Light Chain, Alkali, Smooth Muscle (Gb:U02629), Smooth Muscle, Alt. Splice 4 |
| Uterus_A 5 deno | 0.7029994 | 0.6652874 | 0.557462 | 0.41891643 | U71207_at | Eyes absent homolog (Eab1) mRNA |
| Uterus_A 6 deno | 0.6847081 | 0.6558477 | 0.548483 | 0.41156512 | RC_AA1258 08_at | EST: zl29e12.s1 Soares pregnant uterus NbHPU Homo sapiens cDNA clone 503374 3', mRNA sequence. (from Genbank) |
| Uterus_A 7 deno | 0.6783209 | 0.6473196 | 0.544136 | 0.40528116 | X03635_at | ESR Estrogen receptor |
| Uterus_A 8 deno | 0.6780892 | 0.6394708 | 0.537258 | 0.39963865 | M97676_at-2 | Msh (Drosophila) homeo box homolog 1 (formerly homeo box 7) |
| Uterus_A 9 deno | 0.6780892 | 0.63345 | 0.532624 | 0.3945808 | M97676_at | MSX1 Msh (Drosophila) homeo box homolog 1 (formerly homeo box 7) |
| Uterus_A 10 deno | 0.6749753 | 0.629061 | 0.527834 | 0.3909843 | HG4058-HT4328_at | Oncogene Aml1-Evi-1, Fusion Activated |
| Uterus_A 11 deno | 0.63556329 | 0.6277121 | 0.52485 | 0.38738698 | X98833_ma 1_at | Zinc finger protein, Hsal1 |
| Uterus_A 12 deno | 0.6193135 | 0.622245 | 0.521983 | 0.38387653 | X65724_at | NDP Norrie disease (pseudoglioma) protein |
| Uterus_A 13 deno | 0.6115471 | 0.6184411 | 0.517686 | 0.3806994 | AF005037_a t | Secretory carrier membrane protein (SCAMP1) mRNA |
| Uterus_A 14 deno | 0.6094357 | 0.6157311 | 0.514617 | 0.37791827 | U22398_at | Cdk-inhibitor p57KIP2 (KIP2) mRNA |
| Uterus_A 15 deno | 0.6075793 | 0.611495 | 0.512569 | 0.37525558 | U84487_at | CX3C chemokine precursor, mRNA, alternatively spliced |
| Uterus_A 16 deno | 0.6031231 | 0.6084949 | 0.508376 | 0.37256134 | X13839_at | LCAT Lecithin-cholesterol acyltransferase |
| Uterus_A 17 deno | 0.5878692 | 0.6043285 | 0.505912 | 0.3704882 | M29277_at | CELL SURFACE GLYCOPROTEIN MUC18 PRECURSOR |
| Uterus_A 18 deno | 0.5859218 | 0.6012666 | 0.50366 | 0.36809826 | D11151_at | EDNRA Endothelin receptor type A |
| Uterus_A 19 deno | 0.5841683 | 0.5993426 | 0.50194 | 0.36599654 | X03794_s_a t | HOXB5 Homeo box B5 (2.1 protein) |
| Uterus_A 20 deno | 0.5811234 | 0.5960222 | 0.499428 | 0.3636629 | U40271_s_a t | PTK7 Protein-tyrosine kinase 7 |

FIG. 14B

| | | | | | |
|---|---|---|---|---|---|
| 21 | Uterus_A deno | 0.5789183 | 0.5938608 | 0.497127 | RC_AA4769 | EST: zu38e07.s1 Soares ovary tumor NbHOT Homo sapiens cDNA clone 740292 3', mRNA sequence. (from Genbank) |
| 22 | Uterus_A deno | 0.578205 | 0.5909106 | 0.495523 | 0.36174938 M61906_at 44_at | PHOSPHATIDYLINOSITOL 3-KINASE REGULATORY ALPHA SUBUNIT |
| 23 | Uterus_A deno | 0.5779814 | 0.5893356 | 0.493304 | 0.35991812 AB001106_a M61906_at | GLIA MATURATION FACTOR BETA |
| 24 | Uterus_A deno | 0.5712714 | 0.5896418 | 0.490796 | 0.3580341 t | |
| | | | | | 0.3560466 M37721_at | PAM Peptidylglycine alpha-amidating monooxygenase |
| 25 | Uterus_A deno | 0.5687109 | 0.5881904 | 0.489792 | 0.3543079 M11433_at | RBP1 Cellular retinol-binding protein |
| 26 | Uterus_A deno | 0.5675042 | 0.5866073 | 0.487726 | 0.3526019 L06419_at | PLOD Lysyl hydroxylase |
| 27 | Uterus_A deno | 0.5631672 | 0.5845363 | 0.485729 | 0.3512763 X06614_at | Receptor of retinoic acid |
| 28 | Uterus_A deno | 0.5605159 | 0.5819351 | 0.482978 | 0.34989554 U09210_at | SLC18A3 Solute carrier family 18 (vesicular acetylcholine), member 3 |
| 29 | Uterus_A deno | 0.5587613 | 0.5801027 | 0.481242 | 0.34846714 X57766_at | PSG11 Pregnancy-specific beta-1 glycoprotein 11 |
| 30 | Uterus_A deno | 0.5441624 | 0.5795479 | 0.480028 | 0.34698954 X66945_at | FGFR1 Basic fibroblast growth factor (bFGF) receptor (shorter form) |
| 31 | Uterus_A deno | 0.5411475 | 0.5774937 | 0.479182 | 0.34542534 RC_AA1490 51_at | EST: zl46b12.s1 Soares pregnant uterus NbHPU Homo sapiens cDNA clone 504959 3', mRNA sequence. (from Genbank) |
| 32 | Uterus_A deno | 0.5400556 | 0.5752281 | 0.476929 | 0.3443040 M24122_s_a 8 t | MYL3 Myosin, light polypeptide 3, alkali; ventricular, skeletal, slow |
| 33 | Uterus_A deno | 0.538155 | 0.5726066 | 0.476167 | 0.34289116 X04445_rna 1_s_at | InhA gene exon 1 (and joined CDS) |
| 34 | Uterus_A deno | 0.5368542 | 0.57172212 | 0.475155 | 0.34153652 X57351_s_a t | RPS3 Ribosomal protein S3 |
| 35 | Uterus_A deno | 0.5336916 | 0.57011175 | 0.473583 | 0.3404064 57_at U89336_cds | Unknown gene extracted from Human HLA class III region containing NOTCH4 gene, partial sequence, homeobox PBX2 (HPBX) gene, receptor for advanced glycosylation end products (RAGE) gene, and 6 unidentified cds, complete sequence |
| 36 | Uterus_A deno | 0.5327082 | 0.5698232 | 0.47246 | 0.3393251 U65011_at | Preferentially expressed antigen of melanoma (PRAME) mRNA |
| 37 | Uterus_A deno | 0.5303065 | 0.5678923 | 0.471609 | 0.33834442 X95876_at | G-protein coupled receptor |
| 38 | Uterus_A deno | 0.5295582 | 0.5676312 | 0.470674 | 0.3373514 D43772_at | Squamous cell carcinoma of esophagus mRNA for GRB-7 SH2 domain protein |
| 39 | Uterus_A deno | 0.52907 | 0.5675115 | 0.469849 | 0.33613598 D26561_cds 2_at | ORF for E6 protein gene extracted from Human papillomavirus 5b genome integrated into human carcinoma DNA |

FIG. 14C

| | | | | | |
|---|---|---|---|---|---|
| 40 | Uterus_A_deno | 0.5288413 | 0.5658332 | 0.468863 | 0.335508745 | X54162_at | 64 KD AUTOANTIGEN D1 |
| 41 | Uterus_A_deno | 0.5254902 | 0.5642106 | 0.467448 | 0.333385533 | M63573_at | PPIB Peptidylprolyl isomerase B (cyclophilin B) |
| 42 | Uterus_A_deno | 0.5233572 | 0.563261 | 0.466132 | 0.33302793 | M20471_at | CLTA Clathrin light chain A |
| 43 | Uterus_A_deno | 0.5213624 | 0.5627187 | 0.465505 | 0.3319243 | HG2191-HT2261_at | Crystallin, Beta B3 (Gb:X15145) |
| 44 | Uterus_A_deno | 0.5190398 | 0.5617952 | 0.463813 | 0.3309392 | U90911_at | Clone 23652 mRNA sequence |
| 45 | Uterus_A_deno | 0.5183912 | 0.561232 | 0.462951 | 0.330004755 | L40379_at | Thyroid receptor interactor (TRIP10) mRNA, 3' end of cds |
| 46 | Uterus_A_deno | 0.5167332 | 0.5601378 | 0.462157 | 0.3290352 | M33680_at | 26-kDa cell surface protein TAPA-1 mRNA |
| 47 | Uterus_A_deno | 0.5161371 | 0.5597534 | 0.46165 | 0.32830036 | AB000896_a_t | Cadherin FIB2, partial cds |
| 48 | Uterus_A_deno | 0.5144812 | 0.5590842 | 0.460608 | 0.327519185 | RC_AA164851_at | EST: zp02c11.s1 Stratagene ovarian cancer (#937219) Homo sapiens cDNA clone 595220 3', mRNA sequence. (from Genbank) |
| 49 | Uterus_A_deno | 0.5115326 | 0.5586259 | 0.460226 | 0.32664737 | AB000409_a_t | MNK1 |
| 50 | Uterus_A_deno | 0.5110719 | 0.5560495 | 0.459052 | 0.325575965 | U07151_at | GTP binding protein (ARL3) mRNA |
| 51 | Uterus_A_deno | 0.5097631 | 0.5544351 | 0.458455 | 0.3249864 | J05582_s_at | MUC1 Mucin 1, transmembrane |
| 52 | Uterus_A_deno | 0.5078386 | 0.5519333 | 0.457472 | 0.32428867 | M83751_at | Arginine-rich protein (ARP) gene |
| 53 | Uterus_A_deno | 0.5034767 | 0.5498878 | 0.456676 | 0.323348847 | M86752_at | TRANSFORMATION-SENSITIVE PROTEIN IEF SSP 3521 |
| 54 | Uterus_A_deno | 0.5019161 | 0.5495588 | 0.456124 | 0.3226035 | M76732_s_a_t | HOX7 gene, exon 2 and complete cds |
| 55 | Uterus_A_deno | 0.5011715 | 0.5494118 | 0.455008 | 0.32190213 | Z48570_at | Sp17 gene |
| 56 | Uterus_A_deno | 0.5010443 | 0.548682 | 0.45441 | 0.32108003 | RC_AA284879_at | Homo sapiens incomplete cDNA for a mutated allele of a myosin class I, myh-1c |
| 57 | Uterus_A_deno | 0.4986292 | 0.5473639 | 0.453659 | 0.32014886 | X63629_at | CDH3 Cadherin 3 (P-cadherin) |
| 58 | Uterus_A_deno | 0.4959905 | 0.5467969 | 0.453073 | 0.31972706 | R53717_at | EST: yi02e03.r1 Homo sapiens cDNA clone 138076 5'. (from Genbank) |

FIG. 14D

| | | | | |
|---|---|---|---|---|
| Uterus_A 59 deno | 0.4494047 | 0.5464213 | 0.452428 | 0.3190701 AB000449_a_t | VRK1 |
| Uterus_A 60 deno | 0.4938313 | 0.545815 | 0.451704 | 0.3184461 HG2190-HT2260_at | Crystallin, Beta B3 (GbːX15144) |
| Uterus_A 61 deno | 0.493098 | 0.5443705 | 0.451477 | 0.3176218 S81914_at | IEX-1 |
| Uterus_A 62 deno | 0.4930396 | 0.5441296 | 0.451067 | 0.3170374 L41351_at | Prostasin mRNA |
| Uterus_A 63 deno | 0.4914521 | 0.5429288 | 0.44993 | 0.31620046 RC_AA3941 41_at | EST: zt49f05.s1 Soares ovary tumor NbHOT Homo sapiens cDNA clone 725697 3', mRNA sequence. (from Genbank) |
| Uterus_A 64 deno | 0.4908763 | 0.5424645 | 0.449569 | 0.3158707 M26880_at | UBA52 Ubiquitin A-52 residue ribosomal protein fusion product 1 |
| Uterus_A 65 deno | 0.4905528 | 0.5420473 | 0.449265 | 0.31482926 X04412_at | GSN Gelsolin (amyloidosis, Finnish type) |
| Uterus_A 66 deno | 0.4882318 | 0.5410122 | 0.4488 | 0.314291195 X04470_s_a_t | RPL32 Ribosomal protein L32 |
| Uterus_A 67 deno | 0.4876482 | 0.5403776 | 0.44799 | 0.31386706 U15131_at | HTS1 |
| Uterus_A 68 deno | 0.4874155 | 0.5394405 | 0.447206 | 0.313191915 HG3342-HT3519_s_a | Id1 |
| Uterus_A 69 deno | 0.4860205 | 0.5388785 | 0.446016 | 0.3126637 X90908_at | Ileal lipid binding protein mRNA |
| Uterus_A 70 deno | 0.4841321 | 0.5383306 | 0.445569 | 0.31208307 N71513_s_a_t | EST: yw32h09.r1 Homo sapiens cDNA clone 253985 5'. (from Genbank) |
| Uterus_A 71 deno | 0.4841264 | 0.5370155 | 0.445193 | 0.31147408 M95787_at | 22kDa smooth muscle protein (SM22) mRNA |
| Uterus_A 72 deno | 0.4835202 | 0.5358866 | 0.444637 | 0.311105617 AB000450_a_t | VRK2 |
| Uterus_A 73 deno | 0.4826925 | 0.534344 | 0.444267 | 0.310066507 RC_AA2365 33_s_at | Ecotropic viral integration site 1 |
| Uterus_A 74 deno | 0.4823929 | 0.5339963 | 0.443608 | 0.310111337 AB000905_a_t | DNA for H4 histone |
| Uterus_A 75 deno | 0.4802965 | 0.5334052 | 0.443057 | 0.30952204 U68385_at | Meis1-related protein 2 (MRG2), mRNA, partial cds |
| Uterus_A 76 deno | 0.47686 | 0.532887 | 0.442853 | 0.30924416 X64707_at | 60S RIBOSOMAL PROTEIN L13 |
| Uterus_A 77 deno | 0.4761102 | 0.5325905 | 0.442243 | 0.30867124 AA393164_s_at | Mammaglobin 2 |

FIG. 14E

| | | | | | | |
|---|---|---|---|---|---|---|
| 78 | Uterus_A deno | 0.4757585 | 0.5318888 | 0.441369 | 0.30804583 | X73478_at | HPTPA mRNA |
| 79 | Uterus_A deno | 0.4733101 | 0.5317091 | 0.441369 | 0.30752692 | AB000897_a t | Cadherin FIB3, partial cds |
| 80 | Uterus_A deno | 0.4726467 | 0.5311901 | 0.440723 | 0.3069651 | X79683_s_a t | LAMB2 Laminin, beta 2 (laminin S) |
| 81 | Uterus_A deno | 0.4698234 | 0.5305458 | 0.440097 | 0.30624396 | M85289_at | HSPG2 Heparan sulfate proteoglycan |
| 82 | Uterus_A deno | 0.4687507 | 0.5304906 | 0.439276 | 0.3057988 | X01703_at | Alpha-tubulin mRNA |
| 83 | Uterus_A deno | 0.4685047 | 0.5300277 | 0.439009 | 0.30532092 | U06155_at | Chromosome 1q subtelomeric sequence D1S553 |
| 84 | Uterus_A deno | 0.4679755 | 0.5295302 | 0.438081 | 0.30494124 | RC_AA1148 66_s_at | Homo sapiens homeobox A11 (HOXA11) gene, complete cds |
| 85 | Uterus_A deno | 0.4661969 | 0.5290954 | 0.437072 | 0.30458075 | M31211_s_a t | MYL1 Myosin light chain (alkali) |
| 86 | Uterus_A deno | 0.4630819 | 0.5285833 | 0.436526 | 0.30407998 | U40369_rna 1_at | Spermidine/spermine N1-acetyltransferase (SSAT) gene |
| 87 | Uterus_A deno | 0.4607104 | 0.5269665 | 0.43646 | 0.3036926 | D42123_at | ESP1/CRP2 |
| 88 | Uterus_A deno | 0.4566061 | 0.5265443 | 0.435801 | 0.30324993 | U22970_rna 1_s_at | 6-16 gene (interferon-inducible peptide precursor) extracted from Human Interferon-inducible peptide (6-16) gene |
| 89 | Uterus_A deno | 0.4551983 | 0.5255779 | 0.435288 | 0.30284992 | J02947_s_at | SOD3 Superoxide dismutase 3, extracellular |
| 90 | Uterus_A deno | 0.4551933 | 0.5252157 | 0.43494 | 0.30238762 | U31201_cds 2_s_at | Laminin gamma2 chain gene (LAMC2) |
| 91 | Uterus_A deno | 0.4549561 | 0.5250371 | 0.433915 | 0.30181777 | L03411_s_at | RD Radin blood group |
| 92 | Uterus_A deno | 0.4545091 | 0.5248492 | 0.43354 | 0.30125198 | D86975_at | KIAA0222 gene |
| 93 | Uterus_A deno | 0.4530377 | 0.5247809 | 0.433075 | 0.3009687 | U49260_at | Mevalonate pyrophosphate decarboxylase (MPD) mRNA |
| 94 | Uterus_A deno | 0.4521654 | 0.5243944 | 0.432646 | 0.3003403 | D88155_s_a t | Steroidogenic factor 1 mRNA |
| 95 | Uterus_A deno | 0.4497136 | 0.5234382 | 0.432204 | 0.2999253 | U73843_at | Epithelial-specific transcription factor ESE-1b (ESE-1) mRNA |
| 96 | Uterus_A deno | 0.4468888 | 0.5233313 | 0.432046 | 0.299599 | X69910_at | P63 mRNA for transmembrane protein |
| 97 | Uterus_A deno | 0.4462032 | 0.5226997 | 0.431335 | 0.29919237 | X81372_at | Biphenyl hydrolase-related protein |

FIG. 14F

| | | | | | |
|---|---|---|---|---|---|
| Uterus_A deno 98 | 0.444212 | 0.522201 | 0.431001 | 0.298721975_at | J00220_cds | IGHA1 gene extracted from Human Ig germline H-chain G-E-A region A: gamma-3 5' flank |
| Uterus_A deno 99 | 0.4441896 | 0.5215474 | 0.430228 | 0.2984027 | D79205_at | Ribosomal protein L39 |
| Uterus_A deno 100 | 0.4437682 | 0.5215474 | 0.429998 | 0.29797208 | L33930_s_at | CD24 signal transducer mRNA and 3' region |
| Uterus_A deno 101 | 0.4422355 | 0.5205852 | 0.429478 | 0.29751363 | D29963_at | Platelet-endothelial tetraspan antigen 3 mRNA |
| Uterus_A deno 102 | 0.4422316 | 0.5200284 | 0.429269 | 0.2972376 | X98176_at | MACH-alpha-2 protein |
| Uterus_A deno 103 | 0.437993 | 0.5200284 | 0.42907 | 0.29665336 | Z23090_at | HSPB1 Heat shock 2/kD protein 1 |
| Uterus_A deno 104 | 0.4368865 | 0.5199291 | 0.428712 | 0.29648902 | D79985_at | A cell surface protein |
| Uterus_A deno 105 | 0.4365739 | 0.5197809 | 0.427838 | 0.29596934 | U21090_at | DNA polymerase delta small subunit mRNA |
| Uterus_A deno 106 | 0.4364742 | 0.5193853 | 0.427346 | 0.29555844 | AB000466_a_t | mRNA, clone RES4-24C, exon 1, 2, 3 |
| Uterus_A deno 107 | 0.4363791 | 0.5188586 | 0.426986 | 0.29514474 | RC_AA3992 26_at | Homo sapiens chromosome 19, cosmid R28784 |
| Uterus_A deno 108 | 0.4362825 | 0.5186184 | 0.426346 | 0.29460874 | D82060_at | Kidney mRNA for putative membrane protein with histidine rich charge clusters |
| Uterus_A deno 109 | 0.4360177 | 0.5182504 | 0.426339 | 0.29419395 | U79294_at | Clone 23748 mRNA |
| Uterus_A deno 110 | 0.4352084 | 0.5179058 | 0.425803 | 0.29396734 | X87838_at | CTNNB1 Catenin (cadherin-associated protein), beta 1 (88kD) |
| Uterus_A deno 111 | 0.4333916 | 0.5176738 | 0.42561 | 0.29352158 | U45878_s_a t | Inhibitor of apoptosis protein 1 mRNA |
| Uterus_A deno 112 | 0.4333183 | 0.5175284 | 0.425395 | 0.29320568 | D42041_at | KIAA0088 gene, partial cds |
| Uterus_A deno 113 | 0.4328869 | 0.5164073 | 0.42503 | 0.29294837 | M80359_at | PUTATIVE SERINE/THREONINE-PROTEIN KINASE P78 |
| Uterus_A deno 114 | 0.4324418 | 0.5158723 | 0.424115 | 0.29250085 | AB000220_a t | Semaphorin E |
| Uterus_A deno 115 | 0.4320297 | 0.5152394 | 0.423693 | 0.2920456 | M11313_s_a t | A2M Alpha-2-macroglobulin |
| Uterus_A deno 116 | 0.4314195 | 0.5147505 | 0.423252 | 0.29187736 | RC_AA1332 15_at | Homo sapiens mRNA encoding RAMP1 |
| Uterus_A deno 117 | 0.4312667 | 0.5142239 | 0.423077 | 0.29150053 | J02943_at | CBG Corticosteroid binding globulin |

FIG. 14G

| | | | | | |
|---|---|---|---|---|---|
| Uterus_A 118 deno | 0.4299999 | 0.5141617 | 0.422311 | 0.2909744 U90907_at | Clone 23907 mRNA sequence |
| Uterus_A 119 deno | 0.4284449 | 0.5138102 | 0.4219966 | 0.290969677 M10277_s_a t | ACTB Actin, beta |
| Uterus_A 120 deno | 0.427989 | 0.5130066 | 0.421684 | 0.29036683 J05073_at | PGAM2 Phosphoglycerate mutase 2 (muscle) |
| Uterus_A 121 deno | 0.42570557 | 0.51119464 | 0.421185 | 0.29007736 A28102_at | GABAa receptor alpha-3 subunit |
| Uterus_A 122 deno | 0.42542218 | 0.5102274 | 0.420546 | 0.28974798 J04164_at | RPS3 Ribosomal protein S3 |
| Uterus_A 123 deno | 0.42520054 | 0.50966661 | 0.420015 | 0.28945833 RC_AA4901 42_at | EST: ab05f07.s1 Stratagene fetal retina 937202 Homo sapiens cDNA clone 833941 3', mRNA sequence. (from Genbank) |
| Uterus_A 124 deno | 0.4240377 | 0.5092897 | 0.4199698 | 0.2889603 AB000115_a t | mRNA |
| Uterus_A 125 deno | 0.4239099 | 0.509042 | 0.419403 | 0.28858137 D64109_at | Tob family |
| Uterus_A 126 deno | 0.42009878 | 0.5088357 | 0.419145 | 0.2882721 AB0004671 t | mRNA, clone RES4-25, partial cds |
| Uterus_A 127 deno | 0.4207242 | 0.5088357 | 0.418868 | 0.28780168 RC_AA1324 53_at | EST: zo20b01.s1 Stratagene colon (#937204) Homo sapiens cDNA clone 587401 3', mRNA sequence. (from Genbank) |
| Uterus_A 128 deno | 0.4200143 | 0.5085479 | 0.418832 | 0.28747913 RC_AA0571 93_at | EST: zk79g01.s1 Soares pregnant uterus NbHPU Homo sapiens cDNA clone 489072 3', mRNA sequence. (from Genbank) |
| Uterus_A 129 deno | 0.4196011 | 0.5075169 | 0.418567 | 0.28710553 X61755_ma 1_s_at | HOX3D gene for homeoprotein HOX3D |
| Uterus_A 130 deno | 0.41811775 | 0.5070719 | 0.418261 | 0.2867976 AB0004621 t | SH3 binding protein, clone RES4-23A |
| Uterus_A 131 deno | 0.4180424 | 0.5070689 | 0.417722 | 0.28667536 L22548_at | COL18A1 Collagen, type XVIII, alpha 1 |
| Uterus_A 132 deno | 0.4176474 | 0.5066162 | 0.417452 | 0.2863811 RC_AA2584 82_s_at | Homo sapiens mRNA for zinc finger protein, complete cds |
| Uterus_A 133 deno | 0.4173543 | 0.5065996 | 0.416961 | 0.28615442 L31573_at | Sulfite oxidase mRNA |
| Uterus_A 134 deno | 0.4169104 | 0.5063061 | 0.416921 | 0.28591052 J05428_at | UDP-GLUCURONOSYLTRANSFERASE 2B7 PRECURSOR, MICROSOMAL |
| Uterus_A 135 deno | 0.4162971 | 0.50611895 | 0.416733 | 0.28566689 U12595_at | Tumor necrosis factor type 1 receptor associated protein (TRAP1) mRNA, partial cds |
| Uterus_A 136 deno | 0.41557762 | 0.50566785 | 0.416443 | 0.28525978 AFFX-M27830_M_ at-2 | Human 28S ribosomal RNA gene, complete cds. (from Genbank) |

FIG. 14H

| | | | | | |
|---|---|---|---|---|---|
| 137 | Uterus_A_deno | 0.4155762 | 0.5054011 | 0.2848366 | AFFX-M27830_M_at | AFFX-M27830_M_at (endogenous control) |
| 138 | Uterus_A_deno | 0.414838 | 0.5052038 | 0.415906 | X99720_rna1_at | TPRC gene |
| 139 | Uterus_A_deno | 0.412925 | 0.5041894 | 0.415704 | U55054_at | K-Cl cotransporter (hKCC1) mRNA |
| 140 | Uterus_A_deno | 0.4128701 | 0.5039822 | 0.414831 | HG2274-HT2370_at | Rna Polymerase Ii, 14.5 Kda Subunit |
| 141 | Uterus_A_deno | 0.4121329 | 0.5039408 | 0.414825 | Y00318_at | IF I factor (complement) |
| 142 | Uterus_A_deno | 0.4102755 | 0.5031565 | 0.414653 | J02783_at | P4HB Procollagen-proline, 2-oxoglutarate 4-dioxygenase (proline 4-hydroxylase), beta polypeptide (protein disulfide isomerase; thyroid hormone binding protein p55) |
| 143 | Uterus_A_deno | 0.409792 | 0.5023284 | 0.414653 | L25081_at | ARH9 Aplysia ras-related homolog 9 |
| 144 | Uterus_A_deno | 0.4081467 | 0.5023284 | 0.414322 | M92299_s_at | Homeo box B5 |
| 145 | Uterus_A_deno | 0.407142 | 0.5019749 | 0.413557 | M94250_at | MDK Midkine (neurite growth-promoting factor 2) |
| 146 | Uterus_A_deno | 0.4067512 | 0.5016758 | 0.413405 | HG2815-HT2931_at | Myosin, Light Chain, Alkali, Smooth Muscle (Gb:U02629), Non-Muscle, Alt. Splice 2 |
| 147 | Uterus_A_deno | 0.4067289 | 0.5014106 | 0.41308 | X74104_at | SSR2 Signal sequence receptor, beta |
| 148 | Uterus_A_deno | 0.4049592 | 0.5013072 | 0.412883 | L04270_at | LYMPHOTOXIN-BETA RECEPTOR PRECURSOR |
| 149 | Uterus_A_deno | 0.40459341 | 0.4999831 | 0.412349 | D38583_at | Calgizzarin |
| 150 | Uterus_A_deno | 0.4042062 | 0.4991259 | 0.412031 | RC_AA1370173_at | EST: zl02c01.s1 Soares pregnant uterus NbHPU Homo sapiens cDNA clone 491136 3' similar to contains element THR repetitive element:; mRNA sequence. (from Genbank) |
| 151 | Uterus_A_deno | 0.4039962 | 0.4991158 | 0.411938 | U53506_at | Type II lodothyronine deiodinase mRNA |
| 152 | Uterus_A_deno | 0.4036855 | 0.4988249 | 0.411706 | AA043111_s_at | EST: zk48b08.r1 Soares pregnant uterus NbHPU Homo sapiens cDNA clone 486039 5', mRNA sequence. (from Genbank) |
| 153 | Uterus_A_deno | 0.4036092 | 0.4981218 | 0.411481 | M16937_at | Homeo box c1 protein, mRNA |
| 154 | Uterus_A_deno | 0.4032689 | 0.4971882 | 0.411437 | U32907_at | P37NB mRNA |

FIG. 14I

| | | | | | |
|---|---|---|---|---|---|
| 155 | Uterus_A deno | 0.4014092 | 0.4968431 | 0.411241 | 0.279968997 | L13210_at | Mac-2 binding protein mRNA |
| 156 | Uterus_A deno | 0.4012508 | 0.4966155 | 0.410999 | 0.279422207 | U08198_rna1_at | Complement C8 gamma subunit precursor (C8G) gene |
| 157 | Uterus_A deno | 0.4006594 | 0.4958473 | 0.410798 | 0.2792073 | M12125_at | Skeletal beta-tropomyosin |
| 158 | Uterus_A deno | 0.4001233 | 0.4956109 | 0.410675 | 0.2788841 | X87159_at | Beta subunit of epithelial amiloride-sensitive sodium channel |
| 159 | Uterus_A deno | 0.3984343 | 0.4954442 | 0.410111 | 0.27867562 | X69838_at | G9a |
| 160 | Uterus_A deno | 0.3980627 | 0.4954442 | 0.409397 | 0.2784675 | M68864_at | ORF mRNA |
| 161 | Uterus_A deno | 0.3970766 | 0.4950701 | 0.409253 | 0.27812043 | X83857_s_at | PTGER3 Prostaglandin E receptor 3 (subtype EP3) [alternative products] |
| 162 | Uterus_A deno | 0.3970429 | 0.4950701 | 0.409253 | 0.27784884 | U27655_at | RGP3 mRNA |
| 163 | Uterus_A deno | 0.395334 | 0.4948221 | 0.409176 | 0.27775925 | U18919_at | Chromosome 17q12-21 mRNA, clone pOV-2, partial cds |
| 164 | Uterus_A deno | 0.3951663 | 0.4933896 | 0.409168 | 0.27730173 | D86331_s_at | MMP2 Matrix metalloproteinase 2 |
| 165 | Uterus_A deno | 0.3948417 | 0.4920247 | 0.409127 | 0.27709570 | HG371-HT263B8_s_at | Mucin 1, Epithelial, Alt. Splice 9 |
| 166 | Uterus_A deno | 0.3941645 | 0.4918493 | 0.408144 | 0.2768895 | AF009301_at | TEB4 protein mRNA |
| 167 | Uterus_A deno | 0.3931555 | 0.4918493 | 0.408116 | 0.2764627 | Y00264_at | APP Amyloid A4 protein of Alzheimer's disease |
| 168 | Uterus_A deno | 0.3923586 | 0.4915251 | 0.407863 | 0.2762043 | U84720_at | mRNA export protein Rae1 (RAE1) mRNA |
| 169 | Uterus_A deno | 0.3923153 | 0.4915251 | 0.407757 | 0.2758917 | L27624_s_at | TISSUE FACTOR PATHWAY INHIBITOR 2 PRECURSOR |
| 170 | Uterus_A deno | 0.3920158 | 0.4913622 | 0.407555 | 0.27568007 | D29992_at | TISSUE FACTOR PATHWAY INHIBITOR 2 PRECURSOR |
| 171 | Uterus_A deno | 0.3917662 | 0.491362 | 0.40723 | 0.27544108 | D17532_at | PROBABLE ATP-DEPENDENT RNA HELICASE P54 |
| 172 | Uterus_A deno | 0.3899161 | 0.4911715 | 0.407132 | 0.27503148 | U18242_at | CAMLG Calcium modulating ligand |
| 173 | Uterus_A deno | 0.3899072 | 0.4907261 | 0.40615 | 0.27481934 | X99350_rna1_at-2 | Forkhead (Drosophila)-like 13 |

FIG. 14J

| | | | | | | |
|---|---|---|---|---|---|---|
| 174 | Uterus_A_deno | 0.3899072 | 0.4907112 | 0.406119 | 0.274604 | X99350_rna 1_at | HFH4_cds gene extracted from H.sapiens HFH4 gene, exon 1 and joined CDS |
| 175 | Uterus_A_deno | 0.389556 | 0.4902203 | 0.405871 | 0.27439705 | D50663_at | CW-1 mRNA |
| 176 | Uterus_A_deno | 0.3890103 | 0.4899243 | 0.405731 | 0.2740964 | L04751_at | CYP4A11 Cytochrome P450, subfamily IVA, polypeptide 11 |
| 177 | Uterus_A_deno | 0.3889893 | 0.4886434 | 0.40554 | 0.27387777 | AF005043_a_t | Poly(ADP-ribose) glycohydrolase (hPARG) mRNA |
| 178 | Uterus_A_deno | 0.3886735 | 0.4883817 | 0.405248 | 0.27345976 | AA197134_a_t | EST: zq11b11.r1 Stratagene muscle 937209 Homo sapiens cDNA clone 629373 5', mRNA sequence. (from Genbank) |
| 179 | Uterus_A_deno | 0.3885605 | 0.4881 | 0.405248 | 0.2732578 | M68516_rna 1_at | PCI gene (plasminogen activator inhibitor 3) extracted from Human protein C inhibitor gene |
| 180 | Uterus_A_deno | 0.3884962 | 0.4876038 | 0.404647 | 0.27294514 | L18960_at | EIF4C Eukaryotic translation initiation factor 4C (eIF-4C) |
| 181 | Uterus_A_deno | 0.3878335 | 0.4874873 | 0.404321 | 0.27272266 | X76057_at | MPI Mannose phosphate isomerase |
| 182 | Uterus_A_deno | 0.3874409 | 0.4872577 | 0.404207 | 0.2724144 | X82224_at | Glutamine transaminase K |
| 183 | Uterus_A_deno | 0.3870421 | 0.4870125 | 0.403855 | 0.27227134 | AB002332_a_t | KIAA0334 gene |
| 184 | Uterus_A_deno | 0.3863457 | 0.4868404 | 0.403763 | 0.27211398 | D45906_at | LIMK-2 |
| 185 | Uterus_A_deno | 0.3861356 | 0.4867556 | 0.403763 | 0.27183247 | L77213_at | Phosphomevalonate kinase mRNA |
| 186 | Uterus_A_deno | 0.3860179 | 0.4867483 | 0.403653 | 0.27148208 | Y07829_xpt3_at | Exon A1 from H.sapiens gene encoding RING finger protein./htype=DNA /annot=exon |
| 187 | Uterus_A_deno | 0.3858946 | 0.4865684 | 0.403512 | 0.27124965 | AB000895_a_t | Cadherin FIB1, partial cds |
| 188 | Uterus_A_deno | 0.3855798 | 0.4861995 | 0.402921 | 0.27087584 | L19067_at | TRANSCRIPTION FACTOR P65 |
| 189 | Uterus_A_deno | 0.3854379 | 0.4861572 | 0.402748 | 0.27079478 | U36922_at | Fork head domain protein (FKHR) mRNA, 3' end |
| 190 | Uterus_A_deno | 0.384951 | 0.4860813 | 0.402705 | 0.27059072 | X13766_s_at | CSN2 Beta-casein |
| 191 | Uterus_A_deno | 0.3845308 | 0.4860763 | 0.402553 | 0.2703186 | U54778_at | 14-3-3 epsilon mRNA |
| 192 | Uterus_A_deno | 0.384253 | 0.4858058 | 0.402357 | 0.27008152 | X90840_at | Axonal transporter of synaptic vesicles |
| 193 | Uterus_A_deno | 0.3837801 | 0.4852167 | 0.402321 | 0.26898614 | M93036_at | MAJOR GASTROINTESTINAL TUMOR-ASSOCIATED PROTEIN GA733-2 PRECURSOR |

FIG. 14K

| | | | | | |
|---|---|---|---|---|---|
| 194 | Uterus_A_deno | 0.3834412 | 0.4851144 | 0.401799 | 0.26950815 | X78342_at | (clone PK2J) CDC2-related protein kinase (PISSLRE) mRNA |
| 195 | Uterus_A_deno | 0.38311369 | 0.4850967 | 0.401634 | 0.26931265 | L19711_at | Dystroglycan (DAG1) mRNA |
| 196 | Uterus_A_deno | 0.3826602 | 0.4842905 | 0.401283 | 0.26912433 | AB000468_a_t | Zinc finger protein, clone RES4-26 |
| 197 | Uterus_A_deno | 0.38237716 | 0.4840759 | 0.401202 | 0.26903847 | Z24725_at | Mitogen inducible gene mig-2 |
| 198 | Uterus_A_deno | 0.3822301 | 0.4840454 | 0.400843 | 0.26890865 | M13690_s_at | C1NH Complement component 1 inhibitor (angioedema, hereditary) |
| 199 | Uterus_A_deno | 0.3813474 | 0.4837295 | 0.400781 | 0.2685522 | D42073_at | Reticulocalbin |
| 200 | Uterus_A_deno | 0.3812963 | 0.483696 | 0.400064 | 0.2683764 | D00723_at | GCSH Glycine cleavage system protein H (aminomethyl carrier) |
| 201 | Uterus_A_deno | 0.3796422 | 0.4835097 | 0.399878 | 0.268007551 | U33317_rna_at | Defensin 6 (HD-6) gene |
| 202 | Uterus_A_deno | 0.3792752 | 0.4833969 | 0.399773 | 0.26775816 | U62437_at | Neuronal nicotinic acetylcholine receptor beta-2 subunit |
| 203 | Uterus_A_deno | 0.378675 | 0.4833184 | 0.399639 | 0.26748958 | U83411_at | Carboxypeptidase Z precursor, mRNA |
| 204 | Uterus_A_deno | 0.3784726 | 0.4832972 | 0.399602 | 0.2672902 | D38251_s_a_t | DNA-DIRECTED RNA POLYMERASE II 23 KD POLYPEPTIDE |
| 205 | Uterus_A_deno | 0.37835565 | 0.4826117 | 0.399596 | 0.26698871 | X02419_rna_s_at | UPA gene |
| 206 | Uterus_A_deno | 0.378039 | 0.4819224 | 0.399211 | 0.26671186 | M14058_at | C1R Complement component C1r |
| 207 | Uterus_A_deno | 0.377782 | 0.4817348 | 0.399085 | 0.26652628 | X59798_at | CCND1 Cyclin D1 (PRAD1; parathyroid adenomatosis 1) |
| 208 | Uterus_A_deno | 0.3774269 | 0.4816919 | 0.398452 | 0.26627892 | D29805_at | GGTB2 Glycoprotein-4-beta-galactosyltransferase 2 |
| 209 | Uterus_A_deno | 0.3770593 | 0.4816005 | 0.398359 | 0.2661012 | M29971_at | MGMT 6-O-methylguanine-DNA methyltransferase (MGMT) |
| 210 | Uterus_A_deno | 0.37611662 | 0.4812906 | 0.398147 | 0.26592505 | U25138_at | MaxiK potassium channel beta subunit mRNA |
| 211 | Uterus_A_deno | 0.3757033 | 0.481163 | 0.398064 | 0.26572043 | HG1980-HT2023_at | Tubulin, Beta 2 |
| 212 | Uterus_A_deno | 0.3754145 | 0.4808285 | 0.397796 | 0.26655104 | U25182_at | Antioxidant enzyme AOE37-2 mRNA |
| 213 | Uterus_A_deno | 0.3752081 | 0.4807644 | 0.397595 | 0.26524332 | RC_AA1513 33_at | EST: zl41c12.s1 Soares pregnant uterus NbHPU Homo sapiens cDNA clone 504502 3', mRNA sequence. (from Genbank) |

FIG. 14L

| | | | | | |
|---|---|---|---|---|---|
| 214 | Uterus_A deno | 0.3749906 | 0.4801748 | 0.397473 | 0.26498914 | X67325_at | INTERFERON-ALPHA INDUCED 11.5 KD PROTEIN |
| 215 | Uterus_A deno | 0.3744172 | 0.4799234 | 0.39724 | 0.26464757 | X77366_at | TCF11 Transcription factor 11 (basic leucine zipper type) |
| 216 | Uterus_A deno | 0.3740618 | 0.4795054 | 0.397118 | 0.26452804 | U43077_at | CDC37 homolog mRNA |
| 217 | Uterus_A deno | 0.3727394 | 0.4783845 | 0.396897 | 0.26433152 | D63391_at | Platelet activating factor acetylhydrolase IB gamma-subunit |
| 218 | Uterus_A deno | 0.3724615 | 0.4779314 | 0.396417 | 0.26405442 | D17408_s_a t | Calponin |
| 219 | Uterus_A deno | 0.3723084 | 0.4772744 | 0.396346 | 0.2638878 | X94612_at | Type II cGMP-dependent protein kinase |
| 220 | Uterus_A deno | 0.3721785 | 0.4771564 | 0.396224 | 0.263626 | L22524_s_at | MATRILYSIN PRECURSOR |
| 221 | Uterus_A deno | 0.3716648 | 0.4770376 | 0.396123 | 0.26336345 | L25878_s_at | EPHX1 Epoxide hydrolase 1, microsomal (xenobiotic) |
| 222 | Uterus_A deno | 0.3711425 | 0.4769517 | 0.395993 | 0.2631806 | M62403_s_a t | IGFBP4 Insulin-like growth factor-binding protein 4 |
| 223 | Uterus_A deno | 0.3706329 | 0.4767917 | 0.395783 | 0.26291057 | X72964_at | CALT Caltractin (20kD calcium-binding protein) |
| 224 | Uterus_A deno | 0.37059975 | 0.4767409 | 0.395687 | 0.26273605 | HG3395-HT3573_s_a t | DnaJ Homolog (Gb:X63368), Alt. Splice Form 2 |
| 225 | Uterus_A deno | 0.36967799 | 0.4766974 | 0.395679 | 0.26267448 | X69699_at | Pax8 mRNA |
| 226 | Uterus_A deno | 0.3682101 | 0.47627 | 0.395208 | 0.26241487 | AA482319_f_at | EST: ab15c03.r1 Stratagene lung (#937210) Homo sapiens cDNA clone 840868 5', mRNA sequence. (from Genbank) |
| 227 | Uterus_A deno | 0.3671481 | 0.476121 | 0.395109 | 0.26217762 | L26339_at | Autoantigen mRNA |
| 228 | Uterus_A deno | 0.3651912 | 0.4760983 | 0.394917 | 0.2621099 | X68742_at | Integrin, alpha subunit |
| 229 | Uterus_A deno | 0.3649179 | 0.4758993 | 0.394725 | 0.26185763 | AF001548_r na1_at | 815A9.1 gene (myosin heavy chain) extracted from Homo sapiens chromosome 16 BAC clone CIT987SK-815A9 complete sequence |
| 230 | Uterus_A deno | 0.3640831 | 0.4756543 | 0.39457 | 0.26169914 | M84349_at | CD59 CD59 antigen p18-20 (antigen identified by monoclonal antibodies 16.3A5, EJ16, EJ30, EL32 and G344) |
| 231 | Uterus_A deno | 0.3627926 | 0.474995 | 0.394216 | 0.26155105 | M75099_at | FRAP FK506 binding protein 12-rapamycin associated protein |
| 232 | Uterus_A deno | 0.3625371 | 0.4747753 | 0.394134 | 0.26136196 | U27193_at | Protein-tyrosine phosphatase mRNA |

FIG. 14M

| | | | | | |
|---|---|---|---|---|---|
| 233 | Uterus_A_deno | 0.3617034 | 0.47746594 | 0.393886 | 0.2610491 | M64098_at | High density lipoprotein binding protein (HBP) mRNA |
| 234 | Uterus_A_deno | 0.3611303 | 0.47431144 | 0.393644 | 0.26083332 | S62539_at | Insulin receptor substrate-1 [human, skeletal muscle, mRNA, 5828 nt] |
| 235 | Uterus_A_deno | 0.3608667 | 0.4740229 | 0.393412 | 0.2605413 | M55998_s_at | Alpha-1 collagen type I gene, 3' end |
| 236 | Uterus_A_deno | 0.3597587 | 0.4739754 | 0.393398 | 0.26036203 | M81182_s_at | PXMP1 Peroxisomal membrane protein 1 (70kD, Zellweger syndrome) |
| 237 | Uterus_A_deno | 0.3596351 | 0.4736839 | 0.392947 | 0.26010326 | U52696_s_a_t | Adrenal Creb-rp homolog (Creb-rp), and tenascin-X (XB), partial cds, mRNA |
| 238 | Uterus_A_deno | 0.3595874 | 0.4734863 | 0.392907 | 0.26001436 | L07594_at | TGFBR3 Transforming growth factor, beta receptor III (betaglycan, 300kD)) |
| 239 | Uterus_A_deno | 0.3591667 | 0.4725641 | 0.392651 | 0.25984654 | M84739_at | CALR Autoantigen calreticulin |
| 240 | Uterus_A_deno | 0.3587261 | 0.472512 | 0.392112 | 0.25960776 | X75593_at | Rab 13 |
| 241 | Uterus_A_deno | 0.3581595 | 0.4724179 | 0.392011 | 0.25940916 | U79258_at | Clone 23732 mRNA, partial cds |
| 242 | Uterus_A_deno | 0.3570312 | 0.4719178 | 0.391713 | 0.2591425 | U96094_at | Sarcolipin (SLN) mRNA |
| 243 | Uterus_A_deno | 0.356487 | 0.4718776 | 0.39159 | 0.25892106 | J02854_at | 20-kDa myosin light chain (MLC-2) mRNA |
| 244 | Uterus_A_deno | 0.3561977 | 0.4717351 | 0.391412 | 0.25874886 | X53586_rna1_at | Integrin alpha 6 (or alpha E) protein gene extracted from Human mRNA for integrin alpha 6 |
| 245 | Uterus_A_deno | 0.3558232 | 0.4714233 | 0.391104 | 0.25867283 | X03363_s_at | ERBB2 V-erb-b2 avian erythroblastic leukemia viral oncogene homolog 2 (neuro/glioblastoma derived oncogene homolog) |
| 246 | Uterus_A_deno | 0.3556713 | 0.4710527 | 0.390892 | 0.25841162 | M24486_s_at | P4HA Procollagen-proline, 2-oxoglutarate 4-dioxygenase (proline 4-hydroxylase), alpha polypeptide |
| 247 | Uterus_A_deno | 0.3556233 | 0.4709223 | 0.390831 | 0.2583091 | HG2271-HT2367_at | Profilaggrin |
| 248 | Uterus_A_deno | 0.3556163 | 0.4707972 | 0.390526 | 0.25813356 | HG4683-HT5108_s_at | Tumor Necrosis Factor Receptor 2 Associated Protein Trap3 |
| 249 | Uterus_A_deno | 0.3545109 | 0.4703161 | 0.390331 | 0.2579129 | L42379_at | Quiescin (Q6) mRNA, partial cds |
| 250 | Uterus_A_deno | 0.3540901 | 0.4699484 | 0.390185 | 0.257637 | D14823_at | Chimeric mRNA derived from AML1 gene and MTG8(ETO) gene, partial sequence |
| 251 | Uterus_A_deno | 0.3539492 | 0.4696537 | 0.390015 | 0.2574368 | U24576_at | Breast tumor autoantigen mRNA, complete sequence |

FIG. 14N

| | | | | | |
|---|---|---|---|---|---|
| 252 | Uterus_A deno | 0.3535267 | 0.46993585 | 0.389785 | 0.2572328 | AF000573_r na1_at | Homogentisate 1,2-dioxygenase gene |
| 253 | Uterus_A deno | 0.3526265 | 0.46933475 | 0.38973 | 0.257135151 | U26648_at | STX5A Syntaxin 5A |
| 254 | Uterus_A deno | 0.3518513 | 0.46992196 | 0.389601 | 0.2568196 | D13900_at | Mitochondrial short-chain enoyl-CoA hydratase |
| 255 | Uterus_A deno | 0.3518259 | 0.4692048 | 0.389446 | 0.2567428 | U69126_s_a t | FUSE binding protein 2 (FBP2) mRNA, partial cds |
| 256 | Uterus_A deno | 0.3516677 | 0.468998 | 0.389273 | 0.25656405 | D50913_at | KIAA0123 gene, partial cds |
| 257 | Uterus_A deno | 0.3515681 | 0.468677 | 0.389174 | 0.25637862 | L10343_at | PI3 Protease inhibitor 3, skin-derived (SKALP) |
| 258 | Uterus_A deno | 0.3503282 | 0.4685783 | 0.388905 | 0.256120656 9_at | RC_AA4280 | EST: zw57b01.s1 Soares total fetus Nb2HF8 9w Homo sapiens cDNA clone 774121 3', mRNA sequence. (from Genbank) |
| 259 | Uterus_A deno | 0.3501498 | 0.46833319 | 0.388633 | 0.25598252 | D50863_at | TESK1 |
| 260 | Uterus_A deno | 0.349875 | 0.4678672 | 0.388615 | 0.25583646 | L19267_at | 59 protein mRNA, 3' end |
| 261 | Uterus_A deno | 0.3493615 | 0.46699909 | 0.388422 | 0.2556767 | X52151_at | ARSA Arylsulfatase A |
| 262 | Uterus_A deno | | 0.4669909 | 0.388389 | 0.25552478 | M87770_at | FGFR2 Fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 263 | Uterus_A deno | 0.3483551 | 0.4666338 | 0.388296 | 0.255521854 | U90716_at | Cell surface protein HCAR mRNA |
| 264 | Uterus_A deno | 0.3483136 | 0.4666338 | 0.388105 | 0.2551098 | AB000584_a t | Prostate differentiation factor mRNA |
| 265 | Uterus_A deno | 0.3475202 | 0.46652111 | 0.387877 | 0.25487748 | L22005_at | UBIQUITIN-CONJUGATING ENZYME E2-CDC34 COMPLEMENTING |
| 266 | Uterus_A deno | 0.3474691 | 0.4664369 | 0.387862 | 0.25473884 | U90913_at | Clone 23665 mRNA sequence |
| 267 | Uterus_A deno | 0.3471859 | 0.4657836 | 0.387524 | 0.2544843 | M33374_at | Cell adhesion protein (SQM1) mRNA |
| 268 | Uterus_A deno | 0.3469153 | 0.4657298 | 0.387506 | 0.254431052 | RC_AA4302 09_at | Homo sapiens LIM protein mRNA, complete cds |
| 269 | Uterus_A deno | 0.3467862 | 0.4656529 | 0.387342 | 0.2540986 | U09770_at | Cysteine-rich heart protein (hCRHP) mRNA |
| 270 | Uterus_A deno | 0.346028 | 0.4656386 | 0.387128 | 0.25390607 | X66141_at | MYL2 Myosin, light polypeptide 2, regulatory, cardiac, slow |

FIG. 14O

| | | | | | |
|---|---|---|---|---|---|
| 271 | Uterus_A_deno | 0.3456708 | 0.4655994 | 0.386753 | 0.2538055 | RC_AA4466 50_at | EST: zw89g02.s1 Soares total fetus Nb2HF8 9w Homo sapiens cDNA clone 784178 3', mRNA sequence. (from Genbank) |
| 272 | Uterus_A_deno | 0.3454163 | 0.4654715 | 0.386738 | 0.2536321 | U20362_at | Tg737 mRNA |
| 273 | Uterus_A_deno | 0.3453842 | 0.4649046 | 0.386738 | 0.25333798 | U48959_at | Myosin light chain kinase (MLCK) mRNA |
| 274 | Uterus_A_deno | 0.3447059 | 0.4647908 | 0.386716 | 0.253156667 | U62317_rna_at | Hypothetical protein 384D8_7 gene extracted from Chromosome 22q13 BAC Clone CIT987SK-384D8 complete sequence |
| 275 | Uterus_A_deno | 0.3443086 | 0.4642941 | 0.386583 | 0.252983345 | Z18633_at | Retrotransposon |
| 276 | Uterus_A_deno | 0.3441027 | 0.4641958 | 0.386236 | 0.252783363 | M34423_at | GLB1 Beta-D-galactosidase |
| 277 | Uterus_A_deno | 0.3437606 | 0.4637237 | 0.386213 | 0.2525776 | Y08639_at | Nuclear orphan receptor ROR-beta |
| 278 | Uterus_A_deno | 0.3431605 | 0.4636868 | 0.386145 | 0.2523856 | RC_AA4313 51_at | EST: zw72c12.s1 Soares testis NHT Homo sapiens cDNA clone 781750 3', mRNA sequence. (from Genbank) |
| 279 | Uterus_A_deno | 0.3427788 | 0.4636477 | 0.385899 | 0.25221294 | HG3227-HT3404_at | Guanine Nucleotide-Binding Protein Hsr1 |
| 280 | Uterus_A_deno | 0.3424358 | 0.4631247 | 0.385883 | 0.2520823 | Y09267_at | Flavin-containing monooxygenase 2 |
| 281 | Uterus_A_deno | 0.3415793 | 0.4630214 | 0.385833 | 0.25197226 | U72508_at | B7 mRNA |
| 282 | Uterus_A_deno | 0.3415793 | 0.4628754 | 0.385484 | 0.25167248 | U72508_at-2 | Human B7 mRNA, complete cds |
| 283 | Uterus_A_deno | 0.3415338 | 0.4622342 | 0.385347 | 0.25159296 | U20908_at | Clone 350/2 melanoma ubiquitous mutated protein (MUM-1) gene, partial cds |
| 284 | Uterus_A_deno | 0.3410251 | 0.4621983 | 0.385255 | 0.251129947 | RC_AA2561 62_at | EST: zr79b07.s1 Soares NhHMPu S1 Homo sapiens cDNA clone 681877 3', mRNA sequence. (from Genbank) |
| 285 | Uterus_A_deno | 0.3408567 | 0.4619737 | 0.385178 | 0.25111995 | RC_AA4820 31_at | Ribosomal protein L37 |
| 286 | Uterus_A_deno | 0.340582 | 0.4619737 | 0.38501 | 0.2509831 | U76189_at | EXTL2 (EXTL2) mRNA, partial cds |
| 287 | Uterus_A_deno | 0.3400451 | 0.4616603 | 0.384639 | 0.2507244 | L40397_at | (clone S31t125) mRNA, 3' end of cds |
| 288 | Uterus_A_deno | 0.3399361 | 0.4614886 | 0.384433 | 0.25058222 | M19645_at | 78 KD GLUCOSE REGULATED PROTEIN PRECURSOR |
| 289 | Uterus_A_deno | 0.3399325 | 0.4613862 | 0.384144 | 0.25039697 | U73682_at | Meningioma-expressed antigen 6 (MEA6) mRNA |
| 290 | Uterus_A_deno | 0.3393976 | 0.4610066 | 0.384023 | 0.25035813 | Z22533_s_at | Activin A receptor type II-like 1 |

FIG. 14P

| | | | | | |
|---|---|---|---|---|---|
| 291 | Uterus_A_deno | 0.339082 | 0.4604204 | 0.383996 | 0.25013983 | L38517_at | Indian hedgehog protein (IHH) mRNA, 5' end |
| 292 | Uterus_A_deno | 0.3388332 | 0.4604124 | 0.383678 | 0.2499281 | L19686_ma1_at | Macrophage migration inhibitory factor (MIF) gene |
| 293 | Uterus_A_deno | 0.3386539 | 0.4601696 | 0.383378 | 0.24971211 | X55330_at | AGA Aspartylglucosaminidase |
| 294 | Uterus_A_deno | 0.3380552 | 0.4600778 | 0.383313 | 0.24958752 | U02082_at | Guanine nucleotide regulatory protein (tim1) mRNA |
| 295 | Uterus_A_deno | 0.3376188 | 0.4600464 | 0.382766 | 0.24940549 | U37519_at | ALDH8 Aldehyde dehydrogenase 8 |
| 296 | Uterus_A_deno | 0.3372519 | 0.459957 | 0.38273 | 0.24922764 | X62654_ma1_at | ME491 gene extracted from H.sapiens gene for Me491/CD63 antigen |
| 297 | Uterus_A_deno | 0.3371888 | 0.4597787 | 0.382649 | 0.24906518 | X17254_at | GATA1 Transcription factor Eryf1 |
| 298 | Uterus_A_deno | 0.3371089 | 0.4596771 | 0.382618 | 0.24891324 | U89606_at | Pyridoxal kinase mRNA |
| 299 | Uterus_A_deno | 0.3369807 | 0.4593989 | 0.38253 | 0.24873494 | U67849_at | Beta-galactoside alpha2,6-sialyltransferase (SIAT1) mRNA, exon W |
| 300 | Uterus_A_deno | 0.3360791 | 0.459173 | 0.382419 | 0.24852309 | RC_AA3479 73_at | EST: EST54406 Fetal heart II Homo sapiens cDNA 3' end, mRNA sequence. (from Genbank) |
| 301 | Uterus_A_deno | 0.3358634 | 0.4590025 | 0.382309 | 0.24827251 | D85429_at | DNAJ PROTEIN HOMOLOG 1 |
| 302 | Uterus_A_deno | 0.3353862 | 0.458761 | 0.382081 | 0.24812767 | L08044_s_at | TFF3 Trefoil factor 3 (intestinal) |
| 303 | Uterus_A_deno | 0.3353862 | 0.4579214 | 0.382012 | 0.24792191 | L08044_s_at U20536_s_a | Trefoil factor 3 (intestinal) |
| 304 | Uterus_A_deno | 0.3347316 | 0.4572246 | 0.381873 | 0.24772425 | t | Cysteine protease Mch2 isoform alpha (Mch2) mRNA |
| 305 | Uterus_A_deno | 0.3344394 | 0.4572246 | 0.381707 | 0.24762948 | X57025_at | IGF1 Insulin-like growth factor 1 (somatomedia C) |
| 306 | Uterus_A_deno | 0.334328 | 0.4570327 | 0.38159 | 0.24749441 | RC_AA4822 24_f_at | EST: ab15c03.s1 Stratagene lung (#937210) Homo sapiens cDNA clone 840868 3', mRNA sequence. (from Genbank) |
| 307 | Uterus_A_deno | 0.3339888 | 0.4568894 | 0.381433 | 0.24740446 | D86973_at | KIAA0219 gene, partial cds |
| 308 | Uterus_A_deno | 0.3331699 | 0.4556952 | 0.381338 | 0.24726626 | D21262_at | KIAA0035 gene, partial cds |
| 309 | Uterus_A_deno | 0.3329813 | 0.456655 | 0.38128 | 0.24716893 | K03460_at | Alpha-tubulin isotype H2-alpha gene, last exon |
| 310 | Uterus_A_deno | 0.3326526 | 0.4548651 | 0.380931 | 0.24698804 | M11437_cds 2_at | KNG gene (kininogen) extracted from Human kininogen gene |

FIG. 14Q

| | | | | | |
|---|---|---|---|---|---|
| 311 | Uterus_A_deno | 0.33224483 | 0.4548494 | 0.380931 | 0.246704 | M59371_at | TYROSINE-PROTEIN KINASE RECEPTOR ECK PRECURSOR |
| 312 | Uterus_A_deno | 0.3308183 | 0.4547785 | 0.380809 | 0.24665885 | M27492_at | INTERLEUKIN-1 RECEPTOR, TYPE I PRECURSOR |
| 313 | Uterus_A_deno | 0.3305241 | 0.4546936 | 0.380557 | 0.24642128 | M38258_at | RARG Retinoic acid receptor, gamma 1 |
| 314 | Uterus_A_deno | 0.329749 | 0.4545722 | 0.380493 | 0.24626747 | J05633_at | ITGB5 Integrin beta-5 subunit |
| 315 | Uterus_A_deno | 0.3293291 | 0.4545722 | 0.380216 | 0.24603835 | U33202_s_a t | Mdm2-D (mdm2) mRNA |
| 316 | Uterus_A_deno | 0.3292323 | 0.4543243 | 0.380164 | 0.2459015 | Y00282_at | RPN2 Ribophorin II |
| 317 | Uterus_A_deno | 0.3291355 | 0.4540369 | 0.380105 | 0.24576785 | D13636_at | KIAA0011 gene |
| 318 | Uterus_A_deno | 0.3287892 | 0.453737 | 0.379975 | 0.24565186 | U22431_s_a t | MOP1 mRNA |
| 319 | Uterus_A_deno | 0.3287064 | 0.45373188 | 0.379734 | 0.24545638 | X54938_at | ITPKA Inositol 1,4,5-trisphosphate 3-kinase A |
| 320 | Uterus_A_deno | 0.3286694 | 0.4537264 | 0.379662 | 0.24526131 | U24488_s_a t | CYP21 Cytochrome P450, subfamily XXI (steroid 21-hydroxylase, congenital adrenal hyperplasia) |
| 321 | Uterus_A_deno | 0.3284178 | 0.4536604 | 0.379592 | 0.24514027 | D50645_at | SDF2 |
| 322 | Uterus_A_deno | 0.3283114 | 0.45335351 | 0.379519 | 0.24498405 | RC_AA1612 92_s_at | Interferon, alpha-inducible protein 27 |
| 323 | Uterus_A_deno | 0.3280039 | 0.4532845 | 0.379276 | 0.24476415 | L37347_at | NRAMP2 Natural resistance-associated macrophage protein 2 |
| 324 | Uterus_A_deno | 0.3275977 | 0.4529636 | 0.379065 | 0.24466961 | U86602_at | Nucleolar protein p40 mRNA |
| 325 | Uterus_A_deno | 0.3269334 | 0.4529371 | 0.37904 | 0.24453083 | D87292_at | Rhodanese |
| 326 | Uterus_A_deno | 0.3268973 | 0.452558 | 0.37904 | 0.24430916 | X79204_at | SCA1 Ataxin 1 |
| 327 | Uterus_A_deno | 0.3264969 | 0.4522962 | 0.378937 | 0.24416241 | U50330_at | BMP1 Bone morphogenetic protein 1 |
| 328 | Uterus_A_deno | 0.3261698 | 0.4522531 | 0.378848 | 0.24404605 | L76702_at | Protein phosphatase 2A 74 kDa regulatory subunit (delta or B" subunit) |
| 329 | Uterus_A_deno | 0.325877 | 0.4517606 | 0.378592 | 0.24384515 | X52947_at | GJA1 Cardiac gap junction protein |
| 330 | Uterus_A_deno | 0.3253962 | 0.451715 | 0.378352 | 0.24366722 | U35139_at | NECDIN related protein mRNA |

FIG. 14R

| | | | | | |
|---|---|---|---|---|---|
| 331 | Uterus_A_deno | 0.3249705 | 0.4516403 | 0.378289 | 0.24358681 | D84361_at | P52 and p64 isoforms of N-Shc |
| 332 | Uterus_A_deno | 0.3242988 | 0.4515868 | 0.378083 | AC002115_r na2_at | F25451_2 gene extracted from Human DNA from overlapping chromosome 19 cosmids R31396, F25451, and R31076 containing COX6B and UPKA, genomic sequence |
| 333 | Uterus_A_deno | 0.3236986 | 0.4515263 | 0.377919 | 0.24339214 X60673_rna 1_at | AK3 mRNA for adenylate kinase 3 |
| 334 | Uterus_A_deno | 0.323598 | 0.4512817 | 0.377855 | 0.24331963 U59914_at | Chromosome 15 Mad homolog Smad6 mRNA |
| 335 | Uterus_A_deno | 0.3230597 | 0.4510961 | 0.377426 | 0.24318363 D14520_at | GC-Box binding protein BTEB2 |
| 336 | Uterus_A_deno | 0.3230261 | 0.450872 | 0.377287 | 0.24311537 U09953_at | RPL9 Ribosomal protein L9 |
| 337 | Uterus_A_deno | 0.3228814 | 0.4506879 | 0.377256 | 0.24284379 U41515_at | Deleted in split hand/split foot 1 (DSS1) mRNA |
| 338 | Uterus_A_deno | 0.3224655 | 0.450321 | 0.37703 | 0.24268913 U79241_at | Clone 23759 mRNA, partial cds |
| 339 | Uterus_A_deno | 0.3224182 | 0.4501603 | 0.376843 | 0.24238089 S80562_at | CNN3 Calponin 3, acidic |
| 340 | Uterus_A_deno | 0.3222949 | 0.4500964 | 0.376777 | 0.2422535 HG2197-HT2267_s_a t | Collage, Type Vii, Alpha 1 |
| 341 | Uterus_A_deno | 0.3222534 | 0.4499819 | 0.376495 | 0.24220291 U82108_s_a t | SIP-1 mRNA |
| 342 | Uterus_A_deno | 0.3222534 | 0.449921 | 0.376491 | 0.24200976 U82108_s_a t-2 | Solute carrier family 9 (sodium/hydrogen exchanger), isoform 3 regulatory factor 2 |
| 343 | Uterus_A_deno | 0.3218622 | 0.4496649 | 0.376375 | 0.24173036 U65785_at | 150 kDa oxygen-regulated protein ORP150 mRNA |
| 344 | Uterus_A_deno | 0.3213359 | 0.4495851 | 0.37634 | 0.24150029 AD000684_c ds1_at | LISCH7 gene (liver-specific bHLH-Zip transcription factor) extracted from Homo sapiens DNA from chromosome 19-cosmid R30879 containing USF2, genomic sequence |
| 345 | Uterus_A_deno | 0.3212643 | 0.4495544 | 0.376289 | 0.24139899 D49489_at | Protein disulfide isomerase-related protein P5 |
| 346 | Uterus_A_deno | 0.320374 | 0.4493822 | 0.376224 | 0.24126476 RC_AA4497 18_at | EST: zx09b07.s1 Soares total fetus Nb2HF8 9w Homo sapiens cDNA clone 785941 3', mRNA sequence. (from Genbank) |
| 347 | Uterus_A_deno | 0.3199958 | 0.449273 | 0.376102 | 0.2411686 U09550_at | Oviductal glycoprotein mRNA |
| 348 | Uterus_A_deno | 0.3198461 | 0.4487265 | 0.375982 | 0.24103151 D85418_at | Phosphatidylinositol-glycan-class C (PIG-C) |

FIG. 14S

| | | | | | |
|---|---|---|---|---|---|
| 349 | Uterus_A_deno | 0.319664 | 0.4486223 | 0.375716 | 0.24092479 | AA010324_a_t | Zi09c03.r1 Soares fetal liver spleen 1NFLS S1 Homo sapiens cDNA clone 430276 5', mRNA sequence. (from Genbank) |
| 350 | Uterus_A_deno | 0.319585 | 0.4485313 | 0.375704 | 0.24059117 | M55621_at | MGAT1 N-acetylglucosaminyltransferase I |
| 351 | Uterus_A_deno | 0.3194803 | 0.4484961 | 0.375632 | 0.24051295 | D26362_at | KIAA0043 gene |
| 352 | Uterus_A_deno | 0.319375 | 0.4484718 | 0.375542 | 0.24036835 | X65633_at | ACTH-R gene for adrenocorticotropic hormone receptor |
| 353 | Uterus_A_deno | 0.3193633 | 0.4483939 | 0.375487 | 0.24014501 | D86969_at | KIAA0215 gene |
| 354 | Uterus_A_deno | 0.319358 | 0.4480884 | 0.375282 | 0.23999971 | U28386_at | RCH1 RAG (recombination activating gene) cohort 1 |
| 355 | Uterus_A_deno | 0.3184474 | 0.4479365 | 0.3751 | 0.23992673 | D42063_at | RanBP2 (Ran-binding protein 2) |
| 356 | Uterus_A_deno | 0.3182724 | 0.4475956 | 0.375024 | 0.23975044 | U60808_s_a_t | CDP-diacylglycerol synthase (CDS) mRNA |
| 357 | Uterus_A_deno | 0.3180091 | 0.4475429 | 0.374935 | 0.23956417 | X74801_at | T-COMPLEX PROTEIN 1, GAMMA SUBUNIT |
| 358 | Uterus_A_deno | 0.3179981 | 0.4472666 | 0.374915 | 0.23940325 | M10321_s_a_t | VON WILLEBRAND FACTOR PRECURSOR |
| 359 | Uterus_A_deno | 0.3169152 | 0.4468046 | 0.374913 | 0.23922215 | HG2604-HT2700_at | Pan-2 |
| 360 | Uterus_A_deno | 0.3166372 | 0.44668311 | 0.374809 | 0.23907527 | D63874_at | HMG1 High-mobility group (nonhistone chromosomal) protein 1 |
| 361 | Uterus_A_deno | 0.3165043 | 0.44461813 | 0.374809 | 0.23887782 | HG2279-HT2375_at | Triosephosphate Isomerase |
| 362 | Uterus_A_deno | 0.3164686 | 0.4460278 | 0.374463 | 0.23879078 | X01038_rna1_s_at | Fetal gene for apolipoprotein AI precursor |
| 363 | Uterus_A_deno | 0.3164475 | 0.4460184 | 0.37427 | 0.2386381 | U52522_at | Arfaptin 2, putative target protein of ADP-ribosylation factor, mRNA |
| 364 | Uterus_A_deno | 0.3164171 | 0.4458409 | 0.374163 | 0.23852523 | M77698_at | YY1 YY1 transcription factor |
| 365 | Uterus_A_deno | 0.3162109 | 0.4458009 | 0.374067 | 0.23837909 | M35878_at | INSULIN-LIKE GROWTH FACTOR BINDING PROTEIN 3 PRECURSOR |
| 366 | Uterus_A_deno | 0.313632 | 0.4456559 | 0.374018 | 0.23816937 | U85611_at | Snk interacting protein 2-28 mRNA |
| 367 | Uterus_A_deno | 0.3134979 | 0.4455278 | 0.373949 | 0.23811185 | U37690_at | RNA polymerase II subunit (hsRPB10) mRNA |
| 368 | Uterus_A_deno | 0.3134503 | 0.4450367 | 0.373859 | 0.2378677 | D83032_at | Nuclear protein, NP220 |

FIG. 14T

| | | | | | |
|---|---|---|---|---|---|
| 369 | Uterus_A_deno | 0.3132919 | 0.4449785 | 0.373587 | 0.23774242 | Y09305_at | Protein kinase, Dyrk4, partial |
| 370 | Uterus_A_deno | 0.3132757 | 0.4449585 | 0.373442 | 0.23768234 | U19495_s_at | Intercrine-alpha (hIRH) mRNA |
| 371 | Uterus_A_deno | 0.3131782 | 0.4446946 | 0.373256 | 0.23750801 | X99920_at | S100 calcium-binding protein A13 |
| 372 | Uterus_A_deno | 0.3130562 | 0.4443128 | 0.373102 | 0.23729916 | M83738_at | PTPN9 Protein tyrosine phosphatase, non-receptor type 9 |
| 373 | Uterus_A_deno | 0.3129298 | 0.4441189 | 0.372999 | 0.2372462 | D86549_at | P97 homologous protein, partial cds |
| 374 | Uterus_A_deno | 0.3126976 | 0.4440747 | 0.372925 | 0.23715195 | Z21507_at | EEF1D Eukaryotic translation elongation factor 1 delta (guanine nucleotide exchange protein) |
| 375 | Uterus_A_deno | 0.3124268 | 0.4440436 | 0.372856 | 0.23690297 | D38555_at | KIAA0079 gene |
| 376 | Uterus_A_deno | 0.3119838 | 0.4439238 | 0.372554 | 0.23676604 | X16560_at | COX7C Cytochrome c oxidase VIIc subunit |
| 377 | Uterus_A_deno | 0.3117394 | 0.4436725 | 0.372543 | 0.23663512 | U96781_cds1_at | ATP2A1 gene (Ca2+ ATPase of fast-twitch skeletal muscle sarcoplasmic reticulum, neonatal isoform) extracted from Human Ca2+ ATPase of fast-twitch skeletal muscle sarcoplasmic reticulum adult and neonatal isoforms (ATP2A1) gene |
| 378 | Uterus_A_deno | 0.3114388 | 0.4435158 | 0.372542 | 0.23637944 | HG2810-HT2921_at | Homeotic Protein PI2 |
| 379 | Uterus_A_deno | 0.3112756 | 0.443503 | 0.372322 | 0.23630428 | D14662_at | KIAA0106 gene |
| 380 | Uterus_A_deno | 0.3109515 | 0.4434244 | 0.372216 | 0.23615633 | X55740_at | NT5 5' nucleotidase (CD73) |
| 381 | Uterus_A_deno | 0.3106888 | 0.4434243 | 0.372184 | 0.23603478 | X07979_at | ITGB1 Integrin, beta 1 (fibronectin receptor, beta polypeptide, antigen CD29 includes MDF2, MSK12) |
| 382 | Uterus_A_deno | 0.3105853 | 0.4433298 | 0.371859 | 0.23596144 | RC_AA135185_at | EST: zo27a05.s1 Stratagene colon (#937204) Homo sapiens cDNA clone 588080 3', mRNA sequence. (from Genbank) |
| 383 | Uterus_A_deno | 0.310385 | 0.4433153 | 0.371766 | 0.23585297 | D38549_at | KIAA0068 gene, partial cds |
| 384 | Uterus_A_deno | 0.3103142 | 0.4432471 | 0.371539 | 0.23583385 | S80343_at | RARS Arginyl-tRNA synthetase |
| 385 | Uterus_A_deno | 0.3098956 | 0.4432471 | 0.371505 | 0.23558366 | RC_AA454745_at | EST: zx77e03.s1 Soares ovary tumor NbHOT Homo sapiens cDNA clone 809788 3' similar to contains Alu repetitive element; mRNA sequence. (from Genbank) |
| 386 | Uterus_A_deno | 0.309578 | 0.4431233 | 0.371259 | 0.23546126 | U41654_at | RagA protein |

FIG. 14U

| | | | | | |
|---|---|---|---|---|---|
| 387 | Uterus_A deno | 0.3092669 | 0.4430744 | 0.371156 | 0.23524748 | D16532_at | VLDLR Very low density lipoprotein receptor |
| 388 | Uterus_A deno | 0.3088878 | 0.4430103 | 0.371114 | 0.23511226 | GMCSF_at | No description for gene: GMCSF |
| 389 | Uterus_A deno | 0.3088586 | 0.4428861 | 0.370909 | 0.23492418 | RC_AA4060 54_at | EST: zu65a10.s1 Soares testis NHT Homo sapiens cDNA clone 742842 3', mRNA sequence. (from Genbank) |
| 390 | Uterus_A deno | 0.3087997 | 0.4428766 | 0.370874 | 0.2348472 | AA009826_a t | EST: ze82b02.r1 Soares fetal heart NbHH19W Homo sapiens cDNA clone 365451 5', mRNA sequence. (from Genbank) |
| 391 | Uterus_A deno | 0.3075095 | 0.4427666 | 0.370486 | 0.23478754 | HG417-HT417_s_at | Cathepsin B |
| 392 | Uterus_A deno | 0.3074018 | 0.442739 | 0.370318 | 0.23456089 | M34344_at | ITGA2B Integrin, alpha 2b (platelet glycoprotein IIb of IIb/IIIa complex, antigen CD41B) |
| 393 | Uterus_A deno | 0.3073979 | 0.442721 | 0.370079 | 0.23442553 | D00763_at | GAPD Glyceraldehyde-3-phosphate dehydrogenase |
| 394 | Uterus_A deno | 0.3072291 | 0.4426495 | 0.370008 | 0.23429397 | X59434_at | TST Thiosulfate sulfurtransferase (rhodanese) |
| 395 | Uterus_A deno | 0.3070417 | 0.4426138 | 0.36979 | 0.2341576 | D49387_at | NADP dependent leukotriene b4 12-hydroxydehydrogenase, partial cds |
| 396 | Uterus_A deno | 0.3069941 | 0.4425674 | 0.369777 | 0.23400204 | M91083_at | DNA-binding protein (HRC1) mRNA |
| 397 | Uterus_A deno | 0.3059313 | 0.4424902 | 0.369695 | 0.23388658 | U42408_at | Ladinin (LAD) mRNA |
| 398 | Uterus_A deno | 0.3058104 | 0.4419999 | 0.369326 | 0.2338644 | RC_AA4364 71_at | EST: zv08e05.s1 Soares NhHMPu S1 Homo sapiens cDNA clone 753056 3', mRNA sequence. (from Genbank) |
| 399 | Uterus_A deno | 0.3057342 | 0.4419858 | 0.369159 | 0.23367755 | X95240_s_a t | Cysteine-rich secretory protein-3 |
| 400 | Uterus_A deno | 0.3049663 | 0.4419595 | 0.368907 | 0.233571 | L44538_at | EST: Homo sapiens thymus mRNA (randomly primed, normalized), single-pass sequence, mRNA sequence. (from Genbank) |
| 401 | Uterus_A deno | 0.3036065 | 0.4417441 | 0.368834 | 0.23350069 | D83260_s_a t | HXC-26 mRNA |
| 402 | Uterus_A deno | 0.3032684 | 0.4416245 | 0.368779 | 0.23330177 | M57730_at | EPH-RELATED RECEPTOR TYROSINE KINASE LIGAND 1 PRECURSOR |
| 403 | Uterus_A deno | 0.3030933 | 0.4416104 | 0.368694 | 0.233112435 | AA459542_s _at | Regulatory factor X-associated ankyrin-containing protein |
| 404 | Uterus_A deno | 0.3025794 | 0.4415439 | 0.368437 | 0.23291077 | L07033_at | HMGCL 3-hydroxymethyl-3-methylglutaryl-Coenzyme A lyase (hydroxymethylglutaricaciduria) |
| 405 | Uterus_A deno | 0.3025116 | 0.4415279 | 0.368408 | 0.232675 | Z49269_at | Chemokine HCC-1 |

FIG. 14V

| | | | | |
|---|---|---|---|---|
| 406 | Uterus_A_deno | 0.3024692 | 0.4414794 | 0.368154 | 0.23256662 | U30313_at | Diadenosine tetraphosphatase mRNA |
| 407 | Uterus_A_deno | 0.3021389 | 0.4414436 | 0.368094 | 0.23243715 | L04733_at | KINESIN LIGHT CHAIN |
| 408 | Uterus_A_deno | 0.3017629 | 0.4413044 | 0.367995 | 0.23237877 | U94832_at | KH type splicing regulatory protein KSRP mRNA |
| 409 | Uterus_A_deno | 0.3017367 | 0.4411463 | 0.367898 | 0.23224539 | X51441_at | SERUM AMYLOID A PROTEIN PRECURSOR |
| 410 | Uterus_A_deno | 0.3017026 | 0.4411463 | 0.367797 | 0.2320818 | L22647_s_at | Prostaglandin E receptor 1 (subtype EP1), 42kD |
| 411 | Uterus_A_deno | 0.3016791 | 0.4410265 | 0.367663 | 0.23198555 | U33286_at | Chromosome segregation gene homolog CAS mRNA |
| 412 | Uterus_A_deno | 0.3015491 | 0.4409984 | 0.367612 | 0.23177078 | U48807_at | Dual specific protein phosphatase mRNA |
| 413 | Uterus_A_deno | 0.3014864 | 0.4408862 | 0.367598 | 0.23162402 | M60922_at | Surface antigen mRNA |
| 414 | Uterus_A_deno | 0.3011269 | 0.4407882 | 0.367447 | 0.23149961 | H61361_s_at | Immunoglobulin superfamily containing leucine-rich repeat |
| 415 | Uterus_A_deno | 0.3007341 | 0.4407098 | 0.36725 | 0.23141015 | AF000234_a_t | P2x purinoceptor mRNA |
| 416 | Uterus_A_deno | 0.3003851 | 0.4405996 | 0.367212 | 0.23138271 | M32053_at | H19 RNA gene |
| 417 | Uterus_A_deno | 0.3003795 | 0.4404657 | 0.36715 | 0.2311929 | U78190_rna1_at | GTP cyclohydrolase I feedback regulatory protein gene |
| 418 | Uterus_A_deno | 0.3000679 | 0.4403853 | 0.36709 | 0.23111738 | X91249_at | WHITE PROTEIN HOMOLOG |
| 419 | Uterus_A_deno | 0.3000638 | 0.440361 | 0.36694 | 0.23103131 | U33147_at | Mammaglobin mRNA |
| 420 | Uterus_A_deno | 0.2997915 | 0.44034325 | 0.366922 | 0.23085783 | U75370_at | Mitochondrial RNA polymerase mRNA, nuclear gene encoding mitochondrial protein |
| 421 | Uterus_A_deno | 0.2997595 | 0.4400919 | 0.366808 | 0.23081134 | X54326_at | MULTIFUNCTIONAL AMINOACYL-TRNA SYNTHETASE |
| 422 | Uterus_A_deno | 0.299703 | 0.4400919 | 0.366468 | 0.2307061 | M77016_at | TMOD Tropomodulin |
| 423 | Uterus_A_deno | 0.2996863 | 0.4400916 | 0.366457 | 0.2304516 | U84573_at | Lysyl hydroxylase isoform 2 (PLOD2) mRNA |
| 424 | Uterus_A_deno | 0.2996515 | 0.4400395 | 0.366299 | 0.23028168 | U60319_at | HLA-H MHC protein HLA-H (hereditary haemochromatosis) |
| 425 | Uterus_A_deno | 0.2993916 | 0.4399439 | 0.366274 | 0.23024854 | M64497_at | APOLIPOPROTEIN AI REGULATORY PROTEIN-1 |

FIG. 14W

| | | | | | |
|---|---|---|---|---|---|
| 426 | Uterus_A deno | 0.2991064 | 0.4399162 | 0.36622 | 0.230137793 | RC_AA2332 57_at | Transforming growth factor beta 1 induced transcript 1 |
| 427 | Uterus_A deno | 0.2990786 | 0.4397017 | 0.366108 | 0.229932 | M32879_at | CYP11B1 Cytochrome P450 11 beta |
| 428 | Uterus_A deno | 0.2981855 | 0.439625 | 0.365865 | 0.229761169 | X15187_at | TRA1 Homologue of mouse tumor rejection antigen gp96 |
| 429 | Uterus_A deno | 0.2981116 | 0.4396184 | 0.365784 | 0.229629955 | U68494_at | Hbc647 mRNA sequence |
| 430 | Uterus_A deno | 0.2980832 | 0.4391629 | 0.3655689 | 0.229583684 | Z25821_rna 1_s_at | Dodecenoyl-Coenzyme A delta isomerase (3,2 trans-enoyl-Coenzyme A isomerase) |
| 431 | Uterus_A deno | 0.2980207 | 0.438918 | 0.365606 | 0.229509164 | AB001325_a t | AQP3 Aquaporin 3 |
| 432 | Uterus_A deno | 0.2979845 | 0.4387482 | 0.365586 | 0.229923166 | X07767_at | PRKACA Protein kinase, cAMP-dependent, catalytic, alpha |
| 433 | Uterus_A deno | 0.2978371 | 0.4387255 | 0.365414 | 0.22910094 | D13634_at | KIAA0009 gene |
| 434 | Uterus_A deno | 0.297305 | 0.4384107 | 0.365052 | 0.22900726 | X13916_at | LDL-receptor related protein |
| 435 | Uterus_A deno | 0.2971269 | 0.4383769 | 0.364907 | 0.228889222 | Z80777_at | H2A/k gene |
| 436 | Uterus_A deno | 0.2970312 | 0.4382743 | 0.364553 | 0.228881934 | D86956_at | KIAA0201 gene |
| 437 | Uterus_A deno | 0.2969605 | 0.4381124 | 0.364552 | 0.228862452 | U14550_at | Sialyltransferase SThM (sthm) mRNA |
| 438 | Uterus_A deno | 0.2966619 | 0.4377558 | 0.364335 | 0.2285323 | U89505_at | Hlark mRNA |
| 439 | Uterus_A deno | 0.2962874 | 0.4369476 | 0.364117 | 0.228444386 | M89470_s_a t | PAX2 Paired box homeotic gene 2 |
| 440 | Uterus_A deno | 0.2962253 | 0.4367364 | 0.364032 | 0.2283235 | U13369_at | Ribosomal DNA complete repeating unit |
| 441 | Uterus_A deno | 0.2962041 | 0.4366629 | 0.363854 | 0.2282466 | U13991_at | TATA-binding protein associated factor 30 kDa subunit (tafII30) mRNA |
| 442 | Uterus_A deno | 0.2960017 | 0.436625 | 0.363536 | 0.2280918 | U56418_at | Lysophosphatidic acid acyltransferase-beta mRNA |
| 443 | Uterus_A deno | 0.2959577 | 0.4361742 | 0.363456 | 0.22799143 | X16665_at | HOXB2 Homeo box B2 |
| 444 | Uterus_A deno | 0.2954874 | 0.4361716 | 0.36343 | 0.22783183 | AF001900_a t | Secreted frizzled-related protein 1 |
| 445 | Uterus_A deno | 0.2953545 | 0.4361492 | 0.363421 | 0.22774851 | L40391_at | (clone s153) mRNA fragment |

FIG. 14X

| | | | | |
|---|---|---|---|---|
| 446 | Uterus_A deno | 0.2951211 | 0.4360268 | 0.363283 | 0.22761446 | W27993_at | EST: 43e1 Human retina cDNA randomly primed sublibrary Homo sapiens cDNA, mRNA sequence.: (from Genbank) |
| 447 | Uterus_A deno | 0.2948279 | 0.4360268 | 0.363267 | 0.22273876 | R33301_at | EST: yh81g01.r1 Homo sapiens cDNA clone 136176 5' similar to contains MSR1 repetitive element.: (from Genbank) |
| 448 | Uterus_A deno | 0.2947705 | 0.4359609 | 0.363237 | 0.22726029 | Z69043_s_at | mRNA translocon-associated protein delta subunit precursor |
| 449 | Uterus_A deno | 0.2944394 | 0.4358437 | 0.363169 | 0.22710069 | HG3242-HT4231_s_a_t | Calcium Channel, Voltage-Gated, Alpha 1e Subunit, Alt. Splice 3 |
| 450 | Uterus_A deno | 0.2944256 | 0.4357618 | 0.363146 | 0.22701234 | D89667_at | C-myc binding protein |
| 451 | Uterus_A deno | 0.2934274 | 0.4357099 | 0.363121 | 0.22692072 | M98343_at | Amplaxin (EMS1) mRNA |
| 452 | Uterus_A deno | 0.2930351 | 0.435524 | 0.363116 | 0.22685548 | D84294_at | TPRD |
| 453 | Uterus_A deno | 0.2928565 | 0.4351829 | 0.362707 | 0.22678378 | D28137_at | RPS11 Ribosomal protein S11 |
| 454 | Uterus_A deno | 0.2926317 | 0.4351318 | 0.362705 | 0.22662352 | U68566_at | HS1 binding protein HAX-1 mRNA, nuclear gene encoding mitochondrial protein |
| 455 | Uterus_A deno | 0.2924196 | 0.434964 | 0.362467 | 0.22646135 | HG3431-HT3616_s_a_t | Decorin, Alt. Splice 1 |
| 456 | Uterus_A deno | 0.2921097 | 0.4349208 | 0.362298 | 0.22628474 | X54489_rna1_at | Melanoma growth stimulatory activity (MGSA) |
| 457 | Uterus_A deno | 0.2920352 | 0.4348293 | 0.36224 | 0.22619678 | L76687_at-2 | Growth factor receptor-bound protein 14 |
| 458 | Uterus_A deno | 0.2920352 | 0.4348207 | 0.362107 | 0.22610872 | L76687_at | Grb14 mRNA |
| 459 | Uterus_A deno | 0.291668 | 0.4344747 | 0.362004 | 0.22587514 | X87342_at | Giant larvae homolog |
| 460 | Uterus_A deno | 0.2911482 | 0.4344587 | 0.361973 | 0.22579998 | Z35093_at | SURF1 Surfeit 1 |
| 461 | Uterus_A deno | 0.2908663 | 0.4344587 | 0.36181 | 0.22573127 | U51336_at | Inositol 1,3,4-trisphosphate 5/6-kinase mRNA |
| 462 | Uterus_A deno | 0.2902213 | 0.4342676 | 0.361697 | 0.22567737 | D38537_s_a_t | Protoporphyrinogen oxidase |
| 463 | Uterus_A deno | 0.289964 | 0.43423 | 0.361647 | 0.22547948 | X95586_at | PSMB5 Proteasome (prosome, macropain) subunit, beta type, 5 |
| 464 | Uterus_A deno | 0.2899492 | 0.4342046 | 0.361429 | 0.22543862 | X56494_at | PKM2 Pyruvate kinase, muscle |

FIG. 14Y

| | | | | | |
|---|---|---|---|---|---|
| 465 | Uterus_A deno | 0.2898663 | 0.4340635 | 0.225374197 Z11793_at | Selenoprotein P |
| 466 | Uterus_A deno | 0.2894121 | 0.4340261 | 0.361167 | 0.2252011|J04182_at | LAMP1 Lysosome-associated membrane protein 1 |
| 467 | Uterus_A deno | 0.2902282 | 0.4335746 | 0.361124 | 0.22511102 U09646_at | Carnitine palmitoyltransferase (CPT1) mRNA |
| 468 | Uterus_A deno | 0.2886999 | 0.4335316 | 0.361032 | 0.22249325 AA039806_a_t | Msh (Drosophila) homeo box homolog 1 (formerly homeo box 7) |
| 469 | Uterus_A deno | 0.2886791 | 0.4335316 | 0.360986 | 0.2249255 M11119_at | Endogenous retrovirus envelope region mRNA (PL1) |
| 470 | Uterus_A deno | 0.2881754 | 0.4334388 | 0.360814 | 0.22458471 Z68747_at | Imogen 38 |
| 471 | Uterus_A deno | 0.2878524 | 0.4331787 | 0.360799 | 0.22439732 U04847_at | Ini1 mRNA |
| 472 | Uterus_A deno | 0.2877404 | 0.433137 | 0.360665 | 0.22433487 L78132_at | Prostate carcinoma tumor antigen (pcta-1) mRNA |
| 473 | Uterus_A deno | 0.2875306 | 0.4331364 | 0.36066 | 0.22421539 X56681_s_a_t | JunD mRNA |
| 474 | Uterus_A deno | 0.2874659 | 0.4329076 | 0.360556 | 0.22413822 U32986_s_a_t | DDB1 Damage-specific DNA binding protein 1 (127 kD) |
| 475 | Uterus_A deno | 0.2872125 | 0.4324769 | 0.360522 | 0.22404896 RC_AA4046 09_s_at | EST: zt43h04.s1 Soares ovary tumor NbHOT Homo sapiens cDNA clone 725143 3', mRNA sequence. (from Genbank) |
| 476 | Uterus_A deno | 0.2868869 | 0.4321163 | 0.360287 | 0.22386107 U40282_at | Integrin-linked kinase (ILK) mRNA |
| 477 | Uterus_A deno | 0.2859086 | 0.4320048 | 0.360117 | 0.22383574 AD000092_c ds7_s_at | RAD23A gene (human RAD23A homolog) extracted from Homo sapiens DNA from chromosome 19p13.2 cosmids R31240, R30272 and R28549 containing the EKLF, GCDH, CRTC, and RAD23A genes, genomic sequence |
| 478 | Uterus_A deno | 0.2856298 | 0.4318539 | 0.359879 | 0.22371829 R56174_at | EST: yg91d04.r1 Homo sapiens cDNA clone 40987 5'. (from Genbank) |
| 479 | Uterus_A deno | 0.2855813 | 0.4317689 | 0.359874 | 0.22360732 Y00815_at | PTPRF Protein tyrosine phosphatase, receptor type, f polypeptide |
| 480 | Uterus_A deno | 0.28547 | 0.4317689 | 0.359608 | 0.2235196241 RC_AA0558_at | EST: zf20c08.s1 Soares fetal heart NbHH19W Homo sapiens cDNA clone 377486 3', mRNA sequence. (from Genbank) |
| 481 | Uterus_A deno | 0.2852781 | 0.4316954 | 0.359568 | 0.22336929 X75208_at | HEK2 mRNA for protein tyrosine kinase receptor |
| 482 | Uterus_A deno | 0.2847927 | 0.4316029 | 0.359553 | 0.22329307 L41668_rna1_at | UDP-Galactose 4 epimerase (GALE) gene |
| 483 | Uterus_A deno | 0.2845995 | 0.4314997 | 0.359516 | 0.22322224 U86070_at | PMM1 Phosphomannomutase |

FIG. 14Z

| | | | | | |
|---|---|---|---|---|---|
| 484 | Uterus_A deno | 0.2845324 | 0.4313016 | 0.359454 | 0.223101184 | M19961_at | COX5B Cytochrome c oxidase subunit Vb |
| 485 | Uterus_A deno | 0.2841438 | 0.4309928 | 0.359438 | 0.223048858 | D31887_at | KIAA0062 gene, partial cds |
| 486 | Uterus_A deno | 0.2839794 | 0.4307328 | 0.359248 | 0.222733396 | U72515_at | C3f mRNA |
| 487 | Uterus_A deno | 0.2838041 | 0.4305675 | 0.359248 | 0.222603290 | J03474_at | SERUM AMYLOID A PROTEIN PRECURSOR |
| 488 | Uterus_A deno | 0.2834567 | 0.430433 | 0.358861 | 0.222533384 | HG2755-HT2862_at | T-Plastin |
| 489 | Uterus_A deno | 0.2833406 | 0.4302736 | 0.358812 | 0.222436891 | HG3954-HT4224_s_at | Landsteiner-Wiener Blood Group Glycoprotein (Lw) (Gb:L27671) |
| 490 | Uterus_A deno | 0.2832195 | 0.4299765 | 0.358686 | 0.222264229 | RC_AA290991_s_at | EST: zt18g10.s1 Soares ovary tumor NbHOT Homo sapiens cDNA clone 713538 3', mRNA sequence. (from Genbank) |
| 491 | Uterus_A deno | 0.2832159 | 0.4299765 | 0.358633 | 0.222225547 | D87937_at | Alpha(1,2)fucosyltransferase, 5'UTR partial sequence |
| 492 | Uterus_A deno | 0.2831684 | 0.4293582 | 0.3585 | 0.2219732 | J03910_ma1_at | (clone 14VS) metallothionein-IG (MT1G) gene |
| 493 | Uterus_A deno | 0.2831166 | 0.4293129 | 0.358422 | 0.221942907 | U77594_at | Tazarotene-induced gene 2 (TIG2) mRNA |
| 494 | Uterus_A deno | 0.2826918 | 0.4290204 | 0.358257 | 0.221731330 | U33267_at | Glycine receptor beta subunit (GLRB) mRNA |
| 495 | Uterus_A deno | 0.2822928 | 0.4286917 | 0.358122 | 0.221674280 | U08096_at | Peripheral myelin protein-22 (PMP22) gene, non-coding exon 1B |
| 496 | Uterus_A deno | 0.2818125 | 0.4285328 | 0.357958 | 0.221545825 | Z14093_at | BCKDHA Branched chain keto acid dehydrogenase E1, alpha polypeptide (maple syrup urine disease) |
| 497 | Uterus_A deno | 0.2817415 | 0.4284139 | 0.357843 | 0.221389602 | RC_AA293568_at | EST: zi25h08.s1 Soares ovary tumor NbHOT Homo sapiens cDNA clone 714207 3', mRNA sequence. (from Genbank) |
| 498 | Uterus_A deno | 0.281605 | 0.4283401 | 0.357614 | 0.221274731 | X68733_ma_at | Alpha1-antichymotrypsin, exon 1 |
| 499 | Uterus_A deno | 0.2815501 | 0.4281761 | 0.357482 | 0.221148106 | RC_AA227906_at | EST: zr57d06.s1 Soares NbHMPu S1 Homo sapiens cDNA clone 667499 3', mRNA sequence. (from Genbank) |
| 500 | Uterus_A deno | 0.2803111 | 0.4280593 | 0.357412 | 0.221115176 | U49278_at | Putative DNA-binding protein mRNA, partial cds |
| 501 | Uterus_A deno | 0.2799788 | 0.4278757 | 0.357312 | 0.221068890 | U47621_at | Nucleolar autoantigen No55 mRNA |
| 502 | Uterus_A deno | 0.2799 | 0.4277323 | 0.357238 | 0.220984925 | RC_AA037357_f_at | EST: zc03c04.s1 Soares parathyroid tumor NbHPA Homo sapiens cDNA clone 321222 3' similar to contains Alu repetitive element; mRNA sequence. (from Genbank) |

FIG. 14A2

| | | | | | |
|---|---|---|---|---|---|
| 503 | Uterus_A_deno | 0.2797954 | 0.4277055 | 0.356966 | 0.22083832 | D25274_at | Randomly sequenced mRNA |
| 504 | Uterus_A_deno | 0.2797235 | 0.4275312 | 0.356919 | 0.22073737 | U22233_at | MTAP Methylthioadenosine phosphorylase |
| 505 | Uterus_A_deno | 0.279361 | 0.4274165 | 0.356732 | 0.22054973 | HG1869-HT1904_at | Male Enhanced Antigen |
| 506 | Uterus_A_deno | 0.2793272 | 0.4274165 | 0.356695 | 0.22048616 | X64594_at | ERYTHROCYTE PLASMA MEMBRANE 50 KD GLYCOPROTEIN |
| 507 | Uterus_A_deno | 0.2791519 | 0.4273974 | 0.356643 | 0.2202547 | L07493_at | RECA Replication protein A (E coli RecA homolog, RAD51 homolog) |
| 508 | Uterus_A_deno | 0.2788312 | 0.4272924 | 0.356595 | 0.22014561 | M88279_at | FKBP4 FK506-binding protein 4 (59kD) |
| 509 | Uterus_A_deno | 0.2786267 | 0.42726 | 0.356593 | 0.22013626 | L34600_at | INITIATION FACTOR IF-2, MITOCHONDRIAL PRECURSOR |
| 510 | Uterus_A_deno | 0.2784306 | 0.4270774 | 0.356395 | 0.22002916 | X69141_at | FARNESYL-DIPHOSPHATE FARNESYLTRANSFERASE |
| 511 | Uterus_A_deno | 0.2781857 | 0.4268785 | 0.356352 | 0.21991216 | M15353_at | EIF4E Eukaryotic translation initiation factor 4E |
| 512 | Uterus_A_deno | 0.2778782 | 0.4268214 | 0.356271 | 0.21982065 | U32944_at | Cytoplasmic dynein light chain 1 (hdlc1) mRNA |
| 513 | Uterus_A_deno | 0.2776918 | 0.4267844 | 0.35604 | 0.21979056 | L38951_at | Importin beta subunit mRNA |
| 514 | Uterus_A_deno | 0.2768742 | 0.4267413 | 0.35604 | 0.21964961 | D17516_at | PACAP receptor |
| 515 | Uterus_A_deno | 0.2767665 | 0.4266193 | 0.355878 | 0.21955003 | X66785_at | DBT Dihydrolipoamide branched chain transacylase (E2 component of branched chain keto acid dehydrogenase complex) |
| 516 | Uterus_A_deno | 0.2766471 | 0.426542 | 0.355802 | 0.21945575 | M11717_rna1_at | Heat shock protein (hsp 70) gene |
| 517 | Uterus_A_deno | 0.2764907 | 0.4265125 | 0.355705 | 0.2192977 | X15822_at | COX7A2 Cytochrome c oxidase VIIa subunit (liver specific) |
| 518 | Uterus_A_deno | 0.2764285 | 0.4264167 | 0.355598 | 0.21913551 | U31384_at | G protein gamma-11 subunit mRNA |
| 519 | Uterus_A_deno | 0.2760856 | 0.4263303 | 0.355581 | 0.21908528 | HG1800-HT1823_at | Ribosomal Protein S20 |
| 520 | Uterus_A_deno | 0.2757418 | 0.4256781 | 0.355574 | 0.21892498 | AA380393_at | EST: EST93352 Supt cells Homo sapiens cDNA 5' end, mRNA sequence. (from Genbank) |
| 521 | Uterus_A_deno | 0.2756682 | 0.425627 | 0.355367 | 0.2188031 | U15174_at | Nip3 (NIP3) mRNA |
| 522 | Uterus_A_deno | 0.2756592 | 0.4256174 | 0.355355 | 0.21868214 | L19605_at | ANX11 Annexin XI (56kD autoantigen) |

FIG. 14B2

| | | | | | |
|---|---|---|---|---|---|
| 523 | Uterus_A_deno | 0.275585 | 0.4254182 | 0.356352 | 0.2186341 | U53003_at | KNP-1a |
| 524 | Uterus_A_deno | 0.2754003 | 0.4253238 | 0.355232 | 0.2185015 2 | D79996_at | KIAA0174 gene |
| 525 | Uterus_A_deno | 0.2747127 | 0.4251089 | 0.355014 | 0.2183379 4 | M34182_at | CAMP-DEPENDENT PROTEIN KINASE, GAMMA-CATALYTIC SUBUNIT |
| 526 | Uterus_A_deno | 0.2746049 | 0.4250502 | 0.354693 | 0.21827225 | L37043_at | CSNK1E Casein kinase 1, epsilon |
| 527 | Uterus_A_deno | 0.2744762 | 0.4248196 | 0.354578 | 0.2181629 | K03498_xpt1_s_at | Pol protein from Human endogenous retrovirus HERV-K22 pol and envelope ORF region./ntype=DNA /annot=CDS |
| 528 | Uterus_A_deno | 0.2743953 | 0.4248104 | 0.354494 | 0.21808855 | U23430_s_a t | CCKAR Cholecystokinin A receptor |
| 529 | Uterus_A_deno | 0.2743616 | 0.4247392 | 0.354112 | 0.21794364 | U67934_at | 44.9 kDa protein C18B11 homolog gene, partial cds |
| 530 | Uterus_A_deno | 0.2742131 | 0.4247392 | 0.354273 | 0.21775778 | Z49989_at | Smoothelin |
| 531 | Uterus_A_deno | 0.2741227 | 0.4245836 | 0.35426 | 0.21765679 | U68879_at | Bcl-2 binding component 6 (bbc6) mRNA |
| 532 | Uterus_A_deno | 0.2740948 | 0.4245066 | 0.354161 | 0.21757987 | U68488_at | HTR7 5-hydroxytryptamine (serotonin) receptor 7 (adenylate cyclase-coupled) |
| 533 | Uterus_A_deno | 0.2740372 | 0.4244927 | 0.354054 | 0.21749592 | U34252_at | ALDH7 Aldehyde dehydrogenase 7 (NOTE: redefinition of symbol) |
| 534 | Uterus_A_deno | 0.273772 | 0.4244435 | 0.354054 | 0.21742027 | D45213_at | Homo sapiens mRNA for zinc finger protein, complete cds |
| 535 | Uterus_A_deno | 0.2734819 | 0.4243574 | 0.353961 | 0.21736336 | U62015_at | Cyr61 mRNA |
| 536 | Uterus_A_deno | 0.2734786 | 0.4243166 | 0.353913 | 0.21716398 | L27476_at | X104 mRNA |
| 537 | Uterus_A_deno | 0.2727045 | 0.4242801 | 0.353643 | 0.21705322 | L13744_at | AF-9 PROTEIN |
| 538 | Uterus_A_deno | 0.2724741 | 0.4241035 | 0.353609 | 0.21696998 | J03171_at | INTERFERON-ALPHA/BETA RECEPTOR ALPHA CHAIN PRECURSOR |
| 539 | Uterus_A_deno | 0.2723361 | 0.4240243 | 0.353578 | 0.2169383 | RC_AA4240 06_at | EST: zv79h09.s1 Soares total fetus Nb2HF8.9w Homo sapiens cDNA clone 759905 3' similar to WP:B0024.13 CE05157.; mRNA sequence. (from Genbank) |
| 540 | Uterus_A_deno | 0.2721309 | 0.4238304 | 0.353395 | 0.21676736 | U09579_at | CDKN1A Cyclin-dependent kinase inhibitor 1A (p21, Cip1) |
| 541 | Uterus_A_deno | 0.2718317 | 0.4238057 | 0.353252 | 0.21670492 | L07956_at | GBE1 Glucan (1,4-alpha-), branching enzyme 1 (glycogen branching enzyme, Andersen disease, glycogen storage disease type IV) |

FIG. 14C2

| | | | | | |
|---|---|---|---|---|---|
| 542 | Uterus_A_deno | 0.2714271 | 0.4237284 | 0.353227 | 0.216656726 | X04654_s_at | SNRP70 U1 snRNP 70K protein |
| 543 | Uterus_A_deno | 0.2713856 | 0.4236468 | 0.353132 | 0.216379310 | U70322_at | Transportin (TRN) mRNA |
| 544 | Uterus_A_deno | 0.271137 | 0.423574 | 0.353098 | 0.216272190 | U77456_at | Nucleosome assembly protein 2 mRNA |
| 545 | Uterus_A_deno | 0.2709395 | 0.423483 | 0.3528804 | 0.216117190 | M20777_at | , alpha-2 (VI) collagen |
| 546 | Uterus_A_deno | 0.270704 | 0.4233583 | 0.352744 | 0.216081920 | J03589_at | UBIQUITIN-LIKE PROTEIN GDX |
| 547 | Uterus_A_deno | 0.2705061 | 0.4233548 | 0.352632 | 0.215978680 | L49054_at | T(3;5)(q25.1;p34) fusion gene NPM-MLF1 mRNA |
| 548 | Uterus_A_deno | 0.2703614 | 0.4227634 | 0.352512 | 0.2159313 | M14328_s_at | ENO1 Enolase 1, (alpha) |
| 549 | Uterus_A_deno | 0.2699578 | 0.4227304 | 0.352192 | 0.215585877 | U58682_at | RPS28 Ribosomal protein S28 |
| 550 | Uterus_A_deno | 0.2699567 | 0.4227235 | 0.352192 | 0.215574046 | D31763_at | KIAA0065 gene, partial cds |
| 551 | Uterus_A_deno | 0.2696941 | 0.4226134 | 0.352116 | 0.215725730 | X67698_at | Tissue specific mRNA |
| 552 | Uterus_A_deno | 0.269311 | 0.4225569 | 0.352067 | 0.215679730 | RC_AA4638161_at | EST: zx97c05.s1 Soares NhHMPu S1 Homo sapiens cDNA clone 8116688 3' similar to SW:RB25_RABIT P46629 RAS-RELATED PROTEIN RAB-25. ;, mRNA sequence. (from Genbank) |
| 553 | Uterus_A_deno | 0.2688356 | 0.422502 | 0.352013 | 0.215570630 | L25880_s_at | Epoxide hydrolase 1, microsomal (xenobiotic) |
| 554 | Uterus_A_deno | 0.2688137 | 0.4224213 | 0.351914 | 0.215475430 | U47927_at | UBIQUITIN CARBOXYL-TERMINAL HYDROLASE T |
| 555 | Uterus_A_deno | 0.268597 | 0.4223568 | 0.351889 | 0.215331970 | X05855_at | EEF1G Translation elongation factor 1 gamma |
| 556 | Uterus_A_deno | 0.2683244 | 0.4223372 | 0.351782 | 0.215247511 | Z84718_cds1_at | GSTT1 gene extracted from Human DNA sequence from BAC 322B1 on chromosome 22q11.2-qter contains GSTT1, GSTT2 glutathione transferases 4E-binding protein 1 pseudogene, D-dopachrome tautomerase pseudogene ESTs and polymorphic CA repeat |
| 557 | Uterus_A_deno | 0.2681485 | 0.4222952 | 0.351759 | 0.215052910 | HG1078-HT1078_at | Lamin-Like Protein (Gb:M24732) |
| 558 | Uterus_A_deno | 0.2681193 | 0.4221923 | 0.351702 | 0.214997531 | M31520_rna1_s_at | Unknown protein gene extracted from Human ribosomal protein S24 mRNA |

FIG. 14D2

| | | | | | |
|---|---|---|---|---|---|
| 559 | Uterus_A_deno | 0.2680931 | 0.4221517 | 0.21491511 | U18018_at | ETV4 Ets variant gene 4 (E1A enhancer-binding protein, E1AF) |
| 560 | Uterus_A_deno | 0.2680175 | 0.4219514 | 0.2147938 | J04794_at | ALCOHOL DEHYDROGENASE |
| 561 | Uterus_A_deno | 0.2679596 | 0.4217643 | 0.2147124 | U00968_at | SREBP-1 mRNA |
| 562 | Uterus_A_deno | 0.2679467 | 0.4216982 | 0.21459487 | L27706_at | CCT6 Chaperonin containing T-complex subunit 6 |
| 563 | Uterus_A_deno | 0.2677929 | 0.42155668 | 0.21447521 | U02680_at | Protein tyrosine kinase mRNA |
| 564 | Uterus_A_deno | 0.2673985 | 0.4214301 | 0.21439157 | L38490_s_at | ARF4L ADP-ribosylation factor 4-like |
| 565 | Uterus_A_deno | 0.2673255 | 0.4212584 | 0.21421917 | X63358_at | mRNA KKIALRE for serine/threonine protein kinase |
| 566 | Uterus_A_deno | 0.2672976 | 0.4211393 | 0.21419382 | HG270-HT270_at | Lymphocyte Chemoattractant Factor |
| 567 | Uterus_A_deno | 0.2672949 | 0.4211275 | 0.21404296 | M99435_at | TRANSDUCIN-LIKE ENHANCER PROTEIN 1 |
| 568 | Uterus_A_deno | 0.2671263 | 0.421114 | 0.21398836 | K02765_at | COMPLEMENT C3 PRECURSOR |
| 569 | Uterus_A_deno | 0.2670027 | 0.4210816 | 0.21391523 | D43951_at | ATP SYNTHASE GAMMA CHAIN, MITOCHONDRIAL PRECURSOR |
| 570 | Uterus_A_deno | 0.2667579 | 0.4209127 | 0.21382193 | X53961_at | LTF Lactotransferrin |
| 571 | Uterus_A_deno | 0.2667247 | 0.4208286 | 0.21369071 | U43286_at | Selenophosphate synthetase 2 (SPS2) mRNA |
| 572 | Uterus_A_deno | 0.2664374 | 0.4207057 | 0.21353564 | X59543_at | RIBONUCLEOSIDE-DIPHOSPHATE REDUCTASE M1 CHAIN |
| 573 | Uterus_A_deno | 0.2664353 | 0.4206284 | 0.21342973 | R79750_at | Orphan nuclear hormone receptor |
| 574 | Uterus_A_deno | 0.2662248 | 0.4201897 | 0.21331818 | L34155_at-2 | Laminin, alpha 3 (nicein (150kD), kalinin (165kD), BM600 (150kD), epilegrin) |
| 575 | Uterus_A_deno | 0.2662248 | 0.4201707 | 0.2131184 | L34155_at | Laminin-related protein (LamA3) mRNA |
| 576 | Uterus_A_deno | 0.2660847 | 0.4200046 | 0.21306536 | D87446_at | KIAA0257 gene, partial cds |
| 577 | Uterus_A_deno | 0.2659003 | 0.4198795 | 0.21302578 | X89066_at | TRPC1 Transient receptor potential channel 1 |
| 578 | Uterus_A_deno | 0.2658926 | 0.4198719 | 0.21291442 | HG2507-HT2603_at | Potassium Channel, Voltage-Gated Kcnc1 |

FIG. 14E2

| | | | | | |
|---|---|---|---|---|---|
| 579 | Uterus_A_deno | 0.2658202 | 0.4198377 | 0.34964 | 0.21282695 | U67171_at | Selenoprotein W (selW) mRNA |
| 580 | Uterus_A_deno | 0.2657732 | 0.4196101 | 0.349455 | 0.212732 | X76105_at | DAP-1 mRNA |
| 581 | Uterus_A_deno | 0.2649265 | 0.4194946 | 0.349411 | 0.212267319 | X62083_s_at | RING3 PROTEIN |
| 582 | Uterus_A_deno | 0.264836 | 0.4194618 | 0.349288 | 0.21256402 | L25270_at | XE169 PROTEIN |
| 583 | Uterus_A_deno | 0.2648053 | 0.4193648 | 0.349227 | 0.212251966 | U31383_at | G protein gamma-10 subunit mRNA |
| 584 | Uterus_A_deno | 0.264574 | 0.4193594 | 0.349227 | 0.21235517 | J04501_at | GYS1 Glycogen synthase 1 (muscle) |
| 585 | Uterus_A_deno | 0.2644974 | 0.4193333 | 0.349035 | 0.2120827 | L06147_at | (clone SY11) golgin-95 mRNA |
| 586 | Uterus_A_deno | 0.2644895 | 0.4192634 | 0.349007 | 0.21205798 | U52840_at | Cri-du-chat region mRNA, clone CSA1 |
| 587 | Uterus_A_deno | 0.2641734 | 0.4192071 | 0.348987 | 0.21205539 | L25085_at | PROTEIN TRANSPORT PROTEIN SEC61 BETA SUBUNIT |
| 588 | Uterus_A_deno | 0.2638043 | 0.4191681 | 0.348983 | 0.2119637 | U21128_at | LUM Lumican |
| 589 | Uterus_A_deno | 0.2636656 | 0.4191681 | 0.34884 | 0.21184716 | Z56281_at | Interferon regulatory factor 3 |
| 590 | Uterus_A_deno | 0.2636525 | 0.4190968 | 0.34881 | 0.21170548 | HG3492-HT3686_at | Uncoupling Protein Ucp |
| 591 | Uterus_A_deno | 0.2635278 | 0.4188384 | 0.348783 | 0.21163805 | D50920_at | KIAA0130 gene |
| 592 | Uterus_A_deno | 0.2634213 | 0.4184268 | 0.348591 | 0.21163581 | U72514_at | C2f mRNA |
| 593 | Uterus_A_deno | 0.263129 | 0.4183771 | 0.348472 | 0.21144809 | Z15108_at | PRKCZ Protein kinase C, zeta |
| 594 | Uterus_A_deno | 0.2630199 | 0.4183332 | 0.348444 | 0.21138875 | J00277_at | (genomic clones lambda-[SK2-T2, HS578T]; cDNA clones RS-[3,4, 6]) c-Ha-ras1 proto-oncogene, complete coding sequence |
| 595 | Uterus_A_deno | 0.2628559 | 0.4183297 | 0.348396 | 0.21120284 | U18934_at | TYRO3 Receptor protein-tyrosine kinase sky |
| 596 | Uterus_A_deno | 0.2628134 | 0.4182341 | 0.348382 | 0.2111348 | U79751_at | Basic-leucine zipper nuclear factor (JEM-1) mRNA |
| 597 | Uterus_A_deno | 0.2625636 | 0.4180861 | 0.348353 | 0.211101585 | L39061_at | Transcription factor SL1 mRNA, partial cds |
| 598 | Uterus_A_deno | 0.2625419 | 0.4178532 | 0.348108 | 0.21108791 | HG1139-HT4910_at | Fk506-Binding Protein, Alt. Splice 2 |

FIG. 14F2

| | | | | | |
|---|---|---|---|---|---|
| 599 | Uterus_A deno | 0.2623431 | 0.4178353 | 0.348106 | 0.2107923 | X54941_at | CKS1 CDC28 protein kinase 1 |
| 600 | Uterus_A deno | 0.2622514 | 0.4178126 | 0.346098 | 0.21073449 | U78095_at | Placental bikunin mRNA |
| 601 | Uterus_A deno | 0.2620153 | 0.4177389 | 0.348006 | 0.21061045 | HG2788-HT2896_at | Calcyclin |
| 602 | Uterus_A deno | 0.2619094 | 0.4175922 | 0.347977 | 0.21050337 | J04152_rna1_s_at | M1S1 gene extracted from Human gastrointestinal tumor-associated antigen GA733-1 protein gene, clone 05516 |
| 603 | Uterus_A deno | 0.2617883 | 0.4175743 | 0.347748 | 0.2104121 | RC_AA4194 61_at | EST: zu99d05.s1 NCI_CGAP_GCB1 Homo sapiens cDNA clone IMAGE:746121 3', mRNA sequence. (from Genbank) |
| 604 | Uterus_A deno | 0.2616552 | 0.4174962 | 0.347449 | 0.21036696 | M31013_at | MYl!9 Myosin, heavy polypeptide 9, non-muscle |
| 605 | Uterus_A deno | 0.2612912 | 0.4174601 | 0.347378 | 0.21025482 | D84307_at | Phosphoethanolamine cytidylyltransferase |
| 606 | Uterus_A deno | 0.2610937 | 0.4173998 | 0.347358 | 0.21017759 | D86968_at | KIAA0213 gene, partial cds |
| 607 | Uterus_A deno | 0.2608421 | 0.4172757 | 0.347024 | 0.21009575 | U26032_at | Translation initiation factor eIF-2alpha mRNA, 3'UTR |
| 608 | Uterus_A deno | 0.260039 | 0.4170809 | 0.317013 | 0.2100078 | Z22548_at | Thiol-specific antioxidant protein mRNA |
| 609 | Uterus_A deno | 0.2601918 | 0.4169976 | 0.346992 | 0.20975152 | L36818_at | INPPL1 Inositol polyphosphate phosphatase-like protein 1 (51C protein) |
| 610 | Uterus_A deno | 0.2601779 | 0.4169285 | 0.346846 | 0.20966943 | HT1614_at | Protein Phosphatase 1, Alpha Catalytic Subunit |
| 611 | Uterus_A deno | 0.2595922 | 0.4168607 | 0.34657 | 0.209621791 | HG4334-HT4604_s_at | Glycogenin |
| 612 | Uterus_A deno | 0.2595041 | 0.4167566 | 0.346461 | 0.20953403 | M31627_at | X BOX BINDING PROTEIN-1 |
| 613 | Uterus_A deno | 0.2591497 | 0.4165642 | 0.346443 | 0.20938765 | L40380_at | Thyroid receptor interactor (TRIP11) mRNA, 3' end of cds |
| 614 | Uterus_A deno | 0.2589543 | 0.416486 | 0.34636 | 0.20929463 | D00017_at | ANX2 Annexin II (lipocortin II) |
| 615 | Uterus_A deno | 0.2587756 | 0.4162321 | 0.34622 | 0.20926517 | U46569_at | Aquaporin-5 (AQP5) gene |
| 616 | Uterus_A deno | 0.2583682 | 0.4162008 | 0.34603 | 0.20911497 | M10943_at | Metallothionein-1f gene (hMT-1f) |
| 617 | Uterus_A deno | 0.2582242 | 0.4161993 | 0.345788 | 0.20898302 | X75962_at | OX40L RECEPTOR PRECURSOR |

FIG. 14G2

| | | | | | |
|---|---|---|---|---|---|
| 618 | Uterus_A_deno | 0.2578333 | 0.4159587 | 0.345744 | 0.20887521 | U57911_at | Fetal brain (239FB) mRNA, from the WAGR region |
| 619 | Uterus_A_deno | 0.2578289 | 0.4159102 | 0.34551 | 0.20883551 | U22055_at | 100 kDa coactivator mRNA |
| 620 | Uterus_A_deno | 0.2577869 | 0.4159014 | 0.345443 | 0.20866163 | RC_AA0353 66_at | EST: zk26d12.s1 Soares pregnant uterus NbHPU Homo sapiens cDNA clone 471671 3', mRNA sequence. (from Genbank) |
| 621 | Uterus_A_deno | 0.2574125 | 0.4158571 | 0.345349 | 0.20855607 | U35048_at | TSC-22 protein mRNA |
| 622 | Uterus_A_deno | 0.257185 | 0.4156796 | 0.345224 | 0.20841019 | X80199_at | MLN51 mRNA |
| 623 | Uterus_A_deno | 0.2569321 | 0.4154275 | 0.345082 | 0.20836684 | L40027_at | Glycogen synthase kinase 3 mRNA |
| 624 | Uterus_A_deno | 0.2569108 | 0.4154163 | 0.34505 | 0.20825095 | D14822_at | Chimeric mRNA derived from AML1 gene and MTG8(ETO) gene, partial sequence |
| 625 | Uterus_A_deno | 0.2569098 | 0.4153165 | 0.344815 | 0.20813176 | Z29083_at | 5T4 gene for 5T4 Oncofetal antigen |
| 626 | Uterus_A_deno | 0.2567879 | 0.4149506 | 0.344791 | 0.20804895 | L24774_s_at | DCI Dodecenoyl-Coenzyme A delta isomerase (3,2 trans-enoyl-Coenzyme A isomerase) |
| 627 | Uterus_A_deno | 0.2563604 | 0.414668 | 0.344776 | 0.20791467 | D87455_at | KIAA0266 gene |
| 628 | Uterus_A_deno | 0.2563132 | 0.4144479 | 0.344729 | 0.20790617 | D45248_at | Proteasome activator hPA28 subunit beta |
| 629 | Uterus_A_deno | 0.2559661 | 0.4142088 | 0.344678 | 0.20788381 | L11353_at | NF2 Neurofibromin 2 (bilateral acoustic neuroma) |
| 630 | Uterus_A_deno | 0.2559184 | 0.4141757 | 0.344592 | 0.20774677 | U26710_at | Cbl-b mRNA |
| 631 | Uterus_A_deno | 0.2556659 | 0.4141395 | 0.344576 | 0.20763738 | X75252_at | PBP Prostatic binding protein |
| 632 | Uterus_A_deno | 0.2554102 | 0.4138413 | 0.344563 | 0.20748435 | M57703_s_a t | PMCH Pro-melanin-concentrating hormone |
| 633 | Uterus_A_deno | 0.2550506 | 0.4136742 | 0.344456 | 0.20742702 | M11353_at | EEF1G Translation elongation factor 1 gamma |
| 634 | Uterus_A_deno | 0.2550402 | 0.4135049 | 0.344356 | 0.20732033 | D80005_at | KIAA0183 gene, partial cds |
| 635 | Uterus_A_deno | 0.2550168 | 0.4134337 | 0.344282 | 0.20729733 | M65066_at | PRKAR1B Protein kinase, cAMP-dependent, regulatory, type I, beta |
| 636 | Uterus_A_deno | 0.2550134 | 0.413304 | 0.344206 | 0.20722334 | Y00281_at | RPN1 Ribophorin I |
| 637 | Uterus_A_deno | 0.2547998 | 0.41278 | 0.344153 | 0.20709082 | U68142_at | RalGDS-like 2 (RGL2) mRNA, partial cds |

FIG. 14H2

| | | | | | |
|---|---|---|---|---|---|
| 638 | Uterus_A deno | 0.2546377 | 0.4125558 | 0.34411 | 0.2069234 | U90914_at | Clone 23587 mRNA sequence |
| 639 | Uterus_A deno | 0.2544473 | 0.4125383 | 0.343995 | 0.2069172 | D42044_at | KIAA0090 gene, partial cds |
| 640 | Uterus_A deno | 0.2544405 | 0.4123448 | 0.343954 | 0.20680265 | L04656_at | Carbonic anhydrase-related protein VIII (CA8) mRNA, partial cds |
| 641 | Uterus_A deno | 0.2544229 | 0.4122883 | 0.343852 | 0.20664568 | X51521_at | VIL2 Villin 2 (ezrin) |
| 642 | Uterus_A deno | 0.2538336 | 0.4122883 | 0.343824 | 0.20659515 | D13413_rna 1_s_at | Tumor-associated 120 kDa nuclear protein p120, partial cds(carboxyl terminus) |
| 643 | Uterus_A deno | 0.2537045 | 0.4121573 | 0.343672 | 0.20650668 | J03824_at | UROS Uroporphyrinogen III synthase |
| 644 | Uterus_A deno | 0.2533985 | 0.4121376 | 0.343545 | 0.20639172 | M64788_at | RAP1GA1 RAP1, GTPase activating protein 1 |
| 645 | Uterus_A deno | 0.2529826 | 0.4117497 | 0.343459 | 0.20637465 | Z96810_at | DNA sequence from PAC 452H17 on chromosome X contains sodium and chloride-dependent glycine transporter 1 (GLYT-1) like, ESTs |
| 646 | Uterus_A deno | 0.2525482 | 0.4116872 | 0.343439 | 0.20626236 | U90905_at | Clone 23574 mRNA sequence |
| 647 | Uterus_A deno | 0.2520984 | 0.4116798 | 0.343396 | 0.20620517 | M94556_at | SSBP Single-stranded DNA-binding protein |
| 648 | Uterus_A deno | 0.2519337 | 0.4116798 | 0.343351 | 0.20606036 | J04456_at | LGALS1 Ubiquinol-cytochrome c reductase core protein II |
| 649 | Uterus_A deno | 0.2518845 | 0.4116021 | 0.343318 | 0.20592916 | M57710_at | LGALS3 Lectin, galactoside-binding, soluble, 3 (galectin 3) (NOTE: redefinition of symbol) |
| 650 | Uterus_A deno | 0.2518552 | 0.4115909 | 0.343197 | 0.20589109 | M13755_at | G1P2 Interferon, alpha-inducible protein (clone IFI-15K) |
| 651 | Uterus_A deno | 0.2517993 | 0.4115728 | 0.343179 | 0.20581552 | X86691_at | 218kD Mi-2 protein |
| 652 | Uterus_A deno | 0.2516725 | 0.4114385 | 0.343091 | 0.20570503 | X05299_at | CENPB Centromere protein B (80kD) |
| 653 | Uterus_A deno | 0.2511663 | 0.4114146 | 0.342987 | 0.20554873 | X02596_at | Bcr (breakpoint cluster region) gene in Philadelphia chromosome |
| 654 | Uterus_A deno | 0.2509293 | 0.4113905 | 0.342944 | 0.20548111 | M28713_at | NADH-CYTOCHROME B5 REDUCTASE |
| 655 | Uterus_A deno | 0.2508778 | 0.411289 | 0.342787 | 0.20536642 | X74874_rna 1_s_at | RNA polymerase II largest subunit gene extracted from H.sapiens gene for RNA pol II largest subunit, exon 1 |
| 656 | Uterus_A deno | 0.2507451 | 0.4112571 | 0.342761 | 0.20533037 | U83410_at | CUL-2 (cul-2) mRNA |

FIG. 14I2

| | | | | | |
|---|---|---|---|---|---|
| 657 | Uterus_A_deno | 0.2505027 | 0.4112431 | 0.342705 | 0.205311571 | U94592_at | Uncoupling protein homolog (UCPH) mRNA |
| 658 | Uterus_A_deno | 0.2504852 | 0.4111953 | 0.342575 | 0.205188886 | X86809_at | Major astrocytic phosphoprotein PEA-15 |
| 659 | Uterus_A_deno | 0.2504227 | 0.4111344 | 0.342862 | 0.204937562 | M92357_at | B94 PROTEIN |
| 660 | Uterus_A_deno | 0.2503917 | 0.4110905 | 0.342525 | 0.204875504 | U65579_at | Mitochondrial NADH dehydrogenase-ubiquinone Fe-S protein 8, 23 kDa subunit precursor (NDUFS8) nuclear mRNA encoding mitochondrial protein |
| 661 | Uterus_A_deno | 0.2503327 | 0.4110051 | 0.342445 | 0.204827386 | J00207_rna2_at | IFNA gene (interferon alpha-a) extracted from Human leukocyte interferon (leif) alpha-a gene |
| 662 | Uterus_A_deno | 0.2502797 | 0.4108851 | 0.34231 | 0.204668934 | M80783_at | B12 protein mRNA |
| 663 | Uterus_A_deno | 0.250184 | 0.4108338 | 0.342191 | 0.20457756 | U29175_at | Transcriptional activator hSNF2b |
| 664 | Uterus_A_deno | 0.2501272 | 0.4107993 | 0.342164 | 0.204507861 | RC_AA4904_at | EST: aa45a12.s1 Soares NhHMPu S1 Homo sapiens cDNA clone 823870 3', mRNA sequence. (from Genbank) |
| 665 | Uterus_A_deno | 0.2499178 | 0.4107896 | 0.342137 | 0.204455781 | X74929_s_at | KRT8 Keratin 8 |
| 666 | Uterus_A_deno | 0.2498905 | 0.4105617 | 0.341987 | 0.204299668 | D87024_at | Immunoglobulin lambda gene locus DNA, clone:92H4 |
| 667 | Uterus_A_deno | 0.249839 | 0.4104435 | 0.341978 | 0.204205502 | X05345_at | HARS Histidyl-tRNA synthetase |
| 668 | Uterus_A_deno | 0.2498355 | 0.4103316 | 0.341835 | 0.204099995 | X15880_at | COL6A1 Collagen, type VI, alpha 1 |
| 669 | Uterus_A_deno | 0.2495216 | 0.410291 | 0.341788 | 0.203941151 | U01160_at | Transmembrane 4 superfamily protein (SAS) mRNA |
| 670 | Uterus_A_deno | 0.2495123 | 0.4101844 | 0.341773 | 0.203877729 | X99728_at | NDUFV3 gene, exon 3 |
| 671 | Uterus_A_deno | 0.2491593 | 0.41015775 | 0.341508 | 0.20375377 | X97074_at | EEF2 Eukaryotic translation elongation factor 2 |
| 672 | Uterus_A_deno | 0.2491354 | 0.4100405 | 0.341441 | 0.203539641 | N89563_s_at | EST: HFBEST-40 Human fetal brain QBoqini2 Homo sapiens cDNA, mRNA sequence. (from Genbank) |
| 673 | Uterus_A_deno | 0.2486922 | 0.4100121 | 0.341392 | 0.203527386 | HG2147-HT2217_at | Mucin 3, Intestinal (Gb:M55405) |
| 674 | Uterus_A_deno | 0.2485079 | 0.4099067 | 0.341341 | 0.203499816 | HG4518-HT4921_r_at | Transcription Factor Btf3 Homolog (Gb:M90355) |
| 675 | Uterus_A_deno | 0.2485042 | 0.4098116 | 0.341262 | 0.203389808 | U89916_at | Putative OSP like protein mRNA, partial cds |

FIG. 14J2

| | | | | |
|---|---|---|---|---|
| 676 | Uterus_A_deno | 0.2484186 | 0.4097788 | 0.34116 | 0.2033716 | D38305_at | Tob |
| 677 | Uterus_A_deno | 0.2483445 | 0.4096659 | 0.341127 | 0.2033072 | M60614_at | WT1 Wilms tumor 1 |
| 678 | Uterus_A_deno | 0.2483443 | 0.4096152 | 0.341061 | 0.2031555 | D50922_at | KIAA0132 gene |
| 679 | Uterus_A_deno | 0.2481566 | 0.4095904 | 0.341047 | 0.2031367 | D42084_at | KIAA0094 gene, partial cds |
| 680 | Uterus_A_deno | 0.2480698 | 0.4095649 | 0.340946 | 0.2029222 | D14874_at | ADM Adrenomedullin |
| 681 | Uterus_A_deno | 0.2480122 | 0.4092398 | 0.340837 | 0.2029189 | AA004987_a_t | Homo sapiens HRIHFB2017 mRNA, partial cds |
| 682 | Uterus_A_deno | 0.2479959 | 0.4091134 | 0.34083 | 0.2028929 | X81003_at | HCG V mRNA |
| 683 | Uterus_A_deno | 0.2479685 | 0.4087214 | 0.340802 | 0.2028687 | U23070_at | Putative transmembrane protein (nma) mRNA |
| 684 | Uterus_A_deno | 0.2477644 | 0.4085421 | 0.340801 | 0.2027938 | M61176_at | BDNF Brain-derived neurotrophic factor |
| 685 | Uterus_A_deno | 0.2476759 | 0.4085347 | 0.34075 | 0.2025456 | M35851_s_a_t | AR Androgen receptor (dihydrotestosterone receptor; testicular feminization; spinal and bulbar muscular atrophy; Kennedy disease) |
| 686 | Uterus_A_deno | 0.2476614 | 0.4085268 | 0.340482 | 0.2024909 | AA137107_a_t | EST: z02a06.r1 Soares pregnant uterus NbHPU Homo sapiens cDNA clone 491122 5' similar to contains Alu repetitive element;, mRNA sequence. (from Genbank) |
| 687 | Uterus_A_deno | 0.2475609 | 0.408259 | 0.340387 | 0.202427 | D25248_at | Randomly sequenced mRNA |
| 688 | Uterus_A_deno | 0.2474507 | 0.4081624 | 0.340334 | 0.2023903 | S34389_at | HMOX2 Heme oxygenase (decycling) 2 |
| 689 | Uterus_A_deno | 0.2471866 | 0.4081178 | 0.3403 | 0.2023587 | U06631_at | IEF SSP 9502 mRNA |
| 690 | Uterus_A_deno | 0.2471129 | 0.408109 | 0.340285 | 0.2022660 | M36341_at | ARF4 ADP-ribosylation factor 4 |
| 691 | Uterus_A_deno | 0.2470499 | 0.4080699 | 0.340085 | 0.2021473 | L77886_at | Protein tyrosine phosphatase mRNA |
| 692 | Uterus_A_deno | 0.2469575 | 0.4080064 | 0.340005 | 0.2020316 | U85625_at | Ribonuclease 6 precursor |
| 693 | Uterus_A_deno | 0.246885 | 0.4078902 | 0.339905 | 0.2019161 | S74728_at | Antiquitin |
| 694 | Uterus_A_deno | 0.246218 | 0.4078534 | 0.339849 | 0.2018141 | M23114_at | ATP2A2 ATPase, Ca++ transporting, cardiac muscle, slow twitch 2 |

FIG. 14K2

| | | | | | |
|---|---|---|---|---|---|
| 695 | Uterus_A_deno | 0.2457927 | 0.4078249 | 0.339833 | 0.201733362 | J04173_at | PGAM1 Phosphoglycerate mutase 1 (brain) |
| 696 | Uterus_A_deno | 0.245791 | 0.4076308 | 0.339725 | 0.201160927 | D44466_at | Proteasome subunit p112 |
| 697 | Uterus_A_deno | 0.2457024 | 0.4076252 | 0.339718 | 0.201149745 | J03626_ma1_s_at | UMPS gene extracted from Human UMP synthase mRNA |
| 698 | Uterus_A_deno | 0.2451821 | 0.4075416 | 0.339676 | 0.201132491 | M24485_s_a_t | SAT Spermidine/spermine N1-acetyltransferase |
| 699 | Uterus_A_deno | 0.2451198 | 0.4072084 | 0.339456 | 0.201128925 | AA233236_a_t | Human clone p4betaGT/3 beta-1,4-galactosyltransferase mRNA, partial cds |
| 700 | Uterus_A_deno | 0.2449466 | 0.4071463 | 0.339307 | 0.201125899 | M29550_at | SERINE/THREONINE PROTEIN PHOSPHATASE 2B CATALYTIC SUBUNIT, BETA ISOFORM |
| 701 | Uterus_A_deno | 0.2448869 | 0.4070459 | 0.339267 | 0.201145707 | U12404_at | HSPB1 Heat shock 27kD protein 1 |
| 702 | Uterus_A_deno | 0.2448439 | 0.4070299 | 0.339235 | 0.20096983 | D87469_at | KIAA0279 gene, partial cds |
| 703 | Uterus_A_deno | 0.2446809 | 0.4070299 | 0.33905 | 0.20089798 | AA650016_a_t | EST: zx80d02.r1 Soares ovary tumor NbHOT Homo sapiens cDNA clone 8100051 5' similar to TR:G1020091 G1020091 NEUROPSIN. ;contains element LTR3 repetitive element ;, mRNA sequence. (from Genbank) |
| 704 | Uterus_A_deno | 0.2444632 | 0.4069985 | 0.338941 | 0.200084418 | M76378_at | FN1 Fibronectin 1 |
| 705 | Uterus_A_deno | 0.2439893 | 0.4067805 | 0.338838 | 0.200072708 | X78416_s_a_t | CSN1 Casein, alpha S1 |
| 706 | Uterus_A_deno | 0.2439373 | 0.4065297 | 0.338829 | 0.20071137 | U58046_s_a_t | KIAA0139 gene |
| 707 | Uterus_A_deno | 0.2436725 | 0.4061399 | 0.338755 | 0.2006228 | X71490_at | ATP6E ATPase, H+ transporting, lysosomal (vacuolar proton pump) 31kD |
| 708 | Uterus_A_deno | 0.2436445 | 0.4060523 | 0.338715 | 0.200577796 | M34057_at | LTBP1 Latent transforming growth factor beta binding protein 1 |
| 709 | Uterus_A_deno | 0.2434871 | 0.4059398 | 0.338673 | 0.200461787 | Z11899_s_at | POU5F1 Octamer binding protein 3 |
| 710 | Uterus_A_deno | 0.2433659 | 0.405756 | 0.338579 | 0.200309966 | U51432_at | Nuclear protein Skip mRNA |
| 711 | Uterus_A_deno | 0.2432338 | 0.405722 | 0.33844 | 0.20029211 | X85785_ma_1_at | DARC gene |
| 712 | Uterus_A_deno | 0.2430875 | 0.4055416 | 0.338424 | 0.200199995 | RC_AA0538 15_at | EST: ze25h09.s1 Soares fetal heart NbHH19W Homo sapiens cDNA clone 3600065 3', mRNA sequence. (from Genbank) |
| 713 | Uterus_A_deno | 0.2428401 | 0.40552 | 0.338289 | 0.200008457 | AB000460_a_t | mRNA, clone RES4-22A |

FIG. 14L2

| | | | | | |
|---|---|---|---|---|---|
| 714 | Uterus_A deno | 0.2424154 | 0.4049967 | 0.338116 | 0.20004942 | Y08682_rna 1_s_at | Carnitine palmitoyltransferase I type I |
| 715 | Uterus_A deno | 0.2423697 | 0.4049794 | 0.337872 | 0.19983758 | RC_AA6091 13_at | Homo sapiens mRNA, chromosome 1 specific transcript KIAA0503 |
| 716 | Uterus_A deno | 0.2419224 | 0.4049338 | 0.337824 | 0.19976324 | S65738_at | Actin depolymerizing factor [human, fetal brain, mRNA, 1452 nt] |
| 717 | Uterus_A deno | 0.2417723 | 0.4047661 | 0.337817 | 0.19967079 | M99979_at | PTGS1 Prostaglandin-endoperoxide synthase 1 (prostaglandin G/H synthase and cyclooxygenase) |
| 718 | Uterus_A deno | 0.2413999 | 0.4043337 | 0.337802 | 0.19956286 | J03278_at | PDGFRB Platelet-derived growth factor receptor, beta polypeptide |
| 719 | Uterus_A deno | 0.2409703 | 0.4043114 | 0.337776 | 0.19948545 | AA477978_s_at | Short-chain dehydrogenase/reductase 1 |
| 720 | Uterus_A deno | 0.2408781 | 0.4043111 | 0.337591 | 0.19943006 | AA292745_a t | EST: zt55h02.r1 Soares ovary tumor NbHOT Homo sapiens cDNA clone 726291 5' similar to TR:G984317 G984317 TRYPSIN-RELATED PROTEIN.; mRNA sequence. (from Genbank) |
| 721 | Uterus_A deno | 0.2403585 | 0.4041506 | 0.33754 | 0.19932517 | Z35402_rna 1_s_at | Gene encoding E-cadherin, exon 3 and joined CDS |
| 722 | Uterus_A deno | 0.2403563 | 0.4041416 | 0.337367 | 0.19930059 | L42572_at | Motor protein |
| 723 | Uterus_A deno | 0.2401321 | 0.4040065 | 0.337208 | 0.19921875 | D89052_at | Proton-ATPase-like protein |
| 724 | Uterus_A deno | 0.240064 | 0.4037657 | 0.337196 | 0.19912402 | L38941_at | RPL37 Ribosomal protein L37 |
| 725 | Uterus_A deno | 0.2400631 | 0.4037277 | 0.337097 | 0.19908763 | D86985_at | KIAA0232 gene |
| 726 | Uterus_A deno | 0.2399433 | 0.4035304 | 0.337026 | 0.19897778 | RC_AA1570 01_at | EST: zl19f07.s1 Soares pregnant uterus NbHPU Homo sapiens cDNA clone 502405 3', mRNA sequence. (from Genbank) |
| 727 | Uterus_A deno | 0.2396292 | 0.4033691 | 0.336926 | 0.19897367 | D79994_at | KIAA0172 gene, partial cds |
| 728 | Uterus_A deno | 0.239411 | 0.4033173 | 0.336914 | 0.19875854 | M19684_at | Alpha-1-antitrypsin-related protein gene, exons 3, 4 and 5 |
| 729 | Uterus_A deno | 0.2392891 | 0.4031409 | 0.336886 | 0.19874474 | U33632_at | Two P-domain K+ channel TWIK-1 mRNA |
| 730 | Uterus_A deno | 0.2389883 | 0.4029934 | 0.336761 | 0.19868517 | J04611_at | G22P1 Thyroid autoantigen 70kD (Ku antigen) |
| 731 | Uterus_A deno | 0.2389594 | 0.4028815 | 0.336745 | 0.19857195 | X57206_at | ITPKB Inositol 1,4,5-trisphosphate 3-kinase B |
| 732 | Uterus_A deno | 0.2384095 | 0.4028471 | 0.336633 | 0.19854063 | X86163_at | BDKRB2 Bradykinin receptor B2 |

FIG. 14M2

| | | | | | |
|---|---|---|---|---|---|
| Uterus_A_deno 733 | 0.2382978 | 0.4028134 | 0.336622 | 0.19852203 | D21090_at | XP-C repair complementing protein (p58/HHR23B) |
| Uterus_A_deno 734 | 0.2382975 | 0.4026919 | 0.336508 | 0.19836868 | X84709_at | Mediator of receptor-induced toxicity |
| Uterus_A_deno 735 | 0.2382906 | 0.4025623 | 0.336416 | 0.19821739 | Z50749_at | Sds22-like mRNA |
| Uterus_A_deno 736 | 0.237756 | 0.4022265 | 0.336315 | 0.19811869 | J03805_s_at | Phosphatase 2A mRNA, partial cds |
| Uterus_A_deno 737 | 0.2377442 | 0.4022201 | 0.336308 | 0.19802064 | D26598_at | Proteasome subunit HsC10-II |
| Uterus_A_deno 738 | 0.2372837 | 0.4021445 | 0.336276 | 0.19789927 | U41740_at | Golgin-245 mRNA |
| Uterus_A_deno 739 | 0.2365575 | 0.4020128 | 0.336135 | 0.1978727 | L29008_at | SORD Sorbitol dehydrogenase |
| Uterus_A_deno 740 | 0.2365354 | 0.4019688 | 0.33606 | 0.19781926 | D31417_at | EST: Human fetal-lung cDNA 5'-end sequence, mRNA sequence. (from Genbank) |
| Uterus_A_deno 741 | 0.2355048 | 0.4018727 | 0.33599 | 0.1976977 | U90878_at | LIM domain protein CLP-36 mRNA |
| Uterus_A_deno 742 | 0.2364722 | 0.401764 | 0.335974 | 0.19760236 | Y07566_at | Rit mRNA |
| Uterus_A_deno 743 | 0.236228 | 0.4014053 | 0.335891 | 0.19749716 | U94333_at | C1q/MBL/SPA receptor C1qR(p) mRNA |
| Uterus_A_deno 744 | 0.236228 | 0.4013044 | 0.335849 | 0.19748077 | U94333_at-2 | Human C1q/MBL/SPA receptor C1qR(p) mRNA, complete cds |
| Uterus_A_deno 745 | 0.2359193 | 0.4013027 | 0.335762 | 0.19743699 | J03060_at | GBA Glucosidase, beta; acid (includes glucosylceramidase) |
| Uterus_A_deno 746 | 0.2358976 | 0.401016 | 0.335737 | 0.19733785 | U26403_at | EPLG7 Eph-related receptor tyrosine kinase ligand 7 |
| Uterus_A_deno 747 | 0.2357051 | 0.4009982 | 0.335702 | 0.1972428 | M62831_at | Transcription factor ETR101 mRNA |
| Uterus_A_deno 748 | 0.2356204 | 0.400955 | 0.33559 | 0.19721152 | RC_AA2582 03_at | EST: zs35g04.s1 NCI_CGAP_GCB1 Homo sapiens cDNA clone IMAGE:687222 3', mRNA sequence. (from Genbank) |
| Uterus_A_deno 749 | 0.2353946 | 0.400935 | 0.335501 | 0.19706011 | U71087_at | Protein tyrosine kinase t-Ror1 (Ror1) mRNA |
| Uterus_A_deno 750 | 0.2350302 | 0.4007115 | 0.335501 | 0.19669459 | U04520_at | COL4A5 Collagen, type IV, alpha 5 (Alport syndrome) |
| Uterus_A_deno 751 | 0.2347645 | 0.4005196 | 0.3354455 | 0.19685131 | HG3286-HT3463_at | Crystallin, Alpha A |
| Uterus_A_deno 752 | 0.2347376 | 0.4001016 | 0.335351 | 0.19678746 | M17466_at | F12 Coagulation factor XII (Hageman factor) |

FIG. 14N2

| | | | | | |
|---|---|---|---|---|---|
| 753 | Uterus_A deno | 0.2346534 | 0.3999384 | 0.335254 | 0.19669877 | D84110_at | RBP-MS/type 1 |
| 754 | Uterus_A deno | 0.2344288 | 0.3997569 | 0.335208 | 0.19661027 | J03934_s_at | NMOR1 NAD(P)H:menadione oxidoreductase |
| 755 | Uterus_A deno | 0.2343063 | 0.3996253 | 0.335072 | | X55448_cds 2 at | 2-19 gene (2-19 protein) extracted from H.sapiens G6PD gene for glucose-6-phosphate dehydrogenase |
| 756 | Uterus_A deno | 0.2342788 | 0.3992167 | 0.33491 | 0.19651958 | X56932_at | LCAT Lecithin-cholesterol acyltransferase |
| 757 | Uterus_A deno | 0.233977 | 0.3991958 | 0.334874 | 0.19645308 | L76703_at | B56epsilon mRNA |
| 758 | Uterus_A deno | 0.2338666 | 0.3989463 | 0.334818 | 0.19640778 | D87447_at | KIAA0258 gene |
| 759 | Uterus_A deno | 0.2338324 | 0.3988006 | 0.334733 | 0.19628781 | D38521_at | KIAA0077 gene, partial cds |
| 760 | Uterus_A deno | 0.2337794 | 0.3987582 | 0.334612 | 0.19624043 | Y13620_at | BCL9 gene |
| 761 | Uterus_A deno | 0.2335423 | 0.3986899 | 0.334552 | 0.19611062 | HG4541-HT4946_s_a t | Transformation-Related Protein |
| 762 | Uterus_A deno | 0.2333179 | 0.3985928 | 0.33452 | 0.19601315 | HG415-HT415_at | Lectin, Galactoside-Binding, Soluble, 2 |
| 763 | Uterus_A deno | 0.2332674 | 0.3985597 | 0.334392 | 0.19596807 | U79287_at | Clone 23867 mRNA sequence |
| 764 | Uterus_A deno | 0.2331807 | 0.3984479 | 0.334214 | 0.1958741 | U50733_at | Dynamitin mRNA |
| 765 | Uterus_A deno | 0.2328755 | 0.3983392 | 0.334125 | 0.19585091 | X78669_at | ERC-55 mRNA |
| 766 | Uterus_A deno | 0.2328523 | 0.3982097 | 0.33405 | 0.19572631 | RC_AA2838 48_at | EST: zi19h06.s1 Soares ovary tumor NbHOT Homo sapiens cDNA clone 713627 3', mRNA sequence. (from Genbank) |
| 767 | Uterus_A deno | 0.232635 | 0.3981689 | 0.333974 | 0.19562352 | HG613-HT613_at | Ribosomal Protein S12 |
| 768 | Uterus_A deno | 0.2324877 | 0.3981585 | 0.333776 | 0.19558929 | D28476_at | KIAA0045 gene |
| 769 | Uterus_A deno | 0.2321644 | 0.3979635 | 0.333721 | 0.19554922 | X93921_at-2 | Dual specificity phosphatase 7 |
| 770 | Uterus_A deno | 0.2321644 | 0.3978292 | 0.333649 | 0.1954881 | X93921_at | Protein-tyrosine-phosphatase (tissue type: testis) |
| 771 | Uterus_A deno | 0.2320411 | 0.3977866 | 0.333561 | 0.19535936 | U24683_at | Anti-B cell autoantibody IgM heavy chain variable V-D-J region (VH4) gene, clone A23, VH4-55 non-productive rearrangement |

FIG. 14O2

| | | | | | |
|---|---|---|---|---|---|
| 772 | Uterus_A_deno | 0.2314513 | 0.3976886 | 0.333463 | 0.19531338 | U82130_at | Tumor susceptibility protein (TSG101) mRNA |
| 773 | Uterus_A_deno | 0.2311976 | 0.3976808 | 0.333454 | 0.19519822 | X15882_at | COL6A2 Collagen, type VI, alpha 2 |
| 774 | Uterus_A_deno | 0.2311372 | 0.3974064 | 0.333316 | 0.19514258 | X96752_at | L-3-hydroxyacyl-CoA dehydrogenase |
| 775 | Uterus_A_deno | 0.2310928 | 0.3974034 | 0.333158 | 0.19507122 | RC_AA6210 41_at | EST: ag03e04.s1 Soares testis NHT Homo sapiens cDNA clone 1056222 3', mRNA sequence. (from Genbank) |
| 776 | Uterus_A_deno | 0.230896 | 0.3974002 | 0.331121 | 0.19498265 | U03100_at | CTNNA1 Catenin (cadherin-associated protein), alpha 1 (102kD) |
| 777 | Uterus_A_deno | 0.2303467 | 0.3973968 | 0.333 | 0.19475788 | X76180_at | SLC9A1 Solute carrier family 9 (sodium/hydrogen exchanger), isoform 1 (antiporter, Na+/H+, amiloride sensitive) |
| 778 | Uterus_A_deno | 0.2303291 | 0.3973576 | 0.332975 | 0.19468385 | M73780_at | ITGB8 Integrin, beta 8 |
| 779 | Uterus_A_deno | 0.2303227 | 0.3972426 | 0.332936 | 0.19462924 | D31883_at | KIAA0059 gene |
| 780 | Uterus_A_deno | 0.2301527 | 0.3971692 | 0.332872 | 0.19455749 | U59913_at | SMAD5 (Smad5) mRNA |
| 781 | Uterus_A_deno | 0.2300359 | 0.3971491 | 0.332798 | 0.19444549 | U75276_s_a t | TFIIB related factor hBRF (HBRF) mRNA |
| 782 | Uterus_A_deno | 0.2299543 | 0.3971351 | 0.33272 | 0.19431679 | U74324_at | Guanine nucleotide exchange factor mss4 mRNA |
| 783 | Uterus_A_deno | 0.2299016 | 0.3971334 | 0.332608 | 0.19427429 | HG909-HT909_at | Mg81 |
| 784 | Uterus_A_deno | 0.2298452 | 0.3971278 | 0.332523 | 0.1941988 | L06499_at | RPL37A Ribosomal protein L37a |
| 785 | Uterus_A_deno | 0.2297839 | 0.3970439 | 0.332385 | 0.19413875 | M26682_at | LMO1 LIM domain only 1 (rhombotin 1) |
| 786 | Uterus_A_deno | 0.2295767 | 0.3969169 | 0.33227 | 0.19407034 | D87077_at | KIAA0240 gene, partial cds |
| 787 | Uterus_A_deno | 0.2292912 | 0.396898 | 0.332202 | 0.19391732 | AA482319_i_at | EST: ab15c03.r1 Stratagene lung (#937210) Homo sapiens cDNA clone 840868 5', mRNA sequence. (from Genbank) |
| 788 | Uterus_A_deno | 0.2283888 | 0.3967957 | 0.332068 | 0.19390087 | D86960_at | KIAA0205 gene |
| 789 | Uterus_A_deno | 0.2281222 | 0.3965802 | 0.332008 | 0.1938536 | U62293_rna 1_s_at | LIMK1 gene (LIM-kinase1) extracted from Human LIM-kinase1 and alternatively spliced LIM-kinase1 (LIMK1) gene |
| 790 | Uterus_A_deno | 0.2280639 | 0.3964263 | 0.331949 | 0.19381486 | D13642_at | KIAA0017 gene |
| 791 | Uterus_A_deno | 0.2276432 | 0.3963582 | 0.331921 | 0.19370328 | M60752_at | Histone H2A.1 (H2A) gene |

FIG. 14P2

| # | Sample | | | | Accession | Description |
|---|---|---|---|---|---|---|
| 792 | Uterus_A deno | 0.2276348 | 0.3963392 | 0.33182 | 0.19358824 | RC_AA236275_at | EST: zr54e12.s1 Soares NhHMPu S1 Homo sapiens cDNA clone 667246 3', mRNA sequence. (from Genbank) |
| 793 | Uterus_A deno | 0.2274526 | 0.3960518 | 0.331661 | 0.1934462 | RC_D55590_at | EST: Human fetal brain cDNA 3'-end GEN-183D04, mRNA sequence. (from Genbank) |
| 794 | Uterus_A deno | 0.2273864 | 0.3960518 | 0.331624 | 0.19343604 | RC_AA242823_at | EST: zr65e10.s1 Soares NhHMPu S1 Homo sapiens cDNA clone 668298 3', mRNA sequence. (from Genbank) |
| 795 | Uterus_A deno | 0.2273716 | 0.3960055 | 0.33154 | 0.19330831 | X64177_f_at | Metallothionein |
| 796 | Uterus_A deno | 0.2273713 | 0.3958992 | 0.331521 | 0.19328187 | U07231_at | GRSF1 G-rich RNA sequence binding factor 1 |
| 797 | Uterus_A deno | 0.2273325 | 0.3958559 | 0.331473 | 0.19320635 | X05855_s_at | EEF1G Translation elongation factor 1 gamma |
| 798 | Uterus_A deno | 0.2272773 | 0.3956159 | 0.331357 | 0.1931426 | X12876_s_at | KRT18 Keratin 18 |
| 799 | Uterus_A deno | 0.2272036 | 0.3956129 | 0.331346 | 0.19299792 | U59423_at | Mad-related protein MADR1 mRNA |
| 800 | Uterus_A deno | 0.2271893 | 0.3955437 | 0.331226 | 0.19296314 | U41060_at | Breast cancer, estrogen regulated LIV-1 protein (LIV-1) mRNA, partial cds |
| 801 | Uterus_A deno | 0.2271715 | 0.3954002 | 0.331224 | 0.19287054 | X13956_at | 9 KD PROTEIN |
| 802 | Uterus_A deno | 0.2271464 | 0.3953812 | 0.33115 | 0.19285284 | S81083_cds1_at | <beta>-ADD gene extracted from beta -ADD=adducin beta subunit 63 kda isoform/membrane skeleton protein, beta -ADD=adducin beta subunit 63 kda isoform/membrane skeleton protein {alternatively spliced, exon 10 to 13 region} [human, Genomic, 4499 nt 3 segments] |
| 803 | Uterus_A deno | 0.2270525 | 0.3951676 | 0.331136 | 0.19272555 | RC_AA161085_at | EST: zo62h09.s1 Stratagene pancreas (#937208) Homo sapiens cDNA clone 591521 3' similar to SW:PPAP_RAT P20646 PROSTATIC ACID PHOSPHATASE PRECURSOR ;, mRNA sequence. (from Genbank) |
| 804 | Uterus_A deno | 0.2269973 | 0.3949719 | 0.331 | 0.19256632 | X64037_at | GTF2F1 General transcription factor IIF, polypeptide 1 (74kD subunit) |
| 805 | Uterus_A deno | 0.2266253 | 0.3949148 | 0.330948 | 0.19249186 | U90552_s_at | Butyrophilin (BTF5) mRNA |
| 806 | Uterus_A deno | 0.2265343 | 0.3948469 | 0.330855 | 0.19245616 | U79254_at | Clone 23693 mRNA sequence |
| 807 | Uterus_A deno | 0.2263038 | 0.3947555 | 0.330841 | 0.19244628 | RC_AA505141_at | EST: aa65e04.s1 NCI_CGAP_GCB1 Homo sapiens cDNA clone IMAGE:825822 3', mRNA sequence. (from Genbank) |
| 808 | Uterus_A deno | 0.2260586 | 0.3946863 | 0.330795 | 0.19230844 | AF000560_at | TTF-I interacting peptide 20 mRNA, partial cds |

FIG. 14Q2

| | | | | | |
|---|---|---|---|---|---|
| 809 | Uterus_A deno | 0.22559459 | 0.3946484 | 0.330752 | 0.192220942 | L07597_at | RPS6KA2 Ribosomal protein S6 kinase, 90kD, polypeptide 2 |
| 810 | Uterus_A deno | 0.2258458 | 0.3946254 | 0.330721 | 0.19217859 | S81578_at | Dioxin-responsive gene (putative polyadenylation signal region) [human, hepatoma G2 cell line, mRNA Partial, 302 nt] |
| 811 | Uterus_A deno | 0.2254813 | 0.3945528 | 0.330721 | 0.19207966 | RC_AA0355 14_at | EST: zk26b02.s1 Soares pregnant uterus NbHPU Homo sapiens cDNA clone 471627 3', mRNA sequence. (from Genbank) |
| 812 | Uterus_A deno | 0.22551515 | 0.3944922 | 0.330532 | 0.19195788 | M65199_at | EDN2 Endothelin 2 |
| 813 | Uterus_A deno | 0.222493 | 0.394447 | 0.330378 | 0.19189903 | U59752_at | Sec7p-like protein mRNA, partial cds |
| 814 | Uterus_A deno | 0.2246972 | 0.3943978 | 0.330358 | 0.19182348 | HG33-HT33_at | Ribosomal Protein S4, X-Linked |
| 815 | Uterus_A deno | 0.2241652 | 0.3943604 | 0.330248 | 0.19168772 | L13977_at | LYSOSOMAL PRO-X CARBOXYPEPTIDASE PRECURSOR |
| 816 | Uterus_A deno | 0.2232244 | 0.3941782 | 0.330098 | 0.19163452 | U37689_at | RNA polymerase II subunit (hsRPB8) mRNA |
| 817 | Uterus_A deno | 0.2229216 | 0.393858 | 0.329969 | 0.1915269 | U53445_at | Ovarian cancer downregulated myosin heavy chain homolog (Doc1) mRNA |
| 818 | Uterus_A deno | 0.2227192 | 0.393854 | 0.329914 | 0.19140352 | X63131_s_a t | PML Probable transcription factor PML {alternative products} |
| 819 | Uterus_A deno | 0.2225033 | 0.3938192 | 0.329914 | 0.19135886 | M29877_at | FUCA1 Fucosidase, alpha-L- 1, tissue |
| 820 | Uterus_A deno | 0.2224151 | 0.3935809 | 0.329837 | 0.1913415 | U36221_at | Pancreatic zymogen granule membrane protein GP-2 mRNA |
| 821 | Uterus_A deno | 0.222375 | 0.3935244 | 0.329771 | 0.19131549 | AC002115_c ds1_at | COX6B gene (COXG) extracted from Human DNA from overlapping chromosome 19 cosmids R31396, F25451, and R31076 containing COX6B and UPKA, genomic sequence |
| 822 | Uterus_A deno | 0.2223581 | 0.3934557 | 0.329648 | 0.19120951 | L48513_at | Paraoxonase (PON2) mRNA |
| 823 | Uterus_A deno | 0.2222704 | 0.3934314 | 0.329618 | 0.19112635 | X16609_s_a t | ANK1 Ankyrin 1, erythrocytic |
| 824 | Uterus_A deno | 0.2221153 | 0.393402 | 0.32951 | 0.19110092 | J04970_at | CPM Carboxypeptidase M |
| 825 | Uterus_A deno | 0.2220928 | 0.3933518 | 0.3294414 | 0.19100827 | D86972_at | KIAA0218 gene |
| 826 | Uterus_A deno | 0.222042 | 0.3931866 | 0.329368 | 0.19095838 | M96982_at | SPLICING FACTOR U2AF 35 KD SUBUNIT |
| 827 | Uterus_A deno | 0.2218527 | 0.3931613 | 0.329347 | 0.19090745 | M84711_at | RPS3A Ribosomal protein S3A |

FIG. 14R2

| | | | | | |
|---|---|---|---|---|---|
| 828 | Uterus_A_deno | 0.2210563 | 0.3931398 | 0.329226 | 0.19085993 | D25328_at | PFKP Phosphofructokinase, platelet |
| 829 | Uterus_A_deno | 0.2210487 | 0.3930356 | 0.329107 | 0.19082682 | RC_AA1557 63_at | EST: zo52g12.s1 Stratagene pancreas (#937208) Homo sapiens cDNA clone 590566 3', mRNA sequence. (from Genbank) |
| 830 | Uterus_A_deno | 0.2209396 | 0.3927349 | 0.329104 | 0.19061115 | AA094752_a t | Protein phosphatase 3 (formerly 2B), catalytic subunit, beta isoform (calcineurin A beta) |
| 831 | Uterus_A_deno | 0.2208063 | 0.3927211 | 0.329035 | 0.19058026 | X69111_at | ID3 Inhibitor of DNA binding 3, dominant negative helix-loop-helix protein |
| 832 | Uterus_A_deno | 0.2205668 | 0.3927087 | 0.328885 | 0.19050068 | RC_AA2916 24_s_at | EST: zt45e11.s1 Soares ovary tumor NbHOT Homo sapiens cDNA clone 725324 3', mRNA sequence. (from Genbank) |
| 833 | Uterus_A_deno | 0.2203584 | 0.3926899 | 0.328875 | 0.190399 | L09260_at | (chromosome 3p25) membrane protein mRNA |
| 834 | Uterus_A_deno | 0.2203135 | 0.3926258 | 0.328757 | 0.19037071 | Z27113_at | DNA-DIRECTED RNA POLYMERASE II 14.4 KD POLYPEPTIDE |
| 835 | Uterus_A_deno | 0.2202485 | 0.3926057 | 0.328752 | 0.19024087 | RC_AA4632 34_at | KIAA0792 gene product |
| 836 | Uterus_A_deno | 0.22016656 | 0.3925739 | 0.328696 | 0.19013503 | D38128_at | PTGIR Prostaglandin I2 (prostacyclin) receptor (IP) |
| 837 | Uterus_A_deno | 0.2200277 | 0.392552 | 0.328696 | 0.19007593 | X75535_at | 33 KD HOUSEKEEPING PROTEIN |
| 838 | Uterus_A_deno | 0.2196897 | 0.3925354 | 0.328503 | 0.18999046 | L33243_at | PKD1 Polycystic kidney disease protein 1 |
| 839 | Uterus_A_deno | 0.2195956 | 0.3924983 | 0.328482 | 0.18995152 | U26424_at | Stress responsive serine/threonine protein kinase Krs-1 mRNA |
| 840 | Uterus_A_deno | 0.2195145 | 0.3923914 | 0.328342 | 0.18983406 | D23662_at | UBL1 Ubiquitin-like protein |
| 841 | Uterus_A_deno | 0.2194871 | 0.392348 | 0.328262 | 0.18979727 | D80001_at | KIAA0179 gene, partial cds |
| 842 | Uterus_A_deno | 0.2192769 | 0.3922077 | 0.328238 | 0.1897162 | HG2855-HT2995_at | Heat Shock Protein, 70 Kda (Gb:Y00371) |
| 843 | Uterus_A_deno | 0.2188253 | 0.3921473 | 0.328225 | 0.18962407 | M16424_at | BETA-HEXOSAMINIDASE ALPHA CHAIN PRECURSOR |
| 844 | Uterus_A_deno | 0.2186754 | 0.3921363 | 0.328185 | 0.18959355 | D84454_at | UDP-galactose translocator |
| 845 | Uterus_A_deno | 0.2183199 | 0.3920519 | 0.328171 | 0.18950279 | M22403_s_a t | PLATELET GLYCOPROTEIN IB ALPHA CHAIN PRECURSOR |
| 846 | Uterus_A_deno | 0.2181793 | 0.391978 | 0.328158 | 0.18946974 | X72012_at | ENG Endoglin (Osler-Rendu-Weber syndrome 1) |
| 847 | Uterus_A_deno | 0.2181419 | 0.3916428 | 0.328117 | 0.18941845 | L40393_at | (clone S171) mRNA |

FIG. 14S2

| | | | | | |
|---|---|---|---|---|---|
| 848 | Uterus_A_deno | 0.2180451 | 0.3916329 | 0.328019 | 0.18926829 | L38487_at | Estrogen receptor-related protein (hERRa1) mRNA, 3' end, partial cds |
| 849 | Uterus_A_deno | 0.2179884 | 0.3915557 | 0.3279975 | 0.18916298 | D16469_at | ORF, Xq terminal portion |
| 850 | Uterus_A_deno | 0.2179092 | 0.3913852 | 0.3279175 | 0.18909398 | M83186_at | COX7A1 Cytochrome c oxidase subunit VIIa polypeptide 1 (muscle) |
| 851 | Uterus_A_deno | 0.2177311 | 0.39131164 | 0.3278688 | 0.189037866 | AA452625_a_t | Iduronate 2-sulfatase (Hunter syndrome) |
| 852 | Uterus_A_deno | 0.2176722 | 0.3912907 | 0.3278325 | 0.18898879 | D12485_at | Plasma cell membrane glycoprotein (PC-1) mRNA |
| 853 | Uterus_A_deno | 0.2175078 | 0.3912492 | 0.3276815 | 0.18887334 | U39317_at | E2 ubiquitin conjugating enzyme UbcH5B (UBCH5B) mRNA |
| 854 | Uterus_A_deno | 0.2173687 | 0.3912196 | 0.3276575 | 0.18884222 | S67247_s_at | Smooth muscle myosin heavy chain isoform SMemb [human, umbilical cord, fetal aorta, mRNA Partial, 971 nt] |
| 855 | Uterus_A_deno | 0.2170451 | 0.39111894 | 0.3274585 | 0.18879755 | S69272_s_at | Cytoplasmic antiproteinase |
| 856 | Uterus_A_deno | 0.2170184 | 0.391046 | 0.327433 | 0.18871094 | RC_AA489063_at | EST: aa54f09.s1 NCI_CGAP_GCB1 Homo sapiens cDNA clone IMAGE:824777 3', mRNA sequence. (from Genbank) |
| 857 | Uterus_A_deno | 0.2168844 | 0.39100093 | 0.3272985 | 0.18866172 | U41766_s_a_t | Metalloprotease/disintegrin/cysteine-rich protein precursor (MDC9) mRNA |
| 858 | Uterus_A_deno | 0.2165489 | 0.39098258 | 0.3272745 | 0.18848702 | Z74616_s_at | COL1A2 Collagen, type I, alpha-2 |
| 859 | Uterus_A_deno | 0.2165359 | 0.3909965 | 0.327261 | 0.18841834 | D89501_at | PBI gene |
| 860 | Uterus_A_deno | 0.2165359 | 0.39077785 | 0.3272425 | 0.1883928 | D89501_at-2 | Human PBI gene, complete cds |
| 861 | Uterus_A_deno | 0.2164272 | 0.39066802 | 0.3271565 | 0.18835962 | Z31695_at | 43 kDa inositol polyphosphate 5-phosphatase |
| 862 | Uterus_A_deno | 0.2164264 | 0.39063361 | 0.3270385 | 0.18806374 | L13720_at | Growth-arrest-specific protein (gas) mRNA |
| 863 | Uterus_A_deno | 0.216281 | 0.39044407 | 0.3269485 | 0.18799828 | U59309_at | FH Fumarrate hydratase |
| 864 | Uterus_A_deno | 0.2162152 | 0.3904098 | 0.3269385 | 0.18791752 | U20998_at | SRP9 Signal recognition particle 9 kD protein |
| 865 | Uterus_A_deno | 0.2161932 | 0.39026363 | 0.3269365 | 0.18787563 | M60299_at | Alpha-1 collagen type II gene, exons 1, 2 and 3 |
| 866 | Uterus_A_deno | 0.2161681 | 0.39023296 | 0.326826 | 0.18784288 | U55209_at | Myosin VIIa transcript 2 mRNA |
| 867 | Uterus_A_deno | 0.2160996 | 0.39011967 | 0.326678 | 0.18780664 | M37197_at | COUP TRANSCRIPTION FACTOR |

FIG. 14T2

| | | | | | | |
|---|---|---|---|---|---|---|
| 868 | Uterus_A_deno | 0.2159223 | 0.3901786 | 0.326655 | 0.18769714 | AA0369900_a_t | EST: zk29e11.r1 Soares pregnant uterus NbHPU Homo sapiens cDNA clone 471980 5', mRNA sequence. (from Genbank) |
| 869 | Uterus_A_deno | 0.2158823 | 0.390174 | 0.326548 | 0.18764181 | L19314_at | HRY gene |
| 870 | Uterus_A_deno | 0.2158697 | 0.3901598 | 0.32623 | 0.18763767 | D50911_at | KIAA0121 gene |
| 871 | Uterus_A_deno | 0.2157742 | 0.3901439 | 0.326055 | 0.18754317 | AF006609_a_t | RGS3 mRNA, 5' UTR |
| 872 | Uterus_A_deno | 0.2155456 | 0.390073 | 0.325806 | 0.18732888 | Z74792_s_at | CCAAT transcription binding factor subunit gamma |
| 873 | Uterus_A_deno | 0.2154192 | 0.3900648 | 0.32573 | 0.1872749 | L08666_at | VDAC2 Voltage-dependent anion channel 2 |
| 874 | Uterus_A_deno | 0.2153729 | 0.3900135 | 0.325729 | 0.18723059 | M83772_at | FMO2 Flavin-containing monooxygenase 2 |
| 875 | Uterus_A_deno | 0.2152882 | 0.3899862 | 0.325652 | 0.18716176 | J03077_s_at | PSAP Sulfated glycoprotein 1 |
| 876 | Uterus_A_deno | 0.214885 | 0.3899649 | 0.326623 | 0.18699339 | X64330_at | ATP-citrate lyase |
| 877 | Uterus_A_deno | 0.2148609 | 0.38994 | 0.325549 | 0.18695594 | Z50853_at | CLPP |
| 878 | Uterus_A_deno | 0.2146991 | 0.3898827 | 0.325549 | 0.18680224 | M62762_at | ATP6C Vacuolar H+ ATPase proton channel subunit |
| 879 | Uterus_A_deno | 0.2146418 | 0.3898788 | 0.325455 | 0.18680006 | X84908_at | Phosphorylase-kinase, beta subunit |
| 880 | Uterus_A_deno | 0.2141112 | 0.3898322 | 0.325386 | 0.18666598 | RC_AA0404 65_at | EST: zk46h09.s1 Soares pregnant uterus NbHPU Homo sapiens cDNA clone 485921 3', mRNA sequence. (from Genbank) |
| 881 | Uterus_A_deno | 0.2138043 | 0.389818 | 0.32537 | 0.18656534 | D63475_at | KIAA0109 gene |
| 882 | Uterus_A_deno | 0.2137322 | 0.3898152 | 0.325361 | 0.18643631 | U13616_at | ANK3 Ankyrin G |
| 883 | Uterus_A_deno | 0.2136717 | 0.3896319 | 0.325349 | 0.18640657 | RC_AA1131 66_at | EST: zm27e01.s1 Stratagene pancreas (#937208) Homo sapiens cDNA clone 526872 3', mRNA sequence. (from Genbank) |
| 884 | Uterus_A_deno | 0.2134041 | 0.3895733 | 0.325204 | 0.18634397 | RC_AA4343 90_at | EST: zw31a06.s1 Soares ovary tumor NbHOT Homo sapiens cDNA clone 770866 3', mRNA sequence. (from Genbank) |
| 885 | Uterus_A_deno | 0.2133633 | 0.3895175 | 0.325204 | 0.18630908 | Z34897_at | HRH1 Histamine receptor H1 |
| 886 | Uterus_A_deno | 0.2131764 | 0.3893924 | 0.325166 | 0.1862277 | X95808_s_a_t | Protein encoded by a candidate gene, DXS6673E, for mental retardation |
| 887 | Uterus_A_deno | 0.213163 | 0.389187 | 0.325166 | 0.18616542 | U45285_at | Specific 116-kDa vacuolar proton pump subunit (OC-116KDa) mRNA |

FIG. 14U2

| | | | | | |
|---|---|---|---|---|---|
| Uterus_A_deno | 888 | 0.2130594 | 0.3891805 | 0.325129 | 0.18610477 | D88378_at | Proteasome inhibitor hPI31 subunit |
| Uterus_A_deno | 889 | 0.2129396 | 0.3891524 | 0.324892 | 0.186056640 | RC_AA4814_at | EST: zv45a05.s1 Soares ovary tumor NbHOT Homo sapiens cDNA clone 756560 3', mRNA sequence. (from Genbank) |
| Uterus_A_deno | 890 | 0.2128476 | 0.3890407 | 0.324798 | 0.18591115 | C00810_s_at | Homo sapiens clone 24733 mRNA sequence |
| Uterus_A_deno | 891 | 0.2127736 | 0.3889237 | 0.324723 | 0.18574932 | M57567_at | ARF5 ADP-ribosylation factor 5 |
| Uterus_A_deno | 892 | 0.2126237 | 0.3889156 | 0.324492 | 0.18571627 | M27878_at | ZNF84 Zinc finger protein 84 (HPF2) |
| Uterus_A_deno | 893 | 0.212453 | 0.3888914 | 0.324312 | 0.18565921 | AA012885_a_at | EST: ze27f07.r1 Soares retina N2b4HR Homo sapiens cDNA clone 360229 5', mRNA sequence. (from Genbank) |
| Uterus_A_deno | 894 | 0.2124312 | 0.3887673 | 0.32417 | 0.18564533 | U30999_at | U30999 Homo sapiens MV3 melanoma Homo sapiens cDNA clone memd, mRNA sequence |
| Uterus_A_deno | 895 | 0.2124234 | 0.3887493 | 0.324127 | 0.18562196 | AA443230_a_at | Casein kinase 2, alpha 1 polypeptide |
| Uterus_A_deno | 896 | 0.2124129 | 0.3887451 | 0.324108 | 0.18562196 | U67319_at | Mch3 isoform alpha (Mch3) mRNA |
| Uterus_A_deno | 897 | 0.2121364 | 0.3887233 | 0.32399 | 0.18549491 | RC_AA5999 91_at | EST: ag28h10.s1 Jia bone marrow stroma Homo sapiens cDNA clone 1090915 3', mRNA sequence. (from Genbank) |
| Uterus_A_deno | 898 | 0.2118426 | 0.388687 | 0.323895 | 0.18537976 | HG2239-HT2324_at | Potassium Channel Protein (Gb:Z11585) |
| Uterus_A_deno | 899 | 0.2118247 | 0.3886782 | 0.323885 | 0.18536246 | X70476_at | COATOMER BETA' SUBUNIT |
| Uterus_A_deno | 900 | 0.2117503 | 0.3886605 | 0.323654 | 0.18533596 | D87683_at | KIAA0243 gene, partial cds |
| Uterus_A_deno | 901 | 0.2117159 | 0.3886469 | 0.323579 | 0.18531113 | Z35491_at | Novel glucocorticoid receptor-associated protein |
| Uterus_A_deno | 902 | 0.2115579 | 0.3884025 | 0.323459 | 0.1850868 | X04106_at | CAPN4 Calpain, small polypeptide |
| Uterus_A_deno | 903 | 0.2114043 | 0.3883294 | 0.323328 | 0.1850868 | D67029_at | SEC14L SEC14 (S. cerevisiae)-like |
| Uterus_A_deno | 904 | 0.2113917 | 0.3883212 | 0.323286 | 0.18500431 | D83174_s_at | CBP1 Collagen-binding protein 1 |
| Uterus_A_deno | 905 | 0.2111866 | 0.3882014 | 0.323258 | 0.18494545 | D26018_at | KIAA0039 gene, partial cds |
| Uterus_A_deno | 906 | 0.2111419 | 0.3881112 | 0.32316 | 0.18489355 | X05610_at | COL4A2 Collagen, type IV, alpha 2 |
| Uterus_A_deno | 907 | 0.2110081 | 0.3880424 | 0.32316 | 0.18488622 | S54005_s_at | THYMOSIN BETA-10 |

FIG. 14V2

| | | | | | |
|---|---|---|---|---|---|
| 908 | Uterus_A_deno | 0.2109799 | 0.3879155 | 0.323078 | 0.18481722 | M69023_at | Globin gene |
| 909 | Uterus_A_deno | 0.2109658 | 0.3878527 | 0.322567 | 0.18479131 | D87328_at | HLCS Holocarboxylase synthetase (biotin-[propionyl-Coenzyme A-carboxylase (ATP-hydrolysing)] ligase) |
| 910 | Uterus_A_deno | 0.2107844 | 0.3876812 | 0.322459 | 0.18468052 | X95463_s_at | FMR2 Fragile X mental retardation 2 |
| 911 | Uterus_A_deno | 0.2105251 | 0.3876782 | 0.322424 | 0.18454103 | L10678_at | PFN2 Profilin 2 |
| 912 | Uterus_A_deno | 0.210457 | 0.3876768 | 0.322349 | 0.18448296 | U31556_at | E2F5 E2F transcription factor 5, p130-binding |
| 913 | Uterus_A_deno | 0.2102722 | 0.3876626 | 0.322318 | 0.18435511 | L41887_rna1_at | Splicing factor, arginine/serine-rich 7 (SFRS7) gene |
| 914 | Uterus_A_deno | 0.2101955 | 0.3875812 | 0.322317 | 0.18415335 | D15057_at | DEFENDER AGAINST CELL DEATH 1 |
| 915 | Uterus_A_deno | 0.210088 | 0.387547 | 0.322157 | 0.18413876 | M24470_at | G6PD Glucose-6-phosphate dehydrogenase |
| 916 | Uterus_A_deno | 0.2099746 | 0.3874812 | 0.322157 | 0.18408056 | X74764_at | Receptor protein tyrosine kinase |
| 917 | Uterus_A_deno | 0.2098598 | 0.3874781 | 0.322116 | 0.1840193 | U56402_s_at | Chromatin structural protein homolog (SUPT5H) mRNA |
| 918 | Uterus_A_deno | 0.2095785 | 0.3873623 | 0.322079 | 0.1839599 | RC_AA481414_at | Golgi SNAP receptor complex member 1 |
| 919 | Uterus_A_deno | 0.2095201 | 0.3873605 | 0.32201 | 0.18391488 | M14218_at | ASL Argininosuccinate lyase |
| 920 | Uterus_A_deno | 0.2094332 | 0.3873605 | 0.321991 | 0.18377271 | U90313_at | Glutathione-S-transferase homolog mRNA |
| 921 | Uterus_A_deno | 0.2094245 | 0.3872728 | 0.321881 | 0.18374634 | S67156_at | ASPA Aspartoacylase (aminoacylase 2, Canavan disease) |
| 922 | Uterus_A_deno | 0.2092098 | 0.3871981 | 0.321876 | 0.18366695 | J03161_at | SRF Serum response factor (c-fos serum response element-binding transcription factor) |
| 923 | Uterus_A_deno | 0.2090898 | 0.3871684 | 0.321753 | 0.18360771 | U17714_at | Putative tumor suppressor (SNC6) mRNA |
| 924 | Uterus_A_deno | 0.2088551 | 0.3871217 | 0.32172 | 0.1835653 | K03195_at | (HepG2) glucose transporter gene mRNA |
| 925 | Uterus_A_deno | 0.2087249 | 0.3871217 | 0.321546 | 0.18349284 | L34355_at | (clone p4) 50 kD dystrophin-associated glycoprotein mRNA |
| 926 | Uterus_A_deno | 0.2083499 | 0.3870272 | 0.321537 | 0.18341115 | U34683_at | GSS Glutathione synthetase |
| 927 | Uterus_A_deno | 0.208171 | 0.3867586 | 0.321498 | 0.18331729 | AA059327_i_at | EST: zf65e11.r1 Soares retina N2b4HR Homo sapiens cDNA clone 381836 5'. mRNA sequence. (from Genbank) |

FIG. 14W2

| | | | | | |
|---|---|---|---|---|---|
| 928 | Uterus_A_deno | 0.2081375 | 0.3866959 | 0.321457 | 0.18326777 | X87843_at | Cyclin H assembly factor |
| 929 | Uterus_A_deno | 0.2080586 | 0.3864307 | 0.321449 | 0.18320964 | U58048_at | PRSM1 Metallopeptidase 1 (33 kD) |
| 930 | Uterus_A_deno | 0.2079676 | 0.3864307 | 0.321307 | 0.18309739 | X63469_at | GTF2E2 General transcription factor TFIIE beta subunit, 34 kD |
| 931 | Uterus_A_deno | 0.2077635 | 0.3863581 | 0.3213 | 0.18308832 | X59373_at | HOX4D mRNA for a homeobox protein |
| 932 | Uterus_A_deno | 0.207701 | 0.3862331 | 0.321278 | 0.18305522 | M65085_at | FSHR Follicle stimulating hormone receptor |
| 933 | Uterus_A_deno | 0.2073369 | 0.3862174 | 0.321257 | 0.18299128 | U01337_at | ARAF1 V-raf murine sarcoma 3611 viral oncogene homolog 1 |
| 934 | Uterus_A_deno | 0.2072935 | 0.3861527 | 0.321172 | 0.18287313 | Z28407_at | RPL8 Ribosomal protein L8 |
| 935 | Uterus_A_deno | 0.2070523 | 0.3861446 | 0.321143 | 0.18286061 | U20499_at | Estrogen sulfotransferase mRNA |
| 936 | Uterus_A_deno | 0.2069973 | 0.3861243 | 0.32109 | 0.18269487 | X99325_at | Alpha-tubulin mRNA |
| 937 | Uterus_A_deno | 0.206596 | 0.3860807 | 0.32105 | 0.18259509 | L25286_s_at | COL15A1 Collagen, type XV, alpha 1 |
| 938 | Uterus_A_deno | 0.2063607 | 0.3860218 | 0.320913 | 0.1825639 | U60061_at | RPS26 Ribosomal protein S26 |
| 939 | Uterus_A_deno | 0.2062834 | 0.3856179 | 0.320848 | 0.18246435 | U31814_at | Transcriptional regulator homolog RPD3 mRNA |
| 940 | Uterus_A_deno | 0.2060707 | 0.3854891 | 0.320722 | 0.18238516 | R74226_at | Homo sapiens mRNA for ATP synthase subunit e, complete cds |
| 941 | Uterus_A_deno | 0.2060116 | 0.3854598 | 0.320638 | 0.18230672 | D14658_at | KIAA0102 gene |
| 942 | Uterus_A_deno | 0.2056348 | 0.3851745 | 0.320637 | 0.18222739 | U92457_s_a t | Metabotropic glutamate receptor 4 mRNA |
| 943 | Uterus_A_deno | 0.2055781 | 0.3851476 | 0.320055 | 0.18216674 | D83782_at | KIAA0199 gene, partial cds |
| 944 | Uterus_A_deno | 0.2055413 | 0.3849975 | 0.320471 | 0.18203042 | AA381902_a t | EST: EST95112 Activated T-cells I Homo sapiens cDNA 5' end, mRNA sequence. (from Genbank) |
| 945 | Uterus_A_deno | 0.2054722 | 0.3849196 | 0.320453 | 0.18199 | L38810_at | Thyroid receptor interactor (TRIP1) mRNA |
| 946 | Uterus_A_deno | 0.2053742 | 0.38483 | 0.320388 | 0.18195434 | J05016_rna1 _s_at | (clone pA3) protein disulfide isomerase related protein (ERp72) mRNA |
| 947 | Uterus_A_deno | 0.2053574 | 0.384759 | 0.320379 | 0.18187532 | X72727_at | HNRPK Heterogeneous nuclear ribonucleoprotein K |

FIG. 14X2

| | | | | | |
|---|---|---|---|---|---|
| Uterus_A deno 948 | 0.2051738 | 0.3846767 | 0.320379 | 0.18181248 | M37104_at | ATP5 ATP synthase, H+ transporting, mitochondrial |
| Uterus_A deno 949 | 0.2051648 | 0.3846728 | 0.320376 | 0.18171231 | Z34975_at | LDLC mRNA |
| Uterus_A deno 950 | 0.2047711 | 0.3846443 | 0.320233 | 0.18169716 | RC_AA1768 12_at | EST: zp32g12.s1 Stratagene neuroepithelium (#937231) Homo sapiens cDNA clone 611206 3' similar to contains Alu repetitive element;contains element THR repetitive element ;, mRNA sequence. (from Genbank) |
| Uterus_A deno 951 | 0.204708 | 0.3845868 | 0.320215 | 0.18162225 | D85527_at | LIM domain, partial cds |
| Uterus_A deno 952 | 0.2038934 | 0.3845328 | 0.320041 | 0.1814675 | M61832_s_a t | AHCY S-adenosylhomocysteine hydrolase |
| Uterus_A deno 953 | 0.2035943 | 0.3844999 | 0.319954 | 0.18142994 | Z22551_at | Kinectin gene |
| Uterus_A deno 954 | 0.2031818 | 0.3842996 | 0.319953 | 0.18137155 | Z47055_s_at | Partial cDNA sequence, farnesyl pyrophosphate synthetase like-4 |
| Uterus_A deno 955 | 0.2031434 | 0.3842517 | 0.319841 | 0.18130085 | U32324_at | Interleukin 11 receptor isoform (incomplete) |
| Uterus_A deno 956 | 0.202966 | 0.384227 | 0.319793 | 0.18115702 | M63959_at | LRPAP1 Low density lipoprotein-related protein-associated protein 1 (alpha-2-macroglobulin receptor-associated protein 1 |
| Uterus_A deno 957 | 0.2028788 | 0.3841794 | 0.319687 | 0.181098 | RC_AA6003 10_at | EST: ag04b04.s1 Gessler Wilms tumor Homo sapiens cDNA clone 1069327 3', mRNA sequence. (from Genbank) |
| Uterus_A deno 958 | 0.2027138 | 0.3840461 | 0.319645 | 0.18097389 | M31606_at | PHKG2 Phosphorylase kinase, gamma 2 (testis) |
| Uterus_A deno 959 | 0.202657 | 0.3836649 | 0.319586 | 0.18094139 | M20543_at | ACTA1 Actin, alpha 1, skeletal muscle |
| Uterus_A deno 960 | 0.2025842 | 0.3835693 | 0.319555 | 0.18084618 | X57348_s_a t | SFN Stratifin |
| Uterus_A deno 961 | 0.2025773 | 0.3835476 | 0.319551 | 0.18083958 | D63481_at | KIAA0147 gene, partial cds |
| Uterus_A deno 962 | 0.2024769 | 0.38350 17 | 0.319516 | 0.18079516 | U67368_s_a t | EXT2 Exostoses (multiple) 2 |
| Uterus_A deno 963 | 0.2020793 | 0.38347 | 0.31951 | 0.18066691 | X53331_at | MGP Matrix protein gla |
| Uterus_A deno 964 | 0.2020627 | 0.3834036 | 0.319487 | 0.18057793 | L15344_at | High molecular weight B cell growth factor mRNA sequence |
| Uterus_A deno 965 | 0.2018731 | 0.3832868 | 0.319486 | 0.18054484 | AA025333_a t | EST: ze76b01.r1 Soares fetal heart NbHH19W Homo sapiens cDNA clone 364873 5', mRNA sequence. (from Genbank) |
| Uterus_A deno 966 | 0.2018391 | 0.3832596 | 0.319485 | 0.18046394 | U53446_at | Mitogen-responsive phosphoprotein (DOC-2) mRNA |

FIG. 14Y2

| # | Sample | Val1 | Val2 | Val3 | ID1 | ID2 | Description |
|---|---|---|---|---|---|---|---|
| 967 | Uterus_A_deno | 0.2017264 | 0.3831523 | 0.319426 | 0.18038586 | X15525_rna1_at | Lysosomal acid phosphatase gene (EC 3.1.3.2) Exon 1 (and joined CDS) |
| 968 | Uterus_A_deno | 0.2010871 | 0.3830653 | 0.319319 | 0.18034121 | X97335_at | Kinase A anchor protein |
| 969 | Uterus_A_deno | 0.2010566 | 0.382831 | 0.319221 | 0.18029657 | U72209_at | YY1-associated factor 2 (YAF2) mRNA |
| 970 | Uterus_A_deno | 0.2009065 | 0.3828281 | 0.319221 | 0.18026663 | D63881_at | KIAA0160 gene, partial cds |
| 971 | Uterus_A_deno | 0.2006949 | 0.382779 | 0.319187 | 0.18019491 | X63097_at | RHD Rhesus blood group, D antigen |
| 972 | Uterus_A_deno | 0.2006699 | 0.3827249 | 0.319185 | 0.18002176 | HG3494-HT3688_at | Nuclear Factor Nf-Il6 |
| 973 | Uterus_A_deno | 0.2003197 | 0.382712 | 0.319037 | 0.18001038 | X82153_at | CATHEPSIN K PRECURSOR |
| 974 | Uterus_A_deno | 0.2002562 | 0.3826212 | 0.318913 | 0.17992198 | U42359_at | N33 protein form 1 (N33) gene, exon 10 and complete cds |
| 975 | Uterus_A_deno | 0.2002342 | 0.3825721 | 0.318906 | 0.17980315 | D30756_at | KIAA0108 gene |
| 976 | Uterus_A_deno | 0.2001837 | 0.3824891 | 0.318819 | 0.17978184 | Z26876_at | LTBP1 Latent transforming growth factor beta binding protein 1 |
| 977 | Uterus_A_deno | 0.2001304 | 0.3822296 | 0.318788 | 0.1797627 | RC_C14898_at | EST: Human fetal brain cDNA 3'-end GEN-098C12, mRNA sequence. (from Genbank) |
| 978 | Uterus_A_deno | 0.2000882 | 0.3819756 | 0.31873 | 0.17959587 | X04366_at | CALPAIN 1, LARGE |
| 979 | Uterus_A_deno | 0.2000612 | 0.3819015 | 0.318582 | 0.17953672 | U73377_at | SKI V-ski avian sarcoma viral oncogene homolog |
| 980 | Uterus_A_deno | 0.198835 | 0.3817549 | 0.31845 | 0.17951201 | L41690_at | TNF receptor-1 associated protein (TRADD) mRNA, 3' end of cds |
| 981 | Uterus_A_deno | 0.1998273 | 0.3817186 | 0.318386 | 0.17942125 | M60091_at | GALT Galactose-1-phosphate uridyl transferase |
| 982 | Uterus_A_deno | 0.1995483 | 0.3816814 | 0.318254 | 0.17936562 | HG3884-HT4154_at | Homeotic Protein Hpx-42 |
| 983 | Uterus_A_deno | 0.1994757 | 0.381583 | 0.317977 | 0.17929956 | U23028_at | EIF2B Eukaryotic translation initiation factor 2B epsilon |
| 984 | Uterus_A_deno | 0.1993721 | 0.3814793 | 0.317842 | 0.17926472 | M79463_s_at | PML Probable transcription factor PML (alternative products) |
| 985 | Uterus_A_deno | 0.1992306 | 0.3812621 | 0.317814 | 0.17918429 | HG162-HT3165_at | Tyrosine Kinase, Receptor Axl, Alt. Splice 2 |
| 986 | Uterus_A_deno | 0.1992204 | 0.3812349 | 0.317721 | 0.17908818 | U88871_at | Peroxisome targeting signal 2 receptor (Pex7) mRNA |

FIG. 14Z2

| | | | | |
|---|---|---|---|---|
| 987 | Uterus_A_deno | 0.1990439 | 0.3810806 | 0.317703 | 0.179025529 | RC_AA1560 97_s_at | EST: zo45d03.s1 Stratagene endothelial cell 937223 Homo sapiens cDNA clone 589829 3', mRNA sequence. (from Genbank) |
| 988 | Uterus_A_deno | 0.1988667 | 0.38101017 | 0.3178657 | 0.179900302 | U24169_at | JTV-1 (JTV-1) mRNA |
| 989 | Uterus_A_deno | 0.1987205 | 0.380966 | 0.3178656 | 0.178900997 | M31520_at | Ribosomal protein S24 |
| 990 | Uterus_A_deno | 0.1986969 | 0.3809179 | 0.3176508 | 0.178863396 | M34539_at | FKBP1 FK506-binding protein 1 (12kD) |
| 991 | Uterus_A_deno | 0.1985741 | 0.3806631 | 0.3177467 | 0.178793 | AF002020_a_t | Niemann-Pick C disease protein (NPC1) mRNA |
| 992 | Uterus_A_deno | 0.1983639 | 0.3806556 | 0.3177436 | 0.178642256 | U33849_at | Lymphoma proprotein convertase (LPC) mRNA |
| 993 | Uterus_A_deno | 0.1982744 | 0.3803781 | 0.3177378 | 0.178557778 | Y09022_at | Not56-like protein |
| 994 | Uterus_A_deno | 0.19822 | 0.3802463 | 0.3177372 | 0.178849502 | D21260_at | 60S RIBOSOMAL PROTEIN L23 |
| 995 | Uterus_A_deno | 0.1978276 | 0.3800167 | 0.3177316 | 0.178842768 | U58089_at | Hs-cul-3 mRNA, partial cds |
| 996 | Uterus_A_deno | 0.1975586 | 0.379923 | 0.3177306 | 0.178835084 | X78706_at | CRAT Carnitine acetyltransferase |
| 997 | Uterus_A_deno | 0.1975501 | 0.3798698 | 0.3177271 | 0.178829515 | U10362_at | GP36b glycoprotein mRNA |
| 998 | Uterus_A_deno | 0.1974711 | 0.3797584 | 0.3177134 | 0.17820579 | AF007551_a_t | Bet1p homolog (hbet1) mRNA |
| 999 | Uterus_A_deno | 0.1972353 | 0.3796913 | 0.316759 | 0.178101075 | Z29678_at | MitF mRNA |
| 1000 | Uterus_A_deno | 0.1972284 | 0.3794312 | 0.316736 | 0.178061113 | D31764_at | KIAA0064 gene |

FIG. 14A3

GENETIC MARKERS FOR TUMORS

RELATED APPLICATIONS

This application claims the benefit of U.S. Provisional Application Nos. 60/233,534, filed on Sep. 19, 2000, and 60/278,749, filed on Mar. 26, 2001. The entire teachings of the above applications are incorporated herein by reference.

GOVERNMENT SUPPORT

The invention was supported, in whole or in part, by grant NIH-5T32HL07623 from the National Institutes of Health. The U.S. Government has certain rights in the invention.

BACKGROUND OF THE INVENTION

Classification of tumor samples from individuals is not an exact science. In many instances, accurate diagnosis and safe and effective treatment of a disorder depends on being able to discern biological distinctions among morphologically similar samples, such as tumor samples. The classification of a sample from an individual into particular disease classes has typically been difficult and often incorrect or inconclusive. Using traditional methods, such as morphology analyses, histochemical analyses, immunophenotyping and cytogenetic analyses, often only one or two characteristics of the sample are analyzed to determine the sample's classification, resulting in inconsistent and sometimes inaccurate results. Such results can lead to incorrect diagnoses and potentially ineffective or harmful treatment. Thus, a need exists for accurate markers for identifying tumor classes and classifying tumor samples.

SUMMARY OF THE INVENTION

As described herein, sets of genetic markers which are specific to various tumor classes have been identified. The patterns of expression for these genes will be useful in improving the diagnosis and classification of human cancer. This information will be useful for designing genetic or antibody-based tests for the characterization of clinical tumor samples, and in particular, those samples that are difficult to evaluate with present histopathologic techniques. In addition, a number of specific markers may encode secreted or membrane bound proteins. These proteins would prove useful for the early detection of cancer (analogous to the serum prostate specific antigen (PSA) test) or for the treatment of cancer (analogous to antibody-based treatment of breast cancer by targeting the Her-2/Neu gene product). Finally, genes which are specifically expressed by classes of cancer may be involved in the pathogenesis of disease and are potential therapeutic targets.

The invention relates to classification or identification of biological samples, e.g., tumor samples, based on the simultaneous expression monitoring of a set of genes as described herein using DNA microarrays or other methods developed to assess a large number of genes. Microarrays have the attractive property of allowing one to monitor multiple expression events in parallel using a single technique. The method can be used to distinguish among tumor samples (e.g., to distinguish a breast tumor sample from a prostate tumor sample) or between a tumor sample and corresponding normal sample (e.g., to distinguish a breast tumor sample from a normal breast tissue sample) based on the patterns of gene expression of the samples. The markers identified herein can also be used to classify or identify tumors of unknown primary origin. The invention also relates to classification or identification of biological samples, e.g., tumor samples, based on the expression of a set of proteins encoded by a set of marker genes as described herein.

Both nucleic acid- and protein-based monitoring methods of the genes identified in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3 (or their encoded proteins) can be used to predict or aid in the prediction of, diagnose or aid in the diagnosis of, or monitor or aid in the monitoring of cancer, particularly tumor, establishment, progression or regression in an individual.

In one aspect, the invention features a method of identifying a tumor comprising the steps of: a) obtaining a sample derived from an organ or tissue; b) determining the expression pattern of one or more marker genes in the sample, said one or more marker genes selected from the group consisting of the genes in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3; and c) comparing the expression pattern obtained in step b) to the expression pattern of one or more genes specific to a tumor. A marker gene expression pattern in the sample that is similar to the gene expression pattern specific to a tumor identifies a tumor.

In one embodiment, the one or more marker genes are selected from the group consisting of the genes in FIGS. 1A–1R2, whereby the tumor identified is a bladder tumor. In another embodiment, the one or more marker genes are selected from the group consisting of the genes in FIGS. 2A–2T2, whereby the tumor identified is a breast tumor. In another embodiment, the one or more marker genes are selected from the group consisting of the genes in FIGS. 3A–3Z2, whereby the tumor identified is a central nervous system (CNS) tumor. In yet another embodiment, the one or more marker genes are selected from the group consisting of the genes in FIGS. 4A–4S2, whereby the tumor identified is a colorectal tumor. In another embodiment, the one or more marker genes are selected from the group consisting of the genes in FIGS. 5A–5M2, whereby the tumor identified is leukemia. In still another embodiment, the one or more marker genes are selected from the group consisting of the genes in FIGS. 6A–6W2, whereby the tumor identified is a lung tumor. In another embodiment, the one or more marker genes are selected from the group consisting of the genes in FIGS. 7A–7D3, whereby the tumor identified is a lymphoma. In another embodiment, the one or more marker genes are selected from the group consisting of the genes in FIGS. 8A–8X2, whereby the tumor identified is a melanoma. In another embodiment, the one or more marker genes are selected from the group consisting of the genes in FIGS. 9A–9C3, whereby the tumor identified is a mesothelioma. In still another embodiment, the one or more marker genes are selected from the group consisting of the genes in FIGS. 10A–10P2, whereby the tumor identified is an ovarian tumor. In still another embodiment, the one or more marker genes are selected from the group consisting of the genes in 11A–11O2, whereby the tumor identified is a pancreatic tumor. In another embodiment, the one or more marker genes are selected from the group consisting of the genes in FIGS. 12A–12V2, whereby the tumor identified is a prostate tumor. In another embodiment, the one or more marker genes are selected from the group consisting of the genes in FIGS. 13A–13N2, whereby the tumor identified is a renal tumor. In still another embodiment, the one or more marker genes are selected from the group consisting of the genes in FIGS. 14A–14A3, whereby the tumor identified is a uterine tumor.

In other embodiments, the marker gene is DNA or it corresponding mRNA. Preferably, when the marker gene is DNA or mRNA, the gene expression pattern of the marker gene is determined utilizing specific hybridization probes. For example, the gene expression pattern may be determined utilizing oligonucleotide microarrays.

In another embodiment, the marker genes are expressed as polypeptides. Preferably, when the marker genes are expressed as polypeptides, the gene expression pattern is determined utilizing antibodies.

In another aspect, the invention features a method of predicting the likelihood of tumor development in a subject, comprising the steps of: a) obtaining a sample derived from an organ or tissue of a subject; b) determining the expression pattern of one or more marker genes in the sample, said one or more marker genes selected from the group consisting of the genes in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3; and c) comparing the expression pattern obtained in step b) to the expression pattern of one or more genes specific to a tumor. A marker gene expression pattern in the sample that is similar to the gene expression pattern specific to a tumor indicates an increased likelihood of tumor development in the subject.

In one embodiment, the one or more marker genes are selected from the group consisting of the genes in FIGS. 1A–1R2, whereby the tumor for which a likelihood of development is predicted is a bladder tumor. In another embodiment, the one or more marker genes are selected from the group consisting of the genes in FIGS. 2A–2T2, whereby the tumor for which a likelihood of development is predicted is a breast tumor. In another embodiment, the one or more marker genes are selected from the group consisting of the genes in FIGS. 3A–3Z2, whereby the tumor for which a likelihood of development is predicted is a central nervous system (CNS) tumor. In yet another embodiment, the one or more marker genes are selected from the group consisting of the genes in FIGS. 4A–4S2, whereby the tumor for which a likelihood of development is predicted is a colorectal tumor. In another embodiment, the one or more marker genes are selected from the group consisting of the genes in FIGS. 5A–5M2, whereby the tumor for which a likelihood of development is predicted is leukemia. In still another embodiment, the one or more marker genes are selected from the group consisting of the genes in FIGS. 6A–6W2, whereby the tumor for which a likelihood of development is predicted is a lung tumor. In another embodiment, the one or more marker genes are selected from the group consisting of the genes in FIGS. 7A–7D3, whereby the tumor for which a likelihood of development is predicted is a lymphoma. In another embodiment, the one or more marker genes are selected from the group consisting of the genes in FIGS. 8A–8X2, whereby the tumor for which a likelihood of development is predicted is a melanoma. In another embodiment, the one or more marker genes are selected from the group consisting of the genes in FIGS. 9A–9C3, whereby the tumor for which a likelihood of development is predicted is a mesothelioma. In still another embodiment, the one or more marker genes are selected from the group consisting of the genes in FIGS. 10A–10P2, whereby the tumor for which a likelihood of development is predicted is an ovarian tumor. In still another embodiment, the one or more marker genes are selected from the group consisting of the genes in 11A–11O2, whereby the tumor for which a likelihood of development is predicted is a pancreatic tumor. In another embodiment, the one or more marker genes are selected from the group consisting of the genes in FIGS. 12A–12V2, whereby the tumor for which a likelihood of development is predicted is a prostate tumor. In another embodiment, the one or more marker genes are selected from the group consisting of the genes in FIGS. 13A–13N2, whereby the tumor for which a likelihood of development is predicted is a renal tumor. In still another embodiment, the one or more marker genes are selected from the group consisting of the genes in FIGS. 14A–14A3, whereby the tumor for which a likelihood of development is predicted is a uterine tumor.

In other embodiments, the marker gene is DNA or it corresponding mRNA. Preferably, when the marker gene is DNA or mRNA, the gene expression pattern of the marker gene is determined utilizing specific hybridization probes. For example, the gene expression pattern may be determined utilizing oligonucleotide microarrays.

In another embodiment, the marker genes are expressed as polypeptides. Preferably, when the marker genes are expressed as polypeptides, the gene expression pattern is determined utilizing antibodies.

In still another aspect, the invention features a method of diagnosing a tumor in a subject, comprising the steps of: a) obtaining a sample derived from an organ or tissue of a subject; b) determining the expression pattern of one or more marker genes in the sample, said one or more marker genes selected from the group consisting of the genes in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A32; and c) comparing the expression pattern obtained in step b) to the expression pattern of one or more genes specific to a tumor. A marker gene expression pattern in the sample that is similar to the gene expression pattern specific to a tumor indicates the presence of a tumor in the subject.

In one embodiment, the one or more marker genes are selected from the group consisting of the genes in FIGS. 1A–1R2, whereby the tumor that is diagnosed is a bladder tumor. In another embodiment, the one or more marker genes are selected from the group consisting of the genes in FIGS. 2A–2T2, whereby the tumor that is diagnosed is a breast tumor. In another embodiment, the one or more marker genes are selected from the group consisting of the genes in FIGS. 3A–3Z2, whereby the tumor that is diagnosed is a central nervous system (CNS) tumor. In yet another embodiment, the one or more marker genes are selected from the group consisting of the genes in FIGS. 4A–4S2, whereby the tumor that is diagnosed is a colorectal tumor. In another embodiment, the one or more marker genes are selected from the group consisting of the genes in FIGS. 5A–5M2, whereby the tumor that is diagnosed is leukemia. In still another embodiment, the one or more marker genes are selected from the group consisting of the genes in FIGS. 6A–6W2, whereby the tumor that is diagnosed is a lung tumor. In another embodiment, the one or more marker genes are selected from the group consisting of the genes in FIGS. 7A–7D3, whereby the tumor that is diagnosed is a lymphoma. In another embodiment, the one or more marker genes are selected from the group consisting of the genes in FIGS. 8A–8X2, whereby the tumor that is diagnosed is a melanoma. In another embodiment, the one or more marker genes are selected from the group consisting of the genes in FIGS. 9A–9C3, whereby the tumor that is diagnosed is a mesothelioma. In still another embodiment, the one or more marker genes are selected from the group consisting of the genes in FIGS. 10A–10P2, whereby the tumor that is diagnosed is an ovarian tumor. In still another embodiment, the one or more marker genes are selected from the group consisting of the genes in 11A–11O2, whereby the tumor that is diagnosed is a pancreatic tumor. In another embodiment, the one or more marker genes are selected from the group consisting of the genes in FIGS. 12A–12V2, whereby the tumor that is diagnosed is a prostate tumor. In another embodiment, the one or more marker genes are selected from the group consisting of the genes in FIGS. 13A–13N2, whereby the tumor that is diagnosed is a renal tumor. In still another embodiment, the one or more marker genes are selected from the group consisting of the genes in FIGS. 14A–14A3, whereby the tumor that is diagnosed is a uterine tumor.

In other embodiments, the marker gene is DNA or it corresponding mRNA. Preferably, when the marker gene is DNA or mRNA, the gene expression pattern of the marker gene is determined utilizing specific hybridization probes. For example, the gene expression pattern may be determined utilizing oligonucleotide microarrays.

In another embodiment, the marker genes are expressed as polypeptides. Preferably, when the marker genes are expressed as polypeptides, the gene expression pattern is determined utilizing antibodies.

In yet another aspect, the invention features a method of identifying a compound for use in treating cancer, comprising the steps of: a) providing a cell or cell lysate sample; b) contacting the cell or cell lysate sample with a candidate compound; and c) detecting a decrease in expression of one or more genes specific to a tumor, said one or more genes selected from the group consisting of the genes in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3. A candidate compound that decreases the expression of one or more genes specific to a tumor identifies a compound for use in treating cancer.

In one embodiment, the one or more genes are selected from the group consisting of the genes in FIGS. 1A–1R2, whereby the compound identified is useful for treating bladder cancer. In another embodiment, the one or more genes are selected from the group consisting of the genes in FIGS. 2A–2T2, whereby the compound identified is useful for treating breast cancer. In another embodiment, the one or more genes are selected from the group consisting of the genes in FIGS. 3A–3Z2, whereby the compound identified is useful for treating central nervous system (CNS) cancer. In yet another embodiment, the one or more genes are selected from the group consisting of the genes in FIGS. 4A–4S2, whereby the compound identified is useful for treating colorectal cancer. In another embodiment, the one or more genes are selected from the group consisting of the genes in FIGS. 5A–5M2, whereby the compound identified is useful for treating leukemia. In still another embodiment, the one or more genes are selected from the group consisting of the genes in FIGS. 6A–6W2, whereby the compound identified is useful for treating lung cancer. In another embodiment, the one or more genes are selected from the group consisting of the genes in FIGS. 7A–7D3, whereby the compound identified is useful for treating lymphoma. In another embodiment, the one or more genes are selected from the group consisting of the genes in FIGS. 8A–8X2, whereby the compound identified is useful for treating melanoma. In another embodiment, the one or more genes are selected from the group consisting of the genes in FIGS. 9A–9C3, whereby the compound identified is useful for treating mesothelioma. In still another embodiment, the one or more genes are selected from the group consisting of the genes in FIGS. 10A–10P2, whereby the compound identified is useful for treating ovarian cancer. In still another embodiment, the one or more genes are selected from the group consisting of the genes in 11A–11O2, whereby the compound identified is useful for treating pancreatic cancer. In another embodiment, the one or more genes are selected from the group consisting of the genes in FIGS. 12A–12V2, whereby the compound identified is useful for treating prostate cancer. In another embodiment, the one or more genes are selected from the group consisting of the genes in FIGS. 13A–13N2, whereby the compound identified is useful for treating renal cancer. In still another embodiment, the one or more genes are selected from the group consisting of the genes in FIGS. 14A–14A3, whereby the compound identified is useful for treating uterine cancer.

In other embodiments, the gene is DNA or it corresponding mRNA. Preferably, when the marker gene is DNA or mRNA, the gene expression pattern of the marker gene is determined utilizing specific hybridization probes. For example, the gene expression pattern may be determined utilizing oligonucleotide microarrays.

In another embodiment, the genes are expressed as polypeptides. Preferably, when the marker genes are expressed as polypeptides, the gene expression pattern is determined utilizing antibodies.

In another aspect, the invention features an oligonucleotide microarray having immobilized thereon a plurality of oligonucleotide probes specific for one or more tumor specific genes selected from the group consisting of the genes in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3.

In preferred embodiments, the oligonucleotide probes specific for one or more tumor specific genes are selected from the genes in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3, respectively.

In other embodiments, the oligonucleotide probes are DNA or mRNA.

The invention also features a method for modulating tumor development in a subject by decreasing in the subject at least one marker gene shown to be specific to a particular tumor class, for example, any of the marker genes shown herein.

BRIEF DESCRIPTION OF THE DRAWINGS

FIGS. 1A–1R2 are a table of marker genes for bladder tumor types. The second column of the table (entitled "Distinction") shows the type of tumor (bladder) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

FIGS. 2A–2T2 are a table of marker genes for breast tumor types. The second column of the table (entitled "Distinction") shows the type of tumor (breast) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column ("Desc.") provides descriptive information about the marker gene.

FIGS. 3A–3Z2 are a table of marker genes for central nervous system (CNS) tumor types. The second column of the table (entitled "Distinction") shows the type of tumor (CNS) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

FIGS. 4A–4S2 are a table of marker genes for colorectal tumor types. The second column of the table (entitled "Distinction") shows the type of tumor (colorectal) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene. FIGS. 5A–5M2 are a table of marker genes for leukemia. The second column of the table (entitled "Distinction") shows the type of tumor (leukemia) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

FIGS. 6A–6W2 are a table of marker genes for lung tumor types. The second column of the table (entitled "Distinction") shows the type of tumor (lung) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

FIGS. 7A–7D3 are a table of marker genes for lymphoma tumor types. The second column of the table (entitled "Distinction") shows the type of tumor (lymphoma) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

FIGS. 8A–8X2 are a table of marker genes for melanoma tumor types. The second column of the table (entitled "Distinction") shows the type of tumor (melanoma) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

FIGS. 9A–9C3 are a table of marker genes for mesothelioma tumor types. The second column of the table (entitled "Distinction") shows the type of tumor (mesothelioma) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK®

Figure 15:
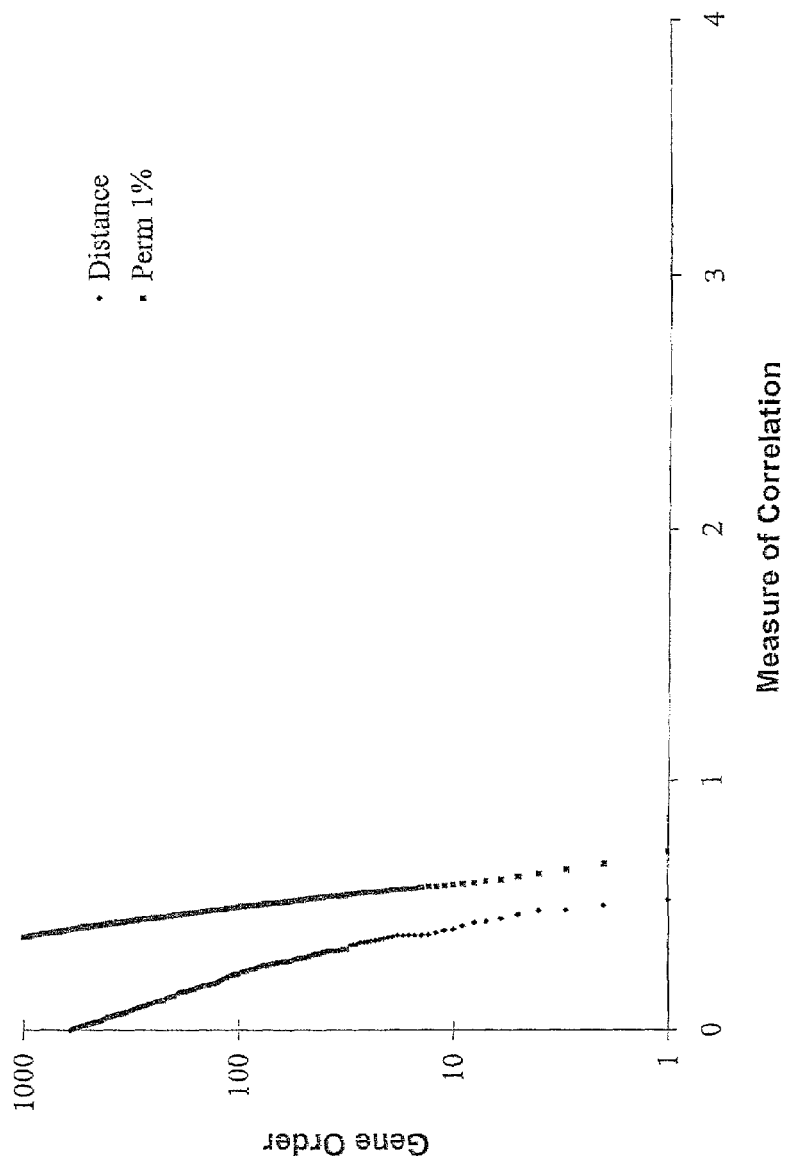

Accession number for the corresponding gene. The eighth column (entitled "Desc.") provides descriptive information about the marker gene.

FIGS. 10A–10P2 are a table of marker genes for ovarian tumor types. The second column of the table (entitled "Distinction") shows the type of tumor (ovarian) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

FIGS. 11A–11O2 are a table of marker genes for pancreatic tumor types. The second column of the table (entitled "Distinction") shows the type of tumor (pancreatic) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

FIGS. 12A–12V2 are a table of marker genes for prostate tumor types. The second column of the table (entitled "Distinction") shows the type of tumor (prostate) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

FIGS. 13A–13N2 are a table of marker genes for renal tumor types. The second column of the table (entitled "Distinction") shows the type of tumor (renal) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

FIGS. 14A–14A3 are a table of marker genes for uterine tumor types. The second column of the table (entitled "Distinction") shows the type of tumor (uterine) for which the marker gene is specific. The third column (entitled "Distance") shows the signal-to-noise distance, which is an indication of the robustness of the marker; the larger the number, the more robust (specific) the marker. The fourth, fifth and sixth columns show the result of permutation tests which are indicators of the possibility that the marker would appear by chance. The seventh column (entitled "Feature") shows the designation assigned to that marker on the AFFYMETRIX® microarray used as described in the Examples. This designation corresponds to a GENBANK® Accession number for the corresponding gene. The eighth column (entitled "Desc.") provides descriptive information about the marker gene.

Figure 16:
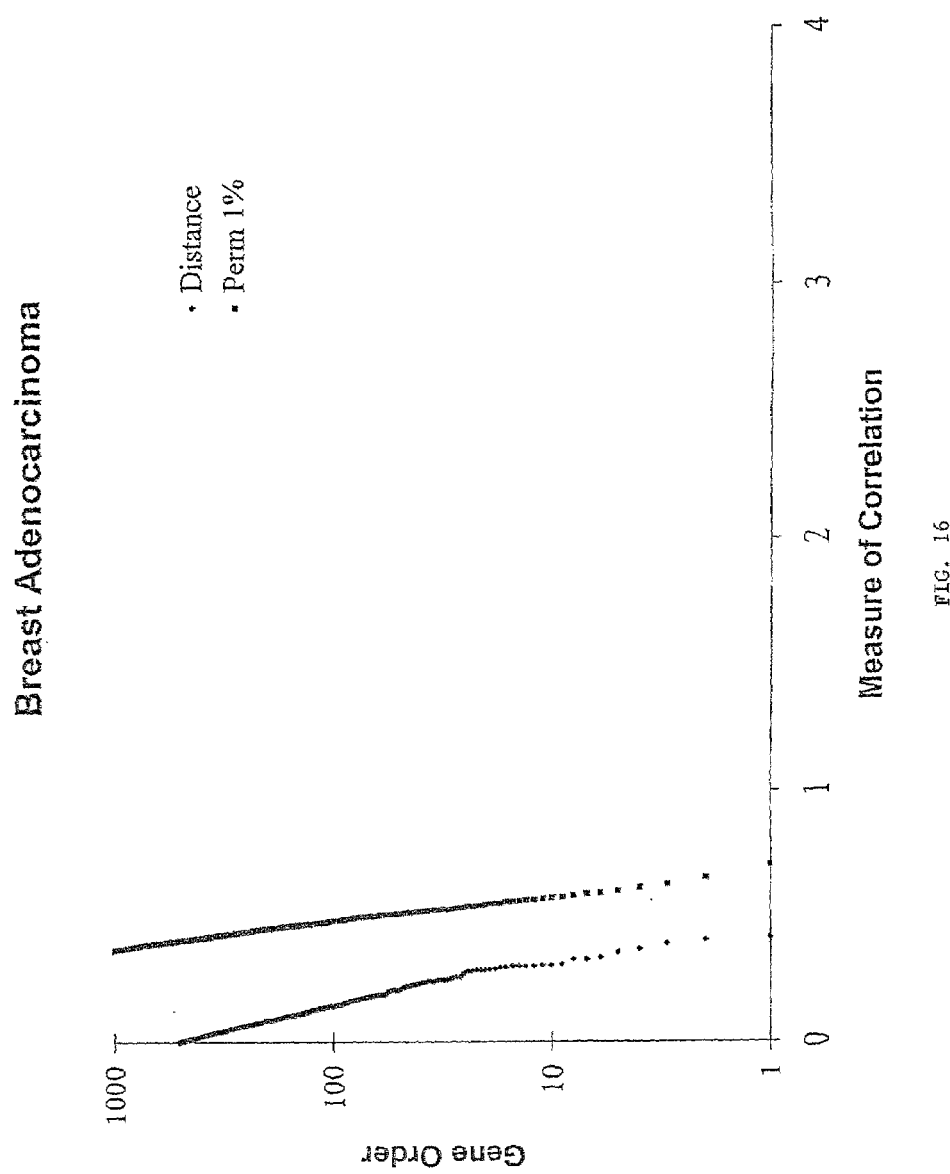
Figure 17:
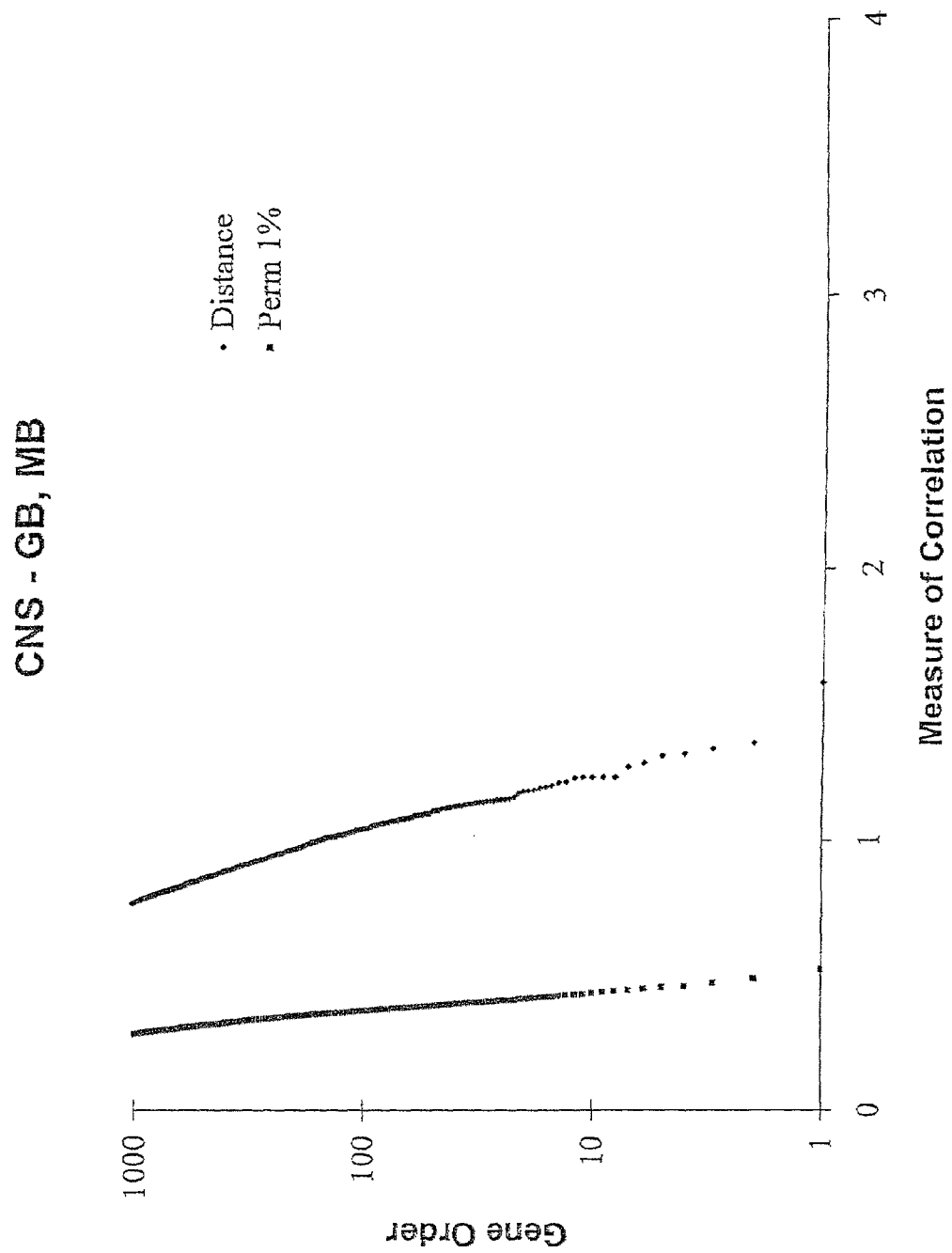
Figure 18:
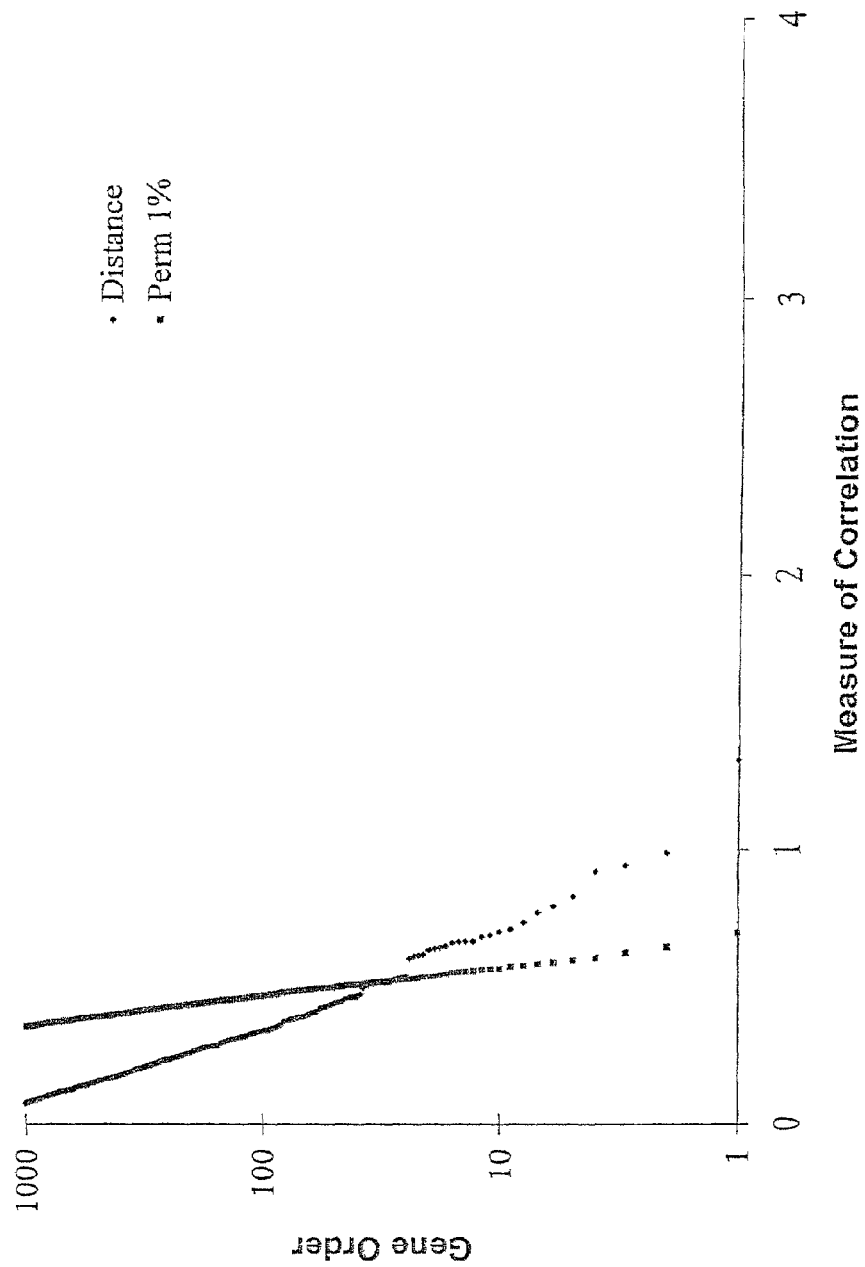
Figure 19:
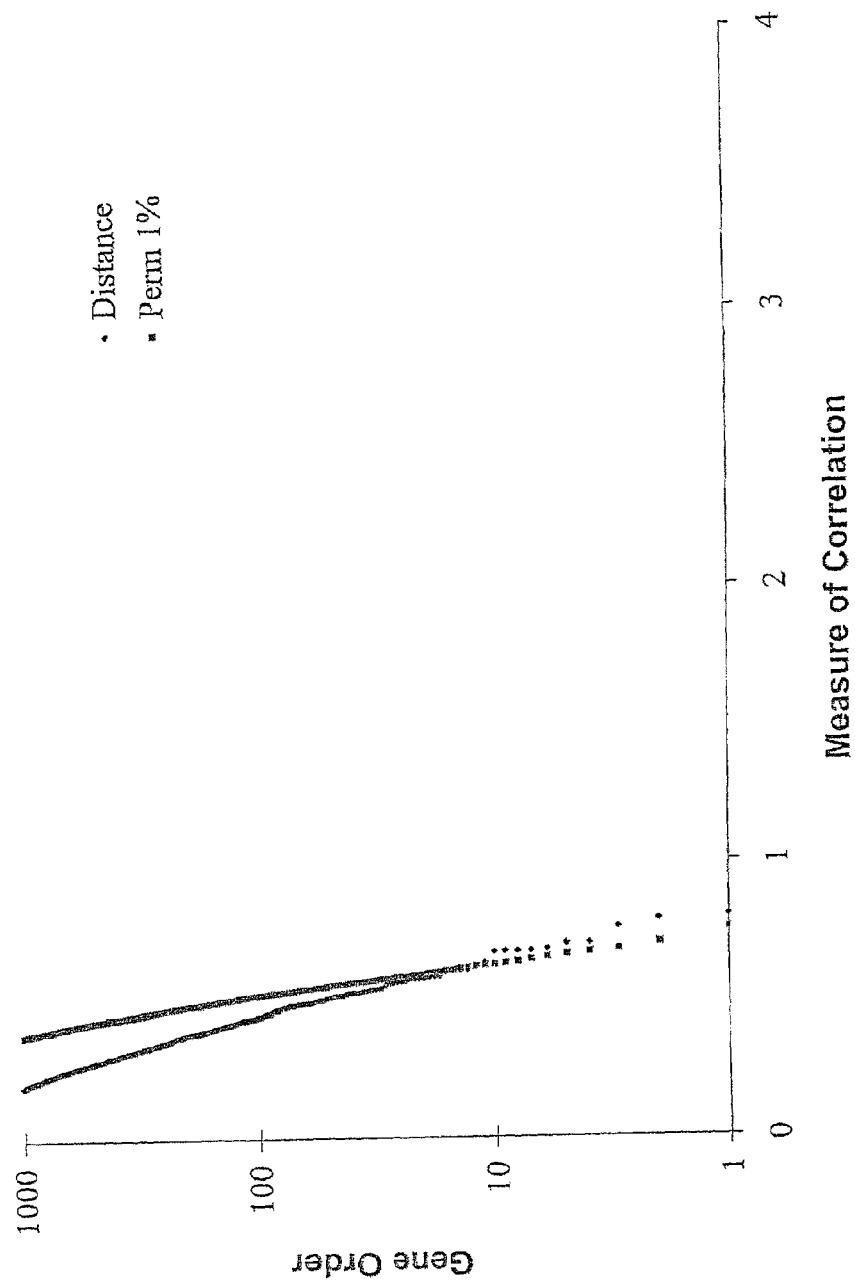
Figure 20:
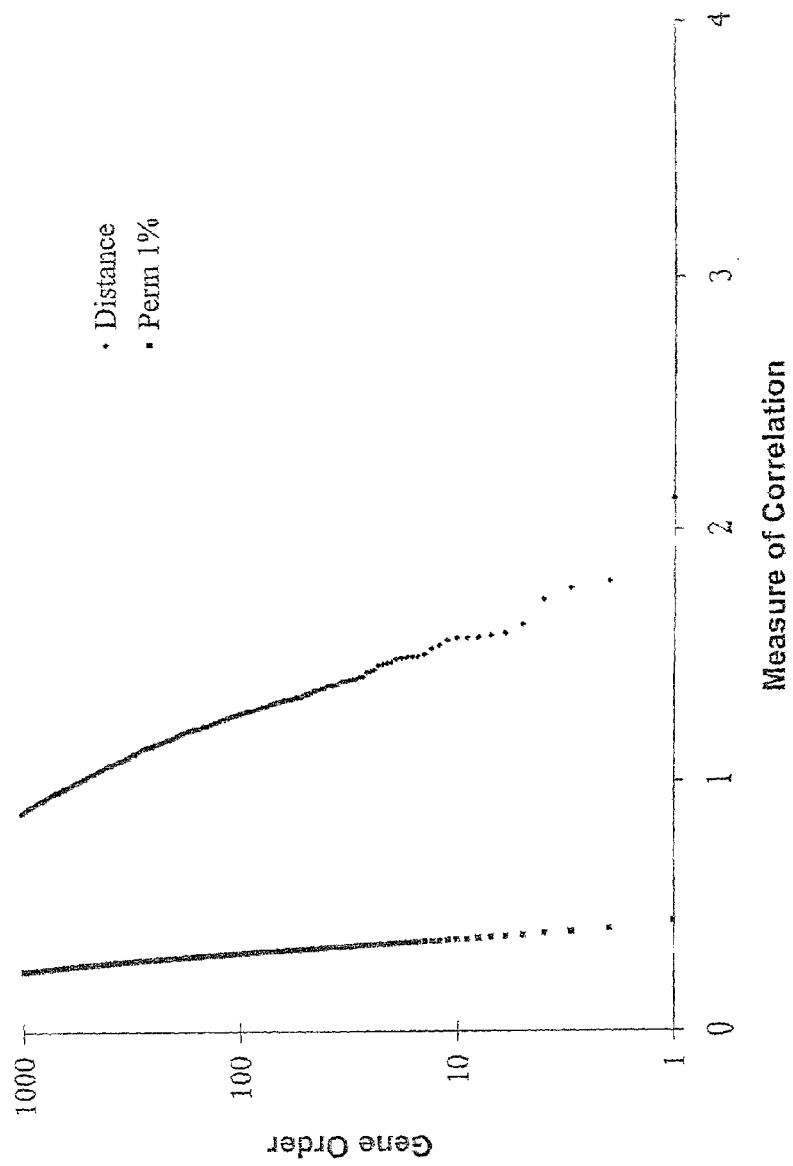
Figure 21:
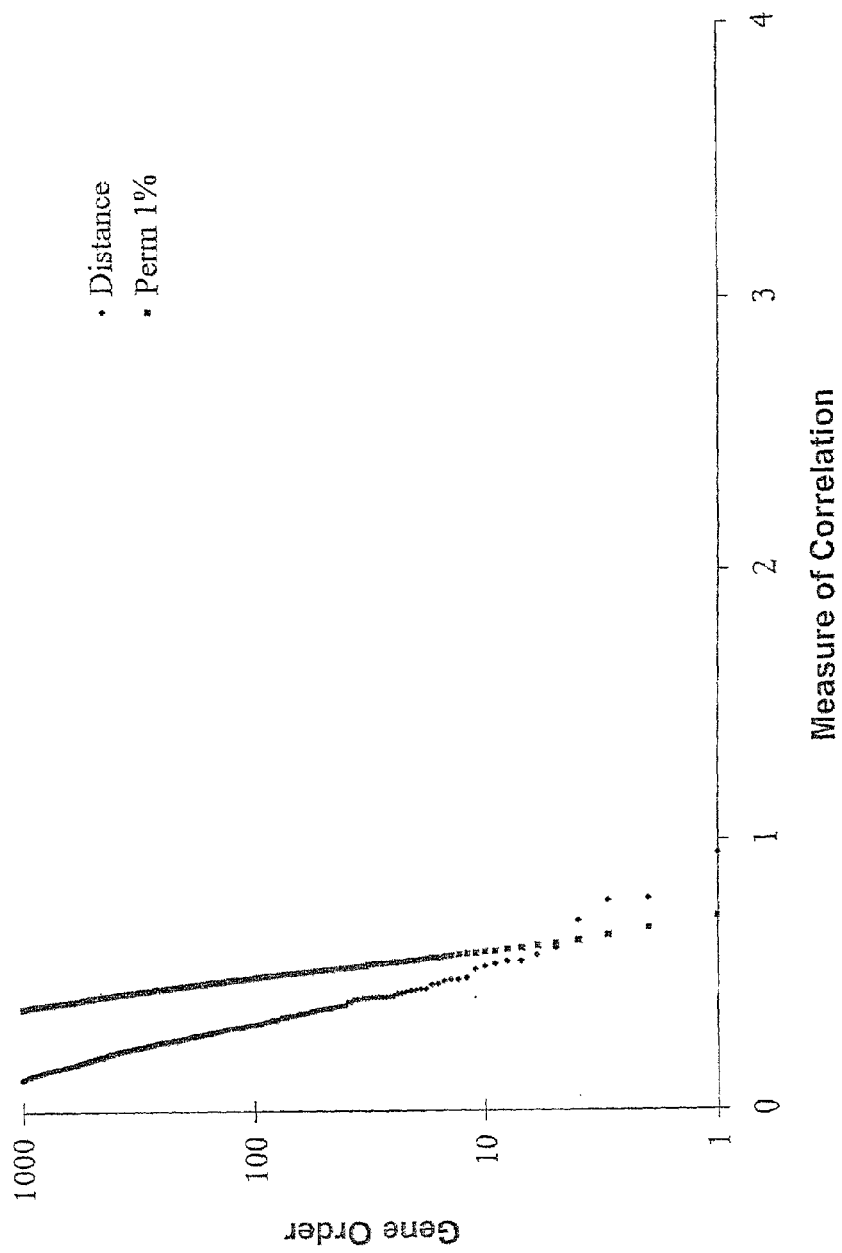
Figure 22:
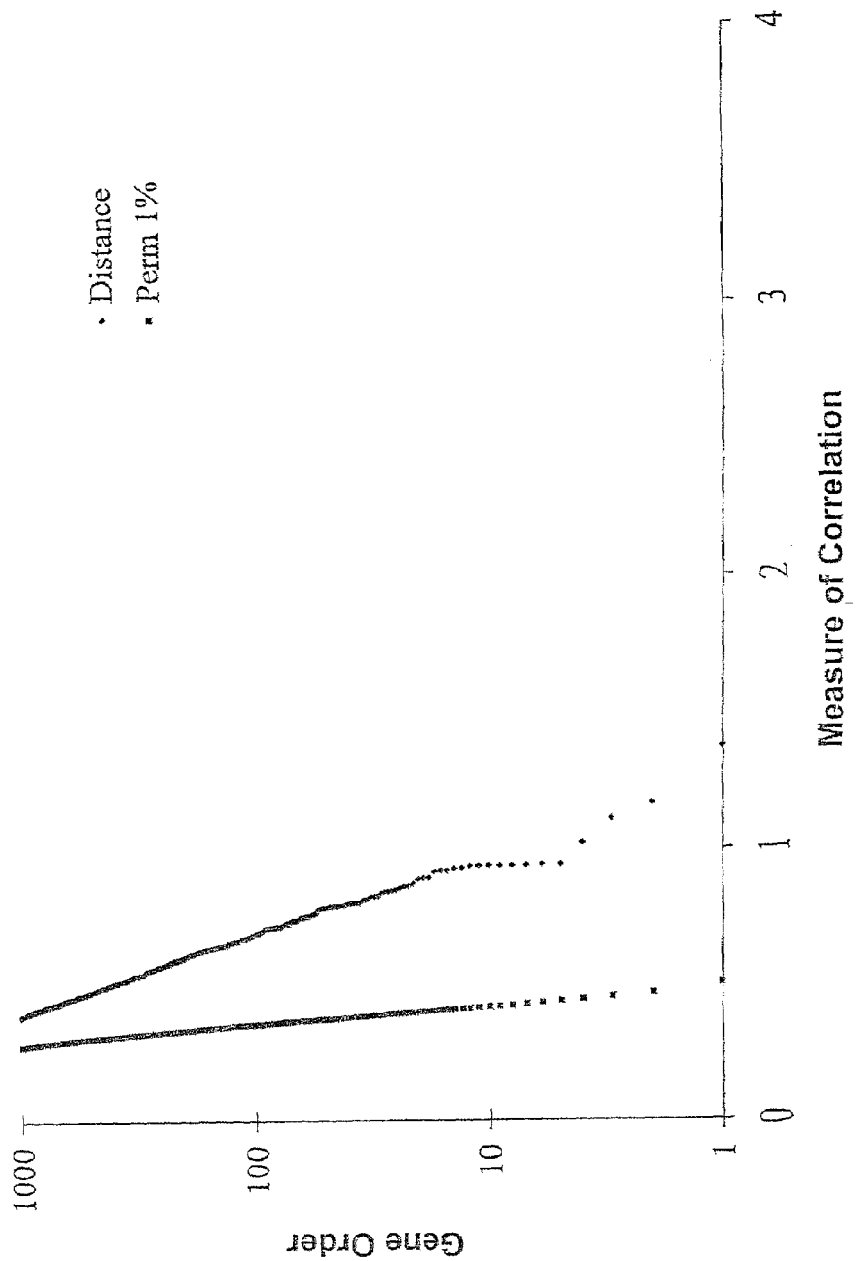
Figure 23:
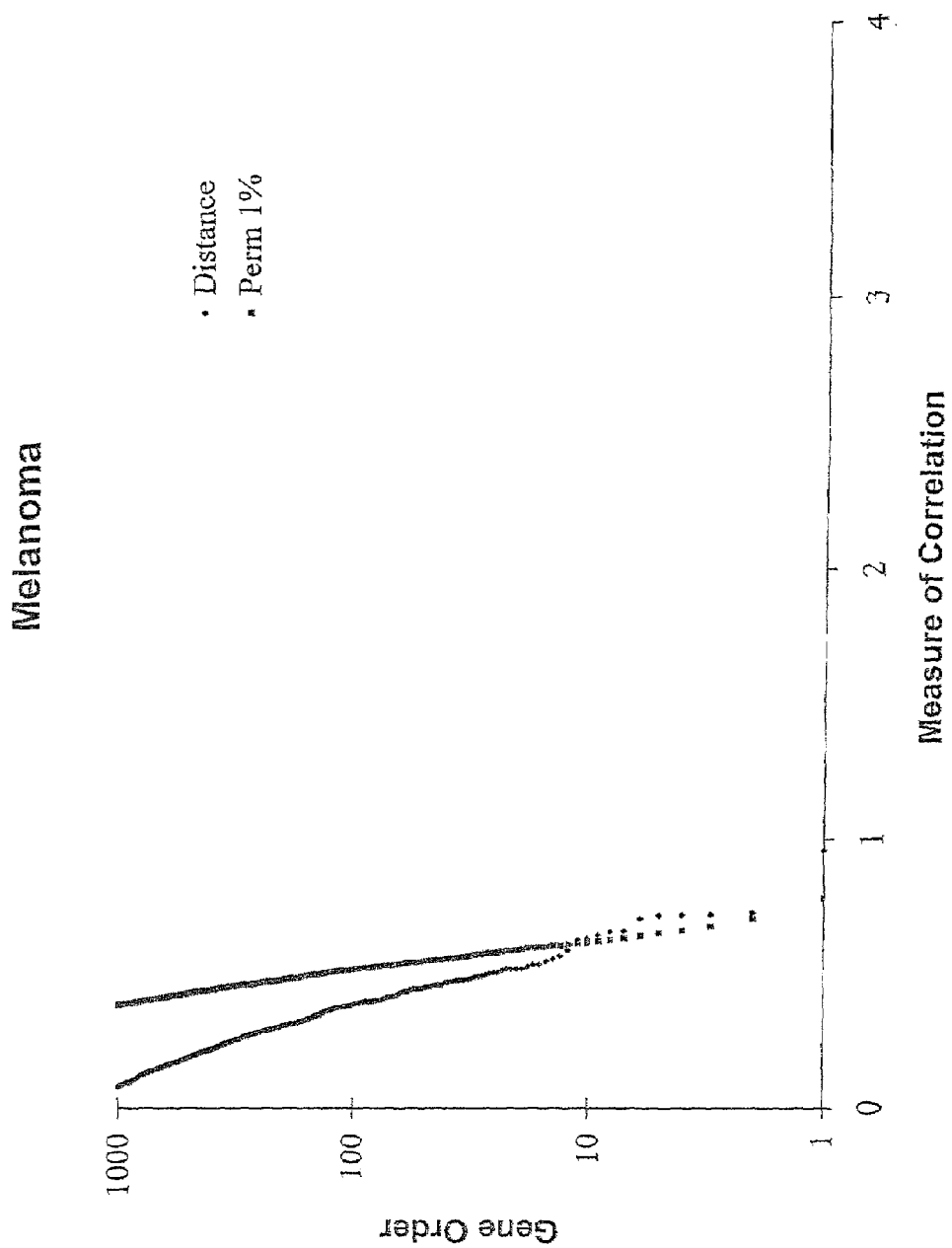
Figure 24:
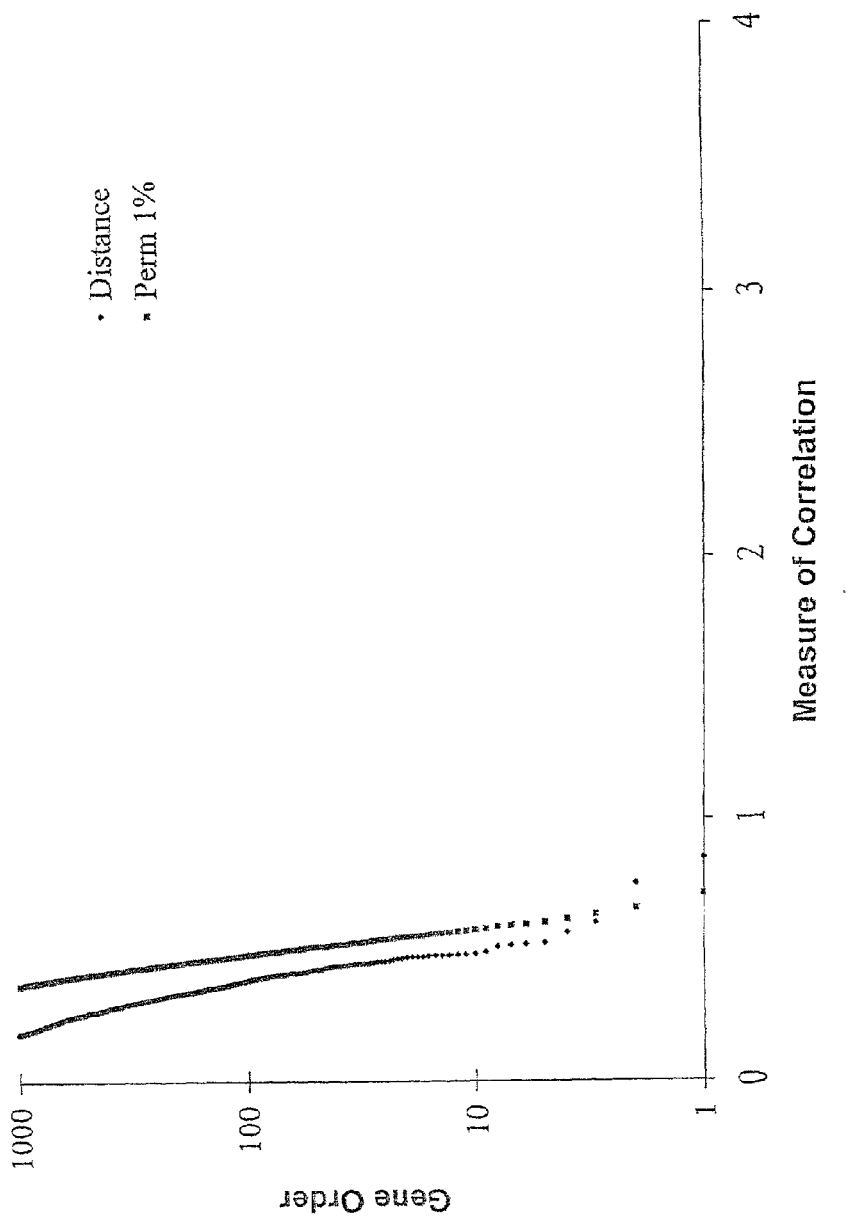
Figure 25:
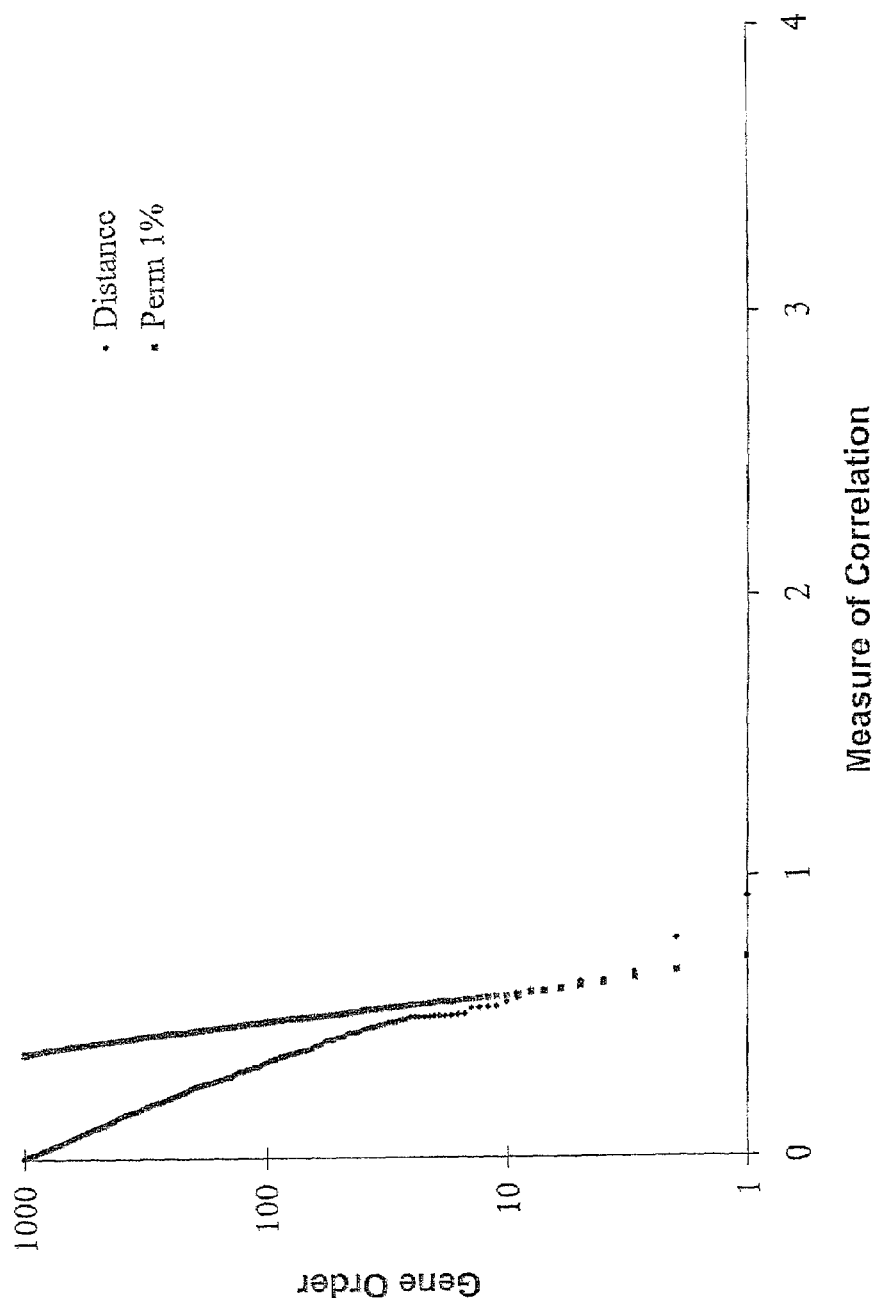
Figure 26:
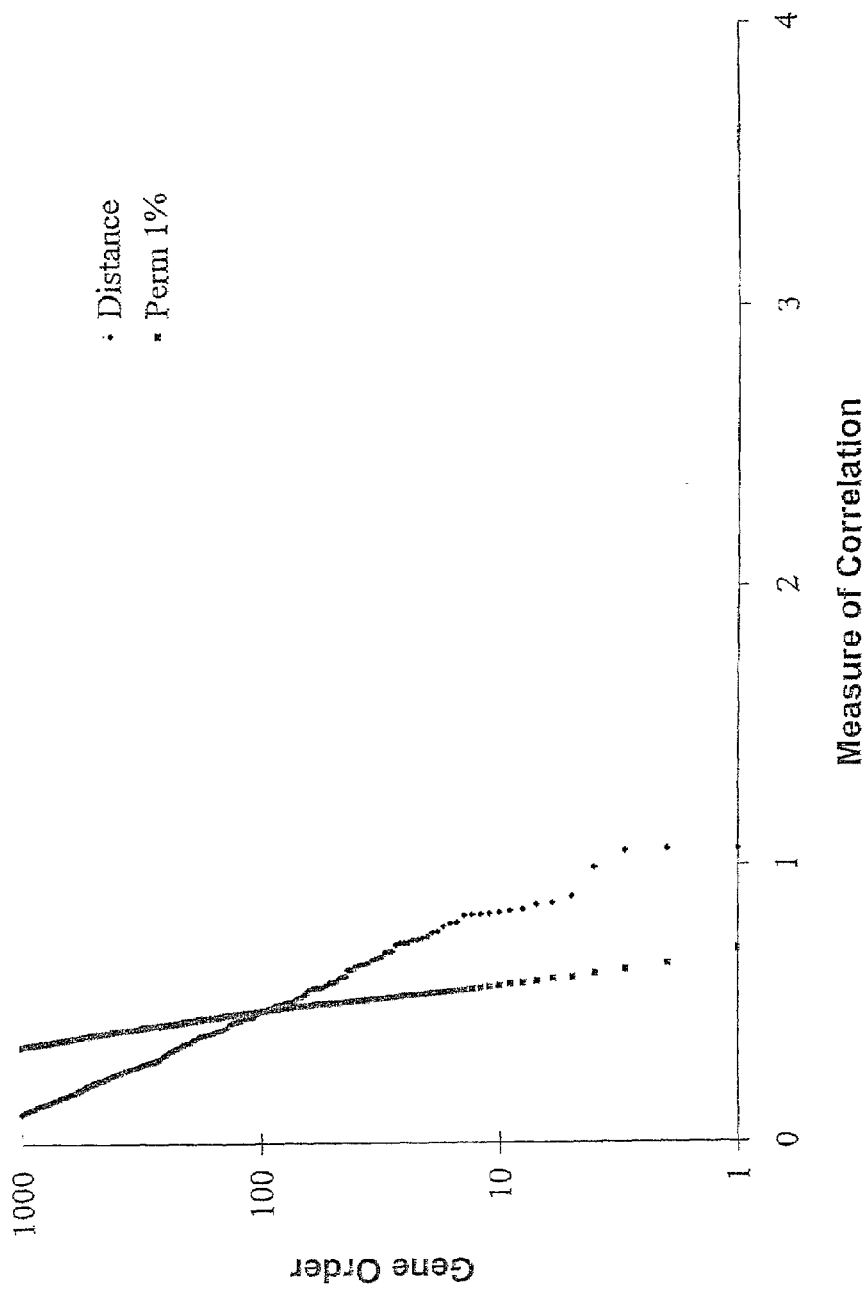
Figure 27:
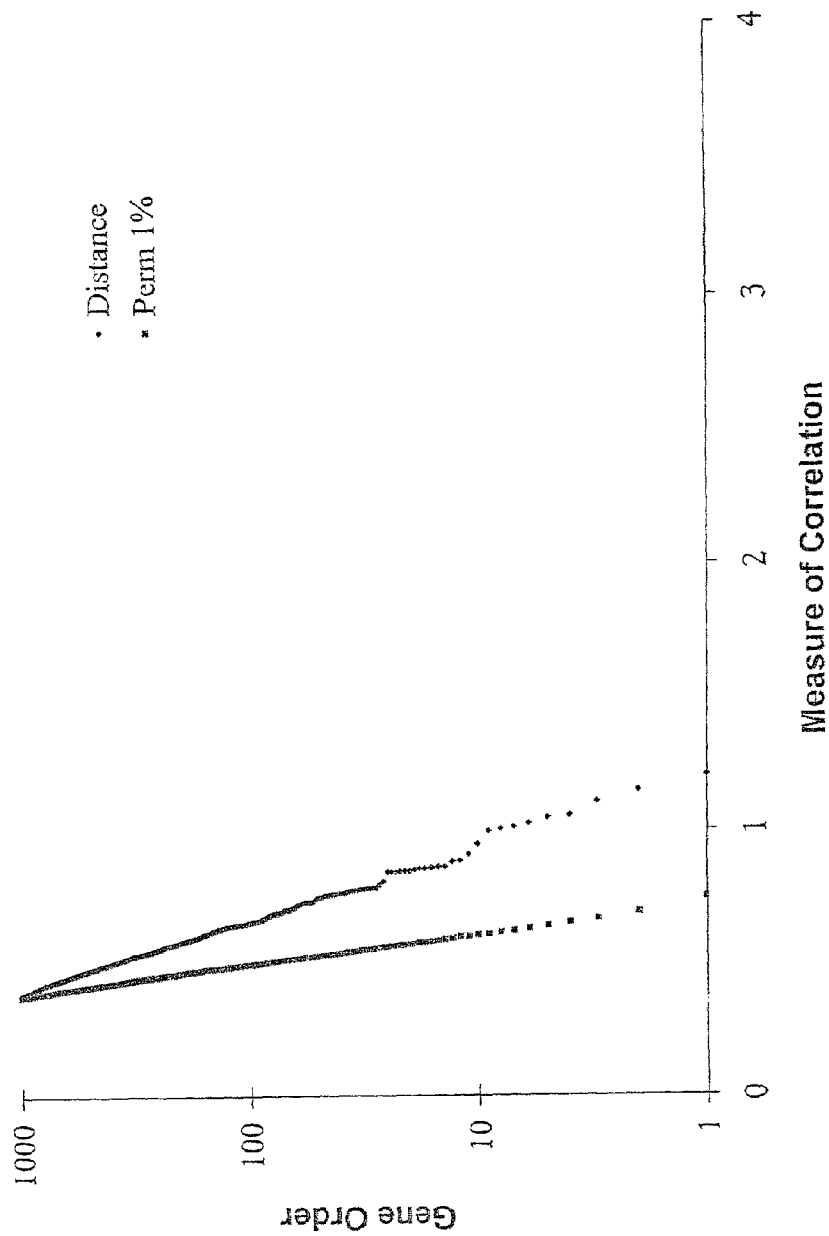

FIGS. 15–27 each show gene order as a function of measure of correlation for a variety of tumors.

DETAILED DESCRIPTION OF THE INVENTION

The invention relates to the identification of sets are marker genes which are specific for particular tumor classes. The marker genes for particular tumor types are shown in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3.

In one embodiment, the genetic markers described herein can be used to identify or classify tumors, such as tumors of unknown primary derivation. In this embodiment, a tumor sample is obtained and the gene expression pattern of a set of genes identified in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3 is determined. For example, the nucleic acid molecules within the sample can be rendered available for hybridization to an oligonucleotide array as described in the Examples. Alternatively, the expression of the proteins encoded by a set of marker genes identified herein can be assessed, e.g., using antibody-based methods. The marker genes (or encoded proteins) to be assessed can be all or a portion of the marker genes associated with a single particular tumor class, or can be all or a portion of the marker genes associated with several different tumor classes.

The expression pattern obtained can then be compared with the expression pattern(s) associated with one or more classes of tumors as described herein, and a classification of the tumor can be made based on the similarity or identity of the sample expression pattern and the pattern characteristic of a particular tumor class. For example, it may be determined that the expression pattern of the marker genes tested correlates most closely with the expression pattern characteristic of tumors of the breast, and a determination can be made that the most likely primary derivation of the tumor sample is breast.

By "gene expression pattern" is meant the level or amount of gene expression of particular genes, for example, marker genes as assessed by methods described herein. The gene expression pattern can comprise data for one or more genes and can be measured at a single time point or over a period of time. For example, the gene expression pattern can be determined using a single marker gene, or it can be determined using two or more marker genes, three or more marker genes, five or more marker genes, eight or more marker genes, twenty or more marker genes, or fifty or more marker genes. A gene expression pattern may include expression levels of marker genes that are not specific to a particular tumor or tumor class, as well as genes that are specific to a particular tumor or tumor class. Classification (e.g., the presence or absence of tumor, or the identification of a compound that modulates tumor development) can be made by comparing the gene expression pattern of the sample with respect to one or more marker genes with one or more gene expression patterns specific to a particular tumor or tumor class (e.g., in a database). Using the methods described herein, expression of numerous genes can be measured simultaneously. The assessment of numerous genes provides for a more accurate evaluation of the sample because there are more genes that can assist in classifying the sample.

As used herein, "marker genes" are proteins, polypeptides, or nucleic acid molecules (e.g., mRNA, tRNA, rRNA, cDNA, or cRNA) that result from transcription or translation of genes. The present invention can be used effectively to analyze proteins, polypeptides, or nucleic acid molecules that are the result of transcription or translation, particularly of the genes identified herein. The nucleic acid molecule levels measured can be derived directly from the gene or, alternatively, from a corresponding regulatory gene or regulatory sequence element. All forms of marker genes can be measured. For example, the nucleic acid molecule can be transcribed to obtain an RNA gene expression product. If desired, the transcript can be translated using, for example, standard in vitro translation methods to obtain a polypeptide gene expression product. Polypeptide marker gene products can be used in protein binding assays, for example, antibody assays, or in nucleic acid binding assays, standardly known in the art, in order to identify tumors or compounds involved in tumor development. Additionally, variants of marker genes including, for example, spliced variants and polymorphic alleles, can be measured. Similarly, gene expression can be measured by assessing the level of a polypeptide or protein or derivative thereof translated from mRNA. The sample to be assessed can be any sample that contains a marker gene. Suitable sources of marker genes, e.g., samples, can include intact cells, lysed cells, cellular material for determining gene expression, or material containing gene expression products. Examples of such samples are cells or tissue derived from the bladder, breast, CNS, colorectal, blood, bone marrow, lung, lymphatic system, skin, mesothelium, ovary, pancreas, prostate, kidney, or uterus. Methods of obtaining such samples are known in the art.

In one embodiment, the marker gene is a protein or polypeptide. As used herein, by "polypeptide" is meant any chain of more than two amino acids, regardless of post-translational modification such as glycosylation or phosphorylation. Examples of polypeptides include, but are not limited to, proteins. In this embodiment the determination of the gene expression pattern is made using techniques for protein detection and quantitation known in the art. For example, antibodies that specifically interact with the protein or polypeptide expression product of one or more genes specific to a particular tumor or tumor class can be obtained using methods that are routine in the art. The specific binding of such antibodies to protein or polypeptide gene expression products can be detected and measured by methods known in the art, for example, Western blot analysis or ELISA techniques.

In a preferred embodiment, the marker is a nucleic acid, for example, DNA or mRNA, and the gene expression levels are obtained by contacting the sample with a suitable microarray on which probes specific for all or a subset of the genes specific to a particular tumor or tumor class have been immobilized, and determining the extent of hybridization of the nucleic acid in the sample to the probes on the microarray. Such microarrays are also within the scope of the invention. Examples of methods of making oligonucleotide microarrays are described, for example, in WO 95/11995. Other methods are readily known to the skilled artisan.

As used herein, "genes specific to a particular tumor or tumor class," refers to a gene or genes whose expression correlates with a particular type of tumor. Expression patterns obtained for genes specific to a particular tumor or tumor class can be used to determine, for example, the presence or absence of a particular tumor in a sample, or if a candidate compound increases or decreases gene expression in a sample. Samples can be classified according to their broad expression pattern, or according to the expression levels of particular genes specific to a particular tumor or tumor class. The genes that are relevant for classification are referred to herein as "genes specific to a particular tumor or tumor class." Not all genes specific to a particular tumor or tumor class for a particular class distinction must be assessed in order to classify a sample. A subset of the genes specific to a particular tumor or tumor class that demonstrate a high correlation with a tumor class distinction can be used in classifying the presence of an that particular tumor type. This subset can be, for example, one or more genes, two or more genes, three or more genes, five or more genes, eight or more genes, twenty or more genes, or fifty or more genes. The genes specific to a particular tumor or tumor class that characterize other classification categories such as, for example, a candidate compound that modulates tumor development, can be the same or different from the genes specific to a particular tumor or tumor class that characterize the presence or absence of a tumor. Typically the accuracy of the classification increases with the number of genes specific to a particular tumor or tumor class that are assessed.

The gene expression value measured or assessed is the numeric value obtained from an apparatus that can measure gene expression levels. Gene expression levels refer to the amount of expression of the gene expression product, as described herein. The values are raw values from the apparatus, or values that are optionally re-scaled, filtered and/or normalized. Such data is obtained, for example, from a GENECHIP® brand probe array or Microarray (Affymetrix, Inc.; U.S. Pat. Nos. 5,631,734, 5,874,219, 5,861,242, 5,858, 659, 5,856,174, 5,843,655, 5,837,832, 5,834,758, 5,770,722, 5,770,456, 5,733,729, 5,556,752, all of which are incorporated herein by reference in their entirety), and the expression levels are calculated with software (e.g., the AFFYMETRIX® GENECHIP® software). For example, nucleic acids (e.g., mRNA or DNA) from a sample that has been subjected to particular stringency conditions hybridize to the probes on the chip. The nucleic acid to be analyzed (e.g., the target) is isolated, amplified and labeled with a detectable label, (e.g., $^{32}P$ or fluorescent label) prior to hybridization to the arrays. After hybridization, the arrays are inserted into a scanner that can detect patterns of hybridization. These patterns are detected by detecting the labeled target now attached to the microarray, e.g., if the target is fluorescently labeled, the hybridization data are collected as light emitted from the labeled groups. Since labeled targets hybridize, under appropriate stringency conditions known to one of skill in the art, specifically to complementary oligonucleotides contained in the microarray, and since the sequence and position of each oligonucleotide in the array are known, the identity of the target nucleic acid applied to the probe is determined.

Quantitation of gene expression patterns from the hybridization of a labeled nucleic acid microarray can be performed by scanning the microarray to measure the amount of hybridization at each position on the microarray with an AFFYMETRIX® scanner (Affymetrix Inc. Santa Clara, Calif.). For each stimulus a time series of nucleic acid levels (C={C1,C2,C3, . . . Cn}) and a corresponding time series of nucleic acid levels (M={M1,M2,M3, . . . Mn}) in control medium in the same experiment as the stimulus is obtained. Quantitative data is then analyzed. Hybridization analysis using microarray is only one method for obtaining gene expression values. Other methods for obtaining gene expression values known in the art or developed in the future can be used with the present invention. Once the gene expression values are determined, the sample can be classified.

Once the gene expression levels of the sample are obtained, the levels are compared or evaluated against a model or control sample(s), and then the sample is classified, for example, based one whether a particular gene in the sample exhibits increased or decreased expression or whether a marker gene expression pattern is similar to the gene expression pattern specific to a tumor. The evaluation of the sample determines whether or not the sample is assigned to a particular tumor class, or whether or not a candidate compounds modulates tumor development.

By "a marker gene expression pattern similar to the gene expression pattern specific to a tumor" is meant that a marker gene is expressed at least 50%, more preferably, at least 60%, 70%, 80%, or 90%, and most preferably at least 95% of the level of a gene specific to a tumor, for example those genes described in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3. Such determinations can be made using methods described herein, as well as methods known in the art. Preferably, when more than one marker gene is being assessed in a give sample, each marker gene is expressed at least 50%, more preferably, at least 60%, 70%, 80%, or 90%, and most preferably at least 95% of the level of a gene specific to a tumor.

The correlation between gene expression and classification can be determined using a variety of methods. Methods for defining classes and classifying samples are described, for example, in U.S. patent application Ser. No. 09/544,627, filed Apr. 6, 2000 by Golub et al., the teachings of which are incorporated herein by reference in their entirety. The information provided by the present invention, alone or in conjunction with other test results, aids in sample classification.

In another embodiment of the invention, a sample is obtained from an individual and an assessment of the expression pattern of a set of marker genes described herein is performed to predict or aid in the prediction or diagnose or aid in the diagnosis of cancer in an individual. A biological sample is obtained from the individual, and the gene expression pattern of a set of genes identified in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3 is determined. For example, the nucleic acid molecules within the sample can be rendered available for hybridization to an oligonucleotide array as described in the Examples. Alternatively, the expression of the proteins encoded by a set of marker genes identified herein can be assessed, e.g., using antibody-based methods. The marker genes (or encoded proteins) to be assessed can be all or a portion of the marker genes associated with a single particular tumor class, or can be all or a portion of the marker genes associated with several different tumor classes.

The expression pattern obtained can be compared with the expression pattern for one or more classes of tumors as described herein. If the expression pattern is substantially similar to that of a tumor class identified herein, a prediction or diagnosis of cancer is likely. The expression pattern can also be compared with the expression pattern obtained from corresponding normal tissue as a control. Similarly, the expression pattern of these marker genes can also be assessed to monitor the effects of treatment in a manner similar to that used in the monitoring of prostate specific antigen for prostate cancer treatment.

Many of the methods described herein for assessment of gene expression require amplification of DNA from target samples. This can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The gene expression of the marker genes identified herein can be analyzed by a variety of methods known in the art, including, but not limited to, gene isolation and sequencing or hybridization of a specific oligonucleotide with amplified gene products. In a preferred embodiment, analysis is performed using chip-based oligonucleotide arrays as described herein and known in the art.

There are a number of genetic markers indicated in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3 for each tumor class. In the methods of the invention it is not necessary that all of the indicated marker genes for any particular class be assessed, although one can assess all marker genes for a particular tumor class or all marker genes for multiple tumor classes. For example, the expression pattern of a subset of these genes can be assessed. In one embodiment, only a single marker gene specific for a particular tumor class is assessed. In another embodiment, multiple marker genes are assessed, each of which is specific for a different tumor class. In a further embodiment, multiple marker genes are assessed, each of which is specific for the same tumor class. For example, it is preferred that at least 2, preferably at least 5, more preferably at least 8, even more preferably at least 20, and even more preferably at least 50 marker genes (or their encoded proteins) are assessed.

The present invention also features methods for identifying compounds that modulate tumor development. Novel compounds identified as described herein are also the subject of the invention. Such methods involve contacting a sample, for example a cell, cell lysate, tissue, or tissue lysate, with a candidate compound, and detecting a decrease in expression of at least one gene specific to a particular tumor or tumor class. A candidate compound that decreases expression of such gene is a compound for use in modulating tumor development. A decrease in an gene specific to a particular tumor or tumor class may be identified using any of the methods described herein (or any analogous method known in the art). For example, oligonucleotide array systems described herein may be used to determine whether the addition of a test compound to a sample modulates expression of a gene specific to a particular tumor or tumor class in that sample.

By "modulating tumor development" is meant increasing or decreasing the likelihood that a tumor will form or develop in a subject. The modulation in tumor formation may be the result of contacting a sample (for example, a cell, tissue, cell or tissue lysate, nucleic acid, or polypeptide) with a candidate compound. It will be appreciated that the degree of modulation provided by a candidate compound in a given assay will vary, but that one skilled in the art can determine the statistically significant change or a therapeutically effective change in the degree or rate of tumor development.

By "tumor development" is meant the formation or progression of a tumor. As used herein leukemias and lymphomas are considered to be types of tumors. Methods for monitoring tumor development are known to those skilled in the art.

By a "candidate compound" is meant a molecule, be it naturally-occurring or artificially derived, that is surveyed for its effects on the gene expression pattern of a marker gene, employing methods described herein. Examples of candidate compounds include, but are not limited to peptides, polypeptides, synthetic organic molecules, naturally occurring organic molecules, nucleic acid molecules, and combinations thereof.

By "decrease in gene expression" is meant a lowering of the level or expression of, and/or the activity of, one or more genes specific to a particular tumor or tumor class in a cell, tissue, cell lysate, or tissue lysate sample relative to a control sample. A decrease in gene expression may occur, for example, when the sample is contacted with a candidate compound for use in modulating tumor development. The control sample may be a cell, tissue, cell lysate, or tissue lysate that was not contacted with the candidate compound or that was contacted with candidate compound vehicle only. Preferably, the decrease in gene expression of a gene specific to a particular tumor or tumor class is at least 25%, more preferably, the decrease is at least 50%, 60%, 70%, 80%, or 90% and most preferably, the decrease is at least one-fold, relative to a control sample.

The expression level of an gene specific to a particular tumor or tumor class may be modulated by modulating transcription, translation, or mRNA or protein turnover, or the activity of the gene expression product, and such modulation may be detected using known methods for measuring mRNA and protein levels and activities, e.g., oligonucleotide microarray hybridization, RT-PCR, and ELISA and nucleic acid and protein binding assays.

While the above described candidate compound screening methods are designed primarily to identify candidate compounds that may be used to decrease tumor development, identification of candidate compounds that increases tumor development is also a feature of the present invention. Such candidate compound identification methods involve contacting a sample, for example, a cell, cell lysate, tissue, or tissue lysate with a candidate compound, and detecting an increase in expression of at least one gene specific for a particular tumor or tumor class. A candidate compound that increases expression of such a gene specific to a particular tumor or tumor class is a compound for use in modulating tumor development.

By "increase in gene expression" is meant a raising of the level of expression, and/or the activity, of one or more genes specific to a particular tumor or tumor class in a cell, tissue, cell lysate, or tissue lysate sample relative to a control sample. An increase in gene expression may occur, for example, when the sample is contacted with a candidate compound for use in modulating tumor development. The control sample may be a cell, tissue, cell lysate, or tissue lysate that was not contacted with the candidate compound or that was contacted with candidate compound vehicle only. Preferably, the increase is at least 1.5-fold, more preferably the increase is at least 2-fold, 5-fold, or 10-fold, and most preferably, the increase is at least 20-fold, relative to a control sample.

In general, novel drugs for modulation of tumor development can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., Chembridge (San Diego, Calif.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their tumor development-modulatory activities should be employed whenever possible.

When a crude extract is found to modulate (i.e., stimulate (increase) or inhibit (decrease)) tumor development, further fractionation of the positive lead extract is desirable to isolate chemical constituents responsible for the observed effect. Thus, the goal of the extraction, fractionation, and purification process is the careful characterization and identification of a chemical entity within the crude extract having an activity that increases or deceases. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases, in which it is desirable to increase or decrease tumor development.

The present invention also features arrays, for example, microarrays that have a plurality of oligonucleotide probes involved in tumor development immobilized thereon. The oligonucleotide probe may be specific for one or more genes specific for a particular tumor or tumor class, selected from those genes described herein. Such genes can be obtained using their GENBANK® Accession Numbers identified in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3. Methods for making oligonucleotide microarrays are well known in the art, and are described, for example, in WO 95/11995, the entire teachings of which are hereby incorporated by reference.

The present invention also provides information regarding the genes that are important in tumor development, thereby providing additional targets for diagnosis and therapy. It is clear that the present invention can be used to generate databases comprising genes specific to a particular tumor or tumor class that will have many applications in medicine, research and industry; such databases are also within the scope of the invention.

The invention will be further illustrated by the following non-limiting examples. The teachings of all references cited herein are incorporated herein by reference in their entirety.

EXAMPLES

Materials and Methods

Approximately 300 human tumor and normal tissue specimens were identified and obtained or purchased from a variety of academic or commercial sources. These specimens represented 30 individual classes of tumor or normal tissue with each class containing between 5 and 20 samples. Total RNA was isolated from these specimens using standard laboratory protocols. "Target" (biotinylated) fragmented complementary RNA (cRNA) was produced from each sample using an established molecular biology protocol. Each Target was hybridized sequentially to two high density AFFYMETRIX® oligonucleotide microarrays (Hu6800FL and Hu35KsubA; Affymetrix, Inc., Santa Clara, Calif.), and gene expression profiles (patterns) were measured using a modified confocal laser scanner according to the manufacturer's instructions.

Analysis of Expression Profile (Pattern) Data

Raw expression data was combined into a master data set containing the expression values for between 6800 and 16,000 genes expressed by each individual sample. A filter was applied to this data set which only allowed those genes expressed at 3-fold above baseline and with an absolute difference in expression value of 100 to pass. A signal-to-noise metric (S2N=mean of class #1-mean of class #2/standard deviation of class #1+standard deviation of class #2) was applied to this filtered data set to determine which genes are expressed in each individual class versus the other classes. Finally, by comparing the sets of genes which are expressed specifically in one class of tumor (e.g., pancreatic adenocarcinoma) versus its accompanying normal tissue (e.g., normal pancreas), we have determined sets of genes which are specific to various tumors and their normal tissue counterparts. The results are shown in FIGS. 1A–1R2, FIGS. 2A–2T2, FIGS. 3A–3Z2, FIGS. 4A–4S2, FIGS. 5A–5M2, FIGS. 6A–6W2, FIGS. 7A–7D3, FIGS. 8A–8X2, FIGS. 9A–9C3, FIGS. 10A–10P2, FIGS. 11A–11O2, FIGS. 12A–12V2, FIGS. 13A–13N2, and FIGS. 14A–14A3.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying a pancreatic tumor comprising the steps of: a) obtaining a sample derived from a pancreas; b) determining the expression pattern of galectin-4 in the sample; and c) comparing the expression pattern obtained in step b) to the expression pattern of galectin-4 specific to a pancreatic tumor, wherein a galectin-4 gene expression pattern in the sample that is similar to the galectin-4 gene expression pattern specific to a tumor identifies a pancreatic tumor.

2. A method according to claim 1, wherein the expression pattern is determined utilizing DNA.

3. A method according to claim 1, wherein the expression pattern is determined utilizing mRNA.

4. A method according to claim 2, wherein the expression pattern is determined utilizing specific hybridization probes.

5. A method according to claim 3, wherein the expression pattern is determined utilizing specific hybridization probes.

6. A method according to claim 2, wherein the expression pattern is determined utilizing oligonucleotide microarrays.

7. A method according to claim 3, wherein the expression pattern is determined using oligonucleotide microarrays.

8. A method according to claim 1, wherein determining the expression pattern occurs by determining the level of a polypeptide encoded by galectin-4.

9. A method according to claim 8, wherein the level of said polypeptide is determined utilizing antibodies.

* * * * *